US012152021B2

(12) United States Patent
Lee et al.

(10) Patent No.: US 12,152,021 B2
(45) Date of Patent: Nov. 26, 2024

(54) HETEROARYL DERIVATIVE, METHOD FOR PRODUCING SAME, AND PHARMACEUTICAL COMPOSITION COMPRISING SAME AS EFFECTIVE COMPONENT

(71) Applicant: VORONOI INC., Incheon (KR)

(72) Inventors: Youn Ho Lee, Incheon (KR); Ju Hee Kang, Incheon (KR); Se In Kang, Incheon (KR); Yi Kyung Ko, Incheon (KR); Eun Hwa Ko, Incheon (KR); Hwan Geun Choi, Seoul (KR); Jung Beom Son, Incheon (KR); Nam Doo Kim, Incheon (KR)

(73) Assignee: VORONOI INC., Incheon (KR)

( * ) Notice: Subject to any disclaimer, the term of this patent is extended or adjusted under 35 U.S.C. 154(b) by 589 days.

(21) Appl. No.: 17/440,630

(22) PCT Filed: Mar. 19, 2020

(86) PCT No.: PCT/KR2020/095044
§ 371 (c)(1),
(2) Date: Sep. 17, 2021

(87) PCT Pub. No.: WO2020/190119
PCT Pub. Date: Sep. 24, 2020

(65) Prior Publication Data
US 2022/0162203 A1    May 26, 2022

(30) Foreign Application Priority Data
Mar. 19, 2019  (KR) .................. 10-2019-0031269
Oct. 28, 2019  (KR) .................. 10-2019-0134472

(51) Int. Cl.
| | |
|---|---|
| *C07D 413/14* | (2006.01) |
| *A61K 31/407* | (2006.01) |
| *A61K 31/506* | (2006.01) |
| *A61K 31/5377* | (2006.01) |
| *A61K 31/5386* | (2006.01) |
| *A61P 35/00* | (2006.01) |
| *C07D 409/14* | (2006.01) |
| *C07D 413/04* | (2006.01) |
| *C07D 417/04* | (2006.01) |
| *C07D 471/04* | (2006.01) |
| *C07D 471/18* | (2006.01) |
| *C07D 487/04* | (2006.01) |
| *C07D 487/08* | (2006.01) |
| *C07D 491/048* | (2006.01) |
| *C07D 491/08* | (2006.01) |
| *C07D 491/107* | (2006.01) |
| *C07D 498/08* | (2006.01) |

(52) U.S. Cl.
CPC ............ *C07D 413/14* (2013.01); *A61P 35/00* (2018.01); *C07D 413/04* (2013.01); *C07D 487/08* (2013.01); *C07D 498/08* (2013.01)

(58) Field of Classification Search
CPC .. C07D 413/14; C07D 413/04; C07D 487/08; C07D 498/08; C07D 417/14; C07D 471/08; C07D 491/048; C07D 487/04; C07D 491/08; C07D 491/107; C07D 409/14; C07D 471/04; A61P 35/00; A61K 31/5377; A61K 31/5386; A61K 31/506; A61K 31/407
See application file for complete search history.

(56) References Cited

U.S. PATENT DOCUMENTS

| | | | |
|---|---|---|---|
| 7,569,561 B2 | 8/2009 | Stadtmueller et al. | |
| 10,377,747 B2 | 8/2019 | Wu et al. | |
| 11,352,352 B2 | 6/2022 | Zhang et al. | |
| 11,466,000 B2 | 10/2022 | Lee et al. | |
| 2016/0102076 A1 | 4/2016 | Suh et al. | |
| 2016/0229837 A1 | 8/2016 | Xi et al. | |
| 2017/0313714 A1 | 11/2017 | Wei et al. | |
| 2018/0208581 A1 | 7/2018 | Zhu et al. | |
| 2019/0127335 A1 | 5/2019 | Betts et al. | |
| 2022/0073505 A1 | 3/2022 | Lee et al. | |
| 2022/0289733 A1 | 9/2022 | Lee et al. | |

FOREIGN PATENT DOCUMENTS

| | | |
|---|---|---|
| CN | 106132957 A | 11/2016 |
| CN | 106478607 A | 3/2017 |
| CN | 108191774 A | 6/2018 |

(Continued)

OTHER PUBLICATIONS

CAS Registry No. 1851548-27-0, entry into Registry STN Jan. 24, 2016, American Chemical Society, 2024.*
U.S. Appl. No. 17/701,478, Lee et al., filed Mar. 22, 2022.
Verweij, M. (2000). "Medical-Ethical Dimensions of Preventive Medicine," Chapter 3 in Preventive Medicine Between Obligation and Aspiration, Springer Science and Business Media, vol. 4, pp. 25-48, 31 pages.

(Continued)

*Primary Examiner* — John M Mauro
(74) *Attorney, Agent, or Firm* — MORRISON & FOERSTER LLP

(57) ABSTRACT

The present invention relates to a 6-(isooxazolidin-2-yl)-N-phenylpyrimidin-4-amine derivative, and a pharmaceutical composition for preventing or treating cancer comprising the compound as an effective component. The compound exhibits high inhibitory activity against an epidermal growth factor receptor (EGFR) variant, or wild-type or variants of one or more of ERBB2 and ERBB4, and thus may be usefully used in the treatment of cancers in which same are expressed. In particular, the compound exhibits excellent inhibitory activity on proliferation of lung cancer cell lines, and thus can be usefully used in the treatment of lung cancer.

29 Claims, 1 Drawing Sheet

(56) References Cited

FOREIGN PATENT DOCUMENTS

| CN | 109280048 A | 1/2019 |
|---|---|---|
| CN | 109608394 A | 4/2019 |
| EP | 3205650 A1 | 8/2017 |
| EP | 3640248 A1 | 4/2020 |
| JP | 2011102241 A | 5/2011 |
| JP | 2017530999 A | 10/2017 |
| JP | 2018520190 A | 7/2018 |
| JP | 2018525431 A | 9/2018 |
| KR | 20090121399 A | 11/2009 |
| KR | 20130053240 A | 5/2013 |
| KR | 20150047855 A | 5/2015 |
| KR | 20150067759 A | 6/2015 |
| KR | 20150131224 A | 11/2015 |
| KR | 1020170066650 A | 6/2017 |
| KR | 1020170118681 A | 10/2017 |
| KR | 20180030190 A | 3/2018 |
| KR | 20190108079 A | 9/2019 |
| KR | 20190108080 A | 9/2019 |
| KR | 102073854 B1 | 2/2020 |
| WO | WO2000232872 A1 | 4/2002 |
| WO | WO2005026129 A1 | 3/2005 |
| WO | WO2006125616 A2 | 11/2006 |
| WO | WO2008115742 A1 | 9/2008 |
| WO | WO2008150118 A2 | 12/2008 |
| WO | WO2011022440 A2 | 2/2011 |
| WO | WO2013109882 A1 | 7/2013 |
| WO | WO2013169401 A1 | 11/2013 |
| WO | WO2014055928 A3 | 6/2014 |
| WO | WO2014128213 A1 | 8/2014 |
| WO | WO2014141104 A1 | 9/2014 |
| WO | WO2015025936 A1 | 2/2015 |
| WO | WO2015061247 A2 | 4/2015 |
| WO | WO2015175632 A1 | 11/2015 |
| WO | WO2015195228 A1 | 12/2015 |
| WO | WO2016060443 A2 | 4/2016 |
| WO | 2016105525 A2 | 6/2016 |
| WO | WO2017096301 A1 | 6/2017 |
| WO | 2017120429 A1 | 7/2017 |
| WO | WO2018109097 A1 | 6/2018 |
| WO | 2018228446 A1 | 12/2018 |
| WO | WO2019010295 A1 | 1/2019 |
| WO | WO2019081486 A1 | 5/2019 |
| WO | WO2019149164 A1 | 8/2019 |
| WO | WO2019177374 A1 | 9/2019 |
| WO | WO2019177375 A1 | 9/2019 |
| WO | WO2019222093 A1 | 11/2019 |
| WO | WO2020190119 A1 | 9/2020 |

OTHER PUBLICATIONS

Balak, M.N. et al. (Nov. 1, 2006). "Novel D761Y And Common Secondary T790M Mutations In Epidermal Growth Factor Receptor—Mutant Lung Adenocarcinomas With Acquired Resistance To Kinase Inhibitors," Clinical Cancer Research, 12(21), 6494-6501.
Carna Biosciences (Feb. 26, 2021). "Drug-Resistant EGFR Mutations in Lung Cancer," Carna Newsletter 9: 2 pages.
Chen, L. et al. (2017). "Recent Progress Of Small-Molecule Epidermal Growth Factor Receptor (EGFR) Inhibitors Against C797S Resistance In Non-Small-Cell Lung Cancer: Miniperspective," Journal Of Medicinal Chemistry 61(10):4290-4300.
Chen, L. et al. (2018, e-pub. Nov. 10, 2018). "The Synthesis Of 4-Arylamido-2-Arylaminoprimidines As Potent EGFR T790M/L858R Inhibitors For NSCLC," Bioorganic & Medicinal Chemistry 26(23-24):6087-6095.
Engelman, J. A. et al. (May 18, 2007). "MET Amplification Leads To Gefitinib Resistance In Lung Cancer By Activating ERRB3 Signaling," Science 316(5827):1039-1043.
Finlay, M. R. V. et al. (2014). "Discovery Of A Potent And Selective EGFR Inhibitor (AZD9291) Of Both Sensitizing And T790M Resistance Mutations That Spares The Wild Type Form Of The Receptor," Journal of Medicinal Chemistry 57:8249-8267.

Fukuoka, M. et al. (Jun. 15, 2003). "Multi-Institutional Randomized Phase II Trial Of Gefitinib For Previously Treated Patients With Advanced Non-Small-Cell Lung Cancer," Journal Of Clinical Oncology 21(12):2237-2246.
Hasako, S. et al. (Aug. 2018, e-pub. May 10, 2018). "TAS6417, A Novel EGFR Inhibitor Targeting Exon 20 Insertion Mutations," Molecular Cancer Therapeutics 17(8):1648-1658.
International Search Report and Written Opinion of the International Searching Authority mailed Jun. 24, 2020, for Patent Application No. PCT/KR2020/095044, filed Mar. 19, 2020, 18 pages. (English Translation).
Jang, J. et al. (Sep. 3, 2018). "Discovery Of A Highly Potent And Broadly Effective Epidermal Growth Factor Receptor And HER2 Exon 20 Insertion Mutant Inhibitor," Angewandte Chemie 130(36):11803-11807, 13 pages.
Kang, J. et al. (Apr. 9-10, 2019). "Discovery Of Selective And Potent EGFR Kinase Inhibitors For Exon 20 Ins Mutation," Poster, presented at Drug Discovery Chemistry, San Diego, CA, one page.
Kim, S. et al. (Oct. 16, 2019). "Abstract B002: Discovery of Selective and Potent EGFR Kinase Inhibitors for Exon20 Insertion Mutations," Molecular Cancer Therapeutics 18(12):3 pages, Abstract Only.
Kim, S. et al. (Oct. 28, 2019). "B002: Discovery of Selective and Potent EGFR Kinase Inhibitors for Exon 20 Insertion Mutations," Poster, presented at AACR-NCI-EORTC International Conference on Molecular Targets and Cancer Therapeutic, Boston, MA, one page.
Kobayashi, S. et al. (Feb. 24, 2005). "EGFR Mutation And Resistance Of Non-Small-Cell Lung Cancer To Gefitinib," New England Journal of Medicine 352(8):786-792.
Kosaka, T. et al. (May 15, 2017, e-pub. Mar. 31, 2017). "Response Heterogeneity Of EGFR And HER2 Exon 20 Insertions To Covalent EGFR And HER2 Inhibitors," Cancer Research 77(10):2712-2721.
Kosaka, T. et al. (Oct. 1, 2006). "Analysis Of Epidermal Growth Factor Receptor Gene Mutation In Patients With Non-Small Cell Lung Cancer And Acquired Resistance To Gefitinib," Clinical Cancer Research 12(19):5764-5769.
Kris, M. G. et al. (Oct. 22-29, 2003). "Efficacy Of Gefitinib, An Inhibitor Of The Epidermal Growth Factor Receptor Tyrosine Kinase, In Symptomatic Patients With Non-Small Cell Lung Cancer: A Randomized Trial," JAMA 290(16):2149-2158.
Lawrence, H. R. et al. (Sep. 13, 2012). "Development Of O-Chlorophenyl Substituted Pyrimidines As Exceptionally Potent Aurora Kinase Inhibitors," Journal Of Medicinal Chemistry 55(17):7392-7416, 56 pages.
Lin, S. Y. et al. (Sep. 28, 2019). "Discovery Of A Furanopyrimidine-Based Epidermal Growth Factor Receptor Inhibitor (DBPR112) As A Clinical Candidate For The Treatment Of Non-Small Cell Lung Cancer," Journal of Medicinal chemistry 62(22):10108-10123.
Lu, X. et al. (Aug. 7, 2017). "Targeting EGFRL858R/T790M And EGFRL858R/T790M/C797S Resistance Mutations In NSCLC: Current Developments In Medicinal Chemistry," Medicinal Research Reviews 38(5):1550-1581.
Lynch, T. J. et al. (May 20, 2004). "Activating Mutations In The Epidermal Growth Factor Receptor Underlying Responsiveness Of Non-Small-Cell Lung Cancer To Gefitinib," New England Journal of Medicine 350(21):2129-2139.
Paez, J. G. et al. (Jun. 4, 2004). "EGFR Mutations In Lung Cancer: Correlation With Clinical Response To Gefitinib Therapy," Science 304(5676):1497-1500.
Pao, W. et al. (Mar. 2005). "Acquired Resistance Of Lung Adenocarcinomas To Gefitinib Or Erlotinib Is Associated With A Second Mutation In The EGFR Kinase Domain," PLoS medicine 2(3):e73, 0225-0235.
Rho, J.K. et al. (Mar. 1, 2017, e-pub. Jan. 12, 2017). "Superior Efficacy And Selectivity Of Novel Small-Molecule Kinase Inhibitors Of T790M-Mutant EGFR In Preclinical Models Of Lung Cancer," Cancer Research 77(5):1200-1211.
Robichaux, J. P. et al. (May 2018). "Mechanisms And Clinical Activity Of An EGFR And HER2 Exon 20-Selective Kinase Inhibitor In Non-Small Cell Lung Cancer," Nature Medicine 24(5):638-646, 22 pages.

(56) References Cited

OTHER PUBLICATIONS

Sharma, S. V. et al. (Mar. 2007). "Epidermal Growth Factor Receptor Mutations In Lung Cancer," Nature Reviews Cancer 7(3):169-181.
Shepherd, F. A. et al. (Jul. 14, 2005). "Erlotinib In Previously Treated Non-Small-Cell Lung Cancer," New England Journal of Medicine 353(2):123-132.
U.S. Appl. No. 17/440,630, Lee et al., filed Sep. 17, 2021.
Udagawa, H. et al. (Nov. 2019, e-pub. Aug. 29, 2019). "TAS6417/CLN-081 Is a Pan-Mutation-Selective EGFR Tyrosine Kinase Inhibitor with a Broad Spectrum of Preclinical Activity against Clinically Relevant EGFR Mutations," Molecular Cancer Research 17(11):2233-2243.
Wang, Y. et al. (Mar. 4, 2020). "Discovery And Sars Of 5-Chloro-N 4-Phenyl-N 2-(Pyridin-2-YI) Pyrimidine-2, 4-Diamine Derivatives As Oral Available And Dual CDK 6 And 9 Inhibitors With Potent Antitumor Activity," Journal Of Medicinal Chemistry 63(6):3327-3347.
Xie, Z. et al. (Feb. 2020, e-pub. Dec. 5, 2019). "Discovery Of 4, 6-Pyrimidinediamine Derivatives As Novel Dual EGFR/FGFR Inhibitors Aimed EGFR/FGFR1-Positive NSCLC," European Journal Of Medicinal Chemistry 187:111943, 18 pages.
Yang, H. et al. (2019, e-pub. Dec. 14, 2019). "Design, Synthesis And Biological Evaluation Of 2-Amino-4-(1, 2, 4-Triazol) Pyridine Derivatives As Potent EGFR Inhibitors To Overcome TKI-Resistance," European Journal Of Medicinal Chemistry 187:111966, 13 pages.
Yu, L. et al. (Jan. 27, 2017, e-pub. Dec. 3, 2016). "A Structure-Guided Optimization Of Pyrido [2, 3-D] Pyrimidin-7-Ones As Selective Inhibitors Of EGFRL858R/T790M Mutant With Improved Pharmacokinetic Properties," European Journal Of Medicinal Chemistry 126:1107-1117.
Zhou, P. et al. (2018). "Design, Synthesis And Evaluation Of The Osimertinib Analogue (C-005) As Potent EGFR Inhibitor Against NSCLC," Bioorganic & Medicinal Chemistry 26:6135-6145.
Burger, A. (1991). "Isosterism And Bioisosterism In Drug Design," Progress in Drug Research/Fortschritte der Arzneimittelforschung/Progrès des Recherches Pharmaceutiques, pp. 287-371.
Shi, Y. et al. (Mar. 31, 2017). "Synthesis and Biological Activities of Novel Cyanoacrylate Derivatives Carrying 5-Arylisoxazole Group," Journal of Chemistry in Colleges and Universities 38(3):421-428. (English Abstract Only).

* cited by examiner

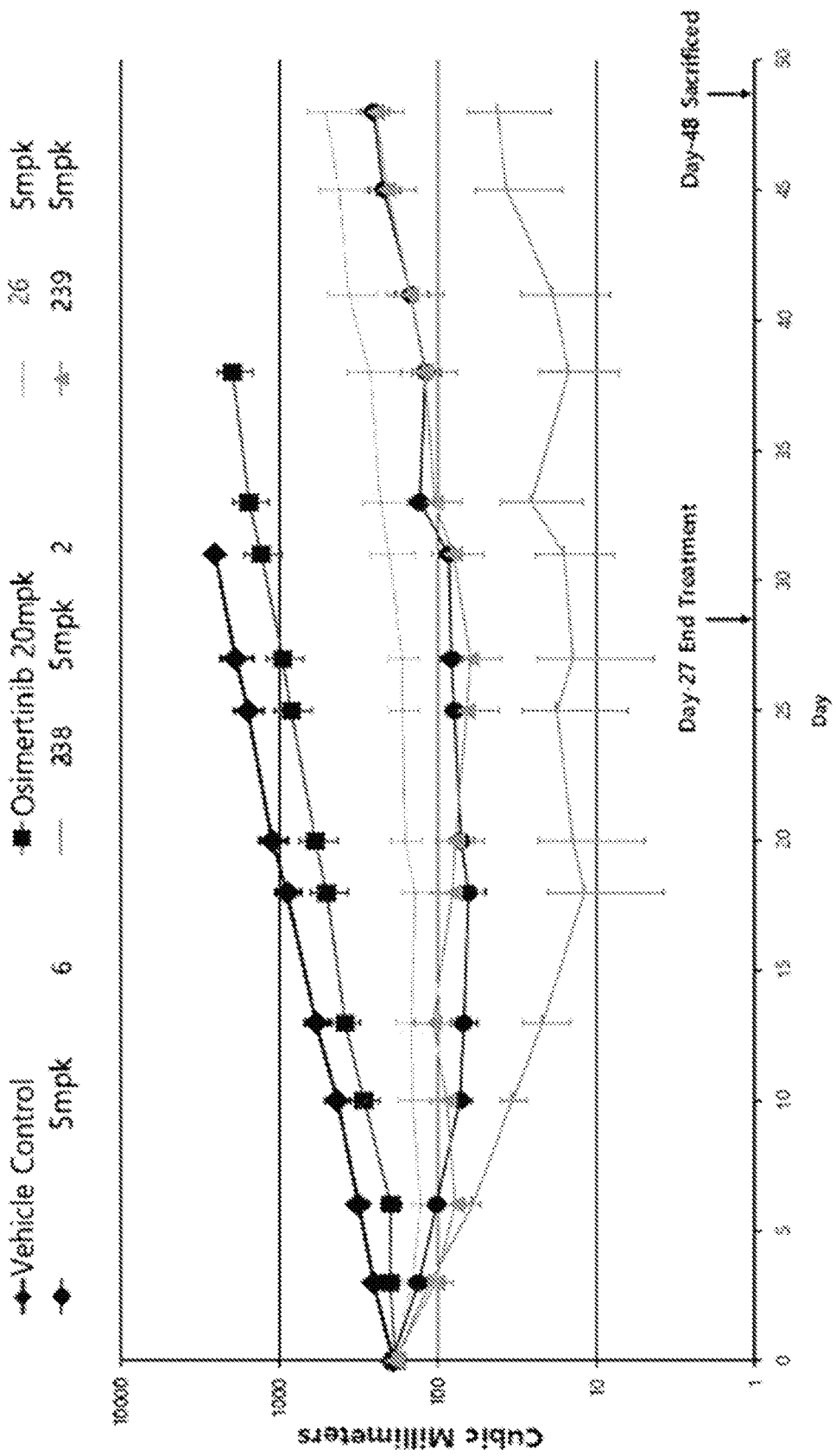

HETEROARYL DERIVATIVE, METHOD FOR PRODUCING SAME, AND PHARMACEUTICAL COMPOSITION COMPRISING SAME AS EFFECTIVE COMPONENT

CROSS REFERENCE TO RELATED APPLICATIONS

This application is a U.S. National Stage Entry under 35 U.S.C. § 371 of International Application No. PCT/KR2020/095044, filed on Mar. 19, 2020, which claims priority to Korean Application No. 10-2019-0031269, filed on Mar. 19, 2019, and Korean Application No. 10-2019-0134472, filed on Oct. 28, 2019, all of which are incorporated herein by reference in their entirety for all purposes.

TECHNICAL FIELD

The present invention relates to a heteroaryl derivative. Specifically, the present invention relates to a 6-(isooxazolidine-2-yl)-N-phenylpyrimidine-4-amine derivative. More specifically, the present relates to the compound, stereoisomers thereof, hydrates thereof, or pharmaceutically acceptable salts thereof, a method for preparation of the same, and a pharmaceutical composition for preventing or treating cancer comprising the same as an effective component.

BACKGROUND ART

The occurrence of cancers is related to a number of environmental factors including chemical substances, radiation, virus, and changes of oncogenes, tumor suppressor genes, genes associated with apoptosis and DNA repair and the like. Recently, the molecular mechanism of cancers is to be understood, and thus, this makes a targeted anticancer therapy, which is a new therapy, become available. Targeted therapeutic agents are generally prepared to show an effect by targeting molecules that cancer cells characteristically have. The molecular targets are genes associated with signal transduction pathway of cancer cells, angiogenesis, cellular matrix, cell cycle regulator, apoptosis and the like. An important targeted therapeutic agent used in the current therapy includes signal transduction pathway inhibitors, including tyrosine kinase inhibitors, and angiogenesis inhibitors and the like. It has been found that a protein tyrosine kinase plays an important role in a number of malignant tumors. In particular, it is known that epidermal growth factor receptor (EGFR), which is a receptor tyrosine kinase of ErbB family, is abnormally activated in a number of epithelial cell tumors including non-small cell lung carcinoma (NSCLC), breast cancer, glioma, squamous cell carcinoma of head and neck, colorectal cancer, rectal adenocarcinoma, head and neck cancer, gastric cancer, and prostate cancer; and the activation of the above EGFR-tyrosine kinase causes a persistent cell proliferation, invasion of the surrounding tissue, remote metastasis, and angiogenesis, and increases a cell survival.

Specifically, the EGFR, which is one of tyrosine kinase receptors of ErbB family, is a transmembrane tyrosine kinase that has an extracellular ligand-binding domain and an intracellular domain including a tyrosine kinase domain, and may include EGFR (referred to as ErbB1 or HER1), HER2 (referred to as ErbB2 or neu), ErbB3, and ErbB4 (referred to as HER4). If a ligand binds to a receptor forming homodimer or heterodimer, a tyrosine kinase in a cell is activated, and a signal stimulated by EGFR as such activates phosphatidylinositol 3-kinase ((PI3K)/AKT/mTOR, RAS/RAF/MAPK, and JAK/STAT) signal transduction pathway (Non-patent Literature 0001). In particular, EGFR is overexpressed in at least a half of non-small cell lung cancer (NSCLC), and thus, a number of studies have been carried out in which EGFR is a target of a therapy. EGFR TKIs (tyrosine kinase inhibitors), which inhibit an activity of EGFR tyrosine kinase, have been developed, and representative drugs include Gefitinib (IRESSA™) erlotinib (TARCEVA™), and lapatinib (TYKERB™, TYVERB™).

On the other hand, it was reported that, in 2004, an activating mutation of EGFR is correlated with a response to gefitinib therapy in non-small cell lung cancer (NSCLC) (Non-patent Literature 0002 and 0003). Specifically, it is known that the above EGFR mutation is largely classified into a sensitizing mutation and a resistant mutation, and a deletion of exon 19 and a L858R point mutation of exon 21 are the most important sensitizing mutations and make up about 85 to 90 percent of a sensitizing mutation, and an exon 19 del mutation is more sensitizing to the TKI. On the other hand, it is known that a T790M point mutation of exon 20 is the most important resistant mutation and is found in at least 50 percent of acquired resistant patients (Non-patent Literature 0004).

Somatic mutations identified hitherto include an in-frame deletion in exon 19 or an insertion in exon 20, as well as, a point mutation in which a single nucleic acid residue is modified within an expressed protein (for example, L858R, G719S, G719C, G719A, L861Q) (Non-patent Literature 0005 to 0007).

Despite an early clinical effect of gefitinib/erlotinib in NSCLC patients with an EGFR mutation, a progressive cancer develops in most patients in the end while these patients are receiving a therapy of these drugs. In an early study of recurred samples, a secondary EGFR mutation, T790M, was identified, which made gefitinib and erlotinib to be ineffective inhibitors of EGFR kinase activity (Non-patent Literature 0008 to 0009). It has been proved in the follow-up study that the EGFR T790M mutation was found in approximately 50 percent (24/48) of tumors derived from patients who acquired a resistance against gefitinib or erlotinib (Non-patent Literature 0010 to 0012). The secondary genetic modification is caused in a position similar to a 'gatekeeper' residue and a secondary resistance allele associated with the same in patients to be treated with a kinase inhibitor (for example, T315I within ABL in imatinib resistant CML).

It has been known for a long time that EGFR del19 or EGFR L858R, which is an EGFR mutation, is a major cause of non-small cell lung cancer and head and neck cancer, and IRESSA and TARCEVA, which are therapeutic drugs of the cancers, were developed and are currently used in clinical trials. However, when such drugs were administered for cancer patients, an acquired resistance caused by an EGFR secondary mutation based on the structure of the drug was observed. In addition, it was found that this was actually a major cause of drug resistance. If first generation inhibitors of EGFR have been used for about ten months in average, an acquired resistance, which is a T790M mutation positioned in a gatekeeper of EGFR kinase, occurs to prevent first generation inhibitors of EGFR exerting a medicinal effect. That is, EGFR del19 T790M or EGFR L858R T790M double mutation occurs to prevent conventional therapeutic agents exerting a medicinal effect.

PRIOR ART LITERATURE

Non-Patent Literature (Non-patent Literature 0001) Nat Rev Cancer 2007; 7:169-81.
(Non-patent Literature 0002) Science 2004; 304:1497-500.
(Non-patent Literature 0003) New England Journal of Medicine 2004; 350:2129-39.
(Non-patent Literature 0004) Clin Cancer Res 2006; 12:6494-6501.
(Non-patent Literature 0005) Fukuoka et al. JCO 2003.
(Non-patent Literature 0006) Kris et al. JAMA 2003.
(Non-patent Literature 0007) Shepherd et al. NEJM 2004.
(Non-patent Literature 0008) Kobayashi et al. NEJM 2005.
(Non-patent Literature 0009) Pao et al. PLOS Medicine 2005.
(Non-patent Literature 0010) Kosaka et al. CCR 2006.
(Non-patent Literature 0011) Balak et al. CCR 2006.
(Non-patent Literature 0012) Engelman et al. Science 2007.

DISCLOSURE

Technical Problem

The purpose of one aspect of the present invention is to provide a compound which exhibits inhibitory effects against wild type or mutant EGFR and is therefore useful in the treating of cancer, and stereoisomers, hydrates, or pharmaceutically acceptable salts of the compound.

The purpose of another aspect of the present invention is to provide a method for preparation of the compound.

The purpose of yet another aspect of the present invention is to provide a pharmaceutical composition for preventing or treating cancer, the composition comprising the compound or stereoisomers, hydrates or pharmaceutically acceptable salts of the same as an effective component.

The purpose of yet another aspect of the present invention is to provide a pharmaceutical composition which suppresses wild type EGFR (epidermal growth factor receptor) or EGFR mutations to prevent or treat cancer.

Technical Solution

To achieve the above-stated purposes,

The present invention provides a compound represented by Chemical Formula 1, stereoisomers of the same, hydrates or the same, or pharmaceutically acceptable salts of the same:

[Chemical Formula 1]

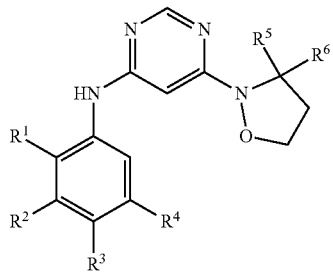

In Chemical Formula 1, $R^1$ is hydrogen, halogen, $C_{1-8}$ alkyl, or $C_{1-8}$ alkoxy, where the $C_{1-8}$ alkyl and $C_{1-8}$ alkoxy of $R^1$ are, respectively and independently, substituted or unsubstituted by at least one halogen, $R^2$ is hydrogen or $-NR^7R^8$, where $R^7$ and $R^8$ are, respectively and independently, hydrogen or $C_{1-8}$ alkyl, or the $R^7$ and $R^8$ are linked together with an N atom to which they are bonded to form a heterocycloalkyl of 3 to 12 atoms, where the $C_{1-8}$ alkyl or heterocycloalkyl of 3 to 12 atoms of $R^7$ and $R^8$ are, respectively and independently, substituted or unsubstituted by at least one substituent selected from a group comprised of $C_{1-8}$ alkyl, $C_{1-8}$ alkoxy and $C_{1-8}$ alkylamino, $R^3$ is hydrogen, $-NR^9R^{10}$ or $-OR^{11}$, where $R^9$, $R^{10}$ and $R^{11}$ are, respectively and independently, halogen or $C_{1-8}$ alkyl, or the $R^9$ and $R^{10}$ are linked together with an N atom to which they are bonded to form a heterocycloalkyl of 3 to 12 atoms or heteroaryl of 3 to 12 atoms, and the $C_{1-8}$ alkyl, heterocycloalkyl of 3 to 12 atoms or heteroaryl of 3 to 12 atoms of $R^9$, $R^{10}$ and $R^{11}$ are, respectively and independently, substituted or unsubstituted by at least one substituent R selected from among a group comprised of hydroxy, $C_{1-8}$ alkyl, $C_{1-8}$ alkoxy, $C_{1-8}$ alkylamino, $C_{1-8}$ alkylcarbonyl, $-NR^{12}R^{13}$, and heterocycloalkyl of 3 to 12 atoms, where the substituents R are, respectively and independently, additionally substituted or unsubstituted by at least one substituent selected from a group comprised of halogen; carbonyl; $C_{1-8}$ alkyl substituted or unsubstituted by hydroxy or $C_{1-8}$ alkylamino; $C_{2-8}$ alkenyl; $C_{1-8}$ alkoxy; $C_{1-8}$ alkylamino; $C_{1-8}$ alkylcarbonyl; and, a heterocycloalkyl of 3 to 12 atoms substituted or unsubstituted by $C_{1-8}$ alkyl, and where the $R^{12}$ and $R^{13}$ are, respectively and independently, hydrogen, $C_{1-8}$ alkyl, $C_{2-8}$ alkenyl, $C_{1-8}$ alkylcarbonyl, $C_{2-8}$ alkenylcarbonyl, or a heterocycloalkyl of 3 to 12 atoms substituted or unsubstituted by $C_{1-8}$ alkyl, $R^4$ is $-NH(C=O)R^{14}C=CR^{15}R^{16}$, where the $R^{14}$, $R^{15}$ and $R^{16}$ are, respectively and independently, hydrogen, halogen, or $C_1$-8 alkyl substituted or unsubstituted by $C_{1-8}$ alkylamino, $R^5$ is $C_1$-8 alkyl, an aryl of 3 to 12 atoms, a heteroaryl of 3 to 12 atoms, or a heterocycloalkyl of 3 to 12 atoms, and the $C_{1-8}$ alkyl, aryl of 3 to 12 atoms, heteroaryl of 3 to 12 atoms, or heterocycloalkyl of 3 to 12 atoms of $R^5$ are, respectively and independently, substituted or unsubstituted by at least one substituent selected from a group comprised of halogen, cyano, $C_{1-8}$ alkyl substituted or unsubstituted by halogen, $C_{2-8}$ alkenyl, $C_{1-8}$ alkoxy, $C_{2-8}$ alkynyl and $C_{1-8}$ alkylamino, and $R^6$ is hydrogen or $C_{1-8}$ alkyl.

Another aspect of the present invention provides:
a method for preparing the compound of Chemical Formula 5, from the compound of Chemical Formula 4;
a step of preparing the compound of Chemical Formula 6 from the compound of Chemical Formula 5; and, a step of preparing the compound of Chemical Formula 1 from the compound of Chemical Formula 6:

[Chemical Formula 4]

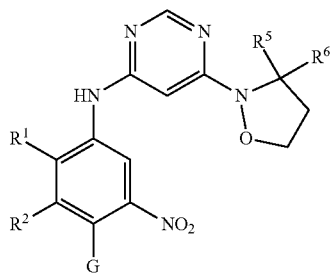

[Chemical Formula 5]

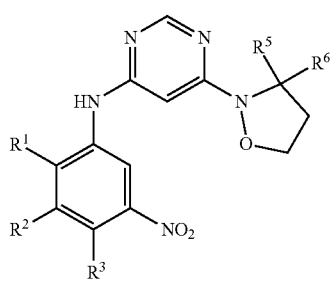

[Chemical Formula 6]

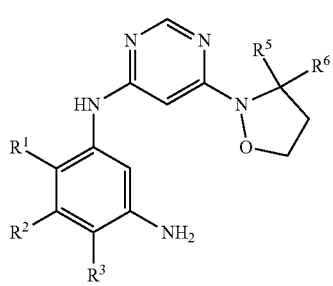

[Chemical Formula 1]

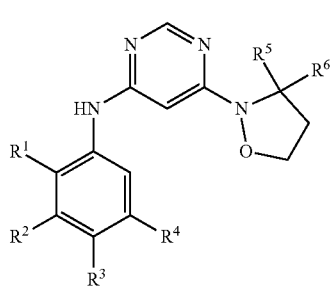

In Chemical Formula 4, G is a leaving group, and $R^1$ and $R^6$ are respectively the same as defined in the above.

Yet another aspect of the present invention provides a pharmaceutical composition for preventing or treating cancer, the composition comprising the compound of the present invention, or stereoisomers, hydrates or pharmaceutically acceptable salts of the same as an effective component.

Benefits of the Invention

The compound provided by one aspect of the present invention, and stereoisomers, hydrates or pharmaceutically acceptable salts thereof exhibit high inhibition activity against not only mutants of EGFR (epidermal growth factor receptor) but also wild type or mutants of at least one of ERBB2 and ERBB4, and therefore can be usefully used in the treatment of cancers in which these kinases are expressed.

BRIEF DESCRIPTION OF THE DRAWINGS

FIG. 1 shows experimental data results in which a PDX (Exon20 ins V769_D770ins ASV) cell line xenograft in vivo was orally administered the Example Compounds for 28 days followed by observation for 21 days without administration to verify whether or not cancer was suppressed.

BEST MODE(S) FOR CARRYING OUT THE INVENTION

In the following, the present invention will be explained in further detail with reference to embodiments.

Embodiments of the present invention may be modified into various different forms, and the scope of the present invention is not limited to the embodiments explained in the following. The embodiments of the present invention are provided so as to provide persons having ordinary skill in the art to which the present invention belongs with a fuller disclosure of the present invention.

Throughout the specification, to "comprise" a certain component element means, unless specifically stated to the contrary, that other components elements may be further comprised, rather than that other component elements are excluded.

In the structural formulae of the present specification, of the symbols which bonds atoms and/or groups to each other, "-" may refer to a single bond, and "=" may refer to a double bond. Such symbols may be omitted, and may be indicated in cases necessary for specifying the bonded atoms or the position of a bond.

In the present specification, atoms being "connected" may include not only cases wherein atoms are connected directly but also cases wherein atoms are connected indirectly using other atoms and/or groups as a medium. Here, the other atoms and/or groups may be, but are not limited to, oxygen, sulfur, $C_{1-8}$ alkylamino or $C_{1-8}$ alkylene groups, and these atoms and/or groups may be substituted or unsubstituted.

In the present specification, the expression "substituted or unsubstituted" may refer to, unless otherwise stated, that one or a plurality of hydrogen atoms is substituted or unsubstituted by another atom or substituent. The substituent may be selected from a group comprised of halogen (chloro (Cl), iodo (I), bromo (Br), fluoro(F)), $C_{1-10}$ alkyl, $C_{2-10}$ alkenyl, $C_{2-10}$ alkynyl, hydroxyl, $C_{1-10}$ alkoxy, amino, nitro, thiol, thioether, imine, cyano, phosphonato, phosphine, carboxy, carbamoyl, carbamic acid, acetal, urea, thiocarbonyl, sulfonyl, sulfonamide, ketone, aldehyde, ester, acetyl, acetoxy, amide, oxygen (=O), haloalkyl (e.g. trifluoromethyl), substituted aminoacyl and aminoalkyl, carbon ring cycloalkyls which are single ring or fused or non-fused multiple ring (e.g. cyclopropyl, cyclobutyl, cyclopentyl or cyclohexyl), hetero cycloalkyls which are single ring or fused or non-fused multiple ring (e.g. pyrrolidinyl, piperidinyl, piperazinyl, morpholinyl, or thiazinyl, carbon ring or hetero ring, single ring or fused or non-fused multiple ring aryls (e.g. phenyl, naphthalenyl, pyrrolyl, indolyl, furanyl, thienyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothienyl, or benzofuranyl), aminos (primary, secondary or tertiary), aryl, aryloxy, and aryl-alkyl, but is not limited hereto. Further, the respective example substituents above may again be substituted or unsubstituted by a substituent selected among these substituents.

In the present specification, "halogen" may be F, Cl, Br or I.

In the present specification, "alkyl" may refer to, unless otherwise stated, a saturated hydrocarbon which is a straight chain or branched chain noncyclic alkyl; a cyclic alkyl; or a combination of the two. Further, "$C_{1-8}$ alkyl" may refer to an alkyl which comprises one to eight carbon atoms. Non-limiting examples of a noncyclic alkyl include methyl, ethyl, N-propyl, N-butyl, N-pentyl, N-hexyl, N-heptyl, N-octyl, isopropyl, secondary (sec)-butyl, tertiary (tert)-butyl, isopentyl, 2-methylpentyl, 3-methylpentyl, 4-methylpentyl and 2,3-dimethylbutyl. Non-examples of a cyclic alkyl include cyclopropyl, cyclobutyl, cyclopentyl, cyclohexyl, cycloheptyl, or cyclooctyl, etc. Non-limiting examples of an alkyl wherein cyclic and non-cyclic alkyls are combined include methylcyclopropyl, cyclopropylmethyl, ethylcyclopropyl, cyclopropylmethyl, methylcyclobutyl, cyclobutylmethyl, ethylcyclopentyl, and cyclopentylmethyl.

In the present specification, "cycloalkyl" may refer to an alkyl, in particular a cycloalkyl, where an alkyl is as defined in the foregoing.

In the present specification, "alkoxy" is an alkyl ether group which may refer to a —(O-alkyl), where an alkyl is as defined in the foregoing. Further, "$C_{1-8}$ alkoxy" may refer to an alkoxy which comprises a $C_{1-8}$ alkyl, that is, —(O—$C_{1-8}$ alkyl), and examples of a $C_{1-8}$ alkoxy may include methoxy, ethoxy, n-propoxy, isopropoxy, n-butoxy, iso-butoxy, sec-butoxy, tert-butoxy, and n-pentoxy, but is not limited hereto.

In the present specification, "heterocycloalkyl" may refer to a ring comprising one to five heteroatoms selected from among N, O and S are ring-forming atoms, which may be saturated or partially unsaturated. Unless otherwise mentioned, a heterocycloalkyl may be a single ring, or a multiple ring such as a spiro ring, a bridge ring or a fused ring. Further, "heterocycloalkyl of 3 to 12 atoms" may refer to a heterocycloalkyl which comprises 3 to 12 ring-forming atoms. Non-limiting examples of a heterocycloalkyl include pyrrolidine, piperidine, N-methyl piperidine, imidazolidine, pyrazolidine, butylolactam, valerolactam, imidazolinone, hydantoin, dioxolane, phthalimide, piperidine, piperidine-2, 4(1H,3H)-dione, 1,4-dioxane, morpholine, thiomorpholine, thiomorpholine-S-oxide, thiomorpholine-S,S-oxide, piperazine, pyran, pyridine, 3-pyrroline, thiopyran, pyrone, tetrahydrofuran, tetrahydrothiophene, quinuclidine, tropane, 2-azaspiro[3.3]heptane, (1R,5S)-3-azabicyclo[3.2.1]octane, (1s,4s)-2-azabicyclo[2.2.2]octane, or (1R,4R)-2-oxa-5-aza bicyclo[2.2.2]octane.

In the present specification, "alkylamino" may refer to —(NR'R"), where R' and R" may, respectively and independently, be selected from a group comprised of hydrogen and $C_{1-8}$ alkyls, where the selected R' and R" may be, respectively and independently, substituted or unsubstituted. Further "$C_{1-8}$ alkylamino" may refer to an amino which comprises a $C_{1-8}$ alkyl, that is, —N—H($C_{1-8}$ alkyl) or —N—($C_{1-8}$ alkyl)$_2$, and may include, but is not limited to dimethylamino, methylethylamino, methylpropylamino, or ethylpropylamino.

In the present specification, "aryl" may refer to an aromatic ring wherein one hydrogen has been removed from an aromatic hydrocarbon ring, and the aryl may be monocyclic or polycyclic. "An aryl of 3 to 12 atoms" may refer to an aryl which includes 3 to 12 ring-forming rings, and non-limiting examples of the same include phenyl, naphthyl, anthracenyl, phenanthryl, biphenyl, and terphenyl.

In the present specification, "heteroaryl" may refer to an aromatic ring which includes at least one heteroatom from among N, O and S as ring-forming atoms, and the heteroaryl may be monocyclic or polycyclic. Further, "heteroaryl of 3 to 12 atoms" may refer to a heteroaryl which includes 3 to 12 ring-forming rings, and non-limiting examples of the same include thienyl, thiophene, furyl, pyrrolyl, pyrazolyl, imidazolyl, thiazolyl, oxazolyl, isothiazolyl, oxadiazolyl, triazolyl, pyridinyl, bipyridyl, pyramidal, triazinyl, triazolyl, acridyl group, pyridazinyl group, pyrazinyl, quinolinyl, quinazoline, quinoxalinyl, phenoxazine, phthalazinyl, pyrimidinyl, pyrido pyrimidinyl, pyrido pyrazinyl, pyrazino pyrazinyl, isoquinoline, indole, carbazole, imidazopyridazinyl, imidazopyridinyl, imidazopyrimidinyl, pyrazolo pyrimidinyl, imidazo pyrazinyl or pyrazolo pyridinyl, N-aryl carbazole, N-heteroaryl carbazole, N-alkyl carbazole group, benzoxazole, benzoimidazole, benzothiazole, benzocarbazole, benzothiophene, dibenzothiophenyl, thienothiophene, benzofuranyl, phenanthroline, isoxazolyl, oxadiazolyl, thiadiazolyl, benzothiazolyl, tetrazolyl, phenothiazolyl, dibenzosilol or dibenzofuranyl, etc.

In the present invention, "hydroxy" may refer to —OH.

In the present specification, "carbonyl" may refer to —(C=(O))—, and may refer to a case wherein a cyclic alkyl, aryl or heterocycloalkyl is substituted by a carbonyl, or a case where a hydrogen atom is substituted by a (=O).

In the present specification, "alkylcarbonyl" may refer to —(C(=O)-alkyl), where the alkyl is as defined in the foregoing. Further, "$C_{1-8}$ alkylcarbonyl" may refer to a carbonyl which includers a $C_{1-8}$ alkyl, that is, —(C(=O)—$C_{1-8}$ alkyl), and non-limiting examples of these include methyl carbonyl (acetyl, —(C=(O)—CH$_3$)), ethyl carbonyl, n-propyl carbonyl, iso-propyl carbonyl, n-butyl carbonyl, sec-butyl carbonyl, isobutyl carbonyl, tert-butyl carbonyl, n-octyl carbonyl, cyclopropyl carbonyl, cyclobutyl carbonyl, cyclopentyl carbonyl, or cyclohexyl carbonyl.

In the present specification, "alkenyl" may refer to, unless otherwise stated, a noncyclic straight chain or branched chain or cyclic hydrocarbon having at least one double bond. Further, "$C_{2-8}$ alkenyl" may refer to an alkenyl which comprises two to eight carbon atoms, and may include, but is not limited to, ethenyl, 1-propenyl, prop-2-en-1-yl[-(CH$_2$CH=CH$_2$)](allyl), 2-butenyl, isopropenyl, 3-butenyl, 4-pentenyl, 5-hexenyl, 1-cyclohexenyl, cyclopentadienyl, 1,3-cyclohexadienyl, 1,4-cyclohexadienyl, 1,3-cycloheptadienyl, or 1,3,5-cycloheptatrienyl.

In the present specification, "alkenylcarbonyl" may refer to —(C(=O)-alkenyl), where alkenyl is as defined in the foregoing. Further, k "$C_{2-8}$ alkeylcarbonyl" may refer to a carbonyl which includes a $C_{2-8}$ alkenyl, that is, —(C(=O)—$C_{2-8}$ alkenyl).

In the present specification, "cyano" may refer to —(CN).

In the present specification, "alkynyl" may refer to a straight chain, branched chain noncyclic or cyclic hydrocarbon having at least one triple bond. Further, "$C_{2-8}$ alkynyl" may refer to an alkynyl which comprises 2 to 8 carbon atoms, and non-limiting examples of such include ethinyl, propynyl, hydroxypropynyl, butene-1-yl, butene-2-yl, pentene-1-yl, 3-methylbutene-1-yl, or hexyn-2-yl.

In the present specification, "aralkyl" may refer to -(alkyl-aryl), where alkyl and aryl are as defined in the foregoing. Further, "aralkyl of 3 to 8 atoms" may refer to an aralkyl which comprises 3 to 8 carbon atoms.

In the present specification, "bicycloalkyl" may mean, unless otherwise stated, a fused, spiro or bridged bicyclic hydrocarbon.

In the present specification, "diazabicycloalkyl" may refer to -(diazabicycloalkyl), that is, may represent a bicycloalkyl which includes two nitrogen atoms in the cycloalkyl. Non-limiting examples of diazabicycloalkyl include diazabicyclo[3,2,1]heptane, diazabicyclo[3,1,1]heptane, and diazabicyclo[2,2,1]heptane.

In the present specification, "oxazabicycloalkyl" may mean -(oxazabicycloalkyl), that is, a bicycloalkyl which comprises one oxygen atom and one nitrogen atom in the cycloalkyl. Non-limiting examples of oxazabicycloalkyl include oxazabicyclo[2,2,1]heptane.

In the present specification, "sulfonic acid ester" may refer to an alkyl sulfonic acid ester or an aryl sulfonic acid ester, where alkyl sulfonic acid ester is represented by —(OS(=O)$_2$-alkyl, and aryl sulfonic acid ester is represented by —(OS)=O$_2$-aryl). Here, alkyl and aryl are as defined in the foregoing.

In the present specification, "hydrate" may refer to the compound of the present invention or a salt thereof, comprising a stoichiometric or non-stoichiometric amount of water bonded by a non-covalent intermolecular force. A hydrate of the compound of the present invention represented by Chemical Formula 1 may comprise a stoichiometric or non-stoichiometric amount of water bonded by a non-covalent intermolecular force. The hydrate may comprise at least one equivalents of water, preferably one to five equivalents. Such hydrate may be prepared by crystallizing, from water or solvent comprising water, the compound of the present invention represented by Chemical Formula 1, isomers of the same, or pharmaceutically acceptable salts thereof.

In the present specification, "solvate" may refer to the compound of the present invention or a salt thereof, comprising a stoichiometric or non-stoichiometric amount of solvent which is bonded by a non-covalent intermolecular force. Preferred solvents include volatile solvents, non-volatile solvents, and/or solvents suitable for administration to humans.

In the present specification, the term "isomer" refers to the compound of the present invention or a salt thereof which has an identical chemical or molecular formula but which is structurally or three-dimensionally different. Included among such isomers are structural isomers such as tautomers, R or S isomers having asymmetric carbon centers, stereoisomers including geometric isomers (trans, cis), and enantiomers. All such isomers and compounds thereof are included in the scope of the present invention.

One aspect of the present invention provides a compound represented by Chemical Formula 1, stereoisomers of the same, hydrates or the same, or pharmaceutically acceptable salts of the same:

In one embodiment:

[Chemical Formula 1]

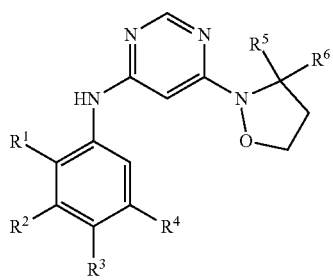

In Chemical Formula 1,
$R^1$ is hydrogen, halogen, $C_{1-8}$ alkyl, or $C_{1-8}$ alkoxy, where the $C_{1-8}$ alkyl and $C_{1-8}$ alkoxy of $R^1$ are, respectively and independently, substituted or unsubstituted by at least one halogen, $R^2$ is hydrogen or —$NR^7R^8$, where $R^7$ and $R^8$ are, respectively and independently, hydrogen or $C_{1-8}$ alkyl, or the $R^7$ and $R^8$ are linked together with an N atom to which they are bonded to form a heterocycloalkyl of 3 to 12 atoms, where the $C_{1-8}$ alkyl or heterocycloalkyl of 3 to 12 atoms of $R^7$ and $R^8$ are, respectively and independently, substituted or unsubstituted by at least one substituent selected from a group comprised of $C_{1-8}$ alkyl, $C_{1-8}$ alkoxy and $C_{1-8}$ alkylamino, $R^3$ is hydrogen, —$NR^9R^{10}$ or —$OR^{11}$, where $R^9$, $R^{10}$ and $R^{11}$ are, respectively and independently, halogen or $C_{1-8}$ alkyl, or the $R^9$ and $R^{10}$ are linked together with an N atom to which they are bonded to form a heterocycloalkyl of 3 to 12 atoms or heteroaryl of 3 to 12 atoms, and the $C_{1-8}$ alkyl, heterocycloalkyl of 3 to 12 atoms or heteroaryl of 3 to 12 atoms of $R^9$, $R^{10}$ and $R^{11}$ are, respectively and independently, substituted or unsubstituted by at least one substituent R selected from among a group comprised of hydroxy, $C_{1-8}$ alkyl, $C_{1-8}$ alkoxy, $C_{1-8}$ alkylamino, $C_{1-8}$ alkylcarbonyl, —$NR^{12}R^{13}$, and heterocycloalkyl of 3 to 12 atoms, where the substituents R are, respectively and independently, additionally substituted or unsubstituted by at least one substituent selected from a group comprised of halogen; carbonyl; $C_{1-8}$ alkyl substituted or unsubstituted by hydroxy or $C_{1-8}$ alkylamino; $C_{2-8}$ alkenyl; $C_{1-8}$ alkoxy; $C_{1-8}$ alkylamino; $C_{1-8}$ alkylcarbonyl; and, a heterocycloalkyl of 3 to 12 atoms substituted or unsubstituted by $C_{1-8}$ alkyl, and where the $R^{12}$ and $R^{13}$ are, respectively and independently, hydrogen, $C_{1-8}$ alkyl, $C_{2-8}$ alkenyl, $C_{1-8}$ alkylcarbonyl, $C_{2-8}$ alkenylcarbonyl, or a heterocycloalkyl of 3 to 12 atoms substituted or unsubstituted by $C_{1-8}$ alkyl, $R^4$ is —$NH(C=O)R^{14}C=CR^{15}R^{16}$, where the $R^{14}$, $R^{15}$ and $R^{16}$ are, respectively and independently, hydrogen, halogen, or $C_1$-8 alkyl substituted or unsubstituted by $C_{1-8}$ alkylamino, $R^5$ is a $C_{1-8}$ alkyl, an aryl of 3 to 12 atoms, a heteroaryl of 3 to 12 atoms, or a heterocycloalkyl of 3 to 12 atoms, and the $C_{1-8}$ alkyl, aryl of 3 to 12 atoms, heteroaryl of 3 to 12 atoms, or heterocycloalkyl of 3 to 12 atoms of $R^5$ are, respectively and independently, halogen, cyano, a $C_{1-8}$ alkyl substituted or unsubstituted by halogen, an aryl of 3 to 12 atoms, a heteroaryl of 3 to 12 atoms, a heterocycloalkyl of 3 to 12 atoms, $C_{2-8}$ alkenyl, $C_{1-8}$ alkoxy, $C_{2-8}$ alkynyl and $C_{1-8}$ alkylamino, where each of the substituents J are, respectively and independently, halogen, $C_{1-8}$ alkyl substituted or unsubstituted by halogen, $C_{1-8}$ alkoxy, and $C_{1-8}$ alkylamino, and $R^6$ may be hydrogen or $C_{1-8}$ alkyl.

In another embodiment, in the compound represented by Chemical Formula 1, $R^1$ is hydrogen, halogen, $C_{1-8}$ alkyl, or $C_{1-8}$ alkoxy, where the $C_{1-8}$ alkoxies of $R^1$ are, respectively and independently, substituted or unsubstituted by at least one halogen, $R^2$ is hydrogen or —$NR^7R^8$, where $R^7$ and $R^8$ are, respectively and independently, hydrogen or $C_{1-8}$ alkyl, or the $R^7$ and $R^8$ are linked together with an N atom to which they are bonded to form a heteroaryl of 3 to 12 atoms, and the $C_{1-8}$ alkyl of $R^7$ and $R^8$ are, respectively and independently, substituted or unsubstituted by at least one substituent selected from a group comprised of $C_{1-8}$ alkoxy and $C_{1-8}$ alkylamino, and the heterocycloalkyl of 3 to 12 atoms formed by the bonding of $R^7$ and $R^8$ is substituted or unsubstituted by at least one substituent selected from among a group comprised of $C_{1-8}$ alkyl and $C_{1-8}$ alkoxy, $R^3$ is hydrogen, $-NR^9R^{10}$ or $-OR^{11}$, where $R^9$, $R^{10}$ and $R^{11}$ are, respectively and independently, halogen or $C_{1-8}$ alkyl, or the $R^9$ and $R^{10}$ are linked together with an N atom to which they are bonded to form a heterocycloalkyl of 3 to 12 atoms or a heteroaryl of 3 to 12 atoms, and the $C_{1-8}$ alkyls of $R^9$, $R^{10}$ and $R^{11}$ are, respectively and independently, substituted or unsubstituted by at least one substituent R selected from among a group comprised of $C_{1-8}$ alkoxy, and $C_{1-8}$ alkylamino, where the heterocycloalkyl of 3 to 12 atoms formed by the bonding of $R^9$ and $R^{10}$ is substituted or unsubstituted by at least one substituent Ra selected from among a group comprised of hydroxy, $C_{1-8}$ alkyl, $C_{1-8}$ alkoxy, $C_{1-8}$ alkylamino, $C_{1-8}$ alkylcarbonyl, $-NR^{12}R^{13}$, and heterocycloalkyl of 3 to 12 atoms, and the $C_{1-8}$ alkyl, $C_{1-8}$ alkylamino, and $C_{1-8}$ alkylcarbonyl of the substituent Ra are, respectively and independently, additionally substituted or unsubstituted by at least one substituent selected from a group comprised of $C_{1-8}$ alkyl, $C_{1-8}$ alkoxy, $C_{1-8}$ alkylamino, and heterocycloalkyl of 3 to 12 atoms, the heterocycloalkyl of 3 to 12 atoms of the substituent Ra is additionally substituted or unsubstituted by at least one substituent selected from among a group comprised of halogen; carbonyl; $C_{1-8}$ alkyl substituted or unsubstituted by a hydroxy or a $C_{1-8}$ alkylamino; $C_{2-8}$ alkenyl; $C_{1-8}$ alkoxy; $C_{1-8}$ alkylamino; $C_{1-8}$ alkylcarbonyl; and, a heterocycloalkyl of 3 to 12 atoms substituted or unsubstituted by $C_{1-8}$ alkyl, where the $R^{12}$ and $R^{13}$ are, respectively and independently, hydrogen, $C_{1-8}$ alkylcarbonyl, $C_{2-8}$ alkenylcarbonyl, or a heterocycloalkyl of 3 to 12 atoms substituted or unsubstituted by $C_{1-8}$ alkyl, heterocycloalkyl of 3 to 12 atoms, and the heteroaryl of 3 to 12 atoms formed by the bonding of $R^9$ and $R^{10}$ is substituted or unsubstituted by $C_{1-8}$ alkyl, $R^4$ is $-NH(C=O)R^{14}C=CR^{15}R^{16}$, where the $R^{14}$ is hydrogen or halogen, and the $R^{15}$ and $R^{16}$ are, respectively and independently, hydrogen or $C_{1-8}$ alkyl substituted or unsubstituted by an alkylamino of $C_{1-8}$, $R^5$ is a $C_{1-8}$ alkyl substituted by a aryl of 3 to 12 atoms or a heteroaryl of 3 to 12 atoms; an aryl of 3 to 12 atoms; or a heteroaryl of 3 to 12 atoms, where the aryl of 3 to 12 atoms and the heteroaryl of 3 to 12 atoms of $R^5$ are, respectively and independently, substituted or unsubstituted by at least one substituent selected from a group comprised of halogen, cyano, $C_{1-8}$ substituted or unsubstituted by halogen, $C_{1-8}$ alkoxy, and $C_{2-8}$ alkynyl, and aryl substituted with a aryl of 3 to 12 atoms or heteroaryl of 3 to 12 atoms of $R^5$ is substituted or unsubstituted by at least one substituent selected from a group comprised of halogen, $C_{1-8}$ alkyl substituted or unsubstituted by halogen, and $C_{1-8}$ alkylamino, and $R^6$ may be hydrogen or $C_{1-8}$ alkyl.

In yet another embodiment, in the compound represented by Chemical Formula 1, $R^1$ is hydrogen, halogen, $C_{1-4}$ alkyl, or $C_{1-4}$ alkoxy, where the $C_{1-4}$ alkoxies of $R^1$ are, respectively and independently, substituted or unsubstituted by at least one halogen, $R^2$ is hydrogen or $-NR^7R^8$, where $R^7$ and $R^8$ are linked, together with the N atoms to which they are bonded, to form a heterocycloalkyl of 3 to 8 atoms, where the heterocycloalkyl of 3 to 8 atoms formed by the bonding of $R^7$ and $R^8$ is substituted or unsubstituted by at least one $C_{1-4}$ alkyl, $R^3$ is hydrogen, $-NR^9R^{10}$ or $-OR^{11}$, where $R^9$, $R^{10}$, and $R^{11}$ are, respectively and independently $C_{1-6}$ alkyl, or $R^9$ and $R^{10}$ are linked together with the N atoms with which they are bonded to form a heterocycloalkyl of 3 to 10 atoms or heteroaryl of 3 to 8 atoms, the $C_{1-6}$ alkyls of $R^9$, $R^{10}$, and $R^{11}$ are, respectively and independently, substituted or unsubstituted by at least one substituent selected from a group comprised of $C_{1-4}$ alkylamino and $C_{1-4}$ alkoxy, and the heterocycloalkyl of 3 to 10 atoms formed by the bonding of $R^9$ and $R^{10}$ is substituted or unsubstituted by at least one substituent $R^b$ selected from among a group comprised of hydroxy, $C_{1-6}$ alkyl, $C_{1-4}$, $C_{1-4}$ alkylamino, $C_{1-4}$ alkylcarbonyl, $-NR^{12}R^{13}$ and heterocycloalkyls of 3 to 10 atoms, the $C_{1-6}$ alkyl, $C_{1-4}$ alkoxy, and $C_{1-4}$ alkylamino of the substituent $R^b$ are, respectively and independently, additionally substituted or unsubstituted by at least one substituent selected from among a group comprised of $C_{1-6}$ alkyl, $C_{1-4}$ alkoxy, and $C_{1-4}$alkylamino, the heterocycloalkyl of 3 to 10 atoms of substituent $R^b$ is additionally substituted or unsubstituted by at least one substituent selected from among a group comprised of halogen; carbonyl; $C_{1-6}$ alkyl substituted or unsubstituted by $C_{1-4}$ alkylamino; $C_{2-4}$ alkenyl; $C_{1-4}$ alkylamino; $C_{1-4}$ alkylcarbonyl; and, a heterocycloalkyl of 3 to 8 atoms substituted or unsubstituted by $C_{1-4}$ alkyl, $R^{12}$ and $R^{13}$ are, respectively and independently, hydrogen, $C_{2-4}$ alkenyl carbonyl or heterocycloalkyl of 3 to 8 atoms substituted or unsubstituted by $C_{1-4}$ alkyl, the heteroaryl of 3 to 8 atoms formed by the bonding of $R^9$ and $R^{10}$ is substituted or unsubstituted by $C_{1-4}$ alkyl, $R^4$ is $-NH(C=O)R^{14}C=CR^{15}R^{16}$, $R^{14}$ is hydrogen or halogen, and $R^{15}$ and $R^{16}$ are, respectively and independently, hydrogen or $C_{1-4}$ alkyl substituted by an alkylamino of $C_{1-4}$, $R^5$ is a $C_{1-4}$ alkyl; an aryl of 3 to 8 atoms; or a heteroaryl of 3 to 8 atoms substituted by an aryl of 3 to 8 atoms or heteroaryl of 3 to 8 atoms; the aryl of 3 to 8 atoms or heteroaryl of 3 to 8 atoms of $R^5$ are, respectively and independently, substituted or unsubstituted by at least one substituent selected from among a group comprised of halogen, cyano, $C_{1-4}$ alkyl substituted or unsubstituted by halogen, $C_{1-4}$ alkoxy, and $C_{2-4}$ alkynyl, the $C_{1-4}$ alkyl substituted by a aryl of 3 to 8 atoms or heteroaryl of 3 to 8 atoms of $R^5$ is substituted or unsubstituted by at least one substituent selected from among a group comprised of halogen, $C_{1-4}$ alkyl substituted or unsubstituted by halogen, and $C_{1-4}$ alkylamino, and $R^6$ may be hydrogen or $C_{1-4}$ alkyl.

In another embodiment, in a compound represented by Chemical Formula 1, $R^1$ is hydrogen, halogen, $C_{1-4}$ alkyl or $C_{1-4}$ alkoxy, where the $C_{1-4}$ alkoxy of $R^1$ is, respectively and independently, substituted or unsubstituted by at least one halogen, $R^2$ is hydrogen or $-NR^7R^8$, where $R^7$ and $R^8$ are linked together with an N atom to which they are bonded to form a heterocycloalkyl of 3 to 8 atoms having one or two N atoms, where the heterocycloalkyl of 3 to 8 atoms formed by the bonding of $R^7$ and $R^8$ is substituted or unsubstituted by at least one $C_{1-4}$ alkyl, $R^3$ is hydrogen, $-NR^9R^{10}$, or $-OR^{11}$, where $R^9$, $R^{10}$ and $R^{11}$ are, respectively and independently, $C_{1-6}$ alkyl, or $R^9$ and $R^{10}$ are linked together with an N atom to which they are bonded to form a heterocycloalkyl of 3 to 10 atoms having one or two heteroatoms selected from a group comprised of N and O, or a heteroaryl of 3 to 8 atoms having one or two heteroatoms selected from a group comprised of N and O, the $C_{1-6}$ alkyl of $R^9$, $R^{10}$ and $R^{11}$ are, respectively and independently, substituted or unsubstituted by at least one substituent selected from among a group comprised of $C_{1-4}$ alkylamino and $C_{1-4}$ alkoxy, the heterocycloalkyl of 3 to 8 atoms formed by the bonding of $R^9$ and $R^{10}$ is substituted or unsubstituted by at least one substituent $R^c$ selected from among a group comprised of a heterocycloalkyl of 3 to 10 atoms having one or two heteroatoms selected from among a group comprised of hydroxy, $C_{1-6}$ alkyl, $C_{1-4}$ alkoxy, $C_{1-4}$ alkylamino, $C_{1-4}$ carbonyl, $-NR^{12}R^{13}$, and heterocycloalkyl of 3 to 10 atoms having one or two heteroatoms selected from the group consisting of N and O, the $C_{1-6}$ alkyl, $C_{1-4}$ alkoxy and $C_{1-4}$ alkylamino of substituents $R^c$ are, respectively and independently, additionally substituted or unsubstituted by at least one substituent selected from among $C_{1-6}$ alkyl, $C_{1-4}$ alkoxy and $C_{1-4}$ alkylamino, the heterocycloalkyl of 3 to 10 atoms of substituents $R^c$ is substituted or unsubstituted by halogen; carbonyl; $C_{1-6}$ alkyl substituted or unsubstituted by $C_{1-4}$ alkylamino; $C_{2-4}$ alkenyl; $C_{1-4}$ alkylamino; $C_{1-4}$ alkylcarbonyl; and $C_{1-4}$ alkyl, and additionally substituted or unsubstituted by at least one substituent selected from among a group comprised of heterocycloalkyl of 3 to 8 atoms having one or two heteroatoms selected from a group comprised of N and O, $R^{12}$ and $R^{13}$ are, respectively and independently, substituted or unsubstituted by hydrogen, $C_{2-4}$ alkenylcarbonyl or $C_{1-4}$ alkyl, are heterocycloalkyl of 3 to 8 atoms having one or two N atoms, the heteroaryl of 3 to 8 atoms formed by the bonding of $R^9$ and $R^{10}$ is substituted or unsubstituted by $C_{1-4}$ alkyl, $R^4$ is $-NH(C=O)R^{14}C=CR^{15}R^{16}$, $R^{14}$ is hydrogen or halogen, and $R^{15}$ and $R^{16}$ are, respectively and independently, $C_{1-4}$ alkyl substituted by hydrogen or $C_{1-4}$ alkylamino, $R^5$ is a $C_{1-4}$ alkyl substituted by a aryl of 3 to 8 atoms or heteroaryl of 3 to 8 atoms; aryl of 3 to 8 atoms; or heteroaryl of 3 to 8 atoms, the aryl of 3 to 8 atoms or heteroaryl of 3 to 8 atoms of $R^5$ is, respectively and independently, substituted or unsubstituted by at least one substituent selected from among a group comprised of halogen, cyano, $C_{1-4}$ alkyl substituted or unsubstituted by halogen, $C_{1-4}$ alkoxy, and $C_{2-4}$ alkynyl, the $C_{1-4}$ substituted by a aryl of 3 to 8 atoms or a heteroaryl of 3 to 8 atoms of $R^5$ is substituted or unsubstituted by at least one substituent selected from among a group comprised of halogen, $C_{1-4}$ alkyl substituted or unsubstituted by halogen, and $C_{1-4}$ alkylamino, and $R^6$ may be hydrogen or $C_{1-4}$ alkyl.

In yet another embodiment, in a compound represented by Chemical Formula 1, $R^1$ is hydrogen, fluoro, chloro, methyl, ethyl, methoxy, ethoxy or propoxy, where the methoxy, ethoxy, or propoxy of $R^1$ is, respectively and independently, substituted or unsubstituted by at least one fluoro or chloro, $R^2$ is hydrogen or $-NR^7R^8$, where $R^7$ and $R^8$ are linked together with an N atom to which they are bonded to form azetidine, pyrrolidine, piperazine, piperidine or diazepane, the azetidine, pyrrolidine, piperazine, piperidine or diazepane formed by the bonding of $R^7$ and $R^8$ substituted or unsubstituted by at least one methyl or ethyl, $R^3$ is hydrogen, $-NR^9R^{10}$, or $-OR^{11}$, where $R^9$, $R^{10}$ and $R^{11}$ are, respectively and independently, methyl, ethyl, propyl, butyl or pentyl, or $R^9$ and $R^{10}$ are linked, together with an N atom to which they are bonded, form an azetidine, pyrrolidine, piperazine, piperidine, diazepane, morpholine, diazabicycloheptane, oxazabicycloheptane, diazabicyclooctane, oxazabicylooctane, imidazole, pyrrole, hexahydropyrrolopyrrole or tetrahydropuropyrrole, the methyl, ethyl, propyl, butyl or pentyl of $R^9$, $R^{10}$ and $R^{11}$ are, respectively and independently, substituted or unsubstituted by at least one substituent selected from among a group comprised of dimethylamino, diethylamino, methylethylamino, methylpropylamino, ethylpropylamino, methoxy or ethoxy, the azetidine, pyrrolidine, piperazine, piperidine, diazepane, morpholine, diazabicycloheptane, oxazabicycloheptane, diazabicyclooctane, oxazabicylooctane, imidazole, pyrrole, hexahydropyrrolopyrrole or tetrahydropuropyrrole formed by the bonding of $R^9$ and $R^{10}$ are, respectively and independently, substituted or unsubstituted by at least one substituent Rd selected from among a group comprised of hydroxy, methyl, ethyl, propyl, butyl, cyclopropyl, cyclobutyl, cyclopentyl, methoxy, ethoxy, dimethylamino, diethylamino, methylethylamino, methylpropylamino, ethylpropylamino, acetyl, azetidine, pyrrolidine, piperazine, piperidine, diazepane, morpholine, oxetane, diazabicycloheptane, oxazabicycloheptane, diazabicyclooctane, oxazabicylooctane, oxazaspiroheptane, azaspirooctane, hexahydropyrrolopirazine, and $-NR^{12}R^{13}$, the methyl, ethyl, propyl, butyl, cyclopropyl, cyclobutyl, cyclopentyl, methoxy, ethoxy, dimethylamino, diethylamino, methylethylamino, methylpropylamino or ethylpropylamino of the substituents Rd are, respectively and independently, additionally substituted or unsubstituted by at least one substituent selected from a group comprised of cyclopropyl, cyclobutyl, methoxy, ethoxy, methylamino, diethylamino and methylethylamino, the azetidine, pyrrolidine, piperazine, piperidine, diazepane, morpholine, oxetane, diazabicycloheptane, oxazabicycloheptane, diazabicyclooctane, oxazabicylooctane, oxazaspiroheptane, azaspirooctane or hexahydropyrrolopirazine of the substituents Rd are, respectively and independently, additionally substituted or unsubstituted by at least one substituent selected from a group comprised of fluoro, chloro, carbonyl, methyl, ethyl, propyl, butyl, cyclopropyl, cyclobutyl, cyclopentyl, methyl substituted by dimethylamino, methyl substituted by diethylamino, ethyl substituted by diethylamino, ethenyl, propenyl, butenyl, dimethylamino, diethylamino, methylethylamino, methylpropylamino, ethylpropylamino, acetyl, azetidine substituted or unsubstituted by methyl or ethyl, pyrrolidine substituted or unsubstituted by methyl or ethyl, piperazine substituted or unsubstituted by methyl or ethyl, piperidine substituted or unsubstituted by methyl or ethyl, diazepane substituted or unsubstituted by methyl or ethyl, morpholine substituted or unsubstituted by methyl or ethyl, and oxetane substituted or unsubstituted by methyl or ethyl, $R^{12}$ is, respectively and independently, hydrogen or prop-2-en-1-on, $R^{13}$ is azetidine substituted or unsubstituted by methyl, ethyl or propyl; pyrrolidine substituted or unsubstituted by methyl, ethyl or propyl; or piperidine substituted or unsubstituted by methyl, ethyl or propyl, the imidazole or pyrrole formed by the bonding of $R^9$ and $R^{10}$ is substituted or unsubstituted by methyl or ethyl, $R^4$ is —NH(C=O)$R^{14}$C=C$R^{15}R^{16}$, $R^{14}$ is hydrogen, fluoro or chloro, $R^{15}$ and $R^{16}$ are, respectively and independently, hydrogen; methyl substituted by dimethylamino or diethylamino; or ethyl substituted by dimethylamino or diethylamino, $R^5$ is methyl substituted by phenyl, naphthyl, pyridine or pyrrole; ethyl substituted by phenyl, naphthyl, pyridine or pyrrole; phenyl; naphthyl; pyrrole; pyridine; or thiophene, the phenyl, naphthyl, pyrrole, pyridine or thiophene of $R^5$ are, respectively and independently, substituted or unsubstituted by at least one substituent selected from among a group comprised of fluoro; chloro; cyano; methyl substituted or unsubstituted by fluoro or chloro; ethyl substituted or unsubstituted by fluoro or chloro; methoxy; ethoxy; and ethinyl, the phenyl, naphthyl, pyridine or pyrrole which is the substituent of the methyl or ethyl of $R^5$ is, respectively and respectively, substituted or unsubstituted by at least one substituent selected from among a group comprised of fluoro; chloro; methyl substituted or unsubstituted by fluoro or chloro; ethyl substituted or unsubstituted by fluoro or chloro; dimethylamino; and diethylamino, and $R^6$ may be hydrogen, methyl or ethyl.

In another embodiment,

A compound represented by Chemical Formula 2, stereoisomers of the same, or pharmaceutically acceptable salts of the same are provided.

[Chemical Formula 2]

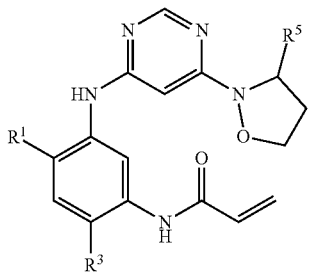

Where, in Chemical Formula 2, $R^1$ is hydrogen or $C_{1-4}$ alkoxy, $R^3$ is —X—Y—Z, where X and Y are, respectively and independently, single bonds or heterocycloalkyl of 3 to 8 atoms comprising at least one N atom, and Z is —$NR^{17}R^{18}$ or is represented by Chemical Formula 3,

[Chemical Formula 3]

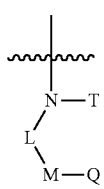

Where, in a case where Z is —$NR^{17}R^{18}$, at least one of X and Y is the heterocycloalkyl of 3 to 8 atoms comprising at least one N atom, where $R^{17}$ and $R^{18}$ are, respectively and independently, a $C_{1-4}$ alkyl substituted or unsubstituted by hydrogen or $C_{1-4}$ alkylamino, or are linked together with an N atom to which they are bonded to form a heterocycloalkyl of 3 to 12 atoms, In a case where Z is Chemical Formula 3, L is an alkylene substituted or unsubstituted by $C_{1-4}$ alkyl, M is —$NR^{19}$ or —O—, T and Q are, respectively and independently, $C_{1-4}$ alkyl substituted or unsubstituted by hydrogen or $C_{1-4}$ alkylamino; T and Q are linked to each other to form a heterocycloalkyl of 3 to 12 atoms substituted or unsubstituted by $C_{1-4}$ alkyl; or T and Q are linked to each other, with additional links between at least two different atoms forming a ring, to form a bridged or fused heterocycloalkyl of 3 to 12 atoms substituted or unsubstituted by a $C_{1-4}$ alkyl, $R^{19}$ is hydrogen, $C_{1-6}$ alkyl, $C_{1-6}$ alkenyl, $C_{1-6}$ alkylcarbonyl, $C_{1-4}$ alkylamino, or a 3 to 8 atom heterocycloalkyl, $R^5$ is a aralkyl of 3 to 8 atoms, aryl of 3 to 8 atoms, or heteroaryl of 3 to 8 atoms, where the aralkyl of 3 to 8 atoms, aryl of 3 to 8 atoms, or heteroaryl of 3 to 8 atoms of $R^5$ may be, respectively and independently, substituted or unsubstituted by at least one substituent selected from among a group comprised of halogen, cyano, $C_{1-4}$ alkyl, and $C_{1-4}$ alkoxy.

In another embodiment,

In the compound represented by Chemical Formula 2, $R^1$ may be hydrogen, methoxy, or ethoxy.

In another embodiment, in the compound represented by Chemical Formula 2, $R^1$ and $R^5$ are as defined in Chemical Formula 2, $R^3$ is —X—Y—Z, where X and Y are, respectively and independently, a single bond, azetidine, pyrrolidine, piperidine or piperazine, and Z is represented by —$NR^{17}R^{18}$ or Chemical Formula 3.

[Chemical Formula 3]

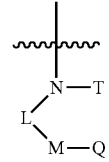

Where, in a case where Z is —$NR^{17}R^{18}$, at least one of X and Y is azetidine, pyrrolidine, piperidine or piperazine, where $R^{17}$ and $R^{18}$ are, respectively and independently methyl or ethyl, or are linked together with an N atom to which they are bonded to be azaspiroctane, In a case where Z is Chemical Formula 3, L is methylene, ethylene, propylene or butylene substituted or unsubstituted by methyl or ethyl, M is —$NR^{19}$ or —O—, and T and Q are, respectively and independently, methyl or ethyl substituted or unsubstituted by dimethyl amino; M is —$NR^{19}$, and T and Q are linked to each other to form a piperazine substituted or unsubstituted by methyl or ethyl; M is —$NR^{19}$, and T and Q are linked together, with additional links between at least two different atoms among the atoms forming the ring, forming a 6 to 8 atom diazabicycloalkyl substituted or unsubstituted by methyl or ethyl; M is —O—, and T and Q are linked together, forming a morpholine substituted or unsubstituted by methyl or ethyl; or M is —O—, and T and Q are linked together, with additional links between at least two different atoms among the atoms forming the ring, forming a 6 to 8 atom oxazabicycloalkyl substituted or unsubstituted by methyl or ethyl, and $R^{19}$ may be methyl, ethyl, propyl, cyclopropyl, cyclopropylmethyl, cyclobutyl, cyclopentyl, prop-2-en-1-yl, acetyl, dimethylamino, or oxetane.

In yet another embodiment,

In the compound represented by Chemical Formula 2, $R^5$ is phenyl, benzyl, pyridine or thiophene, and the phenyl, benzyl, pyridine or thiophene may be, respectively and independently, substituted or unsubstituted by at least one substituent selected from among a group comprised of fluoro, chloro, cyano, methyl substituted or unsubstituted by at least one fluoro, and methoxy.

In another embodiment, in a compound represented by Chemical Formula 2, $R^5$ is as defined in Chemical Formula 2, $R^1$ is hydrogen or methoxy, $R^3$ is —X—Y—Z, where X and Y are, respectively and independently, single bonds, pyrrolidine or piperidine, and Z is dimethylamino, azaspirooctane, or represented by Chemical Formula 3,

[Chemical Formula 3]

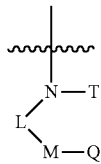

Where, in a case where Z is dimethylamino or azaspirooctane, at least one of X and Y is pyrrolidine or piperidine, In a case where Z is Chemical Formula 3 and X and Y are single bonds, Chemical Formula 3 is piperazine, morpholine, methylethylamino, hexahydropyrrolopyrrole, or tetrahydropuropyrrole substituted or unsubstituted by at least one substituent selected from among a group comprised of methyl, ethyl, propyl, cyclopropyl, cyclobutyl, cyclopentyl, cyclopropylmethyl, and dimethylamino, In a case where Z is Chemical Formula 3 and at least one of X and Y is pyrrolidine or piperidine, Chemical Formula 3 may be piperazine, morpholine, diazabicycloheptane, oxazabicycloheptane, hexahydropyrrolopyrrole, or tetrahydropuropyrrole substituted or unsubstituted by at least one substituent selected from among a group comprised of methyl, ethyl, propyl, oxetane, cyclopropyl, cyclobutyl, cyclopentyl, cyclopropylmethyl, acetyl and dimethylamino.

In yet another embodiment, in a compound represented by Chemical Formula 1, $R^1$ may be hydrogen, fluoro, chloro, methyl, ethyl, methoxy, ethoxy, propoxy, or

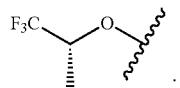

$R^2$ may be hydrogen or

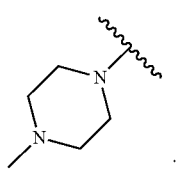 [SMILES: *N1CCN(C)CC1]

$R^3$ may be hydrogen,

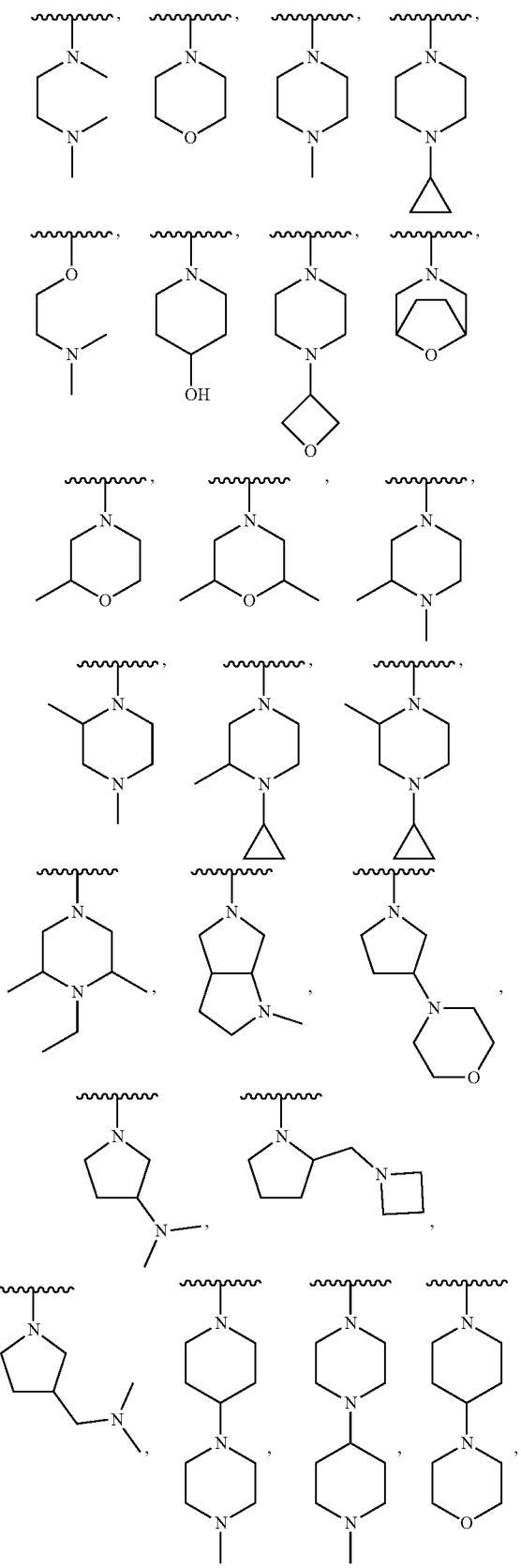

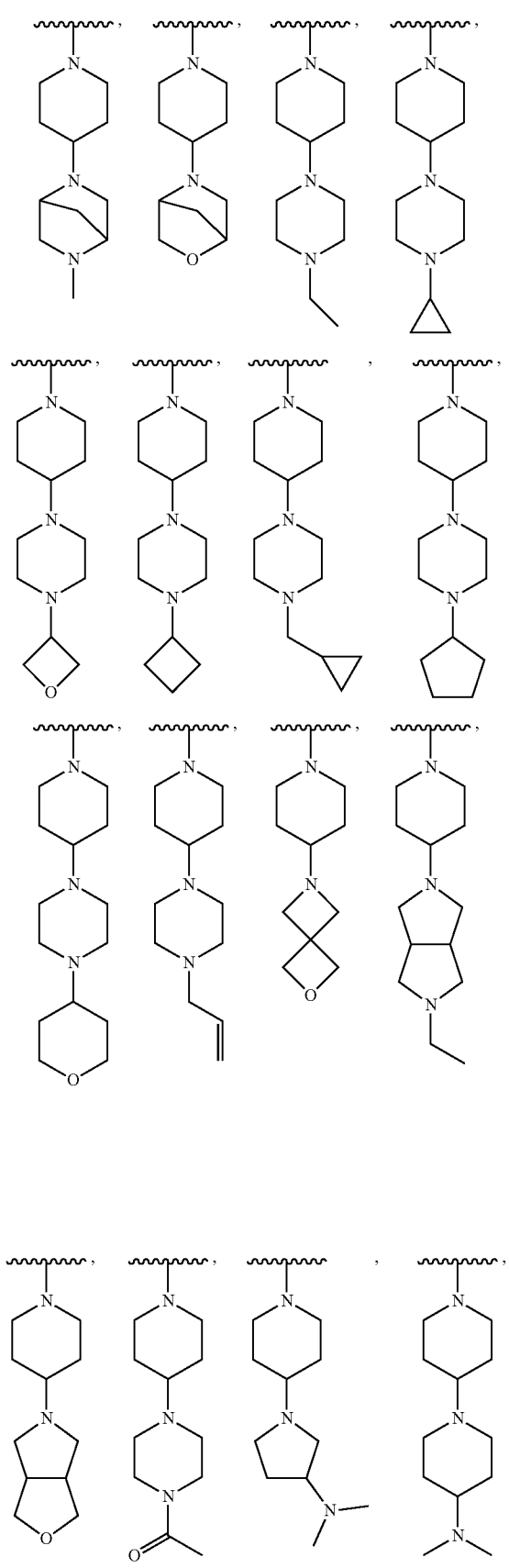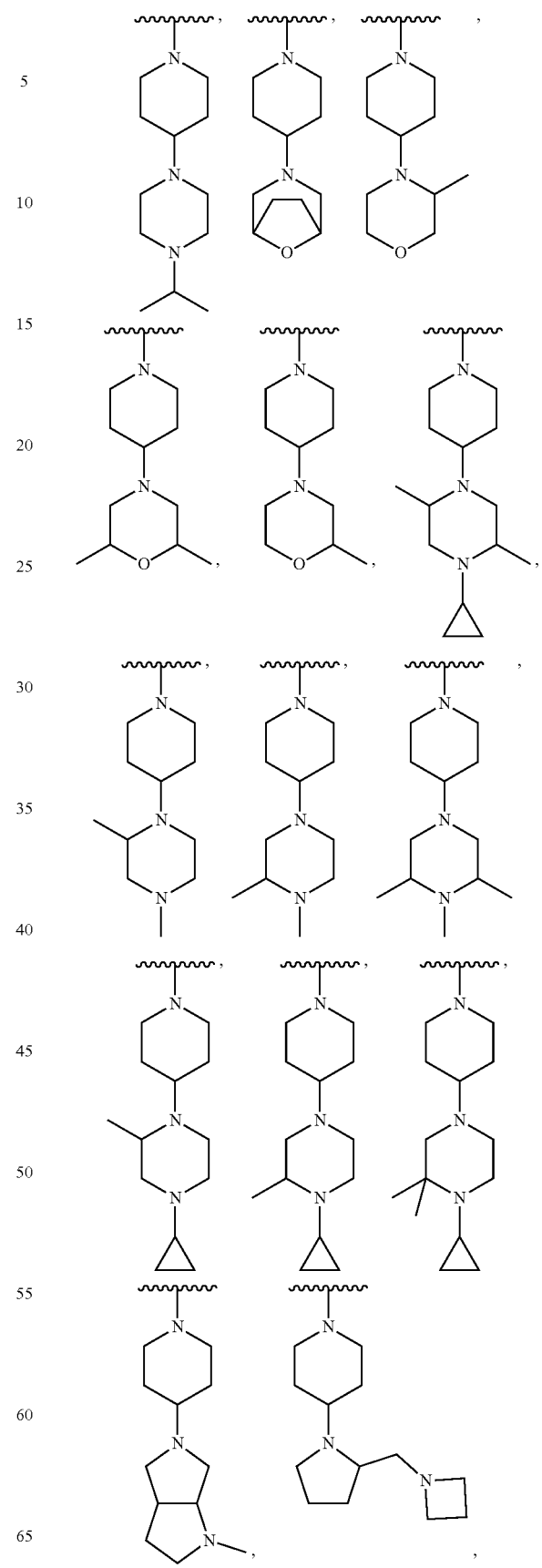

-continued
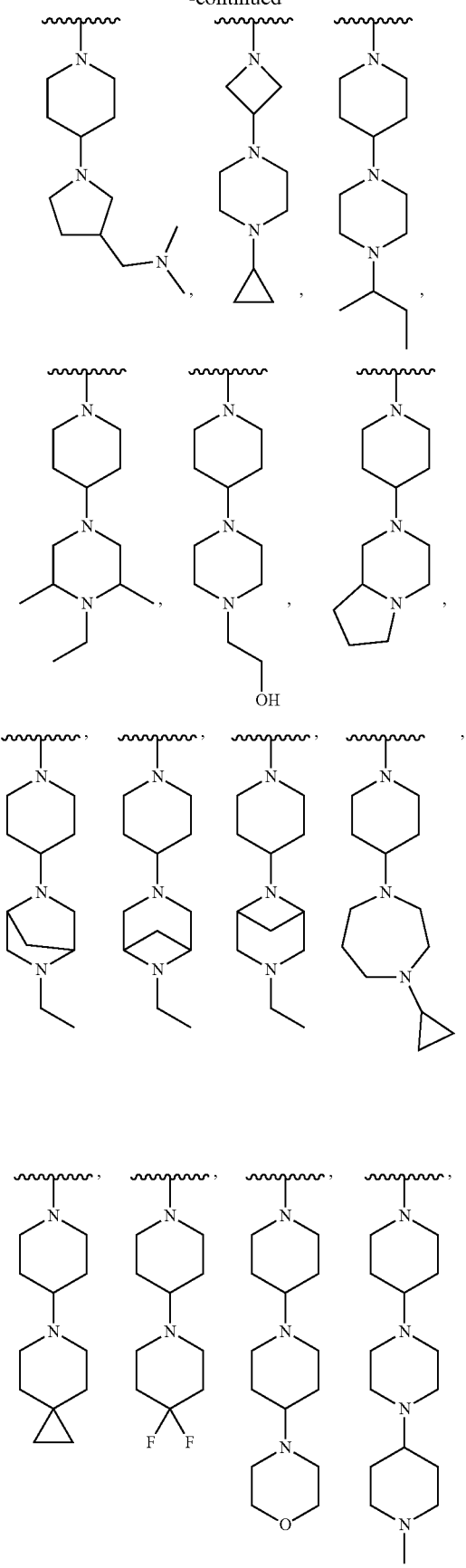
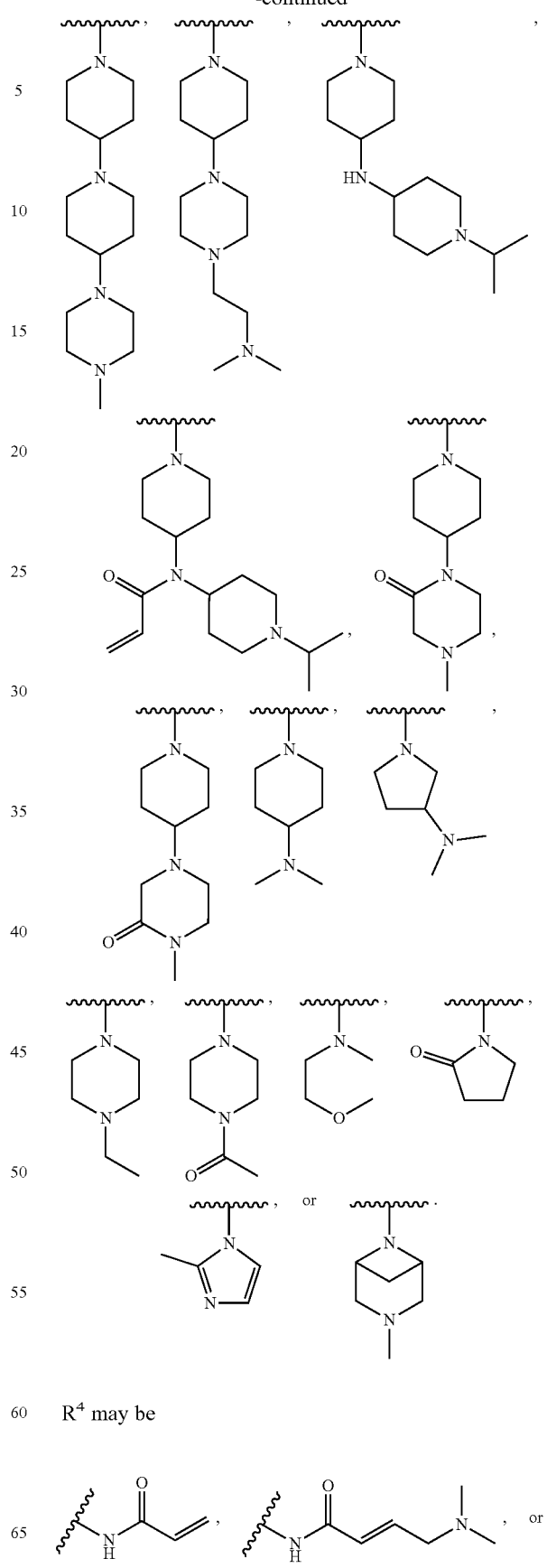
$R^4$ may be

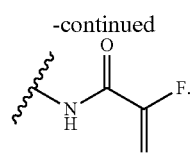
R[5] may be
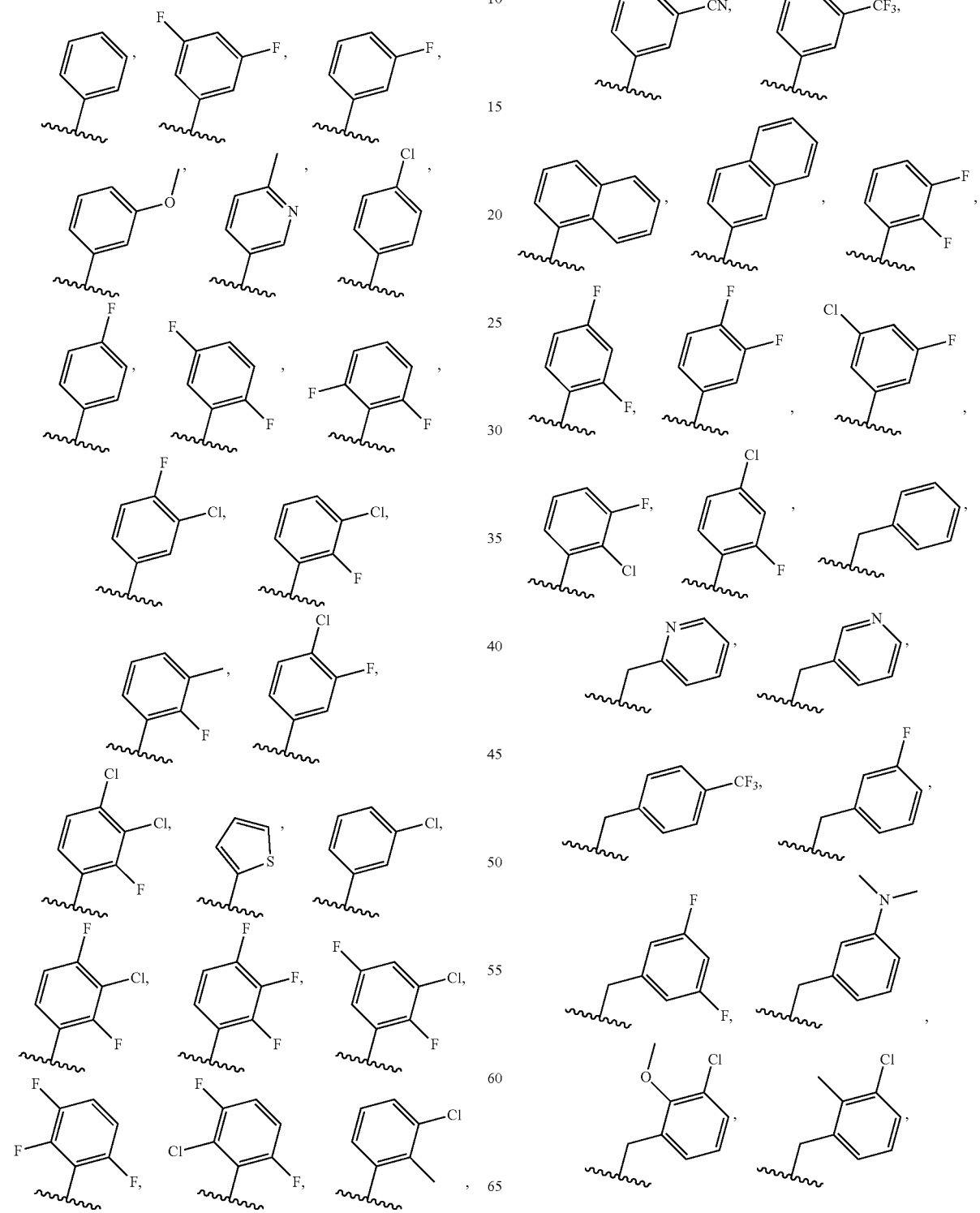
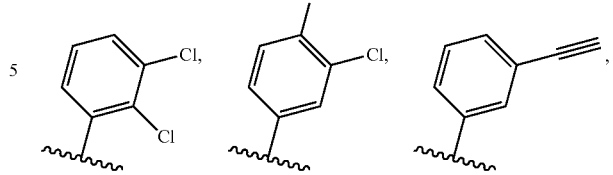
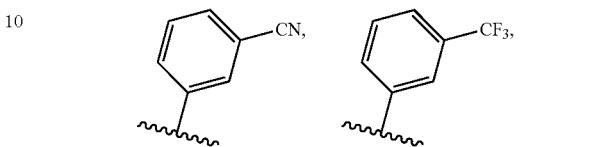
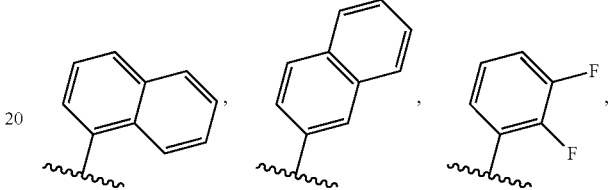
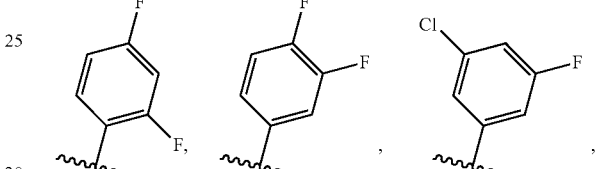
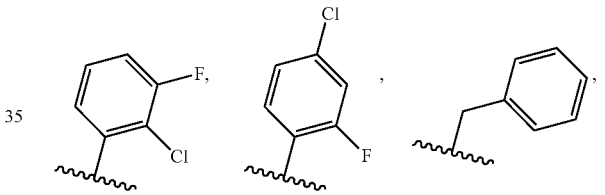
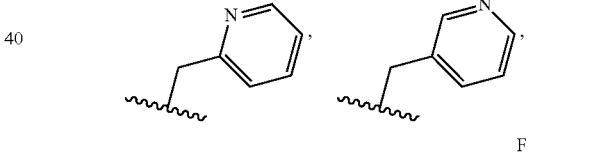
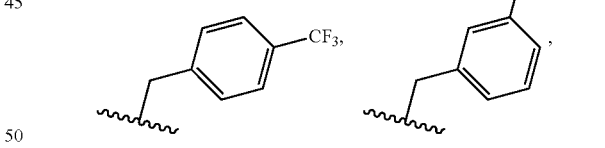
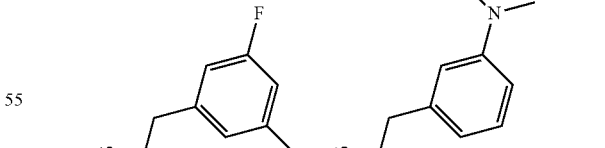
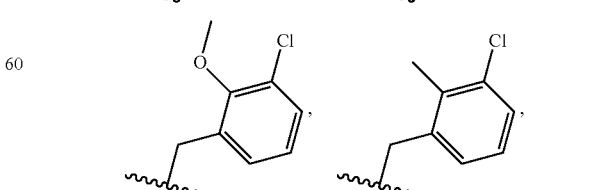

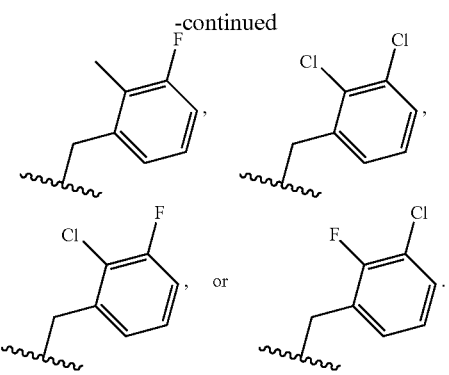

In another embodiment,

The compound represented by Chemical Formula 1 may be any one of Example Compounds 1 through 1059 listed in [Table 1] below.

The compound represented by Chemical Formula 1 of the present invention may be used in the form of pharmaceutically acceptable salts thereof. In particular, the pharmaceutically acceptable salt may be an acid addition salt formed by a free acid. Here, the acid addition salt may be obtained from inorganic acids, such as hydrochloric acid, nitric acid, phosphoric acid, sulfuric acid, hydrobromic acid, hydroiodic acid, nitrous acid, phosphorous acid and the like, nontoxic organic acids, such as aliphatic mono- and dicarboxylate, phenyl-substituted alkanoate, hydroxy alkanoate and alkanthioate, aromatic acids, aliphatic and aromatic sulfonic acids and the like, organic acids, such as acetate, benzoic acid, citric acid, lactic acid, maleic acid, gluconic acid, methanesulfonic acid, 4-toluenesulfonic acid, tartaric acid, fumaric acid and the like. Types of such pharmaceutically acceptable salts include sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzene sulfonate, toluene sulfonate, chlorobenzene sulfonate, xylene sulfonate, phenylacetate, phenylpropionate, phenylbutyrate, citrate, lactate, ß-hydroxybutyrate, glycolate, malate, tartrate, methane sulfonate, propane sulfonate, naphthalene-1-sulfonate, naphthalene-2-sulfonate, mandelate and the like. The acid addition salt may be prepared using a conventional method, for example, by dissolving the derivative of Formula 1 in an organic solvent, such as methanol, ethanol, acetone, methylene chloride, acetonitrile and the like, adding an organic acid or an inorganic acid, filtering the resulting precipitate, and drying, or it may be prepared by distilling a solvent and an acid in excess amount under reduced pressure, then drying, and crystallizing under an organic solvent. Further, the pharmaceutically acceptable salt may be a salt or metal salt obtained using a base. As an example of a metal salt, an alkali metal or alkaline earth metal salt may be obtained, for example, by dissolving the compound in surplus alkali metal hydroxide or alkaline earth metal hydroxide solution, filtering the undissolved compound salt, evaporating the filtrate, and drying. Pharmaceutically suitable alkali metal salts may be sodium, potassium or calcium. In addition, the corresponding salt may be obtained by reacting an alkali metal or alkaline earth metal salt with an appropriate silver salt (for example, silver nitrate).

Further, the present invention may be, not only the compound represented by Chemical Formula 1 and pharmaceutically acceptable salts thereof, but also stereoisomers, in particular, enantiomers of the same and hydrates and/or solvates which may be prepared from the same.

Another aspect of the present invention may provide a method for preparing the compound of Chemical Formula 1.

The method for preparing the compound of Chemical Formula 1 may comprise:
- A step of preparing a compound of Chemical Formula 5 from a compound of Chemical Formula 4;
- A step of preparing a compound of Chemical Formula 6 from the compound of Chemical Formula 5; and,
- A step of preparing the compound of Chemical Formula 1 from the compound of Chemical Formula 6.

[Chemical Formula 4]

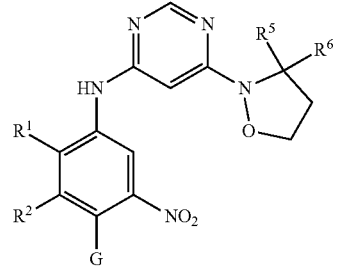

[Chemical Formula 5]

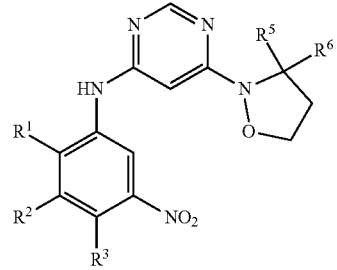

[Chemical Formula 6]

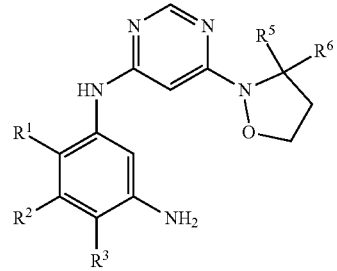

[Chemical Formula 1]

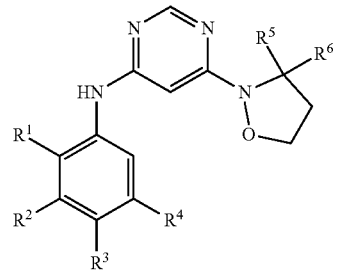

In Chemical Formula 4, G is a leaving group, and $R^1$ and Re are respectively the same as defined in the above. The leaving group may be a functional group such as halogen, sulfonic acid ester or alkoxy, and there is no particular limitation on the functional group so long as it is a functional group where the leaving group can leave from the compound of Chemical Formula 4 to prepare the compound of Chemical Formula 5.

The step of preparing the compound of Chemical Formula 5 from the compound of Chemical Formula 4 may be a step wherein the compound of Chemical Formula 4 reacts with $R^3$—H. The reaction may be carried out in solvent such as dimethylsulfoxide (DMSO). The reaction temperature may be approximately 40 to 100° C., the reaction time may be 90 to 150 minutes, and conditions may not be limited to the above so long as they allow the reaction to carry on smoothly.

Meanwhile, the step of preparing the compound of Chemical Formula 5 from the compound of Chemical Formula 4 may be a step wherein a step of reacting the compound of Chemical Formula 4 with a heterocycloalkyl such as piperidinone is carried out, and then a step of reacting with $R^3$—H is carried out.

The step of preparing the compound of Chemical Formula 6 from the compound of Chemical Formula 5 may be a step of reducing nitro groups existing in a para position from $R^1$, in a meta position from $R^2$, and in an ortho position from $R^3$. In particular, the step may be a step wherein only the nitro groups are reduced, without reducing other functional groups or compounds. Any reducing agent may be used without limitation so long as it is a reducing agent which reduces nitro groups, and for example, $SnCl_2$ may be used.

The step of preparing the compound of Chemical Formula 1 from the compound of Chemical Formula 6 may be a step wherein the compound of Chemical Formula 6 reacts with acrylic acid or acryl halide.

Further, the compound of Chemical Formula 4 may be a compound prepared through a step of preparing a compound of Chemical Formula 8 from a compound of Chemical Formula 7; and, a step of preparing the compound of Chemical Formula 4 from the compound of Chemical Formula 8.

[Chemical Formula 7]

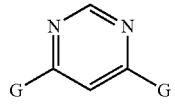

[Chemical Formula 8]

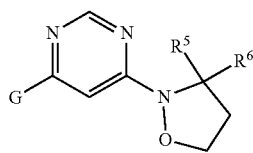

In Chemical Formula 7 or Chemical Formula 8 above, G is, respectively and independently, a leaving group, and $R^5$ and $R^6$ may respectively be the same as defined in the present specification. The leaving group may be a functional group such as halogen, sulfonic acid, ester or alkoxy, and there is no particular limitation on the functional group so long as the compound of Chemical Formula 8 can be prepared from the compound of Chemical Formula 7, and the compound of Chemical Formula 4 can be prepared from the compound of Chemical Formula 8.

The step of preparing the compound of Chemical Formula 8 from the compound of Chemical Formula 7 may be performed in a solvent such as dimethylsulfoxide (DMSO). The reaction temperature may be approximately 60 to 120° C., the reaction time may be approximately 30 to 90 minutes, and there is no particular limitation on the above conditions so long as they allow for the reaction(s) to carry out smoothly.

In the case of the step of preparing the compound of Chemical Formula 4 from the compound of Chemical Formula 8, the reaction temperature may be approximately 80 to 120° C., the reaction time may be approximately 45 to 90 minutes, and there is no particular limitation on the above conditions so long as they allow for the reaction(s) to carry out smoothly.

Yet another aspect of the present invention may provide:

A pharmaceutical composition for preventing or treating cancer, the composition comprising the compound of Chemical Formula 1, stereoisomers of the same, hydrates of the same or pharmaceutically acceptable salts of the same as an effective component.

The compound of Chemical Formula 1 may exhibit inhibitory activity against EGFR (epidermal growth factor receptor) mutants and ERBB2 and ERBB4. In other words, the compound of Chemical Formula 1 can inhibit EGFR (epidermal growth factor receptor) mutants, or wild type or mutant kinases of one of ERBB2 and ERBB4.

The EGFR mutant may be at least one selected from among a group comprised of EGFR Del19/T790M, EGFR L858R/T790M, EGFR L858R, EGFR Exon20 ins NPH, EGFR Exon20 ins SVD, EGFR Exon20 ins FQEA, EGFR Exon20 ins H, and EGFR Exon20 ins ASV.

The ERBB2 mutant may be Her2 Exon20 ins YVMA.

Whereas there is no limitation on the type of cancer, the cancer may be one or more selected from a group comprised of pseudomyxoma, intrahepatic cholangiocarcinoma, hepatoblastoma, liver cancer, thyroid cancer, colon cancer, testis cancer, myelodysplastic syndrome, glioblastoma, oral cancer, lip cancer, mycosis fungoides, acute myeloid leukemia, acute lymphocytic leukemia, basal cell carcinoma, epithelial ovarian cancer, ovarian seminoma, male breast cancer, brain cancer, pituitary adenoma, multiple myeloma, gallbladder cancer, cholangiocarcinoma, colorectal cancer, chronic myeloid leukemia, chronic lymphocytic leukemia, retinoblastoma, choroidal melanoma, ampullar of Vater cancer, bladder cancer, peritoneal cancer, parathyroid cancer, adrenal cancer, nasal and paranasal cavity cancer, non-small cell lung cancer, tongue cancer, astrocytoma, small cell lung cancer, pediatric brain cancer, pediatric lymphoma, pediatric leukemia, small intestine cancer, meningioma, esophageal cancer, glioma, renal pelvis cancer, renal cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, cancer of unknown primary site, gastric lymphoma, gastric cancer, gastric carcinoid, gastrointestinal stromal tumor, Wilms' tumor, breast cancer, sarcoma, penile cancer, pharyngeal cancer, gestational choriocarcinoma, cervical cancer, endometrial cancer, uterine sarcoma, prostate cancer, metastatic bone cancer, metastatic brain cancer, mediastinal cancer, rectal cancer, rectal carcinoid, vaginal cancer, spinal cancer, vestibular schwannoma, pancreatic cancer, salivary gland cancer, Kaposi's sarcoma, Paget's disease, tonsillar cancer, squamous cell cancer, adenocarcinoma of lung, lung cancer, squamous cell lung cancer, skin cancer, anal cancer, rhabdomyosarcoma, laryngeal cancer, pleura cancer, hematologic malignancy, and thymic cancer.

The pharmaceutical composition for preventing or treating cancer according to the present invention may be used for clinical administration, and may be prepared for administration as a variety of oral and non-oral dosage forms.

The pharmaceutical composition of the present invention may comprise pharmaceutically acceptable carriers. Examples of such pharmaceutically acceptable carriers include filling agents, bulking agents, binding agents, wetting agents, disintegrating agents, diluents such as surfactants or excipients, and the composition of the present invention may be formulated together with these.

Solid formulations for oral administration may include tablets, pills, powders, granules and capsules, etc., and such solid formulations may be formulated by mixing, with at least one compound, at least one excipient, for example, starch, calcium carbonate, sucrose, lactose or gelatin, etc. Further, in addition to simple excipients, lubricants such as magnesium stearate or talc may be used in formulation.

Liquid formulations for oral administration may include a suspension, a solution, an emulsion and a syrup, etc. In addition to water commonly used as a simple diluent and liquid paraffin, various excipients, for example, wetting agents, sweetening agents, flavors, preservatives, etc. may be included.

Formulations for non-oral administration include sterilized aqueous solutions, non-aqueous solvents, suspending agents, emulsions, freeze-drying agents, suppositories, etc. Propylene glycol, polyethylene glycol, vegetable oils such as olive oil, injectable esters such as ethyl oleate, etc. may be used as non-aqueous solvents and suspending agents.

Further, non-oral administration may be performed using methods such as subcutaneous injection, intravenous injection, intramuscular injection or intrathoracic injection. Here, for formulation into a dosage form for non-oral administration, the pharmaceutical composition may be prepared by mixing the compound represented by Chemical Formula 1 or a pharmaceutically acceptable salt thereof into water together with a stabilizer or buffer to prepare a solution or suspension, which is then prepared into ampoule or vial type unit doses. The composition is/may be sterilized, may contain preservatives, stabilizing agents, wetting agents or emulsifying agents, salts for osmoregulation, and/or adjuvants such as buffer agents, as well as other therapeutically useful substances, and may be formulated using ordinary mixing, granulation or coating methods.

In the following, the present invention will be explained in detail through embodiments and experimental examples. Provided, that the following embodiments and experimental examples are meant only to exemplify the present invention, and the scope of the present invention is not limited to these.

<Conditions for Analysis and Purification>

The compounds synthesized in the embodiments of the present invention were purified or structurally analyzed according to the following HPLC conditions.

1. Analytical HPLC Conditions
Analytical HPLC Conditions (ACQUITY UPLC H-Class Core System)

A UPLC system (ACQUITY UPLC PDA Detector) manufactured by Waters, equipped with a Waters-manufactured mass QDA Detector was used. The column used was the Waters ACQUITY UPLC® BEH C18 (1.7 µm, 2.1×50 mm), and a column temperature of 30° C. was used.

Water containing 0.1% formic acid was used as mobile phase A, and acetonitrile containing 0.1% formic acid was used as mobile phase B.

Gradient condition (3 minutes with 10-100% B, speed=0.6 ml/min)

Pre-LCMS (Preparative-Liquid Chromatography Mass Spectrometry) for Purification

An autopurification HPLC system (2767 sample manager, 2545 binary gradient module, 2998 photodiode array detector) manufactured by Waters equipped with a Waster-manufactured mass QDA detector was used. The column used was the Waters SunFire® Prep C18 OBD™ (5 µm, 19×50 mm), and the column was carried out at room temperature.

Water containing 0.035% trifluoroacetic acid was used as mobile phase A, and methanol containing 0.035% trifluoroacetic acid was used as mobile phase B.

Gradient condition (10 minutes with 15-100% B, speed=25 ml/min)

Prep-150LC System for Purification (Preparative-Liquid Chromatography UV Spectrometry)

A Prep 150 LC system (2545 quaternary gradient module, 2998 photodiode array detector, Fraction collector[2]) manufactured by Waters was used. The column used was the Waters XTERRA® Prep RP18 OBD™ (10 µm, 30×300 mm), and the column was carried out at room temperature.

Gradient condition (120 minutes with 3-100% B, speed=40 ml/min)

2. NMR Analysis

NMR analysis was carried out using the AVANCE III 400 or AVANCE III 400 HD manufactured by Bruker, and data was presented in ppm (parts per million($\delta$)).

The commercially available reagent used was used without additional purification. In the present invention, room temperature refers to a temperature of about 5° ° C. to 40° C., 10° ° C. to 30° C. in one example, and 20° ° C. to 27° ° C. in another example, but is not limited to within these ranges. For concentration under pressure and removal of solvent through distillation, a rotary evaporator was used.

PREPARATION EXAMPLES

1. Preparation of isoxazolidine derivatives

<Preparation Example 1> Preparation of (S)-3-phenylisoxazolidine

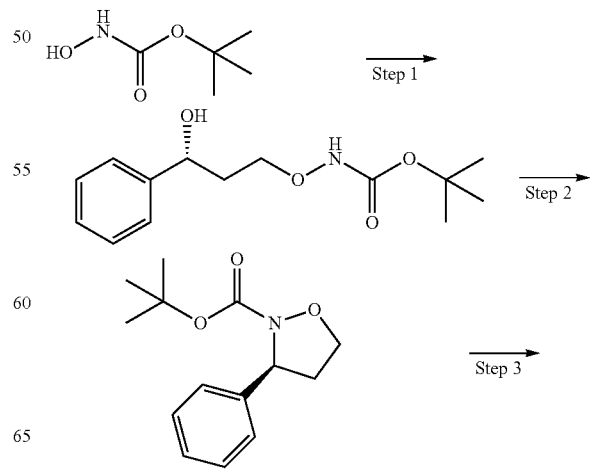

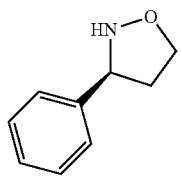

Step 1: Preparation of tert-butyl(R)-(3-hydroxy-3-phenylpropoxy)carbamate tert-butyl hydroxycarbamate (7.8 g, 58.6 mmol) was dissolved in dimethylformamide (140 ml), then sodium hydride (2.58 g, 64.5 mmol) was added at 0° C. and reacted for 30 minutes. Then (R)-3-chloro-1-phenylpropane-1-ol (5 g, 29.3 mmol) dissolved in dimethylformamide (10 ml) was slowly added dropwise over 10 minutes at 0° C., and agitated for 72 hours at room temperature. Aqueous solution of ammonium chloride was added to the reaction mixture to end the reaction, then extraction was performed using ethyl acetate and salt water. The organic layers were added. The organic layer was dried using sodium sulfate and concentrated, then purified with medium pressure liquid chromatography (ethyl acetate/n-hexane) to obtain the target compound tert-butyl(R)-(3-hydroxy-3-phenylpropoxy)carbamate (2.8 g, 68%).

MS (m/z): 150.17 [M+1]+, UPLC r.t. (min): 1.51

Step 2: Preparation of tert-butyl(S)-3-phenylisoxazolidine-2-carboxylate

The tert-butyl(R)-(3-hydroxy-3-phenylpropoxy)carbamate (2.55 g, 94.54 mmol) obtained in Step 1 of Preparation Example 1 above and triethylamine (3.13 ml, 22.44 mmol) were dissolved in dichloromethane (250 ml) and chilled to 0° C. Methanesulfonyl chloride (1 ml, 13 mmol) was added dropwise, then reacted for 2 hours at 0° C. The reaction mixture was extracted with salt water and dichloromethane, and the organic layers were added. The organic layer was dried using sodium sulfate, then vacuum concentrated to obtain the target compound tert-butyl-3-phenylisoxazolidine-2-carboxylate, which was used in the next reaction without purification.

MS (m/z): 194.13 [M+1]+, UPLC r.t. (min): 1.69

Step 3: Preparation of (S)-3-phenylisoxazolidine

The tert-butyl-3-phenylisoxazolidine-2-carboxylate (2.3 g) obtained in Step 2 of Preparation Example 1 above was dissolved in dichloromethane (90 ml), then trifluoroacetic acid (14 ml) was added and reacted for 1 hour at room temperature. The reaction mixture was neutralized with an aqueous solution of sodium bicarbonate, and the organic layers were added. The organic layer was dried using sodium sulfate and vacuum concentrated and purified using medium pressure liquid chromatography (tetrahydrofuran/n-hexane) to obtain the target compound 3-phenylisoxazolidine (1.3 g, 94%).

MS (m/z): 150.08 [M+1]+, UPLC r.t. (min): 0.72

<Preparation Example 2> Preparation of (R)-3-phenylisoxazolidine

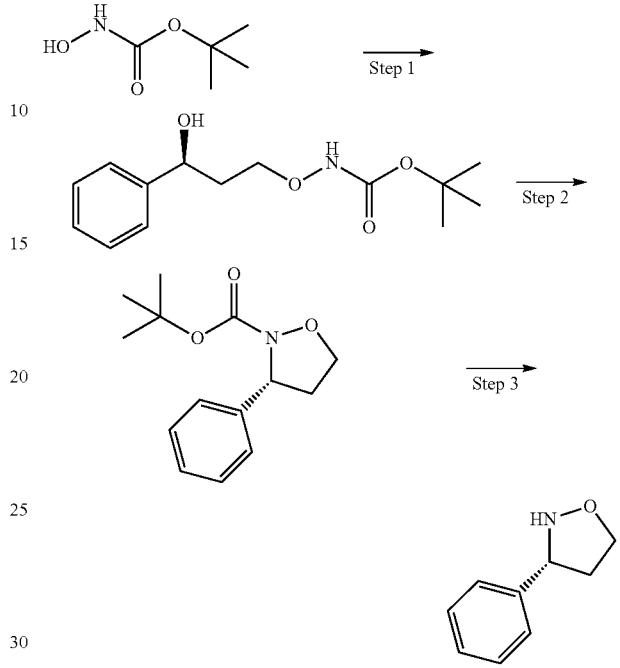

Preparation Example 2 was prepared using method similar to that of Preparation Example 1, and was used in the synthesis of the Example Compounds listed in [Table 1].

MS (m/z): 150.08 [M+1]+, UPLC r.t. (min): 0.72

<Preparation Example 3> Preparation of (R)-3-(3-fluorophenyl)isoxazolidine

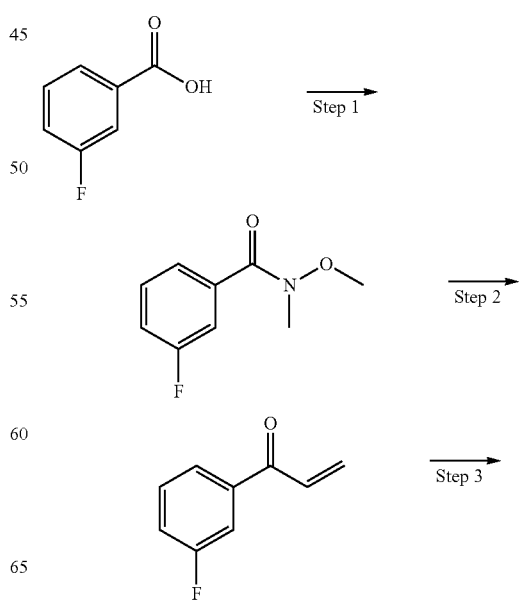

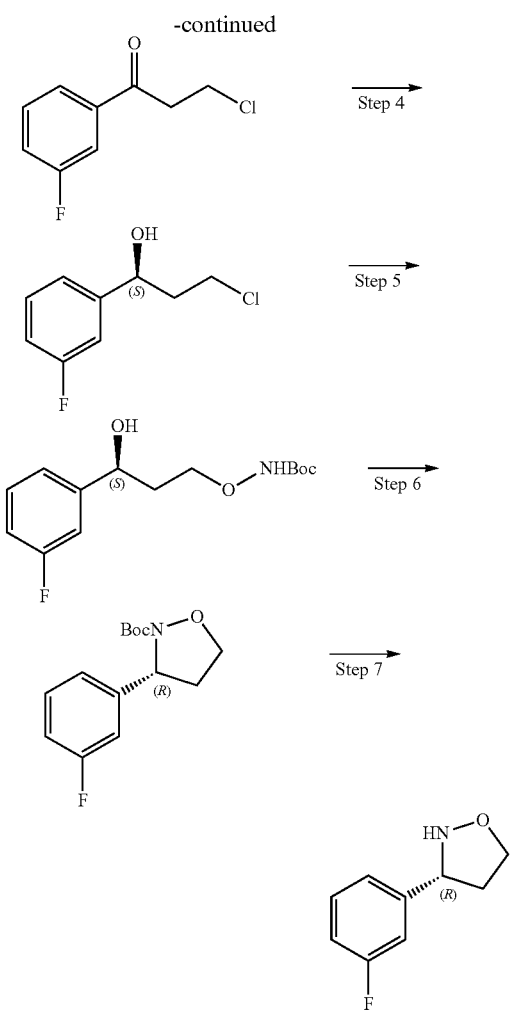

Step 1: Preparation of
3-fluoro-N-methoxy-N-methylbenzamide 3-fluorobenzoic acid (90 g, 642.35 mmol, 1 eq) was dissolved in pyrimidine (150 mL), then N-methoxy methanamine (75.19 g, 770.81 mmol, 1.2 eq, HCl) was added. Thereafter, 1-ethyl-3-(-3-dimethylaminopropyl)carbodiimide (EDCl; 147.77 g, 770.81 mmol. 1.2 eq) was added at 15° C. The reaction mixture was agitated for 30 minutes at 50° C. TLC analysis (PE:EA=3:1) results showed that all of the starting material had disappeared, and new spots with low polarity were detected. Vacuum concentration was performed to remove the pyridine solvent, and dichloromethane (DCM; 500 mL), hydrochloric acid (500 mL, 2N) and salt water (200 mL) were used to extract the organic layer. The organic layer was dried using sodium sulfate and vacuum concentrated to obtain the target compound 3-fluoro-N-methoxy-N-methylbenzamide (110 g, 600.50 mmol, 93.49% yield) in the form of a yellow oil.

1H NMR (400 MHz, CHLOROFORM-d) 0 ppm 7.47-7.40 (m, 1H), 7.39-7.38 (m, 2H), 7.14-7.13 (m, 1H), 3.54 (s, 3H), 3.45 (s, 3H)

Step 2: Preparation of
1-(3-fluorophenyl)prop-2-en-1-one

The 3-fluoro-N-methoxy-N-methylbenzamide (110 g, 600.50 mmol, 1 eq) obtained in Step 1 of Preparation Example 3 was dissolved in tetrahydrofuran (THF; 1 L), and then at 0° C., bromo(vinyl)magnesium (1M, 630.53 mL, 1.05 eq) was added dropwise at 78° C. Then, the reaction mixture was agitated for 30 minutes at 0° C. TLC analysis (PE:EA=4:1) results showed that all of the starting material had disappeared, and new spots having low polarity were detected. Hydrochloric acid (4N, 500 mL) was added to end the reaction, and the organic layer was extracted using methyl tert-butyl ether (MTBE; 2000 mL) and salt water (500 mL). The organic layer was dried using sodium sulfate, then vacuum concentrated. The concentrated compound was purified using chromatography (petroleum ether/ethyl acetate=30/1) to obtain the target compound 1-3-fluorophenyl)prop-2-en-1-one (80 g, 532.80 mmol, 88.73% yield) in the form of a yellow oil.

1H NMR (400 MHZ, CHLOROFORM-d) 0 ppm 7.65 (m, 1H), 7.58-7.52 (m, 1H), 7.39 (m, 1H), 7.24-7.17 (m, 1H), 7.04 (dd, J=17.2, 10.4 Hz, 1H), 6.39 (dd, J=17.2, 1.6 Hz, 1H), 5.90 (dd, J=10.4, 1.6 Hz, 1H)

Step 3: Preparation of
3-chloro-1-(3-fluorophenyl)propan-1-one

The 1-3-fluorophenyl)prop-2-en-1-one (71 g, 472.86 mmol, 1.0 eq) obtained in Step 2 of Preparation Example 3 was dissolved in dichloromethane (DCM; 71 mL), then HCl/dioxane (4M, 295.54 mL, 2.5 eq) was added at 0° C. Then, the reaction mixture was agitated for 1.5 hours at 15° C. TLC analysis (PE:EA=10:1) results showed that all the starting material disappeared, and the target compound was detected. The reaction mixture was concentrated under vacuum, then dichloromethane (DCM; 450 mL) and water (200 mL*5) was added to extract the organic layer, which was dried using sodium sulfate and vacuum concentrated to obtain the target compound 3-chloro-1-(3-fluorophenyl)propan-1-one (73 g, 391.19 mmol. 82.73% yield) in the form of a yellow solid.

1H NMR (400 MHZ, CHLOROFORM-d) δ=7.78-7.72 (m, 1H), 7.69-7.60 (m, 1H), 7.53-7.44 (m, 1H), 7.37-7.24 (m, 1H), 3.93 (t, J=6.8 Hz, 2H), 3.46 (t, J=6.8 Hz, 2H)

Step 4: Preparation of (S)-3-chloro-1-(3-fluorophenyl)propan-1-ol (3aR)-1-methyl-3,3-diphenyl-3a,4,5,6-tetrahydropyrrolo [1,2-c][1,3,2]oxazaborol (1M, 32.15 mL, 0.1 eq) was dissolved in tetrahydrofuran (THF; 1.2 L), then borane tetrahydrofuran (BH3THF; 1M, 186.48 mL, 0.6 eq) was added dropwise at 0° ° C. in a nitrogen atmosphere. The reaction mixture was agitated for 30 minutes at 0° C. Thereafter, the 3-chloro-1-(3-fluorophenyl)propan-1-one obtained in Step 3 of Preparation Example 3 (60 g, 309.02 mmol, 1 eq) diluted in tetrahydrofuran was added dropwise at 0° C. to the reaction mixture. TLC analysis (PE:EA=5:1) results showed that all of the starting material had disappeared, with spots of the target compound detected. The reaction was ended by adding methanol (100 mL) at 0° C., and the solvent was allowed to volatilize in vacuum. The organic layer was extracted from the concentrated compound using dichloromethane (DCM; 100 mL*3) and ammonium chloride (NH4Cl) solution (300 mL). The organic layer was dried using sodium sulfate and vacuum concentrated. The concentrated compound was purified using silica gel chromatography (PE:EA=50:1 to 5:1) to obtain (3)-3-chloro-1-(3-fluorophenyl)propan-1-ol (140 g, 664.2 mmol, 71.65% yield, 89.49% purity, 65.5% e.e) as a colorless oil.

1H NMR (400 MHZ, CHLOROFORM-d) 0 ppm 7.33 (m, 1H), 7.16-7.07 (m, 2H), 7.02-6.96 (m, 1H), 4.96 (m, 1H), 3.75 (m, 1H), 3.57 (m, 1H), 2.26-2.15 (m, 2H)

Step 5: Preparation of tert-butyl(S)-(3-(3-fluorophenyl)-3-hydroxypropoxy)carbamate Tert-butyl hydroxycarbamate (50.4 g, 378.52 mmol, 1.05 eq) was dissolved in dimethylformamide (DMF; 500 mL), and sodium hydride (NaH; 15.86 g, 396.55 mmol, 60% purity, 1.1 eq) was added at 0° ° C. in a nitrogen atmosphere. The reaction mixture was agitated for 1 hour at 10° C., and the (1R)-3-chloro-1-(3-fluorophenyl)propan-1-ol obtained in Step 4 of Preparation Example 3 diluted in dimethyl formamide (DMF; 180 mL) was added dropwise at 0° C., then agitated for 16 hours at 10° C. TLC analysis (PE:EA=2: 1) results showed that all of the starting material had disappeared, and the target compound was detected. An aqueous solution of ammonium chloride (3 L) was added to end the reaction, and the organic layer was extracted using ethyl acetate (2000 mL) and salt water (2000 mL). The organic layer was dried using sodium chlorate, then concentrated under vacuum to obtain tert-butyl(S)-(3-(3-fluorophenyl)-3-hydroxypropoxy)carbamate (176 g, 616.87 mmol, 85.56% yield) in the form of a bright yellow solid.

1H NMR (400 MHZ, CHLOROFORM-d) 0 ppm 7.67-7.64 (m, 1H), 7.23-7.17 (m, 1H), 7.08-7.03 (m, 2H), 6.88-6.81 (m, 1H), 4.99-4.84 (m, 1H), 4.02-3.97 (m, 1H), 3.96-3.89 (m, 1H), 1.95-1.89 (m, 1H), 1.88-1.78 (m, 1H), 1.42-1.39 (m, 9H)

Step 6: Preparation of tert-butyl(R)-3-(3-fluorophenyl)isoxazolidine-2-carboxylate The tert-butyl(S)-(3-(3-fluorophenyl)-3-hydroxypropoxy)carbamate obtained in Step 5 of Preparation Example 3 (88 g, 308.44 mmol, 1 eq) and Et3N (93.63 g, 925.31 mmol, 128.79 mL, 3 eq) were dissolved in dichloromethane (DCM; 1 L), then anhydrous methanesulfonic acid (80.59 g, 462.65 mmol, 1.5 eq) was slowly added at 0° C. The reaction mixture was agitated for 12 hours at 20° C. TLC analysis (PE:EA=3:1) results showed that all of the starting material had disappeared, and new spots were detected. Water (2000 mL) was added to end the reaction, and the organic layer was extracted using dichloromethane (DCM; 200 mL*3). The organic layer was dried using sodium sulfate, then vacuum concentrated. The concentrated compound was purified using chromatography (PE: EA=50:1 to 5:1) to extract 88 g of the target compound having a 82.5% e.e value. The target compound was purified using SFC (column: DAICEL CHIRALPAK AD (250 mm*50 mm, 10 um); mobile phase: [Neu-MeOH]; B %: 15%-15%, 3.4 min; 380 min) to obtain the white solid tert-butyl(R)-3-(3-fluorophenyl)isoxazolidine-2-carboxylate (51 g, 189.66 mmol, 30.74% yield, 99.4% purity).

The enantiomeric purity of the tert-butyl(R)-3-(3-fluorophenyl)isoxazolidine-2-carboxylate obtained in Step 6 was analyzed using the following SFC conditions.
Instrument: CAS-WH-ANA-SFC-C(SHIMADZU LC-30ADsf)
Column: Amycoat 50×4.6 mm I.D., 3 um
Mobile phase: Phase A for CO2, and Phase B for MeOH (0.05% DEA);
Gradient elution: MeOH (0.05% DEA) in CO2 from 5% to 40%
Flow rate: 3 mL/min; Detector: PDA;
Column Temp: 35° C., Back Pressure: 100 Bar In a case where the enantiomeric purity of the tert-butyl (R)-3-(3-fluorophenyl)isoxazolidine-2-carboxylate obtained in Step 6 was low, purification was carried out using the following SFC conditions to obtain the desired enantiomer in the form of a yellow liquid.
(column: DAICEL CHIRALPAK AD-H (250 mm*30 mm, 5 um);
Mobile phase: [0.1% NH3H2O MEOH]; B %: 15%-15%, 3.8 min; 600minmin)

Step 7: Preparation of (R)-3-(3-fluorophenyl)isoxazolidine

Tert-butyl (3R)-3-(3-fluorophenyl)isoxazolidine-2-carboxylate (50 g, 185.94 mmol, 1 eq) was dissolved in ethyl acetate (EA; 200 mL), then HCl/EtOAc (4M, 300 mL, 6.45 eq) was added at 0° C. Then, the reaction mixture was agitated for 1 hour at 10° C. LCMS analysis results showed that all of the starting material had disappeared, and vacuum concentration was performed to obtain a solid. (R)-3-(3-fluorophenyl)isoxazolidine was obtained in the form of a white solid (32 g, 150.26 mmol, 80.81% yield, 95.62% purity, 100% e.e HCl).

MS: m/z 168.2 [M+H]+

1H NMR (400 MHZ, DMSO-d6) 0 ppm 7.53-7.43 (m, 2H), 7.39 (d, J=7.8 Hz, 1H), 7.30-7.23 (m, 1H), 5.01 (t, J=8.0 Hz, 1H), 4.47 (m, 1H), 4.27 (m, 1H), 2.87 (m, 1H), 2.62-2.52 (m, 1H)

In Step 7, the following conditions were used for enantiomeric purification or analysis of the compound.
Instrument: CAS-WH-ANA-SFC-C(SHIMADZU LC-30ADsf)
Column: Chiralpak AY-3 50×4.6 mm I.D., 3 um;
Mobile phase: Phase A for CO2, and Phase B for IPA (0.05% DEA);
Gradient elution: B in A from 5% to 40%;
Flow rate: 3 mL/min; Detector: PDA;
Column Temp: 35° C.; Back Pressure: 100 Bar The compound of Preparation Examples 4 through 52 were prepared using methods similar to those of Preparation Examples 1 through 3 above, and the Example Compounds of the present invention were prepared using the compounds of Preparation Examples 1 through 52.

<Preparation Example 4> Preparation of (R)-3-(3,5-difluorophenyl)isoxazolidine

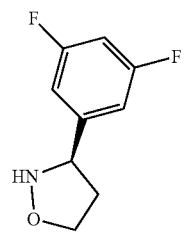 [SMILES: Fc1cc(F)cc([C@H]2CCON2)c1]

1H NMR (400 MHZ, DMSO-d6) δ=7.36-7.27 (m, 3H), 5.04-4.98 (t, J=7.6 Hz, 1H), 4.46-4.36 (m, 1H), 4.25-4.19 (dd, J=7.6, 15.2 Hz, 1H, 2.90-2.78 (m, 1H), 2.56-2.51 (m, 1H)

<Preparation Example 5> Preparation of (R)-3-(2,5-difluorophenyl)isoxazolidine

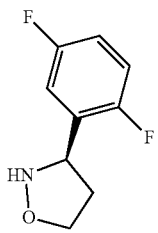

<Preparation Example 6> Preparation of (R)-3-(4-fluorophenyl)isoxazolidine

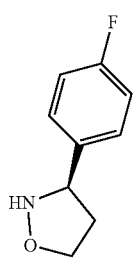 [SMILES: Fc1ccc([C@H]2CCON2)cc1]

<Preparation Example 7> Preparation of (R)-3-(4-chlorophenyl)isoxazolidine

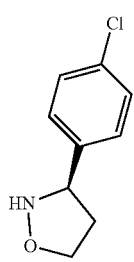

<Preparation Example 8> Preparation of (R)-3-(2,6-difluorophenyl)isoxazolidine

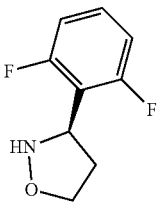 [SMILES: Fc1cccc(F)c1[C@H]1CCON1]

1H NMR (400 MHZ, METHANOL-d4) δ 7.61 (tt, 1H, J=6.4, 8.4 Hz), 7.1-7.2 (m, 2H), 5.49 (t, 1H, J=8.4 Hz), 4.68 (dt, 1H, J=4.0, 8.0 Hz), 4.4-4.5 (m, 1H), 3.0-3.1 (m, 1H), 2.87 (qd, 1H, J=8.4, 12.4 Hz)

<Preparation Example 9> Preparation of (R)-3-(3-chloro-4-fluorophenyl)isoxazolidine

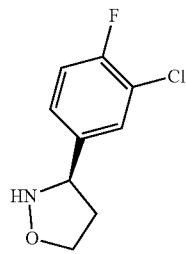

1H NMR (400 MHZ, DMSO-d6) δ=7.82-7.89 (dd, J=2, 7.2, 1H), 7.56-7.51 (s, J=15.6, 2H), 5.0-4.96 (m, 1H), 4.46-4.4 (m, 1H), 4.24-4.20 (m, 1H), 2.85-2.82 (m, 1H), 2.54-2.52 (m, 1H).

<Preparation Example 10> Preparation of (R)-3-(3-chloro-2-fluorophenyl)isoxazolidine

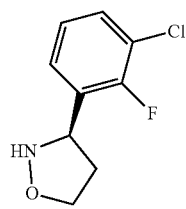

1H NMR (400 MHZ, DMSO-d6) δ=7.49-7.42 (m, 2H), 7.20-7.16 (m, 1H), 6.56 (s, 1H), 4.66-4.65 (m, 1H), 3.96-3.91 (m, 1H), 3.67-3.65 (m, 1H), 2.66-2.61 (m, 1H), 2.08-2.01 (m, 1H).

<Preparation Example 11> Preparation of (R)-3-(2-fluoro-3-methylphenyl)isoxazolidine

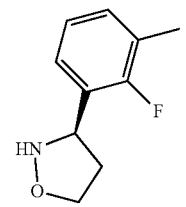

1H NMR (400 MHZ, CHLOROFORM-d) δ 12.6 (s, 1H), 7.46 (t, 1H, J=7.2 Hz), 7.3-7.1 (m, 1H), 7.1-7.0 (m, 1H), 5.25 (t, 1H, J=8.0 Hz), 4.6-4.4 (m, 1H), 4.38 (q, 1H, J=7.6 Hz), 3.0-2.8 (m, 1H), 2.7-2.5 (m, 1H), 2.26 (s, 3H).

<Preparation Example 12> Preparation of (R)-3-(3-methoxyphenyl)isoxazolidine

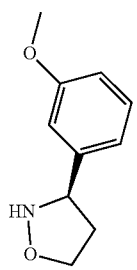

1H NMR (400 MHZ, CDCl₃) δ 7.25-7.20 (m, 2H), 7.11-7.09 (m, 1H), 6.88-6.86 (m, 1H), 4.80-4.76 (m, 1H), 4.46-4.44 (m, 1H), 4.17-4.15 (m, 1H), 3.76 (s, 3H), 2.69-2.66 (m, 2H)

<Preparation Example 13> Preparation of (R)-3-(4-chloro-3-fluorophenyl)isoxazolidine

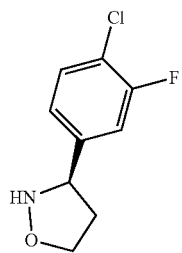 [SMILES: Fc1cc([C@H]2CCON2)ccc1Cl]

<Preparation Example 14> Preparation of (R)-3-(3,4-dichloro-2-fluorophenyl)isoxazolidine

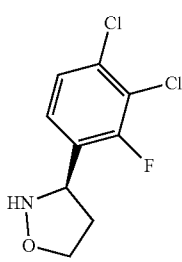

<Preparation Example 15> Preparation of (R)-3-(6-methylpyridine-3-yl)isoxazolidine

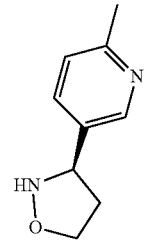

<Preparation Example 16> Preparation of (R)-3-(3-chloro-2,4-difluorophenyl)isoxazolidine

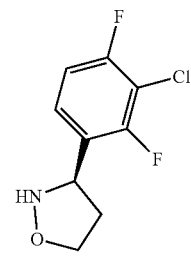

1H NMR (DMSO-d6, 400 MHZ) δ=7.51 (dt, J=6.8, 8.4 Hz, 1H), 7.28 (dt, J=2.0, 8.8 Hz, 1H), 6.60 (br s, 1H), 4.64 (br s, 1H), 3.94 (dt, J=5.2, 8.0 Hz, 1H), 3.76-3.57 (m, 1H), 2.68-2.61 (m, 1H), 2.10-2.01 (m, 1H);

<Preparation Example 17> Preparation of (R)-3-(3,4-dichlorophenyl)isoxazolidine

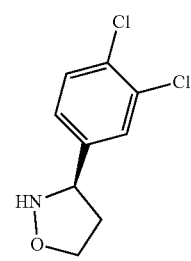

1H NMR (400 MHZ, DMSO-d6) δ=7.83 (d, J=2.0 Hz, 1H), 7.73 (d, J=8.4 Hz, 1H), 7.53 (dd, J=2.0, 8.4 Hz, 1H), 4.99-4.95 (m, 1H), 4.43-4.38 (m, 1H), 4.21-4.17 (m, 1H), 2.85-2.82 (m, 1H), 2.52-2.48 (m, 1H);

<Preparation Example 18> Preparation of (R)-3-(3-ethynylphenyl)isoxazolidine

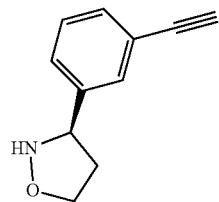

1H NMR (400 MHZ, DMSO-d6) δ=7.49 (s, 1H), 7.43-7.37 (m, 1H), 7.36-7.29 (m, 2H), 6.41 (s, 1H), 4.38 (s, 1H), 4.15 (s, 1H), 3.90 (m, 1H), 3.71 (s, 1H), 2.65-2.53 (m, 1H), 2.11-2.00 (m, 1H)

<Preparation Example 19> Preparation of (S)-3-methyl-3-phenylisoxazolidine

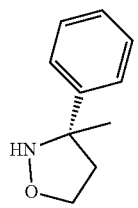

1H NMR (400 MHZ, DMSO-d6) δ 12.86 (br s, 1H), 7.55-7.45 (m, 2H), 7.44-7.37 (m, 2H), 7.35-7.28 (m, 1H), 3.79-3.63 (m, 1H), 3.44-3.32 (m, 1H), 2.75-2.56 (m, 2H), 1.64 (s, 3H)

<Preparation Example 20> Preparation of (R)-3-methyl-3-phenylisoxazolidine

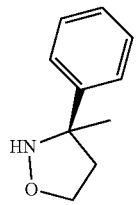

1H NMR (400 MHZ, DMSO-d6) δ 12.88 (br s, 1H), 7.56-7.46 (m, 2H), 7.44-7.36 (m, 2H), 7.34-7.26 (m, 1H), 3.74-3.62 (m, 1H), 3.46-3.28 (m, 1H), 2.72-2.54 (m, 2H), 1.64 (s, 3H)

<Preparation Example 21> Preparation of (R)-3-(2,4-difluorophenyl)isoxazolidine

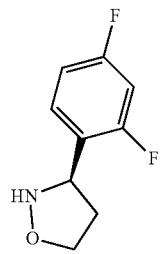 [SMILES: Fc1ccc([C@H]2CCON2)c(F)c1]

1H NMR (400 MHZ, CHLOROFORM-d) 07.52-7.47 (m, 1H), 6.87-6.75 (m, 2H), 5.30 (s, 1H), 4.71-4.68 (m, 1H), 4.09-4.04 (m, 1H), 3.91-3.85 (m, 1H), 2.73-2.64 (3, 1H), 2.24-2.20 (m, 1H)

<Preparation Example 22> Preparation of (R)-3-(2,3-difluorophenyl)isoxazolidine

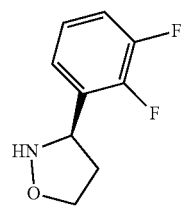 [SMILES: Fc1cccc([C@H]2CCON2)c1F]

1H NMR (CHLOROFORM-d, 400 MHZ) δ 7.27-7.29 (m, 1H), 7.02-7.06 (m, 2H), 5.44 (br s, 1H), 4.75 (dd, J1=4.4 Hz, J2=8.4 Hz, 1H), 4.08 (dt, J1=5.2 Hz, J2=8.0 Hz, 1H), 3.86 (q, J=8.0 Hz, 1H), 2.66-2.76 (m, 1H), 2.19-2.27 (m, 1H).

<Preparation Example 23> Preparation of (R)-3-(3,4-difluorophenyl)isoxazolidine

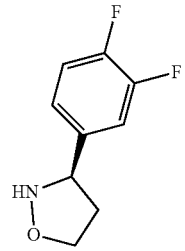 [SMILES: Fc1ccc([C@H]2CCON2)cc1F]

1H NMR (400 MHZ, CHLOROFORM-d) δ=7.24-7.19 (m, 1H), 7.12-7.06 (m, 2H), 5.24 (s, 1H), 4.46 (dd, J1=8.4 Hz, J2=5.6 Hz, 1H), 4.05 (dt, J1=8.0 Hz, J2=5.2 Hz, 1H), 3.91-3.85 (m, 1H), 2.70-2.61 (m, 1H), 2.25-2.17 (m, 1H).

<Preparation Example 24> Preparation of (R)-3-(4-chloro-2-fluorophenyl)isoxazolidine

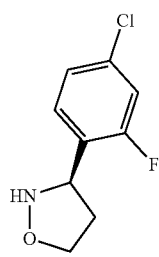 [SMILES: Fc1cc(Cl)ccc1[C@H]1CCON1]

1H NMR (400 MHZ, DEUTERIUM OXIDE) δ 7.48-7.38 (m, 1H), 7.34-7.22 (m, 2H), 5.29-5.20 (m, 1H), 4.58-4.50 (m, 1H), 4.36-4.27 (m, 1H), 2.96-2.84 (m, 1H), 2.79-2.66 (m, 1H).

<Preparation Example 25> Preparation of (R)-3-(naphthalene-2-yl)isoxazolidine

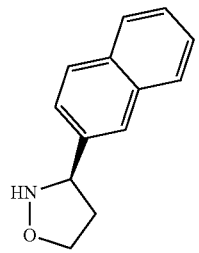 [SMILES: c1ccc2cc([C@H]3CCON3)ccc2c1]

1H NMR (400 MHZ, CHLOROFORM-d) δ 7.91-7.81 (m, 4H), 7.56-7.46 (m, 3H), 5.80-5.00 (m, 1H), 4.68 (t, J=7.2 Hz, 1H), 4.19-3.99 (m, 2H), 2.8-2.72 (m, 1H), 2.45-2.37 (m, 1H).

<Preparation Example 26> Preparation of (R)-3-(naphthelene-1-yl)isoxazolidine

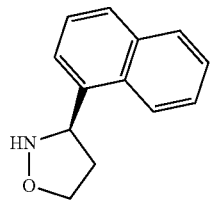 [SMILES: c1ccc2c([C@H]3CCON3)cccc2c1]

1H NMR (400 MHZ, CHLOROFORM-d) δ 8.13 (br s, 1H), 7.9-7.9 (m, 1H), 7.7-7.8 (m, 2H), 7.5-7.6 (m, 3H), 5.3-5.9 (m, 1H), 5.22 (br t, 1H, J=6.4 Hz), 3.9-4.2 (m, 2H), 2.8-2.9 (m, 1H), 2.3-2.5 (m, 1H).

<Preparation Example 27> Preparation of (R)-3-(thiophene-2-yl)isoxazolidine

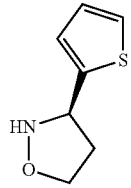

1H NMR (400 MHZ, CHLOROFORM-d) δ 7.23 (d, J=5.0 Hz, 1H), 7.04-6.99 (m, 1H), 6.99-6.94 (m, 1H), 4.97-4.58 (m, 2H), 4.11-3.96 (m, 2H), 2.75-2.58 (m, 1H), 2.44-2.33 (m, 1H).

<Preparation Example 28> Preparation of (R)-3-(2-chloro-3-fluorophenyl)isoxazolidine

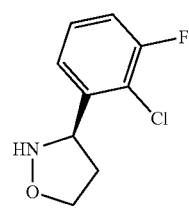 [SMILES: Fc1cccc([C@H]2CCON2)c1Cl]

1H NMR (400 MHZ, CHLOROFORM-d) δ 7.45 (d, J=7.6 Hz, 1H), 7.22 (m, 1H), 7.02 (m, 1H), 5.44 (m, 1H), 4.87 (dd, J=4.0, 8.7 Hz, 1H), 4.10 (m, 1H), 3.79 (m, 1H), 2.86-2.75 (m, 1H), 2.21-2.10 (m, 1H).

<Preparation Example 29> Preparation of (R)-3-(3-chloro-5-fluorophenyl)isoxazolidine

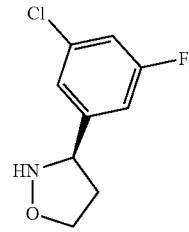 [SMILES: Fc1cc(Cl)cc([C@H]2CCON2)c1]

1H NMR (400 MHZ, CHLOROFORM-d) δ 7.19 (s, 1H), 7.08-6.93 (m, 2H), 5.79-5.03 (m, 1H), 4.56-4.42 (m, 1H), 4.17-4.02 (m, 1H), 3.87 (s, 1H), 2.78-2.63 (m, 1H), 2.32-2.18 (m, 1H).

<Preparation Example 30> Preparation of (R)-3-(3-chlorophenyl)isoxazolidine

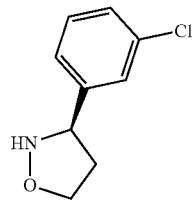 [SMILES: Clc1cccc([C@H]2CCON2)c1]

1H NMR (400 MHZ, DMSO-d6) δ=7.71-7.63 (m, 1H), 7.57-7.41 (m, 3H), 5.01 (t, J=8.0 Hz, 1H), 4.47 (m, 1H), 4.26 (m, 1H), 2.94-2.81 (m, 1H), 2.63-2.52 (m, 1H)

<Preparation Example 31> Preparation of (R)-3-(2,3,4-trifluorophenyl)isoxazolidine

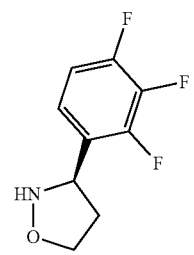

<Preparation Example 32> Preparation of (R)-3-(3-chloro-2,5-difluorophenyl)isoxazolidine

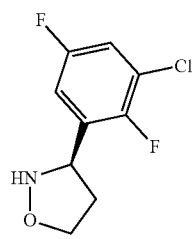 [SMILES: Fc1cc(Cl)c(F)c([C@H]2CCON2)c1]

<Preparation Example 33> Preparation of (R)-3-(2,3,6-trifluorophenyl)isoxazolidine

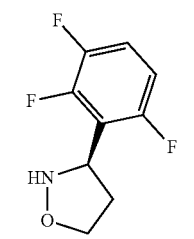

<Preparation Example 34> Preparation of (R)-3-(2-chloro-3,6-difluorophenyl)isoxazolidine

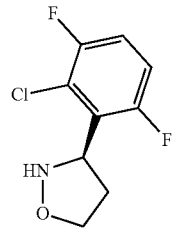 [SMILES: Fc1ccc(F)c([C@H]2CCON2)c1Cl]

<Preparation Example 35> Preparation of (R)-3-(3-chloro-2-methylphenyl)isoxazolidine

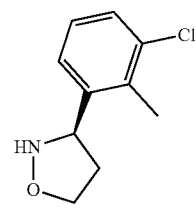

<Preparation Example 36> Preparation of (R)-3-(2,3-dichlorophenyl)isoxazolidine

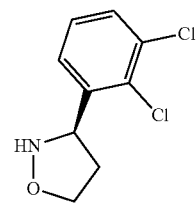

1H NMR (DMSO-d6, 400 MHz) HNMR_7, δ=7.61-7.44 (m, 2H), 7.37-7.30 (m, 1H), 6.67 (d, J=6.0 Hz, 1H), 4.79-4.63 (m, 1H), 3.94 (td, J=4.0, 8.0 Hz, 1H), 3.63 (d, J=8.0 Hz, 1H), 2.78-2.74 (m, 1H), 1.99-1.91 (m, 1H).

<Preparation Example 37> Preparation of (R)-3-(isoxazolidine-3-yl)benzonitrile

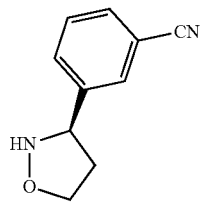 [SMILES: N#Cc1cccc([C@H]2CCON2)c1]

1H NMR (400 MHZ, DMSO-d6) δ=8.04 (s, 1H), 7.90-7.87 (m, 2H), 7.69-7.62 (m, 1H), 5.05 (t, J=7.8 Hz, 1H), 4.48-4.43 (m, 1H), 4.27-4.21 (m, 1H), 2.92-2.82 (m, 1H), 2.62-2.53 (m, 1H).

<Preparation Example 38> Preparation of (R)-3-(3-(trifluoromethyl)phenyl)isoxazolidine

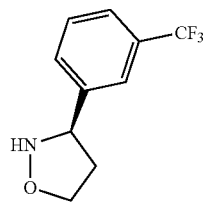 [SMILES: FC(F)(F)c1cccc([C@H]2CCON2)c1]

1H NMR (400 MHZ, Chloroform-d) δ 7.65 (s, 1H), 7.59 (d, J=7.7 Hz, 1H), 7.53 (d, J=7.8 Hz, 1H), 7.46 (t, J=7.7 Hz, 1H), 5.64-5.19 (m, 1H), 4.58 (t, J=7.2 Hz, 1H), 4.11 (td, J=8.2, 5.2 Hz, 1H), 3.94 (s, 1H), 2.80-2.67 (m, 1H), 2.36-2.23 (m, 1H).

<Preparation Example 39> Preparation of (R)-3-benzylisoxazolidine

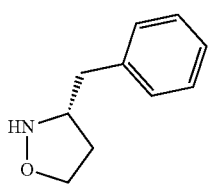 [SMILES: c1ccc(C[C@@H]2CCON2)cc1]

1H NMR (400 MHz, CHLOROFORM-d) δ 12.85-12.47 (m, 1H), 7.37-7.27 (m, 5H), 4.51-4.41 (m, 1H), 4.36-4.18 (m, 2H), 3.60 (dd, J=4.8, 13.6 Hz, 1H), 3.12 (dd, J=10.4, 13.6 Hz, 1H), 2.53-2.42 (m, 1H), 2.41-2.30 (m, 1H).

<Preparation Example 40> Preparation of (S)-3-benzylisoxazolidine

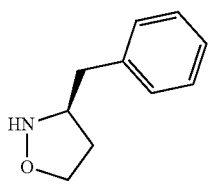

1H NMR (400 MHz, CHLOROFORM-d) δ 12.74-12.40 (m, 1H), 7.28-7.18 (m, 5H), 4.42-4.32 (m, 1H), 4.25-4.10 (m, 2H), 3.50 (dd, J=4.8, 13.6 Hz, 1H), 3.03 (dd, J=10.4, 13.2 Hz, 1H), 2.44-2.33 (m, 1H), 2.32-2.20 (m, 1H).

<Preparation Example 41> Preparation of (S)-3-(3-chloro-2-methoxybenzyl)isoxazolidine

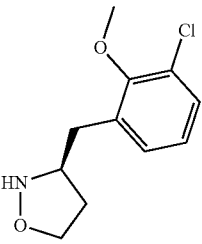

1H NMR (400 MHz, CHLOROFORM-d) δ 12.97-12.35 (m, 2H), 7.34 (dd, J=1.6, 8.0 Hz, 1H), 7.24 (dd, J=1.2, 7.6 Hz, 1H), 7.10-7.00 (m, 1H), 4.44 (dt, J=5.6, 7.6 Hz, 1H), 4.39-4.27 (m, 2H), 3.95 (s, 3H), 3.54 (dd, J=5.2, 13.6 Hz, 1H), 3.22 (dd, J=10.0, 13.6 Hz, 1H), 2.53-2.42 (m, 1H), 2.42-2.29 (m, 1H).

<Preparation Example 42> Preparation of (S)-3-(3-fluoro-2-methylbenzyl)isoxazolidine

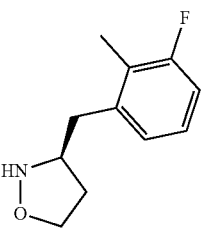

1H NMR (400 MHZ, CHLOROFORM-d) δ=7.14-7.07 (m, 1H), 6.98 (d, J=7.6 Hz, 1H), 6.91 (t, J=8.8 Hz, 1H), 4.08-3.98 (m, 1H), 3.82 (q, J=7.6 Hz, 1H), 3.68-3.59 (m, 1H), 2.96 (dd, J=7.2, 14.0 Hz, 1H), 2.70 (dd, J=7.2, 14.0 Hz, 1H), 2.25 (d, J=2.4 Hz, 3H), 1.98-1.88 (m, 1H).

<Preparation Example 43> Preparation of (S)-3-(3-fluorobenzyl)isoxazolidine

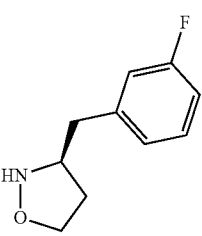 [SMILES: Fc1cccc(C[C@H]2CCON2)c1]

1H NMR (400 MHZ, CHLOROFORM-d) δ 7.26 (dt, J1=6.0 Hz, J2=7.6 Hz, 1H), 7.01 (d, J=7.6 Hz, 1H), 6.96-6.89 (m, 2H), 4.87 (s, 1H), 3.99 (dt, J1=5.6 Hz, J2=8.4 Hz, 1H), 3.80 (q, J=8.0 Hz, 1H), 3.68-3.59 (m, 1H), 2.93 (dd, J1=7.2 Hz, J2=14.0 Hz, 1H), 2.67 (dd, J1=7.2 Hz, J2=14.0 Hz, 1H), 2.31-2.22 (m, 1H), 1.94-1.85 (m, 1H).

<Preparation Example 44> Preparation of (S)-3-(3,5-difluorobenzyl)isoxazolidine

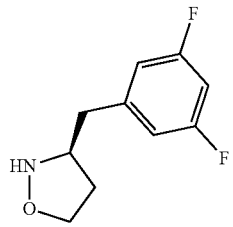 [SMILES: Fc1cc(F)cc(C[C@H]2CCON2)c1]

1H NMR (400 MHZ, CHLOROFORM-d) δ 6.77 (dd, J1=2.4 Hz, J2=8.4 Hz, 2H), 6.66 (tt, J1=2.4 Hz, J2=9.2 Hz, 1H), 4.89 (br s, 1H), 4.02 (dt, J1=5.2 Hz, J2=8.4 Hz, 1H), 3.77 (q, J=8.0 Hz, 1H), 3.66-3.59 (m, 1H), 2.89 (dd, J1=7.6 Hz, J2=14.0 Hz, 1H), 2.65 (dd, J1=6.8 Hz, J2=14.0 Hz, 1H), 2.34-2.26 (m, 1H), 1.93-1.85 (m, 1H).

<Preparation Example 45> Preparation of (S)-3-(isoxazolidine-3-ylmethyl)-N,N-dimethylaniline

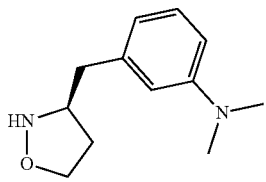

1H NMR (400 MHZ, CHLOROFORM-d) δ 6.77 (dd, J1=2.4 Hz, J2=8.4 Hz, 2H), 6.66 (tt, J1=2.4 Hz, J2=9.2 Hz, 1H), 4.89 (br s, 1H), 4.02 (dt, J1=5.2 Hz, J2=8.4 Hz, 1H), 3.77 (q, J=8.0 Hz, 1H), 3.66-3.59 (m, 1H), 2.89 (dd, J1=7.6 Hz, J2=14.0 Hz, 1H), 2.65 (dd, J1=6.8 Hz, J2=14.0 Hz, 1H), 2.34-2.26 (m, 1H), 1.93-1.85 (m, 1H).

<Preparation Example 46> Preparation of (S)-3-(pyridine-2-ylmethyl)isoxazolidine

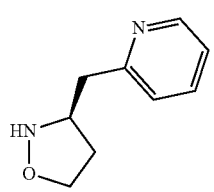 [SMILES: c1ccc(C[C@H]2CCON2)nc1]

1H NMR (DMSO-d6, 400 MHZ) δ=8.54-8.41 (m, 1H), 7.70 (dt, J=2.0, 7.6 Hz, 1H), 7.32-7.18 (m, 2H), 5.98 (br s, 1H), 3.86-3.54 (m, 3H), 2.91-2.70 (m, 2H), 2.18-2.10 (m, 1H), 1.85-1.74 (m, 1H).

<Preparation Example 47> Preparation of (S)-3-(pyridine-3-ylmethyl)isoxazolidine

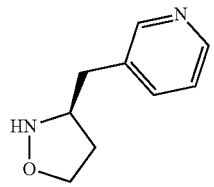 [SMILES: c1cncc(C[C@H]2CCON2)c1]

1H NMR (CDCl3, 400 MHZ) δ 8.55-8.45 (m, 2H), 7.61 (m, 1H), 7.27-7.22 (m, 1H), 4.04 (s, 1H), 3.87-3.73 (m, 1H), 3.70-3.55 (m, 1H), 2.92 (m, 1H), 2.69 (m, 1H), 2.37-2.24 (m, 1H), 1.99-1.82 (m, 1H)

<Preparation Example 48> Preparation of (S)-3-(4-(trifluoromethyl)benzyl)isoxazolidine

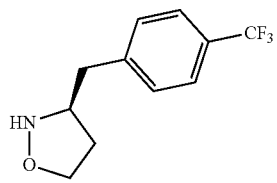 [SMILES: FC(F)(F)c1ccc(C[C@H]2CCON2)cc1]

<Preparation Example 49> Preparation of (S)-3-(3-chloro-2-methylbenzyl)isoxazolidine

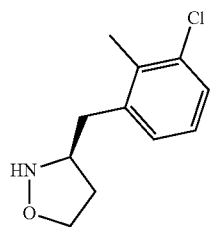

<Preparation Example 50> Preparation of (S)-3-(2,3-dichlorobenzyl)isoxazolidine

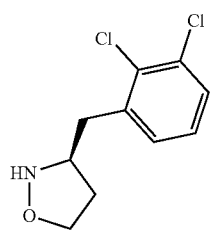

51

<Preparation Example 51> Preparation of (S)-3-(3-chloro-2-fluorobenzyl)isoxazolidine

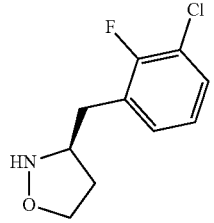

<Preparation Example 52> Preparation of (S)-3-(2-chloro-3-fluorobenzyl)isoxazolidine

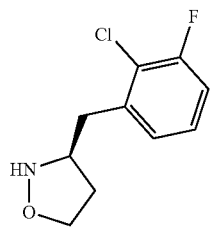 [SMILES: Fc1cccc(C[C@H]2CCON2)c1Cl]

2. Preparation of the Example Compounds of the Present Invention

<Preparation Example 1> Preparation of Example Compound 4

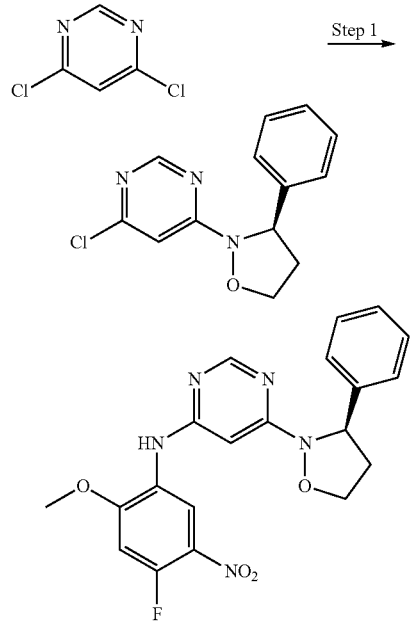

Step 1: Preparation of (R)-2-(6-chloropyrimidine-4-yl)-3-phenylisoxazolidine 4,6-dichloropyrimidine (500 mg, 3.36 mmol) and (R)-3-phenylisoxazolidine (526 mg, 3.52 mmol) were dissolved in a dimethylsulfoxide (DMSO, 7 ml) solvent, and the reaction solution was agitated for 30 minutes at 60° C. After the reaction was completed, extraction was performed using ethylacetate and water. The gathered organic layer was washed with salt water, dried with anhydrous sodium sulfate, then vacuum concentrated, and purified with MPLC (ethylacetate/hexane) to obtain the target compound (R)-2-(6-chloropyrimidine-4-yl)-3phenylisoxazolidine (800 mg, 91%) in the form of a transparent liquid.

MS(m/z): 262.07[M+1], UPLC r.t. (min): 1.58

NMR: 1H NMR (400 MHZ, DMSO-d6) δ 8.48 (s, 1H), 7.42-7.22 (m, 5H), 7.09 (s, 1H), 5.56-5.43 (m, 1H), 4.27-4.17 (m, 1H), 4.00-3.88 (m, 1H), 2.97-2.80 (m, 1H), 2.37-2.22 (m, 1H).

Step 2: Preparation of (R)—N-(4-fluoro-2-methoxy-5-nitrophenyl)-6-(3-phenylisoxazolidine-2-yl)pyrimidine-4-amine The (R)-2-(6-chloropyrimidine-4-yl)-3-phenylisoxazolidine obtained in Step 1 of Preparation Example 1 (800 mg, 3.06 mmol), 4-fluoro-2-methoxy-5-nitroaniline (626 mg, 3.36 mmol) and potassium carbonate (1267 mg, 9.17 mmol) were added to and dissolved in sec-butanol (12 ml), then treated ultrasonically for 5 minutes in a nitrogen atmosphere to remove gases. Tris(dibenzylideneacetone)dipalladium(0) (Pd$_2$(dba)$_3$; 280 mg, 0.306 mmol) and Xphos (146 mg, 0.306 mmol) were added to the reaction mixture, which was then agitated for 1 hour at 100° C. After the reaction was completed, filtration was performed using celite, followed by washing with ethylacetate. The filtrate was concentrated, then purified with MPLC (ethylacetate/hexane) to obtain the target compound (960 mg, 76%).

MS(m/z): 412.13[M+1], UPLC r.t. (min): 1.70,

NMR: 1H NMR (400 MHZ, DMSO-d6) δ 9.08 (s, 1H), 9.01 (s, 1H), 8.34 (s, 1H), 7.47-7.21 (m, 6H), 6.79 (s, 1H), 5.59-5.46 (m, 1H), 4.26-4.14 (m, 1H), 4.01 (s, 3H), 3.94-3.76 (m, 1H), 2.87-2.71 (m, 1H), 2.36-2.19 (m, 1H).

Step 3: Preparation of (R)-N1-(2-(dimethylamino)ethyl)-5-methoxy-N1-methyl-2-nitro-N4-(6-(3-phenylisoxazolidine-2-yl)pyrimidine-4-yl)benzene-1,4-thiamine The (R)—N-(4-fluoro-2-methoxy-5-nitrophenyl)-6-(3-phenylisoxazolidine-2-yl)pyrimidine-4-amine obtained in Step 2 of Preparation Example 1 (100 mg, 0.243 mmol) and potassium carbonate (67.2 mg, 0.486 mmol) were dissolved in dimethyl sulfoxide (DMSO; 1.5 ml). Then N1,N1,N2-trimethylethane-1,2-thiamine (0.035 mL, 0.267 mmol) was added, and agitated for 2 hours at 70° C. After the reaction ended, extraction was performed using ethylacetate and water. The gathered organic layer was washed with salt water, dried with anhydrous sodium sulfate, and concentrated under vacuum to obtain the target compound (110 mg, 92%) which was used in the next reaction without purification.

MS(m/z): 494.24[M+1], UPLC r.t. (min): 1.23

Step 4: Preparation of (R)-N1-(2-(dimethylamino)ethyl)-5-methoxy-N1-methyl-N4-(6-(3-phenylisoxazolidine-2-yl)pyrimidine-4-yl)benzene-1,2,4-triamine The (R)-N1-(2-(dimethylamino)ethyl)-5-methoxy-N1-methyl-2-nitro-N4-(6-(3-phenylisoxazolidine-2-yl)pyrimidine-4-yl)benzene-1,4-thiamine obtained in Step 3 of Preparation Example 1 (110 mg, 0.223 mmol) and SnCl$_2$2H2O (251 mg, 1.114 mmol) were dissolved in ethylacetate (1.5 ml), and agitated for 1 hour at 50° C. The temperature of the reaction solution was brought down to room temperature, and aqueous solution of ammonia was added dropwise until pH5 was reached. Anhydrous sodium carbonate was added to the reaction mixture to adjust to pH 7. The reaction mixture was filtered with celite, and washed multiple times with ethylacetate. The filtrate was concentrated under vacuum to obtain the target compound (90 mg, 87%), which was used in the next reaction without purification.

MS(m/z): 464.27[M+1], UPLC r.t. (min): 1.03

Step 5

(R)—N-(2-((2-(dimethylamino)ethyl)(methyl)amino)-4-methoxy-5-((6-(3-phenylisoxazolidin-2-yl)pyrimidin-4-yl)amino)phenyl)acrylamide was prepared.

The (R)-N1-(2-(dimethylamino)ethyl)-5-methoxy-N1-methyl-N4-(6-(3-phenylisoxazolidine-2-yl)pyrimidine-4-yl)benzene-1,2,4-triamine obtained in Step 4 of Preparation Example 1 (85 mg, 0.183 mmol) was dissolved in tetrahydrofuran (THF; 1.5 ml), and a saturated sodium bicarbonate (NaHCO$_3$; 1.5 ml) aqueous solution was added. While agitating vigorously at 0° C., acryloyl chloride (30 μl, 0.367 mmol) diluted in tetrahydrofuran (THF; 0.5 mL) was added slowly dropwise. After 10 minutes agitation, extraction was performed using ethylacetate and distilled water. The gathered organic layer was dried using anhydrous sodium sulfate. The filtrate was vacuum concentrated, then purified using a Prep-150 LC System to obtain the target compound (58 mg, 61%).

MS(m/z): 518.28[M+1], UPLC r.t. (min): 1.11

NMR: 1H NMR (400 MHZ, Methanol-d4) δ 8.15 (s, 1H), 7.97 (s, 1H), 7.43 (s, 2H), 7.33 (s, 2H), 7.24 (s, 1H), 6.93 (s, 1H), 6.61-6.35 (m, 3H), 5.90-5.75 (m, 1H), 5.60-5.43 (m, 1H), 4.23-4.06 (m, 1H), 4.03-3.93 (m, 1H), 3.91 (s, 3H), 3.45-3.36 (m, 2H), 3.20-3.06 (m, 2H), 2.85-2.79 (m, 1H), 2.77 (s, 6H), 2.73-2.65 (m, 3H), 2.42-2.27 (m, 1H)

<Preparation Example 2> Preparation of Example Compound 56

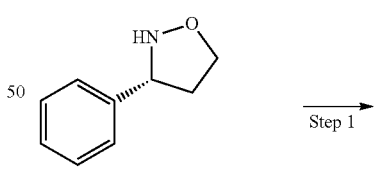

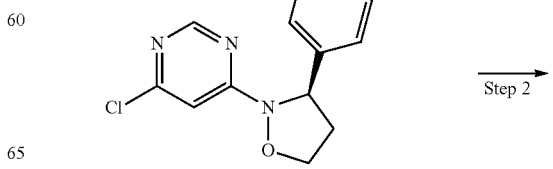

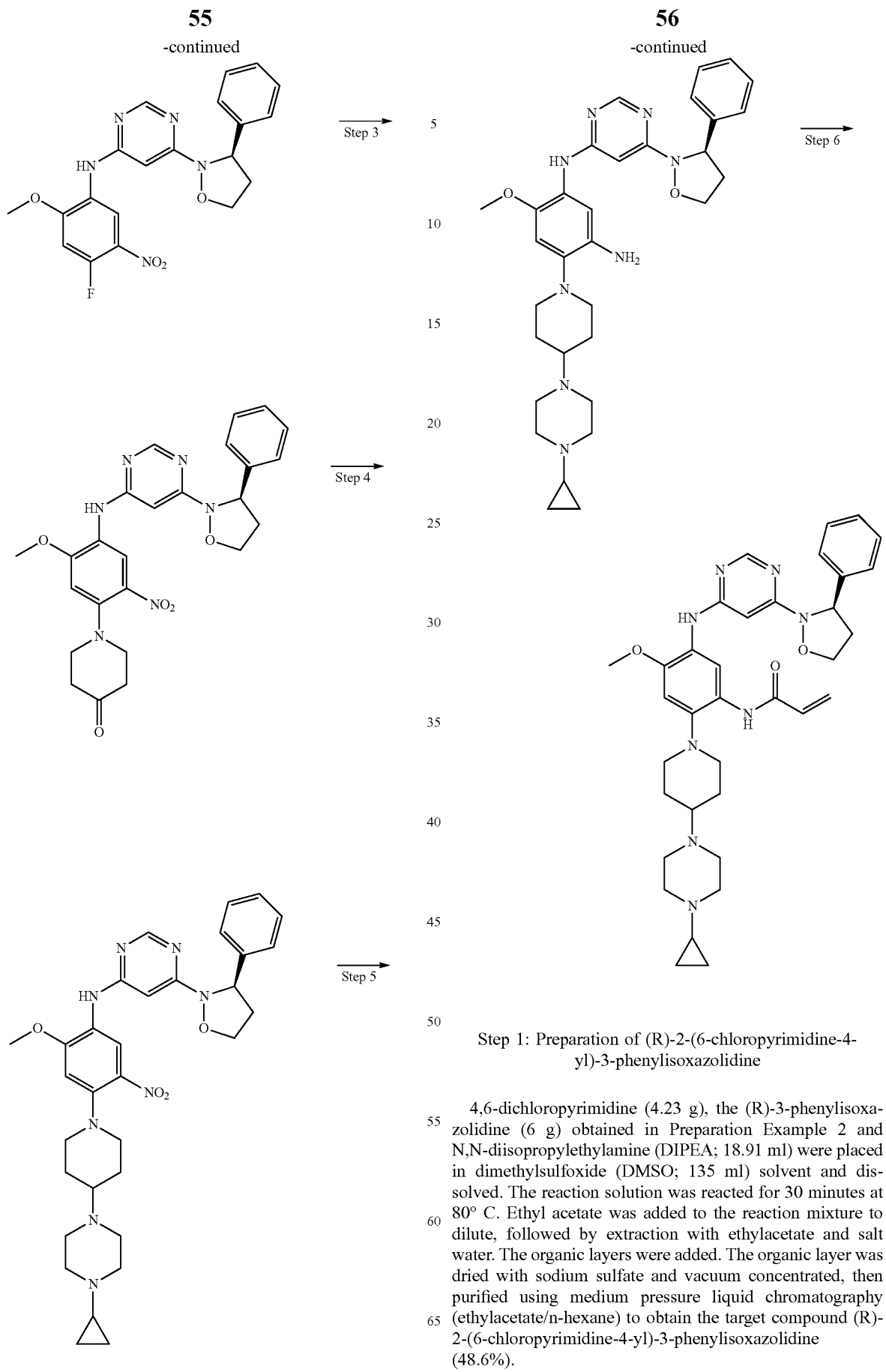

Step 1: Preparation of (R)-2-(6-chloropyrimidine-4-yl)-3-phenylisoxazolidine 4,6-dichloropyrimidine (4.23 g), the (R)-3-phenylisoxazolidine (6 g) obtained in Preparation Example 2 and N,N-diisopropylethylamine (DIPEA; 18.91 ml) were placed in dimethylsulfoxide (DMSO; 135 ml) solvent and dissolved. The reaction solution was reacted for 30 minutes at 80° C. Ethyl acetate was added to the reaction mixture to dilute, followed by extraction with ethylacetate and salt water. The organic layers were added. The organic layer was dried with sodium sulfate and vacuum concentrated, then purified using medium pressure liquid chromatography (ethylacetate/n-hexane) to obtain the target compound (R)-2-(6-chloropyrimidine-4-yl)-3-phenylisoxazolidine (48.6%).

Step 2: Preparation of (R)—N-(4-fluoro-2-methoxy-5-nitrophenyl)-6-(3-phenylisoxazolidine-2-yl)pyrimidine-4-amine 4-fluoro-2-methoxy-5-nitroaniline (4.23 g) the (R)-2-(6-chloropyridine-4-yl)-3-phenylisoxazolidine obtained in Step 1 of Preparation Example 2 (1.84 g) and potassium carbonate (2.56 g) were dissolved in a sec-butanol solvent (20.60 ml). The temperature of the reaction solution was raised to 60° C., then xphos (0.295 g) and tris(dibenzilydeneacetone) dipalladium(0) (Pd$_2$(dba)$_3$; 0.425 g) were placed in the reaction mixture solution. The reaction solution was reacted for 120 minutes at 100° C. After the reaction, the organic layer was vacuum concentrated and purified using medium pressure liquid chromatography (ethylacetate/n-hexane) to obtain the target compound (R)—N-(4-fluoro-2-methoxy-5-nitrophenyl)-6-(3-phenylisoxazolidine-2-yl)pyrimidine-4-amine (58.9% yield).

Step 3: Preparation of (R)-1-(5-methoxy-2-nitro-4((6-(3-phenylisoxazolidine-2-yl)pyrimidine-4-yl)amino)phenyl)piperidine-4-on The (R)—N-(4-fluoro-2-methoxy-5-nitrophenyl)-6-(3-phenylisoxazolidine-2-yl)pyrimidine-4-amine obtained in Step 2 of Preparation Example 2 (1.6 g) was placed in a dimethylsulfoxide (DMSO; 15 ml) solvent and dissolved, and then potassium carbonate (1.98 g) and piperidine-4-on hydrochloride (1.45 g) were added to the reaction solution. Thereafter, the reaction solution was reacted for 120 minutes at 70° C. After the reaction, water was added to the reaction mixture to dilute the reaction solution. Extraction was performed using ethylacetate and salt water, followed by vacuum concentration of the organic layer and purification using medium pressure liquid chromatography (dichloromethane/methanol) to obtain the target compound (R)-1-(5-methoxy-2-nitro-4((6-(3-phenylisoxazolidine-2-yl)pyrimidine-4-yl)amino)phenyl)piperidine-4-on (96% yield).

Step 4: Preparation of (R)—N-(4-(4-(4-cyclopropylpiperazine-1-yl)piperidine-1-yl)-2-methoxy-5-nitrophenyl)-6-(3-phenylisoxazolidine-2-yl)pyrimidine-4-amine The (R)-1-(5-methoxy-2-nitro-4((6-(3-phenylisoxazolidine-2-yl)pyrimidine-4-yl)amino)phenyl)piperidine-4-on obtained in Step 3 of Preparation Example 2 (1.8 g) was placed in a dichloromethane (15 ml) solvent and dissolved, and 1-cyclopropylpiperazine (0.495 mL) and sodium triacetoxy borohydride (1.45 g) was added. The reaction solution was reacted for 16 hours at room temperature. The reaction was ended by adding 2 normal sodium hydroxide aqueous solution, and extraction was carried out using dichloromethane solvent and salt water. The organic layer was vacuum concentrated and purified using medium pressure liquid chromatography (dichloromethane/methanol) to obtain the target compound (R)—N-(4-(4-(4-cyclopropylpiperazine-1-yl)piperidine-1-yl)-2-methoxy-5-nitrophenyl)-6-(3-phenylisoxazolidine-2-yl)pyrimidine-4-amine (73.5% yield).

Step 5: Preparation of (R)-4-(4-(4-cyclopropylpiperazine-1-yl)piperidine-1-yl)-6-methoxy-N1-(6-(3-phenylisoxazolidine-2-yl)pyrimidine-4-yl)benzene-1,3-thiamine The (R)—N-(4-(4-(4-cyclopropylpiperazine-1-yl)piperidine-1-yl)-2-methoxy-5-nitrophenyl)-6-(3-phenylisoxazolidine-2-yl)pyrimidine-4-amine obtained in Step 4 of Preparation Example 2 (1.6 g) was placed in an ethylacetate (20 ml) and methanol (2 ml) solvent and dissolved, then tin(II) chloride dihydrate (2.84 g, 12.56 mmol) was added. Thereafter, the reaction solution was reacted for 120 minutes at 60° C. The reaction was ended by adding aqueous sodium bicarbonate solution, followed by celite filtration and washing with ethylacetate solvent. The filtrate was extracted using ethylacetate and salt water, and the organic layer was vacuum concentrated and purified using medium pressure liquid chromatography (dichloromethane/methanol) to obtain the target compound (R)-4-(4-(4-cyclopropylpiperazine-1-yl)piperidine-1-yl)-6-methoxy-N1-(6-(3-phenylisoxazolidine-2-yl)pyrimidine-4-yl)benzene-1,3-thiamine (77% yield).

Step 6: Preparation of (R)—N-(2-(4-(4-cyclopropylpiperazine-1-yl)piperidine-1-yl)-4-methoxy-5-((6-(3-phenylisoxazolidine-2-yl)pyrimidine-4-yl)amino)phenyl)acrylamide The (R)-4-(4-(4-cyclopropylpiperazine-1-yl)piperidine-1-yl)-6-methoxy-N1-(6-(3-phenylisoxazolidine-2-yl)pyrimidine-4-yl)benzene-1,3-thiamine obtained in Step 5 of Preparation Example 2 (1.18 g) was dissolved in THF solvent (16 mL), then a sodium bicarbonate aqueous solution (16 mL) was added. [The mixture was] placed in an ethylacetate (20 ml) and methanol (2 ml) solvent and dissolved. The temperature of the reaction solution was lowered to 0° ° C., then THE solution (4 ml) in which acryloylchloride (0.315 mL) was dissolved was slowly added dropwise. Thereafter, the reaction solution was reacted for 30 minutes at 0° C., and the reaction was ended by adding sodium bicarbonate aqueous solution to end the reaction, followed by extraction using ethylacetate and salt water. The organic layer was vacuum concentrated and purified using medium pressure liquid chromatography (dichloromethane/methanol) to obtain the target compound (R)—N-(2-(4-(4-cyclopropylpiperazine-1-yl)piperidine-1-yl)-4-methoxy-5-((6-(3-phenylisoxazolidine-2-yl)pyrimidine-4-yl)amino)phenyl)acrylamide (84% yield).

In anot (R)-4-(4-(4-cyclopropylpiperazine-1-yl)piperidine-1-yl)-6-methoxy-N1-(6-(3-phenylisoxazolidine-2-yl)pyrimidine-4-yl)benzene-1,3-thiamine obtained in Step 5 of Preparation Example 2 for the Example Compounds (128 mg) was dissolved in dichloromethane (2 ml), followed by addition of ethylene dichloride (EDC; 48 mg), acrylic acid (0.017 mL) and N,N-diisopropylethylamine (DIPEA; 0.108 mL). The reaction solution was reacted for 1 hour at room temperature, and the reaction was ended using sodium bicarbonate aqueous solution. The compound was extracted using dichloromethane solvent and salt water. The organic layer was vacuum dried, vacuum concentrated, then purified using medium pressure liquid chromatography (dichloromethane/methanol) to obtain the target compound (86% yield).

All of the example compounds of the present invention (Example Compounds 1 through 1059) were prepared using methods similar to those of Preparation Examples 1 or 2, and the name, chemical structural formula, NMR and UPLC analysis results of the respective Example Compounds are given in Table 1 below.

TABLE 1

| Example Compound | Structure | Name of Compound | ¹H NMR[[:]]; MS [M + H]⁺ | UPLC r.t. (min) |
|---|---|---|---|---|
| 1 | 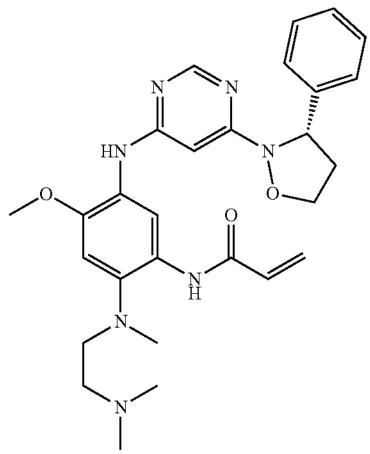 [SMILES: C=CC(=O)Nc1cc(Nc2cc(N3OCC[C@H]3c3ccccc3)ncn2)c(OC)cc1N(C)CCN(C)C] | N-(2((2-(dimethylamino)ethyl)(methyl)amino)-4-methoxy-5-((6-((S)-3-phenylisoxazolidine-2-yl)pyrimidine-4-yl)amino)phenyl)acrylamide | ¹H NMR (400 MHz, Methanol-d₄) δ 8.15 (s, 1H), 7.95 (s, 1H), 7.42 (s, 2H), 7.33 (s, 2H), 7.25 (s, 1H), 6.93 (s, 1H), 6.59-6.36 (m, 3H), 5.90-5.76 (m, 1H), 5.61-5.47 (m, 1H), 4.20-4.08 (m, 1H), 4.02-3.93 (m, 1H), 3.92 (s, 3H), 3.45-3.36 (m, 2H), 3.20-3.07 (m, 2H), 2.85-2.79 (m, 1H), 2.77 (s, 6H), 2.71 (s, 3H), 2.41-2.26 (m, 1H); 518.3 [M + H]⁺ | 1.12 |
| 2 | 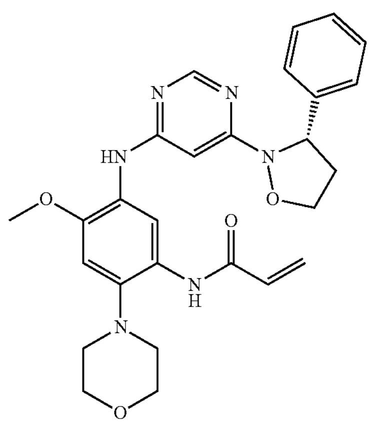 | N-(4-methoxy-2-morpholino-5-((6-((S)-3-phenylisoxazolidine-2-yl)pyrimidine-4-yl)amino)phenyl)acrylamide | ¹H NMR (400 MHz, Methanol-d₄) δ 8.28 (s, 1H), 8.13 (s, 1H), 7.42 (s, 2H), 7.33 (s, 2H), 7.24 (s, 1H), 6.91 (s, 1H), 6.63-6.45 (m, 1H), 6.43-6.27 (m, 2H), 5.85-5.69 (m, 1H), 5.58-5.46 (m, 1H), 4.21-4.09 (m, 1H), 4.02-3.92 (m, 1H), 3.92-3.82 (m, 7H), 2.95-2.88 (m, 4H), 2.85-2.68 (m, 1H), 2.42-2.23 (m, 1H); 503.2 [M + H]⁺ | 1.34 |
| 3 | 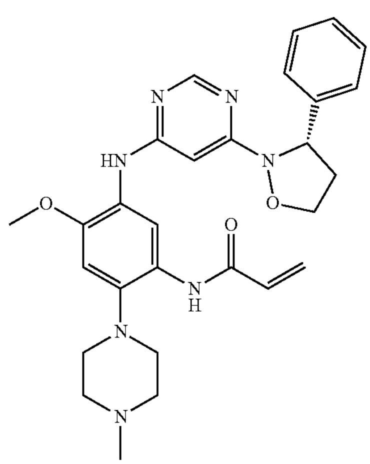 | N-(4-methoxy-2-(4-methylpiperazine-1-yl)-5-((6((S)-3-phenylisoxazolidine-2-yl)pyrimidine-4-yl)amino)phenyl)acrylamide | ¹H NMR (400 MHz, Methanol-d₄) δ 8.31 (s, 1H), 8.14 (s, 1H), 7.42 (s, 2H), 7.33 (s, 2H), 7.24 (s, 1H), 6.92 (s, 1H), 6.62-6.47 (m, 1H), 6.45-6.39 (m, 1H), 6.39-6.30 (m, 1H), 5.86-5.71 (m, 1H), 5.60-5.47 (m, 1H), 4.20-4.07 (m, 1H), 4.01-3.89 (m, 1H), 3.89-3.82 (m, 4H), 3.09-2.95 (m, 7H), 2.87-2.72 (m, 1H), 2.65 (s, 3H), 2.41-2.24 (m, 1H); 516.3 [M + H]⁺ | 1.04 |

TABLE 1-continued

| Example Compound | Structure | Name of Compound | ¹H NMR[[:]]; MS [M + H]⁺ | UPLC r.t. (min) |
|---|---|---|---|---|
| 4 | 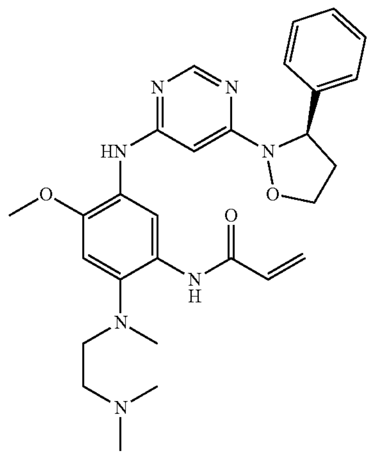 | N-(2-((2-(dimethylamino)ethyl)(methyl)amino)-4-methoxy-5-((6-(R)-3-phenylisoxazolidine-2-yl)pyrimidine-4-yl)amino)phenyl)acrylamide | ¹H NMR (400 MHz, Methanol-d₄) δ 8.15 (s, 1H), 7.97 (s, 1H), 7.43 (s, 2H), 7.33 (s, 2H), 7.24 (s, 1H), 6.93 (s, 1H), 6.61-6.35 (m, 3H), 5.90-5.75 (m, 1H), 5.60-5.43 (m, 1H), 4.23-4.06 (m, 1H), 4.03-3.93 (m, 1H), 3.91 (s, 3H), 3.45-3.36 (m, 2H), 3.20-3.06 (m, 2H), 2.85-2.79 (m, 1H), 2.77 (s, 6H), 2.73-2.65 (m, 3H), 2.42-2.27 (m, 1H); 518.3 [M + H]⁺ | 1.11 |
| 5 | 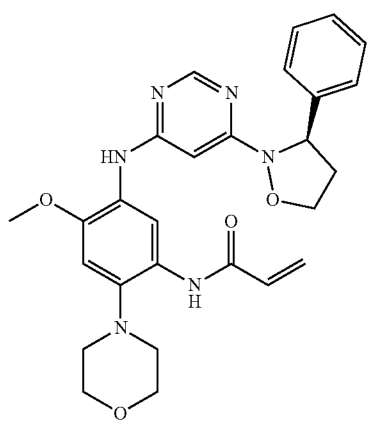 | N-(4-methoxy-2-morpholino-5-((6-((R)-3-phenylisoxazolidine-2-yl)pyrimidine-4-yl)amino)phenyl)acrylamide | ¹H NMR (400 MHz, Methanol-d₄) δ 8.28 (s, 1H), 8.13 (s, 1H), 7.42 (s, 2H), 7.33 (s, 2H), 7.23 (s, 1H), 6.91 (s, 1H), 6.62-6.46 (m, 1H), 6.44-6.26 (m, 2H), 5.85-5.70 (m, 1H), 5.59-5.45 (m, 1H), 4.19-4.07 (m, 1H), 4.01-3.93 (m, 1H) 3.93-3.82 (m, 7H), 2.95-2.87 (m, 4H), 2.86-2.72 (m, 1H), 2.40-2.26 (m, 1H); 503.2 [M + H]⁺ | 1.34 |
| 6 | 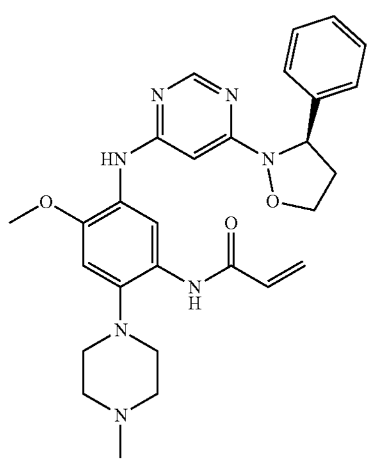 | N-(4-methoxy-2-(4-methylpiperazine-1-yl)-5-((6-((R)-3-phenylisoxazolidine-2-yl)pyrimidine-4-yl)amino)phenyl)acrylamide | ¹H NMR (400 MHz, Methanol-d₄) δ 8.31 (s, 1H), 8.14 (s, 1H), 7.42 (s, 2H), 7.33 (s, 2H), 7.24 (s, 1H), 6.92 (s, 1H), 6.61-6.49 (m, 1H), 6.43 (s, 1H), 6.40-6.29 (m, 1H), 5.87-5.73 (m, 1H), 5.59-5.45 (m, 1H), 4.20-4.02 (m, 1H), 4.02-3.91 (m, 1H), 3.91-3.81 (m, 4H), 3.12-2.92 (m, 7H), 2.85-2.70 (m, 1H), 2.63 (s, 3H), 2.40-2.26 (m, 1H); 516.3 [M + H]₊ | 1.04 |

TABLE 1-continued

| Example Compound | Structure | Name of Compound | ¹H NMR[:]; MS [M + H]⁺ | UPLC r.t. (min) |
|---|---|---|---|---|
| 7 | 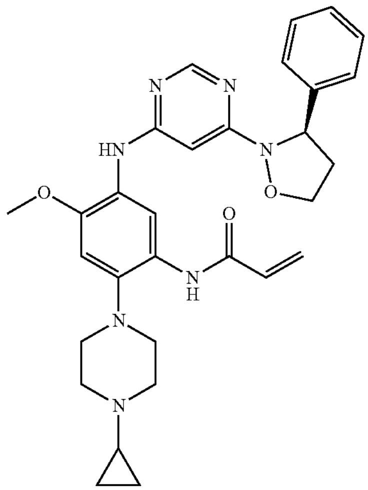 | N-(2-(4-cyclopropylpiperazine-1-yl)-4-methoxy-5-((6-((R)-3-phenylisoxazolidine-2-yl)pyrimidine-4-yl)amino)phenyl) acrylamide | ¹H NMR (400 MHz, DMSO-d₆) δ 9.07 (s, 1H), 8.71 (s, 1H), 8.27 (d, 2H), 7.43-6.98 (m, 5H), 6.79 (d, 2H), 6.36 (s, 1H), 5.52 (d, 2H), 3.81 (s, 3H), 3.15-3.03 (m, 4H), 2.81-2.71 (m, 4H), 2.67 (s, 1H), 2.37 (d, 2H), 2.31-2.21 (m, 3H), 1.91 (s, 1H), 1.11-1.03 (m, 3H), ; 540.3 [M + H]⁺ | 1.14 |
| 8 | 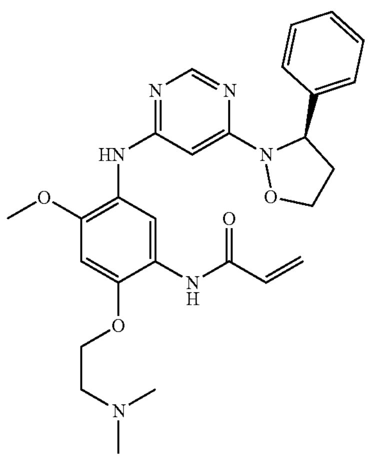 | N-(2-(2-(dimethylamino) ethxy)-4-methoxy-5-((6-(R)-3-phenylisoxazolidine-2-yl)pyrimidine-4-yl-amino)phenyl) acrylamide | 505.3 [M + H]⁺ | 1.07 |
| 9 | 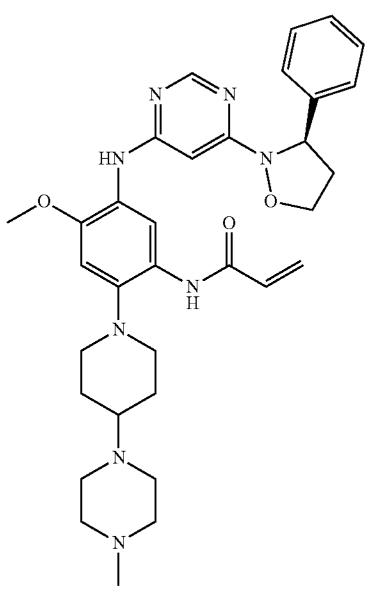 | N-(4-methoxy-2-(4-(4-methylpiperazine-1-yl)piperidine-1-yl)-5-((6-((R)-3-phenylisoxazolidine-2-yl-pyrimidine-4-yl) amino)phenyl) acrylamide | ¹H NMR (400 MHz, DMSO-d₆) δ 8.95 (d, J = 4.0 Hz, 1H), 8.56 (d, J = 4.2 Hz, 1H), 8.15 (t, J = 3.2 Hz, 1H), 7.43-7.23 (m, 5H), 6.82 (d, J = 3.90 Hz, 1H), 6.70-6.60 (m, 1H), 6.34 (d, J = 4.3 Hz, 1H), 6.20 (d, J = 16.7 Hz, 1H), 5.72 (d, J = 10.2 Hz, 1H), 5.53 (s, 1H), 4.13 (t, 1H), 3.39 (t, 2H), 3.32 (s, 3H), 3.09-2.98 (m, 2H), 2.81-2.71 (m, 1H), 2.71-2.60 (m, 4H), 2.40-2.19 (m, 8H), 2.14 (s, 3H), 1.89-1.78 (m, 2H), 1.78-1.63 (m, 2H), ), ; 599.3 [M + H]⁺ | 1.05 |

TABLE 1-continued

| Example Compound | Structure | Name of Compound | ¹H NMR[[:]]; MS [M + H]⁺ | UPLC r.t. (min) |
|---|---|---|---|---|
| 10 | 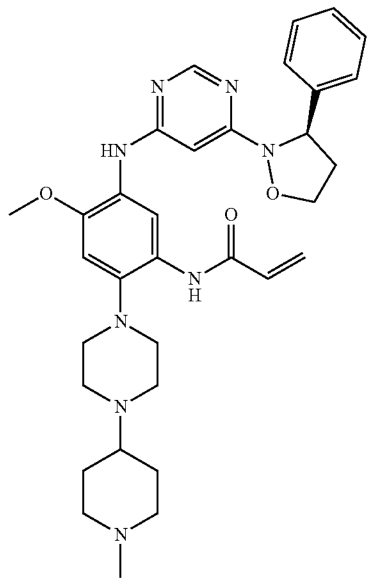 | N-(4-methoxy-2-(4-(1-methylpiperidine-4-yl)piperazine-1-yl)-5-((6-(R)-3-phenylisoxazolidine-2-yl)pyrimidine-4-yl)amino)phenyl) acrylamide | ¹H NMR (400 MHz, Methanol-$d_4$) δ 8.27 (s, 1H), 8.14 (s, 1H), 7.42 (s, 2H), 7.33 (s, 2H), 7.24 (s, 1H), 6.90 (s, 1H), 6.56-6.45 (m, 1H), 6.45-6.26 (m, 2H), 5.85-5.71 (m, 1H), 5.59-5.45 (m, 1H), 4.18-4.03 (m, 1H), 4.03-3.91 (m, 1H), 3.86 (s, 3H), 3.50-3.37 (m, 3H), 3.05-2.95 (m, 4H), 2.94-2.81 (m, 6H), 2.76 (s, 3H), 2.69-2.56 (m, 2H), 2.44-2.25 (m, 1H), 2.23-2.08 (m, 2H); 599.3 [M + H]⁺ | 0.97 |
| 11 | 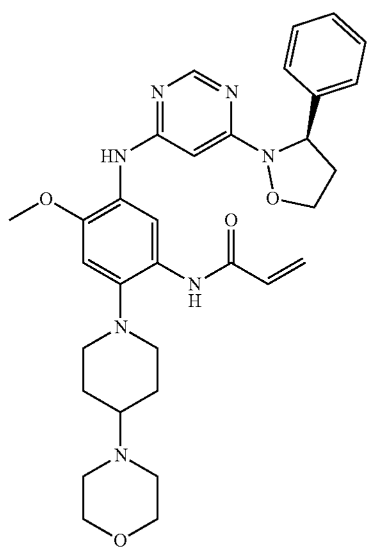 | N-(4-methoxy-2-(4-morpholinopiperidine-1-yl)-5-((6-((R)-3-phenylisoxazolidine-2-yl)pyrimidine-4-yl)amino)phenyl) acrylamide | ¹H NMR (400 MHz, DMSO-$d_6$) δ 9.97 (s, 1H), 9.19 (s, 1H), 8.30 (s, 1H), 7.88 (s, 1H), 7.37 (dd, J = 6.9, 1.3 Hz, 4H), 7.29 (ddd, J = 8.6, 5.4, 2.1 Hz, 1H), 6.90 (s, 1H), 6.67 (dd, J = 17.0, 10.2 Hz, 1H), 6.25 (dd, J = 17.0, 1.9 Hz, 1H), 5.79-5.73 (m, 1H), 5.52 (d, J = 8.1 Hz, 1H), 4.31 (d, J = 4.5 Hz, 1H), 4.07 (d, J = 7.7 Hz, 1H), 3.98 (d, J = 3.9 Hz, 5H), 3.79 (s, 3H), 3.44 (d, J = 12.0 Hz, 2H), 3.36-3.27 (m, 1H), 3.22 (d, J = 11.5 Hz, 2H), 3.14 (d, J = 10.3 Hz, 2H), 2.97-2.90 (m, 1H), 2.77 (s, 2H), 2.37-2.28 (m, 1H), 2.20 (s, 2H), 2.04 (d, J = 13.4 Hz, 2H); 586.3 [M + H]⁺ | 1.11 |

TABLE 1-continued

| Example Compound | Structure | Name of Compound | ¹H NMR[:]; MS [M + H]⁺ | UPLC r.t. (min) |
|---|---|---|---|---|
| 12 | 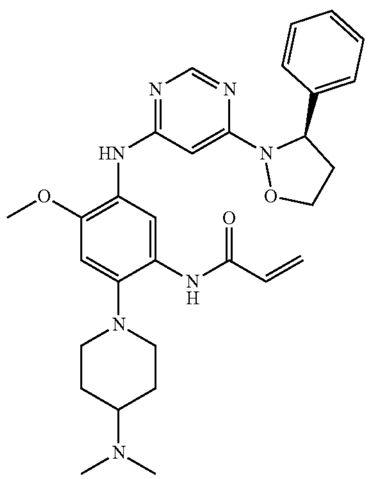 | N-(2-(4-(dimethylamino)piperidine-1-yl)-4-methoxy-5-((6-((R)-3-phenylisoxazolidine-2-yl)pyrimidine-4-yl)amino)phenyl)acrylamide | ¹H NMR (400 MHz, Methanol-$d_4$) δ 8.28 (s, 1H), 8.14 (s, 1H), 7.42 (s, 2H), 7.33 (s, 2H), 7.24 (s, 1H), 6.89 (s, 1H), 6.65-6.48 (m, 1H), 6.47-6.28 (m, 2H), 5.86-5.73 (m, 1H), 5.58-5.43 (m, 1H), 4.20-4.08 (m, 1H), 4.02-3.90 (m, 1H), 3.86 (s, 3H), 3.64-3.55 (m, 4H), 3.26-3.13 (m, 4H), 2.93-2.71 (m, 7H), 2.41-2.28 (m, 1H), 2.21-2.09 (m, 1H); 544.3 [M + H]⁺ | 1.09 |
| 13 | 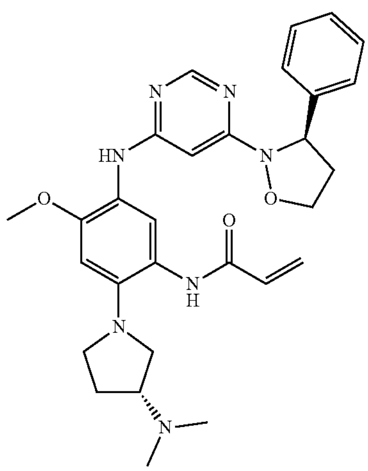 | N-2-((R)-3-(dimethylamino)pyrrolidine-1-yl)-4-methoxy-5-((6-((R)-3-phenylisoxazolidine-2-yl)pyrimidine-4-yl)amino)phenyl)acrylamide | ¹H NMR (400 MHz, Methanol-$d_4$) δ 8.10 (s, 1H), 7.69 (s, 1H), 7.42 (s, 2H), 7.32 (s, 2H), 7.24 (s, 1H), 6.69 (s, 1H), 6.56-6.43 (m, 1H), 6.40-6.23 (m, 2H), 5.87-5.72 (m, 1H), 5.57-5.44 (m, 1H), 4.17-4.04 (m, 1H), 4.00-3.89 (m, 1H), 3.86 (s, 3H), 3.49-3.34 (m, 5H), 2.86-2.72 (m, 1H), 2.63 (s, 6H), 2.41-2.24 (m, 2H), 2.11-2.01 (m, 1H); 530.3 [M + H]⁺ | 1.05 |
| 14 | 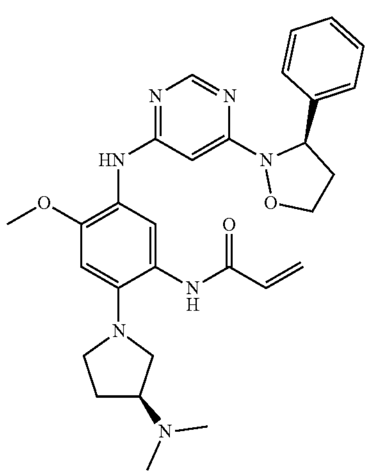 | N-(2-((S)-3-(dimethylamino)pyrrolidine-1-yl)-4-methoxy-5-((6-(R)-3-phenylisoxazolidine-2-yl)pyrimidine-4-yl)amino)phenyl)acrylamide | ¹H NMR (400 MHz, DMSO-$d_6$) δ 9.91 (s, 1H), 9.34 (s, 1H), 9.04 (s, 1H), 8.20 (s, 1H), 7.55 (s, 1H), 7.37 (d, J = 1.7 Hz, 2H), 7.36 (s, 1H), 7.27 (s, 1H), 6.64 (s, 1H), 6.51 (dd, J = 17.1, 10.2 Hz, 1H), 6.21 (dd, J = 17.1, 2.1 Hz, 1H), 6.14 (s, 1H), 5.73 (d, J = 10.4 Hz, 1H), 5.52 (dd, J = 8.7, 5.1 Hz, 2H), 4.23-4.17 (m, 1H), 3.81 (s, 3H), 3.43 (d, J = 6.7 Hz, 2H), 3.34 (d, J = 3.7 Hz, 2H), 3.25 (t, J = 8.2 Hz, 1H), 2.84 (t, J = 5.8 Hz, 6H), 2.35-2.30 (m, 1H), 2.30-2.22 (m, 2H), 2.11 (dd, J = 12.6, 6.7 Hz, 1H), ; 530.4 [M + H]⁺ | 1.07 |

TABLE 1-continued

| Example Compound | Structure | Name of Compound | ¹H NMR[[:]]; MS [M + H]⁺ | UPLC r.t. (min) |
|---|---|---|---|---|
| 15 | 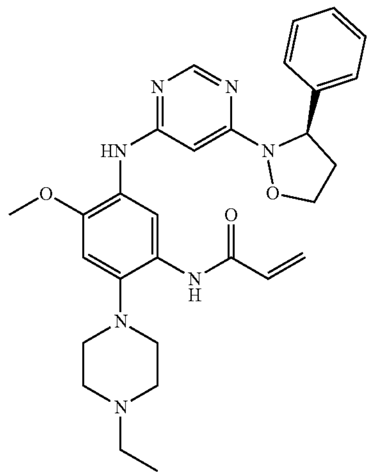 | N-(2-(4-ethylpiperazine-1-yl)-4-methoxy-5-((6-((R)-3-phenylisoxazolidine-2-yl)pyrimidine-4-yl)amino)phenyl) acrylamide | ¹H NMR (400 MHz, Methanol-d₄) δ 8.32 (s, 1H), 8.14 (s, 1H), 7.42 (s, 2H), 7.33 (s, 2H), 7.24 (s, 1H), 6.91 (s, 1H), 6.60-6.47 (m, 1H), 6.47-6.28 (m, 2H), 5.88-5.71 (m, 1H), 5.60-5.42 (m, 1H), 4.20-4.05 (m, 1H), 4.01-3.90 (m, 1H), 3.88 (s, 3H) 3.09 (s, 8H), 3.00-2.87 (m, 2H), 2.87-2.70 (m, 1H), 2.43-2.25 (m, 1H), 1.37-1.20 (m, 3H); 530.3 [M + H]⁺ | 1.06 |
| 16 | 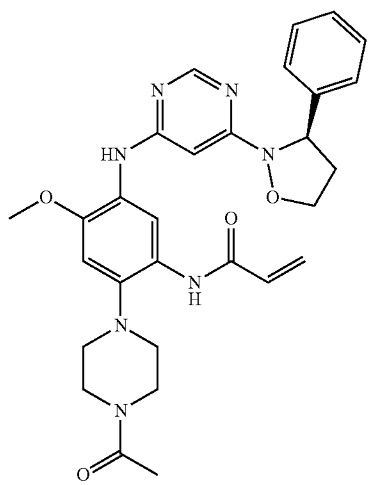 | N-(2-(4-acetylpiperazine-1-yl)-4-methoxy-5-((-6((R)-3-phenylisoxazolidine-2-yl)pyrimidine-4-yl)amino)phenyl) acrylamide | ¹H NMR (400 MHz, DMSO-d₆) δ 9.30 (s, 1H), 8.31 (s, 1H), 8.23 (d, J = 4.1 Hz, 1H), 7.45-7.19 (m, 5H), 7.00 (s, 1H), 6.42 (dd, J = 13.5 Hz, 1H), 6.23 (d, J = 18.3 Hz, 2H), 5.77 (d, J = 9.8 Hz, 1H), 5.52 (s, 1H), 4.23 (s, 1H), 4.02-3.92 (m, 2H), 3.86-3.74 (m, 4H), 3.50 (s, 3H), 3.38-3.29 (m, 4H), 2.80 (s, 3H), 2.36-2.22 (m, 2H), ; 544.3 [M + H]⁺ | 1.27 |
| 17 | 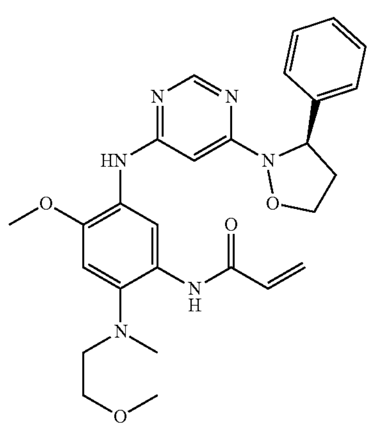 | N-(4-methoxy-2-((2-methoxyethyl)(methyl)amino-5-((6-((R)-3-phenylisoxazolidine-2-yl)pyrimidine-4-yl)amino)phenyl) acrylamide | ¹H NMR (400 MHz, DMSO-d₆) δ 8.45-8.34 (m, 1H), 7.12 (d, J = 4.0 Hz, 1H), 7.01 (s, 1H), 6.91-6.82 (m, 5H), 6.76 (dd, J = 13.8 Hz, 1H), 6.16 (d, J = 16.4 Hz, 1H), 5.99 (s, 1H), 5.75-5.65 (m, 1H), 4.85-4.74 (m, 9H), 4.00 (d, J = 4.3 Hz, 2H), 3.31-3.17 (m, 6H), 3.05 (s, 1H), 1.93-1.76 (m, 2H), ; 505.3 [M + H]⁺ | 1.45 |

TABLE 1-continued

| Example Compound | Structure | Name of Compound | ¹H NMR[[:]]; MS [M + H]⁺ | UPLC r.t. (min) |
|---|---|---|---|---|
| 18 | 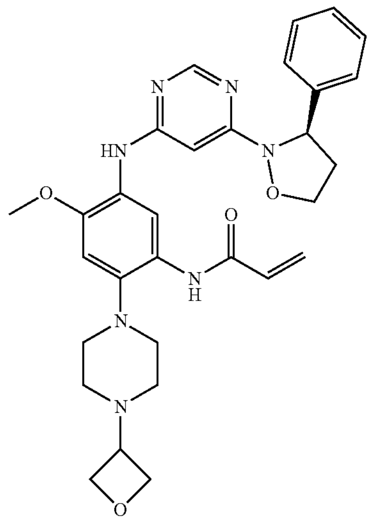 | N-(4-methoxy-2-(4-oxetane-3-yl)piperazine-1-yl)-5-((6-((R)-3-phenylisoxazolidine-2-yl)pyrimidine-4-yl)amino)phenyl)acrylamide | ¹H NMR (400 MHz, Methanol-d₄) δ 8.30 (s, 1H), 8.14 (s, 1H), 7.42 (d, J = 7.3 Hz, 2H), 7.32 (dd, J = 6.8, 8.4 Hz, 2H), 7.27-7.20 (m, 1H), 6.93 (s, 1H), 6.50 (dd, J = 10.2, 17.0 Hz, 1H), 6.41 (d, J = 1.1 Hz, 1H), 6.33 (dd, J = 1.6, 17.0 Hz, 1H), 5.78 (dd, J = 1.6, 10.2 Hz, 1H), 5.52 (dd, J = 4.7, 8.5 Hz, 1H), 4.73 (t, J = 6.7 Hz, 2H), 4.65 (t, J = 6.2 Hz, 2H), 4.17-4.08 (m, 1H), 4.02-3.92 (m, 1H), 3.87 (s, 3H), 3.66-3.57 (m, 1H), 3.03-2.95 (m, 4H), 2.85-2.71 (m, 1H), 2.63-2.51 (m, 4H), 2.38-2.27 (m, 1H); 558.3 [M + H]⁺ | 1.07 |
| 19 | 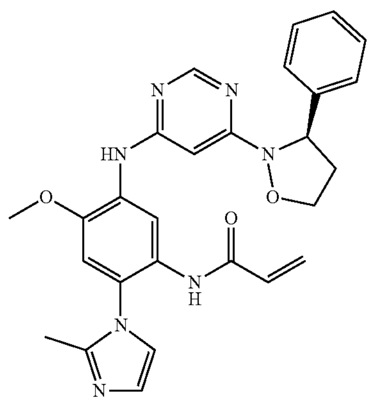 | N-(4-methoxy-2-(2-methyl-1H-imidazole-1-yl)-5-((6((R)-3-phenylisoxazolidine-2-yl)pyrimidine-4-yl)amino)phenyl)acrylamide | ¹H NMR (400 MHz, Methanol-d₄) δ 8.38 (s, 1H), 8.27 (s, 1H), 7.47 (d, J = 7.6 Hz, 2H), 7.37 (t, J = 7.6 Hz, 2H), 7.27 (t, J = 7.2 Hz, 1H), 7.12-7.03 (m, 2H), 7.01 (s, 1H), 6.69 (s, 1H), 6.31-6.23 (m, 2H), 5.73 (dd, J = 2.8, 9.1 Hz, 1H), 5.58 (dd, J = 4.8, 8.5 Hz, 1H), 4.24-4.16 (m, 2H), 4.08-3.98 (m, 2H), 3.96 (s, 3H), 2.30 (s, 3H); 498.3 [M + H]⁺ | 1.19 |
| 20 | 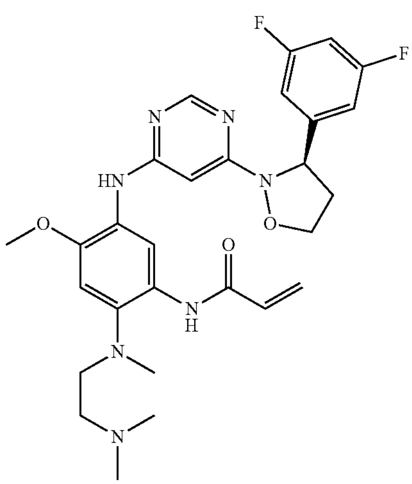 | N-(5-((6-((R)-3-(3,5-difluorophenyl)isoxazolidine-2-yl)pyrimidine-4-yl)amino)-2-((2-(dimethylamino)ethyl)(methylamino)-4-methoxyphenyl)acrylamide | ¹H NMR (400 MHz, Methanol-d₄) δ 8.18 (s, 1H), 7.99 (s, 1H), 7.05 (s, 2H), 6.93 (s, 1H), 6.89-6.77 (m, 1H), 6.60-6.33 (m, 3H), 5.89-5.75 (m, 1H), 5.62-5.42 (m, 1H), 4.19-4.07 (m, 1H), 3.99-3.93 (m, 1H), 3.92 (s, 3H), 3.47-3.35 (m, 2H), 3.20-3.08 (m, 2H), 2.89-2.80 (m, 1H), 2.77 (s, 6H), 2.71 (s, 3H), 2.40-2.25 (m, 1H); 554.3 [M + H]⁺ | 1.23 |

TABLE 1-continued

| Example Compound | Structure | Name of Compound | ¹H NMR[[:]]; MS [M + H]⁺ | UPLC r.t. (min) |
|---|---|---|---|---|
| 21 | 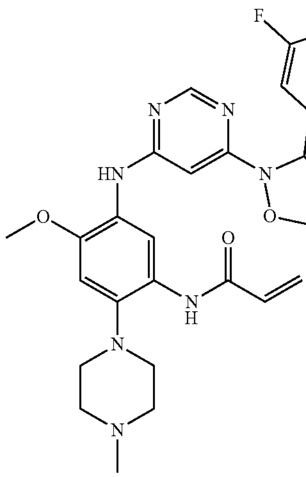 | N-(5-((6-((R)-3-(3,5-difluorophenyl)isoxazolidine-2-yl)pyrimidine-4-yl)amino)-4-methoxy-2-(4-methylpiperazine-1-yl)phenyl)acrylamide | $^1$H NMR (400 MHz, Methanol-$d_4$) δ 8.33 (s, 1H), 8.17 (s, 1H), 7.05 (s, 2H), 6.93 (s, 1H), 6.88-6.74 (m, 1H), 6.59-6.42 (m, 2H), 6.40-6.28 (m, 1H), 5.85-5.72 (m, 1H), 5.61-5.41 (m, 1H), 4.21-4.05 (m, 1H), 4.01-3.91 (m, 1H), 3.88 (s, 3H), 3.10-3.01 (m, 4H), 3.01-2.91 (m, 4H), 2.89-2.74 (m, 1H), 2.62 (s, 3H), 2.40-2.22 (m, 1H); 552.3 [M + H]⁺ | 1.20 |
| 22 | 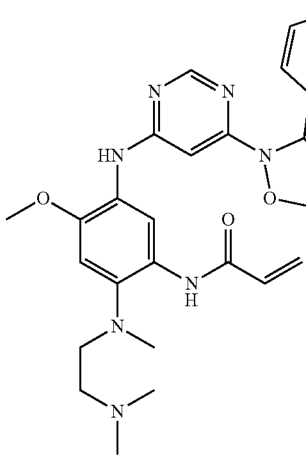 | N-(2-((2-(dimethylamino)ethyl)(methyl)amino)-5-((6-((R)-3-(3-fluorophenyl)isoxazolidine-2-yl)pyrimidine-4-yl)amino)-4-methoxyphenyl)acrylamide | 536.3 [M + H]⁺ | 1.17 |
| 23 | 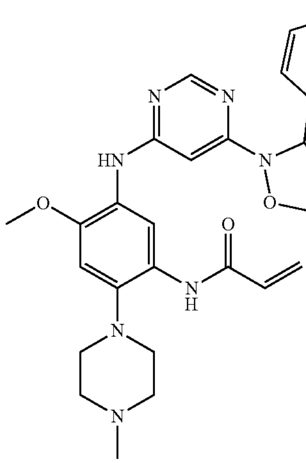 | N-(5-((6-((R)-3-(3-fluorophenyl)isoxazolidine-2-yl)pyrimidine-4-yl)amino)-4-methoxy-2-(4-methylpiperazine-1-yl)phenyl)acrylamide | 534.3 [M + H]⁺ | 1.13 |

TABLE 1-continued

| Example Compound | Structure | Name of Compound | ¹H NMR[[:]]; MS [M + H]⁺ | UPLC r.t. (min) |
|---|---|---|---|---|
| 24 | 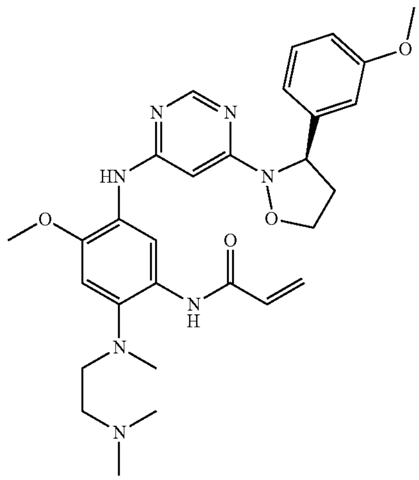 | N-(2-((2-(dimethylamino)ethyl)(methyl)amino)-4-methoxy-5-((6-((R)-3-(3-methoxyphenyl)isoxazolidine-2-yl)pyrimidine-4-yl)amino)phenyl)acrylamide | ¹H NMR (400 MHz, Chloroform-d) δ 9.48 (s, 1H), 8.83 (d, J = 2.9 Hz, 1H), 8.29 (d, J = 2.1 Hz, 1H), 7.70 (s, 1H), 7.25 (td, J = 8.3, 2.0 Hz, 1H), 7.02 (dd, J = 4.3, 2.0 Hz, 2H), 6.81 (d, J = 10.2 Hz, 1H), 6.76 (d, J = 9.4 Hz, 1H), 6.74 (s, 1H), 6.67 (d, J = 2.5 Hz, 1H), 6.45-6.35 (m, 1H), 5.70 (dd, J = 10.1, 2.1 Hz, 1H), 5.65 (dd, J = 8.6, 4.4 Hz, 1H), 4.16 (td, J = 7.9, 4.4 Hz, 1H), 4.12-4.04 (m, 1H), 3.84 (d, J = 2.0 Hz, 3H), 3.80 (d, J = 1.5 Hz, 3H), 3.06 (d, J = 7.1 Hz, 2H), 2.87 (t, J = 5.9 Hz, 2H), 2.76 (tt, J = 8.1, 4.3 Hz, 1H), 2.66 (d, J = 1.9 Hz, 3H), 2.57 (s, 6H), 2.38 (dtd, J = 12.2, 8.0, 4.6 Hz, 1H); 548.3 [M + H]⁺ | 1.11 |
| 25 | 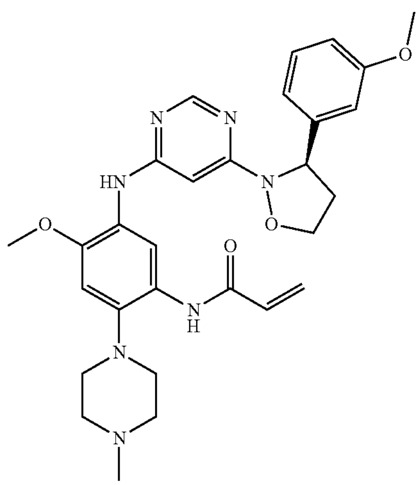 | N-(4-methoxy-5-((6-((R)-3-(3-methoxyphenyl)isoxazolidine-2-yl)pyrimidine-4-yl)amino)-2-(4-methylpiperazine-1-yl)phenyl)acrylamide | ¹H NMR (400 MHz, Chloroform-d) δ 8.71 (s, 1H), 8.44 (s, 1H), 8.27 (d, J = 0.9 Hz, 1H), 7.29 (s, 1H), 7.25 (t, J = 8.1 Hz, 1H), 7.03-6.99 (m, 2H), 6.83-6.76 (m, 2H), 6.57 (s, 1H), 6.41-6.27 (m, 2H), 5.76 (dd, J = 8.9, 2.6 Hz, 1H), 5.64 (dd, J = 8.6, 4.5 Hz, 1H), 4.13 (dd, J = 7.9, 4.4 Hz, 1H), 4.03 (q, J = 8.0 Hz, 1H), 3.86 (s, 3H), 3.80 (s, 3H), 3.07-3.00 (m, 4H), 2.93 (d, J = 6.2 Hz, 4H), 2.80-2.73 (m, 1H), 2.54 (s, 3H), 2.41-2.35 (m, 1H); 546.3 [M + H]⁺ | 1.33 |
| 26 | 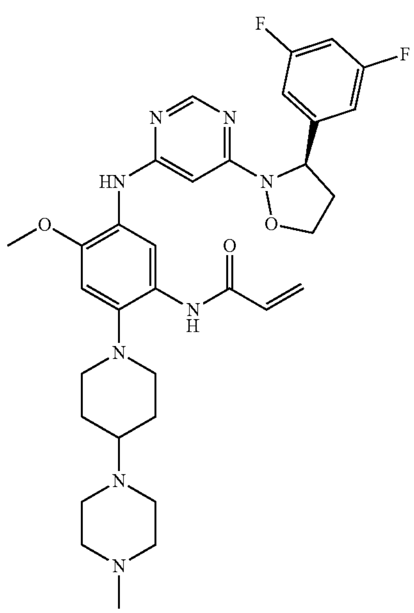 | N-(5-((6-((R)-3-(3,5-difluorophenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, DMSO-d₆) δ 8.95 (s, 1H), 8.63 (s, 1H), 8.20-8.11 (m, 2H), 7.15-7.08 (m, 3H), 6.82 (s, 1H), 6.69-6.61 (m, 1H), 6.35 (s, 1H), 6.21 (dd, J = 17.0, 2.0 Hz, 1H), 5.72 (dd, J = 10.1, 2.0 Hz, 1H), 5.56 (dd, J = 8.7, 4.9 Hz, 1H), 4.16-4.10 (m, 1H), 3.83 (d, J = 8.0 Hz, 1H), 3.80 (s, 3H), 3.16-2.99 (m, 3H), 2.76 (dd, J = 8.1, 4.0 Hz, 1H), 2.68 (d, J = 12.6 Hz, 2H), 2.58-2.52 (m, 3H), 2.38-2.21 (m, 6H), 2.16 (s, 3H), 1.88-1.80 (m, 2H), 1.71 (dd, J = 12.8, 9.2 Hz, 2H); 635.3 [M + H]⁺ | 1.16 |

TABLE 1-continued

| Example Compound | Structure | Name of Compound | ¹H NMR[[:]]; MS [M + H]⁺ | UPLC r.t. (min) |
|---|---|---|---|---|
| 27 | 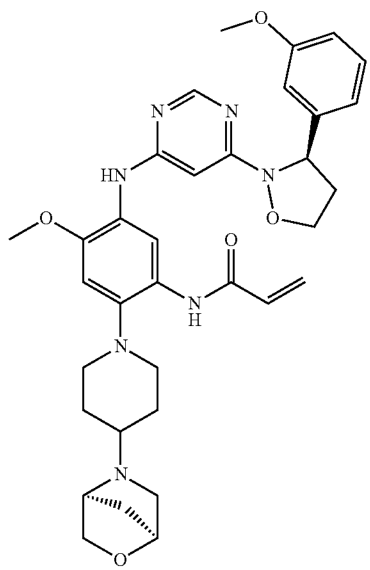 | N-(2-(4-((1S,4S)-2-oxa-5-azabicyclo[2.2.1]heptane-5-yl)piperidine-1-yl)-4-methoxy-5-((6-((R)-3-(3-methoxyphenyl)isoxazolidine-2-yl)pyrimidine-4-yl)amino)phenyl)acrylamide | ¹H NMR (400 MHz, Methanol-d₄) δ 8.05 (d, J = 0.8 Hz, 1H), 7.85 (s, 1H), 7.16 (t, J = 7.9 Hz, 1H), 6.85-6.77 (m, 3H), 6.74 (ddd, J = 8.4, 2.6, 1.0 Hz, 1H), 6.42 (dd, J = 17.0, 10.2 Hz, 1H), 6.27 (dd, J = 17.0, 1.6 Hz, 1H), 5.90 (s, 1H), 5.72 (d, J = 10.1 Hz, 1H), 5.33 (s, 1H), 4.66-4.56 (m, 2H), 4.24 (dd, J = 7.6, 4.4 Hz, 2H), 4.07-3.98 (m, 1H), 3.79 (d, J = 8.8 Hz, 2H), 3.72 (s, 3H), 3.68 (s, 3H), 3.51 (d, J = 13.4 Hz, 2H), 2.90-2.68 (m, 4H), 2.32 (dd, J = 12.9, 5.7 Hz, 2H), 2.12 (d, J = 15.6 Hz, 4H), 1.84 (d, J = 3.7 Hz, 2H); 628.3 [M + H]⁺ | 1.14 |
| 28 | 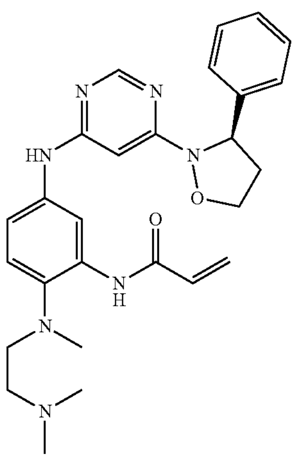 | N-(2-((2-(dimethylamino)ethyl)methyl)amino)-5-((6-((R)-3-phenylisoxazolidine-2-yl)pyrimidine-4-yl)amino)phenyl)acrylamide | ¹H NMR (400 MHz, DMSO-d₆) δ 10.83 (s, 1H), 9.97 (s, 1H), 9.15 (s, 1H), 8.32 (d, J = 4.5 Hz, 1H), 8.25 (s, 1H), 7.44-7.14 (m, 5H), 6.78 (dd, J = 16.2, 10.0 Hz, 1H), 6.29 (d, J = 13.6 Hz, 2H), 5.85-5.76 (m, 1H), 5.51 (s, 1H), 4.26 (s, 1H), 4.05-3.88 (m, 2H), 3.52-3.44 (m, 3H), 3.17 (s, 3H), 3.13-3.05 (m, 4H), 2.82 (s, 3H), 2.37-2.23 (m, 2H), ; 488.3 [M + H]⁺ | 1.11 |
| 29 | 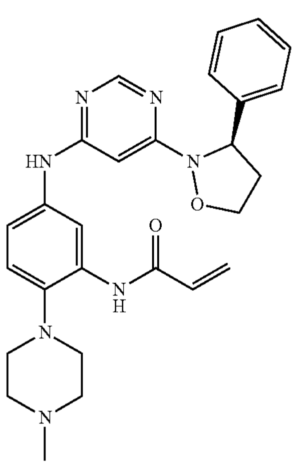 | N-(2-(4-methylpiperazine-1-yl)-5-((6-((R)-3-phenylisoxazolidine-2-yl)pyrimidine-4-yl)amino)phenyl)acrylamide | ¹H NMR (400 MHz, DMSO-d₆) δ 9.13 (s, 1H), 8.22 (d, J = 4.2 Hz, 1H), 8.11 (s, 1H), 7.38 (d, J = 4.9 Hz, 5H), 7.28 (s, 1H), 6.90 (d, J = 3.9 Hz, 1H), 6.67 (s, 1H), 6.20 (s, 2H), 5.74 (d, J = 10.4 Hz, 1H), 5.51 (d, J = 6.6 Hz, 1H), 4.22 (s, 1H), 4.00-3.90 (m, 2H), 3.70-3.59 (m, 4H), 2.85 (dd, J = 15.9, 5.7 Hz, 4H), 2.34-2.23 (m, 2H), 2.05 (s, 3H), ; 486.3 [M + H]⁺ | 1.08 |

TABLE 1-continued

| Example Compound | Structure | Name of Compound | ¹H NMR[:]; MS [M + H]⁺ | UPLC r.t. (min) |
|---|---|---|---|---|
| 30 | 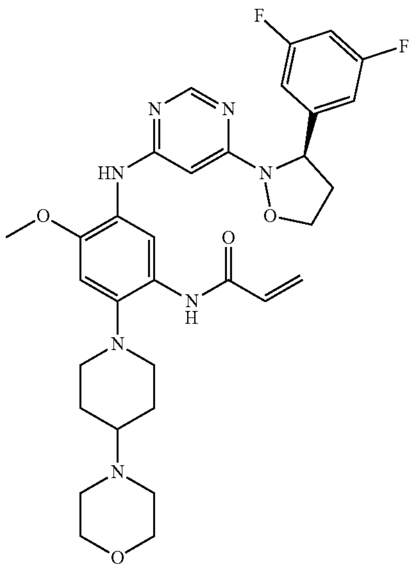 | N-(5-((6-((R)-3-(3,5-difluorophenyl)isoxazolidine-2-yl)pyrimidine-4-yl)amino)-4-methoxy-2-(4-morpholinopiperidine-1-yl)phenyl)acrylamide | ¹H NMR (400 MHz, DMSO-d₆) δ 11.73 (s, 1H), 10.22 (s, 1H), 9.26 (s, 1H), 8.34 (s, 1H), 7.88 (s, 1H), 7.17 (tt, J = 9.3, 2.4 Hz, 1H), 7.10 (h, J = 4.5 Hz, 2H), 6.69 (dd, J = 17.0, 10.2 Hz, 1H), 6.25 (dd, J = 17.0, 1.9 Hz, 1H), 5.79-5.72 (m, 1H), 5.55 (dd, J = 8.6, 5.4 Hz, 1H), 4.05 (d, J = 7.7 Hz, 1H), 4.00-3.96 (m, 4H), 3.81 (s, 3H), 3.43 (d, J = 12.0 Hz, 2H), 3.24 (d, J = 11.4 Hz, 2H), 3.15 (d, J = 12.3 Hz, 2H), 2.93 (qd, J = 7.7, 3.4 Hz, 1H), 2.85-2.74 (m, 2H), 2.26-2.16 (m, 2H), 2.15-1.99 (m, 2H), 1.65-1.54 (m, 1H), 1.53-1.37 (m, 1H), 1.30-1.19 (m, 1H), 0.85 (td, J = 8.0, 7.3, 3.1 Hz, 1H), ; 622.4 [M + H]⁺ | 1.23 |
| 31 | 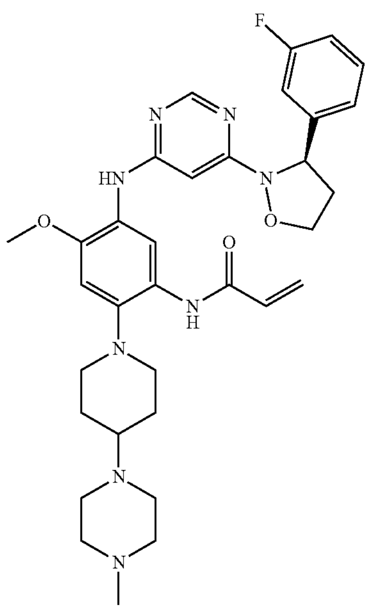 | N-(5-((6-((R)-3-(3-fluorophenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, DMSO-d₆) δ 10.45 (s, 1H), 9.33 (s, 1H), 8.34 (s, 1H), 7.85 (s, 1H), 7.42 (td, J = 8.0, 5.9 Hz, 1H), 7.23-7.06 (m, 3H), 6.94 (s, 1H), 6.75 (dd, J = 16.8, 10.2 Hz, 1H), 6.25 (dd, J = 17.0, 2.0 Hz, 1H), 6.13-6.03 (m, 1H), 5.76 (dd, J = 10.0, 2.0 Hz, 1H), 5.55 (dd, J = 8.4, 5.4 Hz, 2H), 4.08 (q, J = 7.7 Hz, 2H), 3.80 (s, 3H), 3.79-3.70 (m, 4H), 3.61 (q, J = 14.1, 11.7 Hz, 5H), 3.48 (d, J = 16.4 Hz, 1H), 3.25 (d, J = 11.3 Hz, 2H), 3.15 (d, J = 7.9 Hz, 1H), 2.96 (qq, J = 7.3, 4.4 Hz, 2H), 2.84 (s, 5H), 2.32 (dtd, J = 12.6, 7.5, 5.2 Hz, 1H), 2.17 (q, J = 12.3 Hz, 4H), 1.67-1.49 (m, 4H), ; 617.4 [M + H]⁺ | 1.09 |

TABLE 1-continued

| Example Compound | Structure | Name of Compound | $^1$H NMR[[:]]; MS [M + H]$^+$ | UPLC r.t. (min) |
|---|---|---|---|---|
| 32 | 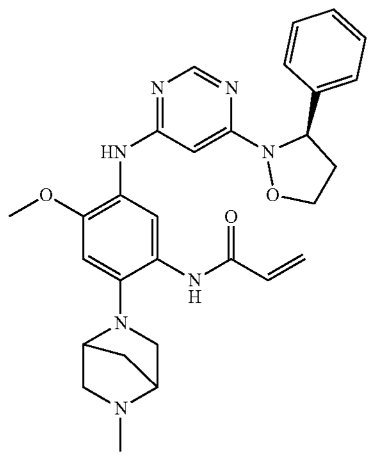 | N-(4-methoxy-2-(5-methyl-2,5-diazabicyclo[2.2.1]heptane-2-yl)-5-((6-((R)-3-phenylisoxazolidine-2-yl)pyrimidine-4-yl)amino)phenyl)acrylamide | 528.3 [M + H]$^+$ | 1.08 |
| 33 | 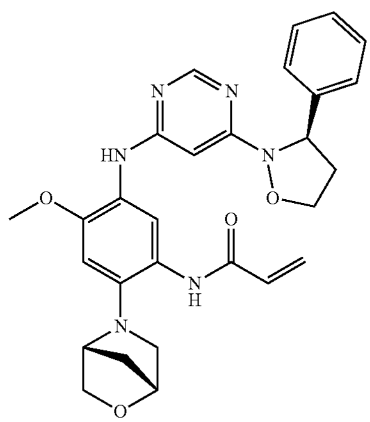 | N-(2-((1R, 4R)-2-oxa-5-azabicyclo[2.2.1]heptane-5-yl)-4-methoxy-5-((6-((R)-3-phenylisoxazolidine-2-yl)pyrimidine-4-yl)amino)phenyl)acrylamide | $^1$H NMR (400 MHz, Methanol-d$_4$) δ 8.10 (s, 1H), 7.41-7.34 (m, 4H), 7.33-7.27 (m, 1H), 7.16 (s, 1H), 6.53-6.42 (m, 2H), 6.38 (dd, J = 17.0, 2.2 Hz, 1H), 5.95 (s, 1H), 5.82 (dd, J = 9.8, 2.1 Hz, 1H), 5.51 (s, 1H), 4.61 (s, 1H), 4.50-4.39 (m, 2H), 4.25-4.16 (m, 1H), 4.10 (d, J = 7.6 Hz, 1H), 3.93-3.88 (m, 1H), 3.81 (s, 3H), 3.65 (dd, J = 9.6, 1.7 Hz, 1H), 3.35 (d, J = 1.7 Hz, 1H), 3.09-2.98 (m, 2H), 2.51-2.40 (m, 1H), 2.07-2.02 (m, 1H), 1.99-1.95 (m, 1H); 515.2 [M + H]$^+$ | 1.15 |
| 34 | 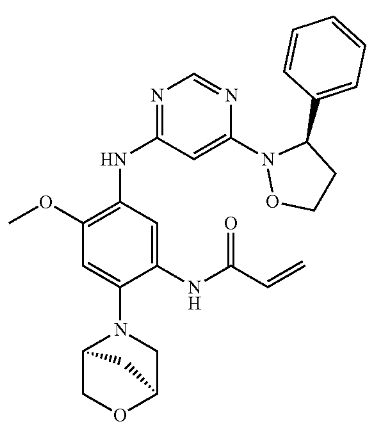 | N-(2-((1S, 4S)-2-oxa-5-azabicyclo[2.2.1]heptane-5-yl)-4-methoxy-5-((6-((R)-3-phenylisoxazolidine-2-yl)pyrimidine-4-yl)amino)phenyl)acrylamide | $^1$H NMR (400 MHz, Methanol-d$_4$) δ 8.11 (s, 1H), 7.49-7.40 (m, 3H), 7.35 (t, J = 7.6 Hz, 2H), 7.26 (t, J = 7.3 Hz, 1H), 6.56 (s, 1H), 6.49 (dd, J = 10.1, 17.0 Hz, 1H), 6.36 (dd, J = 1.8, 17.1 Hz, 1H), 6.27 (d, J = 3.2 Hz, 1H), 5.79 (dd, J = 1.8, 10.1 Hz, 1H), 5.52 (dd, J = 4.6, 8.5 Hz, 1H), 4.18-4.08 (m, 3H), 4.03-3.91 (m, 2H), 3.86 (s, 4H), 3.55-3.48 (m, 1H), 3.17-3.08 (m, 2H), 2.87-2.72 (m, 2H), 2.41-2.27 (m, 1H); 515.2 [M + H]$^+$ | 1.24 |

TABLE 1-continued

| Example Compound | Structure | Name of Compound | ¹H NMR[:]; MS [M + H]⁺ | UPLC r.t. (min) |
|---|---|---|---|---|
| 35 | 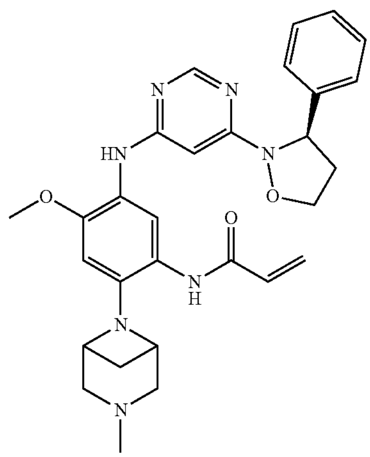 | N-(4-methoxy-2-(3-methyl-3,6-diazabicyclo[3.1.1]heptane-6-yl)-5-((6-((R)-3-phenylisoxazolidine-2-yl)pyrimidine-4-yl)amino)phenyl)acrylamide | ¹H NMR (400 MHz, Methanol-d₄) δ 8.09 (s, 1H), 7.42 (d, J = 7.3 Hz, 2H), 7.33 (dd, J = 7.7, 15.3 Hz, 3H), 7.28-7.17 (m, 1H), 6.46-6.32 (m, 2H), 6.29-6.25 (m, 2H), 5.76 (dd, J = 2.5, 9.4 Hz, 1H), 5.51 (dd, J = 4.6, 8.7 Hz, 1H), 4.38-4.30 (m, 2H), 4.14-4.04 (m, 1H), 3.93 (q, J = 7.9 Hz, 1H), 3.83 (s, 3H), 3.19-3.11 (m, 2H), 3.06-2.96 (m, 2H), 2.82-2.71 (m, 1H), 2.65 (q, J = 6.8 Hz, 1H), 2.38-2.28 (m, 4H), 2.09-2.00 (m, 1H); 528.2 [M + H]⁺ | 1.03 |
| 36 | 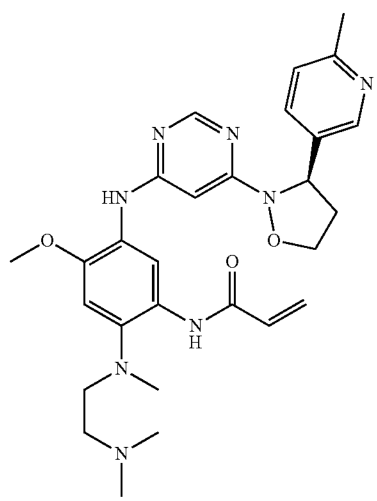 | N-(2-((2-(dimethylamino)ethyl)(methyl)amino)-4-methoxy-5-((6-((R)-3-(6-methylpyridine-3-yl)isoxazolidine-2-yl)pyrimidine-4-yl)amino)phenyl)acrylamide | ¹H NMR (400 MHz, Chloroform-d) δ 10.11 (s, 1H), 8.95 (s, 1H), 8.57 (d, J = 2.4 Hz, 1H), 8.36 (d, J = 0.9 Hz, 1H), 7.71 (dd, J = 8.1, 2.4 Hz, 1H), 7.12 (d, J = 8.0 Hz, 1H), 7.05 (s, 1H), 6.80 (s, 1H), 6.77-6.75 (m, 1H), 6.40 (dd, J =17.0, 2.1 Hz, 1H), 6.31 (dd, J =17.0, 9.8 Hz, 1H), 5.70 (ddd, J = 16.4, 9.0, 3.1 Hz, 2H), 4.18-4.09 (m, 2H), 3.84 (s, 3H), 2.88 (dt, J = 5.0, 2.4 Hz, 2H), 2.71 (s, 3H), 2.53 (s, 3H), 2.35-2.31 (m, 4H), 2.28 (s, 6H); 533.3 [M + H]⁺ | 1.35 |
| 37 | 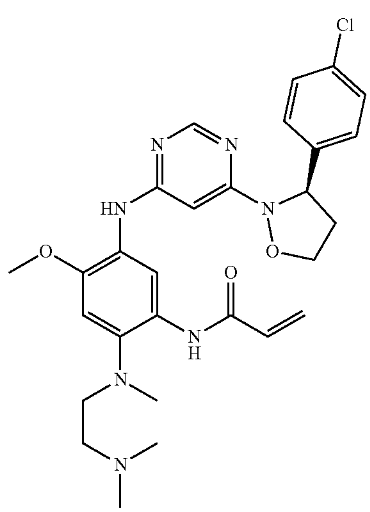 | N-(5-((6-((R)-3-(4-chlorophenyl)isoxazolidine-2-yl)pyrimidine-4-yl)amino)-2-((2-(dimethylamino)ethyl)(methyl)amino)-4-methoxyphenyl)acrylamide | ¹H NMR (400 MHz, Methanol-d₄) δ 8.18 (s, 1H), 8.06 (s, 1H), 7.40 (dd, J = 35.4, 8.1 Hz, 4H), 6.96 (s, 1H), 6.65-6.54 (m, 1H), 6.52-6.39 (m, 2H), 5.85 (dd, J = 10.2, 1.5 Hz, 1H), 5.57-5.50 (m, 1H), 4.16 (td, J = 7.8, 4.6 Hz, 1H), 3.99 (d, J = 7.9 Hz, 1H), 3.93 (s, 3H), 3.42 (t, J = 5.7 Hz, 2H), 3.33 (dt, J = 3.1, 1.6 Hz, 3H), 3.18 (d, J = 13.3 Hz, 2H), 2.80 (d, J = 4.1 Hz, 6H), 2.73 (s, 3H), 2.34 (dt, J = 12.4, 7.5 Hz, 1H); 552.5 [M + H]⁺ | 1.53 |

TABLE 1-continued

| Example Compound | Structure | Name of Compound | ¹H NMR[:]; MS [M + H]⁺ | UPLC r.t. (min) |
|---|---|---|---|---|
| 38 | 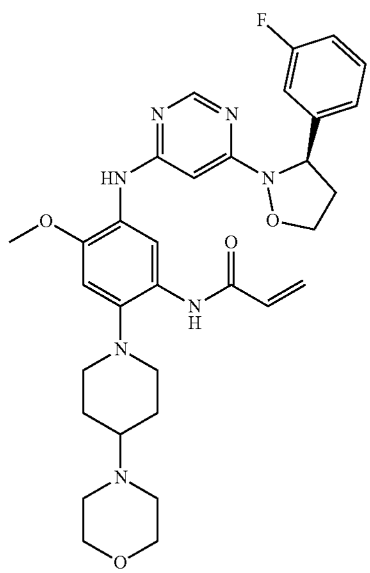 | N-(5-((6-((R)-3-(3-fluorophenyl)isoxazolidine-2-yl)pyrimidine-4-yl)amino)-4-methoxy-2-(4-morpholinopiperidine-1-yl)phenyl)acrylamide | 604.5 [M + H]⁺ | 1.17 |
| 39 | 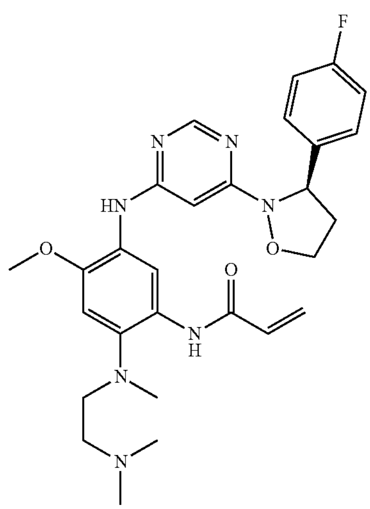 | N-(2-((2-(dimethylamino)ethyl)(methyl)amino)-5-((6-((R)-3-(4-fluorophenyl)isoxazolidine-2-yl)pyrimidine-4-yl)amino)-4-methoxyphenyl)acrylamide | 536.3 [M + H]⁺ KSS-005-068 | |

TABLE 1-continued

| Example Compound | Structure | Name of Compound | $^1$H NMR[[:]]; MS [M + H]$^+$ | UPLC r.t. (min) |
|---|---|---|---|---|
| 40 | 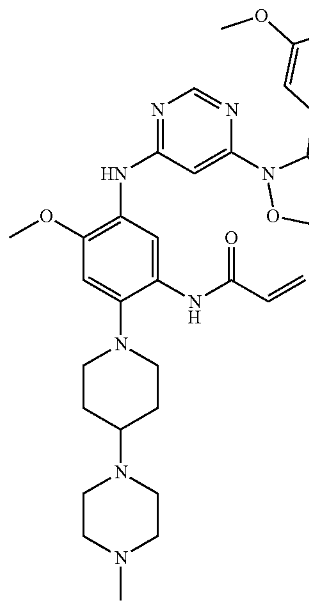 | N-(4-methoxy-5-((6-((R)-3-(3-methoxyphenyl)isoxazolidine-2-yl)pyrimidine-4-yl)amino)-2-(4-(4-methylpiperazine-1-yl)piperidine-1-yl)phenyl)acrylamide | $^1$H NMR (400 MHz, Methanol-d$_4$) δ 8.17 (s, 1H), 7.93 (s, 1H), 7.28 (t, J = 7.8 Hz, 1H), 6.95-6.84 (m, 5H), 6.59 (dd, J = 16.9, 10.2 Hz, 1H), 6.40 (dd, J = 17.0, 1.6 Hz, 1H), 5.84 (dd, J = 10.2, 1.6 Hz, 1H), 5.42 (s, 1H), 4.43 (td, J = 7.5, 4.4 Hz, 1H), 4.19 (td, J = 8.2, 6.6 Hz, 1H), 3.82 (s, 3H), 3.79 (s, 3H), 3.43 (s, 4H), 3.26 (d, J = 12.3 Hz, 5H), 3.02 (dddd, J = 11.1. 8.3, 6.5, 4.3 Hz, 3H), 2.92 (s, 3H), 2.86 (d, J = 11.9 Hz, 2H), 2.50-2.41 (m, 1H), 2.20-2.11 (m, 2H), 2.02-1.89 (m, 3H); 629.3 [M + H]$^+$ | 1.11 |
| 41 | 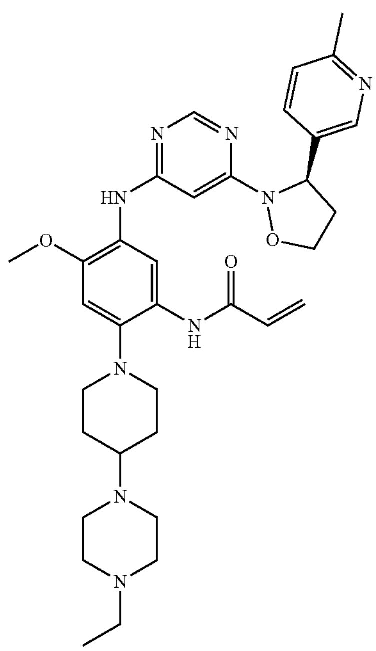 | N-(2-(4-(4-ethylpiperazine-1-yl)piperidine-1-yl)-4-methoxy-5-((6((R)-3-(6-methylpyridine-3-yl)isoxazolidine-2-yl)pyrimidine-4-yl)amino)phenyl)acrylamide | 628.4 [M + H]$^+$ | 0.78 |

TABLE 1-continued

| Example Compound | Structure | Name of Compound | ¹H NMR[[:]]; MS [M + H]⁺ | UPLC r.t. (min) |
|---|---|---|---|---|
| 42 | 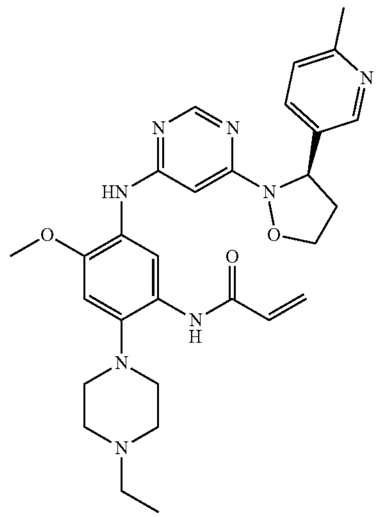 | N-(2-(4-ethylpiperazine-1-yl)-4-methoxy-5-((6((R)-3-(6-methylpyridine-3-yl)isoxazolidine-2-yl)pyrimidine-4-yl)amino)phenyl) acrylamide | 545.3 [M + H]⁺ | 0.74 |
| 43 | 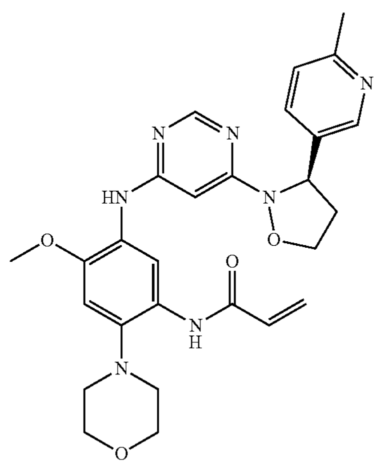 | N-(4-methoxy-5-((6-((R)-3-(6-methylpyridine-3-yl)isoxazolidine-2-yl)pyrimidine-4-yl)amino-2-morpholinophenyl) acrylamide | ¹H NMR (400 MHz, DMSO-d₆) δ 9.95 (d, J = 23.3 Hz, 1H), 9.47 (s, 1H), 9.24 (s, 1H), 8.76 (d, J = 2.1 Hz, 1H), 8.47 (dd, J = 8.4, 2.2 Hz, 1H), 8.30 (d, J = 3.1 Hz, 1H), 7.93 (d, J = 8.4 Hz, 1H), 6.99-6.80 (m, 1H), 6.67 (dd, J = 17.0, 10.2 Hz, 1H), 6.43-6.11 (m, 2H), 5.82-5.63 (m, 2H), 3.84-3.81 (m, 4H), 2.92 (t, J = 4.5 Hz, 3H), 2.76 (s, 3H), 2.50 (q, J = 1.9 Hz, 8H), ; 518.5 [M + H]⁺ | 1.73 |
| 44 | 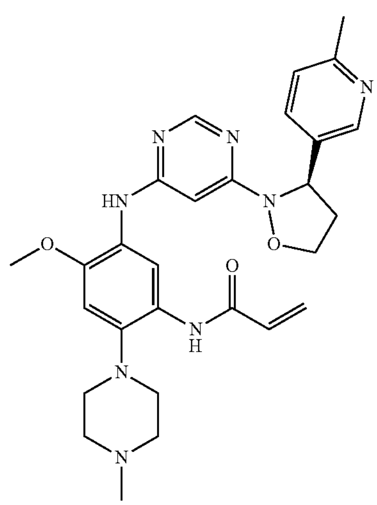 | N-(4-methoxy-2-(4-methylpiperazine-1-yl)-5-((6-((R)-3-(6-methylpyridine-3-yl)isoxazolidine-2-yl)pyrimidine-4-yl)amino)phenyl) acrylamide | ¹H NMR (400 MHz, DMSO-d₆) δ 11.18 (s, 1H) 9.15 (s, 1H), 8.75 (d, J = 2.1 Hz, 1H), 8.45 (dd, J = 8.5, 2.1 Hz, 1H), 8.27 (s, 1H), 8.15 (s, 1H), 7.91 (d, J = 8.4 Hz, 1H), 6.91-6.69 (m, 2H), 6.34 (s, 1H), 6.23 (dd, J = 17.0, 2.0 Hz, 1H), 5.80-5.68 (m, 2H), 4.26 (dd, J = 7.8, 4.1 Hz, 2H), 4.01 (q, J = 7.8 Hz, 2H), 3.84 (s, 3H), 3.60 (ddd, J = 9.0, 6.4, 3.1 Hz, 1H), 3.48 (d, J = 11.4 Hz, 2H), 3.17 (d, J = 6.3 Hz, 4H), 2.81 (d, J = 4.6 Hz, 3H), 2.74 (s, 3H), 2.39 (dq, J = 8.7, 4.9, 3.8 Hz, 1H), ; 531.5 [M + H]⁺ | 1.28 |

TABLE 1-continued

| Example Compound | Structure | Name of Compound | ¹H NMR[[:]]; MS [M + H]⁺ | UPLC r.t. (min) |
|---|---|---|---|---|
| 45 | 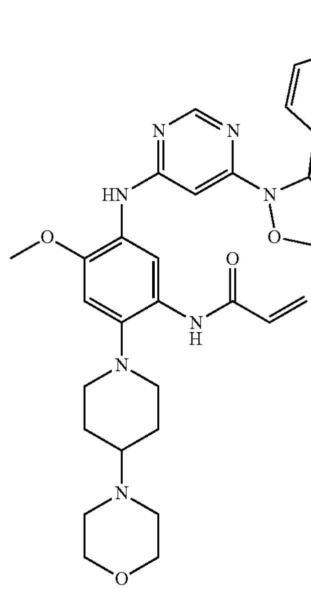 | N-(4-methoxy-5-((6-((R)-3-(6-methylpyridine-3-yl)isoxazolidine-2-yl)pyrimidine-4-yl)amino)-2-(4-morpholinopiperidine-1-yl)phenyl)acrylamide | ¹H NMR (400 MHz, Chloroform-d) δ 8.87 (s, 1H), 8.57 (d, J = 2.3 Hz, 1H), 8.44 (s, 1H), 8.36 (s, 1H), 7.70 (dd, J = 8.0, 2.4 Hz, 1H), 7.12 (d, J = 8.0 Hz, 1H), 6.95 (s, 1H), 6.73 (d, J = 12.7 Hz, 2H), 6.41-6.19 (m, 2H), 5.79-5.67 (m, 2H), 4.20-4.05 (m, 2H), 3.84 (s, 3H), 3.77 (t, J = 4.6 Hz, 4H), 3.12-3.02 (m, 2H), 2.83-2.67 (m, 3H), 2.62 (t, J = 4.7 Hz, 4H), 2.54 (s, 3H), 2.34 (m, 2H), 2.08 (d, J = 12.5 Hz, 2H), 1.65 (m, 2H), ; 601.7 [M + H]⁺ | 1.04 |
| 46 | 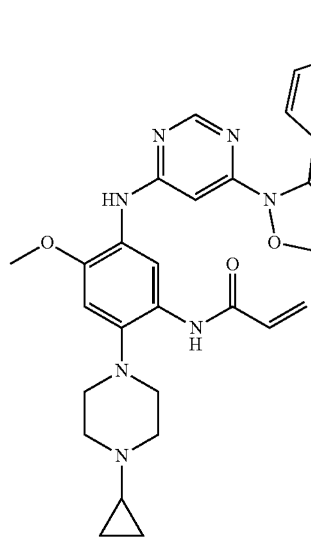 | N-(2-(4-cyclopropylpiperazine-1-yl)-4-methoxy-5-((6-((R)-3-(6-methylpyridine-3-yl)isoxazolidine-2-yl)pyrimidine-4-yl)amino)phenyl)acrylamide | ¹H NMR (400 MHz, Chloroform-d) δ 8.90 (s, 1H), 8.63-8.54 (m, 2H), 8.37 (s, 1H), 7.70 (dd, J = 8.1, 2.4 Hz, 1H), 7.13 (d, J = 8.0 Hz, 1H), 6.96 (s, 1H), 6.79 (s, 1H), 6.72 (s, 1H), 6.35-6.29 (m, 2H), 5.75 (dd, J = 9.7, 1.8 Hz, 1H), 5.73-5.70 (dd, J = 8.5, 4.3 Hz, 1H), 4.16-4.09 (m, 2H), 3.81 (s, 3H), 2.91-2.73 (m, 9H), 2.54 (s, 3H), 2.41-2.32 (m, 1H), 1.73-1.72 (m, 1H), 0.52 (dd, J = 6.5, 4.4 Hz, 2H), 0.47-0.46 (m, 2H), ; 557.6 [M + H]⁺ | 1.03 |

| Example Compound | Structure | Name of Compound | ¹H NMR[:]; MS [M + H]⁺ | UPLC r.t. (min) |
|---|---|---|---|---|
| 47 | 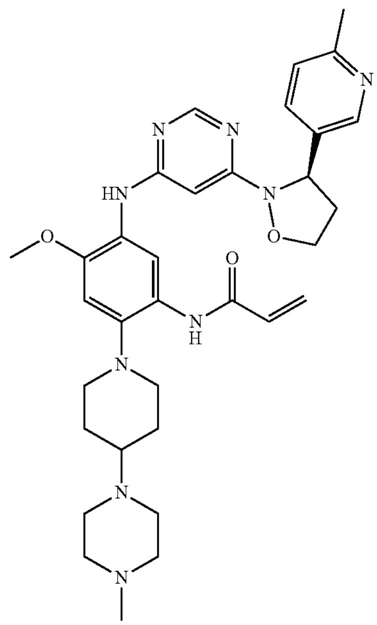 | N-(4-methoxy-2-(4-(4-methylpiperazine-1-yl)piperidine-1-yl)-5-((6((R)-3-(6-methylpyridine-3-yl)isoxazolidine-2-yl)pyrimidine-4-yl)amino)phenyl) acrylamide | ¹H NMR (400 MHz, Chloroform-d) δ 8.87 (s, 1H), 8.78 (s, 1H), 8.57 (d, J = 2.3 Hz, 1H), 8.43-8.36 (m, 2H), 7.70 (dd, J = 8.1, 2.3 Hz, 1H), 7.13 (d, J = 8.0 Hz, 1H), 6.93 (s, 1H), 6.74-6.71 (m, 2H), 6.38-6.21 (m, 1H), 5.74-5.68 (m, 2H), 4.15 (td, J = 8.1, 4.8 Hz, 1H), 4.11-4.03 (m, 1H), 3.91-3.86 (m, 1H), 3.84 (s, 3H), 3.06 (d, J = 10.9 Hz, 2H), 2.85-2.67 (m, 8H), 2.61 (s, 2H), 2.54 (s, 3H), 2.37 (m, 4H), 2.17 (s, 1H), 2.07 (d, J = 11.8 Hz, 2H), 1.70 (d, J = 12.9 Hz, 2H), ; 614.6 [M + H]⁺ | 1.00 |
| 48 | 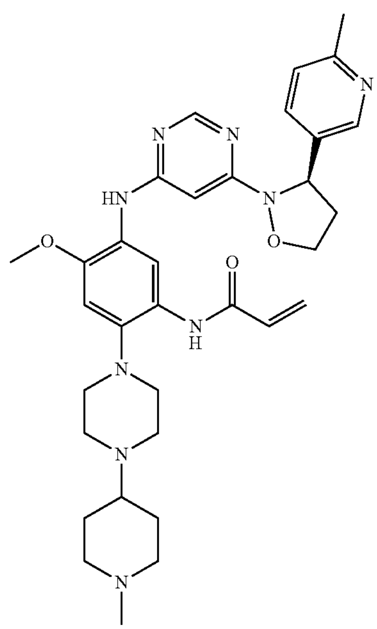 | N-(4-methoxy-2-(4-(1-methylpiperidine-4-yl)piperazine-1-yl)-5-((6-((R)-3-(6-methylpyridine-3-yl)isoxazolidine-2-yl)pyrimidine-4-yl)amino)phenyl) acrylamide | ¹H NMR (400 MHz, Chloroform-d) δ 8.90 (s, 1H), 8.57 (m, 2H), 8.37 (s, 1H), 7.70 (dd, J = 8.0, 2.4 Hz, 1H), 7.13 (d, J = 8.0 Hz, 1H), 6.94 (s, 1H), 6.81 (s, 1H), 6.72 (s, 1H), 6.36 (dd, J = 17.2, 1.6 Hz, 1H), 6.26 (dd, J = 17.0, 9.9 Hz, 1H), 5.74 (m, 1H), 5.72-5.69 (m, 1H), 4.17-4.10 (m, 2H), 3.82 (s, 3H), 2.97 (d, J = 11.2 Hz, 2H), 2.91 (m, 4H), 2.82-2.71 (m, 4H), 2.54 (s, 3H), 2.29 (m, 3H), 2.17 (s, 3H), 2.01 (t, J = 11.7 Hz, 2H), 1.87 (d, J = 12.6 Hz, 2H), 1.73-1.58 (m, 2H), ; 614.5 [M + H]⁺ | 0.90 |

TABLE 1-continued

| Example Compound | Structure | Name of Compound | ¹H NMR[[:]]; MS [M + H]⁺ | UPLC r.t. (min) |
|---|---|---|---|---|
| 49 | 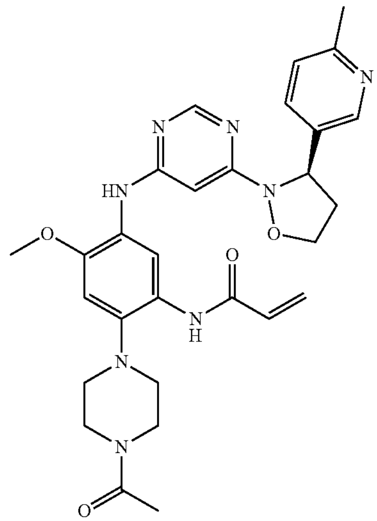 | N-(2-(4-acetylpiperazine-1-yl)-4-methoxy-5-((6-((R)-3-(6-methylpyridine-3-yl)isoxazolidine-2-yl)pyrimidine-4-yl)amino)phenyl) acrylamide | ¹H NMR (400 MHz, Chloroform-d) δ 8.95 (s, 1H), 8.57 (d, J = 2.4 Hz, 1H), 8.44 (s, 1H), 8.38 (d, J = 1.0 Hz, 1H), 7.70 (dd, J = 8.1, 2.4 Hz, 1H), 7.13 (d, J = 8.0 Hz, 1H), 6.98 (s, 1H), 6.72 (d, J = 3.9 Hz, 2H), 6.42-6.33 (m, 1H), 6.26 (dd, J = 16.9, 10.1 Hz, 1H), 5.76 (dd, J = 10.0, 1.5 Hz, 1H), 5.72 (dd, J = 8.7, 4.5 Hz, 1H), 4.17 (td, J = 8.0, 4.4 Hz, 1H), 4.10 (q, J = 8.0 Hz, 1H), 3.85 (s, 3H), 3.67-3.64 (m, 2H), 2.81-2.74 (m, 2H), 2.88 (m, 4H), 2.81-2.74 (m, 1H), 2.54 (s, 3H), 2.37 (dtd, J = 12.4, 8.1, 4.5 Hz, 1H), 2.17 (s, 3H), ; 559.5 [M + H]⁺ | 1.17 |
| 50 | 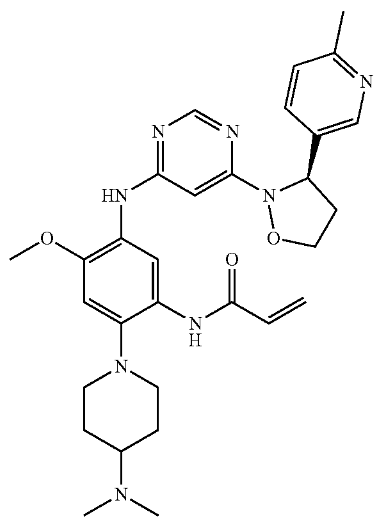 | N-(2-(4-dimethylamino-piperidine-1-yl)-4-methoxy-5-((6-((R)-3-(6-methylpyridine-3-yl)isoxazolidine-2-yl)pyrimidine-4-yl)amino)phenyl) acrylamide | ¹H NMR (400 MHz, Chloroform-d) δ 8.87 (s, 1H), 8.57 (d, J = 2.4 Hz, 1H), 0 8.45 (s, 1H), 8.36 (d, J = 1.1 Hz, 1H), 7.70 (dd, J = 8.0, 2.3 Hz, 1H), 7.13 (d, J = 8.0 Hz, 1H), 6.94 (s, 1H), 6.74 (d, J = 2.6 Hz, 1H), 6.71 (d, J = 7.3 Hz, 1H), 6.39-6.33 (m, 1H), 6.26 (dd, J = 17.0, 9.9 Hz, 1H), 5.77-5.72 (m, 1H), 5.73-5.68 (m, 1H), 4.16 (m, 1H), 4.09 (m, 1H), 3.84 (s, 3H), 3.08 (d, J = 11.3 Hz, 2H), 2.84 (dd, J = 12.0, 5.9 Hz, 1H), 2.80-2.69 (m, 3H), 2.54 (s, 3H), 2.45 (d, J = 4.6 Hz, 6H), 2.39-2.32 (m, 1H), 2.10 (d, J = 12.5 Hz, 2H), 1.76 (t, J = 11.5 Hz, 2H), ; 559.5 [M + H]⁺ | 1.03 |
| 51 | 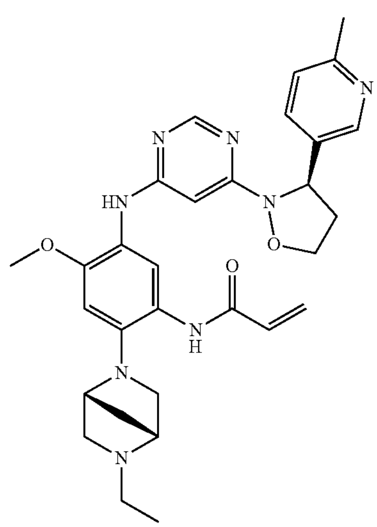 | N-(2-((1R,4R)-5-ethyl-2,5-diazabicyclo[2.2.1]heptane-2-yl)-4-methoxy-5-((6-((R)-3-(6-methylpyridine-3-yl)isoxazolidine-2-yl)pyrimidine-4-yl)amino)phenyl) acrylamide | ¹H NMR (400 MHz, Chloroform-d) δ 8.58-8.53 (m, 2H), 8.34 (s, 1H), 8.00 (s, 1H), 7.70 (dd, J = 8.1, 2.4 Hz, 1H), 7.12 (d, J = 8.0 Hz, 1H), 6.89 (s, 1H), 6.68 (d, J = 16.4 Hz, 2H), 6.38-6.26 (m, 2H), 5.72 (m, 2H), 4.20-4.03 (m, 2H), 3.85 (s, 3H), 3.65-3.54 (m, 2H), 3.07 (dd, J = 9.8, 2.4 Hz, 1H), 2.92-2.81 (m, 1H), 2.86-2.72 (m, 3H), 2.54 (s, 3H), 2.35 (dtt, J = 12.3, 8.6, 4.4 Hz, 1H), 1.33-1.30 (m, 2H), 1.92 (q, J = 9.9 Hz, 2H), 1.15 (t, J = 7.2 Hz, 3H), ; 557.5 [M + H]⁺ | 0.92 |

TABLE 1-continued

| Example Compound | Structure | Name of Compound | ¹H NMR[:]; MS [M + H]⁺ | UPLC r.t. (min) |
|---|---|---|---|---|
| 52 | 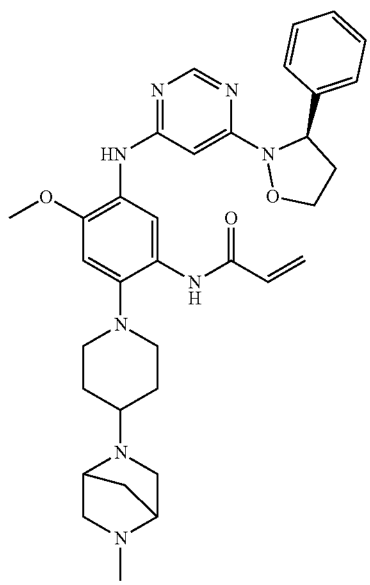 | N-(4-methoxy-2-(4-(5-methyl-2,5-diazabicyclo[2.2.1]heptane-2-yl)piperidine-1-yl)-5-((6-((R)-3-phenylisoxazolidine-2-yl)pyrimidine-1-yl)amino)phenyl)acrylamide | ¹H NMR (400 MHz, DMSO-d6) δ 11.62 (s, 1H), 9.17 (s, 1H), 8.23 (s, 1H), 7.97 (s, 1H), 7.40-7.32 (m, 4H), 7.30-7.24 (m, 1H), 6.87 (d, J = 19.3 Hz, 1H), 6.55 (m, 1H), 6.28-6.14 (m, 2H), 5.75 (d, J = 10.3 Hz, 1H), 5.52 (d, 1H), 4.74 (s, 1H), 4.48 (d, J = 20.0 Hz, 1H), 4.26-4.20 (m, 1H), 3.96 (d, J = 8.9 Hz, 2H), 3.81 (s, 3H), 3.21 (m, 4H), 2.92 (m, 5H), 2.67 (m, 4H), 2.36-2.25 (m, 2H), 2.07 (d, J = 25.9 Hz, ; 4H), 611.6 [M + H]⁺ | 1.35 |
| 53 | 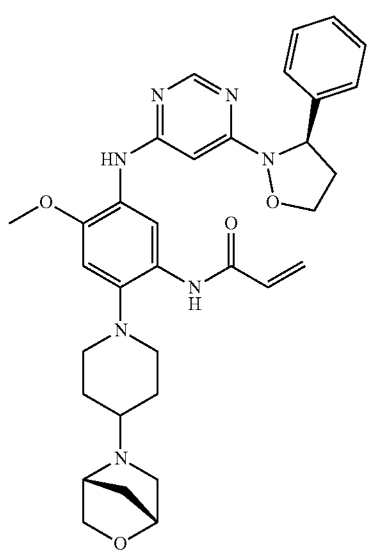 | N-(2-(4-((1R,4R)-2-oxa-5-azabicyclo[2.2.1]heptane-5-yl)piperidine-1-yl)-4-methoxy-5-((6-((R)-3-phenylisoxazolidine-2-yl)pyrimidine-4-yl)amino)phenyl)acrylamide | ¹H NMR (400 MHz, Methanol-d₄) δ 8.08 (s, 1H), 7.77 (s, 1H), 7.26 (dd, J = 7.1. 1.4 Hz, 4H), 7.20 (s, 1H), 6.94 (s, 1H), 6.54 (dd, J = 17.0, 10.2 Hz, 1H), 6.33 (dd, J = 16.9, 1.6 Hz, 1H), 5.77 (d, J = 10.2 Hz, 1H), 5.35 (s, 1H), 4.66 (s, 1H), 4.59 (d, J = 12.7 Hz, 1H), 4.33 (t, J = 3.8 Hz, 1H), 4.14-4.05 (m, 2H), 3.75 (s, 3H), 3.55 (d, J = 11.5 Hz, 1H), 3.38 (d, J = 1.6 Hz, 1H), 3.29 (s, 2H), 3.04-2.88 (m, 3H), 2.37 (ddd, J = 11.8, 8.1, 6.1 Hz, 2H), 2.19 (s, 3H), 2.05 (s, 3H), 1.69-1.58 (m, 1H), 1.45 (s, 1H); 598.3 [M + H]⁺ | 1.1 |

| Example Compound | Structure | Name of Compound | ¹H NMR[[:]]; MS [M + H]⁺ | UPLC r.t. (min) |
|---|---|---|---|---|
| 54 | 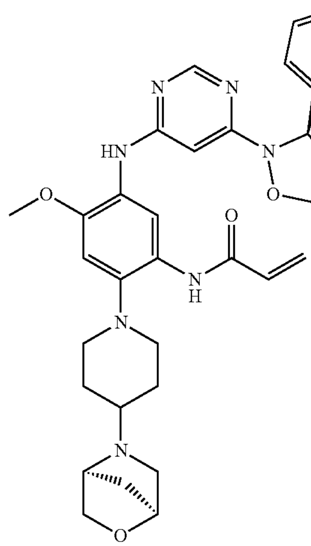 | N-(2-(4-((1S,4S)-2-oxa-5-oxabicyclo[2.2.1]heptane-5-yl)piperidine-1-yl)-4-methoxy-5-((6-((R)-3-phenylisoxazolidine-2-yl)pyrimidine-4-yl)amino)phenyl) acrylamide | ¹H NMR (400 MHz, Methanol-d₄) δ 8.04 (s, 1H), 7.76 (s, 1H), 7.57 (ddd, J = 37.8, 5.8, 3.4 Hz, 1H), 7.28-7.23 (m, 3H), 7.23-7.16 (m, 2H), 6.83 (s, 1H), 6.53 (d, J = 13.9 Hz, 1H), 6.29 (dd, J = 16.9, 1.6 Hz, 1H), 5.73 (d, J = 10.0 Hz, 1H), 5.39 (s, 1H), 4.68-4.54 (m, 2H), 4.33 (d, J = 5.6 Hz, 1H), 4.22 (d, J = 10.7 Hz, 1H) 4.12-4.05 (m, 2H), 3.78 (s, 1H), 3.72 (s, 3H), 3.54 (d, J = 11.6 Hz, 1H), 3.38 (d, J = 2.8 Hz, 1H), 2.93 (d, J = 6.8 Hz, 1H), 2.85-2.74 (m, 2H), 2.40-2.31 (m, 2H), 2.23-2.09 (m, 4H), 1.97 (d, J = 12.3 Hz, 3H); 598.3 [M + H]⁺ | 1.1 |
| 55 | 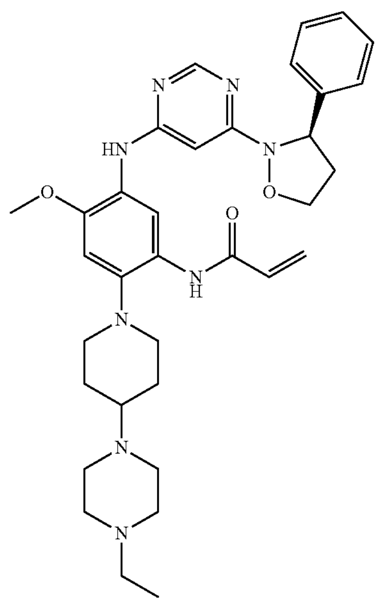 [SMILES: C=CC(=O)Nc1cc(Nc2cc(N3OCC[C@@H]3c3ccccc3)ncn2)c(OC)cc1N1CCC(N2CCN(CC)CC2)CC1] | N-(2-(4-(4-ethylpiperazine-1-yl)piperidine-1-yl)-4-methoxy-5-((6-((R)-3-phenylisoxazolidine-2-yl)pyrimidine-4-yl)amino)phenyl) acrylamide | 613.4 [M + H]⁺ | 1.07 |

TABLE 1-continued

| Example Compound | Structure | Name of Compound | ¹H NMR[:]; MS [M + H]⁺ | UPLC r.t. (min) |
|---|---|---|---|---|
| 56 | 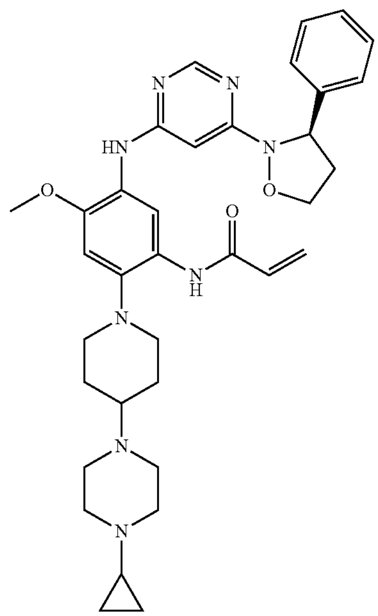 [SMILES: C=CC(=O)Nc1cc(Nc2cc(N3OCC[C@@H]3c3ccccc3)ncn2)c(OC)cc1N1CCC(N2CCN(C3CC3)CC2)CC1] | N-(2-(4-(4-cyclopropylpiperazine-1-yl)piperidine-1-yl)-4-methoxy-5-((6-((R)-3-phenylisoxazolidine-2-yl)pyrimidine-4-yl)amino)phenyl) acrylamide | ¹H NMR (400 MHz, Chloroform-d) δ 8.87 (s, 1H), 8.45 (s, 1H), 8.36 (s, 1H), 7.46 (d, J = 7.4 Hz, 2H), 7.34 (t, J = 7.6 Hz, 2H), 7.23 (d, J = 7.5 Hz, 1H), 6.91 (s, 1H), 6.74 (s, 1H), 6.69 (s, 1H), 6.36 (dd, J = 17.0, 1.6 Hz, 1H), 6.24 (dd, J = 16.9, 10.0 Hz, 1H), 5.76-5.71 (m, 1H), 5.71-5.67 (m, 1H), 4.15 (td, J = 8.0, 4.5 Hz, 1H), 4.07 (q, J = 8.1 Hz, 1H), 3.83 (s, 3H), 3.05 (d, J = 11.3 Hz, 2H), 2.78-2.64 (m, 8H), 2.37 (m, 4H), 2.08 (d, J = 12.4 Hz, 2H), 1.66 (m, 4H), 0.50-0.38 (m, 4H); 625.59 [M + H]⁺ | 1.56 |
| 57 | 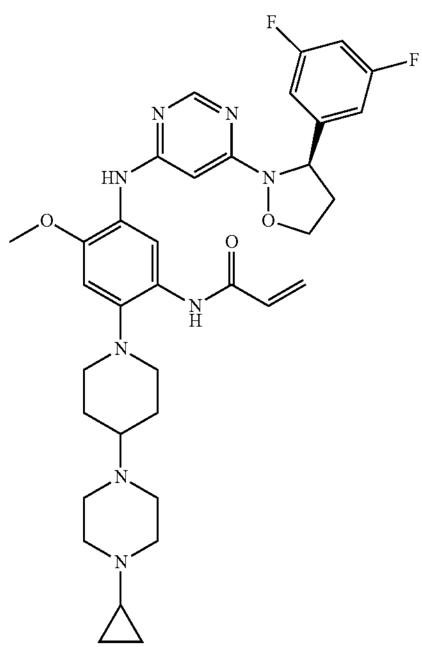 [SMILES: C=CC(=O)Nc1cc(Nc2cc(N3OCC[C@@H]3c3cc(F)cc(F)c3)ncn2)c(OC)cc1N1CCC(N2CCN(C3CC3)CC2)CC1] | N-(2-(4-(4-(cyclopropylpiperazine-1-yl)piperidine-1-yl)-5-((6-((R)-3-(3,5-difluorophenyl)isoxazolidine-2-yl)pyrimidine-4-yl)amino)-4-methoxyphenyl) acrylamide | ¹H NMR (400 MHz, Chloroform-d) δ 8.86 (s, 1H), 8.45 (s, 1H), 8.36 (d, J = 1.0 Hz, 1H), 7.04-6.98 (m, 2H), 6.97 (s, 1H), 6.77-6.64 (m, 3H), 6.42-6.23 (m, 2H), 5.74 (dd, J = 1.6, 10.0 Hz, 1H), 5.67 (dd, J = 4.5, 8.7 Hz, 1H), 4.15 (td, J = 4.2, 8.0 Hz, 1H), 4.06 (q, J = 8.0 Hz, 1H), 3.84 (s, 3H), 3.11-3.01 (m, 2H), 2.82-2.61 (m, 10H), 2.43-2.28 (m, 2H), 2.12-2.04 (m, 2H), 1.74-1.61 (m, 3H), 0.51-0.40 (m, 4H); 661.3 [M + H]⁺ | 1.23 |

TABLE 1-continued

| Example Compound | Structure | Name of Compound | ¹H NMR[[:]]; MS [M + H]⁺ | UPLC r.t. (min) |
|---|---|---|---|---|
| 58 | 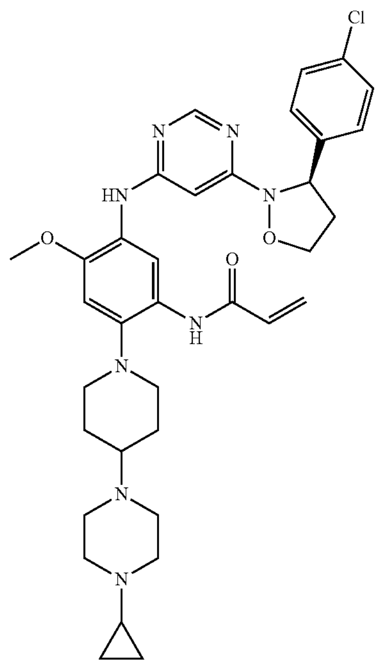 [SMILES: C=CC(=O)Nc1cc(Nc2cc(N3OCC[C@@H]3c3ccc(Cl)cc3)ncn2)c(OC)cc1N1CCC(N2CCN(C3CC3)CC2)CC1] | N-(5-((6-((R)-3-(4-chlorophenyl)isoxazolidine-2-yl)pyrimidine-4-yl)amino)-2-(4-(4-cyclopropylpiperazine-1-yl)piperidine-1-yl)-4-methoxyphenyl)acrylamide | $^1$H NMR (400 MHz, DMSO-$d_6$) δ 9.74 (s, 1H), 9.16 (s, 1H), 8.27 (s, 2H), 7.95 (s, 1H), 7.44-7.33 (m, 7H), 6.88 (s, 2H), 6.68 (dd, J = 17.0, 10.3 Hz, 1H), 6.24 (dd, J = 17.0, 2.0 Hz, 1H), 6.10 (s, 1H), 5.82-5.72 (m, 1H), 5.52 (dd, J = 8.4, 5.4 Hz, 2H), 3.88 (q, J = 5.2, 4.0 Hz, 2H), 3.80 (s, 9H), 3.20 (d, J = 11.7 Hz, 5H), 2.96-2.84 (m, 3H), 2.78 (t, J = 11.5 Hz, 4H), 2.34-2.21 (m, 3H), 2.22-1.95 (m, 8H), 1.03 (d, J = 24.0 Hz, 3H), 0.89-0.69 (m, 4H); 659.56 [M + H]⁺ | 1.34 |
| 59 | 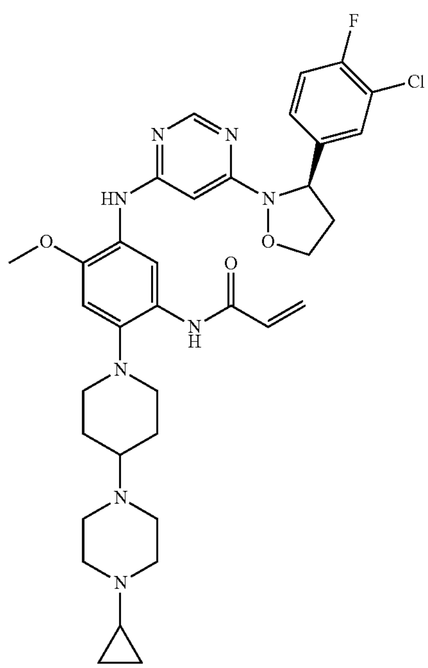 [SMILES: C=CC(=O)Nc1cc(Nc2cc(N3OCC[C@@H]3c3ccc(F)c(Cl)c3)ncn2)c(OC)cc1N1CCC(N2CCN(C3CC3)CC2)CC1] | N-(5-((6-((R)-3-(3-chloro-4-fluorophenyl)isoxazolidine-2-yl)pyrimidine-4-yl)amino)-2-(4-(4-cyclopropylpiperazine-1-yl)piperidine-1-yl)-4-methoxyphenyl)acrylamide; | $^1$H NMR (400 MHz, Methanol-$d_4$) δ 8.18 (d, J = 3.1 Hz, 1H), 8.07 (s, 1H), 7.45 (dd, J = 2.2, 7.1 Hz, 1H), 7.37-7.25 (m, 1H), 7.12 (t, J = 8.8 Hz, 1H), 6.81 (s, 1H), 6.45 (dd, J = 10.2, 17.0 Hz, 1H), 6.34 (s, 1H), 6.26 (d, J = 16.8 Hz, 1H), 5.70 (d, J = 10.3 Hz, 1H), 5.47-5.37 (m, 1H), 4.05 (td, J = 4.3, 8.0 Hz, 1H), 3.87 (q, J = 8.0 Hz, 1H), 3.77 (s, 3H), 3.13-3.05 (m, 2H), 2.97-2.88 (m, 3H), 2.83-2.66 (m, 8H), 2.23 (dtt, J = 3.5, 8.1, 12.6 Hz, 1H), 2.10-1.99 (m, 2H), 1.83-1.68 (m, 3H), 0.83-0.75 (m, 1H), 0.50-0.42 (m, 2H), 0.42-0.34 (m, 2H); 677.3 [M + H]⁺ | 1.32 |

TABLE 1-continued

| Example Compound | Structure | Name of Compound | ¹H NMR[:]; MS [M + H]⁺ | UPLC r.t. (min) |
|---|---|---|---|---|
| 60 | 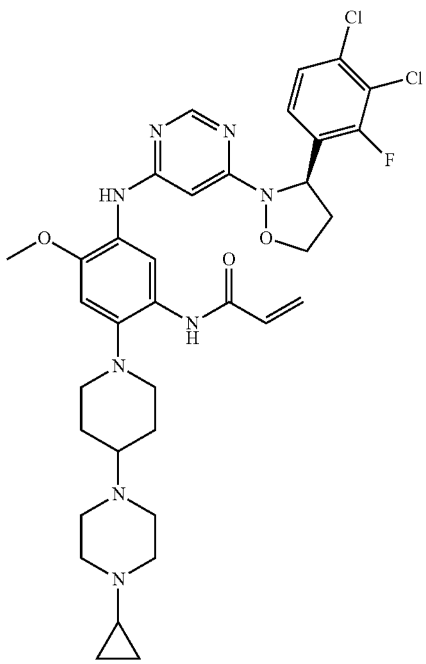 [SMILES: C=CC(=O)Nc1cc(Nc2cc(N3OCC[C@@H]3c3ccc(Cl)c(Cl)c3F)ncn2)c(OC)cc1N1CCC(N2CCN(C3CC3)CC2)CC1] | N-(2-(4-(4-cyclopropylpiperazine-1-yl)piperidine-1-yl)-5-((6-((R)-3-(3,4-dichloro-2-fluorophenyl)isoxazolidine-2-yl)pyrimidine-4-yl)amino)-4-methoxyphenyl)acrylamide; | ¹H NMR (400 MHz, Methanol-d₄) δ 8.18 (d, J = 2.9 Hz, 1H), 8.06 (s, 1H), 7.39 (t, J = 8.0 Hz, 1H), 7.27 (dd, J = 1.6, 8.6 Hz, 1H), 6.81 (s, 1H), 6.45 (dd, J = 10.2, 16.9 Hz, 1H), 6.37 (s, 1H), 6.26 (d, J = 16.6 Hz, 1H), 5.78-5.56 (m, 2H), 4.06 (td, J = 3.9, 7.9 Hz, 1H), 3.88 (q, J = 8.0 Hz, 1H), 3.78 (s, 3H), 3.12-3.03 (m, 2H), 2.95-2.83 (m, 3H), 2.83-2.65 (m, 8H), 2.17 (dtd, J = 4.8, 8.0, 12.8 Hz, 1H), 2.08-1.97 (m, 2H), 1.81-1.66 (m, 3H), 0.83-0.78 (m, 1H), 0.51-0.42 (m, 2H), 0.41-0.33 (m, 2H); 711.3 [M + H]⁺ | 1.52 |
| 61 | 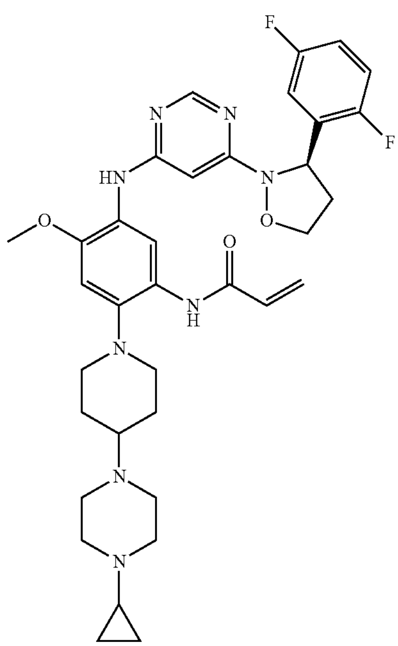 [SMILES: C=CC(=O)Nc1cc(Nc2cc(N3OCC[C@@H]3c3cc(F)ccc3F)ncn2)c(OC)cc1N1CCC(N2CCN(C3CC3)CC2)CC1] | N-(2-(4-(4-cyclopropylpiperazine-1-yl)piperidine-1-yl)-5-((6-((R)-3-(2,5-difluorophenyl)isoxazolidine-2-yl)pyrimidine-4-yl)amino)-4-methoxyphenyl)acrylamide; | ¹H NMR (400 MHz, Methanol-d₄) δ 8.19 (d, J = 8.8 Hz, 1H), 8.07 (s, 1H), 7.14 (ddt, J = 2.8, 5.9, 8.8 Hz, 1H), 7.04 (td, J = 4.4, 9.3 Hz, 1H), 6.92 (tt, J = 3.6, 8.0 Hz, 1H), 6.81 (s, 1H), 6.53-6.34 (m, 2H), 6.26 (d, J = 16.7 Hz, 1H), 5.76-5.60 (m, 2H), 4.04 (td, J = 4.2, 8.0 Hz, 1H), 3.88 (q, J = 8.0 Hz, 1H), 3.78 (s, 3H), 3.13-3.04 (m, 2H), 2.97-2.84 (m, 3H), 2.84-2.65 (m, 8H), 2.16 (dtd, J = 4.6, 8.0, 12.5 Hz, 1H), 2.08-1.98 (m, 2H), 1.82-1.66 (m, 3H), 0.83-0.75 (m, 1H), 0.51-0.42 (m, 2H), 0.40-0.34 (m, 2H); 661.3 [M + H]⁺ | 1.38 |

TABLE 1-continued

| Example Compound | Structure | Name of Compound | ¹H NMR[:]; MS [M + H]⁺ | UPLC r.t. (min) |
|---|---|---|---|---|
| 62 | 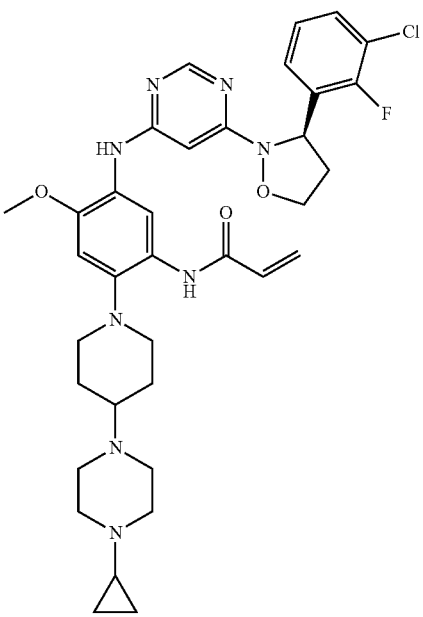 [SMILES: C=CC(=O)Nc1cc(Nc2cc(N3OCC[C@@H]3c3cccc(Cl)c3F)ncn2)c(OC)cc1N1CCC(N2CCN(C3CC3)CC2)CC1] | N-(5-((6-((R)-3-(3-chloro-2-fluorophenyl)isoxazolidine-2-yl)pyrimidine-4-yl)amino)-2-(4-(4-cyclopropylpiperazine-1-yl)piperidine-1-yl)-4-methoxyphenyl)acrylamide | ¹H NMR (400 MHz, Methanol-$d_4$) δ 8.29 (d, J = 8.5 Hz, 1H), 8.17 (s, 1H), 7.49 (t, J = 7.3 Hz, 1H), 7.40 (t, J = 7.6 Hz, 1H), 7.16 (t, J = 7.9 Hz, 1H), 6.92 (s, 1H), 6.56 (dd, J = 10.2, 16.9 Hz, 1H), 6.48 (d, J = 6.0 Hz, 1H), 6.37 (d, J = 16.8 Hz, 1H), 5.80 (t, J = 9.9 Hz, 2H), 4.16 (td, J = 4.2, 8.0 Hz, 1H), 3.99 (q, J = 8.0 Hz, 1H), 3.89 (s, 3H), 3.24-3.16 (m, 2H), 3.08-2.95 (m, 3H), 2.95-2.76 (m, 8H), 2.32-2.22 (m, 1H), 2.19-2.10 (m, 2H), 1.94-1.77 (m, 3H), 0.95-0.88 (m, 1H), 0.61-0.53 (m, 2H), 0.52-0.44 (m, 2H); 677.3 [M + H]⁺ | 1.48 |
| 63 | 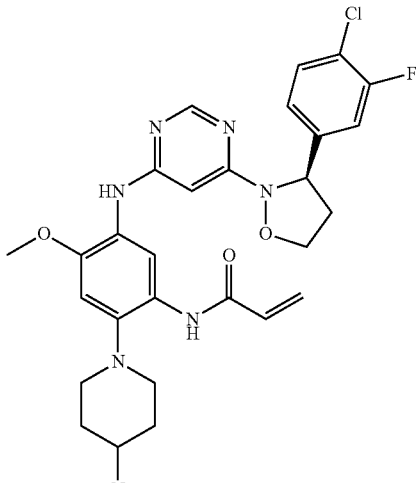 | N-(5-((6-((R)-3-(4-chloro-3-fluorophenyl)isoxazolidine-2-yl)pyrimidine-4-yl)amino)-2-(4-(4-cyclopropylpiperazine-1-yl)piperidine-1-yl)-4-methoxyphenyl)acrylamide | ¹H NMR (400 MHz, Methanol-$d_4$) δ 8.32 (s, 1H), 8.18 (d, J = 0.9 Hz, 1H), 7.45 (t, J = 7.9 Hz, 1H), 7.34 (dd, J = 2.0, 10.5 Hz, 1H), 7.27 (dd, J = 2.0, 8.3 Hz, 1H), 6.92 (s, 1H), 6.57 (dd, J = 10.3, 17.0 Hz, 1H), 6.46 (d, J = 1.0 Hz, 1H), 6.36 (dd, J = 1.5, 17.0 Hz, 1H), 5.81 (dd, J = 1.5, 10.3 Hz, 1H), 5.56 (dd, J = 4.7, 8.6 Hz, 1H), 4.15 (td, J = 4.1, 7.9 Hz, 1H), 3.98 (q, J = 8.0 Hz, 1H), 3.88 (s, 3H), 3.22-3.08 (m, 2H), 2.87-2.72 (m, 11H), 2.57-2.43 (m, 1H), 2.34 (dtd, J = 4.5, 8.0, 12.6 Hz, 1H), 2.17-2.03 (m, 2H) 1.86-1.66 (m, 3H), 0.61-0.48 (m, 2H), 0.48-0.38 (m, 2H); 677.3 [M + H]⁺ | 1.42 |

TABLE 1-continued

| Example Compound | Structure | Name of Compound | $^1$H NMR[:]; MS [M + H]$^+$ | UPLC r.t. (min) |
|---|---|---|---|---|
| 64 | 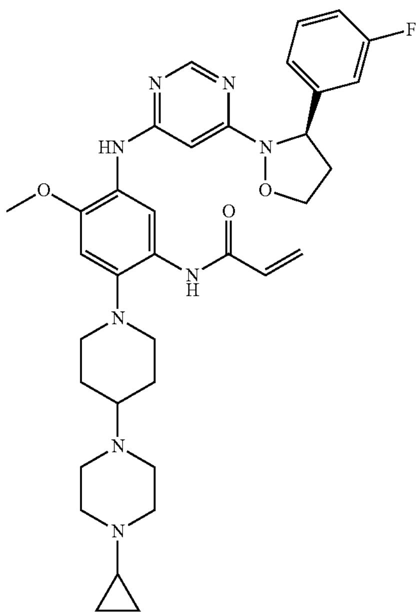 [SMILES: C=CC(=O)Nc1cc(Nc2cc(N3OCC[C@@H]3c3cccc(F)c3)ncn2)c(OC)cc1N1CCC(N2CCN(C3CC3)CC2)CC1] | N-(2-(4-(4-cyclopropylpiperazine-1-yl)piperidine-1-yl)-5-((6-((R)-3-(3-fluorophenyl)isoxazolidine-2-yl)pyrimidine-4-yl)amino)-4-methoxyphenyl)acrylamide | $^1$H NMR (400 MHz, DMSO-d$_6$) δ 9.91 (s, 1H), 9.19 (s, 1H), 8.30 (s, 2H), 7.94 (s, 1H), 7.42 (td, J = 7.9, 6.0 Hz, 2H), 7.24-7.16 (m, 3H), 7.12 (td, J = 8.7, 2.7 Hz, 2H), 6.89 (s, 1H), 6.70 (dd, J = 17.0, 10.2 Hz, 2H), 6.25 (dd, J = 17.0, 1.9 Hz, 2H), 6.11 (s, 1H), 5.81-5.71 (m, 2H), 5.54 (dd, J = 8.5, 5.4 Hz, 2H), 3.89 (t, J = 6.1 Hz, 3H), 3.80 (s, 11H), 3.22 (d, J = 11.5 Hz, 5H), 2.92 (dtd, J = 12.2, 8.0, 7.5, 4.2 Hz, 3H), 2.79 (t, J = 11.7 Hz, 4H), 2.32 (dtd, J = 12.7, 7.6, 5.2 Hz, 2H), 2.23-1.96 (m, 8H), 1.13 (s, 4H), 0.91-0.72 (m, 4H); 643.59 [M + H]$^+$ | 1.34 |
| 65 | 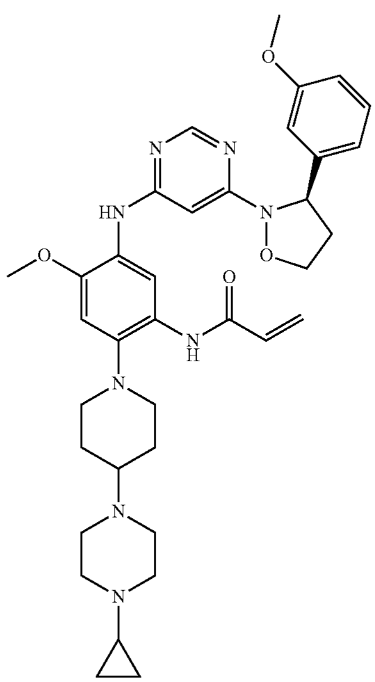 [SMILES: C=CC(=O)Nc1cc(Nc2cc(N3OCC[C@@H]3c3cccc(OC)c3)ncn2)c(OC)cc1N1CCC(N2CCN(C3CC3)CC2)CC1] | N-(2-(4-(4-cyclopropylpiperazine-1-yl)piperidine-1-yl)-4-methoxy-5-((6-((R)-3-(3-methoxyphenyl)isoxazolidine-2-yl)pyrimidine-4-yl)amino)phenyl)acrylamide | $^1$H NMR (400 MHz, DMSO-d$_6$) δ 12.41 (s, 1H), 10.22 (s, 1H), 9.24 (s, 1H), 8.32 (s, 1H), 7.87 (s, 1H), 7.29 (t, J = 7.8 Hz, 1H), 6.89 (dt, J = 14.1, 6.9 Hz, 4H), 6.72 (dd, J = 16.9, 10.3 Hz, 1H), 6.25 (dd, J = 17.0, 1.5 Hz, 1H), 5.76 (d, J = 11.5 Hz, 1H), 5.50-5.44 (m, 1H), 4.33 (dd, J = 11.9, 7.4 Hz, 1H), 4.12-4.05 (m, 3H), 3.79 (s, 3H), 3.75 (s, 3H), 3.23 (d, J = 10.7 Hz, 2H), 3.00-2.87 (m, 2H), 2.81 (t, J = 11.2 Hz, 2H), 2.32 (td, J = 12.7, 7.6 Hz, 1H), 2.22-2.06 (m, 4H), 1.61 (dd, J = 8.2, 4.5 Hz, 3H), 1.46-1.38 (m, 3H), 1.19 (s, 2H), 0.87-0.81 (m, 2H); 655.62 [M + H]$^+$ | 1.13 |

TABLE 1-continued

| Example Compound | Structure | Name of Compound | ¹H NMR[:]; MS [M + H]⁺ | UPLC r.t. (min) |
|---|---|---|---|---|
| 66 | 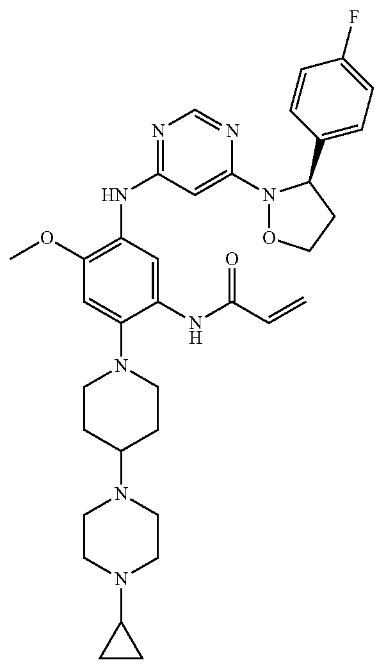 [SMILES: C=CC(=O)Nc1cc(Nc2cc(N3OCC[C@@H]3c3ccc(F)cc3)ncn2)c(OC)cc1N1CCC(N2CCN(C3CC3)CC2)CC1] | N-(2-(4-(4-cyclopropylpiperazine-1-yl)piperidine-1-yl)-5-((6-((R)-3-(4-fluorophenyl)isoxazolidine-2-yl)pyrimidine-4-yl)amino)-4-methoxyphenyl)acrylamide | ¹H NMR (400 MHz, DMSO-d₆) δ 9.88 (s, 1H), 9.18 (s, 1H), 8.29 (s, 1H), 7.93 (s, 1H), 7.40 (dd, J = 8.6, 5.6 Hz, 2H), 7.20 (t, J = 8.8 Hz, 2H), 6.89 (s, 1H), 6.69 (dd, J = 17.0, 10.3 Hz, 1H), 6.25 (dd, J = 17.0, 1.9 Hz, 1H), 6.08 (s, 1H), 5.76 (dd, J = 10.1, 2.0 Hz, 1H), 5.52 (t, J = 7.1 Hz, 1H), 4.32-4.26 (m, 1H), 4.04 (d, J = 7.7 Hz, 3H), 3.80 (s, 3H), 3.71 (s, 4H), 3.41-3.35 (m, 2H), 3.21 (d, J = 11.5 Hz, 2H), 2.90 (d, J = 9.0 Hz, 1H), 2.80 (d, J = 11.8 Hz, 2H), 2.34-2.24 (m, 2H), 2.16 (s, 2H), 2.06 (s, 1H), 1.65-1.56 (m, 1H), 1.48-1.40 (m, 1H), 1.11 (s, 2H), 0.81 (d, J = 7.0 Hz, 2H); 643.34 [M + H]⁺ | 1.14 |
| 67 | 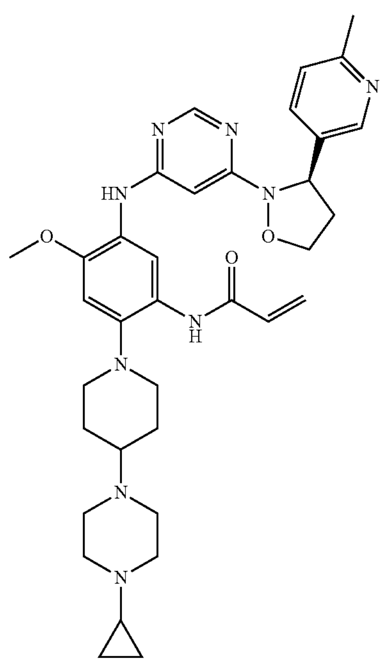 [SMILES: C=CC(=O)Nc1cc(Nc2cc(N3OCC[C@@H]3c3ccc(C)nc3)ncn2)c(OC)cc1N1CCC(N2CCN(C3CC3)CC2)CC1] | N-(2-(4-(4-cyclopropylpiperazine-1-yl)piperidine-1-yl)-4-methoxy-5-((6-((R)-3-(6-methylpyridine-3-yl)isoxazolidine-2-yl)pyrimidine-4-yl)amino)phenyl)acrylamide | ¹H NMR (400 MHz, Chloroform-d) δ 8.86 (s, 1H), 8.57 (d, J = 2.4 Hz, 1H), 8.44 (s, 1H), 8.36 (s, 1H), 7.70 (dd, J = 8.0, 2.4 Hz, 1H), 7.13 (d, J = 8.0 Hz, 1H), 6.94 (s, 1H), 6.74 (s, 1H), 6.71 (s, 1H), 6.45-6.31 (m, 1H), 6.25 (dd, J = 16.9, 10.0 Hz, 1H), 5.74 (dd, J = 9.9, 1.5 Hz, 1H), 5.72-5.68 (m, 1H), 4.15-4.09 (m, 2H), 3.84 (s, 3H), 3.06 (d, J = 12.6 Hz, 2H), 2.74 (m, 8H), 2.54 (s, 3H), 2.36 (ddt, J = 16.1, 7.9, 4.5 Hz, 4H), 2.08 (d, J = 12.4 Hz, 2H), 1.75-1.62 (m, 4H), 0.52-0.39 (m, 4H); 640.63 [M + H]⁺ | 0.85 |

TABLE 1-continued

| Example Compound | Structure | Name of Compound | ¹H NMR[[:]]; MS [M + H]⁺ | UPLC r.t. (min) |
|---|---|---|---|---|
| 68 | 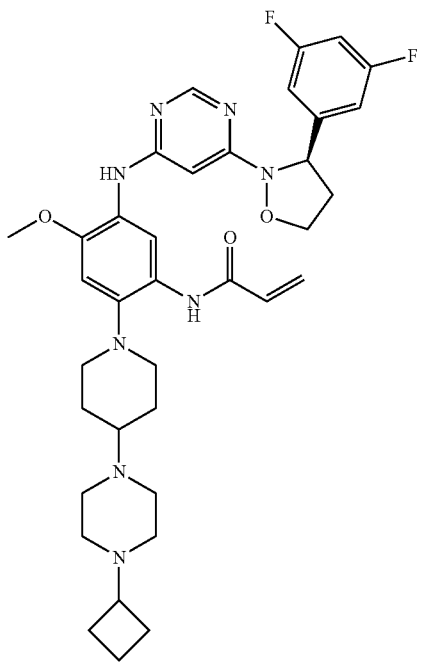 [SMILES: C=CC(=O)Nc1cc(Nc2cc(N3OCC[C@@H]3c3cc(F)cc(F)c3)ncn2)c(OC)cc1N1CCC(N2CCN(C3CCC3)CC2)CC1] | N-(2-(4-(4-cyclobutylpiperazine-1-yl)piperidine-1-yl)-5-((6-((R)-3-(3,5-difluorophenyl)isoxazolidine-2-yl)pyrimidine-4-yl)amino)-4-methoxyphenyl)acrylamide | ¹H NMR (400 MHz, Methanol-d₄) δ 8.18 (s, 1H), 8.07 (s, 1H), 7.01-6.91 (m, 2H), 6.81 (s, 1H), 6.73 (tt, J = 2.4, 9.1 Hz, 1H), 6.44 (dd, J = 10.2, 17.0 Hz, 1H), 6.35 (s, 1H), 6.25 (dd, J = 1.5, 17.0 Hz, 1H), 5.70 (d, J = 10.3 Hz, 1H), 5.46 (dd, J = 4.8, 8.7 Hz, 1H), 4.04 (td, J = 4.1, 7.9 Hz, 1H), 3.86 (q, J = 8.0 Hz, 1H), 3.77 (s, 3H), 3.14-3.03 (m, 3H), 2.88-2.66 (m, 11H), 2.55 (tt, J = 3.7, 11.4 Hz, 1H), 2.29-2.17 (m, 2H), 2.16-2.06 (m, 2H), 2.00-1.92 (m, 4H), 1.77-1.68 (m, 4H); 675.4 [M + H]⁺ | 1.23 |
| 69 | 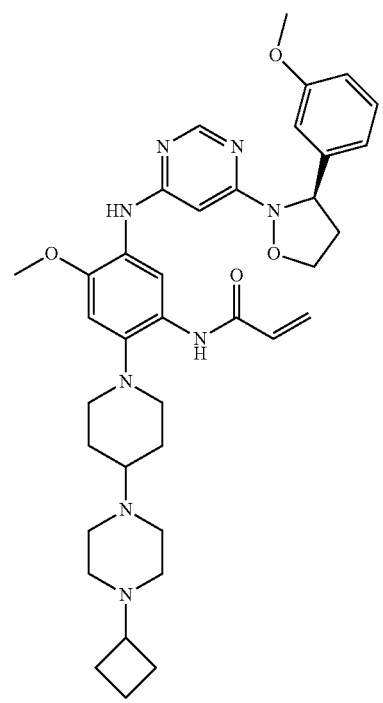 [SMILES: C=CC(=O)Nc1cc(Nc2cc(N3OCC[C@@H]3c3cccc(OC)c3)ncn2)c(OC)cc1N1CCC(N2CCN(C3CCC3)CC2)CC1] | N-(2-(4-(4-cyclobutylpiperazine-1-yl)piperidine-1-yl)-4-methoxy-5-((6-((R)-3-(3-methoxyphenyl)isoxazolidine-2-yl)pyrimidine-4-yl)amino)phenyl)acrylamide | ¹H NMR (400 MHz, DMSO-d₆) δ 12.66 (s, 1H), 10.27 (s, 1H), 9.27 (s, 1H), 8.32 (s, 1H), 7.87 (s, 1H), 7.29 (t, J = 7.8 Hz, 1H), 6.88 (dd, J = 12.2, 7.1 Hz, 4H), 6.74 (dd, J = 16.8, 10.2 Hz, 1H), 6.30-6.21 (m, 1H), 6.00 (s, 1H), 5.77 (d, J = 11.4 Hz, 1H), 5.52-5.42 (m, 1H), 4.33 (dd, J = 11.9, 7.4 Hz, 2H), 4.09 (dd, J = 15.1, 7.6 Hz, 4H), 3.79 (s, 3H), 3.75 (s, 3H), 3.66 (d, J = 12.2 Hz, 4H), 3.46 (d, J = 11.8 Hz, 2H), 3.24 (d, J = 10.6 Hz, 2H), 2.99-2.89 (m, 1H), 2.82 (t, J = 11.0 Hz, 2H), 2.45-2.28 (m, 3H), 2.19 (d, J = 7.8 Hz, 4H), 1.81-1.66 (m, 2H), 1.61 (dd, J = 7.5, 3.8 Hz, 2H), 1.44 (d, J = 2.7 Hz, 2H), 1.24 (s, 1H); 669.62 [M + H]⁺ | 1.10 |

TABLE 1-continued

| Example Compound | Structure | Name of Compound | ¹H NMR[:]; MS [M + H]⁺ | UPLC r.t. (min) |
|---|---|---|---|---|
| 70 | 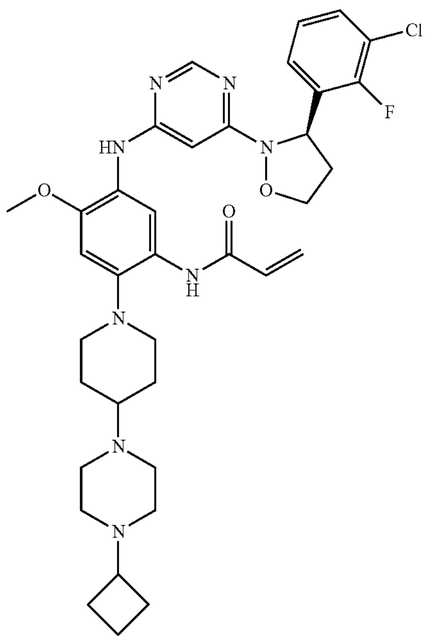 [SMILES: C=CC(=O)Nc1cc(Nc2cc(N3OCC[C@@H]3c3cccc(Cl)c3F)ncn2)c(OC)cc1N1CCC(N2CCN(C3CCC3)CC2)CC1] | N-(5-((6-((R)-3-(3-chloro-2-fluorophenyl)isoxazolidine-2-yl)pyrimidine-4-yl)amino)-2-(4-(4-cyclobutylpiperazine-1-yl)piperidine-1-yl)-4-methoxyphenyl)acrylamide | ¹H NMR (400 MHz, DMSO-d₆) δ 9.99 (s, 1H), 9.16 (s, 1H), 8.67 (t, J = 5.6 Hz, 1H), 8.24 (s, 1H), 8.02 (s, 1H), 7.58-7.48 (m, 1H), 7.43-7.35 (m, 1H), 7.24 (t, J = 7.9 Hz, 1H), 6.88 (s, 1H), 6.69 (ddd, J = 16.5, 10.4, 5.9 Hz, 2H), 6.25 (ddd, J = 17.1, 5.2, 2.0 Hz, 3H), 5.82 (dd, J = 10.3, 2.0 Hz, 1H), 5.78-5.69 (m, 1H), 3.98 (d, J = 7.8 Hz, 1H), 3.81 (s, 3H), 3.69 (q, J = 7.4 Hz, 1H), 3.22-3.16 (m, 2H), 3.09-3.01 (m, 2H), 2.74 (d, J = 4.9 Hz, 8H), 2.42-2.32 (m, 1H), 2.19 (td, J = 14.7, 13.5, 6.9 Hz, 4H), 1.93-1.82 (m, 4H), 1.76 (dd, J = 20.2, 10.2 Hz, 2H), ; 691.5 [M + H]⁺ | 1.26 |
| 71 | 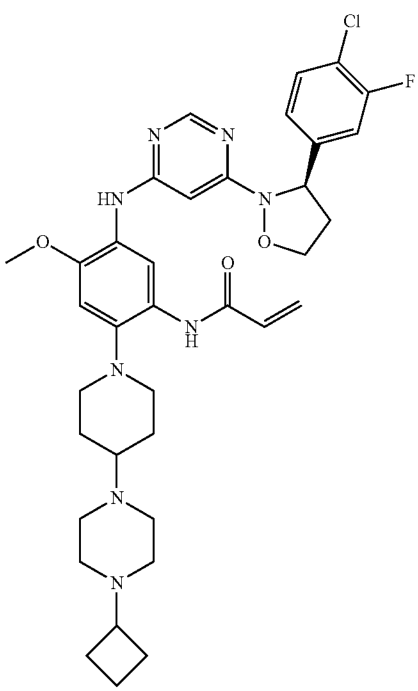 [SMILES: C=CC(=O)Nc1cc(Nc2cc(N3OCC[C@@H]3c3ccc(Cl)c(F)c3)ncn2)c(OC)cc1N1CCC(N2CCN(C3CCC3)CC2)CC1] | N-(5-((6-((R)-3-(4-chloro-3-fluorophenyl)isoxazolidine-2-yl)pyrimidine-4-yl)amino)-2-(4-(4-cyclobutylpiperazine-1-yl)piperidine-1-yl)-4-methoxyphenyl)acrylamide | ¹H NMR (400 MHz, DMSO-d₆) δ 9.19 (s, 1H), 8.29 (d, J = 11.0 Hz, 1H), 8.03-7.88 (m, 1H), 7.59 (t, J = 8.1 Hz, 1H), 7.41 (d, J = 10.7 Hz, 1H), 7.25 (d, J = 8.3 Hz, 1H), 6.89 (d, J = 5.7 Hz, 1H), 6.69 (dd, J = 17.0, 10.2 Hz, 1H), 6.25 (d, J = 16.9 Hz, 1H), 6.14 (s, 1H), 5.76 (d, J = 10.2 Hz, 1H), 5.54 (dd, J = 8.5, 5.4 Hz, 1H), 4.37-4.19 (m, 1H), 3.81 (s, 5H), 3.75 (s, 4H), 3.20 (s, 3H), 2.89 (s, 2H), 2.77 (dd, J = 22.8, 11.2 Hz, 3H), 2.45-2.26 (m, 4H), 2.19 (dd, J = 17.1, 9.1 Hz, 5H), 2.05 (d, J = 12.4 Hz, 2H), 1.74 (dt, J = 28.6, 9.7 Hz, 3H); 691.5 [M + H]⁺ | 1.24 |

TABLE 1-continued

| Example Compound | Structure | Name of Compound | $^1$H NMR[:]; MS [M + H]$^+$ | UPLC r.t. (min) |
|---|---|---|---|---|
| 72 | 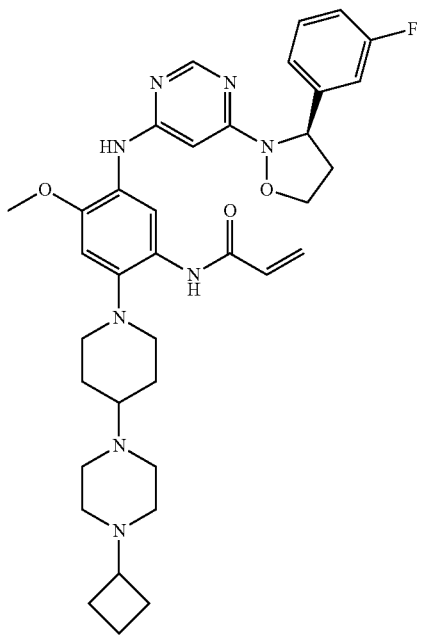 [SMILES: C=CC(=O)Nc1cc(Nc2cc(N3OCC[C@@H]3c3cccc(F)c3)ncn2)c(OC)cc1N1CCC(N2CCN(C3CCC3)CC2)CC1] | N-(2-(4-(4-cyclobutylpiperazine-1-yl)piperidine-1-yl)-5-((6-((R)-3-(3-fluorophenyl)isoxazolidine-2-yl)pyrimidine-4-yl)amino)-4-methoxyphenyl)acrylamide | $^1$H NMR (400 MHz, DMSO-d$_6$) δ 10.12 (s, 1H), 9.24 (s, 1H), 8.31 (s, 1H), 7.90 (s, 1H), 7.43 (q, J = 7.5 Hz, 1H), 7.16 (dt, J = 24.6, 8.5 Hz, 3H), 6.90 (s, 1H), 6.72 (dd, J = 16.9, 10.2 Hz, 1H), 6.26 (d, J = 17.0 Hz, 1H), 6.07 (s, 1H), 5.77 (d, J = 10.3 Hz, 1H), 5.60-5.46 (m, 1H), 4.32 (q, J = 7.0 Hz, 2H), 4.07 (q, J = 7.6 Hz, 2H), 3.80 (s, 3H), 3.23 (d, J = 11.4 Hz, 4H), 2.95 (h, J = 6.8, 6.2 Hz, 2H), 2.80 (t, J = 11.6 Hz, 3H), 2.76 (dd, J = 22.8, 11.2 Hz, 3H), 2.46-2.28 (m, 3H), 2.21 (q, J = 10.9, 9.7 Hz, 5H), 2.15-2.00 (m, 2H), 1.74 (dt, J = 28.4, 9.9 Hz, 2H); 657.57 [M + H]$^+$ | 1.16 |
| 73 | 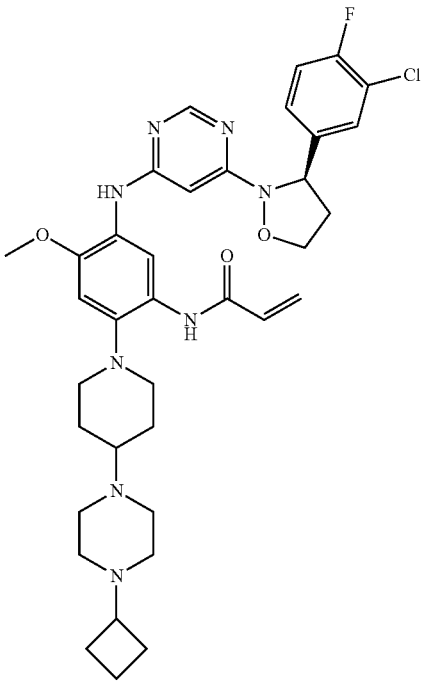 [SMILES: C=CC(=O)Nc1cc(Nc2cc(N3OCC[C@@H]3c3ccc(F)c(Cl)c3)ncn2)c(OC)cc1N1CCC(N2CCN(C3CCC3)CC2)CC1] | N-(5-((6-((R)-3-(3-chloro-4-fluorophenyl)isoxazolidine-2-yl)pyrimidine-4-yl)amino)-2-(4-(4-cyclobutylpiperazine-1-yl)piperidine-1-yl)-4-methoxyphenyl)acrylamide | $^1$H NMR (400 MHz, DMSO-d$_6$) δ 9.94 (s, 1H), 9.20 (s, 1H), 8.30 (d, J = 2.2 Hz, 1H), 7.94 (s, 1H), 7.58 (dd, J = 7.1, 2.1 Hz, 1H), 7.43 (s, 1H), 7.41-7.35 (m, 2H), 6.90 (s, 1H), 6.70 (dd, J = 16.9, 10.3 Hz, 1H), 6.25 (dd, J = 17.0, 1.9 Hz, 1H), 6.13 (s, 1H), 5.76 (dd, J = 9.9, 2.0 Hz, 1H), 5.53 (dd, J = 8.5, 5.4 Hz, 1H), 3.89 (t, J = 6.1 Hz, 7H), 3.80 (d, J = 3.2 Hz, 8H), 3.43 (d, J = 12.3 Hz, 6H), 3.22 (d, J = 11.7 Hz, 4H), 3.12 (qd, J = 7.3, 4.2 Hz, 1H), 2.92 (dt, J = 12.3, 5.4 Hz, 2H), 2.40 (t, J = 9.7 Hz, 3H), 2.36-2.13 (m, 8H), 1.75 (dq, J = 29.1, 10.0, 9.4 Hz, 3H), 1.28 (dd, J = 12.7, 6.7 Hz, 7H); 591.59 [M + H]$^+$ | 1.26 |

TABLE 1-continued

| Example Compound | Structure | Name of Compound | ¹H NMR[[:]]; MS [M + H]⁺ | UPLC r.t. (min) |
|---|---|---|---|---|
| 74 | 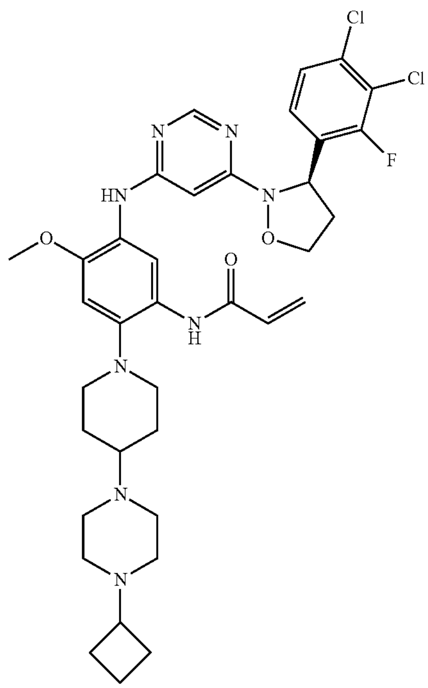 [SMILES: C=CC(=O)Nc1cc(Nc2cc(N3OCC[C@@H]3c3ccc(Cl)c(Cl)c3F)ncn2)c(OC)cc1N1CCC(N2CCN(C3CCC3)CC2)CC1] | N-(2-(4-(4-cyclobutylpiperazine-1-yl)piperidine-1-yl)-5-((6-((R)-3-(3,4-dichloro-2-fluorophenyl)isoxazolidine-2-yl)pyrimidine-4-yl)amino)-4-methoxyphenyl)acrylamide | ¹H NMR (400 MHz, DMSO-d₆) δ 9.47 (s, 1H), 9.15 (s, 1H), 8.25 (s, 1H), 8.03 (s, 1H), 7.53 (dd, J = 8.5, 1.5 Hz, 1H), 7.43 (d, J = 8.0 Hz, 1H), 6.88 (s, 1H), 6.67 (dd, J = 16.9, 10.2 Hz, 1H), 6.24 (dd, J = 17.0, 2.0 Hz, 2H), 5.75 (d, J = 11.0 Hz, 1H), 5.70 (dd, J = 8.7, 5.5 Hz, 1H), 4.28-4.24 (m, 1H), 3.99 (d, J = 7.6 Hz, 1H), 3.81 (s, 3H), 3.38 (q, J = 7.0 Hz, 5H), 3.21 (d, J = 11.4 Hz, 2H), 2.95-2.86 (m, 2H), 2.77 (d, J = 11.7 Hz, 2H), 2.42-2.33 (m, 3H), 2.31-2.24 (m, 2H), 2.20 (d, J = 10.0 Hz, 5H), 2.04 (d, J = 11.8 Hz, 2H) 1.82-1.65 (m, 3H); 725.28 [M + H]⁺ | 1.44 |
| 75 | 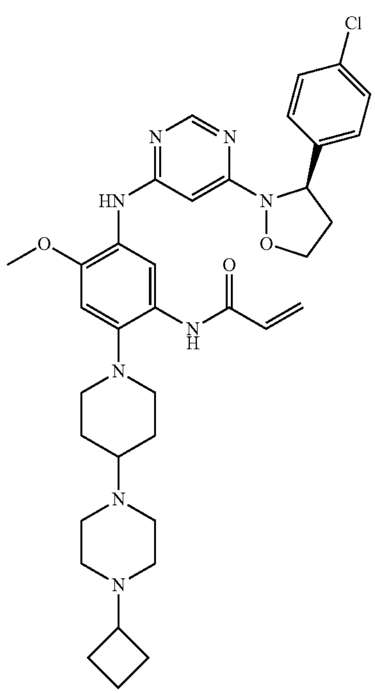 [SMILES: C=CC(=O)Nc1cc(Nc2cc(N3OCC[C@@H]3c3ccc(Cl)cc3)ncn2)c(OC)cc1N1CCC(N2CCN(C3CCC3)CC2)CC1] | N-(5-((6-((R)-3-(4-chlorophenyl)isoxazolidine-2-yl)pyrimidine-4-yl)amino)-2-(4-(4-cyclobutylpiperazine-1-yl)piperidine-1-yl)-4-methoxyphenyl)acrylamide | ¹H NMR (400 MHz, DMSO-d₆) δ 12.68 (s, 1H), 10.33 (s, 1H), 9.30 (s, 1H), 8.33 (s, 1H), 7.87 (s, 1H), 7.41 (dd, J = 24.5, 8.5 Hz, 4H), 6.92 (s, 1H), 6.75 (dd, J = 16.6, 10.3 Hz, 1H), 6.26 (dd, J = 17.0, 1.6 Hz, 1H), 6.05 (s, 1H), 5.77 (d, J = 11.7 Hz, 1H), 5.53 (dd, J = 7.8, 5.7 Hz, 1H), 4.36-4.29 (m, 3H), 4.12-4.05 (m, 4H), 3.81 (s, 3H), 3.66 (d, J = 12.5 Hz, 4H), 3.53-3.40 (m, 3H), 3.25 (d, J = 10.4 Hz, 2H), 3.01-2.90 (m, 1H), 2.84 (d, J = 10.6 Hz, 2H), 2.40 (dd, J = 19.8, 9.9 Hz, 2H), 2.35-2.25 (m, 1H), 2.20 (d, J = 7.7 Hz, 4H), 1.84-1.66 (m, 2H), 1.66-1.52 (m, 2H), 1.50-1.41 (m, 1H), 1.23 (s, 1H); 673.60 [M + H]⁺ | 1.23 |

TABLE 1-continued

| Example Compound | Structure | Name of Compound | ¹H NMR[[:]]; MS [M + H]⁺ | UPLC r.t. (min) |
|---|---|---|---|---|
| 76 | 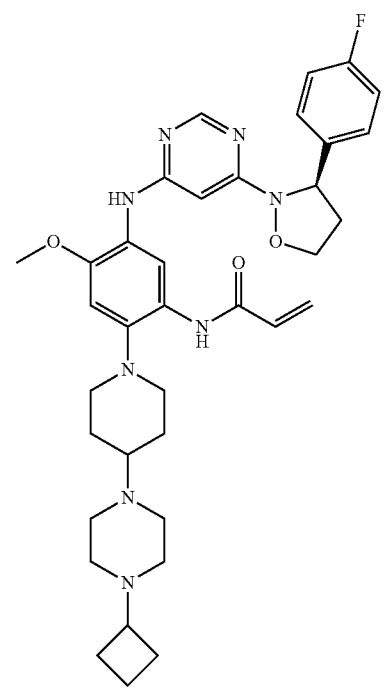 [SMILES: C=CC(=O)Nc1cc(Nc2cc(N3OCC[C@@H]3c3ccc(F)cc3)ncn2)c(OC)cc1N1CCC(N2CCN(C3CCC3)CC2)CC1] | N-(2-(4-(4-cyclobutylpiperazine-1-yl)piperidine-1-yl)-5-((6-((R)-3-(4-fluorophenyl)isoxazolidine-2-yl)pyrimidine-4-yl)amino)-4-methoxyphenyl)acrylamide | ¹H NMR (400 MHz, DMSO-d₆) δ 9.79 (s, 1H), 9.17 (s, 1H), 8.28 (s, 1H), 7.95 (s, 1H), 7.43-7.37 (m, 2H), 7.19 (s, 2H), 6.88 (s, 1H), 6.69 (dd, J = 17.0, 10.4 Hz, 1H), 6.25 (dd, J = 17.0, 1.9 Hz, 1H), 6.09 (s, 1H), 5.76 (d, J = 10.5 Hz, 1H), 5.52 (t, J = 7.1 Hz, 1H), 4.29 (d, J = 4.6 Hz, 1H), 4.03 (d, J = 7.8 Hz, 1H), 3.80 (s, 3H), 3.64 (d, J = 12.5 Hz, 4H), 3.23 (s, 3H), 2.91 (s, 1H), 2.79 (s, 2H), 2.39 (t, J = 9.6 Hz, 2H), 2.34-2.27 (m, 2H), 2.19 (t, J = 11.1 Hz, 5H), 1.83-1.67 (m, 3H), 1.62 (d, J = 5.0 Hz, 2H), 1.43 (d, J = 5.1 Hz, 2H); 657.36 [M + H]⁺ | 1.12 |
| 77 | 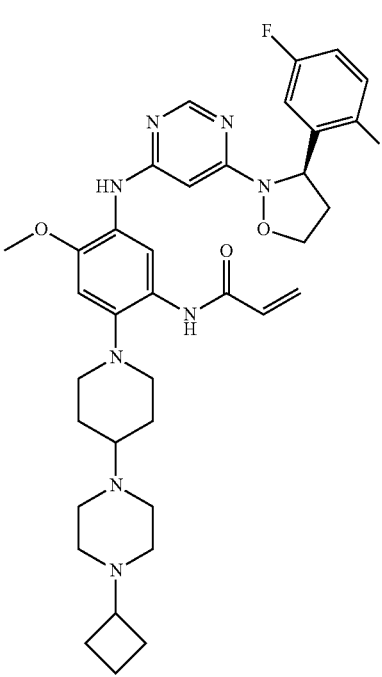 | N-(2-(4-(4-cyclobutylpiperazine-1-yl)piperidine-1-yl)-5-((6-((R)-3-(2,5-difluorophenyl)isoxazolidine-2-yl)pyrimidine-4-yl)amino)-4-methoxyphenyl)acrylamide | ¹H NMR (400 MHz, DMSO-d₆) δ 9.95 (s, 1H), 9.21 (s, 1H), 8.30 (s, 1H), 7.95 (s, 1H), 7.32 (td, J = 9.3, 4.5 Hz, 1H), 7.25-7.12 (m, 3H), 6.90 (s, 1H), 6.71 (dd, J = 16.9, 10.3 Hz, 1H), 6.25 (dd, J = 17.0, 1.9 Hz, 1H), 6.19 (s, 1H), 5.81-5.72 (m, 2H), 5.66 (dd, J = 8.7, 5.6 Hz, 1H), 3.89 (t, J = 6.2 Hz, 1H), 3.81 (s, 4H), 3.53-3.33 (m, 4H), 3.27-3.18 (m, 2H), 3.11 (tt, J = 7.4, 3.7 Hz, 1H), 2.92 (ddd, J = 13.1, 8.7, 5.2 Hz, 2H), 2.40 (t, J = 9.9 Hz, 2H), 2.34-2.00 (m, 9H), 1.73 (dt, J = 29.2, 9.9 Hz, 3H), 1.34-1.21 (m, 8H); 675.67 [M + H]⁺ | 1.20 |

TABLE 1-continued

| Example Compound | Structure | Name of Compound | $^1$H NMR[:]; MS [M + H]$^+$ | UPLC r.t. (min) |
|---|---|---|---|---|
| 78 | 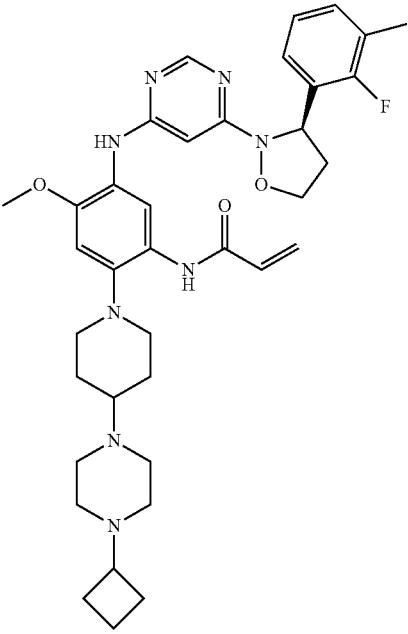 | N-(2-(4-(4-cyclobutylpiperazine-1-yl)piperidine-1-yl)-5-((6-((R)-3-(2-fluoro-3-methylphenyl)isoxazolidine-2-yl)pyrimidine-4-yl)amino)-4-methoxyphenyl)acrylamide | $^1$H NMR (400 MHz, DMSO-d$_6$) δ 8.99 (s, 1H), 8.61 (s, 1H), 8.14 (s, 2H), 7.28 (t, J = 7.4 Hz, 1H), 7.19 (t, J = 7.4 Hz, 1H), 7.06 (t, J = 7.6 Hz, 1H), 6.83 (s, 1H), 6.64 (dd, J = 17.0, 10.2 Hz, 1H), 6.36 (s, 1H), 6.23 (ddd, J = 16.7, 14.9, 1.9 Hz, 2H), 6.08 (dd, J = 17.3, 10.3 Hz, 1H), 5.88 (dd, J = 10.3, 1.9 Hz, 1H), 5.73 (dq, J = 8.6, 4.6 Hz, 2H), 4.14 (td, J = 7.9, 3.8 Hz, 1H), 3.80 (s, 3H), 3.59 (h, J = 6.6 Hz, 4H), 3.15-3.05 (m, 8H), 2.78 (dtd, J = 11.8, 7.9, 3.9 Hz, 2H), 2.26 (d, J = 1.9 Hz, 3H), 2.19-2.09 (m, 2H), 2.04 (s, 4H), 1.77 (s, 2H), 1.68 (q, J = 9.5 Hz, 2H), ; 671.6 [M + H]$^+$ | 1.22 |
| 79 | 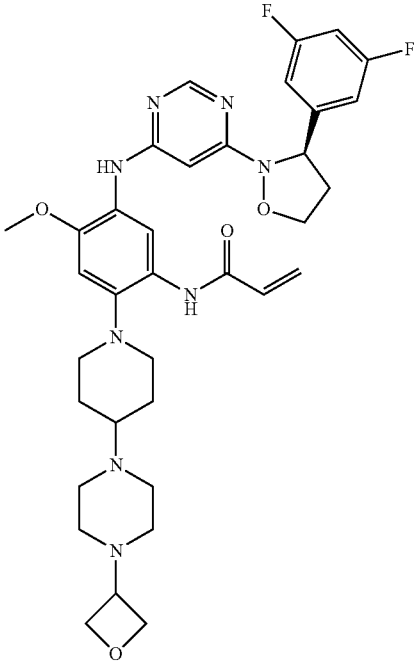 [SMILES: C=CC(=O)Nc1cc(Nc2cc(N3OCC[C@@H]3c3cc(F)cc(F)c3)ncn2)c(OC)cc1N1CCC(N2CCN(C3COC3)CC2)CC1] | N-(5-((6-((R)-3-(3,5-difluorophenyl)isoxazolidine-2-yl)pyrimidine-4-yl)amino)-4-methoxy-2-(4-(4-(oxetane-3-yl)piperazine-1-yl)piperidine-1-yl)phenyl)acrylamide | $^1$H NMR (400 MHz, Methanol-d$_4$) δ 8.18 (s, 1H), 8.07 (s, 1H), 7.04-6.91 (m, 2H), 6.81 (s, 1H), 6.77-6.68 (m, 1H), 6.45 (dd, J = 10.3, 16.9 Hz, 1H), 6.35 (d, J = 3.8 Hz, 1H), 6.25 (dd, J = 1.6, 17.0 Hz, 1H), 5.70 (dd, J = 1.6, 10.2 Hz, 1H), 5.46 (dd, J = 4.8, 8.7 Hz, 1H), 4.04 (td, J = 4.0, 7.8 Hz, 1H), 3.86 (q, J = 8.0 Hz, 1H), 3.77 (s, 3H), 3.51-3.44 (m, 1H), 3.11-3.01 (m, 3H), 2.89-2.62 (m, 8H), 2.60-2.50 (m, 1H), 2.43 (s, 3H), 2.29-2.16 (m, 2H), 2.06-1.96 (m, 2H), 1.77-1.64 (m, 2H), 0.83-0.75 (m, 2H); 677.3 [M + H]$^+$ | 1.26 |

TABLE 1-continued

| Example Compound | Structure | Name of Compound | ¹H NMR[:]; MS [M + H]⁺ | UPLC r.t. (min) |
|---|---|---|---|---|
| 80 | 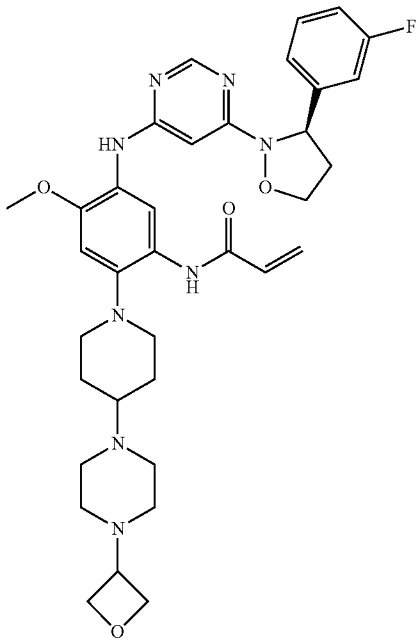 [SMILES: C=CC(=O)Nc1cc(Nc2cc(N3OCC[C@@H]3c3cccc(F)c3)ncn2)c(OC)cc1N1CCC(N2CCN(C3COC3)CC2)CC1] | N-(5-((6-((R)-3-(3-fluorophenyl)isoxazolidine-2-yl)pyrimidine-4-yl)amino)-4-methoxy-2-(4-(4-(oxetane-3-yl)piperazine-1-yl)piperidine-1-yl)phenyl)acrylamide | ¹H NMR (400 MHz, DMSO-d₆) δ 9.28 (s, 1H), 9.08 (s, 1H), 8.24 (s, 1H), 8.04 (s, 1H), 7.41 (q, J = 7.5 Hz, 1H), 7.21 (dd, J = 17.1, 9.1 Hz, 2H), 7.11 (td, J = 8.6, 2.7 Hz, 1H), 6.86 (s, 1H), 6.62 (dd, J = 16.9, 10.3 Hz, 1H), 6.33-6.15 (m, 2H), 5.75 (d, J = 10.3 Hz, 1H), 5.54 (dd, J = 8.6, 5.3 Hz, 1H), 4.61 (t, J = 6.7 Hz, 2H), 4.47 (t, J = 6.1 Hz, 2H), 4.22 (td, J = 7.7, 4.0 Hz, 2H), 3.94 (q, J = 7.8 Hz, 3H), 3.81 (s, 3H), 3.38-3.30 (m, 4H), 3.21-3.13 (m, 2H), 2.85 (dtd, J = 12.0, 7.8, 4.1 Hz, 2H), 2.76 (t, J = 11.7 Hz, 3H), 2.28 (ddd, J = 12.8, 10.5, 6.6 Hz, 2H), 2.13 (d, J = 11.9 Hz, 2H), 1.94 (tt, J = 14.2, 7.0 Hz, 2H); 659.56 [M + H]⁺ | 1.16 |
| 81 | 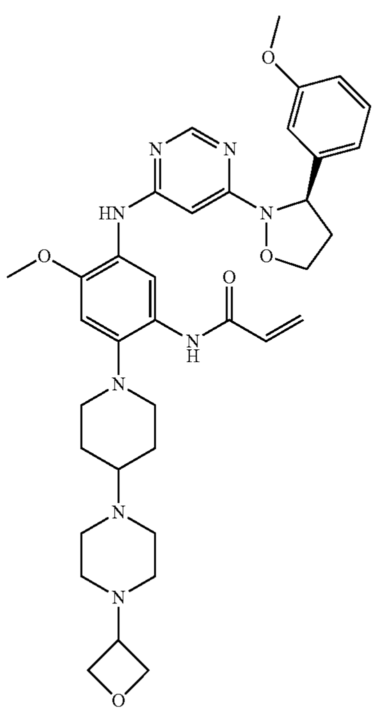 [SMILES: C=CC(=O)Nc1cc(Nc2cc(N3OCC[C@@H]3c3cccc(OC)c3)ncn2)c(OC)cc1N1CCC(N2CCN(C3COC3)CC2)CC1] | N-(4-methoxy-5-((6-((R)-3-(3-methoxyphenyl)isoxazolidine-2-yl)pyrimidine-4-yl)amino)-2-(4-(4-(oxetane-3-yl)piperazine-1-yl)piperidine-1-yl)phenyl)acrylamide | ¹H NMR (400 MHz, DMSO-d₆) δ 10.12 (s, 1H), 9.16 (d, J = 5.5 Hz, 1H), 8.33 (s, 1H), 7.85 (s, 1H), 7.33-7.25 (m, 1H), 6.91-6.86 (m, 4H), 6.76-6.67 (m, 1H), 6.25 (dd, J = 17.0, 1.9 Hz, 2H), 5.49-5.42 (m, 2H), 4.77 (d, J = 6.4 Hz, 2H), 4.62 (t, J = 3.8 Hz, 1H), 4.34 (td, J = 7.5, 4.4 Hz, 1H), 4.10 (q, J = 7.7 Hz, 1H), 3.79 (s, 3H), 3.75 (s, 3H), 3.34 (s, 2H), 3.24 (d, J = 11.3 Hz, 2H), 2.95 (dp, J = 12.3, 4.6, 3.6 Hz, 1H), 2.84 (t, J = 11.6 Hz, 2H), 2.39-2.25 (m, 2H), 2.16 (d, J = 12.3 Hz, 2H), 2.08 (s, 8H), 1.29-1.22 (m, 2H); 671.65 [M + H]⁺ | 1.11 |

TABLE 1-continued

| Example Compound | Structure | Name of Compound | ¹H NMR[:]; MS [M + H]⁺ | UPLC r.t. (min) |
|---|---|---|---|---|
| 82 | 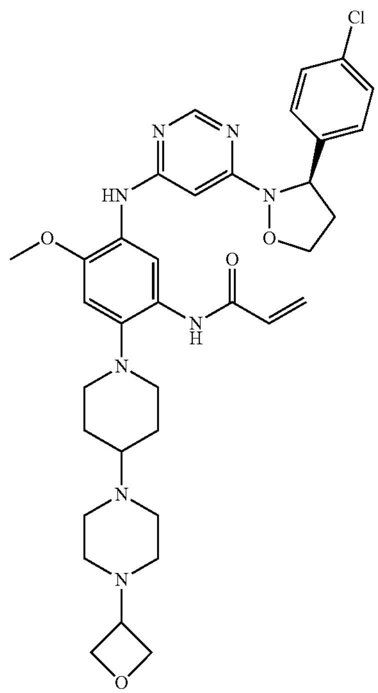 [SMILES: C=CC(=O)Nc1cc(Nc2cc(N3OCC[C@@H]3c3ccc(Cl)cc3)ncn2)c(OC)cc1N1CCC(N2CCN(C3COC3)CC2)CC1] | N-(5-(6-((R)-3-(4-chlorophenyl)isoxazolidine-2-yl)pyrimidine-4-yl)amino)-4-methoxy-2-(4-(4-(oxetane-3-yl)piperazine-1-yl)piperidine-1-yl)phenyl)acrylamide | 676.23 [M + H]⁺ | 1.21 |
| 83 | 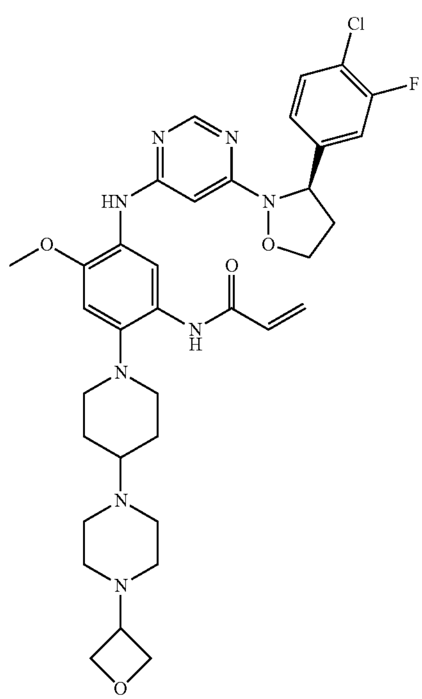 [SMILES: C=CC(=O)Nc1cc(Nc2cc(N3OCC[C@@H]3c3ccc(Cl)c(F)c3)ncn2)c(OC)cc1N1CCC(N2CCN(C3COC3)CC2)CC1] | N-(5-((6-((R)-3-(4-chloro-3-fluorophenyl)isoxazolidine-2-yl)pyrimidine-4-yl)amino)-4-methoxy-2-(4-(4-(oxetane-3-yl)piperazine-1-yl)piperidine-1-yl)phenyl)acrylamide | ¹H NMR (400 MHz, DMSO-d₆) δ 10.10 (s, 1H), 9.15 (d, J = 4.7 Hz, 1H), 8.33 (s, 1H), 7.87 (s, 1H), 7.60 (t, J = 8.1 Hz, 1H), 7.41 (dd, J = 10.3, 2.0 Hz, 1H), 7.24 (dd, J = 8.4, 1.9 Hz, 1H), 6.91 (s, 1H), 6.70 (ddd, J = 15.7, 10.4, 4.2 Hz, 1H), 6.31-6.17 (m, 1H), 6.05 (d, J = 31.5 Hz, 1H), 5.77 (d, J = 10.4 Hz, 1H), 5.53 (dd, J = 8.5, 5.5 Hz, 1H), 4.74 (t, J = 6.0 Hz, 2H), 4.32 (dd, J = 7.6, 4.4 Hz, 2H), 3.80 (s, 3H), 3.32 (d, J = 3.2 Hz, 2H), 3.23 (d, J = 11.4 Hz, 4H), 3.05-2.89 (m, 2H), 2.89-2.63 (m, 2H), 2.44 (s, 8H), 2.40-2.23 (m, 2H), 2.22-1.94 (m, 2H); 693.5 [M + H]⁺ | 1.25 |

TABLE 1-continued

| Example Compound | Structure | Name of Compound | ¹H NMR[[:]]; MS [M + H]⁺ | UPLC r.t. (min) |
|---|---|---|---|---|
| 84 | 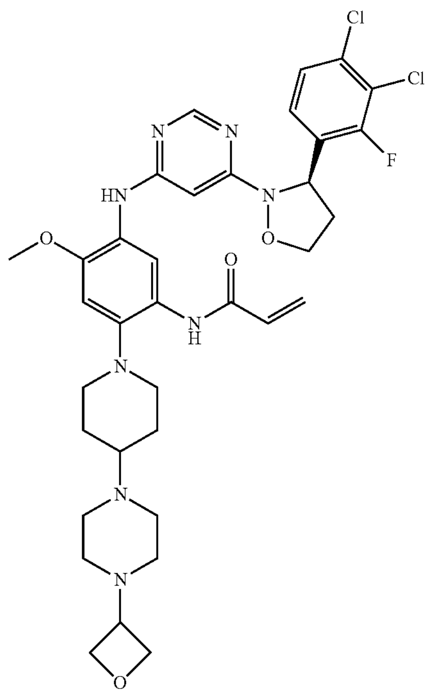 [SMILES: C=CC(=O)Nc1cc(Nc2cc(N3OCC[C@@H]3c3ccc(Cl)c(Cl)c3F)ncn2)c(OC)cc1N1CCC(N2CCN(C3COC3)CC2)CC1] | N-(5-((6-((R)-3-(3,4-dichloro-2-fluorophenyl)isoxazolidine-2-yl)pyrimidine-4-yl)amino)-4-methoxy-2-(4-(4-(oxetane-3-yl)piperazine-1-yl)piperidine-1-yl)phenyl)acrylamide | ¹H NMR (400 MHz, DMSO-d₆) δ 9.95 (s, 1H), 9.12 (d, J = 4.7 Hz, 1H), 8.32 (s, 1H), 7.91 (s, 1H), 7.54 (dd, J = 8.6, 1.6 Hz, 1H), 7.38 (t, J = 8.1 Hz, 1H), 6.90 (s, 1H), 6.66 (d, J = 13.4 Hz, 1H), 6.25 (d, J = 16.5 Hz, 1H), 6.11 (s, 1H), 5.77 (s, 1H), 5.68 (t, J = 7.2 Hz, 1H), 4.67 (d, J = 27.0 Hz, 5H), 4.34 (d, J = 4.2 Hz, 1H), 4.07 (d, J = 7.8 Hz, 2H), 3.81 (s, 3H), 3.71 (d, J = 16.1 Hz, 3H), 3.41 (dd, J = 22.8, 7.0 Hz, 5H), 3.01-2.95 (m, 1H), 2.79 (d, J = 8.6 Hz, 3H), 2.14 (s, 2H); 727.26 [M + H]⁺ | 1.42 |
| 85 | 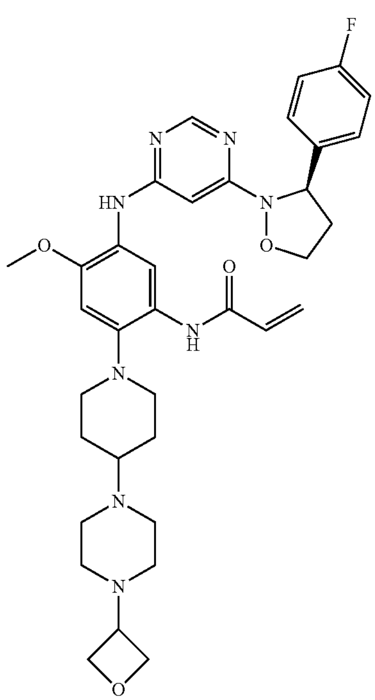 [SMILES: C=CC(=O)Nc1cc(Nc2cc(N3OCC[C@@H]3c3ccc(F)cc3)ncn2)c(OC)cc1N1CCC(N2CCN(C3COC3)CC2)CC1] | N-(5-((6-((R)-3-(4-fluorophenyl)isoxazolidine-2-yl)pyrimidine-4-yl)amino)-4-methoxy-2-(4-(4-(oxetane-3-yl)piperazine-1-yl)piperidine-1-yl)phenyl)acrylamide | ¹H NMR (400 MHz, DMSO-d₆) δ 9.78 (s, 1H), 9.10 (s, 1H), 8.30 (s, 1H), 7.92 (s, 1H), 7.44-7.36 (m, 2H), 7.20 (t, J = 8.8 Hz, 2H), 6.88 (s, 1H), 6.67 (dd, J = 17.0, 10.2 Hz, 1H), 6.25 (dd, J = 17.0, 1.9 Hz, 1H), 6.03 (s, 1H), 5.80-5.73 (m, 1H), 5.51 (s, 1H), 4.64 (d, J = 6.8 Hz, 2H), 4.55 (s, 2H), 4.30 (s, 1H), 4.05 (d, J = 7.7 Hz, 1H), 3.80 (s, 3H), 3.63 (s, 2H), 3.38 (d, J = 6.9 Hz, 3H), 3.20 (d, J = 11.6 Hz, 6H), 2.91 (dd, J = 8.5, 4.6 Hz, 1H), 2.77 (d, J = 11.9 Hz, 2H), 2.33-2.27 (m, 1H), 2.14 (d, J = 11.2 Hz, 2H), 2.01 (s, 2H), 1.10 (d, J = 7.0 Hz, 1H); 659.34 [M + H]⁺ | 1.15 |

| Example Compound | Structure | Name of Compound | ¹H NMR[[:]]; MS [M + H]⁺ | UPLC r.t. (min) |
|---|---|---|---|---|
| 86 | 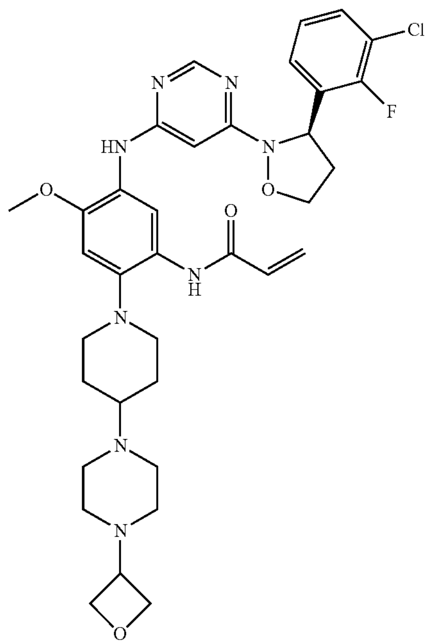 [SMILES: C=CC(=O)Nc1cc(Nc2cc(N3OCC[C@@H]3c3cccc(Cl)c3F)ncn2)c(OC)cc1N1CCC(N2CCN(C3COC3)CC2)CC1] | N-(5-((6-((R)-3-(3-chloro-2-fluorophenyl)isoxazolidine-2-yl)pyrimidine-4-yl)amino)-4-methoxy-2-(4-(4-(oxetane-3-yl)piperazine-1-yl)piperidine-1-yl)phenyl)acrylamide | ¹H NMR (400 MHz, DMSO-$d_6$) δ 9.05 (s, 1H), 8.89 (s, 1H), 8.19 (s, 1H), 8.11 (s, 1H), 7.52 (t, J = 7.5 Hz, 1H), 7.43 (t, J = 7.3 Hz, 1H), 7.23 (t, J = 7.9 Hz, 1H), 6.85 (s, 1H), 6.60 (dd, J = 17.0, 10.1 Hz, 1H), 6.34 (s, 1H), 6.29-6.18 (m, 1H), 5.73 (td, J = 9.2, 8.4, 3.8 Hz, 2H), 4.60 (t, J = 6.6 Hz, 2H), 4.46 (t, J = 6.1 Hz, 2H), 4.20 (dd, J = 8.0, 3.7 Hz, 1H), 3.89 (t, J = 8.0 Hz, 1H), 3.81 (s, 3H), 3.16 (d, J = 12.0 Hz, 8H), 2.97 (s, 2H), 2.85 (dtd, J = 11.8, 7.7, 3.5 Hz, 2H), 2.75 (t, J = 11.8 Hz, 2H), 2.31-2.16 (m, 2H), 2.12 (d, J = 11.5 Hz, 2H), 1.98-1.81 (m, 2H); 693.5 [M + H]⁺ | 1.30 |
| 87 | 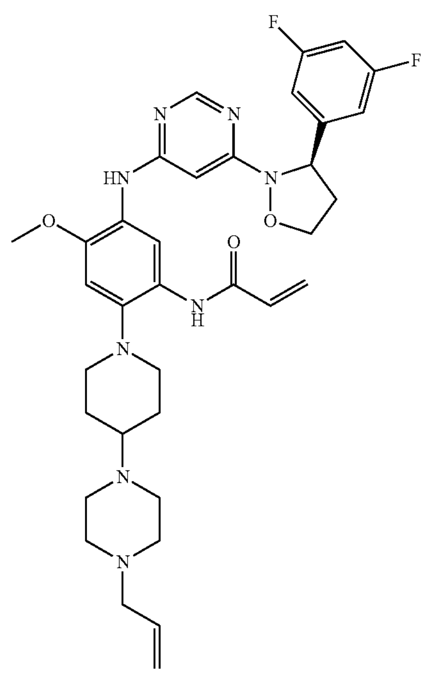 [SMILES: C=CCN1CCN(C2CCN(c3cc(OC)c(Nc4cc(N5OCC[C@@H]5c5cc(F)cc(F)c5)ncn4)cc3NC(=O)C=C)CC2)CC1] | N-(2-(4-(4-allylpiperazine-1-yl)piperidine-1-yl)-5-((6-((R)-3-(3,5-difluorophenyl)isoxazolidine-2-yl)pyrimidine-4-yl)amino)-4-methoxyphenyl)acrylamide | ¹H NMR (400 MHz, DMSO-$d_6$) δ 9.74 (s, 1H), 9.17 (s, 1H), 8.29 (s, 1H), 7.97 (s, 1H), 7.21-7.05 (m, 4H), 6.89 (s, 1H), 6.68 (dd, J = 17.0, 10.2 Hz, 1H), 6.31-6.12 (m, 3H), 6.07-5.91 (m, 2H), 5.76 (dd, J = 10.1, 2.0 Hz, 1H), 5.63 (d, J = 17.0 Hz, 2H), 3.81 (s, 13H), 3.57 (s, 8H), 3.21 (d, J = 11.6 Hz, 3H), 2.96-2.86 (m, 2H), 2.81 (q, J = 14.1, 11.5 Hz, 3H), 2.32 (dq, J = 12.8, 7.6 Hz, 2H), 2.23-1.96 (m, 6H); 661.59 [M + H]⁺ | 1.61 |

TABLE 1-continued

| Example Compound | Structure | Name of Compound | ¹H NMR[:]; MS [M + H]⁺ | UPLC r.t. (min) |
|---|---|---|---|---|
| 88 | 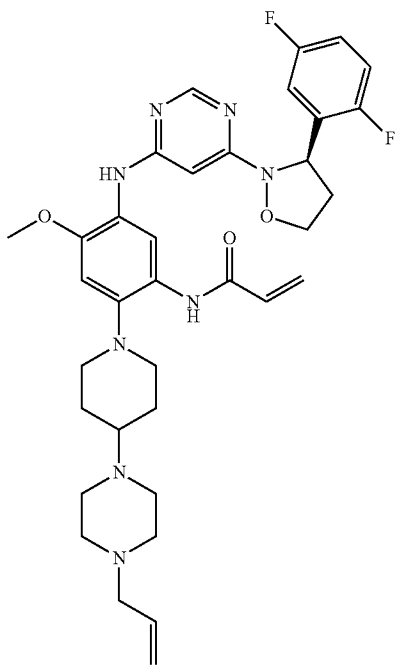 [SMILES: C=CCN1CCN(C2CCN(c3cc(OC)c(Nc4cc(N5OCC[C@@H]5c5cc(F)ccc5F)ncn4)cc3NC(=O)C=C)CC2)CC1] | N-(2-(4-(4-allylpiperazine-1-yl)piperidine-1-yl)-5-((6-((R)-3-(2,5-difluorophenyl)isoxazolidine-2-yl)pyrimidine-4-yl)amino)-4-methoxyphenyl)acrylamide | ¹H NMR (400 MHz, DMSO-d₆) δ 9.90 (s, 1H), 9.19 (s, 1H), 8.30 (s, 1H), 7.95 (s, 1H), 7.32 (td, J = 9.3, 4.4 Hz, 1H), 7.26-7.11 (m, 2H), 6.90 (s, 1H), 6.69 (dd, J = 16.9, 10.2 Hz, 1H), 6.31-6.10 (m, 2H), 5.99 (ddt, J = 17.1, 10.2, 7.0 Hz, 1H), 5.80-5.71 (m, 2H), 5.70-5.52 (m, 3H), 3.81 (s, 4H), 3.74-3.49 (m, 8H), 3.22 (d, J = 11.4 Hz, 2H), 2.92 (ddd, J = 11.9, 7.7, 4.4 Hz, 1H), 2.80 (t, J = 11.7 Hz, 2H), 2.36-2.22 (m, 1H), 2.22-2.00 (m, 4H); 661.54 [M + H]⁺ | 1.16 |
| 89 | 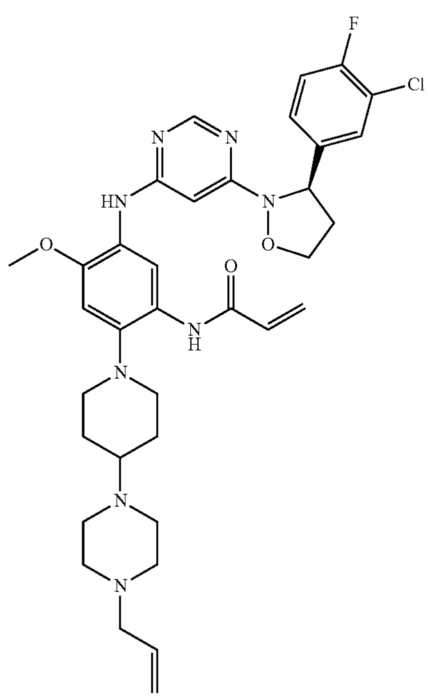 [SMILES: C=CCN1CCN(C2CCN(c3cc(OC)c(Nc4cc(N5OCC[C@@H]5c5ccc(F)c(Cl)c5)ncn4)cc3NC(=O)C=C)CC2)CC1] | N-(2-(4-(4-allylpiperazine-1-yl)piperidine-1-yl)-5-((6-((R)-3-(3-chloro-4-fluorophenyl)isoxazolidine-2-yl)pyrimidine-4-yl)amino)-4-methoxyphenyl)acrylamide | ¹H NMR (400 MHz, DMSO-d₆) δ 12.53 (s, 1H), 10.39 (s, 1H), 9.31 (s, 1H), 8.35 (s, 1H), 7.88 (s, 1H), 7.58 (dd, J = 7.1, 2.0 Hz, 1H), 7.40 (ddd, J = 11.7, 8.6, 6.2 Hz, 2H), 6.93 (s, 1H), 6.73 (td, J = 16.1, 10.3 Hz, 1H), 6.31-6.18 (m, 1H), 6.10 (dd, J = 17.1, 10.2 Hz, 1H), 6.06-5.95 (m, 1H), 5.76 (dd, J = 7.1, 4.5 Hz, 1H), 5.64 (d, J = 16.8 Hz, 1H), 5.59-5.48 (m, 2H), 4.36-4.30 (m, 3H), 3.82 (s, 3H), 3.73-3.69 (m, 3H), 3.29-3.16 (m, 3H), 2.84 (s, 2H), 2.71 (d, J = 4.9 Hz, 3H), 2.33 (dd, J = 12.9, 5.1 Hz, 1H), 2.13 (dd, J = 23.6, 14.7 Hz, 3H); 677.56 [M + H]⁺ | 1.27 |

TABLE 1-continued

| Example Compound | Structure | Name of Compound | ¹H NMR[:]; MS [M + H]⁺ | UPLC r.t. (min) |
|---|---|---|---|---|
| 90 | 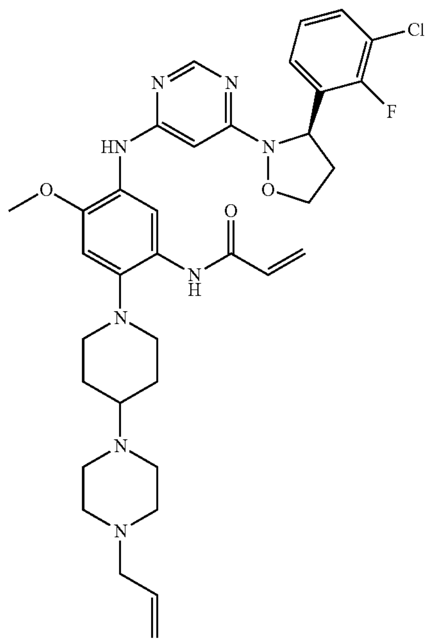 [SMILES: C=CCN1CCN(C2CCN(c3cc(OC)c(Nc4cc(N5OCC[C@@H]5c5cccc(Cl)c5F)ncn4)cc3NC(=O)C=C)CC2)CC1] | N-(2-(4-(4-allylpiperazine-1-yl)piperidine-1-yl)-5-((6-(R-3-(3-chloro-2-fluorophenyl)isoxazolidine-2-yl)pyrimidine-4-yl)amino)-4-methoxyphenyl)acrylamide | ¹H NMR (400 MHz, DMSO-d₆) δ 9.04 (s, 1H), 8.88 (s, 1H), 8.19 (s, 1H), 8.11 (s, 1H), 7.52 (t, J = 7.5 Hz, 1H), 7.43 (t, J = 7.3 Hz, 1H), 7.23 (t, J = 7.9 Hz, 1H), 6.84 (s, 1H), 6.61 (dd, J = 17.0, 10.2 Hz, 1H), 6.34 (s, 1H), 6.23 (d, J = 16.9 Hz, 1H), 5.86 (dt, J = 16.6, 8.0 Hz, 1H), 5.78-5.67 (m, 2H), 5.46 (s, 1H), 5.41 (d, J = 8.5 Hz, 1H), 4.20 (td, J = 8.0, 3.5 Hz, 2H), 3.89 (q, J = 6.9, 5.5 Hz, 2H), 3.81 (s, 3H), 3.17 (s, 4H), 3.13 (s, 2H), 2.90-2.79 (m, 2H), 2.73 (t, J = 11.7 Hz, 2H), 2.27-2.14 (m, 1H), 2.08-1.99 (m, 2H), 1.91 (s, 4H), 1.85 (s, 2H); 677.51 [M + H]⁺ | 1.25 |
| 91 | 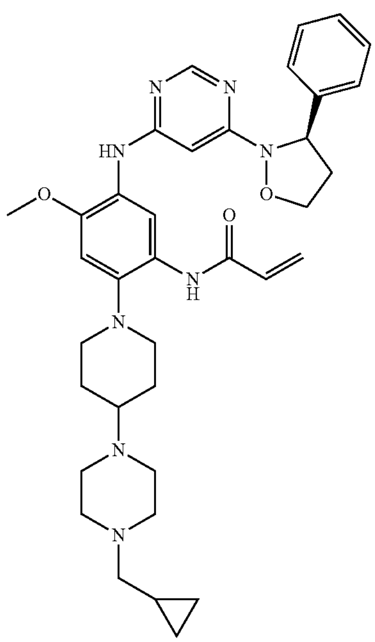 [SMILES: C=CC(=O)Nc1cc(Nc2cc(N3OCC[C@@H]3c3ccccc3)ncn2)c(OC)cc1N1CCC(N2CCN(CC3CC3)CC2)CC1] | N-(2-(4-(4-(cyclopropylmethyl)piperazine-1-yl)piperidine-1-yl)-4-methoxy-5-((6-((R)-3-phenylisoxazolidine-2-yl)pyrimidine-4-yl)amino)phenyl)acrylamide | ¹H NMR (400 MHz, Chloroform-d) δ 8.87 (s, 1H), 8.46 (s, 1H), 8.37 (s, 1H), 7.46 (d, J = 7.2 Hz, 2H), 7.34 (t, J = 7.6 Hz, 2H), 7.24 (dd, J = 8.4, 6.5 Hz, 1H), 6.91 (s, 1H), 6.75 (s, 1H), 6.69 (s, 1H), 6.36 (dd, J = 16.9, 1.5 Hz, 1H), 6.24 (dd, J = 16.9, 10.0 Hz, 1H), 5.72 (ddd, J = 14.4, 9.3, 3.0 Hz, 2H), 4.15 (td, J = 8.0, 4.5 Hz, 1H), 4.07 (q, J = 8.0 Hz, 1H), 3.84 (s, 3H), 3.06 (d, J = 11.2 Hz, 2H), 2.79-2.68 (m, 6H), 2.38 (dtt, J = 16.3, 8.2, 4.2 Hz, 2H), 2.29 (d, J = 6.6 Hz, 2H), 2.09 (d, J = 12.5 Hz, 2H), 1.89-1.75 (m, 3H), 1.68 (td, J = 12.0, 3.7 Hz, 3H), 0.93-0.83 (m, 2H), 0.57-0.49 (m, 2H), 0.12 (dt, J = 5.9, 4.5 Hz, 2H); 639.67 [M + H]⁺ | 1.33 |

TABLE 1-continued

| Example Compound | Structure | Name of Compound | ¹H NMR[:]; MS [M + H]⁺ | UPLC r.t. (min) |
|---|---|---|---|---|
| 92 | 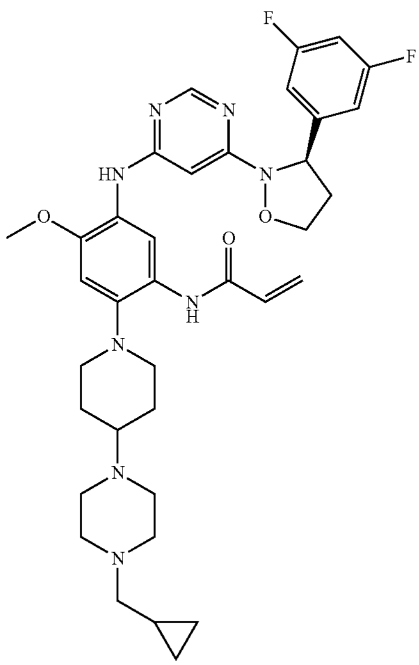 [SMILES: C=CC(=O)Nc1cc(Nc2cc(N3OCC[C@@H]3c3cc(F)cc(F)c3)ncn2)c(OC)cc1N1CCC(N2CCN(CC3CC3)CC2)CC1] | N-(2-(4-(4-(cyclopropylmethyl) piperazine-1-yl)piperidine-1-yl)-5-((6-((R)-3-(3,5-difluorophenyl) isoxazolidine-2-yl)pyrimidine-4-yl)amino)-4-methoxyphenyl) acrylamide | ¹H NMR (400 MHz, Methanol-d₄) δ 8.32 (s, 1H), 8.19 (s, 1H), 7.11-7.00 (m, 2H), 6.92 (s, 1H), 6.84 (tt, J = 2.4, 9.0 Hz, 1H), 6.56 (dd, J = 10.3, 17.0 Hz, 1H), 6.48 (s, 1H), 6.36 (dd, J = 1.6, 17.0 Hz, 1H), 5.81 (dd, J = 1.6, 10.2 Hz, 1H), 5.58 (dd, J = 4.7, 8.7 Hz, 1H), 4.20-4.11 (m, 1H), 3.98 (q, J = 8.0 Hz, 1H), 3.88 (s, 3H), 3.20-3.11 (m, 2H), 3.03-2.69 (m, 11H), 2.61-2.56 (m, 2H), 2.56-2.47 (m, 1H), 2.41-2.26 (m, 1H), 2.10-2.02 (m, 2H), 1.87-1.71 (m, 2H), 1.06-0.94 (m, 1H), 0.69-0.61 (m, 2H), 0.28 (dt, J = 4.6, 6.1 Hz, 2H); 675.3 [M + H]⁺ | 1.23 |
| 93 | 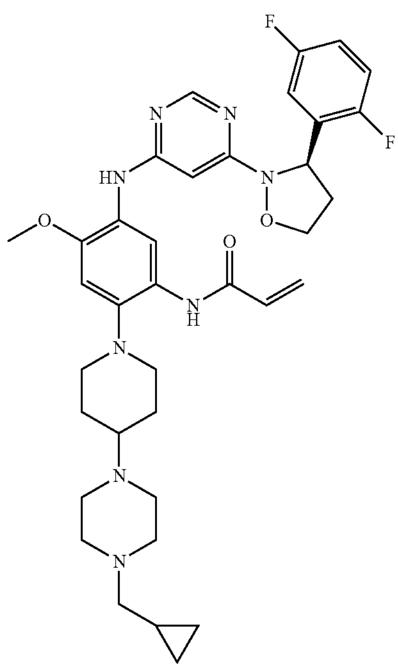 [SMILES: C=CC(=O)Nc1cc(Nc2cc(N3OCC[C@@H]3c3cc(F)ccc3F)ncn2)c(OC)cc1N1CCC(N2CCN(CC3CC3)CC2)CC1] | N-(2-(4-(4-(cyclopropylmethyl) piperazine-1-yl)piperidine-1-yl)-5-((6-((R)-3-(2,5-difluorophenyl) isoxazolidine-2-yl)pyrimidine-4-yl)amino)-4-methoxyphenyl) acrylamide | ¹H NMR (400 MHz, Methanol-d₄) δ 8.32 (s, 1H), 8.18 (d, J = 1.0 Hz, 1H), 7.26 (ddd, J = 3.3, 5.8, 9.1 Hz, 1H), 7.15 (td, J = 4.4, 9.3 Hz, 1H), 7.08-6.99 (m, 1H), 6.93 (s, 1H), 6.62-6.46 (m, 2H), 6.36 (dd, J = 1.6, 17.0 Hz, 1H), 5.79 (td, J = 3.1, 9.3, 9.8 Hz, 2H), 4.19-4.10 (m, 1H), 4.00 (q, J = 8.0 Hz, 1H), 3.20-3.13 (m, 2H), 3.02-2.74 (m, 11H), 2.61-2.55 (m, 2H), 2.55-2.48 (m, 1H), 2.32-2.23 (m, 1H), 2.11-2.03 (m, 2H), 1.86-1.72 (m, 2H), 1.04-0.95 (m, 1H), 0.69-0.61 (m, 2H), 0.31-0.23 (m, 2H); 675.4 [M + H]⁺ | 1.17 |

| Example Compound | Structure | Name of Compound | ¹H NMR[:]; MS [M + H]⁺ | UPLC r.t. (min) |
|---|---|---|---|---|
| 94 | 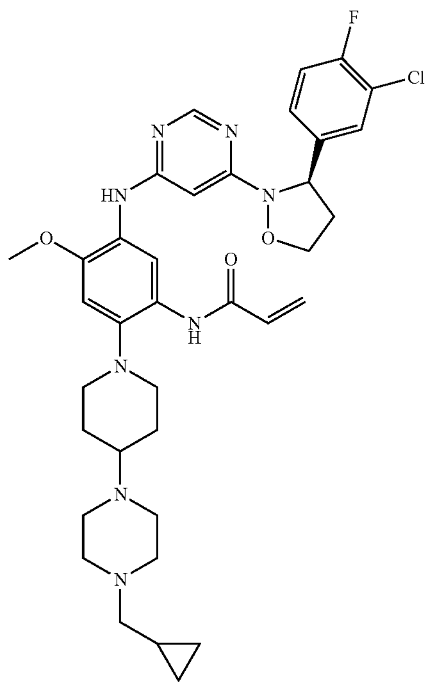 [SMILES: C=CC(=O)Nc1cc(Nc2cc(N3OCC[C@@H]3c3ccc(F)c(Cl)c3)ncn2)c(OC)cc1N1CCC(N2CCN(CC3CC3)CC2)CC1] | N-(5-((6-((R)-3-(3-chloro-4-fluorophenyl)isoxazolidine-2-yl)pyrimidine-4-yl)amino)-2-(4-(4-(cyclopropylmethyl)piperazine-1-yl)piperidine-1-yl)-4-methoxyphenyl)acrylamide | ¹H NMR (400 MHz, DMSO-d₆) δ 12.20 (s, 1H), 10.35 (s, 1H), 9.30 (s, 1H), 8.35 (s, 1H), 7.88 (s, 1H), 7.58 (dd, J = 7.0, 2.0 Hz, 1H), 7.46-7.35 (m, 3H), 6.93 (s, 1H), 6.74 (dt, J = 16.7, 8.4 Hz, 1H), 6.26 (dd, J = 17.0, 1.6 Hz, 1H), 6.12 (s, 1H), 5.77 (d, J = 11.7 Hz, 1H), 5.55 (dd, J = 8.0, 5.5 Hz, 1H), 4.32 (dd, J = 7.2, 4.4 Hz, 2H), 4.07 (dd, J = 15.4, 7.8 Hz, 3H), 3.82 (s, 3H), 3.50 (d, J = 11.3 Hz, 4H), 3.25 (d, J = 10.2 Hz, 4H), 3.11 (d, J = 7.5 Hz, 3H), 2.99-2.82 (m, 6H), 2.71 (d, J = 4.9 Hz, 1H), 2.32 (dt, J = 12.7, 6.4 Hz, 1H), 2.17 (d, J = 19.0 Hz, 4H), 2.09 (s, 1H), 2.05 (s, 1H), 1.28 (ddd, J = 16.7, 13.1, 8.3 Hz, 3H), 1.12 (ddd, J = 21.3, 10.8, 5.9 Hz, 3H), 0.69-0.59 (m, 4H), 0.46 (q, J = 4.8 Hz, 3H), 0.43-0.37 (m, 1H); 691.59 [M + H]⁺ | 1.26 |
| 95 | 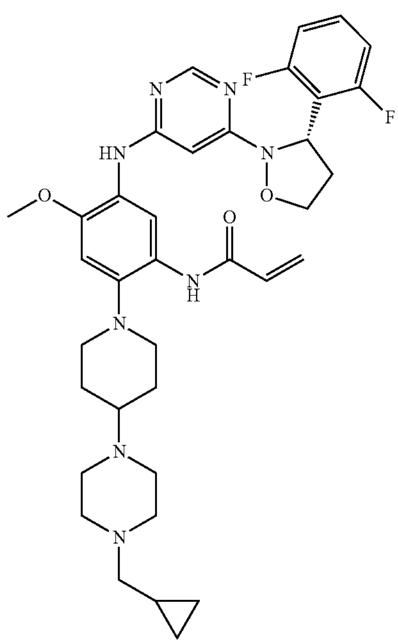 | N-(2-(4-(4-(cyclopropylmethyl)piperazine-1-yl)piperidine-1-yl)-5-((6-((S)-3-(2,6-difluorophenyl)isoxazolidine-2-yl)pyrimidine-4-yl)amino)-4-methoxyphenyl)acrylamide | ¹H NMR (400 MHz, DMSO-d₆) δ 10.34 (s, 1H), 9.28 (s, 1H), 8.30 (s, 1H), 7.84 (s, 1H), 7.48-7.39 (m, 1H), 7.13 (t, J = 8.5 Hz, 2H), 6.93 (s, 1H), 6.80-6.71 (m, 1H), 6.25 (dd, J = 17.0, 1.9 Hz, 1H), 5.95 (s, 1H), 5.76 (dd, J = 10.1, 1.9 Hz, 1H), 5.70 (s, 1H), 4.53-4.48 (m, 1H), 4.10-4.03 (m, 1H), 3.79 (s, 3H), 3.66 (s, 2H), 3.43 (t, J = 5.4 Hz, 7H), 3.14-3.07 (m, 2H), 2.94 (dd, J = 6.0, 3.0 Hz, 1H), 2.85 (t, J = 11.6 Hz, 2H), 2.46, (d, J = 4.2 Hz, 1H), 2.17 (d, J = 19.8 Hz, 4H), 1.09 (t, J = 7.0 Hz, 3H), 0.68-0.60 (m, 2H), 0.50-0.41 (m, 2H); 643.34 [M + H]⁺ | 1.18 |

TABLE 1-continued

| Example Compound | Structure | Name of Compound | ¹H NMR[[:]]; MS [M + H]⁺ | UPLC r.t. (min) |
|---|---|---|---|---|
| 96 | 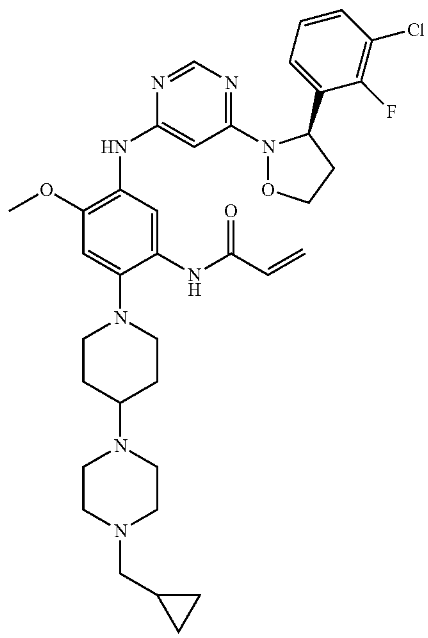 [SMILES: C=CC(=O)Nc1cc(Nc2cc(N3OCC[C@@H]3c3cccc(Cl)c3F)ncn2)c(OC)cc1N1CCC(N2CCN(CC3CC3)CC2)CC1] | N-(5-((6-((R)-3-(3-chloro-2-fluorophenyl)isoxazolidine-2-yl)pyrimidine-4-yl)amino)-2-(4-(4-(cyclopropylmethyl)piperazine-1-yl)piperidine-1-yl)-4-methoxyphenyl)acrylamide | ¹H NMR (400 MHz, DMSO-d$_6$) δ 8.96 (s, 1H), 8.63 (s, 1H), 8.14 (d, J = 8.3 Hz, 2H), 7.55-7.47 (m, 1H), 7.47-7.41 (m, 1H), 7.23 (t, J = 7.9 Hz, 1H), 6.83 (s, 1H), 6.65 (dd, J = 16.9, 10.2 Hz, 1H), 6.35 (s, 1H), 6.21 (dd, J = 16.9, 2.0 Hz, 1H), 5.77-5.67 (m, 2H), 4.07 (s, 4H), 3.90-3.81 (m, 2H), 3.80 (s, 3H), 3.05 (d, J = 11.1 Hz, 2H), 2.81 (dd, J = 8.4, 4.0 Hz, 2H), 2.71-2.62 (m, 2H), 2.15 (d, J = 6.5 Hz, 2H), 1.91 (s, 4H), 1.85 (d, J = 12.0 Hz, 2H), 1.69 (d, J = 11.5 Hz, 2H), 1.18 (t, J = 7.1 Hz, 1H), 0.82 (dd, J = 12.6, 5.5 Hz, 1H), 0.45 (dt, J = 8.5, 2.9 Hz, 2H), 0.06 (q, J = 4.8 Hz, 2H); 691.59 [M + H]⁺ | 1.28 |
| 97 | 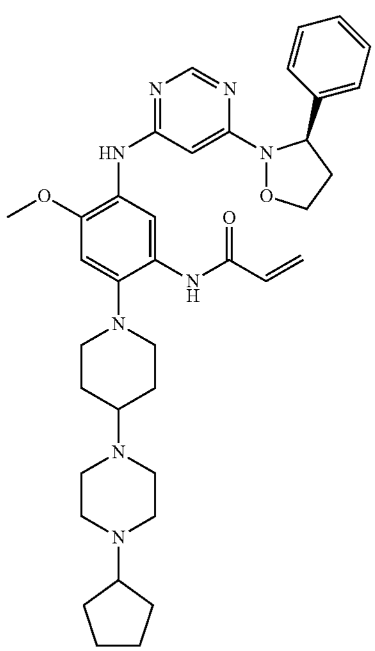 [SMILES: C=CC(=O)Nc1cc(Nc2cc(N3OCC[C@@H]3c3ccccc3)ncn2)c(OC)cc1N1CCC(N2CCN(C3CCCC3)CC2)CC1] | N-(2-(4-(4-cyclopentylpiperazine-1-yl)piperidine-1-yl)-4-methoxy-5-((6-((R)-3-phenylisoxazolidine-2-yl)pyrimidine-4-yl)amino)phenyl)acrylamide | ¹H NMR (400 MHz, Chloroform-d) δ 8.87 (s, 1H), 8.47 (s, 1H), 8.35 (s, 1H), 7.46 (d, J = 7.2 Hz, 2H), 7.35 (d, J = 3.5 Hz, 2H), 7.25 (q, J = 6.9 Hz, 1H), 6.96 (s, 1H), 6.76 (s, 1H), 6.67 (s, 1H), 6.40-6.32 (m, 1H), 6.25 (dd, J = 16.9, 9.9 Hz, 1H), 5.79-5.64 (m, 2H), 4.15 (td, J = 7.7, 4.3 Hz, 1H), 4.06 (q, J = 7.6 Hz, 1H), 3.84 (s, 3H), 3.06 (d, J = 11.0 Hz, 2H), 2.80-2.70 (m, 4H), 2.59 (dq, J = 3.9, 2.5, 1.9 Hz, 2H), 2.50 (s, 2H), 2.33 (s, 6H), 2.09 (d, J = 12.2 Hz, 2H), 1.89 (s, 2H), 1.76-1.64 (m, 4H), 1.57 (t, J = 6.2 Hz, 2H), 1.42 (d, J = 9.7 Hz, 2H); 653.61 [M + H]⁺ | 1.29 min |

TABLE 1-continued

| Example Compound | Structure | Name of Compound | ¹H NMR[[:]]; MS [M + H]⁺ | UPLC r.t. (min) |
|---|---|---|---|---|
| 98 | 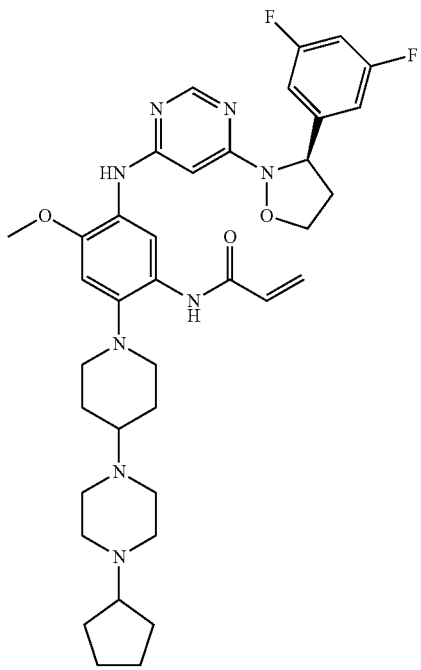 [SMILES: C=CC(=O)Nc1cc(Nc2cc(N3OCC[C@@H]3c3cc(F)cc(F)c3)ncn2)c(OC)cc1N1CCC(N2CCN(C3CCCC3)CC2)CC1] | N-(2-(4-(4-cyclopentylpiperazine-1-yl)piperidine-1-yl)-5-((6-((R)-3-(3,5-difluorophenyl)isoxazolidine-2-yl)pyrimidine-4-yl)amino)-4-methoxyphenyl)acrylamide | ¹H NMR (400 MHz, Methanol-d₄) δ 8.20 (s, 1H), 8.06 (s, 1H), 7.00-6.89 (m, 2H), 6.80 (s, 1H), 6.72 (tt, J = 2.4, 9.1 Hz, 1H), 6.44 (dd, J = 10.3, 17.0 Hz, 1H), 6.35 (s, 1H), 6.24 (dd, J = 1.5, 16.9 Hz, 1H), 5.68 (dd, J = 1.6, 10.3 Hz, 1H), 5.46 (dd, J = 4.7, 8.7 Hz, 1H), 4.08-3.97 (m, 1H), 3.85 (q, J = 7.9 Hz, 1H), 3.76 (s, 3H), 3.09-2.98 (m, 3H), 2.86-2.58 (m, 12H), 2.44-2.32 (m, 1H), 2.22 (dtd, J = 4.6, 8.1, 12.6 Hz, 1H), 1.98-1.86 (m, 5H), 1.73-1.60 (m, 5H), 1.58-1.48 (m, 2H), 1.45-1.36 (m, 2H); 689.3 [M + H]⁺ | 1.23 |
| 99 | 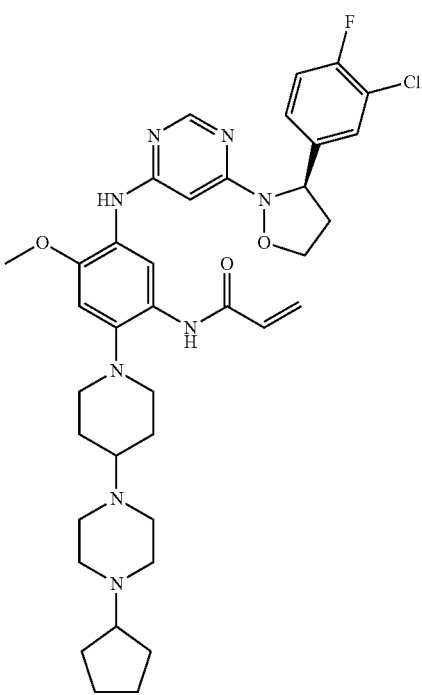 [SMILES: C=CC(=O)Nc1cc(Nc2cc(N3OCC[C@@H]3c3ccc(F)c(Cl)c3)ncn2)c(OC)cc1N1CCC(N2CCN(C3CCCC3)CC2)CC1] | N-(5-((6-((R)-3-(3-chloro-4-fluorophenyl)isoxazolidine-2-yl)pyrimidine-4-yl)amino)-2-(4-(4-cyclopentylpiperazine-1-yl)piperidine-1-yl)-4-methoxyphenyl)acrylamide | ¹H NMR (400 MHz, DMSO-d₆) δ 12.42 (s, 1H), 10.33 (s, 1H), 9.30 (s, 1H), 8.34 (s, 1H), 7.89 (s, 1H), 7.58 (dd, J = 7.0, 2.0 Hz, 13H), 7.47-7.35 (m, 2H), 6.93 (s, 1H), 6.74 (dt, J = 16.7, 8.3 Hz, 1H), 6.26 (dd, J = 17.0, 1.6 Hz, 1H), 6.11 (s, 1H), 5.77 (d, J = 11.6 Hz, 1H), 5.58-5.51 (m, 1H), 4.37-4.28 (m, 2H), 4.07 (dd, J = 15.5, 7.8 Hz, 4H), 3.81 (s, 3H), 3.44 (d, J = 7.6 Hz, 2H), 3.25 (d, J = 10.6 Hz, 2H), 3.00-2.88 (m, 2H), 2.83 (t, J = 10.6 Hz, 3H), 2.72 (d, J = 4.9 Hz, 1H), 2.33 (td, J = 12.7, 7.6 Hz, 2H), 2.16 (d, J = 15.4 Hz, 3H), 2.05 (s, 4H), 1.88-1.67 (m, 6H), 1.63-1.48 (m, 5H), 1.28 (ddd, J = 16.5, 13.1, 8.4 Hz, 2H); 705.58 [M + H]⁺. | 1.28 |

TABLE 1-continued

| Example Compound | Structure | Name of Compound | ¹H NMR[[:]]; MS [M + H]⁺ | UPLC r.t. (min) |
|---|---|---|---|---|
| 100 | 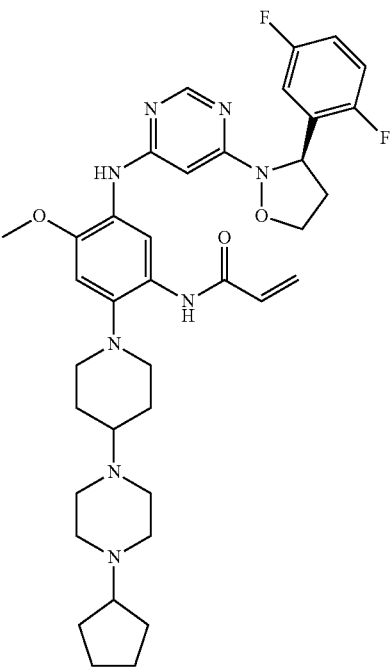 [SMILES: C=CC(=O)Nc1cc(Nc2cc(N3OCC[C@@H]3c3cc(F)ccc3F)ncn2)c(OC)cc1N1CCC(N2CCN(C3CCCC3)CC2)CC1] | N-(2-(4-(4-cyclopentylpiperazine-1-yl)piperidine-1-yl)-5-((6-((R)-3-(2,5-difluorophenyl)isoxazolidine-2-yl)pyrimidine-4-yl)amino)-4-methoxyphenyl)acrylamide | ¹H NMR (400 MHz, Methanol-d₄) δ 8.33 (s, 1H), 8.18 (d, J = 0.9 Hz, 1H), 7.26 (ddd, J = 3.2, 5.8, 9.1 Hz, 1H), 7.15 (td, J = 4.3, 9.3 Hz, 1H), 7.08-6.98 (m, 1H), 6.92 (s, 1H), 6.61-6.49 (m, 2H), 6.36 (dd, J = 1.6, 17.0 Hz, 1H), 5.79 (td, J = 3.1, 9.2, 9.7 Hz, 2H), 4.19-4.10 (m, 1H), 3.99 (q, J = 8.0 Hz, 1H), 3.89 (s, 3H), 3.20-3.12 (m, 2H), 3.06-2.76 (m, 12H), 2.59-2.50 (m, 1H), 2.27 (dtd, J = 4.6, 8.1, 12.7 Hz, 1H), 2.11-2.00 (m, 5H), 1.87-1.73 (m, 5H), 1.72-1.63 (m, 2H), 1.62-1.51 (m, 2H); 689.4 [M + H]⁺ | 1.22 |
| 101 | 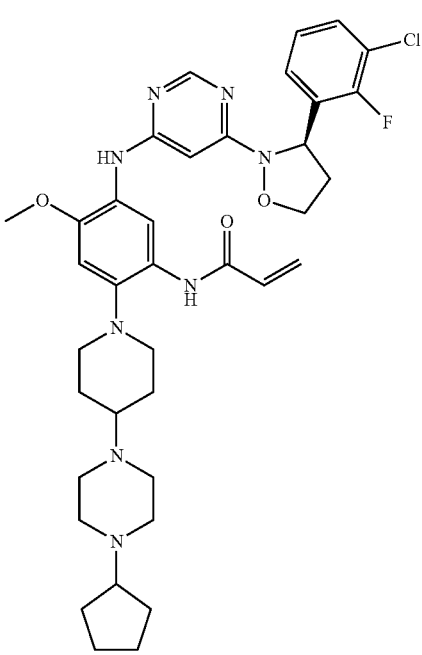 [SMILES: C=CC(=O)Nc1cc(Nc2cc(N3OCC[C@@H]3c3cccc(Cl)c3F)ncn2)c(OC)cc1N1CCC(N2CCN(C3CCCC3)CC2)CC1] | N-(5-((6-((R)-3-(3-chloro-2-fluorophenyl)isoxazolidine-2-yl)pyrimidine-4-yl)amino)-2-(4-(4-cyclopentylpiperazine-1-yl)piperidine-1-yl)-4-methoxyphenyl)acrylamide | ¹H NMR (400 MHz, DMSO-d₆) δ 8.96 (s, 1H), 8.63 (s, 1H), 8.14 (d, J = 7.9 Hz, 2H), 7.51 (t, J = 7.5 Hz, 1H), 7.45 (t, J = 7.1 Hz, 1H), 7.23 (t, J = 7.9 Hz, 1H), 6.83 (s, 1H), 6.64 (dd, J = 16.9, 10.2 Hz, 1H), 6.35 (s, 1H), 6.21 (d, J = 17.9 Hz, 1H), 5.73 (dd, J = 9.1, 5.0 Hz, 2H), 4.17 (td, J = 7.9, 3.6 Hz, 2H), 3.85 (q, J = 8.0 Hz, 2H), 3.79 (s, 3H), 3.17 (s, 2H), 3.04 (d, J = 11.0 Hz, 2H), 2.81 (dtd, J = 12.1, 8.1, 3.6 Hz, 2H), 2.72-2.61 (m, 2H), 2.41 (q, J = 8.1 Hz, 2H), 2.21 (tdd, J = 12.7, 9.5, 5.8 Hz, 2H), 1.88 (s, 4H), 1.76 (td, J = 11.0, 5.9 Hz, 2H), 1.68 (d, J = 11.1 Hz, 2H), 1.66-1.54 (m, 2H), 1.50 (ddt, J = 12.4, 9.3, 3.7 Hz, 2H), 1.37-1.20 (m, 2H); 705.62 [M + H]⁺ | 1.28 |

TABLE 1-continued

| Example Compound | Structure | Name of Compound | $^1$H NMR[:]; MS [M + H]$^+$ | UPLC r.t. (min) |
|---|---|---|---|---|
| 102 | 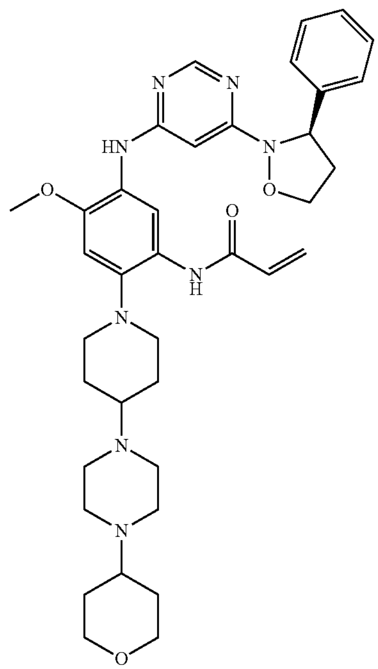 [SMILES: C=CC(=O)Nc1cc(Nc2cc(N3OCC[C@@H]3c3ccccc3)ncn2)c(OC)cc1N1CCC(N2CCN(C3CCOCC3)CC2)CC1] | N-(4-methoxy-5-((6-((R)-3-phenylisoxazolidine-2-yl)pyrimidine-4-yl)amino)-2-(4-(4-(tetrahydro-2H-pyran-4-yl)piperazine-1-yl)piperidine-1-yl)phenyl)acrylamide | $^1$H NMR (400 MHz, Chloroform-d) δ 8.87 (s, 1H), 8.36 (s, 1H), 7.46 (d, J = 7.3 Hz, 2H), 7.34 (t, J = 7.6 Hz, 2H), 7.24 (t, J = 7.3 Hz, 1H), 6.91 (s, 1H), 6.74 (s, 1H), 6.69 (s, 1H), 6.36 (d, J = 16.2 Hz, 1H), 6.24 (dd, J = 16.9, 10.0 Hz, 1H), 5.76-5.71 (m, 1H), 5.71-5.66 (m, 1H), 4.15 (td, J = 7.9, 4.4 Hz, 1H), 4.10-4.05 (m, 1H), 4.05-3.99 (m, 2H), 3.84 (s, 3H), 3.39 (td, J = 11.9, 1.9 Hz, 2H), 3.06 (d, J = 11.2 Hz, 2H), 2.73 (dt, J = 22.3, 7.0 Hz, 11H), 2.49-2.32 (m, 4H), 2.09 (d, J = 12.3 Hz, 2H), 1.85-1.77 (m, 2H), 1.74-1.54 (m, 4H); 669.75 [M + H]$^+$ | 1.87 |
| 103 | 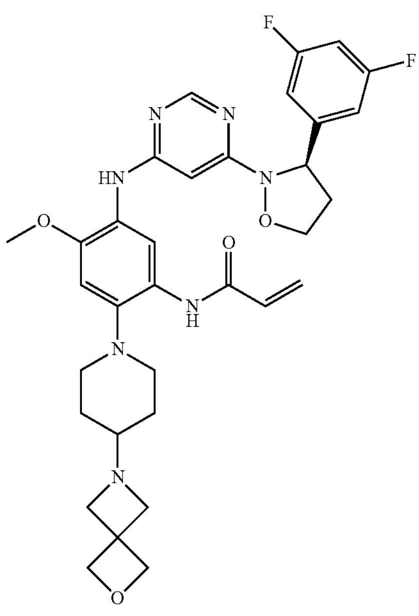 [SMILES: C=CC(=O)Nc1cc(Nc2cc(N3OCC[C@@H]3c3cc(F)cc(F)c3)ncn2)c(OC)cc1N1CCC(N2CC3(COC3)C2)CC1] | N-(2-(4-(2-oxa-6-azaspiro[3.3]heptane-6-yl)piperidine-1-yl)-5-((6-((R)-3-(3,5-difluorophenyl)isoxazolidine-2-yl)pyrimidine-4-yl)amino)-4-methoxyphenyl)acrylamide | $^1$H NMR (400 MHz, DMSO) δ 9.00 (s, 1H), 8.64 (s, 1H), 8.17 (s, 1H), 8.12 (s, 1H), 7.17-7.06 (m, 3H), 6.84 (s, 1H), 6.63-6.52 (m, 1H), 6.36 (s, 1H), 6.20 (d, J = 17.4 Hz, 1H), 5.72 (d, J = 10.5 Hz, 1H), 5.56 (dd, J = 8.6, 5.0 Hz, 1H), 4.83-4.68 (m, 1H), 4.62 (s, 3H), 4.43-4.20 (m, 2H), 4.13 (td, J = 7.8, 4.0 Hz, 1H), 3.88-3.75 (m, 4H), 3.67-3.54 (m, 1H), 3.22-2.92 (m, 5H), 2.80-2.58 (m, 4H), 2.30-2.19 (m, 1H), 2.09-1.85 (m, 2H); 634.54 [M + H]$^+$. | 1.39 |

TABLE 1-continued

| Example Compound | Structure | Name of Compound | ¹H NMR[[:]]; MS [M + H]⁺ | UPLC r.t. (min) |
|---|---|---|---|---|
| 104 | 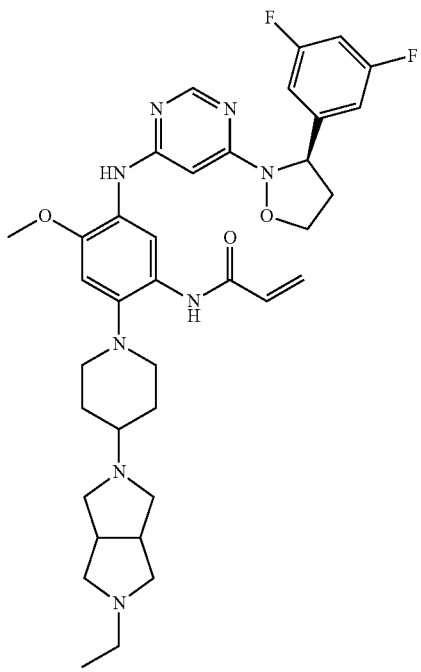 [SMILES: C=CC(=O)Nc1cc(Nc2cc(N3OCC[C@@H]3c3cc(F)cc(F)c3)ncn2)c(OC)cc1N1CCC(N2CC3CN(CC)CC3C2)CC1] | N-(5-((6-((R)-3-(3,5-difluorophenyl)isoxazolidine-2-yl)pyrimidine-4-yl)amino)-2-(4-(5-ethylhexahydropyrrolo[3,4-c]pyrrole-2(1H)-yl)piperidine-1-yl)-4-methoxyphenyl)acrylamide | ¹H NMR (400 MHz, DMSO) δ 8.98 (s, 1H), 8.64 (s, 1H), 8.16 (s, 1H), 8.11 (s, 1H), 7.16-7.08 (m, 3H), 6.82 (s, 1H), 6.62 (dd, J = 16.9, 10.3 Hz, 1H), 6.35 (s, 1H), 6.24-6.17 (m, 1H), 5.87 (dd, J = 10.3, 1.8 Hz, 1H), 5.72 (d, J = 11.0 Hz, 1H), 5.56 (dd, J = 8.6, 5.0 Hz, 1H), 4.13 (td, J = 7.8, 3.9 Hz, 1H), 3.97-3.76 (m, 5H), 3.62-3.47 (m, 2H), 3.12-2.98 (m, 5H), 2.90-2.62 (m, 9H), 2.29-2.16 (m, 2H), 1.98-1.88 (m, 2H), 1.78-1.66 (m, 2H), 1.14 (t, J = 10.7 Hz, 3H); 675.62 [M + H]⁺ | 1.28 |
| 105 | 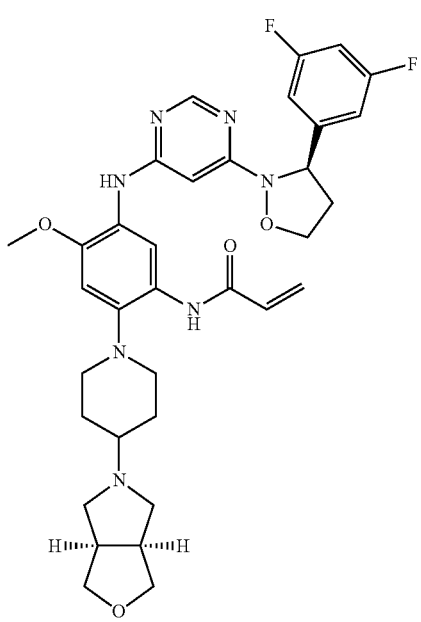 [SMILES: C=CC(=O)Nc1cc(Nc2cc(N3OCC[C@@H]3c3cc(F)cc(F)c3)ncn2)c(OC)cc1N1CCC(N2C[C@H]3COC[C@H]3C2)CC1] | N-(5-((6-((R)-3-(3,5-difluorophenyl)isoxazolidine-2-yl)pyrimidine-4-yl)amino)-4-methoxy-2-(4-((3aR,6aS)-tetrahydro-1H-puro[3,4-c]pyrrole-5(3H)-yl)piperidine-1-yl)phenyl)acrylamide | ¹H NMR (400 MHz, DMSO) δ 9.12-8.91 (m, 1H), 8.65 (s, 1H), 8.17 (s, 1H), 8.12 (s, 1H), 7.17-7.07 (m, 3H), 6.84 (s, 1H), 6.56 (s, 1H), 6.38 (s, 1H), 6.22 (d, J = 17.0 Hz, 1H), 5.77-5.67 (m, 1H), 5.56 (dd, J = 8.6, 5.0 Hz, 1H), 4.13 (td, J = 7.8, 3.9 Hz, 1H), 3.94-3.69 (m, 7H), 3.66-3.44 (m, 3H), 3.19-2.97 (m, 5H), 2.81-2.64 (m, 4H), 2.29-2.18 (m, 1H), 2.14-1.82 (m, 4H); 648.57 [M + H]⁺ | 1.42 |

TABLE 1-continued

| Example Compound | Structure | Name of Compound | ¹H NMR[[:]]; MS [M + H]⁺ | UPLC r.t. (min) |
|---|---|---|---|---|
| 106 | 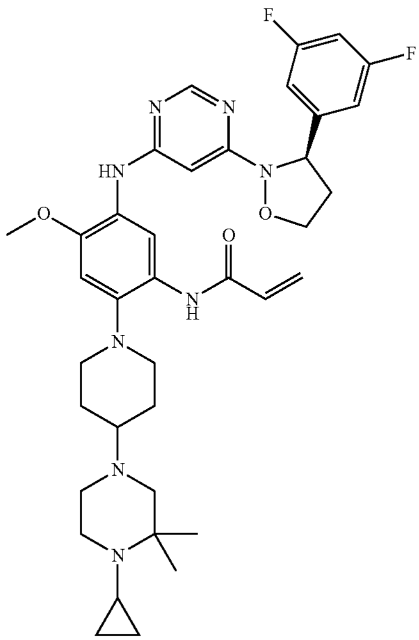 [SMILES: C=CC(=O)Nc1cc(Nc2cc(N3OCC[C@@H]3c3cc(F)cc(F)c3)ncn2)c(OC)cc1N1CCC(N2CCN(C3CC3)C(C)(C)C2)CC1] | N-(2-(4-(4-cyclopropyl-3,3-dimethylpiperazine-1-yl)piperidine-1-yl)-5-((6-((R)-3-(3,5-difluorophenyl)isoxazolidine-2-yl)pyrimidine-4-yl)amino)-4-methoxyphenyl)acrylamide | 689.7 [M + H]⁺ | 1.33 |
| 107 | 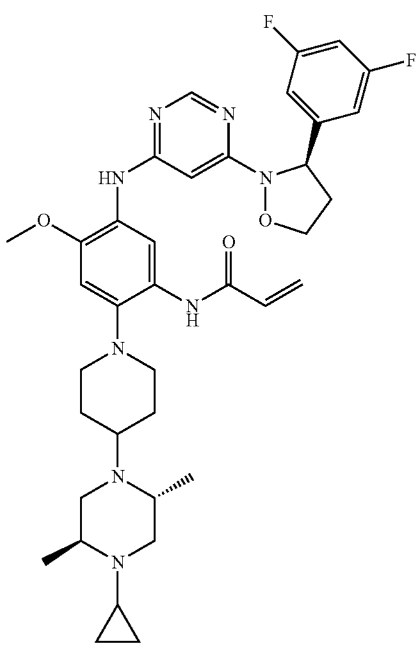 [SMILES: C=CC(=O)Nc1cc(Nc2cc(N3OCC[C@@H]3c3cc(F)cc(F)c3)ncn2)c(OC)cc1N1CCC(N2C[C@H](C)N(C3CC3)C[C@H]2C)CC1] | N-(2-(4-((2R,5S)-4-cyclopropyl-2,5-dimethylpiperazine-1-yl)piperidine-1-yl)-5-((6-((R)-3-(3,5-difluorophenyl)isoxazolidine-2-yl)pyrimidine-4-yl)amino)-4-methoxyphenyl)acrylamide | ¹H NMR (400 MHz, DMSO-d₆) δ 8.95 (s, 1H), 8.62 (s, 1H), 8.16 (s, 1H), 7.12 (ddd, J = 8.2, 6.2, 3.2 Hz, 3H), 6.84 (s, 1H), 6.68 (dd, J = 16.9, 10.1 Hz, 1H), 6.34 (s, 1H), 6.21, (dd, J = 16.9, 2.1 Hz, 1H), 5.72 (d, J = 10.9 Hz, 1H), 5.55 (dt, J = 10.5, 5.1 Hz, 1H), 3.85 (dd, J = 15.5, 7.4 Hz, 2H), 3.79 (s, 3H), 3.17 (s, 2H), 3.05 (q, J = 14.6, 13.2 Hz, 4H), 2.88, (d, J = 11.5 Hz, 2H), 2.80 (d, J = 2.4 Hz, 1H), 2.75 (dt, J = 12.6, 3.8 Hz, 3H), 2.67 (q, J = 1.8 Hz, 1H), 2.55 (d, J = 6.1 Hz, 1H), 2.39-2.32 (m, 2H), 2.30-2.19 (m, 2H), 2.00 (td, J = 10.6, 5.5 Hz, 4H), 1.71 (s, 3H), 1.23 (s, 3H), 1.11 (d, J = 6.2, Hz, 3H), 0.99 (d, J = 6.1 Hz, 2H), ; 689.6 [M + H]⁺ | 1.32 |

TABLE 1-continued

| Example Compound | Structure | Name of Compound | ¹H NMR[:]; MS [M + H]⁺ | UPLC r.t. (min) |
|---|---|---|---|---|
| 108 | 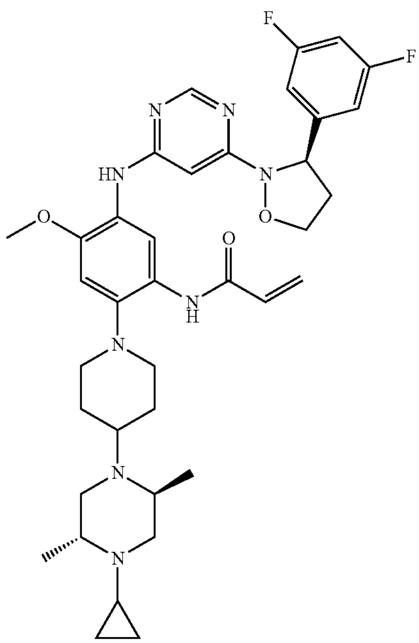 [SMILES: C=CC(=O)Nc1cc(Nc2cc(N3OCC[C@@H]3c3cc(F)cc(F)c3)ncn2)c(OC)cc1N1CCC(N2C[C@@H](C)N(C3CC3)C[C@@H]2C)CC1] | N-(2-(4-((2S,5R)-4-cyclopropyl-2,5-dimethylpiperazine-1-yl)piperidine-1-yl)-5-((6-((R)-3-(3,5-difluorophenyl)isoxazolidine-2-yl)pyrimidine-4-yl)amino)-4-methoxyphenyl)acrylamide | 689.6 [M + H]⁺ | 1.29 |
| 109 | 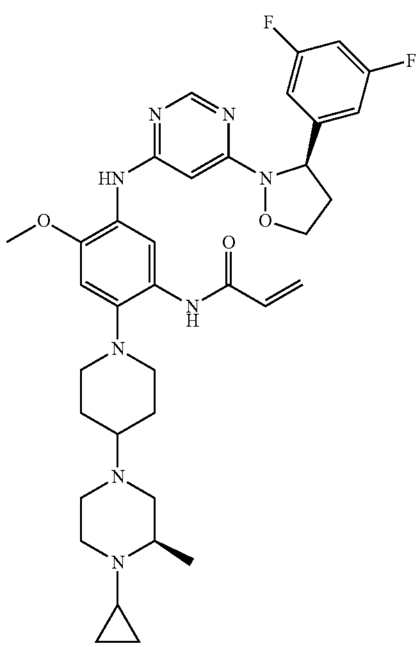 [SMILES: C=CC(=O)Nc1cc(Nc2cc(N3OCC[C@@H]3c3cc(F)cc(F)c3)ncn2)c(OC)cc1N1CCC(N2CCN(C3CC3)[C@H](C)C2)CC1] | N-(2-(4-((R)-4-cyclopropyl-3-methylpiperazine-1-yl)piperidine-1-yl)-5-((6-((R)-3-(3,5-difluorophenyl)isoxazolidine-2-yl)pyrimidine-4-yl)amino)-4-methoxyphenyl)acrylamide | ¹H NMR (400 MHz, Methanol-d₄) δ 8.23 (s, 1H), 8.11 (s, 1H), 7.00 (d, J = 4.3 Hz, 2H), 6.85 (s, 1H), 6.77 (tt, J = 2.5, 9.1 Hz, 1H), 6.50 (dd, J = 10.2, 17.0 Hz, 1H), 6.39 (s, 1H), 6.30 (d, J = 16.4 Hz, 1H), 5.75 (d, J = 10.6 Hz, 1H), 5.50 (dd, J = 4.8, 8.6 Hz, 1H), 4.12-4.05 (m, 1H), 3.91 (q, J = 8.0 Hz, 1H), 3.82 (s, 3H), 3.14-3.05 (m, 4H), 2.80-2.70 (m, 3H), 2.68-2.58 (m, 2H), 2.58-2.50 (m, 2H), 2.33-2.19 (m, 2H), 2.11-2.00 (m, 2H), 1.83-1.71 (m, 2H), 1.71-1.59 (m, 1H), 1.22 (d, 3H), 0.67 (dt, J = 5.8, 11.5 Hz, 1H), 0.58 (dt, J = 4.8, 10.2 Hz, 1H), 0.49 (q, J = 7.5, 9.1 Hz, 1H), 0.32 (dt, J = 5.4, 10.8 Hz, 1H); 675.4 [M + H]⁺ | 1.41 |

TABLE 1-continued

| Example Compound | Structure | Name of Compound | ¹H NMR[:]; MS [M + H]⁺ | UPLC r.t. (min) |
|---|---|---|---|---|
| 110 | 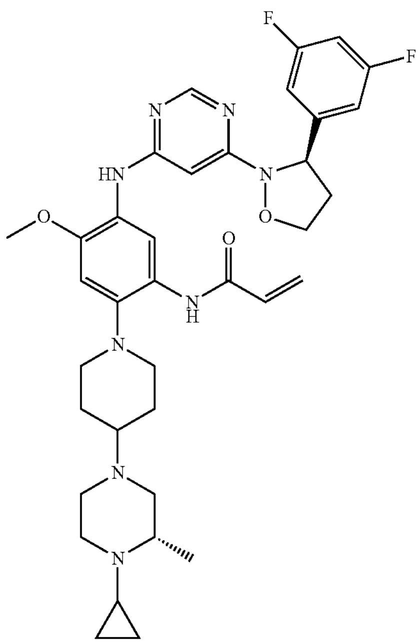 [SMILES: C=CC(=O)Nc1cc(Nc2cc(N3OCC[C@@H]3c3cc(F)cc(F)c3)ncn2)c(OC)cc1N1CCC(N2CCN(C3CC3)[C@@H](C)C2)CC1] | N-(2-(4-((S)-4-cyclopropyl-3-methylpiperazine-1-yl)piperidine-1-yl)-5-((6-((R)-3-(3,5-difluorophenyl)isoxazolidine-2-yl)pyrimidine-4-yl)amino)-4-methoxyphenyl)acrylamide | ¹H NMR (400 MHz, Methanol-d₄) δ 8.29 (s, 1H), 8.18 (s, 1H), 7.07 (d, J = 4.5 Hz, 2H), 6.92 (s, 1H), 6.84 (tt, J = 2.5, 9.1 Hz, 1H), 6.57 (dd, J = 10.3, 17.0 Hz, 1H), 6.46 (s, 1H), 6.37 (d, J = 16.8 Hz, 1H), 5.82 (d, J = 10.4 Hz, 1H), 5.57 (dd, J = 4.7, 8.7 Hz, 1H), 4.15 (dd, J = 4.2, 7.9 Hz, 1H), 3.97 (q, J = 8.0 Hz, 1H), 3.89 (s, 3H), 3.22-3.15 (m, 4H), 2.86-2.70 (m, 5H), 2.68-2.58 (m, 2H), 2.42-2.28 (m, 2H), 2.17-2.08 (m, 2H), 1.89-1.79 (m, 2H), 1.78-1.68 (m, 1H), 1.30 (d, J = 6.5 Hz, 3H), 0.75 (dt, J = 5.8, 11.6 Hz, 1H), 0.65 (dt, J = 4.8, 10.2 Hz, 1H), 0.61-0.51 (m, 1H), 0.39 (dt, J = 5.2, 10.5 Hz, 1H); 675.4 [M + H]⁺ | 1.41 |
| 111 | 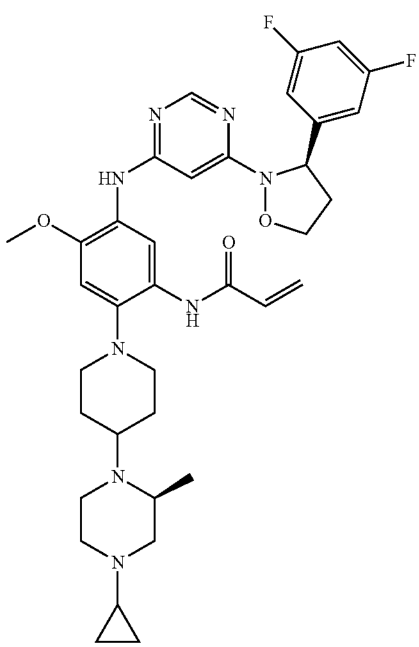 [SMILES: C=CC(=O)Nc1cc(Nc2cc(N3OCC[C@@H]3c3cc(F)cc(F)c3)ncn2)c(OC)cc1N1CCC(N2CCN(C3CC3)C[C@@H]2C)CC1] | N-(2-(4-((S)-4-cyclopropyl-2-methylpiperazine-1-yl)piperidine-1-yl)-5-((6-((R)-3-(3,5-difluorophenyl)isoxazolidine-2-yl)pyrimidine-4-yl)amino)-4-methoxyphenyl)acrylamide | ¹H NMR (400 MHz, Methanol-d₄) δ 8.30 (s, 1H), 8.18 (s, 1H), 7.14-7.02 (m, 2H), 6.94 (m, 1H), 6.87-6.78 (m, 1H), 6.57 (dd, J = 10.3, 17.0 Hz, 1H), 6.47 (s, 1H), 6.37 (dd, J = 1.5, 17.0 Hz, 1H), 5.82 (d, J = 9.8 Hz, 1H), 5.57 (dd, J = 4.8, 8.7 Hz, 1H), 4.19-4.12 (m, 2H), 3.98 (q, J = 7.9 Hz, 2H), 3.89 (s, 3H), 3.21 (d, J = 11.5 Hz, 4H), 3.14 (d, J = 8.0 Hz, 1H), 3.08-3.02 (m, 2H), 2.96-2.81 (m, 5H), 2.76-2.57 (m, 2H), 2.53-2.44 (m, 1H), 2.39-2.31 (m, 1H), 1.30 (d, J = 6.4 Hz, 3H), 0.56 (d, J = 6.3 Hz, 2H), 0.47 (s, 2H); 675.4 [M + H]⁺ | 1.3 |

TABLE 1-continued

| Example Compound | Structure | Name of Compound | ¹H NMR[:]; MS [M + H]⁺ | UPLC r.t. (min) |
|---|---|---|---|---|
| 112 | 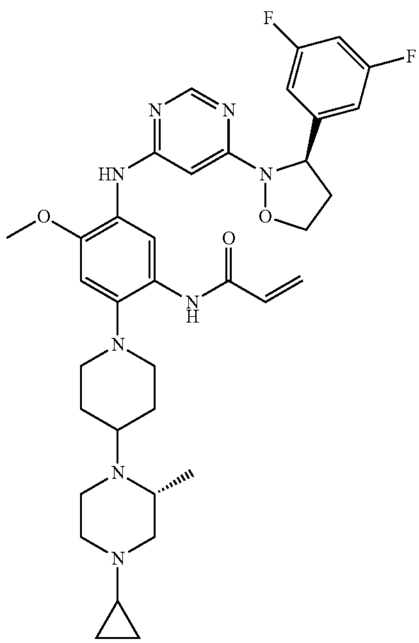 [SMILES: C=CC(=O)Nc1cc(Nc2cc(N3OCC[C@@H]3c3cc(F)cc(F)c3)ncn2)c(OC)cc1N1CCC(N2CCN(C3CC3)C[C@H]2C)CC1] | N-(2-(4-((R)-4-cyclopropyl-2-methylpiperazine-1-yl)piperidine-1-yl)-5-((6-((R)-3-(3,5-difluorophenyl)isoxazolidine-2-yl)pyrimidine-4-yl)amino)-4-methoxyphenyl)acrylamide | ¹H NMR (400 MHz, Methanol-d₄) δ 8.30 (s, 1H), 8.18 (s, 1H), 7.11-7.02 (m, 2H), 6.94 (s, 1H), 6.91-6.78 (m, 1H), 6.57 (dd, J = 10.2, 16.9 Hz, 1H), 6.47 (s, 1H), 6.37 (dd, J = 1.5, 16.8 Hz, 1H), 5.82 (d, J = 10.3 Hz, 1H), 5.57 (dd, J = 4.8, 8.6 Hz, 1H), 4.19-4.12 (m, 2H), 3.98 (q, J = 7.9 Hz, 2H), 3.89 (s, 3H), 3.21 (d, J = 12.7 Hz, 4H), 3.10-3.01 (m, 3H), 2.99-2.79 (m, 5H), 2.65 (d, J = 18.7 Hz, 2H), 2.54-2.42 (m, 1H), 2.36-2.29 (m, 1H), 1.32-1.30 (m, 3H), 0.56 (d, J = 6.4 Hz, 2H), 0.47 (s, 2H); 675.4 [M + H]⁺ | 1.31 |
| 113 | 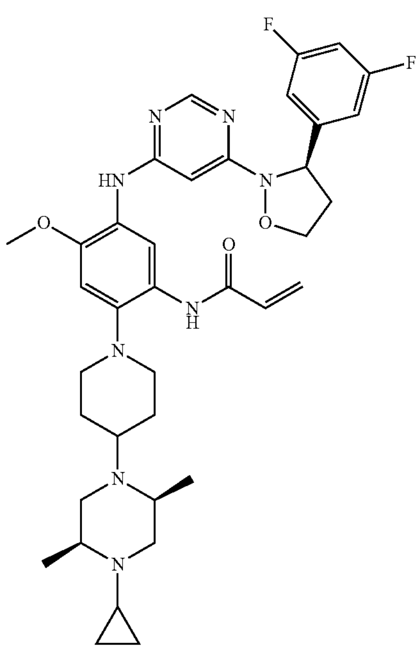 [SMILES: C=CC(=O)Nc1cc(Nc2cc(N3OCC[C@@H]3c3cc(F)cc(F)c3)ncn2)c(OC)cc1N1CCC(N2C[C@H](C)N(C3CC3)C[C@@H]2C)CC1] | N-(2-(4-((2S,5S)-4-cyclopropyl-2,5-dimethylpiperazine-1-yl)piperidine-1-yl)-5-((6-((R)-3-(3,5-difluorophenyl)isoxazolidine-2-yl)pyrimidine-4-yl)amino)-4-methoxyphenyl)acrylamide | ¹H NMR (400 MHz, DMSO-d₆) δ 10.01 (s, 1H), 9.29 (s, 1H), 8.32 (s, 1H), 7.22-7.06 (m, 4H), 6.94 (d, J = 18.2 Hz, 1H), 6.65 (ddd, J = 52.1, 16.8, 10.2 Hz, 1H), 6.25 (d, J = 17.0 Hz, 1H), 6.15 (s, 1H), 5.81-5.71 (m, 2H), 5.55 (dd, J = 8.6, 5.4 Hz, 2H), 4.04 (q, J = 7.7 Hz, 2H), 3.81 (d, J = 4.2 Hz, 6H), 3.57 (s, 6H), 3.21 (d, J = 33.4 Hz, 5H), 3.03-2.87 (m, 4H), 2.88-2.63 (m, 2H), 2.39-2.23 (m, 3H), 2.11 (d, J = 20.3 Hz, 3H), 1.74 (s, 2H), 1.57 (s, 6H), ; 689.6 [M + H]⁺ | 1.40 |

TABLE 1-continued

| Example Compound | Structure | Name of Compound | ¹H NMR[[:]]; MS [M + H]⁺ | UPLC r.t. (min) |
|---|---|---|---|---|
| 114 | 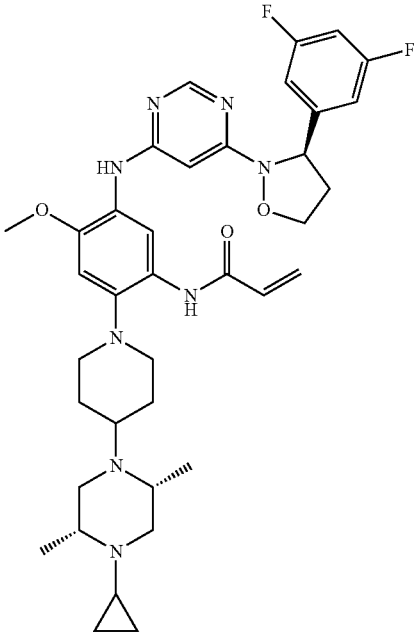 [SMILES: C=CC(=O)Nc1cc(Nc2cc(N3OCC[C@@H]3c3cc(F)cc(F)c3)ncn2)c(OC)cc1N1CCC(N2C[C@@H](C)N(C3CC3)C[C@H]2C)CC1] | N-(2-(4-((2R,5R)-4-cyclopropyl-2,5-dimethylpiperazine-1-yl)piperidine-1-yl)-5-((6-((R)-3-(3,5-difluorophenyl)isoxazolidine-2-yl)pyrimidine-4-yl)amino)-4-methoxyphenyl)acrylamide | ¹H NMR (400 MHz, DMSO-d₆) δ 8.94 (s, 1H), 8.62 (s, 1H), 8.16 (d, J = 1.0 Hz, 1H), 7.12 (dq, J = 7.7, 3.0, 1.7 Hz, 4H), 6.83 (s, 1H), 6.65 (dd, J = 16.9, 10.2 Hz, 1H), 6.34 (s, 1H), 6.20 (dd, J = 17.0, 2.0 Hz, 1H), 5.75-5.67 (m, 1H), 5.56 (dd, J = 8.7. 5.0 Hz, 1H), 4.13 (d, J = 3.9 Hz, 1H), 3.79 (s, 4H), 3.32 (s, 3H), 3.11-2.93 (m, 4H), 2.77 (ddd, J = 12.1, 8.3, 3.9 Hz, 1H), 2.73-2.64 (m, 3H), 2.60 (dd, J = 10.9, 4.9 Hz, 3H), 2.44 (dd, J = 11.0, 3.2 Hz, 2H), 2.31-2.18 (m, 3H), 1.88-1.77 (m, 3H), 1.77-1.65 (m, 2H), 1.55 (d, J = 10.4 Hz, 2H), 1.09 (d, J = 6.2 Hz, 4H), 0.95 (d, J = 6.3 Hz, 4H), 0.58-0.49 (m, 1H), 0.42-0.31 (m, 3H), 0.13 (d, J = 9.6 Hz, 1H), ; 689.6 [M + H]⁺ | 1.41 |
| 115 | 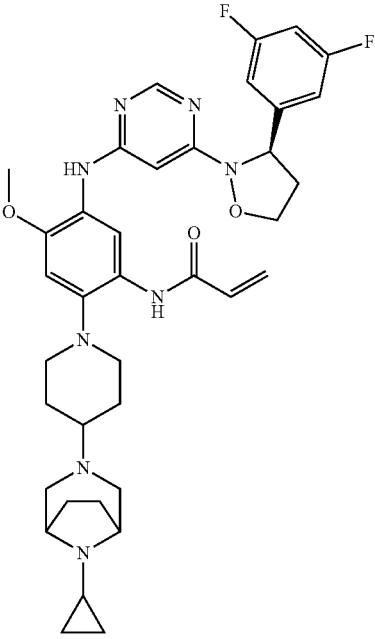 [SMILES: C=CC(=O)Nc1cc(Nc2cc(N3OCC[C@@H]3c3cc(F)cc(F)c3)ncn2)c(OC)cc1N1CCC(N2CC3CCC(C2)N3C2CC2)CC1] | N-(2-(4-((1R,5S)-8-cyclopropyl-3,8-diazabicyclo[3.2.1]octan-3-yl)piperidine-1-yl)-5-((6-((R)-3-(3,5-difluorophenyl)isoxazolidine-2-yl)pyrimidine-4-yl)amino)-4-methoxyphenyl)acrylamide | ¹H NMR (400 MHz, CDCl₃) δ 8.81 (s, 1H), 8.44 (s, 1H), 8.34 (s, 1H), 7.16 (s, 1H), 7.01 (s, 1H), 6.99 (s, 1H), 6.75 (s, 1H), 6.71-6.65 (m, 2H), 6.40-6.23 (m, 2H), 5.77-5.72 (m, 1H), 5.66 (dd, J = 8.7, 4.5 Hz, 1H), 4.18-4.11 (m, 1H), 4.05 (q, J = 8.0 Hz, 1H), 3.84 (s, 3H), 3.37 (s, 2H), 3.06-2.99 (m, 2H), 2.82-2.63 (m, 5H), 2.55-2.49 (m, 2H), 2.38-2.28 (m, 2H), 2.01-1.85 (m, 7H), 1.69-1.57 (m, 2H), 0.63-0.56 (m, 2H), 0.50-0.43 (m, 2H); 687.53 [M + H]⁺ | 1.21 |

TABLE 1-continued

| Example Compound | Structure | Name of Compound | ¹H NMR[[:]]; MS [M + H]⁺ | UPLC r.t. (min) |
|---|---|---|---|---|
| 116 | 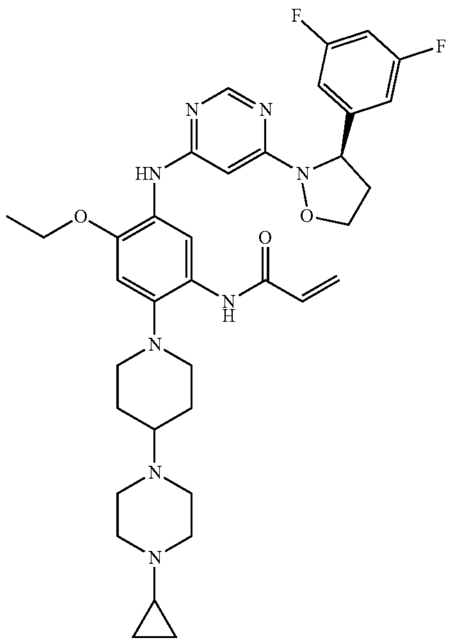 [SMILES: C=CC(=O)Nc1cc(Nc2cc(N3OCC[C@@H]3c3cc(F)cc(F)c3)ncn2)c(OCC)cc1N1CCC(N2CCN(C3CC3)CC2)CC1] | N-(2-(4-(4-cyclopropylpiperazine-1-yl)piperidine-1-yl)-5-((6-((R)-3-(3,5-difluorophenyl)isoxazolidine-2-yl)pyrimidine-4-yl)amino)-4-ethoxyphenyl)acrylamide | ¹H NMR (400 MHz, Methanol-$d_4$) δ 8.17 (s, 2H), 7.11-7.02 (m, 2H), 6.91-6.77 (m, 2H), 6.58 (dd, J = 10.3, 16.9 Hz, 1H), 6.36 (d, J = 18.5 Hz, 2H), 5.79 (dd, J = 1.6, 10.2 Hz, 1H), 5.56 (dd, J = 4.9, 8.6 Hz, 1H), 4.23-4.11 (m, 4H), 3.96 (t, J = 8.0 Hz, 1H), 3.02-2.89 (m, 4H), 2.91-2.76 (m, 7H), 2.76-2.68 (m, 2H), 2.41-2.28 (m, 2H), 2.10-2.03 (m, 2H), 1.82-1.70 (m, 2H), 1.59 (td, J = 4.1, 12.0 Hz, 1H), 1.48 (t, J = 7.0 Hz, 3H), 0.54 (dd, J = 4.5, 6.7 Hz, 2H), 0.49-0.40 (m, 2H); 675.4 [M + H]⁺ | 1.33 |
| 117 | 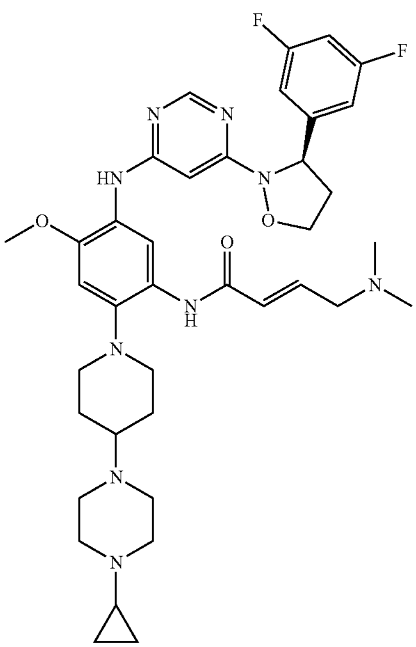 | N-(2-(4-(4-cyclopropylpiperazine-1-yl)piperidine-1-yl)-5-((6-((R)-3-(3,5-difluorophenyl)isoxazolidine-2-yl)pyrimidine-4-yl)amino)-4-methoxyphenyl)-(E)-4-(dimethylamino)but-2-enamide | ¹H NMR (400 MHz, Methanol-$d_4$) δ 8.32 (s, 1H), 8.18 (s, 1H), 7.11-7.02 (m, 2H), 6.95-6.80 (m, 4H), 6.76-6.72 (m, 2H), 6.56-6.44 (m, 2H), 5.57 (dd, J = 4.8, 8.7 Hz, 1H), 4.16 (td, J = 3.9, 7.7 Hz, 2H), 3.97 (d, J = 8.0 Hz, 1H), 3.89 (s, 4H), 3.16 (s, 3H), 3.03 (s, 3H), 2.89-2.78 (m, 10H), 2.41-2.28 (m, 2H), 2.14-2.09 (m, 2H), 1.87-1.76 (m, 4H), 0.59-0.53 (m, 2H), 0.50-0.44 (m, 2H); 718.4 [M + H]⁺ | 1.1 |

TABLE 1-continued

| Example Compound | Structure | Name of Compound | ¹H NMR[[:]]; MS [M + H]⁺ | UPLC r.t. (min) |
|---|---|---|---|---|
| 118 | 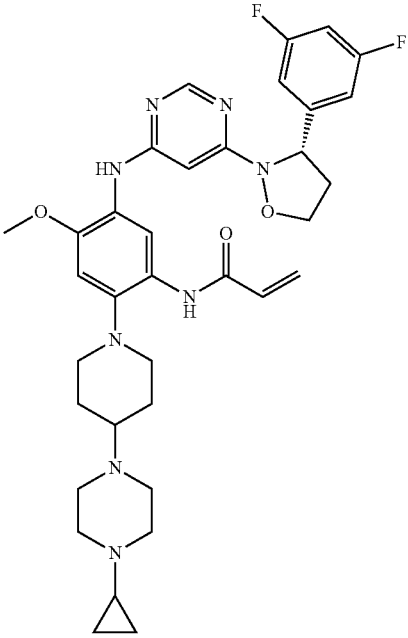 [SMILES: C=CC(=O)Nc1cc(Nc2cc(N3OCC[C@H]3c3cc(F)cc(F)c3)ncn2)c(OC)cc1N1CCC(N2CCN(C3CC3)CC2)CC1] | N-(2-(4-(4-cyclopropylpiperazine-1-yl)piperidine-1-yl)-5-((6-((S)-3-(3,5-difluorophenyl)isoxazolidine-2-yl)pyrimidine-4-yl)amino)-4-methoxyphenyl)acrylamide | ¹H NMR (400 MHz, CDCl₃) δ 8.86 (s, 1H), 8.44 (s, 1H), 8.36 (s, 1H), 7.04-6.97 (m, 2H), 6.94 (s, 1H), 6.75 (s, 1H), 6.73-6.64 (m, 2H), 6.39-6.19 (m, 2H), 5.74 (d, J = 11.1 Hz, 1H), 5.67 (dd, J = 8.7, 4.5 Hz, 1H), 4.19-4.11 (m, 1H), 4.06 (q, J = 8.0 Hz, 1H), 3.84 (s, 3H), 3.12-3.00 (m, 2H), 2.81-2.59 (m, 10H), 2.40-2.29 (m, 2H), 2.14-2.03 (m, 2H), 1.76-1.60 (m, 4H), 0.51-0.38 (m, 4H); 661.54 [M + H]⁺ | 1.19 |
| 119 | 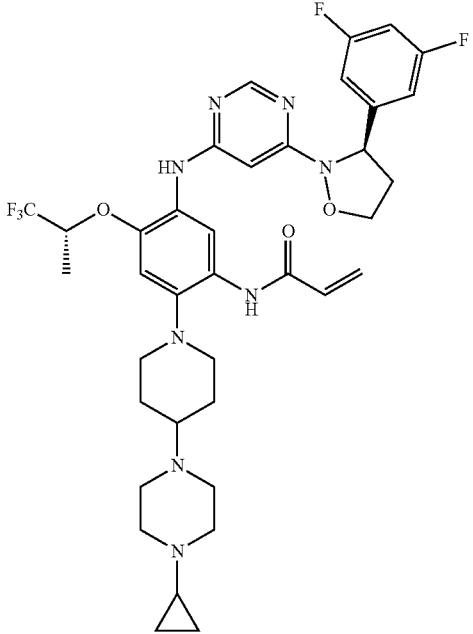 [SMILES: C=CC(=O)Nc1cc(Nc2cc(N3OCC[C@@H]3c3cc(F)cc(F)c3)ncn2)c(O[C@H](C)C(F)(F)F)cc1N1CCC(N2CCN(C3CC3)CC2)CC1] | N-(2-(4-(4-cyclopropylpiperazine-1-yl)piperidine-1-yl)-5-((6-((R)-3-(3,5-difluorophenyl)isoxazolidine-2-yl)pyrimidine-4-yl)amino)-4-(((R)-1,1,1-trifluoropropane-2-yl)oxy)phenyl)acrylamide | ¹H NMR (400 MHz, Methanol-d₄) δ 8.25 (s, 1H), 8.17 (s, 1H), 7.11-6.98 (m, 3H), 6.90-6.77 (m, 1H), 6.63-6.49 (m, 1H), 6.41 (d, J = 6.0 Hz, 2H), 5.83 (d, J = 10.3 Hz, 1H), 5.57 (dd, J = 4.8, 8.7 Hz, 1H), 4.19-4.13 (m, 1H), 3.97 (q, J = 8.0 Hz, 1H), 3.23-3.14 (m, 3H), 3.06-2.91 (m, 4H), 2.91-2.76 (m, 8H), 2.40-2.29 (m, 1H), 2.17-2.11 (m, 2H), 1.93-1.75 (m, 4H), 1.44 (d, J = 6.5 Hz, 3H), 0.60-0.52 (m, 2H), 0.52-0.45 (m, 2H); 743.3 [M + H]⁺ | 1.42 |

TABLE 1-continued

| Example Compound | Structure | Name of Compound | ¹H NMR[[:]]; MS [M + H]⁺ | UPLC r.t. (min) |
|---|---|---|---|---|
| 120 | 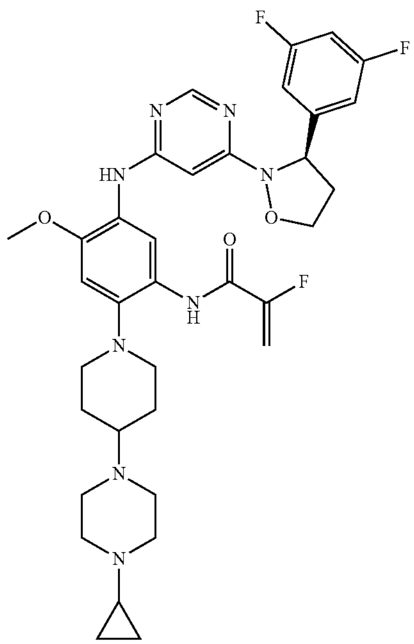 [SMILES: C=C(F)C(=O)Nc1cc(Nc2cc(N3OCC[C@@H]3c3cc(F)cc(F)c3)ncn2)c(OC)cc1N1CCC(N2CCN(C3CC3)CC2)CC1] | N-(2-(4-(4-cyclopropylpiperazine-1-yl)piperidine-1-yl)-5-((6-((R)-3-(3,5-difluorophenyl)isoxazolidine-2-yl)pyrimidine-4-yl)amino)-4-methoxyphenyl)-2-fluoroacrylamide | ¹H NMR (400 MHz, DMSO-$d_6$) δ 9.30 (d, J = 3.6 Hz, 1H), 8.70 (s, 1H), 8.42 (d, J = 1.2 Hz, 1H), 8.19 (s, 1H), 7.13 (ddd, J = 7.9, 5.4, 2.9 Hz, 3H), 6.95 (s, 1H), 6.44 (s, 1H), 5.79-5.61 (m, 1H), 5.29 (dd, J = 13.9, 3.0 Hz, 1H), 4.14 (td, J = 7.9, 3.9 Hz, 1H), 3.82 (s, 4H), 3.06 (d, J = 11.4 Hz, 2H), 2.88 (d, J = 30.1 Hz, 5H), 2.77 (ddt, J = 15.4, 7.4, 4.0 Hz, 8H), 2.32-2.18 (m, 1H), 2.11-2.03 (m, 2H), 1.65 (td, J = 11.9, 3.6 Hz, 2H), 1.24 (dd, J = 4.6, 2.5 Hz, 2H), 0.45 (dt, J = 6.2, 2.9 Hz, 2H), 0.36 (q, J = 3.4, 2.9 Hz, 2H), ; 679.5 [M + H]⁺ | 1.35 |
| 121 | 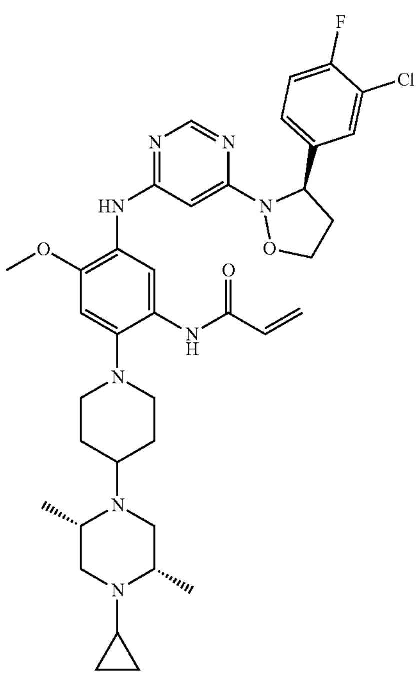 [SMILES: C=CC(=O)Nc1cc(Nc2cc(N3OCC[C@@H]3c3ccc(F)c(Cl)c3)ncn2)c(OC)cc1N1CCC(N2C[C@H](C)N(C3CC3)C[C@@H]2C)CC1] | N-(5-((6-((R)-3-(3-chloro-4-fluorophenyl)isoxazolidine-2-yl)pyrimidine-4-yl)amino)-2-(4-((2S,5S)-4-cyclopropyl-2,5-dimethylpiperazine-1-yl)piperidine-1-yl)-4-methoxyphenyl)acrylamide | ¹H NMR (400 MHz, DMSO-$d_6$) δ 10.31 (s, 1H), 9.38 (s, 1H), 8.35 (s, 1H), 7.88 (d, J = 73.3 Hz, 1H), 7.59 (dd, J = 7.1, 2.2 Hz, 1H), 7.46-7.34 (m, 2H), 6.96 (d, J = 22.5 Hz, 1H), 6.68 (ddd, J = 55.9, 17.0, 10.2 Hz, 1H), 6.25 (d, J = 17.0 Hz, 1H), 6.13 (s, 1H), 5.77 (dd, J = 10.1, 1.9 Hz, 1H), 5.54 (t, J = 7.0 Hz, 1H), 4.32 (d, J = 4.6 Hz, 1H), 4.19-4.00 (m, 3H), 3.97 (s, 1H), 3.82 (d, J = 4.1 Hz, 3H), 3.71 (s, 1H), 3.57 (d, J = 2.2 Hz, 2H), 3.44-3.35 (m, 1H), 3.24 (d, J = 30.2 Hz, 3H), 2.96 (ddd, J = 17.0, 8.7, 4.8 Hz, 3H), 2.83-2.67 (m, 1H), 2.33 (dt, J = 9.5, 5.2 Hz, 2H), 2.15 (s, 2H), 1.77 (s, 2H), 1.61 (d, J = 13.5 Hz, 4H), 1.46-1.34 (m, 1H), 0.84 (d, J = 6.8 Hz, 3H), ; 705.3 [M + H]⁺ | 1.45 |

TABLE 1-continued

| Example Compound | Structure | Name of Compound | ¹H NMR[[:]]; MS [M + H]⁺ | UPLC r.t. (min) |
|---|---|---|---|---|
| 122 | 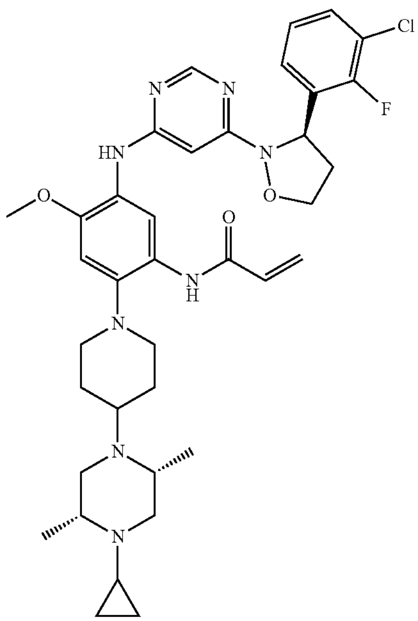 [SMILES: C=CC(=O)Nc1cc(Nc2cc(N3OCC[C@@H]3c3cccc(Cl)c3F)ncn2)c(OC)cc1N1CCC(N2C[C@@H](C)N(C3CC3)C[C@H]2C)CC1] | N-(5-((6-((R)-3-(3-chloro-2-fluorophenyl)isoxazolidine-2-yl)pyrimidine-4-yl)amino)-2-(4-((2R,5R)-4-cyclopropyl-2,5-dimethylpiperazine-1-yl)piperidine-1-yl)-4-methoxyphenyl)acrylamide | ¹H NMR (400 MHz, DMSO-d₆) δ 9.04 (d, J = 35.7 Hz, 3H), 8.21 (s, 1H), 7.56-7.49 (m, 1H), 7.46-7.39 (m, 2H), 7.23 (t, J = 7.9 Hz, 2H), 6.85 (s, 1H), 6.51 (t, J = 13.9 Hz, 1H), 6.32 (s, 2H), 6.28-6.17 (m, 2H), 5.80-5.67 (m, 4H), 4.21 (dt, J = 7.9, 4.1 Hz, 2H), 3.91 (q, J = 7.9 Hz, 2H), 3.81 (s, 6H), 3.45 (d, J = 9.5 Hz, 1H), 3.16 (d, J = 9.3 Hz, 3H), 2.94 (d, J = 12.1 Hz, 2H), 2.89-2.77 (m, 4H), 2.68 (d, J = 11.1 Hz, 4H), 2.22 (dq, J = 13.1, 7.8, 6.6 Hz, 3H), 2.14 (s, 2H), 1.79 (s, 2H), 1.60 (s, 1H), 1.32-1.14 (m, 10H), 0.67 (s, 2H), 0.48 (d, J = 35.5 Hz, 3H), ; 705.6 [M + H]⁺ | 1.42 |
| 123 | 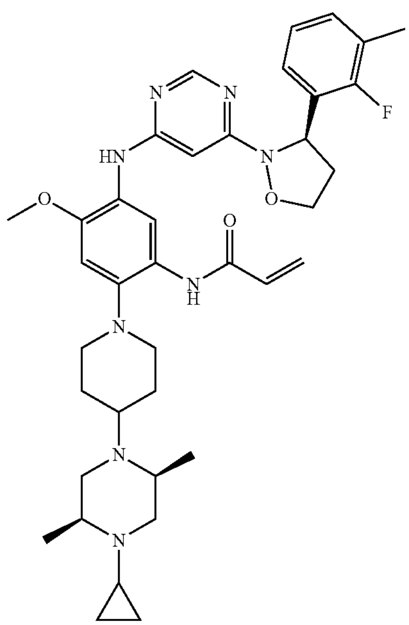 | N-(2-(4-((2S,5S)-4-cyclopropyl-2,5-dimethylpiperazine-1-yl)piperidine-1-yl)-5-((6-((R)-3-(2-fluoro-3-methylphenyl)isoxazolidine-2-yl)pyrimidine-4-yl)amino)-4-methoxyphenyl)acrylamide | ¹H NMR (400 MHz, DMSO-d₆) δ 8.94 (s, 1H), 8.59 (s, 1H), 8.14 (s, 1H), 7.28 (t, J = 7.6 Hz, 1H), 7.19 (t, J = 7.3 Hz, 1H), 7.06 (t, J = 7.6 Hz, 1H), 6.83 (s, 1H), 6.66 (dd, J = 16.9, 10.2 Hz, 1H), 6.34 (s, 1H), 6.20 (dd, J = 16.9, 2.0 Hz, 1H), 5.72 (dd, J = 9.3, 4.4 Hz, 2H), 4.14 (td, J = 7.8, 3.8 Hz, 1H), 3.84 (q, J = 8.0 Hz, 1H), 3.79 (s, 3H), 3.02 (d, J = 11.0 Hz, 2H), 2.95 (s, 1H), 2.77 (dt, J = 8.1, 4.2 Hz, 1H), 2.67 (q, J = 9.5, 8.4 Hz, 2H), 2.64-2.54 (m, 3H), 2.43 (dd, J = 11.0, 3.2 Hz, 2H), 2.26 (d, J = 2.0 Hz, 3H), 2.22-2.09 (m, 2H), 1.82 (t, J = 12.9 Hz, 2H), 1.55 (d, J = 11.1 Hz, 2H), 1.24 (s, 3H), 1.09 (d, J = 6.2 Hz, 3H), 0.94 (d, J = 6.3 Hz, 3H), 0.53 (q, J = 6.0 Hz, 1H), 0.42-0.31 (m, 2H), ; 685.6 [M + H]⁺ | 1.40 |

TABLE 1-continued

| Example Compound | Structure | Name of Compound | $^1$H NMR[[:]]; MS [M + H]$^+$ | UPLC r.t. (min) |
|---|---|---|---|---|
| 124 | 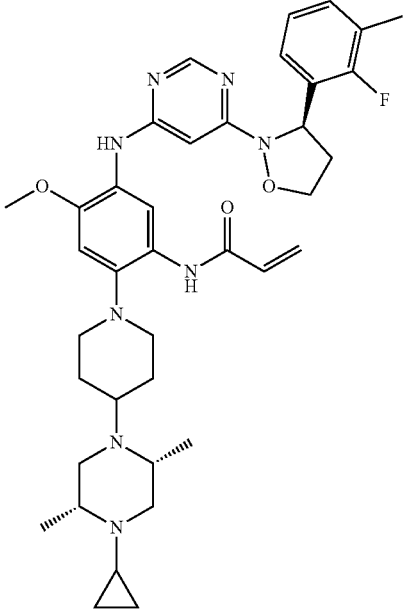 | N-(2-(4-((2R,5R)-4-cyclopropyl-2,5-dimethylpiperazine-1-yl)piperidine-1-yl)-5-((6-((R)-3-(2-fluoro-3-methylphenyl)isoxazolidine-2-yl)pyrimidine-4-yl)amino)-4-methoxyphenyl)acrylamide | $^1$H NMR (400 MHz, DMSO-d$_6$) δ 9.09 (s, 1H), 8.21 (s, 1H), 8.03 (s, 1H), 7.22 (dt, J = 13.8, 7.4 Hz, 2H), 7.07 (t, J = 7.6 Hz, 1H), 6.86 (s, 1H), 6.51 (t, J = 13.9 Hz, 1H), 6.32-6.17 (m, 2H), 5.74 (dd, J = 10.4 Hz, 1H), 5.70 (dd, J = 8.7, 5.2 Hz, 1H), 4.21 (q, J = 6.0, 4.7 Hz, 1H), 3.92 (q, J = 7.9 Hz, 1H), 3.81 (s, 3H), 3.45 (s, 1H), 3.15 (s, 3H), 3.02-2.88 (m, 1H), 2.84 (d, J = 8.3 Hz, 2H), 2.69 (d, J = 13.1 Hz, 3H), 2.54 (s, 1H), 2.26 (d, J = 2.0 Hz, 3H), 2.24-2.08 (m, 3H), 1.80 (s, 2H), 1.57 (d, J = 19.0 Hz, 1H), 1.38-1.12 (m, 8H), 0.67 (s, 1H), 0.49 (d, J = 35.7 Hz, 2H), 0.21 (s, 1H), ; 685.7 [M + H]$^+$ | 1.41 |
| 125 | 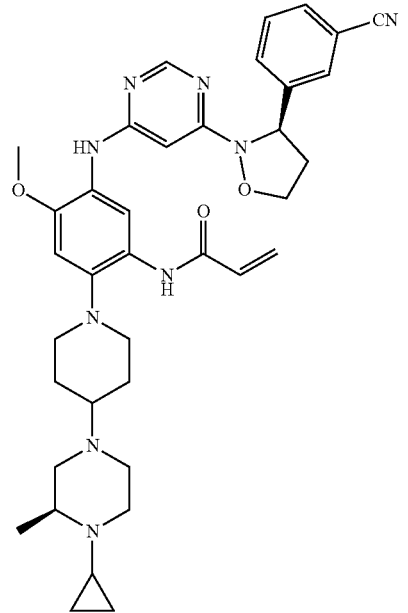 [SMILES: C=CC(=O)Nc1cc(Nc2cc(N3OCC[C@@H]3c3cccc(C#N)c3)ncn2)c(OC)cc1N1CCC(N2CCN(C3CC3)[C@@H](C)C2)CC1] | N-(5-((6-((R)-3-(3-cyanophenyl)isoxazolidine-2-yl)pyrimidine-4-yl)amino)-2-(4-((S)-4-cyclopropyl-3-methylpiperazine-1-yl)piperidine-1-yl)-4-methoxyphenyl)acrylamide | $^1$H NMR (400 MHz, CDCl$_3$) δ 8.81 (s, 1H), 8.44 (s, 1H), 8.33 (s, 1H), 7.78 (s, 1H), 7.70 (d, J = 7.8 Hz, 1H), 7.54 (d, J = 7.7 Hz, 1H), 7.45 (t, J = 7.8 Hz, 1H), 6.75 (s, 1H), 6.70 (s, 1H), 6.40-6.23 (m, J = 17.0, 12.9 Hz, 2H), 5.77-5.68 (m, 2H), 4.19-4.13 (m, 1H), 4.08 (q, J = 8.0 Hz, 1H), 3.84 (s, 3H), 3.11-3.02 (m, 4H), 2.99-2.92 (m, 1H), 2.85-2.68 (m, 3H), 2.65-2.51 (m, 2H), 2.49-2.29 (m, 3H), 2.14-2.08 (m, 3H), 1.79-1.67 (m, 2H), 1.61-1.53 (m, 1H), 1.23 (d, J = 6.3 Hz, 3H), 0.70-0.58 (m, 2H), 0.50-0.30 (m, 2H); 664.54 [M + H]$^+$ | 1.10 |

TABLE 1-continued

| Example Compound | Structure | Name of Compound | ¹H NMR[[:]]; MS [M + H]⁺ | UPLC r.t. (min) |
|---|---|---|---|---|
| 126 | 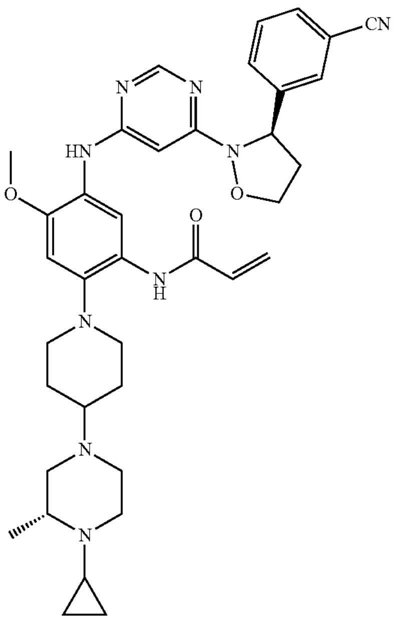 [SMILES: C=CC(=O)Nc1cc(Nc2cc(N3OCC[C@@H]3c3cccc(C#N)c3)ncn2)c(OC)cc1N1CCC(N2CCN(C3CC3)[C@H](C)C2)CC1] | N-(5-((6-((R)-3-(3-cyanophenyl)isoxazolidine-2-yl)pyrimidine-4-yl)amino)-2-(4-((R)-4-cyclopropyl-3-methylpiperazine-1-yl)piperidine-1-yl)-4-methoxyphenyl)acrylamide | ¹H NMR (400 MHz, CDCl$_3$) δ 8.78 (s, 1H), 8.43 (s, 1H), 8.31 (s, 1H), 7.78 (s, 1H), 7.70 (d, J = 7.9 Hz, 1H), 7.55 (d, J = 7.7 Hz, 1H), 7.48-7.41 (m, 2H), 6.73 (d, J = 13.3 Hz, 1H), 6.68 (s, 1H), 6.40-6.24 (m, 2H), 5.78-5.67 (m, 2H), 4.20-4.12 (m, 1H), 4.07 (q, J = 8.0 Hz, 1H), 3.84 (s, 3H), 3.15-3.00 (m, 5H), 2.84-2.46 (m, 7H), 2.38-2.28 (m, 1H), 2.22-2.08 (m, 3H), 1.83-1.72 (m, 2H), 1.66-1.56 (m, 1H), 1.24 (d, J = 6.3 Hz, 3H), 0.72-0.61 (m, 2H), 0.51-0.33 (m, 2H); 664.59 [M + H]⁺ | 1.10 |
| 127 | 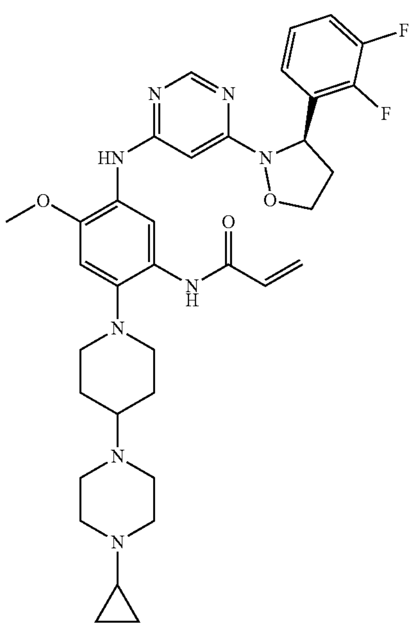 [SMILES: C=CC(=O)Nc1cc(Nc2cc(N3OCC[C@@H]3c3cccc(F)c3F)ncn2)c(OC)cc1N1CCC(N2CCN(C3CC3)CC2)CC1] | N-(2-(4-(4-cyclopropylpiperazine-1-yl)piperidine-1-yl)-5-((6-((R)-3-(2,3-difluorophenyl)isoxazolidine-2-yl)pyrimidine-4-yl)amino)-4-methoxyphenyl)acrylamide | ¹H NMR (400 MHz, DMSO-d$_6$) δ 8.95 (s, 1H), 8.62 (s, 1H), 8.16 (s, 1H), 7.40-7.25 (m, 2H), 7.24-7.15 (m, 1H), 6.82 (s, 1H), 6.65 (dd, J = 16.9, 10.2 Hz, 1H), 6.35 (s, 1H), 6.20 (dd, J = 16.9, 2.0 Hz, 1H), 5.75 (d, J = 3.9 Hz, 2H), 5.74-5.69 (m, 1H), 3.85 (q, J = 7.9 Hz, 1H), 3.79 (s, 3H), 3.04 (d, J = 11.1 Hz, 3H), 2.81 (dtd, J = 12.0, 8.0, 3.7 Hz, 1H), 2.70-2.60 (m, 3H), 2.34-2.15 (m, 3H), 1.91 (s, 7H), 1.82 (t, J = 7.2 Hz, 2H), 1.70 (tt, J = 12.8, 6.6 Hz, 3H), 1.57 (dq, J = 6.7, 3.4 Hz, 1H), 1.23 (s, 1H), 0.39 (dt, J = 6.2, 3.0 Hz, 2H), 0.27 (p, J = 3.9 Hz, 2H), ; 661.5 [M + H]⁺ | 1.23 |

TABLE 1-continued

| Example Compound | Structure | Name of Compound | ¹H NMR[[:]]; MS [M + H]⁺ | UPLC r.t. (min) |
|---|---|---|---|---|
| 128 | 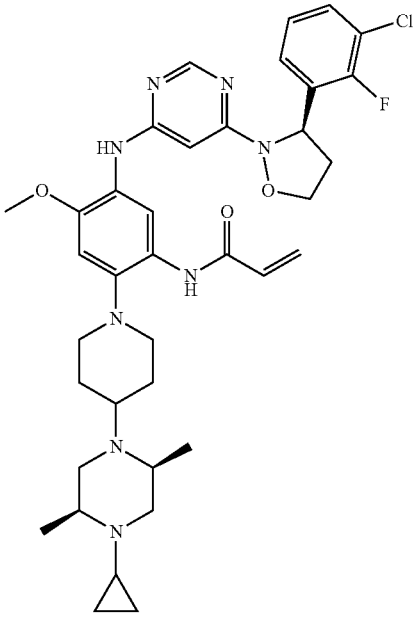 [SMILES: C=CC(=O)Nc1cc(Nc2cc(N3OCC[C@@H]3c3cccc(Cl)c3F)ncn2)c(OC)cc1N1CCC(N2C[C@H](C)N(C3CC3)C[C@@H]2C)CC1] | N-(5-((6-((R)-3-(3-chloro-2-fluorophenyl)isoxazolidine-2-yl)pyrimidine-4-yl)amino)-2-(4-((2S,5S)-4-cyclopropyl-2,5-dimethylpiperazine-1-yl)piperidine-1-yl)-4-methoxyphenyl)acrylamide | ¹H NMR (400 MHz, DMSO-$d_6$) δ 8.94 (s, 1H), 8.63 (s, 1H), 8.15 (s, 1H), 7.55-7.48 (m, 1H), 7.45 (t, J = 7.1 Hz, 1H), 7.22 (t, J = 8.0 Hz, 1H), 6.83 (s, 1H), 6.66 (dd, J = 17.0, 10.2 Hz, 1H), 6.35 (s, 1H), 6.20 (dd, J = 17.0, 2.0 Hz, 1H), 5.72 (dt, J = 9.5, 4.2 Hz, 2H), 4.17 (td, J = 7.9, 3.7 Hz, 1H), 3.90-3.82 (m, 1H), 3.79 (s, 3H), 3.02 (d, J = 11.0 Hz, 2H), 2.86-2.75 (m, 1H), 2.69 (d, J = 12.4 Hz, 2H), 2.64-2.53 (m, 2H), 2.26 (t, J = 10.0 Hz, 1H), 2.22-2.15 (m, 1H), 1.87 (s, 6H), 1.80 (d, J = 13.5 Hz, 2H), 1.61-1.50 (m, 2H), 1.09 (d, J = 6.2 Hz, 3H), 0.94 (d, J = 6.3 Hz, 3H), 0.57-0.49 (m, 1H), 0.37 (d, J = 7.0 Hz, 2H), 0.13 (d, J = 9.8 Hz, 1H), ; 705.5 [M + H]⁺ | 1.43 |
| 129 | 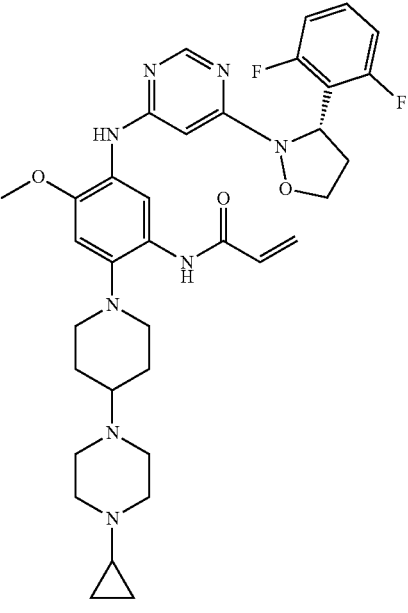 [SMILES: C=CC(=O)Nc1cc(Nc2cc(N3OCC[C@H]3c3c(F)cccc3F)ncn2)c(OC)cc1N1CCC(N2CCN(C3CC3)CC2)CC1] | N-(2-(4-(4-cyclopropylpiperazine-1-yl)piperidine-1-yl)-5-((6-((S)-3-(2,6-difluorophenyl)isoxazolidine-2-yl)pyrimidine-4-yl)amino)-4-methoxyphenyl)acrylamide | ¹H NMR (400 MHz, DMSO-$d_6$) δ 9.87 (s, 1H), 9.17 (s, 1H), 8.26 (s, 1H), 7.90 (s, 1H) 7.42 (ddd, J = 8.5, 6.5, 2.0 Hz, 1H), 7.12 (t, J = 8.5 Hz, 2H), 6.89 (s, 1H), 6.69 (dd, J = 17.0, 10.3 Hz, 1H), 6.24 (dd, J = 17.0, 2.0 Hz, 1H), 5.99 (s, 1H), 5.76 (dd, J = 10.2, 1.9 Hz, 1H), 5.69 (s, 1H), 4.48-4.41 (m, 1H), 4.01 (d, J = 11.2 Hz, 2H), 3.79 (s, 3H), 3.70 (s, 4H), 3.57 (s, 2H), 3.21 (d, J = 11.4 Hz, 2H), 2.91 (s, 1H), 2.79 (t, J = 11.8 Hz, 2H), 2.46 (s, 1H), 2.16 (s, 2H), 2.09 (s, 3H), 1.24 (s, 2H), 1.10 (s, 2H), 0.80 (d, J = 6.4 Hz, 2H), ; 661.3 [M + H]⁺ | 1.14 |

TABLE 1-continued

| Example Compound | Structure | Name of Compound | ¹H NMR[[:]]; MS [M + H]⁺ | UPLC r.t. (min) |
|---|---|---|---|---|
| 130 | 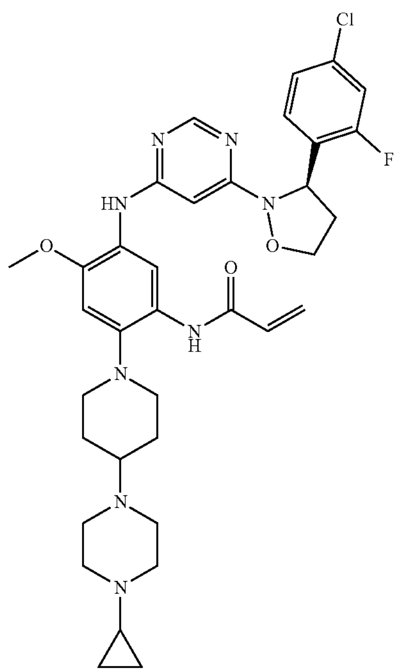 [SMILES: C=CC(=O)Nc1cc(Nc2cc(N3OCC[C@@H]3c3ccc(Cl)cc3F)ncn2)c(OC)cc1N1CCC(N2CCN(C3CC3)CC2)CC1] | N-(5-((6-((R)-3-(4-chloro-2-fluorophenyl)isoxazolidine-2-yl)pyrimidine-4-yl)amino)-2-(4-(4-cyclopropylpiperazine-1-yl)piperidine-1-yl)-4-methoxyphenyl)acrylamide | 676.3 [M + H]⁺ | 1.34 |
| 131 | 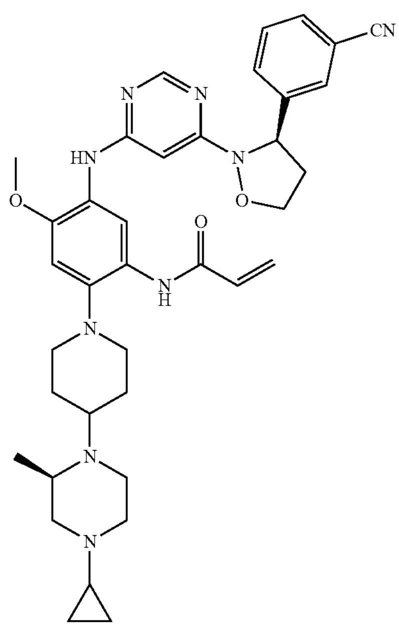 [SMILES: C=CC(=O)Nc1cc(Nc2cc(N3OCC[C@@H]3c3cccc(C#N)c3)ncn2)c(OC)cc1N1CCC(N2CCN(C3CC3)C[C@H]2C)CC1] | N-(5-((6-((R)-3-(3-cyanophenyl)isoxazolidine-2-yl)pyrimidine-4-yl)amino)-2-(4-((R)-4-cyclopropyl-2-methylpiperazine-1-yl)piperidine-1-yl)-4-methoxyphenyl)acrylamide | ¹H NMR (400 MHz, CDCl₃) δ 8.79 (s, 1H), 8.42 (s, 1H), 8.31 (s, 1H), 7.78 (s, 1H), 7.70 (d, J = 7.9 Hz, 1H), 7.55 (d, J = 7.7 Hz, 1H), 7.50-7.42 (m, 2H), 6.76 (s, 1H), 6.68 (s, 1H), 6.40-6.24 (m, 2H), 5.76 (dd, J = 9.7, 1.6 Hz, 1H), 5.71 (dd, J = 8.7, 4.6 Hz, 1H), 4.19-4.11 (m, 1H), 4.07 (q, J = 8.0 Hz, 1H), 3.84 (s, 3H), 3.17-3.04 (m, 3H), 3.02-2.91 (m, 4H), 2.87-2.77 (m, 2H), 2.76-2.58 (m, 3H), 2.45-2.28 (m, 2H), 2.00-1.87 (m, 3H), 1.76-1.65 (m, 2H), 1.18 (d, J = 6.3 Hz, 3H), 0.53-0.42 (m, J = 5.7 Hz, 4H); 664.54 [M + H]⁺ | 1.12 |

TABLE 1-continued

| Example Compound | Structure | Name of Compound | ¹H NMR[[:]]; MS [M + H]⁺ | UPLC r.t. (min) |
|---|---|---|---|---|
| 132 | 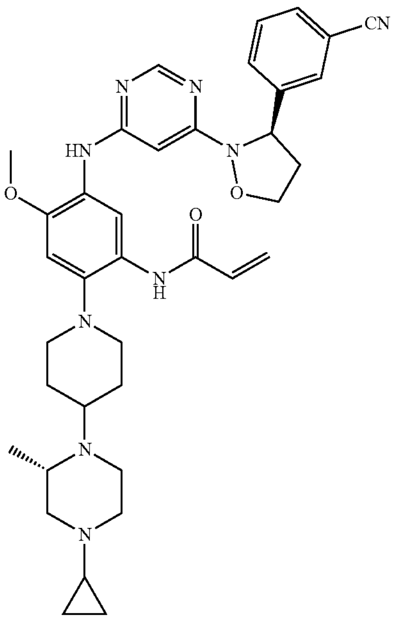 [SMILES: C=CC(=O)Nc1cc(Nc2cc(N3OCC[C@@H]3c3cccc(C#N)c3)ncn2)c(OC)cc1N1CCC(N2CCN(C3CC3)C[C@@H]2C)CC1] | N-(5-((6-((R)-3-(3-cyanophenyl)isoxazolidine-2-yl)pyrimidine-4-yl)amino)-2-(4-((S)-4-cyclopropyl-2-methylpiperazine-1-yl)piperidine-1-yl)-4-methoxyphenyl)acrylamide | ¹H NMR (400 MHz, CDCl₃) δ 8.79 (s, 1H), 8.42 (s, 1H), 8.32 (s, 1H), 7.78 (s, 1H), 7.70 (d, J = 7.8 Hz, 1H), 7.55 (d, J = 7.7 Hz, 1H), 7.45 (t, J = 7.8 Hz, 1H), 7.38 (s, 1H), 6.76 (s, 1H), 6.69 (s, 1H), 6.39-6.23 (m, 2H), 5.76 (dd, J = 9.8, 1.6 Hz, 1H), 5.71 (dd, J = 8.7, 4.6 Hz, 1H), 4.19-4.13 (m, 1H), 4.08 (q, J = 8.0 Hz, 1H), 3.84 (s, 3H), 3.12-3.04 (m, 3H), 3.00-2.89 (m, 4H), 2.86-2.78 (m, 2H), 2.72-2.55 (m, 3H), 2.41-2.29 (m, 2H), 1.98-1.86 (m, 3H), 1.74-1.63 (m, 2H), 1.16 (d, J = 6.2 Hz, 3H), 0.52-0.43 (m, 4H); 664.59 [M + H]⁺ | 1.12 |
| 133 | 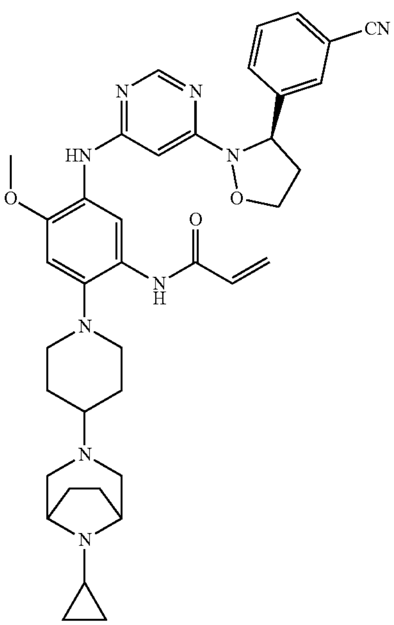 [SMILES: C=CC(=O)Nc1cc(Nc2cc(N3OCC[C@@H]3c3cccc(C#N)c3)ncn2)c(OC)cc1N1CCC(N2CC3CCC(C2)N3C2CC2)CC1] | N-(5-((6-((R)-3-(3-cyanophenyl)isoxazolidine-2-yl)pyrimidine-4-yl)amino)-2-(4-(8-cyclopropyl-3,8-diazabicyclo[3.2.1]octan-3-yl)piperidine-1-yl)-4-methoxyphenyl)acrylamide | ¹H NMR (400 MHz, CDCl₃) δ 8.78 (s, 1H), 8.44 (s, 1H), 8.31 (s, 1H), 7.78 (s, 1H), 7.70 (d, J = 7.9 Hz, 1H), 7.54 (d, J = 7.7 Hz, 1H), 7.47-7.38 (m, 2H), 6.75 (s, 1H), 6.68 (s, 1H), 6.40-6.24 (m, 2H), 5.75 (dd, J = 9.7, 1.6 Hz, 1H), 5.71 (dd, J = 8.6, 4.6 Hz, 1H), 4.19-4.11 (m, 1H), 4.07 (q, J = 8.1 Hz, 1H), 3.84 (s, 3H), 3.49 (s, 2H), 3.08-2.98 (m, 2H), 2.85-2.65 (m, 7H), 2.44-2.29 (m, 2H), 2.04-1.91 (m, 7H), 1.73-1.60 (m, 2H), 0.81-0.73 (m, 2H), 0.56-0.48 (m, 2H); 676.59 [M + H]⁺ | 1.13 |

TABLE 1-continued

| Example Compound | Structure | Name of Compound | ¹H NMR[:]; MS [M + H]⁺ | UPLC r.t. (min) |
|---|---|---|---|---|
| 134 | 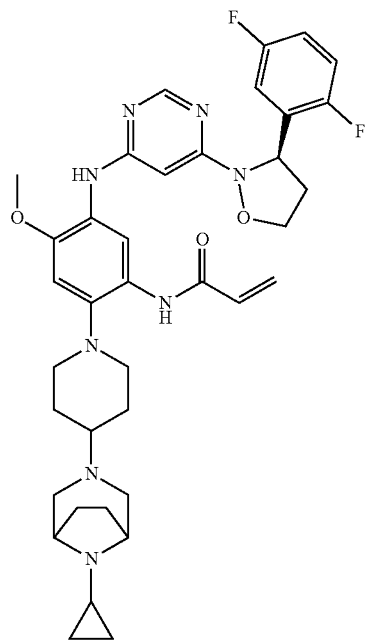 [SMILES: C=CC(=O)Nc1cc(Nc2cc(N3OCC[C@@H]3c3cc(F)ccc3F)ncn2)c(OC)cc1N1CCC(N2CC3CCC(C2)N3C2CC2)CC1] | N-(2-(4-(8-cyclopropyl-3,8-diazabicyclo[3.2.1]octan-3-yl)piperidine-1-yl)-5-((6-((R)-3-(2,5-difluorophenyl)isoxazolidine-2-yl)pyrimidine-4-yl)amino)-4-methoxyphenyl)acrylamide | ¹H NMR (400 MHz, CDCl₃) δ 8.83 (s, 1H), 8.44 (s, 1H), 8.34 (s, 1H), 7.35-7.28 (m, 1H), 7.12 (s, 1H), 7.03-6.95 (m, 1H), 6.93-6.85 (m, 1H), 6.75 (s, 1H), 6.74 (s, 1H), 6.40-6.23 (m, 2H), 5.89 (dd, J = 8.7, 4.4 Hz, 1H), 5.75 (dd, J = 9.8, 1.6 Hz, 1H), 4.14-4.03 (m, 2H), 3.84 (s, 3H), 3.35 (s, 2H), 3.06-2.99 (m, 2H), 2.87-2.78 (m, 1H), 2.74-2.63 (m, 4H), 2.53-2.46 (m, 2H), 2.36-2.25 (m, 2H), 1.99-1.83 (m, 7H), 1.68-1.57 (m, 2H), 0.59-0.52 (m, 2H), 0.49-0.41 (m, 2H); 687.53 [M + H]⁺ | 1.22 |
| 135 | 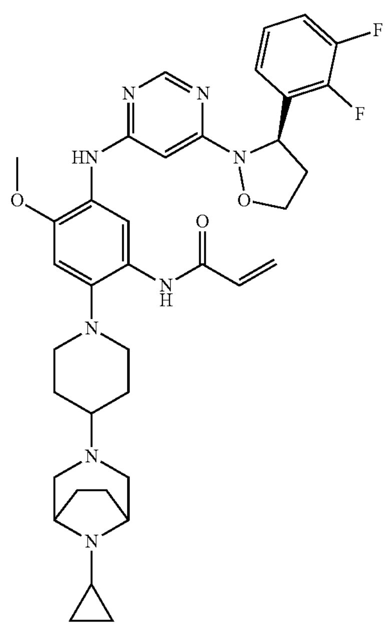 [SMILES: C=CC(=O)Nc1cc(Nc2cc(N3OCC[C@@H]3c3cccc(F)c3F)ncn2)c(OC)cc1N1CCC(N2CC3CCC(C2)N3C2CC2)CC1] | N-(2-(4-(8-cyclopropyl-3,8-diazabicyclo[3.2.1]octan-3-yl)piperidine-1-yl)-5-((6-((R)-3-(2,3-difluorophenyl)isoxazolidine-2-yl)pyrimidine-4-yl)amino)-4-methoxyphenyl)acrylamide | ¹H NMR (400 MHz, CDCl₃) δ 8.80 (s, 1H), 8.43 (s, 1H), 8.32 (s, 1H), 7.37-7.28 (m, 2H), 7.10-7.00 (m, 2H), 6.75 (s, 1H), 6.71 (s, 1H), 6.40-6.23 (m, 2H), 5.92 (dd, J = 8.5, 4.5 Hz, 1H), 5.75 (dd, J = 9.8, 1.6 Hz, 1H), 4.16-4.02 (m, 2H), 3.84 (s, 3H), 3.42 (s, 2H), 3.08-2.98 (m, 2H), 2.92-2.53 (m, 7H), 2.40-2.26 (m, 2H), 2.03-1.87 (m, 7H), 1.71-1.58 (m, 2H), 0.71-0.62 (m, 2H), 0.53-0.44 (m, 2H); 687.53 [M + H]⁺ | 1.22 |

TABLE 1-continued

| Example Compound | Structure | Name of Compound | ¹H NMR[:]; MS [M + H]⁺ | UPLC r.t. (min) |
|---|---|---|---|---|
| 136 | 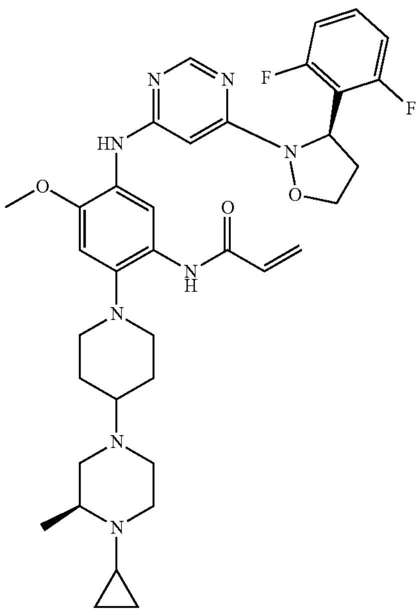 [SMILES: C=CC(=O)Nc1cc(Nc2cc(N3OCC[C@@H]3c3c(F)cccc3F)ncn2)c(OC)cc1N1CCC(N2CCN(C3CC3)[C@@H](C)C2)CC1] | N-(2-(4-((S)-4-cyclopropyl-3-methylpiperazine-1-yl)piperidine-1-yl)-5-((6-((R)-3-(2,6-difluorophenyl)isoxazolidine-2-yl)pyrimidine-4-yl)amino)-4-methoxyphenyl)acrylamide | ¹H NMR (400 MHz, Chloroform-d) δ 8.82 (s, 1H), 8.42 (s, 1H), 8.35 (s, 1H), 7.82 (s, 1H), 7.24-7.20 (m, 1H), 6.91-6.87 (m, 2H), 6.73 (s, 1H), 6.40-6.31 (m, 1H), 6.25 (dd, J = 16.9, 10.0 Hz, 1H), 5.94-5.88 (m, 1H), 5.78-5.64 (m, 2H), 4.45-4.30 (m, 2H), 3.97 (p, J = 7.5 Hz, 2H), 3.00 (d, J = 26.2 Hz, 4H), 2.90 (d, J = 10.8 Hz, 1H), 2.82-2.67 (m, 4H), 2.61-2.53 (m, 2H), 2.48 (d, J = 11.2 Hz, 1H), 2.33 (t, J = 10.8 Hz, 2H), 1.69-1.64 (m, 2H), 1.56-1.53 (m, 1H), 1.21 (d, J = 6.3 Hz, 3H), 0.67-0.57 (m, 2H), 0.48-0.41 (m, 1H), 0.36-0.29 (m, 1H); 675.6 [M + H]⁺ | 1.11 |
| 137 | 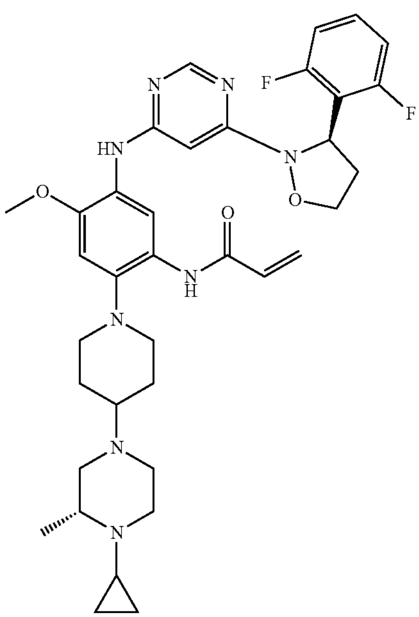 [SMILES: C=CC(=O)Nc1cc(Nc2cc(N3OCC[C@@H]3c3c(F)cccc3F)ncn2)c(OC)cc1N1CCC(N2CCN(C3CC3)[C@H](C)C2)CC1] | N-(2-(4-((R)-4-cyclopropyl-3-methylpiperazine-1-yl)piperidine-1-yl)-5-((6-((R)-3-(2,6-difluorophenyl)isoxazolidine-2-yl)pyrimidine-4-yl)amino)-4-methoxyphenyl)acrylamide | ¹H NMR (400 MHz, Chloroform-d) δ 8.80 (s, 1H), 8.41 (s, 1H), 8.34 (d, J = 1.0 Hz, 1H), 7.83 (s, 1H), 7.24-7.20 (m, 1H), 6.90-6.88 (m, 2H), 6.72 (s, 1H), 6.39-6.32 (m, 1H), 6.25 (dd, J = 16.9, 9.9 Hz, 1H), 5.91 (dd, J = 9.0, 6.5 Hz, 1H), 5.76-5.68 (m, 2H), 4.44-4.33 (m, 2H), 3.97 (p, J = 7.2 Hz, 2H), 3.81 (s, 3H), 3.08-2.98 (m, 4H), 2.92 (d, J = 11.1 Hz, 1H), 2.78-2.67 (m, 4H), 2.61-2.56 (m, 2H), 2.54-2.48 (m, 1H), 2.40-2.33 (m, 2H), 1.73-1.65 (m, 2H), 1.55 (dt, J = 6.7, 3.2 Hz, 1H), 1.22 (d, J = 6.3 Hz, 3H), 0.67-0.59 (m, 2H), 0.48-0.40 (m, 1H), 0.37-0.30 (m, 1H); 675.6 [M + H]⁺ | 1.10 |

TABLE 1-continued

| Example Compound | Structure | Name of Compound | ¹H NMR[[:]]; MS [M + H]⁺ | UPLC r.t. (min) |
|---|---|---|---|---|
| 138 | 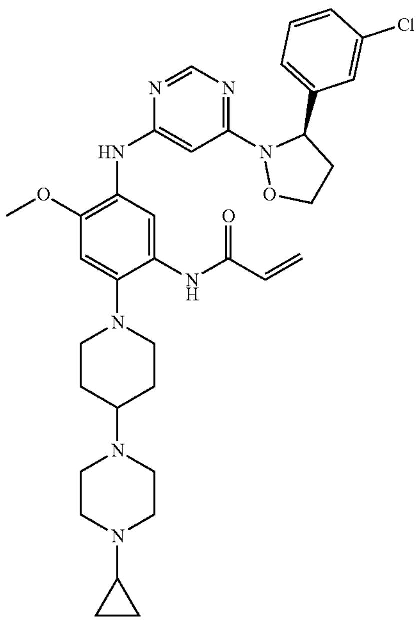 [SMILES: C=CC(=O)Nc1cc(Nc2cc(N3OCC[C@@H]3c3cccc(Cl)c3)ncn2)c(OC)cc1N1CCC(N2CCN(C3CC3)CC2)CC1] | N-(5-((6-((R)-3-(3-chlorophenyl)isoxazolidine-2-yl)pyrimidine-4-yl)amino)-2-(4-(4-cyclopropylpiperazine-1-yl)piperidine-1-yl)-4-methoxyphenyl)acrylamide | ¹H NMR (400 MHz, DMSO-$d_6$) δ 9.20 (s, 1H), 9.06 (s, 1H), 8.23 (d, J = 2.1 Hz, 1H), 8.05 (s, 1H), 7.43 (d, J = 3.6 Hz, 1H), 7.39 (d, J = 7.5 Hz, 1H), 7.37-7.33 (m, 2H), 6.85 (s, 1H), 6.61 (dd, J = 17.0, 10.2 Hz, 1H), 6.28-6.19 (m, 2H), 5.74 (d, J = 10.3 Hz, 1H), 5.53 (dd, J = 8.6, 5.3 Hz, 1H), 4.26-4.18 (m, 2H), 3.91 (t, J = 7.9 Hz, 3H), 3.80 (s, 3H), 3.29 (d, J = 11.6 Hz, 2H), 3.22-3.09 (m, 4H), 2.85 (d, J = 9.0 Hz, 2H), 2.74 (t, J = 11.7 Hz, 3H), 2.28 (dtd, J = 17.0, 9.1, 7.9, 4.8 Hz, 1H), 2.09 (d, J = 11.9 Hz, 3H), 1.98-1.84 (m, 2H), 0.63-0.44 (m, 4H), ; 659.5 [M + H]⁺ | 1.19 |
| 139 | 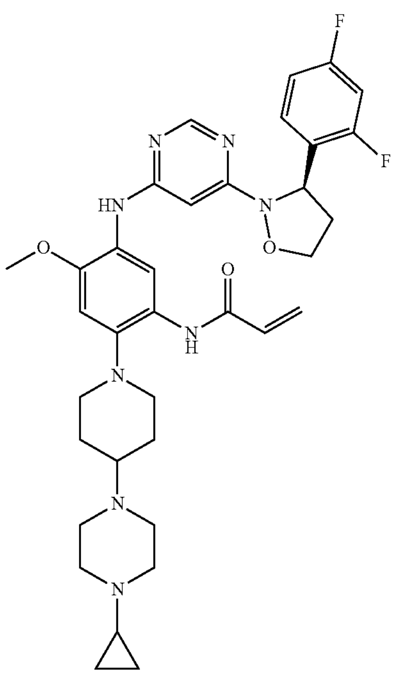 [SMILES: C=CC(=O)Nc1cc(Nc2cc(N3OCC[C@@H]3c3ccc(F)cc3F)ncn2)c(OC)cc1N1CCC(N2CCN(C3CC3)CC2)CC1] | N-(2-(4-(4-cyclopropylpiperazine-1-yl)piperidine-1-yl)-5-((6-((R)-3-(2,4-difluorophenyl)isoxazolidine-2-yl)pyrimidine-4-yl)amino)-4-methoxyphenyl)acrylamide | ¹H NMR (400 MHz, DMSO-$d_6$) δ 9.67 (s, 1H), 9.15 (s, 1H), 8.27 (s, 1H), 7.98 (s, 1H), 7.49-7.38 (m, 1H), 7.35-7.25 (m, 1H), 7.09 (td, J = 8.4, 2.6 Hz, 1H), 6.89 (s, 1H), 6.67 (dd, J = 16.9, 10.2 Hz, 1H), 6.29-6.12 (m, 2H), 5.76 (d, J = 10.3 Hz, 1H), 5.66 (t, J = 7.3 Hz, 1H), 4.29 (q, J = 7.7, 6.4 Hz, 2H), 4.05-3.98 (m, 4H), 3.81 (s, 3H), 3.76-3.58 (m, 5H), 3.21 (d, J = 11.5 Hz, 2H), 2.94-2.85 (m, 1H), 2.78 (t, J = 11.6 Hz, 2H), 2.30-2.22 (m, 1H), 2.20-2.11 (m, 2H), 2.09-1.93 (m, 2H), 1.26-1.22 (m, 1H), 0.89-0.67 (m, 4H); 661.5 [M + H]⁺ | 1.19 |

TABLE 1-continued

| Example Compound | Structure | Name of Compound | ¹H NMR[[:]]; MS [M + H]⁺ | UPLC r.t. (min) |
|---|---|---|---|---|
| 140 | 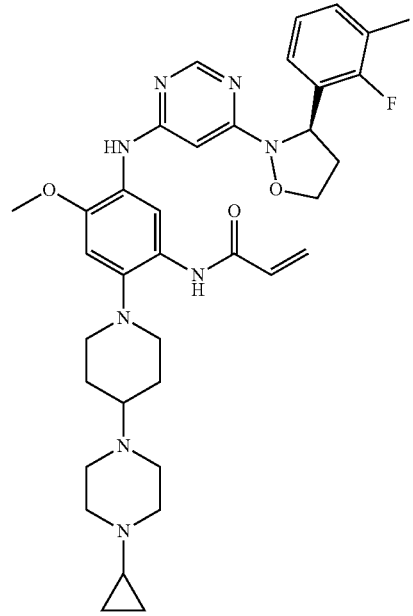 | N-(2-(4-(4-cyclopropylpiperazine-1-yl)piperidine-1-yl)-5-((6-((R)-3-(2-fluoro-3-methylphenyl)isoxazolidine-2-yl)pyrimidine-4-yl)amino)-4-methoxyphenyl)acrylamide | ¹H NMR (400 MHz, DMSO-$d_6$) δ 8.94 (s, 1H), 8.59 (s, 1H), 8.14 (d, J = 1.0 Hz, 2H), 7.28 (t, J = 7.4 Hz, 1H), 7.18 (t, J = 6.9 Hz, 2H), 7.06 (t, J = 7.6 Hz, 1H), 6.82 (s, 1H), 6.65 (dd, J = 16.9, 10.2 Hz, 1H), 6.35 (s, 1H), 6.20 (dd, J = 17.0, 2.0 Hz, 1H), 5.70 (s, 1H), 4.14 (td, J = 8.0, 3.9 Hz, 1H), 3.79 (s, 3H), 3.17 (s, 2H), 3.03 (dd, J = 12.0, 6.7 Hz, 3H), 2.95-2.85 (m, 1H), 2.82-2.71 (m, 2H), 2.66 (t, J = 11.6 Hz, 3H), 2.21-2.06 (m, 2H), 1.88 (s, 8H), 1.83 (d, J = 12.3 Hz, 3H), 1.70 (d, J = 12.1 Hz, 3H), 1.58 (tt, J = 6.6, 3.7 Hz, 1H), 0.39 (dt, J = 6.2, 3.0 Hz, 3H), 0.30-0.26 (m, 2H), ; 657.5 [M + H]⁺ | 1.26 |
| 141 | 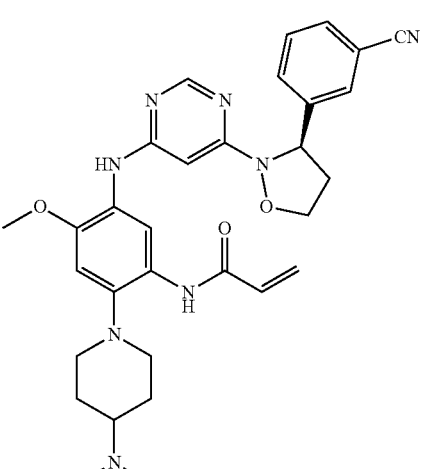 | N-(5-((6-((R)-3-(3-cyanophenyl)isoxazolidine-2-yl)pyrimidine-4-yl)amino)-2-(4-(4-cyclopropylpiperazine-1-yl)piperidine-1-yl)-4-methoxyphenyl)acrylamide | ¹H NMR (400 MHz, DMSO-$d_6$) δ 9.93 (s, 1H), 9.19 (s, 1H), 8.30 (s, 1H), 7.94 (s, 1H), 7.83 (d, J = 1.8 Hz, 1H), 7.78 (d, J = 7.5 Hz, 2H), 7.72 (d, J = 7.9 Hz, 1H), 7.60 (t, J = 7.8 Hz, 1H), 6.90 (s, 1H), 6.69 (dd, J = 17.0, 10.2 Hz, 1H), 6.25 (dd, J = 17.0, 1.9 Hz, 1H), 6.14 (s, 1H), 5.80-5.72 (m, 1H), 5.58 (dd, J = 8.5, 5.5 Hz, 1H), 3.89 (t, J = 6.1 Hz, 1H), 3.81 (s, 3H), 3.57 (s, 2H), 3.43 (d, J = 16.8 Hz, 2H), 3.37 (t, J = 7.0 Hz, 1H), 3.22 (d, J = 11.6 Hz, 2H), 3.07-2.58 (m, 7H), 2.40-2.28 (m, 2H), 2.16 (s, 3H), 2.13-2.00 (m, 3H), 1.15 (d, J = 7.0 Hz, 2H), 0.82 (d, J = 7.0 Hz, 3H), ; 650.5 [M + H]⁺ | 1.15 |

TABLE 1-continued

| Example Compound | Structure | Name of Compound | ¹H NMR[[:]]; MS [M + H]⁺ | UPLC r.t. (min) |
|---|---|---|---|---|
| 142 | 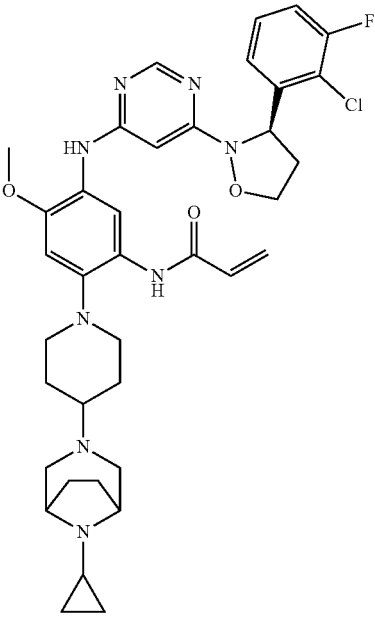 [SMILES: C=CC(=O)Nc1cc(Nc2cc(N3OCC[C@@H]3c3cccc(F)c3Cl)ncn2)c(OC)cc1N1CCC(N2CC3CCC(C2)N3C2CC2)CC1] | N-(5-((6-((R)-3-(2-chloro-3-fluorophenyl)isoxazolidine-2-yl)pyrimidine-4-yl)amino)-2-(4-(8-cyclopropyl-3,8-diazabicyclo[3.2.1]octan-3-yl)piperidine-1-yl)-4-methoxyphenyl)acrylamide | ¹H NMR (400 MHz, CDCl₃) δ 8.80 (s, 1H), 8.44 (s, 1H), 8.32 (d, J = 0.6 Hz, 1H), 7.46 (d, J = 7.9 Hz, 1H), 7.24-7.18 (m, 1H), 7.07-7.02 (m, 1H), 6.75 (s, 1H), 6.72 (s, 1H), 6.40-6.24 (m, 2H), 5.95 (dd, J = 8.7, 4.4 Hz, 1H), 5.75 (dd, J = 9.8, 1.7 Hz, 1H), 4.14-4.04 (m, 2H), 3.84 (s, 3H), 3.41 (s, 2H), 3.08-2.99 (m, 2H), 2.99-2.88 (m, 1H), 2.76-2.63 (m, 4H), 2.62-2.53 (m, 2H), 2.40-2.32 (m, 1H), 2.28-2.19 (m, 1H), 2.03-1.86 (m, 7H), 1.70-1.57 (m, 2H), 0.69-0.61 (m, 2H), 0.52-0.45 (m, 2H); 703.50 [M + H]⁺ | 1.37 |
| 143 | 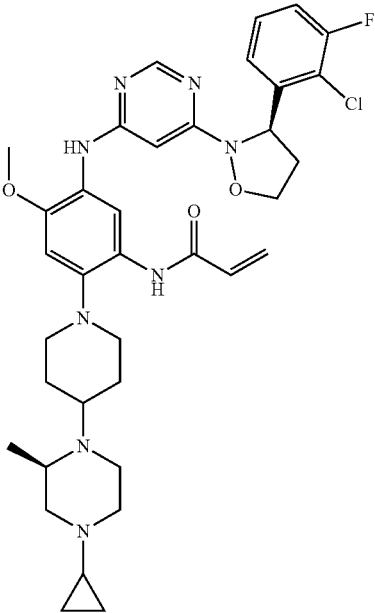 [SMILES: C=CC(=O)Nc1cc(Nc2cc(N3OCC[C@@H]3c3cccc(F)c3Cl)ncn2)c(OC)cc1N1CCC(N2CCN(C3CC3)C[C@H]2C)CC1] | N-(5-((6-((R)-3-(2-chloro-3-fluorophenyl)isoxazolidine-2-yl)pyrimidine-4-yl)amino)-2-(4-((R)-4-cyclopropyl-2-methylpiperazine-1-yl)piperidine-1-yl)-4-methoxyphenyl)acrylamide | ¹H NMR (400 MHz, CDCl₃) δ 8.80 (s, 1H), 8.43 (s, 1H), 8.32 (s, 1H), 7.46 (d, J = 7.9 Hz, 1H), 7.32 (s, 1H), 7.24-7.18 (m, 1H), 7.05 (dd, J = 12.3, 4.7 Hz, 1H), 6.74 (d, J = 7.1 Hz, 1H), 6.71 (s, 1H), 6.39-6.23 (m, 2H), 5.94 (dd, J = 8.7, 4.4 Hz, 1H), 5.74 (dd, J = 9.8, 1.6 Hz, 1H), 4.13-4.03 (m, 2H), 3.84 (s, 3H), 3.10-3.01 (m, 4H), 2.99-2.89 (m, 2H), 2.79-2.67 (m, 2H), 2.67-2.51 (m, 2H), 2.50-2.37 (m, 2H), 2.29-2.19 (m, 1H), 2.14-2.07 (m, 3H), 1.80-1.67 (m, 2H), 1.61-1.54 (m, 1H), 1.23 (d, J = 6.3 Hz, 3H), 0.69-0.59 (m, 2H), 0.50-0.31 (m, 2H); 691.45 [M + H]⁺ | 1.34 |

TABLE 1-continued

| Example Compound | Structure | Name of Compound | ¹H NMR[:]; MS [M + H]⁺ | UPLC r.t. (min) |
|---|---|---|---|---|
| 144 | 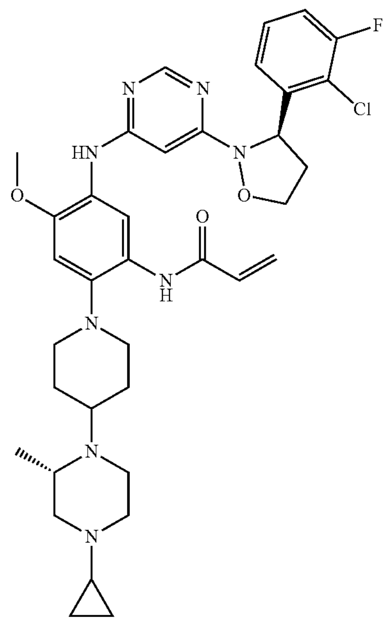 [SMILES: C=CC(=O)Nc1cc(Nc2cc(N3OCC[C@@H]3c3cccc(F)c3Cl)ncn2)c(OC)cc1N1CCC(N2CCN(C3CC3)C[C@@H]2C)CC1] | N-(5-((6-((R)-3-(2-chloro-3-fluorophenyl)isoxazolidine-2-yl)pyrimidine-4-yl)amino)-2-(4-((S)-4-cyclopropyl-2-methylpiperazine-1-yl)piperidine-1-yl)-4-methoxyphenyl)acrylamide | ¹H NMR (400 MHz, CDCl₃) δ 8.78 (s, 1H), 8.42 (s, 1H), 8.31 (s, 1H), 7.48-7.40 (m, 2H), 7.08-7.01 (m, 1H), 6.74 (s, 1H), 6.71 (s, 1H), 6.40-6.24 (m, 2H), 5.94 (dd, J = 8.7, 4.4 Hz, 1H), 5.74 (dd, J = 9.7, 1.7 Hz, 1H), 4.15-4.02 (m, 2H), 3.84 (s, 3H), 3.14-2.89 (m, 6H), 2.79-2.43 (m, 6H), 2.27-2.20 (m, 1H), 2.15-2.07 (m, 3H), 1.82-1.70 (m, 2H), 1.64-1.55 (m, 1H), 1.24 (d, J = 6.3 Hz, 3H), 0.71-0.60 (m, 2H), 0.51-0.32 (m, 2H); 691.50 [M + H]⁺ | 1.32 |
| 145 | 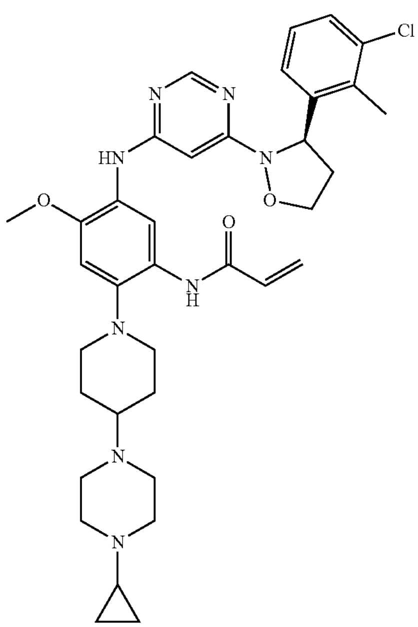 | N-(5-((6-((R)-3-(3-chloro-2-methylphenyl)isoxazolidine-2-yl)pyrimidine-4-yl)amino)-2-(4-(4-cyclopropylpiperazine-1-yl)piperidine-1-yl)-4-methoxyphenyl)acrylamide | ¹H NMR (400 MHz, DMSO-d₆) δ 8.94 (s, 1H), 8.58 (s, 1H), 8.14 (d, J = 1.0 Hz, 1H), 7.40 (d, J = 7.8 Hz, 2H), 7.34 (dd, J = 8.0, 1.3 Hz, 2H), 7.20 (t, J = 7.9 Hz, 2H), 6.82 (s, 1H), 6.65 (dd, J = 16.9, 10.2 Hz, 1H), 6.34 (s, 1H), 6.20 (dd, J = 17.1, 2.0 Hz, 1H), 5.69 (dd, J = 8.9, 4.6 Hz, 2H), 4.16-4.13 (m, 1H), 3.79 (s, 3H), 2.89 (t, J = 6.2 Hz, 1H), 2.86-2.78 (m, 2H), 2.65 (d, J = 11.4 Hz, 4H), 2.27 (s, 2H), 2.11-2.07 (m, 1H), 1.89 (s, 8H), 1.83 (d, J = 12.4 Hz, 3H), 1.71 (s, 2H), 1.58 (dt, J = 6.5, 3.1 Hz, 2H), 0.39 (dd, J = 6.4, 2.2 Hz, 2H), 0.28-0.26 (m, 2H), ; 673.5 [M + H]⁺ | 1.31 |

| Example Compound | Structure | Name of Compound | ¹H NMR[[:]]; MS [M + H]⁺ | UPLC r.t. (min) |
|---|---|---|---|---|
| 146 | 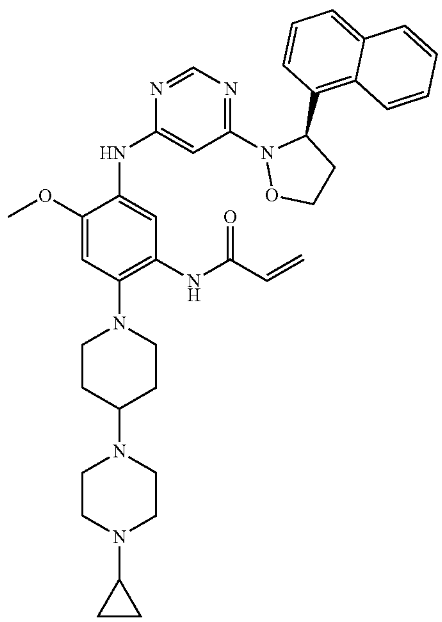 [SMILES: C=CC(=O)Nc1cc(Nc2cc(N3OCC[C@@H]3c3cccc4ccccc34)ncn2)c(OC)cc1N1CCC(N2CCN(C3CC3)CC2)CC1] | N-(2-(4-(4-cyclopropylpiperazine-1-yl)piperidine-1-yl)-4-methoxy-5-((6-((R)-3-(naphthalene-1-yl)isoxazolidine-2-yl)pyrimidine-4-yl)amino)phenyl) acrylamide | ¹H NMR (400 MHz, Chloroform-d) δ 8.90 (s, 1H), 8.45 (s, 1H), 8.36 (s, 1H), 8.15 (d, J = 8.3 Hz, 1H), 7.88 (dd, J = 8.0, 1.5 Hz, 1H), 7.79-7.75 (m, 2H), 7.55-7.45 (m, 3H), 6.91 (s, 1H), 6.78-6.75 (m, 2H), 6.42-6.21 (m, 4H), 5.74 (dd, J = 9.9, 1.6 Hz, 1H), 4.20-4.15 (m, 2H), 3.84 (s, 3H), 3.09-3.03 (m, 2H), 2.99-2.94 (m, 1H), 2.75-2.60 (m, 10H), 2.42-2.32 (m, 2H), 2.10-2.05 (m, 2H), 1.72-1.66 (m, 2H), 0.49-0.42 (m, 4H); 675.5 [M + H]⁺ | 1.24 |
| 147 | 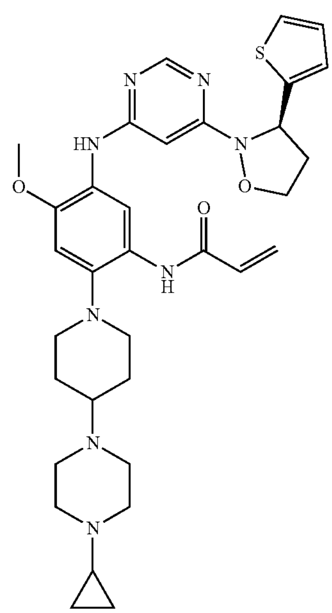 [SMILES: C=CC(=O)Nc1cc(Nc2cc(N3OCC[C@@H]3c3cccs3)ncn2)c(OC)cc1N1CCC(N2CCN(C3CC3)CC2)CC1] | N-(2-(4-(4-cyclopropylpiperazine-1-yl)piperidine-1-yl)-4-methoxy-5-((6-((R)-3-(thiophene-2-yl)isoxazolidine-2-yl)pyrimidine-4-yl)amino)phenyl) acrylamide | ¹H NMR (400 MHz, CDCl₃) δ 8.79 (s, 1H), 8.41 (s, 1H), 8.36 (s, 1H), 7.43 (s, 1H), 7.19 (d, J = 5.1 Hz, 1H), 7.06 (d, J = 3.4 Hz, 1H), 6.95 (dd, J = 4.9, 3.6 Hz, 1H), 6.72 (s, 1H), 6.62 (s, 1H), 6.39-6.11 (m, 2H), 5.99 (dd, J = 8.2, 3.2 Hz, 1H), 5.80 (d, J = 10.4 Hz, 1H), 5.73 (dd, J = 9.8, 1.5 Hz, 1H), 4.23-4.16 (m, 1H), 4.12 (q, J = 7.9 Hz, 1H), 3.82 (s, 3H), 3.12-3.01 (m, 2H), 2.98-2.61 (m, 12H), 2.55-2.46 (m, 1H), 2.16-2.08 (m, 2H), 1.87-1.70 (m, 3H), 0.55-0.46 (m, 4H); 631.50 [M + H]⁺ | 1.17 |

TABLE 1-continued

| Example Compound | Structure | Name of Compound | ¹H NMR[[:]]; MS [M + H]⁺ | UPLC r.t. (min) |
|---|---|---|---|---|
| 148 | 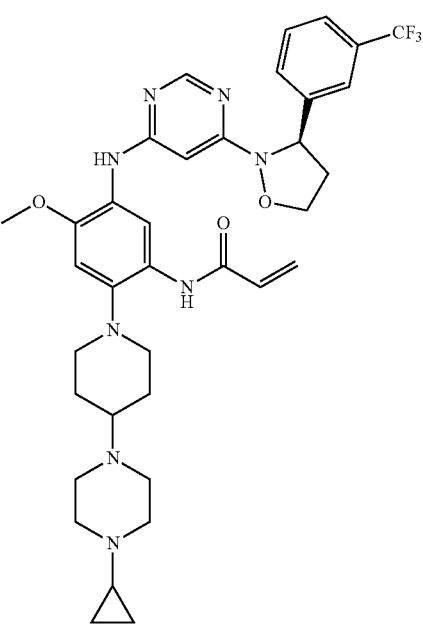 [SMILES: C=CC(=O)Nc1cc(Nc2cc(N3OCC[C@@H]3c3cccc(C(F)(F)F)c3)ncn2)c(OC)cc1N1CCC(N2CCN(C3CC3)CC2)CC1] | N-(2-(4-(4-cyclopropylpiperazine-1-yl)piperidine-1-yl)-4-methoxy-5-((6-((R)-3-(3-(trifluoromethyl)phenyl)isoxazolidine-2-yl)pyrimidine-4-yl)amino)phenyl)acrylamide | ¹H NMR (400 MHz, Chloroform-d) δ 8.86 (s, 1H), 8.45 (s, 1H), 8.36 (d, J = 1.0 Hz, 1H), 7.73 (s, 1H), 7.66 (d, J = 7.6 Hz, 1H), 7.50-7.44 (m, 2H), 6.95 (s, 1H), 6.74 (d, J = 6.5 Hz, 2H), 6.38-6.20 (m, 3H), 5.77-5.73 (m, 2H), 4.17-4.07 (m, 2H), 3.84 (s, 3H), 3.07-3.03 (m, 2H), 2.78-2.61 (m, 12H), 2.36-2.33 (m, 1H), 2.10-2.05 (m, 2H), 1.72-1.65 (m, 2H), 0.47-0.42 (m, 4H); 693.5 [M + H]⁺ | 1.42 |
| 149 | 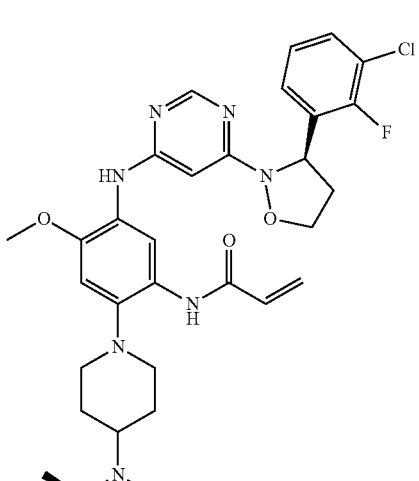 | N-(5-((6-((R)-3-(3-chloro-2-fluorophenyl)isoxazolidine-2-yl)pyrimidine-4-yl)amino)-2-(4-((R)-4-cyclopropyl-2-methylpiperazine-1-yl)piperidine-1-yl)-4-methoxyphenyl)acrylamide | ¹H NMR (400 MHz, DMSO-d₆) δ 9.06 (d, J = 26.6 Hz, 2H), 8.21 (d, J = 3.5 Hz, 1H), 7.53 (td, J = 7.6, 1.7 Hz, 1H), 7.42 (t, J = 6.9 Hz, 1H), 7.23 (t, J = 7.9 Hz, 1H), 6.85 (s, 1H), 6.65 (d, J = 11.5 Hz, 1H), 6.33-6.17 (m, 2H), 5.79-5.65 (m, 2H), 4.22 (dt, J = 7.9, 4.3 Hz, 2H), 3.93 (d, J = 8.0 Hz, 4H), 3.80 (s, 3H), 3.47 (d, J = 31.1 Hz, 4H), 3.22 (s, 2H), 3.15 (d, J = 13.8 Hz, 3H), 2.88 (d, J = 13.8 Hz, 3H), 2.23 (h, J = 7.6 Hz, 1H), 2.14 (s, 1H), 2.00-1.83 (m, 2H), 1.31 (d, J = 6.2 Hz, 3H), 0.61-0.39 (m, 4H), ; 691.5 [M + H]⁺ | 1.41 |

TABLE 1-continued

| Example Compound | Structure | Name of Compound | ¹H NMR[[:]]; MS [M + H]⁺ | UPLC r.t. (min) |
|---|---|---|---|---|
| 150 | 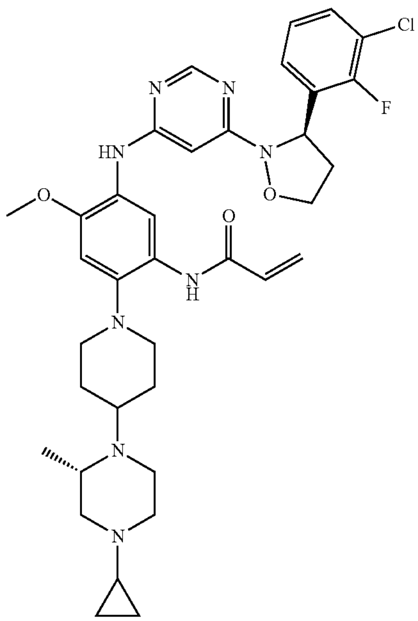 [SMILES: C=CC(=O)Nc1cc(Nc2cc(N3OCC[C@@H]3c3cccc(Cl)c3F)ncn2)c(OC)cc1N1CCC(N2CCN(C3CC3)C[C@@H]2C)CC1] | N-(5-((6-((R)-3-(3-chloro-2-fluorophenyl)isoxazolidine-2-yl)pyrimidine-4-yl)amino)-2-(4-((S)-4-cyclopropyl-2-methylpiperazine-1-yl)piperidine-1-yl)-4-methoxyphenyl)acrylamide | ¹H NMR (400 MHz, DMSO-d₆) δ 9.22 (d, J = 24.5 Hz, 1H), 9.05 (s, 1H), 8.23 (d, J = 2.5 Hz, 1H), 7.53 (td, J = 7.6, 1.7 Hz, 1H), 7.45-7.37 (m, 1H), 7.23 (t, J = 7.9 Hz, 1H), 6.86 (s, 1H), 6.66 (s, 1H), 6.31-6.20 (m, 2H), 5.73 (td, J = 9.7, 8.8, 3.6 Hz, 2H), 4.30-4.17 (m, 4H), 3.95 (td, J = 9.9, 8.7, 5.9 Hz, 3H), 3.80 (s, 3H), 3.63 (s, 1H), 3.50 (d, J = 24.8 Hz, 2H), 3.27 (s, 2H), 3.14 (t, J = 10.9 Hz, 2H), 2.95-2.72 (m, 4H), 2.33-2.21 (m, 1H), 2.15 (s, 1H), 2.02-1.84 (m, 2H), 1.32 (d, J = 6.2 Hz, 3H), 0.53 (d, J = 25.6 Hz, 4H); 691.5 [M + H]⁺ | 1.41 |
| 151 | 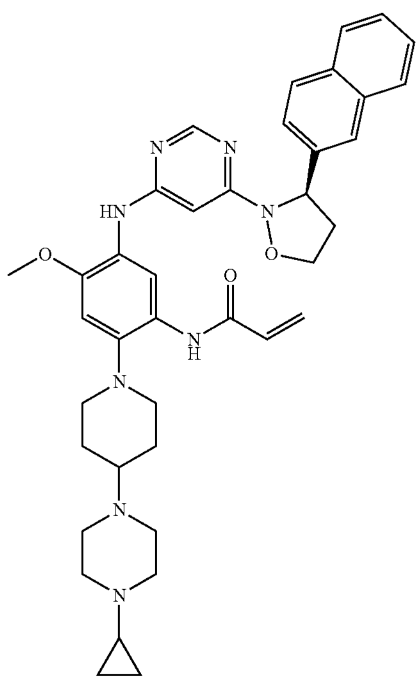 [SMILES: C=CC(=O)Nc1cc(Nc2cc(N3OCC[C@@H]3c3ccc4ccccc4c3)ncn2)c(OC)cc1N1CCC(N2CCN(C3CC3)CC2)CC1] | N-(2-(4-(4-cyclopropylpiperazine-1-yl)piperidine-1-yl)-4-methoxy-5-((6-((R)-3-(naphthalene-2-yl)isoxazolidine-2-yl)pyrimidine-4-yl)amino)phenyl)acrylamide | ¹H NMR (400 MHz, DMSO-d₆) δ 12.05 (s, 2H), 9.85 (s, 1H), 9.16 (s, 1H), 8.28 (s, 1H), 8.00-7.83 (m, 5H), 7.61-7.44 (m, 3H), 6.86 (s, 1H), 6.68 (dd, J = 17.0, 10.2 Hz, 1H), 6.25 (dd, J = 17.0, 1.9 Hz, 1H), 6.10 (s, 1H), 5.84-5.71 (m, 1H), 5.67 (s, 1H), 4.37 (d, J = 4.7 Hz, 1H), 4.10 (q, J = 7.7 Hz, 3H), 3.77 (s, 3H), 3.70 (s, 4H), 3.20 (d, J = 11.3 Hz, 2H), 3.00 (d, J = 6.4 Hz, 1H), 2.77 (t, J = 11.9 Hz, 2H), 2.41 (dq, J = 12.9, 7.3 Hz, 2H), 2.17 (d, J = 11.0 Hz, 2H), 2.07 (d, J = 16.1 Hz, 2H), 1.32-1.20 (m, 1H), 1.09 (t, J = 7.0 Hz, 2H), 0.80 (s, 2H); 675.53 [M + H]⁺ | 1.26 |

TABLE 1-continued

| Example Compound | Structure | Name of Compound | ¹H NMR[[:]]; MS [M + H]⁺ | UPLC r.t. (min) |
|---|---|---|---|---|
| 152 | 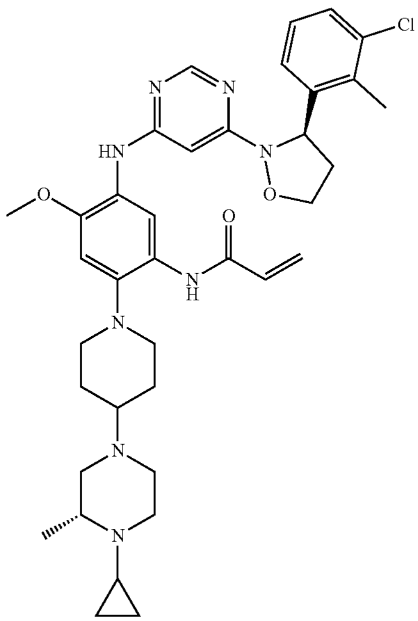 [SMILES: C=CC(=O)Nc1cc(Nc2cc(N3OCC[C@@H]3c3cccc(Cl)c3C)ncn2)c(OC)cc1N1CCC(N2CCN(C3CC3)[C@H](C)C2)CC1] | N-(5-((6-((R)-3-(3-chloro-2-methylphenyl)isoxazolidine-2-yl)pyrimidine-4-yl)amino)-2-(4-((R)-4-cyclopropyl-3-methylpiperazine-1-yl)piperidine-1-yl)-4-methoxyphenyl)acrylamide | ¹H NMR (400 MHz, DMSO-$d_6$) δ 9.00 (s, 1H), 8.63 (s, 1H), 8.20-8.10 (m, 2H), 7.39 (dd, J = 7.8, 1.3 Hz, 1H), 7.34 (dd, J = 8.1, 1.4 Hz, 1H), 7.20 (t, J = 7.9 Hz, 1H), 6.83 (s, 1H), 6.61 (dd, J = 16.9, 10.2 Hz, 1H), 6.38 (s, 1H), 6.22 (dd, J = 16.9, 1.9 Hz, 1H), 5.71 (ddd, J = 14.0, 9.4, 3.5 Hz, 2H), 4.15 (td, J = 7.9, 3.8 Hz, 1H), 3.81 (s, 3H), 3.44-3.27 (m, 8H), 3.12 (t, J = 10.9 Hz, 4H), 2.84 (tq, J = 8.0, 3.9 Hz, 2H), 2.72 (s, 4H), 2.42 (s, 4H), 2.08 (ddq, J = 12.8, 8.1, 5.2 Hz, 3H), 1.91 (s, 2H), 1.23 (d, J = 14.1 Hz, 4H), ; 687.5 [M + H]⁺ | 1.32 |
| 153 | 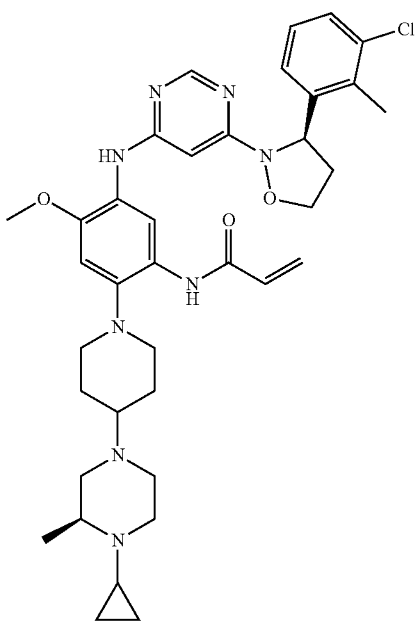 [SMILES: C=CC(=O)Nc1cc(Nc2cc(N3OCC[C@@H]3c3cccc(Cl)c3C)ncn2)c(OC)cc1N1CCC(N2CCN(C3CC3)[C@@H](C)C2)CC1] | N-(5-((6-((R)-3-(3-chloro-2-methylphenyl)isoxazolidine-2-yl)pyrimidine-4-yl)amino)-2-(4-((S)-4-cyclopropyl-3-methylpiperazine-1-yl)piperidine-1-yl)-4-methoxyphenyl)acrylamide | ¹H NMR (400 MHz, DMSO-$d_6$) δ 8.94 (s, 1H), 8.58 (s, 1H), 8.14 (t, J = 1.6 Hz, 2H), 7.40 (dd, J = 7.8, 1.3 Hz, 1H), 7.34 (dd, J = 7.9, 1.3 Hz, 1H), 7.20 (t, J = 7.9 Hz, 1H), 6.81 (s, 1H), 6.66 (dd, J = 17.0, 10.2 Hz, 1H), 6.34 (s, 1H), 6.20 (dd, J = 17.0, 2.0 Hz, 1H), 5.71 (td, J = 9.0, 8.3, 3.5 Hz, 2H), 4.14 (td, J = 7.9, 3.8 Hz, 1H), 3.79 (s, 3H), 3.32 (s, 6H), 3.04 (d, J = 11.0 Hz, 2H), 2.89-2.60 (m, 7H), 2.42 (s, 3H), 2.36-2.15 (m, 4H), 1.92 (t, J = 9.7 Hz, 1H), 1.83 (d, J = 11.8 Hz, 2H), 1.76-1.63 (m, 3H), 1.10 (d, J = 6.3 Hz, 3H), ; 687.5 [M + H]⁺ | 1.31 |

TABLE 1-continued

| Example Compound | Structure | Name of Compound | ¹H NMR[[:]]; MS [M + H]⁺ | UPLC r.t. (min) |
|---|---|---|---|---|
| 154 | 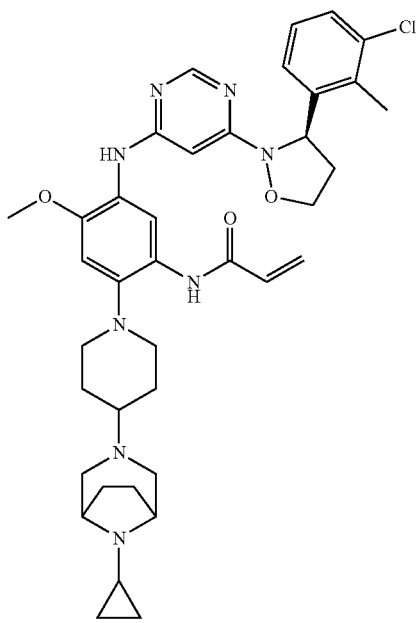 [SMILES: C=CC(=O)Nc1cc(Nc2cc(N3OCC[C@@H]3c3cccc(Cl)c3C)ncn2)c(OC)cc1N1CCC(N2CC3CCC(C2)N3C2CC2)CC1] | N-(5-((6-((R)-3-(3-chloro-2-methylphenyl)isoxazolidine-2-yl)pyrimidine-4-yl)amino)-2-(4-(8-cyclopropyl-3,8-diazabicyclo[3.2.1]octan-3-yl)piperidine-1-yl)-4-methoxyphenyl)acrylamide | ¹H NMR (400 MHz, DMSO-$d_6$) δ 8.95 (s, 1H), 8.58 (s, 1H), 8.14 (d, J = 1.0 Hz, 1H), 7.40 (dd, J = 7.7, 1.3 Hz, 1H), 7.34 (dd, J = 8.0, 1.3 Hz, 1H), 7.20 (t, J = 7.9 Hz, 1H), 6.80 (s, 1H), 6.66 (dd, J = 17.0, 10.2 Hz, 1H), 6.34 (s, 1H), 6.20 (dd, J = 17.0, 2.0 Hz, 1H), 5.70 (ddd, J = 8.6, 5.6, 3.4 Hz, 2H), 4.14 (td, J = 7.9, 3.8 Hz, 1H), 3.79 (s, 3H), 3.32 (s, 2H), 3.19 (s, 2H), 3.03 (d, J = 11.1 Hz, 2H), 2.82 (dtd, J = 11.9, 7.9, 3.8 Hz, 1H), 2.63 (ddd, J = 14.5, 10.1, 2.8 Hz, 4H), 2.42 (s, 3H), 2.28 (d, J = 9.6 Hz, 2H), 2.18 (dq, J = 10.4, 5.6, 3.4 Hz, 1H), 2.14-2.02 (m, 1H), 1.92-1.75 (m, 5H), 1.66 (dq, J = 20.8, 8.9, 6.4 Hz, 4H), 0.36 (dd, J = 6.4, 4.1 Hz, 2H), 0.30 (d, J = 3.5 Hz, 2H), ; 699.5 [M + H]⁺ | 1.35 |
| 155 | 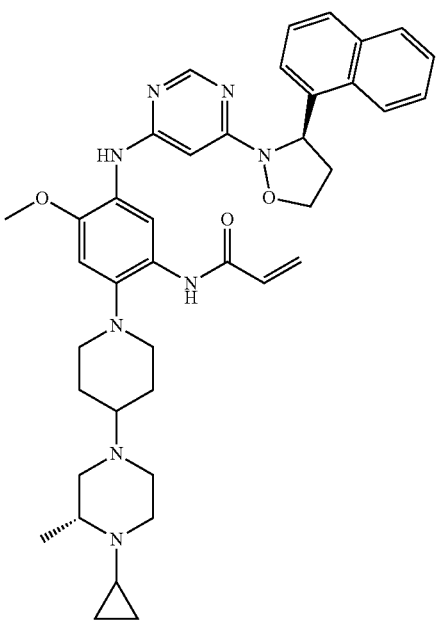 [SMILES: C=CC(=O)Nc1cc(Nc2cc(N3OCC[C@@H]3c3cccc4ccccc34)ncn2)c(OC)cc1N1CCC(N2CCN(C3CC3)[C@H](C)C2)CC1] | N-(2-(4-((R)-4-cyclopropyl-3-methylpiperazine-1-yl)piperidine-1-yl)-4-methoxy-5-((6-((R)-3-(naphthalene-1-yl)isoxazolidine-2-yl)pyrimidine-4-yl)amino)phenyl)acrylamide | ¹H NMR (400 MHz, Chloroform-d) δ 8.90 (s, 1H), 8.45 (s, 1H), 8.37 (s, 1H), 8.15 (d, J = 8.4 Hz, 1H), 7.88 (dd, J = 8.1, 1.5 Hz, 1H), 7.79-7.75 (m, 2H), 7.55-7.45 (m, 3H), 6.92 (s, 1H), 6.78-6.75 (m, 2H), 6.43-6.21 (m, 4H), 5.75-5.72 (m, 1H), 4.20-4.15 (m, 2H), 3.84 (s, 3H), 3.05-2.85 (m, 7H), 2.75-2.67 (m, 2H), 2.50-2.41 (m, 2H), 2.31-2.28 (m, 1H), 2.08-1.97 (m, 3H), 1.68-1.64 (m, 2H), 1.56-1.51 (m, 1H), 1.21 (d, J = 6.3 Hz, 3H), 0.66-0.59 (m, 2H), 0.46-0.41 (m, 1H), 0.35-0.29 (m, 1H); 689.5 [M + H]⁺ | 1.26 |

TABLE 1-continued

| Example Compound | Structure | Name of Compound | ¹H NMR[:]; MS [M + H]⁺ | UPLC r.t. (min) |
|---|---|---|---|---|
| 156 | 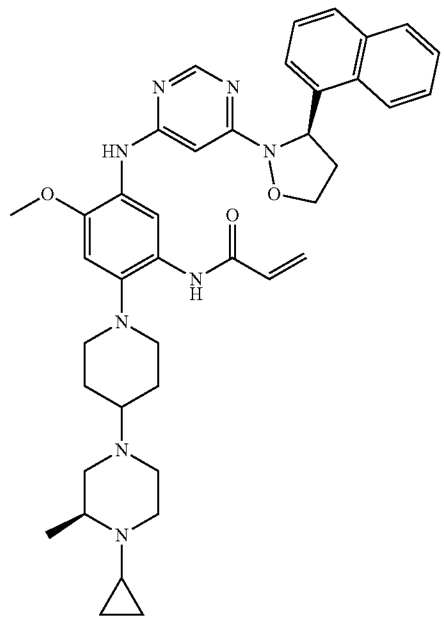 [SMILES: C=CC(=O)Nc1cc(Nc2cc(N3OCC[C@@H]3c3cccc4ccccc34)ncn2)c(OC)cc1N1CCC(N2CCN(C3CC3)[C@@H](C)C2)CC1] | N-(2-(4-((S)-4-cyclopropyl-3-methylpiperazine-1-yl)piperidine-1-yl)-4-methoxy-5-((6-((R)-3-(naphthalene-1-yl)isoxazolidine-2-yl)pyrimidine-4-yl)amino)phenyl) acrylamide | ¹H NMR (400 MHz, Chloroform-d) δ 8.90 (s, 1H), 8.45 (s, 1H), 8.37 (d, J = 1.0 Hz, 1H), 8.16-8.13 (m, 1H), 7.90-7.86 (m, 1H), 7.77 (dd, J = 7.8, 6.4 Hz, 2H), 7.56-7.44 (m, 3H), 6.92 (s, 1H), 6.76 (d, J = 11.9 Hz, 2H), 6.43-6.20 (m, 4H), 5.74 (dd, J = 10.0, 1.6 Hz, 1H), 4.20-4.15 (m, 2H), 3.84 (s, 3H), 3.08-2.86 (m, 7H), 2.76-2.68 (m, 2H), 2.52-2.42 (m, 2H), 2.32-2.28 (m, 1H), 2.02 (dd, J = 22.0, 11.6 Hz, 3H), 1.69-1.64 (m, 2H), 1.56-1.51 (m, 1H), 1.21 (d, J = 6.4 Hz, 3H), 0.66-0.58 (m, 2H), 0.47-0.41 (m, 1H), 0.34-0.28 (m, 1H); 689.5 [M + H]⁺ | 1.27 |
| 157 | 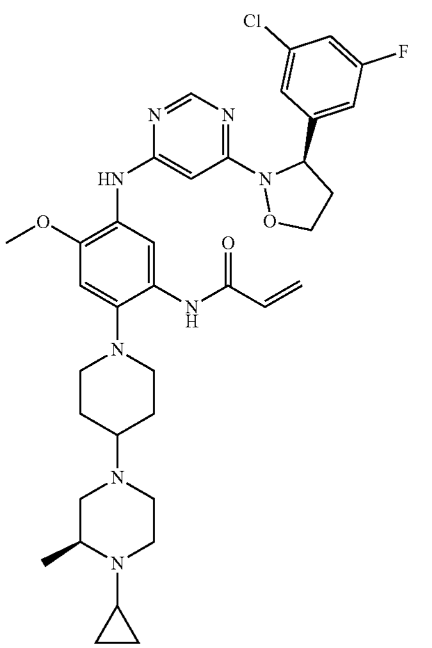 [SMILES: C=CC(=O)Nc1cc(Nc2cc(N3OCC[C@@H]3c3cc(F)cc(Cl)c3)ncn2)c(OC)cc1N1CCC(N2CCN(C3CC3)[C@@H](C)C2)CC1] | N-(5-((6-((R)-3-(3-chloro-5-fluorophenyl)isoxazolidine-2-yl)pyrimidine-4-yl)amino)-2-(4-((S)-4-cyclopropyl-3-methylpiperazine-1-yl)piperidine-1-yl)-4-methoxyphenyl) acrylamide | ¹H NMR (400 MHz, CDCl₃) δ 8.86 (s, 1H), 8.45 (s, 1H), 8.36 (s, 1H), 7.10 (d, J = 9.4 Hz, 1H), 6.99-6.94 (m, 1H), 6.92 (s, 1H), 6.75 (s, 1H), 6.71 (s, 1H), 6.39-6.11 (m, 2H), 5.77-5.70 (m, 2H), 5.66 (dd, J = 8.7, 4.5 Hz, 1H), 4.19-4.12 (m, 1H), 4.06 (q, J = 8.0 Hz, 1H), 3.84 (s, 3H), 3.10-2.85 (m, 5H), 2.81-2.67 (m, 3H), 2.57-2.44 (m, 2H), 2.38-2.25 (m, 3H), 2.11-1.96 (m, 3H), 1.72-1.65 (m, 2H), 1.57-1.50 (m, 1H), 1.21 (d, J = 6.3 Hz, 3H), 0.69-0.55 (m, 2H), 0.48-0.28 (m, 2H); 691.45 [M + H]⁺ | 1.34 |

TABLE 1-continued

| Example Compound | Structure | Name of Compound | ¹H NMR[[:]]; MS [M + H]⁺ | UPLC r.t. (min) |
|---|---|---|---|---|
| 158 | 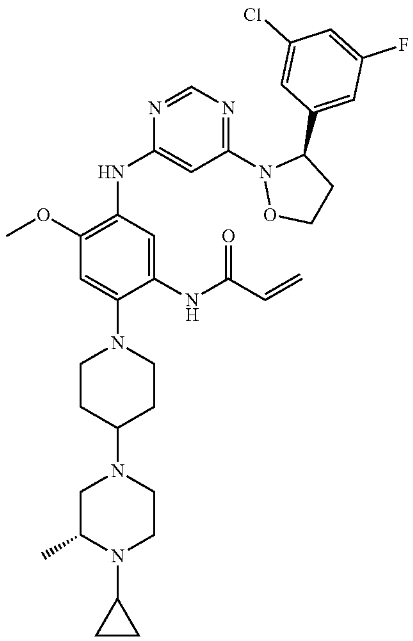 [SMILES: C=CC(=O)Nc1cc(Nc2cc(N3OCC[C@@H]3c3cc(F)cc(Cl)c3)ncn2)c(OC)cc1N1CCC(N2CCN(C3CC3)[C@H](C)C2)CC1] | N-(5-((6-((R)-3-(3-chloro-5-fluorophenyl)isoxazolidine-2-yl)pyrimidine-4-yl)amino)-2-(4-((R)-4-cyclopropyl-3-methylpiperazine-1-yl)piperidine-1-yl)-4-methoxyphenyl)acrylamide | ¹H NMR (400 MHz, CDCl₃) δ 8.86 (s, 1H), 8.44 (s, 1H), 8.36 (s, 1H), 7.10 (d, J = 9.4 Hz, 1H), 6.97 (dt, J = 8.4, 2.0 Hz, 1H) 6.93 (s, 1H), 6.75 (s, 1H), 6.71 (s, 1H), 6.40-6.19 (m, 2H), 5.74 (dd, J = 10.0, 1.3 Hz, 1H), 5.66 (dd, J = 8.7, 4.6 Hz, 1H), 4.15 (dt, J = 8.0, 4.1 Hz, 1H), 4.06 (q, J = 8.1 Hz, 1H), 3.84 (s, 3H), 3.09-2.86 (m, 5H), 2.81-2.67 (m, 3H), 2.57-2.43 (m, 2H), 2.38-2.26 (m, 3H), 2.11-1.97 (m, 3H), 1.69-1.60 (m, 2H), 1.57-1.49 (m, 1H), 1.21 (d, J = 6.3 Hz, 3H), 0.68-0.56 (m, 2H), 0.47-0.27 (m, 2H); 691.50 [M + H]⁺ | 1.32 |
| 159 | 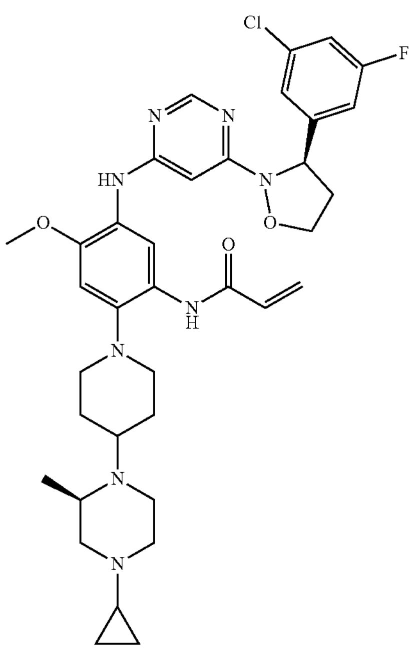 [SMILES: C=CC(=O)Nc1cc(Nc2cc(N3OCC[C@@H]3c3cc(F)cc(Cl)c3)ncn2)c(OC)cc1N1CCC(N2CCN(C3CC3)C[C@H]2C)CC1] | N-(5-((6-((R)-3-(3-chloro-5-fluorophenyl)isoxazolidine-2-yl)pyrimidine-4-yl)amino)-2-(4-((R)-4-cyclopropyl-2-methylpiperazine-1-yl)piperidine-1-yl)-4-methoxyphenyl)acrylamide | ¹H NMR (400 MHz, CDCl₃) δ 8.86 (s, 1H), 8.44 (s, 1H), 8.36 (s, 1H), 7.10 (d, J = 9.4 Hz, 1H), 6.97 (dt, J = 8.5, 2.0 Hz, 1H), 6.94 (s, 1H), 6.76 (s, 1H), 6.71 (s, 1H), 6.40-6.22 (m, 2H), 5.75 (dd, J = 10.0, 1.4 Hz, 1H), 5.66 (dd, J = 8.7. 4.6 Hz, 1H), 4.15 (td, J = 8.0, 4.2 Hz, 1H), 4.06 (q, J = 8.0 Hz, 1H), 3.84 (s, 3H), 3.12-3.01 (m, 2H), 2.99-2.66 (m, 8H), 2.57-2.41 (m, 2H), 2.38-2.28 (m, 1H), 2.26-2.19 (m, 1H), 1.93-1.81 (m, 3H), 1.64-1.55 (m, 2H), 1.09 (d, J = 6.1 Hz, 3H), 0.50-0.37 (m, 4H); 691.45 [M + H]⁺ | 1.35 |

TABLE 1-continued

| Example Compound | Structure | Name of Compound | ¹H NMR[:]; MS [M + H]⁺ | UPLC r.t. (min) |
|---|---|---|---|---|
| 160 | 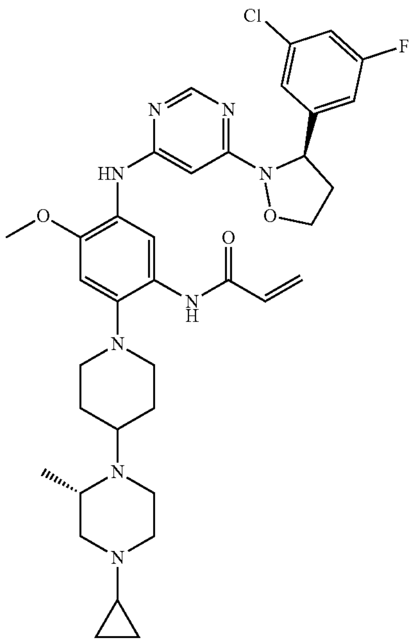 [SMILES: C=CC(=O)Nc1cc(Nc2cc(N3OCC[C@@H]3c3cc(F)cc(Cl)c3)ncn2)c(OC)cc1N1CCC(N2CCN(C3CC3)C[C@@H]2C)CC1] | N-(5-((6-((R)-3-(3-chloro-5-fluorophenyl)isoxazolidine-2-yl)pyrimidine-4-yl)amino)-2-(4-((S)-4-cyclopropyl-2-methylpiperazine-1-yl)piperidine-1-yl)-4-methoxyphenyl)acrylamide | ¹H NMR (400 MHz, CDCl₃) δ 8.86 (s, 1H), 8.44 (s, 1H), 8.36 (s, 1H), 7.10 (d, J = 9.4 Hz, 1H), 6.99-6.95 (m, 1H), 6.93 (s, 1H), 6.76 (s, 1H), 6.71 (s, 1H), 6.29 (dt, J = 16.9, 13.3 Hz, 2H), 5.77-5.73 (m, 1H), 5.66 (dd, J = 8.6, 4.6 Hz, 1H), 4.16 (td, J = 8.1, 4.3 Hz, 1H), 4.06 (q, J = 8.1 Hz, 1H), 3.84 (s, 3H), 3.11-3.02 (m, 2H), 2.99-2.63 (m, 8H), 2.57-2.41 (m, 2H), 2.38-2.28 (m, 1H), 2.27-2.10 (m, 1H), 1.94-1.81 (m, 3H), 1.60-1.53 (m, 2H), 1.09 (d, J = 6.2 Hz, 3H), 0.49-0.37 (m, 4H); 691.45 [M + H]⁺ | 1.36 |
| 161 | 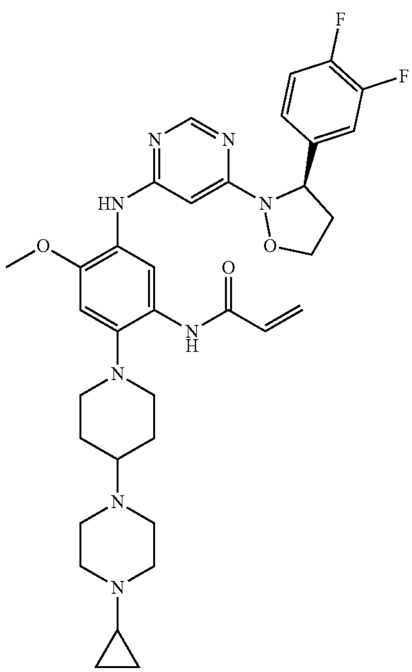 [SMILES: C=CC(=O)Nc1cc(Nc2cc(N3OCC[C@@H]3c3ccc(F)c(F)c3)ncn2)c(OC)cc1N1CCC(N2CCN(C3CC3)CC2)CC1] | N-(2-(4-(4-cyclopropylpiperazine-1-yl)piperidine-1-yl)-5-((6-((R)-3-(3,4-difluorophenyl)isoxazolidine-2-yl)pyrimidine-4-yl)amino)-4-methoxyphenyl)acrylamide | ¹H NMR (400 MHz, Methanol-d₄) δ 8.31 (s, 1H), 8.17 (s, 1H), 7.40-7.32 (m, 1H), 7.28-7.21 (m, 2H), 6.91 (s, 1H), 6.57 (dd, J = 17.0, 10.3 Hz, 1H), 6.45 (s, 1H), 6.36 (dd, J = 17.0, 1.3 Hz, 1H), 5.81 (d, J = 10.4 Hz, 1H), 5.54 (dd, J = 8.5, 4.6 Hz, 1H), 4.15 (td, J = 7.9, 4.3 Hz, 1H), 3.98 (q, J = 7.9 Hz, 1H), 3.88 (s, 3H), 3.17 (d, J = 11.0 Hz, 2H), 2.67 (t, J = 11.5 Hz, 1H), 2.40-2.27 (m, 1H), 2.16-2.06 (m, 2H), 1.89-1.74 (m, 3H), 1.30 (s, 1H), 0.59-0.51 (m, 2H), 0.51-0.43 (m, 2H); 661.5 [M + H]⁺ | 1.25 |

TABLE 1-continued

| Example Compound | Structure | Name of Compound | ¹H NMR[:]; MS [M + H]⁺ | UPLC r.t. (min) |
|---|---|---|---|---|
| 162 | 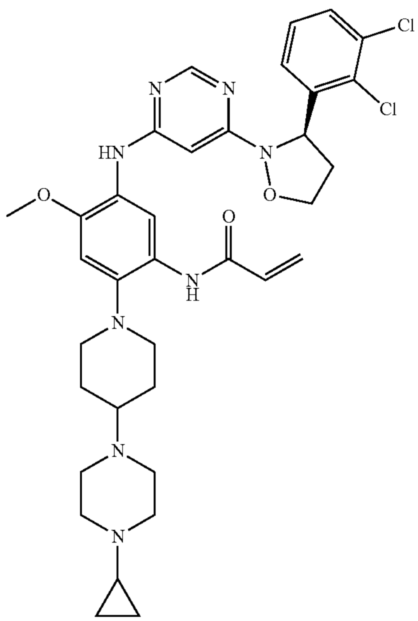 [SMILES: C=CC(=O)Nc1cc(Nc2cc(N3OCC[C@@H]3c3cccc(Cl)c3Cl)ncn2)c(OC)cc1N1CCC(N2CCN(C3CC3)CC2)CC1] | N-(2-(4-(4-cyclopropylpiperazine-1-yl)piperidine-1-yl)-5-((6-((R)-3-(2,3-dichlorophenyl)isoxazolidine-2-yl)pyrimidine-4-yl)amino)-4-methoxyphenyl)acrylamide | ¹H NMR (400 MHz, Chloroform-d) δ 8.84 (s, 1H), 8.44 (s, 1H), 8.35 (d, J = 1.0 Hz, 1H), 7.59 (dd, J = 7.8, 1.6 Hz, 1H), 7.37 (dd, J = 7.9, 1.6 Hz, 1H), 7.19 (t, J = 7.9 Hz, 1H), 6.96 (s, 1H), 6.75 (s, 2H), 6.36 (dd, J = 17.0, 1.6 Hz, 1H), 6.26 (dd, J = 16.9, 9.9 Hz, 1H), 5.96 (dd, J = 8.8, 4.4 Hz, 1H), 5.74 (dd, J = 9.9, 1.7 Hz, 1H), 4.15-4.02 (m, 2H), 3.85 (s, 3H), 3.65 (p, J = 6.7 Hz, 1H), 3.08 (d, J = 7.4 Hz, 2H), 2.95 (dtd, J = 12.3, 8.0, 4.3 Hz, 1H), 2.81-2.66 (m, 8H), 2.11 (d, J = 12.3 Hz, 2H), 1.83 (s, 6H), 1.55 (t, J = 7.4 Hz, 2H), 0.50-0.40 (m, 4H), ; 693.5 [M + H]⁺ | 1.35 |
| 163 | 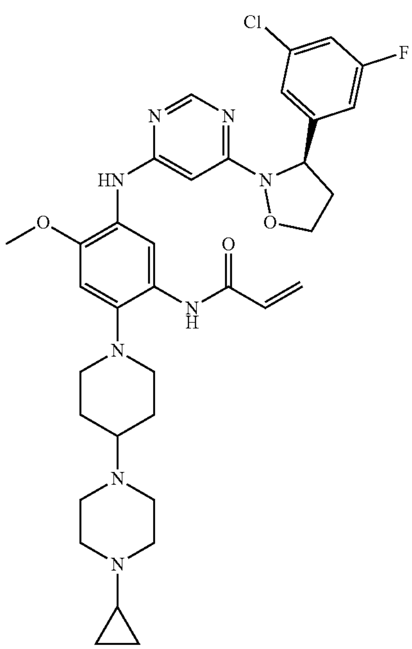 [SMILES: C=CC(=O)Nc1cc(Nc2cc(N3OCC[C@@H]3c3cc(F)cc(Cl)c3)ncn2)c(OC)cc1N1CCC(N2CCN(C3CC3)CC2)CC1] | N-(5-((6-((R)-3-(3-chloro-5-fluorophenyl)isoxazolidine-2-yl)pyrimidine-4-yl)amino)-2-(4-(4-cyclopropylpiperazine-1-yl)piperidine-1-yl)-4-methoxyphenyl)acrylamide | 677.5 [M + H]⁺ | 1.33 |

TABLE 1-continued

| Example Compound | Structure | Name of Compound | ¹H NMR[:]; MS [M + H]⁺ | UPLC r.t. (min) |
|---|---|---|---|---|
| 164 | 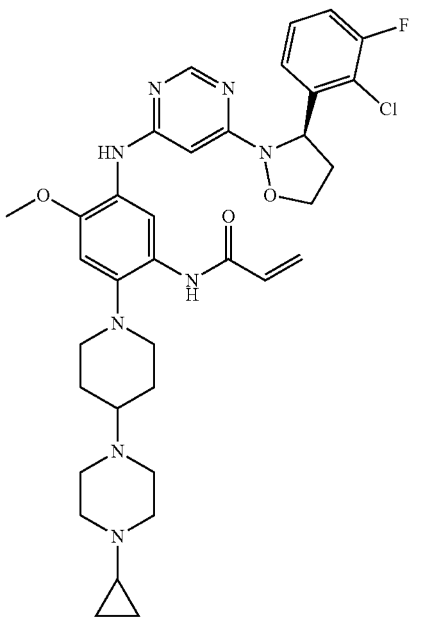 [SMILES: C=CC(=O)Nc1cc(Nc2cc(N3OCC[C@@H]3c3cccc(F)c3Cl)ncn2)c(OC)cc1N1CCC(N2CCN(C3CC3)CC2)CC1] | N-(5-((6-((R)-3-(2-chloro-3-fluorophenyl)isoxazolidine-2-yl)pyrimidine-4-yl)amino)-2-(4-(4-cyclopropylpiperazine-1-yl)piperidine-1-yl)-4-methoxyphenyl)acrylamide | ¹H NMR (400 MHz, Chloroform-d) δ 8.81 (s, 1H), 8.43 (s, 1H), 8.35 (s, 1H), 7.46 (d, J = 7.9 Hz, 1H), 7.20 (dt, J = 8.1, 4.1 Hz, 1H), 6.74 (d, J = 8.6 Hz, 2H), 6.42-6.16 (m, 2H), 5.95 (dd, J = 8.8, 4.4 Hz, 1H), 5.74 (dd, J = 9.9, 1.7 Hz, 1H), 4.17-3.98 (m, 2H), 3.84 (s, 3H), 3.81-3.74 (m, 2H), 3.06 (dd, J = 9.4, 5.2 Hz, 2H), 2.81-2.67 (m, 7H), 2.06 (s, 3H), 1.43 (s, 5H), 1.39 (d, J = 6.7 Hz, 3H), 0.95 (t, J = 7.3 Hz, 4H), ; 677.5 [M + H]⁺ | 1.30 |
| 165 | 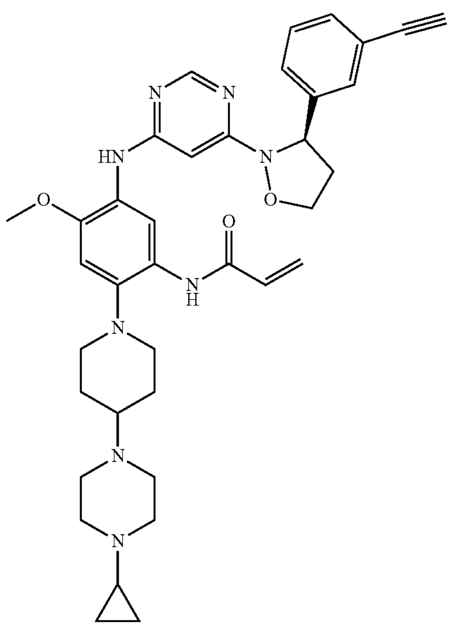 [SMILES: C#Cc1cccc([C@H]2CCON2c2cc(Nc3cc(NC(=O)C=C)c(N4CCC(N5CCN(C6CC6)CC5)CC4)cc3OC)ncn2)c1] | N-(2-(4-(4-cyclopropylpiperazine-1-yl)piperidine-1-yl)-5-((6-((R)-3-(3-ethynylphenyl)isoxazolidine-2-yl)pyrimidine-4-yl)amino)-4-methoxyphenyl)acrylamide | ¹H NMR (400 MHz, DMSO-d₆) δ 10.08 (s, 1H), 9.21 (s, 1H), 8.31 (s, 1H), 7.91 (s, 1H), 7.43 (d, J = 21.5 Hz, 4H), 6.90 (s, 1H), 6.70 (dd, J = 17.0, 10.2 Hz, 1H), 6.25 (dd, J = 17.0, 1.9 Hz, 1H), 6.07 (s, 1H), 5.79-5.74 (m, 1H), 5.56-5.47 (m, 1H), 4.32 (d, J = 4.4 Hz, 1H), 4.24 (s, 1H), 4.10-4.01 (m, 2H), 3.80 (s, 3H), 3.77-3.71 (m, 4H), 3.22 (d, J = 11.3 Hz, 2H), 2.93 (ddt, J = 11.9, 8.6, 4.8 Hz, 2H), 2.80 (t, J = 11.6 Hz, 2H), 2.35-2.26 (m, 1H), 2.17 (s, 2H), 2.09 (s, 2H), 1.67-1.54 (m, 2H), 1.49-1.36 (m, 2H), 1.16 (t, J = 3.6 Hz, 2H), 0.83 (d, J = 7.1 Hz, 2H), ; 649.3 [M + H]⁺ | 1.13 |

| Example Compound | Structure | Name of Compound | ¹H NMR[:]; MS [M + H]⁺ | UPLC r.t. (min) |
|---|---|---|---|---|
| 166 | 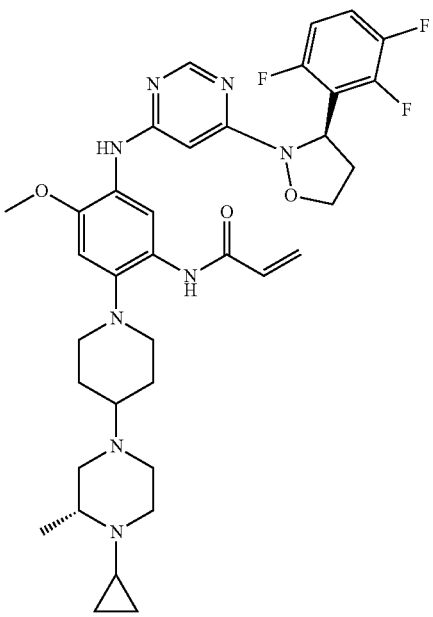 [SMILES: C=CC(=O)Nc1cc(Nc2cc(N3OCC[C@@H]3c3c(F)ccc(F)c3F)ncn2)c(OC)cc1N1CCC(N2CCN(C3CC3)[C@H](C)C2)CC1] | N-(2-(4-((R)-4-cyclopropyl-3-methylpiperazin-1-yl)piperidin-1-yl)-4-methoxy-5-((6-((R)-3-(2,3,6-trifluorophenyl)isoxazolidin-2-yl)pyrimidin-4-yl)amino)phenyl)acrylamide | ¹H NMR (400 MHz, Chloroform-d) δ 8.84 (s, 1H), 8.43 (s, 1H), 8.36 (d, J = 1.0 Hz, 1H), 7.10-7.02 (m, 1H), 6.87-6.80 (m, 2H) 6.73 (s, 1H), 6.65-6.61 (m, 1H), 6.43-6.17 (m, 3H), 5.90 (dd, J = 9.1, 6.6 Hz, 1H), 5.74 (dd, J = 10.0, 1.5 Hz, 1H), 4.40-4.34 (m, 1H), 4.03-3.94 (m, 1H), 3.82 (s, 3H), 3.07-2.86 (m, 6H), 2.77-2.68 (m, 3H), 2.56-2.48 (m, 2H), 2.31-2.27 (m, 1H), 2.09-1.97 (m, 3H), 1.70-1.62 (m, 2H), 1.56-1.50 (m, 1H), 1.21 (d, J = 2.7 Hz, 3H), 0.67-0.57 (m, 2H), 0.46-0.31 (m, 2H); 693.5 [M + H]⁺ | 1.20 |
| 167 | 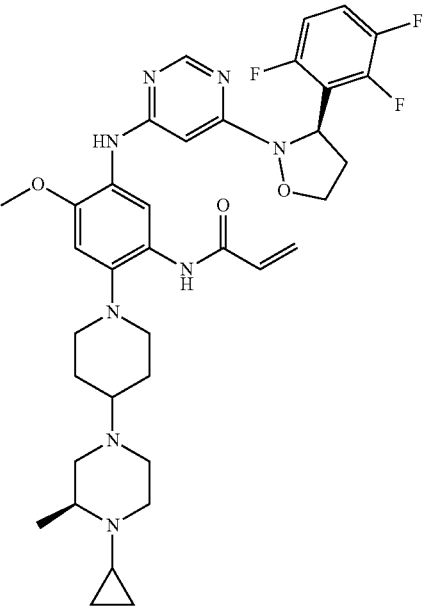 [SMILES: C=CC(=O)Nc1cc(Nc2cc(N3OCC[C@@H]3c3c(F)ccc(F)c3F)ncn2)c(OC)cc1N1CCC(N2CCN(C3CC3)[C@@H](C)C2)CC1] | N-(2-(4-((S)-4-cyclopropyl-3-methylpiperazin-1-yl)piperidin-1-yl)-4-methoxy-5-((6-((R)-3-(2,3,6-trifluorophenyl)isoxazolidin-2-yl)pyrimidin-4-yl)amino)phenyl)acrylamide | ¹H NMR (400 MHz, Chloroform-d) δ 8.84 (s, 1H), 8.43 (s, 1H), 8.36 (d, J = 1.0 Hz, 1H), 7.10-7.01 (m, 1H), 6.87-6.81 (m, 2H), 6.73 (s, 1H), 6.64-6.61 (m, 1H), 6.42-6.18 (m, 3H), 5.90 (dd, J = 9.0, 6.6 Hz, 1H), 5.74 (dd, J = 10.0, 1.5 Hz, 1H), 4.39-4.33 (m, 1H), 4.02-3.95 (m, 1H), 3.82 (s, 3H), 3.07-2.86 (m, 6H), 2.76-2.68 (m, 3H), 2.57-2.49 (m, 2H), 2.32-2.28 (m, 1H), 2.09-1.98 (m, 3H), 1.69-1.59 (m, 2H), 1.56-1.50 (m, 1H), 1.21 (d, 3H), 0.66-0.58 (m, 2H), 0.48-0.40 (m, 1H), 0.35-0.28 (m, 1H); 693.5 [M + H]⁺ | 1.20 |

TABLE 1-continued

| Example Compound | Structure | Name of Compound | ¹H NMR[[:]]; MS [M + H]⁺ | UPLC r.t. (min) |
|---|---|---|---|---|
| 168 | 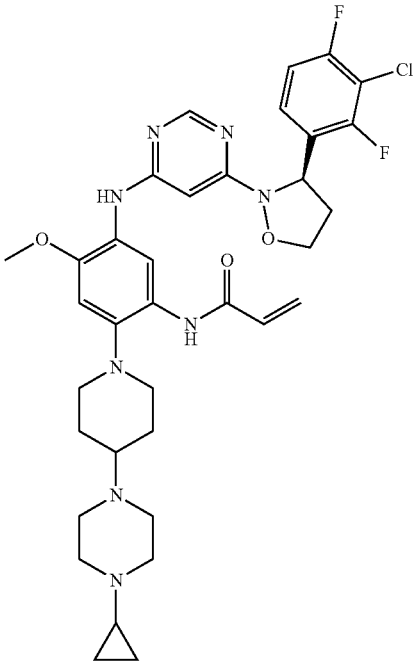 [SMILES: C=CC(=O)Nc1cc(Nc2cc(N3OCC[C@@H]3c3ccc(F)c(Cl)c3F)ncn2)c(OC)cc1N1CCC(N2CCN(C3CC3)CC2)CC1] | N-(5-((6-((R)-3-(3-chloro-2,4-difluorophenyl)isoxazolidine-2-yl)pyrimidine-4-yl)amino)-2-(4-(4-cyclopropylpiperazine-1-yl)piperidine-1-yl)-4-methoxyphenyl)acrylamide | ¹H NMR (400 MHz, Chloroform-d) δ 8.84 (s, 1H), 8.40 (s, 1H), 8.34 (d, J = 1.0 Hz, 1H), 7.49 (td, J = 8.4, 6.0 Hz, 1H), 7.09 (s, 1H), 6.95 (td, J = 8.5, 1.8 Hz, 1H), 6.74 (d, J = 1.8 Hz, 2H), 6.41-6.21 (m, 2H), 5.86 (dd, J = 8.8, 4.6 Hz, 1H), 5.74 (dd, J = 9.7, 1.8 Hz, 1H), 4.19-3.99 (m, 2H), 3.84 (s, 3H), 3.08 (d, J = 11.6 Hz, 2H), 2.80 (dp, J = 24.7, 12.3, 8.2 Hz, 10H), 2.12 (d, J = 12.1 Hz, 2H), 2.07 (s, 1H), 1.91-1.68 (m, 3H), 1.26 (d, J = 4.6 Hz, 1H), 0.92-0.81 (m, 1H), 0.55-0.39 (m, 4H), ; 695.5 [M + H]⁺ | 1.35 |
| 169 | 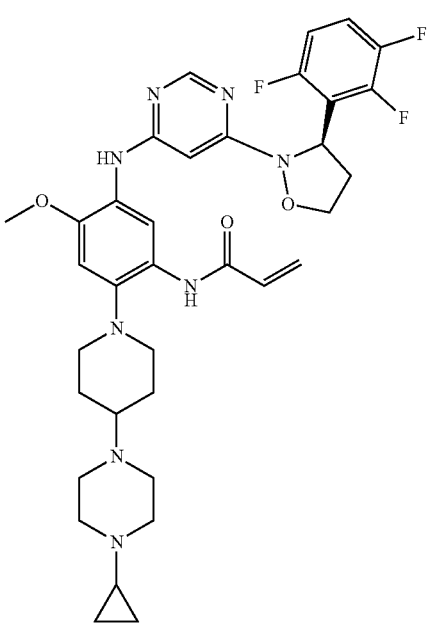 [SMILES: C=CC(=O)Nc1cc(Nc2cc(N3OCC[C@@H]3c3c(F)ccc(F)c3F)ncn2)c(OC)cc1N1CCC(N2CCN(C3CC3)CC2)CC1] | N-(2-(4-(4-cyclopropylpiperazine-1-yl)piperidine-1-yl)-4-methoxy-5-((6-((R)-3-(2,3,6-trifluorophenyl)isoxazolidine-2-yl)pyrimidine-4-yl)amino)phenyl)acrylamide | ¹H NMR (400 MHz, Chloroform-d) δ 8.83 (s, 1H), 8.43 (s, 1H), 8.36 (d, J = 1.0 Hz, 1H), 7.08-7.03 (m, 1H), 6.86-6.82 (m, 2H), 6.73 (s, 1H), 6.63 (s, 1H), 6.42-6.17 (m, 3H), 5.91-5.87 (m, 1H), 5.73 (dd, J = 10.0, 1.5 Hz, 1H), 4.38-4.34 (m, 1H), 4.01-3.96 (m, 1H), 3.82 (s, 3H), 3.07-3.03 (m, 2H), 2.75-2.59 (m, 12H), 2.36-2.30 (m, 1H), 2.09-2.05 (m, 2H), 1.72-1.66 (m, 2H), 0.47-0.42 (m, 4H); 679.5 [M + H]⁺ | 1.23 |

TABLE 1-continued

| Example Compound | Structure | Name of Compound | ¹H NMR[:]; MS [M + H]⁺ | UPLC r.t. (min) |
|---|---|---|---|---|
| 170 | 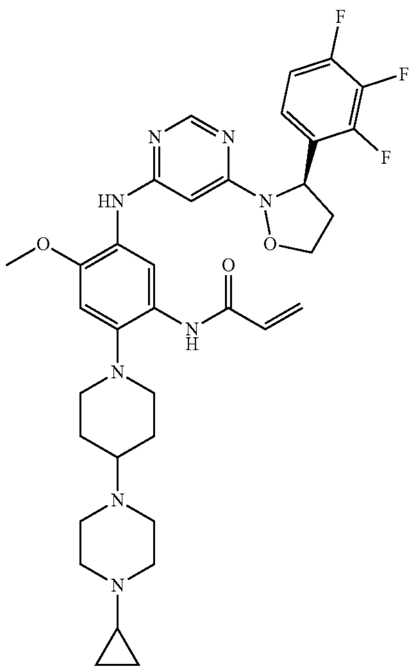 [SMILES: C=CC(=O)Nc1cc(Nc2cc(N3OCC[C@@H]3c3ccc(F)c(F)c3F)ncn2)c(OC)cc1N1CCC(N2CCN(C3CC3)CC2)CC1] | N-(2-(4-(4-cyclopropylpiperazine-1-yl)piperidine-1-yl)-4-methoxy-5-((6-((R)-3-(2,3,4-trifluorophenyl)isoxazolidine-2-yl)pyrimidine-4-yl)amino)phenyl)acrylamide | ¹H NMR (400 MHz, DMSO-d₆) δ 10.17 (s, 1H), 9.25 (s, 1H), 8.33 (s, 1H), 7.91 (s, 1H), 7.33 (dt, J = 9.8, 2.3 Hz, 1H), 7.24 (dd, J = 8.3, 5.3 Hz, 1H), 6.92 (s, 1H), 6.71 (dd, J = 17.0, 10.2 Hz, 1H), 6.29-6.12 (m, 2H), 5.73 (ddd, J = 28.1, 9.3, 3.7 Hz, 2H), 4.37-4.31 (m, 3H), 4.07 (t, J = 7.9 Hz, 2H), 3.77 (s, 4H), 3.67 (s, 2H), 3.50 (d, J = 16.0 Hz, 1H), 3.23 (d, J = 11.5 Hz, 2H), 2.94 (t, J = 6.3 Hz, 2H), 2.82 (s, 2H), 2.37-2.29 (m, 1H), 2.17 (s, 2H), 2.10 (d, J = 7.0 Hz, 2H), 1.61 (d, J = 12.5 Hz, 1H), 1.48-1.38 (m, 1H), 1.23-1.15 (m, 2H), 0.84 (d, J = 7.0 Hz, 2H), ; 679.3 [M + H]⁺ | 1.28 |
| 171 | 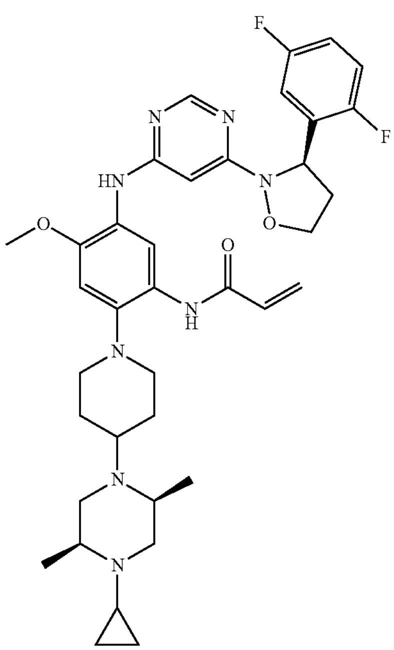 [SMILES: C=CC(=O)Nc1cc(Nc2cc(N3OCC[C@@H]3c3cc(F)ccc3F)ncn2)c(OC)cc1N1CCC(N2C[C@H](C)N(C3CC3)C[C@@H]2C)CC1] | N-(2-(4-((2S,5S)-4-cyclopropyl-2,5-dimethylpiperazine-1-yl)piperidine-1-yl)-5-((6-((R)-3-(2,5-difluorophenyl)isoxazolidine-2-yl)pyrimidine-4-yl)amino)-4-methoxyphenyl)acrylamide | ¹H NMR (400 MHz, DMSO-d₆) δ 9.95 (s, 1H), 9.27 (s, 1H), 8.31 (s, 1H), 7.32 (td, J = 9.3, 4.4 Hz, 1H), 7.26-7.12 (m, 3H), 6.94 (d, J = 17.4 Hz, 1H), 6.80-6.51 (m, 1H), 6.28-6.11 (m, 2H), 5.76 (t, J = 5.3 Hz, 2H), 5.66 (dd, J = 8.6, 5.5 Hz, 2H), 4.03 (d, J = 8.2 Hz, 10H), 3.81 (d, J = 3.8 Hz, 6H), 3.56 (s, 3H), 3.35-3.10 (m, 5H), 3.02-2.87 (m, 4H), 2.86-2.67 (m, 2H), 2.29 (dt, J = 13.1, 6.5 Hz, 3H), 2.13 (s, 3H), 1.73 (s, 2H), 1.56 (s, 6H); 689.6 [M + H]⁺ | 1.41 |

TABLE 1-continued

| Example Compound | Structure | Name of Compound | ¹H NMR[[:]]; MS [M + H]⁺ | UPLC r.t. (min) |
|---|---|---|---|---|
| 172 | 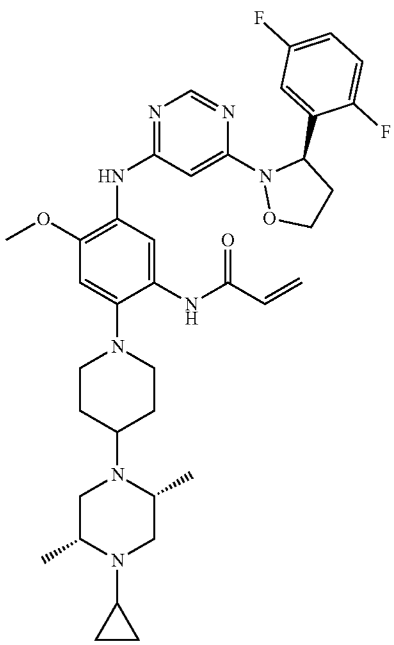 [SMILES: C=CC(=O)Nc1cc(Nc2cc(N3OCC[C@@H]3c3cc(F)ccc3F)ncn2)c(OC)cc1N1CCC(N2C[C@@H](C)N(C3CC3)C[C@H]2C)CC1] | N-(2-(4-((2R,5R)-4-cyclopropyl-2,5-dimethylpiperazine-1-yl)piperidine-1-yl)-5-((6-((R)-3-(2,5-difluorophenyl)isoxazolidine-2-yl)pyrimidine-4-yl)amino)-4-methoxyphenyl)acrylamide | ¹H NMR (400 MHz, DMSO-d$_6$) δ 10.00 (s, 1H), 9.25 (d, J = 28.6 Hz, 1H), 8.31 (s, 1H), 7.32 (td, J = 9.3, 4.5 Hz, 2H), 7.26-7.10 (m, 3H), 6.94 (d, J = 18.3 Hz, 1H), 6.79-6.49 (m, 1H), 6.31-6.12 (m, 3H), 5.75 (d, J = 3.5 Hz, 1H), 5.66 (dd, J = 8.6, 5.6 Hz, 2H), 4.05 (t, J = 7.9 Hz, 4H), 3.81 (d, J = 4.1 Hz, 6H), 3.56 (s, 12H), 3.21 (d, J = 33.4 Hz, 5H), 3.03-2.87 (m, 4H), 2.88-2.64 (m, 3H), 2.36-2.22 (m, 3H), 2.14 (s, 3H), 1.74 (s, 3H), 1.57 (s, 6H), ; 689.6 [M + H]⁺ | 1.38 |
| 173 | 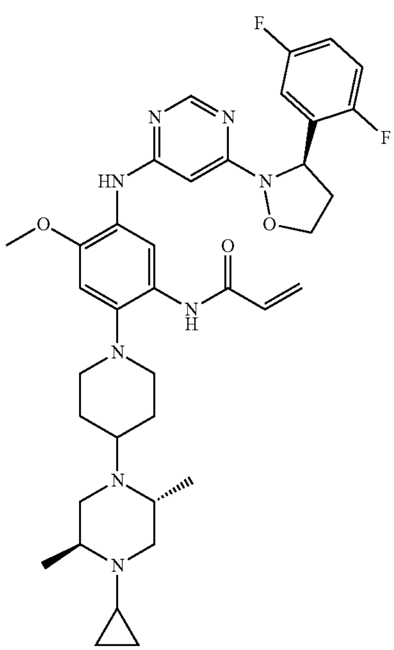 [SMILES: C=CC(=O)Nc1cc(Nc2cc(N3OCC[C@@H]3c3cc(F)ccc3F)ncn2)c(OC)cc1N1CCC(N2C[C@H](C)N(C3CC3)C[C@H]2C)CC1] | N-(2-(4-((2R,5S)-4-cyclopropyl-2,5-dimethylpiperazine-1-yl)piperidine-1-yl)-5-((6-((R)-3-(2,5-difluorophenyl)isoxazolidine-2-yl)pyrimidine-4-yl)amino)-4-methoxyphenyl)acrylamide | 689.6 [M + H]⁺ | 1.37 |

TABLE 1-continued

| Example Compound | Structure | Name of Compound | ¹H NMR[[:]]; MS [M + H]⁺ | UPLC r.t. (min) |
|---|---|---|---|---|
| 174 | 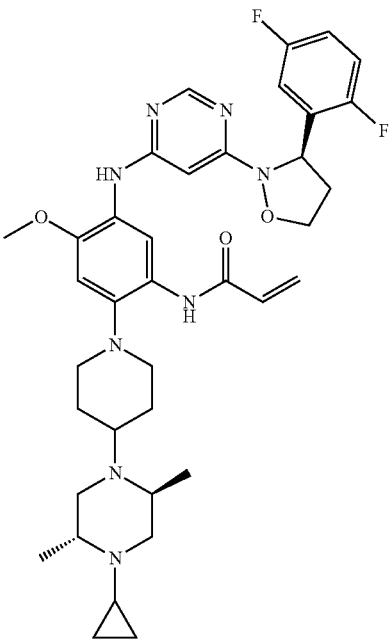 [SMILES: C=CC(=O)Nc1cc(Nc2cc(N3OCC[C@@H]3c3cc(F)ccc3F)ncn2)c(OC)cc1N1CCC(N2C[C@@H](C)N(C3CC3)C[C@@H]2C)CC1] | N-(2-(4-((2S,5R)-4-cyclopropyl-2,5-dimethylpiperazine-1-yl)piperidine-1-yl)-5-((6-((R)-3-(2,5-difluorophenyl)isoxazolidine-2-yl)pyrimidine-4-yl)amino)-4-methoxyphenyl)acrylamide | 689.6 [M + H]⁺ | 1.36 |
| 175 | 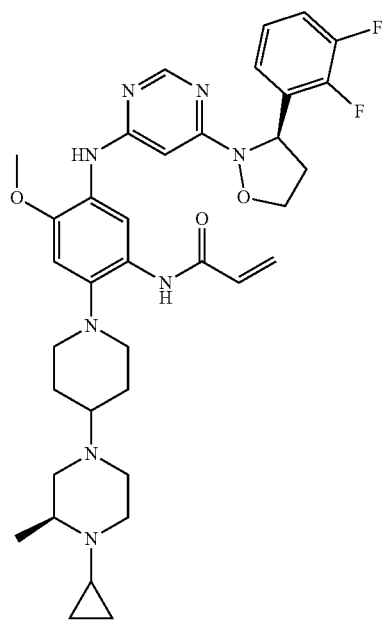 [SMILES: C=CC(=O)Nc1cc(Nc2cc(N3OCC[C@@H]3c3cccc(F)c3F)ncn2)c(OC)cc1N1CCC(N2CCN(C3CC3)[C@@H](C)C2)CC1] | N-(2-(4-((S)-4-cyclopropyl-3-methylpiperazine-1-yl)piperidine-1-yl)-5-((6-((R)-3-(2,3-difluorophenyl)isoxazolidine-2-yl)pyrimidine-4-yl)amino)-4-methoxyphenyl)acrylamide | ¹H NMR (400 MHz, CDCl₃) δ 8.79 (s, 1H), 8.42 (s, 1H), 8.32 (s, 1H), 7.41-7.31 (m, 2H), 7.09-7.00 (m, 2H), 6.74 (s, 1H) 6.70 (s, 1H), 6.39-6.23 (m, 2H), 5.92 (dd, J = 8.6, 4.5 Hz, 1H), 5.74 (dd, J = 9.8, 1.6 Hz, 1H), 4.16-4.10 (m, 1H), 4.05 (q, J = 8.0 Hz, 1H), 3.84 (s, 3H), 3.12-2.97 (m, 5H), 2.90-2.81 (m, 1H), 2.78-2.42 (m, 6H), 2.34-2.25 (m, 1H), 2.18-2.08 (m, 3H), 1.82-1.69 (m, 2H), 1.65-1.55 (m, 1H), 1.24 (d, J = 6.3 Hz, 3H), 0.72-0.59 (m, 2H), 0.51-0.32 (m, 2H); 675.62 [M + H]⁺ | 1.27 |

TABLE 1-continued

| Example Compound | Structure | Name of Compound | ¹H NMR[[:]]; MS [M + H]⁺ | UPLC r.t. (min) |
|---|---|---|---|---|
| 176 | 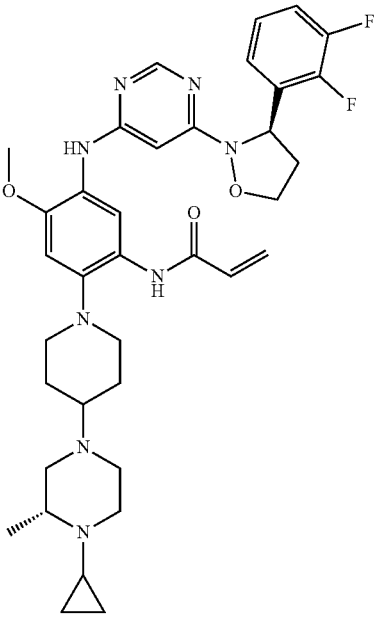 [SMILES: C=CC(=O)Nc1cc(Nc2cc(N3OCC[C@@H]3c3cccc(F)c3F)ncn2)c(OC)cc1N1CCC(N2CCN(C3CC3)[C@H](C)C2)CC1] | N-(2-(4-((R)-4-cyclopropyl-3-methylpiperazine-1-yl)piperidine-1-yl)-5-((6-((R)-3-(2,3-difluorophenyl)isoxazolidine-2-yl)pyrimidine-4-yl)amino)-4-methoxyphenyl)acrylamide | ¹H NMR (400 MHz, CDCl₃) δ 8.79 (s, 1H), 8.42 (s, 1H), 8.32 (s, 1H), 7.41-7.30 (m, 2H), 7.11-6.99 (m, 2H), 6.74 (s, 1H), 6.70 (s, 1H), 6.39-6.23 (m, 2H), 5.92 (dd, J = 8.6, 4.5 Hz, 1H), 5.74 (dd, J = 9.8, 1.6 Hz, 1H), 4.17-4.10 (m, 1H), 4.06 (q, J = 8.1 Hz, 1H), 3.84 (s, 3H), 3.12-3.02 (m, 4H), 3.02-2.96 (m, 1H), 2.90-2.81 (m, 1H), 2.78-2.41 (m, 6H), 2.35-2.26 (m, 1H), 2.17-2.07 (m, 3H), 1.80-1.68 (m, 2H), 1.63-1.55 (m, 1H), 1.23 (d, J = 6.3 Hz, 3H), 0.70-0.58 (m, 2H), 0.50-0.32 (m, 2H); 675.58 [M + H]⁺ | 1.25 |
| 177 | 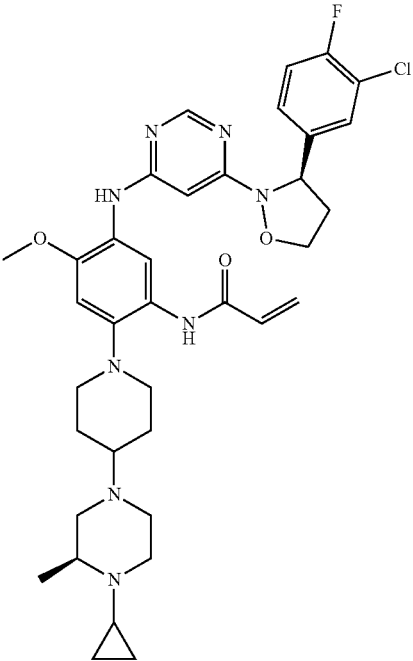 [SMILES: C=CC(=O)Nc1cc(Nc2cc(N3OCC[C@@H]3c3ccc(F)c(Cl)c3)ncn2)c(OC)cc1N1CCC(N2CCN(C3CC3)[C@@H](C)C2)CC1] | N-(5-((6-((R)-3-(3-chloro-4-fluorophenyl)isoxazolidine-2-yl)pyrimidine-4-yl)amino)-2-(4-((S)-4-cyclopropyl-3-methylpiperazine-1-yl)piperidine-1-yl)-4-methoxyphenyl)acrylamide | ¹H NMR (400 MHz, DMSO-d₆) δ 10.25 (s, 1H), 9.25 (s, 1H), 8.34 (s, 1H), 7.90 (s, 1H), 7.58 (dd, J = 7.1, 2.1 Hz, 1H), 7.46-7.35 (m, 2H), 6.92 (s, 1H), 6.78-6.68 (m, 1H), 6.26 (dd, J = 16.9, 2.0 Hz, 1H), 6.12 (s, 1H), 5.81-5.74 (m, 1H), 5.54 (dd, J = 8.5, 5.4 Hz, 1H), 4.35-4.27 (m, 1H), 4.15-4.05 (m, 2H), 3.81 (s, 3H), 3.74-3.66 (m, 2H), 3.54-3.37 (m, 3H), 3.23 (s, 2H), 3.00-2.75 (m, 5H), 2.33 (dt, J = 7.8, 5.2 Hz, 1H), 2.25-2.09 (m, 4H), 1.58-1.49 (m, 3H), 1.43 (s, 1H), 0.91 (d, J = 52.0 Hz, 4H), ; 691.3 [M + H]⁺ | 1.32 |

TABLE 1-continued

| Example Compound | Structure | Name of Compound | ¹H NMR[[:]]; MS [M + H]⁺ | UPLC r.t. (min) |
|---|---|---|---|---|
| 178 | 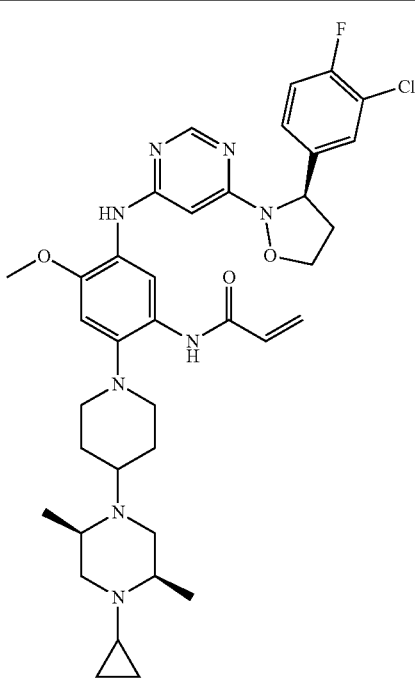 | N-(5-((6-((R)-3-(3-chloro-4-fluorophenyl)isoxazolidine-2-yl)pyrimidine-4-yl)amino)-2-(4-((2R,5R)-4-cyclopropyl-2,5-dimethylpiperazine-1-yl)piperidine-1-yl)-4-methoxyphenyl)acrylamide | ¹H NMR (400 MHz, DMSO-d₆) δ 10.35 (s, 1H), 9.40 (s, 1H), 8.35 (s, 1H), 7.88 (d, J = 69.9 Hz, 1H), 7.59 (dd, J = 7.1, 2.2 Hz, 1H), 7.46-7.35 (m, 2H), 6.97 (d, J = 21.7 Hz, 1H), 6.80-6.55 (m, 1H), 6.26 (dd, J = 16.9, 1.9 Hz, 1H), 6.13 (s, 1H), 5.77 (dd, J = 10.2, 1.9 Hz, 1H), 5.54 (dd, J = 8.4, 5.5 Hz, 1H), 4.37-4.29 (m, 2H), 4.14-4.01 (m, 3H), 3.82 (d, J = 3.5 Hz, 3H), 3.72 (s, 1H), 3.67-3.53 (m, 2H), 3.38 (d, J = 6.7 Hz, 1H), 3.22 (dd, J = 29.9, 15.5 Hz, 3H), 3.08-2.88 (m, 3H), 2.81 (d, J = 29.2 Hz, 1H), 2.32 (dd, J = 7.9, 5.0 Hz, 2H), 2.17 (d, J = 14.7 Hz, 2H), 1.77 (d, J = 7.0 Hz, 2H), 1.65-1.57 (m, 4H), 1.46-1.33 (m, 1H), 0.94-0.74 (m, 3H), ; 705.3 [M + H]⁺ | 1.39 |
| 179 | 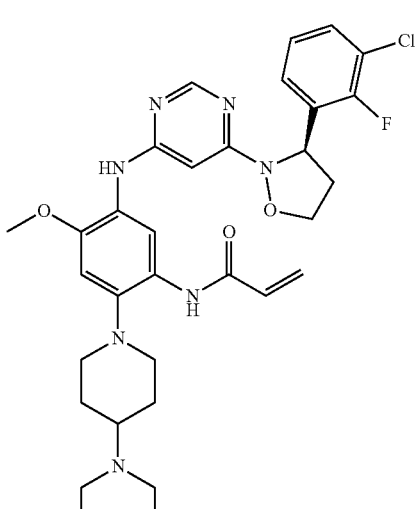 | N-(5-((6-((R)-3-(3-chloro-2-fluorophenyl)isoxazolidine-2-yl)pyrimidine-4-yl)amino)-2-(4-((S)-4-cyclopropyl-3-methylpiperazine-1-yl)piperidine-1-yl)-4-methoxyphenyl)acrylamide | 1H NMR (400 MHz, DMSO-d6) δ 9.08 (s, 1H), 8.22 (s, 1H), 8.07 (s, 1H), 7.56-7.50 (m, 1H), 7.41 (t, J = 7.3 Hz, 1H), 7.23 (t, J = 7.9 Hz, 1H), 6.86 (s, 1H), 6.65 (dd, J = 16.8, 10.0 Hz, 1H), 6.33-6.19 (m, 2H), 5.79-5.68 (m, 2H), 4.29-4.19 (m, 1H), 3.94 (q, J = 8.1 Hz, 2H), 3.81 (s, 3H), 3.18 (d, J = 11.1 Hz, 4H), 2.87 (d, J = 9.3 Hz, 2H), 2.75 (t, J = 11.5 Hz, 3H), 2.29-2.20 (m, 2H), 2.16 (s, 3H), 1.99 (s, 3H), 1.91 (s, 3H), 1.38 (d, J = 16.4 Hz, 3H), 1.24 (s, 3H), ; 691.5 [M + H]+ | 1.38 |

TABLE 1-continued

| Example Compound | Structure | Name of Compound | ¹H NMR[:]; MS [M + H]⁺ | UPLC r.t. (min) |
|---|---|---|---|---|
| 180 | 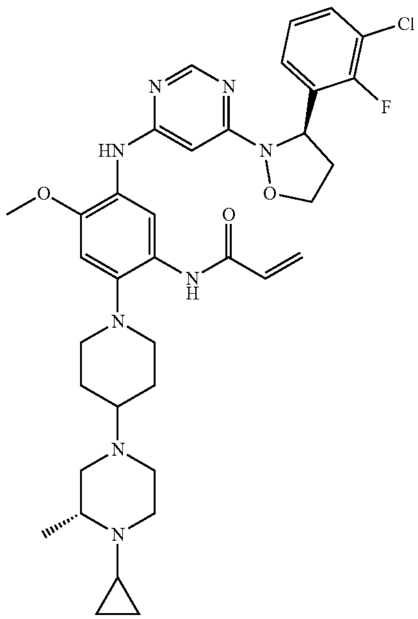 [SMILES: C=CC(=O)Nc1cc(Nc2cc(N3OCC[C@@H]3c3cccc(Cl)c3F)ncn2)c(OC)cc1N1CCC(N2CCN(C3CC3)[C@H](C)C2)CC1] | N-(5-((6-((R)-3-(3-chloro-2-fluorophenyl)isoxazolidine-2-yl)pyrimidine-4-yl)amino)-2-(4-((R)-4-cyclopropyl-3-methylpiperazine-1-yl)piperidine-1-yl)-4-methoxyphenyl)acrylamide | ¹H NMR (400 MHz, DMSO-$d_6$) δ 9.03 (s, 1H), 8.76 (s, 1H), 8.18 (s, 1H), 7.52 (t, J = 7.4 Hz, 1H), 7.48-7.38 (m, 1H), 7.23 (t, J = 7.9 Hz, 1H), 6.84 (s, 1H), 6.60 (d, J = 12.0 Hz, 1H), 6.37 (s, 1H), 6.29-6.17 (m, 1H), 5.73 (t, J = 7.5 Hz, 2H), 4.19 (d, J = 3.8 Hz, 1H), 3.88 (q, J = 7.9 Hz, 1H), 3.81 (s, 3H), 3.15 (d, J = 11.1 Hz, 4H), 2.83 (d, J = 8.7 Hz, 2H), 2.72 (s, 3H), 2.25-2.05 (m, 5H), 1.91 (s, 5H), 1.28-1.21 (m, 4H), 1.17 (s, 4H), ; 691.5 [M + H]⁺ | 1.38 |
| 181 | 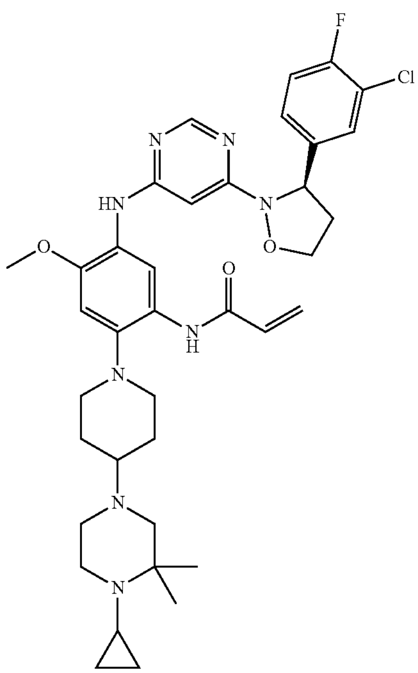 [SMILES: C=CC(=O)Nc1cc(Nc2cc(N3OCC[C@@H]3c3ccc(F)c(Cl)c3)ncn2)c(OC)cc1N1CCC(N2CCN(C3CC3)C(C)(C)C2)CC1] | N-(5-((6-((R)-3-(3-chloro-4-fluorophenyl)isoxazolidine-2-yl)pyrimidine-4-yl)amino)-2-(4-(4-cyclopropyl-3,3-dimethylpiperazine-1-yl)piperidine-1-yl)-4-methoxyphenyl)acrylamide | ¹H NMR (400 MHz, Methanol-$d_4$) δ 8.28 (s, 1H), 8.16 (s, 1H), 7.54 (dd, J = 7.1, 2.3 Hz, 1H), 7.39 (ddd, J = 8.6, 4.6, 2.3 Hz, 1H), 7.21 (t, J = 8.9 Hz, 1H), 6.89 (s, 1H), 6.53 (dd, J = 17.0, 10.2 Hz, 1H), 6.43 (s, 1H), 6.35 (dd, J = 17.0, 1.6 Hz, 1H), 5.84-5.76 (m, 1H), 5.52 (dd, J = 8.6, 4.7 Hz, 1H), 4.14 (td, J = 7.9, 4.2 Hz, 1H), 3.96 (q, J = 8.0 Hz, 1H), 3.86 (s, 3H), 3.15 (d, J = 11.6 Hz, 2H), 3.09 (t, J = 5.2 Hz, 2H), 2.82-2.76 (m, 2H), 2.72-2.64 (m, 2H), 2.35-2.28 (m, 1H), 2.20 (tt, J = 7.1, 3.9 Hz, 1H), 2.03 (d, J = 12.1 Hz, 2H), 1.87-1.77 (m, 2H), 1.37 (s, 6H), 1.28 (s, 4H), 0.74 (d, J = 6.9 Hz, 2H), 0.69-0.59 (m, 2H); 705.5 [M + H]⁺ | 1.33 |

TABLE 1-continued

| Example Compound | Structure | Name of Compound | ¹H NMR[[:]]; MS [M + H]⁺ | UPLC r.t. (min) |
|---|---|---|---|---|
| 182 | 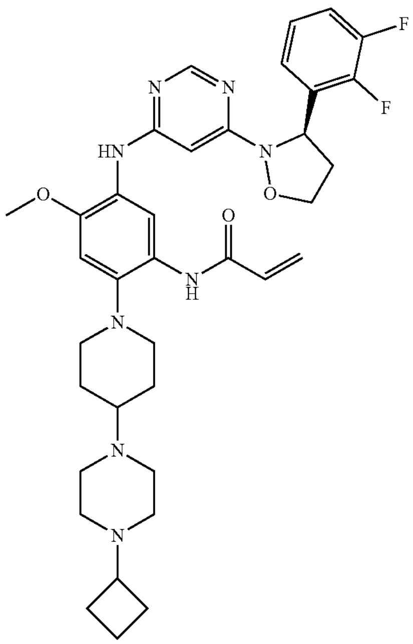 [SMILES: C=CC(=O)Nc1cc(Nc2cc(N3OCC[C@@H]3c3cccc(F)c3F)ncn2)c(OC)cc1N1CCC(N2CCN(C3CCC3)CC2)CC1] | N-(2-(4-(4-cyclobutylpiperazine-1-yl)piperidine-1-yl)-5-((6-((R)-3-(2,3-difluorophenyl)isoxazolidine-2-yl)pyrimidine-4-yl)amino)-4-methoxyphenyl)acrylamide | ¹H NMR (400 MHz, DMSO-d₆) δ 8.95 (s, 1H), 8.63 (s, 1H), 8.16 (s, 1H), 7.41-7.13 (m, 4H), 6.82 (s, 1H), 6.65 (dd, J = 17.0, 10.2 Hz, 1H), 6.35 (s, 1H), 6.20 (dd, J = 17.0, 2.0 Hz, 1H), 5.75 (d, J = 4.6 Hz, 2H), 5.74-5.69 (m, 1H), 3.85 (q, J = 8.1 Hz, 2H), 3.79 (s, 4H), 3.04 (d, J = 11.1 Hz, 3H), 2.88-2.74 (m, 2H), 2.71-2.59 (m, 4H), 2.38-2.14 (m, 6H), 1.94 (dq, J = 9.6, 5.8, 5.2 Hz, 3H), 1.82 (s, 8H), 1.80-1.66 (m, 5H), 1.66-1.56 (m, 3H), 1.23 (s, 1H), ; 675.6 [M + H]⁺ | 1.21 |
| 183 | 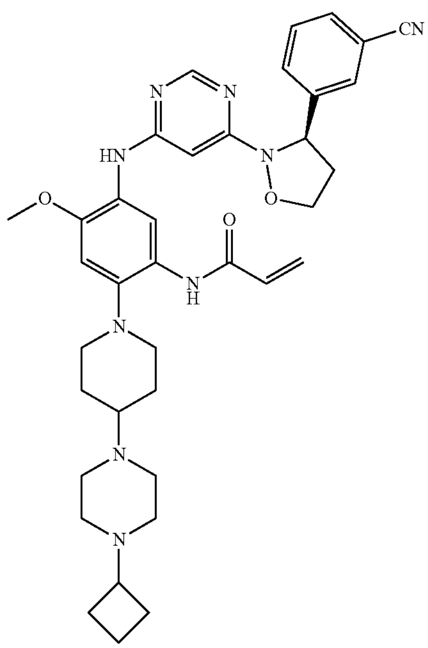 [SMILES: C=CC(=O)Nc1cc(Nc2cc(N3OCC[C@@H]3c3cccc(C#N)c3)ncn2)c(OC)cc1N1CCC(N2CCN(C3CCC3)CC2)CC1] | N-(5-((6-((R)-3-(3-cyanophenyl)isoxazolidine-2-yl)pyrimidine-4-yl)amino)-2-(4-(4-cyclobutylpiperazine-1-yl)piperidine-1-yl)-4-methoxyphenyl)acrylamide | ¹H NMR (400 MHz, DMSO-d₆) δ 8.95 (s, 1H), 8.62 (s, 1H), 8.16 (s, 1H), 7.83 (d, J = 1.8 Hz, 1H), 7.79-7.72 (m, 2H), 7.58 (t, J = 7.8 Hz, 1H), 6.82 (s, 1H), 6.65 (dd, J = 17.0, 10.2 Hz, 1H), 6.36 (s, 1H), 6.20 (dd, J = 17.0, 2.0 Hz, 1H), 5.71 (dd, J = 10.1, 2.0 Hz, 1H), 5.59 (dd, J = 8.7, 5.0 Hz, 1H), 4.14 (td, J = 7.9, 3.9 Hz, 1H), 3.79 (s, 3H), 3.33 (s, 8H), 3.04 (d, J = 11.1 Hz, 2H), 2.78 (dtd, J = 12.0, 7.8, 3.9 Hz, 2H), 2.71-2.60 (m, 4H), 2.25 (tq, J = 8.2, 5.1 Hz, 6H), 2.08 (s, 3H), 2.01-1.90 (m, 3H), 1.66-1.56 (m, 3H), ; 664.5 [M + H]⁺ | 1.09 |

TABLE 1-continued

| Example Compound | Structure | Name of Compound | ¹H NMR[:]; MS [M + H]⁺ | UPLC r.t. (min) |
|---|---|---|---|---|
| 184 | 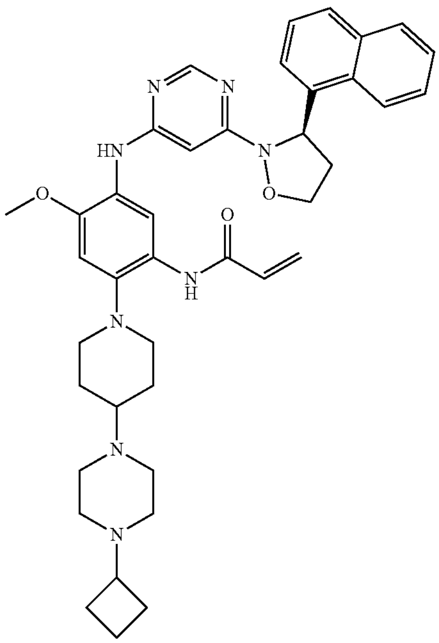 [SMILES: C=CC(=O)Nc1cc(Nc2cc(N3OCC[C@@H]3c3cccc4ccccc34)ncn2)c(OC)cc1N1CCC(N2CCN(C3CCC3)CC2)CC1] | N-(2-(4-(4-cyclobutylpiperazine-1-yl)piperidine-1-yl)-4-methoxy-5-((6-((R)-3-(naphthalene-1-yl)isoxazolidine-2-yl)pyrimidine-4-yl)amino)phenyl) acrylamide | ¹H NMR (400 MHz, Chloroform-d) δ 8.90 (s, 1H), 8.46 (s, 1H), 8.37 (s, 1H), 8.15 (d, J = 8.3 Hz, 1H), 7.89-7.87 (m, 1H), 7.79-7.75 (m, 2H), 7.55-7.45 (m, 3H), 6.93 (s, 1H), 6.78-6.75 (m, 2H), 6.41-6.21 (m, 4H), 5.73 (dd, J = 10.0, 1.6 Hz, 1H), 4.20-4.15 (m, 2H), 3.85 (s, 3H), 3.08-3.04 (m, 2H), 2.99-2.94 (m, 1H), 2.78-2.64 (m, 8H), 2.41-2.31 (m, 4H), 2.10-2.07 (m, 2H), 1.95-1.83 (m, 4H), 1.75-1.69 (m, 4H); 689.6 [M + H]⁺ | 1.24 |
| 185 | 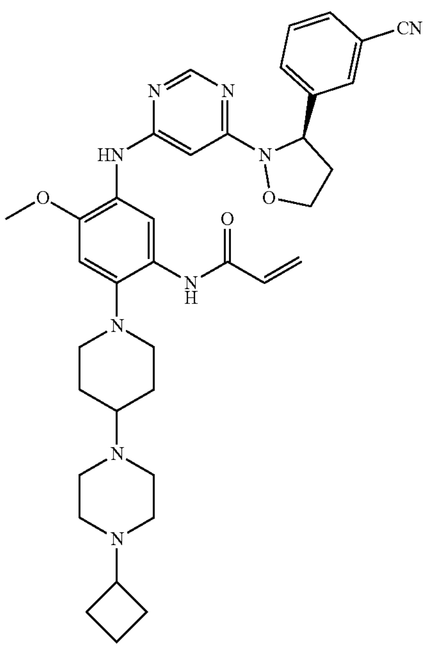 [SMILES: C=CC(=O)Nc1cc(Nc2cc(N3OCC[C@@H]3c3cccc(C#N)c3)ncn2)c(OC)cc1N1CCC(N2CCN(C3CCC3)CC2)CC1] | N-(5-((6-((R)-3-(3-chlorophenyl)isoxazolidine-2-yl)pyrimidine-4-yl)amino)-2-(4-(4-cyclobutylpiperazine-1-yl)piperidine-1-yl)-4-methoxyphenyl) acrylamide | 1H NMR (400 MHz, DMSO-d6) δ 9.07 (s, 1H), 8.23 (d, J = 3.1 Hz, 1H), 8.06 (s, 1H), 7.43 (q, J = 2.9, 2.4 Hz, 1H), 7.39 (d, J = 7.5 Hz, 1H), 7.35 (ddd, J = 7.4, 5.0, 1.8 Hz, 2H), 6.85 (s, 1H), 6.63 (dd, J = 17.0, 10.2 Hz, 1H), 6.28-6.19 (m, 2H), 5.77-5.70 (m, 1H), 5.53 (dd, J = 8.6, 5.3 Hz, 1H), 4.21 (dq, J = 7.4, 3.7, 2.8 Hz, 4H), 3.91 (ddd, J = 13.2, 8.5, 4.8 Hz, 4H), 3.81 (s, 5H), 3.17 (d, J = 11.5 Hz, 4H), 2.89-2.81 (m, 1H), 2.76 (t, J = 11.7 Hz, 3H), 2.28 (dq, J = 8.9, 5.1, 3.8 Hz, 1H), 2.18 (d, J = 8.9 Hz, 4H), 2.04 (s, 2H), 1.94-1.83 (m, 2H), 1.75 (dt, J = 18.8, 10.1 Hz, 2H), ; 673.5 | 1.22 |

TABLE 1-continued

| Example Compound | Structure | Name of Compound | ¹H NMR[[:]]; MS [M + H]⁺ | UPLC r.t. (min) |
|---|---|---|---|---|
| 186 | 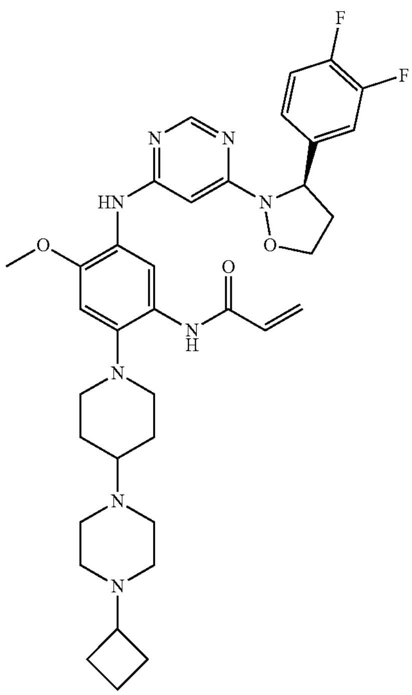 [SMILES: C=CC(=O)Nc1cc(Nc2cc(N3OCC[C@@H]3c3ccc(F)c(F)c3)ncn2)c(OC)cc1N1CCC(N2CCN(C3CCC3)CC2)CC1] | N-(2-(4-(4-cyclobutylpiperazine-1-yl)piperidine-1-yl)-5-((6-((R)-3-(3,4-difluorophenyl)isoxazolidine-2-yl)pyrimidine-4-yl)amino)-4-methoxyphenyl)acrylamide | $^1$H NMR (400 MHz, DMSO-d$_6$) δ 10.11 (s, 1H), 9.23 (s, 1H), 8.32 (s, 1H), 7.92 (s, 1H), 7.49-7.38 (m, 2H), 7.22 (dq, J = 7.9, 2.7 Hz, 1H), 6.91 (s, 1H), 6.72 (dd, J = 16.9, 10.2 Hz, 1H), 6.25 (dd, J = 17.0, 1.9 Hz, 1H), 6.12 (s, 1H), 5.75 (d, J = 5.4 Hz, 1H), 5.53 (dd, J = 8.5, 5.4 Hz, 1H), 4.29 (dd, J = 7.6, 4.5 Hz, 1H), 4.10-4.00 (m, 1H), 3.81 (s, 3H), 3.63 (s, 6H), 3.46 (d, J = 13.8 Hz, 3H), 3.23 (d, J = 11.5 Hz, 2H), 2.97-2.87 (m, 1H), 2.81 (t, J = 11.8 Hz, 2H), 2.44-2.29 (m, 3H), 2.24-2.14 (m, 4H), 2.09 (s, 1H), 1.84-1.69 (m, 2H), 1.63-1.55 (m, 1H), 1.48-1.40 (m, 1H), ; 675.3 [M + H]⁺ | 1.21 |
| 187 | 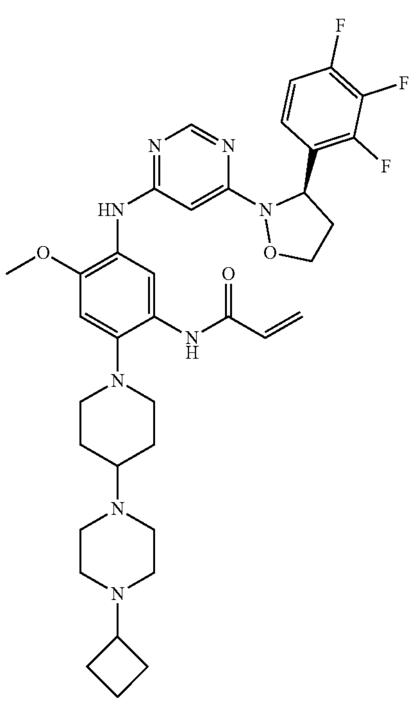 [SMILES: C=CC(=O)Nc1cc(Nc2cc(N3OCC[C@@H]3c3ccc(F)c(F)c3F)ncn2)c(OC)cc1N1CCC(N2CCN(C3CCC3)CC2)CC1] | N-(2-(4-(4-cyclobutylpiperazine-1-yl)piperidine-1-yl)-4-methoxy-5-((6-((R)-3-(2,3,4-trifluorophenyl)isoxazolidine-2-yl)pyrimidine-4-yl)amino)phenyl)acrylamide | $^1$H NMR (400 MHz, DMSO-d$_6$) δ 9.70 (s, 1H), 9.17 (s, 1H), 8.28 (s, 1H), 7.99 (s, 1H), 7.40-7.24 (m, 2H), 6.89 (s, 1H), 6.69 (dd, J = 16.9, 10.2 Hz, 1H), 6.24 (dd, J = 17.1, 2.0 Hz, 2H), 5.78-5.74 (m, 1H), 5.70 (dd, J = 8.6, 5.5 Hz, 1H), 4.30 (d, J = 4.2 Hz, 1H), 4.09 (d, J = 5.2 Hz, 1H), 4.01 (d, J = 7.9 Hz, 1H), 3.81 (s, 3H), 3.74 (s, 1H), 3.65 (d, J = 12.7 Hz, 3H), 3.47-3.35 (m, 3H), 3.22 (d, J = 11.3 Hz, 2H), 2.96-2.88 (m, 1H), 2.79 (t, J = 11.8 Hz, 2H), 2.39 (s, 1H), 2.34-2.28 (m, 1H), 2.19 (t, J = 11.3 Hz, 4H), 2.07 (d, J = 16.0 Hz, 3H), 1.74 (dd, J = 20.6, 10.5 Hz, 2H), 1.63-1.54 (m, 1H), 1.46-1.39 (m, 1H), ; 693.3 [M + H]⁺ | 1/28 |

TABLE 1-continued

| Example Compound | Structure | Name of Compound | ¹H NMR[:]; MS [M + H]⁺ | UPLC r.t. (min) |
|---|---|---|---|---|
| 188 | 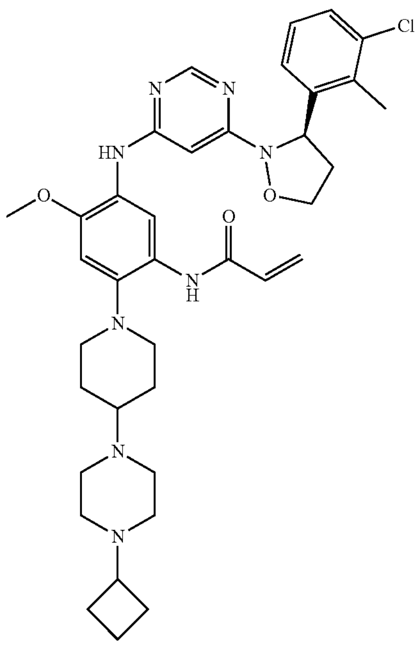 [SMILES: C=CC(=O)Nc1cc(Nc2cc(N3OCC[C@@H]3c3cccc(Cl)c3C)ncn2)c(OC)cc1N1CCC(N2CCN(C3CCC3)CC2)CC1] | N-(5-((6-((R)-3-(3-chloro-2-methylphenyl)isoxazolidine-2-yl)pyrimidine-4-yl)amino)-2-(4-(4-cyclobutylpiperazine-1-yl)piperidine-1-yl)-4-methoxyphenyl)acrylamide | ¹H NMR (400 MHz, DMSO-d₆) δ 8.95 (s, 1H), 8.59 (s, 1H), 8.14 (t, J = 1.4 Hz, 2H), 7.40 (dd, J = 7.8, 1.3 Hz, 1H), 7.34 (dd, J = 8.0, 1.3 Hz, 1H), 7.20 (t, J = 7.9 Hz, 1H), 6.82 (s, 1H), 6.65 (dd, J = 16.9, 10.2 Hz, 1H), 6.35 (s, 1H), 6.20 (dd, J = 17.0, 2.0 Hz, 1H), 5.70 (td, J = 9.2, 8.5, 3.5 Hz, 2H), 4.15 (td, J = 7.9, 3.8 Hz, 1H), 3.79 (s, 3H), 3.05 (d, J = 11.1 Hz, 2H), 2.83 (dtd, J = 12.0, 7.9, 3.7 Hz, 2H), 2.71-2.62 (m, 3H), 2.54 (s, 1H), 2.42 (s, 4H), 2.37-2.16 (m, 5H), 2.13-2.04 (m, 2H), 1.96 (s, 3H), 1.83 (s, 3H), 1.64 (d, J = 6.4 Hz, 2H), 1.24 (d, J = 6.0 Hz, 5H), ; 687.5 [M + H]⁺ | 1.25 |
| 189 | 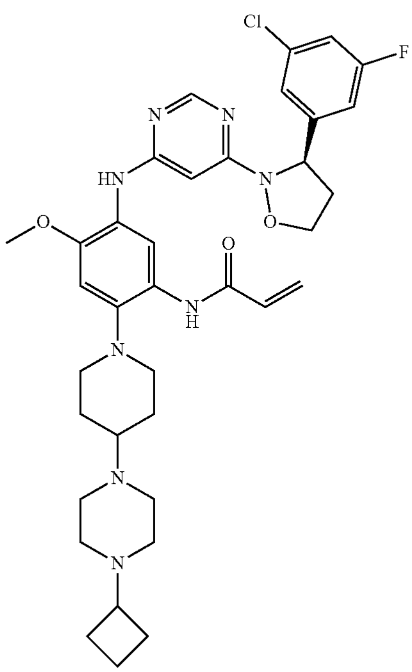 [SMILES: C=CC(=O)Nc1cc(Nc2cc(N3OCC[C@@H]3c3cc(F)cc(Cl)c3)ncn2)c(OC)cc1N1CCC(N2CCN(C3CCC3)CC2)CC1] | N-(5-((6-((R)-3-(3-chloro-5-fluorophenyl)isoxazolidine-2-yl)pyrimidine-4-yl)amino)-2-(4-(4-cyclobutylpiperazine-1-yl)piperidine-1-yl)-4-methoxyphenyl)acrylamide | 691.45 [M + H]⁺ | 1.28 |

TABLE 1-continued

| Example Compound | Structure | Name of Compound | ¹H NMR[[:]]; MS [M + H]⁺ | UPLC r.t. (min) |
|---|---|---|---|---|
| 190 | 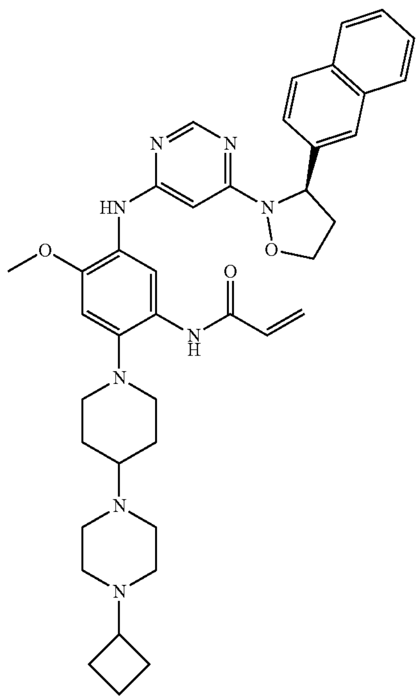 [SMILES: C=CC(=O)Nc1cc(Nc2cc(N3OCC[C@@H]3c3ccc4ccccc4c3)ncn2)c(OC)cc1N1CCC(N2CCN(C3CCC3)CC2)CC1] | N-(2-(4-(4-cyclobutylpiperazine-1-yl)piperidine-1-yl)-4-methoxy-5-((6-((R)-3-(naphthalene-2-yl)isoxazolidine-2-yl)pyrimidine-4-yl)amino)phenyl) acrylamide | ¹H NMR (400 MHz, DMSO-$d_6$) δ 9.06 (s, 1H), 8.22 (d, J = 3.7 Hz, 1H), 8.07 (s, 1H), 7.96-7.85 (m, 4H), 7.52 (dtd, J = 14.9, 8.1, 7.4, 3.5 Hz, 3H), 6.84 (s, 1H), 6.63 (dd, J = 16.9, 10.2 Hz, 1H), 6.24 (dd, J = 17.0, 1.9 Hz, 2H), 5.78-5.62 (m, 2H), 4.26 (dd, J = 8.4, 4.5 Hz, 2H), 4.01-3.93 (m, 2H), 3.79 (s, 3H), 3.67-3.59 (m, 6H), 3.16 (d, J = 11.4 Hz, 4H), 2.96-2.85 (m, 2H), 2.73 (q, J = 14.7, 13.3 Hz, 2H), 2.37 (tdd, J = 11.2, 5.9, 3.9 Hz, 1H), 2.16 (d, J = 9.6 Hz, 4H), 2.02 (s, 2H), 1.89 (d, J = 15.9 Hz, 2H), 1.73 (dd, J = 18.6, 9.5 Hz, 2H), ; 689.6 [M + H]⁺ | 1.23 |
| 191 | 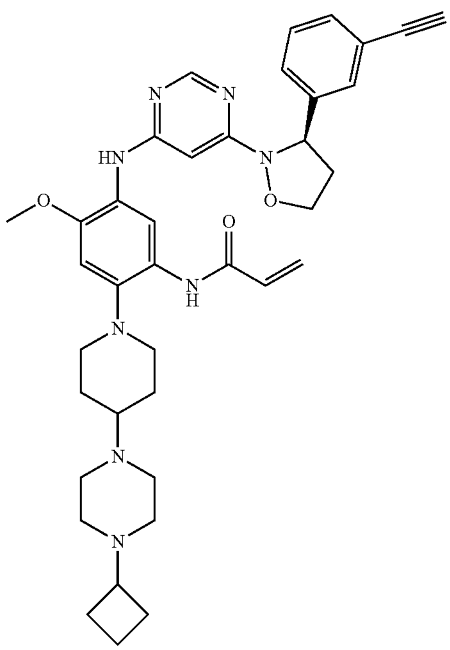 [SMILES: C#Cc1cccc([C@H]2CCON2c2cc(Nc3cc(NC(=O)C=C)c(N4CCC(N5CCN(C6CCC6)CC5)CC4)cc3OC)ncn2)c1] | N-(2-(4-(4-cyclobutylpiperazine-1-yl)piperidine-1-yl)-5-((6-((R)-3-(3-ethynylphenyl)isoxazolidine-2-yl)pyrimidine-4-yl)amino)-4-methoxyphenyl) acrylamide | ¹H NMR (400 MHz, DMSO-$d_6$) δ 10.13 (s, 1H), 9.22 (s, 1H), 8.32 (s, 1H), 7.91 (s, 1H), 7.46 (s, 1H), 7.40 (s, 3H), 6.90 (s, 1H), 6.72 (dd, J = 17.0, 10.3 Hz, 1H), 6.25 (dd, J = 17.0, 1.9 Hz, 1H), 5.79-5.74 (m, 2H), 5.52 (dd, J = 8.4, 5.6 Hz, 1H), 4.32 (d, J = 4.4 Hz, 1H), 4.24 (s, 1H), 4.06 (d, J = 7.8 Hz, 1H), 3.80 (s, 3H), 3.75 (s, 1H), 3.65 (d, J = 12.4 Hz, 4H), 3.45 (d, J = 13.8 Hz, 3H), 3.23 (d, J = 11.3 Hz, 2H), 2.94 (dd, J = 8.2, 4.4 Hz, 1H), 2.80 (t, J = 11.5 Hz, 2H), 2.41 (t, J = 10.2 Hz, 2H), 2.35-2.29 (m, 1H), 2.25-2.16 (m, 4H), 2.09 (d, J = 6.6 Hz, 2H), 1.73 (dd, J = 20.1, 10.2 Hz, 2H), 1.64-1.58 (m, 1H), 1.47-1.39 (m, 1H), 663.4 [M + H]⁺ | 1.09 |

TABLE 1-continued

| Example Compound | Structure | Name of Compound | ¹H NMR[[:]]; MS [M + H]⁺ | UPLC r.t. (min) |
|---|---|---|---|---|
| 192 | 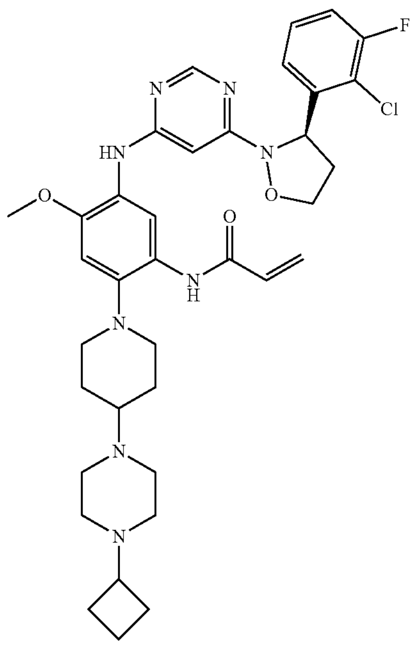 [SMILES: C=CC(=O)Nc1cc(Nc2cc(N3OCC[C@@H]3c3cccc(F)c3Cl)ncn2)c(OC)cc1N1CCC(N2CCN(C3CCC3)CC2)CC1] | N-(5-((6-((R)-3-(2-chloro-3-fluorophenyl)isoxazolidine-2-yl)pyrimidine-4-yl)amino)-2-(4-(4-cyclobutylpiperazine-1-yl)piperidine-1-yl)-4-methoxyphenyl)acrylamide | $^1$H NMR (400 MHz, DMSO-$d_6$) δ 9.09 (d, J = 13.7 Hz, 1H), 8.22 (s, 1H), 8.08 (s, 1H), 7.44-7.31 (m, 3H), 6.85 (s, 1H), 6.62 (dd, J = 17.0, 10.2 Hz, 1H), 6.33-6.18 (m, 2H), 5.82-5.70 (m, 2H), 4.20 (td, J = 7.9, 4.0 Hz, 3H), 3.95 (d, J = 8.0 Hz, 4H), 3.81 (s, 3H), 3.71 (s, 3H), 3.17 (d, J = 11.6 Hz, 4H), 2.94 (dtd, J = 12.1, 7.9, 4.0 Hz, 2H), 2.76 J = 11.7 Hz, 2H), 2.23-2.08 (m, 5H), 2.04 (d, J = 11.6 Hz, 2H), 1.90 (d, J = 10.4 Hz, 2H), 1.75 (dt, J = 18.8, 8.6 Hz, 2H), ; 691.5 [M + H]⁺ | 1.21 |
| 193 | 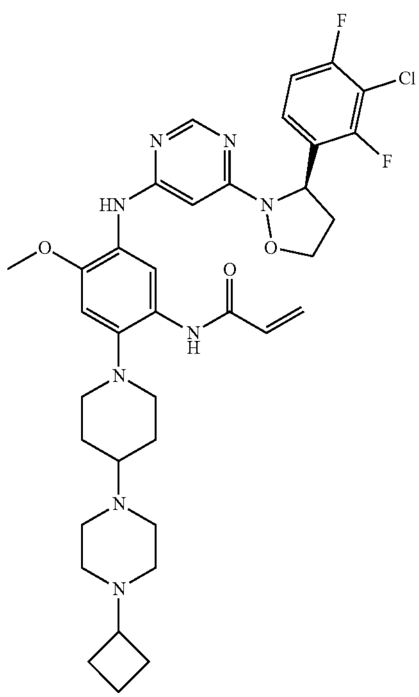 [SMILES: C=CC(=O)Nc1cc(Nc2cc(N3OCC[C@@H]3c3ccc(F)c(Cl)c3F)ncn2)c(OC)cc1N1CCC(N2CCN(C3CCC3)CC2)CC1] | N-(5-((6-((R)-3-(3-chloro-2,4-difluorophenyl)isoxazolidine-2-yl)pyrimidine-4-yl)amino)-2-(4-(4-cyclobutylpiperazine-1-yl)piperidine-1-yl)-4-methoxyphenyl)acrylamide | $^1$H NMR (400 MHz, DMSO-$d_6$) δ 9.04 (d, J = 15.4 Hz, 1H), 8.21 (d, J = 2.2 Hz, 1H), 8.10 (s, 1H), 7.47 (td, J = 8.5, 6.1 Hz, 1H), 7.32 (td, J = 8.8, 1.7 Hz, 1H), 6.84 (s, 1H), 6.62 (dd, J = 17.0, 10.2 Hz, 1H), 6.32 (s, 1H), 6.23 (dd, J = 16.9, 1.9 Hz, 1H), 5.78-5.66 (m, 2H), 4.22 (td, J = 7.9, 3.6 Hz, 2H), 3.91 (s, 4H), 3.81 (s, 3H), 3.43 (t, J = 7.0 Hz, 4H), 3.20-3.11 (m, 4H), 2.85 (dq, J = 8.5, 5.6, 4.3 Hz, 2H), 2.80-2.71 (m, 2H), 2.28-2.21 (m, 1H), 2.16 (q, J = 10.9, 10.3 Hz, 4H), 2.03 (d, J = 11.2 Hz, 2H), 1.89 (d, J = 16.1 Hz, 2H), 1.74 (dt, J = 18.6, 9.6 Hz, 2H), : 709.5 [M + H]⁺ | 1.33 |

TABLE 1-continued

| Example Compound | Structure | Name of Compound | ¹H NMR[:]; MS [M + H]⁺ | UPLC r.t. (min) |
|---|---|---|---|---|
| 194 | 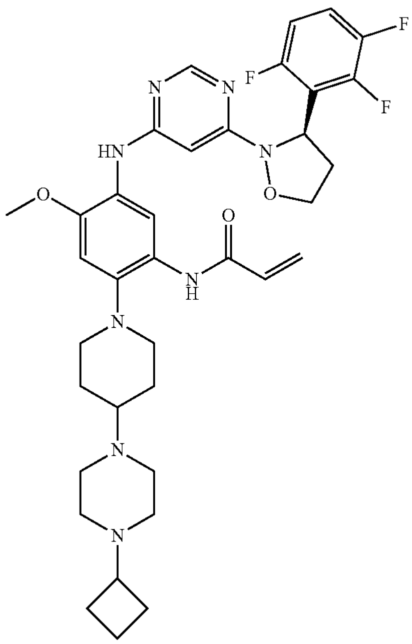 [SMILES: C=CC(=O)Nc1cc(Nc2cc(N3OCC[C@@H]3c3c(F)ccc(F)c3F)ncn2)c(OC)cc1N1CCC(N2CCN(C3CCC3)CC2)CC1] | N-(2-(4-(4-cyclobutylpiperazine-1-yl)piperidine-1-yl)-4-methoxy-5-((6-((R)-3-(2,3,6-trifluorophenyl)isoxazolidine-2-yl)pyrimidine-4-yl)amino)phenyl)acrylamide | ¹H NMR (400 MHz, Chloroform-d) δ 8.84 (s, 1H), 8.43 (s, 1H), 8.36 (d, J = 1.0 Hz, 1H), 7.08-7.03 (m, 1H), 6.86-6.82 (m, 2H), 6.74 (s, 1H), 6.63 (s, 1H), 6.45-6.14 (m, 3H), 5.91-5.87 (m, 1H), 5.73 (dd, J = 10.0, 1.5 Hz, 1H), 4.38-4.32 (m, 1H), 4.01-3.95 (m, 1H), 3.82 (s, 3H), 3.07-3.02 (m, 2H), 2.77-2.54 (m, 12H), 2.34-2.30 (m, 1H), 2.10-2.07 (m, 2H), 1.94-1.83 (m, 4H), 1.72-1.64 (m, 4H); 693.5 [M + H]⁺ | 1.19 |
| 195 | 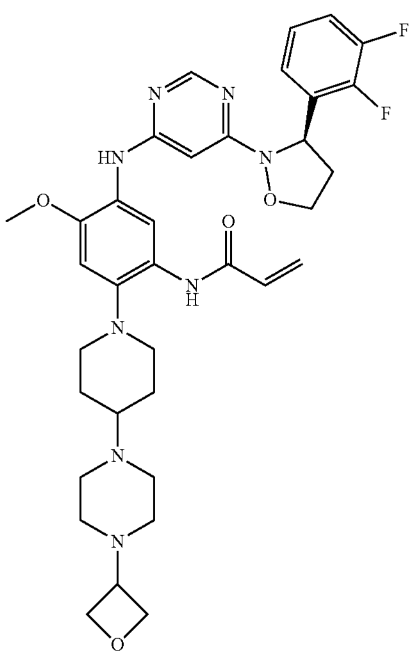 [SMILES: C=CC(=O)Nc1cc(Nc2cc(N3OCC[C@@H]3c3cccc(F)c3F)ncn2)c(OC)cc1N1CCC(N2CCN(C3COC3)CC2)CC1] | N-(5-((6-((R)-3-(2,3-difluorophenyl)isoxazolidine-2-yl)pyrimidine-4-yl)amino)-4-methoxy-2-(4-(4-(oxetane-3-yl)piperazine-1-yl)piperidine-1-yl)phenyl)acrylamide | ¹H NMR (400 MHz, Chloroform-d) δ 8.87 (s, 1H), 8.43 (s, 1H), 8.36 (d, J = 1.0 Hz, 1H), 7.37-7.33 (m, 1H), 7.07-7.02 (m, 2H), 6.94 (s, 1H), 6.76-6.74 (m, 2H), 6.39-6.20 (m, 3H), 5.94-5.91 (m, 1H), 5.75-5.72 (m, 1H), 4.70-4.63 (m, 4H), 4.17-4.04 (m, 3H), 3.85 (s, 3H), 3.55-3.51 (m, 1H), 3.09-3.04 (m, 2H), 2.90-2.70 (m, 7H), 2.42-2.29 (m, 4H), 2.11-2.06 (m, 2H), 1.70-1.67 (m, 2H); 677.5 [M + H]⁺ | 1.24 |

TABLE 1-continued

| Example Compound | Structure | Name of Compound | $^1$H NMR[[:]]; MS [M + H]$^+$ | UPLC r.t. (min) |
|---|---|---|---|---|
| 196 | 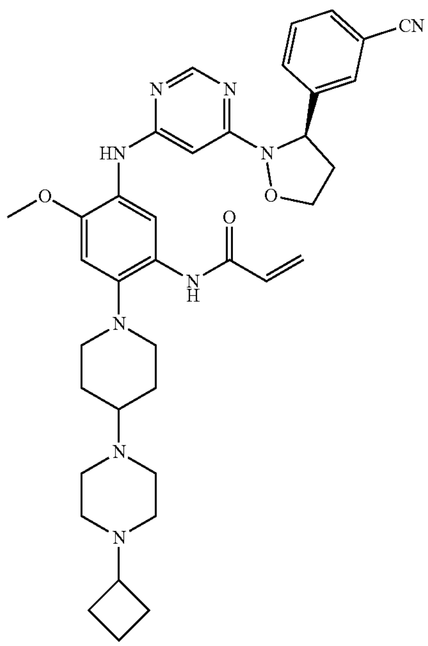 [SMILES: C=CC(=O)Nc1cc(Nc2cc(N3OCC[C@@H]3c3cccc(C#N)c3)ncn2)c(OC)cc1N1CCC(N2CCN(C3CCC3)CC2)CC1] | N-(5-((6-((R)-3-(3-cyanophenyl)isoxazolidine-2-yl)pyrimidine-4-yl)amino)-4-methoxy-2-(4-(4-(oxetane-3-yl)piperazine-1-yl)piperidine-1-yl)phenyl)acrylamide | $^1$H NMR (400 MHz, Chloroform-d) δ 8.87 (s, 1H), 8.45 (s, 1H), 8.36 (d, J = 1.0 Hz, 1H), 7.79 (d, J = 1.9 Hz, 1H), 7.71 (d, J = 7.8 Hz, 1H), 7.56-7.52 (m, 1H), 7.45 (t, J = 7.8 Hz, 1H), 6.94 (s, 1H), 6.76-6.71 (m, 2H), 6.45-6.14 (m, 3H), 5.76-5.70 (m, 2H), 4.70-4.62 (m, 4H), 4.18-4.07 (m, 2H), 3.85 (s, 3H), 3.55-3.46 (m, 2H), 3.09-3.03 (m, 2H), 2.86-2.67 (m, 7H), 2.43-2.31 (m, 4H), 2.10-2.04 (m, 2H), 1.71-1.66 (m, 2H); 666.5 [M + H]$^+$ | 1.10 |
| 197 | 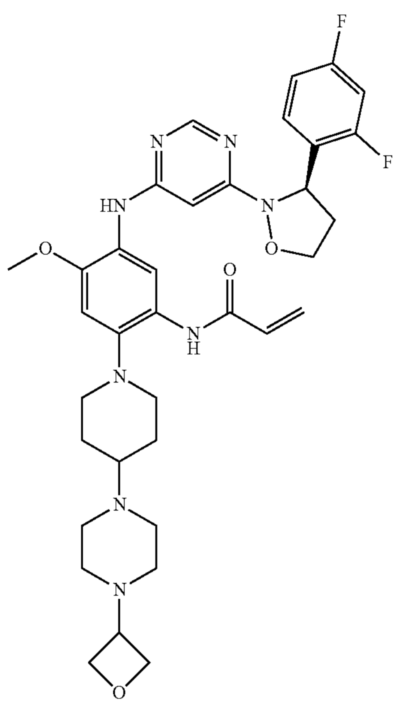 [SMILES: C=CC(=O)Nc1cc(Nc2cc(N3OCC[C@@H]3c3ccc(F)cc3F)ncn2)c(OC)cc1N1CCC(N2CCN(C3COC3)CC2)CC1] | N-(5-((6-((R)-3-(2,4-difluorophenyl)isoxazolidine-2-yl)pyrimidine-4-yl)amino)-4-methoxy-2-(4-(4-(oxetane-3-yl)piperazine-1-yl)piperidine-1-yl)phenyl)acrylamide | $^1$H NMR (400 MHz, Chloroform-d) δ 8.87 (s, 1H), 8.43 (s, 1H), 8.37 (s, 1H), 7.56 (m, 1H), 6.92 (s, 1H), 6.79 (m, 4H), 6.36 (d, J = 16.8 Hz, 1H), 6.26 m, 1H), 5.87 (m, 1H), 5.74 (d, J = 10.3 Hz, 1H), 4.10 (m, 2H), 3.85 (s, 3H), 3.51 (m, 2H), 3.07 (d, J = 11.7 Hz, 2H), 2.87-2.63 (m, 8H), 2.36 (d, J = 67.9 Hz, 6H), 2.11-2.04 (m, 2H), 1.68 (m, 4H); 677.5 [M + H]$^+$ | 1.21 |

TABLE 1-continued

| Example Compound | Structure | Name of Compound | ¹H NMR[:]; MS [M + H]⁺ | UPLC r.t. (min) |
|---|---|---|---|---|
| 198 | 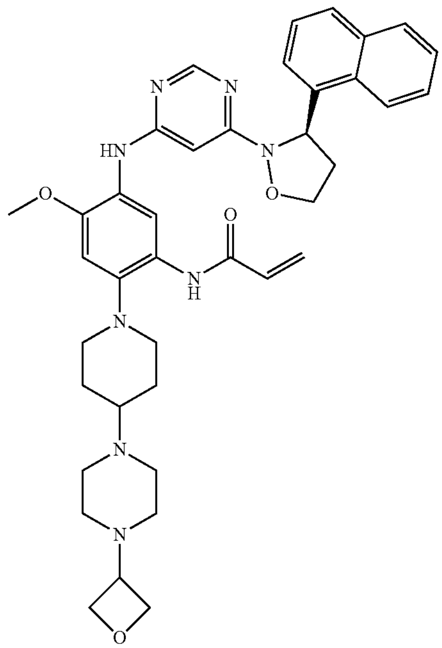 [SMILES: C=CC(=O)Nc1cc(Nc2cc(N3OCC[C@@H]3c3cccc4ccccc34)ncn2)c(OC)cc1N1CCC(N2CCN(C3COC3)CC2)CC1] | N-(4-methoxy-5-((6-((R)-3-(naphthalene-1-yl)isoxazolidine-2-yl)pyrimidine-4-yl)amino)-2-(4-(4-(oxetane-3-yl)piperazine-1-yl)piperidine-1-yl)phenyl)acrylamide | ¹H NMR (400 MHz, Chloroform-d) δ 8.91 (s, 1H), 8.44 (s, 1H), 8.37 (s, 1H), 8.15 (d, J = 8.3 Hz, 1H), 7.88 (d, J = 7.8 Hz, 1H), 7.77 (dd, J = 7.8, 4.7 Hz, 2H), 7.55-7.44 (m, 3H), 6.94 (s, 1H), 6.77 (d, J = 10.4 Hz, 2H), 6.43-6.22 (m, 4H), 5.74 (dd, J = 9.9, 1.6 Hz, 1H), 4.69-4.63 (m, 4H), 4.20-4.14 (m, 2H), 3.85 (s, 3H), 3.55-3.47 (m, 2H), 3.10-3.05 (m, 2H), 2.98-2.94 (m, 1H), 2.78-2.68 (m, 6H), 2.45-2.38 (m, 4H), 2.10-2.05 (m, 2H), 1.70-1.67 (m, 2H); 691.5 [M + H]⁺ | 1.22 |
| 199 | 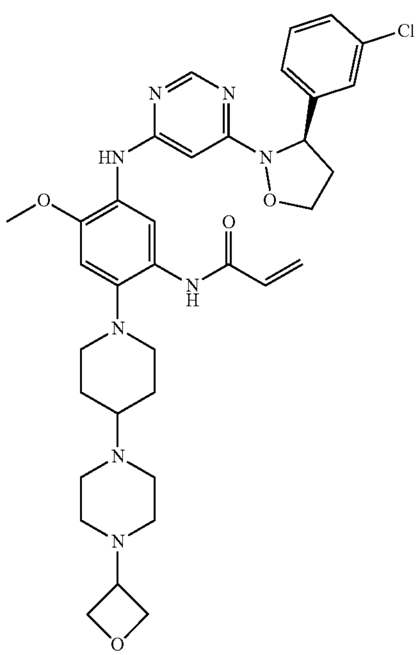 [SMILES: C=CC(=O)Nc1cc(Nc2cc(N3OCC[C@@H]3c3cccc(Cl)c3)ncn2)c(OC)cc1N1CCC(N2CCN(C3COC3)CC2)CC1] | N-(5-((6-((R)-3-(3-chlorophenyl)isoxazolidine-2-yl)pyrimidine-4-yl)amino)-4-methoxy-2-(4-(4-(oxetane-3-yl)piperazine-1-yl)piperidine-1-yl)phenyl)acrylamide | ¹H NMR (400 MHz, DMSO-d₆) δ 9.21 (s, 1H), 9.07 (s, 1H), 8.24 (s, 1H), 8.05 (s, 1H), 7.43 (d, J = 1.9 Hz, 1H), 7.42-7.39 (m, 1H), 7.36 (dd, J = 4.7, 2.5 Hz, 2H), 6.86 (s, 1H), 6.62 (dd, J = 16.9, 10.2 Hz, 1H), 6.28-6.20 (m, 2H), 5.75 (d, J = 10.3 Hz, 1H), 5.53 (dd, J = 8.6, 5.3 Hz, 1H), 4.60 (t, J = 6.6 Hz, 2H), 4.47 (t, J = 6.1 Hz, 2H), 4.22 (td, J = 7.8, 3.9 Hz, 3H), 3.81 (s, 3H), 3.63 (q, J = 6.2 Hz, 2H), 3.32 (s, 2H), 3.17 (t, J = 6.1 Hz, 4H), 3.06-2.93 (m, 2H), 2.85 (dtd, J = 12.0, 7.6, 3.9 Hz, 1H), 2.75 (t, J = 11.7 Hz, 2H), 2.28 (tdd, J = 12.8, 9.7, 5.7 Hz, 2H), 2.10 (d, J = 10.1 Hz, 2H), 1.92 (d, J = 10.1 Hz, 2H), ; 675.5 [M + H]⁺ | 1.24 |

| Example Compound | Structure | Name of Compound | ¹H NMR[[:]]; MS [M + H]⁺ | UPLC r.t. (min) |
|---|---|---|---|---|
| 200 | 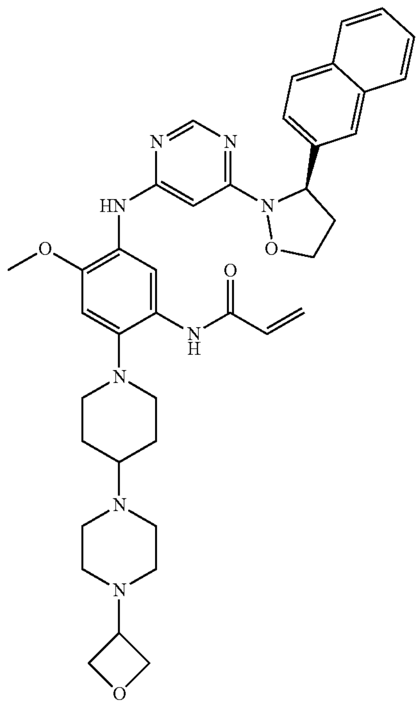 [SMILES: C=CC(=O)Nc1cc(Nc2cc(N3OCC[C@@H]3c3ccc4ccccc4c3)ncn2)c(OC)cc1N1CCC(N2CCN(C3COC3)CC2)CC1] | N-(4-methoxy-5-((6-((R)-3-(naphthalene-2-yl)isoxazolidine-2-yl)pyrimidine-4-yl)amino)-2-(4-(4-(oxetane-3-yl)piperazine-1-yl)piperidine-1-yl)phenyl)acrylamide | ¹H NMR (400 MHz, DMSO-d₆) δ 9.07 (d, J = 3.3 Hz, 1H), 8.24 (d, J = 6.6 Hz, 1H), 8.04 (d, J = 8.3 Hz, 1H), 7.97-7.88 (m, 4H), 7.52 (qt, J = 7.5, 3.4 Hz, 3H), 6.85 (s, 1H), 6.68-6.58 (m, 1H), 6.28-6.18 (m, 2H), 5.79-5.63 (m, 2H), 4.60 (t, J = 6.6 Hz, 2H), 4.47 (dt, J = 9.5, 4.7 Hz, 2H), 4.33-4.24 (m, 2H), 3.99 (dd, J = 16.2, 7.9 Hz, 4H), 3.79 (s, 3H), 3.65-3.58 (m, 2H), 3.32 (s, 2H), 3.16 (d, J = 4.6 Hz, 4H), 3.00-2.91 (m, 1H), 2.75 (t, J = 11.8 Hz, 2H), 2.43-2.30 (m, 2H), 2.12 (dd, J = 17.1, 7.3 Hz, 2H), 1.92 (d, J = 10.5 Hz, 2H), ; 691.5 [M + H]⁺ | 1.23 |
| 201 | 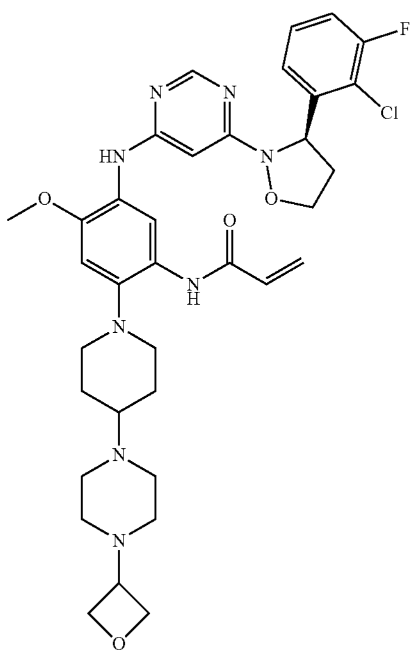 [SMILES: C=CC(=O)Nc1cc(Nc2cc(N3OCC[C@@H]3c3cccc(F)c3Cl)ncn2)c(OC)cc1N1CCC(N2CCN(C3COC3)CC2)CC1] | N-(5-((6-((R)-3-(2-chloro-3-fluorophenyl)isoxazolidine-2-yl)pyrimidine-4-yl)amino)-4-methoxy-2-(4-(4-(oxetane-3-yl)piperazine-1-yl)piperidine-1-yl)phenyl)acrylamide | ¹H NMR (400 MHz, DMSO-d₆) δ 9.06 (s, 1H), 8.22 (s, 1H), 8.07 (s, 1H), 7.45-7.31 (m, 3H), 6.86 (s, 1H), 6.62 (dd, J = 17.0, 10.2 Hz, 1H), 6.34-6.17 (m, 2H), 5.83-5.71 (m, 2H), 4.60 (t, J = 6.6 Hz, 2H), 4.47 (t, J = 6.1 Hz, 2H), 4.21 (td, J = 7.8, 3.9 Hz, 2H), 3.97-3.95 (m, 4H), 3.81 (s, 3H), 3.62 (p, J = 6.4 Hz, 2H), 3.44 (q, J = 7.0 Hz, 1H), 3.32 (t, J = 12.1 Hz, 1H), 3.21-3.11 (m, 3H), 2.96 (tq, J = 8.1, 3.9 Hz, 2H), 2.75 (t, J = 11.9 Hz, 2H), 2.32 (s, 1H), 2.14 (ddd, J = 12.3, 8.1, 4.5 Hz, 3H), 1.98-1.86 (m, 2H), ; 693.5 [M + H]⁺ | 1.25 |

TABLE 1-continued

| Example Compound | Structure | Name of Compound | ¹H NMR[:]; MS [M + H]⁺ | UPLC r.t. (min) |
|---|---|---|---|---|
| 202 | 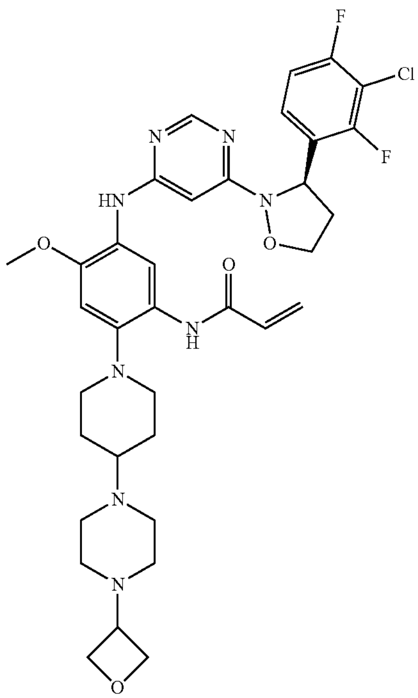 [SMILES: C=CC(=O)Nc1cc(Nc2cc(N3OCC[C@@H]3c3ccc(F)c(Cl)c3F)ncn2)c(OC)cc1N1CCC(N2CCN(C3COC3)CC2)CC1] | N-(5-((6-((R)-3-(3-chloro-2,4-difluorophenyl)isoxazolidine-2-yl)pyrimidine-4-yl)amino)-4-methoxy-2-(4-(4-(oxetane-3-yl)piperazine-1-yl)piperidine-1-yl)phenyl)acrylamide | ¹H NMR (400 MHz, DMSO-$d_6$) δ 9.05 (s, 1H), 8.21 (s, 1H), 8.10 (s, 1H), 7.47 (td, J = 8.6, 6.2 Hz, 1H), 7.32 (td, J = 8.8, 1.7 Hz, 1H), 6.85 (s, 1H), 6.61 (dd, J = 17.0, 10.2 Hz, 1H), 6.33 (s, 1H), 6.23 (dd, J = 17.0, 1.9 Hz, 1H), 5.77-5.66 (m, 2H), 4.60 (t, J = 6.6 Hz, 2H), 4.46 (t, J = 6.1 Hz, 2H), 4.22 (td, J = 7.8, 3.7 Hz, 1H), 3.91 (q, J = 8.2 Hz, 3H), 3.81 (s, 3H), 3.44 (d, J = 7.0 Hz, 1H), 3.31 (s, 2H), 3.17 (d, J = 11.7 Hz, 4H), 2.99 (s, 2H), 2.84 (qd, J = 8.2, 3.9 Hz, 1H), 2.73 (q, J = 18.0, 15.1 Hz, 2H), 2.34-2.19 (m, 3H), 2.11 (t, J = 10.0 Hz, 2H), 1.90 (dd, J = 15.0, 9.0 Hz, 2H), ; 711.4 [M + H]⁺ | 1.33 |
| 203 | 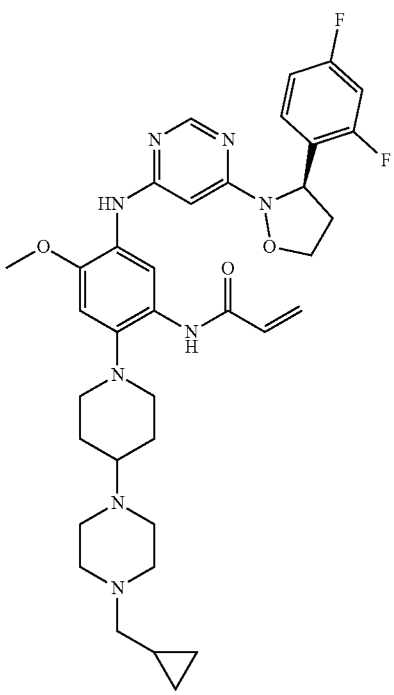 [SMILES: C=CC(=O)Nc1cc(Nc2cc(N3OCC[C@@H]3c3ccc(F)cc3F)ncn2)c(OC)cc1N1CCC(N2CCN(CC3CC3)CC2)CC1] | N-(2-(4-(4-(cyclopropylmethyl)piperazine-1-yl)piperidine-1-yl)-5-((6-((R)-3-(2,4-difluorophenyl)isoxazolidine-2-yl)pyrimidine-4-yl)amino)-4-methoxyphenyl)acrylamide | ¹H NMR (400 MHz, Chloroform-d) δ 8.87 (s, 1H), 8.45 (s, 1H), 8.36 (s, 1H), 7.56 (q, J = 8.2 Hz, 1H), 6.93 (s, 1H), 6.82 (td, J = 12.6, 11.4, 7.9 Hz, 2H), 6.75 (d, J = 3.0 Hz, 2H), 6.39-6.32 (m, 1H), 6.24 (dd, J = 17.0, 10.0 Hz, 1H), 5.87 (dd, J = 8.6, 4.3 Hz, 1H), 5.73 (dd, J = 10.0, 1.6 Hz, 1H), 4.14-4.06 (m, 2H), 3.85 (s, 3H), 3.06 (d, J = 11.3 Hz, 2H), 2.83-2.65 (m, 8H), 2.35-2.26 (m, 4H), 2.09 (d, J = 12.8 Hz, 2H), 0.90-0.82 (m, 6H), 0.53 (d, J = 7.7 Hz, 2H), 0.13 (d, J = 5.0 Hz, 2H), ; 675.5 [M + H]⁺ | 1.18 |

TABLE 1-continued

| Example Compound | Structure | Name of Compound | ¹H NMR[[:]]; MS [M + H]⁺ | UPLC r.t. (min) |
|---|---|---|---|---|
| 204 | 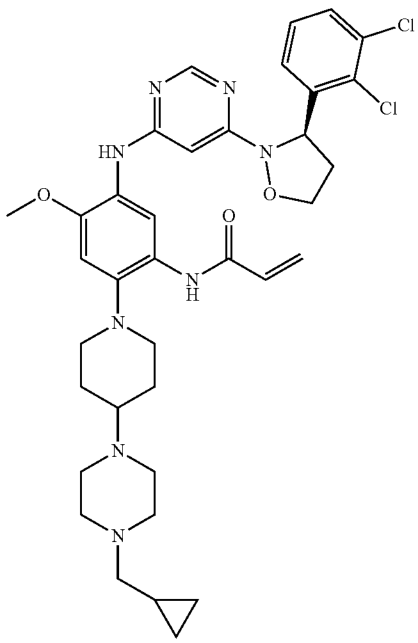 [SMILES: C=CC(=O)Nc1cc(Nc2cc(N3OCC[C@@H]3c3cccc(Cl)c3Cl)ncn2)c(OC)cc1N1CCC(N2CCN(CC3CC3)CC2)CC1] | N-(2-(4-(4-(cyclopropylmethyl)piperazine-1-yl)piperidine-1-yl)-5-((6-((R)-3-(2,3-dichlorophenyl)isoxazolidine-2-yl)pyrimidine-4-yl)amino)-4-methoxyphenyl)acrylamide | ¹H NMR (400 MHz, Chloroform-d) δ 8.87 (s, 1H), 8.42 (s, 1H), 8.36 (d, J = 1.0 Hz, 1H), 7.60 (dd, J = 7.9, 1.6 Hz, 1H), 7.37 (dd, J = 8.0, 1.6 Hz, 1H), 7.19 (t, J = 7.9 Hz, 1H), 6.93 (s, 1H), 6.75 (s, 2H), 6.40-6.32 (m, 1H), 6.30-6.21 (m, 1H), 5.96 (dd, J = 8.8, 4.4 Hz, 1H), 5.74 (dd, J = 10.0, 1.6 Hz, 1H), 4.15-4.04 (m, 2H), 3.85 (s, 3H), 3.64 (s, 2H), 3.07 (d, J = 10.7 Hz, 4H), 3.00-2.90 (m, 2H), 2.88-2.68 (m, 7H), 2.45-2.30 (m, 3H), 2.27-2.19 (m, 1H), 2.14-2.04 (m, 2H), 0.91-0.80 (m, 1H), 0.60 (s, 2H), 0.20 (s, 2H); 707.4 [M + H]⁺ | 1.31 |
| 205 | 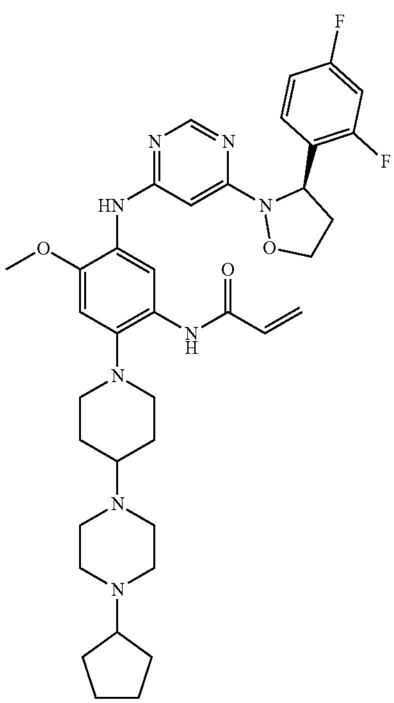 [SMILES: C=CC(=O)Nc1cc(Nc2cc(N3OCC[C@@H]3c3ccc(F)cc3F)ncn2)c(OC)cc1N1CCC(N2CCN(C3CCCC3)CC2)CC1] | N-(2-(4-(4-cyclopentylpiperazine-1-yl)piperidine-1-yl)-5-((6-((R)-3-(2,4-difluorophenyl)isoxazolidine-2-yl)pyrimidine-4-yl)amino)-4-methoxyphenyl)acrylamide | ¹H NMR (400 MHz, Chloroform-d) δ 8.87 (s, 1H), 8.44 (s, 1H), 8.36 (s, 1H), 7.56 (q, J = 8.3 Hz, 1H), 6.93 (s, 1H), 6.87-6.74 (m, 4H), 6.35 (d, J = 17.3 Hz, 1H), 6.24 (dd, J = 17.0, 10.1 Hz, 1H), 5.87 (dd, J = 8.7, 4.3 Hz, 1H), 5.74 (dd, J = 10.2, 1.5 Hz, 1H), 4.14-4.05 (m, 2H), 3.85 (s, 3H), 3.06 (d, J = 11.8 Hz, 4H), 2.87-2.66 (m, 8H), 2.32-2.21 (m, 2H), 2.09 (d, J = 12.4 Hz, 2H), 1.91 (s, 2H), 1.70 (s, 4H), 1.45 (s, 6H), ; 689.5 [M + H]⁺ | 1.22 |

TABLE 1-continued

| Example Compound | Structure | Name of Compound | $^1$H NMR[[:]]; MS [M + H]$^+$ | UPLC r.t. (min) |
|---|---|---|---|---|
| 206 | 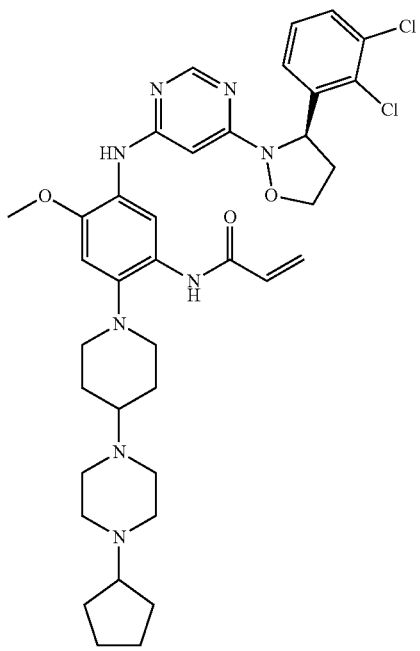 [SMILES: C=CC(=O)Nc1cc(Nc2cc(N3OCC[C@@H]3c3cccc(Cl)c3Cl)ncn2)c(OC)cc1N1CCC(N2CCN(C3CCCC3)CC2)CC1] | N-(2-(4-(4-cyclopentylpiperazine-1-yl)piperidine-1-yl)-5-((6-((R)-3-(2,3-dichlorophenyl)isoxazolidine-2-yl)pyrimidine-4-yl)amino)-4-methoxyphenyl)acrylamide | $^1$H NMR (400 MHz, Chloroform-d) δ 8.85 (s, 1H), 8.39-8.34 (m, 2H), 7.59 (d, J = 7.2 Hz, 1H), 7.37 (d, J = 7.9 Hz, 1H), 7.19 (t, J = 7.9 Hz, 1H), 7.06 (s, 1H), 6.74 (s, 2H), 6.39-6.33 (m, 1H), 6.31-6.21 (m, 1H), 5.96 (dd, J = 8.8, 4.4 Hz, 1H), 5.75 (d, J = 10.1 Hz, 1H), 4.15-4.03 (m, 2H), 3.85 (s, 3H), 3.66 (hept, J = 6.6 Hz, 6H), 3.12-3.05 (m, 10H), 2.79-2.69 (m, 3H), 2.11-1.99 (m, 6H), 1.93-1.81 (m, 3H); 721.5 [M + H]$^+$ | 1.35 |
| 207 | 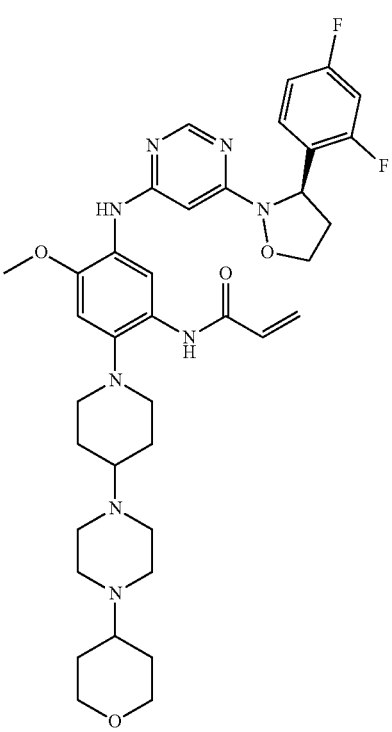 [SMILES: C=CC(=O)Nc1cc(Nc2cc(N3OCC[C@@H]3c3ccc(F)cc3F)ncn2)c(OC)cc1N1CCC(N2CCN(C3CCOCC3)CC2)CC1] | N-(5-((6-((R)-3-(2,4-difluorophenyl)isoxazolidine-2-yl)pyrimidine-4-yl)amino)-4-methoxy-2-(4-(4-(tetrahydro-2H-pyran-4-yl)piperazine-1-yl)piperidine-1-yl)phenyl)acrylamide | $^1$H NMR (400 MHz, Chloroform-d) δ 8.88 (s, 1H), 8.37 (s, 2H), 7.56 (m, 1H), 6.95 (s, 1H), 6.82 (m, 2H), 6.75 (m, 2H), 6.35 (m, 2H), 5.80 (m, 1H), 5.75 (d, J = 11.2 Hz, 1H), 4.08 (s, 4H), 3.85 (s, 3H), 3.40 (m, 5H), 3.31 (s, 2H), 3.08 (m, 4H), 2.79 (m, 7H), 2.30 (s, 4H), 1.44 (d, J = 6.5 Hz, 1H), 1.23-1.13 (m, 3H); 705.5 [M + H]$^+$ | 1.21 |

TABLE 1-continued

| Example Compound | Structure | Name of Compound | ¹H NMR[:]; MS [M + H]⁺ | UPLC r.t. (min) |
|---|---|---|---|---|
| 208 | 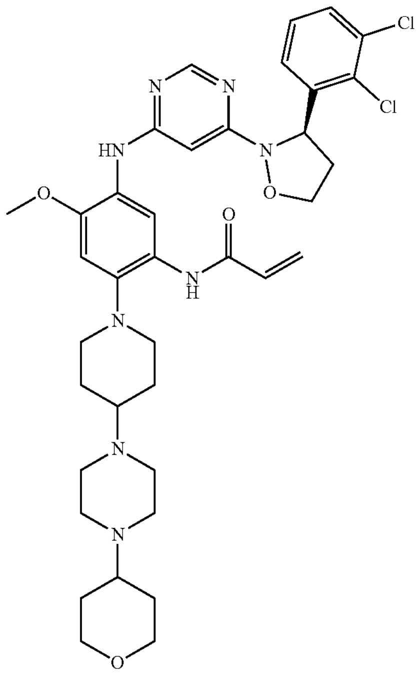 [SMILES: C=CC(=O)Nc1cc(Nc2cc(N3OCC[C@@H]3c3cccc(Cl)c3Cl)ncn2)c(OC)cc1N1CCC(N2CCN(C3CCOCC3)CC2)CC1] | N-(5-((6-((R)-3-(2,3-dichlorophenyl)isoxazolidine-2-yl)pyrimidine-4-yl)amino)-4-methoxy-2-(4-(4-(tetrahydro-2H-pyran-4-yl)piperazine-1-yl)piperidine-1-yl)phenyl)acrylamide | ¹H NMR (400 MHz, Chloroform-d) δ 8.87 (s, 1H), 8.36 (s, 1H), 7.59 (d, J = 7.9 Hz, 1H), 7.37 (d, J = 8.0 Hz, 1H), 7.19 (t, J = 7.9 Hz, 2H), 6.98 (s, 1H), 6.74 (d, J = 8.9 Hz, 2H), 6.49-6.21 (m, 2H), 5.96 (dd, J = 8.7, 4.4 Hz, 1H), 5.74 (d, J = 10.1 Hz, 1H), 4.12-4.03 (m, 3H), 3.85 (s, 3H), 3.40 (t, J = 11.9 Hz, 2H), 3.35-3.27 (m, 2H), 3.15 3.04 (m, 3H), 3.01-2.86 (m, 3H), 2.86-2.67 (m, 6H), 2.27-2.18 (m, 2H), 2.10-2.02 (m, 2H), 1.48-1.42 (m, 4H), 1.39 (d, J = 6.7 Hz, 3H); 737.5 [M + H]⁺ | 1.30 |
| 209 | 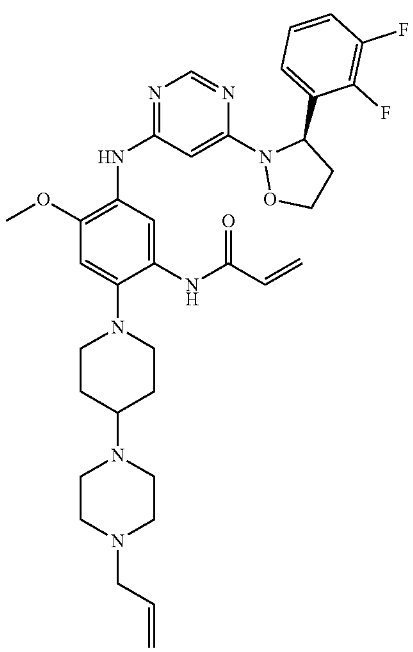 [SMILES: C=CCN1CCN(C2CCN(c3cc(OC)c(Nc4cc(N5OCC[C@@H]5c5cccc(F)c5F)ncn4)cc3NC(=O)C=C)CC2)CC1] | N-(2-(4-(4-allylpiperazine-1-yl)piperidine-1-yl)-5-((6-((R)-3-(2,3-difluorophenyl)isoxazolidine-2-yl)pyrimidine-4-yl)amino)-4-methoxyphenyl)acrylamide | ¹H NMR (400 MHz, DMSO-d₆) δ 8.95 (s, 1H), 8.63 (s, 1H), 8.16 (s, 1H), 7.40-7.26 (m, 2H), 7.25-7.15 (m, 1H), 6.82 (s, 1H), 6.65 (dd, J = 17.0, 10.2 Hz, 1H), 6.35 (s, 1H), 6.20 (dd, J = 16.9, 2.0 Hz, 1H), 5.74 (d, J = 10.1 Hz, 4H), 5.22-5.06 (m, 2H), 3.85 (q, J = 8.0 Hz, 2H), 3.79 (s, 4H), 3.04 (d, J = 11.0 Hz, 3H), 2.92 (d, J = 6.4 Hz, 2H), 2.81 (dtd, J = 12.0, 7.9, 3.7 Hz, 2H), 2.71-2.61 (m, 3H), 2.46-2.29 (m, 4H), 2.22 (dddd, J = 20.8, 12.9, 7.8, 4.3 Hz, 2H), 1.85 (s, 8H), 1.78-1.63 (m, 2H), ; 661.5 [M + H]⁺ | 1.20 |

TABLE 1-continued

| Example Compound | Structure | Name of Compound | ¹H NMR[:]; MS [M + H]⁺ | UPLC r.t. (min) |
|---|---|---|---|---|
| 210 | 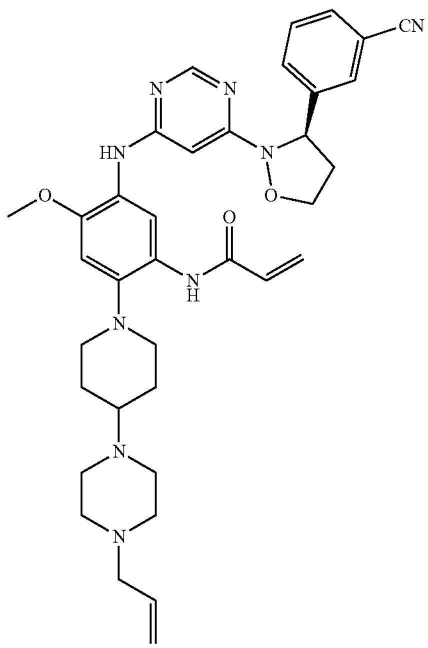 [SMILES: C=CCN1CCN(C2CCN(c3cc(OC)c(Nc4cc(N5OCC[C@@H]5c5cccc(C#N)c5)ncn4)cc3NC(=O)C=C)CC2)CC1] | N-(2-(4-(4-allylpiperazine-1-yl)piperidine-1-yl)-5-((6-((R)-3-(3-cyanophenyl)isoxazolidine-2-yl)pyrimidine-4-yl)amino)-4-methoxyphenyl)acrylamide | 650.5 [M + H]⁺ | 1.11 |
| 211 | 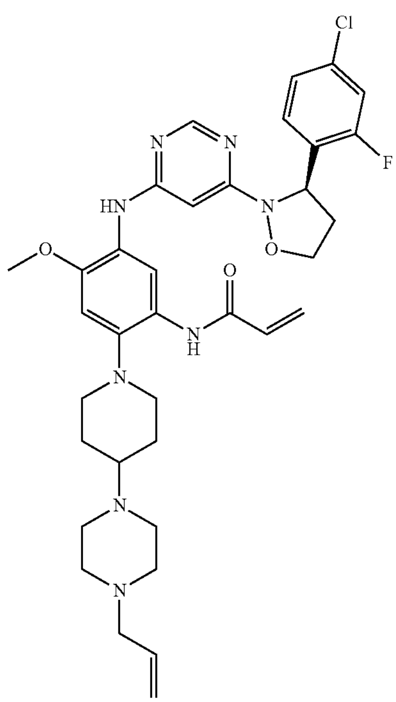 [SMILES: C=CCN1CCN(C2CCN(c3cc(OC)c(Nc4cc(N5OCC[C@@H]5c5ccc(Cl)cc5F)ncn4)cc3NC(=O)C=C)CC2)CC1] | N-(2-(4-(4-allylpiperazine-1-yl)piperidine-1-yl)-5-((6-((R)-3-(4-chloro-2-fluorophenyl)isoxazolidine-2-yl)pyrimidine-4-yl)amino)-4-methoxyphenyl)acrylamide | ¹H NMR (400 MHz, Methanol-d₄) δ 8.35 (s, 1H), 8.17 (d, J = 0.7 Hz, 1H), 7.54 (t, J = 8.2 Hz, 1H), 7.26-7.16 (m, 2H), 6.91 (s, 1H), 6.57 (dd, J = 17.0, 10.3 Hz, 1H), 6.50 (s, 1H), 6.36 (dd, J = 17.0, 1.4 Hz, 1H), 5.97-5.83 (m, 2H), 5.82-5.72 (m, 2H), 5.25 (d, J = 11.0 Hz, 3H), 4.14 (td, J = 7.9, 4.3 Hz, 1H), 4.00 (t, J = 8.0 Hz, 1H), 3.88 (s, 6H), 3.64-3.54 (m, 1H), 3.10 (d, J = 6.9 Hz, 3H), 2.81-2.73 (m, 4H), 2.52 (dd, J = 10.9, 5.7 Hz, 1H), 2.49-2.41 (m, 2H), 2.26 (ddd, J = 20.5, 10.3, 6.5 Hz, 1H), 2.06 (d, J = 11.4 Hz, 2H), 1.77 (tt, J = 11.7, 6.0 Hz, 2H); 677.5 [M + H]⁺ | 1.29 |

TABLE 1-continued

| Example Compound | Structure | Name of Compound | ¹H NMR[[:]]; MS [M + H]⁺ | UPLC r.t. (min) |
|---|---|---|---|---|
| 212 | 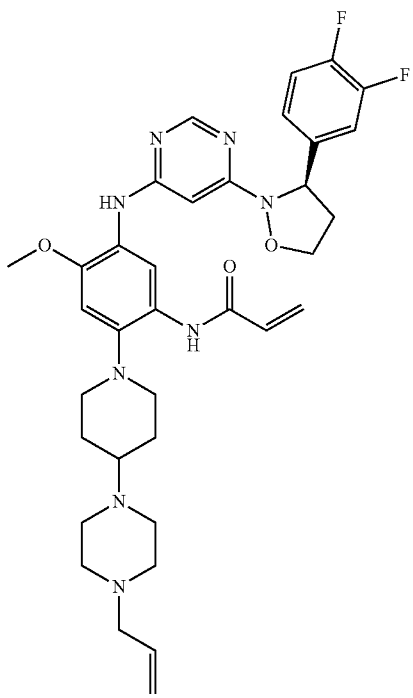 [SMILES: C=CCN1CCN(C2CCN(c3cc(OC)c(Nc4cc(N5OCC[C@@H]5c5ccc(F)c(F)c5)ncn4)cc3NC(=O)C=C)CC2)CC1] | N-(2-(4-(4-allylpiperazine-1-yl)piperidine-1-yl)-5-((6-((R)-3-(3,4-difluorophenyl) isoxazolidine-2-yl)pyrimidine-4-yl)amino)-4-methoxyphenyl) acrylamide | ¹H NMR (400 MHz, Methanol-d₄) δ 8.34 (s, 1H), 8.18 (s, 1H), 7.40-7.32 (m, 1H), 7.27-7.23 (m, 2H), 6.92 (s, 1H), 6.60 (dd, J = 16.9, 10.3 Hz, 1H), 6.47 (s, 1H), 6.39 (s, 1H), 6.34 (d, J = 1.8 Hz, 1H), 6.29 (d, J = 1.8 Hz, 1H), 6.14 (dd, J = 17.3, 10.3 Hz, 2H), 5.99-5.87 (m, 2H), 5.82 (dt, J = 7.6, 2.3 Hz, 2H), 5.55 (dd, J = 8.5, 4.6 Hz, 1H), 5.39 (s, 1H), 4.15 (td, J = 7.9, 4.3 Hz, 1H), 3.98 (q, J = 7.9 Hz, 1H), 3.88 (s, 3H), 3.38-3.34 (m, 2H), 3.18 (s, 4H), 2.98 (d, J = 3.4 Hz, 4H), 2.81 (dt, J = 7.8, 6.2 Hz, 3H), 2.39-2.28 (m, 1H), 2.15 (d, J = 10.9 Hz, 2H), 1.95 (dt, J = 23.4, 11.8 Hz, 3H); 661.5 [M + H]⁺ | 1.18 |
| 213 | 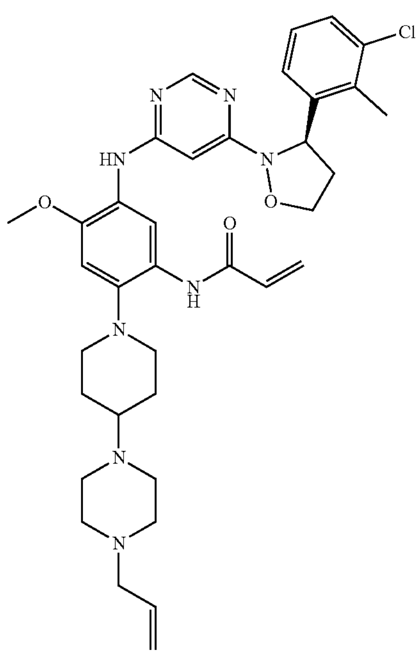 [SMILES: C=CCN1CCN(C2CCN(c3cc(OC)c(Nc4cc(N5OCC[C@@H]5c5cccc(Cl)c5C)ncn4)cc3NC(=O)C=C)CC2)CC1] | N-(2-(4-(4-allylpiperazine-1-yl)piperidine-1-yl)-5-((6-((R)-3-(3-chloro-2-methylphenyl) isoxazolidine-2-yl)pyrimidine-4-yl)amino)-4-methoxyphenyl) acrylamide | ¹H NMR (400 MHz, DMSO-d₆) δ 8.95 (s, 1H), 8.59 (s, 1H), 8.15-8.14 (m, 2H), 7.40 (dd, J = 7.8, 1.3 Hz, 1H), 7.34 (dd, J = 8.0, 1.3 Hz, 1H), 7.21 (d, J = 7.9 Hz, 1H), 6.82 (s, 1H), 6.65 (dd, J = 16.9, 10.2 Hz, 1H), 6.35 (s, 1H), 6.20 (dd, J = 17.0, 2.0 Hz, 1H), 5.87-5.74 (m, 1H), 5.70 (td, J = 8.9, 8.2, 3.4 Hz, 2H), 5.23-5.10 (m, 2H), 4.14 (td, J = 7.9, 3.9 Hz, 1H), 3.79 (s, 3H), 3.09-3.01 (m, 3H), 2.95 (d, J = 6.4 Hz, 3H), 2.83 (dtd, J = 12.1, 8.0, 3.8 Hz, 2H), 2.66 (t, J = 11.6 Hz, 3H), 2.58 (s, 3H), 2.54 (s, 2H), 2.42 (s, 4H), 2.08 (dtd, J = 12.6, 8.1, 5.0 Hz, 2H), 1.91 (s, 4H), 1.85 (d, J = 12.0 Hz, 3H), 1.78-1.65 (m, 3H), ; 673.5 [M + H]⁺ | 1.28 |

TABLE 1-continued

| Example Compound | Structure | Name of Compound | ¹H NMR[[:]]; MS [M + H]⁺ | UPLC r.t. (min) |
|---|---|---|---|---|
| 214 | 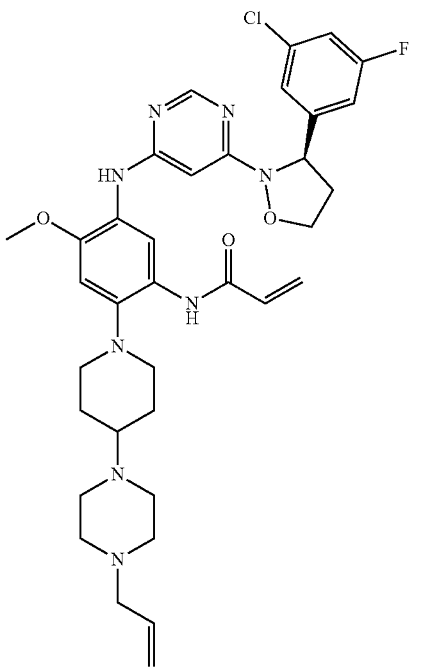 [SMILES: C=CCN1CCN(C2CCN(c3cc(OC)c(Nc4cc(N5OCC[C@@H]5c5cc(F)cc(Cl)c5)ncn4)cc3NC(=O)C=C)CC2)CC1] | N-(2-(4-(4-allylpiperazine-1-yl)piperidine-1-yl)-5-((6-((R)-3-(3-chloro-5-fluorophenyl)isoxazolidine-2-yl)pyrimidine-4-yl)amino)-4-methoxyphenyl)acrylamide | 677.4 [M + H]⁺ | 1.29 |
| 215 | 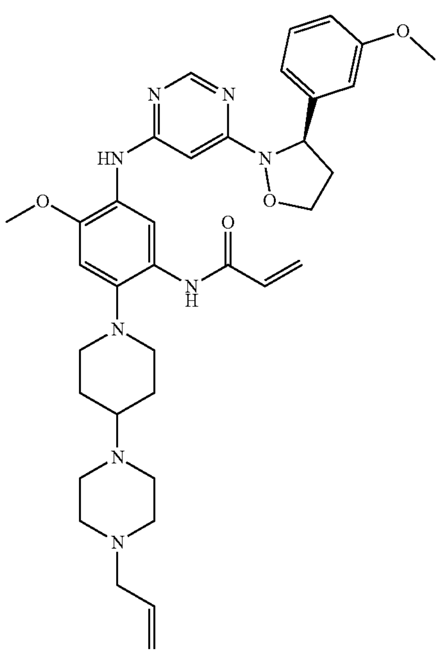 | N-(2-(4-(4-allylpiperazine-1-yl)piperidine-1-yl)-4-methoxy-5-((6-((R)-3-(3-methoxyphenyl)isoxazolidine-2-yl)pyrimidine-4-yl)amino)phenyl)acrylamide | ¹H NMR (400 MHz, Methanol-d₄) δ 8.29 (s, 1H), 8.17 (s, 1H), 7.26 (t, J = 8.2 Hz, 1H), 7.00 (d, J = 6.8 Hz, 2H), 6.91 (s, 1H), 6.83 (dd, J = 8.2, 1.7 Hz, 1H), 6.63 (dd, J = 16.9, 10.3 Hz, 1H), 6.41-6.32 (m, 2H), 5.98-5.88 (m, 1H), 5.81 (d, J = 11.3 Hz, 1H), 5.50 (dd, J = 8.4, 4.8 Hz, 1H), 5.41 (t, J = 14.1 Hz, 2H), 4.19 (td, J = 7.8, 4.5 Hz, 1H), 4.01 (q, J = 7.9 Hz, 1H), 3.86 (s, 3H), 3.80 (s, 3H), 3.18 (s, 2H), 2.87-2.78 (m, 3H), 2.41-2.30 (m, 1H), 2.18 (s, 2H), 1.99 (d, J = 9.8 Hz, 2H); 655.5 [M + H]⁺ | 1.08 |

TABLE 1-continued

| Example Compound | Structure | Name of Compound | ¹H NMR[[:]]; MS [M + H]⁺ | UPLC r.t. (min) |
|---|---|---|---|---|
| 216 | 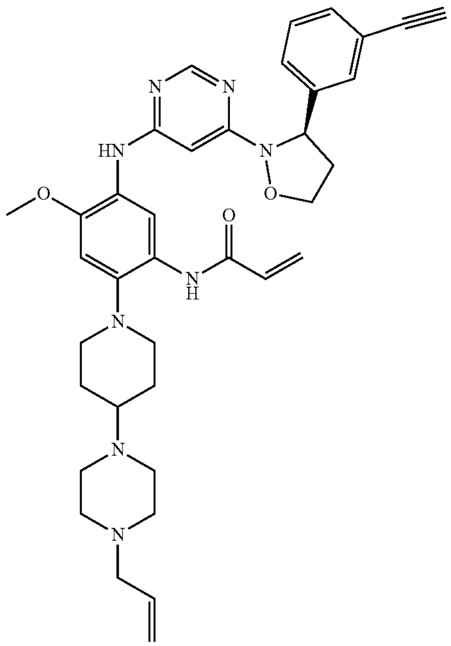 [SMILES: C#Cc1cccc([C@H]2CCON2c2cc(Nc3cc(NC(=O)C=C)c(N4CCC(N5CCN(CC=C)CC5)CC4)cc3OC)ncn2)c1] | N-(2-(4-(4-allylpiperazine-1-yl)piperidine-1-yl)-5-((6-((R)-3-(3-ethynylphenyl)isoxazolidine-2-yl)pyrimidine-4-yl)amino)-4-methoxyphenyl)acrylamide | ¹H NMR (400 MHz, Methanol-d$_4$) δ 8.17 (s, 1H), 8.03 (s, 1H), 7.48 (s, 1H), 7.39 (s, 1H), 6.93 (s, 1H), 6.58 (dd, J = 17.0, 10.2 Hz, 1H), 6.39 (dd, J = 17.0, 1.3 Hz, 1H), 6.09 (s, 1H), 5.94 (dd, J = 17.1, 10.2 Hz, 1H), 5.83 (d, J = 11.3 Hz, 1H), 5.53-5.42 (m, 3H), 4.36 (td, J = 7.6, 4.3 Hz, 1H), 4.13 (dd, J = 15.3, 8.0 Hz, 1H), 3.85 (s, 3H), 3.55 (s, 1H), 3.49 (d, J = 6.5 Hz, 2H), 3.25 (d, J = 11.2 Hz, 4H), 2.90-2.80 (m, 2H), 2.47-2.36 (m, 1H), 2.20-2.11 (m, 2H), 2.01 (s, 2H) 1.95 (d, J = 8.7 Hz, 1H), 1.31 (s, 1H); 649.5 [M + H]⁺ | 1.17 |
| 217 | 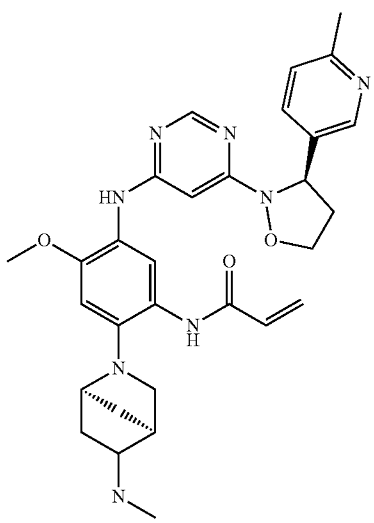 [SMILES: C=CC(=O)Nc1cc(Nc2cc(N3OCC[C@@H]3c3ccc(C)nc3)ncn2)c(OC)cc1N1C[C@@H]2C[C@H]1CC2NC] | N-(2-((1S,4S)-5-ethyl-2,5-diazabicyclo[2.2.1]heptane-2-yl)-4-methoxy-5-((6-((R)-3-(6-methylpyridine-3-yl)isoxazolidine-2-yl)pyrimidine-4-yl)amino)phenyl)acrylamide | ¹H NMR (400 MHz, Chloroform-d) δ 8.58-8.51 (m, 2H), 8.35 (s, 1H), 8.03 (s, 1H), 7.70 (dd, J = 8.1, 2.4 Hz, 1H), 7.13 (d, J = 8.0 Hz, 1H), 6.88 (s, 1H), 6.77 (s, 1H), 6.62 (s, 1H), 6.38 (s, 2H), 5.79-5.61 (m, 2H), 4.22-4.13 (m, 1H), 4.03 (q, J = 7.9 Hz, 1H), 3.91 (t, J = 6.3 Hz, 2H), 3.87 (s, 3H), 3.18-3.11 (m, 1H), 2.92-2.88 (m, 1H), 2.79-2.70 (m, 2H), 2.54 (s, 3H), 2.43-2.24 (m, 2H), 2.01 (s, 2H), 1.47-1.30 (m, 2H), 1.22-1.02 (m, 3H), ; 557.5 [M + H]⁺ | 0.93 |

TABLE 1-continued

| Example Compound | Structure | Name of Compound | ¹H NMR[[:]]; MS [M + H]⁺ | UPLC r.t. (min) |
|---|---|---|---|---|
| 218 | 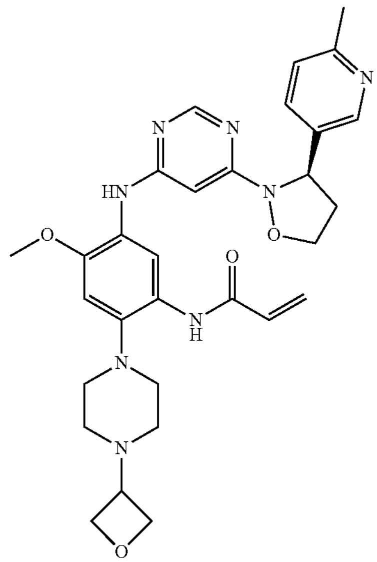 [SMILES: C=CC(=O)Nc1cc(Nc2cc(N3OCC[C@@H]3c3ccc(C)nc3)ncn2)c(OC)cc1N1CCN(C2COC2)CC1] | N-(4-methoxy-5-((6-((R)-3-(6-methylpyridine-3-yl)isoxazolidine-2-yl)pyrimidine-4-yl)amino)-2-(4-(oxetane-3-yl)piperazine-1-yl)phenyl)acrylamide | ¹H NMR (400 MHz, Chloroform-d) δ 8.91 (s, 1H), 8.57 (d, J = 2.4 Hz, 1H), 8.49 (s, 1H), 8.37 (s, 1H), 7.70 (dd, J = 8.1, 2.4 Hz, 1H), 7.13 (d, J = 8.0 Hz, 1H), 7.00 (s, 1H), 6.81 (s, 1H), 6.72 (s, 1H), 6.36 (dd, J = 16.9, 1.6 Hz, 1H), 6.25 (dd, J = 17.0, 10.0 Hz, 1H), 5.74 (dd, J = 10.0, 1.5 Hz, 1H), 5.72-5.69 (m, 1H), 4.69 (dt, J = 21.2, 6.3 Hz, 4H), 4.20-4.06 (m, 2H), 3.84 (s, 3H), 3.61 (p, J = 6.4 Hz, 1H), 2.95 (dt, J = 4.6, 2.7 Hz, 4H), 2.84-2.73 (m, 2H), 2.54 (s, 6H), 2.37 (dp, J = 11.8, 3.9, 3.5 Hz, 1H), ; 573.4 [M + H]⁺ | 0.99 |
| 219 | 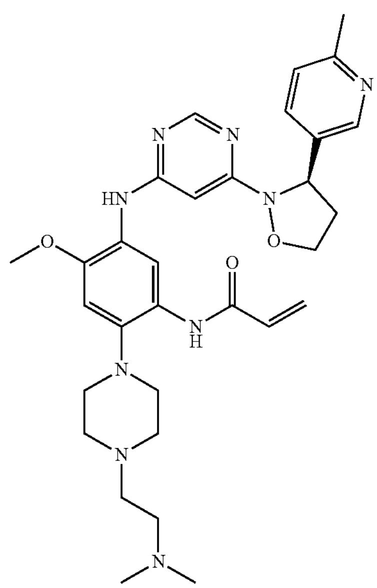 [SMILES: C=CC(=O)Nc1cc(Nc2cc(N3OCC[C@@H]3c3ccc(C)nc3)ncn2)c(OC)cc1N1CCN(CCN(C)C)CC1] | N-(2-(4-(2-(dimethylamino)ethyl)piperazine-1-yl)-4-methoxy-5-((6-((R)-3-(6-methylpyridine-3-yl)isoxazolidine-2-yl)pyrimidine-4-yl)amino)phenyl)acrylamide | ¹H NMR (400 MHz, Chloroform-d) δ 8.89 (s, 1H), 8.57 (d, J = 2.3 Hz, 1H), 8.52 (s, 1H), 8.36 (s, 1H), 7.70 (dd, J = 8.0, 2.4 Hz, 1H), 7.13 (d, J = 8.0 Hz, 1H), 6.99 (s, 1H), 6.80 (s, 1H), 6.71 (s, 1H), 6.36 (dd, J = 16.9, 1.7 Hz, 1H), 6.26-6.23 (m, 1H), 5.75 (dd, J = 9.8, 1.7 Hz, 1H), 5.71-5.69 (m, 1H), 4.20-4.04 (m, 2H), 3.84 (s, 3H), 3.67-3.63 (m, 1H), 2.96-2.91 (m, 4H), 2.80-2.70 (m, 8H), 2.53-2.52 (m, 8H), 2.36 (dq, J = 11.8, 3.6 Hz, 2H), ; 588.5 [M + H]⁺ | 0.96 |

| Example Compound | Structure | Name of Compound | $^1$H NMR[[:]]; MS [M + H]$^+$ | UPLC r.t. (min) |
|---|---|---|---|---|
| 220 | 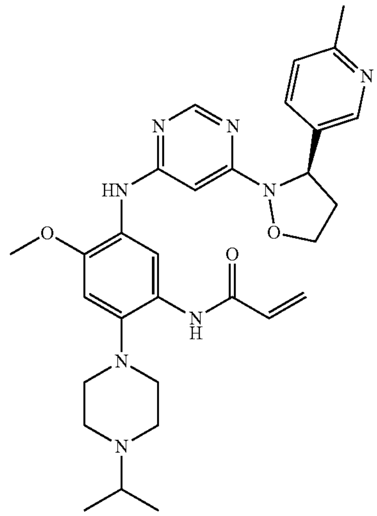 | N-(2-(4-isopropylpiperazine-1-yl)-4-methoxy-5-((6-((R)-3-(6-methylpyridine-3-yl)isoxazolidine-2-yl)pyrimidine-4-yl)amino)phenyl) acrylamide | $^1$H NMR (400 MHz, DMSO-d$_6$) δ 11.09 (s, 1H), 9.36 (s, 1H), 9.27 (s, 1H), 8.75 (d, J = 2.1 Hz, 1H), 8.46 (dd, J = 8.3, 2.1 Hz, 1H), 8.28 (s, 1H), 8.11 (s, 1H), 7.92 (d, J = 8.4 Hz, 1H), 6.82 (s, 1H), 6.40-6.14 (m, 2H), 5.78-5.68 (m, 2H), 4.29 (q, J = 7.0, 6.4 Hz, 2H), 4.03 (q, J = 7.8 Hz, 2H), 3.84 (s, 3H), 3.60 (dd, J = 6.6, 2.7 Hz, 1H), 3.57 (s, 3H), 3.41 (s, 3H), 3.34 (d, J = 11.7 Hz, 2H), 3.25-3.16 (m, 2H), 3.11 (tt, J = 7.3, 3.7 Hz, 2H), 2.92 (dq, J = 11.9, 7.5, 6.0 Hz, 1H), 2.75 (s, 3H), 2.40 (td, J = 13.0, 7.8 Hz, 1H), ; 589.5 [M + H]$^+$ | 1.03 |
| 221 | 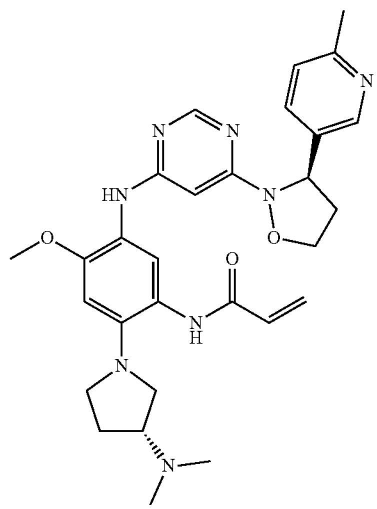 [SMILES: C=CC(=O)Nc1cc(Nc2cc(N3OCC[C@@H]3c3ccc(C)nc3)ncn2)c(OC)cc1N1CC[C@@H](N(C)C)C1] | N-(2-((R)-3-(dimethylamino)pyrolidine-1-yl)-4-methoxy-5-((6-((R)-3-(6-methylpyridine-3-yl)isoxazolidine-2-yl)pyrimidine-4-yl)amino)phenyl) acrylamide | $^1$H NMR (400 MHz, DMSO-d$_6$) δ 11.27 (s, 1H), 9.98 (s, 1H), 9.66 (s, 1H), 8.76 (d, J = 2.1 Hz, 1H), 8.46 (d, J = 8.4 Hz, 1H), 8.30 (s, 1H), 7.93 (d, J = 8.3 Hz, 1H), 7.59 (s, 1H), 6.88 (dd, J = 17.2, 10.1 Hz, 1H), 6.69 (s, 1H), 6.21 (dd, J = 17.1, 2.1 Hz, 1H), 5.72 (td, J = 11.9, 10.1, 4.7 Hz, 2H), 4.31 (s, 1H), 4.07-4.02 (m, 3H), 3.88 (t, J = 6.1 Hz, 3H), 3.82 (s, 3H), 3.63 (d, J = 10.4 Hz, 3H), 3.57 (s, 2H), 3.51 (s, 1H), 3.43-3.36 (m, 1H), 3.17 (s, 1H), 3.06 (q, J = 8.2 Hz, 1H), 2.96 (d, J = 6.4 Hz, 1H), 2.80 (d, J = 2.8 Hz, 3H), 2.76 (s, 1H), 2.30 (s, 1H), ; 545.5 [M + H]$^+$ | 0.92 |
| 222 | 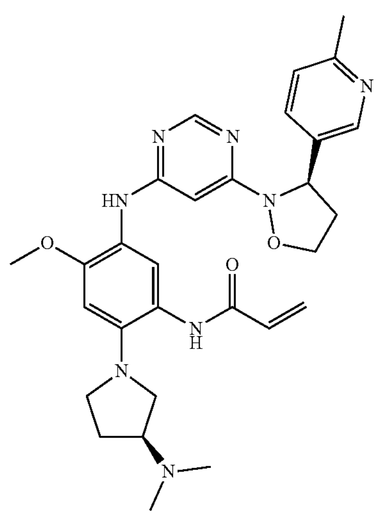 [SMILES: C=CC(=O)Nc1cc(Nc2cc(N3OCC[C@@H]3c3ccc(C)nc3)ncn2)c(OC)cc1N1CC[C@H](N(C)C)C1] | N-(2-((S)-3-(dimethylamino)pyrolidine-1-yl)-4-methoxy-5-((6-((R)-3-(6-methylpyridine-3-yl)isoxazolidine-2-yl)pyrimidine-4-yl)amino)phenyl) acrylamide | $^1$H NMR (400 MHz, DMSO-d$_6$) δ 11.18 (s, 1H), 9.61 (s, 1H), 8.75 (d, J = 2.1 Hz, 1H), 8.44 (d, J = 8.5 Hz, 1H), 8.27 (s, 1H), 7.91 (d, J = 8.4 Hz, 1H), 7.65 (s, 1H), 6.94-6.81 (m, 1H), 6.69 (s, 1H), 6.21 (dd, J = 17.1. 2.1 Hz, 2H), 5.77-5.68 (m, 2H), 4.28 (d, J = 6.2 Hz, 1H), 4.06-4.00 (m, 1H), 3.88 (d, J = 5.8 Hz, 1H), 3.82 (d, J = 3.2 Hz, 3H), 3.57 (s, 3H), 3.09 (s, 1H), 3.05-2.98 (m, 3H), 2.80 (dd, J = 8.0, 4.7 Hz, 5H), 2.74 (s, 3H), 2.30 (dq, J = 13.1, 6.3, 5.3 Hz, 2H), ; 545.5 [M + H]$^+$ | 0.93 |

TABLE 1-continued

| Example Compound | Structure | Name of Compound | ¹H NMR[[:]]; MS [M + H]⁺ | UPLC r.t. (min) |
|---|---|---|---|---|
| 223 | 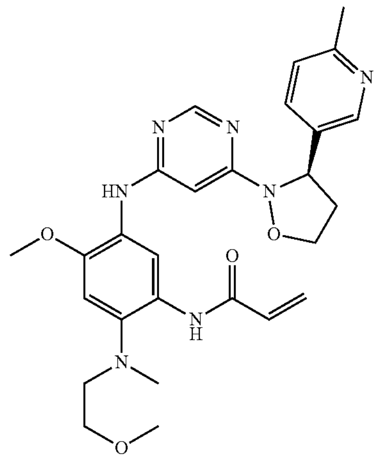 [SMILES: C=CC(=O)Nc1cc(Nc2cc(N3OCC[C@@H]3c3ccc(C)nc3)ncn2)c(OC)cc1N(C)CCOC] | N-(4-methoxy-2-((2-methoxyethyl)(methyl)amino)-5-((6-((R)-3-(6-methylpyridine-3-yl)isoxazolidine-2-yl)pyrimidine-4-yl)amino)phenyl)acrylamide | ¹H NMR (400 MHz, DMSO-d₆) δ 9.67 (s, 2H), 8.76 (d, J = 2.1 Hz, 1H), 8.48 (d, J = 8.7 Hz, 1H), 8.32 (d, J = 7.4 Hz, 2H), 7.93 (d, J = 8.7 Hz, 1H), 7.17 (s, 1H), 6.48 (s, 2H), 6.25 (d, J = 16.8 Hz, 1H), 5.82-5.71 (m, 2H), 4.32-4.24 (m, 2H), 4.04 (d, J = 8.7 Hz, 2H), 3.86 (s, 3H), 3.57 (s, 1H), 3.47 (s, 2H), 3.28 (s, 3H), 2.93 (s, 3H), 2.76 (s, 3H), 2.44-2.37 (m, 1H), ; 520.5 [M + H]⁺ | 1.23 |
| 224 | 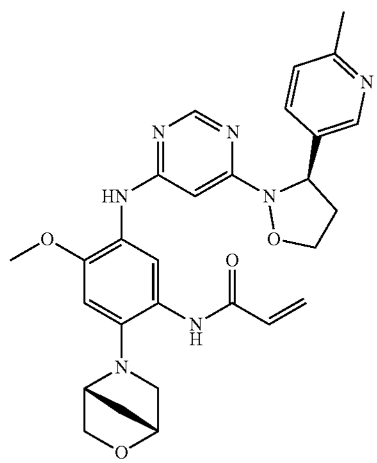 [SMILES: C=CC(=O)Nc1cc(Nc2cc(N3OCC[C@@H]3c3ccc(C)nc3)ncn2)c(OC)cc1N1C[C@H]2C[C@@H]1CO2] | N-(2-((1R,4R)-2-oxa-5-azabicyclo[2.2.1]heptane-5-yl)-4-methoxy-5-((6-((R)-3-(6-methylpyridine-3-yl)isoxazolidine-2-yl)pyrimidine-4-yl)amino)phenyl)acrylamide | ¹H NMR (400 MHz, DMSO-d₆) δ 9.64 (s, 1H), 9.36 (d, J = 24.6 Hz, 1H), 8.75 (d, J = 2.2 Hz, 1H), 8.43 (d, J = 8.4 Hz, 1H), 8.26 (d, J = 2.4 Hz, 1H), 7.90 (d, J = 8.4 Hz, 1H), 7.16 (d, J = 47.7 Hz, 1H), 6.47 (d, J = 11.2 Hz, 1H), 6.19 (dd, J = 17.1, 2.1 Hz, 1H), 5.78-5.66 (m, 2H), 4.60-4.45 (m, 2H), 4.29 (td, J = 7.6, 4.0 Hz, 1H), 4.04 (t, J = 7.8 Hz, 1H), 3.95 (dd, J = 7.8, 2.6 Hz, 1H), 3.86 (t, J = 6.3 Hz, 2H), 3.80 (d, J = 4.2 Hz, 3H), 3.57 (s, 2H), 2.96-2.92 (m, 1H), 2.79 (t, J = 6.1 Hz, 1H), 2.73 (s, 3H), 2.44-2.37 (m, 1H), 1.85 (q, J = 9.8 Hz, 2H), ; 530.4 [M + H]⁺ | 1.08 |
| 225 | 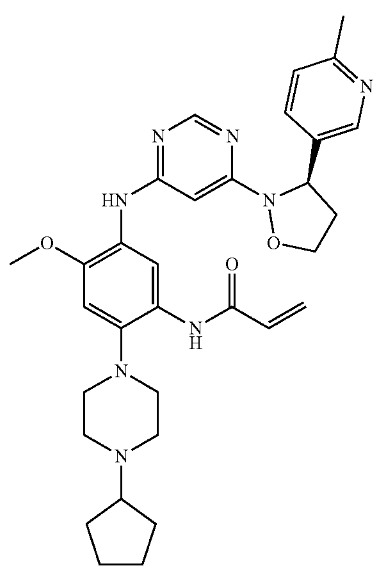 [SMILES: C=CC(=O)Nc1cc(Nc2cc(N3OCC[C@@H]3c3ccc(C)nc3)ncn2)c(OC)cc1N1CCN(C2CCCC2)CC1] | N-(2-(4-cyclopentylpiperazine-1-yl)-4-methoxy-5-((6-((R)-3-(6-methylpyridine-3-yl)isoxazolidine-2-yl)pyrimidine-4-yl)amino)phenyl)acrylamide | ¹H NMR (400 MHz, Chloroform-d) δ 8.91 (s, 1H), 8.59-8.57 (s, 2H), 8.37 (s, 1H), 7.70 (dd, J = 8.1, 2.4 Hz, 1H), 7.13 (d, J = 8.0 Hz, 1H), 6.95 (s, 1H), 6.83 (s, 1H), 6.72 (s, 1H), 6.36 (dd, J = 16.9, 1.6 Hz, 1H), 6.30-6.23 (m, 1H), 5.77-5.73 (m, 1H), 5.73-5.69 (m, 1H), 4.20-4.05 (m, 2H), 3.82 (s, 3H), 2.94 (t, J = 5.0 Hz, 4H), 2.80-2.72 (m, 3H), 2.63-2.60 (m, 2H), 2.54 (s, 3H), 2.40-2.32 (m, 1H), 2.18 (d, J = 7.7 Hz, 1H), 1.97-1.89 (m, 2H), 1.78-1.71 (m, 2H), 1.65-1.58 (m, 2H), 1.50-1.42 (m, 2H), ; 585.6 [M + H]⁺ | 0.89 |

TABLE 1-continued

| Example Compound | Structure | Name of Compound | ¹H NMR[:]; MS [M + H]⁺ | UPLC r.t. (min) |
|---|---|---|---|---|
| 226 | 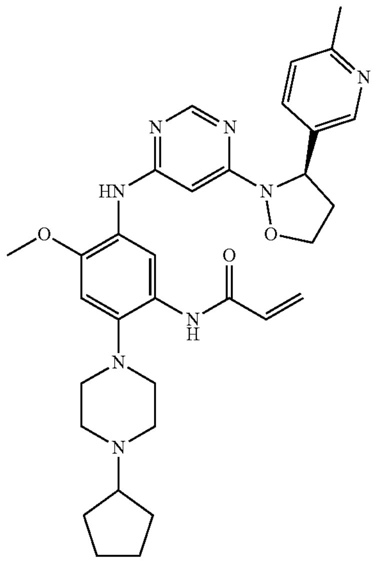 | N-(2-(4-cyclopentylpiperazine-1-yl)-4-methoxy-5-((6-((R)-3-(6-methylpyridine-3-yl)isoxazolidine-2-yl)pyrimidine-4-yl)amino)phenyl) acrylamide | ¹H NMR (400 MHz, Chloroform-d) δ 8.87 (s, 1H), 8.57 (d, J = 2.3 Hz, 1H), 8.47 (s, 1H), 8.36 (s, 1H), 7.70 (dd, J = 8.1, 2.4 Hz, 1H), 7.13 (d, J = 8.0 Hz, 1H), 6.92 (s, 1H), 6.75 (s, 1H), 6.72 (s, 1H), 6.40-6.31 (m, 1H), 6.26 (dd, J = 16.9, 9.9 Hz, 1H), 5.77-5.73 (m, 1H), 5.73-5.69 (m, 1H), 4.21-4.06 (m, 2H), 3.84 (s, 3H), 3.27-3.15 (m, 4H), 3.05 (d, J = 11.5 Hz, 2H), 2.82-2.62 (m, 6H), 2.48-2.42 (m, 3H), 2.37 (s, 3H), 2.29 (s, 3H), 2.27 (s, 6H), ; 616.6 [M + H]⁺ | 0.46 |
| 227 | 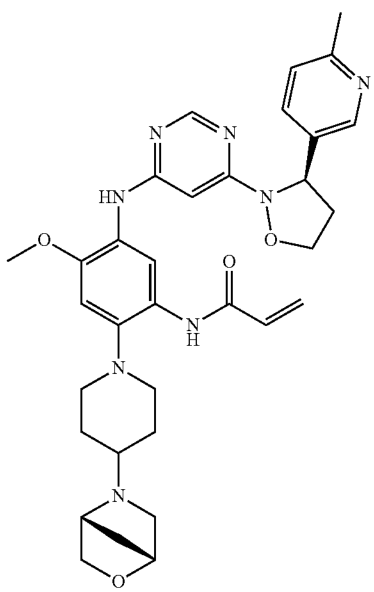 [SMILES: C=CC(=O)Nc1cc(Nc2cc(N3OCC[C@@H]3c3ccc(C)nc3)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-4-methoxy-5-((6-((R)-3-(6-methylpyridine-3-yl)isoxazolidine-2-yl)pyrimidine-4-yl)amino)phenyl) acrylamide | ¹H NMR (400 MHz, Chloroform-d) δ 8.87 (s, 1H), 8.57 (d, J = 2.4 Hz, 1H), 8.48 (s, 1H), 8.36 (s, 1H), 7.70 (dd, J = 8.1, 2.4 Hz, 1H), 7.13 (d, J = 8.0 Hz, 1H), 6.94 (s, 1H), 6.76 (s, 1H), 6.72 (s, 1H), 6.35 (dd, J = 17.0, 1.5 Hz, 1H), 6.24 (dd, J = 16.9, 10.0 Hz, 1H), 5.72 (m, 2H), 4.21-4.04 (m, 3H), 3.85 (s, 3H), 3.78 (s, 1H), 3.67 (dd, J = 8.0, 1.6 Hz, 1H), 3.20-3.13 (m, 1H), 3.03 (d, J = 11.7 Hz, 2H), 2.83-2.71 (m, 3H), 2.54 (m, 5H), 2.36 (m, 1H), 2.10-1.91 (m, 4H), 1.83 (d, J = 9.8 Hz, 1H), 1.68 (m, 2H), ; 613.6 [M + H]⁺ | 0.75 |

TABLE 1-continued

| Example Compound | Structure | Name of Compound | ¹H NMR[:]; MS [M + H]⁺ | UPLC r.t. (min) |
|---|---|---|---|---|
| 228 | 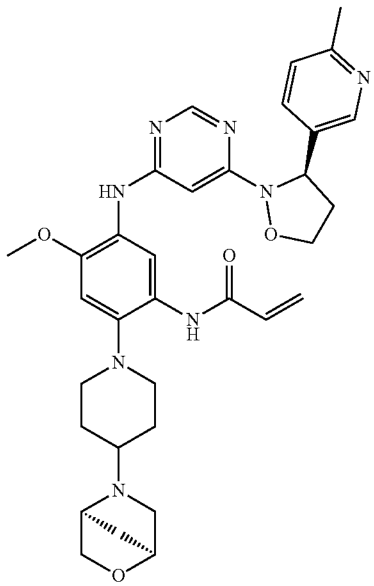 [SMILES: C=CC(=O)Nc1cc(Nc2cc(N3OCC[C@@H]3c3ccc(C)nc3)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-4-methoxy-5-((6-((R)-3-(6-methylpyridine-3-yl)isoxazolidine | ¹H NMR (400 MHz, Chloroform-d) δ 8.87 (s, 1H), 8.57 (d, J = 2.3 Hz, 1H), 8.48 (s, 1H), 8.36 (s, 1H), 7.70 (dd, J = 8.1, 2.4 Hz, 1H), 7.13 (d, J = 8.0 Hz, 1H), 6.96 (s, 1H), 6.76 (s, 1H), 6.72 (s, 1H), 6.44-6.32 (m, 1H), 6.24 (dd, J = 17.0, 10.0 Hz, 1H), 5.81-5.68 (m, 2H), 4.20-4.07 (m, 3H), 3.85 (s, 3H), 3.78 (m, 1H), 3.67 (dd, J = 7.9, 1.7 Hz, 1H), 3.15 (d, J = 9.8 Hz, 1H), 3.03 (m, 2H), 2.76 (m, 3H), 2.63-2.48 (m, 5H), 2.35 (m, 1H), 2.08-1.90 (m, 4H), 1.83 (d, J = 9.5 Hz, 1H), 1.68 (t, J = 11.1 Hz, 2H), ; 613.6 [M + H]⁺ | 0.81 |
| 229 | 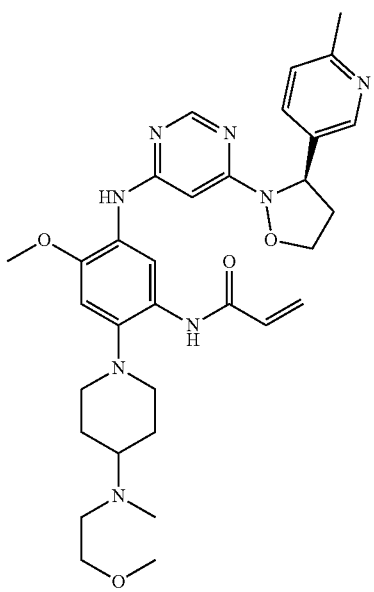 [SMILES: C=CC(=O)Nc1cc(Nc2cc(N3OCC[C@@H]3c3ccc(C)nc3)ncn2)c(OC)cc1N1CCC(N(C)CCOC)CC1] | N-(4-methoxy-2-(4-((2-methoxyethyl)(methyl)amino)piperidine-1-yl)-5-((6-((R)-3-(6-methylpyridine-3-yl)isoxazolidine-2-yl)pyrimidine-4-yl)amino)phenyl)acrylamide | ¹H NMR (400 MHz, Chloroform-d) δ 8.87 (s, 1H), 8.57 (d, J = 2.2 Hz, 1H), 8.46 (s, 1H), 8.36 (s, 1H), 7.70 (dd, J = 8.0, 2.3 Hz, 1H), 7.13 (d, J = 8.1 Hz, 1H), 6.93 (s, 1H), 6.73 (d, J = 13.1 Hz, 2H), 6.43-6.19 (m, 2H), 5.79-5.66 (m, 2H), 4.22-4.05 (m, 2H), 3.84 (s, 3H), 3.53 (t, J = 5.7 Hz, 2H), 3.39 (s, 3H), 3.06 (d, J = 11.0 Hz, 2H), 2.83-2.66 (m, 5H), 2.54 (s, 3H), 2.41 (s, 3H), 2.00 (m, 2H), 1.92-1.79 (m, 2H), 1.70 (m, 2H), ; 603.5 [M + H]⁺ | 0.83 |

TABLE 1-continued

| Example Compound | Structure | Name of Compound | ¹H NMR[[:]]; MS [M + H]⁺ | UPLC r.t. (min) |
|---|---|---|---|---|
| 230 | 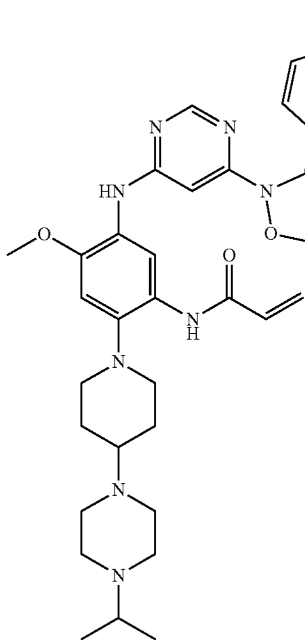 | N-(2-(4-(4-isopropylpiperazine-1-yl)piperidine-1-yl)-4-methoxy-5-((6-((R)-3-(6-methylpyridine-3-yl)isoxazolidine-2-yl)pyrimidine-4-yl)amino)phenyl) acrylamide | ¹H NMR (400 MHz, Chloroform-d) δ 8.86 (s, 1H), 8.57 (d, J = 2.3 Hz, 1H), 8.41 (s, 1H), 8.36 (s, 1H), 7.71 (dd, J = 8.1, 2.4 Hz, 1H), 7.13 (d, J = 8.1 Hz, 1H), 6.97 (s, 1H), 6.73 (d, J = 10.5 Hz, 2H), 6.36 (dd, J = 16.9, 1.6 Hz, 1H), 6.28-6.16 (m, 1H), 5.76-5.73 (m, 1H), 5.71 (m 1H), 4.16 (tt, J = 8.7, 4.3 Hz, 1H), 4.12-4.06 (m, 1H), 3.84 (s, 3H), 3.06 (dd, J = 9.6, 4.8 Hz, 4H), 2.94 (s, 8H), 2.82-2.68 (m, 4H), 2.46 (d, J = 4.5 Hz, 1H), 2.36 (dtd, J = 12.3, 8.0, 4.4 Hz, 2H), 2.12-2.05 (m, 2H), 1.69 (d, J = 11.9 Hz, 2H), 1.26 (d, J = 6.2 Hz, 6H), ; 642.6 [M + H]⁺ | 0.80 |
| 231 | 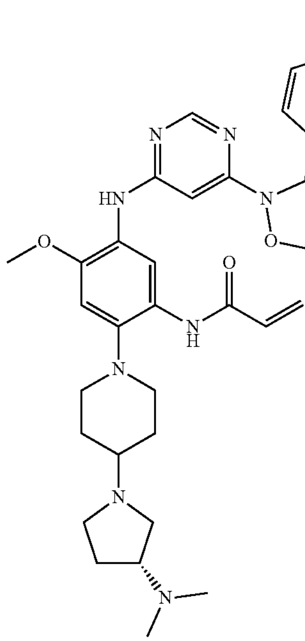 | N-(2-(4-((R)-3-(dimethylamino) pyrolidine-1-yl)piperidine-1-yl)-4-methoxy-5-((6-((R)-3-(6-methylpyridine-3-yl)isoxazolidine-2-yl)pyrimidine-4-yl)amino)phenyl) acrylamide | ¹H NMR (400 MHz, Chloroform-d) δ 8.86 (s, 1H), 8.57 (d, J = 2.3 Hz, 1H), 8.49 (s, 1H), 8.36 (s, 1H), 7.73-7.69 (m, 1H), 7.13 (d, J = 8.0 Hz, 1H), 6.92 (s, 1H), 6.75 (s, 1H), 6.72 (s, 1H), 6.34 (dd, J = 16.7, 1.4 Hz, 1H), 6.23 (dd, J = 16.9, 10.1 Hz, 1H), 5.72 (m, 2H), 4.19-4.07 (m, 2H), 3.84 (s, 3H), 3.29-3.14 (m, 5H), 3.12-2.99 (m, 3H), 2.94 (m, 1H), 2.83-2.68 (m, 5H), 2.54 (s, 3H), 2.47 (t, J = 6.3 Hz, 2H), 2.35 (m, 2H), 2.30 (s, 6H), ; 628.6 [M + H]⁺ | 0.36 |

TABLE 1-continued

| Example Compound | Structure | Name of Compound | ¹H NMR[[:]]; MS [M + H]⁺ | UPLC r.t. (min) |
|---|---|---|---|---|
| 232 | 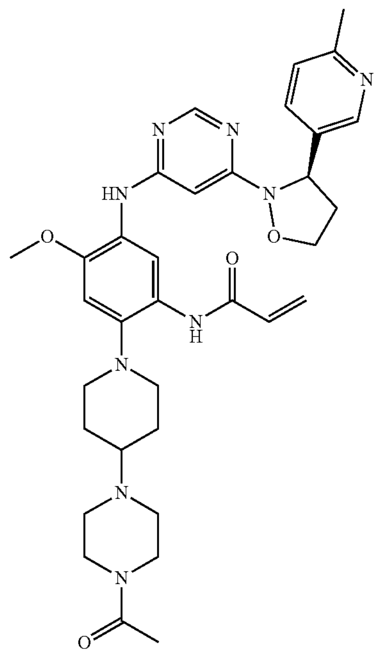 [SMILES: C=CC(=O)Nc1cc(Nc2cc(N3OCC[C@@H]3c3ccc(C)nc3)ncn2)c(OC)cc1N1CCC(N2CCN(C(C)=O)CC2)CC1] | N-(2-(4-(4-acetylpiperazine-1-yl)piperidine-1-yl)-4-methoxy-5-((6-((R)-3-(6-methylpyridine-3-yl)isoxazolidine-2-yl)pyrimidine-4-yl)amino)phenyl)acrylamide | ¹H NMR (400 MHz, Chloroform-d) δ 8.86 (s, 1H), 8.57 (d, J = 2.4 Hz, 1H), 8.41 (s, 1H), 8.36 (d, J = 1.0 Hz, 1H), 7.73-7.68 (m, 1H), 7.13 (d, J =8.0 Hz, 1H), 7.01 (s, 1H), 6.73 (d, J = 13.9 Hz, 2H), 6.43-6.34 (m, 1H), 6.28-6.11 (m, 1H), 5.77-5.73 (m, 1H), 5.73-5.69 (m, 1H), 4.15 (dd, J = 8.0, 4.5 Hz, 1H), 4.10 (d, J = 8.0 Hz, 1H), 3.84 (s, 3H), 3.67 (m, 2H), 3.52 (t, J = 5.0 Hz, 2H), 3.07 (m, 2H), 2.81-2.69 (m, 4H), 2.62 (dt, J = 14.2, 5.1 Hz, 4H), 2.44-2.32 (m, 4H), 2.11 (s, 3H), 2.04 (m, 2H), 1.68 (m, 2H), ; 642.6 [M + H]⁺ | 0.76 |
| 233 | 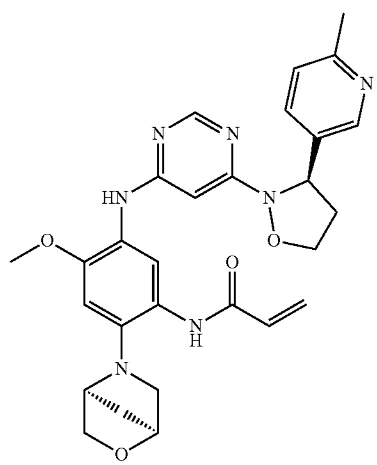 [SMILES: C=CC(=O)Nc1cc(Nc2cc(N3OCC[C@@H]3c3ccc(C)nc3)ncn2)c(OC)cc1N1C[C@@H]2C[C@H]1CO2] | N-(2-((1S,4S)-2-oxa-5-azabicyclo[2.2.1]heptane-5-yl)-4-methoxy-5-((6-((R)-3-(6-methylpyridine-3-yl)isoxazolidine-2-yl)pyrimidine-4-yl)amino)phenyl)acrylamide | ¹H NMR (400 MHz, Chloroform-d) δ 8.67 (s, 1H), 8.57 (d, J = 2.3 Hz, 1H), 8.36 (s, 1H), 7.97 (s, 1H), 7.70 (dd, J = 8.1, 2.4 Hz, 1H), 7.13 (d, J = 8.0 Hz, 1H), 6.88 (s, 1H), 6.67 (d, J = 26.7 Hz, 2H), 6.39 (d, J = 17.2 Hz, 1H), 6.28 (dd, J = 16.9, 10.0 Hz, 1H), 5.75 (d, J = 10.0 Hz, 1H), 5.70 (dd, J = 8.7, 4.4 Hz, 1H), 4.65 (s, 1H), 4.15 (td, J = 8.0, 4.5 Hz, 1H), 4.05 (d, J = 7.7 Hz, 2H), 3.86 (s, 4H), 3.75 (d, J = 7.8 Hz, 1H), 3.42 (d, J = 10.2 Hz, 1H), 3.24 (d, J = 10.1 Hz, 1H), 2.76 (dtd, J = 12.5, 8.2, 4.5 Hz, 1H), 2.54 (s, 3H), 2.36 (dtd, J = 12.3, 7.9, 4,4 Hz, 1H), 2.08 (d, J = 9.9 Hz, 1H), 1.99 (d, J = 9.8 Hz, 1H), ; 530.5 [M + H]⁺ | 0.87 |

TABLE 1-continued

| Example Compound | Structure | Name of Compound | ¹H NMR[[:]]; MS [M + H]⁺ | UPLC r.t. (min) |
|---|---|---|---|---|
| 234 | 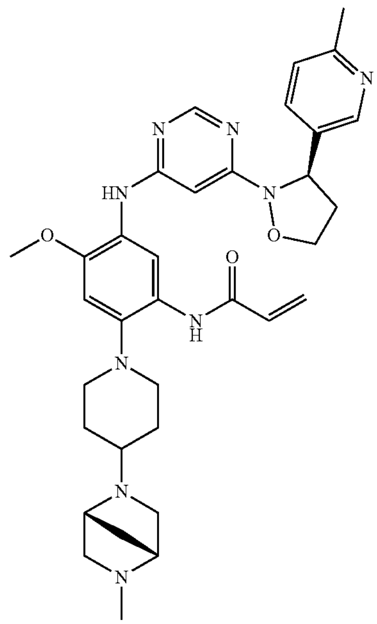 [SMILES: C=CC(=O)Nc1cc(Nc2cc(N3OCC[C@@H]3c3ccc(C)nc3)ncn2)c(OC)cc1N1CCC(N2C[C@H]3C[C@@H]2CN3C)CC1] | N-(4-methoxy-2-(4-((1R,4R)-5-methyl-2,5-diazabicyclo[2.2.1]heptane-2-yl)piperidine-1-yl)-5-((6-((R)-3-(6-methylpyridine-3-yl)isoxazolidine-2-yl)pyrimidine-4-yl)amino)phenyl)acrylamide | ¹H NMR (400 MHz, Chloroform-d) δ 8.87 (s, 1H), 8.57 (d, J = 2.4 Hz, 1H), 8.35 (s, 1H), 7.72 (dd, J = 8.1, 2.4 Hz, 1H), 7.15 (d, J = 8.1 Hz, 1H), 7.04 (s, 1H), 6.76 (s, 1H), 6.69 (s, 1H), 6.54 (s, 2H), 6.34 (s, 1H), 5.77-5.68 (m, 2H), 5.61 (s, 2H), 4.17 (td, J = 8.0, 4.3 Hz, 1H), 4.09 (q, J = 8.0 Hz, 1H), 3.86 (s, 3H), 3.35 (q, J = 6.0 Hz, 5H), 3.19 (dd, J = 7.2, 5.6 Hz, 4H), 3.13 (t, J = 6.9 Hz, 5H), 2.55 (s, 3H), 2.01 (p, J = 6.6 Hz, 6H), ; 626.6 [M + H]⁺ | 0.74 |
| 235 | 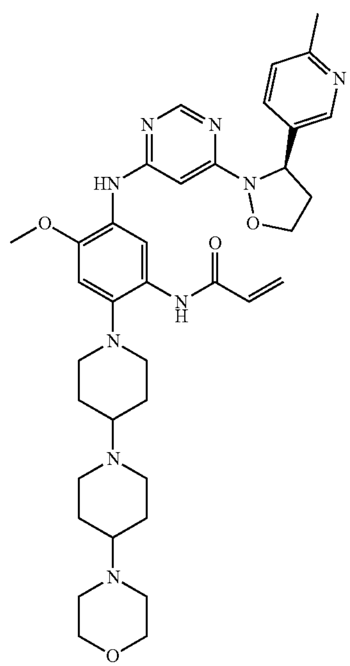 [SMILES: C=CC(=O)Nc1cc(Nc2cc(N3OCC[C@@H]3c3ccc(C)nc3)ncn2)c(OC)cc1N1CCC(N2CCC(N3CCOCC3)CC2)CC1] | N-(4-methoxy-5-((6-((R)-3-(6-methylpyridine-3-yl)isoxazolidine-2-yl)pyrimidine-4-yl)amino)-2-(4-morpholino-[1,4'-bipiperidine]-1'-yl)phenyl)acrylamide | ¹H NMR (400 MHz, DMSO-d₆) δ 8.94 (s, 1H), 8.59 (s, 1H), 8,47 (d, J = 2.3 Hz, 1H), 8.15 (d, J = 8.6 Hz, 2H), 7.67 (dd, J = 8.1, 2.4 Hz, 1H), 7.23 (d, J = 8.0 Hz, 1H), 6.81 (s, 1H), 6.65 (dd, J = 16.9, 10.2 Hz, 1H), 6.33 (s, 1H), 6.20 (dd, J = 16.9, 2.0 Hz, 1H), 5.72 (d, J = 10.3 Hz, 1H), 5.54 (dd, J = 8.6, 4.9 Hz, 1H), 4.15 (td, J = 7.9, 4.1 Hz, 1H), 3.86 (q, J = 7.9 Hz, 1H), 3.79 (s, 2H), 3.56 (t, J = 4.6 Hz, 3H), 3.33 (s, 10H), 3.05 (d, J = 10.4 Hz, 2H), 3.00-2.91 (m, 2H), 2.74 (dt, J = 8.3, 4.2 Hz, 1H), 2,70-2.61 (m, 2H), 2.45 (s, 3H), 1.86-1.64 (m, 6H), 1.36 (d, J = 12.2 Hz, 2H), 1.24 (s, 1H), ; 684.6 [M + H]⁺ | 0.45 |

TABLE 1-continued

| Example Compound | Structure | Name of Compound | ¹H NMR[[:]]; MS [M + H]⁺ | UPLC r.t. (min) |
|---|---|---|---|---|
| 236 | 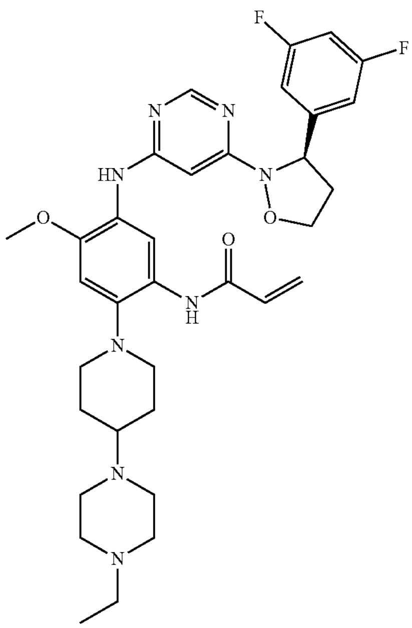 [SMILES: C=CC(=O)Nc1cc(Nc2cc(N3OCC[C@@H]3c3cc(F)cc(F)c3)ncn2)c(OC)cc1N1CCC(N2CCN(CC)CC2)CC1] | N-(5-((6-((R)-3-(3,5-difluorophenyl)isoxazolidine-2-yl)pyrimidine-4-yl)amino)-2-(4-(4-ethylpiperazine-1-yl)piperidine-1-yl)-4-methoxyphenyl)acrylamide | ¹H NMR (400 MHz, Methanol-$d_4$) δ 8.30 (s, 1H), 8.18 (s, 1H), 7.12-7.01 (m, 2H), 6.92 (s, 1H), 6.84 (tt, J = 2.5, 9.1 Hz, 1H), 6.55 (dd, J = 10.2, 17.0 Hz, 1H), 6.46 (s, 1H), 6.36 (dd, J = 1.5, 17.0 Hz, 1H), 5.81 (d, J = 10.3 Hz, 1H), 5.57 (dd, J = 4.7, 8.7 Hz, 1H), 4.19-4.11 (m, 1H), 3.97 (q, J = 8.0 Hz, 1H), 3.88 (s, 3H), 3.22-3.12 (m, 2H), 3.08-2.87 (m, 9H), 2.87-2.74 (m, 4H), 2.66-2.58 (m, 1H), 2.38-2.29 (m, 1H), 2.10-2.02 (m, 2H), 1.88-1.75 (m, 2H), 1.27 (t, J = 7.3 Hz, 3H); 649.3 [M + H]⁺ | 1.15 |
| 237 | 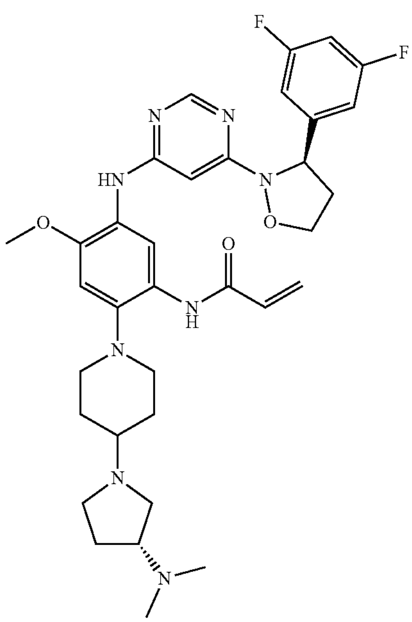 [SMILES: C=CC(=O)Nc1cc(Nc2cc(N3OCC[C@@H]3c3cc(F)cc(F)c3)ncn2)c(OC)cc1N1CCC(N2CC[C@@H](N(C)C)C2)CC1] | N-(5-((6-((R)-3-(3,5-difluorophenyl)ioxazolidine-2-yl)pyrimidine-4-yl)amino)-2-(4-((R)-3-(dimethylamino)pyrolidine-1-yl)piperidine-1-yl)-4-methoxyphenyl)acrylamide | ¹H NMR (400 MHz, Methanol-$d_4$) δ 8.29 (s, 1H), 8.18 (s, 1H), 7.10-7.02 (m, 2H), 6.92 (s, 1H), 6.90-6.80 (m, 1H), 6.61-6.51 (m, 1H), 6.47 (s, 1H), 6.42-6.31 (m, 1H), 5.81 (d, J = 10.5 Hz, 1H), 5.57 (dd, J = 4.8, 8.7 Hz, 1H), 4.20-4.12 (m, 1H), 3.98 (q, J = 8.0 Hz, 1H), 3.89 (s, 3H), 3.26-3.19 (m, 1H), 3.19-3.10 (m, 3H), 3.06-2.97 (m, 2H), 2.92-2.75 (m, 4H), 2.63-2.53 (m, 7H), 2.38-2.20 (m, 2H), 2.17-2.09 (m, 2H), 1.87-1.75 (m, 2H); 649.3 [M + H]⁺ | 1.09 |

TABLE 1-continued

| Example Compound | Structure | Name of Compound | ¹H NMR[:]; MS [M + H]⁺ | UPLC r.t. (min) |
|---|---|---|---|---|
| 238 | 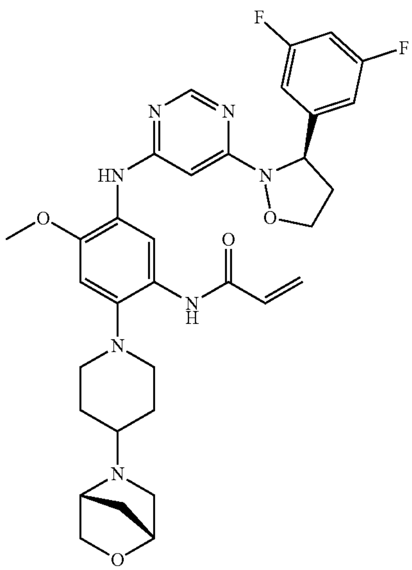 [SMILES: C=CC(=O)Nc1cc(Nc2cc(N3OCC[C@@H]3c3cc(F)cc(F)c3)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-5-((6-((R)-3-(3,5-difluorophenyl)isoxazolidine-2-yl)pyrimidine-4-yl)amino)-4-methoxyphenyl)acrylamide | ¹H NMR (400 MHz, Methanol-$d_4$) δ 8.33 (s, 1H), 8.18 (d, J = 1.0 Hz, 1H), 7.10-7.03 (m, 2H), 6.93 (s, 1H), 6.87-6.81 (m, 1H), 6.58 (dd, J = 17.0, 10.3 Hz, 1H), 6.47 (d, J = 1.0 Hz, 1H), 6.36 (dd, J. 17.0, 1.6 Hz, 1H), 5.80 (dd, J = 10.3, 1.6 Hz, 1H), 5.57 (dd, J = 8.6, 4.8 Hz, 1H), 4.47 (t, J = 2.0 Hz, 1H), 4.19-4.10 (m, 2H), 3.98 (d, J = 8.0 Hz, 1H), 3.88 (s, 4H), 3.67 (dd, J = 8.3, 1.7 Hz, 1H), 3.15-3.08 (m, 3H), 2.88-2.78 (m, 3H), 2.70-2.59 (m, 2H), 2.36-2.30 (m, 1H), 2.11-1.93 (m, 3H), 1.89-1.84 (m, 1H), 1.73 (d, J = 12.0 Hz, 2H); 634.3 [M + H]⁺ | 1.2 |
| 239 | 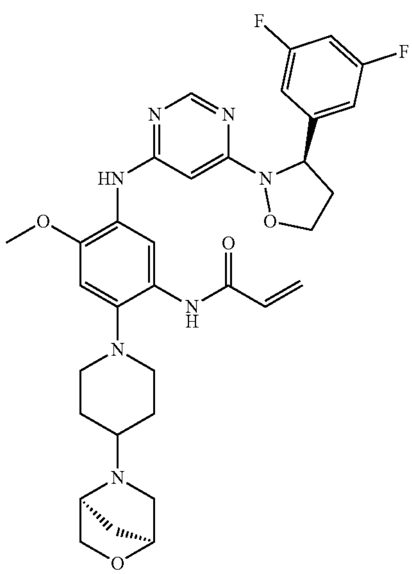 [SMILES: C=CC(=O)Nc1cc(Nc2cc(N3OCC[C@@H]3c3cc(F)cc(F)c3)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((R)-3-(3,5-difluorophenyl)isoxazolidine-2-yl)pyrimidine-4-yl)amino)-4-methoxyphenyl)acrylamide | ¹H NMR (400 MHz, Methanol-$d_4$) δ 8.33 (s, 1H), 8.18 (d, J = 1.0 Hz, 1H), 7.09-7.03 (m, 2H), 6.92 (s, 1H), 6.87-6.81 (m, 1H), 6.58 (dd, J = 17.0, 10.3 Hz, 1H), 6.47 (d, J = 1.0 Hz, 1H), 6.36 (dd, J = 17.0, 1.5 Hz, 1H), 5.80 (dd, J = 10.3, 1.6 Hz, 1H), 5.57 (dd, J = 8.7, 4.7 Hz, 1H), 4.47 (t, J = 2.0 Hz, 1H), 4.17-4.10 (m, 2H), 3.97 (q, J = 8.0 Hz, 1H), 3.90 (s, 1H), 3.88 (s, 3H), 3.67 (dd, J = 8.3, 1.7 Hz, 1H), 3.13-3.07 (m, 3H), 2.85-2.76 (m, 3H), 2.70-2.58 (m, 2H), 2.37-2.31 (m, 1H), 2.06 (d, J = 13.6 Hz, 1H), 2.02 (d, J = 3.4 Hz, 1H), 1.94 (dd, J = 10.2, 2.1 Hz, 1H), 1.86 (d, J = 10.1 Hz, 1H), 1.77-1.67 (m, 2H); 634.3 [M + H]⁺ | 1.21 |

TABLE 1-continued

| Example Compound | Structure | Name of Compound | ¹H NMR[[:]]; MS [M + H]⁺ | UPLC r.t. (min) |
|---|---|---|---|---|
| 240 | 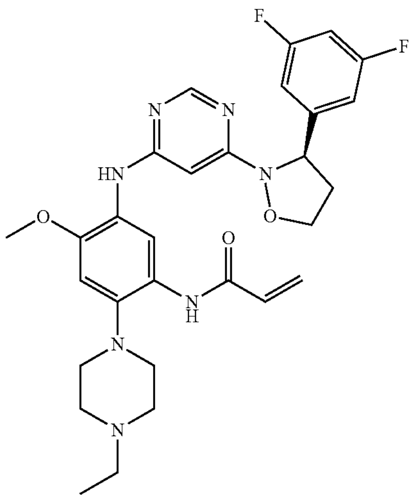 [SMILES: C=CC(=O)Nc1cc(Nc2cc(N3OCC[C@@H]3c3cc(F)cc(F)c3)ncn2)c(OC)cc1N1CCN(CC)CC1] | N-(5-((6-((R)-3-(3,5-difluorophenyl)isoxazolidine-2-yl)pyrimidine-4-yl)amino)-2-(4-ethylpiperazine-1-yl)-4-methoxyphenyl)acrylamide | ¹H NMR (400 MHz, DMSO-d₆) δ 11.34 (s, 1H), 10.19 (s, 1H), 9.31 (s, 1H), 8.32 (s, 1H), 7.16 (tt, J = 9.4, 2.5 Hz, 1H), 7.10 (h, J = 4.4 Hz, 2H), 6.88 (q, J = 9.6, 9.0 Hz, 2H), 6.24 (dd, J = 17.0, 2.0 Hz, 1H), 5.74 (dd, J = 10.1, 2.0 Hz, 1H), 5.56 (dd, J = 8.6, 5.4 Hz, 1H), 4.04 (q, J = 7.8 Hz, 3H), 3.82 (s, 3H), 3.50 (d, J = 11.2 Hz, 2H), 3.41 (d, J = 10.2 Hz, 2H), 3.31-3.19 (m, 4H), 3.20-3.10 (m, 3H), 2.92 (qd, J = 7.8, 3.5 Hz, 1H), 2.32 (dtd, J = 12.8, 7.7, 5.2 Hz, 1H), 1.32 (t, J = 7.2 Hz, 3H), 1.23 (d, J = 3.4 Hz, 1H), 0.88-0.78 (m, 1H), ; 566.3 [M + H]⁺ | 1.16 |
| 241 | 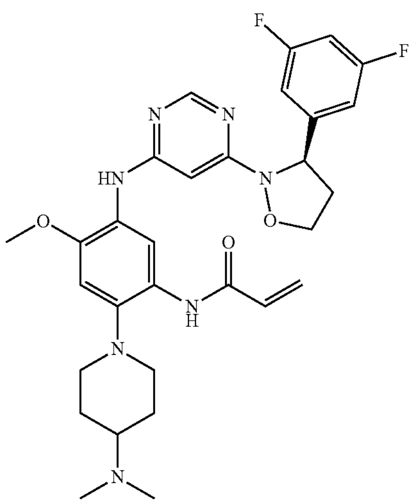 [SMILES: C=CC(=O)Nc1cc(Nc2cc(N3OCC[C@@H]3c3cc(F)cc(F)c3)ncn2)c(OC)cc1N1CCC(N(C)C)CC1] | N-(5-((6-((R)-3-(3,5-difluorophenyl)isoxazolidine-2-yl)pyrimidine-4-yl)amino)-2-(4-(dimethylamino)piperidine-1-yl)-4-methoxyphenyl)acrylamide | ¹H NMR (400 MHz, DMSO-d₆) δ 10.48 (s, 1H), 9.49-9.24 (m, 1H), 8.36 (s, 1H), 7.87 (s, 1H), 7.17 (tt, J = 9.3, 2.4 Hz, 1H), 7.10 (h, J = 4.5 Hz, 3H), 6.96 (s, 1H), 6.78 (dd, J = 16.9, 10.2 Hz, 1H), 6.25 (dd, J = 16.9, 1.9 Hz, 2H), 6.14 (s, 1H), 5.79-5.71 (m, 1H), 5.56 (dd, J = 8.6, 5.4 Hz, 1H), 4.06 (q, J = 7.7 Hz, 1H), 3.81 (s, 4H), 3.25 (d, J = 12.2 Hz, 2H), 3.00-2.80 (m, 4H), 2.73 (d, J = 4.9 Hz, 7H), 2.33 (dtd, J = 12.7, 7.6, 5.3 Hz, 1H), 2.20-2.00 (m, 5H), 1.23 (d, J = 3.4 Hz, 2H), 0.84 (td, J = 7.6. 7.1, 3.1 Hz, 1H), ; 580.4 [M + H]⁺ | 1.13 |
| 242 | 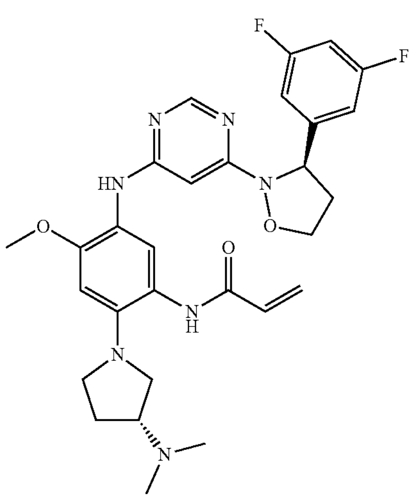 [SMILES: C=CC(=O)Nc1cc(Nc2cc(N3OCC[C@@H]3c3cc(F)cc(F)c3)ncn2)c(OC)cc1N1CC[C@@H](N(C)C)C1] | N-(5-((6-((R)-3-(3,5-difluorophenyl)isoxazolidine-2-yl)pyrimidine-4-yl)amino)-2-((R)-3-(dimethylamino)pyrolidine-1-yl)-4-methoxyphenyl)acrylamide | ¹H NMR (400 MHz, Chloroform-d) δ 8.63 (s, 1H), 8.34 (s, 1H), 8.20 (s, 1H), 6.93 (s, 1H), 6.73 (s, 1H), 6.71-6.63 (m, 2H), 6.41-6.25 (m, 2H), 5.72 (dd, J = 9.5, 2.2 Hz, 1H), 5.66 (dd, J = 8.8, 4.6 Hz, 1H), 4.04 (q, J = 8.2 Hz, 1H), 3.83 (s, 3H), 3.22-3.04 (m, 4H), 2.93-2.68 (m, 2H), 2.29 (s, 8H), 2.16 (ddd, J = 16.5, 9.4, 3.3 Hz, 3H), ; 566.3 [M + H]⁺ | 1.11 |

TABLE 1-continued

| Example Compound | Structure | Name of Compound | ¹H NMR[[:]]; MS [M + H]⁺ | UPLC r.t. (min) |
|---|---|---|---|---|
| 243 | 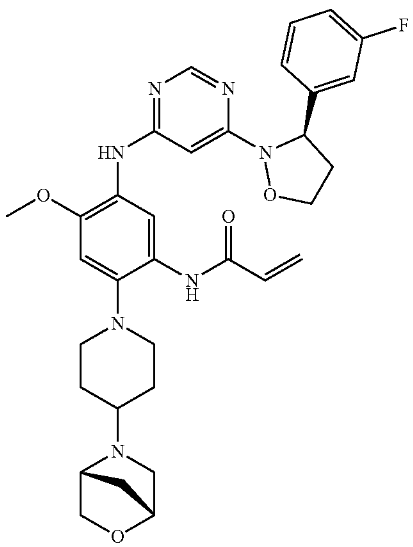 [SMILES: C=CC(=O)Nc1cc(Nc2cc(N3OCC[C@@H]3c3cccc(F)c3)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-5-((6-((R)-3-(3-fluorophenyl)isoxazolidine-2-yl)pyrimidine-4-yl)amino)-4-methoxyphenyl)acrylamide | ¹H NMR (400 MHz, DMSO-d₆) δ 8.94 (s, 1H), 8.60 (s, 1H), 8.17 (d, J = 4.7 Hz, 2H), 7.40 (td, J = 8.0, 6.1 Hz, 1H), 7.26 (d, J = 7.7 Hz, 1H), 7.20 (dt, J = 10.3, 2.2 Hz, 1H), 7.08 (td, J = 8.6, 2.7 Hz, 1H), 6.84 (s, 1H), 6.68-6.61 (m, 1H), 6.35 (s, 1H), 6.21 (dd, J = 17.0, 1.9 Hz, 1H), 5.72, (dd, J = 10.0, 2.0 Hz, 1H), 5.56 (dd, J = 8.7, 5.0 Hz, 1H), 4.34 (d, J = 2.6 Hz, 1H), 4.12 (dd, J = 7.9, 3.9 Hz, 1H), 3.90-3.83 (m, 2H), 3.80 (s, 3H), 3.70 (s, 1H), 3.54-3.50 (m, 1H), 3.05-2.94 (m, 3H), 2.78-2.67 (m, 3H), 2.47 (d, J = 4.6 Hz, 1H), 2.35 (d, J = 9.7 Hz, 1H), 2.29-2.19 (m, H1), 1.83 (s, 2H), 1.69-1.57 (m, 4H); 616.3 [M + H]⁺ | 1.13 |
| 244 | 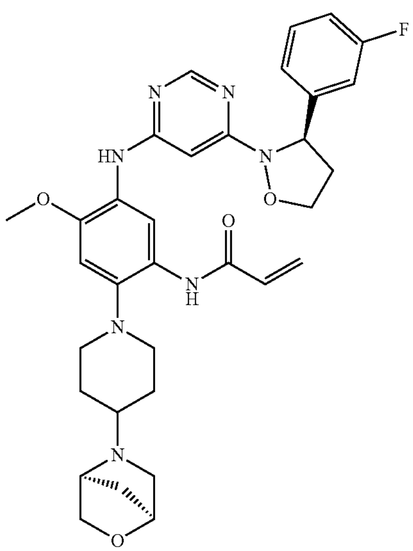 [SMILES: C=CC(=O)Nc1cc(Nc2cc(N3OCC[C@@H]3c3cccc(F)c3)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((R)-3-(3-fluorophenyl)isoxazolidine-2-yl)pyrimidine-4-yl)amino)-4-methoxyphenyl)acrylamide | ¹H NMR (400 MHz, Methanol-d₄) δ 8.18 (s, 1H), 7.89 (s, 1H), 7.39 (dd, J = 8.0, 5.8 Hz, 1H), 7.22-7.17 (m, 1H), 7.12 (dd, J = 9.8, 2.0 Hz, 1H), 7.05 (d, J = 2.6 Hz, 1H), 6.97 (d, J = 3.6 Hz, 1H), 6.64 (ddd, J = 17.0, 10.3, 2.1 Hz, 1H), 6.44-6.37 (m, 1H), 6.01 (s, 1H), 5.85 (dd, J = 10.3, 1.6 Hz, 1H), 5.52 (d, J = 6.6 Hz, 1H), 4.82-4.67 (m, 3H), 4.44 (td, J = 7.6, 4.3 Hz, 1H), 4.34 (d, J = 10.7 Hz, 1H), 4.20 (td, J = 8.4, 6.7 Hz, 2H), 3.92-3.89 (m, 1H), 3.87 (s, 3H), 3.66 (d, J = 15.6 Hz, 2H), 3.10-3.00 (m, 1H), 2.91 (dd, J = 23.9, 11.8 Hz, 2H), 2.53-2.43 (m, 2H), 2.31-2.05 (m, 6H); 616.3 [M + H]⁺ | 1.13 |
| 245 | 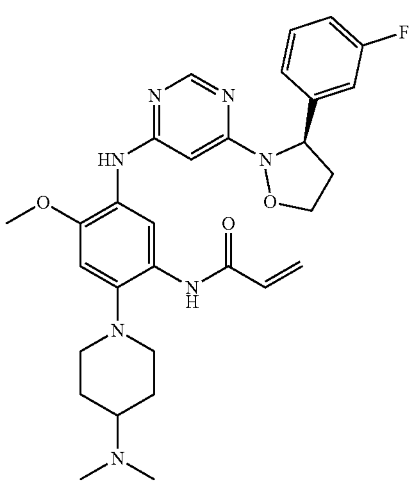 [SMILES: C=CC(=O)Nc1cc(Nc2cc(N3OCC[C@@H]3c3cccc(F)c3)ncn2)c(OC)cc1N1CCC(N(C)C)CC1] | N-(2-(4-(dimethylamino)piperidine-1-yl)-5-((6-((R)-3-(3-fluorophenyl)isoxazolidine-2-yl)pyrimidine-4-yl)amino)-4-methoxyphenyl)acrylamide | ¹H NMR (400 MHz, DMSO-d₆) δ 9.04 (s, 1H), 8.63 (s, 1H), 8.18 (d, J = 4.9 Hz, 2H), 7.40 (td, J = 7.9, 6.1 Hz, 1H), 7.26 (d, J = 7.7 Hz, 1H), 7.20 (dd, J = 10.4, 2.0 Hz, 1H), 7.09 (td, J = 8.6, 2.6 Hz, 1H), 6.84 (s, 1H), 6.69 (dd, J = 16.9, 10.2 Hz, 1H), 6.37 (s, 1H), 6.23 (dd, J = 17.1, 2.0 Hz, 1H), 5.76-5.68 (m, 1H), 5.56 (dd, J = 8.7, 5.0 Hz, 1H), 4.14 (td, J = 7.8, 3.8 Hz, 1H), 3.87-3.83 (m, 1H), 3.81 (s, 3H), 3.17 (s, 3H), 3.12 (d, J = 11.7 Hz, 2H), 3.01-2.90 (m, 1H), 2.78-2.71 (m, 2H), 2.60 (s, 6H), 2.25 (ddt, J = 11.8, 7.8, 4.0 Hz, 1H), 2.03 (d, J = 11.7 Hz, 2H); 562.3 [M + H]⁺ | 1.14 |

TABLE 1-continued

| Example Compound | Structure | Name of Compound | ¹H NMR[[:]]; MS [M + H]⁺ | UPLC r.t. (min) |
|---|---|---|---|---|
| 246 | 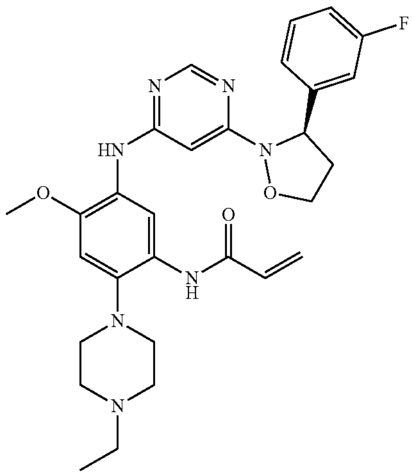 [SMILES: C=CC(=O)Nc1cc(Nc2cc(N3OCC[C@@H]3c3cccc(F)c3)ncn2)c(OC)cc1N1CCN(CC)CC1] | N-(2-(4-ethylpiperazine-1-yl)-5-((6-((R)-3-(3-fluorophenyl)isoxazolidine-2-yl)pyrimidine-4-yl)amino)-4-methoxyphenyl)acrylamide | ¹H NMR (400 MHz, Methanol-d₄) δ 8.19 (d, J = 2.8 Hz, 1H), 8.00 (s, 1H), 7.44-7.39 (m, 1H), 7.22-7.19 (m, 1H), 7.14-6.97 (m, 3H), 6.72-6.66 (m, 1H), 6.42 (dd, J = 16.9, 1.6 Hz, 1H), 6.00 (s, 1H), 5.85 (dd, J = 10.3, 1.6 Hz, 1H), 5.53 (s, 1H), 4.43 (dt, J = 7.5, 3.9 Hz, 1H), 4.23-4.17 (m, 1H), 3.96 (t, J = 5.7 Hz, 1H), 3.88 (d, J = 3.2 Hz, 3H), 3.70 (d, J = 11.8 Hz, 2H), 3.47-3.35 (m, 4H), 3.29-3.22 (m, 2H), 3.10-3.00 (m, 2H), 2.48 (dddd, J = 12.6, 8.4, 7.1, 5.8 Hz, 1H), 1.46 (t, J = 7.3 Hz, 3H); 548.3 [M + H]⁺ | 1.14 |
| 247 | 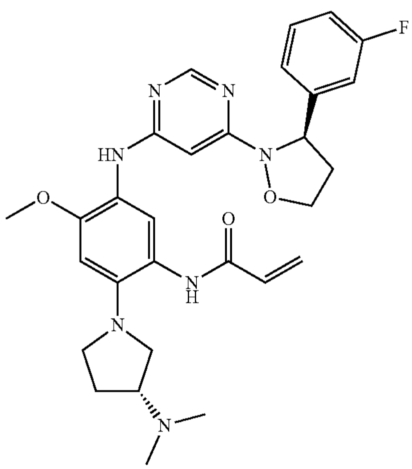 [SMILES: C=CC(=O)Nc1cc(Nc2cc(N3OCC[C@@H]3c3cccc(F)c3)ncn2)c(OC)cc1N1CC[C@@H](N(C)C)C1] | N-(2-((R)-3-(dimethylamino)pyrrolidine-1-yl)-5-((6-((R)-3-(3-fluorophenyl)isoxazolidine-2-yl)pyrimidine-4-yl)amino)-4-methoxyphenyl)acrylamide | ¹H NMR (400 MHz, DMSO-d₆) δ 9.40 (s, 1H), 8.50 (s, 1H), 8.14 (d, J = 1.0 Hz, 1H), 7.46 (s, 1H), 7.38 (dd, J = 8.0, 6.1 Hz, 1H), 7.26 (d, J = 7.8 Hz, 1H), 7.20 (dt, J = 10.3, 2.1 Hz, 1H), 7.09 (dd, J = 8.4, 2.4 Hz, 1H), 6.58-6.50 (m, 2H), 6.26-6.16 (m, 2H), 5.60 (dd, J = 10.1, 2.1 Hz, 1H), 5.57-5.50 (m, 1H), 4.12 (q, J = 4.0 Hz, 1H), 3.82 (s, 1H), 3.80 (s, 3H), 3.27 (dd, J = 11.8, 5.7 Hz, 4H), 2.92 (d, J = 7.5 Hz, 1H), 2.79-2.71 (m, 1H), 2.29 (s, 6H), 2.26-2.21 (m, 1H), 2.16-2.06 (m, 1H), 1.87-1.76 (m, 1H); 548.3 [M + H]⁺ | 1.09 |
| 248 | 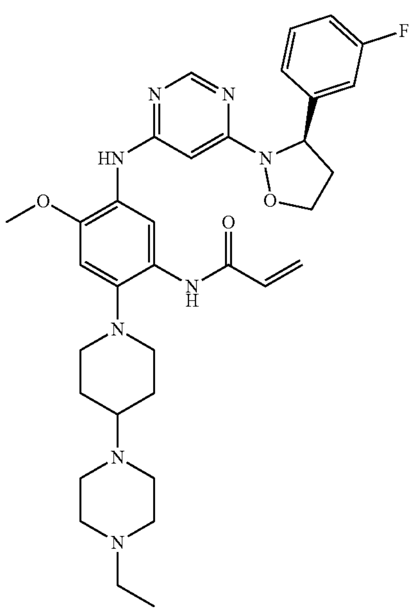 [SMILES: C=CC(=O)Nc1cc(Nc2cc(N3OCC[C@@H]3c3cccc(F)c3)ncn2)c(OC)cc1N1CCC(N2CCN(CC)CC2)CC1] | N-(2-(4-(4-ethylpiperazine-1-yl)piperidine-1-yl)-5-((6-((R)-3-(3-fluorophenyl)isoxazolidine-2-yl)pyrimidine-4-yl)amino)-4-methoxyphenyl)acrylamide | ¹H NMR (400 MHz, DMSO-d₆) δ 8.95 (s, 1H), 8.60 (s, 1H), 8.15 (d, J = 3.4 Hz, 2H), 7.40 (td, J = 7.9, 6.1 Hz, 1H), 7.29-7.18 (m, 2H), 7.08 (td, J = 8.6, 2.7 Hz, 1H), 6.82 (s, 1H), 6.65 (dd, J = 16.9, 10.3 Hz, 1H), 6.34 (s, 1H), 6.23-6.15 (m, 1H), 5.77-5.69 (m, 1H), 5.55 (dd, J = 8.7, 5.0 Hz, 1H), 4.13 (d, J = 4.0 Hz, 1H), 3.83 (d, J = 8.1 Hz, 1H), 3.80 (s, 3H), 3.05 (d, J = 11.1 Hz, 2H), 2.80-2.72 (m, 1H), 2.66 (ddd, J = 12.2, 9.4, 3.6 Hz, 2H), 2.54 (s, 3H), 2.37 (s, 2H), 2.34-2.19 (m, 6H), 1.83 (s, 3H), 1.70 (dd, J = 11.7, 3.7 Hz, 2H), 0.99 (t, J = 7.2 Hz, 3H); 631.3 [M + H]⁺ | 1.08 |

TABLE 1-continued

| Example Compound | Structure | Name of Compound | ¹H NMR[[:]]; MS [M + H]⁺ | UPLC r.t. (min) |
|---|---|---|---|---|
| 249 | 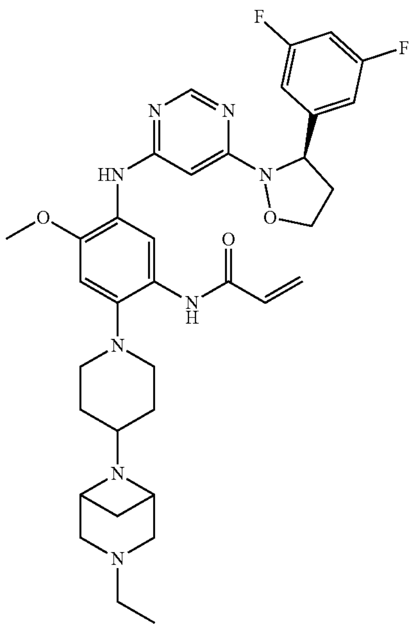 [SMILES: C=CC(=O)Nc1cc(Nc2cc(N3OCC[C@@H]3c3cc(F)cc(F)c3)ncn2)c(OC)cc1N1CCC(N2C3CC2CN(CC)C3)CC1] | N-(5-((6-((R)-3-(3,5-difluorophenyl)isoxazolidine-2-yl)pyrimidine-4-yl)amino)-2-(4-(3-ethyl-3,6-diazabicyclo[3.1.1]heptane-6-yl)piperidine-1-yl)-4-methoxyphenyl)acrylamide | ¹H NMR (400 MHz, Methanol-d₄) δ 8.29 (s, 1H), 8.19 (s, 1H), 7.10-7.04 (m, 2H), 6.94 (s, 1H), 6.84 (tt, J = 2.4, 9.1 Hz, 1H), 6.60-6.43 (m, 2H), 6.42-6.29 (m, 1H), 5.82 (d, J = 10.2 Hz, 1H), 5.57 (dd, J = 4.8, 8.7 Hz, 1H), 4.36-4.28 (m, 2H), 4.18-4.12 (m, 1H), 3.97 (q, J = 8.0 Hz, 1H), 3.89 (s, 3H), 3.42-3.34 (m, 2H), 3.22-3.13 (m, 4H), 2.98-2.79 (m, 7H), 2.40-2.26 (m, 2H), 2.23-2.02 (m, 3H), 1.71 (td, J = 3.7, 11.7 Hz, 1H), 1.23 (t, J = 7.2 Hz, 3H); 661.3 [M + H]⁺ | 1.13 |
| 250 | 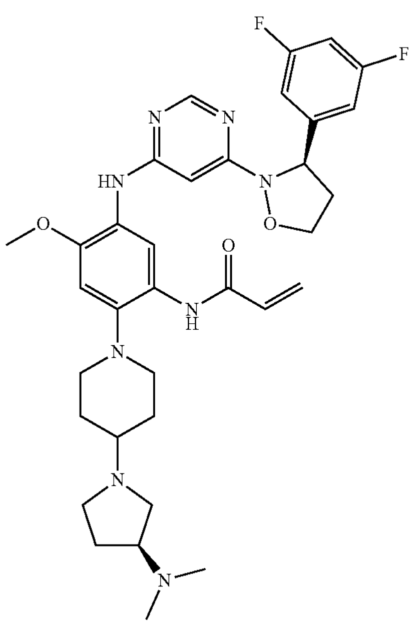 [SMILES: C=CC(=O)Nc1cc(Nc2cc(N3OCC[C@@H]3c3cc(F)cc(F)c3)ncn2)c(OC)cc1N1CCC(N2CC[C@H](N(C)C)C2)CC1] | N-(5-((6-((R)-3-(3,5-difluorophenyl)isoxazolidine-2-yl)pyrimidine-4-yl)amino)-2-(4-((S)-3-(dimethylamino)pyrrolidine-1-yl)piperidine-1-yl)-4-methoxyphenyl)acrylamide | ¹H NMR (400 MHz, Methanol-d₄) δ 8.29 (s, 1H), 8.18 (s, 1H), 7.10-7.02 (m, 2H), 6.92 (s, 1H), 6.90-6.80 (m, 1H), 6.61-6.51 (m, 1H), 6.47 (s, 1H), 6.42-6.31 (m, 1H), 5.81 (d, J = 10.5 Hz, 1H), 5.57 (dd, J = 4.8, 8.7 Hz, 1H), 4.20-4.12 (m, 1H), 3.98 (q, J = 8.0 Hz, 1H), 3.89 (s, 3H), 3.26-3.19 (m, 1H), 3.19-3.10 (m, 3H), 3.06-2.97 (m, 2H), 2.92-2.75 (m, 4H), 2.63-2.53 (m, 7H), 2.38-2.20 (m, 2H), 2.17-2.09 (m, 2H), 1.87-1.75 (m, 2H); 649.3 [M + H]⁺ | 1.10 |

TABLE 1-continued

| Example Compound | Structure | Name of Compound | ¹H NMR[[:]]; MS [M + H]⁺ | UPLC r.t. (min) |
|---|---|---|---|---|
| 251 | 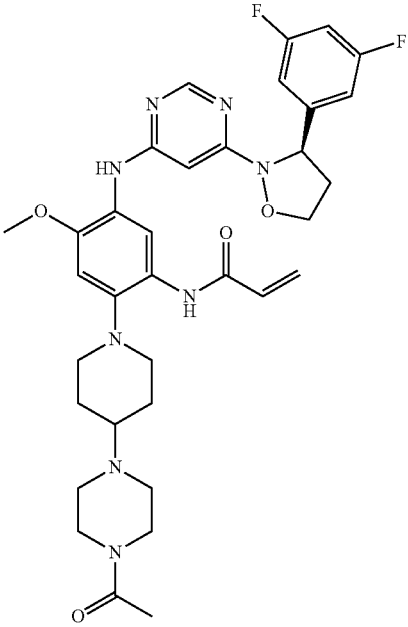 [SMILES: C=CC(=O)Nc1cc(Nc2cc(N3OCC[C@@H]3c3cc(F)cc(F)c3)ncn2)c(OC)cc1N1CCC(N2CCN(C(C)=O)CC2)CC1] | N-(2-(4-(4-acetylpiperazine-1-yl)piperidine-1-yl)-5-((6-((R)-3-(3,5-difluorophenyl)isoxazolidine-2-yl)pyrimidine-4-yl)amino)-4-methoxyphenyl)acrylamide | ¹H NMR (400 MHz, Methanol-d₄) δ 8.30 (s, 1H), 8.18 (s, 1H), 7.11-7.00 (m, 2H), 6.92 (s, 1H), 6.89-6.77 (m, 1H), 6.56 (dd, J = 10.2, 17.0 Hz, 1H), 6.46 (s, 1H), 6.36 (d, J = 16.9 Hz, 1H), 5.81 (d, J = 10.3 Hz, 1H), 5.56 (dd, J = 4.8, 8.7 Hz, 1H), 4.18-4.12 (m, 1H), 3.97 (q, J = 8.0 Hz, 1H), 3.88 (s, 3H), 3.71-3.57 (m, 4H), 3.20-3.11 (m, 2H), 2.88-2.73 (m, 5H), 2.73-2.65 (m, 2H), 2.59-2.47 (m, 1H), 2.39-2.28 (m, 1H), 2.13 (s, 3H), 2.05 (d, J = 12.2 Hz, 2H), 1.86-1.72 (m, 2H); 663.3 [M + H]⁺ | 1.18 |
| 252 | 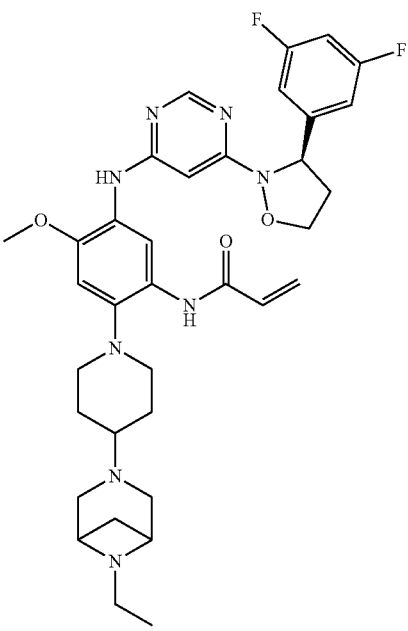 [SMILES: C=CC(=O)Nc1cc(Nc2cc(N3OCC[C@@H]3c3cc(F)cc(F)c3)ncn2)c(OC)cc1N1CCC(N2CC3CC(C2)N3CC)CC1] | N-(5-((6-((R)-3-(3,5-difluorophenyl)isoxazolidine-2-yl)pyrimidine-4-yl)amino)-2-(4-(6-ethyl-3,6-diazabicyclo[3.1.1]heptane-3-yl)piperidine-1-yl)-4-methoxyphenyl)acrylamide | ¹H NMR (400 MHz, Methanol-d₄) δ 8.29 (s, 1H), 8.18 (s, 1H), 7.13-7.00 (m, 2H), 6.94 (s, 1H), 6.91-6.78 (m, 1H), 6.54 (dd, J = 10.2, 17.0 Hz, 1H), 6.46 (s, 1H), 6.37 (d, J = 16.9 Hz, 1H), 5.81 (d, J = 10.2 Hz, 1H), 5.57 (dd, J = 4.8, 8.7 Hz, 1H), 4.16 (td, J = 4.1, 7.9 Hz, 1H), 3.98 (q, J = 8.0 Hz, 1H), 3.89 (s, 3H), 3.53-3.39 (m, 3H), 3.30-3.23 (m, 3H), 3.21-3.12 (m, 3H), 2.91-2.70 (m, 5H), 2.41-2.31 (m, 2H), 2.15-2.03 (m, 2H), 1.93-1.77 (m, 3H), 1.35-1.26 (m, 3H); 661.3 [M + H]⁺ | 1.20 |

TABLE 1-continued

| Example Compound | Structure | Name of Compound | ¹H NMR[[:]]; MS [M + H]⁺ | UPLC r.t. (min) |
|---|---|---|---|---|
| 253 | 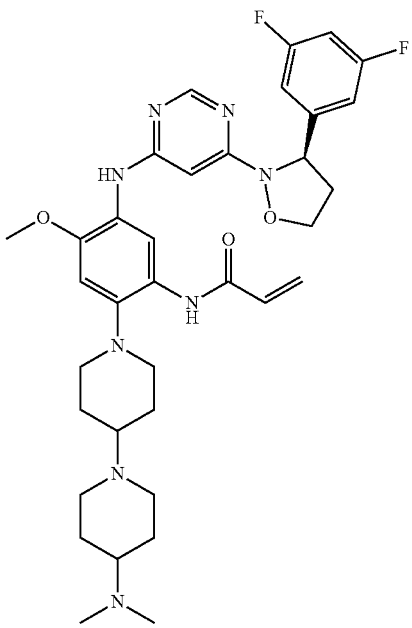 [SMILES: C=CC(=O)Nc1cc(Nc2cc(N3OCC[C@@H]3c3cc(F)cc(F)c3)ncn2)c(OC)cc1N1CCC(N2CCC(N(C)C)CC2)CC1] | N-(5-((6-((R)-3-(3,5-difluorophenyl)isoxazolidine-2-yl)pyrimidine-4-yl)amino)-2-4-(dimethylamino)-1,4'-bipiperidine-1'-yl)-4-methoxyphenyl)acrylamide | ¹H NMR (400 MHz, Methanol-$d_4$) δ 8.29 (s, 1H), 8.18 (s, 1H), 7.12-7.01 (m, 2H), 6.92 (s, 1H), 6.88-6.79 (m, 1H), 6.56 (dd, J = 10.2, 17.0 Hz, 1H), 6.46 (s, 1H), 6.37 (d, J = 16.9 Hz, 1H), 5.81 (d, J = 10.3 Hz, 1H), 5.57 (dd, J = 4.8, 8.7 Hz, 1H), 4.16 (td, J = 4.1, 7.9 Hz, 1H), 3.97 (q, J = 7.9 Hz, 1H), 3.88 (s, 3H), 3.23-3.13 (m, 2H), 3.05-2.94 (m, 1H), 2.91-2.75 (m, 4H), 2.73 (s, 7H), 2.61-2.50 (m, 2H), 2.40-2.29 (m, 1H), 2.15 (dd, J = 6.3, 9.4 Hz, 2H), 2.07 (d, J = 11.9 Hz, 2H), 1.92-1.70 (m, 5H); 663.4 [M + H]⁺ | 1.08 |
| 254 | 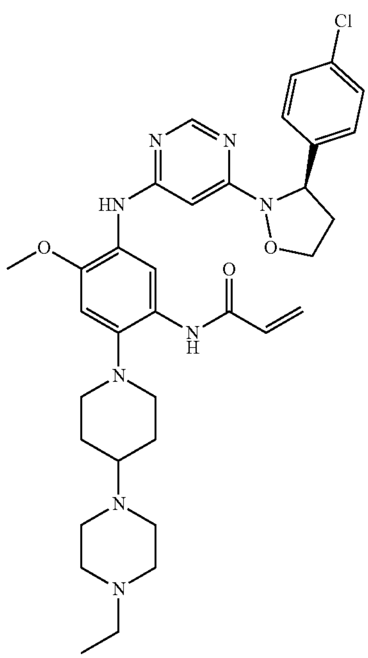 [SMILES: C=CC(=O)Nc1cc(Nc2cc(N3OCC[C@@H]3c3ccc(Cl)cc3)ncn2)c(OC)cc1N1CCC(N2CCN(CC)CC2)CC1] | N-(5-((6-((R)-3-(4-chlorophenyl)isoxazolidine-2-yl)pyrimidine-4-yl)amino)-2-(4-(4-ethylpiperazine-1-yl)piperidine-1-yl)-4-methoxyphenyl)acrylamide | 647.3 [M + H]⁺ | 1.18 |

TABLE 1-continued

| Example Compound | Structure | Name of Compound | ¹H NMR[:]; MS [M + H]⁺ | UPLC r.t. (min) |
|---|---|---|---|---|
| 255 | 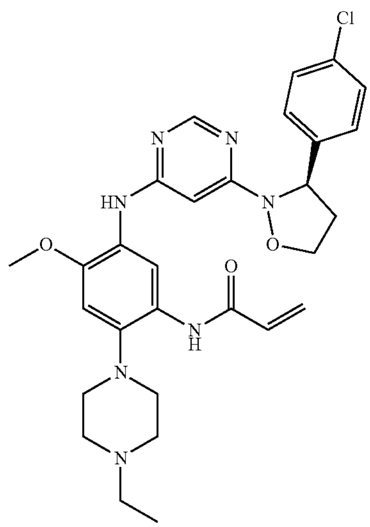 [SMILES: C=CC(=O)Nc1cc(Nc2cc(N3OCC[C@@H]3c3ccc(Cl)cc3)ncn2)c(OC)cc1N1CCN(CC)CC1] | N-(5-((6-((R)-3-(4-chlorophenyl)isoxazolidine-2-yl)pyrimidine-4-yl)amino)-2-(4-ethylpiperazine-1-yl)-4-methoxyphenyl)acrylamide | 564.2 [M + H]⁺ | 1.23 |
| 256 | 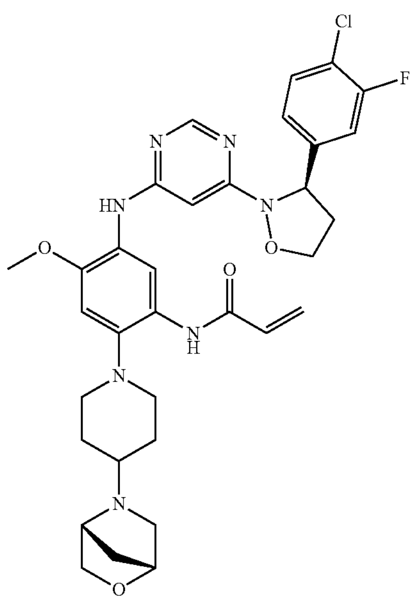 [SMILES: C=CC(=O)Nc1cc(Nc2cc(N3OCC[C@@H]3c3ccc(Cl)c(F)c3)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-5-((6-((R)-3-(4-chloro-3-fluorophenyl)isoxazolidine-2-yl)pyrimidine-4-yl)amino)-4-methoxyphenyl)acrylamide | ¹H NMR (400 MHz, DMSO-d₆) δ 9.85 (s, 1H), 9.24 (d, J = 32.0 Hz, 1H), 8.30 (d, J = 6.7 Hz, 1H), 7.88 (s, 1H), 7.59 (t, J = 8.0 Hz, 1H), 7.42 (dd, J = 10.4, 2.0 Hz, 1H), 7.25 (d, J = 8.4 Hz, 1H), 6.90 (s, 1H), 6.59 (s, 1H), 6.28-6.20 (m, 1H), 6.13 (s, 1H), 5.76 (d, J = 10.4 Hz, 1H), 5.54 (dd, J = 8.6, 5.4 Hz, 1H), 4.72-4.55 (m, 3H), 4.28 (s, 1H), 4.20 (d, J = 10.2 Hz, 1H), 3.82 (d, J = 2.0 Hz, 3H), 3.71 (d, J = 9.7 Hz, 1H), 3.47 (t, J = 9.4 Hz, 2H), 3.19 (d, J = 20.5 Hz, 3H), 2.87 (d, J = 35.1 Hz, 3H), 2.31 (d, J = 13.0 Hz, 2H), 2.12 (d, J = 38.0 Hz, 5H); 650.3 [M + H]⁺ | 1.27 |

TABLE 1-continued

| Example Compound | Structure | Name of Compound | ¹H NMR[:]; MS [M + H]⁺ | UPLC r.t. (min) |
|---|---|---|---|---|
| 257 | 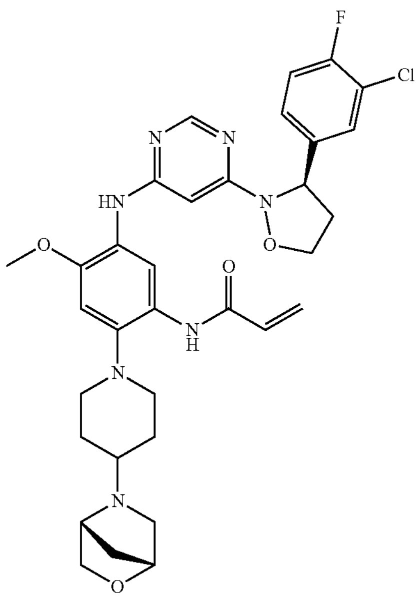 [SMILES: C=CC(=O)Nc1cc(Nc2cc(N3OCC[C@@H]3c3ccc(F)c(Cl)c3)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-5-((6-((R)-3-(3-chloro-4-fluorophenyl)isoxazolidine-2-yl)pyrimidine-4-yl)amino)-4-methoxyphenyl)acrylamide | ¹H NMR (400 MHz, DMSO-d₆) δ 10.10 (s, 1H), 9.29 (d, J = 33.0 Hz, 1H), 8.33 (s, 1H), 7.86 (d, J = 12.2 Hz, 1H), 7.58 (dd, J = 7.1, 2.1 Hz, 1H), 7.45-7.36 (m, 2H), 6.92 (d, J = 9.0 Hz, 1H), 6.71-6.53 (m, 1H), 6.29-6.23 (m, 1H), 6.12 (s, 1H), 5.76 (d, J = 10.4 Hz, 1H), 5.54 (dd, J = 8.5, 5.4 Hz, 1H), 4.73-4.56 (m, 3H), 4.46 (d, J = 9.2 Hz, 1H), 4.31 (d, J = 4.3 Hz, 1H), 4.22 (s, 1H), 4.06 (s, 2H), 3.82 (d, J = 2.3 Hz, 3H), 3.72-3.68 (m, 1H), 3.50-3.41 (m, 2H), 3.24 (d, J = 11.4 Hz, 2H), 2.97-2.78 (m, 3H), 2.33 (t, J = 6.6 Hz, 2H), 2.11-2.03 (m, 3H); 650.3 [M + H]⁺ | 1.27 |
| 258 | 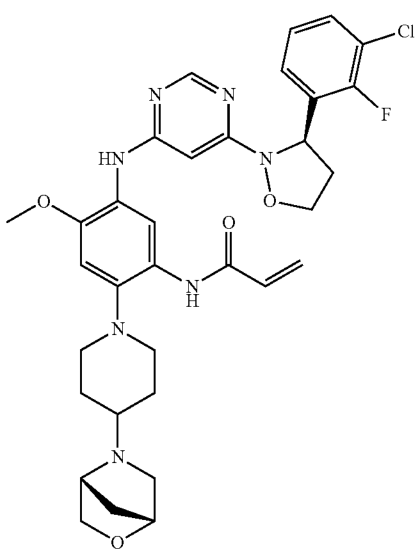 [SMILES: C=CC(=O)Nc1cc(Nc2cc(N3OCC[C@@H]3c3cccc(Cl)c3F)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-5-((6-((R)-3-(3-chloro-2-fluorophenyl)isoxazolidine-2-yl)pyrimidine-4-yl)amino)-4-methoxyphenyl)acrylamide | ¹H NMR (400 MHz, DMSO-d₆) δ 10.01 (s, 1H), 9.27 (d, J = 33.1 Hz, 1H), 8.31 (s, 1H), 7.88 (d, J = 12.1 Hz, 1H), 7.57-7.52 (m, 1H), 7.36 (t, J = 7.1 Hz, 1H), 7.24 (t, J = 7.9 Hz, 1H), 6.92 (d, J = 8.2 Hz, 1H), 6.63 (dt, J = 17.7, 8.8 Hz, 1H), 6.27-6.14 (m, 2H), 5.77-5.68 (m, 2H), 4.72-4.64 (m, 2H), 4.57 (s, 1H), 4.44 (d, J = 9.2 Hz, 1H), 4.32 (d, J = 4.1 Hz, 1H), 4.19 (s, 1H), 3.82 (d, J = 2.1 Hz, 3H), 3.71 (d, J = 3.2 Hz, 1H), 3.46 (t, J = 9.6 Hz, 3H), 3.23 (d, J = 11.2 Hz, 2H), 3.00-2.94 (m, 1H), 2.84 (t, J = 11.2 Hz, 2H), 2.31 (d, J = 10.6 Hz, 3H), 2.12-2.05 (m, 3H); 650.3 [M + H]⁺ | 1.29 |

TABLE 1-continued

| Example Compound | Structure | Name of Compound | $^1$H NMR[[:]]; MS [M + H]$^+$ | UPLC r.t. (min) |
|---|---|---|---|---|
| 259 | 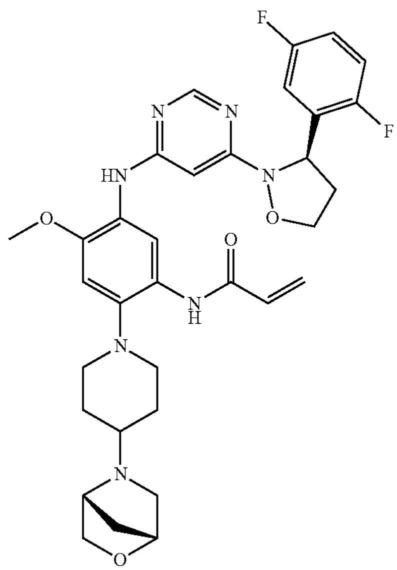 [SMILES: C=CC(=O)Nc1cc(Nc2cc(N3OCC[C@@H]3c3cc(F)ccc3F)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-5-((6-((R)-3-(2,5-difluorophenyl)isoxazolidine-2-yl)pyrimidine-4-yl)amino)-4-methoxyphenyl)acrylamide | $^1$H NMR (400 MHz, DMSO-d$_6$) δ 10.23 (s, 1H), 9.33 (d, J = 35.9 Hz, 1H), 8.34 (s, 1H), 7.85 (d, J = 11.6 Hz, 1H), 7.33 (td, J = 9.3, 4.4 Hz, 1H), 7.19 (dtd, J = 18.1, 9.1, 8.7, 3.7 Hz, 2H), 6.95 (d, J = 10.9 Hz, 1H), 6.64 (ddd, J = 21.2, 16.9, 10.2 Hz, 1H), 6.29-6.15 (m, 2H), 5.77 (dd, J = 10.0, 1.9 Hz, 1H), 5.66 (dd, J = 8.6, 5.6 Hz, 1H), 4.73-4.64 (m, 2H), 4.57 (s, 1H), 4.49 (s, 1H), 4.33 (d, J = 3.7 Hz, 1H), 3.83 (d, J = 2.2 Hz, 3H), 3.70 (td, J = 5.7, 3.0 Hz, 1H), 3.51-3.42 (m, 2H), 3.25 (d, J = 11.7 Hz, 2H), 3.15 (dd, J = 11.4, 3.6 Hz, 1H), 2.99-2.80 (m, 3H), 2.37-2.27 (m, 2H), 2.08 (d, J = 10.8 Hz, 3H); 634.3 [M + H]$^+$ | 1.23 |
| 260 | 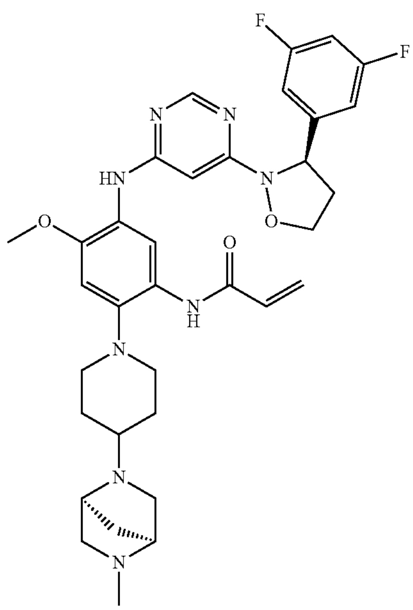 [SMILES: C=CC(=O)Nc1cc(Nc2cc(N3OCC[C@@H]3c3cc(F)cc(F)c3)ncn2)c(OC)cc1N1CCC(N2C[C@@H]3C[C@H]2CN3C)CC1] | N-(5-((6-((R)-3-(3,5-difluorophenyl)isoxazolidine-2-yl)pyrimidine-4-yl)amino)-4-methoxy-2-(4-((1S,4S)-5-methyl-2,5-diazabicyclo[2.2.1]heptane-2-yl)piperidine-1-yl)phenyl)acrylamide | $^1$H NMR (400 MHz, DMSO-d$_6$) δ 10.06 (s, 1H), 9.29 (s, 1H), 8.33 (s, 1H), 7.85 (s, 1H), 7.19-7.14 (m, 1H), 7.12-7.08 (m, 2H), 6.93 (d, J = 23.4 Hz, 1H), 6.58 (d, J = 21.7 Hz, 1H), 6.25 (dd, J = 17.0, 1.8 Hz, 1H), 6.14 (s, 1H), 5.80-5.70 (m, 1H), 5.55 (dd, J = 8.6, 5.4 Hz, 1H), 4.70 (s, 2H), 4.48 (s, 1H), 4.29 (dd, J = 7.6, 4.3 Hz, 2H), 4.05 (s, 2H), 3.82 (s, 3H), 3.69 (s, 2H), 3.25 (s, 3H), 2.98-2.92 (m, 2H), 2.88 (d, J = 4.1 Hz, 3H), 2.75 (d, J = 9.3 Hz, 2H), 2.33 (dq, J = 10.4, 3.9, 2.5 Hz, 2H), 2.08 (d, J = 35.2 Hz, 3H); 647.3 [M + H]$^+$ | 1.13 |

TABLE 1-continued
| Example Compound | Structure | Name of Compound | ¹H NMR[[:]]; MS [M + H]⁺ | UPLC r.t. (min) |
|---|---|---|---|---|
| 261 | 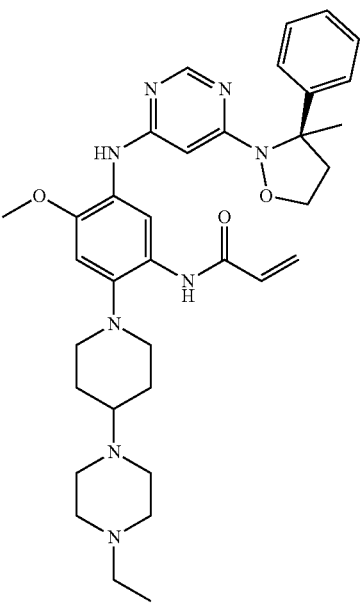 [SMILES: C=CC(=O)Nc1cc(Nc2cc(N3OCC[C@]3(C)c3ccccc3)ncn2)c(OC)cc1N1CCC(N2CCN(CC)CC2)CC1] | N-(2-(4-(4-ethylpiperazine-1-yl)piperidine-1-yl)-4-methoxy-5-((6-(3-methyl-3-phenylisoxazolidine-2-yl)pyrimidine-4-yl)amino)phenyl) acrylamide | 627.6 [M + H]⁺ | 1.06 |
| 262 | 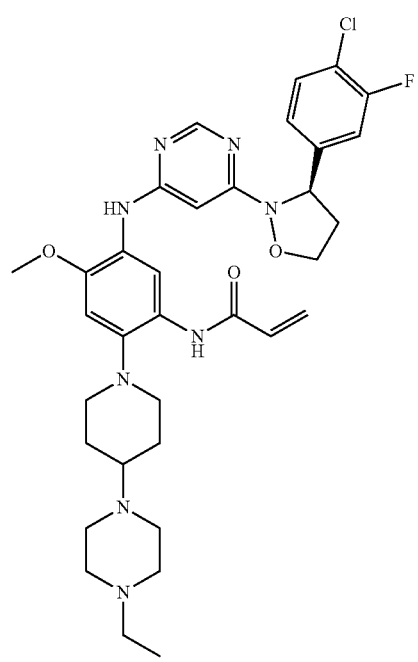 [SMILES: C=CC(=O)Nc1cc(Nc2cc(N3OCC[C@@H]3c3ccc(Cl)c(F)c3)ncn2)c(OC)cc1N1CCC(N2CCN(CC)CC2)CC1] | N-(5-((6-((R)-3-(4-chloro-3-fluorophenyl) isoxazolidine-2-yl)pyrimidine-4-yl)amino)-2-(4-(4-ethylpiperazine-1-yl)piperidine-1-yl)-4-methoxyphenyl) acrylamide | 665.5 [M + H]⁺ | 1.27 |

TABLE 1-continued

| Example Compound | Structure | Name of Compound | ¹H NMR[:]; MS [M + H]⁺ | UPLC r.t. (min) |
|---|---|---|---|---|
| 263 | 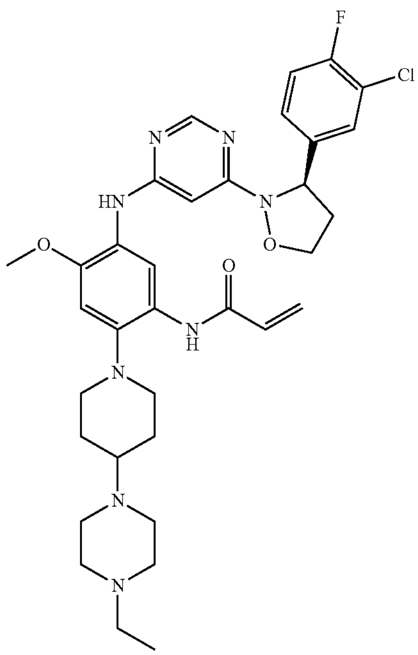 [SMILES: C=CC(=O)Nc1cc(Nc2cc(N3OCC[C@@H]3c3ccc(F)c(Cl)c3)ncn2)c(OC)cc1N1CCC(N2CCN(CC)CC2)CC1] | N-(5-(((6-((R)-3-(3-chloro-4-fluorophenyl)isoxazolidine-2-yl)pyrimidine-4-yl)amino)-2-(4-(4-ethylpiperazine-1-yl)piperidine-1-yl)-methoxyphenyl)acrylamide | 665.5 [M + H]⁺ | 1.26 |
| 264 | 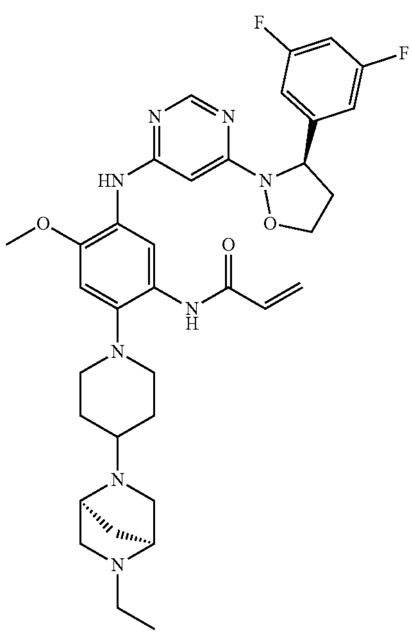 [SMILES: C=CC(=O)Nc1cc(Nc2cc(N3OCC[C@@H]3c3cc(F)cc(F)c3)ncn2)c(OC)cc1N1CCC(N2C[C@@H]3C[C@H]2CN3CC)CC1] | N-(5-(((6-((R)-3-(3,5-difluorophenyl)isoxazolidine-2-yl)pyrimidine-4-yl)amino)-2-(4-((1S,4S)-5-ethyl-2,5-diazabicyclo[2.2.1]heptane-2-yl)piperidine-1-yl)-4-methoxyphenyl)acrylamide | 661.3 [M + H]⁺ | 1.17 |

TABLE 1-continued

| Example Compound | Structure | Name of Compound | ¹H NMR[:]; MS [M + H]⁺ | UPLC r.t. (min) |
|---|---|---|---|---|
| 265 | 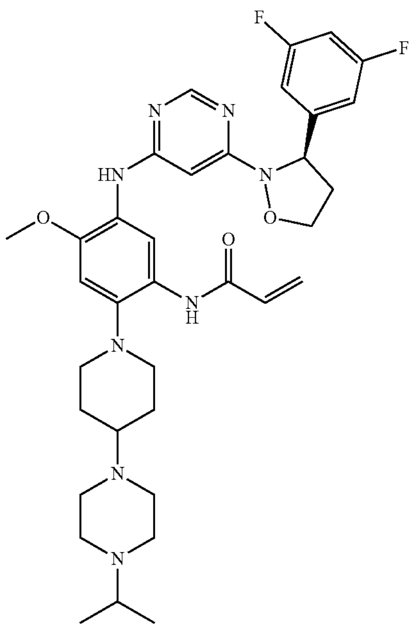 [SMILES: C=CC(=O)Nc1cc(Nc2cc(N3OCC[C@@H]3c3cc(F)cc(F)c3)ncn2)c(OC)cc1N1CCC(N2CCN(C(C)C)CC2)CC1] | N-(5-((6-((R)-3-(3,5-difluorophenyl)isoxazolidine-2-yl)pyrimidine-4-yl)amino)-2-(4-(4-isopropylpiperazine-1-yl)piperidine-1-yl)-4-methoxyphenyl)acrylamide | ¹H NMR (400 MHz, Methanol-$d_4$) δ 8.30 (s, 1H), 8.18 (s, 1H), 7.12-7.02 (m, 2H), 6.92 (s, 1H), 6.90-6.79 (m, 1H), 6.55 (dd, J = 10.2, 17.0 Hz, 1H), 6.46 (s, 1H), 6.37 (dd, J = 1.5, 17.0 Hz, 1H), 5.81 (d, J = 10.3 Hz, 1H), 5.57 (dd, J = 4.7, 8.7 Hz, 1H), 4.16 (td, J = 4.1, 7.9 Hz, 1H), 3.97 (q, J = 8.0 Hz, 1H), 3.88 (s, 3H), 3.30-3.23 (m, 2H), 3.19-3.10 (m, 5H), 2.97 (s, 4H), 2.88-2.75 (m, 3H), 2.68-2.56 (m, 1H), 2.40-2.28 (m, 1H), 2.10-2.01 (m, 2H), 1.89-1.74 (m, 2H), 1.33-1.29 (m, 6H); 663.4 [M + H]⁺ | 1.18 |
| 266 | 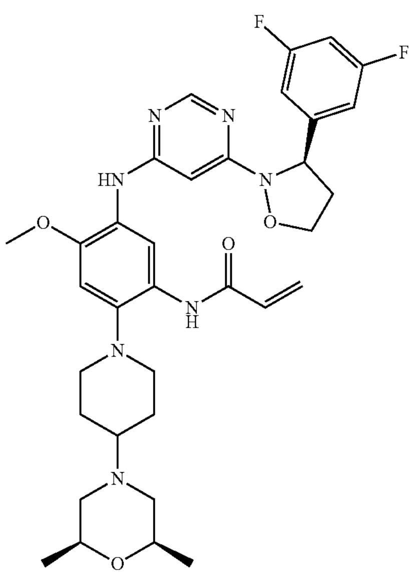 [SMILES: C=CC(=O)Nc1cc(Nc2cc(N3OCC[C@@H]3c3cc(F)cc(F)c3)ncn2)c(OC)cc1N1CCC(N2C[C@@H](C)O[C@@H](C)C2)CC1] | N-(5-((6-((R)-3-(3,5-difluorophenyl)isoxazolidine-2-yl)pyrimidine-4-yl)amino)-2-(4-((2S,6R)-2,6-dimethylmorpholino)piperidine-1-yl)-4-methoxyphenyl)acrylamide | ¹H NMR (400 MHz, Methanol-$d_4$) δ 8.30 (s, 1H), 8.18 (s, 1H), 7.11-7.01 (m, 2H), 6.92 (s, 1H), 6.84 (tt, J = 2.5, 9.1 Hz, 1H), 6.57 (dd, J = 10.3, 17.0 Hz, 1H), 6.46 (s, 1H), 6.37 (d, J = 16.9 Hz, 1H), 5.81 (d, J = 10.3 Hz, 1H), 5.56 (dd, J = 4.8, 8.7 Hz, 1H), 4.16 (td, J = 4.1, 7.9 Hz, 1H), 3.97 (q, J = 7.9 Hz, 1H), 3.88 (s, 3H), 3.77 (dt, J = 6.5, 12.4 Hz, 2H), 3.22-3.14 (m, 2H), 3.14-3.07 (m, 2H), 2.87-2.75 (m, 3H), 2.66-2.56 (m, 1H), 2.38-2.28 (m, 1H), 2.14-2.09 (m, 2H), 1.87-1.75 (m, 2H), 1.25-1.18 (m, 6H); 650.3 [M + H]⁺ | 1.31 |

TABLE 1-continued

| Example Compound | Structure | Name of Compound | ¹H NMR[:]; MS [M + H]⁺ | UPLC r.t. (min) |
|---|---|---|---|---|
| 267 | 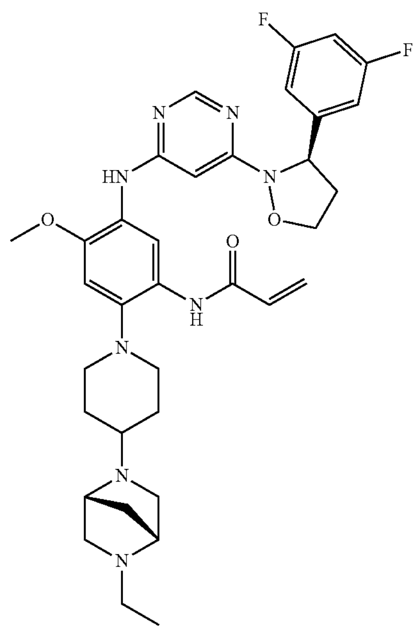 [SMILES: C=CC(=O)Nc1cc(Nc2cc(N3OCC[C@@H]3c3cc(F)cc(F)c3)ncn2)c(OC)cc1N1CCC(N2C[C@H]3C[C@@H]2CN3CC)CC1] | N-(5-((6-((R)-3-(3,5-difluorophenyl)isoxazolidine-2-yl)pyrimidine-4-yl)amino)-2-(4-((1R,4R)-5-ethyl-2,5-diazabicyclo[2.2.1]heptane-2-yl)piperidine-1-yl)-4-methoxyphenyl)acrylamide | ¹H NMR (400 MHz, CDCl₃) δ 8.84 (s, 1H), 8.48 (s, 1H), 8.35 (s, 1H), 7.06 (s, 1H), 7.03-6.98 (m, 2H), 6.75 (s, 1H), 6.72-6.65 (m, 2H), 6.38-6.22 (m, 2H), 5.73 (dd, J = 9.8, 1.5 Hz, 1H), 5.66 (dd, J = 8.7, 4.5 Hz, 1H), 4.15 (td, J = 8.0, 4.2 Hz, 1H), 4.06 (q, J = 8.0 Hz, 1H), 3.85 (s, 3H), 3.74 (d, J = 18.2 Hz, 2H), 3.26-3.20 (m, 1H), 3.10-3.06 (m, 1H), 3.04-2.99 (m, 2H), 2.96-2.87 (m, 4H), 2.83-2.73 (m, 7H), 2.67-2.62 (m, 1H), 2.38-2.29 (m, 1H), 1.78-1.66 (m, 2H), 1.21 (t, J = 7.2 Hz, 3H); 661.6 [M + H]⁺ | 1.2 |
| 268 | 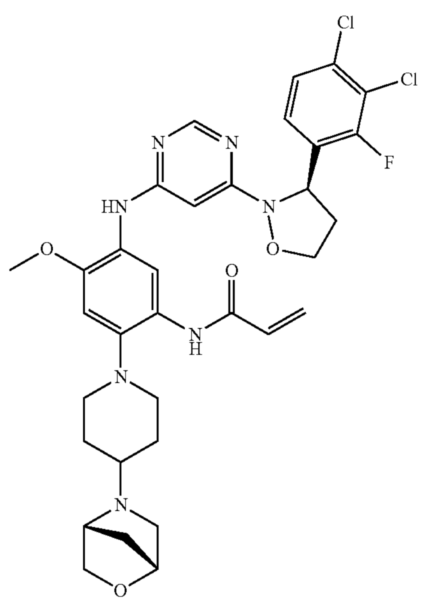 [SMILES: C=CC(=O)Nc1cc(Nc2cc(N3OCC[C@@H]3c3ccc(Cl)c(Cl)c3F)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-5-((6-((R)-3-(3,4-dichloro-2-fluorophenyl)isoxazolidine-2-yl)pyrimidine-4-yl)amino)-4-methoxyphenyl)acrylamide | ¹H NMR (400 MHz, Methanol-d₄) δ 8.29 (s, 1H), 8.18 (s, 1H), 7.50 (t, J = 8.0 Hz, 1H), 7.38 (d, J = 8.6 Hz, 1H), 6.93 (s, 1H), 6.56 (dd, J = 10.2, 17.0 Hz, 1H), 6.49 (s, 1H), 6.37 (d, J = 16.9 Hz, 1H), 5.87-5.70 (m, 2H), 4.23-4.14 (m, 3H), 3.99 (q, J = 8.0 Hz, 1H), 3.89 (s, 3H), 3.77 (d, J = 9.0 Hz, 1H), 3.31-3.25 (m, 2H), 3.20-3.12 (m, 2H), 3.01-2.79 (m, 5H), 2.34-2.22 (m, 1H), 2.22-2.13 (m, 1H), 2.13-2.02 (m, 3H), 1.87-1.73 (m, 2H); 684.2 [M + H]⁺ | 1.51 |

TABLE 1-continued

| Example Compound | Structure | Name of Compound | ¹H NMR[[:]]; MS [M + H]⁺ | UPLC r.t. (min) |
|---|---|---|---|---|
| 269 | 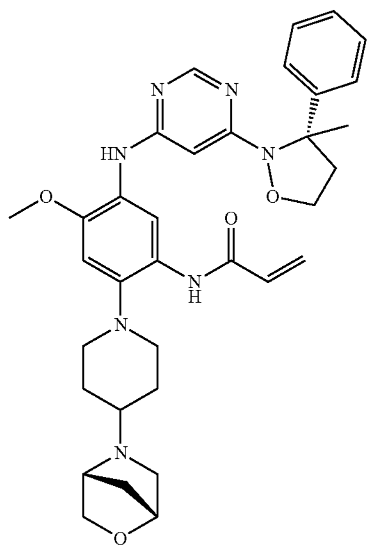 [SMILES: C=CC(=O)Nc1cc(Nc2cc(N3OCC[C@@]3(C)c3ccccc3)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-4-methoxy-5-((6-((S)-3-methyl-3-phenylisoxazolidine-2-yl)pyrimidine-4-yl)amino)phenyl)acrylamide | ¹H NMR (400 MHz, Methanol-d₄) δ 8.26 (s, 1H), 8.12 (s, 1H), 7.48 (d, J = 8.0 Hz, 2H), 7.33 (t, J = 7.6 Hz, 2H), 7.25 (t, J = 7.3 Hz, 1H), 6.93 (s, 1H), 6.55 (dd, J = 10.3, 17.0 Hz, 1H), 6.39-6.30 (m, 2H), 5.80 (d, J = 10.3 Hz, 1H), 4.23-4.19 (m, 1H), 4.19-4.14 (m, 1H), 3.98 (td, J = 5.0, 9.0 Hz, 1H), 3.89 (s, 3H), 3.79-3.73 (m, 1H), 3.73-3.63 (m, 1H), 3.31-3.25 (m, 2H), 3.19-3.13 (m, 2H), 3.02-2.90 (m, 2H), 2.90-2.77 (m, 2H), 2.73-2.64 (m, 1H), 2.56-2.46 (m, 1H), 2.21-2.10 (m, 1H), 2.12-2.01 (m, 3H), 1.85-1.75 (m, 2H), 1.62 (s, 3H); 612.3 [M + H]⁺ | 1.27 |
| 270 | 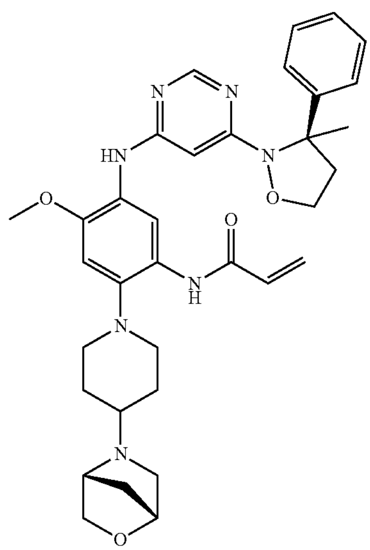 [SMILES: C=CC(=O)Nc1cc(Nc2cc(N3OCC[C@]3(C)c3ccccc3)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-4-methoxy-5-((6-((R)-3-methyl-3-phenylisoxazolidine-2-yl)pyrimidine-4-yl)amino)phenyl)acrylamide | ¹H NMR (400 MHz, Methanol-d₄) δ 8.27 (s, 1H), 8.12 (s, 1H), 7.48 (d, J = 7.6 Hz, 2H), 7.33 (t, J = 7.6 Hz, 2H), 7.25 (t, J = 7.3 Hz, 1H), 6.93 (s, 1H), 6.55 (dd, J = 10.2, 17.0 Hz, 1H), 6.40-6.28 (m, 2H), 5.79 (d, J = 10.3 Hz, 1H), 4.29-4.22 (m, 1H), 4.21-4.12 (m, 1H), 4.03-3.92 (m, 1H), 3.89 (s, 3H), 3.81-3.74 (m, 1H), 3.74-3.62 (m, 1H), 3.32-3.27 (m, 2H), 3.22-3.11 (m, 2H), 3.06-2.94 (m, 2H), 2.91-2.78 (m, 2H), 2.73-2.63 (m, 1H), 2.58-2.46 (m, 1H), 2.24-2.13 (m, 1H), 2.13-2.02 (m, 3H), 1.88-1.75 (m, 2H), 1.62 (s, 3H), ; 612.3 [M + H]⁺ | 1.26 |

TABLE 1-continued

| Example Compound | Structure | Name of Compound | ¹H NMR[[:]]; MS [M + H]⁺ | UPLC r.t. (min) |
|---|---|---|---|---|
| 271 | 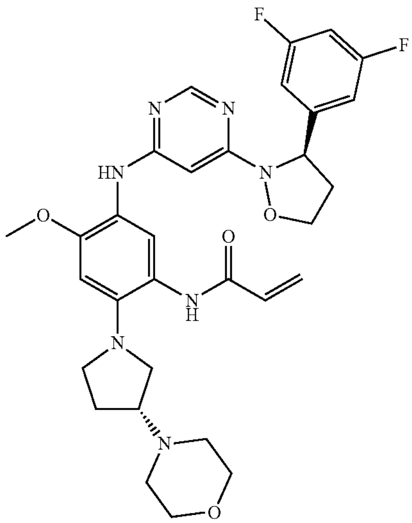 [SMILES: C=CC(=O)Nc1cc(Nc2cc(N3OCC[C@@H]3c3cc(F)cc(F)c3)ncn2)c(OC)cc1N1CC[C@@H](N2CCOCC2)C1] | N-(5-((6-((R)-3-(3,5-difluorophenyl)isoxazolidine-2-yl)pyrimidine-4-yl)amino)-4-methoxy-2-((R)-3-morpholinopyrolidine-1-yl)phenyl)acrylamide | ¹H NMR (400 MHz, DMSO-d₆) δ 11.91 (d, J = 9.5 Hz, 1H), 10.22 (s, 1H), 9.70 (s, 1H), 7.56 (s, 1H), 7.18 (tt, J = 9.3, 2.4 Hz, 1H), 7.12-7.06 (m, 2H), 6.89 (dd, J = 17.0, 10.2 Hz, 1H), 6.71 (s, 1H), 6.22 (dd, J = 17.0, 2.1 Hz, 1H), 6.05 (s, 1H), 5.71 (dd, J = 10.1, 2.1 Hz, 1H), 5.56 (dd, J = 8.6, 5.4 Hz, 1H), 4.11-4.03 (m, 1H), 3.96 (tp, J = 18.1, 5.8, 5.1 Hz, 6H), 3.82 (s, 3H), 3.73 (dd, J = 11.0, 4.5 Hz, 1H), 3.61-3.45 (m, 4H), 3.41 (dd, J = 10.9, 6.3 Hz, 1H), 3.13 (dt, J = 24.6, 7.8 Hz, 4H), 3.00-2.88 (m, 1H), 2.47-2.26 (m, 4H), ; 608.5 [M + H]⁺ | 1.34 |
| 272 | 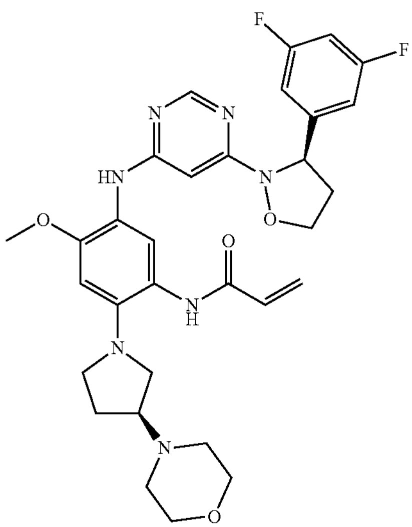 [SMILES: C=CC(=O)Nc1cc(Nc2cc(N3OCC[C@@H]3c3cc(F)cc(F)c3)ncn2)c(OC)cc1N1CC[C@H](N2CCOCC2)C1] | N-(5-((6-((R)-3-(3,5-difluorophenyl)isoxazolidine-2-yl)pyrimidine-4-yl)amino)-4-methoxy-2-((S)-3-morpholinopyrolidine-1-yl)phenyl)acrylamide | ¹H NMR (400 MHz, DMSO-d₆) δ 11.93 (d, J = 9.4 Hz, 1H), 10.28 (s, 1H), 9.72 (s, 1H), 7.55 (s, 1H), 7.18 (tt, J = 9.3, 2.4 Hz, 1H), 7.10 (h, J = 4.5 Hz, 2H), 6.90 (dd, J = 17.0, 10.2 Hz, 1H), 6.71 (s, 1H), 6.22 (dd, J = 16.9, 2.1 Hz, 1H), 6.06 (s, 1H), 5.71 (dd, J = 10.1, 2.1 Hz, 1H), 5.56 (dd, J = 8.6, 5.4 Hz, 1H), 4.11-4.04 (m, 1H), 3.97 (q, J = 12.6, 9.9 Hz, 5H), 3.82 (s, 3H), 3.73 (dd, J = 11.0, 4.5 Hz, 1H), 3.54 (dtd, J = 17.8, 12.9, 11.4, 7.3 Hz, 3H), 3.42 (dd, J = 11.0, 6.3 Hz, 1H), 3.14 (dt, J = 28.6, 9.4 Hz, 4H), 3.00-2.89 (m, 1H), 2.36 (dddd, J = 26.2, 13.2, 10.7, 6.7 Hz, 3H), ; 608.5 [M + H]⁺ | 1.32 |

TABLE 1-continued

| Example Compound | Structure | Name of Compound | ¹H NMR[:]; MS [M + H]⁺ | UPLC r.t. (min) |
|---|---|---|---|---|
| 273 | 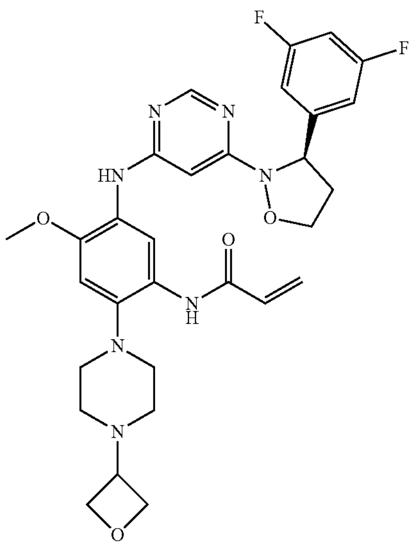 [SMILES: C=CC(=O)Nc1cc(Nc2cc(N3OCC[C@@H]3c3cc(F)cc(F)c3)ncn2)c(OC)cc1N1CCN(C2COC2)CC1] | N-(5-((6-((R)-3-(3,5-difluorophenyl)isoxazolidine-2-yl)pyrimidine-4-yl)amino)-4-methoxy-2-(4-(oxetane-3-yl)piperazine-1-yl)phenyl)acrylamide | 594.5 [M + H]⁺ | 1.37 |
| 274 | 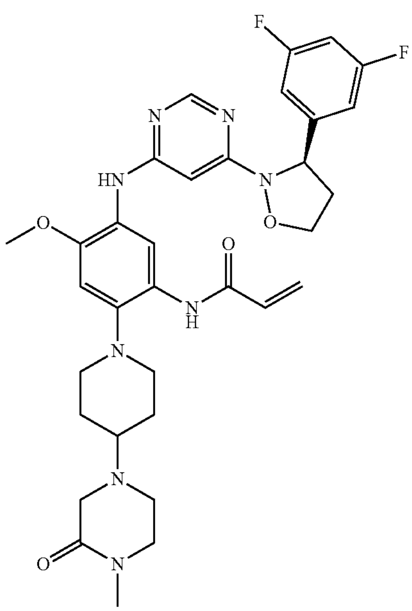 [SMILES: C=CC(=O)Nc1cc(Nc2cc(N3OCC[C@@H]3c3cc(F)cc(F)c3)ncn2)c(OC)cc1N1CCC(N2CCN(C)C(=O)C2)CC1] | N-(5-((6-((R)-3-(3,5-difluorophenyl)isoxazolidine-2-yl)pyrimidine-4-yl)amino)-4-methoxy-2-(4-(4-methyl-3-oxopiperazine-1-yl)piperidine-1-yl)phenyl)acrylamide | ¹H NMR (400 MHz, Chloroform-d) δ 8.71 (s, 1H), 8.41 (s, 1H), 8.27 (d, J = 0.9 Hz, 1H), 6.97 (h, J = 4.5 Hz, 3H), 6.74 (s, 1H), 6.66 (tt, J = 8.9, 2.4 Hz, 1H), 6.62 (s, 1H), 6.40 - 6.20 (m, 2H), 5.74 (dd, J = 9.8, 1.7 Hz, 1H), 5.62 (dd, J = 8.8, 4.6 Hz, 1H), 4.02 (q, J = 8.0 Hz, 1H), 3.83 (s, 3H), 3.46 (s, 2H), 3.35 (d, J = 8.1 Hz, 4H), 3.11 - 3.02 (m, 2H), 2.97 (s, 3H), 2.84 (dd, J = 6.3, 4.6 Hz, 2H), 2.82 - 2.67 (m, 4H), 2.44 (tt, J = 11.0, 3.8 Hz, 1H), 2.31 (dtd, J = 12.6, 8.1, 4.7 Hz, 1H), 2.04 - 1.97 (m, 2H), 1.74 - 1.62 (m, 2H), ; 649.5 [M + H]⁺ | 1.38 |

| Example Compound | Structure | Name of Compound | $^1$H NMR[[:]]; MS [M + H]$^+$ | UPLC r.t. (min) |
|---|---|---|---|---|
| 275 | 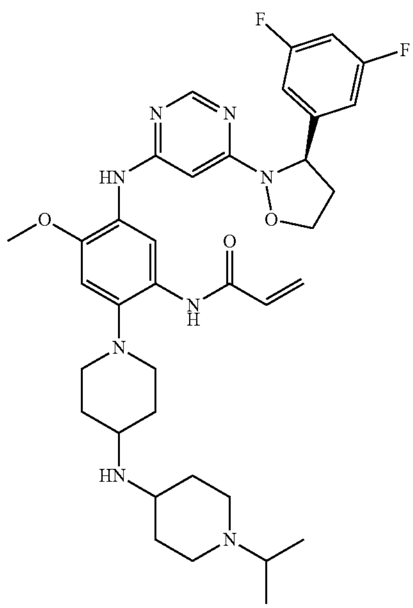 [SMILES: C=CC(=O)Nc1cc(Nc2cc(N3OCC[C@@H]3c3cc(F)cc(F)c3)ncn2)c(OC)cc1N1CCC(NC2CCN(C(C)C)CC2)CC1] | N-(5-((6-((R)-3-(3,5-difluorophenyl) isoxazolidine-2-yl)pyrimidine-4-yl)amino)-2-(4-((1-isopropylpiperidine-4-yl)amino)piperidine-1-yl)-4-methoxyphenyl) acrylamide | 677.5 [M + H]$^+$ | 1.31 |
| 276 | 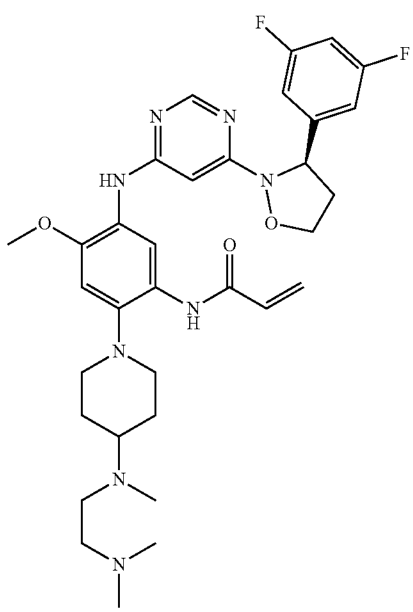 [SMILES: C=CC(=O)Nc1cc(Nc2cc(N3OCC[C@@H]3c3cc(F)cc(F)c3)ncn2)c(OC)cc1N1CCC(N(C)CCN(C)C)CC1] | N-(5-((6-((R)-3-(3,5-difluorophenyl) isoxazolidine-2-yl)pyrimidine-4-yl)amino)-2-(4-((2-(dimethylamino)ethyl) (methyl)amino) piperidine-1-yl)-4-methoxyphenyl) acrylamide | $^1$H NMR (400 MHz, CDCl$_3$) δ 8.87 (s, 1H), 8.45 (s, 1H), 8.37 (s, 1H), 7.03-6.99 (m, 2H) 6.93 (s, 1H), 6.75 (s, 1H), 6.72-6.65 (m, 2H), 6.40-6.25 (m, 2H), 5.75 (dd, J = 9.7, 1.8 Hz, 1H), 5.67 (dd, J = 8.8, 4.5 Hz, 1H), 4.15 (td, J = 8.1, 4.3 Hz, 1H), 4.11-3.84 (m, 4H), 3.85 (s, 2H), 3.11-3.02 (m, 2H), 2.80-2.59 (m, 8H), 2.49-2.29 (m, 10H), 2.02-1.96 (m, 2H), 1.78-1.67 (m, 2H), ; 637.6 [M + H]$^+$ | 1.25 |

TABLE 1-continued

| Example Compound | Structure | Name of Compound | ¹H NMR[[:]]; MS [M + H]⁺ | UPLC r.t. (min) |
|---|---|---|---|---|
| 277 | 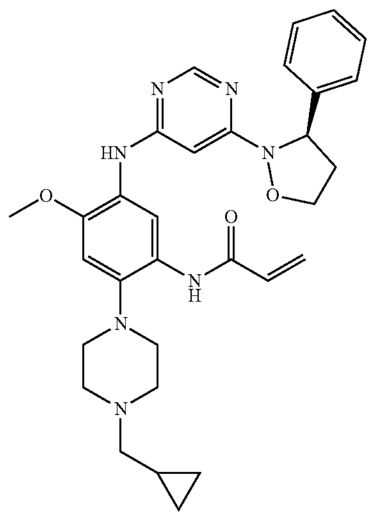 [SMILES: C=CC(=O)Nc1cc(Nc2cc(N3OCC[C@@H]3c3ccccc3)ncn2)c(OC)cc1N1CCN(CC2CC2)CC1] | N-(2-(4-(cyclopropylmethyl)piperazine-1-yl)-4-methoxy-5-((6-((R)-3-phenylisoxazolidine-2-yl)pyrimidine-4-yl)amino)phenyl)acrylamide | ¹H NMR (400 MHz, CDCl₃) δ 8.92 (s, 1H), 8.57 (s, 1H), 8.37 (s, 1H), 7.47 (d, J = 7.6 Hz, 2H), 7.34 (t, J = 7.6 Hz, 2H), 7.24 (s, 1H), 6.92 (s, 1H), 6.83 (s, 1H), 6.70 (s, 1H), 6.37 (d, J = 16.8 Hz, 1H), 6.26 (dd, J = 16.9, 10.0 Hz, 1H), 5.77-5.73 (m, 1H), 5.73-5.68 (m, 1H), 4.16 (td, J = 7.9, 4.6 Hz, 1H), 4.07 (q, J = 7.9 Hz, 1H), 3.83 (s, 3H), 2.95 (s, 4H), 2.81-2.72 (m, 3H), 2.44-2.38 (m, 1H), 2.36 (d, J = 6.8 Hz, 2H), 0.87 (m, 3H), 0.63-0.52 (m, 2H), 0.17 (m, 2H), ; 556.5 [M + H]⁺ | 1.38 |
| 278 | 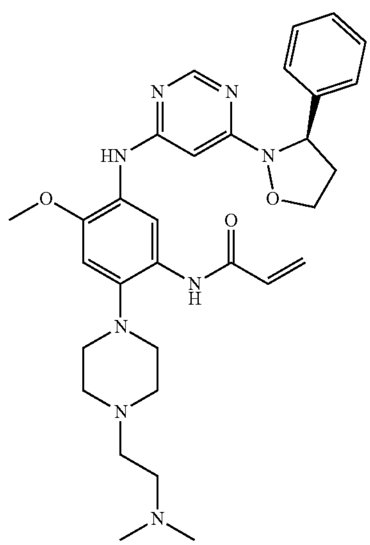 [SMILES: C=CC(=O)Nc1cc(Nc2cc(N3OCC[C@@H]3c3ccccc3)ncn2)c(OC)cc1N1CCN(CCN(C)C)CC1] | N-(2-(4-(2-(dimethylamino)ethyl)piperazine-1-yl)-4-methoxy-5-((6-((R)-3-phenylisoxazolidine-2-yl)pyrimidine-4-yl)amino)phenyl)acrylamide | ¹H NMR (400 MHz, CDCl₃) δ 8.90 (s, 1H), 8.55 (s, 1H), 8.37 (s, 1H), 7.46 (d, J = 7.6 Hz, 2H), 7.34 (t, J = 7.6 Hz, 2H), 7.23 (t, J = 7.3 Hz, 1H), 6.94 (s, 1H), 6.80 (s, 1H), 6.69 (s, 1H), 6.36 (d, J = 16.0 Hz, 1H), 6.27 (dd, J = 16.9, 9.9 Hz, 1H), 5.78-5.73 (m, 1H), 5.71-5.65 (m, 1H), 4.16 (td, J = 7.9, 4.6 Hz, 1H), 4.06 (dt, J = 8.0, 5.8 Hz, 1H), 3.82 (s, 3H), 2.98-2.88 (m, 4H), 2.80-2.64 (m, 4H), 2.62-2.57 (m, 2H), 2.54-2.48 (m, 2H), 2.44-2.34 (m, 2H), 2.31 (s, 6H), ; 573.5 [M + H]⁺ | 1.28 |
| 279 | 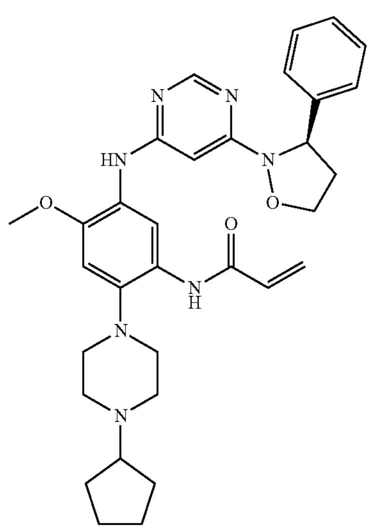 [SMILES: C=CC(=O)Nc1cc(Nc2cc(N3OCC[C@@H]3c3ccccc3)ncn2)c(OC)cc1N1CCN(C2CCCC2)CC1] | N-(2-(4-cyclopentylpiperazine-1-yl)-4-methoxy-5-((6-((R)-3-phenylisoxazolidine-2-yl)pyrimidine-4-yl)amino)phenyl)acrylamide | ¹H NMR (400 MHz, CDCl₃) δ 8.91 (s, 1H), 8.59 (s, 1H), 8.37 (s, 1H), 7.46 (d, J = 7.5 Hz, 2H), 7.34 (t, J = 7.6 Hz, 2H), 7.23 (dt, J = 7.3 Hz, 1H), 6.95 (s, 1H), 6.82 (s, 1H), 6.70 (s, 1H), 6.36 (d, J = 16.9 Hz, 1H), 6.27 (dd, J = 16.9, 9.9 Hz, 1H), 5.74 (dd, J = 10.0, 1.4 Hz, 1H), 5.72-5.67 (m, 1H), 4.16 (td, J = 7.9, 4.6 Hz, 1H), 4.07 (q, J = 7.9 Hz, 1H), 3.82 (s, 3H), 2.94 (s, 4H), 2.80-2.66 (m, 3H), 2.64-2.54 (m, 2H), 2.44-2.30 (m, 2H), 1.92 (m, 2H), 1.73 (m, 2H), 1.61 (m, 2H), 1.52-1.39 (m, 2H), ; 570.5 [M + H]⁺ | 1.41 |

TABLE 1-continued

| Example Compound | Structure | Name of Compound | ¹H NMR[[:]]; MS [M + H]⁺ | UPLC r.t. (min) |
|---|---|---|---|---|
| 280 | 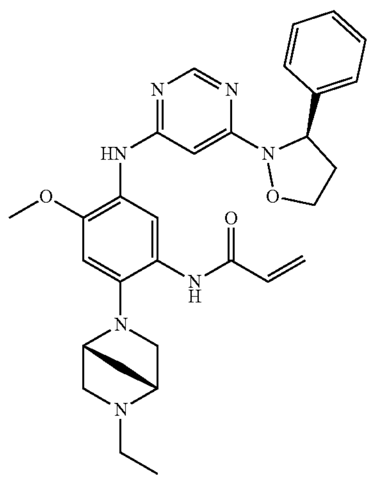 [SMILES: C=CC(=O)Nc1cc(Nc2cc(N3OCC[C@@H]3c3ccccc3)ncn2)c(OC)cc1N1C[C@H]2C[C@@H]1CN2CC] | N-(2-((1R,4R)-5-ethyl-2,5-diazabicyclo[2.2.1]heptane-2-yl)-4-methoxy-5-((6-((R)-3-phenylisoxazolidine-2-yl)pyrimidine-4-yl)amino)phenyl) acrylamide | ¹H NMR (400 MHz, CDCl₃) δ 8.56 (s, 1H), 8.35 (s, 1H), 7.95 (s, 1H), 7.46 (d, J = 7.6 Hz, 2H), 7.34 (t, J = 7.6 Hz, 2H), 7.23 (d, J = 7.3 Hz, 1H), 6.80 (s, 1H), 6.68 (s, 1H), 6.64 (s, 1H), 6.38 (d, J = 16.7 Hz, 1H), 6.28 (dd, J = 16.8, 10.0 Hz, 1H), 5.74 (d, J = 10.6 Hz, 1H), 5.70 (dd, J = 8.6, 4.5 Hz, 1H), 4.21-4.12 (m, 1H), 4.05 (dd, J = 15.9, 8.1 Hz, 1H), 3.84 (s, 3H), 3.73 (s, 1H), 3.57 (s, 1H), 3.48 (d, J = 9.2 Hz, 1H), 3.07 (d, J = 8.1 Hz, 1H), 2.81 (s, 2H), 2.78-2.70 (m, 2H), 2.58 (m, 1H), 2.44-2.33 (m, 1H), 1.90 (dd, J = 21.0, 9.5 Hz, 2H), 1.13 (t, J = 7.0 Hz, 3H), ; 542.5 [M + H]⁺ | 1.34 |
| 281 | 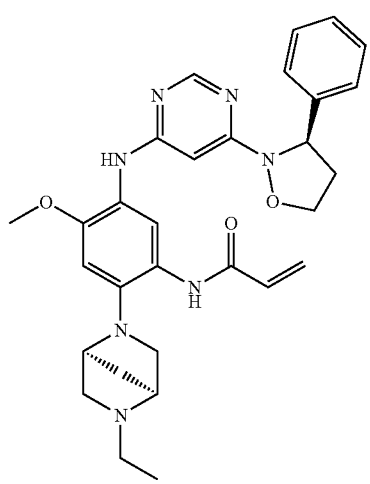 [SMILES: C=CC(=O)Nc1cc(Nc2cc(N3OCC[C@@H]3c3ccccc3)ncn2)c(OC)cc1N1C[C@@H]2C[C@H]1CN2CC] | N-(2-((1S,4S)-5-ethyl-2,5-diazabicyclo[2.2.1]heptane-2-yl)-4-methoxy-5-((6-((R)-3-phenylisoxazolidine-2-yl)pyrimidine-4-yl)amino)phenyl) acrylamide | ¹H NMR (400 MHz, CDCl₃) δ 8.55 (s, 1H), 8.34 (s, 1H), 7.95 (s, 1H), 7.46 (d, J = 7.6 Hz, 2H), 7.33 (t, J = 7.6 Hz, 2H), 7.24 (m, 1H), 6.86 (s, 1H), 6.65 (s, 1H), 6.60 (s, 1H), 6.38 (d, J = 16.5 Hz, 1H), 6.29 (dd, J = 16.9, 9.9 Hz, 1H), 5.73 (d, J = 10.5 Hz, 1H), 5.69 (dd, J = 8.6, 4.4 Hz, 1H), 4.14 (td, J = 7.8, 4.6 Hz, 1H), 4.02 (q, J = 7.8 Hz, 1H), 3.83 (s, 3H), 3.72 (s, 1H), 3.58 (s, 1H), 3.46 (d, J = 9.6 Hz, 1H), 3.11 (d, J = 8.2 Hz, 1H), 2.82 (s, 2H), 2.79-2.66 (m, 2H), 2.58 (m, 1H), 2.43-2.33 (m, 1H), 1.90 (dd, J = 21.0, 9.6 Hz, 2H), 1.12 (t, J = 7.1 Hz, 3H), ; 542.4 [M + H]⁺ | 1.35 |
| 282 | 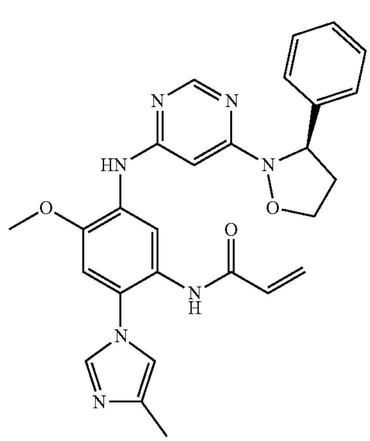 [SMILES: C=CC(=O)Nc1cc(Nc2cc(N3OCC[C@@H]3c3ccccc3)ncn2)c(OC)cc1-n1cnc(C)c1] | N-(4-methoxy-2-(4-methyl-1H-imidazole-1-yl)-5-((6-((R)-3-phenylisoxazolidine-2-yl)pyrimidine-4-yl)amino)phenyl) acrylamide | ¹H NMR (400 MHz, CDCl₃) δ 9.40 (s, 1H), 8.92 (s, 1H), 8.42 (s, 1H), 7.50-7.43 (m, 3H), 7.36 (t, J = 7.6 Hz, 2H), 7.28-7.25 (m, 1H), 7.15 (s, 1H), 6.79 (s, 1H), 6.75 (s, 1H), 6.72 (s, 1H), 6.44-6.31 (m, 1H), 6.27-6.15 (m, 1H), 5.80-5.73 (m, 1H), 5.73-5.66 (m, 1H), 4.20 (m, 1H), 4.11-3.99 (m, 1H), 3.88 (s, 3H), 2.77 (m, 1H), 2.49-2.37 (m, 1H), 2.23 (s, 3H), ; 498.4 [M + H]⁺ | 1.49 |

| Example Compound | Structure | Name of Compound | ¹H NMR[[:]]; MS [M + H]⁺ | UPLC r.t. (min) |
|---|---|---|---|---|
| 283 | 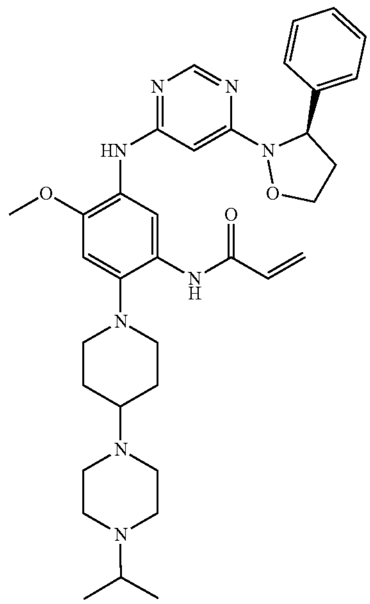 | N-(2-(4-(4-isopropylpiperazine-1-yl)piperidine-1-yl)-4-methoxy-5-((6-((R)-3-phenylisoxazolidine-2-yl)pyrimidine-4-yl)amino)phenyl) acrylamide | ¹H NMR (400 MHz, Chloroform-d) δ 8.88 (s, 1H), 8.45 (s, 1H), 8.37 (s, 1H), 7.46 (d, J = 7.3 Hz, 2H), 7.34 (dd, J = 8.3, 6.8 Hz, 2H), 7.24 (s, 1H), 6.89 (s, 1H), 6.74 (s, 1H), 6.69 (s, 1H), 6.35 (dd, J = 16.9, 1.5 Hz, 1H), 6.24 (dd, J = 16.9, 10.1 Hz, 1H), 5.72 (ddd, J = 13.2, 9.3. 3.0 Hz, 2H), 4.15 (td, J = 7.9, 4.4 Hz, 1H), 4.07 (q, J = 8.0 Hz, 1H), 3.84 (s, 3H), 3.06 (d, J = 11.4 Hz, 2H), 2.76-2.70 (m, 4H), 2.44-2.25 (m, 3H), 2.09 (d, J = 12.0 Hz, 2H), 1.69-1.64 (m, 3H), 1.09 (d, J = 6.5 Hz, 8H), ; 627.6 [M + H]⁺ | 1.10 |
| 284 | 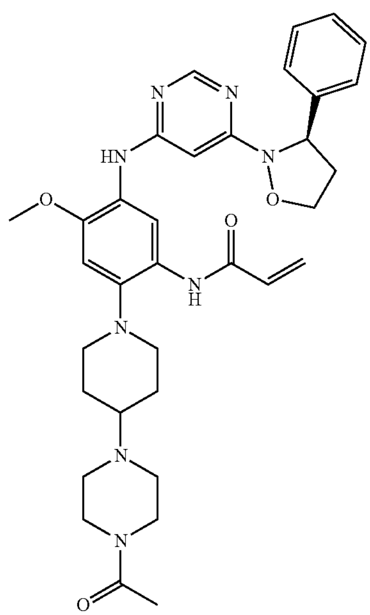 [SMILES: C=CC(=O)Nc1cc(Nc2cc(N3OCC[C@@H]3c3ccccc3)ncn2)c(OC)cc1N1CCC(N2CCN(C(C)=O)CC2)CC1] | N-(2-(4-(4-acetylpiperazine-1-yl)piperidine-1-yl)-4-methoxy-5-((6-((R)-3-phenylisoxazolidine-2-yl)pyrimidine-4-yl)amino)phenyl) acrylamide | ¹H NMR (400 MHz, Chloroform-d) δ 8.87 (s, 1H), 8.42 (s, 1H), 8.38-8.34 (m, 1H), 7.46 (d, J = 7.3 Hz, 2H), 7.33 (dd, J = 8.4, 6.8 Hz, 2H), 7.26-7.21 (m, 1H), 6.97 (s, 1H), 6.74 (s, 1H), 6.69 (s, 1H), 6.37 (dd, J = 17.0, 1.6 Hz, 1H), 6.25 (dd, J = 16.9, 10.0 Hz, 1H), 5.72 (ddd, J = 18.4, 9.3, 3.0 Hz, 2H), 4.15 (td, J = 8.0, 4.4 Hz, 1H), 4.06 (q, J = 8.0 Hz, 1H), 3.83 (s, 3H), 3.66 (t, J = 5.1 Hz, 2H), 3.51 (t, J = 5.0 Hz, 2H), 3.06 (d, J = 11.0 Hz, 2H), 2.77-2.60 (m, 3H), 2.62-2.58 (m, 3H), 2.40 (ddd, J = 10.5, 8.2, 4.3 Hz, 2H), 2.10 (s, 3H), 2.03 (d, J = 13.6 Hz, 2H), 1.71-1.61 (m, 2H), 1.26 (s, 1H), ; 627.6 [M + H]⁺ | 1.35 |

TABLE 1-continued

| Example Compound | Structure | Name of Compound | ¹H NMR[:]; MS [M + H]⁺ | UPLC r.t. (min) |
|---|---|---|---|---|
| 285 | 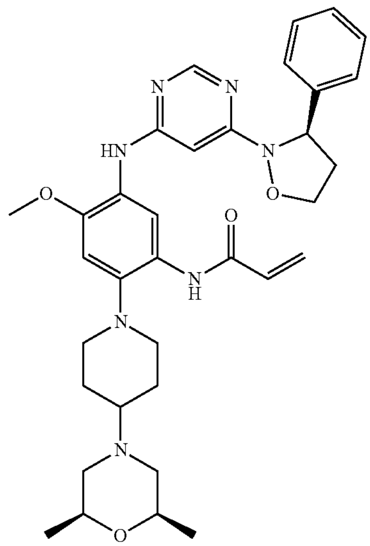 [SMILES: C=CC(=O)Nc1cc(Nc2cc(N3OCC[C@@H]3c3ccccc3)ncn2)c(OC)cc1N1CCC(N2C[C@@H](C)O[C@@H](C)C2)CC1] | N-(2-(4-((2S,6R)-2,6-dimethylmorpholino)piperidine-1-yl)-4-methoxy-5-((6-((R)-3-phenylisoxazolidine-2-yl)pyrimidine-4-yl)amino)phenyl)acrylamide | ¹H NMR (400 MHz, Chloroform-d) δ 8.87 (s, 1H), 8.43 (s, 1H), 8.37 (s, 1H), 7.46 (d, J = 7.6 Hz, 2H), 7.34 (d, J = 7.6 Hz, 2H), 7.23 (d, J = 7.3 Hz, 1H), 6.96 (s, 1H), 6.74 (s, 1H), 6.69 (s, 1H), 6.41-6.33 (m, 1H), 6.26 (dd, J = 16.9, 9.8 Hz, 1H), 5.72 (ddd, J = 16.7, 9.3, 3.0 Hz, 2H), 4.16 (td, J = 7.9, 4.5 Hz, 1H), 4.07 (q, J = 8.0 Hz, 1H), 3.84 (s, 3H), 3.72 (s, 2H), 3.07 (d, J = 11.2 Hz, 2H), 2.89 (d, J = 10.7 Hz, 2H), 2.77-2.67 (m, 3H), 2.42-2.35 (m, 1H), 2.30 (dd, J = 13.2, 7.6 Hz, 2H), 2.07 (d, J = 13.3 Hz, 3H), 1.91 (t, J = 10.1 Hz, 3H), 1.73-1.63 (m, 5H), ; 614.6 [M + H]⁺ | 1.33 |
| 286 | 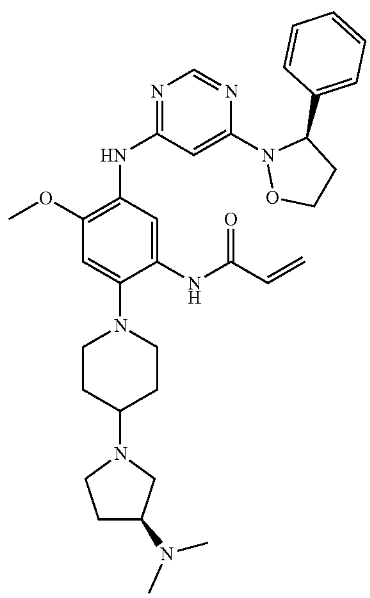 [SMILES: C=CC(=O)Nc1cc(Nc2cc(N3OCC[C@@H]3c3ccccc3)ncn2)c(OC)cc1N1CCC(N2CC[C@H](N(C)C)C2)CC1] | N-(2-(4-((S)-3-(dimethylamino)pyrolidine-1-yl)piperidine-1-yl)-4-methoxy-5-((6-((R)-3-phenylisoxazolidine-2-yl)pyrimidine-4-yl)amino)phenyl)acrylamide | ¹H NMR (400 MHz, Chloroform-d) δ 8.86 (s, 1H), 8.49 (s, 1H), 8.36 (d, J = 1.0 Hz, 1H), 7.48-7.44 (m, 2H), 7.33 (dd, J = 8.5, 6.8 Hz, 2H), 7.26-7.20 (m, 1H), 6.94 (s, 1H), 6.75 (s, 1H), 6.69 (s, 1H), 6.34 (dd, J = 16.9, 1.5 Hz, 1H), 6.23 (dd, J = 16.9, 10.0 Hz, 1H), 5.71 (ddd, J = 12.4, 9.3, 3.0 Hz, 2H), 4.15 (td, J = 8.0, 4.5 Hz, 1H), 4.07 (q, J = 8.0 Hz, 1H), 3.84 (s, 3H), 3.05 (ddd, J = 21.8, 9.9, 5.4 Hz, 3H), 2.93 (td, J = 8.4, 5.1 Hz, 1H), 2.75 (tdd, J = 11.7, 5.7, 2.4 Hz, 4H), 2.56 (td, J = 9.0, 6.5 Hz, 1H), 2.42-2.34 (m, 2H), 2.26 (s, 6H), 2.22-2.16 (m, 1H), 2.10-2.01 (m, 3H), 1.81-1.67 (m, 3H), ; 613.6 [M + H]⁺ | 1.27 |

TABLE 1-continued

| Example Compound | Structure | Name of Compound | $^1$H NMR[[:]]; MS [M + H]$^+$ | UPLC r.t. (min) |
|---|---|---|---|---|
| 287 | 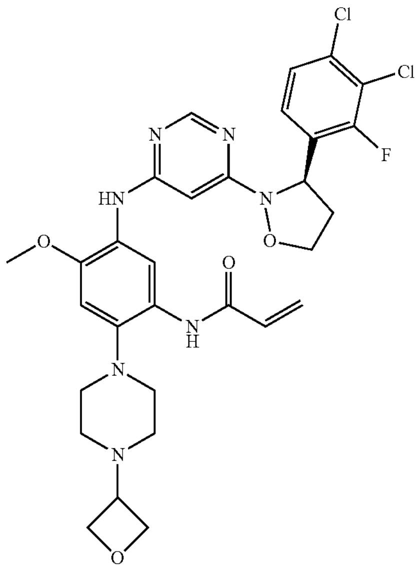 [SMILES: C=CC(=O)Nc1cc(Nc2cc(N3OCC[C@@H]3c3ccc(Cl)c(Cl)c3F)ncn2)c(OC)cc1N1CCN(C2COC2)CC1] | N-(5-((6-((R)-3-(3,4-dichloro-2-fluorophenyl)isoxazolidine-2-yl)pyrimidine-4-yl)amino)-4-methoxy-2-(4-(oxetane-3-yl)piperazine-1-yl)phenyl)acrylamide | $^1$H NMR (400 MHz, DMSO-d$_6$) δ 9.95 (s, 1H), 9.18 (s, 1H), 8.32 (s, 1H), 8.04-7.99 (m, 1H), 7.54 (dd, J = 8.5, 1.5 Hz, 1H), 7.38 (t, J = 8.1 Hz, 1H), 6.92 (s, 1H), 6.70 (dd, J = 17.0, 10.2 Hz, 1H), 6.24 (dd, J = 17.0, 2.0 Hz, 1H), 6.13 (s, 1H), 5.76 (dd, J = 9.7, 2.3 Hz, 1H), 5.68 (dd, J = 8.7, 5.7 Hz, 1H), 4.85-4.77 (m, 4H), 4.54 (s, 1H), 4.07 (d, J = 7.8 Hz, 2H), 3.83 (s, 3H), 3.52 (s, 2H), 3.39-3.34 (m, 1H), 3.26 (s, 4H), 3.16 (d, J = 12.1 Hz, 2H), 2.97 (d, J = 8.0 Hz, 1H); 644.2 [M + H]$^+$ | 1.65 |
| 288 | 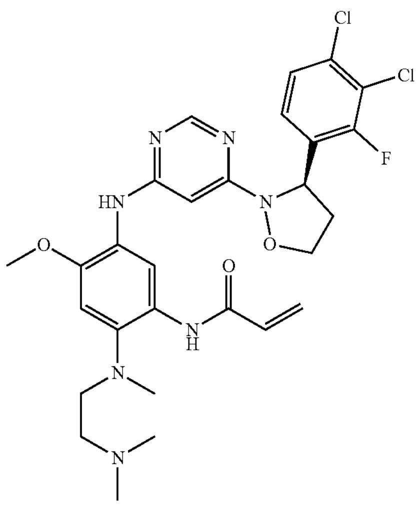 | N-(5-((6-((R)-3-(3,4-dichloro-2-fluorophenyl)isoxazolidine-2-yl)pyrimidine-4-yl)amino)-2-((2-(dimethylamino)ethyl)(methyl)amino)-4-methoxyphenyl)acrylamide | $^1$H NMR (400 MHz, DMSO-d$_6$) δ 9.88 (s, 1H), 9.73 (s, 1H), 8.28 (s, 1H), 8.09 (s, 1H), 7.53 (dd, J = 8.6, 1.5 Hz, 1H), 7.41 (t, J = 8.1 Hz, 1H), 7.20 (dd, J = 17.0, 10.2 Hz, 1H), 6.96 (s, 1H), 6.30-6.19 (m, 2H), 5.73-5.66 (m, 2H), 4.33-4.27 (m, 1H), 4.03 (d, J = 7.9 Hz, 1H), 3.83 (s, 3H), 3.32 (s, 4H), 2.93 (d, J = 8.3 Hz, 1H), 2.73 (d, J = 4.8 Hz, 6H), 2.61 (s, 3H), 2.30 (dd, J = 13.2, 6.1 Hz, 1H); 604.2 [M + H]$^+$ | 1.76 |
| 289 | 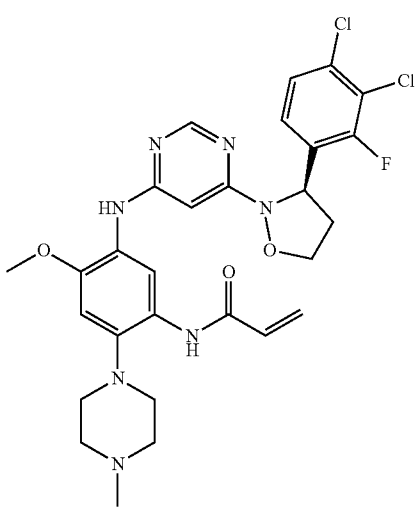 | N-(5-((6-((R)-3-(3,4-dichloro-2-fluorophenyl)isoxazolidine-2-yl)pyrimidine-4-yl)amino)-4-methoxy-2-(4-methylpiperazine-1-yl)phenyl)acrylamide | $^1$H NMR (400 MHz, DMSO-d$_6$) δ 9.77 (s, 1H), 9.17 (s, 1H), 8.28 (s, 1H), 8.07 (s, 1H), 7.53 (dd, J = 8.6, 1.5 Hz, 1H), 7.40 (t, J = 8.1 Hz, 1H), 6.88 (s, 1H), 6.81-6.72 (m, 1H), 6.28-6.18 (m, 2H), 5.78-5.65 (m, 2H), 4.28 (dd, J = 7.8, 4.0 Hz, 1H), 4.03 (s, 1H), 3.83 (s, 3H), 3.48 (d, J = 11.5 Hz, 2H), 3.42-3.36 (m, 2H), 3.20 (s, 4H), 2.97-2.87 (m, 1H), 2.82 (d, J = 4.6 Hz, 3H), 2.36-2.24 (m, 1H), ; 602.2 [M + H]$^+$ | 1.64 |

TABLE 1-continued

| Example Compound | Structure | Name of Compound | ¹H NMR[:]; MS [M + H]⁺ | UPLC r.t. (min) |
|---|---|---|---|---|
| 290 | 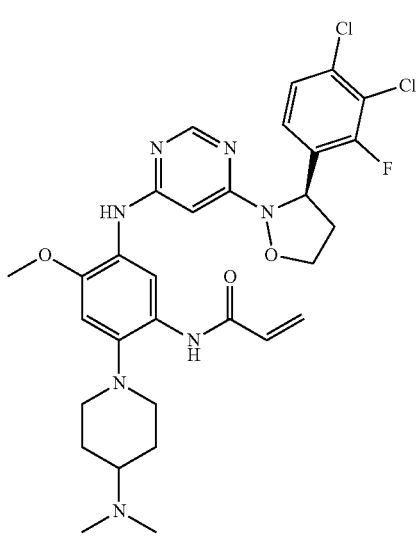 | N-(5-((6-((R)-3-(3,4-dichloro-2-fluorophenyl)isoxazolidine-2-yl)pyrimidine-4-yl)amino)-2-(4-(dimethylamino)piperidine-1-yl)-4-methoxyphenyl)acrylamide | ¹H NMR (400 MHz, DMSO-d₆) δ 9.25 (s, 1H), 8.75 (s, 1H), 8.32 (s, 1H), 7.93 (s, 1H), 7.53 (dd, J = 8.5, 1.5 Hz, 1H), 7.39 (t, J = 8.1 Hz, 1H), 6.92 (s, 1H), 6.75 (dd, J = 16.9, 10.2 Hz, 1H), 6.25 (dd, J = 17.0, 1.9 Hz, 2H), 5.79-5.74 (m, 1H), 5.71-5.66 (m, 1H), 4.33-4.30 (m, 1H), 4.06 (d, J = 7.8 Hz, 1H), 3.82 (s, 3H), 3.68 (d, J = 7.3 Hz, 1H), 3.38 (d, J = 6.9 Hz, 1H), 3.08 (s, 1H), 2.95 (d, J = 4.9 Hz, 1H), 2.81 (s, 1H), 2.73 (d, J = 5.5 Hz, 6H), 2.36-2.28 (m, 1H), 2.13 (d, J = 9.5 Hz, 2H), 2.03 (d, J = 11.0 Hz, 2H), 1.90 (d, J = 7.1 Hz, 1H), ; 630.2 [M + H]⁺ | 1.72 |
| 291 | 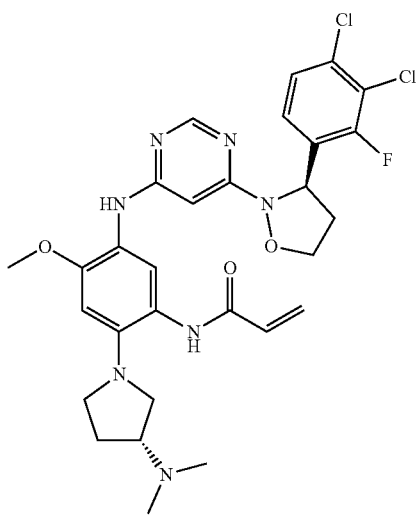 [SMILES: C=CC(=O)Nc1cc(Nc2cc(N3OCC[C@@H]3c3ccc(Cl)c(Cl)c3F)ncn2)c(OC)cc1N1CC[C@@H](N(C)C)C1] | N-(5-((6-((R)-3-(3,4-dichloro-2-fluorophenyl)isoxazolidine-2-yl)pyrimidine-4-yl)amino)-2-((R)-3-(dimethylamino)pyrolidine-1-yl)-4-methoxyphenyl)acrylamide | ¹H NMR (400 MHz, DMSO-d₆) δ 9.54 (d, J = 30.1 Hz, 1H), 8.25 (d, J = 2.9 Hz, 1H), 7.64 (s, 1H), 7.53 (dd, J = 8.5, 1.5 Hz, 1H), 7.40 (t, J = 8.1 Hz, 2H), 6.85 (dd, J = 17.0, 10.2 Hz, 1H), 6.66 (d, J = 21.0 Hz, 1H), 6.25-6.08 (m, 2H), 5.74-5.65 (m, 2H), 4.27 (q, J = 6.7, 5.3 Hz, 1H), 3.99 (d, J = 7.8 Hz, 1H), 3.88 (s, 1H), 3.81 (d, J = 3.1 Hz, 3H), 3.59 (s, 1H), 3.48 (s, 1H), 3.41-3.36 (m, 1H), 3.05 (d, J = 8.4 Hz, 1H), 2.80 (dd, J = 8.3, 4.6 Hz, 6H), 2.36-2.21 (m, 4H), ; 616.2 [M + H]⁺ | 1.64 |

TABLE 1-continued

| Example Compound | Structure | Name of Compound | ¹H NMR[[:]]; MS [M + H]⁺ | UPLC r.t. (min) |
|---|---|---|---|---|
| 292 | 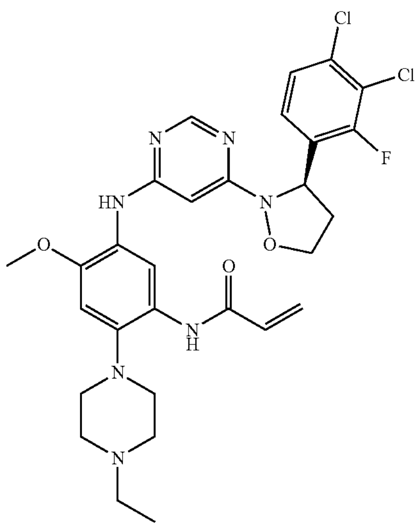 [SMILES: C=CC(=O)Nc1cc(Nc2cc(N3OCC[C@@H]3c3ccc(Cl)c(Cl)c3F)ncn2)c(OC)cc1N1CCN(CC)CC1] | N-(5-((6-((R)-3-(3,4-dichloro-2-fluorophenyl)isoxazolidine-2-yl)pyrimidine-4-yl)amino)-2-(4-ethylpiperazine-1-yl)-4-methoxyphenyl)acrylamide | ¹H NMR (400 MHz, DMSO-d$_6$) δ 9.81 (s, 1H), 9.21 (s, 1H), 8.29 (s, 1H), 8.07 (s, 1H), 7.53 (dd, J = 8.5, 1.5 Hz, 1H), 7.40 (t, J = 8.1 Hz, 1H), 6.90-6.72 (m, 2H), 6.31-6.17 (m, 2H), 5.73 (ddd, J = 23.7, 9.4, 3.8 Hz, 2H), 4.31-4.27 (m, 1H), 4.02 (d, J = 8.0 Hz, 2H), 3.83 (s, 3H), 3.52 (d, J = 11.3 Hz, 2H), 3.40-3.29 (m, 3H), 3.22-3.14 (m, 4H), 2.93 (dd, J = 8.1, 4.3 Hz, 1H), 2.34-2.24 (m, 1H), 1.32 (t, J = 7.2 Hz, 3H); 616.2 [M + H]⁺ | 1.68 |
| 293 | 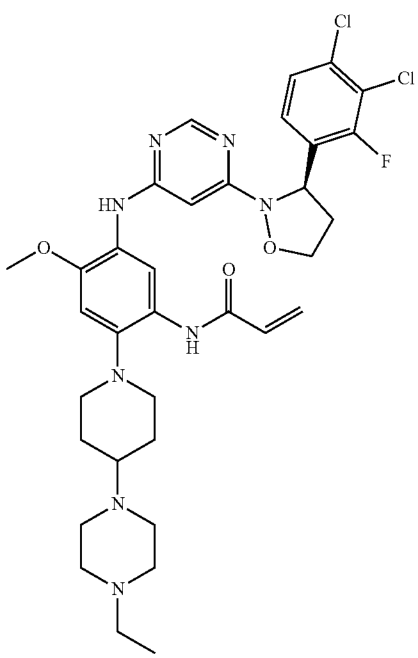 | N-(5-((6-((R)-3-(3,4-dichloro-2-fluorophenyl)isoxazolidine-2-yl)pyrimidine-4-yl)amino)-2-(4-(4-ethylpiperazine-1-yl)piperidine-1-yl)-4-methoxyphenyl)acrylamide | 698.3 [M + H]⁺ | 1.63 |

TABLE 1-continued

| Example Compound | Structure | Name of Compound | $^1$H NMR[:]; MS [M + H]$^+$ | UPLC r.t. (min) |
|---|---|---|---|---|
| 294 | 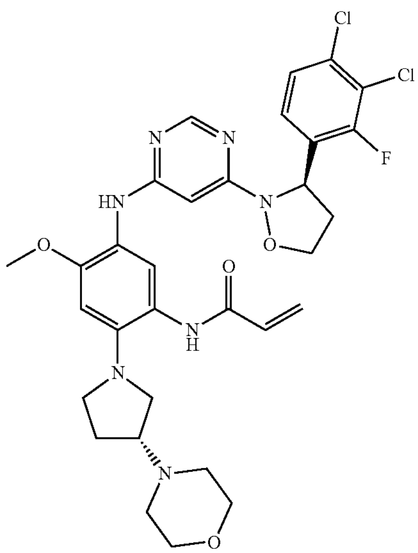 [SMILES: C=CC(=O)Nc1cc(Nc2cc(N3OCC[C@@H]3c3ccc(Cl)c(Cl)c3F)ncn2)c(OC)cc1N1CC[C@@H](N2CCOCC2)C1] | N-(5-((6-((R)-3-(3,4-dichloro-2-fluorophenyl)isoxazolidine-2-yl)pyrimidine-4-yl)amino)-4-methoxy-2-((R)-3-morpholinopyrolidine-1-yl)phenyl)acrylamide | $^1$H NMR (400 MHz, DMSO-d$_6$) δ 9.67 (s, 1H), 9.60 (s, 1H), 8.26 (s, 1H), 7.64 (s, 1H), 7.53 (dd, J = 8.6, 1.5 Hz, 1H), 7.39 (t, J = 8.1 Hz, 1H), 6.86 (dd, J = 17.0, 10.2 Hz, 1H), 6.70 (s, 1H), 6.21 (dd, J = 17.0, 2.1 Hz, 1H), 6.13 (s, 1H), 5.70 (dd, J = 9.9, 2.4 Hz, 2H), 4.31-4.27 (m, 1H), 3.97 (s, 2H), 3.82 (s, 3H), 3.56 (d, J = 12.1 Hz, 2H), 3.50-3.47 (m, 1H), 3.38 (d, J = 7.0 Hz, 3H), 3.11 (dd, J = 15.7, 7.3 Hz, 4H), 2.98-2.87 (m, 1H), 2.32 (dd, J = 14.0, 6.7 Hz, 3H), 1.09 (t, J = 7.0 Hz, 2H), ; 658.4 [M + H]$^+$ | 1.37 |
| 295 | 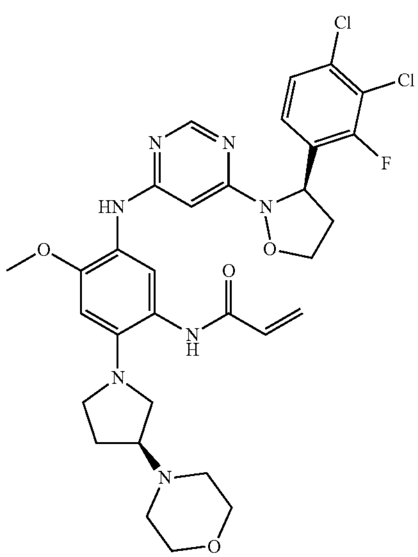 [SMILES: C=CC(=O)Nc1cc(Nc2cc(N3OCC[C@@H]3c3ccc(Cl)c(Cl)c3F)ncn2)c(OC)cc1N1CC[C@H](N2CCOCC2)C1] | N-(5-((6-((R)-3-(3,4-dichloro-2-fluorophenyl)isoxazolidine-2-yl)pyrimidine-4-yl)amino)-4-methoxy-2-((S)-3-morpholinopyrolidine-1-yl)phenyl)acrylamide | $^1$H NMR (400 MHz, DMSO-d$_6$) δ 9.79 (s, 1H), 9.59 (d, J = 33.2 Hz, 1H), 8.27 (d, J = 2.6 Hz, 1H), 7.62 (s, 1H), 7.53 (dd, J = 8.6, 1.5 Hz, 1H), 7.40 (dd, J = 8.1, 2.3 Hz, 1H), 6.87 (dd, J = 17.0, 10.2 Hz, 1H), 6.68 (d, J = 22.7 Hz, 1H), 6.21 (dd, J = 17.0, 2.1 Hz, 1H), 6.12 (s, 1H), 5.73-5.66 (m, 2H), 4.31-4.26 (m, 1H), 4.05 (s, 1H), 3.81 (d, J = 3.2 Hz, 3H), 3.53 (d, J = 20.3 Hz, 4H), 3.43-3.38 (m, 1H), 3.16 (d, J = 7.6 Hz, 4H), 2.96 (d, J = 6.3 Hz, 2H), 2.44-2.27 (m, 4H), 1.65-1.55 (m, 1H), 1.50-1.40 (m, 1H), ; 658.4 [M + H]$^+$ | 1.38 |

TABLE 1-continued

| Example Compound | Structure | Name of Compound | ¹H NMR[[:]]; MS [M + H]⁺ | UPLC r.t. (min) |
|---|---|---|---|---|
| 296 | 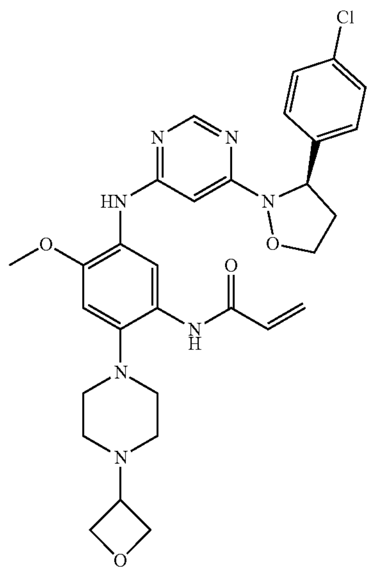 [SMILES: C=CC(=O)Nc1cc(Nc2cc(N3OCC[C@@H]3c3ccc(Cl)cc3)ncn2)c(OC)cc1N1CCN(C2COC2)CC1] | N-(5-((6-((R)-3-(4-chlorophenyl)isoxazolidine-2-yl)pyrimidine-4-yl)amino)-4-methoxy-2-(4-(oxetane-3-yl)piperazine-1-yl)phenyl)acrylamide | 592.5 [M + H]⁺ | 1.48 |
| 297 | 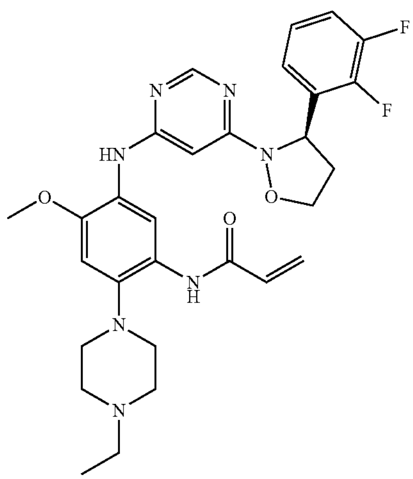 [SMILES: C=CC(=O)Nc1cc(Nc2cc(N3OCC[C@@H]3c3cccc(F)c3F)ncn2)c(OC)cc1N1CCN(CC)CC1] | N-(5-((6-((R)-3-(2,3-difluorophenyl)isoxazolidine-2-yl)pyrimidine-4-yl)amino)-2-(4-ethylpiperazine-1-yl)-4-methoxyphenyl)acrylamide | ¹H NMR (400 MHz, Chloroform-d) δ 8.90 (s, 1H), 8.56 (s, 1H), 8.37 (d, J = 1.0 Hz, 1H), 7.40-7.31 (m, 1H), 7.08-7.01 (m, 2H), 6.98 (s, 1H), 6.82 (s, 1H), 6.75 (s, 1H), 6.37 (dd, J = 17.0, 1.6 Hz, 1H), 6.26 (dd, J = 16.9, 9.9 Hz, 1H), 5.93 (dd, J = 8.8, 4.5 Hz, 1H), 5.75 (dd, J = 9.9, 1.6 Hz, 1H), 4.19-4.11 (m, 1H), 4.11-4.01 (m, 1H), 3.83 (s, 3H), 2.96-2.91 (m, 4H), 2.88-2.81 (m, 1H), 2.75-2.55 (m, 4H), 2.52 (q, J = 7.2 Hz, 2H), 2.36-2.27 (m, 1H), 1.16 (t, J = 7.2 Hz, 3H); 566.4 [M + H]⁺ | 1.21 |
| 298 | 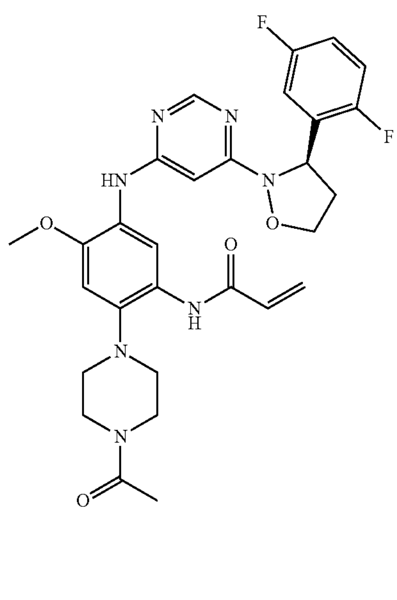 [SMILES: C=CC(=O)Nc1cc(Nc2cc(N3OCC[C@@H]3c3cc(F)ccc3F)ncn2)c(OC)cc1N1CCN(C(C)=O)CC1] | N-(2-(4-acetylpiperazine-1-yl)-5-((6-((R)-3-(2,5-difluorophenyl)isoxazolidine-2-yl)pyrimidine-4-yl)amino)-4-methoxyphenyl)acrylamide | ¹H NMR (400 MHz, CDCl₃) δ 8.91 (s, 1H), 8.43 (s, 1H), 8.36 (s, 1H), 7.35-7.28 (m, 1H), 7.21 (s, 1H), 7.04-6.94 (m, 1H), 6.94-6.86 (m, 1H), 6.75 (s, 1H), 6.73 (s, 1H), 6.30 (dt, J = 16.9, 13.2 Hz, 2H), 5.90 (dd, J = 8.7, 4.3 Hz, 1H), 5.77 (dd, J = 10.0, 1.2 Hz, 1H), 4.16-4.03 (m, 2H), 3.86 (s, 3H), 3.84-3.75 (m, 2H), 3.68-3.63 (m, 2H), 2.93-2.80 (m, 5H), 2.34-2.26 (m, 1H), 2.17 (s, 3H) 580.4 [M + H]⁺ | 1.41 |

TABLE 1-continued

| Example Compound | Structure | Name of Compound | ¹H NMR[[:]]; MS [M + H]⁺ | UPLC r.t. (min) |
|---|---|---|---|---|
| 299 | 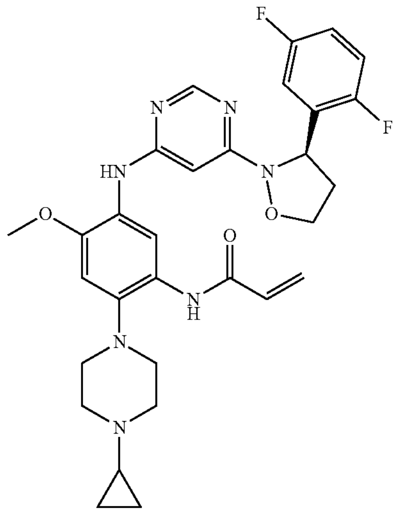 [SMILES: C=CC(=O)Nc1cc(Nc2cc(N3OCC[C@@H]3c3cc(F)ccc3F)ncn2)c(OC)cc1N1CCN(C2CC2)CC1] | N-(2-(4-cyclopropylpiperazine-1-yl)-5-((6-((R)-3-(2,5-difluorophenyl)isoxazolidine-2-yl)pyrimidine-4-yl)amino)-4-methoxyphenyl)acrylamide | ¹H NMR (400 MHz, CDCl₃) δ 8.91 (s, 1H), 8.60 (s, 1H), 8.37 (s, 1H), 7.36-7.28 (m, J = 9.0, 5.8, 3.2 Hz, 1H), 7.00 (td, J = 9.2, 4.4 Hz, 1H), 6.95 (s, 1H), 6.93-6.86 (m, 1H), 6.80 (s, 1H), 6.77 (s, 1H), 6.40-6.25 (m, 2H), 5.90 (dd, J = 8.7, 4.3 Hz, 1H), 5.75 (dd, J = 9.8, 1.6 Hz, 1H), 4.16-4.04 (m, 2H), 3.82 (s, 3H), 2.92-2.77 (m, 9H), 2.34-2.24 (m, 1H), 1.76-1.70 (m, 1H), 0.55-0.50 (m, 2H), 0.49-0.43 (m, 2H); 578.5 [M + H]⁺ | 1.23 |
| 300 | 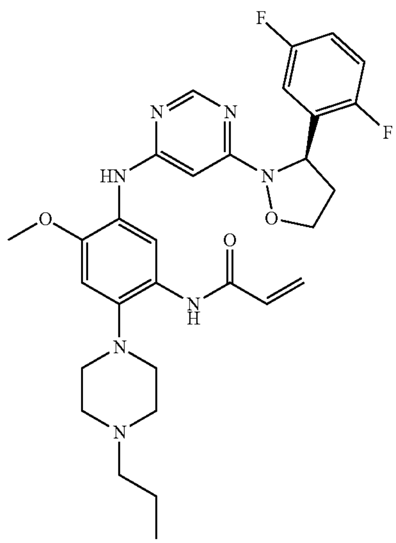 [SMILES: C=CC(=O)Nc1cc(Nc2cc(N3OCC[C@@H]3c3cc(F)ccc3F)ncn2)c(OC)cc1N1CCN(CCC)CC1] | N-(5-((6-((R)-3-(2,5-difluorophenyl)isoxazolidine-2-yl)pyrimidine-4-yl)amino)-4-methoxy-2-(4-propylpiperazine-1-yl)phenyl)acrylamide | ¹H NMR (400 MHz, CDCl₃) δ 8.91 (s, 1H), 8.57 (s, 1H), 8.37 (s, 1H), 7.36-7.28 (m, 1H), 7.04-6.94 (m, 2H), 6.93-6.87 (m, 1H), 6.82 (s, 1H), 6.77 (s, 1H), 6.30 (dt, J = 17.0, 13.1 Hz, 2H), 5.90 (dd, J = 8.6, 4.2 Hz, 1H), 5.74 (dd, J = 10.0, 1.1 Hz, 1H), 4.16-4.03 (m, 2H), 3.84 (m, 3H), 2.96-2.88 (m, 4H), 2.87-2.79 (m, 1H), 2.70-2.63 (m, 2H), 2.43-2.38 (m, 2H), 2.34-2.24 (m, 1H), 1.64-1.53 (m, 4H), 0.95 (t, J = 7.4 Hz, 3H); 580.5 [M + H]⁺ | 1.24 |
| 301 | 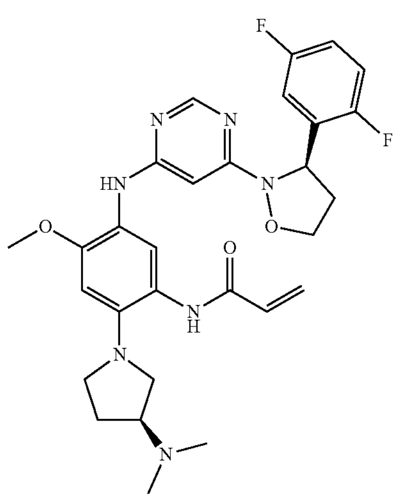 [SMILES: C=CC(=O)Nc1cc(Nc2cc(N3OCC[C@@H]3c3cc(F)ccc3F)ncn2)c(OC)cc1N1CC[C@H](N(C)C)C1] | N-(5-((6-((R)-3-(2,5-difluorophenyl)isoxazolidine-2-yl)pyrimidine-4-yl)amino)-2-((S)-3-(dimethylamino)pyrolidine-1-yl)-4-methoxyphenyl)acrylamide | ¹H NMR (400 MHz, CDCl₃) δ 8.71 (s, 1H), 8.36 (s, 1H), 8.17 (s, 1H), 7.35-7.29 (m, 1H), 7.00 (td, J = 9.2, 4.4 Hz, 1H), 6.92-6.85 (m, J = 10.9, 5.4 Hz, 2H), 6.77 (s, 1H), 6.72 (s, 1H), 6.42-6.23 (m, 2H), 5.90 (dd, J = 8.6, 4.1 Hz, 1H), 5.73 (dd, J = 10.0, 1.3 Hz, 1H), 4.15-4.01 (m, 2H), 3.85 (s, 3H), 3.22-3.03 (m, 3H) 2.93-2.76 (m, 2H), 2.35-2.12 (m, 9H), 1.99-1.89 (m, 1H) 566.5 [M + H]⁺ | 1.17 |

TABLE 1-continued

| Example Compound | Structure | Name of Compound | ¹H NMR[[:]]; MS [M + H]⁺ | UPLC r.t. (min) |
|---|---|---|---|---|
| 302 | 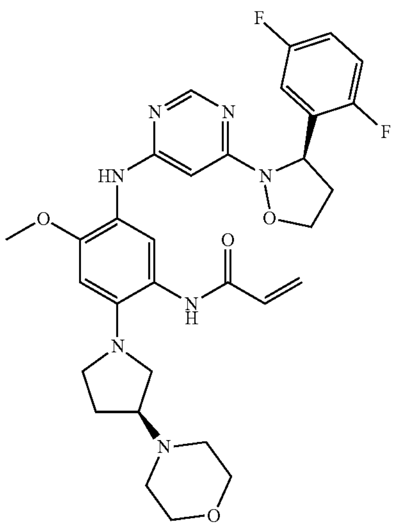 [SMILES: C=CC(=O)Nc1cc(Nc2cc(N3OCC[C@@H]3c3cc(F)ccc3F)ncn2)c(OC)cc1N1CC[C@H](N2CCOCC2)C1] | N-(5-((6-((R)-3-(2,5-difluorophenyl)isoxazolidine-2-yl)pyrimidine-4-yl)amino)-4-methoxy-2-((S)-3-morpholinopyrrolidine-1-yl)phenyl)acrylamide | ¹H NMR (400 MHz, CDCl₃) δ 8.73 (s, 1H), 8.36 (s, 1H), 8.14 (s, 1H), 7.35-7.29 (m, 1H), 7.02-6.87 (m, 3H), 6.77 (s, 1H), 6.72 (s, 1H), 6.41-6.22 (m, 2H), 5.90 (dd, J = 8.6, 4.2 Hz, 1H), 5.76-5.71 (m, 1H), 4.15-4.01 (m, 2H), 3.85 (s, 1H), 3.78-3.74 (m, 4H), 3.21-3.08 (m, 3H), 3.02-2.96 (m, 1H), 2.85-2.77 (m, 1H), 2.60-2.55 (m, 2H), 2.52-2.44 (m, 2H), 2.33-2.14 (m, 3H), 2.00-1.90 (m, 1H); 608.46 [M + H]⁺ | 1.18 |
| 303 | 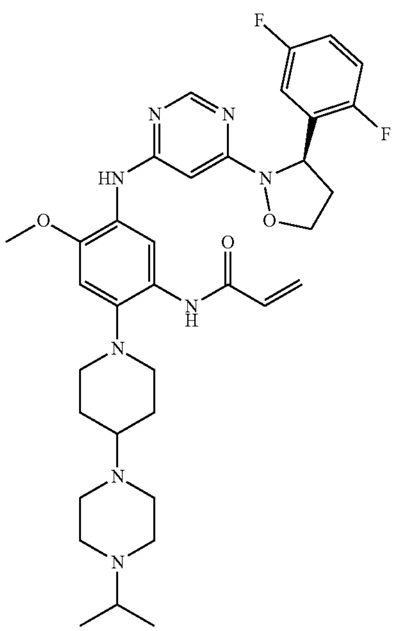 [SMILES: C=CC(=O)Nc1cc(Nc2cc(N3OCC[C@@H]3c3cc(F)ccc3F)ncn2)c(OC)cc1N1CCC(N2CCN(C(C)C)CC2)CC1] | N-(5-((6-((R)-3-(2,5-difluorophenyl)isoxazolidine-2-yl)pyrimidine-4-yl)amino)-2-(4-(4-isopropylpiperazine-1-yl)piperidine-1-yl)-4-methoxyphenyl)acrylamide | ¹H NMR (400 MHz, Methanol-d₄) δ 8.29 (s, 1H), 8.18 (s, 1H), 7.29-7.20 (m, 1H), 7.15 (td, J = 4.3, 9.3 Hz, 1H), 7.04 (tt, J = 3.6, 8.2 Hz, 1H), 6.93 (s, 1H), 6.63-6.45 (m, 2H), 6.45-6.27 (m, 1H), 5.88-5.68 (m, 2H), 4.16 (dt, J = 4.0, 8.1 Hz, 1H), 3.99 (q, J = 8.0 Hz, 1H), 3.89 (s, 3H), 3.29-3.21 (m, 1H), 3.20-3.09 (m, 6H), 3.05-2.92 (m, 3H), 2.92-2.74 (m, 4H), 2.67-2.57 (m, 1H), 2.33-2.21 (m, 1H), 2.11-2.02 (m, 2H), 1.89-1.73 (m, 2H), 1.32 (s, 3H), 1.30 (s, 3H); 663.4 [M + H]⁺ | 1.19 |

TABLE 1-continued

| Example Compound | Structure | Name of Compound | ¹H NMR[:]; MS [M + H]⁺ | UPLC r.t. (min) |
|---|---|---|---|---|
| 304 | 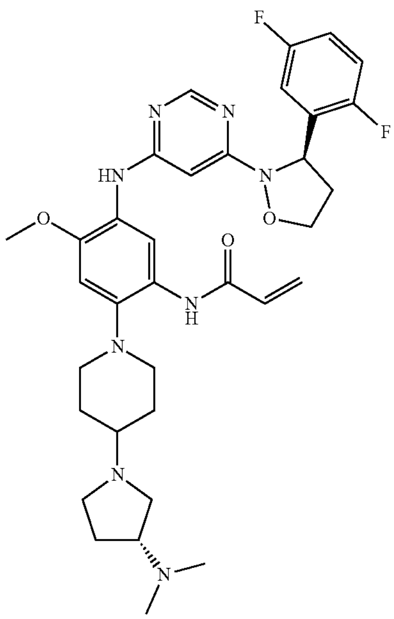 [SMILES: C=CC(=O)Nc1cc(Nc2cc(N3OCC[C@@H]3c3cc(F)ccc3F)ncn2)c(OC)cc1N1CCC(N2CC[C@@H](N(C)C)C2)CC1] | N-(5-((6-((R)-3-(2,5-difluorophenyl)isoxazolidine-2-yl)pyrimidine-4-yl)amino)-2-(4-((R)-3-(dimethylamino)pyrolidine-1-yl)piperidine-1-yl)-4-methoxyphenyl)acrylamide | ¹H NMR (400 MHz, Methanol-d₄) δ 8.17 (s, 1H), 8.06 (s, 1H), 7.17-7.08 (m, 1H), 7.08-6.98 (m, 1H), 6.98-6.87 (m, 1H), 6.81 (s, 1H), 6.49-6.34 (m, 2H), 6.31-6.20 (m, 1H), 5.73-5.60 (m, 2H), 4.04 (td, J = 4.2, 7.9 Hz, 1H), 3.88 (q, J = 8.0 Hz, 1H), 3.78 (s, 3H), 3.29-3.22 (m, 2H), 3.15-3.08 (m, 1H), 3.08-2.99 (m, 3H), 2.97-2.84 (m, 2H), 2.83-2.65 (m, 4H), 2.47 (s, 6H), 2.22-2.10 (m, 2H), 2.07-1.98 (m, 2H), 1.76-1.63 (m, 2H); 649.3 [M + H]⁺ | 1.11 |
| 305 | 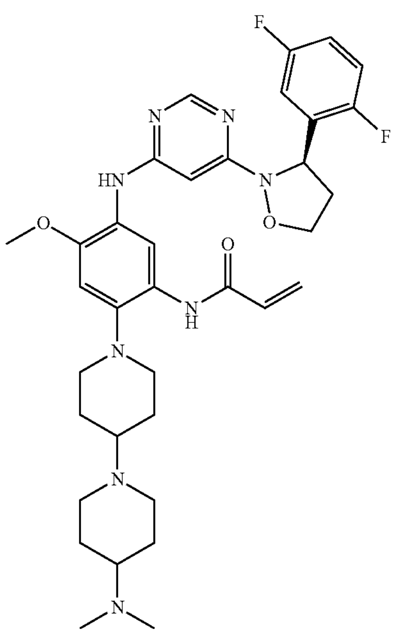 | N-(5-((6-((R)-3-(2,5-difluorophenyl)isoxazolidine-2-yl)pyrimidine-4-yl)amino)-2-(4-(dimethylamino)-(1,4'-bipiperidine)-1'-yl)-4-methoxyphenyl)acrylamide | ¹H NMR (400 MHz, Methanol-d₄) δ 8.18 (s, 1H), 8.06 (s, 1H), 7.18-7.08 (m, 1H), 7.08-6.98 (m, 1H), 6.98-6.87 (m, 1H), 6.80 (s, 1H), 6.52-6.35 (m, 2H), 6.28-6.20 (m, 1H), 5.75-5.59 (m, 2H), 4.08-3.98 (m, 1H), 3.87 (q, J = 8.0 Hz, 1H), 3.77 (s, 3H), 3.12-3.01 (m, 5H), 2.98-2.92 (m, 1H), 2.91-2.80 (m, 1H), 2.80-2.63 (m, 7H), 2.48-2.37 (m, 2H), 2.21-2.10 (m, 1H), 2.07-1.99 (m, 2H), 1.99-1.90 (m, 2H), 1.80-1.59 (m, 5H); 649.3 [M + H]⁺ | 1.11 |

TABLE 1-continued

| Example Compound | Structure | Name of Compound | ¹H NMR[[:]]; MS [M + H]⁺ | UPLC r.t. (min) |
|---|---|---|---|---|
| 306 | 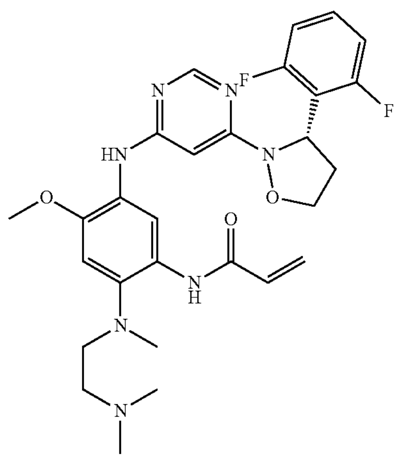 [SMILES: C=CC(=O)Nc1cc(Nc2cc(N3OCC[C@H]3c3c(F)cccc3F)ncn2)c(OC)cc1N(C)CCN(C)C] | N-(5-((6-((S)-3-(2,6-difluorophenyl)isoxazolidine-2-yl)pyrimidine-4-yl)amino)-2-((2-(dimethylamino)ethyl)(methyl)amino)-4-methoxyphenyl)acrylamide | ¹H NMR (400 MHz, DMSO-d₆) δ 9.85 (s, 1H), 8.25 (s, 1H), 8.02 (s, 1H), 7.46-7.37 (m, 1H), 7.20-7.09 (m, 3H), 6.96 (s, 1H), 6.23 (dd, J = 17.0, 2.2 Hz, 1H), 6.05 (s, 1H), 5.71 (dd, J = 10.1, 2.2 Hz, 1H), 4.46 (t, J = 8.0 Hz, 1H), 3.80 (s, 3H), 3.32 (s, 4H), 2.94-2.86 (m, 1H), 2.73 (d, J = 4.8 Hz, 6H), 2.61 (s, 3H), 2.44 (s, 1H), 1.53 (d, J = 72.7 Hz, 2H); 554.5 [M + H]⁺ | 1.16 |
| 307 | 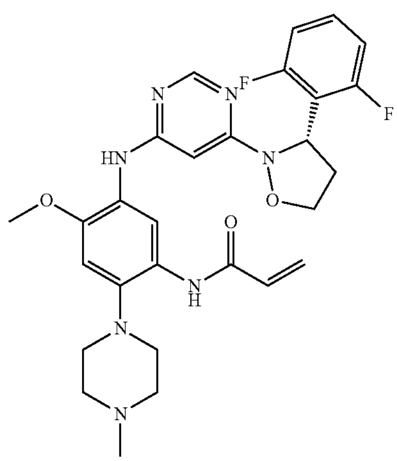 [SMILES: C=CC(=O)Nc1cc(Nc2cc(N3OCC[C@H]3c3c(F)cccc3F)ncn2)c(OC)cc1N1CCN(C)CC1] | N-(5-((6-((S)-3-(2,6-difluorophenyl)isoxazolidine-2-yl)pyrimidine-4-yl)amino)-4-methoxy-2-(4-methylpiperazine-1-yl)phenyl)acrylamide | ¹H NMR (400 MHz, DMSO-d₆) δ 9.73 (s, 1H), 9.14 (s, 1H), 8.25 (s, 1H), 8.02 (s, 1H), 7.42 (ddd, J = 14.7, 8.4, 6.4 Hz, 1H), 7.12 (t, J = 8.4 Hz, 2H), 6.88 (s, 1H), 6.76 (dd, J = 17.0, 10.3 Hz, 1H), 6.24 (dd, J = 17.0, 2.0 Hz, 1H), 6.02 (s, 1H), 5.76 (dd, J = 10.1, 2.0 Hz, 1H), 5.68 (t, J = 7.7 Hz, 1H), 4.44 (t, J = 7.5 Hz, 1H), 3.80 (s, 3H), 3.50 (d, J = 11.6 Hz, 2H), 3.35 (d, J = 10.8 Hz, 2H), 3.21-3.14 (m, 4H), 2.93-2.86 (m, 1H), 2.83 (d, J = 4.5 Hz, 3H), 2.47-2.42 (m, 1H), 1.64-1.40 (m, 2H); 552.5 [M + H]⁺ | 1.11 |
| 308 | 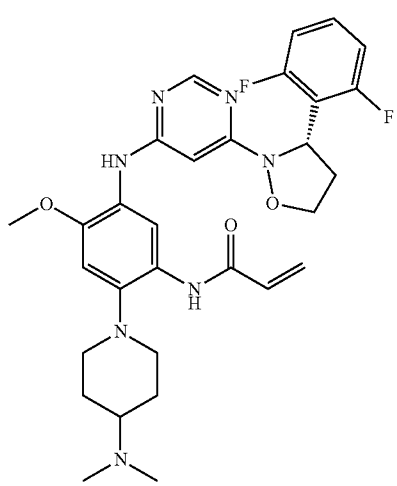 [SMILES: C=CC(=O)Nc1cc(Nc2cc(N3OCC[C@H]3c3c(F)cccc3F)ncn2)c(OC)cc1N1CCC(N(C)C)CC1] | N-(5-((6-((S)-3-(2,6-difluorophenyl)isoxazolidine-2-yl)pyrimidine-4-yl)amino)-2-(4-(dimethylamino)piperidine-1-yl)-4-methoxyphenyl)acrylamide | ¹H NMR (400 MHz, DMSO-d₆) δ 10.03 (s, 1H), 9.17 (s, 1H), 8.27 (s, 1H), 7.88 (s, 1H), 7.46-7.37 (m, 1H), 7.12 (t, J = 8.5 Hz, 2H), 6.90 (s, 1H), 6.72 (dd, J = 16.9, 10.2 Hz, 1H), 6.25 (dd, J = 17.0, 1.9 Hz, 1H), 5.96 (s, 1H), 5.76 (dd, J = 10.1, 2.0 Hz, 1H), 5.68 (t, 2H), 4.49-4.45 (m, 1H), 4.05-4.02 (m, 1H), 3.79 (s, 3H), 3.30 (d, J = 14.0 Hz, 1H), 3.21 (d, J = 11.5 Hz, 2H), 2.96-2.88 (m, 1H), 2.80 (d, J = 11.6 Hz, 2H), 2.75 (d, J = 4.9 Hz, 6H), 2.12 (d, J = 11.8 Hz, 2H), 2.05-1.95 (m, 2H); 580.5 [M + H]⁺ | 1.14 |

TABLE 1-continued

| Example Compound | Structure | Name of Compound | $^1$H NMR[[:]]; MS [M + H]$^+$ | UPLC r.t. (min) |
|---|---|---|---|---|
| 309 | 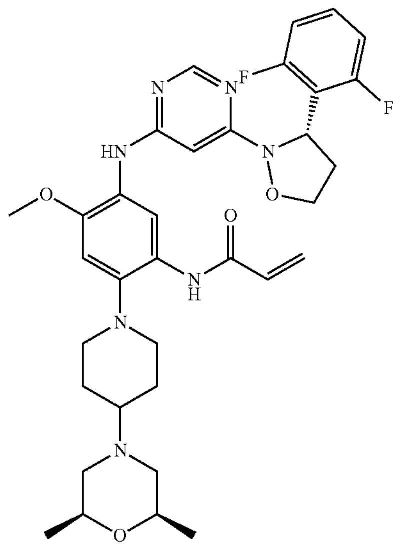 [SMILES: C=CC(=O)Nc1cc(Nc2cc(N3OCC[C@H]3c3c(F)cccc3F)ncn2)c(OC)cc1N1CCC(N2C[C@@H](C)O[C@@H](C)C2)CC1] | N-(5-((6-((S)-3-(2,6-difluorophenyl)isoxazolidine-2-yl)pyrimidine-4-yl)amino)-2-(4-((2S,6R)-2,6-dimethylmorpholino)piperidine-1-yl)-4-methoxyphenyl)acrylamide | $^1$H NMR (400 MHz, DMSO-d$_6$) δ 10.41 (s, 1H), 9.29 (s, 1H), 8.31 (s, 1H), 7.80 (s, 1H), 7.43 (ddd, J = 8.5, 6.4, 2.0 Hz, 1H), 7.14 (d, J = 8.5 Hz, 2H), 6.95 (s, 1H), 6.73 (dd, J = 17.0, 10.2 Hz, 1H), 6.25 (dd, J = 17.0, 1.9 Hz, 1H), 5.96 (s, 1H), 5.77 (dd, J = 10.2, 1.9 Hz, 1H), 5.72-5.67 (m, 1H), 4.52-4.45 (m, 1H), 4.23-4.12 (m, 2H), 4.11-4.02 (m, 1H), 3.80 (s, 3H), 3.49-3.43 (m, 2H), 3.38 (q, J = 7.0 Hz, 2H), 3.26 (d, J = 11.4 Hz, 2H), 2.98-2.90 (m, 1H), 2.83 (d, J = 11.6 Hz, 2H), 2.75-2.64 (m, 2H), 2.26 (d, J = 11.3 Hz, 2H), 2.20-2.09 (m, 2H), 1.17 (d, J = 6.3 Hz, 6H), ; 650.3 [M + H]$^+$ | 1.23 |
| 310 | 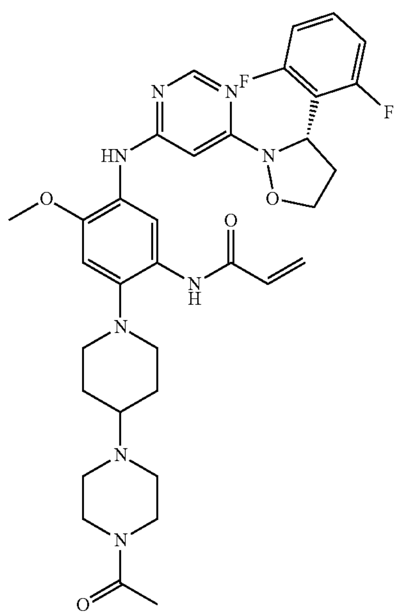 [SMILES: C=CC(=O)Nc1cc(Nc2cc(N3OCC[C@H]3c3c(F)cccc3F)ncn2)c(OC)cc1N1CCC(N2CCN(C(C)=O)CC2)CC1] | N-(2-(4-(4-acetylpiperazine-1-yl)piperidine-1-yl)-5-((6-((S)-3-(2,6-difluorophenyl)isoxazolidine-2-yl)pyrimidine-4-yl)amino)-4-methoxyphenyl)acrylamide | $^1$H NMR (400 MHz, DMSO-d$_6$) δ 10.37 (s, 1H), 9.31 (s, 1H), 8.31 (s, 1H), 7.80 (s, 1H), 7.46-7.41 (m, 1H), 7.13 (t, J = 8.5 Hz, 2H), 6.93 (s, 1H), 6.74 (dd, J = 17.0, 10.2 Hz, 1H), 6.27-6.23 (m, 1H), 5.96 (s, 1H), 5.78-5.67 (m, 2H), 4.53-4.46 (m, 2H), 4.09-4.00 (m, 2H), 3.79 (s, 3H), 3.73 (d, J = 12.9 Hz, 1H), 3.48 (d, J = 8.8 Hz, 2H), 3.39-3.36 (m, 3H), 3.05-2.93 (m, 2H), 2.83 (s, 2H), 2.51 (q, J = 1.9 Hz, 3H), 2.48-2.43 (m, 1H), 2.20 (s, 2H), 2.12 (s, 1H), 2.07 (s, 3H), ; 663.6 [M + H]$^+$ | 1.17 |

TABLE 1-continued

| Example Compound | Structure | Name of Compound | ¹H NMR[:]; MS [M + H]⁺ | UPLC r.t. (min) |
|---|---|---|---|---|
| 311 | 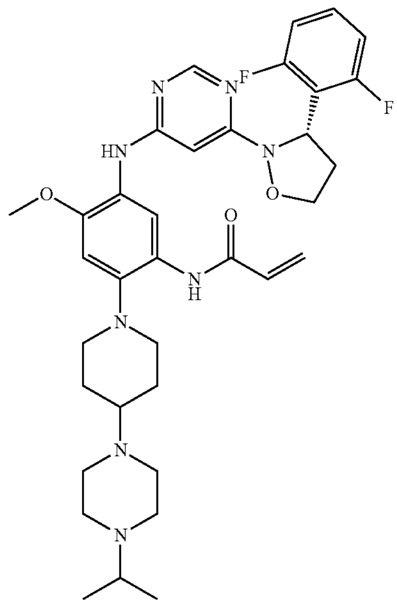 [SMILES: C=CC(=O)Nc1cc(Nc2cc(N3OCC[C@H]3c3c(F)cccc3F)ncn2)c(OC)cc1N1CCC(N2CCN(C(C)C)CC2)CC1] | N-(5-((6-((S)-3-(2,6-difluorophenyl)isoxazolidine-2-yl)pyrimidine-4-yl)amino)-2-(4-(4-isopropylpiperazine-1-yl)piperidine-1-yl)-methoxyphenyl)acrylamide | ¹H NMR (400 MHz, DMSO-d₆) δ 10.29 (s, 1H), 9.26 (s, 1H), 8.29 (s, 1H), 7.86 (s, 1H), 7.43 (ddd, J = 8.4, 6.4, 2.0 Hz, 1H), 7.13 (t, J = 8.5 Hz, 2H), 6.91 (s, 1H), 6.76 (dd, J = 16.9, 10.3 Hz, 1H), 6.25 (dd, J = 17.0, 1.9 Hz, 1H), 5.97 (s, 1H), 5.80-5.74 (m, 1H), 5.69 (s, 1H), 4.52-4.48 (m, 1H), 4.08-4.01 (m, 1H), 3.79 (s, 7H), 3.69 (s, 4H), 3.60 (t, J = 6.7 Hz, 1H), 3.53-3.45 (m, 1H), 3.41-3.35 (m, 1H), 3.24 (d, J = 11.1 Hz, 2H), 2.97-2.90 (m, 1H), 2.82 (t, J = 11.4 Hz, 2H), 2.46 (d, J = 8.8 Hz, 1H), 2.15 (d, J = 15.1 Hz, 4H), 1.32 (d, J = 6.6 Hz, 6H), ; 663.3 [M + H]⁺ | 1.14 |
| 312 | 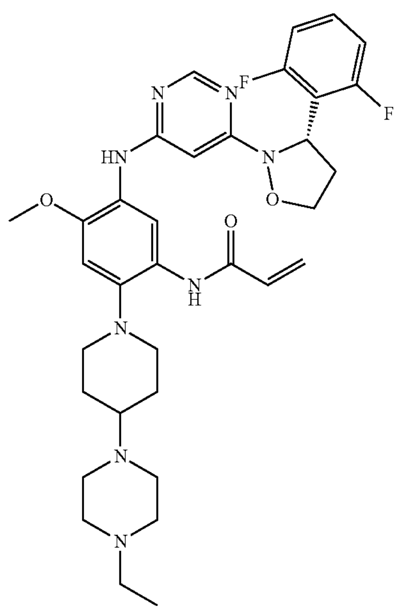 [SMILES: C=CC(=O)Nc1cc(Nc2cc(N3OCC[C@H]3c3c(F)cccc3F)ncn2)c(OC)cc1N1CCC(N2CCN(CC)CC2)CC1] | N-(5-((6-((S)-3-(2,6-difluorophenyl)isoxazolidine-2-yl)pyrimidine-4-yl)amino)-2-(4-(4-ethylpiperazine-1-yl)piperidine-1-yl)-4-methoxyphenyl)acrylamide | 649.6 [M + H]⁺ | 1.10 |

TABLE 1-continued

| Example Compound | Structure | Name of Compound | ¹H NMR[[:]]; MS [M + H]⁺ | UPLC r.t. (min) |
|---|---|---|---|---|
| 313 | 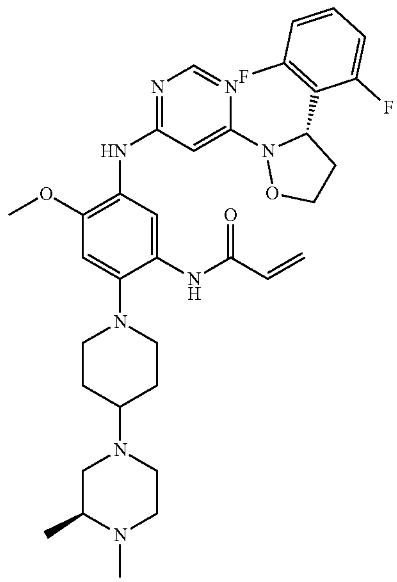 [SMILES: C=CC(=O)Nc1cc(Nc2cc(N3OCC[C@H]3c3c(F)cccc3F)ncn2)c(OC)cc1N1CCC(N2CCN(C)[C@@H](C)C2)CC1] | N-(5-((6-((S)-3-(2,6-difluorophenyl)isoxazolidine-2-yl)pyrimidine-4-yl)amino)-2-(4-((S)-3,4-dimethylpiperazine-1-yl)piperidine-1-yl)-4-methoxyphenyl)acrylamide | ¹H NMR (400 MHz, DMSO-d₆) δ 10.31 (s, 1H), 9.25 (s, 1H), 8.30 (s, 1H), 7.84 (s, 1H), 7.43 (ddd, J = 8.4, 6.4, 2.0 Hz, 1H), 7.13 (t, J = 8.5 Hz, 2H), 6.92 (s, 1H), 6.77-6.69 (m, 1H), 6.25 (dd, J = 17.0, 1.9 Hz, 1H), 5.98 (d, J = 20.2 Hz, 1H), 5.77 (dd, J = 10.1, 1.9 Hz, 1H), 5.70 (s, 1H), 4.51-4.46 (m, 1H), 4.10-4.02 (m, 1H), 3.84 (d, J = 12.7 Hz, 2H), 3.79 (s, 3H), 3.76 (s, 1H), 3.66 (d, J = 8.9 Hz, 2H), 3.50-3.36 (m, 3H), 3.29-3.22 (m, 2H), 2.93 (d, J = 3.2 Hz, 1H), 2.84 (s, 3H), 2.80 (d, J = 12.4 Hz, 1H), 2.45 (d, J = 3.7 Hz, 1H), 2.26-2.06 (m, 4H), 1.62 (dd, J = 5.1, 2.7 Hz, 1H), 1.42 (d, J = 6.1 Hz, 3H), ; 649.3 [M + H]⁺ | 1.13 |
| 314 | 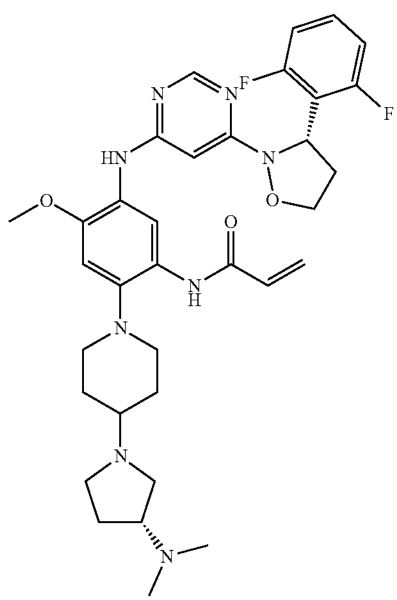 [SMILES: C=CC(=O)Nc1cc(Nc2cc(N3OCC[C@H]3c3c(F)cccc3F)ncn2)c(OC)cc1N1CCC(N2CC[C@@H](N(C)C)C2)CC1] | N-(5-((6-((S)-3-(2,6-difluorophenyl)isoxazolidine-2-yl)pyrimidine-4-yl)amino)-2-(4-((R)-3-(dimethylamino)pyrolidine-1-yl)piperidine-1-yl)-4-methoxyphenyl)acrylamide | 649.5 [M + H]⁺ | 1.10 |

TABLE 1-continued

| Example Compound | Structure | Name of Compound | $^1$H NMR[:]; MS [M + H]$^+$ | UPLC r.t. (min) |
|---|---|---|---|---|
| 315 | 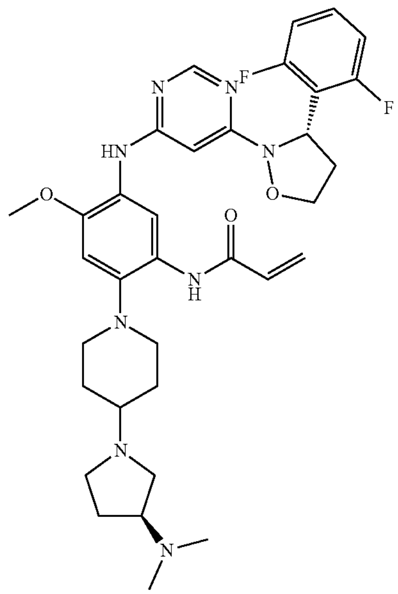 [SMILES: C=CC(=O)Nc1cc(Nc2cc(N3OCC[C@H]3c3c(F)cccc3F)ncn2)c(OC)cc1N1CCC(N2CC[C@H](N(C)C)C2)CC1] | N-(5-((6-((S)-3-(2,6-difluorophenyl)isoxazolidine-2-yl)pyrimidine-4-yl)amino)-2-(4-((S)-3-(dimethylamino)pyrolidine-1-yl)piperidine-1-yl)-4-methoxyphenyl)acrylamide | 649.5 [M + H]$^+$ | 1.04 |
| 316 | 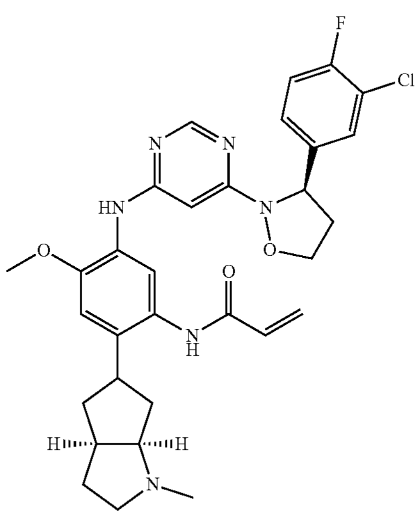 [SMILES: C=CC(=O)Nc1cc(Nc2cc(N3OCC[C@@H]3c3ccc(F)c(Cl)c3)ncn2)c(OC)cc1C1C[C@@H]2CCN(C)[C@@H]2C1] | N-(5-((6-((R)-3-(3-chloro-4-fluorophenyl)isoxazolidine-2-yl)pyrimidine-4-yl)amino)-4-methoxy-2-((3aS,6aS)-1-methylhexahydropyrrolo[3,4-b]pyrrole-5(1H)-yl)phenyl)acrylamide | $^1$H NMR (400 MHz, Methanol-d$_4$) δ 8.05 (d, J = 1.2 Hz, 1H), 7.44 (dd, J = 7.1, 2.0 Hz, 1H), 7.31-7.25 (m, 1H), 7.10 (t, J = 8.9 Hz, 1H), 6.74 (s, 1H), 6.49 (dd, J = 17.0, 10.2 Hz, 1H), 6.28 (dd, J = 17.8, 2.4 Hz, 1H), 5.68 (dd, J = 10.3, 1.5 Hz, 1H), 5.41 (dd, J = 8.5, 4.7 Hz, 1H), 4.03 (td, J = 7.8, 4.2 Hz, 1H), 3.84 (dd, J = 15.9, 7.9 Hz, 1H), 3.75 (s, 3H), 3.21 (dt, J = 3.2, 1.6 Hz, 4H), 3.01 (dt, J = 11.6, 5.9 Hz, 1H), 2.92 (t, J = 8.0 Hz, 12H), 2.84-2.63 (m, 4H), 2.39 (s, 2H), 2.31-2.05 (m, 3H); 594.1 [M + H]$^+$ | 1.30 |

TABLE 1-continued

| Example Compound | Structure | Name of Compound | ¹H NMR[[:]]; MS [M + H]⁺ | UPLC r.t. (min) |
|---|---|---|---|---|
| 317 | 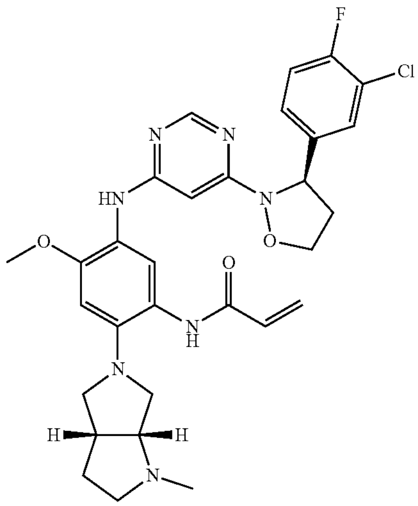 [SMILES: C=CC(=O)Nc1cc(Nc2cc(N3OCC[C@@H]3c3ccc(F)c(Cl)c3)ncn2)c(OC)cc1N1C[C@H]2CCN(C)[C@H]2C1] | N-(5-((6-((R)-3-(3-chloro-4-fluorophenyl)isoxazolidine-2-yl)pyrimidine-4-yl)amino)-4-methoxy-2-((3aR,6aR)-1-methylhexahydropyrrolo[3,4-b]pyrrole-5(1H)-yl)phenyl)acrylamide | ¹H NMR (400 MHz, Methanol-d₄) δ 8.15 (d, J = 3.7 Hz, 1H), 7.56-7.47 (m, 1H), 7.41-7.32 (m, 1H), 7.20 (td, J = 8.9, 2.3 Hz, 1H), 6.84 (s, 1H), 6.59 (dd, J = 17.0, 10.2 Hz, 1H), 6.42-6.38 (m, 1H), 5.77 (dd, J = 10.3, 1.4 Hz, 1H), 5.51 (dd, J = 8.4, 4.8 Hz, 1H), 4.12 (td, J = 7.9, 4.2 Hz, 1H), 3.99-3.91 (m, 1H), 3.84 (s, 3H), 3.33-3.27 (m, 3H), 3.14-3.06 (m, 1H), 3.01 (dd, J = 11.4, 7.1 Hz, 2H), 2.93-2.72 (m, 4H), 2.48 (s, 3H), 2.40-2.14 (m, 3H), 1.68 (ddd, J = 19.5, 12.2, 7.3 Hz, 1H); 594.4 [M + H]⁺ | 1.30 |
| 318 | 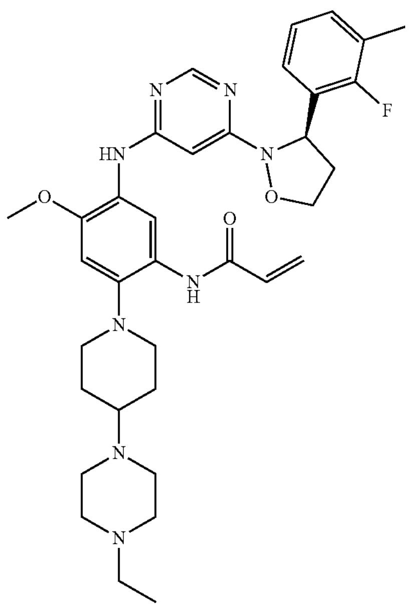 | N-(2-(4-(4-ethylpiperazine-1-yl)piperidine-1-yl)-5-((6-((R)-3-(2-fluoro-3-methylphenyl)isoxazolidine-2-yl)pyrimidine-4-yl)amino)-4-methoxyphenyl)acrylamide | ¹H NMR (400 MHz, DMSO-d₆) δ 9.28 (s, 1H), 8.33 (s, 1H), 7.89 (s, 1H), 7.23 (t, J = 7.5, 1.9 Hz, 1H), 7.15 (t, J = 7.4 Hz, 1H), 7.08 (t, J = 7.5 Hz, 1H), 6.93 (s, 1H), 6.74 (dtd, J = 21.5, 10.7, 4.0 Hz, 1H), 6.26 (dd, J = 17.0, 2.0 Hz, 1H), 6.12 (s, 1H), 5.81-5.73 (m, 1H), 5.69 (dd, J = 8.6, 5.5 Hz, 1H), 4.32 (td, J = 7.6, 4.3 Hz, 2H), 4.09 (q, J = 7.7 Hz, 2H), 3.82 (s, 4H), 3.70 (q, J = 12.8, 10.0 Hz, 3H), 3.64-3.56 (m, 2H), 3.30-3.14 (m, 5H), 2.83 (t, J = 11.2 Hz, 2H), 2.71 (d, J = 4.8 Hz, 1H), 2.29-2.05 (m, 8H), 1.36-1.24 (m, 4H), ; 645.5 [M + H]⁺ | 1.16 |
| 319 | 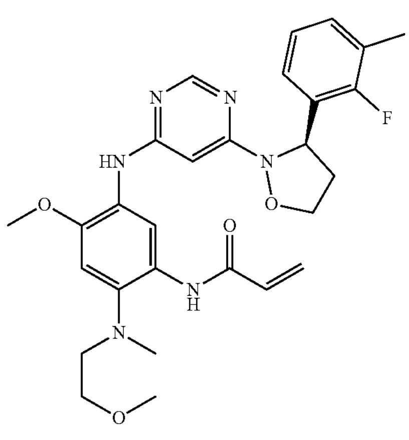 | N-(5-((6-((R)-3-(2-fluoro-3-methylphenyl)isoxazolidine-2-yl)pyrimidine-4-yl)amino)-4-methoxy-2-((2-methoxyethyl)(methyl)amino)phenyl)acrylamide | ¹H NMR (400 MHz, Chloroform-d) δ 9.12 (s, 1H), 8.89 (s, 1H), 8.28 (s, 1H), 7.32 (s, 1H), 7.08 (t, J = 7.3 Hz, 1H), 6.99 (t, J = 7.6 Hz, 1H), 6.78 (s, 1H), 6.60 (s, 1H), 6.40 (dd, J = 17.0, 1.9 Hz, 1H), 6.30 (dd, J = 16.9, 9.9 Hz, 1H), 5.89 (dd, J = 8.8, 4.5 Hz, 1H), 5.69 (dd, J = 9.9, 1.9 Hz, 1H), 4.18-4.04 (m, 2H), 3.84 (s, 3H), 3.47 (t, J = 4.9 Hz, 2H), 3.43 (s, 3H), 2.98 (h, J = 4.1 Hz, 2H), 2.85 (dtd, J = 12.7, 8.0, 4.7 Hz, 1H), 2.76 (s, 3H), 2.38-2.23 (m, 5H), ; 537.3 [M + H]⁺ | 1.58 |

TABLE 1-continued

| Example Compound | Structure | Name of Compound | $^1$H NMR[:]; MS [M + H]$^+$ | UPLC r.t. (min) |
|---|---|---|---|---|
| 320 | 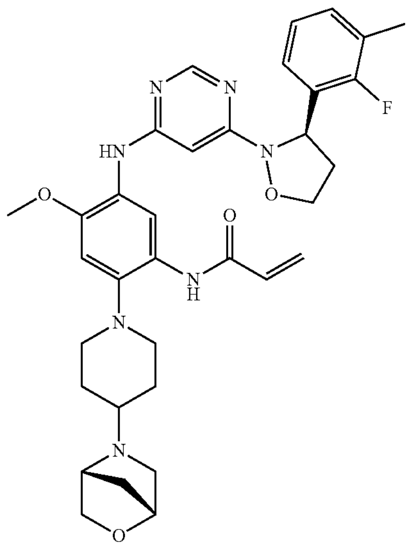 | N-(2-(4-((1R,4R)-2-oxa-5-azabicyclo[2.2.1]heptane-5-yl)piperidine-1-yl)-5-((6-((R)-3-(2-fluoro-3-methylphenyl)isoxazolidine-2-yl)pyrimidine-4-yl)amino)-4-methoxyphenyl)acrylamide | $^1$H NMR (400 MHz, DMSO-d$_6$) δ 10.32 (s, 1H), 8.33 (s, 1H), 7.83 (d, J = 13.0 Hz, 1H), 7.23 (td, J = 7.5, 1.9 Hz, 1H), 7.15 (t, J = 7.3 Hz, 1H), 7.08 (t, J = 7.5 Hz, 1H), 6.95 (d, J = 11.7 Hz, 1H), 6.65 (ddd, J = 25.1, 17.0, 10.2 Hz, 1H), 6.25 (dt, J = 17.1, 2.1 Hz, 1H), 6.12 (s, 1H), 5.77 (dd, J = 10.0, 1.9 Hz, 1H), 5.68 (dd, J = 8.6, 5.5 Hz, 1H), 4.74-4.68 (m, 1H), 4.65 (d, J = 2.5 Hz, 1H), 4.57 (s, 1H), 4.51 (d, J = 9.1 Hz, 1H), 4.32 (td, J = 7.6, 4.3 Hz, 1H), 4.21 (d, J = 10.2 Hz, 1H), 4.09 (q, J = 7.7 Hz, 1H), 3.83 (d, J = 2.6 Hz, 3H), 3.69 (td, J = 7.2, 6.7, 3.7 Hz, 1H), 3.60 (pt, J = 6.6, 3.5 Hz, 1H), 3.49-3.42 (m, 1H), 3.29 (dd, J = 30.1, 12.5 Hz, 2H), 3.11 (tt, J = 7.3, 3.6 Hz, 1H), 2.97 (ddd, J = 12.4, 7.7, 4.4 Hz, 1H), 2.87 (p, J = 11.5, 9.2 Hz, 1H), 2.35 (d, J = 10.8 Hz, 1H), 2.26 (d, J = 2.0 Hz, 4H), 2.08 (t, J = 8.8 Hz, 3H), 1.33 (s, 2H), ; 630.4 [M + H]$^+$ | 1.21 |
| 321 | 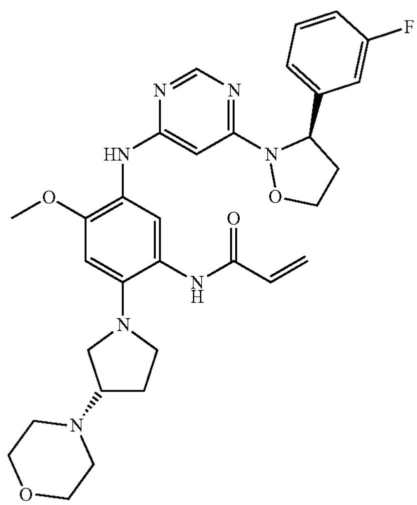 | N-(5-((6-((R)-3-(3-fluorophenyl)isoxazolidine-2-yl)pyrimidine-4-yl)amino)-4-methoxy-2-((S)-3-morpholinopyrrolidine-1-yl)phenyl)acrylamide | $^1$H NMR (400 MHz, DMSO-d$_6$) δ 9.43-9.25 (m, 1H), 8.49 (s, 1H), 8.13 (s, 1H), 7.39 (td, J = 8.0, 6.1 Hz, 2H), 7.28-7.14 (m, 2H), 7.08 (td, J = 8.6, 2.7 Hz, 1H), 6.49 (s, 1H), 6.26-6.14 (m, 2H), 5.68 (dd, J = 10.1, 2.1 Hz, 1H), 5.54 (dd, J = 8.7, 5.0 Hz, 1H), 4.12 (td, J = 7.9, 3.8 Hz, 1H), 3.80 (s, 5H), 3.59 (s, 3H), 3.17 (d, J = 36.8 Hz, 3H), 2.75 (dtd, J = 12.0, 8.0, 3.8 Hz, 3H), 2.38 (s, 2H), 2.29-2.15 (m, 2H), 2.10 (s, 1H), 1.72 (s, 1H), 1.26 (td, J = 7.2, 4.8 Hz, 2H); 590.4 [M + H]$^+$ | 1.11 |

| Example Compound | Structure | Name of Compound | ¹H NMR[[:]]; MS [M + H]⁺ | UPLC r.t. (min) |
|---|---|---|---|---|
| 322 | 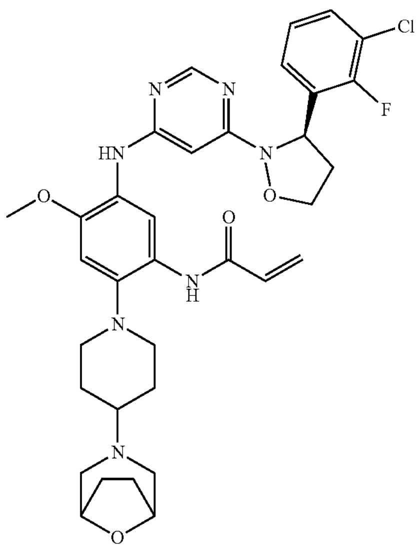 [SMILES: C=CC(=O)Nc1cc(Nc2cc(N3OCC[C@@H]3c3cccc(Cl)c3F)ncn2)c(OC)cc1N1CCC(N2CC3CCC(C2)O3)CC1] | N-(2-(4-((1R,5S)-8-oxa-3-azabicyclo[3.2.1]octan-3-yl)piperidine-1-yl)-5-((6-((R)-3-(3-chloro-2-fluorophenyl)isoxazolidine-2-yl)pyrimidine-4-yl)amino)-4-methoxyphenyl)acrylamide | ¹H NMR (400 MHz, DMSO-$d_6$) δ 10.00 (s, 1H), 9.02 (s, 1H), 8.23 (s, 1H), 8.05 (s, 1H), 7.53 (t, J = 7.4 Hz, 1H), 7.40 (t, J = 7.3 Hz, 1H), 7.23 (t, J = 7.9 Hz, 1H), 6.88 (s, 1H), 6.59 (dd, J = 17.1, 10.2 Hz, 1H), 6.24 (d, J = 17.4 Hz, 2H), 5.81-5.65 (m, 2H), 4.51 (s, 2H), 4.29-4.20 (m, 2H), 3.81 (s, 3H), 3.40-3.33 (m, 3H), 3.28 (dd, J = 10.8, 5.7 Hz, 2H), 3.20-3.12 (m, 3H), 2.88 (s, 1H), 2.73 (t, J = 11.8 Hz, 2H), 2.21 (d, J = 7.9 Hz, 3H), 2.12 (s, 2H), 2.06 (d, J = 11.6 Hz, 1H), 1.95 (s, 2H); 664.5 [M + H]⁺ | 1.24 |
| 323 | 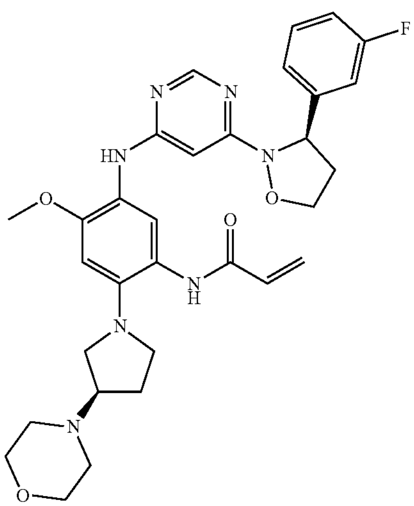 [SMILES: C=CC(=O)Nc1cc(Nc2cc(N3OCC[C@@H]3c3cccc(F)c3)ncn2)c(OC)cc1N1CC[C@@H](N2CCOCC2)C1] | N-(5-((6-((R)-3-(3-fluorophenyl)isoxazolidine-2-yl)pyrimidine-4-yl)amino)-4-methoxy-2-((R)-3-morpholinopyrrolidine-1-yl)phenyl)acrylamide | ¹H NMR (400 MHz, DMSO-$d_6$) δ 9.34 (s, 1H), 8.48 (s, 1H), 8.12 (s, 1H), 7.45-7.33 (m, 2H), 7.25 (d, J = 7.8 Hz, 1H), 7.22-7.16 (m, 1H), 7.08 (td, J = 8.6, 2.6 Hz, 1H), 6.50 (d, J = 3.0 Hz, 1H), 6.48-6.42 (m, 1H), 6.20 (d, J = 2.2 Hz, 2H), 5.68 (dd, J = 10.2, 2.1 Hz, 1H), 5.54 (dd, J = 8.7, 4.9 Hz, 1H), 4.12 (td, J = 7.9, 3.9 Hz, 1H), 3.80 (s, 4H), 3.59 (t, J = 4.7 Hz, 4H), 3.38 (dt, J = 9.5, 4.8 Hz, 1H), 3.28 (t, J = 8.1 Hz, 1H), 3.24-3.15 (m, 2H), 2.84-2.69 (m, 2H), 2.47-2.42 (m, 2H), 2.38 (q, J = 5.7, 5.1 Hz, 2H), 2.23 (dtd, J = 12.7, 8.0, 4.9 Hz, 1H), 2.09 (d, J = 7.4 Hz, 1H), 1.77-1.66 (m, 1H); 590.5 [M + H]⁺ | 1.10 |
| 324 | 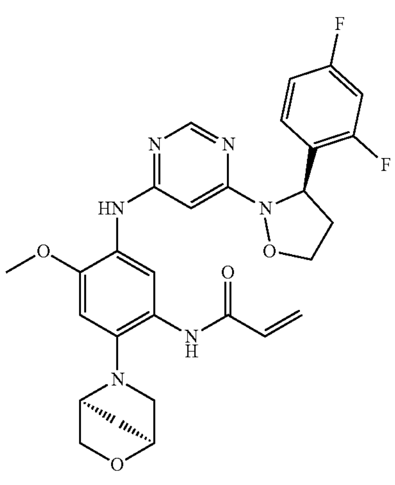 [SMILES: C=CC(=O)Nc1cc(Nc2cc(N3OCC[C@@H]3c3ccc(F)cc3F)ncn2)c(OC)cc1N1C[C@@H]2C[C@H]1CO2] | N-(2-((1S,4S)-2-oxa-5-azabicyclo[2.2.1]heptane-5-yl)-5-((6-((R)-3-(2,4-difluorophenyl)isoxazolidine-2-yl)pyrimidine-4-yl)amino)-4-methoxyphenyl)acrylamide | ¹H NMR (400 MHz, Chloroform-d) δ 8.68 (s, 1H), 8.36 (s, 1H), 7.95 (s, 1H), 7.56 (d, J = 7.0 Hz, 1H), 6.90 (s, 1H), 6.82 (m, 3H), 6.69 (d, J = 15.8 Hz, 1H), 6.39 (d, J = 16.7 Hz, 1H), 6.32-6.23 (m, 1H), 5.85 (s, 1H), 5.75 (d, J = 10.0 Hz, 1H), 4.65 (s, 1H), 4.11 (d, J = 4.5 Hz, 1H), 4.06 (d, J = 7.8 Hz, 1H), 3.86 (s, 3H), 3.75 (d, J = 7.5 Hz, 1H), 3.43 (d, J = 10.2 Hz, 1H), 3.24 (d, J = 10.1 Hz, 1H), 2.79 (d, J = 12.3 Hz, 1H), 2.35-2.22 (m, 1H), 2.17 (s, 2H), 2.08 (d, J = 10.1 Hz, 1H), 1.99 (d, J = 9.6 Hz, 1H), ; 551.4 [M + H]⁺ | 1.36 |

TABLE 1-continued

| Example Compound | Structure | Name of Compound | $^1$H NMR[[:]]; MS [M + H]$^+$ | UPLC r.t. (min) |
|---|---|---|---|---|
| 325 | 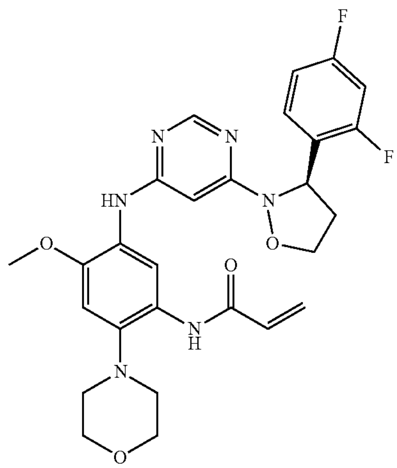 [SMILES: C=CC(=O)Nc1cc(Nc2cc(N3OCC[C@@H]3c3ccc(F)cc3F)ncn2)c(OC)cc1N1CCOCC1] | N-(5-((6-((R)-3-(2,4-difluorophenyl)isoxazolidine-2-yl)pyrimidine-4-yl)amino)-4-methoxy-2-morpholinophenyl)acrylamide | $^1$H NMR (400 MHz, Chloroform-d) δ 8.93 (s, 1H), 8.51 (s, 1H), 8.38 (d, J = 1.0 Hz, 1H), 7.56 (dt, J = 14.6, 7.1 Hz, 1H), 6.96 (s, 1H), 6.88-6.80 (m, 2H), 6.77 (d, J = 7.7 Hz, 2H), 6.42-6.34 (m, 1H), 6.27 (dd, J = 17.0, 10.0 Hz, 1H), 5.88 (dd, J = 8.7, 4.4 Hz, 1H), 5.76 (dd, J = 9.9, 1.5 Hz, 1H), 4.16-4.04 (m, 2H), 3.91-3.87 (m, 6H), 2.89 (q, J = 3.8 Hz, 4H), 2.81 (ddt, J = 12.7, 8.2, 4.2 Hz, 1H), 2.33-2.23 (m, 1H), 2.17 (s, 1H), ; 539.4 [M + H] | 1.50 |
| 326 | 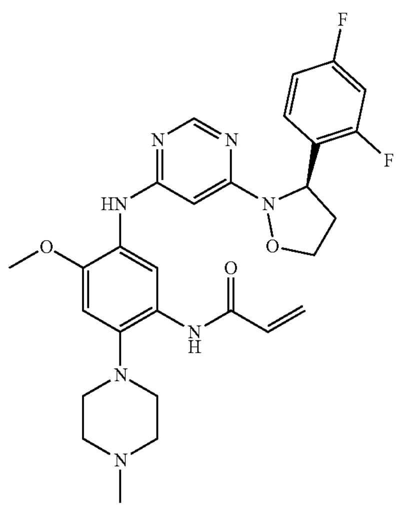 [SMILES: C=CC(=O)Nc1cc(Nc2cc(N3OCC[C@@H]3c3ccc(F)cc3F)ncn2)c(OC)cc1N1CCN(C)CC1] | N-(5-((6-((R)-3-(2,4-difluorophenyl)isoxazolidine-2-yl)pyrimidine-4-yl)amino)-4-methoxy-2-(4-methylpiperazine-1-yl)phenyl)acrylamide | $^1$H NMR (400 MHz, Chloroform-d) δ 8.91 (s, 1H), 8.53 (s, 1H), 8.37 (s, 1H), 7.56 (dt, J = 15.2, 7.4 Hz, 1H), 6.94 (s, 1H), 6.87-6.78 (m, 3H), 6.75 (s, 1H), 6.43-6.34 (m, 1H), 6.27 (dd, J = 16.9, 9.9 Hz, 1H), 5.88 (dd, J = 8.6, 4.4 Hz, 1H), 5.75 (dd, J = 9.9, 1.6 Hz, 1H), 4.14-4.06 (m, 2H), 3.84 (s, 3H), 2.92 (s, 3H), 2.84-2.76 (m, 1H), 2.40 (s, 3H), 2.31-2.25 (m, 1H), 2.23 (s, 1H), 2.17 (s, 1H), 2.02 (s, 1H), 1.26 (s, 1H), 1.19 (t, J = 7.3 Hz, 1H), ; 552.4 [M + H] | 1.21 |
| 327 | 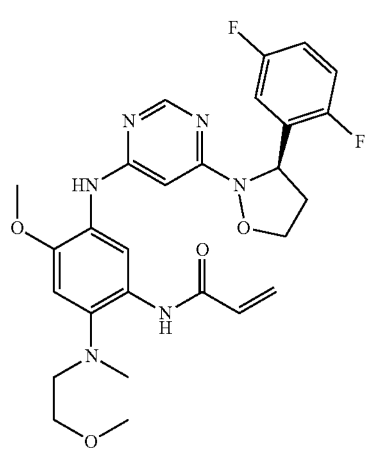 [SMILES: C=CC(=O)Nc1cc(Nc2cc(N3OCC[C@@H]3c3cc(F)ccc3F)ncn2)c(OC)cc1N(C)CCOC] | N-(5-((6-((R)-3-(2,5-difluorophenyl)isoxazolidine-2-yl)pyrimidine-4-yl)amino)-4-methoxy-2-((2-methoxyethyl)(methyl)amino)phenyl)acrylamide | $^1$H NMR (400 MHz, CDCl$_3$) δ 9.13 (s, 1H), 8.99 (s, 1H), 8.37 (s, 1H), 7.36-7.28 (m, 1H), 7.04-6.96 (m, 2H), 6.92-6.85 (m, 1H), 6.79 (s, 1H), 6.78 (s, 1H), 6.35 (qd, J = 16.9, 5.8 Hz, 2H), 5.90 (dd, J = 8.7, 4.3 Hz, 1H), 5.69 (dd, J = 9.8, 1.9 Hz, 1H), 4.15-4.06 (m, 2H), 3.85 (s, 3H), 3.47 (t, J = 4.9 Hz, 2H), 3.43 (s, 3H), 3.02-2.93 (m, 2H), 2.88-2.78 (m, 1H), 2.76 (s, 3H), 2.35-2.24 (m, 1H); 541.5 [M + H]$^+$ | 1.63 |

TABLE 1-continued

| Example Compound | Structure | Name of Compound | ¹H NMR[[:]]; MS [M + H]⁺ | UPLC r.t. (min) |
|---|---|---|---|---|
| 328 | 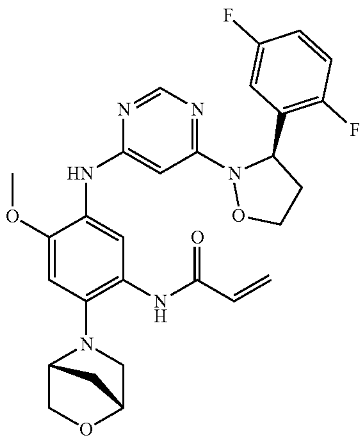 [SMILES: C=CC(=O)Nc1cc(Nc2cc(N3OCC[C@@H]3c3cc(F)ccc3F)ncn2)c(OC)cc1N1C[C@H]2C[C@@H]1CO2] | N-(2-((1R,4R)-2-oxa-5-azabicyclo[2.2.1]heptane-5-yl)-5-((6-((R)-3-(2,5-difluorophenyl)isoxazolidine-2-yl)pyrimidine-4-yl)amino)-4-methoxyphenyl)acrylamide | ¹H NMR (400 MHz, CDCl₃) δ 8.59 (s, 1H), 8.33 (s, 1H), 7.94 (s, 1H), 7.35-7.28 (m, 1H), 7.14 (s, 1H), 7.00 (td, J = 9.2, 4.3 Hz, 1H), 6.93-6.87 (m, 1H), 6.73 (s, 1H), 6.71 (s, 1H), 6.41-6.24 (m, 2H), 5.89 (dd, J = 8.3, 4.0 Hz, 1H), 5.78-5.73 (m, 1H), 4.65 (s, 1H), 4.19-4.03 (m, 4H), 3.91-3.88 (m, 1H), 3.86 (s, 3H), 3.80-3.74 (m, 2H), 3.48-3.43 (m, 1H), 3.23-3.18 (m, 1H), 2.87-2.78 (m, 1H), 2.34-2.24 (m, 1H); 551.4 [M + H]⁺ | 1.28 |
| 329 | 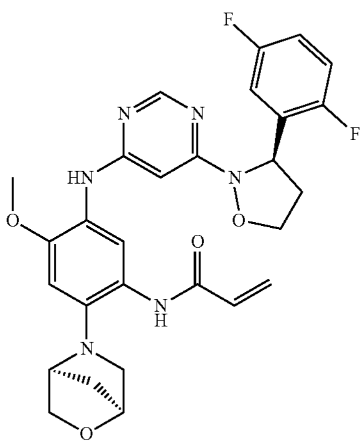 [SMILES: C=CC(=O)Nc1cc(Nc2cc(N3OCC[C@@H]3c3cc(F)ccc3F)ncn2)c(OC)cc1N1C[C@@H]2C[C@H]1CO2] | N-(2-((1S,4S)-2-oxa-5-azabicyclo[2.2.1]heptane-5-yl)-5-((6-((R)-3-(2,5-difluorophenyl)isoxazolidine-2-yl)pyrimidine-4-yl)amino)-4-methoxyphenyl)acrylamide | ¹H NMR (400 MHz, CDCl₃) δ 8.66 (s, 1H), 8.35 (s, 1H), 7.95 (s, 1H), 7.35-7.28 (m, 1H), 7.07-6.96 (m, 2H), 6.93-6.86 (m, 1H), 6.71 (s, 1H), 6.67 (s, 1H), 6.42-6.23 (m, 2H), 5.89 (dd, J = 8.6, 4.3 Hz, 1H), 5.79-5.72 (m, 1H), 4.26-3.97 (m, 4H), 3.91-3.83 (m, 4H), 3.83-3.72 (m, 2H), 3.46-3.38 (m, 1H), 3.28-3.20 (m, 1H), 2.86-2.76 (m, 1H), 2.34-2.22 (m, 2H); 551.4 [M + H]⁺ | 1.28 |
| 330 | 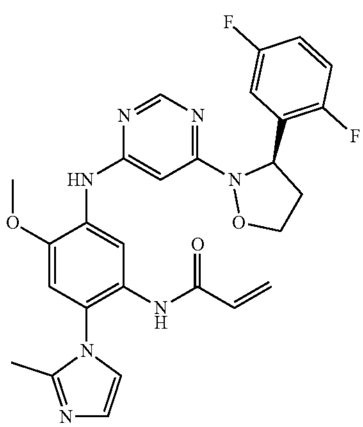 [SMILES: C=CC(=O)Nc1cc(Nc2cc(N3OCC[C@@H]3c3cc(F)ccc3F)ncn2)c(OC)cc1-n1ccnc1C] | N-(5-((6-((R)-3-(2,5-difluorophenyl)isoxazolidine-2-yl)pyrimidine-4-yl)amino)-4-methoxy-2-(2-methyl-1H-imidazole-1-yl)phenyl)acrylamide | ¹H NMR (400 MHz, CDCl₃) δ 9.06 (s, 1H), 8.43 (s, 1H), 7.40 (s, 1H), 7.35-7.28 (m, 1H), 7.15 (s, 1H), 7.02 (td, J = 9.1, 4.3 Hz, 1H), 6.96-6.88 (m, 2H), 6.82 (s, 1H), 6.79-6.72 (m, 2H), 6.29 (d, J = 16.9 Hz, 1H), 6.06 (dd, J = 16.8, 10.3 Hz, 1H), 5.91 (dd, J = 8.5, 4.5 Hz, 1H), 5.74-5.68 (m, 1H), 4.18 (td, J = 7.9, 4.3 Hz, 1H), 4.06 (q, J = 8.0 Hz, 1H), 3.90 (s, 3H), 2.90-2.79 (m, 1H), 2.37-2.30 (m, 1H), 2.26 (s, 3H); 534.4 [M + H]⁺ | 1.26 |

TABLE 1-continued

| Example Compound | Structure | Name of Compound | ¹H NMR[[:]]; MS [M + H]⁺ | UPLC r.t. (min) |
|---|---|---|---|---|
| 331 | 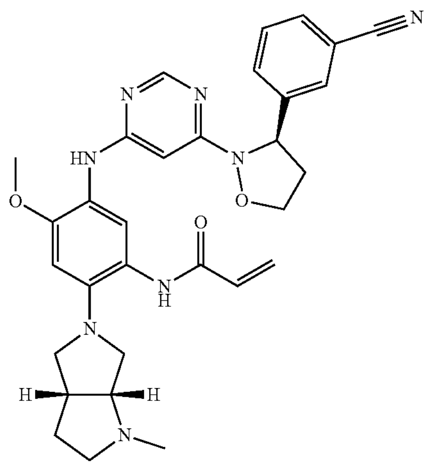 [SMILES: C=CC(=O)Nc1cc(Nc2cc(N3OCC[C@@H]3c3cccc(C#N)c3)ncn2)c(OC)cc1N1C[C@H]2CCN(C)[C@H]2C1] | N-(5-((6-((R)-3-(3-cyanophenyl)isoxazolidine-2-yl)pyrimidine-4-yl)amino)-4-methoxy-2-((3aR,6aR)-1-methylhexahydropyrrolo[3,4-b]pyrrole-5(1H)-yl)phenyl)acrylamide | ¹H NMR (400 MHz, CDCl₃) δ 9.40 (s, 1H), 8.45 (s, 1H), 8.30 (s, 1H), 7.78 (s, 1H), 7.71 (d, J = 7.9 Hz, 1H), 7.54 (d, J = 7.6 Hz, 1H), 7.45 (t, J = 7.8 Hz, 1H), 6.68-6.59 (m, 2H), 6.56-6.42 (m, 2H), 5.77-5.64 (m, 2H), 4.16 (td, J = 8.0, 4.1 Hz, 1H), 4.04 (q, J = 8.1 Hz, 1H), 3.83 (s, 3H), 3.65-3.54 (m, 2H), 3.31-3.23 (m, 1H), 3.09-3.02 (m, 1H), 3.00-2.87 (m, 2H), 2.85-2.70 (m, 2H), 2.63 (s, 3H), 2.51-2.40 (m, 1H), 2.38-2.23 (m, 2H), 1.89-1.77 (m, 1H); 567.5 [M + H]⁺ | 1.03 |
| 332 | 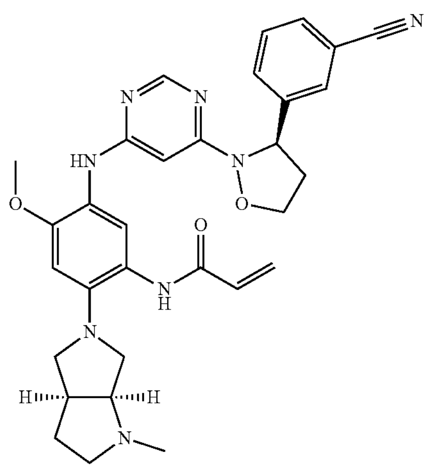 [SMILES: C=CC(=O)Nc1cc(Nc2cc(N3OCC[C@@H]3c3cccc(C#N)c3)ncn2)c(OC)cc1N1C[C@@H]2CCN(C)[C@@H]2C1] | N-(5-((6-((R)-3-(3-cyanophenyl)isoxazolidine-2-yl)pyrimidine-4-yl)amino)-4-methoxy-2-((3aS,6aS)-1-methylhexahydropyrrolo[3,4-b]pyrrole-5(1H)-yl)phenyl)acrylamide | ¹H NMR (400 MHz, CDCl₃) δ 9.25 (s, 1H), 8.52 (s, 1H), 8.31 (s, 1H), 7.79 (s, 1H), 7.71 (d, J = 7.8 Hz, 1H), 7.54 (d, J = 7.7 Hz, 1H), 7.45 (t, J = 7.8 Hz, 1H), 7.21 (s, 1H), 6.71-6.62 (m, 2H), 6.52-6.41 (m, 2H), 5.72 (dd, J = 7.8, 4.2 Hz, 2H), 4.16 (td, J = 8.0, 4.1 Hz, 1H), 4.07 (q, J = 8.0 Hz, 1H), 3.83 (s, 3H), 3.51-3.41 (m, 2H), 3.23-3.17 (m, 1H), 3.08-3.01 (m, 1H), 2.99-2.88 (m, 1H), 2.88-2.75 (m, 3H), 2.64-2.54 (m, 3H), 2.47-2.38 (m, 1H), 2.38-2.22 (m, 2H), 1.88-1.75 (m, 1H); 567.5 [M + H]⁺ | 1.04 |
| 333 | 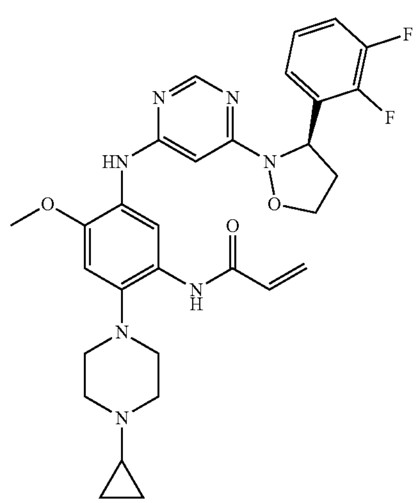 [SMILES: C=CC(=O)Nc1cc(Nc2cc(N3OCC[C@@H]3c3cccc(F)c3F)ncn2)c(OC)cc1N1CCN(C2CC2)CC1] | N-(2-(4-cyclopropylpiperazine-1-yl)-5-((6-((R)-3-(2,3-difluorophenyl)isoxazolidine-2-yl)pyrimidine-4-yl)amino)-4-methoxyphenyl)acrylamide | ¹H NMR (400 MHz, Chloroform-d) δ 8.90 (s, 1H), 8.59 (s, 1H), 8.37 (s, 1H), 7.40-7.30 (m, 1H), 7.12-7.00 (m, 2H), 6.96 (s, 1H), 6.82-6.73 (m, 2H), 6.42-6.33 (m, 1H), 6.33-6.23 (m, 1H), 5.93 (dd, J = 8.9, 4.6 Hz, 1H), 5.75 (dd, J = 9.9, 1.7 Hz, 1H), 4.19-4.10 (m, 1H), 4.10-4.01 (m, 1H), 3.82 (s, 3H), 2.93-2.66 (m, 9H), 2.38-2.25 (m, 1H), 1.76-1.70 (m, 1H), 0.57-0.42 (m, 4H); 578.4 [M + H]⁺ | 1.17 |

TABLE 1-continued

| Example Compound | Structure | Name of Compound | ¹H NMR[[:]]; MS [M + H]⁺ | UPLC r.t. (min) |
|---|---|---|---|---|
| 334 | 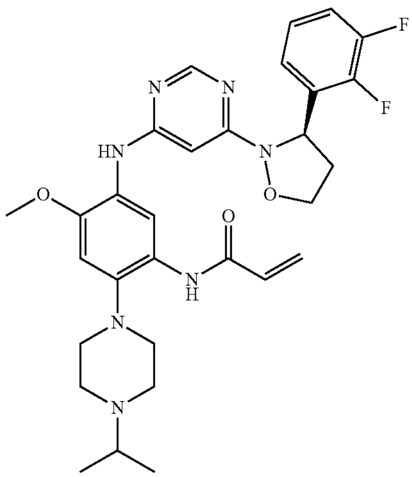 [SMILES: C=CC(=O)Nc1cc(Nc2cc(N3OCC[C@@H]3c3cccc(F)c3F)ncn2)c(OC)cc1N1CCN(C(C)C)CC1] | N-(5-((6-((R)-3-(2,3-difluorophenyl)isoxazolidine-2-yl)pyrimidine-4-yl)amino)-2-(4-isopropylpiperazine-1-yl)-4-methoxyphenyl)acrylamide | 1H NMR (400 MHz, Chloroform-d) δ 8.89 (s, 1H), 8.56 (s, 1H), 8.36 (d, J = 1.0 Hz, 1H), 7.40-7.31 (m, 1H), 7.12-7.01 (m, 2H), 7.00 (s, 1H), 6.83 (s, 1H), 6.75 (s, 1H), 6.37 (dd, J = 16.8, 1.7 Hz, 1H), 6.27 (dd, J = 17.0, 9.9 Hz, 1H), 5.93 (dd, J = 8.8, 4.6 Hz, 1H), 5.75 (dd, J = 9.9, 1.7 Hz, 1H), 4.19-4.12 (m, 1H), 4.12-4.01 (m, 1H), 3.83 (s, 3H), 2.99-2.91 (m, 4H), 2.90-2.84 (m, 1H), 2.83-2.78 (m, 1H), 2.77-2.68 (m, 4H), 2.35-2.26 (m, 1H), 1.13 (d, J = 6.5 Hz, 6H); 580.5 [M + H]⁺ | 1.21 |
| 335 | 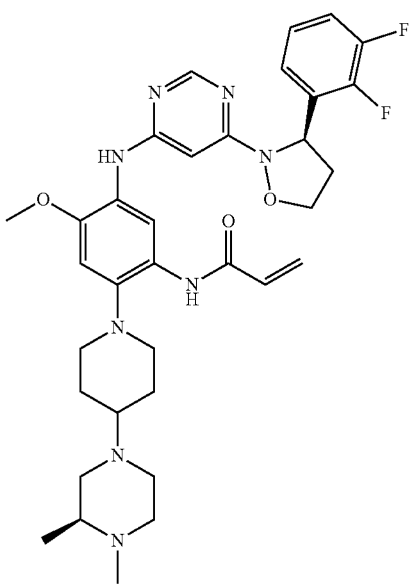 [SMILES: C=CC(=O)Nc1cc(Nc2cc(N3OCC[C@@H]3c3cccc(F)c3F)ncn2)c(OC)cc1N1CCC(N2CCN(C)[C@@H](C)C2)CC1] | N-(5-((6-((R)-3-(2,3-difluorophenyl)isoxazolidine-2-yl)pyrimidine-4-yl)amino)-2-(4-((S)-3,4-dimethylpiperazine-1-yl)piperidine-1-yl)-4-methoxyphenyl)acrylamide | ¹H NMR (400 MHz, Chloroform-d) δ 8.87 (s, 1H), 8.44 (s, 1H), 8.36 (d, J = 0.9 Hz, 1H), 7.40-7.31 (m, 1H), 7.12-6.98 (m, 2H), 6.93 (s, 1H), 6.75 (d, J = 2.4 Hz, 2H), 6.36 (dd, J = 17.0, 1.6 Hz, 1H), 6.25 (dd, J = 16.9, 10.0 Hz, 1H), 5.93 (dd, J = 8.8, 4.6 Hz, 1H), 5.74 (dd, J = 9.9, 1.6 Hz, 1H), 4.19-4.11 (m, 1H), 4.10-4.03 (m, 1H), 3.85 (s, 3H), 3.10-3.02 (m, 2H), 3.02-2.95 (m, 1H), 2.94-2.79 (m, 3H), 2.78-2.66 (m, 2H), 2.43-2.34 (m, 2H), 2.32 (s, 3H), 2.32-2.27 (m, 2H), 2.21-2.14 (m, 1H), 2.11-2.05 (m, 2H), 2.05-1.98 (m, 1H), 1.70-1.60 (m, 2H), 1.10 (d, J = 6.1 Hz, 3H); 649.5 [M + H]⁺ | 1.10 |

TABLE 1-continued

| Example Compound | Structure | Name of Compound | ¹H NMR[:]; MS [M + H]⁺ | UPLC r.t. (min) |
|---|---|---|---|---|
| 336 | 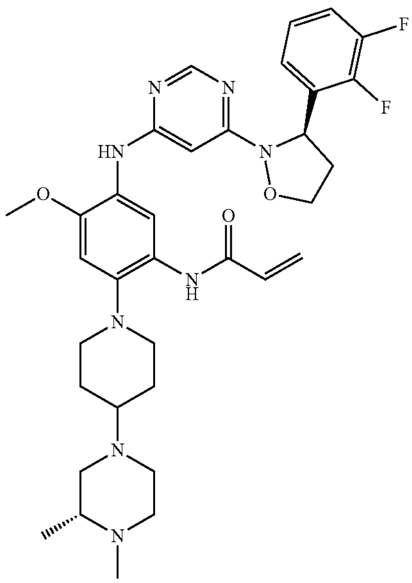 [SMILES: C=CC(=O)Nc1cc(Nc2cc(N3OCC[C@@H]3c3cccc(F)c3F)ncn2)c(OC)cc1N1CCC(N2CCN(C)[C@H](C)C2)CC1] | N-(5-((6-((R)-3-(2,3-difluorophenyl)isoxazolidine-2-yl)pyrimidine-4-yl)amino)-2-(4-((R)-3,4-dimethylpiperazine-1-yl)piperidine-1-yl)-4-methoxyphenyl)acrylamide | ¹H NMR (400 MHz, Chloroform-d) δ 8.87 (s, 1H), 8.44 (s, 1H), 8.36 (d, J = 1.0 Hz, 1H), 7.39-7.31 (m, 1H), 7.12-6.98 (m, 2H), 6.94 (s, 1H), 6.75 (d, J = 1.9 Hz, 2H), 6.36 (dd, J = 17.0, 1.6 Hz, 1H), 6.25 (dd, J = 16.9, 10.0 Hz, 1H), 5.93 (dd, J = 8.8, 4.5 Hz, 1H), 5.74 (dd, J = 9.9, 1.6 Hz, 1H), 4.19-4.10 (m, 1H), 4.10-4.01 (m, 1H), 3.85 (s, 3H), 3.10-3.02 (m, 2H), 3.02-2.95 (m, 1H), 2.95-2.81 (m, 3H), 2.78-2.65 (m, 2H), 2.45-2.35 (m, 2H), 2.33 (s, 3H), 2.32-2.27 (m, 2H), 2.24-2.13 (m, 1H), 2.12-1.99 (m, 3H), 1.72-1.61 (m, 2H), 1.11 (d, J = 6.2 Hz, 3H); 649.5 [M + H]⁺ | 1.09 |
| 337 | 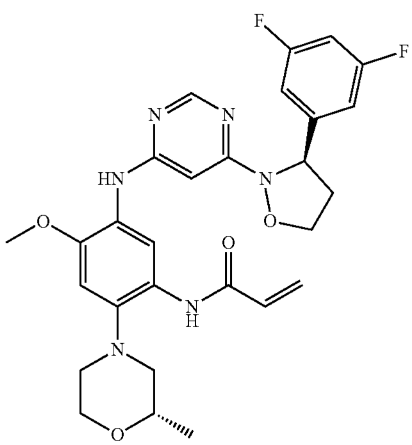 [SMILES: C=CC(=O)Nc1cc(Nc2cc(N3OCC[C@@H]3c3cc(F)cc(F)c3)ncn2)c(OC)cc1N1CCO[C@@H](C)C1] | N-(5-((6-((R)-3-(3,5-difluorophenyl)isoxazolidine-2-yl)pyrimidine-4-yl)amino)-4-methoxy-2-((S)-2-methylmorpholino)phenyl)acrylamide | ¹H NMR (400 MHz, DMSO-d₆) δ 9.06 (s, 1H), 8.65 (s, 1H), 8.18 (d, J = 2.6 Hz, 2H), 7.13 (ddd, J = 8.2, 5.8, 3.2 Hz, 4H), 6.86 (s, 1H), 6.62 (dd, J = 17.0, 10.2 Hz, 1H), 6.37 (s, 1H), 6.20 (dd, J = 17.0, 2.0 Hz, 1H), 5.72 (dd, J = 10.1, 2.0 Hz, 1H), 5.56 (dd, J = 8.7, 5.0 Hz, 1H), 4.13 (td, J = 7.9, 3.9 Hz, 1H), 3.87-3.74 (m, 9H), 2.87-2.70 (m, 4H), 1.78 (s, 2H), 1.11 (d, J = 6.2 Hz, 4H), ; 553.3 [M + H]⁺ | 1.51 |
| 338 | 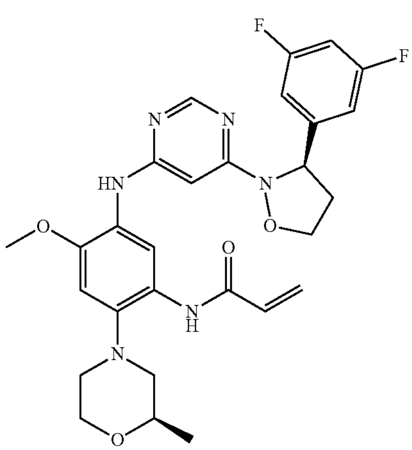 [SMILES: C=CC(=O)Nc1cc(Nc2cc(N3OCC[C@@H]3c3cc(F)cc(F)c3)ncn2)c(OC)cc1N1CCO[C@H](C)C1] | N-(5-((6-((R)-3-(3,5-difluorophenyl)isoxazolidine-2-yl)pyrimidine-4-yl)amino)-4-methoxy-2-((R)-2-methylmorpholino)phenyl)acrylamide | ¹H NMR (400 MHz, DMSO-d₆) δ 9.07 (s, 1H), 8.71 (s, 1H), 8.18 (s, 1H), 7.13 (td, J = 7.7, 7.1, 3.1 Hz, 3H), 6.86 (s, 1H), 6.62 (dd, J = 17.0, 10.2 Hz, 1H), 6.36 (s, 1H), 6.21 (dd, J = 17.0, 2.0 Hz, 1H), 5.72 (dd, J = 10.2, 1.9 Hz, 1H), 5.56 (dd, J = 8.8, 5.0 Hz, 1H), 4.14 (td, J = 7.9, 3.9 Hz, 1H), 3.82 (d, J = 7.8 Hz, 8H), 2.93-2.71 (m, 4H), 2.30-2.19 (m, 1H), 1.91 (s, 1H), 1.10 (d, J = 6.2 Hz, 3H), ; 553.4 [M + H]⁺ | 1.52 |

TABLE 1-continued

| Example Compound | Structure | Name of Compound | ¹H NMR[:]; MS [M + H]⁺ | UPLC r.t. (min) |
|---|---|---|---|---|
| 339 | 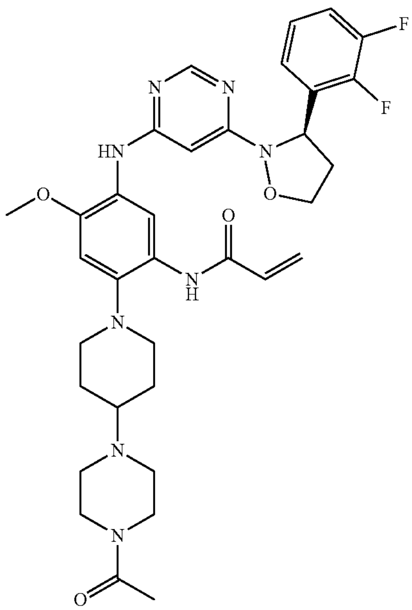 [SMILES: C=CC(=O)Nc1cc(Nc2cc(N3OCC[C@@H]3c3cccc(F)c3F)ncn2)c(OC)cc1N1CCC(N2CCN(C(C)=O)CC2)CC1] | N-(2-(4-(4-acetylpiperazine-1-yl)piperidine-1-yl)-5-((6-((R)-3-(2,3-difluorophenyl)isoxazolidine-2-yl)pyrimidine-4-yl)amino)-4-methoxyphenyl)acrylamide | ¹H NMR (400 MHz, DMSO-d₆) δ 8.96 (s, 1H), 8.63 (s, 1H), 8.16 (s, 1H), 7.40-7.24 (m, 2H), 7.20 (td, J = 8.1, 4.6 Hz, 1H), 6.82 (s, 1H), 6.65 (dd, J = 16.9, 10.2 Hz, 1H), 6.35 (s, 1H), 6.21 (dd, J = 17.0, 2.0 Hz, 1H), 5.80-5.68 (m, 2H), 3.85 (q, J = 8.0 Hz, 1H), 3.79 (s, 3H), 3.06 (d, J = 11.3 Hz, 3H), 2.88-2.75 (m, 1H), 2.72-2.61 (m, 2H), 2.41-2.29 (m, 2H), 2.27-2.12 (m, 2H), 1.99 (s, 4H), 1.88-1.69 (m, 5H), 1.67 (s, 4H), 1.24 (s, 5H), 0.89-0.79 (m, 1H), ; 663.5 [M + H]⁺ | 1.21 |
| 340 | 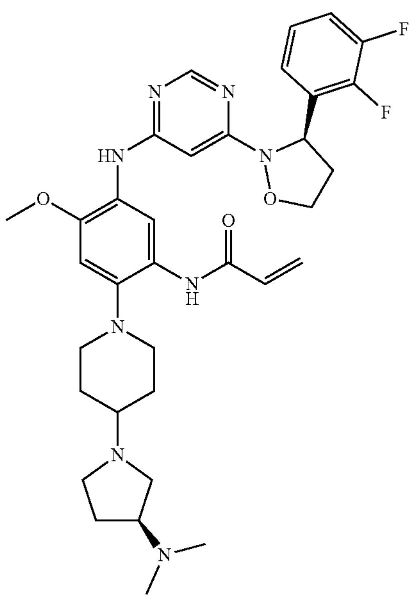 [SMILES: C=CC(=O)Nc1cc(Nc2cc(N3OCC[C@@H]3c3cccc(F)c3F)ncn2)c(OC)cc1N1CCC(N2CC[C@H](N(C)C)C2)CC1] | N-(5-((6-((R)-3-(2,3-difluorophenyl)isoxazolidine-2-yl)pyrimidine-4-yl)amino)-2-(4-((S)-3-(dimethylamino)pyrrolidine-1-yl)piperidine-1-yl)-4-methoxyphenyl)acrylamide | ¹H NMR (400 MHz, DMSO-d₆) δ 8.95 (s, 1H), 8.63 (s, 1H), 8.16 (s, 1H), 7.39-7.24 (m, 3H), 7.20 (td, J = 8.0, 4.7 Hz, 2H), 6.82 (s, 1H), 6.64 (dd, J = 16.9, 10.2 Hz, 1H), 6.35 (s, 1H), 6.20 (dd, J = 17.0, 2.0 Hz, 1H), 5.73 (s, 1H), 3.84 (dd, J = 9.0, 7.2 Hz, 3H), 3.80 (s, 5H), 3.10 (d, J = 11.9 Hz, 2H), 3.01 (d, J = 11.4 Hz, 5H), 2.86-2.75 (m, 4H), 2.73-2.58 (m, 6H), 2.35-2.26 (m, 2H), 2.25-2.15 (m, 2H), 1.96-1.80 (m, 5H), 1.72-1.52 (m, 5H), 1.24 (s, 2H), ; 649.5 [M + H]⁺ | 1.10 |

TABLE 1-continued

| Example Compound | Structure | Name of Compound | ¹H NMR[[:]]; MS [M + H]⁺ | UPLC r.t. (min) |
|---|---|---|---|---|
| 341 | 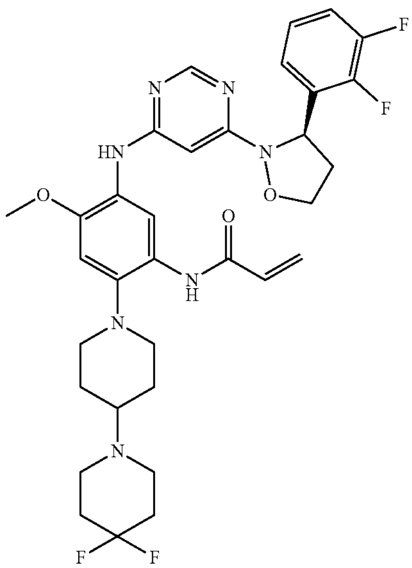 [SMILES: C=CC(=O)Nc1cc(Nc2cc(N3OCC[C@@H]3c3cccc(F)c3F)ncn2)c(OC)cc1N1CCC(N2CCC(F)(F)CC2)CC1] | N-(2-(4,4-difluoro-[1,4'-bipiperidine]-1'-yl)-5-((6-((R)-3-(2,3-difluorophenyl)isoxazolidine-2-yl)pyrimidine-4-yl)amino)-4-methoxyphenyl)acrylamide | ¹H NMR (400 MHz, DMSO-d₆) δ 9.00 (s, 1H), 8.67 (s, 1H), 8.25-8.09 (m, 2H), 7.42-7.26 (m, 2H), 7.26-7.11 (m, 1H), 6.83 (s, 1H), 6.62 (dd, J = 17.0, 10.2 Hz, 1H), 6.39 (s, 1H), 6.23 (dd, J = 16.9, 1.9 Hz, 1H), 5.75 (s, 1H), 3.87 (t, J = 8.1 Hz, 1H), 3.81 (s, 3H), 3.37 (s, 8H), 3.14 (d, J = 10.2 Hz, 3H), 2.88-2.65 (m, 4H), 2.27-2.16 (m, 2H), 2.08 (d, J = 7.8 Hz, 2H), 1.91 (s, 7H), ; 656.5 [M + H]⁺ | 1.29 |
| 342 | 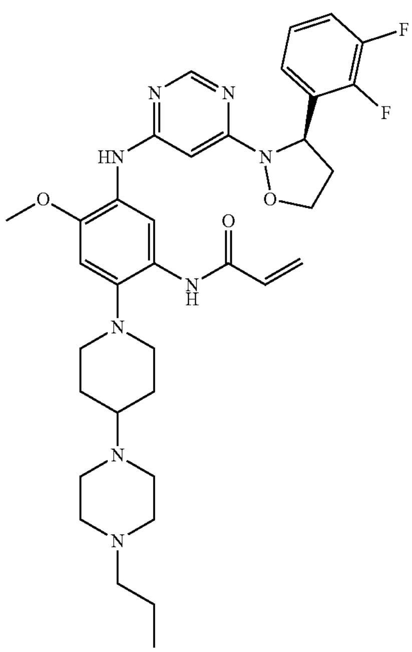 [SMILES: C=CC(=O)Nc1cc(Nc2cc(N3OCC[C@@H]3c3cccc(F)c3F)ncn2)c(OC)cc1N1CCC(N2CCN(CCC)CC2)CC1] | N-(5-((6-((R)-3-(2,3-difluorophenyl)isoxazolidine-2-yl)pyrimidine-4-yl)amino)-4-methoxy-2-(4-(4-propylpiperazine-1-yl)piperidine-1-yl)phenyl)acrylamide | ¹H NMR (400 MHz, DMSO-d₆) δ 8.95 (s, 1H), 8.63 (s, 1H), 8.16 (s, 1H), 7.39-7.25 (m, 3H), 7.20 (qd, J = 7.7, 6.7, 3.0 Hz, 2H), 6.82 (s, 1H), 6.65 (dd, J = 16.6, 10.1 Hz, 1H), 6.35 (s, 1H), 6.20 (dd, J = 16.9, 2.0 Hz, 1H), 5.77-5.71 (m, 2H), 4.16 (dt, J = 7.9, 4.0 Hz, 1H), 3.79 (s, 3H), 3.05 (d, J = 10.8 Hz, 4H), 2.97 (td, J = 7.1, 5.7 Hz, 2H), 2.88-2.75 (m, 3H), 2.71-2.61 (m, 3H), 2.18 (dt, J = 14.4, 7.3 Hz, 8H), 2.09 (s, 2H), 1.84 (d, J = 12.0 Hz, 3H), 1.69 (d, J = 11.4 Hz, 2H), 1.23 (s, 3H), ; 663.6 [M + H]⁺ | 1.19 |

TABLE 1-continued

| Example Compound | Structure | Name of Compound | ¹H NMR[[:]]; MS [M + H]⁺ | UPLC r.t. (min) |
|---|---|---|---|---|
| 343 | 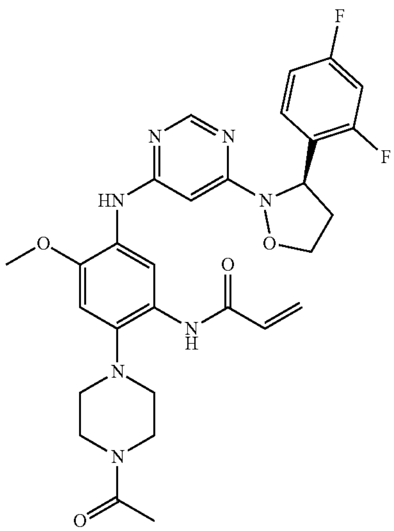 [SMILES: C=CC(=O)Nc1cc(Nc2cc(N3OCC[C@@H]3c3ccc(F)cc3F)ncn2)c(OC)cc1N1CCN(C(C)=O)CC1] | N-(2-(4-acetylpiperazine-1-yl)-5-((6-((R)-3-(2,4-difluorophenyl)isoxazolidine-2-yl)pyrimidine-4-yl)amino)-4-methoxyphenyl)acrylamide | ¹H NMR (400 MHz, Chloroform-d) δ 8.95 (s, 1H), 8.44 (s, 1H), 8.38 (s, 1H), 7.56 (d, J = 6.7 Hz, 1H), 6.98 (s, 1H), 6.82 (s, 2H), 6.74 (d, J = 14.8 Hz, 2H), 6.38 (d, J = 16.6 Hz, 1H), 6.31-6.22 (m, 1H), 5.87 (s, 1H), 5.76 (d, J = 11.1 Hz, 1H), 4.16-4.03 (m, 2H), 3.85 (s, 3H), 3.80 (s, 2H), 3.65 (s, 2H), 2.89 (s, 4H), 2.80 (d, J = 4.4 Hz, 1H), 2.28 (d, J = 16.7 Hz, 1H), 2.17 (s, 3H), ; 580.5 [M + H]⁺ | 1.40 |
| 344 | 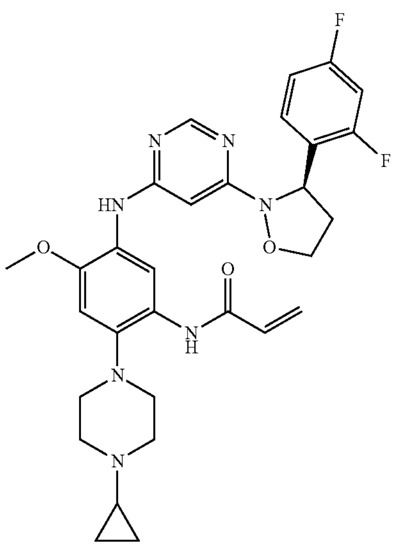 [SMILES: C=CC(=O)Nc1cc(Nc2cc(N3OCC[C@@H]3c3ccc(F)cc3F)ncn2)c(OC)cc1N1CCN(C2CC2)CC1] | N-(2-(4-cyclopropylpiperazine-1-yl)-5-((6-((R)-3-(2,4-difluorophenyl)isoxazolidine-2-yl)pyrimidine-4-yl)amino)-4-methoxyphenyl)acrylamide | ¹H NMR (400 MHz, Chloroform-d) δ 8.91 (s, 1H), 8.59 (s, 1H), 8.37 (s, 1H), 7.57 (d, J = 6.7 Hz, 1H), 6.94 (s, 1H), 6.82 (d, J = 17.0 Hz, 3H), 6.75 (s, 1H), 6.37 (d, J = 16.9 Hz, 1H), 6.28 (dd, J = 17.0, 9.8 Hz, 1H), 5.88 (s, 1H), 5.75 (d, J = 9.8 Hz, 1H), 4.11 (d, J = 16.8 Hz, 2H), 3.82 (s, 3H), 2.88 (s, 4H), 2.82 (s, 2H), 2.29 (m, 2H), 1.74 (m, 2H), 0.96 (dd, 1H), 0.52 (d, J = 6.5 Hz, 2H), 0.47 (d, J = 3.4 Hz, 2H), ; 578.4 [M + H]⁺ | 1.21 |

TABLE 1-continued

| Example Compound | Structure | Name of Compound | ¹H NMR[[:]]; MS [M + H]⁺ | UPLC r.t. (min) |
|---|---|---|---|---|
| 345 | 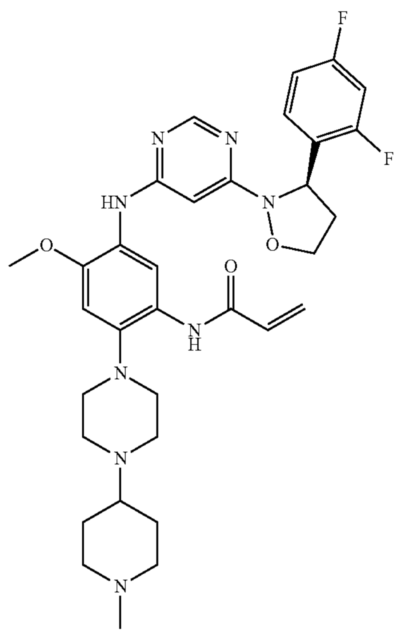 [SMILES: C=CC(=O)Nc1cc(Nc2cc(N3OCC[C@@H]3c3ccc(F)cc3F)ncn2)c(OC)cc1N1CCN(C2CCN(C)CC2)CC1] | N-(5-((6-((R)-3-(2,4-difluorophenyl)isoxazolidine-2-yl)pyrimidine-4-yl)amino)-4-methoxy-2-(4-(1-methylpiperidine-4-yl)piperazine-1-yl)phenyl)acrylamide | ¹H NMR (400 MHz, Chloroform-d) δ 8.89 (s, 1H), 8.55 (s, 1H), 8.36 (s, 1H), 7.56 (d, J = 6.9 Hz, 1H), 7.02 (s, 1H), 6.78 (d, J = 29.1 Hz, 4H), 6.39-6.22 (m, 2H), 5.88 (m, 1H), 5.74 (d, J = 10.6 Hz, 1H), 4.12 (s, 2H), 3.83 (s, 3H), 2.92 (s, 6H), 2.75 (s, 5H), 2.29 (s, 5H), 1.99 (t, 2H), 1.88 (d, 2H), 1.65 (m, 2H), ; 635.5 [M + H]⁺ | 1.06 |
| 346 | 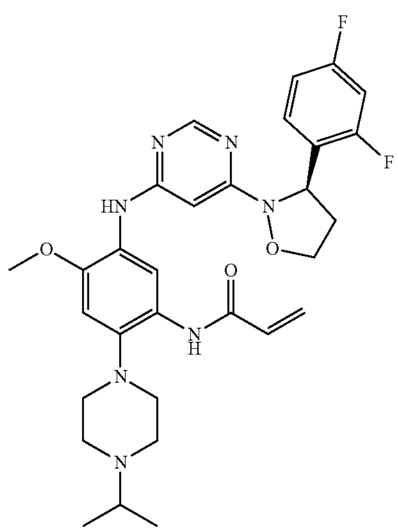 [SMILES: C=CC(=O)Nc1cc(Nc2cc(N3OCC[C@@H]3c3ccc(F)cc3F)ncn2)c(OC)cc1N1CCN(C(C)C)CC1] | N-(5-((6-((R)-3-(2,4-difluorophenyl)isoxazolidine-2-yl)pyrimidine-4-yl)amino)-2-(4-isopropylpiperazine-1-yl)-4-methoxyphenyl)acrylamide | ¹H NMR (400 MHz, Chloroform-d) δ 8.91 (s, 1H), 8.58 (s, 1H), 8.37 (s, 1H), 7.57 (d, J = 6.6 Hz, 1H), 6.94 (s, 1H), 6.88-6.74 (m, 4H), 6.37 (d, J = 16.5 Hz, 1H), 6.27 (dd, J = 16.9, 10.0 Hz, 1H), 5.88 (m, 1H), 5.75 (d, J = 9.9 Hz, 1H), 4.11 (d, J = 16.8 Hz, 2H), 3.83 (s, 3H), 2.93 (s, 4H), 2.72 (s, 6H), 2.25 (s, 1H), 1.59 (s, 6H), ; 580.5 [M + H]⁺ | 1.24 |

TABLE 1-continued

| Example Compound | Structure | Name of Compound | ¹H NMR[:]; MS [M + H]⁺ | UPLC r.t. (min) |
|---|---|---|---|---|
| 347 | 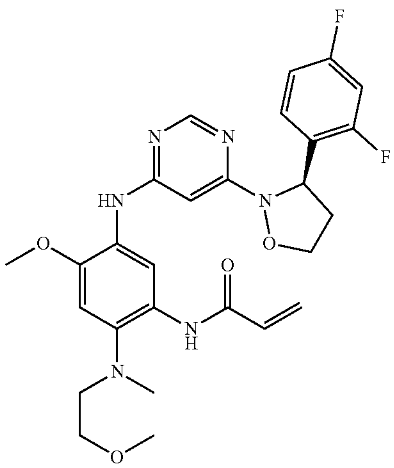 [SMILES: C=CC(=O)Nc1cc(Nc2cc(N3OCC[C@@H]3c3ccc(F)cc3F)ncn2)c(OC)cc1N(C)CCOC] | N-(5-((6-((R)-3-(2,4-difluorophenyl)isoxazolidine-2-yl)pyrimidine-4-yl)amino)-4-methoxy-2-((2-methoxyethyl)(methyl)amino)phenyl)acrylamide | ¹H NMR (400 MHz, Chloroform-d) δ 9.13 (s, 1H), 8.99 (s, 1H), 8.37 (s, 1H), 7.57 (d, J = 6.7 Hz, 1H), 6.94 (s, 1H), 6.81 (m, J = 25.7 Hz, 4H), 6.40 (d, J = 18.7 Hz, 1H), 6.32 (d, J = 9.8 Hz, 1H), 5.86 (m, 1H), 5.69 (d, J = 11.7 Hz, 1H), 4.11 (t, J = 7.8 Hz, 2H), 3.85 (s, 3H), 3.47 (d, J = 4.9 Hz, 2H), 3.43 (s, 3H), 2.97 (m, 2H), 2.79 (s, 1H), 2.76 (s, 3H), 2.28 (s, 1H), ; 541.4 [M + H]⁺ | 1.55 |
| 348 | 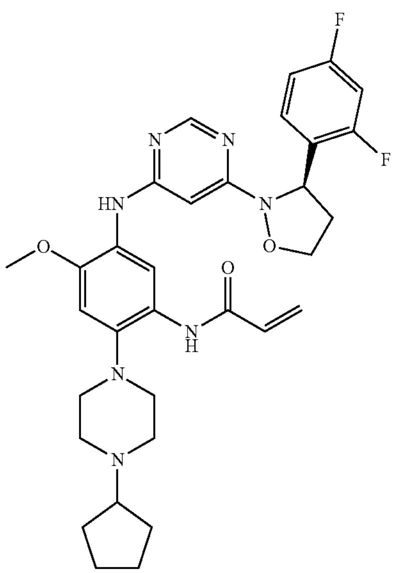 [SMILES: C=CC(=O)Nc1cc(Nc2cc(N3OCC[C@@H]3c3ccc(F)cc3F)ncn2)c(OC)cc1N1CCN(C2CCCC2)CC1] | N-(2-(4-cyclopentylpiperazine-1-yl)-5-((6-((R)-3-(2,4-difluorophenyl)isoxazolidine-2-yl)pyrimidine-4-yl)amino)-4-methoxyphenyl)acrylamide | ¹H NMR (400 MHz, Chloroform-d) δ 8.91 (s, 1H), 8.59 (s, 1H), 8.37 (s, 1H), 7.57 (d, J = 6.7 Hz, 1H), 6.94 (s, 1H), 6.83 (m, 3H), 6.75 (s, 1H), 6.36 (d, J = 16.1 Hz, 1H), 6.29 (m, 1H), 5.86 (m, 1H), 5.75 (d, J = 10.0 Hz, 1H), 4.16-4.04 (m, 2H), 3.82 (s, 3H), 2.94 (s, 4H), 2.81 (d, J = 8.0 Hz, 2H), 2.71 (s, 2H), 2.62-2.58 (m, 4H), 2.27 (m, 1H), 1.92 (m, 2H), 1.74 (m, 2H), 1.52-1.40 (m, 2H), ; 606.5 [M + H]⁺ | 1.25 |

TABLE 1-continued

| Example Compound | Structure | Name of Compound | ¹H NMR[:]; MS [M + H]⁺ | UPLC r.t. (min) |
|---|---|---|---|---|
| 349 | 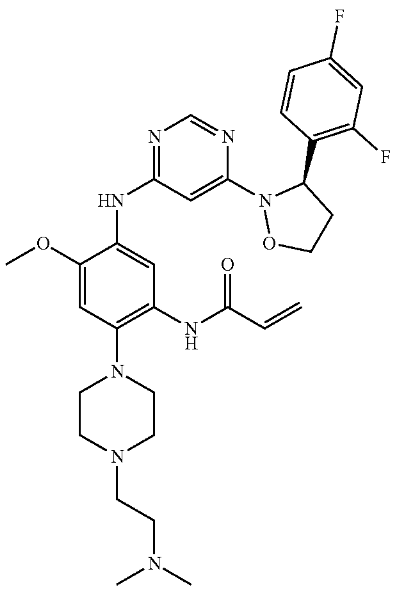 [SMILES: C=CC(=O)Nc1cc(Nc2cc(N3OCC[C@@H]3c3ccc(F)cc3F)ncn2)c(OC)cc1N1CCN(CCN(C)C)CC1] | N-(5-((6-((R)-3-(2,4-difluorophenyl)isoxazolidine-2-yl)pyrimidine-4-yl)amino)-2-(4-(2-(dimethylamino)ethyl)piperazine-1-yl)-4-methoxyphenyl)acrylamide | ¹H NMR (400 MHz, Chloroform-d) δ 8.90 (s, 1H), 8.54 (s, 1H), 8.37 (s, 1H), 7.57 (m, 1H), 6.94 (s, 1H), 6.82 (m, 3H), 6.75 (s, 1H), 6.36 (d, J = 18.1 Hz, 1H), 6.30-6.21 (m, 1H), 5.89 (m, 1H), 5.75 (d, J = 11.3 Hz, 1H), 4.10 (d, J = 13.1 Hz, 2H), 3.84 (s, 3H), 2.94 (s, 4H), 2.82 (m, 3H), 2.66 (s, 6H), 2.37 (s, 5H), 2.27 (dt, J = 8.3, 4.4 Hz, 2H), ; 609.5 [M + H]⁺ | 1.14 |
| 350 | 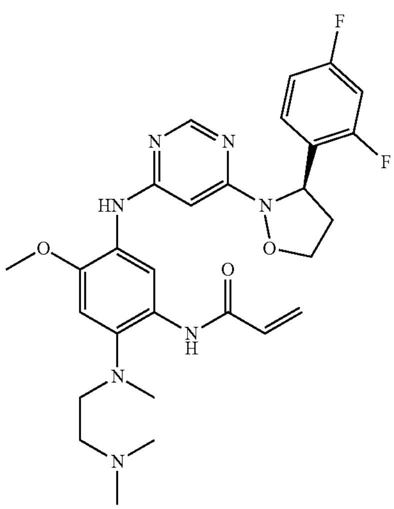 [SMILES: C=CC(=O)Nc1cc(Nc2cc(N3OCC[C@@H]3c3ccc(F)cc3F)ncn2)c(OC)cc1N(C)CCN(C)C] | N-(5-((6-((R)-3-(2,4-difluorophenyl)isoxazolidine-2-yl)pyrimidine-4-yl)amino)-2-((2-(dimethylamino)ethyl)(methyl)amino)-4-methoxyphenyl)acrylamide | ¹H NMR (400 MHz, Chloroform-d) δ 10.11 (s, 1H), 8.96 (s, 1H), 8.37 (d, J = 1.0 Hz, 1H), 7.57 (td, J = 8.6, 6.5 Hz, 1H), 6.96 (s, 1H), 6.87-6.82 (m, 1H), 6.80 (d, J = 1.3 Hz, 3H), 6.40 (dd, J = 17.0, 1.9 Hz, 1H), 6.28 (dd, J = 17.0, 10.0 Hz, 1H), 5.88 (dd, J = 8.7, 4.3 Hz, 1H), 5.68 (dd, J = 9.9, 1.9 Hz, 1H), 4.15-4.09 (m, 2H), 3.85 (s, 3H), 2.87 (q, J = 2.6 Hz, 2H), 2.72 (s, 3H), 2.32 (t, J = 5.5 Hz, 2H), 2.27 (s, 6H), 1.26 (s, 2H), ; 554.5 [M + H] | 1.24 |

TABLE 1-continued

| Example Compound | Structure | Name of Compound | $^1$H NMR[[:]]; MS [M + H]$^+$ | UPLC r.t. (min) |
|---|---|---|---|---|
| 351 | 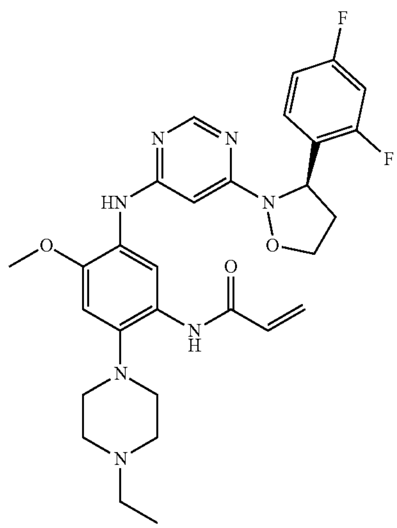 [SMILES: C=CC(=O)Nc1cc(Nc2cc(N3OCC[C@@H]3c3ccc(F)cc3F)ncn2)c(OC)cc1N1CCN(CC)CC1] | N-(5-((6-((R)-3-(2,4-difluorophenyl)isoxazolidine-2-yl)pyrimidine-4-yl)amino)-2-(4-ethylpiperazine-1-yl)-4-methoxyphenyl)acrylamide | $^1$H NMR (400 MHz, Chloroform-d) δ 8.91 (s, 1H), 8.56 (s, 1H), 8.37 (s, 1H), 7.61-7.53 (m, 1H), 6.95 (s, 1H), 6.87-6.78 (m, 3H), 6.75 (s, 1H), 6.40-6.33 (m, 1H), 6.26 (dd, J = 16.9, 9.9 Hz, 1H), 5.88 (dd, J = 8.6, 4.3 Hz, 1H), 5.75 (dd, J = 9.9, 1.6 Hz, 1H), 4.15-4.04 (m, 2H), 3.83 (s, 3H), 2.93 (d, J = 5.0 Hz, 4H), 2.52 (q, J = 7.2 Hz, 2H), 1.61 (s, 4H), 1.25 (s, 2H), 1.15 (t, J = 7.2 Hz, 3H), ; 566.4 [M + H] | 1.21 |
| 352 | 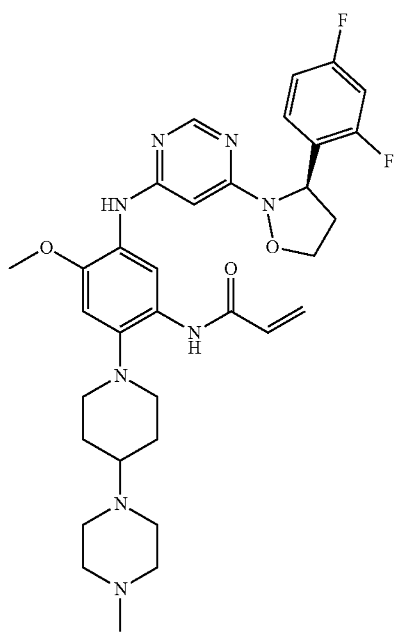 [SMILES: C=CC(=O)Nc1cc(Nc2cc(N3OCC[C@@H]3c3ccc(F)cc3F)ncn2)c(OC)cc1N1CCC(N2CCN(C)CC2)CC1] | N-(5-((6-((R)-3-(2,4-difluorophenyl)isoxazolidine-2-yl)pyrimidine-4-yl)amino)-4-methoxy-2-(4-(4-methylpiperazine-1-yl)piperidine-1-yl)phenyl)acrylamide | $^1$H NMR (400 MHz, Chloroform-d) δ 8.87 (s, 1H), 8.45 (s, 1H), 8.36 (d, J = 1.0 Hz, 1H), 7.56 (td, J = 8.6, 6.5 Hz, 1H), 6.92 (s, 1H), 6.87-6.77 (m, 2H), 6.75 (d, J = 2.1 Hz, 2 H), 6.36 (dd, J = 17.0, 1.6 Hz, 1H), 6.24 (dd, J = 16.9, 10.0 Hz, 1H), 5.87 (dd, J = 8.6, 4.3 Hz, 1H), 5.74 (dd, J = 10.0, 1.6 Hz, 1H), 4.14-4.05 (m, 2H), 3.85 (s, 3H), 3.06 (d, J = 11.6 Hz, 2H), 2.80 (dt, J = 11.6, 3.6 Hz, 1H), 2.76-2.71 (m, 2H), 2.52 (s, 2H), 2.32 (s, 3H), 2.17 (s, 1H), 2.08 (d, J = 12.5 Hz, 2H), 1.66 (d, J = 19.2 Hz, 8H), 1.26 (d, J = 2.2 Hz, 1H), ; 635.5 [M + H] | 1.14 |

TABLE 1-continued

| Example Compound | Structure | Name of Compound | ¹H NMR[[:]]; MS [M + H]⁺ | UPLC r.t. (min) |
|---|---|---|---|---|
| 353 | 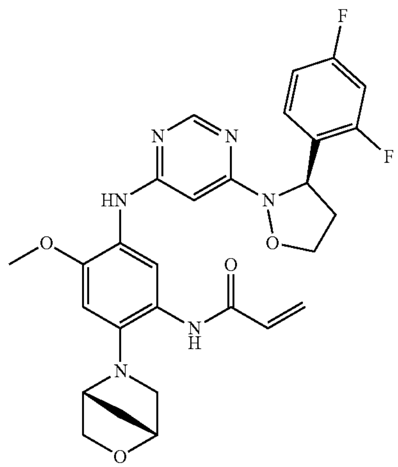 [SMILES: C=CC(=O)Nc1cc(Nc2cc(N3OCC[C@@H]3c3ccc(F)cc3F)ncn2)c(OC)cc1N1C[C@H]2C[C@@H]1CO2] | N-(2-((1R,4R)-2-oxa-5-azabicyclo[2.2.1]heptane-5-yl)-5-((6-((R)-3-(2,4-difluorophenyl)isoxazolidine-2-yl)pyrimidine-4-yl)amino)-4-methoxyphenyl)acrylamide | ¹H NMR (400 MHz, Chloroform-d) δ 8.64 (s, 1H), 8.36 (s, 1H), 7.95 (s, 1H), 7.56 (d, J = 7.9 Hz, 1H), 6.90-6.77 (m, 3H), 6.73 (s, 2H), 6.39 (d, J = 16.9 Hz, 1H), 6.28 (dd, J = 16.9, 10.0 Hz, 1H), 5.88 (dd, J = 8.7, 4.5 Hz, 1H), 5.76 (d, J = 10.0 Hz, 1H), 4.65 (s, 1H), 4.16-4.03 (m, 3H), 3.86 (s, 3H), 3.75 (d, J = 7.9 Hz, 1H), 3.46 (d, J = 10.1 Hz, 1H), 3.20 (d, J = 10.1 Hz, 1H), 2.85-2.75 (m, 1H), 2.33-2.23 (m, 1H), 2.17 (s, 1H), 2.09 (d, J = 10.0 Hz, 1H), 2.00 (d, J = 9.7 Hz, 1H), ; 551.4 [M + H] | 1.32 |
| 354 | 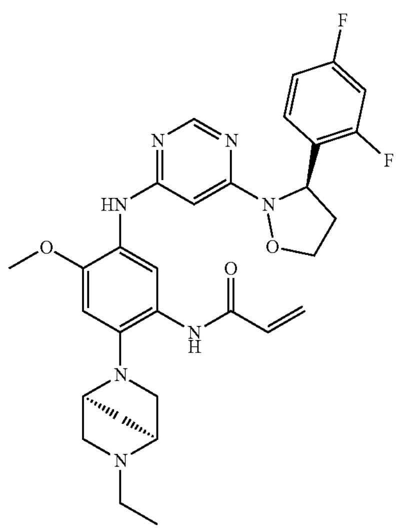 [SMILES: C=CC(=O)Nc1cc(Nc2cc(N3OCC[C@@H]3c3ccc(F)cc3F)ncn2)c(OC)cc1N1C[C@@H]2C[C@H]1CN2CC] | N-(5-((6-((R)-3-(2,4-difluorophenyl)isoxazolidine-2-yl)pyrimidine-4-yl)amino)-2-((1S,4S)-5-ethyl-2,5-diazabicyclo[2.2.1]heptane-2-yl)-4-methoxyphenyl)acrylamide | ¹H NMR (400 MHz, Chloroform-d) δ 8.58 (s, 1H), 8.34 (s, 1H), 7.93 (s, 1H), 7.55 (d, J = 13.5, 6.9 Hz, 1H), 6.87-6.77 (m, 3H), 6.67 (s, 2H), 6.38 (d, J = 16.8 Hz, 1H), 6.28 (dd, J = 17.0, 10.0 Hz, 1H), 5.87 (dd, J = 8.7, 4.3 Hz, 1H), 5.74 (d, J = 9.9 Hz, 1H), 4.10 (dd, J = 8.1, 4.6 Hz, 1H), 4.03 (q, J = 7.9 Hz, 1H), 3.85 (s, 3H), 3.72 (s, 1H), 3.58 (s, 1H), 3.45 (d, J = 9.6 Hz, 1H), 3.11 (d, J = 9.7 Hz, 1H), 2.82 (s, 2H), 2.31-2.22 (m, 1H), 2.17 (s, 1H), 1.92 (t, J = 11.4 Hz, 2H), 1.26 (s, 2H), 1.12 (t, J = 7.1 Hz, 3H), ; 578.5 [M + H] | 1.16 |
| 355 | 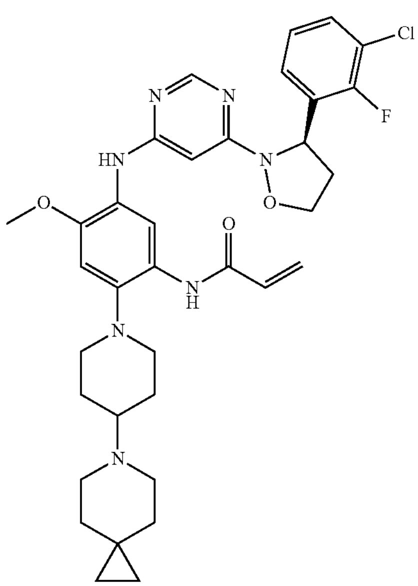 [SMILES: C=CC(=O)Nc1cc(Nc2cc(N3OCC[C@@H]3c3cccc(Cl)c3F)ncn2)c(OC)cc1N1CCC(N2CCC3(CC2)CC3)CC1] | N-(2-(4-(6-azaspiro[2.5]octan-6-yl)piperidine-1-yl)-5-((6-((R)-3-(3-chloro-2-fluorophenyl)isoxazolidine-2-yl)pyrimidine-4-yl)amino)-4-methoxyphenyl)acrylamide | ¹H NMR (400 MHz, DMSO-d₆) δ 9.01 (s, 1H), 8.17 (d, J = 12.9 Hz, 2H), 7.56-7.48 (m, 1H), 7.44 (t, J = 7.1 Hz, 1H), 7.23 (t, J = 7.9 Hz, 1H), 6.84 (s, 1H), 6.63 (dd, J = 16.9, 10.1 Hz, 1H), 6.36 (s, 1H), 6.24 (dd, J = 17.0, 1.9 Hz, 1H), 5.77-5.70 (m, 2H), 4.24-4.14 (m, 1H), 3.88 (q, J = 7.9 Hz, 1H), 3.82 (s, 3H), 3.51 (d, J = 11.5 Hz, 2H), 3.17 (d, J = 11.3 Hz, 2H), 3.08 (q, J = 11.4 Hz, 2H), 2.88-2.81 (m, 1H), 2.76 (t, J = 12.0 Hz, 2H), 2.26-2.16 (m, 2H), 2.13 (d, J = 14.6 Hz, 4H), 1.98 (d, J = 12.0 Hz, 2H), 1.23 (s, 1H), 1.17 (d, J = 13.8 Hz, 2H), 0.51-0.36 (m, 4H), ; 662.5 [M + H]⁺ | 1.40 |

TABLE 1-continued

| Example Compound | Structure | Name of Compound | ¹H NMR[[:]]; MS [M + H]⁺ | UPLC r.t. (min) |
|---|---|---|---|---|
| 356 | 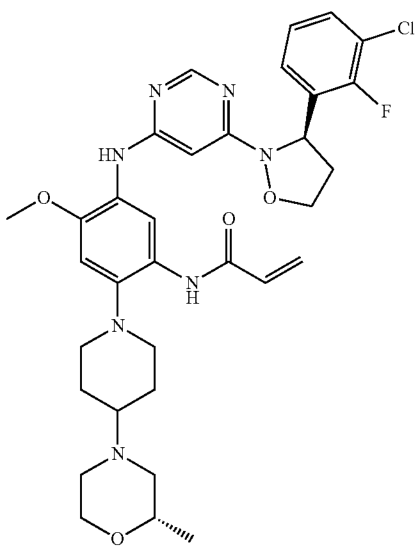 [SMILES: C=CC(=O)Nc1cc(Nc2cc(N3OCC[C@@H]3c3cccc(Cl)c3F)ncn2)c(OC)cc1N1CCC(N2CCO[C@@H](C)C2)CC1] | N-(5-((6-((R)-3-(3-chloro-2-fluorophenyl)isoxazolidine-2-yl)pyrimidine-4-yl)amino)-4-methoxy-2-(4-((S)-2-methylmorpholino)piperidin-1-yl)phenyl)acrylamide | ¹H NMR (400 MHz, DMSO-d₆) δ 9.03 (s, 1H), 8.68 (s, 1H), 8.17 (s, 1H), 7.56-7.47 (m, 1H), 7.47-7.39 (m, 1H), 7.23 (t, J = 7.8 Hz, 1H), 6.84 (s, 1H), 6.59 (s, 1H), 6.39 (s, 1H), 6.23 (dd, J = 17.1, 1.9 Hz, 1H), 5.73 (dd, J = 8.9, 4.9 Hz, 2H), 4.18 (td, J = 8.0, 3.7 Hz, 1H), 4.05 (d, J = 12.7 Hz, 1H), 3.87 (t, J = 8.1 Hz, 1H), 3.82 (s, 3H), 3.62 (td, J = 6.7, 4.0 Hz, 1H), 3.14 (qd, J = 7.4, 4.1 Hz, 4H), 2.81 (dd, J = 8.1, 4.1 Hz, 2H), 2.78-2.68 (m, 2H), 2.25-2.17 (m, 1H), 2.15 (d, J = 9.8 HZ, 2H), 1.91 (s, 3H), 1.25 (q, J = 7.2, 6.7 Hz, 4H), 1.18 (d, J = 6.2 Hz, 2H), ; 652.4 [M + H]⁺ | 1.32 |
| 357 | 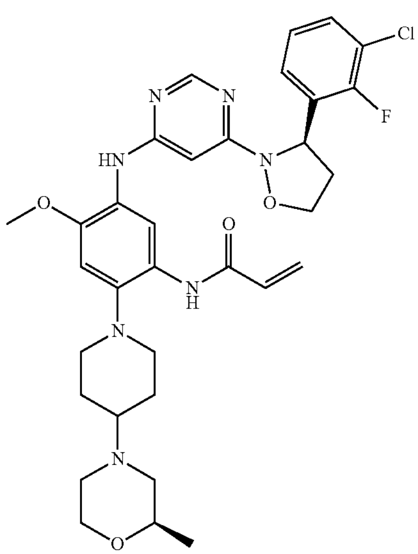 [SMILES: C=CC(=O)Nc1cc(Nc2cc(N3OCC[C@@H]3c3cccc(Cl)c3F)ncn2)c(OC)cc1N1CCC(N2CCO[C@H](C)C2)CC1] | N-(5-((6-((R)-3-(3-chloro-2-fluorophenyl)isoxazolidine-2-yl)pyrimidine-4-yl)amino)-4-methoxy-2-(4-((R)-2-methylmorpholino)piperidin-1-yl)phenyl)acrylamide | ¹H NMR (400 MHz, DMSO-d₆) δ 8.95 (s, 1H), 8.64 (s, 1H), 8.15 (s, 1H), 7.51 (t, J = 7.5 Hz, 1H), 7.45 (t, J = 7.1 Hz, 1H), 7.22 (t, J = 7.9 Hz, 1H), 6.83 (s, 1H), 6.64 (s, 1H), 6.36 (s, 1H), 6.21 (d, J = 17.0 Hz, 1H), 5.77-5.71 (m, 2H), 4.17 (dt, J = 9.1, 4.5 Hz, 1H), 3.86 (q, J = 8.0 Hz, 1H), 3.80 (s, 3H), 3.06 (s, 3H), 2.89-2.75 (m, 3H), 2.18 (dt, J = 12.8, 6.9 Hz, 4H), 1.91 (s, 3H), 1.87 (s, 3H), 1.73 (d, J = 14.7 Hz, 2H), 1.07 (d, J = 6.5 Hz, 4H), ; 652.4 [M + H]⁺ | 1.32 |

TABLE 1-continued

| Example Compound | Structure | Name of Compound | ¹H NMR[[:]]; MS [M + H]⁺ | UPLC r.t. (min) |
|---|---|---|---|---|
| 358 | 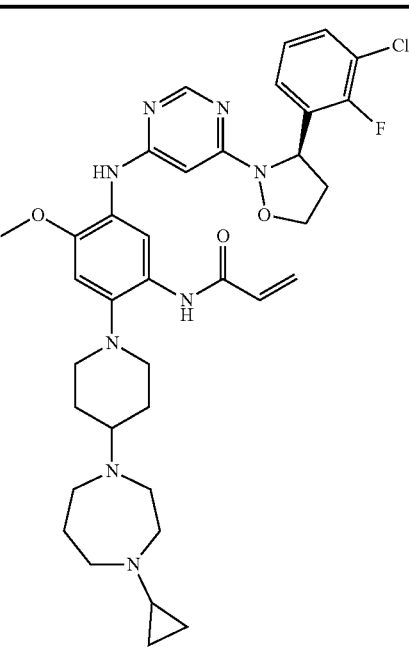 | N-(5-((6-((R)-3-(3-chloro-2-fluorophenyl)isoxazolidine-2-yl)pyrimidine-4-yl)amino)-2-(4-(4-cyclopropyl-1,4-diazepane-1-yl)piperidine-1-yl)-4-methoxyphenyl)acrylamide | ¹H NMR (400 MHz, DMSO-d₆) δ 8.96 (s, 1H), 8.67 (s, 1H), 8.16 (s, 1H), 7.57-7.47 (m, 1H), 7.47-7.40 (m, 1H), 7.23 (t, J = 7.9 Hz, 1H), 6.82 (s, 1H), 6.66 (dd, J = 16.8, 10.1 Hz, 1H), 6.39 (s, 1H), 6.24 (dd, J = 17.0, 2.0 Hz, 1H), 5.74 (dt, J = 8.7, 4.8 Hz, 2H), 4.18 (td, J = 8.0, 3.7 Hz, 1H), 3.87 (t, J = 8.1 Hz, 1H), 3.81 (s, 4H), 3.13 (d, J = 11.5 Hz, 3H), 3.05 (s, 2H), 2.88 (s, 2H), 2.86-2.78 (m, 2H), 2.74 (t, J = 11.6 Hz, 2H), 2.26-2.14 (m, 2H), 2.05 (d, J = 14.8 Hz, 3H), 1.95 (s, 2H), 1.91 (s, 5H), 0.48 (d, J = 30.7 Hz, 3H), ; 691.5 [M + H]⁺ | 1.20 |
| 359 | 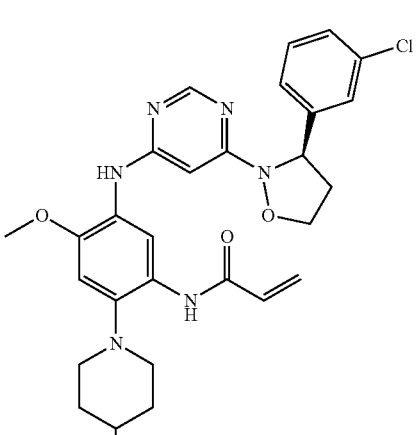 | N-(5-((6-((R)-3-(3-chlorophenyl)isoxazolidine-2-yl)pyrimidine-4-yl)amino)-2-((2-(dimethylamino)ethyl)(methyl)amino)-4-methoxyphenyl)acrylamide | ¹H NMR (400 MHz, DMSO-d₆) δ 10.05 (s, 1H), 8.62 (s, 1H), 8.47 (s, 1H), 8.17 (s, 1H), 7.48-7.27 (m, 4H), 6.99 (s, 1H), 6.46-6.31 (m, 2H), 6.22 (dd, J = 16.9, 2.2 Hz, 1H), 5.81-5.65 (m, 1H), 5.54 (dd, J = 8.7, 5.1 Hz, 1H), 4.14 (td, J = 7.9, 3.8 Hz, 1H), 3.80 (s, 3H), 2.87 (t, J = 5.8 Hz, 2H), 2.78 (dtd, J = 12.0, 7.8, 3.7 Hz, 1H), 2.71 (s, 3H), 2.33 (s, 2H), 2.21 (s, 8H); 552.4 [M + H]⁺ | 1.21 |

TABLE 1-continued

| Example Compound | Structure | Name of Compound | ¹H NMR[[:]]; MS [M + H]⁺ | UPLC r.t. (min) |
|---|---|---|---|---|
| 360 | 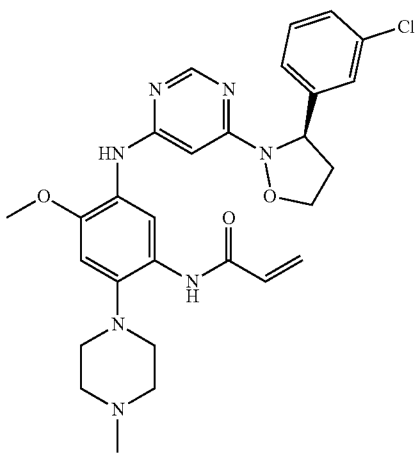 [SMILES: C=CC(=O)Nc1cc(Nc2cc(N3OCC[C@@H]3c3cccc(Cl)c3)ncn2)c(OC)cc1N1CCN(C)CC1] | N-(5-((6-((R)-3-(3-chlorophenyl) isoxazolidine-2-yl)pyrimidine-4-yl) amino)-4-methoxy-2-(4-methylpiperazine-1-yl)phenyl)acrylamide | ¹H NMR (400 MHz, DMSO-d₆) δ 8.97 (s, 1H), 8.62 (s, 1H), 8.14 (d, J = 13.7 Hz, 2H), 7.48-7.30 (m, 4H), 6.84 (s, 1H), 6.59 (dd, J = 17.0, 10.2 Hz, 1H), 6.36 (s, 1H), 6.21 (dt, J = 17.0, 3.9 Hz, 1H), 5.72 (d, J = 10.6 Hz, 1H), 5.54 (dd, J = 8.6, 5.1 Hz, 1H), 4.14 (td, J = 7.9, 3.7 Hz, 1H), 3.88-3.76 (m, 4H), 2.88 (t, J = 4.8 Hz, 4H), 2.77 (qq, J = 7.7, 3.7 Hz, 1H), 2.55 (d, J = 10.5 Hz, 3H), 2.36-2.16 (m, 5H); 550.4 [M + H]⁺ | 1.16 |
| 361 | 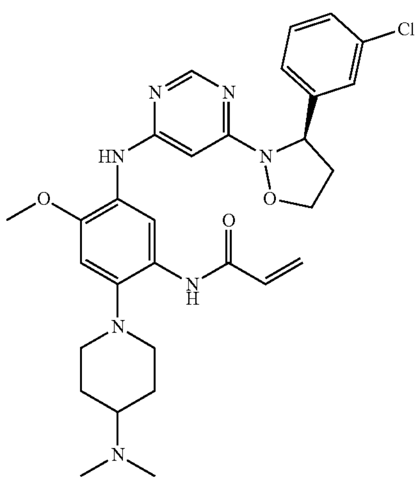 [SMILES: C=CC(=O)Nc1cc(Nc2cc(N3OCC[C@@H]3c3cccc(Cl)c3)ncn2)c(OC)cc1N1CCC(N(C)C)CC1] | N-(5-((6-((R)-3-(3-chlorophenyl) isoxazolidine-2-yl)pyrimidine-4-yl)amino)-2-(4-(dimethylamino) piperidine-1-yl)-4-methoxyphenyl) acrylamide | ¹H NMR (400 MHz, DMSO-d₆) δ 8.98 (s, 1H), 8.61 (s, 1H), 8.15 (d, J = 6.5 Hz, 2H), 7.47-7.30 (m, 4H), 6.83 (s, 1H), 6.65 (dd, J = 17.0, 10.1 Hz, 1H), 6.35 (s, 1H), 6.23 (ddd, J = 17.0. 12.9, 2.0 Hz, 1H), 5.77-5.68 (m, 1H), 5.54 (dd, J = 8.7, 5.1 Hz, 1H), 4.14 (td, J = 7.9, 3.8 Hz, 1H), 3.80 (s, 4H), 3.09-3.03 (m, 2H), 2.77 (dtd, J = 12.0, 7.9, 3.7 Hz, 1H), 2.71-2.63 (m, 2H), 2.30 (s, 6H), 1.86 (d, J = 11.5 Hz, 2H), 1.78-1.64 (m, 2H), 1.13-1.02 (m, 2H); 578.4 [M + H]⁺ | 1.18 |
| 362 | 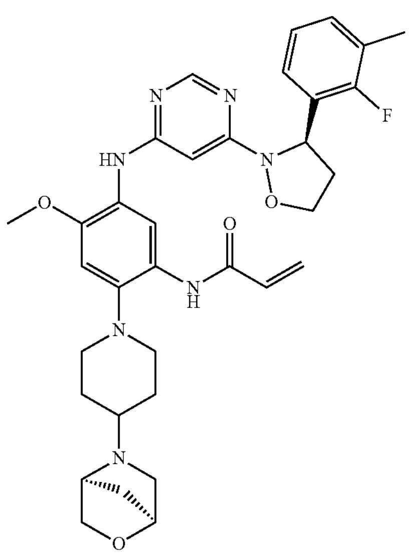 | N-(2-(4-((1S,4S)-2-oxa-5-azabicyclo[2.2.1]heptane-5-yl)piperidine-1-yl)-5-((6-((R)-3-(2-fluoro-3-methylphenyl) isoxazolidine-2-yl)pyrimidine-4-yl)amino)-4-methoxyphenyl) acrylamide | ¹H NMR (400 MHz, Chloroform-d) δ 8.88 (s, 1H), 8.46 (s, 1H), 8.37 (d, J = 1.0 Hz, 1H), 7.44-7.33 (m, 1H), 7.11-7.03 (m, 1H), 6.99 (t, J = 7.6 Hz, 1H), 6.92 (s, 1H), 6.74 (d, J = 8.9 Hz, 2H), 6.41-6.16 (m, 2H), 5.91 (dd, J = 8.8, 4.4 Hz, 1H), 5.73 (dd, J = 9.8, 1.6 Hz, 1H), 4.47 (s, 1H), 4.16-4.01 (m, 3H), 3.85 (s, 3H), 3.66 (dq, J = 13.3, 7.3, 6.6 Hz, 2H), 3.08 (dd, J = 15.6, 8.1 Hz, 3H), 2.79 (dtdd, J = 20.3, 11.7, 8.3, 3.4 Hz, 4H), 2.36-2.22 (m, 4H), 1.97 (d, J = 12.6 Hz, 2H), 1.55-1.41 (m, 5H), ; 630.5 [M + H]⁺ | 1.15 |

TABLE 1-continued

| Example Compound | Structure | Name of Compound | ¹H NMR[[:]]; MS [M + H]⁺ | UPLC r.t. (min) |
|---|---|---|---|---|
| 363 | 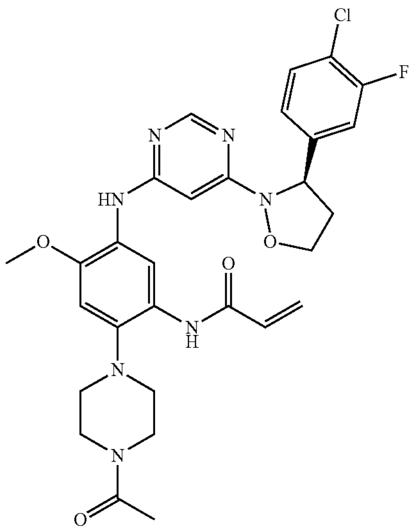 [SMILES: C=CC(=O)Nc1cc(Nc2cc(N3OCC[C@@H]3c3ccc(Cl)c(F)c3)ncn2)c(OC)cc1N1CCN(C(C)=O)CC1] | N-(2-(4-acetylpiperazine-1-yl)-5-((6-((R)-3-(4-chloro-3-fluorophenyl)isoxazolidine-2-yl)pyrimidine-4-yl)amino)-4-methoxyphenyl)acrylamide | ¹H NMR (400 MHz, Chloroform-d) δ 8.95 (s, 1H), 8.44 (s, 1H), 8.38 (d, J = 1.0 Hz, 1H), 7.36 (t, J = 7.9 Hz, 1H), 7.29 (dd, J = 10.1, 2.0 Hz, 1H), 7.19 (dd, J = 8.4, 2.0 Hz, 1H), 6.98 (s, 1H), 6.72 (s, 2H), 6.38 (dd, J = 16.9, 1.5 Hz, 1H), 6.26 (dd, J = 16.9, 10.0 Hz, 1H), 5.77 (dd, J = 10.0, 1.5 Hz, 1H), 5.66 (dd, J = 8.7, 4.6 Hz. 1H), 4.16 (td, J = 8.0, 4.2 Hz, 1H), 4.06 (q, J = 8.1 Hz, 1H), 3.85 (s, 3H), 3.80 (s, 1H), 3.65 (t, J = 5.0 Hz, 2H), 2.88 (td, J = 6.3, 3.2 Hz, 4H), 2.77 (dtd, J = 12.2, 8.0, 4.2 Hz, 1H), 2.34 (dtd, J = 12.5, 8.1, 4.6 Hz, 1H), 2.17 (s, 3H), 1.66-1.59 (m, 1H), ; 596.3 [M + H]⁺ | 1.44 |
| 364 | 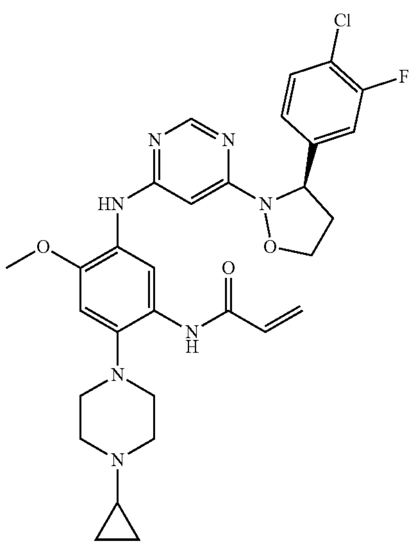 [SMILES: C=CC(=O)Nc1cc(Nc2cc(N3OCC[C@@H]3c3ccc(Cl)c(F)c3)ncn2)c(OC)cc1N1CCN(C2CC2)CC1] | N-(5-((6-((R)-3-(4-chloro-3-fluorophenyl)isoxazolidine-2-yl)pyrimidine-4-yl)amino)-2-(4-cyclopropylpiperazine-1-yl)-4-methoxyphenyl)acrylamide | ¹H NMR (400 MHz, Chloroform-d) δ 8.90 (s, 1H), 8.60 (s, 1H), 8.36 (d, J = 1.0 Hz, 1H), 7.35 (t, J = 7.9 Hz, 1H), 7.29 (dd, J = 10.2, 2.1 Hz, 1H), 7.19 (dd, J = 8.3, 2.0 Hz, 1H), 6.94 (s, 1H), 6.79 (s, 1H), 6.37 (dd, J = 16.9, 1.7 Hz, 1H), 6.28 (dd, J = 16.9, 9.8 Hz, 1H), 5.76 (dd, J = 9.8, 1.7 Hz, 1H), 5.66 (dd, J = 8.7, 4.5 Hz, 1H), 4.15 (td, J = 8.0, 4.2 Hz, 1H), 4.07 (q, J = 8.0 Hz, 1H), 3.81 (s, 3H), 2.92-2.71 (m, 9H), 2.33 (dtd, J = 12.5, 8.1, 4.6 Hz, 1H), 1.72 (tt, J = 6.6, 3.7 Hz, 1H), 0.57-0.38 (m, 4H), ; 594.4 [M + H]⁺ | 1.28 |

TABLE 1-continued

| Example Compound | Structure | Name of Compound | $^1$H NMR[:]; MS [M + H]$^+$ | UPLC r.t. (min) |
|---|---|---|---|---|
| 365 | 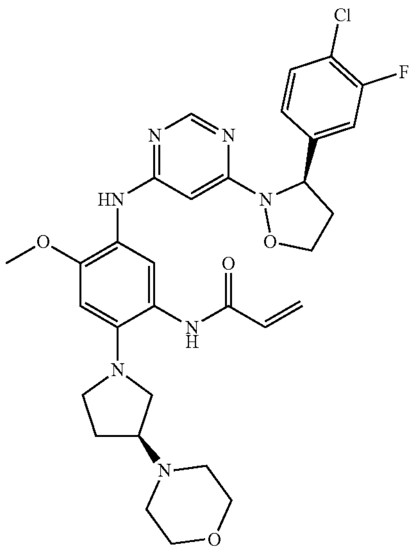 | N-(5-((6-((R)-3-(4-chloro-3-fluorophenyl)isoxazolidine-2-yl)pyrimidine-4-yl)amino)-4-methoxy-2-((S)-3-morpholinopyrolidine-1-yl)phenyl)acrylamide | $^1$H NMR (400 MHz, Chloroform-d) δ 8.71 (s, 1H), 8.35 (s, 1H), 8.16 (s, 1H), 7.35 (t, J = 7.9 Hz, 1H), 7.29 (dd, J = 10.2, 2.0 Hz, 1H), 7.19 (dd, J = 8.3, 2.0 Hz, 1H), 6.91 (s, 1H), 6.77 (s, 1H), 6.67 (s, 1H), 6.45-6.20 (m, 2H), 5.74 (dd, J = 10.0, 1.6 Hz, 1H), 5.65 (dd, J = 8.7, 4.6 Hz, 1H), 4.14 (td, J = 7.9, 4.2 Hz, 1H), 4.04 (q, J = 8.0 Hz, 1H), 3.84 (s, 3H), 3.76 (t, J = 4.7 Hz, 3H), 3.24-2.94 (m, 4H), 2.76 (dtd, J = 12.3, 8.0, 4.2 Hz, 1H), 2.64-2.42 (m, 4H), 2.33 (dtd, J = 12.3, 8.0, 4.5 Hz, 1H), 2.26-2.13 (m, 1H), 2.02 (s, 3H), ; 624.4 [M + H]$^+$ | 1.23 |
| 366 | 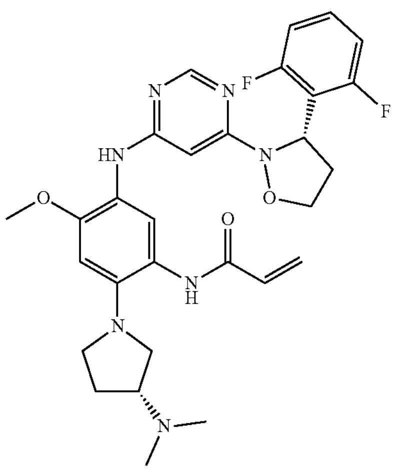 [SMILES: C=CC(=O)Nc1cc(Nc2cc(N3OCC[C@H]3c3c(F)cccc3F)ncn2)c(OC)cc1N1CC[C@@H](N(C)C)C1] | N-(5-((6-((S)-3-(2,6-difluorophenyl)isoxazolidine-2-yl)pyrimidine-4-yl)amino)-2-((R)-3-(dimethylamino)pyrolidine-1-yl)-4-methoxyphenyl)acrylamide | 566.5 [M + H]$^+$ | 1.06 |
| 367 | 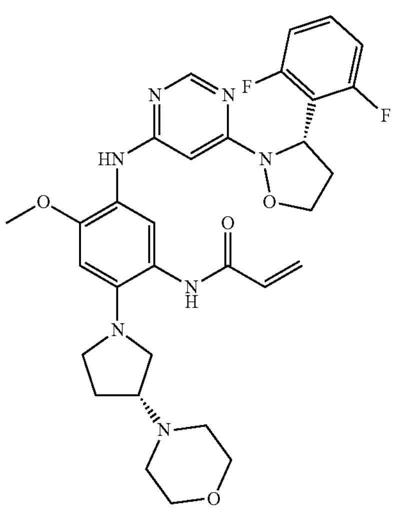 [SMILES: C=CC(=O)Nc1cc(Nc2cc(N3OCC[C@H]3c3c(F)cccc3F)ncn2)c(OC)cc1N1CC[C@@H](N2CCOCC2)C1] | N-(5-((6-((S)-3-(2,6-difluorophenyl)isoxazolidine-2-yl)pyrimidine-4-yl)amino)-4-methoxy-2-((R)-3-morpholinopyrolidine-1-yl)phenyl)acrylamide | 1H NMR (400 MHz, Methanol-d4) δ 7.99 (s, 1H), 7.55 (s, 1H), 7.25-7.14 (m, 1H), 6.83 (t, J = 8.4 Hz, 2H), 6.52 (s, 1H), 6.41 (dd, J = 17.0, 10.2 Hz, 1H), 6.23 (d, J = 16.3 Hz, 1H), 6.11 (s, 1H), 5.63 (dd, J = 19.9, 9.7 Hz, 2H), 4.19 (dd, J = 7.7. 6.1 Hz, 1H), 3.80-3.74 (m, 1H), 3.71 (s, 3H), 3.64 (t, J = 4.0 Hz, 4H), 3.45 (ddd, J = 17.1, 11.1, 5.4 Hz, 2H), 3.21 (dt. J = 3.2, 1.6 Hz, 3H), 3.17 (d, J = 7.1 Hz, 2H), 2.99-2.92 (m, 1H), 2.70-2.46 (m, 5H), 2.39 (dt, J = 11.7, 7.7 Hz, 2H), 2.12 (d, J = 4.8 Hz, 1H), 1.88 (s, 5H); 608.5 [M + H]+ | 1.05 |

TABLE 1-continued

| Example Compound | Structure | Name of Compound | ¹H NMR[[:]]; MS [M + H]⁺ | UPLC r.t. (min) |
|---|---|---|---|---|
| 368 | 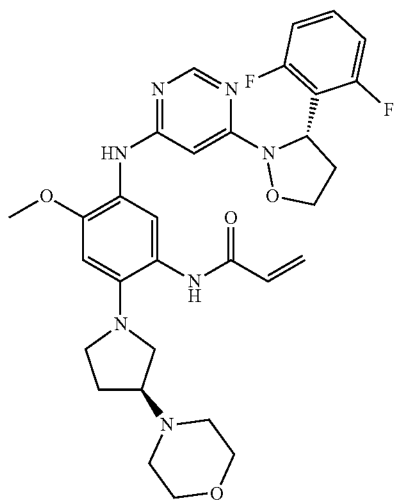 [SMILES: C=CC(=O)Nc1cc(Nc2cc(N3OCC[C@H]3c3c(F)cccc3F)ncn2)c(OC)cc1N1CC[C@H](N2CCOCC2)C1] | N-(5-((6-((S)-3-(2,6-difluorophenyl)isoxazolidine-2-yl)pyrimidine-4-yl)amino)-4-methoxy-2-((S)-3-morpholinopyrrolidine-1-yl)phenyl)acrylamide | $^1$H NMR (400 MHz, Methanol-$d_4$) δ 8.09 (s, 1H), 7.64 (s, 1H), 7.34-7.25 (m, 1H), 6.93 (t, J = 8.4 Hz, 2H), 6.62 (s, 1H), 6.51 (dd, J = 17.0, 10.2 Hz, 1H), 6.37-6.29 (m, 1H), 6.22 (s, 1H), 5.73 (dd, J = 17.8, 9.8 Hz, 2H), 4.29 (dd, J = 7.9, 5.9 Hz, 1H), 3.87 (dd, J = 11.6, 6.3 Hz, 2H), 3.82 (s, 3H), 3.72 (t, J = 4.5 Hz, 4H), 3.55 (ddd, J = 17.1, 11.1, 5.4 Hz, 1H), 3.32-3.29 (m, 2H), 3.24 (dd, J = 14.3, 7.3 Hz, 2H), 3.02-2.90 (m, 1H), 2.75 (dt, J = 9.0, 8.2 Hz, 1H), 2.67-2.45 (m, 4H), 2.25-2.14 (m, 1H), 1.97 (s, 4H); 608.5 [M + H]⁺ | 1.07 |
| 369 | 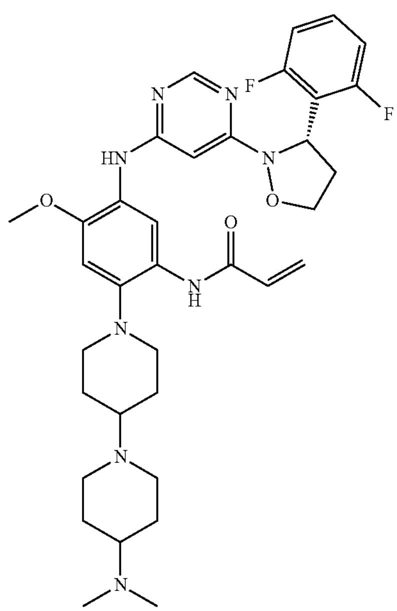 [SMILES: C=CC(=O)Nc1cc(Nc2cc(N3OCC[C@H]3c3c(F)cccc3F)ncn2)c(OC)cc1N1CCC(N2CCC(N(C)C)CC2)CC1] | N-(5-((6-((S)-3-(2,6-difluorophenyl)isoxazolidine-2-yl)pyrimidine-4-yl)amino)-2-(4-(dimethylamino)-[1,4'-bipiperidine]-1'-yl)-4-methoxyphenyl)acrylamide | 663.6 [M + H]⁺ | 0.99 |

TABLE 1-continued

| Example Compound | Structure | Name of Compound | ¹H NMR[:]; MS [M + H]⁺ | UPLC r.t. (min) |
|---|---|---|---|---|
| 370 | 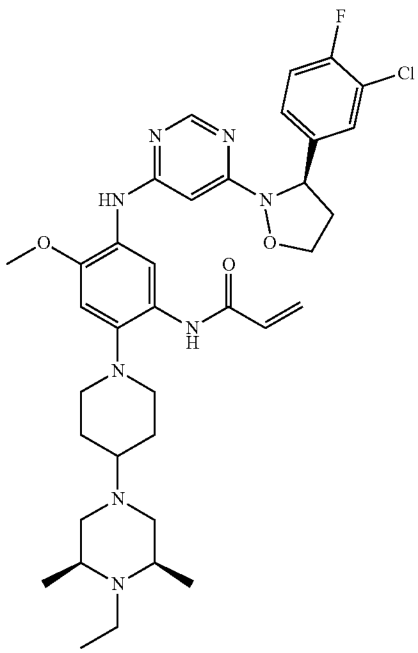 [SMILES: C=CC(=O)Nc1cc(Nc2cc(N3OCC[C@@H]3c3ccc(F)c(Cl)c3)ncn2)c(OC)cc1N1CCC(N2C[C@@H](C)N(CC)[C@@H](C)C2)CC1] | N-(5-((6-((R)-3-(3-chloro-4-fluorophenyl)isoxazolidine-2-yl)pyrimidine-4-yl)amino)-2-(4-((3S,5R)-4-ethyl-3,5-dimethylpiperazine-1-yl)piperidine-1-yl)-4-methoxyphenyl)acrylamide | ¹H NMR (400 MHz, CDCl₃) δ 8.80 (s, 1H), 8.42 (s, 1H), 8.32 (s, 1H), 7.52 (dd, J = 7.0, 1.8 Hz, 1H), 7.37 (s, 1H), 7.34-7.29 (m, 1H), 7.10 (t, J = 8.7 Hz, 1H), 6.74 (s, 1H), 6.67 (s, 1H), 6.31 (dt, J = 16.9, 13.1 Hz, 2H), 5.75 (d, J = 10.8 Hz, 1H), 5.63 (dd, J = 8.5, 4.6 Hz, 1H), 4.15 (td, J = 7.9, 4.2 Hz, 1H), 4.05 (q, J = 8.0 Hz, 1H), 3.84 (s, 3H), 3.15-2.92 (m, 8H), 2.81-2.65 (m, 3H), 2.54-2.38 (m, 3H), 2.38-2.26 (m, 1H), 2.08 (d, J = 12.1 Hz, 2H), 2.04 (s, 4H), 1.72 (dd, J = 21.0, 11.5 Hz, 2H), 1.22 (d, J = 6.1 Hz, 6H), 1.02 (t, J = 7.1 Hz, 3H); 693.6 [M + H]⁺ | 1.22 |
| 371 | 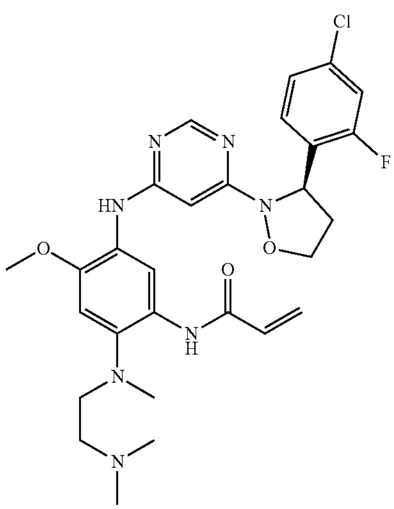 [SMILES: C=CC(=O)Nc1cc(Nc2cc(N3OCC[C@@H]3c3ccc(Cl)cc3F)ncn2)c(OC)cc1N(C)CCN(C)C] | N-(5-((6-((R)-3-(4-chloro-2-fluorophenyl)isoxazolidine-2-yl)pyrimidine-4-yl)amino)-2-((2-(dimethylamino)ethyl)(methyl)amino)-4-methoxyphenyl)acrylamide | ¹H NMR (400 MHz, Chloroform-d) δ 9.87 (s, 1H), 8.93 (s, 1H), 8.34 (s, 1H), 7.54 (t, J = 8.3 Hz, 1H), 7.18 (s, 1H), 7.13-7.06 (m, 2H), 6.78 (d, J = 2.2 Hz, 2H), 6.40 (s, 1H), 6.39 (s, 1H), 5.87 (dd, J = 8.8, 4.4 Hz, 1H), 5.68 (t, J = 5.9 Hz, 1H), 4.11 (td, J = 8.0, 6.5, 3.1 Hz, 2H), 3.85 (s, 3H), 2.93 (dt, J = 5.6, 2.9 Hz, 2H), 2.86-2.79 (m, 1H), 2.70 (s, 3H), 2.44 (t, J = 5.7 Hz, 2H), 2.33 (s, 6H), 2.29-2.24 (m, 1H); 570.4 [M + H]⁺ | 1.33 |

TABLE 1-continued

| Example Compound | Structure | Name of Compound | ¹H NMR[[:]]; MS [M + H]⁺ | UPLC r.t. (min) |
|---|---|---|---|---|
| 372 | 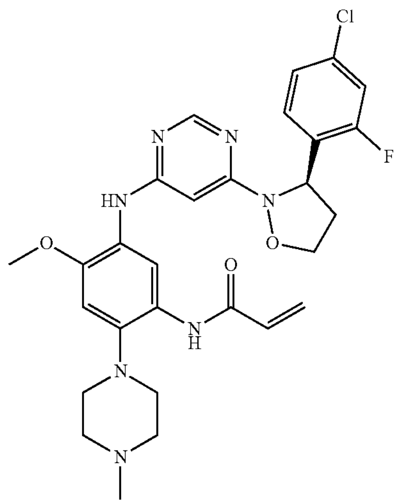 [SMILES: C=CC(=O)Nc1cc(Nc2cc(N3OCC[C@@H]3c3ccc(Cl)cc3F)ncn2)c(OC)cc1N1CCN(C)CC1] | N-(5-((6-((R)-3-(4-chloro-2-fluorophenyl)isoxazolidine-2-yl)pyrimidine-4-yl)amino)-4-methoxy-2-(4-methylpiperazine-1-yl)phenyl)acrylamide | ¹H NMR (400 MHz, Methanol-d₄) δ 8.32 (s, 1H), 8.15 (d, J = 5.0 Hz, 1H), 7.52 (t, J = 8.2 Hz, 1H), 7.24-7.16 (m, 2H), 6.92 (d, J = 13.1 Hz, 1H), 6.53 (dd, J = 16.9, 10.2 Hz, 1H), 6.48 (d, J = 3.7 Hz, 1H), 6.35 (d, J = 16.8 Hz, 1H), 5.80 (d, J = 10.2 Hz, 1H), 5.73 (dd, J = 8.7, 4.7 Hz, 1H), 4.13 (td, J = 8.0, 4.2 Hz, 1H), 3.99 (d, J = 7.8 Hz, 1H), 3.88 (d, J = 2.3 Hz, 3H), 3.04 (t, J = 4.9 Hz, 4H), 2.99-2.88 (m, 4H), 2.82 (ddd, J = 12.5, 8.2, 4.4 Hz, 1H), 2.57 (d, J = 7.6 Hz, 3H), 2.28-2.21 (m, 1H); 568.4 [M + H]⁺ | 1.29 |
| 373 | 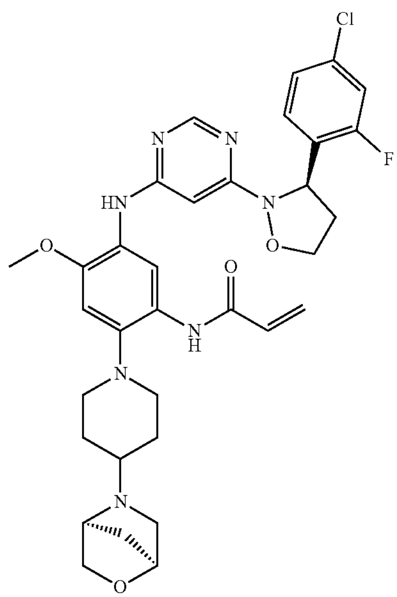 [SMILES: C=CC(=O)Nc1cc(Nc2cc(N3OCC[C@@H]3c3ccc(Cl)cc3F)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((R)-3-(4-chloro-2-fluorophenyl)isoxazolidine-2-yl)pyrimidine-4-yl)amino)-4-methoxyphenyl)acrylamide | ¹H NMR (400 MHz, DMSO-d₆) δ 10.89 (s, 1H), 9.23 (d, J = 30.9 Hz, 1H), 8.26 (s, 1H), 7.95 (d, J = 12.8 Hz, 1H), 7.51-7.40 (m, 2H), 7.30 (dd, J = 8.4, 2.1 Hz, 1H), 6.88 (d, J = 5.6 Hz, 1H), 6.59 (td, J = 15.9, 10.2 Hz, 1H), 6.24 (dt, J = 17.0, 2.4 Hz, 2H), 5.78-5.62 (m, 2H), 4.72-4.54 (m, 3H), 3.82 (d, J = 1.3 Hz, 3H), 3.70 (d, J = 9.7 Hz, 1H), 3.37 (d, J = 4.8 Hz, 4H), 2.95-2.66 (m, 4H), 2.34-2.17 (m, 3H), 2.08 (d, J = 11.5 Hz, 3H), ; 650.3 [M + H]⁺ | 1.38 |

TABLE 1-continued

| Example Compound | Structure | Name of Compound | $^1$H NMR[[:]]; MS [M + H]$^+$ | UPLC r.t. (min) |
|---|---|---|---|---|
| 374 | 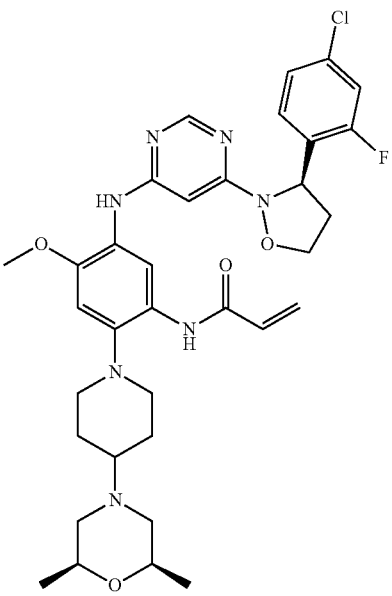 [SMILES: C=CC(=O)Nc1cc(Nc2cc(N3OCC[C@@H]3c3ccc(Cl)cc3F)ncn2)c(OC)cc1N1CCC(N2C[C@@H](C)O[C@@H](C)C2)CC1] | N-(5-((6-((R)-3-(4-chloro-2-fluorophenyl)isoxazolidine-2-yl)pyrimidine-4-yl)amino)-2-(4-((2S,6R)-2,6-dimethylmorpholino)piperidine-1-yl)-4-methoxyphenyl)acrylamide | $^1$H NMR (400 MHz, DMSO-d$_6$) δ 10.36 (s, 1H), 9.28 (s, 1H), 8.34 (s, 1H), 7.86 (s, 1H), 7.50 (dd, J = 10.3, 2.1 Hz, 1H), 7.38 (t, J = 8.3 Hz, 1H), 7.31 (dd, J = 8.4, 2.1 Hz, 1H), 6.94 (s, 1H), 6.72 (dd, J = 17.0, 10.2 Hz, 1H), 6.26 (dd, J = 17.0, 1.9 Hz, 1H), 6.15 (s, 1H), 5.77 (dd, J = 10.1, 1.9 Hz, 1H), 5.67 (dd, J = 8.6, 5.6 Hz, 1H), 4.36-4.31 (m, 1H), 4.17 (ddd, J = 9.8, 6.8, 3.4 Hz, 2H), 4.08 (d, J = 7.7 Hz, 1H), 3.82 (s, 3H), 3.36 (dd, J = 10.9, 5.1 Hz, 5H), 2.95 (dd, J = 7.9, 4.1 Hz, 1H), 2.81 (s, 2H), 2.70 (d, J = 10.6 Hz, 2H), 2.31-2.22 (m, 3H), 2.16-2.05 (m, 2H), 1.17 (d, J = 6.3 Hz, 6H), ; 666.3 [M + H]$^+$ | 1.32 |
| 375 | 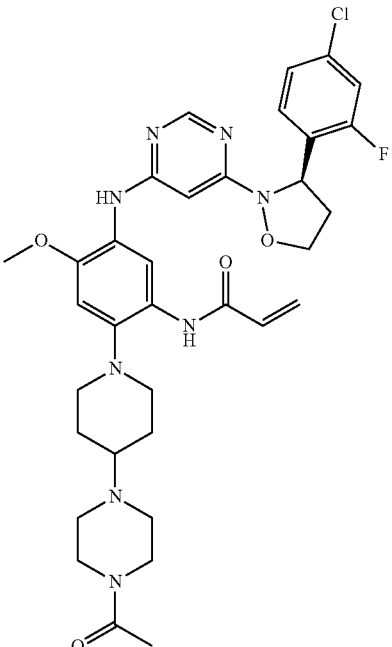 | N-(2-(4-(4-acetylpiperazine-1-yl)piperidine-1-yl)-5-((6-((R)-3-(4-chloro-2-fluorophenyl)isoxazolidine-2-yl)pyrimidine-4-yl)amino)-4-methoxyphenyl)acrylamide | $^1$H NMR (400 MHz, DMSO-d$_6$) δ 9.67 (s, 1H), 9.15 (s, 1H), 8.27 (s, 1H), 7.96 (s, 1H), 7.52-7.37 (m, 2H), 7.30 (dd, J = 8.3, 2.1 Hz, 1H), 6.89 (s, 1H), 6.67 (dd, J = 17.0, 10.2 Hz, 1H), 6.28-6.15 (m, 2H), 5.80-5.63 (m, 2H), 4.50 (d, J = 14.0 Hz, 1H), 4.28 (s, 1H), 4.01 (s, 2H), 3.81 (s, 3H), 3.49 (s, 3H), 3.34 (s, 2H), 3.18 (d, J = 10.4 Hz, 4H), 3.05-2.88 (m, 3H), 2.77 (s, 2H), 2.17 (s, 3H), 2.06 (s, 3H), ; 679.3 [M + H]$^+$ | 1.28 |

TABLE 1-continued

| Example Compound | Structure | Name of Compound | ¹H NMR[[:]]; MS [M + H]⁺ | UPLC r.t. (min) |
|---|---|---|---|---|
| 376 | 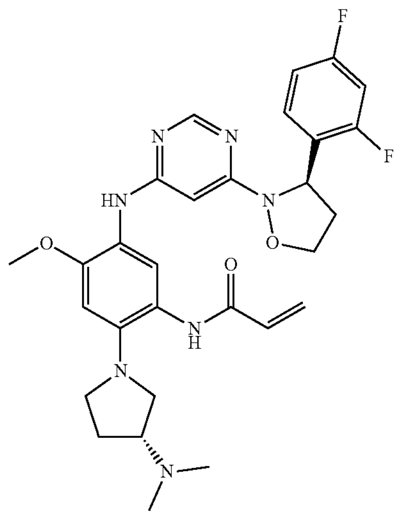 [SMILES: C=CC(=O)Nc1cc(Nc2cc(N3OCC[C@@H]3c3ccc(F)cc3F)ncn2)c(OC)cc1N1CC[C@@H](N(C)C)C1] | N-(5-((6-((R)-3-(2,4-difluorophenyl)isoxazolidine-2-yl)pyrimidine-4-yl)amino)-2-((R)-3-(dimethylamino)pyrolidine-1-yl)-4-methoxyphenyl)acrylamide | ¹H NMR (400 MHz, Chloroform-d) δ 8.67 (s, 1H), 8.35 (s, 1H), 8.14 (s, 1H), 7.56 (q, J = 8.1 Hz, 1H), 6.88-6.77 (m, 3H), 6.74 (d, J = 11.0 Hz, 2H), 6.41-6.35 (m, 1H), 6.28 (dd, J = 16.9, 9.8 Hz, 1H), 5.88 (dd, J = 8.7, 4.3 Hz, 1H), 5.73 (dd, J = 9.9, 1.8 Hz, 1H), 4.15-4.04 (m, 2H), 3.84 (s, 3H), 3.19 (q, J = 7.9 Hz, 1H), 3.11 (d, J = 7.0 Hz, 2H), 2.90-2.75 (m, 2H), 2.30 (s, 6H), 1.62 (s, 4H), ; 566.4 [M + H] | 1.15 |
| 377 | 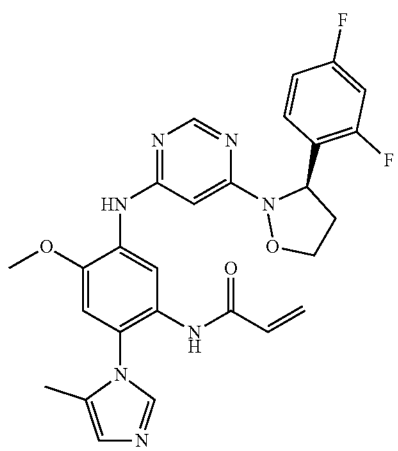 [SMILES: C=CC(=O)Nc1cc(Nc2cc(N3OCC[C@@H]3c3ccc(F)cc3F)ncn2)c(OC)cc1-n1cncc1C] | N-(5-((6-((R)-3-(2,4-difluorophenyl)isoxazolidine-2-yl)pyrimidine-4-yl)amino)-4-methoxy-2-(5-methyl-1H-imidazole-1-yl)phenyl)acrylamide | ¹H NMR (400 MHz, Chloroform-d) δ 9.11 (s, 1H), 8.45 (s, 1H), 7.56 (q, J = 8.0 Hz, 1H), 7.21 (s, 1H), 7.14 (d, J = 1.4 Hz, 1H), 6.95 (d, J = 1.4 Hz, 1H), 6.84 (dd, J = 19.1, 9.0 Hz, 3H), 6.75 (s, 1H), 6.68 (s, 1H), 6.27 (d, J = 16.9 Hz, 1H), 6.03 (dd, J = 16.8, 10.3 Hz, 1H), 5.89 (dd, J = 8.7, 4.7 Hz, 1H), 5.71 (d, J = 10.3 Hz, 1H), 4.17 (dt, J = 7.9, 3.9 Hz, 1H), 4.06 (q, J = 7.9 Hz, 1H), 3.90 (s, 3H), 2.25 (s, 2H), 2.17 (s, 3H), ; 534.4 [M + H] | 1.26 |
| 378 | 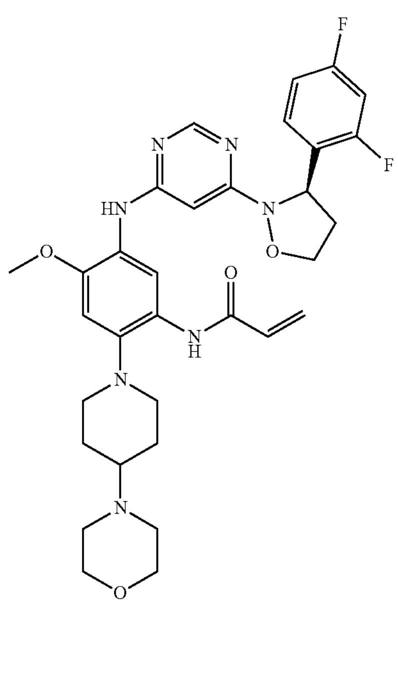 [SMILES: C=CC(=O)Nc1cc(Nc2cc(N3OCC[C@@H]3c3ccc(F)cc3F)ncn2)c(OC)cc1N1CCC(N2CCOCC2)CC1] | N-(5-((6-((R)-3-(2,4-difluorophenyl)isoxazolidine-2-yl)pyrimidine-4-yl)amino)-4-methoxy-2-(4-morpholinopiperidine-1-yl)phenyl)acrylamide | ¹H NMR (400 MHz, Chloroform-d) δ 8.88 (s, 1H), 8.44 (s, 1H), 8.37 (d, J = 1.0 Hz, 1H), 7.56 (td, J = 8.6, 6.5 Hz, 1H), 6.93 (s, 1H), 6.87-6.78 (m, 2H), 6.75 (d, J = 1.8 Hz, 2H), 6.36 (dd, J = 17.0, 1.5 Hz, 1H), 6.24 (dd, J = 16.9, 10.0 Hz, 1H), 5.88 (dd, J = 8.7, 4.3 Hz, 1H), 5.74 (dd, J = 10.0, 1.6 Hz, 1H), 4.16-4.04 (m, 2H), 3.85 (s, 3H), 3.78 (t, J = 4.7 Hz, 4H), 3.07 (d, J = 11.6 Hz, 2H), 2.80 (dt, J = 11.7, 3.7 Hz, 1H), 2.77-2.67 (m, 2H), 2.62 (t, J = 4.7 Hz, 4H), 2.29 (ddd, J = 12.5, 9.8, 5.8 Hz, 2H), 2.08 (d, J = 12.5 Hz, 2H), 1.70-1.61 (m, 2H), ; 622.5[M + H] | 1.14 |

TABLE 1-continued

| Example Compound | Structure | Name of Compound | ¹H NMR[[:]]; MS [M + H]⁺ | UPLC r.t. (min) |
|---|---|---|---|---|
| 379 | 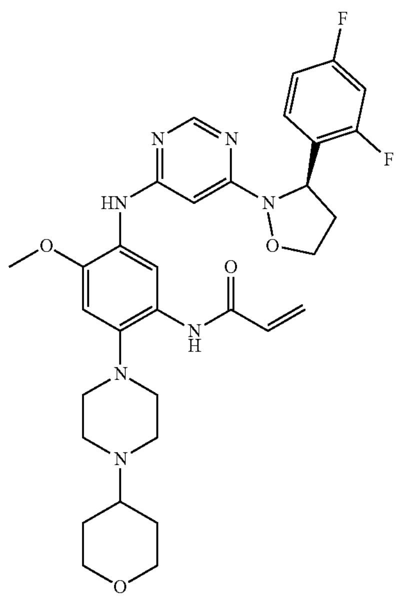 | N-(5-((6-((R)-3-(2,4-difluorophenyl)isoxazolidine-2-yl)pyrimidine-4-yl)amino)-4-methoxy-2-(4-(tetrahydro-2H-pyran-4-yl)piperazine-1-yl)phenyl)acrylamide | ¹H NMR (400 MHz, Chloroform-d) δ 8.91 (s, 1H), 8.54 (s, 1H), 8.37 (s, 1H), 7.61-7.53 (m, 1H), 6.96 (s, 1H), 6.87-6.78 (m, 3H), 6.75 (s, 1H), 6.40-6.34 (m, 1H), 6.26 (dd, J = 17.0, 9.9 Hz, 1H), 5.88 (dd, 8.6, 4.3 Hz, 1H), 5.75 (dd, J = 9.9, 1.6 Hz, 1H), 4.14-4.04 (m, 4H), 3.83 (s, 3H), 3.42 (dd, J = 12.7, 10.7 Hz, 2H), 2.93 (q, J = 3.9 Hz, 4H), 2.83-2.74 (m, 4H), 2.52 (ddd, J = 11.3, 7.5, 3.8 Hz, 1H), 1.84 (d, J = 12.6 Hz, 2H), 1.66 (dd, J = 12.1, 4.4 Hz, 4H), ; 635.6 [M + H] | 1.20 |
| 380 | 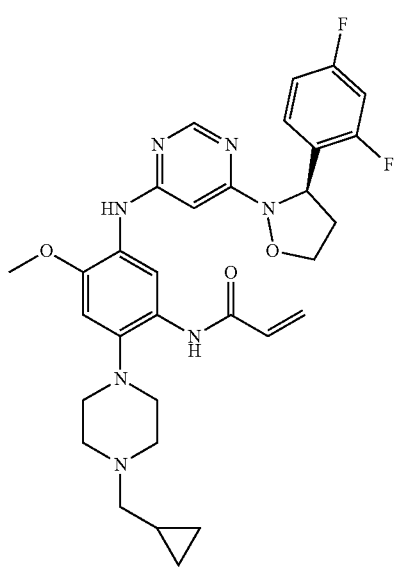 [SMILES: C=CC(=O)Nc1cc(Nc2cc(N3OCC[C@@H]3c3ccc(F)cc3F)ncn2)c(OC)cc1N1CCN(CC2CC2)CC1] | N-(2-(4-(cyclopropylmethyl)piperazine-1-yl)-5-((6-((R)-3-(2,4-difluorophenyl)isoxazolidine-2-yl)pyrimidine-4-yl)amino)-4-methoxyphenyl)acrylamide | ¹H NMR (400 MHz, Chloroform-d) δ 8.92 (s, 1H), 8.57 (s, 1H), 8.37 (d, J = 1.0 Hz, 1H), 7.60-7.53 (m, 1H), 6.94 (s, 1H), 6.87-6.75 (m, 4H), 6.40-6.33 (m, 1H), 6.26 (dd, J = 16.9, 9.9 Hz, 1H), 5.88 (dd, J = 8.7, 4.3 Hz, 1H), 5.74 (dd, J = 9.9, 1.6 Hz, 1H), 4.14-4.05 (m, 2H), 3.84 (s, 3H), 2.94 (d, J = 5.1 Hz, 4H), 2.80 (ddd, J = 12.8, 8.4, 4.7 Hz, 2H), 2.36 (d, J = 6.6 Hz, 2H), 2.28 (dq, J = 12.0, 3.7 Hz, 1H), 2.17 (s, 4H), 0.60-0.54 (m, 2H), 0.16 (q, J = 5.0 Hz, 2H), ; 592.5 [M + H] | 1.20 |

TABLE 1-continued

| Example Compound | Structure | Name of Compound | ¹H NMR[[:]]; MS [M + H]⁺ | UPLC r.t. (min) |
|---|---|---|---|---|
| 381 | 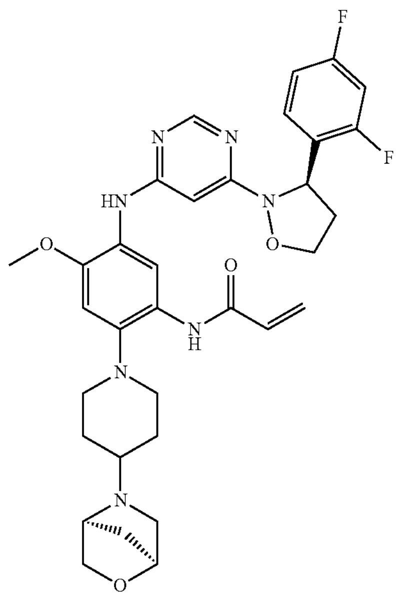 [SMILES: C=CC(=O)Nc1cc(Nc2cc(N3OCC[C@@H]3c3ccc(F)cc3F)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((R)-3-(2,4-difluorophenyl)isoxazolidine-2-yl)pyrimidine-4-yl)amino)-4-methoxyphenyl)acrylamide | ¹H NMR (400 MHz, Chloroform-d) δ 8.88 (s, 1H), 8.48 (s, 1H), 8.37 (d, J = 0.9 Hz, 1H), 7.61-7.53 (m, 1H), 6.93 (s, 1H), 6.82 (dddd, J = 12.9, 11.2, 8.6, 2.6 Hz, 2H), 6.76 (d, J = 5.3 Hz, 2H), 6.35 (dd, J = 17.0, 1.5 Hz, 1H), 6.23 (dd, J = 16.9, 10.1 Hz, 1H), 5.88 (dd, J = 8.7, 4.3 Hz, 1H), 5.73 (dd, J = 10.1, 1.5 Hz, 1H), 4.44 (s, 1H), 4.09 (q, J = 7.9, 7.3 Hz, 3H), 3.86 (s, 3H), 3.77 (d, J = 2.2 Hz, 1H), 3.66 (dd, J = 8.1, 1.6 Hz, 1H), 3.14 (dd, J = 9.9, 1.8 Hz, 1H), 3.03 (dd, J = 12.0, 3.7 Hz, 2H), 2.78 (ddd, J = 12.0, 8.4, 3.3 Hz, 2H), 2.62-2.55 (m, 1H), 2.50 (d, J = 9.9 Hz, 1H), 2.27 (dtd, J = 12.3, 8.0, 4.2 Hz, 1H), 2.04 (d, J = 13.1 Hz, 1H), 2.00-1.89 (m, 2H), 1.83 (d, J = 9.8 Hz, 1H), 1.65 (dd, J = 22.6, 11.4 Hz, 3H), ; 634.5 [M + H] | 1.15 |
| 382 | 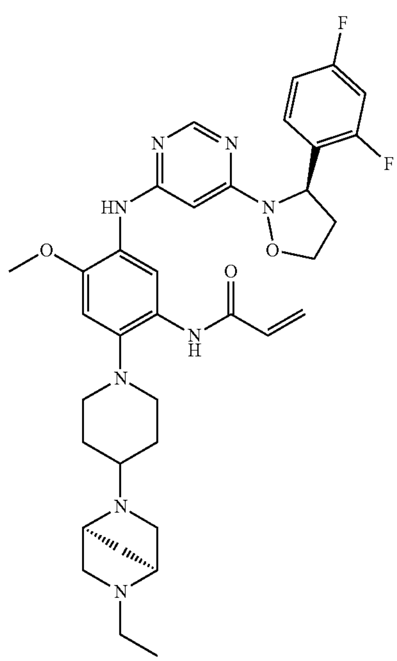 [SMILES: C=CC(=O)Nc1cc(Nc2cc(N3OCC[C@@H]3c3ccc(F)cc3F)ncn2)c(OC)cc1N1CCC(N2C[C@@H]3C[C@H]2CN3CC)CC1] | N-(5-((6-((R)-3-(2,4-difluorophenyl)isoxazolidine-2-yl)pyrimidine-4-yl)amino)-2-(4-((1S,4S)-5-ethyl-2,5-diazabicyclo[2.2.1]heptane-2-yl)piperidine-1-yl)-4-methoxyphenyl)acrylamide | ¹H NMR (400 MHz, Chloroform-d) δ 8.88 (s, 1H), 8.47 (s, 1H), 8.37 (s, 1H), 7.56 (q, J = 8.2 Hz, 1H), 6.92 (s, 1H), 6.87-6.77 (m, 2H), 6.75 (d, J = 3.4 Hz, 2H), 6.39-6.31 (m, 1H), 6.29-6.19 (m, 1H), 5.87 (dd, J = 8.6, 4.3 Hz, 1H), 5.73 (d, J = 10.1 Hz, 1H), 4.15-4.05 (m, 2H), 3.85 (s, 3H), 3.66 (s, 1H), 3.02 (s, 3H), 2.85-2.73 (m, 4H), 2.30-2.23 (m, 1H), 2.17 (s, 3H), 2.06 (d, J = 12.8 Hz, 1H), 1.90 (s, 2H), 1.69 (d, J = 31.5 Hz, 4H), 1.28 (d, J = 18.2 Hz, 3H), 1.17 (s, 2H), ; 661.5 [M + H] | 1.07 |

TABLE 1-continued

| Example Compound | Structure | Name of Compound | ¹H NMR[:]; MS [M + H]⁺ | UPLC r.t. (min) |
|---|---|---|---|---|
| 383 | 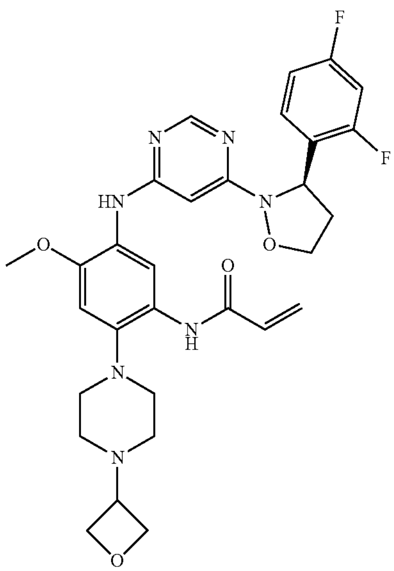 [SMILES: C=CC(=O)Nc1cc(Nc2cc(N3OCC[C@@H]3c3ccc(F)cc3F)ncn2)c(OC)cc1N1CCN(C2COC2)CC1] | N-(5-((6-((R)-3-(2,4-difluorophenyl)isoxazolidine-2-yl)pyrimidine-4-yl)amino)-4-methoxy-2-(4-(oxetane-3-yl)piperazine-1-yl)phenyl)acrylamide | ¹H NMR (400 MHz, Chloroform-d) δ 8.92 (s, 1H), 8.49 (s, 1H), 8.38 (s, 1H), 7.56 (d, J = 6.7 Hz, 1H), 6.97 (s, 1H), 6.79 (m, 4H), 6.36 (d, J = 16.2 Hz, 2H), 6.27 (m, 1H), 5.88 (m, 1H), 5.74 (d, J = 11.3 Hz, 1H), 4.69 (td, J = 21.8 Hz, 4H), 4.08 (m, 2H), 3.85 (s, 3H), 3.61 (m, 1H), 2.96 (s, 4H), 2.81 (m, 1H), 2.54 (s, 4H), 2.28 (s, 1H), ; 594.4 [M + H]⁺ | 1.16 |
| 384 | 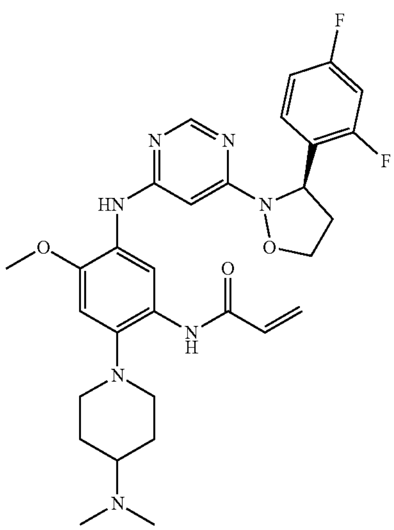 [SMILES: C=CC(=O)Nc1cc(Nc2cc(N3OCC[C@@H]3c3ccc(F)cc3F)ncn2)c(OC)cc1N1CCC(N(C)C)CC1] | N-(5-((6-((R)-3-(2,4-difluorophenyl)isoxazolidine-2-yl)pyrimidine-4-yl)amino)-2-(4-(dimethylamino)piperidine-1-yl)-4-methoxyphenyl)acrylamide | ¹H NMR (400 MHz, Chloroform-d) δ 8.87 (s, 1H), 8.49 (s, 1H), 8.37 (s, 1H), 7.57 (m, 1H), 6.92 (s, 1H), 6.79 (m, 4H), 6.35 (d, J = 15.9 Hz, 1H), 6.27 (m, 1H), 5.87 (m, 1H), 5.74 (d, J = 11.3 Hz, 1H), 4.08 (m, 2H), 3.85 (s, 3H), 3.06 (d, J = 11.6 Hz, 2H), 2.80 (m, 1H), 2.73 (m, 2H), 2.36 (s, 6H), 2.27 (m, 2H), 2.06 (d, J = 13.9 Hz, 2H), 1.66 (d, J = 9.9 Hz, 2H), ; 580.5 [M + H]⁺ | 1.19 |

TABLE 1-continued

| Example Compound | Structure | Name of Compound | ¹H NMR[[:]]; MS [M + H]⁺ | UPLC r.t. (min) |
|---|---|---|---|---|
| 385 | 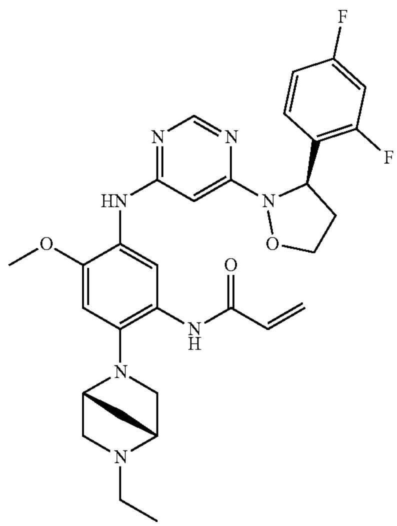 [SMILES: C=CC(=O)Nc1cc(Nc2cc(N3OCC[C@@H]3c3ccc(F)cc3F)ncn2)c(OC)cc1N1C[C@H]2C[C@@H]1CN2CC] | N-(5-((6-((R)-3-(2,4-difluorophenyl)isoxazolidine-2-yl)pyrimidine-4-yl)amino)-2-((1R,4R)-5-ethyl-2,5-diazabicyclo[2.2.1]heptane-2-yl)-4-methoxyphenyl)acrylamide | ¹H NMR (400 MHz, Chloroform-d) δ 8.56 (s, 1H), 8.34 (s, 1H), 7.96 (s, 1H), 7.56 (m, 1H), 6.85 (m, 3H), 6.69 (s, 2H), 6.38 (m, 1H), 6.31 (m, 1H), 5.89 (m, 1H), 5.74 (d, J = 10.2 Hz, 1H), 4.15-4.02 (m, 2H), 3.85 (s, 3H), 3.73 (s, 1H), 3.57 (s, 1H), 3.49 (d, 1H), 3.06 (d, J = 9.4 Hz, 1H), 2.75 (m, 4H), 2.60 (m, 1H), 2.27 (m, 1H), 1.91 (q, J = 10.6. 10.0 Hz, 2H), 1.13 (t, J = 7.1 Hz, 3H), ; 578.4 [M + H]⁺ | 1.14 |
| 386 | 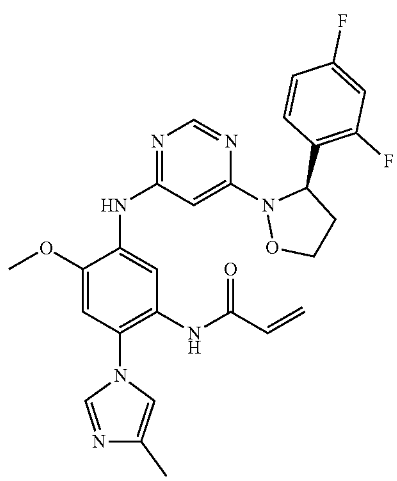 [SMILES: C=CC(=O)Nc1cc(Nc2cc(N3OCC[C@@H]3c3ccc(F)cc3F)ncn2)c(OC)cc1-n1cnc(C)c1] | N-(5-((6-((R)-3-(2,4-difluorophenyl)isoxazolidine-2-yl)pyrimidine-4-yl)amino)-4-methoxy-2-(4-methyl-1H-imidazole-1-yl)phenyl)acrylamide | ¹H NMR (400 MHz, Chloroform-d) δ 8.96 (s, 1H), 8.47-8.38 (m, 1H), 7.61-7.52 (m, 1H), 7.51-7.45 (m, 1H), 7.15 (d, J = 8.0 Hz, 1H), 6.90-6.72 (m, 6H), 6.44-6.25 (m, 1H), 6.13 (dd, J = 16.8, 10.3 Hz, 1H), 5.88 (dd, J = 8.6, 4.5 Hz, 1H), 5.80-5.67 (m, 1H), 4.17 (td, J = 8.0, 4.3 Hz, 1H), 4.09-4.03 (m, 1H), 3.90 (s, 3H), 2.90-2.77 (m, 1H), 2.30 (s, 3H), 1.82 (p, J = 7.0 Hz, 1H), ; 534.3 [M + H]⁺ | 1.29 |

TABLE 1-continued

| Example Compound | Structure | Name of Compound | ¹H NMR[:]; MS [M + H]⁺ | UPLC r.t. (min) |
|---|---|---|---|---|
| 387 | 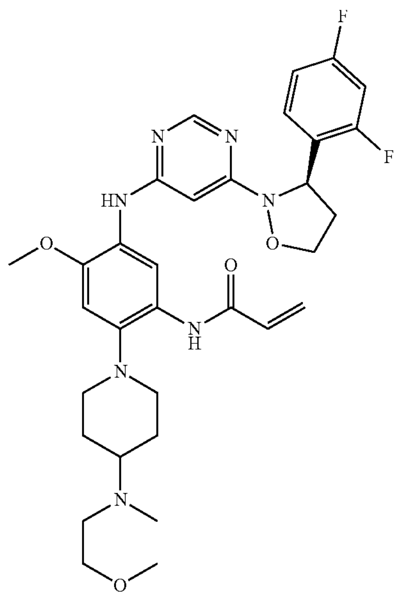 [SMILES: C=CC(=O)Nc1cc(Nc2cc(N3OCC[C@@H]3c3ccc(F)cc3F)ncn2)c(OC)cc1N1CCC(N(C)CCOC)CC1] | N-(5-((6-((R)-3-(2,4-difluorophenyl)isoxazolidine-2-yl)pyrimidine-4-yl)amino)-4-methoxy-2-(4-((2-methoxyethyl)(methyl)amino)piperidine-1-yl)phenyl)acrylamide | ¹H NMR (400 MHz, Chloroform-d) δ 8.87 (s, 1H), 8.45 (s, 1H), 8.36 (s, 1H), 7.62-7.51 (m, 1H), 6.94 (s, 1H), 6.89-6.71 (m, 4H), 6.40-6.33 (m, 1H), 6.31-6.22 (m, 1H), 5.90-5.85 (m, 1H), 5.75 (d, J = 10.1 Hz, 1H), 4.16-4.03 (m, 2H), 3.85 (s, 3H), 3.59-3.51 (m, 2H), 3.39 (s, 3H), 3.35-3.26 (m, 1H), 3.07 (d, J = 11.1 Hz, 2H), 2.87-2.67 (m, 7H), 2.61 (s, 2H), 2.44 (s, 4H), ; 624.5 [M + H]⁺ | 1.19 |
| 388 | 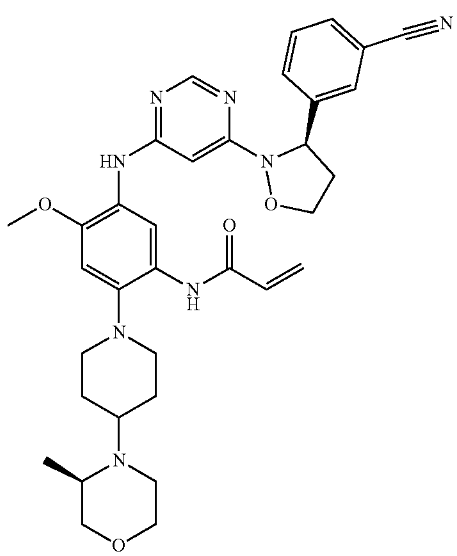 [SMILES: C=CC(=O)Nc1cc(Nc2cc(N3OCC[C@@H]3c3cccc(C#N)c3)ncn2)c(OC)cc1N1CCC(N2CCOC[C@H]2C)CC1] | N-(5-((6-((R)-3-(3-cyanophenyl)isoxazolidine-2-yl)pyrimidine-4-yl)amino)-4-methoxy-2-(4-((R)-3-methylmorpholino)piperidine-1-yl)phenyl)acrylamide | ¹H NMR (400 MHz, CDCl₃) δ 8.79 (s, 1H), 8.44 (s, 1H), 8.31 (s, 1H), 7.78 (s, 1H), 7.70 (d, J = 7.9 Hz, 1H), 7.58-7.50 (m, 2H), 7.45 (t, J = 7.8 Hz, 1H), 6.77 (s, 1H), 6.68 (s, 1H), 6.40-6.23 (m, 2H), 5.76 (dd, J = 9.9, 1.5 Hz, 1H), 5.71 (dd, J = 8.7, 4.6 Hz, 1H), 4.16 (td, J = 8.0, 4.1 Hz, 1H), 4.07 (q, J = 8.1 Hz, 1H), 3.89-3.81 (m, 4H), 3.78-3.70 (m, 2H), 3.47-3.38 (m, 1H), 3.13-3.03 (m, 2H), 2.98-2.89 (m, 2H), 2.86-2.64 (m, 5H), 2.39-2.29 (m, 1H), 1.98-1.79 (m, 3H), 1.74-1.61 (m, 1H), 1.08 (d, J = 6.4 Hz, 3H), ; 625.5 [M + H]⁺ | 1.08 |

TABLE 1-continued

| Example Compound | Name of Compound | ¹H NMR[[:]]; MS [M + H]⁺ | UPLC r.t. (min) |
|---|---|---|---|
| 389 | N-(2-(4-((1R,4R)-2-oxa-5-azabicyclo[2.2.1]heptane-5-yl)piperidine-1-yl)-5-((6-((R)-3-(3-cyanophenyl)isoxazolidine-2-yl)pyrimidine-4-yl)amino)-4-methoxyphenyl)acrylamide | ¹H NMR (400 MHz, CDCl₃) δ 8.87 (s, 1H), 8.49 (s, 1H), 8.36 (s, 1H), 7.79 (s, 1H), 7.71 (d, J = 7.9 Hz, 1H), 7.55 (d, 7.7 Hz, 1H), 7.45 (t, J = 7.8 Hz, 1H), 6.96 (s, 1H), 6.77 (s, 1H), 6.74 (s, 1H), 6.39-6.20 (s, 2H), 5.77-5.69 (m, 2H), 4.44 (s, 1H), 4.17 (td, J = 8.1, 4.2 Hz, 1H), 4.12-4.05 (m, 2H), 3.86 (s, 3H), 3.81-3.74 (m, 1H), 3.69-3.64 (m, 1H), 3.17-3.11 (m, 1H), 3.07-2.99 (m, 2H), 2.86-2.71 (m, 3H), 2.63-2.54 (m, 1H), 2.53-2.47 (m, 1H), 2.39-2.29 (m, 1H), 2.09-2.00 (m, 1H), 1.99-1.90 (m, 2H), 1.86-1.80 (m, 1H), 1.74-1.62 (m, 2H); 623.5 [M + H]⁺ | 1.05 |
| 390 | N-(5-((6-((R)-3-(3-cyanophenyl)isoxazolidine-2-yl)pyrimidine-4-yl)amino)-2-(4-hydroxypiperidine-1-yl)-4-methoxyphenyl)acrylamide | ¹H NMR (400 MHz, CDCl₃) δ 8.87 (s, 1H), 8.35 (s, 1H), 7.79 (s, 1H), 7.71 (d, J = 7.8 Hz, 1H), 7.55 (d, 7.7 Hz, 1H), 7.45 (t, J = 7.7 Hz, 1H), 7.04 (s, 1H), 6.78 (s, 1H), 6.73 (s, 1H), 6.30 (dt, J = 16.9, 13.4 Hz, 2H), 5.78-5.70 (m, 2H), 4.17 (td, J = 7.9, 4.1 Hz, 1H), 4.08 (q, J = 8.0 Hz, 1H), 3.98-3.91 (m, 1H), 3.85 (s, 3H), 3.10-3.01 (m, 2H), 2.86-2.72 (m, 3H), 2.40-2.29 (m, 1H), 2.11-2.03 (m, 2H), 1.81-1.73 (m, 2H); 542.4 [M + H]⁺ | 1.21 |
| 391 | N-(5-((6-((R)-3-(3-cyanophenyl)isoxazolidine-2-yl)pyrimidine-4-yl)amino)-4-methoxy-2-(4-(oxetane-3-yl)piperazine-1-yl)phenyl)acrylamide | ¹H NMR (400 MHz, Chloroform-d) δ 8.92 (s, 1H), 8.50 (s, 1H), 8.37 (d, J = 0.9 Hz, 1H), 7.79 (d, 1.8 Hz, 1H), 7.75-7.67 (m, 1H), 7.58-7.51 (m, 1H), 7.45 (t, J = 7.8 Hz, 1H), 6.98 (s, 1H), 6.82 (s, 1H), 6.74 (s, 1H), 6.36 (dd, J = 17.0, 1.5 Hz, 1H), 6.26 (dd, J = 16.9, 10.0 Hz, 1H), 5.79-5.69 (m, 2H), 4.69 (dt, J = 21.4, 6.3 Hz, 4H), 4.22-4.14 (m, 1H), 4.14-4.03 (m, 1H), 3.85 (s, 3H), 3.66-3.55 (m, 1H), 3.02-2.91 (m, 4H), 2.88-2.75 (m, 1H), 2.63-2.43 (m, 4H), 2.41-2.28 (m, 1H); 583.4 [M + H]⁺ | 1.09 |

TABLE 1-continued

| Example Compound | Structure | Name of Compound | ¹H NMR[[:]]; MS [M + H]⁺ | UPLC r.t. (min) |
|---|---|---|---|---|
| 392 | 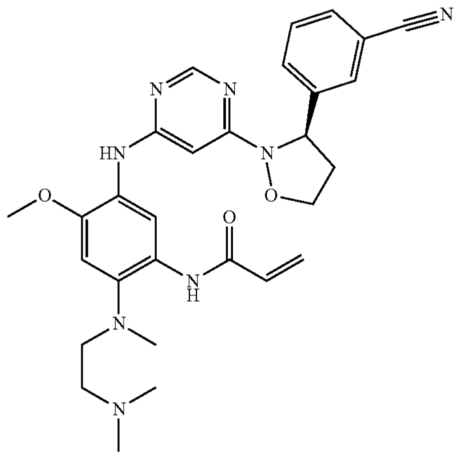 [SMILES: C=CC(=O)Nc1cc(Nc2cc(N3OCC[C@@H]3c3cccc(C#N)c3)ncn2)c(OC)cc1N(C)CCN(C)C] | N-(5-((6-((R)-3-(3-cyanophenyl)isoxazolidine-2-yl)pyrimidine-4-yl)amino)-2-((2-(dimethylamino)ethyl)(methyl)amino)-4-methoxyphenyl)acrylamide | ¹H NMR (400 MHz, Chloroform-d) δ 10.12 (s, 1H), 8.96 (s, 1H), 8.37 (d, J = 1.0 Hz, 1H), 7.79 (d, J = 1.8 Hz, 1H), 7.72 (dt, J = 8.0, 1.7 Hz, 1H), 7.54 (dt, J = 7.6, 1.5 Hz, 1H), 7.45 (t, J = 7.8 Hz, 1H), 6.98 (s, 1H), 6.81-6.78 (m, 2H), 6.40 (dd, J = 17.0, 2.0 Hz, 1H), 6.34-6.22 (m, 1H), 5.74 (dd, J = 8.8, 4.5 Hz, 1H), 5.72-5.65 (m, 1H), 4.19-4.10 (m, 2H), 3.85 (s, 3H), 2.91-2.86 (m, 2H), 2.84-2.78 (m, 1H), 2.72 (s, 3H), 2.37-2.31 (m, 3H), 2.29 (s, 6H), ; 543.5 [M + H]⁺ | 1.08 |
| 393 | 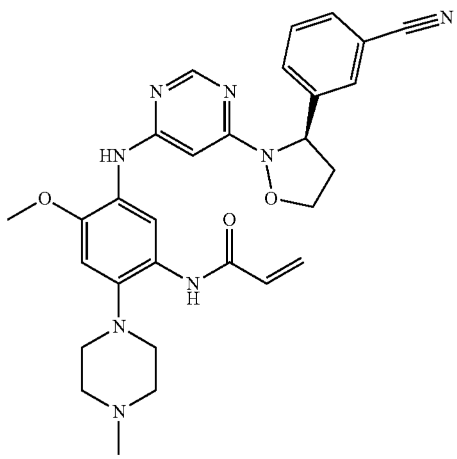 [SMILES: C=CC(=O)Nc1cc(Nc2cc(N3OCC[C@@H]3c3cccc(C#N)c3)ncn2)c(OC)cc1N1CCN(C)CC1] | N-(5-((6-((R)-3-(3-cyanophenyl)isoxazolidine-2-yl)pyrimidine-4-yl)amino)-4-methoxy-2-(4-methylpiperazine-1-yl)phenyl)acrylamide | ¹H NMR (400 MHz, Chloroform-d) δ 8.90 (s, 1H), 8.54 (s, 1H), 8.36 (d, J = 1.0 Hz, 1H), 7.79 (d, J = 1.8 Hz, 1H), 7.71 (dt, J = 7.8, 1.7 Hz, 1H), 7.55 (dt, J = 7.7, 1.5 Hz, 1H), 7.45 (t, J = 7.7 Hz, 1H), 6.99 (s, 1H), 6.80 (s, 1H), 6.73 (s, 1H), 6.37 (dd, J = 17.1, 1.6 Hz, 1H), 6.27 (dd, J = 17.0, 9.9 Hz, 1H), 5.79-5.68 (m, 2H), 4.22-4.13 (m, 1H), 4.13-4.03 (m, 1H), 3.84 (s, 3H), 2.96-2.89 (m, 4H), 2.86-2.77 (m, 1H), 2.73-2.53 (m, 4H), 2.40 (s, 3H), 2.37-2.28 (m, 1H); 541.5 [M + H]⁺ | 1.02 |
| 394 | 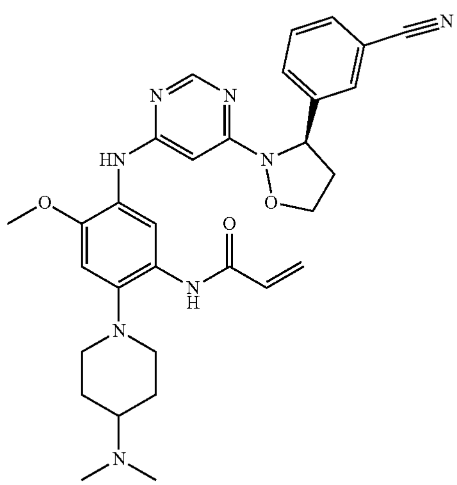 [SMILES: C=CC(=O)Nc1cc(Nc2cc(N3OCC[C@@H]3c3cccc(C#N)c3)ncn2)c(OC)cc1N1CCC(N(C)C)CC1] | N-(5-((6-((R)-3-(3-cyanophenyl)isoxazolidine-2-yl)pyrimidine-4-yl)amino)-2-(4-(dimethylamino)piperidine-1-yl)-4-methoxyphenyl)acrylamide | ¹H NMR (400 MHz, Chloroform-d) δ 8.87 (s, 1H), 8.46 (s, 1H), 8.36 (d, J = 0.9 Hz, 1H), 7.79 (d, J = 1.9 Hz, 1H), 7.74-7.67 (m, 1H), 7.55 (dt, J = 7.8, 1.5 Hz, 1H), 7.45 (t, J = 7.8 Hz, 1H), 6.95 (s, 1H), 6.75 (d, J = 8.4 Hz, 2H), 6.36 (dd, J = 17.0, 1.7 Hz, 1H), 6.27 (dd, J = 16.9, 9.9 Hz, 1H), 5.79-5.68 (m, 2H), 4.22-4.14 (m, 1H), 4.14-4.03 (m, 1H), 3.85 (s, 3H), 3.12-3.05 (m, 2H), 2.86-2.77 (m, 1H), 2.79-2.70 (m, 2H), 2.45 (s, 6H), 2.37 (dd, J = 8.1, 4.5 Hz, 1H), 2.34-2.29 (m, 1H), 2.15-2.07 (m, 2H), 1.80-1.68 (m, 2H); 569.5 [M + H]⁺ | 1.05 |

TABLE 1-continued

| Example Compound | Structure | Name of Compound | ¹H NMR[[:]]; MS [M + H]⁺ | UPLC r.t. (min) |
|---|---|---|---|---|
| 395 | 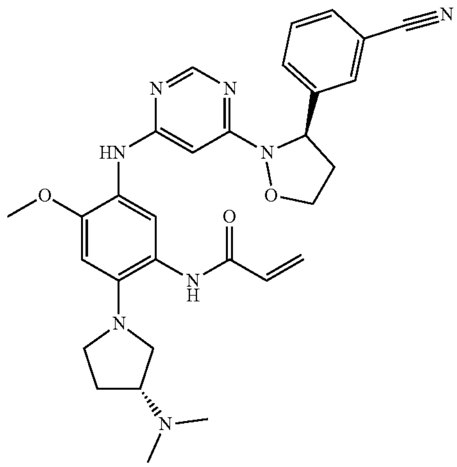 [SMILES: C=CC(=O)Nc1cc(Nc2cc(N3OCC[C@@H]3c3cccc(C#N)c3)ncn2)c(OC)cc1N1CC[C@@H](N(C)C)C1] | N-(5-((6-((R)-3-(3-cyanophenyl)isoxazolidine-2-yl)pyrimidine-4-yl)amino)-2-((R)-3-(dimethylamino)pyrolidine-1-yl)-4-methoxyphenyl)acrylamide | ¹H NMR (400 MHz, Chloroform-d) δ 8.67 (s, 1H), 8.35 (s, 1H), 8.17 (s, 1H), 7.79 (d, J = 1.7 Hz, 1H), 7.71 (d, J = 7.8 Hz, 1H), 7.55 (dt, J = 7.7, 1.5 Hz, 1H), 7.45 (t, J = 7.8 Hz, 1H), 6.90 (s, 1H), 6.76 (s, 1H), 6.71 (s, 1H), 6.43-6.35 (m, 1H), 6.30 (dd, J = 16.9, 9.8 Hz, 1H), 5.77-5.69 (m, 2H), 4.22-4.13 (m, 1H), 4.13-4.03 (m, 1H), 3.84 (s, 3H), 3.24-3.15 (m, 1H), 3.13-3.09 (m, 2H), 2.95-2.74 (m, 2H), 2.40-2.31 (m, 1H), 2.31 (s, 6H), 2.20-2.16 (m, 1H), 2.01-1.88 (m, 1H), 1.72-1.69 (m, 1H); 555.5 [M + H]⁺ | 1.00 |
| 396 | 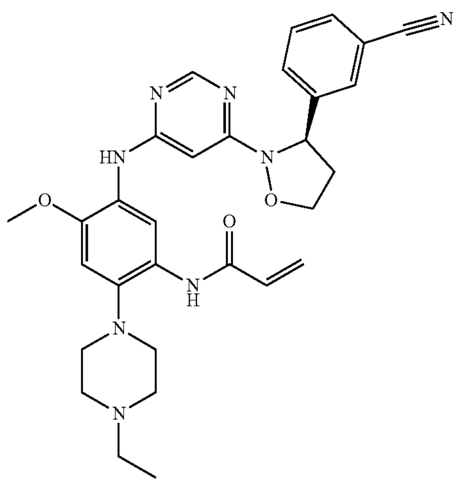 [SMILES: C=CC(=O)Nc1cc(Nc2cc(N3OCC[C@@H]3c3cccc(C#N)c3)ncn2)c(OC)cc1N1CCN(CC)CC1] | N-(5-((6-((R)-3-(3-cyanophenyl)isoxazolidine-2-yl)pyrimidine-4-yl)amino)-2-(4-ethylpiperazine-1-yl)-4-methoxyphenyl)acrylamide | ¹H NMR (400 MHz, Chloroform-d) δ 8.91 (s, 1H), 8.57 (s, 1H), 8.37 (d, J = 0.9 Hz, 1H), 7.79 (d, J = 1.8 Hz, 1H), 7.71 (dt, J = 7.9, 1.6 Hz, 1H), 7.55 (dt, J = 7.7, 1.5 Hz, 1H), 7.45 (t, J = 7.7 Hz, 1H), 6.96 (s, 1H), 6.83 (s, 1H), 6.74 (s, 1H), 6.37 (dd, J = 16.9, 1.6 Hz, 1H), 6.27 (dd, J = 16.9, 9.9 Hz, 1H), 5.77-5.71 (m, 2H), 4.22-4.14 (m, 1H), 4.14-4.03 (m, 1H), 3.83 (s, 3H), 2.96-2.92 (m, 4H), 2.86-2.77 (m, 1H), 2.74-2.56 (m, 4H), 2.52 (q, J = 7.2 Hz, 2H), 2.39-2.30 (m, 1H), 1.16 (t, J = 7.2 Hz, 3H); 555.5 [M + H]⁺ | 1.05 |
| 397 | 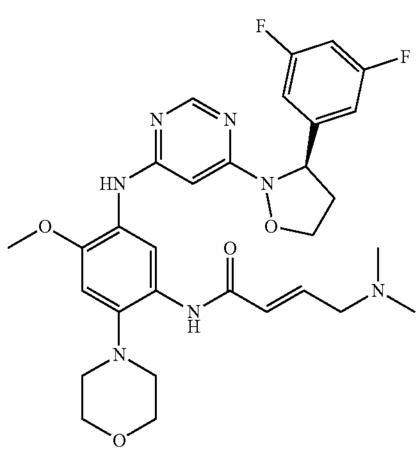 | N-(5-((6-((R)-3-(3,5-difluorophenyl)isoxazolidine-2-yl)pyrimidine-4-yl)amino)-4-methoxy-2-morpholinophenyl)-(E)-4-(dimethylamino)but-2-enamide | ¹H NMR (400 MHz, DMSO-d₆) δ 8.97 (s, 1H), 8.64 (s, 1H), 8.17 (s, 2H), 7.12 (dq, J = 9.0, 3.0 Hz, 4H), 6.86 (s, 1H), 6.74-6.61 (m, 2H), 5.56 (dd, J = 8.7, 5.0 Hz, 2H), 4.13 (td, J = 8.0, 3.9 Hz, 2H), 3.88-3.75 (m, 9H), 2.85 (t, J = 4.6 Hz, 4H), 2.76 (dtd, J = 12.2, 7.8, 3.8 Hz, 3H), 2.25 (ddt, J = 12.1, 7.9, 3.7 Hz, 2H), 1.77 (s, 3H), 1.23 (s, 4H), ; 596.4 [M + H]⁺ | 1.15 |

TABLE 1-continued

| Example Compound | Structure | Name of Compound | ¹H NMR[[:]]; MS [M + H]⁺ | UPLC r.t. (min) |
|---|---|---|---|---|
| 398 | 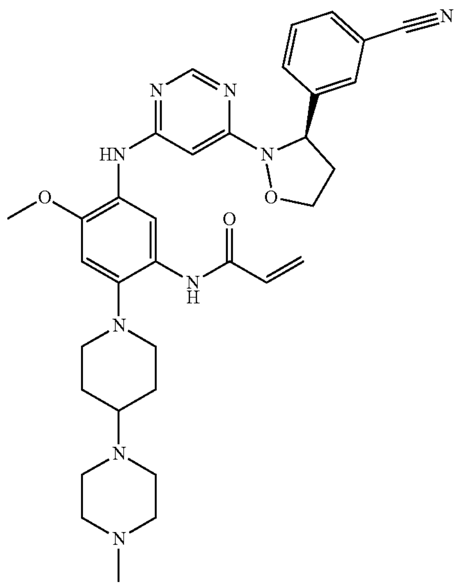 [SMILES: C=CC(=O)Nc1cc(Nc2cc(N3OCC[C@@H]3c3cccc(C#N)c3)ncn2)c(OC)cc1N1CCC(N2CCN(C)CC2)CC1] | N-(5-((6-((R)-3-(3-cyanophenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, DMSO-d₆) δ 8.97 (s, 1H), 8.63 (s, 1H), 8.16 (s, 1H), 8.14 (s, 1H), 7.79-7.72 (m, 2H), 7.58 (t, J = 7.8 Hz, 1H), 6.82 (s, 1H), 6.70-6.59 (m, 1H), 6.36 (s, 1H), 6.25-6.17 (m, 1H), 5.72 (dd, J = 10.1, 2.0 Hz, 1H), 5.59 (dd, J = 8.7, 5.1 Hz, 1H), 4.15 (td, J = 7.9, 3.9 Hz, 1H), 3.80 (s, 3H), 3.07 (d, J = 11.4 Hz, 3H), 2.98-2.59 (m, 11H), 2.56 (s, 1H), 2.30-2.21 (m, 1H), 1.94-1.65 (m, 5H), 1.25 (dd, J = 11.4, 4.7 Hz, 4H), ; 624.4 [M + H]⁺ | 1.21 |
| 399 | 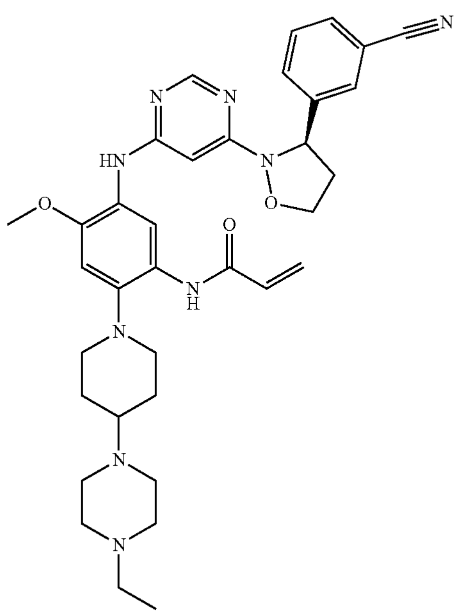 [SMILES: C=CC(=O)Nc1cc(Nc2cc(N3OCC[C@@H]3c3cccc(C#N)c3)ncn2)c(OC)cc1N1CCC(N2CCN(CC)CC2)CC1] | N-(5-((6-((R)-3-(3-cyanophenyl)isoxazolidine-2-yl)pyrimidine-4-yl)amino)-2-(4-(4-ethylpiperazine-1-yl)piperidine-1-yl)-4-methoxyphenyl)acrylamide | ¹H NMR (400 MHz, DMSO-d₆) δ 8.98 (s, 1H), 8.63 (s, 1H), 8.16 (s, 1H), 7.83 (d, J = 1.9 Hz, 1H), 7.75 (dd, J = 8.8, 6.9 Hz, 2H), 7.58 (t, J = 7.8 Hz, 1H), 6.82 (s, 1H), 6.67 (ddd, J = 19.8, 16.8, 10.3 Hz, 2H), 6.36 (s, 1H), 6.23 (q, J = 2.3 Hz, 1H), 5.75-5.70 (m, 1H), 5.59 (dd, J = 8.6, 5.1 Hz, 1H), 4.15 (td, J = 7.9, 3.9 Hz, 1H), 3.80 (s, 3H), 3.58 (q, J = 5.1, 3.4 Hz, 2H), 2.78 (dq, J = 8.2, 4.2 Hz, 3H), 2.60 (s, 3H), 2.31-2.21 (m, 2H), 1.78-1.64 (m, 3H), 1.26 (t, J = 7.1 Hz, 15H), 1.16 (s, 3H), ; 638.5 [M + H]⁺ | 1.21 |

TABLE 1-continued

| Example Compound | Structure | Name of Compound | ¹H NMR[[:]]; MS [M + H]⁺ | UPLC r.t. (min) |
|---|---|---|---|---|
| 400 | 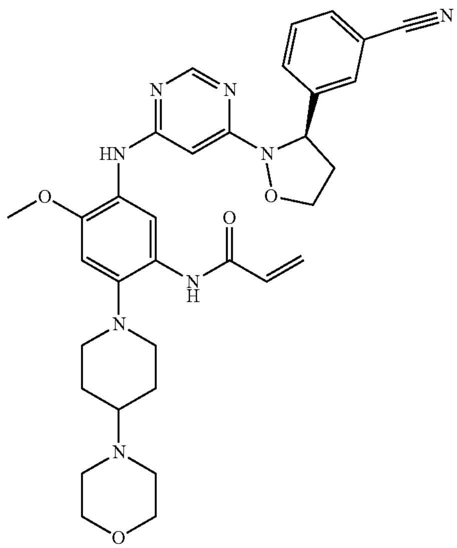 [SMILES: C=CC(=O)Nc1cc(Nc2cc(N3OCC[C@@H]3c3cccc(C#N)c3)ncn2)c(OC)cc1N1CCC(N2CCOCC2)CC1] | N-(5-((6-((R)-3-(3-cyanophenyl)isoxazolidine-2-yl)pyrimidine-4-yl)amino)-4-methoxy-2-(4-morpholinopiperidine-1-yl)phenyl)acrylamide | ¹H NMR (400 MHz, DMSO-d$_6$) δ 8.95 (s, 1H), 8.62 (s, 1H), 8.16 (d, J = 2.9 Hz, 2H), 7.83 (d, J = 1.8 Hz, 1H), 7.79-7.72 (m, 2H), 7.58 (t, J = 7.8 Hz, 1H), 6.83 (s, 1H), 6.65 (dd, J = 17.0, 10.2 Hz, 1H), 6.36 (s, 1H), 6.21 (dd, J = 17.0, 2.0 Hz, 1H), 5.72 (dd, J = 10.1, 2.0 Hz, 1H), 5.59 (dd, J = 8.7, 5.0 Hz, 1H), 4.15 (td, J = 7.9, 3.9 Hz, 1H), 3.80 (s, 3H), 3.59 (t, J = 4.5 Hz, 4H), 3.33 (s, 6H), 3.05 (d, J = 11.0 Hz, 2H), 2.78 (dtd, J = 12.1, 7.9, 3.8 Hz, 1H), 2.66 (ddd, J = 12.4, 9.5, 3.9 Hz, 2H), 2.26 (dtd, J = 12.6, 8.2, 4.9 Hz, 2H), 1.91-1.80 (m, 2H), 1.75-1.62 (m, 2H), 1.24 (d, J = 3.4 Hz, 2H), 0.85 (td, J = 8.1, 7.4, 3.1 Hz, 1H), ; 611.4 [M + H]⁺ | 1.22 |
| 401 | 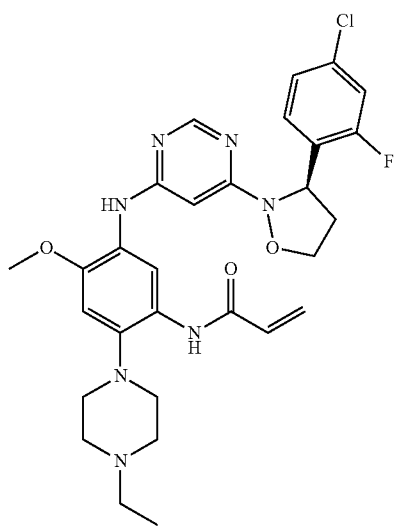 [SMILES: C=CC(=O)Nc1cc(Nc2cc(N3OCC[C@@H]3c3ccc(Cl)cc3F)ncn2)c(OC)cc1N1CCN(CC)CC1] | N-(5-((6-((R)-3-(4-chloro-2-fluorophenyl)isoxazolidine-2-yl)pyrimidine-4-yl)amino)-2-(4-ethylpiperazine-1-yl)-4-methoxyphenyl)acrylamide | ¹H NMR (400 MHz, Chloroform-d) δ 8.87 (s, 1H), 8.53 (s, 1H), 8.34 (d, J = 1.0 Hz, 1H), 7.53 (t, J = 8.2 Hz, 1H), 7.18 (s, 1H), 7.13-7.06 (m, 2H), 6.82 (s, 1H), 6.73 (s, 1H), 6.36 (dd, J = 17.0, 1.5 Hz, 1H), 6.26 (dd, J = 17.0, 10.0 Hz, 1H), 5.87 (dd, J = 8.8, 4.4 Hz, 1H), 5.75 (dd, J = 9.9, 1.6 Hz, 1H), 4.11 (td, J = 7.2, 6.2, 3.5 Hz, 1H), 4.06 (q, J = 8.0, 7.0 Hz, 1H), 3.84 (s, 3H), 3.02-2.90 (m, 4H), 2.84-2.78 (m, 1H), 2.76-2.58 (m, 4H), 2.56 (q, J = 7.2 Hz, 2H), 2.30-2.23 (m, 1H), 1.16 (t, J = 7.2 Hz, 3H); 582.4 [M + H]⁺ | 1.25 |

| Example Compound | Structure | Name of Compound | ¹H NMR[:]; MS [M + H]⁺ | UPLC r.t. (min) |
|---|---|---|---|---|
| 402 | 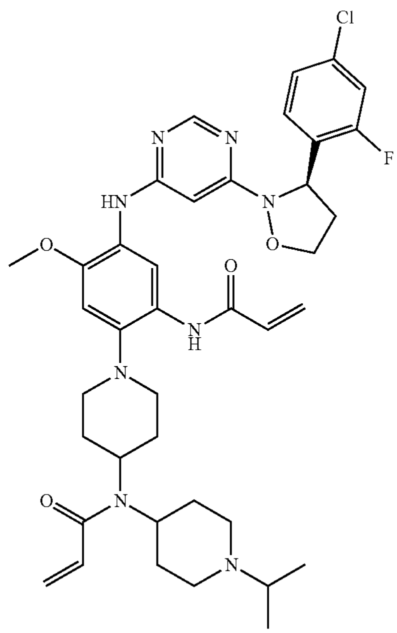 [SMILES: C=CC(=O)Nc1cc(Nc2cc(N3OCC[C@@H]3c3ccc(Cl)cc3F)ncn2)c(OC)cc1N1CCC(N(C(=O)C=C)C2CCN(C(C)C)CC2)CC1] | N-(1-(2-acrylamido-4-((6-((R)-3-(4-chloro-2-fluorophenyl)isoxazolidine-2-yl)pyrimidine-4-yl)amino)-5-methoxyphenyl)piperidine-4-yl)-N-(1-isopropylpiperidine-4-yl)acrylamide | ¹H NMR (400 MHz, DMSO-$d_6$) δ 10.10 (s, 1H), 9.48 (s, 1H), 8.31 (s, 1H), 7.95 (s, 1H), 7.51-7.47 (m, 1H), 7.40 (t, J = 8.3 Hz, 1H), 7.30 (dd, J = 8.4, 2.0 Hz, 1H), 6.90 (d, J = 38.7 Hz, 2H), 6.25 (dd, J = 17.0, 2.0 Hz, 2H), 6.08 (d, J = 16.5 Hz, 1H), 5.82-5.59 (m, 4H), 4.30 (dd, J = 7.7, 4.1 Hz, 2H), 4.06 (d, J = 7.8 Hz, 1H), 3.83 (s, 3H), 3.43 (s, 2H), 3.39-3.24 (m, 6H), 3.19 (d, J = 16.3 Hz, 2H), 3.04-2.87 (m, 4H), 2.30-2.21 (m, 1H), 1.69 (s, 5H), 1.29 (d, J = 6.6 Hz, 6H), ; 747.3 [M + H]⁺ | 1.5 |
| 403 | 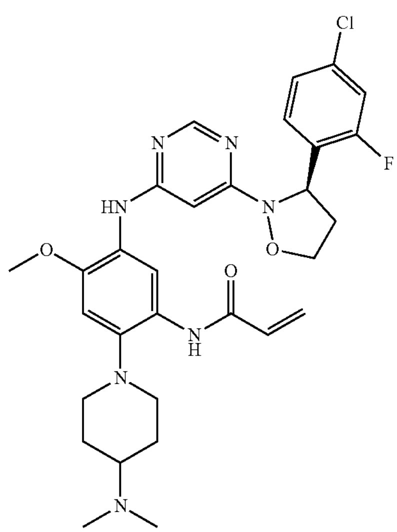 [SMILES: C=CC(=O)Nc1cc(Nc2cc(N3OCC[C@@H]3c3ccc(Cl)cc3F)ncn2)c(OC)cc1N1CCC(N(C)C)CC1] | N-(5-((6-((R)-3-(4-chloro-2-fluorophenyl)isoxazolidine-2-yl)pyrimidine-4-yl)amino)-2-(4-(dimethylamino)piperidine-1-yl)-4-methoxyphenyl)acrylamide | ¹H NMR (400 MHz, Chloroform-d) δ 8.79 (s, 1H), 8.44 (s, 1H), 8.32 (d, J = 1.0 Hz, 1H), 7.52 (t, J = 8.3 Hz, 1H), 7.33 (s, 1H), 7.13-7.06 (m, 2H), 6.74 (s, 1H), 6.71 (s, 1H), 6.42-6.27 (m, 2H), 5.86 (dd, J = 8.7, 4.4 Hz, 1H), 5.75 (dd, J = 9.0, 2.5 Hz, 1H), 4.12 (dt, J = 8.0, 4.0 Hz, 1H), 4.09-4.01 (m, 1H), 3.85 (s, 3H), 3.11 (d, J = 11.9 Hz, 2H), 2.73 (d, J = 12.3 Hz, 4H), 2.54 (s, 6H), 2.30-2.24 (m, 1H), 2.12 (d, J = 12.8 Hz, 2H), 1.88-1.79 (m, 2H); 596.4 [M + H]⁺ | 1.24 |

TABLE 1-continued

| Example Compound | Structure | Name of Compound | ¹H NMR[:]; MS [M + H]⁺ | UPLC r.t. (min) |
|---|---|---|---|---|
| 404 | 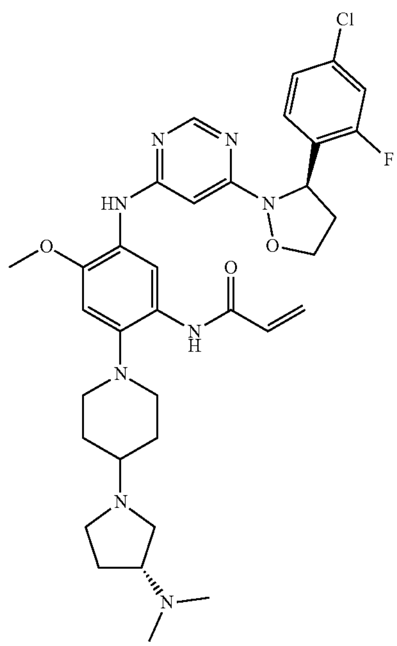 [SMILES: C=CC(=O)Nc1cc(Nc2cc(N3OCC[C@@H]3c3ccc(Cl)cc3F)ncn2)c(OC)cc1N1CCC(N2CC[C@@H](N(C)C)C2)CC1] | N-(5-((6-((R)-3-(4-chloro-2-fluorophenyl) isoxazolidine-2-yl)pyrimidine-4-yl)amino)-2-(4-((R)-3-(dimethylamino) pyrolidine-1-yl)piperidine-1-yl)-4-methoxyphenyl) acrylamide | ¹H NMR (400 MHz, Methanol-d₄) δ 8.05 (s, 1H), 7.91 (s, 1H), 7.28 (t, J = 8.2 Hz, 1H), 7.15-7.07 (m, 2H), 6.83 (s, 1H), 6.49 (dd, J = 16.9, 10.2 Hz, 1H), 6.30-6.23 (m, 1H), 6.08 (s, 1H), 5.69 (d, J = 10.8 Hz, 1H), 5.62 (dd, 8.4, 5.6 Hz, 1H), 4.23 (td, J = 7.6, 4.3 Hz, 1H), 4.14-4.07 (m, 1H), 4.02 (dd, J = 15.4, 8.0 Hz, 1H), 3.85 (s, 2H), 3.76 (s, 3H), 3.69 (s, 1H), 3.43 (d, J = 5.8 Hz, 1H), 3.29 (s, 1H), 3.25-3.18 (m, 3H), 3.13 (d, J = 11.3 Hz, 2H), 2.89 (s, 7H), 2.76 (t, J = 12.4 Hz, 2H), 2.62-2.50 (m, 1H), 2.28 (td, J = 12.6, 5.2 Hz, 2H), 2.18 (d, J = 9.5 Hz, 2H), 1.98 (d, J = 11.4 Hz, 2H), 1.89 (s, 2H); 665.5 [M + H]⁺ | 1.18 |
| 405 | 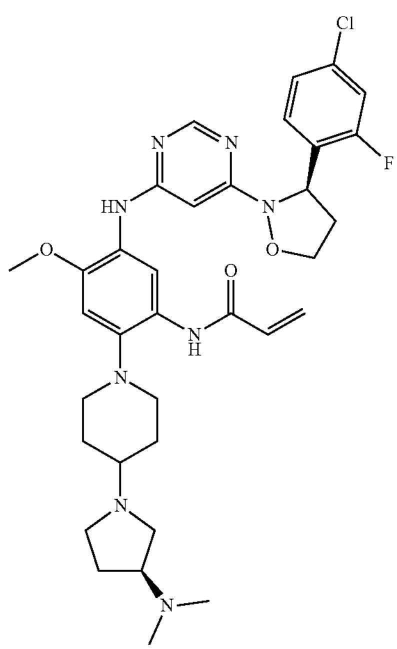 [SMILES: C=CC(=O)Nc1cc(Nc2cc(N3OCC[C@@H]3c3ccc(Cl)cc3F)ncn2)c(OC)cc1N1CCC(N2CC[C@H](N(C)C)C2)CC1] | N-(5-((6-((R)-3-(4-chloro-2-fluorophenyl) isoxazolidine-2-yl)pyrimidine-4-yl)amino)-2-(4-((S)-3-(dimethylamino) pyrolidine-1-yl)piperidine-1-yl)-4-methoxyphenyl) acrylamide | ¹H NMR (400 MHz, CDCl₃) δ 11.08 (s, 1H), 8.36 (d, J = 9.3 Hz, 2H), 8.08 (s, 1H), 7.23 (t, J = 8.3 Hz, 1H), 7.15-7.08 (m, 2H), 6.74 (s, 1H), 6.35 (d, J = 4.3 Hz, 2H), 6.09 (s, 1H), 5.75 (dd, J = 8.5, 4.9 Hz, 2H), 4.22 (dd, J = 12.7, 7.4 Hz, 1H), 4.08 (dd, J = 15.3, 7.6 Hz, 1H), 3.82 (s, 3H), 3.12 (s, 2H), 2.93 (s, 6H), 2.81 (d, J = 10.1 Hz, 2H), 2.35 (dt, J = 12.5, 7.2 Hz, 1H), 2.20 (s, 3H), 2.06 (s, 2H), ; 665.5 [M + H]⁺ | 1.20 |

… TABLE 1-continued

| Example Compound | Structure | Name of Compound | $^1$H NMR[[:]]; MS [M + H]$^+$ | UPLC r.t. (min) |
|---|---|---|---|---|
| 406 | 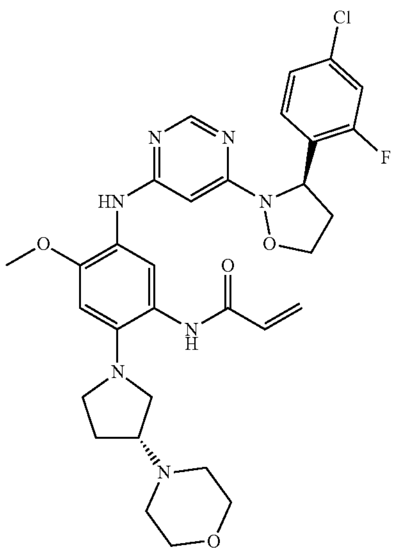 [SMILES: C=CC(=O)Nc1cc(Nc2cc(N3OCC[C@@H]3c3ccc(Cl)cc3F)ncn2)c(OC)cc1N1CC[C@@H](N2CCOCC2)C1] | N-(5-(((6-((R)-3-(4-chloro-2-fluorophenyl)isoxazolidine-2-yl)pyrimidine-4-yl)amino)-4-methoxy-2-((R)-3-morpholinopyrrolidine-1-yl)phenyl)acrylamide | $^1$H NMR (400 MHz, CDCl$_3$) δ 9.29 (s, 1H), 8.70 (s, 1H), 8.17 (s, 2H), 7.37 (t, J = 8.1 Hz, 1H), 7.11 (d, J = 9.1 Hz, 2H), 6.69-6.58 (m, 2H), 6.42-6.30 (m, 2H), 5.79 (dd, J = 8.4, 4.6 Hz, 1H), 5.71 (d, J = 10.3 Hz, 1H), 4.18 (dd, J = 12.5, 7.7 Hz, 1H), 4.06 (dd, J = 15.8, 7.9 Hz, 1H), 3.97 (d, J = 3.1 Hz, 4H), 3.81 (s, 3H), 3.74 (d, J = 11.0 Hz, 1H), 3.51 (s, 1H), 3.23 (d, J = 7.0 Hz, 2H), 3.11-3.02 (m, 2H), 2.83 (ddd, J = 24.6, 12.9, 7.1 Hz, 2H), 2.41 (d, J = 6.5 Hz, 1H), 2.38-2.24 (m, 2H), 2.06 (s, 2H); 624.4 [M + H]$^+$ | 1.29 |
| 407 | 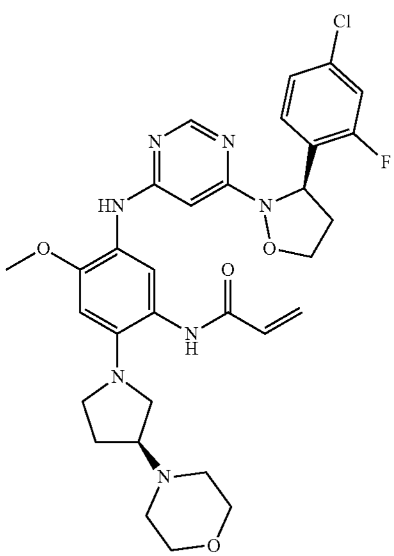 [SMILES: C=CC(=O)Nc1cc(Nc2cc(N3OCC[C@@H]3c3ccc(Cl)cc3F)ncn2)c(OC)cc1N1CC[C@H](N2CCOCC2)C1] | N-(5-(((6-((R)-3-(4-chloro-2-fluorophenyl)isoxazolidine-2-yl)pyrimidine-4-yl)amino)-4-methoxy-2-((S)-3-morpholinopyrrolidine-1-yl)phenyl)acrylamide | $^1$H NMR (400 MHz, CDCl$_3$) δ 10.96 (s, 1H), 8.86 (s, 1H), 8.06 (s, 1H), 7.94 (s, 1H), 7.23 (t, J = 8.3 Hz, 1H), 7.15-7.08 (m, 2H), 6.69 (dd, J = 16.8, 10.2 Hz, 1H), 6.57 (s, 1H), 6.32 (d, J = 16.8 Hz, 1H), 5.84 (s, 1H), 5.76-5.65 (m, 2H), 4.20 (dd, J = 12.8, 7.5 Hz, 1H), 4.03 (dd, J = 15.0, 7.2 Hz, 5H), 3.81 (s, 1H), 3.79 (s, 3H), 3.65 (d, J = 4.6 Hz, 1H), 3.25 (s, 1H), 2.98 (dd, J = 16.5, 8.2 Hz, 1H), 2.93-2.84 (m, 1H), 2.58 (dd, J = 10.8, 7.8 Hz, 1H), 2.45-2.28 (m, 3H), 2.06 (s, 2H); 624.5 [M + H]$^+$ | 1.29 |

TABLE 1-continued

| Example Compound | Structure | Name of Compound | ¹H NMR[[:]]; MS [M + H]⁺ | UPLC r.t. (min) |
|---|---|---|---|---|
| 408 | 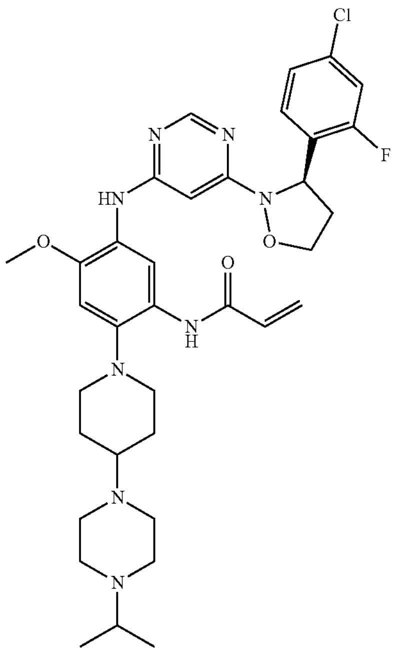 [SMILES: C=CC(=O)Nc1cc(Nc2cc(N3OCC[C@@H]3c3ccc(Cl)cc3F)ncn2)c(OC)cc1N1CCC(N2CCN(C(C)C)CC2)CC1] | N-(5-((6-((R)-3-(4-chloro-2-fluorophenyl)isoxazolidine-2-yl)pyrimidine-4-yl)amino)-2-(4-(4-isopropylpiperazine-1-yl)piperidine-1-yl)-4-methoxyphenyl)acrylamide | ¹H NMR (400 MHz, DMSO-$d_6$) δ 9.70 (s, 1H), 9.17 (s, 1H), 8.27 (s, 1H), 8.00 (s, 1H), 7.52-7.35 (m, 2H), 7.30 (dd, J = 8.4, 2.0 Hz, 1H), 6.90 (s, 1H), 6.70 (dd, J = 16.9, 10.2 Hz, 1H), 6.25 (dd, J = 17.1, 2.0 Hz, 2H), 5.71 (ddd, J = 35.7, 8.4, 4.3 Hz, 2H), 4.29-4.25 (m, 1H), 4.01 (d, J = 7.9 Hz, 1H), 3.81 (s, 3H), 3.76 (s, 6H), 3.42 (d, J = 5.4 Hz, 1H), 3.38-3.33 (m, 1H), 3.30-3.25 (m, 1H), 3.21 (d, J = 10.8 Hz, 2H), 2.93-2.87 (m, 1H), 2.79 (t, J = 11.8 Hz, 2H), 2.29-2.02 (m, 6H), 1.32 (d, J = 6.5 Hz, 6H), ; 679.3 [M + H]⁺ | 1.41 |
| 409 | 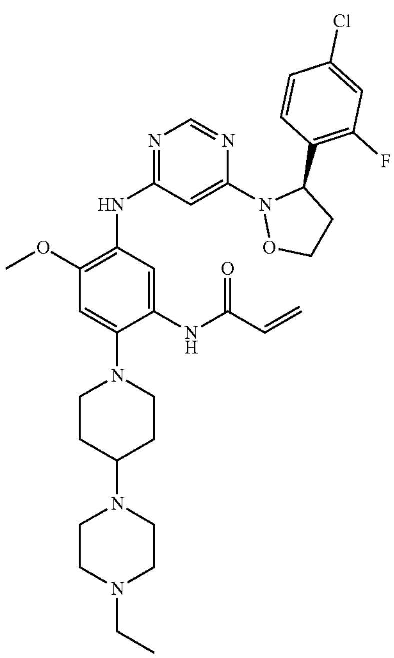 [SMILES: C=CC(=O)Nc1cc(Nc2cc(N3OCC[C@@H]3c3ccc(Cl)cc3F)ncn2)c(OC)cc1N1CCC(N2CCN(CC)CC2)CC1] | N-(5-((6-((R)-3-(4-chloro-2-fluorophenyl)isoxazolidine-2-yl)pyrimidine-4-yl)amino)-2-(4-(4-ethylpiperazine-1-yl)piperidine-1-yl)-4-methoxyphenyl)acrylamide | ¹H NMR (400 MHz, DMSO-$d_6$) δ 10.05 (s, 1H), 9.22 (s, 1H), 8.30 (s, 1H), 7.93 (s, 1H), 7.49 (dd, J = 10.3, 2.0 Hz, 1H), 7.40 (t, J = 8.3 Hz, 1H), 7.30 (dd, J = 8.3, 2.1 Hz, 1H), 6.91 (s, 1H), 6.77-6.64 (m, 1H), 6.25 (dd, J = 17.0, 1.9 Hz, 2H), 5.83-5.62 (m, 2H), 4.36-4.30 (m, 4H), 4.06 (d, J = 7.8 Hz, 1H), 3.81 (s, 3H), 3.67 (s, 2H), 3.57 (d, J = 11.1 Hz, 2H), 3.45 (s, 1H), 3.22 (s, 4H), 2.93 (d, J = 8.9 Hz, 1H), 2.81 (s, 2H), 2.30-2.01 (m, 6H), 1.29 (t, J = 7.2 Hz, 3H), ; 665.3 [M + H]⁺ | 1.4 |

TABLE 1-continued

| Example Compound | Structure | Name of Compound | ¹H NMR[:]; MS [M + H]⁺ | UPLC r.t. (min) |
|---|---|---|---|---|
| 410 | 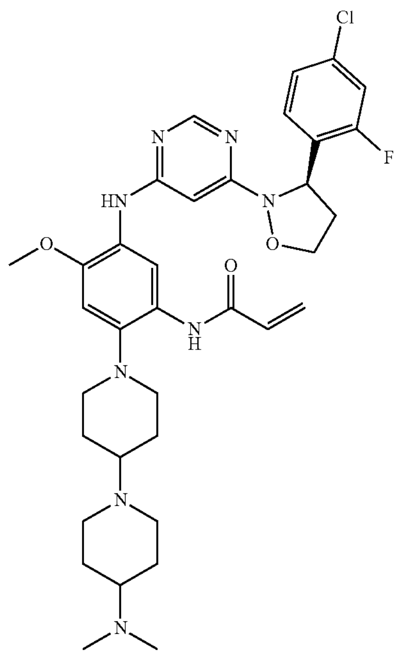 | N-(5-((6-((R)-3-(4-chloro-2-fluorophenyl)isoxazolidine-2-yl)pyrimidine-4-yl)amino)-2-(4-(dimethylamino)-[1,4'-bipiperidine]-1'-yl)-4-methoxyphenyl)acrylamide | ¹H NMR (400 MHz, DMSO-$d_6$) δ 10.07 (s, 1H), 9.24 (s, 1H), 8.31 (s, 1H), 7.92 (s, 1H), 7.49 (dd, J = 10.3, 2.1 Hz, 1H), 7.39 (d, J = 8.3 Hz, 1H), 7.30 (dd, J = 8.4, 2.0 Hz, 1H), 6.90 (s, 1H), 6.75 (dd, J = 17.0, 10.3, Hz, 1H), 6.28-6.14 (m, 2H), 5.71 (dd, J = 24.9, 3.9 Hz, 2H), 4.31 (td, J = 7.5, 4.1 Hz, 1H), 4.05 (q, J = 7.8 Hz, 1H), 3.82 (d, J = 2.6 Hz, 3H), 3.63 (s, 1H), 3.50 (d, J = 8.0 Hz, 1H), 3.40-3.33 (m, 1H), 3.23 (d, J = 11.1 Hz, 2H), 3.14 (s, 2H), 2.97-2.88 (m, 1H), 2.79 (s, 2H), 2.71 (d, J = 4.6 Hz, 6H), 2.54 (s, 1H), 2.30 (d, J = 8.8 Hz, 5H), 2.18 (d, J = 10.3 Hz, 2H), 2.08 (d, J = 11.9 Hz, 2H), ; 679.3 [M + H]⁺ | 1.33 |
| 411 | 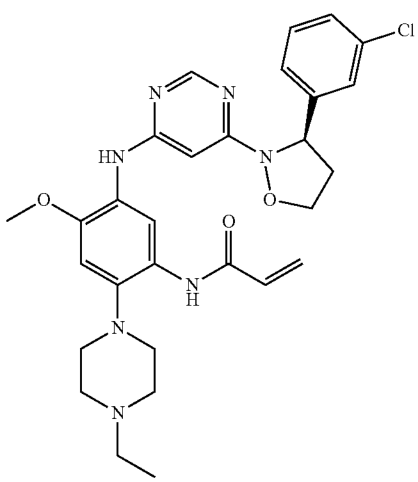 [SMILES: C=CC(=O)Nc1cc(Nc2cc(N3OCC[C@@H]3c3cccc(Cl)c3)ncn2)c(OC)cc1N1CCN(CC)CC1] | N-(5-((6-((R)-3-(3-chlorophenyl)isoxazolidine-2-yl)pyrimidine-4-yl)amino)-2-(4-ethylpiperazine-1-yl)-4-methoxyphenyl)acrylamide | ¹H NMR (400 MHz, DMSO-$d_6$) δ 8.98 (s, 1H), 8.62 (s, 1H), 8.18-8.11 (m, 2H), 7.47-7.29 (m, 4H), 6.86 (s, 1H), 6.59 (dd, J = 17.0, 10.2 Hz, 1H), 6.36 (s, 1H), 6.20 (dd, J = 16.9, 2.0 Hz, 1H), 5.72 (dd, J = 9.9, 2.0 Hz, 1H), 5.54 (dd, J = 8.7, 5.0 Hz, 1H), 4.14 (td, J = 7.9, 3.8 Hz, 1H), 3.89-3.75 (m, 4H), 2.87 (t, J = 4.8 Hz, 4H), 2.77 (dtd, J = 12.0, 7.8, 3.8 Hz, 2H), 2.57 (s, 3H), 2.40 (q, J = 7.1 Hz, 2H), 2.30-2.17 (m, 1H), 1.04 (t, J = 7.1 Hz, 3H); 564.5 [M + H]⁺ | 1.15 |

TABLE 1-continued

| Example Compound | Structure | Name of Compound | $^1$H NMR[[:]]; MS [M + H]$^+$ | UPLC r.t. (min) |
|---|---|---|---|---|
| 412 | 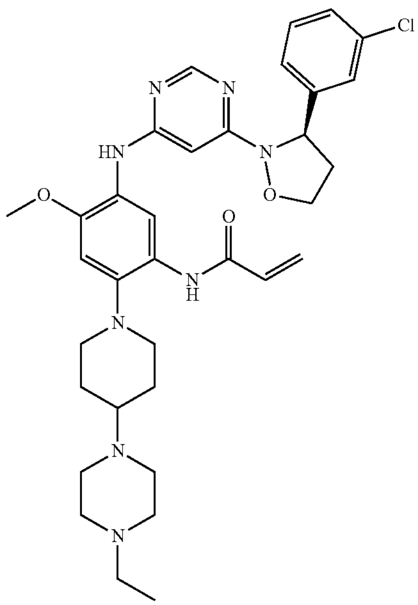 [SMILES: C=CC(=O)Nc1cc(Nc2cc(N3OCC[C@@H]3c3cccc(Cl)c3)ncn2)c(OC)cc1N1CCC(N2CCN(CC)CC2)CC1] | N-(5-((6-((R)-3-(3-chlorophenyl) isoxazolidine-2-yl)pyrimidine-4-yl)amino)-2-(4-(4-ethylpiperazine-1-yl)piperidine-1-yl)-4-methoxyphenyl) acrylamide | $^1$H NMR (400 MHz, DMSO-d$_6$) δ 8.95 (s, 1H), 8.60 (s, 1H), 8.15 (d, J = 4.8 Hz, 2H), 7.47-7.28 (m, 4H), 6.82 (s, 1H), 6.65 (dd, J = 16.9, 10.2 Hz, 1H), 6.34 (s, 1H), 6.21 (dd, J = 17.0, 2.0 Hz, 1H), 5.77-5.66 (m, 1H), 5.54 (dd, J = 8.7, 5.1 Hz, 1H), 4.14 (td, J = 7.9, 3.8 Hz, 1H), 3.87-3.75 (m, 4H), 3.05 (d, J = 11.1 Hz, 2H), 2.77 (dtd, J = 11.6, 7.8, 3.5 Hz, 1H), 2.72-2.61 (m, 3H), 2.53 (s, 3H), 2.44-2.17 (m, 8H), 1.85 (d, J = 12.0 Hz, 2H), 1.76-1.61 (m, 2H), 0.99 (t, J = 7.1 Hz, 3H); 647.5 [M + H]$^+$ | 1.14 |
| 413 | 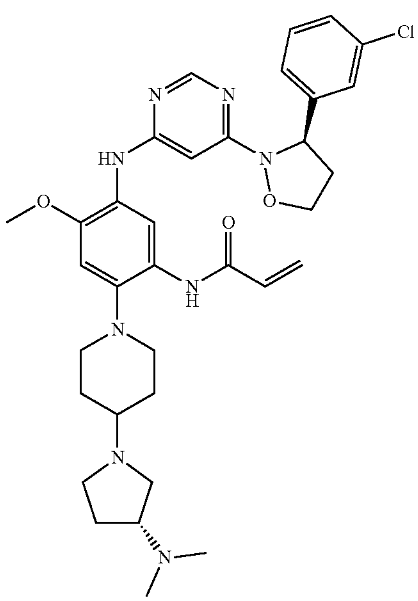 [SMILES: C=CC(=O)Nc1cc(Nc2cc(N3OCC[C@@H]3c3cccc(Cl)c3)ncn2)c(OC)cc1N1CCC(N2CC[C@@H](N(C)C)C2)CC1] | N-(5-((6-((R)-3-(3-chlorophenyl) isoxazolidine-2-yl)pyrimidine-4-yl)amino)-2-(4-((R)-3-(dimethylamino) pyrolidine-1-yl)piperidine-1-yl)-4-methoxyphenyl) acrylamide | $^1$H NMR (400 MHz, DMSO-d$_6$) δ 8.95 (s, 1H), 8.60 (s, 1H), 8.15 (d, J = 5.2 Hz, 2H), 7.48-7.29 (m, 4H), 6.82 (s, 1H), 6.64 (dd, J = 17.0, 10.2 Hz, 1H), 6.34 (s, 1H), 6.20 (dd, J = 17.0, 2.0 Hz, 1H), 5.71 (d, J = 10.3 Hz, 1H), 5.54 (dd, J = 8.7, 5.1 Hz, 1H), 4.14 (td, J = 7.9, 3.8 Hz, 1H), 3.89-3.74 (m, 4H), 3.01 (d, J = 11.3 Hz, 2H), 2.86-2.72 (m, 2H), 2.67 (t, J = 10.6 Hz, 4H), 2.34 (d, J = 8.5 Hz, 1H), 2.29-2.18 (m, 1H), 2.12 (s, 6H), 1.97-1.77 (m, 4H), 1.76-1.52 (m, 4H); 647.5 [M + H]$^+$ | 1.06 |

TABLE 1-continued

| Example Compound | Structure | Name of Compound | ¹H NMR[[:]]; MS [M + H]⁺ | UPLC r.t. (min) |
|---|---|---|---|---|
| 414 | 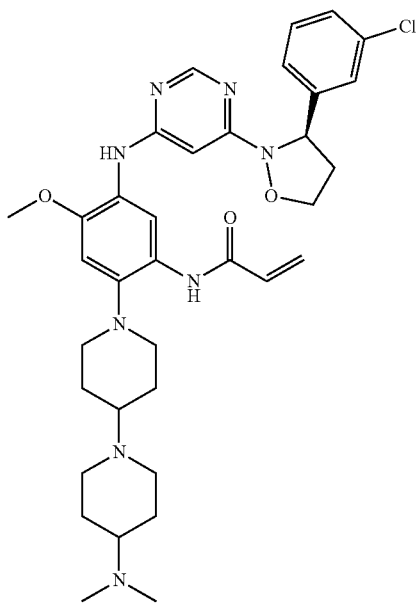 [SMILES: C=CC(=O)Nc1cc(Nc2cc(N3OCC[C@@H]3c3cccc(Cl)c3)ncn2)c(OC)cc1N1CCC(N2CCC(N(C)C)CC2)CC1] | N-(5-((6-((R)-3-(3-chlorophenyl)isoxazolidine-2-yl)pyrimidine-4-yl)amino)-2-(4-(dimethylamino)-[1,4'-bipiperidine]-1'-yl)-4-methoxyphenyl)acrylamide | ¹H NMR (400 MHz, DMSO-$d_6$) δ 8.95 (s, 1H), 8.60 (s, 1H), 8.15 (d, J = 6.3 Hz, 2H), 7.46-7.29 (m, 4H), 6.82 (s, 1H), 6.65 (dd, J = 16.9, 10.2 Hz, 1H), 6.34 (s, 1H), 6.21 (dd, J = 17.0, 2.0 Hz, 1H), 5.72 (d, J = 10.3 Hz, 1H), 5.54 (dd, J = 8.7, 5.1 Hz, 1H), 4.14 (td, J = 7.8, 3.7 Hz, 1H), 3.89-3.75 (m, 4H), 3.01 (dd, J = 31.8, 11.2 Hz, 4H), 2.77 (dtd, J = 11.9, 7.8, 3.6 Hz, 1H), 2.72-2.60 (m, 2H), 2.35 (d, J = 13.0 Hz, 1H), 2.24 (s, 6H), 2.17 (q, J = 11.9, 9.8 Hz, 4H), 1.85-1.65 (m, 6H), 1.37 (d, J = 11.9 Hz, 2H); 661.5 [M + H]⁺ | 1.04 |
| 415 | 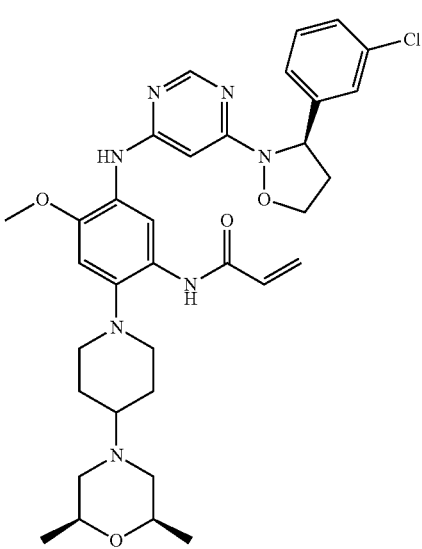 [SMILES: C=CC(=O)Nc1cc(Nc2cc(N3OCC[C@@H]3c3cccc(Cl)c3)ncn2)c(OC)cc1N1CCC(N2C[C@@H](C)O[C@@H](C)C2)CC1] | N-(5-((6-((R)-3-(3-chlorophenyl)isoxazolidine-2-yl)pyrimidine-4-yl)amino)-2-(4-((2S,6R)-2,6-dimethylmorpholino)piperidine-1-yl)-4-methoxyphenyl)acrylamide | ¹H NMR (400 MHz, DMSO-$d_6$) δ 9.05 (s, 1H), 8.20 (d, J = 16.0 Hz, 1H), 8.06 (s, 1H), 7.44 (s, 1H), 7.41-7.29 (m, 3H), 6.86 (s, 1H), 6.62 (t, J = 13.9 Hz, 1H), 6.30-6.21 (m, 2H), 5.75 (d, J = 10.4 Hz, 1H), 5.53 (t, J = 6.9 Hz, 1H), 4.20 (s, 1H), 3.89 (d, J = 22.7 Hz, 4H), 3.81 (s, 3H), 3.51 (d, J = 11.9 Hz, 4H), 3.29 (s, 1H), 3.18 (d, J = 11.4 Hz, 2H), 2.74 (t, J = 11.3 Hz, 4H), 2.27 (s, 1H), 2.15 (d, J = 11.7 Hz, 2H), 1.99-1.77 (m, 2H), 1.18 (d, J = 6.2 Hz, 5H), ; 648.5 [M + H]⁺ | 1.25 |

TABLE 1-continued

| Example Compound | Structure | Name of Compound | ¹H NMR[[:]]; MS [M + H]⁺ | UPLC r.t. (min) |
|---|---|---|---|---|
| 416 | 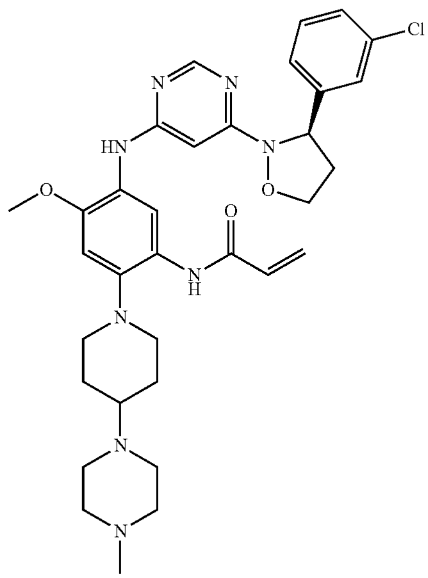 [SMILES: C=CC(=O)Nc1cc(Nc2cc(N3OCC[C@@H]3c3cccc(Cl)c3)ncn2)c(OC)cc1N1CCC(N2CCN(C)CC2)CC1] | N-(5-((6-((R)-3-(3-chlorophenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, DMSO-d₆) δ 9.06 (s, 1H), 8.24 (s, 1H), 8.06 (s, 1H), 7.43 (q, J = 2.3 Hz, 1H), 7.42-7.32 (m, 3H), 6.86 (s, 1H), 6.63 (dd, J = 17.0, 10.2 Hz, 1H), 6.24 (d, J = 16.6 Hz, 2H), 5.74 (d, J = 10.4 Hz, 1H), 5.53 (dd, J = 8.5, 5.2 Hz, 1H), 4.21 (s, 1H), 3.93 (d, J = 8.5 Hz, 1H), 3.81 (s, 3H), 3.63 (s, 2H), 3.17 (d, J = 11.7 Hz, 8H), 2.93-2.82 (m, 4H), 2.76 (t, J = 10.9 Hz, 3H), 2.30 (dd, J = 15.8, 10.4 Hz, 2H), 2.05 (s, 2H), 1.89 (d, J = 13.3 Hz, 2H), ; 633.5 [M + H]⁺ | 1.13 |
| 417 | 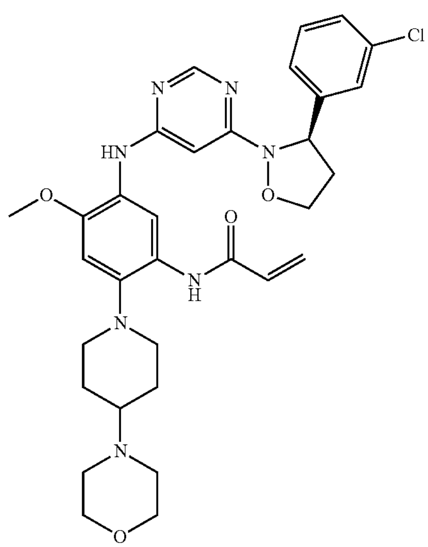 [SMILES: C=CC(=O)Nc1cc(Nc2cc(N3OCC[C@@H]3c3cccc(Cl)c3)ncn2)c(OC)cc1N1CCC(N2CCOCC2)CC1] | N-(5-((6-((R)-3-(3-chlorophenyl)isoxazolidine-2-yl)pyrimidine-4-yl)amino)-4-methoxy-2-(4-morpholinopiperidine-1-yl)phenyl)acrylamide | ¹H NMR (400 MHz, DMSO-d₆) δ 9.08 (d, J = 10.5 Hz, 1H), 8.22 (d, J = 11.7 Hz, 1H), 8.06 (s, 1H), 7.43 (d, J = 6.2 Hz, 1H), 7.42-7.28 (m, 3H), 6.86 (s, 1H), 6.59 (d, J = 11.0 Hz, 1H), 6.32-6.16 (m, 2H), 5.74 (d, J = 10.4 Hz, 1H), 5.53 (dd, J = 8.6, 5.2 Hz, 1H), 4.20 (s, 1H), 4.05 (d, J = 12.6 Hz, 3H), 3.97-3.85 (m, 2H), 3.81 (s, 3H), 3.71 (s, 3H), 3.49 (d, J = 12.2 Hz, 2H), 3.32 (s, 1H), 3.18 (d, J = 9.5 Hz, 4H), 2.90-2.67 (m, 2H), 2.35-2.20 (m, 1H), 2.14 (d, J = 11.4 Hz, 2H), 1.91 (s, 1H), ; 620.5 [M + H]⁺ | 1.16 |

TABLE 1-continued

| Example Compound | Structure | Name of Compound | ¹H NMR[[:]]; MS [M + H]⁺ | UPLC r.t. (min) |
|---|---|---|---|---|
| 418 | 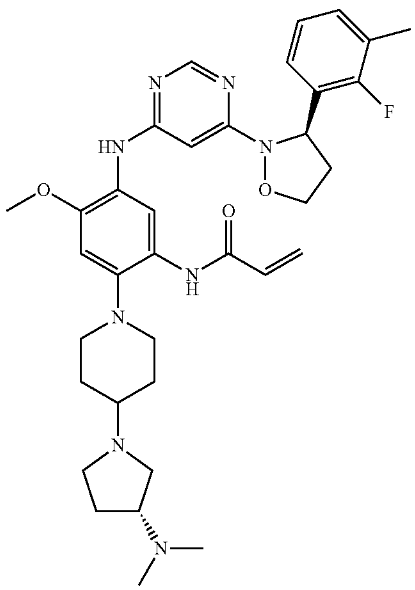 | N-(2-(4-((R)-3-(dimethylamino)pyrolidine-1-yl)piperidine-1-yl)-5-((6-((R)-3-(2-fluoro-3-methylphenyl)isoxazolidine-2-yl)pyrimidine-4-yl)amino)-4-methoxyphenyl)acrylamide | ¹H NMR (400 MHz, Chloroform-d) δ 8.85 (s, 1H), 8.48 (s, 1H), 8.35 (s, 1H), 7.39 (td, J = 7.5, 1.9 Hz, 1H), 7.12-7.04 (m, 1H), 7.02-6.94 (m, 2H), 6.73 (d, J = 11.0 Hz, 2H), 6.39-6.27 (m, 1H), 6.27-6.20 (m, 1H), 5.90 (dd, J = 8.8, 4.4 Hz, 1H), 5.73 (dd, J = 9.8, 1.7 Hz, 1H), 4.17-4.01 (m, 2H), 3.84 (s, 3H), 3.55 (h, J = 6.7 Hz, 1H), 3.09-2.88 (m, 7H), 2.83-2.62 (m, 4H), 2.53 (dd, J = 9.1, 7.2 Hz, 1H), 2.33 (s, 6H), 2.14-2.00 (m, 3H), 1.93-1.66 (m, 3H), 1.36 (d, J = 6.6 Hz, 3H), ; 645.6 [M + H]⁺ | 1.05 |
| 419 | 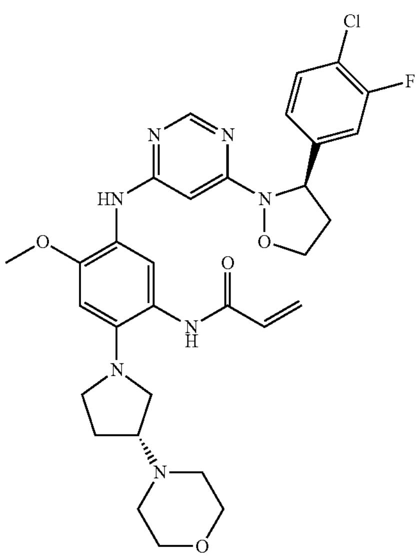 [SMILES: C=CC(=O)Nc1cc(Nc2cc(N3OCC[C@@H]3c3ccc(Cl)c(F)c3)ncn2)c(OC)cc1N1CC[C@@H](N2CCOCC2)C1] | N-(5-((6-((R)-3-(4-chloro-3-fluorophenyl)isoxazolidine-2-yl)pyrimidine-4-yl)amino)-4-methoxy-2-((R)-3-morpholinopyrrolidine-1-yl)phenyl)acrylamide | ¹H NMR (400 MHz, Chloroform-d) δ 8.65 (s, 1H), 8.34 (s, 1H), 8.16 (s, 1H), 7.35 (t, J = 7.9 Hz, 1H), 7.31-7.28 (m, 1H), 7.18 (dd, J = 8.4, 2.0 Hz, 1H), 6.95 (s, 1H), 6.75 (s, 1H), 6.67 (s, 1H), 6.43-6.23 (m, 2H), 5.74 (dd, J = 9.7, 1.8 Hz, 1H), 5.65 (dd, J = 8.7, 4.5 Hz, 1H), 4.15 (td, J = 8.0, 4.2 Hz, 1H), 4.05 (q, J = 8.0 Hz, 1H), 3.83 (s, 3H), 3.76 (t, J = 4.7 Hz, 4H), 3.25-3.05 (m, 4H), 2.98 (p, J = 7.4 Hz, 1H), 2.76 (dtd, J = 12.3, 8.1, 4.2 Hz, 1H), 2.53 (ddt, J = 39.6, 11.1, 4.6 Hz, 4H), 2.33 (ddt, J = 11.9, 7.9, 4.0 Hz, 1H), 2.19 (dtd, J = 12.1, 7.6, 4.3 Hz, 1H), 1.99-1.91 (m, 1H), ; 624.4 [M + H]⁺ | 1.15 |

TABLE 1-continued

| Example Compound | Structure | Name of Compound | ¹H NMR[[:]]; MS [M + H]⁺ | UPLC r.t. (min) |
|---|---|---|---|---|
| 420 | 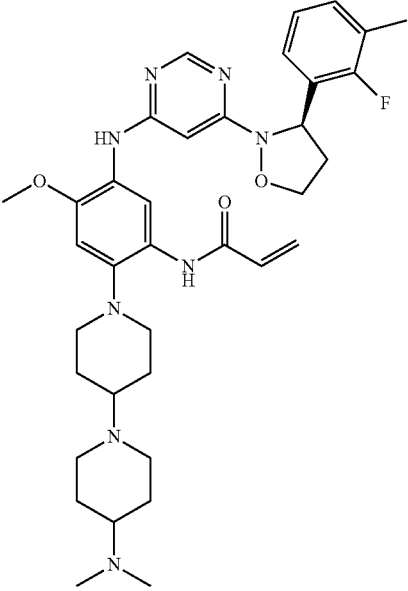 | N-(2-(4-(dimethylamino)-[1,4'-bipiperidine]-1'-yl)-5-((6-((R)-3-(2-fluoro-3-methylphenyl)isoxazolidine-2-yl)pyrimidine-4-yl)amino)-4-methoxyphenyl)acrylamide | ¹H NMR (400 MHz, Methanol-d₄) δ 8.23 (s, 1H), 7.93 (s, 1H), 7.19 (dt, J = 24.4, 7.6 Hz, 3H), 7.08 (t, J = 7.6 Hz, 1H), 6.72 (dd, J = 16.9, 10.2 Hz, 1H), 6.48 (d, J = 16.9 Hz, 1H), 6.10 (s, 1H), 5.90 (d, J = 10.4 Hz, 1H), 5.73 (t, J = 7.0 Hz, 1H), 4.44 (td, J = 7.5, 4.4 Hz, 1H), 4.23 (q, J = 7.7 Hz, 1H), 3.93 (d, J = 8.2 Hz, 5H), 3.79-3.64 (m, 2H), 3.53 (ddq, J = 12.7, 8.5, 4.1 Hz, 2H), 3.37 (d, J = 12.1 Hz, 2H), 3.30-3.22 (m, 1H), 3.07 (ddd, J = 13.4, 8.5, 5.5 Hz, 1H), 2.97 (s, 6H), 2.91 (d, J = 3.6 Hz, 2H), 2.48 (dd, J = 19.1, 12.2 Hz, 5H), 2.39-2.24 (m, 7H), ; 659.6 [M + H]⁺ | 1.06 |
| 421 | 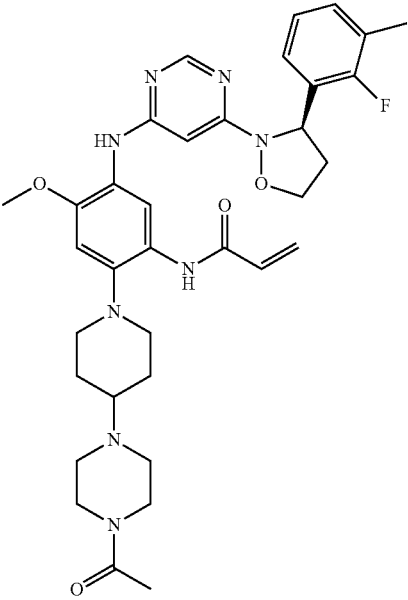 | N-(2-(4-(4-acetylpiperazine-1-yl)piperidine-1-yl)-5-((6-((R)-3-(2-fluoro-3-methylphenyl)isoxazolidine-2-yl)pyrimidine-4-yl)amino)-4-methoxyphenyl)acrylamide | ¹H NMR (400 MHz, Chloroform-d) δ 8.87 (s, 1H), 8.42 (s, 1H), 8.36 (d, J = 0.9 Hz, 1H), 7.39 (td, J = 7.4, 1.9 Hz, 1H), 7.07 (dt, J = 7.4, 3.8 Hz, 1H), 7.02-6.91 (m, 2H), 6.73 (d, J = 8.9 Hz, 2H), 6.45-6.20 (m, 2H), 5.90 (dd, J = 8.8, 4.4 Hz, 1H), 5.78-5.71 (m, 1H), 4.17-4.03 (m, 2H), 3.84 (s, 3H), 3.66 (t, J = 5.0 Hz, 2H), 3.51 (t, J = 5.0 Hz, 2H), 3.12-3.03 (m, 2H), 2.84 (td, J = 8.1, 4.3 Hz, 1H), 2.73 (qd, J = 11.9, 2.2 Hz, 2H), 2.61 (dt, J = 13.8, 5.0 Hz, 4H), 2.28 (d, J = 2.0 Hz, 3H), 2.11 (s, 3H), 2.06-2.00 (m, 2H), 1.67 (qd, J = 12.0, 3.9 Hz, 2H), 1.43 (d, J = 6.6 Hz, 2H), ; 659.5 [M + H]⁺ | 1.15 |

TABLE 1-continued

| Example Compound | Structure | Name of Compound | ¹H NMR[:]; MS [M + H]⁺ | UPLC r.t. (min) |
|---|---|---|---|---|
| 422 | 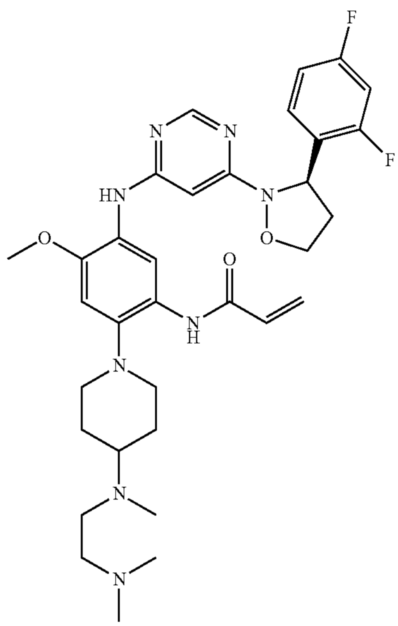 [SMILES: C=CC(=O)Nc1cc(Nc2cc(N3OCC[C@@H]3c3ccc(F)cc3F)ncn2)c(OC)cc1N1CCC(N(C)CCN(C)C)CC1] | N-(5-((6-((R)-3-(2,4-difluorophenyl) isoxazolidine-2-yl)pyrimidine-4-yl)amino)-2-(4-((2-(dimethylamino)ethyl) (methyl)amino) piperidine-1-yl)-4-methoxyphenyl) acrylamide | ¹H NMR (400 MHz, Chloroform-d) δ 8.88 (s, 1H), 8.46 (s, 1H), 8.37 (s, 1H), 7.56 (dt, J = 14.8, 7.4 Hz, 1H), 6.92 (s, 1H), 6.87-6.70 (m, 4H), 6.40-6.22 (m, 2H), 5.88 (dd, J = 8.9, 4.3 Hz, 1H), 5.80-5.71 (m, 1H), 4.16-4.03 (m, 2H), 3.85 (s, 3H), 3.06 (d, J = 11.6 Hz, 2H), 2.86-2.62 (m, 5H), 2.37 (s, 3H), 2.30 (s, 6H), 1.99 (d, J = 12.5 Hz, 2H), 1.80-1.68 (m, 6H), ; 637.6 [M + H]⁺ | 1.06 |
| 423 | 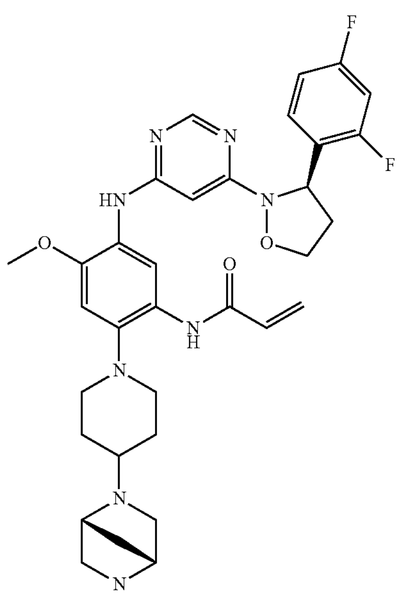 [SMILES: C=CC(=O)Nc1cc(Nc2cc(N3OCC[C@@H]3c3ccc(F)cc3F)ncn2)c(OC)cc1N1CCC(N2C[C@H]3C[C@@H]2CN3)CC1] | N-(2-(4-((1R,4R)-2-oxa-5-azabicyclo[2.2.1] heptane-5-yl) piperidine-1-yl)-5-((6-((R)-3-(2,4-difluorophenyl) isoxazolidine-2-yl)pyrimidine-4-yl)amino)-4-methoxyphenyl) acrylamide | ¹H NMR (400 MHz, Chloroform-d) δ 8.90-8.85 (s, 1H), 8.48 (s, 1H), 8.37 (s, 1H), 7.56 (d, J = 8.6 Hz, 1H), 6.93 (s, 1H), 6.80 (m, 4H), 6.35 (d, J = 16.6 Hz, 1H), 6.26 (m, 1H), 5.88 (m, 1H), 5.73 (d, J = 11.0 Hz, 1H), 4.44 (s, 1H), 4.09 (m, 4H), 3.86 (s, 3H), 3.77 (s, 1H), 3.67 (d, J = 7.7 Hz, 1H), 3.14 (d, J = 9.6 Hz, 1H), 3.03 (d, J = 11.8 Hz, 2H), 2.78 (m, 4H), 2.58 (m, 1H), 2.50 (d, J = 9.8 Hz, 1H), 2.27 (m, 1H), 2.06 (m, 1H), 1.92 (d, J = 11.3 Hz, 2H), 1.84 (s, 1H), ; 634.5 [M + H]⁺ | 1.16 |

TABLE 1-continued

| Example Compound | Structure | Name of Compound | ¹H NMR[[:]]; MS [M + H]⁺ | UPLC r.t. (min) |
|---|---|---|---|---|
| 424 | 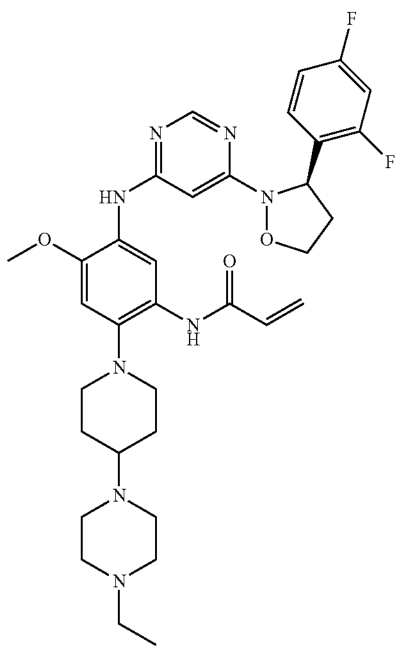 [SMILES: C=CC(=O)Nc1cc(Nc2cc(N3OCC[C@@H]3c3ccc(F)cc3F)ncn2)c(OC)cc1N1CCC(N2CCN(CC)CC2)CC1] | N-(5-((6-((R)-3-(2,4-difluorophenyl) isoxazolidine-2-yl)pyrimidine-4-yl)amino)-2-(4-(4-ethylpiperazine-1-yl)piperidine-1-yl)-4-methoxyphenyl) acrylamide | ¹H NMR (400 MHz, Chloroform-d) δ 8.87 (s, 1H), 8.45 (s, 1H), 8.36 (s, 1H), 7.56 (m, 1H), 6.92 (s, 1H), 6.83 (q, 2H), 6.75 (s, 2H), 6.35 (d, J = 16.8 Hz, 1H), 6.26 (m, 1H), 5.87 (m, 1H), 5.73 (d, J = 10.3 Hz, 1H), 4.10 (s, 2H), 3.85 (s, 3H), 3.06 (d, J = 11.5 Hz, 2H), 2.86-2.63 (m, 8H), 2.54 (s, 3H), 2.44 (m, 3H), 2.30 (m, 3H), 2.09 (d, J = 5.0 Hz, 2H), 1.11 (s, 3H), ; 649.5 [M + H]⁺ | 1.10 |
| 425 | 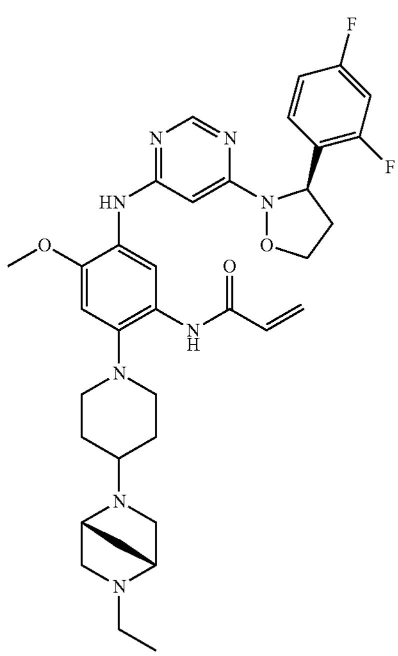 [SMILES: C=CC(=O)Nc1cc(Nc2cc(N3OCC[C@@H]3c3ccc(F)cc3F)ncn2)c(OC)cc1N1CCC(N2C[C@H]3C[C@@H]2CN3CC)CC1] | N-(5-((6-((R)-3-(2,4-difluorophenyl) isoxazolidine-2-yl)pyrimidine-4-yl)amino)-2-(4-((1R,4R)-5-ethyl-2,5-diazabicyclo[2.2.1] heptane-2-yl) piperidine-1-yl)-4-methoxyphenyl) acrylamide | ¹H NMR (400 MHz, Chloroform-d) δ 8.87 (s, 1H), 8.47 (s, 1H), 7.56 (m, 1H), 6.91 (s, 1H), 6.80 (m, 4H), 6.34 (d, J = 16.9 Hz, 1H), 6.25 (m, 1H), 5.86 (m, 1H), 5.72 (d, J = 11.0 Hz, 1H), 4.09 (m, 2H), 3.85 (s, 3H), 3.61 (s, 1H), 3.36 (s, 1H), 3.00 (m, 3H), 2.88 (d, J = 9.9 Hz, 2H), 2.76 (d, J = 23.4 Hz, 3H), 2.58 (m, 6H), 2.27 (m, 1H), 2.02 (m, 1H), 1.91 (m, 1H), 1.80 (m, 2H), 1.10 (t, 3H), ; 661.5 [M + H]⁺ | 1.07 |

TABLE 1-continued

| Example Compound | Structure | Name of Compound | ¹H NMR[[:]]; MS [M + H]⁺ | UPLC r.t. (min) |
|---|---|---|---|---|
| 426 | 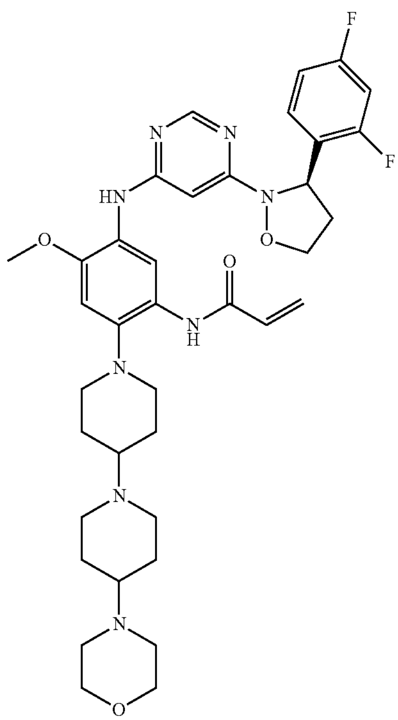 [SMILES: C=CC(=O)Nc1cc(Nc2cc(N3OCC[C@@H]3c3ccc(F)cc3F)ncn2)c(OC)cc1N1CCC(N2CCC(N3CCOCC3)CC2)CC1] | N-(5-((6-((R)-3-(2,4-difluorophenyl)isoxazolidine-2-yl)pyrimidine-4-yl)amino)-4-methoxy-2-(4-morpholino-[1,4'-bipiperidine]-1'-yl)phenyl)acrylamide | ¹H NMR (400 MHz, Chloroform-d) δ 8.87 (s, 1H), 8.44 (s, 1H), 8.36 (s, 1H), 7.56 (m, 1H), 6.92 (s, 1H), 6.82 (s, 2H), 6.75 (m, 2H), 6.36 (d, J = 17.0 Hz, 1H), 6.27 (m, 1H), 5.87 (m, 1H), 5.74 (d, J = 10.9 Hz, 1H), 4.10 (d, J = 11.3 Hz, 3H), 3.85 (s, 3H), 3.73 (m, 4H), 3.15-3.02 (m, 4H), 2.79 (m, 2H), 2.72 (m, 2H), 2.57 (m, 4H), 2.38 (m, 2H), 2.22 (m, 5H), 2.03 (d, J = 14.6 Hz, 2H), 1.87 (d, J = 13.5 HZ, 2H), ; 705.6 [M + H]⁺ | 1.12 |
| 427 | 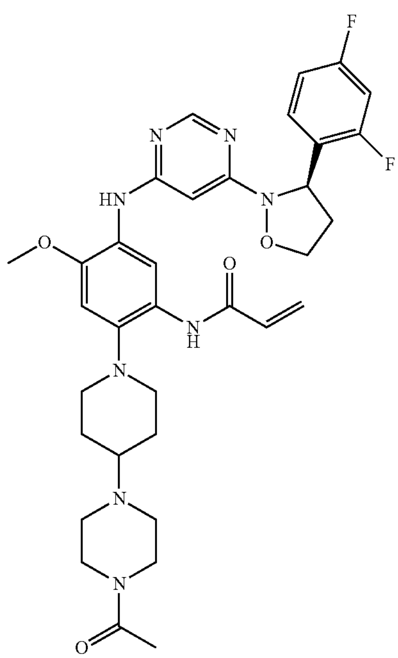 [SMILES: C=CC(=O)Nc1cc(Nc2cc(N3OCC[C@@H]3c3ccc(F)cc3F)ncn2)c(OC)cc1N1CCC(N2CCN(C(C)=O)CC2)CC1] | N-(2-(4-(4-acetylpiperazine-1-yl)piperidine-1-yl)-5-((6-((R)-3-(2,4-difluorophenyl)isoxazolidine-2-yl)pyrimidine-4-yl)amino)-4-methoxyphenyl)acrylamide | ¹H NMR (400 MHz, Chloroform-d) δ 8.88 (s, 1H), 8.41 (s, 1H), 8.37 (d, J = 0.9 Hz, 1H), 7.56 (q, J = 8.4 Hz, 1H), 6.93 (s, 1H), 6.87-6.78 (m, 2H), 6.75 (s, 2H), 6.40-6.33 (m, 1H), 6.25 (dd, J = 16.9, 10.0 Hz, 1H), 5.88 (dd, J = 8.7, 4.3 Hz, 1H), 5.74 (dd, J = 10.0, 1.5 Hz, 1H), 4.14-4.05 (m, 2H), 3.85 (s, 3H), 3.67 (t, J = 5.1 Hz, 2H), 3.52 (t, J = 5.1 Hz, 2H), 3.07 (d, J = 11.5 Hz, 2H), 2.81 (dd, J = 8.2, 4.2 Hz, 1H), 2.77-2.68 (m, 2H), 2.61 (dt, J = 13.9, 5.0 Hz, 4H), 2.44-2.36 (m, 1H), 2.32-2.23 (m, 1H), 2.11 (s, 3H), 2.04 (d, J = 12.4 Hz, 2H), 1.69 (t, J = 11.8 Hz, 2H), ; 663.5 [M + H] | 1.33 |

TABLE 1-continued

| Example Compound | Structure | Name of Compound | ¹H NMR[[:]]; MS [M + H]⁺ | UPLC r.t. (min) |
|---|---|---|---|---|
| 428 | 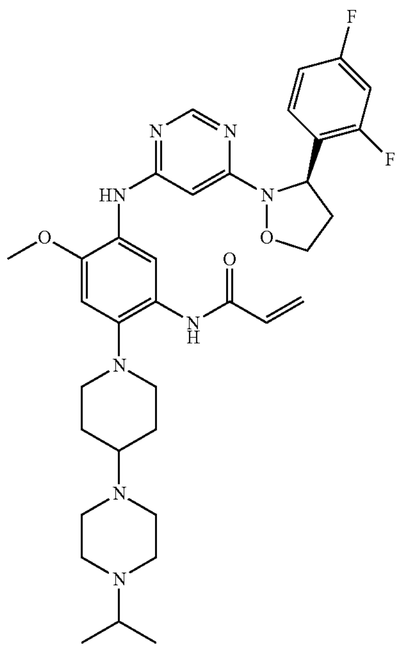 [SMILES: C=CC(=O)Nc1cc(Nc2cc(N3OCC[C@@H]3c3ccc(F)cc3F)ncn2)c(OC)cc1N1CCC(N2CCN(C(C)C)CC2)CC1] | N-(5-((6-((R)-3-(2,4-difluorophenyl)isoxazolidine-2-yl)pyrimidine-4-yl)amino)-2-(4-(4-isopropylpiperazine-1-yl)piperidine-1-yl)-4-methoxyphenyl)acrylamide | ¹H NMR (400 MHz, Chloroform-d) δ 8.87 (s, 1H), 8.45 (s, 1H), 8.36 (s, 1H), 7.56 (td, J = 8.6, 6.5 Hz, 1H), 6.92 (s, 1H), 6.87-6.77 (m, 2H), 6.75 (d, J = 2.4 Hz, 2H), 6.39-6.32 (m, 1H), 6.24 (dd, J = 16.9, 10.0 Hz, 1H), 5.87 (dd, J = 8.8, 4.3 Hz, 1H), 5.73 (dd, J = 9.9, 1.5 Hz, 1H), 4.15-4.05 (m, 2H), 3.84 (s, 3H), 3.06 (d, J = 11.5 Hz, 2H), 2.82-2.61 (m, 10H), 2.35-2.22 (m, 2H), 2.10 (d, J = 12.4 Hz, 2H), 1.72-1.60 (m, 4H), 1.08 (d, J = 6.5 Hz, 6H), ; 663.6 [M + H] | 1.09 |
| 429 | 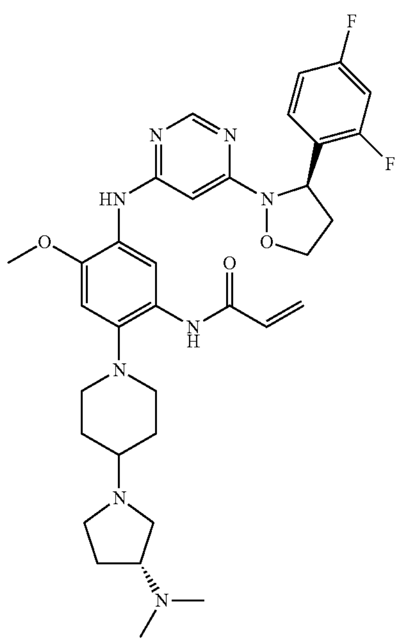 [SMILES: C=CC(=O)Nc1cc(Nc2cc(N3OCC[C@@H]3c3ccc(F)cc3F)ncn2)c(OC)cc1N1CCC(N2CC[C@@H](N(C)C)C2)CC1] | N-(5-((6-((R)-3-(2,4-difluorophenyl)isoxazolidine-2-yl)pyrimidine-4-yl)amino)-2-(4-((R)-3-(dimethylamino)pyrolidine-1-yl)piperidine-1-yl)-4-methoxyphenyl)acrylamide | ¹H NMR (400 MHz, Chloroform-d) δ 8.86 (s, 1H), 8.48 (s, 1H), 8.36 (s, 1H), 7.56 (q, J = 8.3 Hz, 1H), 6.99 (s, 1H), 6.88-6.77 (m, 2H), 6.75 (s, 1H), 6.38-6.31 (m, 1H), 6.30-6.12 (m, 2H), 5.87 (dd, J = 8.8, 4.3 Hz, 1H), 5.75-5.70 (m, 1H), 4.14-4.04 (m, 2H), 3.85 (s, 3H), 3.01 (t, J = 16.2 Hz, 5H), 2.87-2.60 (m, 5H), 2.53 (d, J = 8.7 Hz, 1H), 2.34 (s, 6H), 2.07 (d, J = 10.6 Hz, 2H), 1.88 (t, J = 10.2 Hz, 1H), 1.75 (t, J = 11.2 Hz, 2H), 1.38 (s, 2H), ; 649.5 [M + H] | 1.04 |

| Example Compound | Structure | Name of Compound | ¹H NMR[[:]]; MS [M + H]⁺ | UPLC r.t. (min) |
|---|---|---|---|---|
| 430 | 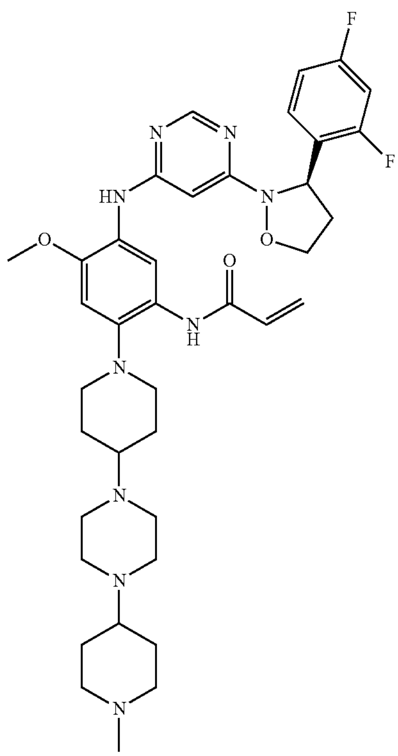 [SMILES: C=CC(=O)Nc1cc(Nc2cc(N3OCC[C@@H]3c3ccc(F)cc3F)ncn2)c(OC)cc1N1CCC(N2CCN(C3CCN(C)CC3)CC2)CC1] | N-(5-((6-((R)-3-(2,4-difluorophenyl)isoxazolidine-2-yl)pyrimidine-4-yl)amino)-4-methoxy-2-(4-(4-(1-methylpiperidine-4-yl)piperazine-1-yl)piperidine-1-yl)phenyl)acrylamide | ¹H NMR (400 MHz, Chloroform-d) δ 8.87 (s, 1H), 8.44 (s, 1H), 8.36 (s, 1H), 7.56 (q, J = 8.0 Hz, 1H), 6.92 (s, 1H), 6.87-6.77 (m, 2H), 6.75 (s, 2H), 6.35 (d, J = 16.9 Hz, 1H), 6.23 (dd, J = 16.8, 10.0 Hz, 1H), 5.87 (dd, J = 8.8, 4.3 Hz, 1H), 5.73 (d, J = 10.4 Hz, 1H), 4.14-4.04 (m, 2H), 3.84 (s, 3H), 3.24 (t, J = 6.1 Hz, 2H), 3.19-3.16 (m, 2H), 3.06 (d, J = 11.7 Hz, 2H), 2.92 (d, J = 11.2 Hz, 2H), 2.66 (s, 4H), 2.39 (t, J = 6.2 Hz, 2H), 2.27 (s, 3H), 2.09 (d, J = 12.5 Hz, 2H), 1.95 (t, J = 11.6 Hz, 2H), 1.83 (d, J = 12.3 Hz, 2H), 1.65 (t, J = 6.2 Hz, 4H), 1.14 (t, J = 7.2 Hz, 4H), ; 718.6 [M + H] | 1.13 |
| 431 | 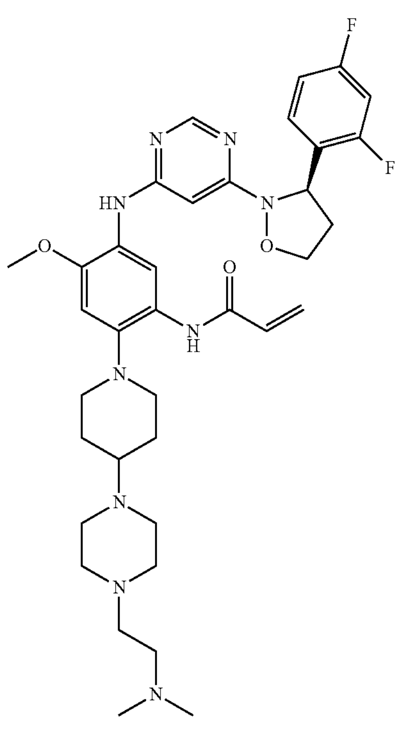 [SMILES: C=CC(=O)Nc1cc(Nc2cc(N3OCC[C@@H]3c3ccc(F)cc3F)ncn2)c(OC)cc1N1CCC(N2CCN(CCN(C)C)CC2)CC1] | N-(5-((6-((R)-3-(2,4-difluorophenyl)isoxazolidine-2-yl)pyrimidine-4-yl)amino)-2-(4-(4-(2-(dimethylamino)ethyl)piperazine-1-yl)piperidine-1-yl)-4-methoxyphenyl)acrylamide | ¹H NMR (400 MHz, Chloroform-d) δ 8.87 (s, 1H), 8.46 (d, J = 10.8 Hz, 1H), 8.35 (d, J = 8.7 Hz, 1H), 7.58-7.52 (m, 1H), 6.93 (d, J = 4.0 Hz, 1H), 6.88-6.78 (m, 3H), 6.75 (s, 1H), 6.35 (d, J = 17.1 Hz, 1H), 6.24 (dd, J = 16.8, 10.1 Hz, 1H), 5.85 (s, 1H), 5.74 (d, J = 10.0 Hz, 1H), 4.14-4.07 (m, 2H), 3.94 (d, J = 7.7 Hz, 1H), 3.85 (s, 3H), 3.27 (dd, J = 7.7, 4.5 Hz, 4H), 3.22 (d, J = 4.5 Hz, 2H), 3.18 (dd, J = 7.3, 5.5 Hz, 4H), 2.60-2.55 (m, 8H), 2.39 (s, 6H), 1.77-1.72 (m, 4H), ; 692.6 [M + H] | 1.12 |

TABLE 1-continued

| Example Compound | Structure | Name of Compound | ¹H NMR[[:]]; MS [M + H]⁺ | UPLC r.t. (min) |
|---|---|---|---|---|
| 432 | 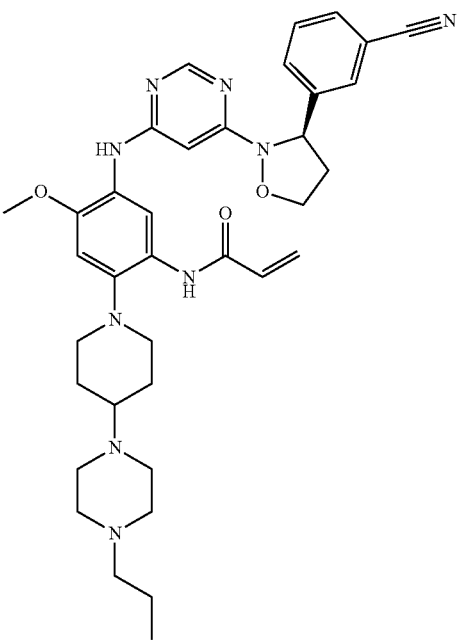 [SMILES: C=CC(=O)Nc1cc(Nc2cc(N3OCC[C@@H]3c3cccc(C#N)c3)ncn2)c(OC)cc1N1CCC(N2CCN(CCC)CC2)CC1] | N-(5-((6-((R)-3-(3-cyanophenyl)isoxazolidine-2-yl)pyrimidine-4-yl)amino)-4-methoxy-2-(4-(4-propylpiperazine-1-yl)piperidine-1-yl)phenyl)acrylamide | ¹H NMR (400 MHz, DMSO-d₆) δ 9.05 (s, 1H), 8.69 (s, 1H), 8.17 (d, J = 1.0 Hz, 1H), 7.83 (d, J = 1.8 Hz, 1H), 7.80-7.72 (m, 2H), 7.58 (t, J = 7.8 Hz, 1H), 6.84 (s, 1H), 6.66 (dd, J = 16.9, 10.2 Hz, 1H), 6.37 (s, 1H), 6.22 (dd, J = 17.0, 2.0 Hz, 1H), 5.73 (d, J = 10.4 Hz, 1H), 5.59 (dd, J = 8.7, 5.1 Hz, 1H), 4.15 (td, J = 7.9, 3.8 Hz, 1H), 3.81 (s, 3H), 3.59 (pd, J = 6.6, 3.9 Hz, 7H), 3.34 (s, 14H), 3.11 (dt, J = 7.4, 3.7 Hz, 6H), 2.08 (s, 3H), ; 652.5 [M + H]⁺ | 1.10 |
| 433 | 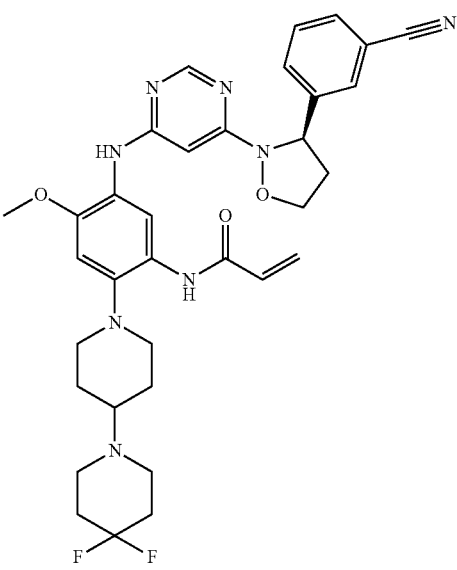 [SMILES: C=CC(=O)Nc1cc(Nc2cc(N3OCC[C@@H]3c3cccc(C#N)c3)ncn2)c(OC)cc1N1CCC(N2CCC(F)(F)CC2)CC1] | N-(5-((6-((R)-3-(3-cyanophenyl)isoxazolidine-2-yl)pyrimidine-4-yl)amino)-2-(4,4-difluoro-[1,4'-bipiperidine]-1'-yl)-4-methoxyphenyl)acrylamide | ¹H NMR (400 MHz, DMSO-d₆) δ 8.95 (s, 1H), 8.62 (s, 1H), 8.16 (s, 1H), 7.83 (d, J = 1.9 Hz, 1H), 7.81-7.70 (m, 2H), 7.58 (t, J = 7.8 Hz, 1H), 6.82 (s, 1H), 6.66 (dd, J = 16.9, 10.2 Hz, 1H), 6.36 (s, 1H), 6.21 (dd, J = 17.0, 2.0 Hz, 1H), 5.72 (dd, J = 10.3, 2.0 Hz, 1H), 5.59 (dd, J = 8.7, 5.0 Hz, 1H), 4.15 (td, J = 7.9, 3.9 Hz, 1H), 3.80 (s, 3H), 3.33 (s, 5H), 3.06 (d, J = 11.1 Hz, 2H), 2.78 (dtd, J = 12.0, 7.9, 3.8 Hz, 1H), 2.72-2.55 (m, 6H), 2.31-2.20 (m, 1H), 1.95 (tt, J = 13.8, 5.4 Hz, 4H), 1.84-1.70 (m, 4H), ; 645.4 [M + H]⁺ | 1.18 |

TABLE 1-continued

| Example Compound | Structure | Name of Compound | ¹H NMR[:]; MS [M + H]⁺ | UPLC r.t. (min) |
|---|---|---|---|---|
| 434 | 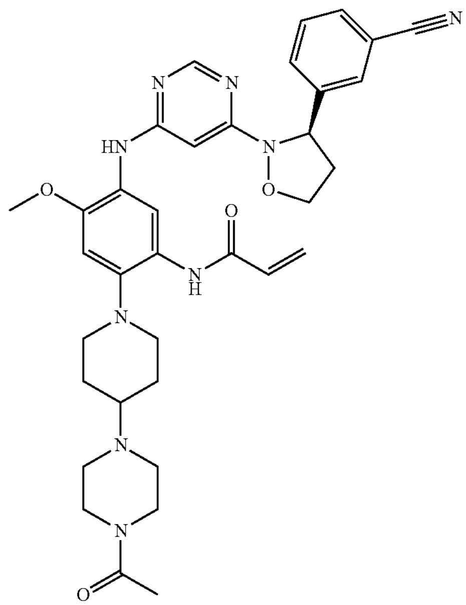 [SMILES: C=CC(=O)Nc1cc(Nc2cc(N3OCC[C@@H]3c3cccc(C#N)c3)ncn2)c(OC)cc1N1CCC(N2CCN(C(C)=O)CC2)CC1] | N-(2-(4-(4-acetylpiperazine-1-yl)piperidine-1-yl)-5-((6-((R)-3-(3-cyanophenyl)isoxazolidine-2-yl)pyrimidine-4-yl)amino)-4-methoxyphenyl)acrylamide | ¹H NMR (400 MHz, DMSO-d₆) δ 8.96 (s, 1H), 8.62 (s, 1H), 8.16 (s, 1H), 7.83 (d, J = 1.8 Hz, 1H), 7.80-7.72 (m, 2H), 7.58 (t, J = 7.8 Hz, 1H), 6.82 (s, 1H), 6.65 (dd, J = 16.9, 10.2 Hz, 1H), 6.36 (s, 1H), 6.23 (dd, J = 33.1, 2.0 Hz, 2H), 5.72 (dd, J = 10.2, 2.0 Hz, 1H), 5.59 (dd, J = 8.6, 5.0 Hz, 1H), 4.15 (td, J = 7.8, 3.8 Hz, 1H), 3.80 (s, 3H), 3.46-3.21 (m, 8H), 3.06 (d, J = 11.1 Hz, 2H), 2.78 (dtd, J = 12.0, 7.9, 3.8 Hz, 1H), 2.66 (td, J = 10.4, 9.6, 6.0 Hz, 2H), 2.53 (t, J = 4.9 Hz, 2H), 2.47 (d, J = 4.4 Hz, 2H), 1.99 (s, 3H), 1.87-1.79 (m, 2H), 1.79-1.66 (m, 2H), ; 652.5 [M + H]⁺ | 1.10 |
| 435 | 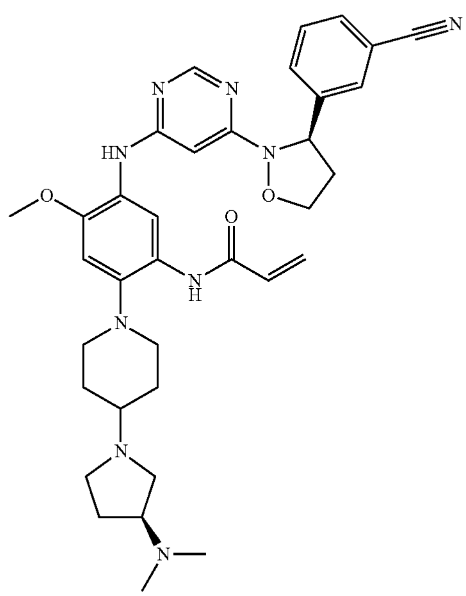 [SMILES: C=CC(=O)Nc1cc(Nc2cc(N3OCC[C@@H]3c3cccc(C#N)c3)ncn2)c(OC)cc1N1CCC(N2CC[C@H](N(C)C)C2)CC1] | N-(5-((6-((R)-3-(3-cyanophenyl)isoxazolidine-2-yl)pyrimidine-4-yl)amino)-2-(4-((S)-3-(dimethylamino)pyrolidine-1-yl)piperidine-1-yl)-4-methoxyphenyl)acrylamide | 638.6 [M + H]⁺ | 1.01 |

TABLE 1-continued

| Example Compound | Structure | Name of Compound | ¹H NMR[[:]]; MS [M + H]⁺ | UPLC r.t. (min) |
|---|---|---|---|---|
| 436 | 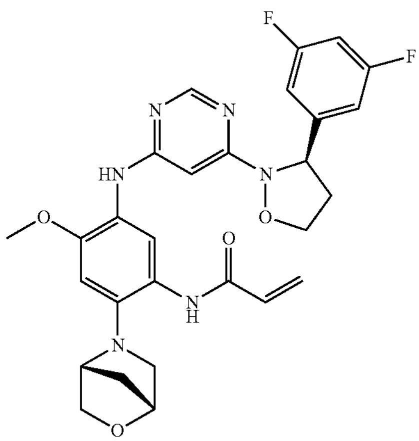 [SMILES: C=CC(=O)Nc1cc(Nc2cc(N3OCC[C@@H]3c3cc(F)cc(F)c3)ncn2)c(OC)cc1N1C[C@H]2C[C@@H]1CO2] | N-(2-((1R,4R)-2-oxa-5-azabicyclo[2.2.1]heptane-5-yl)-5-((6-((R)-3-(3,5-difluorophenyl)isoxazolidine-2-yl)pyrimidine-4-yl)amino)-4-methoxyphenyl) acrylamide | ¹H NMR (400 MHz, MeOD) δ 8.13 (s, 1H), 7.52 (s, 1H), 7.07 (d, J = 6.6 Hz, 2H), 6.84 (dd, J = 10.1, 8.0 Hz, 1H), 6.57 (s, 1H), 6.48 (dd, J = 17.0, 10.1 Hz, 1H), 6.41-6.26 (m, 2H), 5.79 (dd, J = 10.1, 1.7 Hz, 1H), 5.56 (dd, J = 8.5, 4.8 Hz, 1H), 4.60 (s, 1H), 4.38 (s, 1H), 4.17-4.10 (m, 2H), 3.98-3.84 (m, 5H), 3.51 (d, J = 8.3 Hz, 1H), 3.14 (d, J = 9.2 Hz, 1H), 2.88-2.75 (m, 1H), 2.33 (dt, J = 8.7, 6.4 Hz, 1H), 2.06 (d, J = 8.3 Hz, 1H), 1.98-1.89 (m, 1H), ; 551.4 [M + H]⁺ | 1.38 |
| 437 | 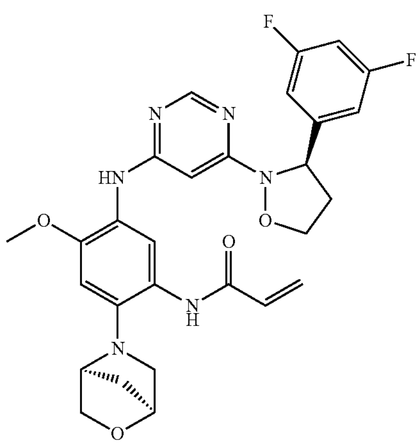 [SMILES: C=CC(=O)Nc1cc(Nc2cc(N3OCC[C@@H]3c3cc(F)cc(F)c3)ncn2)c(OC)cc1N1C[C@@H]2C[C@H]1CO2] | N-(2-((1S,4S)-2-oxa-5-azabicyclo[2.2.1]heptane-5-yl)-5-((6-((R)-3-(3,5-difluorophenyl)isoxazolidine-2-yl)pyrimidine-4-yl)amino)-4-methoxyphenyl) acrylamide | ¹H NMR (400 MHz, MeOD) δ 8.14 (s, 1H), 7.52 (s, 1H), 7.08 (t, J = 6.4 Hz, 2H), 6.84 (ddd, J = 9.1, 5.7, 2.2 Hz, 1H), 6.57 (s, 1H), 6.49 (dd, J = 17.0, 10.1 Hz, 1H), 6.41-6.33 (m, 2H), 5.79 (dd, J = 10.1, 1.7 Hz, 1H), 5.56 (dd, J = 8.6, 4.6 Hz, 1H), 4.60 (s, 1H), 4.38 (s, 1H), 4.20-4.09 (m, 2H), 3.98-3.86 (m, 5H), 3.53 (d, J = 9.5 Hz, 1H), 3.13 (d, J = 9.6 Hz, 1H), 2.87-2.73 (m, 1H), 2.38-2.26 (m, 1H), 2.06 (d, J = 8.2 Hz, 1H), 1.98-1.90 (m, 1H), ; 551.4 [M + H]⁺ | 1.37 |
| 438 | 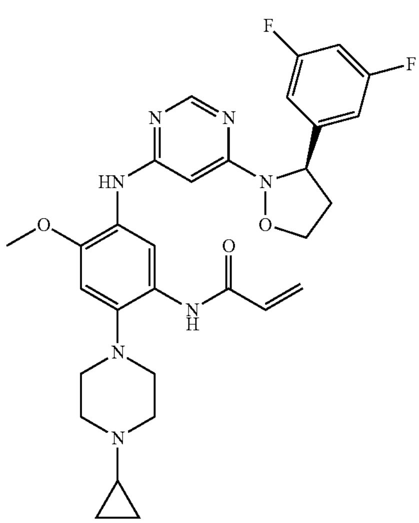 [SMILES: C=CC(=O)Nc1cc(Nc2cc(N3OCC[C@@H]3c3cc(F)cc(F)c3)ncn2)c(OC)cc1N1CCN(C2CC2)CC1] | N-(2-(4-cyclopropylpiperazine-1-yl)-5-((6-((R)-3-(3,5-difluorophenyl)isoxazolidine-2-yl)pyrimidine-4-yl)amino)-4-methoxyphenyl) acrylamide | ¹H NMR (400 MHz, MeOD) δ 8.35 (s, 1H), 8.20 (d, J = 7.2 Hz, 1H), 7.07 (d, J = 6.7 Hz, 2H), 6.92 (s, 1H), 6.84 (ddd, J = 9.1, 5.6, 2.2 Hz, 1H), 6.58-6.46 (m, 2H), 6.37 (dd, J = 17.0, 1.3 Hz, 1H), 5.82 (d, J = 10.5 Hz, 1H), 5.57 (dd, J = 8.6, 4.8 Hz, 1H), 4.15 (td, J = 7.8, 4.2 Hz, 1H), 3.97 (q, J = 8.0 Hz, 1H), 3.89 (d, J = 7.7 Hz, 3H), 2.97-2.78 (m, 9H), 2.38-2.28 (m, 1H), 1.86-1.77 (m, 1H), 0.52 (ddd, J = 14.7, 10.7, 6.9 Hz, 4H), ; 578.4 [M + H]⁺ | 1.26 |

TABLE 1-continued

| Example Compound | Structure | Name of Compound | ¹H NMR[[:]]; MS [M + H]⁺ | UPLC r.t. (min) |
|---|---|---|---|---|
| 439 | 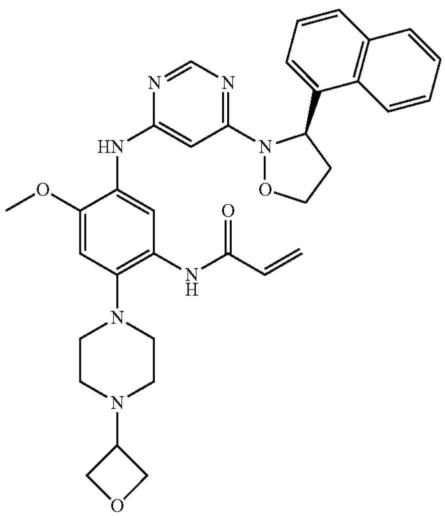 [SMILES: C=CC(=O)Nc1cc(Nc2cc(N3OCC[C@@H]3c3cccc4ccccc34)ncn2)c(OC)cc1N1CCN(C2COC2)CC1] | N-(4-methoxy-5-((6-((R)-3-(naphthalene-1-yl)isoxazolidine-2-yl)pyrimidine-4-yl)amino)-2-(4-(oxetane-3-yl)piperazine-1-yl)phenyl)acrylamide | ¹H NMR (400 MHz, Chloroform-d) δ 8.96 (s, 1H), 8.50 (s, 1H), 8.38 (d, J = 0.9 Hz, 1H), 8.15 (d, J = 8.4 Hz, 1H), 7.92-7.85 (m, 1H), 7.77 (dd, J = 7.7, 4.6 Hz, 2H), 7.60-7.41 (m, 3H), 6.95 (s, 1H), 6.81 (d, J = 11.5 Hz, 2H), 6.45-6.32 (m, 2H), 6.25 (dd, J = 16.9, 10.0 Hz, 1H), 5.74 (dd, J = 10.0, 1.5 Hz, 1H), 4.69 (dt, J = 20.7, 6.3 Hz, 4H), 4.22-4.12 (m, 2H), 3.85 (s, 3H), 3.61 (p, J = 6.4 Hz, 1H), 3.03-2.90 (m, 5H), 2.63-2.43 (m, 4H), 2.46-2.37 (m, 1H), ; 608.5 [M + H]⁺ | 1.25 |
| 440 | 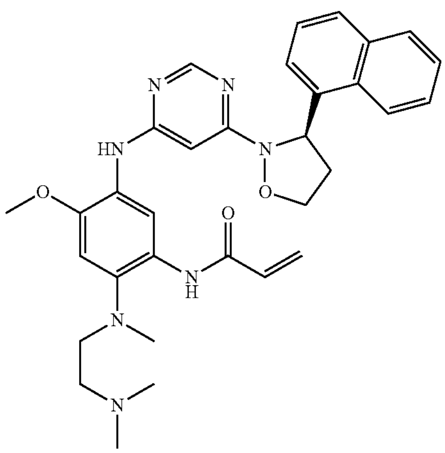 [SMILES: C=CC(=O)Nc1cc(Nc2cc(N3OCC[C@@H]3c3cccc4ccccc34)ncn2)c(OC)cc1N(C)CCN(C)C] | N-(2-((2-(dimethylamino)ethyl)(methyl)amino)-4-methoxy-5-((6-((R)-3-(naphthalene-1-yl)isoxazolidine-2-yl)pyrimidine-4-yl)amino)phenyl)acrylamide | ¹H NMR (400 MHz, Chloroform-d) δ 10.10 (s, 1H), 9.00 (s, 1H), 8.37 (d, J = 1.0 Hz, 1H), 8.16 (d, J = 8.4 Hz, 1H), 7.88 (dd, J = 8.0, 1.5 Hz, 1H), 7.78 (dd, J = 10.6, 7.7 Hz, 2H), 7.60-7.41 (m, 3H), 6.96 (s, 1H), 6.86-6.77 (m, 2H), 6.45-6.36 (m, 2H), 6.29 (dd, J = 17.0, 10.0 Hz, 1H), 5.68 (dd, J = 9.9, 2.0 Hz, 1H), 4.27-4.11 (m, 2H), 3.85 (s, 3H), 3.04-2.92 (m, 1H), 2.92-2.84 (m, 2H), 2.72 (s, 3H), 2.45-2.37 (m, 1H), 2.36-2.30 (m, 2H), 2.28 (s, 6H), ; 568.4 [M + H]⁺ | 1.29 |
| 441 | 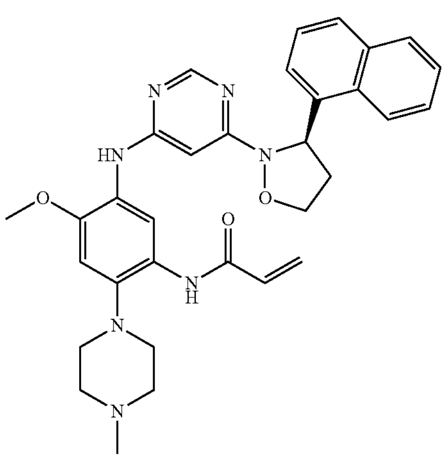 [SMILES: C=CC(=O)Nc1cc(Nc2cc(N3OCC[C@@H]3c3cccc4ccccc34)ncn2)c(OC)cc1N1CCN(C)CC1] | N-(4-methoxy-2-(4-methylpiperazine-1-yl)-5-((6-((R)-3-(naphthalene-1-yl)isoxazolidine-2-yl)pyrimidine-4-yl)amino)phenyl)acrylamide | ¹H NMR (400 MHz, Chloroform-d) δ 8.95 (s, 1H), 8.53 (s, 1H), 8.37 (d, J = 1.0 Hz, 1H), 8.15 (d, J = 8.3 Hz, 1H), 7.92-7.85 (m, 1H), 7.77 (t, J = 6.9 Hz, 2H), 7.60-7.41 (m, 3H), 6.95 (s, 1H), 6.79 (d, J = 6.6 Hz, 2H), 6.45-6.33 (m, 2H), 6.27 (dd, J = 17.0, 10.0 Hz, 1H), 5.75 (dd, J = 9.9, 1.6 Hz, 1H), 4.24-4.11 (m, 2H), 3.85 (s, 3H), 3.03-2.90 (m, 5H), 2.74-2.50 (m, 4H), 2.47-2.35 (m, 4H), ; 566.4 [M + H]⁺ | 1.23 |

TABLE 1-continued

| Example Compound | Structure | Name of Compound | ¹H NMR[[:]]; MS [M + H]⁺ | UPLC r.t. (min) |
|---|---|---|---|---|
| 442 | 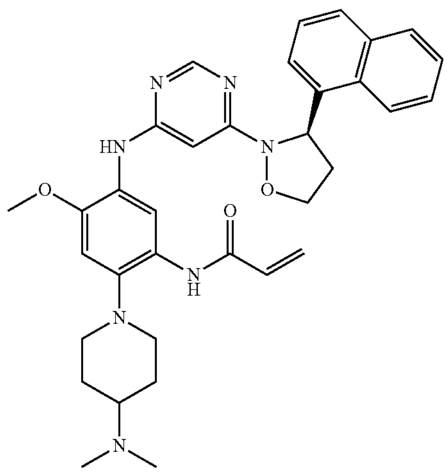 [SMILES: C=CC(=O)Nc1cc(Nc2cc(N3OCC[C@@H]3c3cccc4ccccc34)ncn2)c(OC)cc1N1CCC(N(C)C)CC1] | N-(2-(4-(dimethylamino)piperidine-1-yl)-4-methoxy-5-((6-((R)-3-(naphthalene-1-yl)isoxazolidine-2-yl)pyrimidine-4-yl)amino)phenyl)acrylamide | ¹H NMR (400 MHz, Chloroform-d) δ 8.91 (s, 1H), 8.48 (s, 1H), 8.37 (d, J = 0.9 Hz, 1H), 8.15 (d, J = 8.4 Hz, 1H), 7.88 (dd, J = 8.0, 1.5 Hz, 1H), 7.77 (t, J = 6.8 Hz, 2H), 7.60-7.41 (m, 3H), 6.93 (s, 1H), 6.77 (d, J = 11.0 Hz, 2H), 6.45-6.40 (m, 1H), 6.40-6.31 (m, 1H), 6.26 (dd, J = 16.9, 10.0 Hz, 1H), 5.74 (dd, J = 10.0, 1.6 Hz, 1H), 4.25-4.11 (m, 2H), 3.85 (s, 3H), 3.11-3.02 (m, 2H), 3.01-2.92 (m, 1H), 2.80-2.67 (m, 2H), 2.45-2.40 (m, 1H), 2.39 (s, 6H), 2.35-2.24 (m, 1H), 2.11-2.03 (m, 2H), 1.72-1.62 (m, 2H), ; 594.5 [M + H]⁺ | 1.24 |
| 443 | 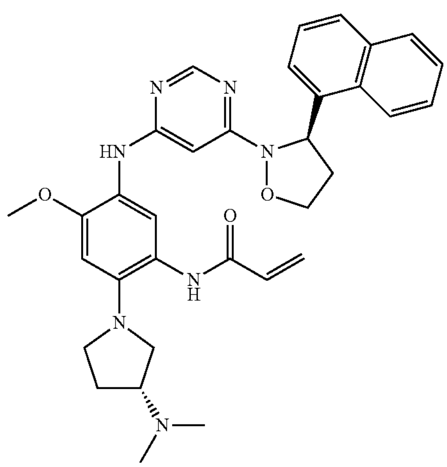 [SMILES: C=CC(=O)Nc1cc(Nc2cc(N3OCC[C@@H]3c3cccc4ccccc34)ncn2)c(OC)cc1N1CC[C@@H](N(C)C)C1] | N-(2-((R)-3-(dimethylamino)pyrolidine-1-yl)-4-methoxy-5-((6-((R)-3-(naphthalene-1-yl)isoxazolidine-2-yl)pyrimidine-4-yl)amino)phenyl)acrylamide | ¹H NMR (400 MHz, Chloroform-d) δ 8.71 (s, 1H), 8.35 (s, 1H), 8.18-8.12 (m, 2H), 7.88 (dd, J = 7.9, 1.5 Hz, 1H), 7.81-7.73 (m, 2H), 7.60-7.41 (m, 3H), 6.88 (s, 1H), 6.76 (d, J = 2.1 Hz, 2H), 6.45-6.34 (m, 2H), 6.29 (dd, J = 16.9, 9.8 Hz, 1H), 5.73 (dd, J = 9.9, 1.8 Hz, 1H), 4.24-4.13 (m, 2H), 3.84 (s, 3H), 3.24-3.15 (m, 1H), 3.13-3.10 (m, 2H), 3.00-2.93 (m, 1H), 2.93-2.86 (m, 1H), 2.47-2.35 (m, 1H), 2.30 (s, 6H), 2.19 (d, J = 7.5 Hz, 1H), 2.01-1.87 (m, 2H), ; 580.5 [M + H]⁺ | 1.21 |
| 444 | 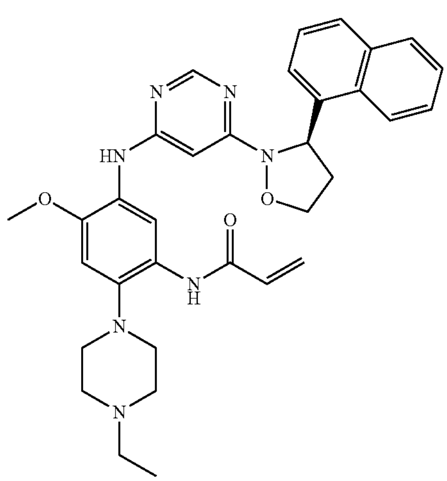 [SMILES: C=CC(=O)Nc1cc(Nc2cc(N3OCC[C@@H]3c3cccc4ccccc34)ncn2)c(OC)cc1N1CCN(CC)CC1] | N-(2-(4-ethylpiperazine-1-yl)-4-methoxy-5-((6-((R)-3-(naphthalene-1-yl)isoxazolidine-2-yl)pyrimidine-4-yl)amino)phenyl)acrylamide | ¹H NMR (400 MHz, Chloroform-d) δ 8.95 (s, 1H), 8.57 (s, 1H), 8.37 (d, J = 1.0 Hz, 1H), 8.15 (d, J = 8.3 Hz, 1H), 7.88 (dd, J = 8.0, 1.5 Hz, 1H), 7.81-7.73 (m, 2H), 7.60-7.41 (m, 3H), 6.95 (s, 1H), 6.81 (d, J = 13.3 Hz, 2H), 6.45-6.32 (m, 2H), 6.27 (dd, J = 16.9, 9.9 Hz, 1H), 5.74 (dd, J = 9.9, 1.6 Hz, 1H), 4.24-4.11 (m, 2H), 3.84 (s, 3H), 3.03-2.88 (m, 5H), 2.76-2.53 (m, 4H), 2.51 (t, J = 7.2 Hz, 2H), 2.47-2.35 (m, 1H), 1.16 (t, J = 7.2 Hz, 3H), ; 580.4 [M + H]⁺ | 1.25 |

TABLE 1-continued

| Example Compound | Structure | Name of Compound | ¹H NMR[:]; MS [M + H]⁺ | UPLC r.t. (min) |
|---|---|---|---|---|
| 445 | 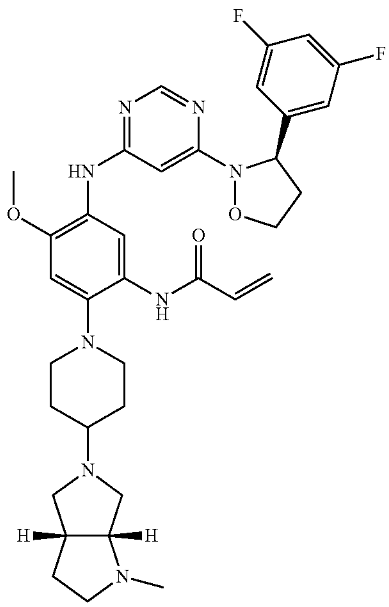 [SMILES: C=CC(=O)Nc1cc(Nc2cc(N3OCC[C@@H]3c3cc(F)cc(F)c3)ncn2)c(OC)cc1N1CCC(N2C[C@H]3CCN(C)[C@H]3C2)CC1] | N-(5-((6-((R)-3-(3,5-difluorophenyl)isoxazolidine-2-yl)pyrimidine-4-yl)amino)-4-methoxy-2-(4-((3aR,6aR)-1-methylhexahydropyrrolo[3,4-b]pyrrole-5(1H)-yl)piperidine-1-yl)phenyl)acrylamide | ¹H NMR (400 MHz, CDCl₃) δ 8.80 (s, 1H), 8.47 (s, 1H), 8.33 (s, 1H), 7.23 (s, 1H), 7.04-6.96 (m, 2H), 6.74 (s, 1H), 6.72-6.64 (m, 2H), 6.39-6.23 (m, 2H), 5.75 (dd, J = 9.7, 1.7 Hz, 1H), 5.66 (dd, J = 8.6, 4.5 Hz, 1H), 4.14 (td, J = 7.9, 4.2 Hz, 1H), 4.06 (q, J = 16.0, 8.0 Hz, 1H), 3.84 (s, 3H), 3.18-3.10 (m, 2H), 3.07-2.97 (m, 3H), 2.85-2.67 (m, 5H), 2.63-2.56 (m, 1H), 2.55-2.48 (m, 2H), 2.46 (s, 3H), 2.37-2.28 (m, 1H), 2.26-2.18 (m, 1H), 2.13-1.95 (m, 3H), 1.87-1.65 (m, 3H); 661.50 [M + H]⁺ | 1.14 |
| 446 | 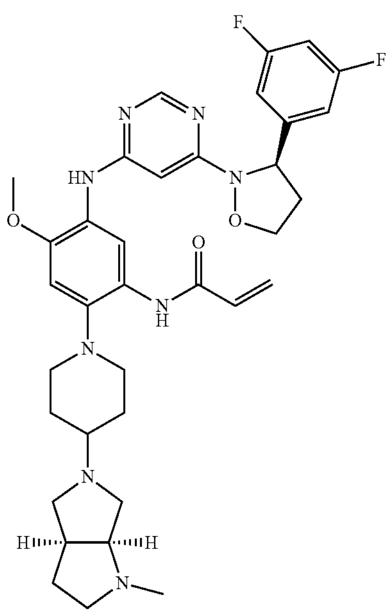 [SMILES: C=CC(=O)Nc1cc(Nc2cc(N3OCC[C@@H]3c3cc(F)cc(F)c3)ncn2)c(OC)cc1N1CCC(N2C[C@@H]3CCN(C)[C@@H]3C2)CC1] | N-(5-((6-((R)-3-(3,5-difluorophenyl)isoxazolidine-2-yl)pyrimidine-4-yl)amino)-4-methoxy-2-(4-((3aS,6aS)-1-methylhexahydropyrrolo[3,4-b]pyrrole-5(1H)-yl)piperidine-1-yl)phenyl)acrylamide | ¹H NMR (400 MHz, CDCl₃) δ 8.81 (s, 1H), 8.48 (s, 1H), 8.33 (s, 1H), 7.20 (s, 1H), 7.03-6.97 (m, 2H), 6.74 (s, 1H), 6.71-6.65 (m, 2H), 6.38-6.23 (m, 2H), 5.75 (dd, J = 9.7, 1.6 Hz, 1H), 5.66 (dd, J = 8.6, 4.5 Hz, 1H), 4.14 (td, J = 8.1, 4.3 Hz, 1H), 4.06 (q, J = 8.1 Hz, 1H), 3.84 (s, 3H), 3.16-3.07 (m, 2H), 3.05-2.99 (m, 3H), 2.83-2.67 (m, 5H), 2.60-2.53 (m, 1H), 2.51-2.40 (m, 5H), 2.38 2.29 (m, 1H), 2.25-2.16 (m, 1H), 2.11-2.00 (m, 3H), 1.86-1.64 (m, 3H); 661.50 [M + H]⁺ | 1.14 |

TABLE 1-continued

| Example Compound | Structure | Name of Compound | ¹H NMR[[:]]; MS [M + H]⁺ | UPLC r.t. (min) |
|---|---|---|---|---|
| 447 | 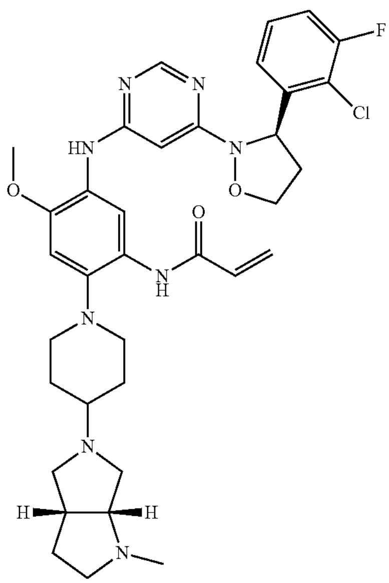 [SMILES: C=CC(=O)Nc1cc(Nc2cc(N3OCC[C@@H]3c3cccc(F)c3Cl)ncn2)c(OC)cc1N1CCC(N2C[C@H]3CCN(C)[C@H]3C2)CC1] | N-(5-((6-((R)-3-(2-chloro-3-fluorophenyl)isoxazolidine-2-yl)pyrimidine-4-yl)amino)-4-methoxy-2-(4-((3aR,6aR)-1-methylhexahydro-pyrrolo[3,4-b]pyrrole-5(1H)-yl)piperidine-1-yl)phenyl)acrylamide | ¹H NMR (400 MHz, CDCl₃) δ 8.80 (s, 1H), 8.47 (s, 1H), 8.32 (s, 1H), 7.46 (d, J = 7.8 Hz, 1H), 7.24-7.18 (m, 2H), 7.05 (t, J = 8.0 Hz, 1H), 6.75 (s, 1H), 6.73 (s, 1H), 6.38-6.23 (m, 2H), 5.95 (dd, J = 8.8, 4.4 Hz, 1H), 5.74 (dd, J = 9.7, 1.6 Hz, 1H), 4.14-4.03 (m, 2H), 3.85 (s, 3H), 3.15-3.07 (m, 2H), 3.05-2.98 (m, 3H), 2.97-2.89 (m, 1H), 2.85-2.64 (m, 5H), 2.60-2.53 (m, 1H), 2.51-2.45 (m, 2H), 2.44 (s, 3H), 2.27-2.18 (m, 2H), 2.11-2.00 (m, 2H), 1.86-1.66 (m, 3H); 677.56 [M + H]⁺ | 1.19 |
| 448 | 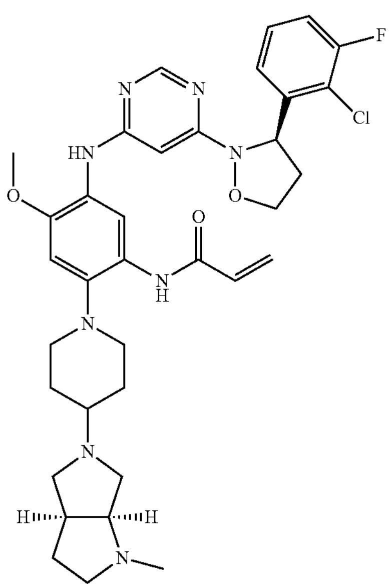 [SMILES: C=CC(=O)Nc1cc(Nc2cc(N3OCC[C@@H]3c3cccc(F)c3Cl)ncn2)c(OC)cc1N1CCC(N2C[C@@H]3CCN(C)[C@@H]3C2)CC1] | N-(5-((6-((R)-3-(2-chloro-3-fluorophenyl)isoxazolidine-2-yl)pyrimidine-4-yl)amino)-4-methoxy-2-(4-((3aS,6aS)-1-methylhexahydro-pyrrolo[3,4-b]pyrrole-5(1H)-yl)piperidine-1-yl)phenyl)acrylamide | ¹H NMR (400 MHz, CDCl₃) δ 8.81 (s, 1H), 8.48 (s, 1H), 8.33 (s, 1H), 7.46 (d, 7.8 Hz, 1H), 7.24-7.17 (m, 2H), 7.12 (s, 1H), 7.05 (t, J = 7.9 Hz, 1H), 6.76-6.71 (m, 2H), 6.38-6.22 (m, 2H), 5.95 (dd, J = 8.8, 4.4 Hz, 1H), 5.77-5.71 (m, 1H), 4.14-4.03 (m, 2H), 3.85 (s, 3H), 3.13-3.05 (m, 1H), 3.05-2.90 (m, 5H), 2.81-2.64 (m, 5H), 2.52-2.40 (m, 5H), 2.28-2.12 (m, 2H), 2.04-1.99 (m, 2H), 1.84-1.72 (m, 2H), 1.69-1.62 (m, 1H); 677.47 [M + H]⁺ | 1.18 |

TABLE 1-continued

| Example Compound | Structure | Name of Compound | $^1$H NMR[[:]]; MS [M + H]$^+$ | UPLC r.t. (min) |
|---|---|---|---|---|
| 449 | 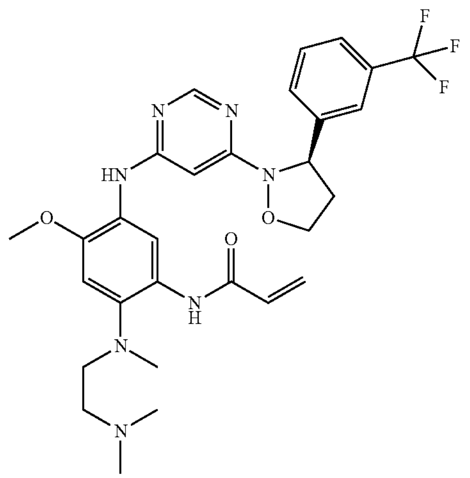 [SMILES: C=CC(=O)Nc1cc(Nc2cc(N3OCC[C@@H]3c3cccc(C(F)(F)F)c3)ncn2)c(OC)cc1N(C)CCN(C)C] | N-(2-((2-(dimethylamino)ethyl)(methyl)amino)-4-methoxy-5-((6-((R)-3-(3-(trifluoromethyl)phenyl)isoxazolidine-2-yl)pyrimidine-4-yl)amino)phenyl)acrylamide | $^1$H NMR (400 MHz, CDCl$_3$) δ 9.53 (s, 1H), 8.77 (s, 1H), 8.33 (s, 1H), 7.73 (s, 1H), 7.65 (d, J = 7.5 Hz, 1H), 7.48 (dt, J = 15.3, 7.7 Hz, 2H), 6.72 (d, J = 25.1 Hz, 2H), 6.40 (dd, J = 16.8, 1.8 Hz, 1H), 5.76 (dd, J = 8.6, 4.5 Hz, 1H), 5.70 (dd, J = 10.2, 1.7 Hz, 1H), 4.20 (td, J = 8.0, 4.3 Hz, 1H), 4.11 (q, J = 8.0 Hz, 1H), 3.85 (s, 3H), 3.32-3.14 (m, 4H), 3.09 (q, J = 7.4 Hz, 2H), 2.81 (s, 6H), 2.72 (s, 3H), 2.41-2.33 (m, 1H), 1.54 (t, J = 7.4 Hz, 4H); 586.4 [M + H]$^+$ | 1.31 |
| 450 | 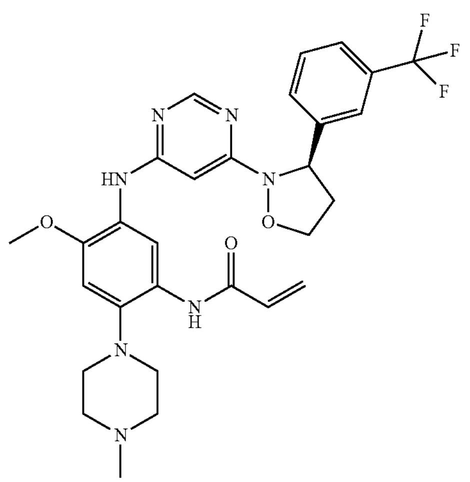 [SMILES: C=CC(=O)Nc1cc(Nc2cc(N3OCC[C@@H]3c3cccc(C(F)(F)F)c3)ncn2)c(OC)cc1N1CCN(C)CC1] | N-(4-methoxy-2-(4-methylpiperazine-1-yl)-5-((6-((R)-3-(3-(trifluoromethyl)phenyl)isoxazolidine-2-yl)pyrimidine-4-yl)amino)phenyl)acrylamide | $^1$H NMR (400 MHz, CDCl$_3$) δ 8.81 (s, 1H), 8.52 (s, 1H), 8.34 (s, 1H), 7.71 (s, 1H), 7.65 (d, J = 7.7 Hz, 1H), 7.48 (dt, J = 15.5, 7.8 Hz, 2H), 7.31 (s, 1H), 6.78 (s, 1H), 6.67 (s, 1H), 6.45-6.32 (m, 2H), 5.73 (dd, J = 8.9, 2.5 Hz, 1H), 4.16 (td, J = 7.9, 4.2 Hz, 1H), 4.05 (dd, J = 16.1, 8.0 Hz, 1H), 3.84 (s, 3H), 3.10 (d, J = 5.9 Hz, 4H), 3.09-3.02 (m, 4H), 2.86-2.73 (m, 1H), 2.64 (s, 3H), 2.41-2.30 (m, 1H), 1.51 (t, J = 7.4 Hz, 1H); 584.4 [M + H]$^+$ | 1.31 |
| 451 | 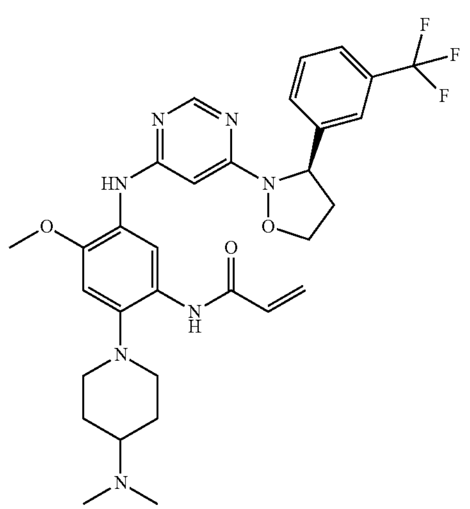 [SMILES: C=CC(=O)Nc1cc(Nc2cc(N3OCC[C@@H]3c3cccc(C(F)(F)F)c3)ncn2)c(OC)cc1N1CCC(N(C)C)CC1] | N-(2-(4-(dimethylamino)piperidine-1-yl)-4-methoxy-5-((6-((R)-3-(3-(trifluoromethyl)phenyl)isoxazolidine-2-yl)pyrimidine-4-yl)amino)phenyl)acrylamide | $^1$H NMR (400 MHz, Chloroform-d) δ 8.85 (s, 1H), 8.46 (s, 1H), 8.35 (d, J = 1.0 Hz, 1H), 7.73 (s, 1H), 7.66 (d, J = 7.6 Hz, 1H), 7.48 (dt, J = 15.3, 7.7 Hz, 2H), 6.75 (d, J = 1.1 Hz, 1H), 6.72 (d, J = 1.9 Hz, 1H), 6.35 (d, J = 1.8 Hz, 1H), 6.29 (dd, J = 17.0, 9.6 Hz, 1H), 5.75 (ddd, J = 9.7, 6.6, 3.3 Hz, 2H), 4.17 (td, J = 8.1, 4.3 Hz, 1H), 4.08 (q, J = 8.0 Hz, 1H), 3.84 (s, 3H), 3.10-3.05 (m, 2H), 2.83-2.68 (m, 4H), 2.44 (d, J = 1.3 Hz, 6H), 2.38 (q, J = 3.8 Hz, 1H), 2.08 (d, J = 12.7 Hz, 2H), 1.74 (dt, J = 12.5, 6.2 Hz, 2H); 612.5 [M + H]$^+$ | 1.29 |

TABLE 1-continued

| Example Compound | Structure | Name of Compound | ¹H NMR[[:]]; MS [M + H]⁺ | UPLC r.t. (min) |
|---|---|---|---|---|
| 452 | 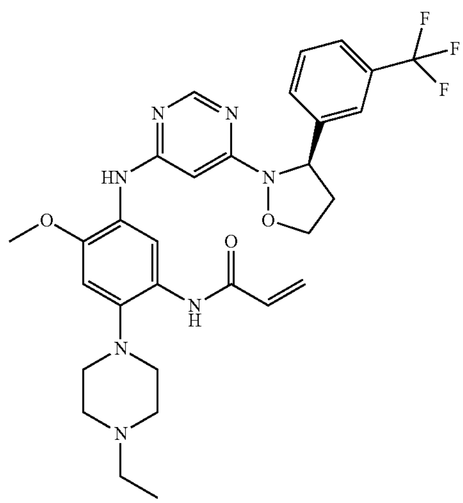 [SMILES: C=CC(=O)Nc1cc(Nc2cc(N3OCC[C@@H]3c3cccc(C(F)(F)F)c3)ncn2)c(OC)cc1N1CCN(CC)CC1] | N-(2-(4-ethylpiperazine-1-yl)-4-methoxy-5-((6-((R)-3-(3-(trifluoromethyl)phenyl)isoxazolidine-2-yl)pyrimidine-4-yl)amino)phenyl)acrylamide | ¹H NMR (400 MHz, CDCl₃) δ 8.90 (s, 1H), 8.50 (s, 1H), 8.37 (s, 1H), 7.73 (s, 1H), 7.66 (d, J = 7.5 Hz, 1H), 7.48 (dt, J = 15.3, 7.7 Hz, 2H), 7.09 (s, 1H), 6.82 (s, 1H), 6.72 (s, 1H), 6.40-6.26 (m, 2H), 5.78-5.72 (m, 2H), 4.17 (td, J = 8.0, 4.2 Hz, 1H), 4.07 (q, J = 8.0 Hz, 1H), 3.84 (s, 3H), 3.04 (d, J = 13.0 Hz, 4H), 2.81 (dtd, J = 12.1, 8.1, 4.3 Hz, 4H), 2.66 (dd, J = 13.9, 6.8 Hz, 2H), 2.41-2.32 (m, 1H), 1.23 (t, J = 7.2 Hz, 3H); 598.4 [M + H]⁺ | 1.30 |
| 453 | 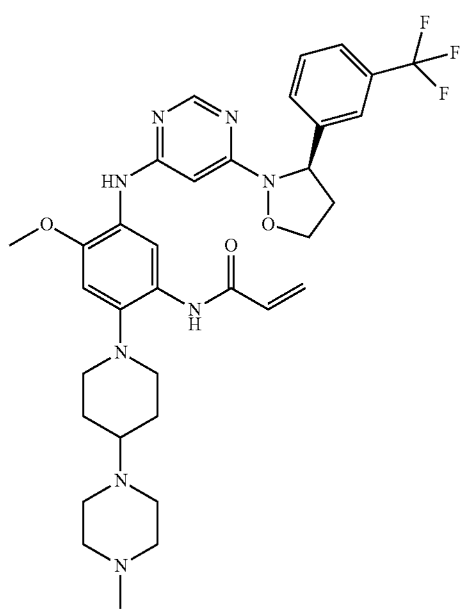 [SMILES: C=CC(=O)Nc1cc(Nc2cc(N3OCC[C@@H]3c3cccc(C(F)(F)F)c3)ncn2)c(OC)cc1N1CCC(N2CCN(C)CC2)CC1] | N-(4-methoxy-2-(4-(4-methylpiperazine-1-yl)piperidine-1-yl)-5-((6-((R)-3-(3-(trifluoromethyl)phenyl)isoxazolidine-2-yl)pyrimidine-4-yl)amino)phenyl)acrylamide | 667.5 [M + H]⁺ | 1.21 |

TABLE 1-continued

| Example Compound | Structure | Name of Compound | ¹H NMR[:]; MS [M + H]⁺ | UPLC r.t. (min) |
|---|---|---|---|---|
| 454 | 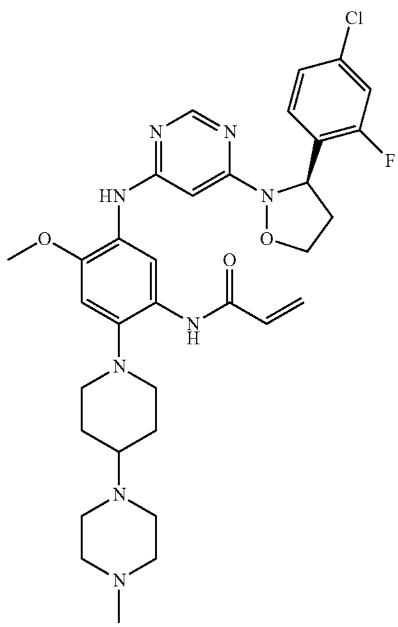 [SMILES: C=CC(=O)Nc1cc(Nc2cc(N3OCC[C@@H]3c3ccc(Cl)cc3F)ncn2)c(OC)cc1N1CCC(N2CCN(C)CC2)CC1] | N-(5-((6-((R)-3-(4-chloro-2-fluorophenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, Chloroform-d) δ 8.84 (s, 1H), 8.43 (s, 1H), 8.34 (d, J = 1.0 Hz, 1H), 7.53 (t, J = 8.2 Hz, 1H), 7.09 (td, J = 7.1, 6.6, 4.0 Hz, 3H), 6.75 (s, 1H), 6.73 (s, 1H), 6.40-6.31 (m, 1H), 6.25 (dd, J = 16.9, 10.0 Hz, 1H), 5.86 (dd, J = 8.7, 4.4 Hz, 1H), 5.74 (dd, J = 9.9, 1.6 Hz, 1H), 4.13-4.04 (m, 2H), 3.85 (s, 3H), 3.06 (d, J = 11.5 Hz, 2H), 2.82 (dd, J = 8.1, 4.4 Hz, 1H), 2.80-2.53 (m, 10H), 2.40 (d, J = 11.1 Hz, 1H), 2.35 (s, 3H), 2.30-2.25 (m, 1H), 2.12-2.06 (m, 2H), 1.68 (d, J = 11.5 Hz, 2H); 651.5 [M + H]⁺ | 1.18 |
| 455 | 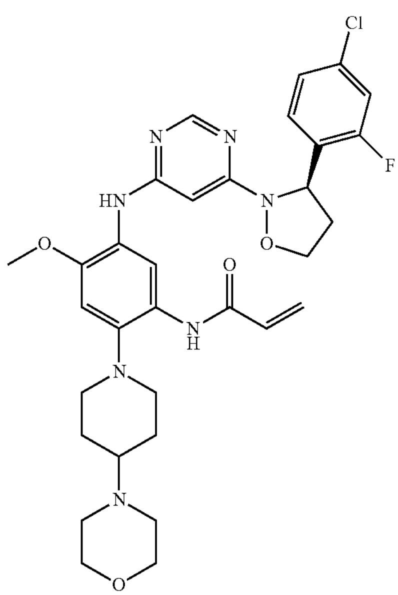 [SMILES: C=CC(=O)Nc1cc(Nc2cc(N3OCC[C@@H]3c3ccc(Cl)cc3F)ncn2)c(OC)cc1N1CCC(N2CCOCC2)CC1] | N-(5-((6-((R)-3-(4-chloro-2-fluorophenyl)isoxazolidine-2-yl)pyrimidine-4-yl)amino)-4-methoxy-2-(4-morpholinopiperidine-1-yl)phenyl)acrylamide | ¹H NMR (400 MHz, Chloroform-d) δ 8.81 (s, 1H), 8.43 (s, 1H), 8.32 (d, J = 1.0 Hz, 1H), 7.52 (t, J = 8.5 Hz, 1H), 7.33 (s, 1H), 7.14-7.05 (m, 2H), 6.75 (s, 1H), 6.71 (s, 1H), 6.36 (dd, J = 17.0, 1.6 Hz, 1H), 6.26 (dd, J = 16.9, 9.9 Hz, 1H), 5.86 (dd, J = 8.8, 4.4 Hz, 1H), 5.74 (dd, J = 9.9, 1.6 Hz, 1H), 4.16-4.07 (m, 1H), 4.09-4.03 (m, 1H), 3.85 (s, 3H), 3.79 (t, J = 4.7 Hz, 4H), 3.08 (d, J = 11.4 Hz, 2H), 2.88-2.77 (m, 1H), 2.74 (q, J = 12.3 Hz, 2H), 2.65 (t, J = 4.7 Hz, 4H), 2.41-2.31 (m, 1H), 2.32-2.20 (m, 1H), 2.13-2.08 (m, 2H), 1.69 (qd, J = 13.7, 13.0, 3.6 Hz, 2H); 638.4 [M + H]⁺ | 1.27 |

TABLE 1-continued

| Example Compound | Structure | Name of Compound | ¹H NMR[[:]]; MS [M + H]⁺ | UPLC r.t. (min) |
|---|---|---|---|---|
| 456 | 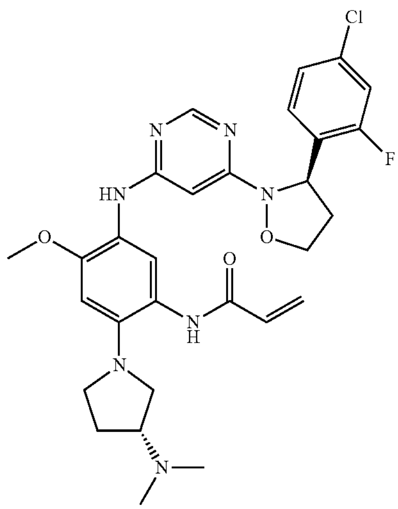 [SMILES: C=CC(=O)Nc1cc(Nc2cc(N3OCC[C@@H]3c3ccc(Cl)cc3F)ncn2)c(OC)cc1N1CC[C@@H](N(C)C)C1] | N-(5-((6-((R)-3-(4-chloro-2-fluorophenyl)isoxazolidine-2-yl)pyrimidine-4-yl)amino)-2-((R)-3-(dimethylamino)pyrolidine-1-yl)-4-methoxyphenyl)acrylamide | ¹H NMR (400 MHz, CDCl₃) δ 8.73 (s, 1H), 8.24 (d, J = 16.6 Hz, 2H), 7.44 (t, J = 8.3 Hz, 1H), 7.14-7.04 (m, 2H), 6.60 (s, 1H), 6.50 (s, 1H), 6.40 (d, J = 16.8 Hz, 1H), 5.81 (dd, J = 8.4, 4.5 Hz, 1H), 5.71 (d, J = 10.8 Hz, 1H), 4.15 (dd, J = 12.3, 7.8 Hz, 1H), 4.04 (q, J = 7.8 Hz, 1H), 3.82 (s, 3H), 3.74 (d, J = 11.0 Hz, 1H), 3.60 (s, 1H), 3.37 (s, 1H), 3.05-2.92 (m, 2H), 2.85 (s, 6H), 2.37 (d, J = 4.4 Hz, 2H), 2.32-2.23 (m, 1H); 582.4 [M + H]⁺ | 1.26 |
| 457 | 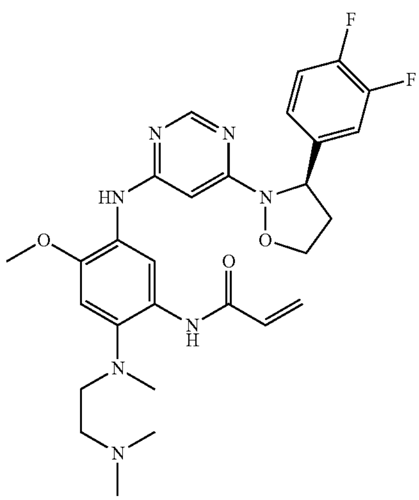 [SMILES: C=CC(=O)Nc1cc(Nc2cc(N3OCC[C@@H]3c3ccc(F)c(F)c3)ncn2)c(OC)cc1N(C)CCN(C)C] | N-(5-((6-((R)-3-(3,4-difluorophenyl)isoxazolidine-2-yl)pyrimidine-4-yl)amino)-2-((2-(dimethylamino)ethyl)(methyl)amino)-4-methoxyphenyl)acrylamide | ¹H NMR (400 MHz, DMSO-d₆) δ 10.19 (s, 1H), 9.95 (s, 1H), 8.33 (s, 1H), 8.02 (s, 1H), 7.45 (tdd, J = 10.4, 7.3, 4.1 Hz, 2H), 7.33-7.20 (m, 2H), 6.97 (s, 1H), 6.26-6.11 (m, 2H), 5.70 (dd, J = 10.1, 2.2 Hz, 1H), 5.54 (dd, J = 8.4, 5.3 Hz, 1H), 4.32 (dt, J = 7.6, 3.7 Hz, 1H), 4.08 (t, J = 7.7 Hz, 1H), 3.82 (s, 3H), 3.32 (s, 4H), 2.97-2.88 (m, 1H), 2.72 (d, J = 4.8 Hz, 6H), 2.62 (s, 3H), 2.34 (ddd, J = 9.9, 7.7, 5.2 Hz, 1H), ; 554.3 [M + H]⁺ | 1.26 |
| 458 | 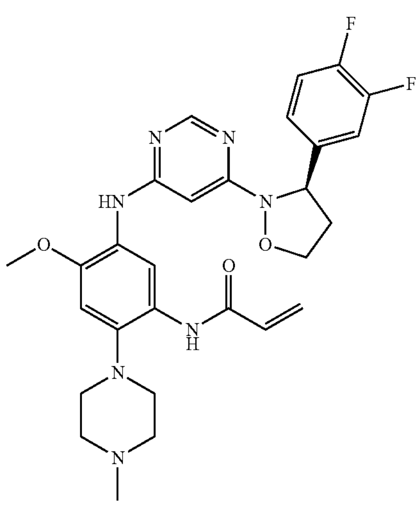 [SMILES: C=CC(=O)Nc1cc(Nc2cc(N3OCC[C@@H]3c3ccc(F)c(F)c3)ncn2)c(OC)cc1N1CCN(C)CC1] | N-(5-((6-((R)-3-(3,4-difluorophenyl)isoxazolidine-2-yl)pyrimidine-4-yl)amino)-4-methoxy-2-(4-methylpiperazine-1-yl)phenyl)acrylamide | ¹H NMR (400 MHz, DMSO-d₆) δ 9.75 (s, 1H), 9.17 (s, 1H), 8.29 (s, 1H), 8.07 (s, 1H), 7.48-7.39 (m, 2H), 7.27-7.20 (m, 1H), 6.88 (s, 1H), 6.82-6.74 (m, 1H), 6.28-6.12 (m, 2H), 5.76 (dd, J = 10.2, 2.0 Hz, 1H), 5.53 (dd, J = 8.5, 5.2 Hz, 1H), 4.26 (q, J = 4.5, 4.0 Hz, 1H), 4.01 (t, J = 7.8 Hz, 1H), 3.83 (s, 3H), 3.48 (d, J = 11.6 Hz, 2H), 3.37 (d, J = 10.6 Hz, 2H), 3.18 (d, J = 8.8 Hz, 4H), 2.93-2.87 (m, 1H), 2.82 (d, J = 4.5 Hz, 3H), 2.31 (dt, J = 12.8, 3.8 Hz, 1H), ; 552.3 [M + H]⁺ | 1.20 |

TABLE 1-continued

| Example Compound | Structure | Name of Compound | ¹H NMR[[:]]; MS [M + H]⁺ | UPLC r.t. (min) |
|---|---|---|---|---|
| 459 | 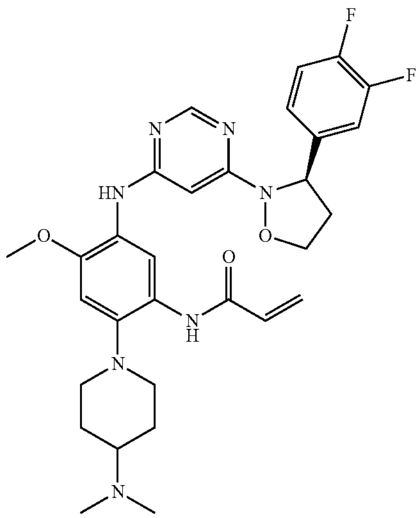 [SMILES: C=CC(=O)Nc1cc(Nc2cc(N3OCC[C@@H]3c3ccc(F)c(F)c3)ncn2)c(OC)cc1N1CCC(N(C)C)CC1] | N-(5-((6-((R)-3-(3,4-difluorophenyl)isoxazolidine-2-yl)pyrimidine-4-yl)amino)-2-(4-(dimethylamino)piperidine-1-yl)-4-methoxyphenyl)acrylamide | ¹H NMR (400 MHz, DMSO-d₆) δ 10.03 (s, 1H), 9.20 (s, 1H), 8.32 (s, 1H), 7.93 (s, 1H), 7.47-7.39 (m, 2H), 7.22 (d, J = 8.4 Hz, 1H), 6.90 (s, 1H), 6.73 (dd, J = 17.0, 10.2 Hz, 1H), 6.25 (dd, J = 17.0, 2.0 Hz, 1H), 6.12 (s, 1H), 5.79-5.72 (m, 1H), 5.53 (dd, J = 8.4, 5.2 Hz, 1H), 4.29 (td, J = 7.5, 4.3 Hz, 1H), 4.04 (q, J = 7.7 Hz, 1H), 3.81 (s, 3H), 3.33-3.16 (m, 3H), 2.97-2.88 (m, 1H), 2.80 (d, J = 11.8 Hz, 2H), 2.75 (d, J = 5.0 Hz, 6H), 2.33 (ddd, J = 13.0, 8.5, 5.4 Hz, 1H), 2.12 (d, J = 11.5 Hz, 2H), 2.01 (d, J = 12.1 Hz, 2H), ; 580.3 [M + H]⁺ | 1.22 |
| 460 | 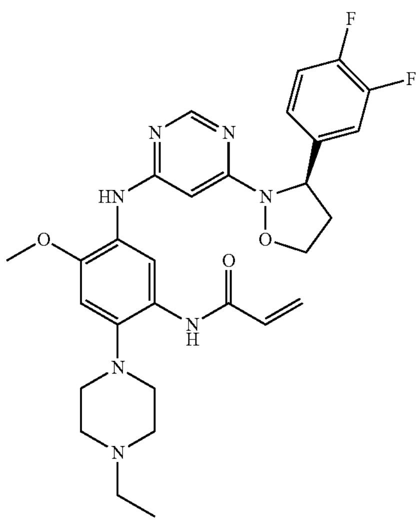 [SMILES: C=CC(=O)Nc1cc(Nc2cc(N3OCC[C@@H]3c3ccc(F)c(F)c3)ncn2)c(OC)cc1N1CCN(CC)CC1] | N-(5-((6-((R)-3-(3,4-difluorophenyl)isoxazolidine-2-yl)pyrimidine-4-yl)amino)-2-(4-ethylpiperazine-1-yl)-4-methoxyphenyl)acrylamide | ¹H NMR (400 MHz, DMSO-d₆) δ 9.80 (s, 1H), 9.22 (s, 1H), 8.29 (s, 1H), 8.06 (s, 1H), 7.44 (tdd, J = 10.8, 6.8, 4.0 Hz, 2H), 7.23 (dq, J = 7.7, 2.6 Hz, 1H), 6.83 (d, J = 27.4 Hz, 2H), 6.27-6.14 (m, 2H), 5.78-5.70 (m, 1H), 5.53 (dd, J = 8.5, 5.3 Hz, 1H), 4.27 (d, J = 4.4 Hz, 1H), 4.02 (t, J = 7.8 Hz, 1H), 3.83 (s, 3H), 3.52 (d, J = 11.3 Hz, 2H), 3.33 (s, 2H), 3.19 (ddd, J = 19.8, 7.7, 4.1 Hz, 6H), 2.94-2.82 (m, 1H), 2.31 (dd, J = 12.8, 5.1 Hz, 1H), 1.32 (t, J = 7.2 Hz, 3H), ; 566.3 [M + H]⁺ | 1.21 |

TABLE 1-continued

| Example Compound | Structure | Name of Compound | ¹H NMR[[:]]; MS [M + H]⁺ | UPLC r.t. (min) |
|---|---|---|---|---|
| 461 | 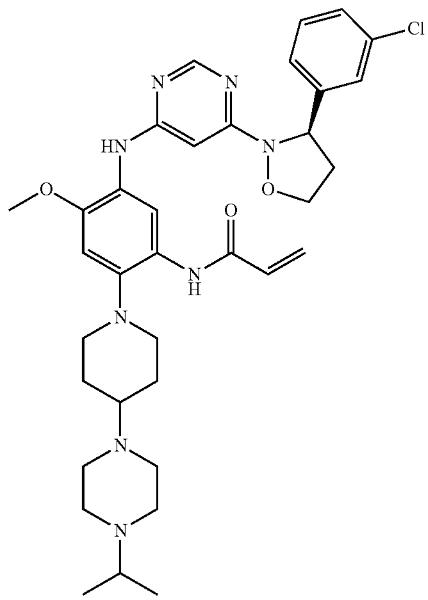 [SMILES: C=CC(=O)Nc1cc(Nc2cc(N3OCC[C@@H]3c3cccc(Cl)c3)ncn2)c(OC)cc1N1CCC(N2CCN(C(C)C)CC2)CC1] | N-(5-((6-((R)-3-(3-chlorophenyl)isoxazolidine-2-yl)pyrimidine-4-yl)amino)-2-(4-(4-isopropylpiperazine-1-yl)piperidine-1-yl)-4-methoxyphenyl)acrylamide | ¹H NMR (400 MHz, DMSO-d₆) δ 9.05 (s, 1H), 8.21 (s, 1H), 8.09 (s, 1H), 7.43 (d, J = 5.9 Hz, 1H), 7.41-7.32 (m, 3H), 6.84 (s, 1H), 6.62 (dd, J = 17.1, 10.3 Hz, 1H), 6.31-6.25 (m, 1H), 6.21 (d, J = 2.0 Hz, 1H), 5.74 (d, J = 10.4 Hz, 1H), 5.53 (dd, J = 8.6, 5.2 Hz, 1H), 4.20 (td, J = 7.8, 3.8 Hz, 2H), 3.95-3.86 (m, 2H), 3.81 (s, 3H), 3.16 (d, J = 11.2 Hz, 6H), 2.89-2.64 (m, 5H), 2.39-2.16 (m, 2H), 2.10-1.96 (m, 2H), 1.87 (t, J = 15.5 Hz, 3H), 1.26 (d, J = 6.5 Hz, 7H), ; 661.5 [M + H]⁺ | 1.10 |
| 462 | 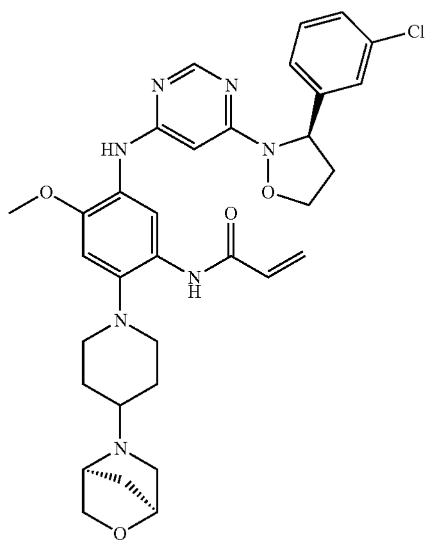 [SMILES: C=CC(=O)Nc1cc(Nc2cc(N3OCC[C@@H]3c3cccc(Cl)c3)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((R)-3-(3-chlorophenyl)isoxazolidine-2-yl)pyrimidine-4-yl)amino)-4-methoxyphenyl)acrylamide | ¹H NMR (400 MHz, DMSO-d₆) δ 9.10 (d, J = 17.9 Hz, 1H), 8.24 (d, J = 6.0 Hz, 1H), 8.02 (s, 1H), 7.43 (d, J = 2.7 Hz, 1H), 7.41-7.31 (m, 3H), 6.85 (s, 1H), 6.62-6.50 (m, 1H), 6.23 (dd, J = 16.3, 3.1 Hz, 2H), 5.79-5.69 (m, 1H), 5.53 (dd, J = 8.6, 5.3 Hz, 1H), 4.72 (s, 1H), 4.66 (d, J = 7.7 Hz, 2H), 4.22 (dd, J = 9.0, 5.0 Hz, 2H), 3.96 (dt, J = 23.7, 8.8 Hz, 2H), 3.81 (s, 3H), 3.75 (t, J = 9.8 Hz, 1H), 3.55-3.36 (m, 2H), 3.28-3.10 (m, 3H), 2.93-2.65 (m, 3H), 2.38-2.21 (m, 1H), 2.21-1.99 (m, 3H), 1.88 (d, J = 21.4 Hz, 2H), ; 632.5 [M + H]⁺ | 1.14 |

TABLE 1-continued

| Example Compound | Structure | Name of Compound | $^1$H NMR[[:]]; MS [M + H]$^+$ | UPLC r.t. (min) |
|---|---|---|---|---|
| 463 | 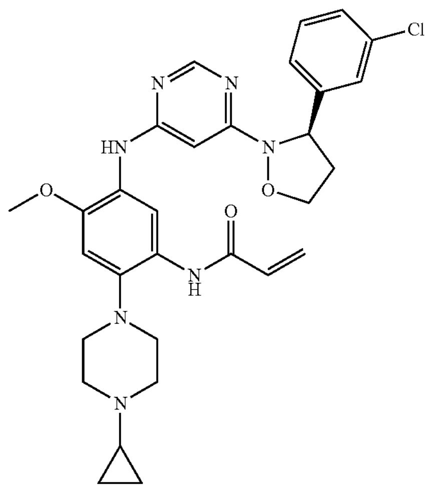 [SMILES: C=CC(=O)Nc1cc(Nc2cc(N3OCC[C@@H]3c3cccc(Cl)c3)ncn2)c(OC)cc1N1CCN(C2CC2)CC1] | N-(5-((6-((R)-3-(3-chlorophenyl)isoxazolidine-2-yl)pyrimidine-4-yl)amino)-2-(4-cyclopropylpiperazine-1-yl)-4-methoxyphenyl)acrylamide | $^1$H NMR (400 MHz, DMSO-d$_6$) δ 9.13 (s, 2H), 8.22 (s, 1H), 8.13 (s, 1H), 7.43 (q, J = 3.9, 3.0 Hz, 1H), 7.37 (dt, J = 12.7, 7.3 Hz, 3H), 6.90 (s, 1H), 6.67 (dd, J = 16.9, 10.2 Hz, 1H), 6.25 (d, J = 1.9 Hz, 1H), 5.74 (dd, J = 10.0, 2.0 Hz, 1H), 5.53 (dd, J = 8.6, 5.3 Hz, 1H), 4.21 (td, J = 7.7, 3.9 Hz, 4H), 3.92 (q, J = 7.9 Hz, 3H), 3.80 (s, 3H), 3.65 (q, J = 5.9, 5.3 Hz, 4H), 2.84 (dt, J = 16.2, 5.0 Hz, 4H), 2.34-2.20 (m, 1H), 2.05 (s, 3H), ; 576.4 [M + H]$^+$ | 1.25 |
| 464 | 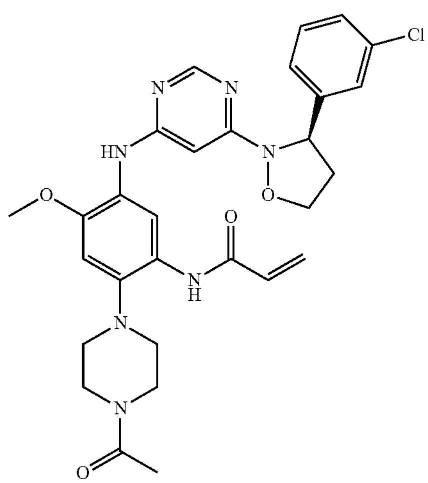 [SMILES: C=CC(=O)Nc1cc(Nc2cc(N3OCC[C@@H]3c3cccc(Cl)c3)ncn2)c(OC)cc1N1CCN(C(C)=O)CC1] | N-(2-(4-acetylpiperazine-1-yl)-5-((6-((R)-3-(3-chlorophenyl)isoxazolidine-2-yl)pyrimidine-4-yl)amino)-4-methoxyphenyl)acrylamide | $^1$H NMR (400 MHz, DMSO-d$_6$) δ 8.83 (d, J = 26.2 Hz, 2H), 8.26-8.15 (m, 1H), 7.43 (d, J = 8.1 Hz, 1H), 7.35 (dt, J = 19.1, 6.1 Hz, 4H), 6.96-6.74 (m, 1H), 6.39 (d, J = 33.6 Hz, 1H), 5.54 (dd, J = 8.9, 5.4 Hz, 1H), 4.17 (s, 1H), 3.83 (qd, J = 11.6, 11.0, 6.0 Hz, 5H), 3.30 (s, 3H), 3.17 (s, 2H), 3.13-3.00 (m, 3H), 2.88-2.74 (m, 2H), 2.33-2.19 (m, 2H), 1.91 (s, 3H), ; 578.4 [M + H]$^+$ | 1.41 |
| 465 | 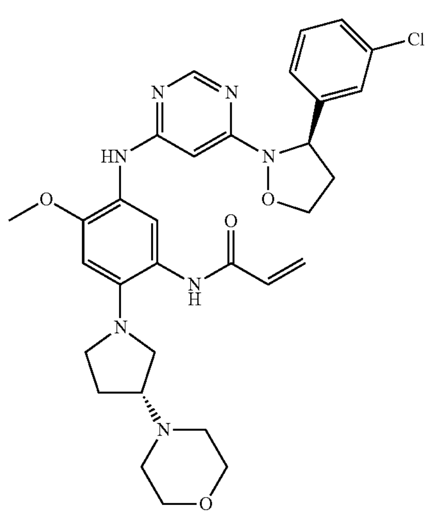 [SMILES: C=CC(=O)Nc1cc(Nc2cc(N3OCC[C@@H]3c3cccc(Cl)c3)ncn2)c(OC)cc1N1CC[C@@H](N2CCOCC2)C1] | N-(5-((6-((R)-3-(3-chlorophenyl)isoxazolidine-2-yl)pyrimidine-4-yl)amino)-4-methoxy-2-((R)-3-morpholinopyrolidine-1-yl)phenyl)acrylamide | $^1$H NMR (400 MHz, Chloroform-d) δ 8.67 (s, 1H), 8.35 (s, 1H), 8.14 (s, 1H), 7.47 (t, J = 1.9 Hz, 1H), 7.34 (dt, J = 7.5, 1.6 Hz, 1H), 7.29-7.18 (m, 2H), 6.93 (s, 1H), 6.75 (s, 1H), 6.67 (s, 1H), 6.42-6.23 (m, 2H), 5.73 (dd, J = 9.9, 1.8 Hz, 1H), 5.67 (dd, J = 8.7, 4.5 Hz, 1H), 4.21-3.99 (m, 2H), 3.83 (s, 3H), 3.76 (t, J = 4.7 Hz, 4H), 3.26-3.05 (m, 4H), 2.98 (p, J = 7.4 Hz, 1H), 2.76 (dtd, J = 12.3, 8.0, 4.2 Hz, 1H), 2.53 (ddt, J = 39.6, 10.6, 4.6 Hz, 4H), 2.35 (dtd, J = 12.4, 8.1, 4.5 Hz, 1H), 2.19 (dtd, J = 12.1, 7.5, 4.5 Hz, 1H), 2.02-1.88 (m, 1H), ; 606.3 [M + H]$^+$ | 1.18 |

TABLE 1-continued

| Example Compound | Structure | Name of Compound | ¹H NMR[[:]]; MS [M + H]⁺ | UPLC r.t. (min) |
|---|---|---|---|---|
| 466 | 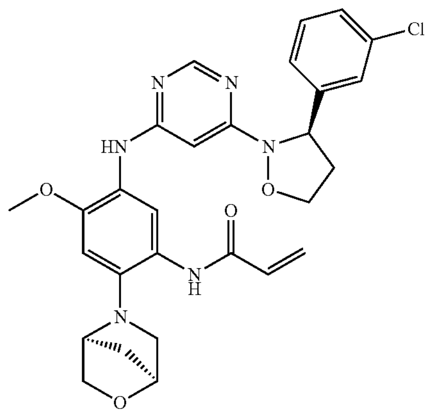 [SMILES: C=CC(=O)Nc1cc(Nc2cc(N3OCC[C@@H]3c3cccc(Cl)c3)ncn2)c(OC)cc1N1C[C@@H]2C[C@H]1CO2] | N-(2-((1S,4S)-2-oxa-5-azabicyclo[2.2.1]heptane-5-yl)-5-((6-((R)-3-(3-chlorophenyl)isoxazolidine-2-yl)pyrimidine-4-yl)amino)-4-methoxyphenyl)acrylamide | 1H NMR (400 MHz, Chloroform-d) δ 8.67 (s, 1H), 8.36 (s, 1H), 7.97 (s, 1H), 7.47 (d, J = 2.0 Hz, 1H), 7.34 (dt, J = 7.6, 1.7 Hz, 1H), 7.29-7.19 (m, 2H), 6.90 (s, 1H), 6.66 (d, J = 29.6 Hz, 2H), 6.32 (tq, J = 26.5, 16.6, 15.3 Hz, 2H), 5.75 (dd, J = 10.0, 1.5 Hz, 1H), 5.67 (dd, J = 8.7, 4.5 Hz, 1H), 4.65 (s, 1H), 4.13 (qd, J = 9.0, 8.5, 5.7 Hz, 1H), 4.03 (dd, J = 15.5, 7.9 Hz, 2H), 3.86 (s, 3H), 3.42 (d, J = 10.1 Hz, 1H), 3.24 (d, J = 10.1 Hz, 1H), 2.76 (dtd, J = 12.3, 8.0, 4.2 Hz, 1H), 2.61 (s, 2H), 2.35 (dtd, J = 12.5, 8.1, 4.6 Hz, 1H), 2.08 (d, J = 9.9 Hz, 1H), 1.99 (d, J = 10.3, Hz, 1H), ; 549.3 [M + H]⁺ | 1.37 |
| 467 | 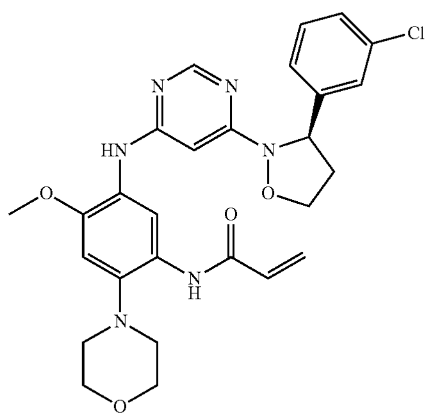 [SMILES: C=CC(=O)Nc1cc(Nc2cc(N3OCC[C@@H]3c3cccc(Cl)c3)ncn2)c(OC)cc1N1CCOCC1] | N-(5-((6-((R)-3-(3-chlorophenyl)isoxazolidine-2-yl)pyrimidine-4-yl)amino)-4-methoxy-2-morpholinophenyl)acrylamide | ¹H NMR (400 MHz, Chloroform-d) δ 8.93 (s, 1H), 8.51 (s, 1H), 8.38 (d, J = 0.9 Hz, 1H), 7.47 (d, J = 1.9 Hz, 1H), 7.34 (dt, J = 7.7, 1.6 Hz, 1H), 7.28-7.19 (m, 2H), 7.00 (s, 1H), 6.77 (s, 1H), 6.71 (s, 1H), 6.43-6.20 (m, 2H), 5.76 (dd, J = 9.9, 1.6 Hz, 1H), 5.68 (dd, J = 8.7, 4.5 Hz, 1H), 4.21-4.01 (m, 2H), 3.88 (t, J = 4.5 Hz, 4H), 3.86 (s, 3H), 2.80 (td, J = 4.1, 1.7 Hz, 4H), 2.77 (dtd, J = 12.3, 8.0, 4.2 Hz, 1H), 2.36 (dtd, J = 12.5, 8.1, 4.6 Hz, 1H), ; 537.2 [M + H]⁺ | 1.51 |
| 468 | 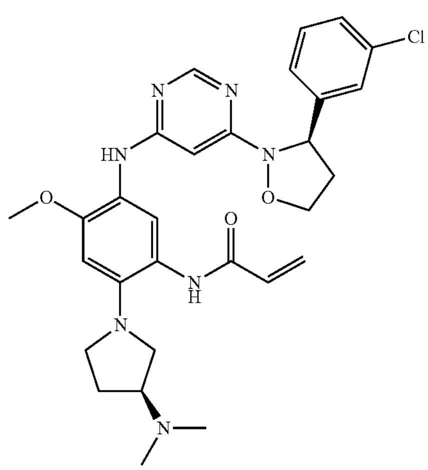 [SMILES: C=CC(=O)Nc1cc(Nc2cc(N3OCC[C@@H]3c3cccc(Cl)c3)ncn2)c(OC)cc1N1CC[C@H](N(C)C)C1] | N-(5-((6-((R)-3-(3-chlorophenyl)isoxazolidine-2-yl)pyrimidine-4-yl)amino)-2-((S)-3-(dimethylamino)pyrrolidine-1-yl)-4-methoxyphenyl)acrylamide | ¹H NMR (400 MHz, Chloroform-d) δ 8.62 (s, 1H), 8.44 (s, 1H), 8.33 (s, 1H), 7.47 (t, J = 1.9 Hz, 1H), 7.37-7.28 (m, 1H), 7.27-7.15 (m, 2H), 7.01 (s, 1H), 6.68 (d, J = 29.5 Hz, 1H), 6.47-6.38 (m, 1H), 6.24-6.08 (m, 1H), 5.82-5.55 (m, 2H), 4.14 (tt, J = 7.2, 3.7 Hz, 1H), 4.02 (q, J = 8.0 Hz, 1H), 3.83 (s, 3H), 3.60 (p, J = 6.7 Hz, 1H), 3.24 (ddt, J = 21.5, 8.6, 4.7 Hz, 2H), 3.14-3.06 (m, 2H), 3.03 (q, J = 7.4 Hz, 2H), 2.76 (dtd, J = 12.3, 8.0, 4.2 Hz, 1H), 2.63 (dd, J = 25.4, 15.0 Hz, 1H), 2.41 (s, 4H), 2.21 (td, J = 12.3, 6.6 Hz, 1H), 1.43 (d, J = 15.6 Hz, 3H), ; 564.4 [M + H]⁺ | 1.17 |

TABLE 1-continued

| Example Compound | Structure | Name of Compound | ¹H NMR[[:]]; MS [M + H]⁺ | UPLC r.t. (min) |
|---|---|---|---|---|
| 469 | 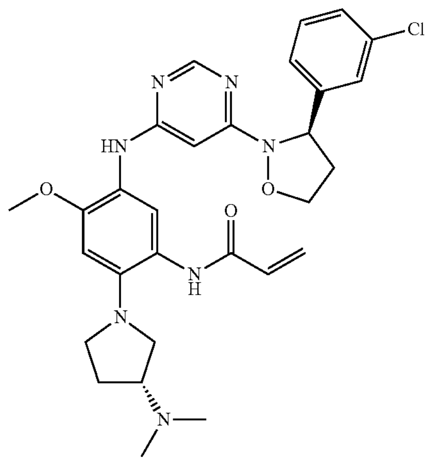 [SMILES: C=CC(=O)Nc1cc(Nc2cc(N3OCC[C@@H]3c3cccc(Cl)c3)ncn2)c(OC)cc1N1CC[C@@H](N(C)C)C1] | N-(5-((6-((R)-3-(3-chlorophenyl)isoxazolidine-2-yl)pyrimidine-4-yl)amino)-2-((R)-3-(dimethylamino)pyrolidine-1-yl)-4-methoxyphenyl)acrylamide | ¹H NMR (400 MHz, DMSO-$d_6$) δ 9.91 (s, 1H), 9.33 (s, 1H), 8.87 (s, 1H), 8.19 (s, 1H), 7.60 (s, 1H), 7.49-7.31 (m, 4H), 6.64 (s, 1H), 6.51 (dd, J = 17.0, 10.2 Hz, 1H), 6.25-6.20 (m, 1H), 5.80-5.69 (m, 1H), 5.53 (dd, J = 8.7, 5.2 Hz, 1H), 4.17 (td, J = 7.7, 3.8 Hz, 1H), 3.93 (q, J = 7.1, 6.5 Hz, 1H), 3.90-3.77 (m, 4H), 3.47-3.40 (m, 2H), 3.32 (t, J = 4.6 Hz, 1H), 3.22 (q, J = 8.2 Hz, 1H), 2.84 (t, J = 5.7 Hz, 7H), 2.39-2.20 (m, 2H), 2.12 (dt, J = 13.4, 7.3 Hz, 1H), ; 564.4 [M + H]⁺ | 1.19 |
| 470 | 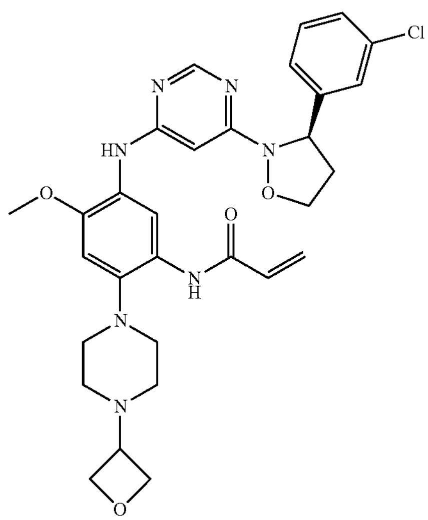 [SMILES: C=CC(=O)Nc1cc(Nc2cc(N3OCC[C@@H]3c3cccc(Cl)c3)ncn2)c(OC)cc1N1CCN(C2COC2)CC1] | N-(5-((6-((R)-3-(3-chlorophenyl)isoxazolidine-2-yl)pyrimidine-4-yl)amino)-4-methoxy-2-(4-(oxetane-3-yl)piperazine-1-yl)phenyl)acrylamide | ¹H NMR (400 MHz, DMSO-$d_6$) δ 9.05 (s, 1H), 8.75 (s, 1H), 8.25 (s, 1H), 8.18 (s, 1H), 7.46-7.30 (m, 4H), 6.84 (s, 1H), 6.63 (dd, J = 17.1, 10.2 Hz, 1H), 6.39 (s, 1H), 6.23 (dd, J = 17.1, 2.0 Hz, 1H), 5.74 (d, J = 9.7 Hz, 1H), 5.54 (dd, J = 8.7, 5.1 Hz, 1H), 4.76 (s, 4H), 4.20-4.10 (m, 1H), 3.84 (s, 4H), 3.63 (s, 4H), 3.42-3.35 (m, 1H), 3.17 (s, 4H), 2.83-2.73 (m, 1H), 2.30-2.18 (m, 1H); 592.4 [M + H]⁺ | 1.22 |

TABLE 1-continued

| Example Compound | Structure | Name of Compound | ¹H NMR[[:]]; MS [M + H]⁺ | UPLC r.t. (min) |
|---|---|---|---|---|
| 471 | 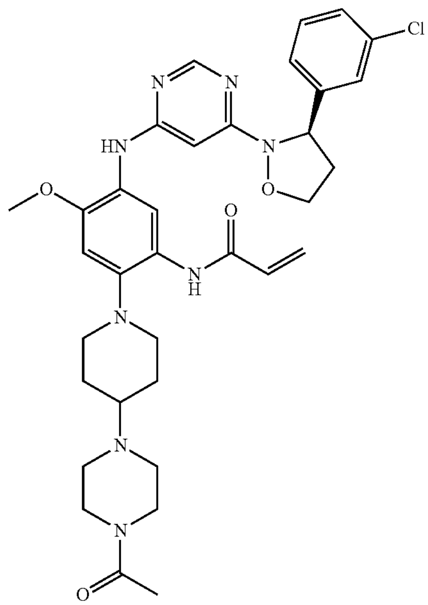 [SMILES: C=CC(=O)Nc1cc(Nc2cc(N3OCC[C@@H]3c3cccc(Cl)c3)ncn2)c(OC)cc1N1CCC(N2CCN(C(C)=O)CC2)CC1] | N-(2-(4-(4-acetylpiperazine-1-yl)piperidine-1-yl)-5-((6-((R)-3-(3-chlorophenyl)isoxazolidine-2-yl)pyrimidine-4-yl)amino)-4-methoxyphenyl)acrylamide | ¹H NMR (400 MHz, DMSO-d₆) δ 10.53 (s, 1H), 9.20 (s, 1H), 9.08 (s, 1H), 8.25 (s, 1H), 8.10 (s, 1H), 7.48-7.30 (m, 4H), 6.87 (s, 1H), 6.66 (dd, J = 17.0, 10.2 Hz, 1H), 6.30-6.23 (m, 1H), 5.82-5.66 (m, 1H), 5.54 (dd, J = 8.6, 5.3 Hz, 1H), 4.21 (td, J = 7.8, 3.9 Hz, 1H), 4.06 (s, 1H), 3.93 (t, J = 7.9 Hz, 1H), 3.82 (s, 3H), 3.52 (s, 3H), 3.39 (dq, J = 11.7, 7.6, 6.2 Hz, 2H), 3.18 (d, J = 11.5 Hz, 3H), 3.10-2.91 (m, 2H), 2.85 (tt, J = 8.1, 4.0 Hz, 1H), 2.77 (t, J = 12.8 Hz, 2H), 2.32-2.20 (m, 1H), 2.12 (d, J = 11.4 Hz, 2H), 2.08 (s, 3H), 2.00 (dt, J = 12.1, 6.4 Hz, 2H), ; 661.4 [M + H]⁺ | 1.22 |
| 472 | 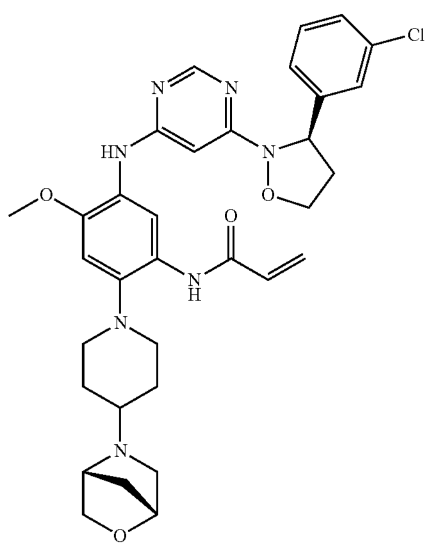 [SMILES: C=CC(=O)Nc1cc(Nc2cc(N3OCC[C@@H]3c3cccc(Cl)c3)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-5-((6-((R)-3-(3-chlorophenyl)isoxazolidine-2-yl)pyrimidine-4-yl)amino)-4-methoxyphenyl)acrylamide | ¹H NMR (400 MHz, DMSO-d₆) δ 9.08 (d, J = 16.7 Hz, 1H), 8.71 (s, 1H), 8.18 (s, 1H), 8.11 (s, 1H), 7.47-7.29 (m, 4H), 6.82 (s, 1H), 6.52 (dt, J = 19.2, 10.2 Hz, 1H), 6.37 (s, 1H), 6.22 (d, J = 16.9 Hz, 1H), 5.74 (d, J = 10.1 Hz, 1H), 5.54 (dd, J = 8.6, 5.2 Hz, 1H), 4.76-4.61 (m, 2H), 4.15 (dd, J = 7.9, 3.9 Hz, 1H), 3.90-3.79 (m, 4H), 3.75 (t, J = 10.5 Hz, 2H), 3.44-3.36 (m, 3H), 3.23 (d, J = 11.8 Hz, 1H), 3.18-3.07 (m, 2H), 2.81-2.73 (m, 2H), 2.65 (d, J = 12.3 Hz, 1H), 2.33 (s, 1H), 2.29-2.20 (m, 1H), 2.16 (d, J = 14.6 Hz, 1H), 2.01 (d, J = 11.4 Hz, 1H), 1.87-1.73 (m, 2H), ; 632.5 [M + H]⁺ | 1.24 |

TABLE 1-continued

| Example Compound | Structure | Name of Compound | $^1$H NMR[:]; MS [M + H]$^+$ | UPLC r.t. (min) |
|---|---|---|---|---|
| 473 | 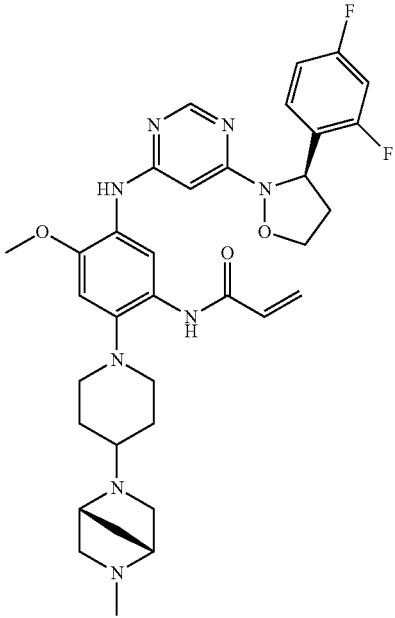 [SMILES: C=CC(=O)Nc1cc(Nc2cc(N3OCC[C@@H]3c3ccc(F)cc3F)ncn2)c(OC)cc1N1CCC(N2C[C@H]3C[C@@H]2CN3C)CC1] | N-(5-((6-((R)-3-(2,4-difluorophenyl) isoxazolidine-2-yl)pyrimidine-4-yl)amino)-4-methoxy-2-(4-((1R,4R)-5-methyl-2,5-diazabicyclo[2.2.1] heptane-2-yl)piperidine-1-yl)phenyl)acrylamide | $^1$H NMR (400 MHz, Chloroform-d) δ 8.88 (s, 1H), 8.47 (s, 1H), 8.37 (s, 1H), 7.56 (q, J = 8.3 Hz, 1H), 6.93 (s, 1H), 6.87-6.73 (m, 4H), 6.38-6.31 (m, 1H), 6.24 (dd, J = 17.0, 10.0 Hz, 1H), 5.87 (dd, J = 8.7, 4.3 Hz, 1H), 5.73 (d, J = 10.1 Hz, 1H), 4.14-4.05 (m, 2H), 3.86 (s, 3H), 3.02 (s, 2H), 2.78 (q, J = 11.7, 9.9 Hz, 4H), 2.50 (d, J = 9.6 Hz, 2H), 2.32-2.24 (m, 1H), 2.06 (d, J = 10.5 Hz, 2H), 1.90 (s, 2H), 1.25 (s, 3H), ; 647.5 [M + H] | 1.13 |
| 474 | 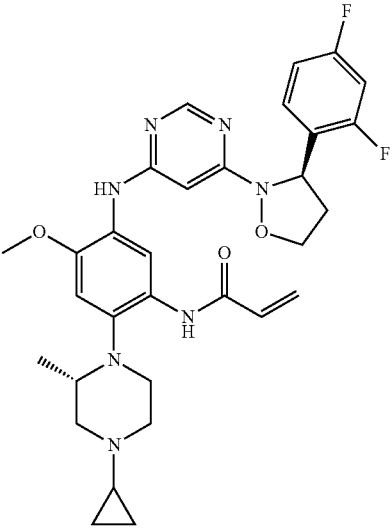 [SMILES: C=CC(=O)Nc1cc(Nc2cc(N3OCC[C@@H]3c3ccc(F)cc3F)ncn2)c(OC)cc1N1CCN(C2CC2)C[C@@H]1C] | N-(2-((S)-4-cyclopropyl-2-methylpiperazine-1-yl)-5-((6-((R)-3-(2,4-difluorophenyl) isoxazolidine-2-yl)pyrimidine-4-yl)amino)-4-methoxyphenyl) acrylamide | $^1$H NMR (400 MHz, Chloroform-d) δ 9.02 (s, 1H), 8.96 (s, 1H), 8.38 (s, 1H), 7.57 (q, J = 8.3 Hz, 1H), 7.07 (s, 1H), 6.81 (dd, J = 12.2, 8.4 Hz, 4H), 6.35-6.23 (m, 2H), 5.88 (dd, J = 8.7, 4.1 Hz, 1H), 5.74 (dd, J = 9.6, 1.9 Hz, 1H), 4.15-4.08 (m, 2H), 3.80 (s, 3H), 3.16-2.97 (m, 4H), 2.85-2.79 (m, 2H), 2.53-2.45 (m, 1H), 2.31-2.24 (m, 1H), 2.20 (t, J = 10.4 Hz, 1H), 1.70 (d, J = 4.1 Hz, 1H), 0.82 (d, J = 6.1 Hz, 3H), 0.50 (dd, J = 17.3, 5.1 Hz, 4H), ; 592.4 [M + H] | 1.31 |

TABLE 1-continued

| Example Compound | Structure | Name of Compound | ¹H NMR[:]; MS [M + H]⁺ | UPLC r.t. (min) |
|---|---|---|---|---|
| 475 | 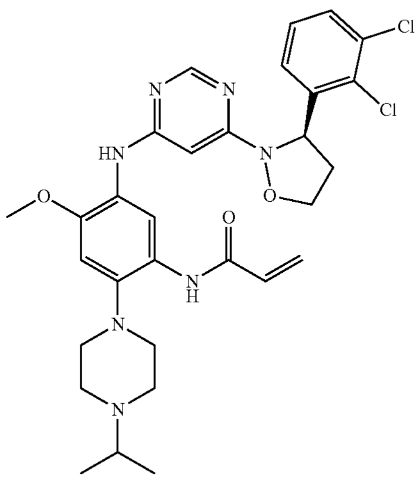 [SMILES: C=CC(=O)Nc1cc(Nc2cc(N3OCC[C@@H]3c3cccc(Cl)c3Cl)ncn2)c(OC)cc1N1CCN(C(C)C)CC1] | N-(5-((6-((R)-3-(2,3-dichlorophenyl)isoxazolidine-2-yl)pyrimidine-4-yl)amino)-2-(4-isopropylpiperazine-1-yl)-4-methoxyphenyl)acrylamide | ¹H NMR (400 MHz, Chloroform-d) δ 8.90 (s, 1H), 8.57 (s, 1H), 8.36 (s, 1H), 7.60 (d, J = 7.8 Hz, 1H), 7.39-7.34 (m, 1H), 7.19 (t, J = 7.9 Hz, 1H), 6.95 (s, 1H), 6.84 (s, 1H), 6.76 (s, 1H), 6.37 (d, J = 16.7 Hz, 1H), 6.27 (dd, J = 16.9, 9.9 Hz, 1H), 5.97 (dd, J = 8.9, 4.4 Hz, 1H), 5.77-5.72 (m, 1H), 4.10 (dt, J = 10.3, 6.3 Hz, 2H), 3.83 (s, 3H), 2.94 (dt, J = 8.1, 4.1 Hz, 4H), 2.78-2.67 (m, 4H), 2.23 (dtd, J = 12.6, 8.2, 4.4 Hz, 1H), 1.64 (s, 2H), 1.13 (d, J = 6.4 Hz, 6H), ; 612.3 [M + H] | 1.37 |
| 476 | 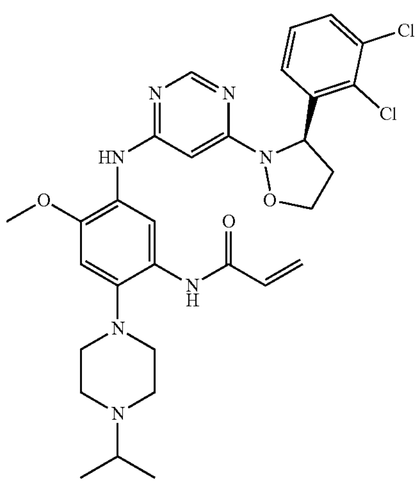 [SMILES: C=CC(=O)Nc1cc(Nc2cc(N3OCC[C@@H]3c3cccc(Cl)c3Cl)ncn2)c(OC)cc1N1CCN(C(C)C)CC1] | N-(5-((6-((R)-3-(2,3-dichlorophenyl)isoxazolidine-2-yl)pyrimidine-4-yl)amino)-2-(4-(dimethylamino)piperidine-1-yl)-4-methoxyphenyl)acrylamide | ¹H NMR (400 MHz, Chloroform-d) δ 8.86 (s, 1H), 8.43 (s, 1H), 8.35 (s, 1H), 7.59 (dd, J = 7.8, 1.6 Hz, 1H), 7.37 (dd, J = 7.9, 1.6 Hz, 1H), 7.19 (t, J = 7.9 Hz, 1H), 7.05 (s, 1H), 6.75 (s, 1H), 6.36-6.26 (m, 2H), 6.16 (dd, J = 17.3, 10.1 Hz, 1H), 5.96 (dd, J = 8.8, 4.4 Hz, 1H), 5.73 (ddd, J = 16.3, 9.8, 2.0 Hz, 1H), 4.16-4.05 (m, 2H), 3.85 (s, 3H), 2.96 (ddt, J = 12.2, 8.1, 4.0 Hz, 2H), 2.81-2.71 (m, 2H), 2.53 (s, 6H), 2.23 (dq, J = 12.2, 3.8 Hz, 1H), 1.88-1.76 (m, 2H), 1.33-1.22 (m, 4H), ; 612.4 [M + H] | 1.34 |

TABLE 1-continued

| Example Compound | Structure | Name of Compound | ¹H NMR[[:]]; MS [M + H]⁺ | UPLC r.t. (min) |
|---|---|---|---|---|
| 477 | 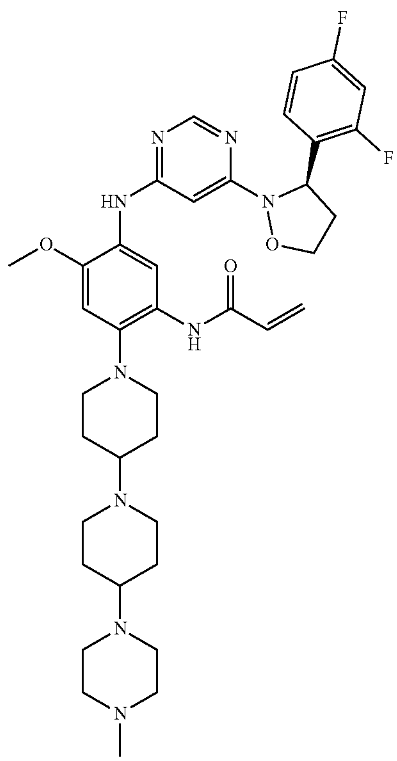 [SMILES: C=CC(=O)Nc1cc(Nc2cc(N3OCC[C@@H]3c3ccc(F)cc3F)ncn2)c(OC)cc1N1CCC(N2CCC(N3CCN(C)CC3)CC2)CC1] | N-(5-((6-((R)-3-(2,4-difluorophenyl)isoxazolidine-2-yl)pyrimidine-4-yl)amino)-4-methoxy-2-(4-(4-methylpiperazine-1-yl)-[1,4'-bipiperidine]-1'-yl)phenyl)acrylamide | ¹H NMR (400 MHz, Chloroform-d) δ 8.86 (s, 1H), 8.44 (s, 1H), 8.36 (s, 1H), 7.56 (m, 1H), 6.92 (s, 1H), 6.84 (m, 2H), 6.75 (m, 2H), 6.34 (m, 1H), 6.27 (d, J = 10.1 Hz, 1H), 5.89 (m, 1H), 5.74 (d, J = 11.1 Hz, 1H), 4.08 (d, J = 16.0 Hz, 2H), 3.85 (s, 3H), 3.12 (m, 5H), 2.79 (m, 2H), 2.72 m, 2H), 2.63 (m, 5H), 2.50 (m, 3H), 2.30 (m, 5H), 2.02 (m, 3H), 1.86 (m, 3H), 1.71 (m, 3H), ; 718.6 [M + H]⁺ | 1.11 |
| 478 | 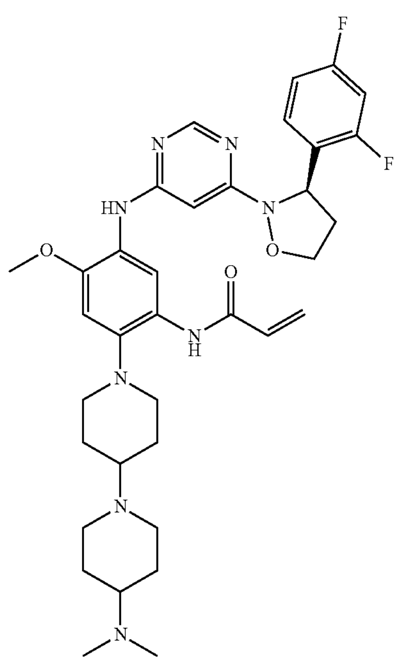 [SMILES: C=CC(=O)Nc1cc(Nc2cc(N3OCC[C@@H]3c3ccc(F)cc3F)ncn2)c(OC)cc1N1CCC(N2CCC(N(C)C)CC2)CC1] | N-(5-((6-((R)-3-(2,4-difluorophenyl)isoxazolidine-2-yl)pyrimidine-4-yl)amino)-2-(4-(dimethylamino)-[1,4'-bipiperidine]-1'-yl)-4-methoxyphenyl)acrylamide | ¹H NMR (400 MHz, Chloroform-d) δ 9.25 (s, 1H), 8.86 (s, 1H), 8.43 (s, 2H), 8.36 (s, 1H), 8.31 (s, 1H), 7.54 (m, 2H), 6.94 (s, 1H), 6.36 (d, J = 17.4 Hz, 1H), 6.26 (dd, J = 16.7, 10.4 Hz, 1H), 5.83 (m, 1H), 5.75 (d, J = 10.4 Hz, 1H), 4.14-4.04 (m, 2H), 3.85 (s, 3H), 3.78-3.69 (m, 4H), 3.44-3.36 (m, 3H), 3.31-3.26 (m, 5H), 2.40 (s, 6H), 1.81-1.73 (m, 4H), 1.71-1.56 (m, 4H), ; 663.5 [M + H]⁺ | 1.11 |

| Example Compound | Structure | Name of Compound | ¹H NMR[[:]]; MS [M + H]⁺ | UPLC r.t. (min) |
|---|---|---|---|---|
| 479 | 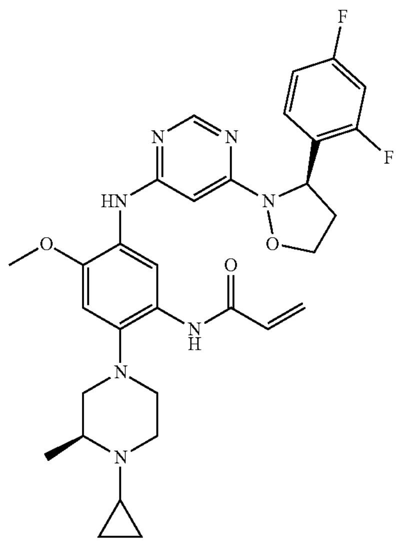 [SMILES: C=CC(=O)Nc1cc(Nc2cc(N3OCC[C@@H]3c3ccc(F)cc3F)ncn2)c(OC)cc1N1CCN(C2CC2)[C@@H](C)C1] | N-(2-((S)-4-cyclopropyl-3-methylpiperazine-1-yl)-5-((6-((R)-3-(2,4-difluorophenyl)isoxazolidine-2-yl)pyrimidine-4-yl)amino)-4-methoxyphenyl)acrylamide | ¹H NMR (400 MHz, Chloroform-d) δ 8.90 (s, 1H), 8.60 (s, 1H), 8.37 (s, 1H), 7.56 (m, 1H), 6.93 (s, 1H), 6.80 (m, 4H), 6.35 (m, 1H), 6.28 (m, 1H), 5.89 (m, 1H), 5.75 (d, J = 11.0 Hz, 1H), 4.11 (m, 2H), 3.82 (s, 3H), 3.12 (d, J = 11.7 Hz, 1H), 2.89 (m, 2H), 2.82 (m, 2H), 2.69 (m, 1H), 2.64-2.55 (m, 1H), 2.27 (m, 1H), 1.66 (s, 1H), 1.57 (s, 1H), 1.26 (d, J = 6.2 Hz, 3H), 0.65 (d, J = 32.1 Hz, 2H), 0.50 (m, 1H), 0.36 (m, 1H), ; 592.4 [M + H]⁺ | 1.24 |
| 480 | 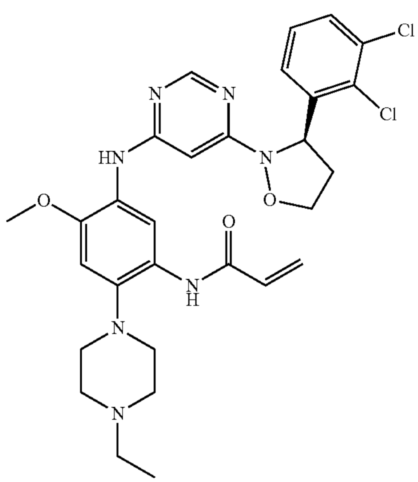 [SMILES: C=CC(=O)Nc1cc(Nc2cc(N3OCC[C@@H]3c3cccc(Cl)c3Cl)ncn2)c(OC)cc1N1CCN(CC)CC1] | N-(5-((6-((R)-3-(2,3-dichlorophenyl)isoxazolidine-2-yl)pyrimidine-4-yl)amino)-2-(4-ethylpiperazine-1-yl)-4-methoxyphenyl)acrylamide | ¹H NMR (400 MHz, Chloroform-d) δ 8.90 (s, 1H), 8.56 (s, 1H), 8.36 (s, 1H), 7.60 (d, J = 7.8 Hz, 1H), 7.37 (d, J = 9.0 Hz, 1H), 7.19 (t, J = 7.9 Hz, 1H), 6.95 (s, 1H), 6.82 (s, 1H), 6.76 (s, 1H), 6.36 (d, J = 16.2 Hz, 1H), 6.29 (d, J = 10.0 Hz, 1H), 5.98 (m, 1H), 5.75 (d, J = 11.1 Hz, 1H), 4.09 (m, 2H), 3.84 (s, 3H), 3.07 (m, 1H), 2.94 (m, 5H), 2.66 (s, 3H), 2.53 (m, 2H), 2.24 (m, 1H), 1.16 (t, J = 7.2 Hz, 3H), ; 598.3 [M + H]⁺ | 1.35 |
| 481 | 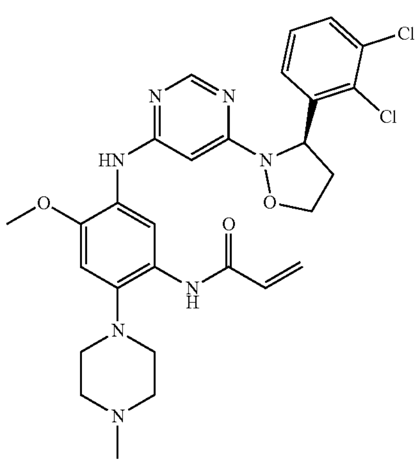 [SMILES: C=CC(=O)Nc1cc(Nc2cc(N3OCC[C@@H]3c3cccc(Cl)c3Cl)ncn2)c(OC)cc1N1CCN(C)CC1] | N-(5-((6-((R)-3-(2,3-dichlorophenyl)isoxazolidine-2-yl)pyrimidine-4-yl)amino)-4-methoxy-2-(4-methylpiperazine-1-yl)phenyl)acrylamide | ¹H NMR (400 MHz, Chloroform-d) δ 11.33 (s, 1H), 8.92 (s, 1H), 8.37 (s, 1H), 7.58 (s, 1H), 7.38 (s, 1H), 7.19 (s, 1H), 6.98 (s, 1H), 6.81 (s, 1H), 6.75 (s, 1H), 6.36 (s, 1H), 6.30 (d, J = 10.4 Hz, 1H), 5.98 (m, 1H), 5.75 (d, J = 11.1 Hz, 1H), 4.08 (m, 2H), 3.84 (s, 3H), 3.65 (m, 2H), 3.08 (m, 2H), 2.91 (m, 2H), 2.49 (m, 2H), 2.22 (m, 2H), 1.45 (d, J = 6.6 Hz, 3H), ; 584.3 [M + H]⁺ | 1.33 |

TABLE 1-continued

| Example Compound | Structure | Name of Compound | ¹H NMR[:]; MS [M + H]⁺ | UPLC r.t. (min) |
|---|---|---|---|---|
| 482 | 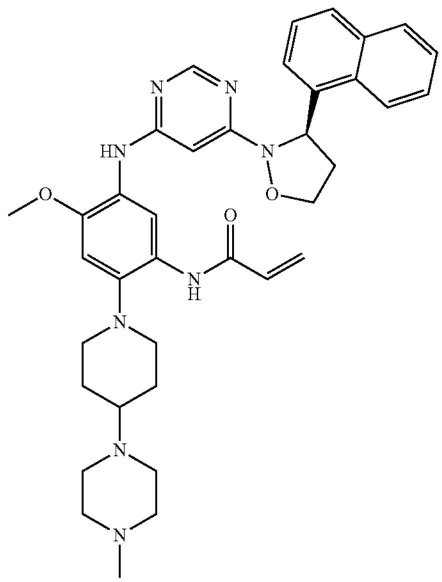 [SMILES: C=CC(=O)Nc1cc(Nc2cc(N3OCC[C@@H]3c3cccc4ccccc34)ncn2)c(OC)cc1N1CCC(N2CCN(C)CC2)CC1] | N-(4-methoxy-2-(4-(4-methylpiperazine-1-yl)piperidine-1-yl)-5-((6-((R)-3-(naphthalene-1-yl)isoxazolidine-2-yl)pyrimidine-4-yl)amino)phenyl) acrylamide | ¹H NMR (400 MHz, Chloroform-d) δ 8.89 (s, 1H), 8.44 (s, 1H), 8.36 (s, 1H), 8.14 (d, J = 8.3 Hz, 1H), 7.88 (dd, J = 8.0, 1.5 Hz, 1H), 7.57-7.42 (m, 4H), 6.98 (s, 1H), 6.77 (s, 1H), 6.74 (s, 1H), 6.43-6.37 (m, 2H), 6.34 (d, J = 1.6 Hz, 1H), 6.25 (dd, J = 16.9, 10.0 Hz, 1H), 5.74 (dd, J = 10.0, 1.6 Hz, 1H), 4.16 (d, J = 6.5 Hz, 2H), 3.84 (s, 4H), 3.35-3.17 (m, 2H), 3.16-3.00 (m, 4H), 2.84 (s, 1H), 2.72 (tdd, J = 11.6, 9.3, 8.8, 4.5 Hz, 8H), 2.67-2.50 (m, 5H), 2.07 (d, J = 12.9 Hz, 2H), 1.71-1.65 (m, 2H), ; 649.5 [M + H]⁺ | 1.20 |
| 483 | 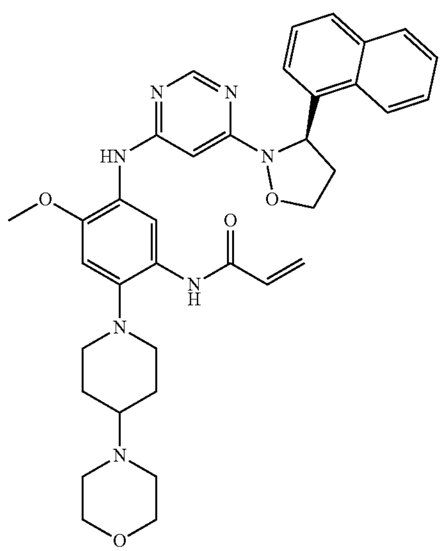 | N-(4-methoxy-2-(4-morpholinopiperidine-1-yl)-5-((6-((R)-3-(naphthalene-1-yl)isoxazolidine-2-yl)pyrimidine-4-yl)amino)phenyl) acrylamide | ¹H NMR (400 MHz, Chloroform-d) δ 8.89 (s, 1H), 8.44 (s, 1H), 8.36 (s, 1H), 8.14 (d, J = 8.3 Hz, 1H), 7.87 (dd, J = 7.9, 1.4 Hz, 1H), 7.63-7.36 (m, 4H), 7.00 (s, 1H), 6.76 (d, J = 10.8 Hz, 2H), 6.43-6.18 (m, 4H), 5.74 (dd, J = 9.9, 1.6 Hz, 1H), 4.16 (d, J = 7.0 Hz, 1H), 3.84 (s, 3H), 3.77 (t, J = 4.6 Hz, 4H), 3.06 (dq, J = 9.4, 3.3 Hz, 2H), 3.01-2.89 (m, 1H), 2.79-2.66 (m, 2H), 2.61 (dd, J = 7.6, 3.3 Hz, 5H), 2.40 (dtd, J = 11.8, 7.8, 3.9 Hz, 1H), 2.30 (tt, J = 11.1, 3.8 Hz, 1H), 2.07 (d, J = 12.7 Hz, 3H), 1.65 (qd, J = 12.1, 3.9 Hz, 3H), 1.33-1.22 (m, 2H), ; 363.5 [M + H]⁺ | 1.23 |

TABLE 1-continued

| Example Compound | Structure | Name of Compound | ¹H NMR[[:]]; MS [M + H]⁺ | UPLC r.t. (min) |
|---|---|---|---|---|
| 484 | 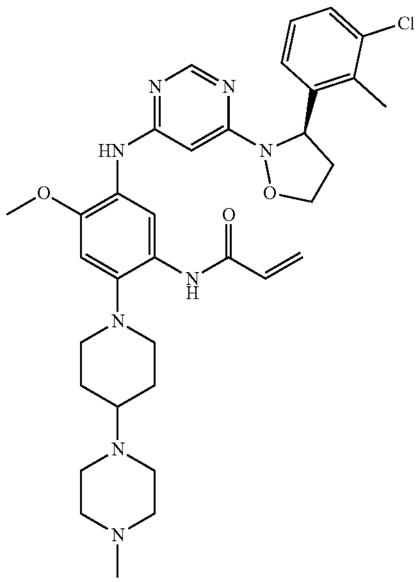 | N-(2-(4-(4-ethylpiperazine-1-yl)piperidine-1-yl)-4-methoxy-5-((6-((R)-3-(naphthalene-1-yl)isoxazolidine-2-yl)pyrimidine-4-yl)amino)phenyl)acrylamide | ¹H NMR (400 MHz, DMSO-$d_6$) δ 9.02 (s, 1H), 8.63 (s, 1H), 8.27 (d, J = 8.2 Hz, 1H), 8.16 (d, J = 9.4 Hz, 2H), 7.99-7.94 (m, 1H), 7.84 (d, J = 8.2 Hz, 1H), 7.64 (d, J = 7.2 Hz, 1H), 7.63-7.52 (m, 2H), 7.48 (t, J = 7.7 Hz, 1H), 6.83 (s, 1H), 6.73-6.66 (m, 1H), 6.26-6.20 (m, 2H), 5.76 (s, 2H), 3.95 (q, J = 8.0 Hz, 1H), 3.81 (s, 3H), 3.57 (p, J = 6.6 Hz, 3H), 3.05-2.96 (m, 4H), 2.22 (ddt, J = 12.1, 8.0, 4.2 Hz, 1H), 1.32-1.25 (m, 12H), 1.21 (d, J = 6.8 Hz, 4H), 1.08 (td, J = 7.4, 5.2 Hz, 3H), ; 663.5 [M + H]⁺ | 1.14 |
| 485 | 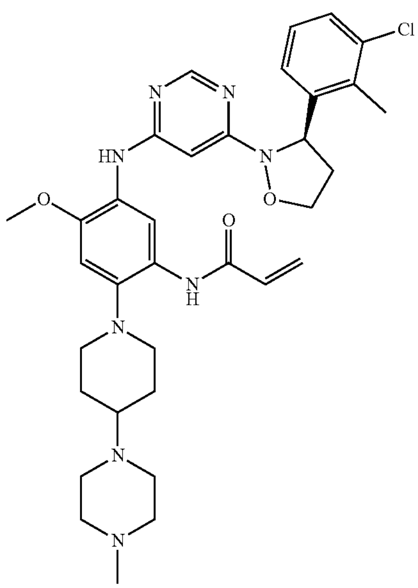 [SMILES: C=CC(=O)Nc1cc(Nc2cc(N3OCC[C@@H]3c3cccc(Cl)c3C)ncn2)c(OC)cc1N1CCC(N2CCN(C)CC2)CC1] | N-(5-((6-((R)-3-(3-chloro-2-methylphenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, Chloroform-d) δ 8.82 (s, 1H), 8.43 (s, 1H), 8.32 (s, 1H), 7.48 (d, J = 7.8 Hz, 1H), 7.16-7.07 (m, 2H), 6.74 (s, 1H), 6.69 (s, 1H), 6.39-6.31 (m, 1H), 6.25 (dd, J = 16.9, 9.9 Hz, 1H), 5.83 (dd, J = 8.8, 4.5 Hz, 1H), 5.74 (dd, J = 9.9, 1.6 Hz, 1H), 4.13 (dd, J = 8.0, 4.2 Hz, 2H), 3.84 (s, 4H), 3.06 (d, J = 11.6 Hz, 3H), 2.90-2.52 (m, 13H), 2.47 (s, 4H), 2.37 (s, 4H), 2.17 (dtd, J = 12.5, 8.1, 4.5 Hz, 2H), 2.06 (d, J = 12.0 Hz, 3H), 1.68 (qd, J = 12.1, 3.9 Hz, 3H), ; 647.5 [M + H]⁺ | 1.24 |

TABLE 1-continued

| Example Compound | Structure | Name of Compound | ¹H NMR[[:]]; MS [M + H]⁺ | UPLC r.t. (min) |
|---|---|---|---|---|
| 486 | 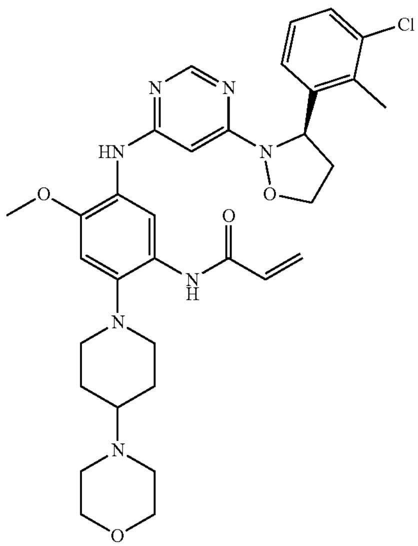 [SMILES: C=CC(=O)Nc1cc(Nc2cc(N3OCC[C@@H]3c3cccc(Cl)c3C)ncn2)c(OC)cc1N1CCC(N2CCOCC2)CC1] | N-(5-((6-((R)-3-(3-chloro-2-methylphenyl) isoxazolidine-2-yl)pyrimidine-4-yl)amino)-4-methoxy-2-(4-morpholinopiperidine-1-yl)phenyl)acrylamide | ¹H NMR (400 MHz, Chloroform-d) δ 8.84 (s, 1H), 8.44 (s, 1H), 8.33 (d, J = 1.0 Hz, 1H), 7.49 (dd, J = 7.8, 1.3 Hz, 1H), 7.15-7.05 (m, 2H), 6.75 (s, 1H), 6.70 (d, J = 1.1 Hz, 1H), 6.36 (dd, J = 16.9, 1.5 Hz, 1H), 6.25 (dd, J = 16.9, 10.0 Hz, 1H), 5.84, (dd, J = 8.8, 4.5 Hz, 1H), 5.74 (dd, J = 10.0, 1.6 Hz, 1H), 4.14 (td, J = 8.1, 4.2 Hz, 1H), 3.84 (s, 3H), 3.78 (t, J = 4.7 Hz, 4H), 3.07 (d, J = 11.4 Hz, 2H), 2.87-2.66 (m, 4H), 2.63 (t, J = 4.6 Hz, 4H), 2.47 (s, 4H), 2.31 (dtd, J = 12.9, 9.2, 8.3, 4.6 Hz, 3H), 2.18 (dtd, J = 12.5, 8.1, 4.5 Hz, 3H), 1.72-1.60 (m, 3H), ; 634.4 [M + H]⁺ | 1.27 |
| 487 | 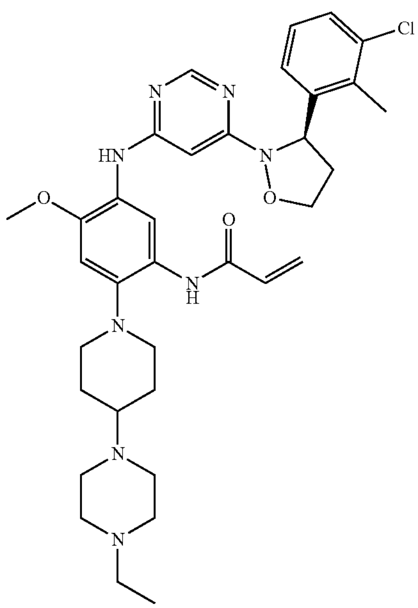 [SMILES: C=CC(=O)Nc1cc(Nc2cc(N3OCC[C@@H]3c3cccc(Cl)c3C)ncn2)c(OC)cc1N1CCC(N2CCN(CC)CC2)CC1] | N-(5-((6-((R)-3-(3-chloro-2-methylphenyl) isoxazolidine-2-yl)pyrimidine-4-yl)amino)-2-(4-(4-ethylpiperazine-1-yl)piperidine-1-yl)-4-methoxyphenyl) acrylamide | 661.5 [M + H]⁺ | 1.25 |

TABLE 1-continued

| Example Compound | Structure | Name of Compound | ¹H NMR[:]; MS [M + H]⁺ | UPLC r.t. (min) |
|---|---|---|---|---|
| 488 | 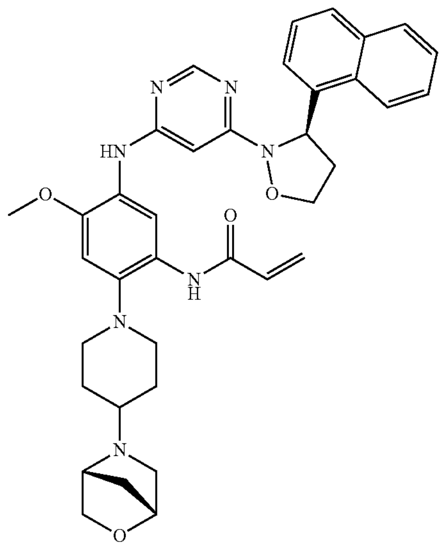 [SMILES: C=CC(=O)Nc1cc(Nc2cc(N3OCC[C@@H]3c3cccc4ccccc34)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-4-methoxy-5-((6-((R)-3-(naphthalene-1-yl)isoxazolidine-2-yl)pyrimidine-4-yl)amino)phenyl) acrylamide | ¹H NMR (400 MHz, Chloroform-d) δ 8.91 (s, 1H), 8.49 (s, 1H), 8.37 (d, J = 0.9 Hz, 1H), 8.15 (d, J = 8.4 Hz, 1H), 7.88 (d, J = 8.0 Hz, 1H), 7.81-7.73 (m, 2H), 7.60-7.41 (m, 3H), 6.92 (s, 1H), 6.78 (d, J = 8.9 Hz, 2H), 6.45-6.40 (m, 1H), 6.40-6.31 (m, 1H), 6.24 (dd, J = 17.0, 10.0 Hz, 1H), 5.73 (dd, J = 10.0, 1.5 Hz, 1H), 4.44 (s, 1H), 4.25-4.12 (m, 2H), 4.09 (d, J = 7.9 Hz, 1H), 3.86 (s, 3H), 3.77 (s, 1H), 3.67 (dd, J = 7.9, 1.6 Hz, 1H), 3.14 (dd, J = 9.8, 1.7 Hz, 1H), 3.07-3.00 (m, 2H), 2.99-2.92 (m, 1H), 2.83-2.70 (m, 2H), 2.61-2.56 (m, 1H), 2.51 (d, J = 9.9 Hz, 1H), 2.47-2.35 (m, 1H), 2.04 (d, 1H), 2.00-1.88 (m, 2H), 1.83 (d, J = 9.8 Hz, 1H), 1.72-1.62 (m, 2H), ; 648.5 [M + H]⁺ | 1.25 |
| 489 | 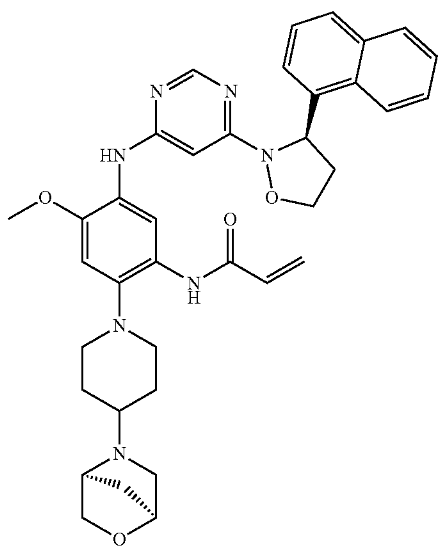 [SMILES: C=CC(=O)Nc1cc(Nc2cc(N3OCC[C@@H]3c3cccc4ccccc34)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-4-methoxy-5-((6-((R)-3-(naphthalene-1-yl)isoxazolidine-2-yl)pyrimidine-4-yl)amino)phenyl) acrylamide | ¹H NMR (400 MHz, Chloroform-d) δ 8.91 (s, 1H), 8.49 (s, 1H), 8.37 (s, 1H), 8.15 (d, J = 8.3 Hz, 1H), 7.88 (d, J = 8.0 Hz, 1H), 7.77 (dd, J = 7.6, 5.7 Hz, 2H), 7.60-7.41 (m, 3H), 6.92 (s, 1H), 6.78 (d, J = 7.5 Hz, 2H), 6.45-6.31 (m, 2H), 6.24 (dd, J = 16.9, 10.0 Hz, 1H), 5.73 (dd, J = 10.0, 1.5 Hz, 1H), 4.44 (s, 1H), 4.24-4.12 (m, 2H), 4.09 (d, J = 7.9 Hz, 1H), 3.86 (s, 3H), 3.77 (s, 1H), 3.67 (dd, J = 7.9, 1.6 Hz, 1H), 3.14 (dd, J = 10.0, 1.8 Hz, 1H), 3.07-2.99 (m, 2H), 2.99-2.92 (m, 1H), 2.82-2.71 (m, 2H), 2.61-2.56 (m, 1H), 2.51 (d, J = 9.9 Hz, 1H), 2.47-2.35 (m, 1H), 2.04 (d, J = 13.7 Hz, 1H), 1.99-1.88 (m, 2H), 1.83 (d, J = 9.8 Hz, 1H), 1.73-1.64 (m, 2H), ; 648.5 [M + H]⁺ | 1.25 |

TABLE 1-continued

| Example Compound | Structure | Name of Compound | ¹H NMR[[:]]; MS [M + H]⁺ | UPLC r.t. (min) |
|---|---|---|---|---|
| 490 | 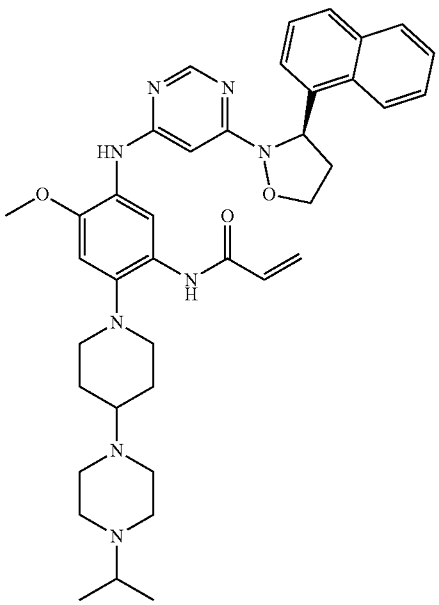 [SMILES: C=CC(=O)Nc1cc(Nc2cc(N3OCC[C@@H]3c3cccc4ccccc34)ncn2)c(OC)cc1N1CCC(N2CCN(C(C)C)CC2)CC1] | N-(2-(4-(4-isopropylpiperazine-1-yl)piperidine-1-yl)-4-methoxy-5-((6-((R)-3-(naphthalene-1-yl)isoxazolidine-2-yl)pyrimidine-4-yl)amino)phenyl) acrylamide | ¹H NMR (400 MHz, Chloroform-d) δ 8.90 (s, 1H), 8.46 (s, 1H), 8.37 (s, 1H), 8.15 (d, J = 8.4 Hz, 1H), 7.91-7.85 (m, 1H), 7.81-7.73 (m, 2H), 7.60-7.41 (m, 3H), 6.91 (s, 1H), 6.77 (d, J = 10.2 Hz, 2H), 6.43-6.31 (m, 2H), 6.24 (dd, J = 17.0, 10.0 Hz, 1H), 5.74 (dd, J = 9.9, 1.6 Hz, 1H), 4.24-4.11 (m, 2H), 3.85 (s, 3H), 3.06 (d, J = 9.6 Hz, 2H), 3.01-2.92 (m, 1H), 2.82-2.53 (m, 11H), 2.45-2.36 (m, 1H), 2.30 (d, J = 10.9 Hz, 1H), 2.10 (d, J = 12.5 Hz, 2H), 1.73-1.64 (m, 2H), 1.08 (d, J = 6.5 Hz, 6H), ; 677.5 [M + H]⁺ | 1.22 |
| 491 | 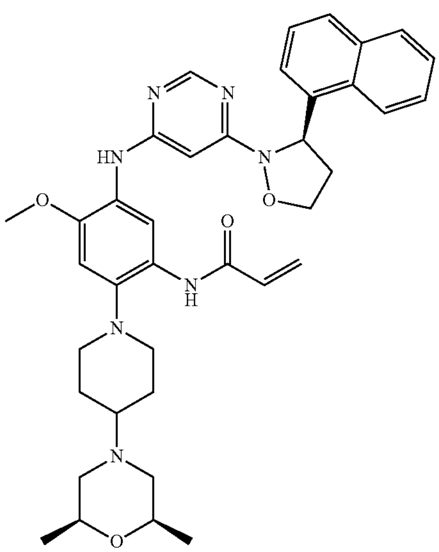 [SMILES: C=CC(=O)Nc1cc(Nc2cc(N3OCC[C@@H]3c3cccc4ccccc34)ncn2)c(OC)cc1N1CCC(N2C[C@@H](C)O[C@@H](C)C2)CC1] | N-(2-(4-((2S,6R)-2,6-dimethylmorpholino)piperidine-1-yl)-4-methoxy-5-((6-((R)-3-(naphthalene-1-yl)isoxazolidine-2-yl)pyrimidine-4-yl)amino)phenyl) acrylamide | ¹H NMR (400 MHz, Chloroform-d) δ 8.90 (s, 1H), 8.44 (s, 1H), 8.37 (s, 1H), 8.15 (d, J = 8.3 Hz, 1H), 7.88 (dd, J = 7.7, 1.4 Hz, 1H), 7.77 (dd, J = 7.7, 5.2 Hz, 2H), 7.60-7.41 (m, 3H), 6.92 (s, 1H), 6.77 (d, J = 12.4 Hz, 2H), 6.45-6.33 (m, 2H), 6.26 (dd, J = 16.9, 10.0 Hz, 1H), 5.74 (dd, J = 9.9, 1.6 Hz, 1H), 4.24-4.11 (m, 2H), 3.85 (s, 3H), 3.78-3.65 (m, 2H), 3.06 (s, 2H), 3.03-2.91 (m, 1H), 2.88 (d, J = 10.8 Hz, 2H), 2.72 (dt, J = 12.7, 10.3 Hz, 2H), 2.41 (dtd, J = 11.9, 7.9, 3.9 Hz, 1H), 2.29 (d, J = 4.0 Hz, 1H), 2.07 (d, J = 12.4 Hz, 2H), 1.90 (t, J = 10.6 Hz, 2H), 1.67 (dt, J = 12.2, 6.0 Hz, 2H), 1.21 (d, J = 6.2 Hz, 6H), ; 664.5 [M + H]⁺ | 1.30 |

TABLE 1-continued

| Example Compound | Structure | Name of Compound | ¹H NMR[:]; MS [M + H]⁺ | UPLC r.t. (min) |
|---|---|---|---|---|
| 492 | 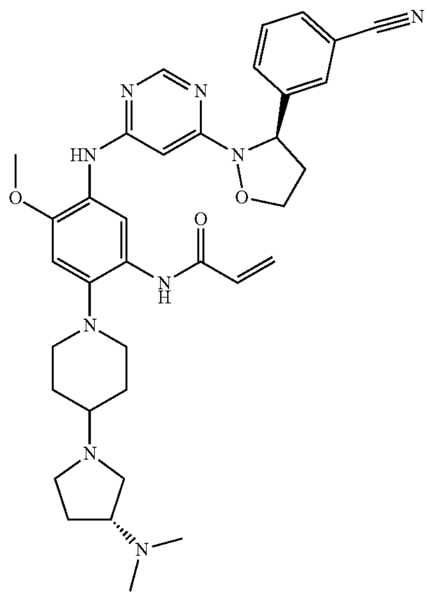 [SMILES: C=CC(=O)Nc1cc(Nc2cc(N3OCC[C@@H]3c3cccc(C#N)c3)ncn2)c(OC)cc1N1CCC(N2CC[C@@H](N(C)C)C2)CC1] | N-(5-((6-((R)-3-(3-cyanophenyl)isoxazolidine-2-yl)pyrimidine-4-yl)amino)-2-(4-((R)-3-(dimethylamino)pyrolidine-1-yl)piperidine-1-yl)-4-methoxyphenyl)acrylamide | ¹H NMR (400 MHz, CDCl₃) δ 8.85 (s, 1H), 8.49 (s, 1H), 8.35 (s, 1H), 7.79 (s, 1H), 7.71 (d, J = 7.9 Hz, 1H), 7.54 (d, J = 7.7 Hz, 1H), 7.45 (t, J = 7.8 Hz, 1H), 7.01 (s, 1H), 6.75 (s, 1H), 6.73 (s, 1H), 6.38-6.12 (m, 2H), 5.75-5.65 (m, 2H), 4.16 (td, J = 8.0, 4.1 Hz, 1H), 4.08 (q, J = 8.0 Hz, 1H), 3.85 (s, 3H), 3.13-3.06 (m, 1H), 3.06-2.98 (m, 2H), 2.98-2.90 (m, 2H), 2.85-2.69 (m, 3H), 2.68-2.62 (m, 1H), 2.54-2.47 (m, 1H), 2.38-2.23 (m, 8H), 2.13-2.02 (m, 3H), 1.90-1.68 (m, 3H); 638.56 [M + H]⁺ | 0.99 |
| 493 | 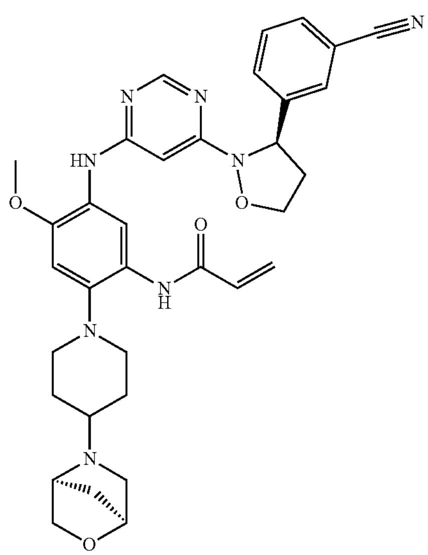 [SMILES: C=CC(=O)Nc1cc(Nc2cc(N3OCC[C@@H]3c3cccc(C#N)c3)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((R)-3-(3-cyanophenyl)isoxazolidine-2-yl)pyrimidine-4-yl)amino)-4-methoxyphenyl)acrylamide | ; 623.60 [M + H]⁺ | 1.11 |

TABLE 1-continued

| Example Compound | Structure | Name of Compound | ¹H NMR[[:]]; MS [M + H]⁺ | UPLC r.t. (min) |
|---|---|---|---|---|
| 494 | 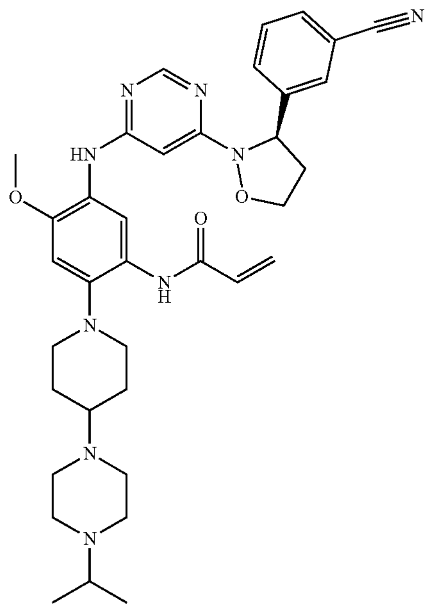 [SMILES: C=CC(=O)Nc1cc(Nc2cc(N3OCC[C@@H]3c3cccc(C#N)c3)ncn2)c(OC)cc1N1CCC(N2CCN(C(C)C)CC2)CC1] | N-(5-((6-((R)-3-(3-cyanophenyl)isoxazolidine-2-yl)pyrimidine-4-yl)amino)-2-(4-(4-isopropylpiperazine-1-yl)piperidine-1-yl)-4-methoxyphenyl)acrylamide | ¹H NMR (400 MHz, CDCl₃) δ 8.86 (s, 1H), 8.46 (s, 1H), 8.36 (s, 1H), 7.79 (s, 1H), 7.71 (d, J = 7.9 Hz, 1H), 7.54 (d, J = 7.7 Hz, 1H), 7.45 (t, J = 7.8 Hz, 1H), 6.93 (s, 1H), 6.76 (s, 1H), 6.73 (s, 1H), 6.38-6.20 (m, 2H), 5.76-5.69 (m, 2H), 4.16 (td, J = 8.0, 4.1 Hz, 1H), 4.08 (q, J = 8.0 Hz, 1H), 3.85 (s, 3H), 3.10-3.02 (m, 2H), 2.86-2.68 (m, 7H), 2.38-2.29 (m, 2H), 2.14-2.06 (m, 2H), 1.73-1.60 (m, 7H), 1.10 (s, 3H), 1.08 (s, 3H); 652.68 [M + H]⁺ | 1.07 |
| 495 | 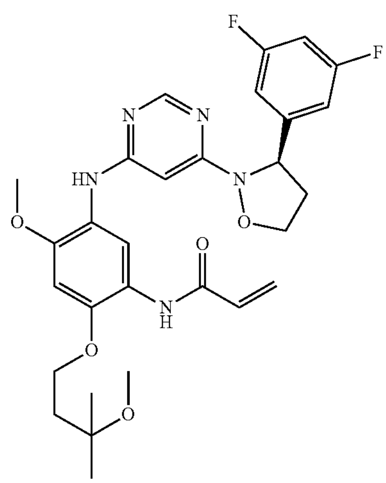 [SMILES: C=CC(=O)Nc1cc(Nc2cc(N3OCC[C@@H]3c3cc(F)cc(F)c3)ncn2)c(OC)cc1OCCC(C)(C)OC] | N-(5-((6-((R)-3-(3,5-difluorophenyl)isoxazolidine-2-yl)pyrimidine-4-yl)amino)-4-methoxy-2-(3-methoxy-3-methylbutoxy)phenyl)acrylamide | ¹H NMR (400 MHz, CDCl₃) δ 8.79 (s, 1H), 8.33 (s, 1H), 8.15 (s, 1H), 7.03-6.97 (m, 2H), 6.75 (s, 1H), 6.71-6.64 (m, 1H), 6.61 (s, 1H), 6.58 (s, 1H), 6.42-6.26 (m, 2H), 5.72 (dd, J = 9.7, 1.9 Hz, 1H), 5.66 (dd, J = 8.6, 4.5 Hz, 1H), 4.18-4.09 (m, 3H), 4.06-3.99 (m, 1H), 3.84 (s, 3H), 3.27 (s, 3H), 2.80-2.72 (m, 1H), 2.37-2.28 (m, 1H), 2.04 (t, J = 6.5 Hz, 2H), 1.29 (s, 6H); 570.38 [M + H]⁺ | 1.60 |
| 496 | 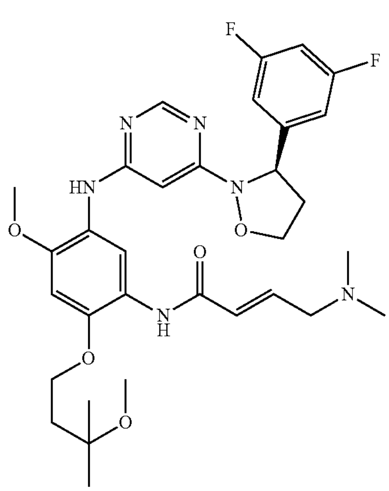 [SMILES: COc1cc(OCCC(C)(C)OC)c(NC(=O)/C=C/CN(C)C)cc1Nc1cc(N2OCC[C@@H]2c2cc(F)cc(F)c2)ncn1] | N-(5-((6-((R)-3-(3,5-difluorophenyl)isoxazolidine-2-yl)pyrimidine-4-yl)amino)-4-methoxy-2-(3-methoxy-3-methylbutoxy)phenyl)-(E)-4-(dimethylamino)but-2-enamide | ¹H NMR (400 MHz, CDCl₃) δ 8.75 (s, 1H), 8.31 (s, 1H), 7.99 (s, 1H), 7.04-6.85 (m, 4H), 6.70-6.64 (m, 1H), 6.60 (s, 1H), 6.57 (s, 1H), 6.15 (d, J = 15.3 Hz, 1H), 5.66 (dd, J = 8.6, 4.6 Hz, 1H), 4.18-4.09 (m, 3H), 4.03 (q, J = 8.0 Hz, 1H), 3.84 (s, 3H), 3.27 (s, 3H), 3.15 (d, J = 6.1 Hz, 2H), 2.80-2.71 (m, 1H), 2.35-2.28 (m, 7H), 2.07-2.02 (m, 2H), 1.29 (s, 6H); 627.53 [M + H]⁺ | 1.29 |

TABLE 1-continued

| Example Compound | Structure | Name of Compound | $^1$H NMR[[:]]; MS [M + H]$^+$ | UPLC r.t. (min) |
|---|---|---|---|---|
| 497 | 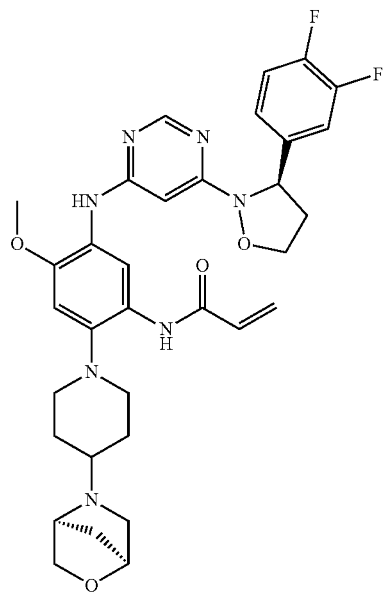 [SMILES: C=CC(=O)Nc1cc(Nc2cc(N3OCC[C@@H]3c3ccc(F)c(F)c3)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((R)-3-(3,4-difluorophenyl)isoxazolidine-2-yl)pyrimidine-4-yl)amino)-4-methoxyphenyl)acrylamide | 634.4 [M + H]$^+$ | 1.21 |
| 498 | 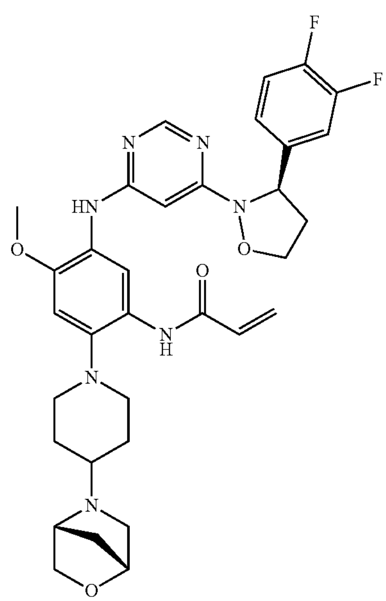 [SMILES: C=CC(=O)Nc1cc(Nc2cc(N3OCC[C@@H]3c3ccc(F)c(F)c3)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-5-((6-((R)-3-(3,4-difluorophenyl)isoxazolidine-2-yl)pyrimidine-4-yl)amino)-4-methoxyphenyl)acrylamide | 634.5 [M + H]$^+$ | 1.22 |

TABLE 1-continued

| Example Compound | Structure | Name of Compound | ¹H NMR[[:]]; MS [M + H]⁺ | UPLC r.t. (min) |
|---|---|---|---|---|
| 499 | 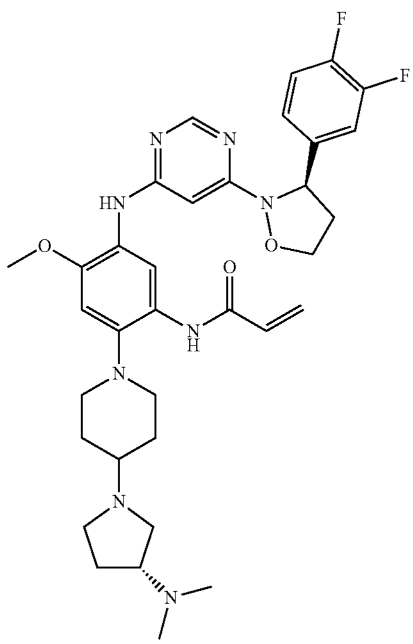 [SMILES: C=CC(=O)Nc1cc(Nc2cc(N3OCC[C@@H]3c3ccc(F)c(F)c3)ncn2)c(OC)cc1N1CCC(N2CC[C@@H](N(C)C)C2)CC1] | N-(5-((6-((R)-3-(3,4-difluorophenyl)isoxazolidine-2-yl)pyrimidine-4-yl)amino)-2-(4-((R)-3-(dimethylamino)pyrolidine-1-yl)piperidine-1-yl)-4-methoxyphenyl)acrylamide | ¹H NMR (400 MHz, DMSO-d₆) δ 10.50 (s, 1H), 9.47 (s, 1H), 8.37 (s, 1H), 7.83 (s, 1H), 7.48-7.39 (m, 2H), 7.26-7.20 (m, 1H), 7.02 (s, 1H), 6.79-6.68 (m, 1H), 6.27 (dd, J = 17.0, 1.9 Hz, 1H), 6.17-6.08 (m, 1H), 5.80-5.76 (m, 1H), 5.58-5.54 (m, 2H), 4.32 (dd, J = 7.6, 4.5 Hz, 1H), 4.12-3.95 (m, 3H), 3.84 (s, 3H), 3.65 (d, J = 9.5 Hz, 2H), 3.46 (s, 1H), 3.34-3.27 (m, 2H), 2.95 (dd, J = 8.1, 4.4 Hz, 1H), 2.85 (s, 9H), 2.46 (d, J = 8.9 Hz, 2H), 2.38-2.31 (m, 1H), 2.21 (d, J = 25.6 Hz, 4H), ; 631.3 [M + H]⁺ | 1.17 |
| 500 | 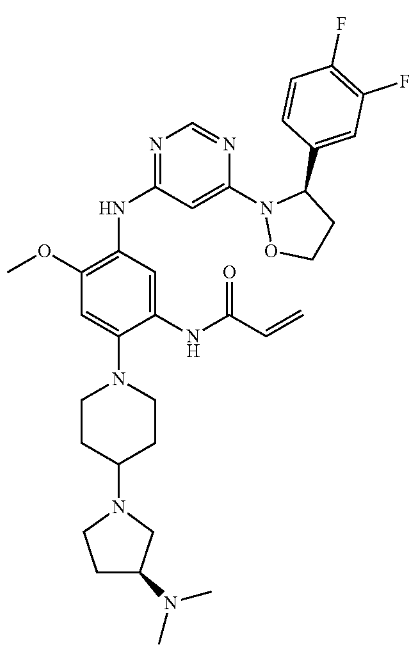 [SMILES: C=CC(=O)Nc1cc(Nc2cc(N3OCC[C@@H]3c3ccc(F)c(F)c3)ncn2)c(OC)cc1N1CCC(N2CC[C@H](N(C)C)C2)CC1] | N-(5-((6-((R)-3-(3,4-difluorophenyl)isoxazolidine-2-yl)pyrimidine-4-yl)amino)-2-(4-((S)-3-(dimethylamino)pyrolidine-1-yl)piperidine-1-yl)-4-methoxyphenyl)acrylamide | ¹H NMR (400 MHz, DMSO-d₆) δ 10.25 (s, 1H), 9.34 (s, 1H), 8.34 (s, 1H), 7.85 (s, 1H), 7.44 (dtd, J = 10.5, 8.5, 7.2, 3.0 Hz, 2H), 7.26-7.16 (m, 1H), 6.96 (d, J = 7.6 Hz, 1H), 6.76-6.66 (m, 1H), 6.25 (dd, J = 17.0, 1.9 Hz, 1H), 6.11 (s, 1H), 5.76 (dd, J = 10.1, 1.9 Hz, 1H), 5.54 (dd, J = 8.5, 5.3 Hz, 1H), 4.31 (q, J = 3.2 Hz, 2H), 4.04 (dd, J = 18.6, 11.1 Hz, 3H), 3.82 (s, 3H), 3.75 (s, 1H), 3.66-3.50 (m, 2H), 3.39 (d, J = 11.8 Hz, 1H), 3.26 (d, J = 11.4 Hz, 2H), 2.93 (ddd, J = 18.3, 9.0, 5.0 Hz, 1H), 2.87-2.77 (m, 8H), 2.47-2.39 (m, 1H), 2.36-2.28 (m, 1H), 2.24-2.05 (m, 4H), ; 631.3 [M + H]⁺ | 1.1 |

TABLE 1-continued

| Example Compound | Structure | Name of Compound | ¹H NMR[[:]]; MS [M + H]⁺ | UPLC r.t. (min) |
|---|---|---|---|---|
| 501 | 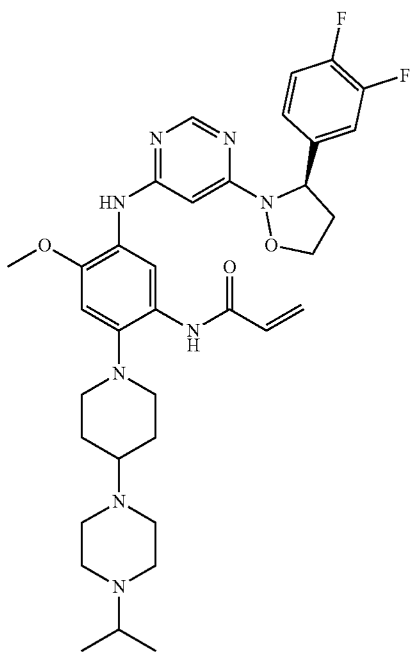 [SMILES: C=CC(=O)Nc1cc(Nc2cc(N3OCC[C@@H]3c3ccc(F)c(F)c3)ncn2)c(OC)cc1N1CCC(N2CCN(C(C)C)CC2)CC1] | N-(5-((6-((R)-3-(3,4-difluorophenyl)isoxazolidine-2-yl)pyrimidine-4-yl)amino)-2-(4-(4-isopropylpiperazine-1-yl)piperidine-1-yl)-4-methoxyphenyl)acrylamide | 663.5 [M + H]⁺ | 1.16 |
| 502 | 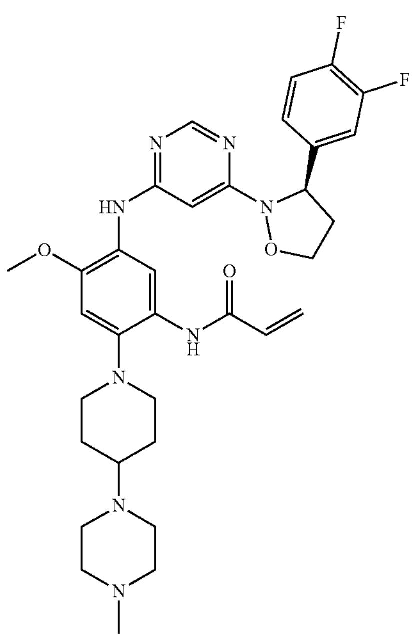 [SMILES: C=CC(=O)Nc1cc(Nc2cc(N3OCC[C@@H]3c3ccc(F)c(F)c3)ncn2)c(OC)cc1N1CCC(N2CCN(C)CC2)CC1] | N-(5-((6-((R)-3-(3,4-difluorophenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, DMSO-d₆) δ 10.19 (s, 1H), 9.24 (s, 1H), 8.33 (s, 1H), 7.90 (s, 1H), 7.48-7.41 (m, 2H), 7.25-7.19 (m, 1H), 6.92 (s, 1H), 6.75-6.67 (m, 1H), 6.25 (dd, J = 17.0, 1.9 Hz, 1H), 6.11 (s, 1H), 5.76 (dd, J = 10.0, 2.0 Hz, 1H), 5.53 (dd, J = 8.5, 5.4 Hz, 1H), 4.31 (d, J = 4.5 Hz, 1H), 4.06 (d, J = 7.8 Hz, 1H), 3.81 (s, 3H), 3.76 (d, J = 18.4 Hz, 3H), 3.62 (d, J = 8.9 Hz, 5H), 3.44 (d, J = 5H), 3.24 (d, J = 11.3 Hz, 2H), 2.92 (dd, J = 8.2, 4.4 Hz, 1H), 2.83 (d, J = 14.2 Hz, 5H), 2.37-2.28 (m, 1H), 2.23-2.06 (m, 4H), ; 635.3 [M + H]⁺ | 1.13 |

TABLE 1-continued

| Example Compound | Structure | Name of Compound | ¹H NMR[[:]]; MS [M + H]⁺ | UPLC r.t. (min) |
|---|---|---|---|---|
| 503 | 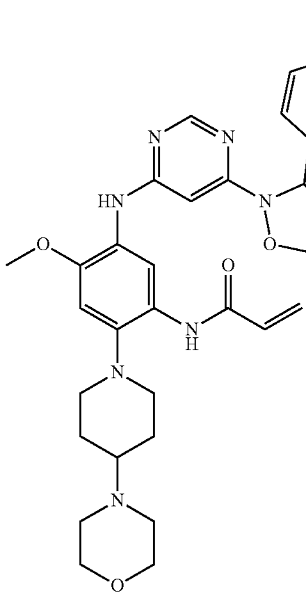 | N-(5-((6-((R)-3-(3,4-difluorophenyl)isoxazolidine-2-yl)pyrimidine-4-yl)amino)-4-methoxy-2-(4-morpholinopiperidine-1-yl)phenyl)acrylamide | ¹H NMR (400 MHz, DMSO-$d_6$) δ 10.11 (s, 1H), 9.23 (s, 1H), 8.33 (s, 1H), 7.89 (s, 1H), 7.44 (ddq, J = 11.4, 6.3, 3.0, 2.3 Hz, 2H), 7.26-7.20 (m, 1H), 6.92 (s, 1H), 6.69 (dd, J = 17.0, 10.2 Hz, 1H), 6.25 (dd, J = 17.0, 1.9 Hz, 1H), 6.11 (s, 1H), 5.76 (dd, J = 10.1, 1.9 Hz, 1H), 5.56-5.52 (m, 1H), 4.29 (dd, J = 7.6, 4.4 Hz, 1H), 4.08-4.03 (m, 1H), 3.99 (d, J = 7.5 Hz, 4H), 3.44 (d, J = 12.0 Hz, 2H), 3.24 (d, J = 11.3 Hz, 3H), 3.17-3.08 (m, 2H), 2.97-2.87 (m, 1H), 2.79 (t, J = 11.8 Hz, 2H), 2.33 (ddd, J = 10.0, 7.8, 5.2 Hz, 1H), 2.22 (d, J = 10.3 Hz, 2H), 2.13-2.01 (m, 2H), ; 622.3 [M + H]⁺ | 1.17 |
| 504 | 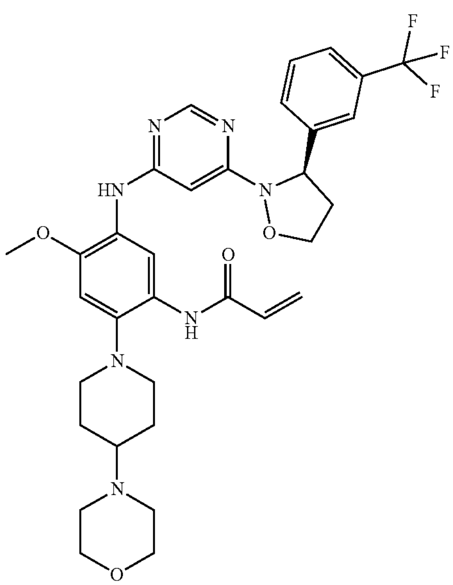 [SMILES: C=CC(=O)Nc1cc(Nc2cc(N3OCC[C@@H]3c3cccc(C(F)(F)F)c3)ncn2)c(OC)cc1N1CCC(N2CCOCC2)CC1] | N-(4-methoxy-2-(4-morpholinopiperidine-1-yl)-5-((6-((R)-3-(3-(trifluoromethyl)phenyl)isoxazolidine-2-yl)pyrimidine-4-yl)amino)phenyl)acrylamide | ¹H NMR (400 MHz, Chloroform-d) δ 8.74 (s, 1H), 8.44 (s, 1H), 8.29 (s, 1H), 7.75 (s, 1H), 7.71 (s, 1H), 7.65 (d, J = 7.6 Hz, 1H), 7.48 (dt, J = 15.3, 7.7 Hz, 2H), 6.75 (s, 1H), 6.66 (s, 1H), 6.40-6.33 (m, 1H), 6.28 (dd, J = 16.9, 9.7 Hz, 1H), 5.74 (dt, J = 9.0, 2.4 Hz, 2H), 4.15 (td, J = 8.0, 4.2 Hz. 1H), 4.07 (q, J = 8.0 Hz, 1H), 3.84 (s, 3H), 3.81 (t, J = 4.7 Hz, 4H), 3.08 (t, J = 8.8 Hz, 2H), 2.83 (tt, J = 8.1, 4.0 Hz, 1H), 2.77 (d, J = 11.7 Hz, 2H), 2.73 (d, J = 3.8 Hz, 4H), 2.45 (tt, J = 11.2, 3.8 Hz, 1H), 2.36 (dq, J = 11.9, 3.5 Hz, 1H), 2.12-2.07 (m, 2H), 1.74 (qd, J = 12.1, 4.0 Hz, 2H); 654.5 [M + H]⁺ | 1.29 |

TABLE 1-continued

| Example Compound | Structure | Name of Compound | ¹H NMR[[:]]; MS [M + H]⁺ | UPLC r.t. (min) |
|---|---|---|---|---|
| 505 | 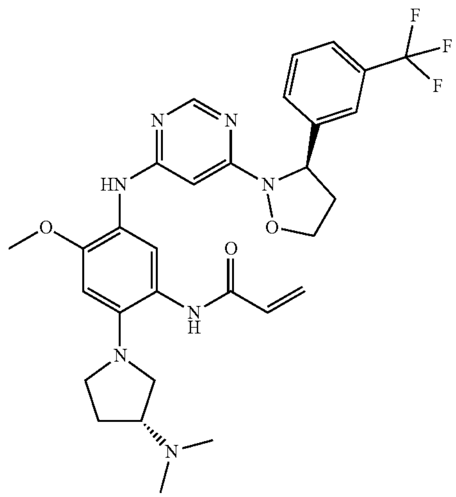 [SMILES: C=CC(=O)Nc1cc(Nc2cc(N3OCC[C@@H]3c3cccc(C(F)(F)F)c3)ncn2)c(OC)cc1N1CC[C@@H](N(C)C)C1] | N-(2-((R)-3-(dimethylamino)pyrolidine-1-yl)-4-methoxy-5-((6-((R)-3-(3-(trifluoromethyl)phenyl)isoxazolidine-2-yl)pyrimidine-4-yl)amino)phenyl)acrylamide | 598.4 [M + H]⁺ | 1.24 |
| 506 | 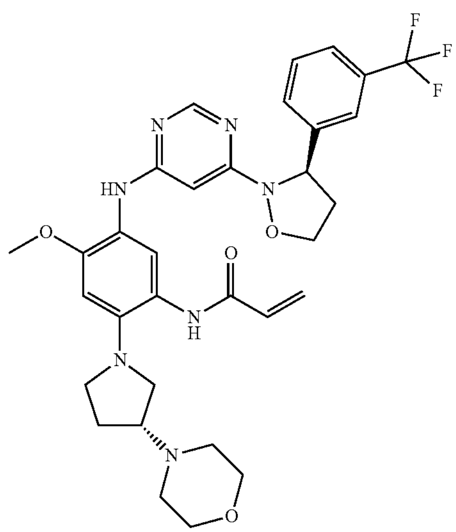 [SMILES: C=CC(=O)Nc1cc(Nc2cc(N3OCC[C@@H]3c3cccc(C(F)(F)F)c3)ncn2)c(OC)cc1N1CC[C@@H](N2CCOCC2)C1] | N-(4-methoxy-2-((R)-3-morpholinopyrolidine-1-yl)-5-((6-((R)-3-(3-(trifluoromethyl)phenyl)isoxazolidine-2-yl)pyrimidine-4-yl)amino)phenyl)acrylamide | ¹H NMR (400 MHz, Methanol-$d_4$) δ 8.15 (d, J = 0.5 Hz, 1H), 7.78-7.69 (m, 3H), 7.60-7.53 (m, 2H), 6.71 (s, 1H), 6.58 (dd, J = 17.0, 10.3 Hz, 1H), 6.41-6.32 (m, 2H), 5.80 (dd, = 10.3, 1.4 Hz, 1H), 5.65 (dd, J = 8.5, 4.8 Hz, 1H), 4.17 (td, J = 7.9, 4.2 Hz, 1H), 4.01-3.94 (m, 1H), 3.88 (s, 3H), 3.84 (t, J = 4.4 Hz, 4H), 3.39-3.29 (m, 8H), 2.95-2.83 (m, 4H), 2.40-2.28 (m, 2H), 2.05 (t, J = 15.6 Hz, 1H); 640.4 [M + H]⁺ | 1.25 |
| 507 | 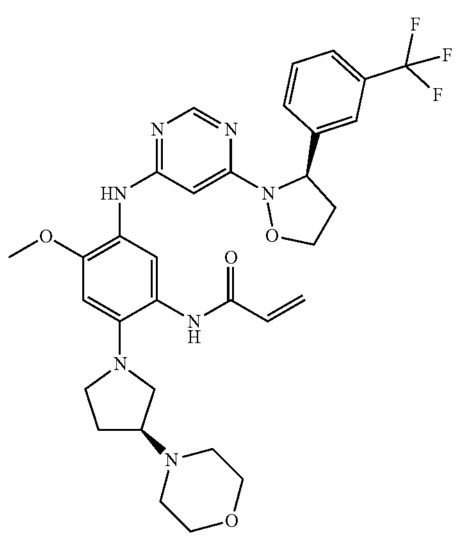 [SMILES: C=CC(=O)Nc1cc(Nc2cc(N3OCC[C@@H]3c3cccc(C(F)(F)F)c3)ncn2)c(OC)cc1N1CC[C@H](N2CCOCC2)C1] | N-(4-methoxy-2-((S)-3-morpholinopyrolidine-1-yl)-5-((6-((R)-3-(3-(trifluoromethyl)phenyl)isoxazolidine-2-yl)pyrimidine-4-yl)amino)phenyl)acrylamide | ¹H NMR (400 MHz, Methanol-$d_4$) δ 8.14 (s, 1H), 7.73 (t, J = 11.3 Hz, 3H), 7.60-7.51 (m, 2H), 6.67 (s, 1H), 6.54 (dd, J = 17.0, 10.2 Hz, 1H), 6.40-6.31 (m, 2H), 5.79 (dd, J = 10.3, 1.5 Hz, 1H), 5.64 (dd, J = 8.5, 4.8 Hz, 1H), 4.15 (td, J = 7.9, 4.2 Hz, 1H), 3.97 (d, J = 7.9 Hz, 1H), 3.87 (s, 3H), 3.77 (t, J = 4.6 Hz, 4H), 3.39-3.25 (m, 7H), 3.11-3.01 (m, 1H), 2.91-2.78 (m, 1H), 2.76-2.56 (m, 4H), 2.40-2.30 (m, 1H), 2.25 (dtd, J = 12.9, 6.5, 3.3 Hz, 1H), 2.01-1.86 (m, 1H); 640.4 [M + H]⁺ | 1.22 |

TABLE 1-continued

| Example Compound | Structure | Name of Compound | ¹H NMR[[:]]; MS [M + H]⁺ | UPLC r.t. (min) |
|---|---|---|---|---|
| 508 | 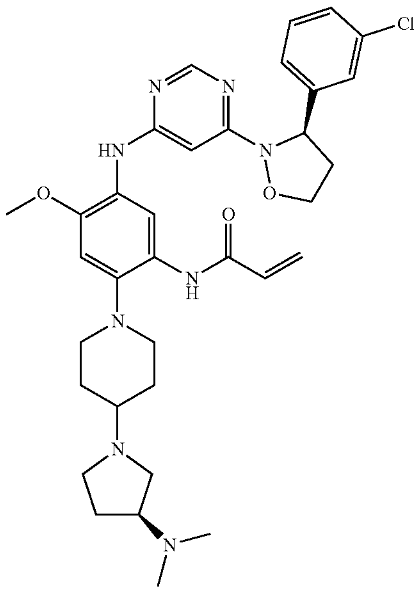 [SMILES: C=CC(=O)Nc1cc(Nc2cc(N3OCC[C@@H]3c3cccc(Cl)c3)ncn2)c(OC)cc1N1CCC(N2CC[C@H](N(C)C)C2)CC1] | N-(5-((6-((R)-3-(3-chlorophenyl)isoxazolidine-2-yl)pyrimidine-4-yl)amino)-2-(4-((S)-3-(dimethylamino)pyrolidine-1-yl)piperidine-1-yl)-4-methoxyphenyl)acrylamide | ; 647.5 [M + H]⁺ | 1.14 |
| 509 | 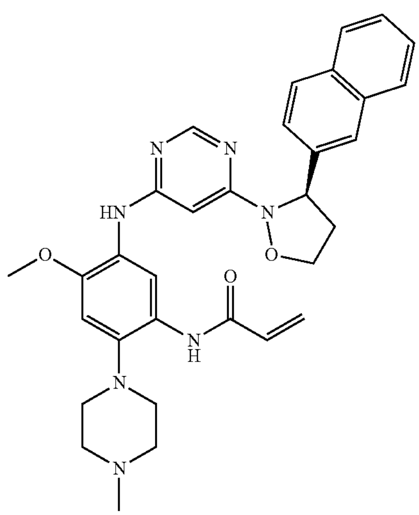 [SMILES: C=CC(=O)Nc1cc(Nc2cc(N3OCC[C@@H]3c3ccc4ccccc4c3)ncn2)c(OC)cc1N1CCN(C)CC1] | N-(4-methoxy-2-(4-methylpiperazine-1-yl)-5-((6-((R)-3-(naphthalene-2-yl)isoxazolidine-2-yl)pyrimidine-4-yl)amino)phenyl)acrylamide | ¹H NMR (400 MHz, Chloroform-d) δ 8.92 (s, 1H), 8.54 (s, 1H), 8.38 (d, J = 0.9 Hz, 1H), 7.94 (d, J = 1.7 Hz, 1H), 7.85-7.79 (m, 3H), 7.44 (td, J = 7.4, 6.7, 3.8 Hz, 2H), 6.97 (s, 1H), 6.77 (d, J = 24.0 Hz, 2H), 6.44-6.22 (m, 2H), 5.85 (dd, J = 8.7, 4.5 Hz, 1H), 5.76 (dd, J = 9.9, 1.6 Hz, 1H), 4.20 (td, J = 7.9, 4.4 Hz, 1H), 4.11 (q, J = 7.9 Hz, 1H), 3.84 (s, 3H), 3.64-3.57 (m, 2H), 3.03 (d, J = 7.4 Hz, 2H), 2.94-2.90 (m, 3H), 2.40 (s, 3H), 1.51 (t, J = 7.4 Hz, 4H), ; 566.4 [M + H]⁺ | 1.21 |

TABLE 1-continued

| Example Compound | Structure | Name of Compound | ¹H NMR[[:]]; MS [M + H]⁺ | UPLC r.t. (min) |
|---|---|---|---|---|
| 510 | 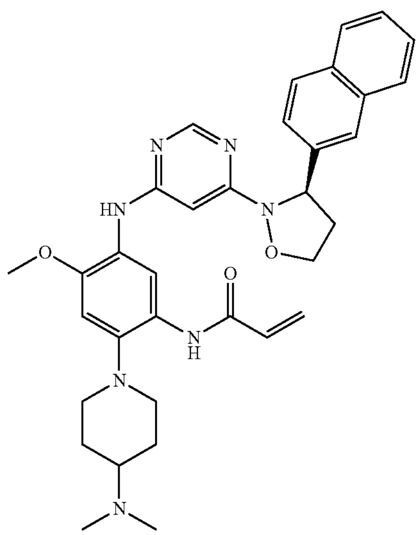 [SMILES: C=CC(=O)Nc1cc(Nc2cc(N3OCC[C@@H]3c3ccc4ccccc4c3)ncn2)c(OC)cc1N1CCC(N(C)C)CC1] | N-(2-(4-(dimethylamino)piperidine-1-yl)-4-methoxy-5-((6-((R)-3-(naphthalene-2-yl)isoxazolidine-2-yl)pyrimidine-4-yl)amino)phenyl)acrylamide | ¹H NMR (400 MHz, Chloroform-d) δ 8.87 (s, 1H), 8.37 (d, J = 1.0 Hz, 1H), 7.94 (s, 1H), 7.81 (dt, J = 9.3, 3.7 Hz, 2H), 7.44 (ddt, J = 9.1, 6.8, 3.3 Hz, 2H), 7.02 (s, 1H), 6.73 (d, J = 5.2 Hz, 2H), 6.41-6.27 (m, 2H), 6.22-6.17 (m, 1H), 5.85 (dd, J = 8.6, 4.5 Hz, 1H), 5.75 (dd, J = 9.7, 1.8 Hz, 1H), 5.62 (dd, J = 9.1, 3.1 Hz, 1H), 4.20 (td, J = 8.0, 4.5 Hz, 1H), 4.11 (q, J = 7.9 Hz, 1H), 3.84 (s, 3H), 3.72 (dd, J = 14.8, 5.8 Hz, 2H), 3.55 (h, J = 6.7 Hz, 2H), 2.99 (t, J = 7.4 Hz, 1H), 2.77-2.71 (m, 2H), 2.46 (s, 6H), 2.09 (d, J = 12.4 Hz, 2H), 1.76 (qd, J = 12.1, 3.9 Hz, 2H), 1.41 (d, J = 7.4 Hz, 1H), ; 594.4 [M + H]⁺ | 1.21 |
| 511 | 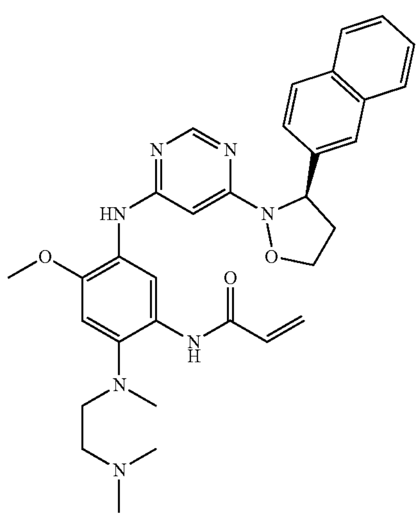 [SMILES: C=CC(=O)Nc1cc(Nc2cc(N3OCC[C@@H]3c3ccc4ccccc4c3)ncn2)c(OC)cc1N(C)CCN(C)C] | N-(2-((2-(dimethylamino)ethyl)(methyl)amino)-4-methoxy-5-((6-((R)-3-(naphthalene-2-yl)isoxazolidine-2-yl)pyrimidine-4-yl)amino)phenyl)acrylamide | ¹H NMR (400 MHz, Chloroform-d) δ 9.57 (s, 1H), 8.87 (s, 1H), 8.36 (s, 1H), 7.94 (s, 1H), 7.81 (dd, J = 8.2, 3.8 Hz, 3H), 7.57 (dd, J = 8.5, 1.8 Hz, 1H), 7.44 (dq, J = 7.6, 5.3, 3.9 Hz, 2H), 7.10 (s, 1H), 6.73 (d, J = 28.7 Hz, 2H), 6.42 (dd, J = 16.8, 2.1 Hz, 1H), 5.85 (dd, J = 8.7 4.6 Hz, 1H), 5.71 (dd, J = 10.1, 2.0 Hz, 1H), 4.23 (td, J = 7.9, 4.3 Hz, 1H), 4.15 (t, J = 8.0 Hz, 1H), 3.84 (s, 3H), 3.69-3.62 (m, 2H), 3.23-3.19 (m, 2H), 3.12-3.07 (m, 2H), 2.99 (s, 1H), 2.72 (s, 3H), 2.70 (s, 6H), ; 568.4 [M + H]⁺ | 1.28 |

TABLE 1-continued

| Example Compound | Structure | Name of Compound | ¹H NMR[[:]]; MS [M + H]⁺ | UPLC r.t. (min) |
|---|---|---|---|---|
| 512 | 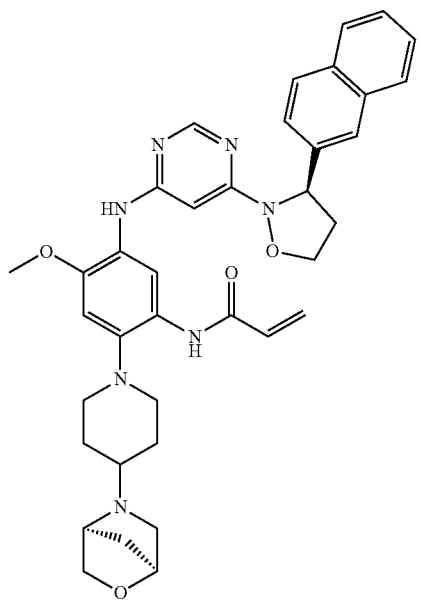 [SMILES: C=CC(=O)Nc1cc(Nc2cc(N3OCC[C@@H]3c3ccc4ccccc4c3)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-4-methoxy-5-((6-((R)-3-(naphthalene-2-yl)isoxazolidine-2-yl)pyrimidine-4-yl)amino)phenyl) acrylamide | ¹H NMR (400 MHz, Chloroform-d) δ 8.80 (s, 1H), 8.52 (s, 1H), 8.35 (s, 1H), 7.93 (d, J = 1.7 Hz, 1H), 7.86-7.79 (m, 3H), 7.56 (dd, J = 8.5, 1.8 Hz, 1H), 7.45 (qd, J = 7.4, 3.6 Hz, 2H), 6.70 (d, J = 3.7 Hz, 2H), 6.54-6.34 (m, 2H), 5.83 (dd, J = 8.7, 4.7 Hz, 1H), 5.77 (dd, J = 9.6, 2.0 Hz, 1H), 4.61 (s, 1H), 4.39 (s, 1H), 4.22 (tt, J = 7.9, 4.6 Hz, 2H), 4.11 (q, J = 7.9 Hz, 1H), 3.83 (d, J = 4.7 Hz, 3H), 3.69-3.62 (m, 3H), 3.12 (d, J = 8.5 Hz, 3H), 2.89-2.68 (m, 4H), 2.60-2.38 (m, 4H), 2.07 (dt, J = 33.4, 13.3 Hz, 3H), ; 648.6 [M + H]⁺ | 1.24 |
| 513 | 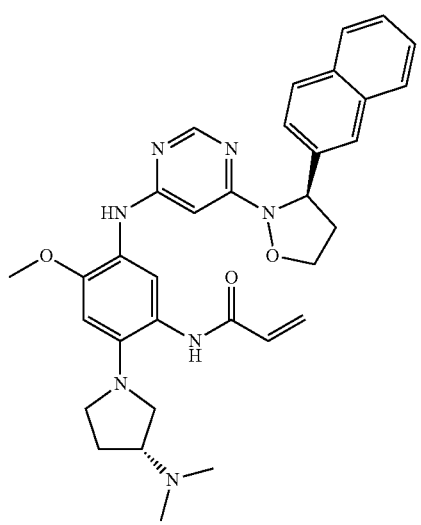 [SMILES: C=CC(=O)Nc1cc(Nc2cc(N3OCC[C@@H]3c3ccc4ccccc4c3)ncn2)c(OC)cc1N1CC[C@@H](N(C)C)C1] | N-(2-((R)-3-(dimethylamino)pyrolidine-1-yl)-4-methoxy-5-((6-((R)-3-(naphthalene-2-yl)isoxazolidine-2-yl)pyrimidine-4-yl)amino)phenyl) acrylamide | ¹H NMR (400 MHz, DMSO-d₆) δ 9.33 (s, 1H), 8.53 (s, 1H), 8.14 (s, 1H), 7.90 (td, J = 7.5, 6.8, 3.3 Hz, 4H), 7.61-7.44 (m, 4H), 6.59 (s, 1H), 6.49 (dd, J = 17.1, 10.2 Hz, 1H), 6.30 (s, 1H), 6.20 (dd, J = 17.1, 2.1 Hz, 1H), 5.70 (dq, J = 11.1, 5.1, 3.6 Hz, 2H), 4.18 (td, J = 7.8, 3.7 Hz, 1H), 3.90-3.79 (m, 4H), 3.32 (s, 6H), 2.83 (dtd, J = 12.1, 8.1, 3.8 Hz, 2H), 2.65 (d, J = 19.7 Hz, 3H), 2.39-2.31 (m, 2H), 2.25 (s, 1H), 1.97 (s, 1H), ; 580.4 [M + H]⁺ | 1.19 |

TABLE 1-continued

| Example Compound | Structure | Name of Compound | ¹H NMR[[:]]; MS [M + H]⁺ | UPLC r.t. (min) |
|---|---|---|---|---|
| 514 | 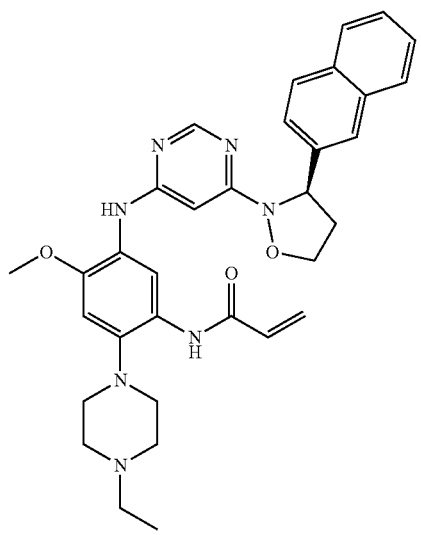 [SMILES: C=CC(=O)Nc1cc(Nc2cc(N3OCC[C@@H]3c3ccc4ccccc4c3)ncn2)c(OC)cc1N1CCN(CC)CC1] | N-(2-(4-ethylpiperazine-1-yl)-4-methoxy-5-((6-((R)-3-(naphthalene-2-yl)isoxazolidine-2-yl)pyrimidine-4-yl)amino)phenyl) acrylamide | ¹H NMR (400 MHz, DMSO-d₆) δ 9.54 (s, 1H), 9.06 (s, 1H), 8.86 (s, 1H), 8.26 (s, 1H), 8.20 (s, 1H), 7.94-7.88 (m, 3H), 7.56 (dd, J = 8.5, 1.7 Hz, 1H), 7.50 (tt, J = 8.1, 3.7 Hz, 2H), 6.84 (s, 1H), 6.66 (dd, J = 17.1, 10.2 Hz, 1H), 6.38 (s, 1H), 6.25 (dd, J = 17.0, 1.9 Hz, 1H), 5.79-5.74 (m, 1H), 5.70 (dd, J = 8.6, 5.3 Hz, 1H), 4.23 (d, J = 3.9 Hz, 1H), 3.92 (t, J = 7.9 Hz, 1H), 3.83 (s, 3H), 3.58 (d, J = 11.6 Hz, 2H), 3.22 (d, J = 11.8 Hz, 6H), 3.04 (t, J = 12.5 Hz, 2H), 2.91-2.82 (m, 1H), 2.36 (dt, J = 8.8, 5.1 Hz, 2H), 1.28 (t, J = 7.2 Hz, 3H), ; 580.4 [M + H]⁺ | 1.25 |
| 515 | 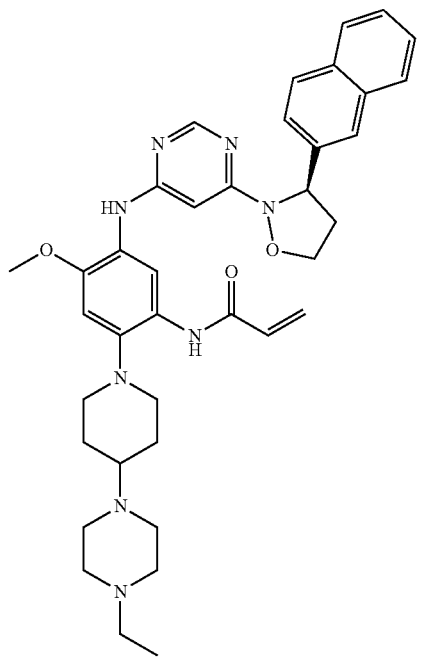 [SMILES: C=CC(=O)Nc1cc(Nc2cc(N3OCC[C@@H]3c3ccc4ccccc4c3)ncn2)c(OC)cc1N1CCC(N2CCN(CC)CC2)CC1] | N-(2-(4-(4-ethylpiperazine-1-yl)piperidine-1-yl)-4-methoxy-5-((6-((R)-3-(naphthalene-2-yl)isoxazolidine-2-yl)pyrimidine-4-yl)amino)phenyl) acrylamide | ¹H NMR (400 MHz, DMSO-d₆) δ 9.01 (s, 1H), 8.76 (s, 1H), 8.16 (d, J = 16.7 Hz, 2H), 7.95-7.86 (m, 4H), 7.56 (dd, J = 8.4, 1.8 Hz, 1H), 7.50 (qd, J = 7.6, 6.9, 3.7 Hz, 2H), 6.83 (s, 1H), 6.63 (dd, J = 16.9, 10.2 Hz, 1H), 6.35 (s, 1H), 6.23 (dd, J = 17.0, 1.9 Hz, 1H), 5.77-5.62 (m, 2H), 4.21 (dd, J = 7.7, 3.9 Hz, 1H), 3.91 (q, J = 8.1 Hz, 1H), 3.81 (s, 3H), 3.51 (s, 3H), 3.31 (s, 2H), 3.11 (d, J = 11.6 Hz, 4H), 2.94 (s, 1H), 2.91-2.81 (m, 2H), 2.72 (t, J = 11.8 Hz, 3H), 2.41-2.32 (m, 2H), 1.94 (s, 2H), 1.79 (s, 2H), 1.20 (t, J = 7.2 Hz, 3H), ; 663.5 [M + H]⁺ | 1.2 |

TABLE 1-continued

| Example Compound | Structure | Name of Compound | ¹H NMR[[:]]; MS [M + H]⁺ | UPLC r.t. (min) |
|---|---|---|---|---|
| 516 | 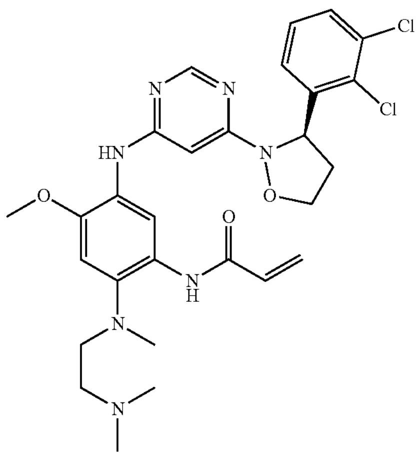 [SMILES: C=CC(=O)Nc1cc(Nc2cc(N3OCC[C@@H]3c3cccc(Cl)c3Cl)ncn2)c(OC)cc1N(C)CCN(C)C] | N-(5-((6-((R)-3-(2,3-dichlorophenyl)isoxazolidine-2-yl)pyrimidine-4-yl)amino)-2-((2-(dimethylamino)ethyl)(methyl)amino)-4-methoxyphenyl)acrylamide | ¹H NMR (400 MHz, Chloroform-d) δ 11.32 (s, 1H), 9.96 (s, 1H), 8.92 (s, 1H), 8.36 (s, 1H), 7.60 (d, J = 8.9 Hz, 1H), 7.37 (d, J = 9.4 Hz, 1H), 7.19 (t, J = 7.9 Hz, 1H), 6.96 (s, 1H), 6.82 (s, 1H), 6.77 (s, 1H), 6.40 (d, J = 16.5 Hz, 1H), 5.99 (s, 1H), 5.69 (d, J = 11.9 Hz, 1H), 4.12 (m, 2H), 3.85 (s, 3H), 3.69-3.61 (m, 1H), 3.08 (d, J = 7.4 Hz, 1H), 2.95 (d, J = 3.3 Hz, 2H), 2.73 (s, 3H), 2.43 (s, 6H), 2.24 (d, J = 12.4 Hz, 2H), ; 586.3 [M + H]⁺ | 1.37 |
| 517 | 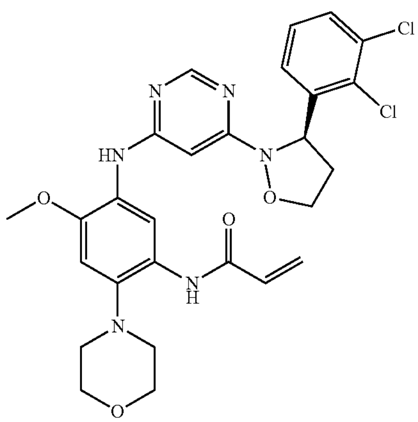 [SMILES: C=CC(=O)Nc1cc(Nc2cc(N3OCC[C@@H]3c3cccc(Cl)c3Cl)ncn2)c(OC)cc1N1CCOCC1] | N-(5-((6-((R)-3-(2,3-dichlorophenyl)isoxazolidine-2-yl)pyrimidine-4-yl)amino)-4-methoxy-2-morpholinophenyl)acrylamide | ¹H NMR (400 MHz, Chloroform-d) δ 8.93 (s, 1H), 8.51 (s, 1H), 8.37 (s, 1H), 7.60 (d, J = 8.8 Hz, 1H), 7.37 (d, J = 9.2 Hz, 1H), 7.19 (t, J = 7.9 Hz, 1H), 6.96 (s, 1H), 6.78 (d, J = 4.6 Hz, 2H), 6.37 (d, J = 17.0 Hz, 1H), 6.28 (m, 1H), 5.96 (m, 1H), 5.76 (d, J = 11.3 Hz, 1H), 4.11 (m, 2H), 3.87 (m, 7H), 2.96 (m, 1H), 2.89 (m, 4H), 2.24 (m, 1H), ; 571.3 [M + H]⁺ | 1.64 |
| 518 | 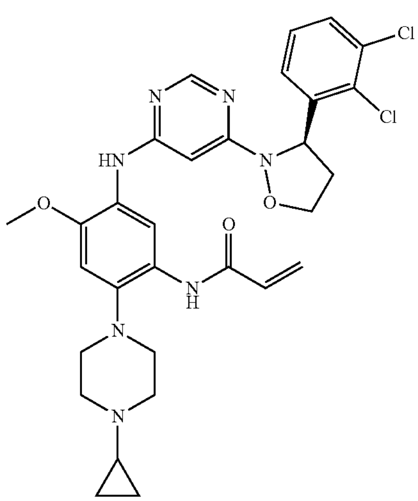 [SMILES: C=CC(=O)Nc1cc(Nc2cc(N3OCC[C@@H]3c3cccc(Cl)c3Cl)ncn2)c(OC)cc1N1CCN(C2CC2)CC1] | N-(2-(4-cyclopropylpiperazine-1-yl)-5-((6-((R)-3-(2,3-dichlorophenyl)isoxazolidine-2-yl)pyrimidine-4-yl)amino)-4-methoxyphenyl)acrylamide | ¹H NMR (400 MHz, Chloroform-d) δ 8.90 (s, 1H), 8.60 (s, 1H), 8.36 (s, 1H), 7.60 (d, J = 7.7 Hz, 1H), 7.37 (d, J = 9.3 Hz, 1H), 7.19 (t, J = 7.9 Hz, 1H), 6.94 (s, 1H), 6.78 (d, J = 13.6 Hz, 2H), 6.37 (d, J = 18.3 Hz, 1H), 6.30 (m, 1H), 5.96 (m, 1H), 5.75 (d, J = 9.8 Hz, 1H), 4.11 (m, 2H), 3.82 (s, 3H), 2.90 (m, 8H), 2.23 (m, 2H), 1.73 (m, 1H), 0.52 (d, J = 6.4 Hz, 2H), 0.47 (t, J = 3.8 Hz, 2H), ; 610.3 [M + H]⁺ | 1.36 |

TABLE 1-continued

| Example Compound | Structure | Name of Compound | ¹H NMR[[:]]; MS [M + H]⁺ | UPLC r.t. (min) |
|---|---|---|---|---|
| 519 | 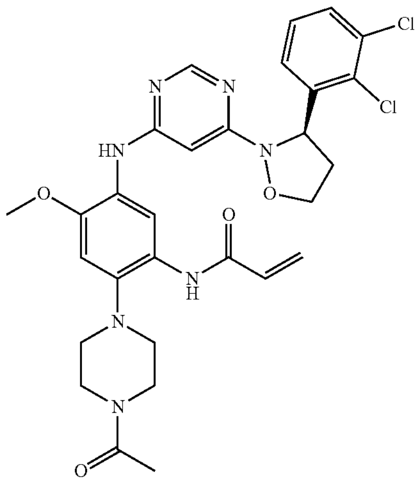 [SMILES: C=CC(=O)Nc1cc(Nc2cc(N3OCC[C@@H]3c3cccc(Cl)c3Cl)ncn2)c(OC)cc1N1CCN(C(C)=O)CC1] | N-(2-(4-acetylpiperazine-1-yl)-5-((6-((R)-3-(2,3-dichlorophenyl)isoxazolidine-2-yl)pyrimidine-4-yl)amino)-4-methoxyphenyl)acrylamide | ¹H NMR (400 MHz, Chloroform-d) δ 8.94 (s, 1H), 8.44 (s, 1H), 8.37 (s, 1H), 7.60 (d, J = 8.9 Hz, 1H), 7.36 (d, J = 9.3 Hz, 1H), 7.19 (t, J = 7.9 Hz, 1H), 6.98 (s, 1H), 6.75 (d, J = 17.0 Hz, 2H), 6.38 (d, J = 16.0 Hz, 1H), 6.28 (m, 1H), 5.96 (m, 1H), 5.76 (d, J = 10.0 Hz, 1H), 4.09 (m, 2H), 3.86 (s, 3H), 3.80 (s, 2H), 3.64 (m, 2H), 2.96 (m, 1H), 2.87 (m, 3H), 2.61 (s, 3H), 2.21 (m, 1H), 2.02 (s, 1H), ; 612.3 [M + H]⁺ | 1.54 |
| 520 | 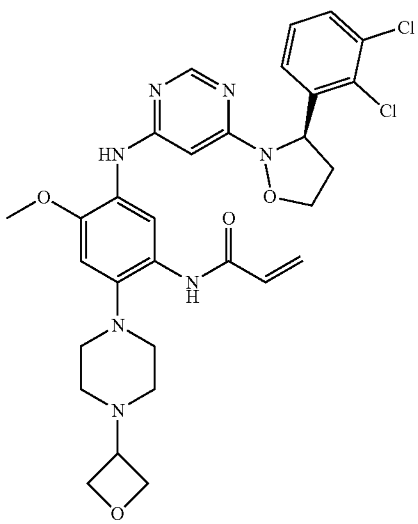 [SMILES: C=CC(=O)Nc1cc(Nc2cc(N3OCC[C@@H]3c3cccc(Cl)c3Cl)ncn2)c(OC)cc1N1CCN(C2COC2)CC1] | N-(5-((6-((R)-3-(2,3-dichlorophenyl)isoxazolidine-2-yl)pyrimidine-4-yl)amino)-4-methoxy-2-(4-(oxetane-3-yl)piperazine-1-yl)phenyl)acrylamide | ¹H NMR (400 MHz, Chloroform-d) δ 8.92 (s, 1H), 8.49 (s, 1H), 8.37 (d, J = 1.0 Hz, 1H), 7.63-7.56 (m, 1H), 7.37 (dd, J = 7.9, 1.5 Hz, 1H), 7.19 (t, J = 7.9 Hz, 1H), 6.96 (s, 1H), 6.82 (s, 1H), 6.76 (s, 1H), 6.36 (dd, J = 17.0, 1.5 Hz, 1H), 6.25 (dd, J = 16.9, 10.0 Hz, 1H), 5.97 (dd, J = 8.8, 4.4 Hz, 1H), 5.74 (dd, J = 10.0, 1.5 Hz, 1H), 4.72 (t, J = 6.6 Hz, 2H), 4.67 (t, J = 6.2 Hz, 2H), 4.16-4.03 (m, 2H), 3.85 (s, 3H), 3.61 (p, J = 6.5 Hz, 1H), 3.01-2.89 (m, 5H), 2.64-2.45 (m, 4H), 2.24 (dp, J = 12.1, 4.1 Hz, 1H), ; 626.33 [M + H]⁺ | 1.34 |
| 521 | 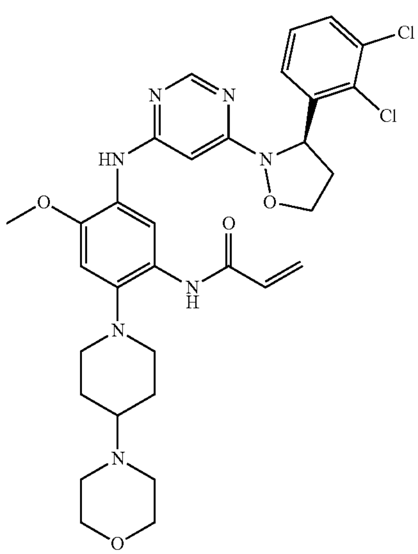 | N-(5-((6-((R)-3-(2,3-dichlorophenyl)isoxazolidine-2-yl)pyrimidine-4-yl)amino)-4-methoxy-2-(4-morpholinopiperidine-1-yl)phenyl)acrylamide | ¹H NMR (400 MHz, Chloroform-d) δ 8.87 (s, 1H), 8.44 (s, 1H), 8.36 (s, 1H), 7.60 (d, J = 7.8 Hz, 1H), 7.37 (dd, J = 7.8, 1.5 Hz, 1H), 7.19 (t, J = 7.9 Hz, 1H), 6.93 (s, 1H), 6.76 (s, 2H), 6.36 (d, J = 16.8 Hz, 1H), 6.25 (dd, J = 16.9, 10.0 Hz, 1H), 5.96 (dd, J = 8.8, 4.4 Hz, 1H), 5.81-5.70 (m, 1H), 4.16-4.04 (m, 2H), 3.85 (s, 3H), 3.78 (t, J = 4.7 Hz, 4H), 3.07 (d, J = 11.4 Hz, 2H), 3.00-2.90 (m, 1H), 2.73 (q, J = 12.3 Hz, 3H), 2.65-2.56 (m, 4H), 2.37-2.17 (m, 3H), 2.08 (d, J = 12.5 Hz, 2H), ; 654.4 [M + H]⁺ | 1.34 |

TABLE 1-continued

| Example Compound | Structure | Name of Compound | ¹H NMR[[:]]; MS [M + H]⁺ | UPLC r.t. (min) |
|---|---|---|---|---|
| 522 | 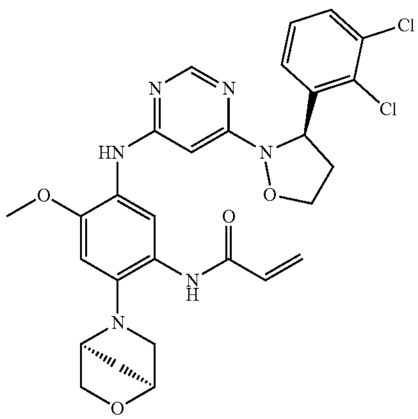 [SMILES: C=CC(=O)Nc1cc(Nc2cc(N3OCC[C@@H]3c3cccc(Cl)c3Cl)ncn2)c(OC)cc1N1C[C@@H]2C[C@H]1CO2] | N-(2-((1S,4S)-2-oxa-5-azabicyclo[2.2.1]heptane-5-yl)-5-((6-((R)-3-(2,3-dichlorophenyl)isoxazolidine-2-yl)pyrimidine-4-yl)amino)-4-methoxyphenyl)acrylamide | ¹H NMR (400 MHz, Chloroform-d) δ 8.68 (s, 1H), 8.35 (s, 1H), 7.95 (s, 1H), 7.60 (d, J = 7.8 Hz, 1H), 7.37 (dd, J = 8.0, 1.6 Hz, 1H), 7.19 (t, J = 7.9 Hz, 1H), 6.90 (s, 1H), 6.69 (d, J = 13.7 Hz, 2H), 6.39 (d, J = 16.8 Hz, 1H), 6.28 (dd, J = 16.8, 10.0 Hz, 1H), 5.96 (dd, J = 8.8, 4.5 Hz, 1H), 5.75 (d, J = 10.2 Hz, 1H), 4.65 (s, 1H), 4.14-3.99 (m, 3H), 3.86 (s, 3H), 3.76 (d, J = 7.8 Hz, 1H), 3.43 (d, J = 10.1 Hz, 1H), 3.24 (d, J = 10.1 Hz, 1H), 2.94 (dtd, J = 12.4, 8.1, 4.2 Hz, 1H), 2.61 (s, 1H), 2.22 (tdd, J = 12.9, 8.7, 4.6 Hz, 1H), 2.09 (d, J = 9.8 Hz, 1H), 1.99 (d, J = 10.6 Hz, 1H), ; 583.3 [M + H] | 1.48 |
| 523 | 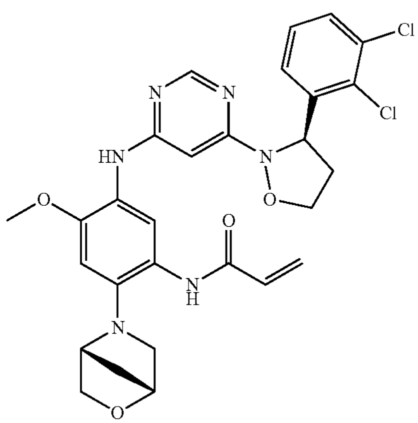 [SMILES: C=CC(=O)Nc1cc(Nc2cc(N3OCC[C@@H]3c3cccc(Cl)c3Cl)ncn2)c(OC)cc1N1C[C@H]2C[C@@H]1CO2] | N-(2-((1R,4R)-2-oxa-5-azabicyclo[2.2.1]heptane-5-yl)-5-((6-((R)-3-(2,3-dichlorophenyl)isoxazolidine-2-yl)pyrimidine-4-yl)amino)-4-methoxyphenyl)acrylamide | ¹H NMR (400 MHz, Chloroform-d) δ 8.64 (s, 1H), 8.35 (s, 1H), 7.95 (s, 1H), 7.59 (d, J = 7.8 Hz, 1H), 7.37 (dd, J = 7.9, 1.6 Hz, 1H), 7.19 (t, J = 7.9 Hz, 1H), 6.88 (s, 1H), 6.73 (s, 2H), 6.39 (d, J = 16.8 Hz, 1H), 6.28 (dd, J = 17.0, 10.0 Hz, 1H), 5.97 (dd, J = 8.8, 4.4 Hz, 1H), 5.76 (d, J = 9.9 Hz, 1H), 4.65 (s, 1H), 4.16-4.01 (m, 3H), 3.86 (s, 3H), 3.75 (d, J = 7.8 Hz, 1H), 3.46 (d, J = 10.1 Hz, 1H), 3.20 (d, J = 10.1 Hz, 1H), 3.00-2.89 (m, 1H), 2.62 (s, 1H), 2.23 (dtd, J = 12.6, 8.2, 4.6 Hz, 1H), 2.09 (d, J = 10.0 Hz, 1H), 2.00 (d, J = 9.9 Hz, 1H), ; 583.3 [M + H] | 1.48 |
| 524 | 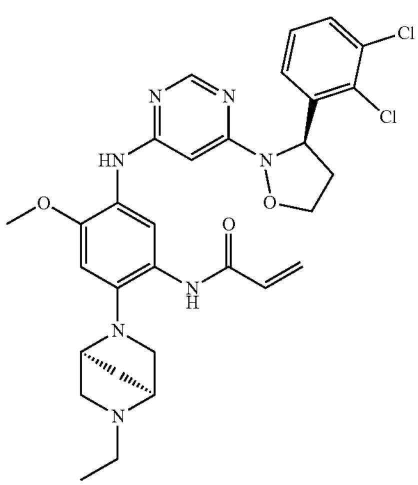 [SMILES: C=CC(=O)Nc1cc(Nc2cc(N3OCC[C@@H]3c3cccc(Cl)c3Cl)ncn2)c(OC)cc1N1C[C@@H]2C[C@H]1CN2CC] | N-(5-((6-((R)-3-(2,3-dichlorophenyl)isoxazolidine-2-yl)pyrimidine-4-yl)amino)-2-((1S,4S)-5-ethyl-2,5-diazabicyclo[2.2.1]heptane-2-yl)-4-methoxyphenyl)acrylamide | ¹H NMR (400 MHz, Chloroform-d) δ 8.65 (s, 1H), 8.34 (s, 1H), 8.15 (s, 1H), 7.59 (d, J = 7.8 Hz, 1H), 7.37 (dd, J = 7.9, 1.6 Hz, 1H), 7.19 (t, J = 7.9 Hz, 1H), 6.95 (s, 1H), 6.81 (s, 1H), 6.66 (s, 1H), 6.39 (d, J = 16.5 Hz, 1H), 6.26-6.13 (m, 1H), 5.95 (dd, J = 8.8, 4.4 Hz, 1H), 5.75-5.66 (m, 1H), 4.09 (dd, J = 7.9, 4.2 Hz, 1H), 4.03 (q, J = 8.1 Hz, 1H), 3.88 (s, 3H), 3.13 (d, J = 9.6 Hz, 1H), 2.98-2.90 (m, 1H), 2.83 (d, J = 10.8 Hz, 1H), 2.35 (d, J = 25.1 Hz, 1H), 2.22 (dtd, J = 12.6, 8.2, 4.5 Hz, 1H), 1.51 (t, J = 7.6 Hz, 1H), 1.45 (d, J = 6.7 Hz, 2H), 1.37-1.21 (m, 7H), ; 610.3 [M + H] | 1.29 |

TABLE 1-continued

| Example Compound | Structure | Name of Compound | ¹H NMR[[:]]; MS [M + H]⁺ | UPLC r.t. (min) |
|---|---|---|---|---|
| 525 | 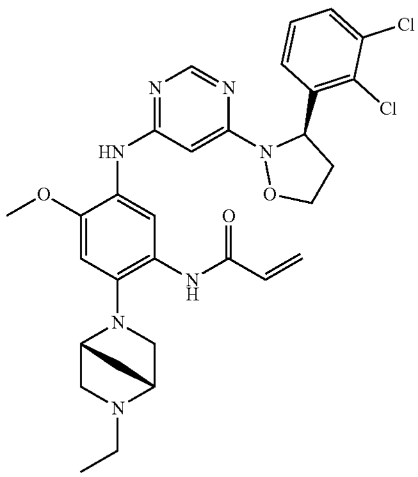 [SMILES: C=CC(=O)Nc1cc(Nc2cc(N3OCC[C@@H]3c3cccc(Cl)c3Cl)ncn2)c(OC)cc1N1C[C@H]2C[C@@H]1CN2CC] | N-(5-((6-((R)-3-(2,3-dichlorophenyl)isoxazolidine-2-yl)pyrimidine-4-yl)amino)-2-((1R,4R)-5-ethyl-2,5-diazabicyclo[2.2.1]heptane-2-yl)-4-methoxyphenyl)acrylamide | ¹H NMR (400 MHz, Chloroform-d) δ 8.62 (s, 1H), 8.34 (s, 1H), 8.09 (s, 1H), 7.59 (d, J = 7.8 Hz, 1H), 7.37 (dd, J = 8.0, 1.6 Hz, 1H), 7.19 (t, J = 7.9 Hz, 1H), 6.92 (s, 1H), 6.73 (s, 1H), 6.38 (d, J = 15.9 Hz, 1H), 6.32-6.14 (m, 1H), 5.96 (dd, J = 8.7, 4.4 Hz, 1H), 5.78-5.66 (m, 2H), 4.14-4.04 (m, 2H), 3.88 (s, 3H), 3.09 (d, J = 10.5 Hz, 1H), 2.95 (ddt, J = 12.2, 8.0, 4.0 Hz, 2H), 2.80 (s, 2H), 2.32 (d, J = 21.0 Hz, 1H), 2.25-2.20 (m, 1H), 2.07 (s, 2H), 1.39-1.17 (m, 6H), ; 610.3 [M + H] | 1.29 |
| 526 | 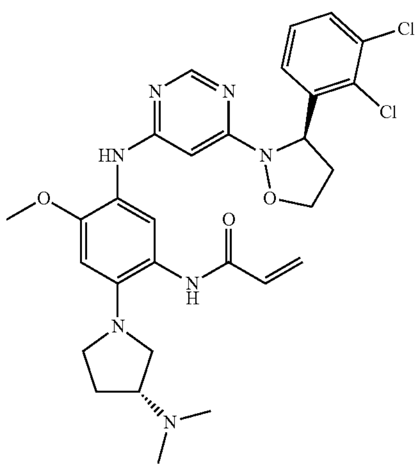 [SMILES: C=CC(=O)Nc1cc(Nc2cc(N3OCC[C@@H]3c3cccc(Cl)c3Cl)ncn2)c(OC)cc1N1CC[C@@H](N(C)C)C1] | N-(5-((6-((R)-3-(2,3-dichlorophenyl)isoxazolidine-2-yl)pyrimidine-4-yl)amino)-2-((R)-3-(dimethylamino)pyrolidine-1-yl)-4-methoxyphenyl)acrylamide | ¹H NMR (400 MHz, Chloroform-d) δ 11.35 (s, 1H), 8.58 (s, 1H), 8.33 (d, J = 1.0, Hz, 1H), 7.60 (d, J = 8.0 Hz, 1H), 7.36 (dd, J = 8.0, 1.6 Hz, 1H), 7.19 (t, J = 7.9 Hz, 1H), 6.86 (s, 1H), 6.74 (s, 1H), 6.68 (s, 1H), 6.41 (d, J = 16.3 Hz, 1H), 5.96 (dd, J = 8.8, 4.4 Hz, 1H), 5.72 (d, J = 11.7 Hz, 1H), 4.14-4.02 (m, 2H), 3.84 (s, 3H), 3.69-3.61 (m, 1H), 3.32 (dd, J = 7.3, 5.3 Hz, 1H), 3.12-3.05 (m, 2H), 2.95 (dq, J = 8.4, 4.0 Hz, 1H), 2.32 (d, J = 18.1 Hz, 1H), 2.23 (ddd, J = 12.4, 8.3, 4.4 Hz, 1H), 1.58-1.52 (m, 3H), 1.45 (d, J = 6.6 Hz, 2H), 1.26 (d, J = 4.8 Hz, 3H), 1.19 (t, J = 7.3 527Hz, 1H), ; 598.4 [M + H] | 1.29 |
| 527 | 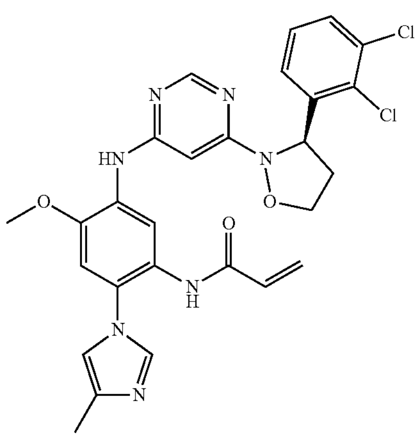 [SMILES: C=CC(=O)Nc1cc(Nc2cc(N3OCC[C@@H]3c3cccc(Cl)c3Cl)ncn2)c(OC)cc1-n1cnc(C)c1] | N-(5-((6-((R)-3-(2,3-dichlorophenyl)isoxazolidine-2-yl)pyrimidine-4-yl)amino)-4-methoxy-2-(4-methyl-1H-imidazole-1-yl)phenyl)acrylamide | ¹H NMR (400 MHz, Chloroform-d) δ 8.96 (s, 1H), 8.43 (dd, J = 7.8, 1.0 Hz, 1H), 7.59 (dd, J = 7.9, 1.6 Hz, 1H), 7.53-7.47 (m, 1H), 7.39 (dd, J = 8.0, 1.6 Hz, 1H), 7.24-7.14 (m, 2H), 6.99 (d, J = 9.0 Hz, 1H), 6.82-6.76 (m, 2H), 6.33 (d, J = 17.0 Hz, 1H), 6.11 (dd, J = 17.0, 10.2 Hz, 1H), 5.98 (dd, J = 8.7, 4.5 Hz, 1H), 5.73 (dd, J = 10.3, 1.2 Hz, 1H), 4.16 (td, J = 8.0, 4.1 Hz, 1H), 4.06 (q, J = 8.1 Hz, 1H), 3.90 (d, J = 2.4 Hz, 3H), 2.97 (dtd, J = 12.4, 7.9, 4.1 Hz, 1H), 2.31 (d, J = 1.0 Hz, 3H), 2.29-2.24 (m, 1H), 2.07-2.01 (m, 1H), ; 566.3 [M + H] | 1.46 |

TABLE 1-continued

| Example Compound | Structure | Name of Compound | ¹H NMR[[:]]; MS [M + H]⁺ | UPLC r.t. (min) |
|---|---|---|---|---|
| 528 | 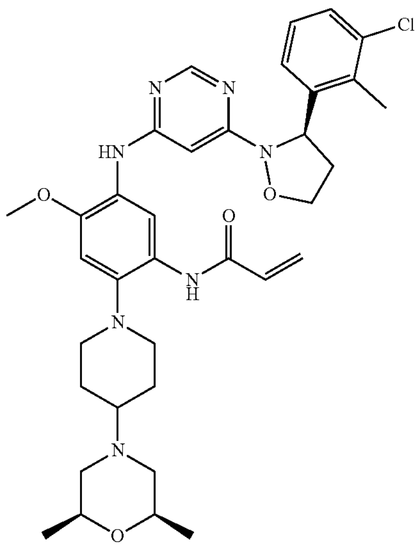 [SMILES: C=CC(=O)Nc1cc(Nc2cc(N3OCC[C@@H]3c3cccc(Cl)c3C)ncn2)c(OC)cc1N1CCC(N2C[C@@H](C)O[C@@H](C)C2)CC1] | N-(5-((6-((R)-3-(3-chloro-2-methylphenyl)isoxazolidine-2-yl)pyrimidine-4-yl)amino)-2-(4-((2S,6R)-2,6-dimethylmorpholino)piperidine-1-yl)-4-methoxyphenyl)acrylamide | ¹H NMR (400 MHz, DMSO-d6) δ 8.94 (s, 1H), 8.59 (s, 1H), 8.14 (d, J = 1.0 Hz, 2H), 7.40 (dd, J = 7.8, 1.3 Hz, 1H), 7.34 (dd, J = 8.0, 1.3 Hz, 1H), 7.20 (t, J = 7.9 Hz, 1H), 6.82 (s, 1H), 6.66 (dd, 16.9, 10.2 Hz, 1H), 6.34 (s, 1H), 6.21 (dd, J = 16.9, 2.0 Hz, 1H), 5.74-5.66 (m, 2H), 4.14 (td, J = 7.9, 3.8 Hz, 1H), 3.79 (s, 3H), 3.54 (dqd, J = 12.5, 6.1, 3.1 Hz, 2H), 3.05 (d, J = 11.1 Hz, 2H), 2.88-2.77 (m, 3H), 2.65 (td, J = 10.9, 9.6, 6.1 Hz, 2H), 2.42 (s, 3H), 2.25 (dq, J = 11.0, 5.6, 3.7 Hz, 1H), 2.12-2.02 (m, 1H), 1.91-1.77 (m, 6H), 1.70 (qd, J = 11.3, 10.5, 3.2 Hz, 2H), 1.06 (d, J = 6.3 Hz, 6H), ; 662.5 [M + H]⁺ | 1.33 |
| 529 | 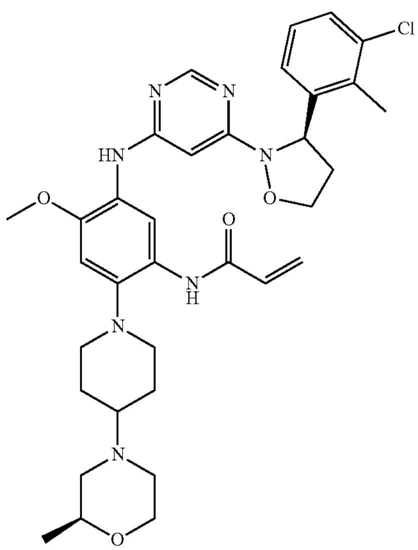 [SMILES: C=CC(=O)Nc1cc(Nc2cc(N3OCC[C@@H]3c3cccc(Cl)c3C)ncn2)c(OC)cc1N1CCC(N2CCO[C@@H](C)C2)CC1] | N-(5-((6-((R)-3-(3-chloro-2-methylphenyl)isoxazolidine-2-yl)pyrimidine-4-yl)amino)-4-methoxy-2-(4-((S)-2-methylmorpholino)piperidine-1-yl)phenyl)acrylamide | ¹H NMR (400 MHz, DMSO-d₆) δ 8.95 (s, 1H), 8.59 (s, 1H), 8.17-8.12 (m, 2H), 7.40 (dd, J = 7.9, 1.3 Hz, 1H) 7.34 (dd, J = 8.0, 1.3 Hz, 1H), 7.20 (t, J = 7.9 Hz, H), 6.82 (s, 1H), 6.65 (dd, J = 16.9, 10.2 Hz, 1H), 6.35 (s, 1H), 6.21 (dd, J = 17.0, 2.0 Hz, 1H), 5.71 (td, J = 9.4, 3.4 Hz, 2H), 4.15 (td, J = 7.8, 3.7 Hz, 1H), 3.80 (s, 3H), 3.50 (t, J = 10.6 Hz, 2H), 3.42-3.22 (m, 4H), 3.11-3.00 (m, 3H), 2.83 (dtd, J = 11.9, 7.9, 3.7 Hz, 4H), 2.67 (t, J = 11.4 Hz, 2H), 2.36-2.18 (m, 2H), 2.08 (dtd, J = 12.6, 8.1, 5.0 Hz, 2H), 1.91 (s, 3H), 1.87 (s, 2H), 1.71 (d, J = 12.4 Hz, 3H), 1.07 (d, J = 6.2 Hz, 3H), ; 648.6 [M + H]⁺ | 1.30 |

TABLE 1-continued

| Example Compound | Structure | Name of Compound | ¹H NMR[[:]]; MS [M + H]⁺ | UPLC r.t. (min) |
|---|---|---|---|---|
| 530 | 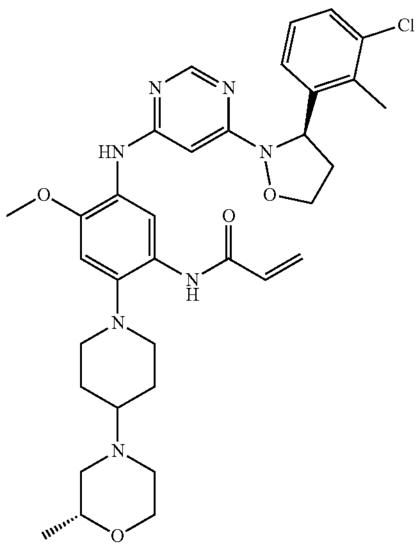 [SMILES: C=CC(=O)Nc1cc(Nc2cc(N3OCC[C@@H]3c3cccc(Cl)c3C)ncn2)c(OC)cc1N1CCC(N2CCO[C@H](C)C2)CC1] | N-(5-((6-((R)-3-(3-chloro-2-methylphenyl)isoxazolidine-2-yl)pyrimidine-4-yl)amino)-4-methoxy-2-(4-((R)-2-methylmorpholino)piperidine-1-yl)phenyl)acrylamide | ¹H NMR (400 MHz, DMSO-d$_6$) δ 8.95 (s, 1H), 8.59 (s, 1H), 8.14 (d, J = 1.0 Hz, 2H), 7.40 (dd, J = 7.8, 1.3 Hz, 1H), 7.34 (dd, J = 8.0, 1.3 Hz, 1H), 7.20 (t, J = 7.9 Hz, 1H), 6.82 (s, 1H), 6.65 (dd, J = 16.9, 10.2 Hz, 1H), 6.35 (s, 1H), 6.21 (dd, J = 17.0, 2.0 Hz, 1H), 5.71 (td, J = 9.0, 3.4 Hz, 2H), 4.14 (td, J = 7.8, 3.8 Hz, 1H), 3.80 (s, 3H), 3.53-3.45 (m, 2H), 3.33 (s, 4H), 3.12-3.00 (m, 3H), 2.87-2.71 (m, 4H), 2.66 (td, J = 10.5, 9.4, 6.1 Hz, 2H), 2.42 (s, 3H), 2.34-2.16 (m, 2H), 2.14-2.02 (m, 1H), 1.91 (s, 2H), 1.86 (d, J = 12.6 Hz, 3H), 1.79-1.63 (m, 3H), 1.07 (d, J = 6.3 Hz, 4H), ; 648.5 [M + H]⁺ | 1.29 |
| 531 | 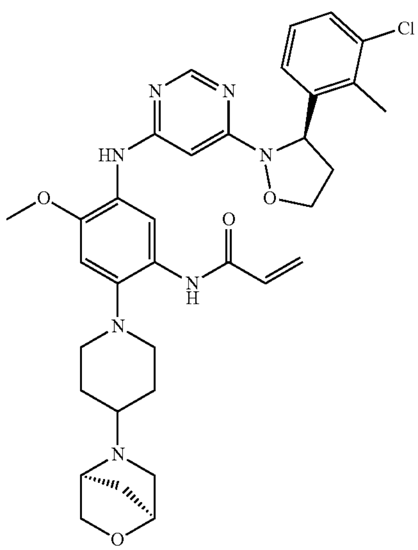 [SMILES: C=CC(=O)Nc1cc(Nc2cc(N3OCC[C@@H]3c3cccc(Cl)c3C)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((R)-3-(3-chloro-2-methylphenyl)isoxazolidine-2-yl)pyrimidine-4-yl)amino)-4-methoxyphenyl)acrylamide | ¹H NMR (400 MHz, DMSO-d$_6$) δ 8.94 (s, 1H), 8.59 (s, 1H), 8.14 (d, J = 1.0 Hz, 1H), 7.40 (dd, J = 7.8, 1.3 Hz, 1H), 7.34 (dd, J = 8.0, 1.3 Hz, 1H), 7.20 (t, J = 7.9 Hz, 1H), 6.83 (s, 1H), 6.64 (dd, J = 16.9, 10.2 Hz, 1H), 6.35 (s, 1H), 6.20 (dd, J = 17.0, 2.0 Hz, 1H), 5.70 (td, J = 8.8, 7.7, 3.4 Hz, 2H), 4.15 (td, J = 7.9, 3.8 Hz, 1H), 3.87 (dd, J = 12.8, 7.8 Hz, 2H), 3.80 (s, 3H), 3.04-2.90 (m, 4H), 2.83 (dtd, J = 11.9, 8.0, 3.8 Hz, 2H), 2.70 (tdd, J = 10.9, 7.8, 2.3 Hz, 2H), 2.42 (s, 3H), 2.34 (d, J = 9.7 Hz, 1H), 2.14-2.01 (m, 2H), 1.90 (s, 5H), 1.76-1.52 (m, 5H), ; 646.5 [M + H]⁺ | 1.27 |

TABLE 1-continued

| Example Compound | Structure | Name of Compound | ¹H NMR[[:]]; MS [M + H]⁺ | UPLC r.t. (min) |
|---|---|---|---|---|
| 532 | 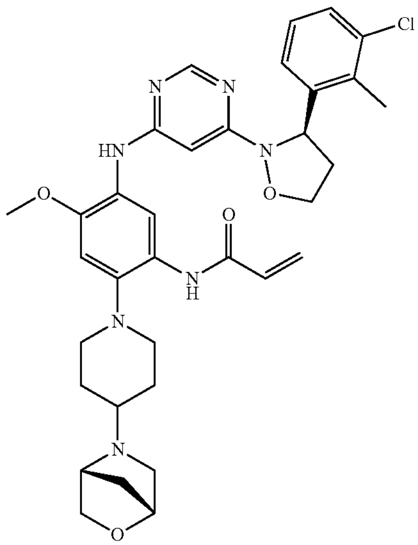 [SMILES: C=CC(=O)Nc1cc(Nc2cc(N3OCC[C@@H]3c3cccc(Cl)c3C)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-5-((6-((R)-3-(3-chloro-2-methylphenyl)isoxazolidine-2-yl)pyrimidine-4-yl)amino)-4-methoxyphenyl)acrylamide | ¹H NMR (400 MHz, DMSO-d₆) δ 8.94 (s, 1H), 8.59 (s, 1H), 8.14 (d, J = 1.0 Hz, 1H), 7.40 (dd, J = 7.9, 1.4 Hz, 1H), 7.34 (dd, J = 8.0, 1.3 Hz, 1H), 7.20 (t, J = 7.9 Hz, 1H), 6.83 (s, 1H), 6.64 (dd, J = 17.0, 10.2 Hz, 1H), 6.34 (s, 1H), 6.20 (dd, J = 17.0, 2.0 Hz, 1H), 5.70 (td, J = 8.9, 7.8, 3.4 Hz, 2H), 4.15 (td, J = 7.9, 3.8 Hz, 1H), 3.87 (dd, J = 12.9, 7.8 Hz, 3H), 3.80 (s, 3H), 3.04-2.93 (m, 4H), 2.82 (dq, J = 8.0, 4.1 Hz, 1H), 2.71 (dt, J = 11.4, 9.1 Hz, 3H), 2.42 (s, 4H), 2.34 (d, J = 9.7 Hz, 1H), 2.10-2.05 (m, 1H), 1.90 (s, 6H), 1.73-1.55 (m, 5H), ; 646.5 [M + H]⁺ | 1.26 |
| 533 | 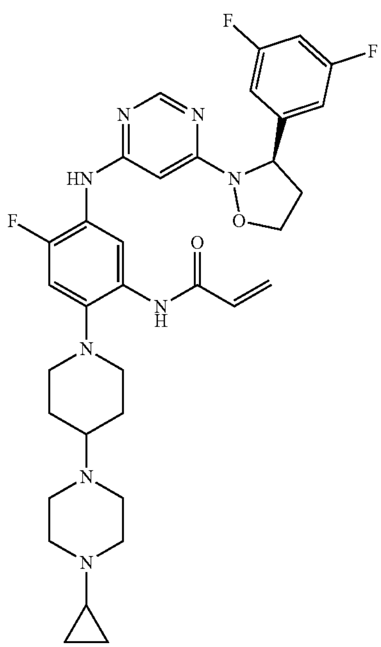 [SMILES: C=CC(=O)Nc1cc(Nc2cc(N3OCC[C@@H]3c3cc(F)cc(F)c3)ncn2)c(F)cc1N1CCC(N2CCN(C3CC3)CC2)CC1] | N-(2-(4-(4-cyclopropylpiperazine-1-yl)piperidine-1-yl)-5-((6-((R)-3-(3,5-difluorophenyl)isoxazolidine-2-yl)pyrimidine-4-yl)amino)-4-fluorophenyl)acrylamide | ¹H NMR (400 MHz, Methanol-d₄) δ 8.32 (d, J = 8.4 Hz, 1H), 8.19 (s, 1H), 7.14-7.01 (m, 3H), 6.88-6.80 (m, 1H), 6.57 (dd, J = 10.1, 17.0 Hz, 1H), 6.46-6.33 (m, 2H), 5.84 (d, J = 10.3 Hz, 1H), 5.61-5.52 (m, 1H), 4.20-4.14 (m, 1H), 4.00-3.94 (m, 1H), 3.23-3.16 (m, 2H), 3.08-2.94 (m, 4H), 2.91-2.73 (m, 8H), 2.38-2.31 (m, 1H), 2.18-2.09 (m, 2H), 1.92-1.78 (m, 3H), 0.59-0.53 (m, 2H), 0.53-0.44 (m, 2H), ; 649.3 [M + H]⁺ | 1.34 |

TABLE 1-continued

| Example Compound | Structure | Name of Compound | ¹H NMR[[:]]; MS [M + H]⁺ | UPLC r.t. (min) |
|---|---|---|---|---|
| 534 | 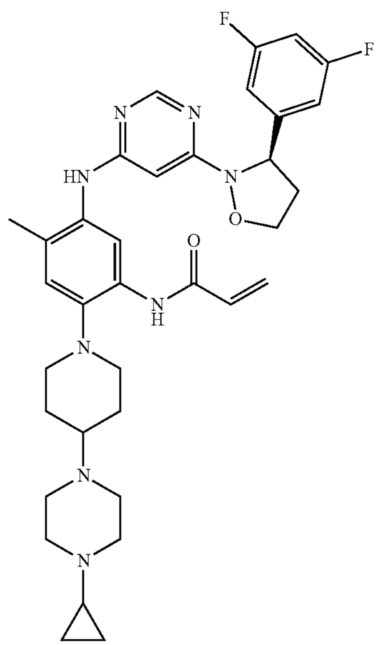 [SMILES: C=CC(=O)Nc1cc(Nc2cc(N3OCC[C@@H]3c3cc(F)cc(F)c3)ncn2)c(C)cc1N1CCC(N2CCN(C3CC3)CC2)CC1] | N-(2-(4-(4-cyclopropylpiperazine-1-yl)piperidine-1-yl)-5-((6-((R)-3-(3,5-difluorophenyl)isoxazolidine-2-yl)pyrimidine-4-yl)amino)-4-methylphenyl)acrylamide | ¹H NMR (400 MHz, Methanol-$d_4$) δ 8.13 (s, 1H), 8.06 (s, 1H), 7.17 (s, 1H), 7.09-7.00 (m, 2H), 6.84 (tt, J = 2.5, 9.1 Hz, 1H), 6.56 (dd, J = 10.3, 17.0 Hz, 1H), 6.43-6.32 (m, 1H), 6.21 (s, 1H), 5.82 (d, J = 10.3 Hz, 1H), 5.55 (dd, J = 4.8, 8.7 Hz, 1H), 4.16-4.09 (m, 1H), 3.94 (q, J = 7.9 Hz, 1H), 3.21-3.14 (m, 2H), 3.10-2.95 (m, 4H), 2.93-2.76 (m, 8H), 2.37-2.28 (m, 1H), 2.23 (s, 3H), 2.20-2.11 (m, 2H), 1.93-1.79 (m, 3H), 0.60-0.53 (m, 2H), 0.52-0.45 (m, 2H), ; 645.3 [M + H]⁺ | 1.24 |
| 535 | 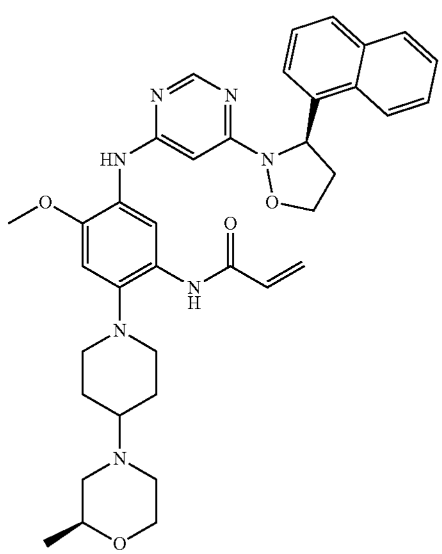 | N-(4-methoxy-2-(4-((S)-2-methylmorpholino)piperidine-1-yl)-5-((6-((R)-3-(naphthalene-1-yl)isoxazolidine-2-yl)pyrimidine-4-yl)amino)phenyl)acrylamide | 650.5 [M + H]⁺ | 1.28 |

TABLE 1-continued

| Example Compound | Structure | Name of Compound | ¹H NMR[[:]]; MS [M + H]⁺ | UPLC r.t. (min) |
|---|---|---|---|---|
| 536 | 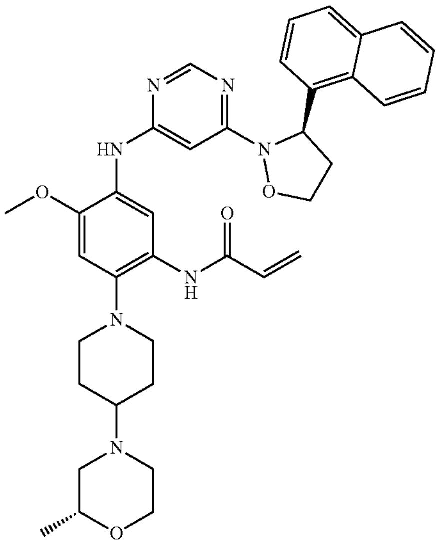 | N-(4-methoxy-2-(4-((R)-2-methylmorpholino)piperidin-1-yl)-5-((6-((R)-3-(naphthalene-1-yl)isoxazolidine-2-yl)pyrimidine-4-yl)amino)phenyl)acrylamide | 1H NMR (400 MHz, Chloroform-d) δ 8.91 (s, 1H), 8.44 (s, 1H), 8.37 (s, 1H), 8.15 (d, J = 8.3 Hz, 1H), 7.88 (dd, J = 8.0, 1.5 Hz, 1H), 7.77 (dd, J = 7.7, 5.2 Hz, 2H), 7.60-7.41 (m, 3H), 6.93 (s, 1H), 6.77 (d, J = 12.2 Hz, 2H), 6.45-6.32 (m, 2H), 6.25 (dd, J = 16.9, 10.0 Hz, 1H), 5.74 (dd, J = 10.0, 1.6 Hz, 1H), 4.24-4.09 (m, 2H), 3.96-3.90 (m, 1H), 3.85 (s, 3H), 3.76-3.60 (m, 2H), 3.12-3.02 (m, 2H), 3.01-2.93 (m, 1H), 2.93-2.82 (m, 2H), 2.80-2.66 (m, 2H), 2.45-2.37 (m, 1H), 2.34-2.26 (m, 2H), 2.11-2.04 (m, 2H), 1.69-1.63 (m, 3H), 1.26 (s, 3H), ; 650.5 [M + H]+ | 1.27 |
| 537 | 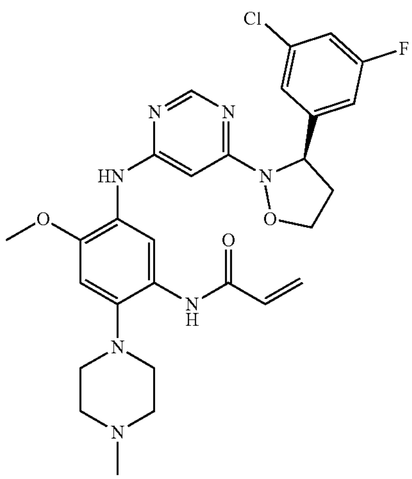 | N-(5-((6-((R)-3-(3-chloro-5-fluorophenyl)isoxazolidine-2-yl)pyrimidine-4-yl)amino)-4-methoxy-2-(4-methylpiperazine-1-yl)phenyl)acrylamide | ; 568.35 [M + H]⁺ | 1.29 |
| 538 | 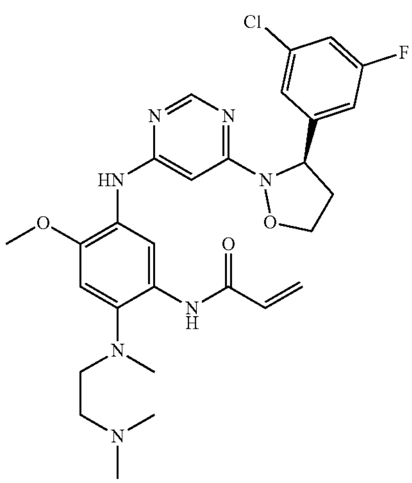 | N-(5-((6-((R)-3-(3-chloro-5-fluorophenyl)isoxazolidine-2-yl)pyrimidine-4-yl)amino)-2-((2-(dimethylamino)ethyl)(methyl)amino)-4-methoxyphenyl)acrylamide | ; 570.38 [M + H]⁺ | 1.31 |

TABLE 1-continued

| Example Compound | Structure | Name of Compound | ¹H NMR[[:]]; MS [M + H]⁺ | UPLC r.t. (min) |
|---|---|---|---|---|
| 539 | 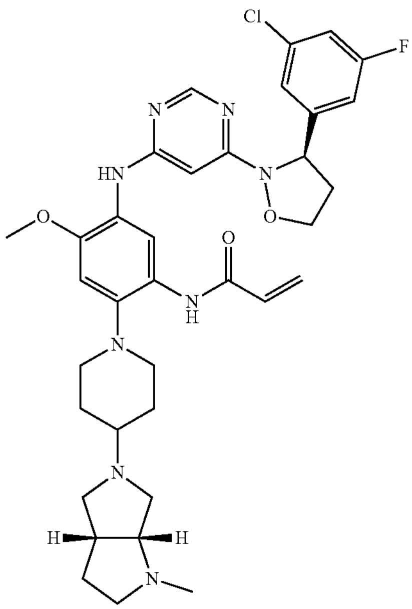 | N-(5-((6-((R)-3-(3-chloro-5-fluorophenyl)isoxazolidine-2-yl)pyrimidine-4-yl)amino)-4-methoxy-2-(4-((3aR,6aR)-1-methylhexahydropyrrolo[3,4-b]pyrrole-5(1H)-yl)piperidine-1-yl)phenyl)acrylamide | ; 677.47 [M + H]⁺ | 1.21 |
| 540 | 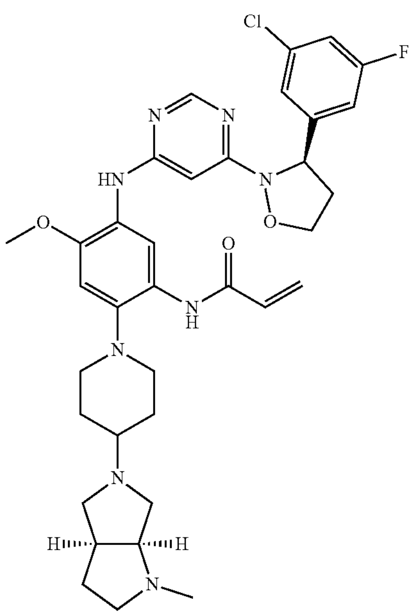 | N-(5-((6-((R)-3-(3-chloro-5-fluorophenyl)isoxazolidine-2-yl)pyrimidine-4-yl)amino)-4-methoxy-2-(4-((3aS,6aS)-1-methylhexahydropyrrolo[3,4-b]pyrrole-5(1H)-yl)piperidine-1-yl)phenyl)acrylamide | ; 677.47 [M + H]⁺ | 1.21 |

TABLE 1-continued

| Example Compound | Structure | Name of Compound | ¹H NMR[[:]]; MS [M + H]⁺ | UPLC r.t. (min) |
|---|---|---|---|---|
| 541 | 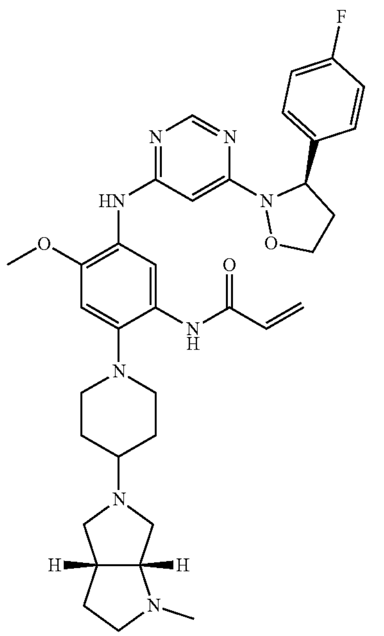 | N-(5-((6-((R)-3-(4-fluorophenyl)isoxazolidine-2-yl)pyrimidine-4-yl)amino)-4-methoxy-2-(4-((3aR,6aR)-1-methylhexahydropyrrolo[3,4-b]pyrrole-5(1H)-yl)piperidine-1-yl)phenyl)acrylamide | ; 643.3 [M + H]⁺ | 1.18 |
| 542 | 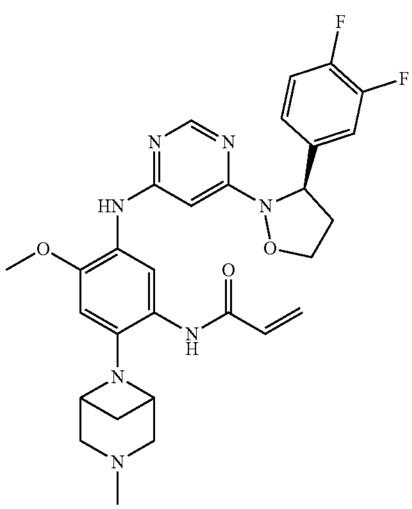 | N-(5-((6-((R)-3-(3,4-difluorophenyl)isoxazolidine-2-yl)pyrimidine-4-yl)amino)-4-methoxy-2-(3-methyl-3,6-diazabicyclo[3.1.1]heptane-6-yl)phenyl)acrylamide | ; 564.4 [M + H]⁺ | 1.16 |

TABLE 1-continued

| Example Compound | Structure | Name of Compound | ¹H NMR[[:]]; MS [M + H]⁺ | UPLC r.t. (min) |
|---|---|---|---|---|
| 543 | 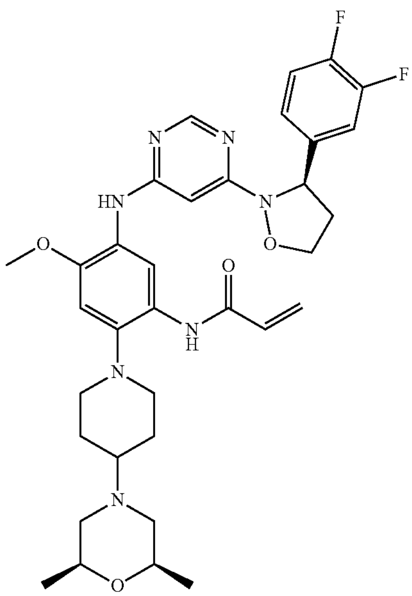 | N-(5-((6-((R)-3-(3,4-difluorophenyl)isoxazolidine-2-yl)pyrimidine-4-yl)amino)-2-(4-((2S,6R)-2,6-dimethylmorpholino)piperidine-1-yl)-4-methoxyphenyl)acrylamide | ¹H NMR (400 MHz, DMSO-d₆) δ 10.08 (s, 1H), 9.20 (s, 1H), 8.32 (s, 1H), 7.89 (s, 1H), 7.43 (ddt, J = 10.5, 4.7, 2.7 Hz, 2H), 7.26-7.21 (m, 1H), 6.92 (s, 1H), 6.69 (dd, J = 16.9, 10.2 Hz, 1H), 6.25 (dd, J = 17.0, 1.9 Hz, 1H), 6.11 (s, 1H), 5.78 (d, J = 1.9 Hz, 1H), 5.53 (dd, J = 8.4, 5.3 Hz, 1H), 4.30 (d, J = 4.5 Hz, 1H), 4.15 (dt, J = 7.7, 4.0 Hz, 2H), 4.05 (d, J = 7.7 Hz, 1H), 3.81 (s, 3H), 3.46 (d, J = 11.7 Hz, 2H), 3.23 (d, J = 11.8 Hz, 3H), 2.93-2.87 (m, 1H), 2.78 (s, 2H), 2.69 (d, J = 10.7 Hz, 2H), 2.32 (d, J = 7.7 Hz, 1H), 2.24 (d, J = 11.4 Hz, 2H), 2.13-2.03 (m, 2H), 1.17 (d, J = 6.2 Hz, 6H), ; 650.3 [M + H]⁺ | 1.28 |
| 544 | 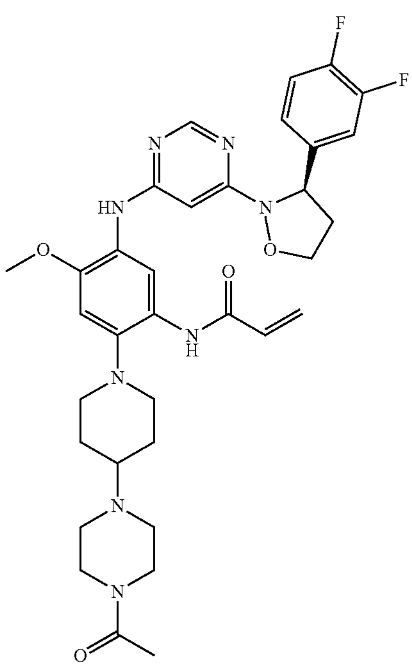 | N-(2-(4-(4-acetylpiperazine-1-yl)piperidine-1-yl)-5-((6-((R)-3-(3,4-difluorophenyl)isoxazolidine-2-yl)pyrimidine-4-yl)amino)-4-methoxyphenyl)acrylamide | ; 663.5 [M + H]⁺ | 1.20 |

TABLE 1-continued

| Example Compound | Structure | Name of Compound | ¹H NMR[[:]]; MS [M + H]⁺ | UPLC r.t. (min) |
|---|---|---|---|---|
| 545 | 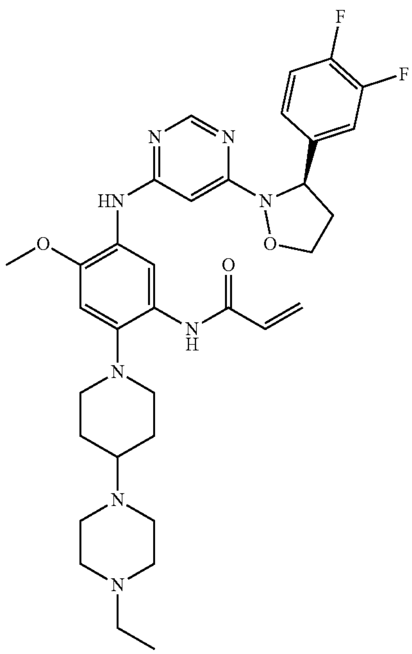 | N-(5-((6-((R)-3-(3,4-difluorophenyl)isoxazolidine-2-yl)pyrimidine-4-yl)amino)-2-(4-(4-ethylpiperazine-1-yl)piperidine-1-yl)-4-methoxyphenyl)acrylamide | ; 649.5 [M + H]⁺ | 1.18 |
| 546 | 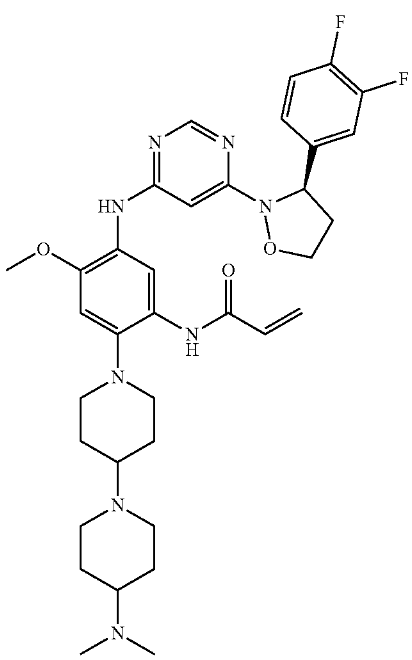 | N-(5-((6-((R)-3-(3,4-difluorophenyl)isoxazolidine-2-yl)pyrimidine-4-yl)amino)-2-(4-(dimethylamino)-[1,4'-bipiperidine]-1'-yl)-4-methoxyphenyl)acrylamide | ; 663.5 [M + H]⁺ | 1.09 |

TABLE 1-continued

| Example Compound | Structure | Name of Compound | ¹H NMR[[:]]; MS [M + H]⁺ | UPLC r.t. (min) |
|---|---|---|---|---|
| 547 | 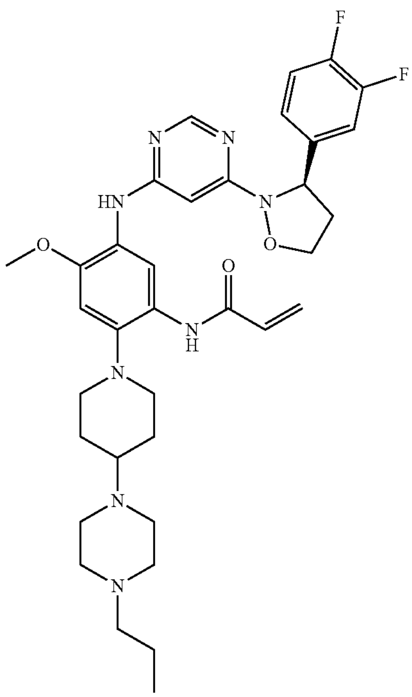 | N-(5-((6-((R)-3-(3,4-difluorophenyl)isoxazolidine-2-yl)pyrimidine-4-yl)amino)-4-methoxy-2-(4-(4-propylpiperazine-1-yl)piperidine-1-yl)phenyl)acrylamide | ¹H NMR (400 MHz, Methanol-$d_4$) δ 8.29 (s, 1H), 8.08 (s, 1H), 7.24 (dd, J = 11.8, 7.7 Hz, 1H), 7.13 (dd, J = 9.2, 4.5 Hz, 2H), 6.78 (s, 1H), 6.53 (dd, J = 16.9, 10.3 Hz, 1H), 6.36 (s, 1H), 6.26-6.20 (m, 1H), 5.78-5.65 (m, 1H), 5.41 (dd, J = 8.4, 4.8 Hz, 1H), 4.05 (td, J = 7.8, 4.3 Hz, 1H), 3.87 (d, J = 7.9 Hz, 1H), 3.75 (s, 3H), 3.22-3.19 (m, 1H), 3.00 (dd, J = 7.1, 4.0 Hz, 5H), 2.81-2.74 (m, 2H), 2.73-2.62 (m, 4H), 2.26-2.16 (m, 1H), 2.05 (s, 1H), 1.95 (d, J = 10.7 Hz, 2H), 1.79 (dd, J = 16.3, 7.3 Hz, 2H), 1.66-1.58 (m, 2H), 0.88 (t, J = 7.4 Hz, 3H); 663.5 [M + H]⁺ | 1.08 |
| 548 | 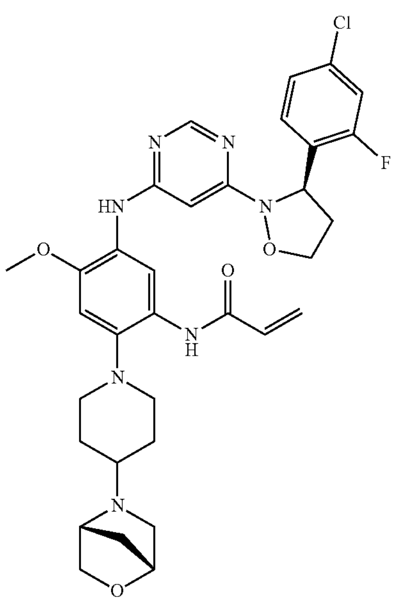 | N-(2-(4-((1R,4R)-2-oxa-5-azabicyclo[2.2.1]heptane-5-yl)piperidine-1-yl)-5-((6-((R)-3-(4-chloro-2-fluorophenyl)isoxazolidine-2-yl)pyrimidine-4-yl)amino)-4-methoxyphenyl)acrylamide | ¹H NMR (400 MHz, DMSO-$d_6$) δ 9.92 (s, 1H), 9.26 (d, J = 33.7 Hz, 1H), 8.30 (s, 1H), 7.89 (d, J = 12.7 Hz, 1H), 7.49 (dd, J = 10.3, 2.1 Hz, 1H), 7.40 (t, J = 8.3 Hz, 1H), 7.30 (dd, J = 8.4, 2.1 Hz, 1H), 6.92 (d, J = 7.7 Hz, 1H), 6.59 (dd, J = 17.3, 10.3 Hz, 1H), 6.29-6.13 (m, 2H), 5.75 (d, J = 4.5 Hz, 1H), 5.66 (dd, J = 8.6, 5.5 Hz, 1H), 4.71-4.55 (m, 2H), 4.33-4.25 (m, 1H), 4.20 (d, J = 10.3 Hz, 1H), 4.04 (d, J = 7.8 Hz, 1H), 3.82 (d, J = 1.8 Hz, 3H), 3.70 (d, J = 9.9 Hz, 1H), 3.52-3.40 (m, 2H), 3.30-3.13 (m, 3H), 2.95-2.67 (m, 4H), 2.29 (dd, J = 18.8, 10.0 Hz, 2H), 2.18-2.02 (m, 4H), ; 650.3 [M + H]⁺ | 1.3 |

TABLE 1-continued

| Example Compound | Structure | Name of Compound | ¹H NMR[:]; MS [M + H]⁺ | UPLC r.t. (min) |
|---|---|---|---|---|
| 549 | 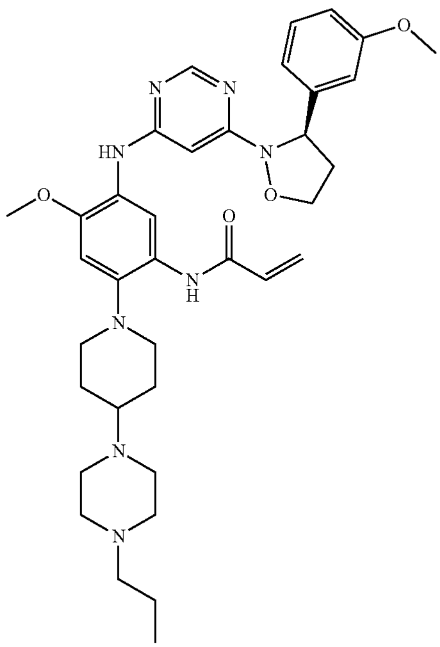 | N-(4-methoxy-5-((6-((R)-3-(3-methoxyphenyl)isoxazolidine-2-yl)pyrimidine-4-yl)amino)-2-(4-(4-propylpiperazine-1-yl)piperidine-1-yl)phenyl)acrylamide | ¹H NMR (400 MHz, Methanol-d₄) δ 8.10 (s, 1H), 8.07 (s, 1H), 7.15 (t, J = 8.2 Hz, 1H), 6.85 (s, 1H), 6.80 (s, 1H), 6.75-6.69 (m, 1H), 6.54 (dd, J = 16.9, 10.3 Hz, 1H), 6.30-6.21 (m, 1H), 6.14 (s, 1H), 5.70 (d, J = 10.5 Hz, 1H), 5.36 (dd, J = 8.3, 5.2 Hz, 1H), 4.14 (td, J = 7.6, 4.4 Hz, 1H), 3.93 (dd, J = 15.7, 7.8 Hz, 1H), 3.73 (s, 3H), 3.23-3.19 (m, 3H), 3.05-3.00 (m, 3H), 2.78 (ddd, J = 23.2, 18.3, 11.7 Hz, 7H), 2.31-2.19 (m, 1H), 2.06 (s, 3H), 2.01 (d, J = 10.6 Hz, 1H), 1.85 (d, J = 10.1 Hz, 1H), 1.77-1.69 (m, 2H), 1.65 (dd, J = 15.7, 7.8 Hz, 2H), 0.92 (t, J = 7.3 Hz, 3H), ; 657.5 [M + H]⁺ | 1.10 |
| 550 | 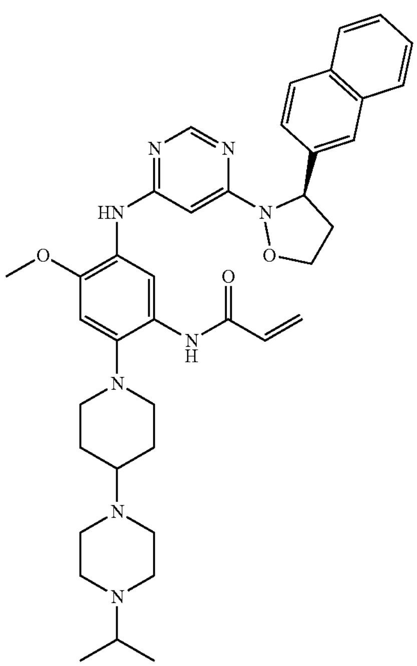 | N-(2-(4-(4-isopropylpiperazine-1-yl)piperidine-1-yl)-4-methoxy-5-((6-((R)-3-(naphthalene-2-yl)isoxazolidine-2-yl)pyrimidine-4-yl)amino)phenyl)acrylamide | ¹H NMR (400 MHz, DMSO-d₆) δ 8.97 (s, 1H), 8.59 (s, 1H), 8.16 (s, 1H), 7.95-7.86 (m, 4H), 7.49 (qd, J = 7.4, 7.0, 3.4 Hz, 2H), 6.83 (s, 1H), 6.66 (dd, J = 16.9, 10.2 Hz, 1H), 6.38 (s, 1H), 6.25-6.02 (m, 2H), 5.76-5.65 (m, 2H), 4.19 (td, J = 7.9, 3.8 Hz, 1H), 3.88 (q, J = 7.9 Hz, 1H), 3.80 (s, 3H), 3.11-3.02 (m, 2H), 2.94-2.79 (m, 2H), 2.68 (q, J = 11.7, 9.6 Hz, 5H), 2.34 (dtd, J = 13.7, 9.3, 8.7, 5.8 Hz, 2H), 1.86 (d, J = 12.1 Hz, 2H), 1.78-1.63 (m, 2H), 1.17 (d, J = 6.6 Hz, 6H), 1.02 (d, J = 6.5 Hz, 6H), ; 677.5 [M + H]⁺ | 1.18 |

TABLE 1-continued

| Example Compound | Structure | Name of Compound | ¹H NMR[[:]]; MS [M + H]⁺ | UPLC r.t. (min) |
|---|---|---|---|---|
| 551 | 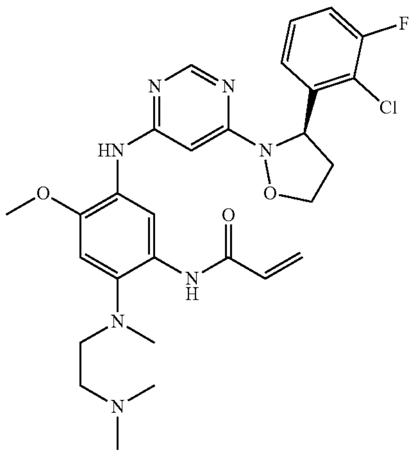 | N-(5-((6-((R)-3-(2-chloro-3-fluorophenyl)isoxazolidine-2-yl)pyrimidine-4-yl)amino)-2-((2-(dimethylamino)ethyl)(methyl)amino)-4-methoxyphenyl)acrylamide | ¹H NMR (400 MHz, Chloroform-d) δ 8.84 (s, 1H), 8.36-8.30 (m, 1H), 7.49-7.43 (m, 1H), 7.24-7.17 (m, 1H), 7.05 (td, J = 8.5, 1.6 Hz, 1H), 6.76 (d, J = 13.8 Hz, 2H), 6.45-6.24 (m, 2H), 6.21-6.09 (m, 1H), 5.95 (dd, J = 8.7, 4.4 Hz, 1H), 5.70 (dt, J = 8.3, 3.1 Hz, 1H), 4.16-4.07 (m, 2H), 3.85 (s, 3H), 3.70 (d, J = 7.5 Hz, 1H), 3.16 (d, J = 5.3 Hz, 2H), 2.92-2.88 (m, 2H), 2.70 (s, 3H), 2.63 (s, 6H), 2.24 (dtd, J = 12.4, 8.1, 5.0 Hz, 2H), ; 570.3 [M + H]⁺ | 1.26 |
| 552 | 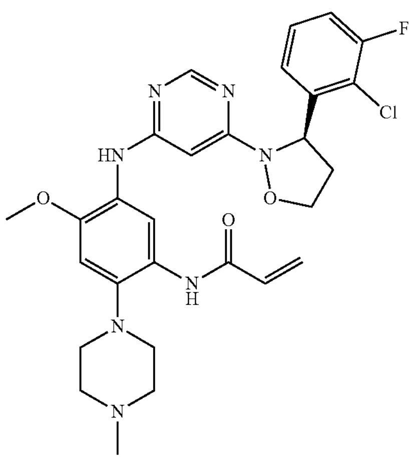 | N-(5-((6-((R)-3-(2-chloro-3-fluorophenyl)isoxazolidine-2-yl)pyrimidine-4-yl)amino)-4-methoxy-2-(4-methylpiperazine-1-yl)phenyl)acrylamide | ¹H NMR (400 MHz, Chloroform-d) δ 8.53 (s, 1H), 8.23 (d, J = 9.4 Hz, 1H), 7.46 (d, J = 7.8 Hz, 1H), 7.35 (d, J = 7.6 Hz, 1H), 7.21 (td, J = 8.0, 5.3 Hz, 1H), 7.09-6.93 (m, 2H), 6.73 (s, 1H), 6.42-6.24 (m, 2H), 5.95 (dd, J = 8.7, 4.5 Hz, 1H), 5.78-5.70 (m, 1H), 4.17-3.98 (m, 3H), 3.85 (s, 3H), 3.74 (s, 3H), 3.15 (s, 3H), 2.96 (dt, J = 20.7, 3.7 Hz, 3H), 2.78 (s, 4H), ; 568.3 [M + H]⁺ | 1.24 |
| 553 | 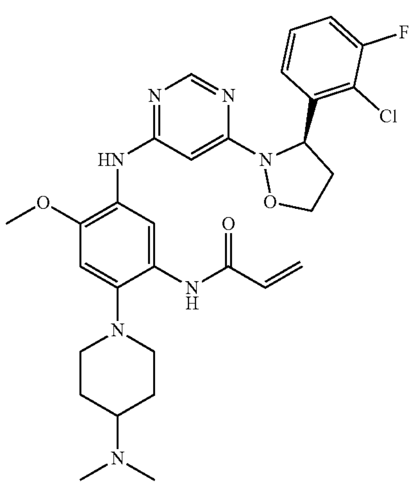 | N-(5-((6-((R)-3-(2-chloro-3-fluorophenyl)isoxazolidine-2-yl)pyrimidine-4-yl)amino)-2-(4-(dimethylamino)piperidine-1-yl)-4-methoxyphenyl)acrylamide | ¹H NMR (400 MHz, Chloroform-d) δ 8.84 (s, 1H), 8.40 (s, 1H), 8.35 (d, J = 1.0 Hz, 1H), 7.46 (d, J = 7.8 Hz, 1H), 7.21 (td, J = 8.0, 5.3 Hz, 1H), 7.13 (s, 1H), 7.05 (td, J = 8.5, 1.5 Hz, 1H), 6.73 (s, 1H), 6.36 (d, J = 2.9 Hz, 1H), 6.33-6.11 (m, 1H), 5.95 (dd, J = 8.8, 4.4 Hz, 1H), 5.73 (ddd, J = 20.7, 9.5, 2.5 Hz, 1H), 4.16-4.03 (m, 3H), 3.85 (s, 3H), 3.13 (d, J = 11.7 Hz, 2H), 2.94 (dtd, J = 12.3, 8.0, 4.3 Hz, 1H), 2.87-2.70 (m, 3H), 2.63 (s, 6H), 2.29-2.14 (m, 3H), 2.00-1.84 (m, 2H), ; 596.4 [M + H]⁺ | 1.24 |

TABLE 1-continued

| Example Compound | Structure | Name of Compound | ¹H NMR[[:]]; MS [M + H]⁺ | UPLC r.t. (min) |
|---|---|---|---|---|
| 554 | 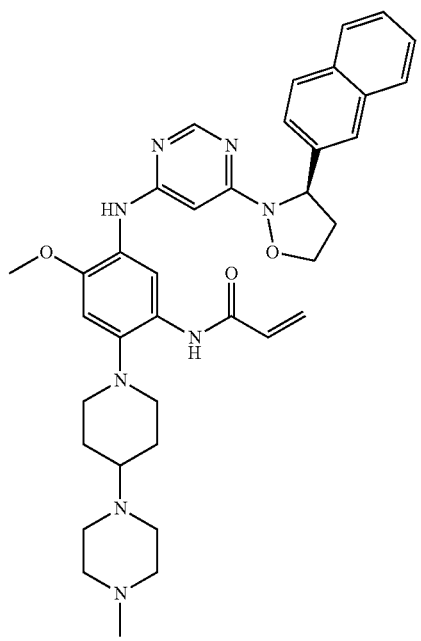 | N-(4-methoxy-2-(4-(4-methylpiperazine-1-yl)piperidine-1-yl)-5-((6-((R)-3-(naphthalene-2-yl)isoxazolidine-2-yl)pyrimidine-4-yl)amino)phenyl) acrylamide | ¹H NMR (400 MHz, DMSO-$d_6$) δ 9.06 (s, 1H), 8.25 (s, 1H), 8.05 (s, 1H), 7.95-7.88 (m, 4H), 7.56-7.48 (m, 3H), 6.85 (s, 1H), 6.64 (dd, J = 17.0, 10.2 Hz, 1H), 6.24 (dd, J = 17.1, 1.9 Hz, 2H), 5.79-5.64 (m, 2H), 4.28 (dd, J = 7.9, 4.0 Hz, 1H), 4.01 (d, J = 8.2 Hz, 1H), 3.79 (s, 3H), 3.61 (s, 2H), 3.17 (d, J = 12.0 Hz, 4H), 3.01-2.91 (m, 1H), 2.87 (s, 3H), 2.75 (t, J = 11.6 Hz, 4H), 2.45-2.31 (m, 1H), 2.05 (s, 4H), 1.90 (d, J = 10.8 Hz, 4H), ; 649.5 [M + H]⁺ | 1.13 |
| 555 | 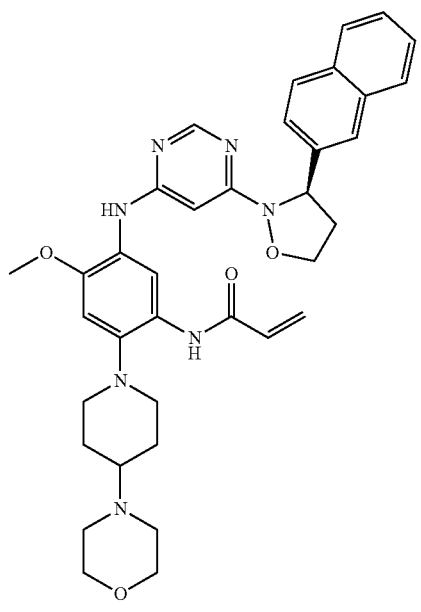 | N-(4-methoxy-2-(4-morpholinopiperidine-1-yl)-5-((6-((R)-3-(naphthalene-2-yl)isoxazolidine-2-yl)pyrimidine-4-yl)amino)phenyl) acrylamide | ¹H NMR (400 MHz, DMSO-$d_6$) δ 9.07 (s, 1H), 8.24 (s, 1H), 8.04 (s, 1H), 7.97-7.88 (m, 4H), 7.59-7.48 (m, 3H), 6.84 (s, 1H), 6.64 (dd, J = 17.0, 10.2 Hz, 1H), 6.24 (dd, J = 17.0, 1.9 Hz, 2H), 5.80-5.64 (m, 2H), 4.54 (d, J = 13.4 Hz, 1H), 4.34-4.21 (m, 1H), 4.03 (dt, J = 16.1, 10.8 Hz, 2H), 3.79 (s, 3H), 3.57 (d, J = 35.8 Hz, 2H), 3.47-3.34 (m, 2H), 3.18 (d, J = 11.7 Hz, 2H), 2.93 (d, J = 9.3 Hz, 2H), 2.75 (t, J = 11.7 Hz, 2H), 2.39 (dt, J = 13.0, 3.8 Hz, 1H), 2.07 (s, 5H), 2.02-1.87 (m, 2H), ; 636.5 [M + H]⁺ | 1.25 |

TABLE 1-continued

| Example Compound | Structure | Name of Compound | ¹H NMR[[:]]; MS [M + H]⁺ | UPLC r.t. (min) |
|---|---|---|---|---|
| 556 | 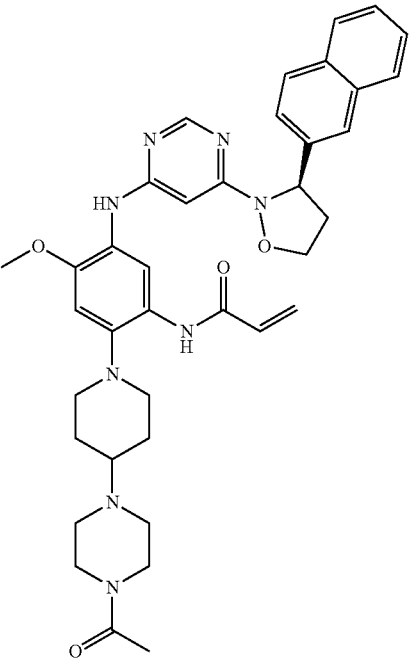 | N-(2-(4-(4-acetylpiperazine-1-yl)piperidine-1-yl)-4-methoxy-5-((6-((R)-3-(naphthalene-2-yl)isoxazolidine-2-yl)pyrimidine-4-yl)amino)phenyl) acrylamide | ¹H NMR (400 MHz, DMSO-d₆) δ 9.08 (s, 1H), 8.24 (d, J = 3.6 Hz, 1H), 8.03 (s, 1H), 7.96-7.87 (m, 4H), 7.52 (qd, J = 7.5, 3.7 Hz, 3H), 6.85 (s, 1H), 6.62 (dd, J = 17.0, 10.2 Hz, 1H), 6.24 (dd, J = 17.1, 1.9 Hz, 2H), 5.71 (ddd, J = 29.2, 9.4, 3.8 Hz, 2H), 4.29 (s, 1H), 4.02 (td, J = 16.2, 14.9, 9.8 Hz, 4H), 3.79 (s, 3H), 3.72 (t, J = 12.3 Hz, 3H), 3.49 (d, J = 12.1 Hz, 2H), 3.33 (s, 1H), 3.18 (d, J = 11.3 Hz, 4H), 2.93 (s, 1H), 2.75 (t, J = 11.8 Hz, 4H), 2.39 (dq, J = 13.1, 7.5 Hz, 1H), 2.22-2.09 (m, 2H), 2.02-1.84 (m, 2H), ; 677.5 [M + H]⁺ | 1.23 |
| 557 | 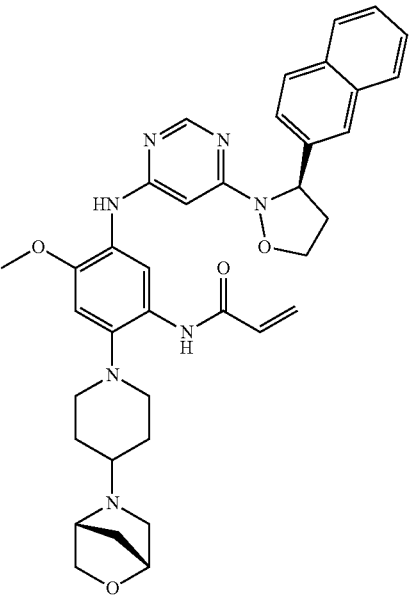 | N-(2-(4-((1R,4R)-2-oxa-5-azabicyclo[2.2.1]heptane-5-yl)piperidine-1-yl)-4-methoxy-5-((6-((R)-3-(naphthalene-2-yl)isoxazolidine-2-yl)pyrimidine-4-yl)amino)phenyl) acrylamide | ¹H NMR (400 MHz, DMSO-d₆) δ 9.09 (d, J = 16.6 Hz, 1H), 8.93 (s, 1H), 8.21 (s, 1H), 8.08 (s, 1H), 7.92 (dt, J = 8.6, 4.3 Hz, 4H), 7.59-7.46 (m, 3H), 6.83 (s, 1H), 6.54 (dt, J = 17.0, 10.2 Hz, 1H), 6.33 (s, 1H), 6.23 (dd, J = 16.4, 3.3 Hz, 1H), 5.72 (ddd, J = 19.7, 9.5, 4.5 Hz, 2H), 4.72 (s, 1H), 4.66 (d, J = 7.0 Hz, 1H), 4.23 (dd, J = 8.6, 4.6 Hz, 2H), 3.93 (t, J = 7.9 Hz, 1H), 3.81 (s, 3H), 3.75 (t, J = 10.1 Hz, 2H), 3.57-3.43 (m, 2H), 3.15 (t, J = 9.9 Hz, 2H), 2.92-2.73 (m, 3H), 2.36 (ddd, J = 12.8, 8.5, 4.1 Hz, 2H), 2.18-2.02 (m, 3H), 1.83 (s, 2H), ; 648.5 [M + H]⁺ | 1.24 |

TABLE 1-continued

| Example Compound | Structure | Name of Compound | ¹H NMR[[:]]; MS [M + H]⁺ | UPLC r.t. (min) |
|---|---|---|---|---|
| 558 | 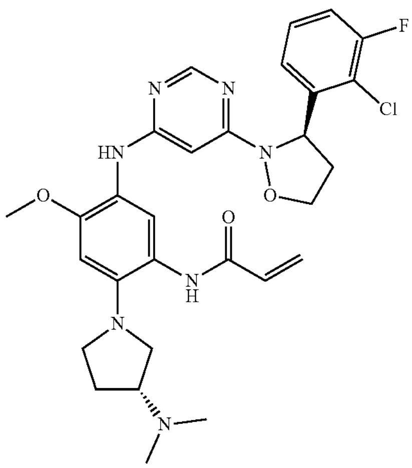 | N-(5-((6-((R)-3-(2-chloro-3-fluorophenyl)isoxazolidine-2-yl)pyrimidine-4-yl)amino)-2-((R)-3-(dimethylamino)pyrolidine-1-yl)-4-methoxyphenyl)acrylamide | ¹H NMR (400 MHz, DMSO-d₆) δ 9.94 (s, 1H), 9.33 (s, 1H), 8.86 (s, 1H), 8.18 (s, 1H), 7.62 (s, 1H), 7.38-7.35 (m, 2H), 6.65 (s, 1H), 6.51 (dd, J = 17.0, 10.2 Hz, 1H), 6.31-6.16 (m, 2H), 5.78 (dd, J = 8.8, 4.9 Hz, 1H), 5.73 (dd, J = 10.2, 2.0 Hz, 1H), 4.17 (td, J = 7.9, 3.8 Hz, 1H), 3.92-3.87 (m, 1H), 3.83 (s, 3H), 3.46-3.39 (m, 2H), 3.37-3.29 (m, 1H), 3.22 (q, J = 8.3 Hz, 1H), 2.92 (dt, J = 8.4, 4.0 Hz, 1H), 2.84 (d, J = 5.6 Hz, 6H), 2.40-2.29 (m, 2H), 2.11 (ddd, J = 12.3, 8.3, 3.5 Hz, 2H), ; 582.4 [M + H]⁺ | 1.22 |
| 559 | 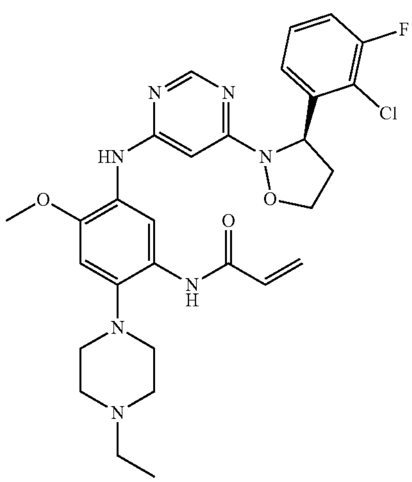 | N-(5-((6-((R)-3-(2-chloro-3-fluorophenyl)isoxazolidine-2-yl)pyrimidine-4-yl)amino)-2-(4-ethylpiperazine-1-yl)-4-methoxyphenyl)acrylamide | ¹H NMR (400 MHz, DMSO-d₆) δ 9.69 (s, 1H), 9.07 (s, 1H), 8.81 (s, 1H), 8.28 (s, 1H), 8.19 (s, 1H), 7.41-7.37 (m, 2H), 6.85 (s, 1H), 6.66 (dd, J = 17.0, 10.1 Hz, 1H), 6.43 (s, 1H), 6.24 (dd, J = 17.0, 2.0 Hz, 1H), 5.78 (ddd, J = 16.5, 9.4, 3.4 Hz, 2H), 4.17 (td, J = 7.9, 3.8 Hz, 1H), 3.91 (t, J = 8.1 Hz, 1H), 3.84 (s, 3H), 3.58 (d, J = 11.7 Hz, 2H), 3.29-3.16 (m, 6H), 3.05 (t, J = 12.2 Hz, 2H), 2.90 (qd, J = 8.3, 4.0 Hz, 1H), 2.12 (dtd, J = 12.8, 8.2, 5.0 Hz, 1H), 1.28 (t, J = 7.3 Hz, 3H), ; 582.4 [M + H]⁺ | 1.26 |
| 560 | 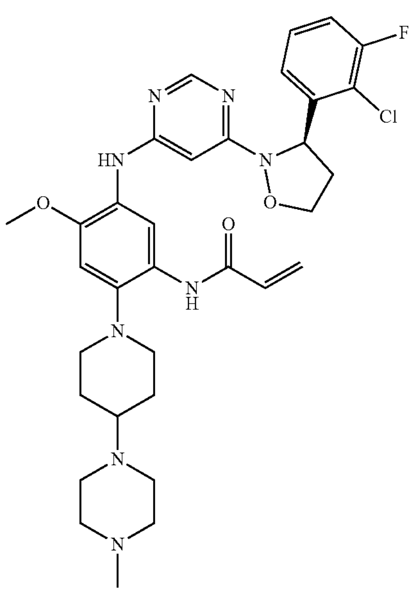 | N-(5-((6-((R)-3-(2-chloro-3-fluorophenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, DMSO-d₆) δ 9.10 (d, J = 30.3 Hz, 2H), 8.22 (s, 1H), 8.09 (s, 1H), 7.45-7.31 (m, 3H), 6.86 (s, 1H), 6.63 (dd, J = 16.9, 10.2 Hz, 1H), 6.35-6.18 (m, 2H), 5.85-5.68 (m, 2H), 4.20 (td, J = 7.9, 4.0 Hz, 1H), 3.96 (q, J = 8.0 Hz, 1H), 3.81 (s, 3H), 3.74-3.27 (m, 7H), 3.17 (d, J = 11.9 Hz, 4H), 2.95 (qt, J = 7.6, 3.8 Hz, 1H), 2.87 (s, 3H), 2.76 (t, J = 11.7 Hz, 2H), 2.15 (dp, J = 11.6, 3.9, 3.0 Hz, 1H), 2.07 (d, J = 11.5 Hz, 2H), 1.89 (d, J = 15.3 Hz, 2H), ; 651.5 [M + H]⁺ | 1.20 |

TABLE 1-continued

| Example Compound | Structure | Name of Compound | ¹H NMR[[:]]; MS [M + H]⁺ | UPLC r.t. (min) |
|---|---|---|---|---|
| 561 | 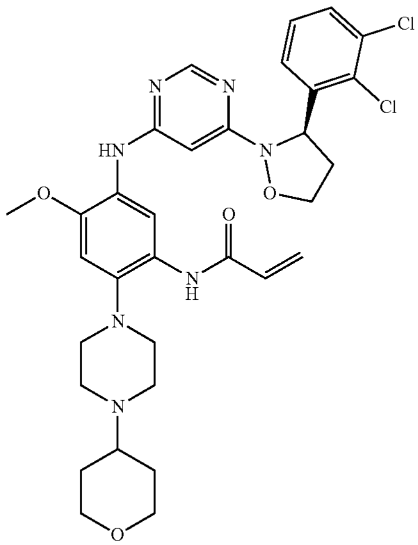 | N-(5-((6-((R)-3-(2,3-dichlorophenyl)isoxazolidine-2-yl)pyrimidine-4-yl)amino)-4-methoxy-2-(4-(tetrahydro-2H-pyran-4-yl)piperazine-1-yl)phenyl)acrylamide | ¹H NMR (400 MHz, Chloroform-d) δ 8.90 (s, 1H), 8.54 (s, 1H), 8.36 (d, J = 1.0 Hz, 1H), 7.62-7.57 (m, 1H), 7.37 (dd, J = 8.0, 1.6 Hz, 1H), 7.19 (t, J = 7.9 Hz, 1H), 6.96 (s, 1H), 6.82 (s, 1H), 6.76 (s, 1H), 6.40-6.31 (m, 1H), 6.26 (dd, J = 17.0, 9.9 Hz, 1H), 5.97 (dd, J = 8.8, 4.4 Hz, 1H), 5.75 (dd, J = 9.9, 1.6 Hz, 1H), 4.14-4.03 (m, 4H), 3.83 (s, 3H), 3.47-3.37 (m, 2H), 2.93 (s, 4H), 2.76 (s, 4H), 2.23 (dtd, J = 12.5, 8.2, 4.5 Hz, 1H), 1.84 (d, J = 12.6 Hz, 2H), 1.64 (ddd, J = 23.0, 13.6, 7.7 Hz, 4H), ; 654.4 [M + H] | 1.35 |
| 562 | 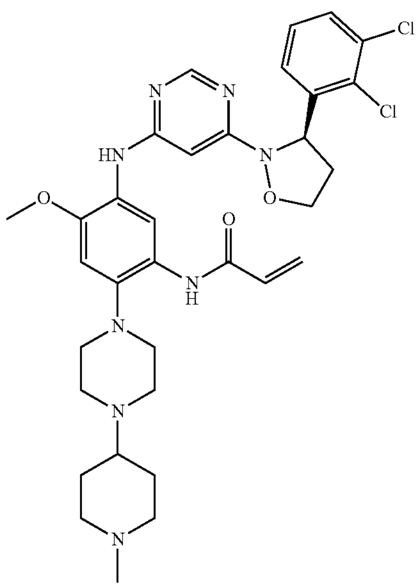 | N-(5-((6-((R)-3-(2,3-dichlorophenyl)isoxazolidine-2-yl)pyrimidine-4-yl)amino)-4-methoxy-2-(4-(1-methylpiperidine-4-yl)piperazine-1-yl)phenyl)acrylamide | ¹H NMR (400 MHz, Chloroform-d) δ 8.48 (s, 1H), 8.35 (dd, J = 8.9, 1.0 Hz, 1H), 7.57 (d, J = 8.9 Hz, 1H), 7.37 (ddd, J = 8.0, 4.1, 1.5 Hz, 1H), 7.20 (dt, J = 7.9, 4.0 Hz, 1H), 7.03-6.94 (m, 2H), 6.81-6.75 (m, 1H), 6.55 (d, J = 1.0 Hz, 1H), 6.39-6.22 (m, 1H), 5.95 (td, J = 8.8, 4.5 Hz, 1H), 5.75 (dd, J = 10.0, 1.6 Hz, 1H), 5.55 (s, 1H), 4.10 (q, J = 7.9 Hz, 2H), 3.96 (q, J = 8.1 Hz, 1H), 3.85 (d, J = 3.9 Hz, 4H), 3.30 (s, 3H), 3.26 (d, J = 7.2 Hz, 2H), 3.23 (s, 3H), 3.20-3.18 (m, 2H), 3.16 (s, 2H), 3.04 (t, J = 6.7 Hz, 4H), 1.99-1.95 (m, 4H), ; 667.4 [M + H] | 1.19 |

TABLE 1-continued

| Example Compound | Structure | Name of Compound | ¹H NMR[:]; MS [M + H]⁺ | UPLC r.t. (min) |
|---|---|---|---|---|
| 563 | 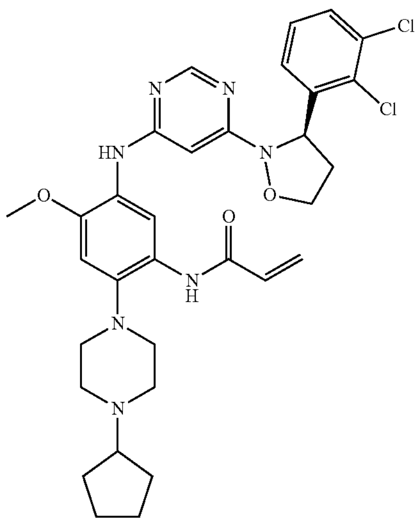 | N-(2-(4-cyclopentylpiperazine-1-yl)-5-((6-((R)-3-(2,3-dichlorophenyl)isoxazolidine-2-yl)pyrimidine-4-yl)amino)-4-methoxyphenyl)acrylamide | ¹H NMR (400 MHz, Chloroform-d) δ 8.90 (s, 1H), 8.59 (s, 1H), 8.36 (d, J = 1.0 Hz, 1H), 7.60 (dd, J = 7.9, 1.6 Hz, 1H), 7.37 (dd, J = 8.0, 1.6 Hz, 1H), 7.19 (t, J = 7.9 Hz, 1H), 6.95 (s, 1H), 6.83 (s, 1H), 6.76 (s, 1H), 6.40-6.21 (m, 2H), 5.97 (dd, J = 8.8, 4.4 Hz, 1H), 5.75 (dd, J = 9.8, 1.7 Hz, 1H), 4.15-4.04 (m, 2H), 3.82 (s, 3H), 3.00-2.91 (m, 4H), 2.70 (s, 2H), 2.59 (p, J = 7.8 Hz, 2H), 2.23 (dtd, J = 12.6, 8.2, 4.4 Hz, 1H), 1.93 (s, 2H), 1.79-1.70 (m, 2H), 1.60 (d, J = 6.9 Hz, 4H), 1.47 (q, J = 11.4, 9.8 Hz, 2H), ; 638.4 [M + H] | 1.39 |
| 564 | 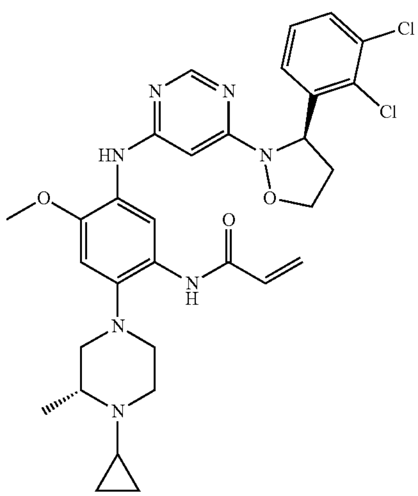 | N-(2-((R)-4-cyclopropyl-3-methylpiperazine-1-yl)-5-((6-((R)-3-(2,3-dichlorophenyl)isoxazolidine-2-yl)pyrimidine-4-yl)amino)-4-methoxyphenyl)acrylamide | ¹H NMR (400 MHz, Chloroform-d) δ 8.90 (s, 1H), 8.60 (s, 1H), 8.36 (d, J = 1.0 Hz, 1H), 7.63-7.57 (m, 1H), 7.37 (dd, J = 7.9, 1.6 Hz, 1H), 7.19 (t, J = 7.9 Hz, 1H), 6.94 (s, 1H), 6.78 (d, J = 9.8 Hz, 2H), 6.41-6.22 (m, 2H), 5.97 (dd, J = 8.7, 4.4 Hz, 1H), 5.75 (dd, J = 9.9, 1.7 Hz, 1H), 4.15-4.04 (m, 2H), 3.82 (s, 3H), 3.13 (d, J = 11.8 Hz, 1H), 2.96 (ddt, J = 12.1, 7.9, 4.1 Hz, 1H), 2.90 (d, J = 9.1 Hz, 1H), 2.83 (d, J = 10.3 Hz, 1H), 2.63-2.55 (m, 2H), 2.23 (dp, J = 12.1, 4.1 Hz, 1H), 1.56 (s, 3H), 1.26 (d, J = 6.2 Hz, 3H), 0.66 (ddt, J = 28.0, 10.2, 5.5 Hz, 2H), 0.49 (dq, J = 10.9, 5.9 Hz, 1H), 0.37 (dt, J = 10.5, 5.4 Hz, 1H), ; 624.4 [M + H] | 1.38 |

TABLE 1-continued

| Example Compound | Structure | Name of Compound | ¹H NMR[:]; MS [M + H]⁺ | UPLC r.t. (min) |
|---|---|---|---|---|
| 565 | 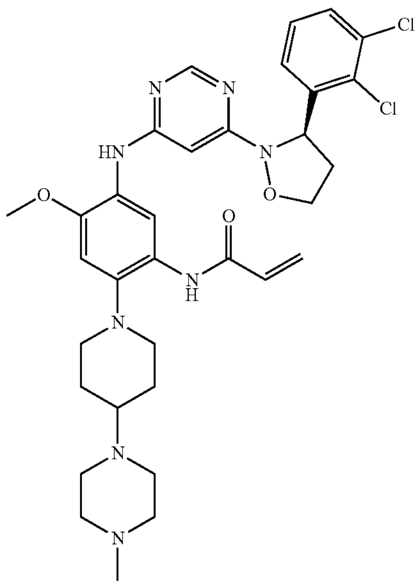 | N-(5-((6-((R)-3-(2,3-dichlorophenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, Chloroform-d) δ 8.87 (s, 1H), 8.43 (s, 1H), 8.36 (s, 1H), 7.60 (d, J = 7.6 Hz, 1H), 7.37 (d, J = 7.8 Hz, 1H), 7.20 (t, J = 7.9 Hz, 1H), 6.92 (s, 1H), 6.75 (s, 2H), 6.36 (d, J = 16.8 Hz, 1H), 6.25 (dd, J = 16.9, 9.9 Hz, 1H), 5.96 (dd, J = 8.8, 4.5 Hz, 1H), 5.74 (d, J = 10.1 Hz, 1H), 4.17-4.04 (m, 2H), 3.85 (s, 3H), 3.40-3.33 (m, 2H), 3.29-3.16 (m, 3H), 3.07 (d, J = 11.6 Hz, 2H), 3.00-2.88 (m, 3H), 2.80-2.70 (m, 4H), 2.46-2.38 (m, 4H), 2.26-2.16 (m, 2H), 2.09 (d, J = 12.4 Hz, 2H), ; 667.4 [M + H]⁺ | 1.28 |
| 566 | 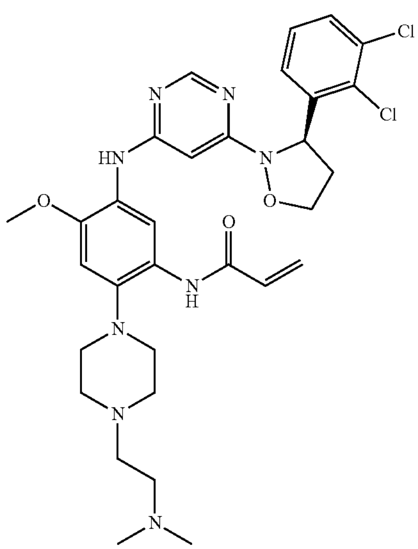 | N-(5-((6-((R)-3-(2,3-dichlorophenyl)isoxazolidine-2-yl)pyrimidine-4-yl)amino)-2-(4-(2-(dimethylamino)ethyl)piperazine-1-yl)-4-methoxyphenyl)acrylamide | ¹H NMR (400 MHz, Chloroform-d) δ 8.90 (s, 1H), 8.36 (d, J = 5.3 Hz, 1H), 7.61-7.57 (m, 1H), 7.36 (d, J = 3.3 Hz, 1H), 7.21-7.19 (m, 1H), 7.00 (s, 1H), 6.80 (d, J = 5.0 Hz, 1H), 6.74 (s, 1H), 6.55 (s, 1H), 6.47-6.39 (m, 1H), 6.35-6.26 (m, 1H), 5.99-5.92 (m, 1H), 5.78-5.71 (m, 1H), 4.09 (q, J = 8.0 Hz, 2H), 3.85 (s, 3H), 3.36 (t, J = 6.1 Hz, 3H), 3.21-3.16 (m, 5H), 3.13 (s, 2H), 3.04 (t, J = 6.4 Hz, 4H), 2.75 (s, 6H), ; 641.51 [M + H]⁺ | 1.26 |

TABLE 1-continued

| Example Compound | Structure | Name of Compound | ¹H NMR[:]; MS [M + H]⁺ | UPLC r.t. (min) |
|---|---|---|---|---|
| 567 | 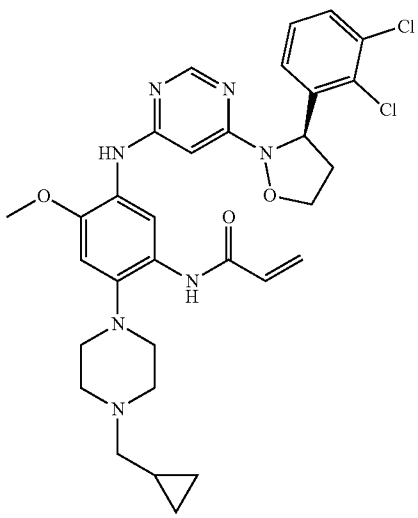 | N-(2-(4-(cyclopropylmethyl)piperazine-1-yl)-5-((6-((R)-3-(2,3-dichlorophenyl)isoxazolidine-2-yl)pyrimidine-4-yl)amino)-4-methoxyphenyl)acrylamide | ¹H NMR (400 MHz, Chloroform-d) δ 8.91 (s, 1H), 8.56 (s, 1H), 8.36 (d, J = 1.0 Hz, 1H), 7.64-7.58 (m, 1H), 7.37 (dd, J = 7.9, 1.6 Hz, 1H), 7.19 (t, J = 7.9 Hz, 1H), 6.95 (s, 1H), 6.84 (s, 1H), 6.76 (s, 1H), 6.41-6.34 (m, 1H), 6.32-6.22 (m, 1H), 5.97 (dd, J = 8.8, 4.4 Hz, 1H), 5.74 (dd, J = 9.9, 1.6 Hz, 1H), 4.16-4.04 (m, 2H), 3.84 (s, 3H), 3.04-2.89 (m, 5H), 2.74 (s, 3H), 2.54 (s, 1H), 2.38 (s, 1H), 2.32-2.16 (m, 2H), 1.56-1.50 (m, 1H), 0.64-0.53 (m, 2H), 0.23-0.15 (m, 2H), ; 624.39 [M + H]⁺ | 1.38 |
| 568 | 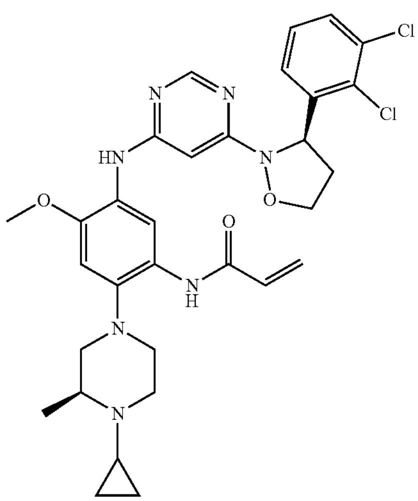 | N-(2-((S)-4-cyclopropyl-3-methylpiperazine-1-yl)-5-((6-((R)-3-(2,3-dichlorophenyl)isoxazolidine-2-yl)pyrimidine-4-yl)amino)-4-methoxyphenyl)acrylamide | ¹H NMR (400 MHz, Chloroform-d) δ 8.89 (s, 1H), 8.60 (s, 1H), 8.36 (d, J = 1.0 Hz, 1H), 7.60 (dd, J = 7.1, 1.1 Hz, 1H), 7.37 (dd, J = 8.0, 1.6 Hz, 1H), 7.19 (t, J = 7.9 Hz, 1H), 6.94 (s, 1H), 6.79 (s, 1H), 6.77 (s, 1H), 6.41-6.34 (m, 1H), 6.27 (dd, J = 17.0, 9.9 Hz, 1H), 5.97 (dd, J = 8.8, 4.4 Hz, 1H), 5.75 (dd, J = 10.0, 1.6 Hz, 1H), 4.15-4.05 (m, 2H), 3.82 (s, 3H), 3.17-3.09 (m, 1H), 3.00-2.92 (m, 1H), 2.90-2.87 (m, 1H), 2.82 (d, J = 11.1 Hz, 1H), 2.70 (s, 1H), 2.64-2.57 (m, 2H), 2.30-2.19 (m, 1H), 1.56 (s, 2H), 1.26 (d, J = 6.2 Hz, 3H), 0.74-0.59 (m, 2H), 0.54-0.45 (m, 1H), 0.44-0.35 (m, 1H), ; 624.4 [M + H]⁺ | 1.38 |

TABLE 1-continued

| Example Compound | Structure | Name of Compound | ¹H NMR[:]; MS [M + H]⁺ | UPLC r.t. (min) |
|---|---|---|---|---|
| 569 | 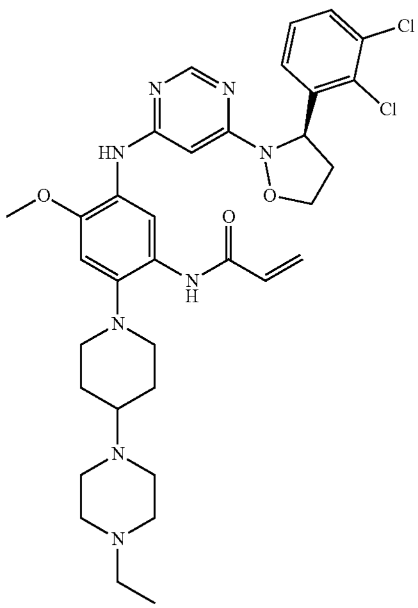 | N-(5-((6-((R)-3-(2,3-dichlorophenyl)isoxazolidine-2-yl)pyrimidine-4-yl)amino)-2-(4-(4-ethylpiperazine-1-yl)piperidine-1-yl)-4-methoxyphenyl)acrylamide | ¹H NMR (400 MHz, Chloroform-d) δ 8.87 (s, 1H), 8.40 (s, 1H), 8.36 (d, J = 1.0 Hz, 1H), 7.60 (dd, J = 7.6, 1.6 Hz, 1H), 7.37 (dd, J = 8.0, 1.6 Hz, 1H), 7.19 (t, J = 7.9 Hz, 1H), 6.94 (s, 1H), 6.77-6.72 (m, 2H), 6.40-6.32 (m, 1H), 6.25 (dd, J = 16.9, 10.1 Hz, 1H), 5.96 (dd, J = 8.8, 4.4 Hz, 1H), 5.74 (dd, J = 9.9, 1.6 Hz, 1H), 4.16-4.05 (m, 1H), 3.85 (s, 3H), 3.46-3.38 (m, 2H), 3.35-3.28 (m, 2H), 3.08 (d, J = 11.7 Hz, 2H), 3.00-2.85 (m, 5H), 2.74 (q, J = 12.4 Hz, 5H), 2.40 (s, 2H), 2.30-2.18 (m, 2H), 2.09 (d, J = 12.1 Hz, 2H), 1.19 (t, J = 7.3 Hz, 3H), ; 681.4 [M + H]⁺ | 1.28 |
| 570 | 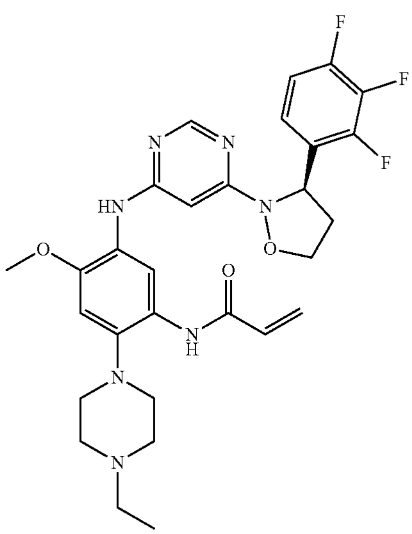 | N-(2-(4-ethylpiperazine-1-yl)-4-methoxy-5-((6-((R)-3-(2,3,4-trifluorophenyl)isoxazolidine-2-yl)pyrimidine-4-yl)amino)phenyl)acrylamide | ¹H NMR (400 MHz, Chloroform-d) δ 8.72 (s, 1H), 8.45 (s, 1H), 8.29 (s, 1H), 7.70 (s, 1H), 7.32-7.26 (m, 1H), 6.93 (tdd, J = 9.2, 6.8, 2.0 Hz, 1H), 6.84 (s, 1H), 6.64 (s, 1H), 6.40-6.28 (m, 2H), 5.83 (dd, J = 8.8, 4.7 Hz, 1H), 5.75 (dd, J = 8.6, 2.9 Hz, 1H), 4.13 (td, J = 8.1, 4.2 Hz, 1H), 4.03 (q, J = 8.0 Hz, 1H), 3.86 (s, 3H), 3.15-3.06 (m, 4H), 3.07-2.93 (m, 4H), 2.85 (dq, J = 8.7, 5.5, 4.6 Hz, 3H), 2.28 (dtd, J = 12.6, 8.1, 4.6 Hz, 1H), 1.28 (t, J = 7.3 Hz, 3H); 584.3 [M + H]⁺ | 1.25 |

TABLE 1-continued

| Example Compound | Structure | Name of Compound | ¹H NMR[:]; MS [M + H]⁺ | UPLC r.t. (min) |
|---|---|---|---|---|
| 571 | 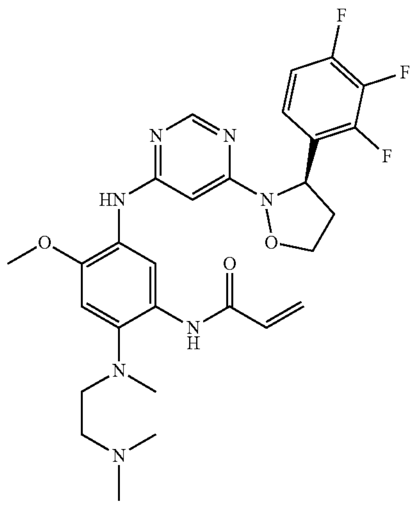 | N-(2-((2-(dimethylamino)ethyl)(methyl)amino)-4-methoxy-5-((6-((R)-3-(2,3,4-trifluorophenyl)isoxazolidine-2-yl)pyrimidine-4-yl)amino)phenyl)acrylamide | ¹H NMR (400 MHz, Chloroform-d) δ 9.38 (s, 1H), 8.78 (s, 1H), 8.28 (d, J = 1.0 Hz, 1H), 7.79 (s, 1H), 7.29 (q, J = 6.1, 5.2 Hz, 1H), 6.97-6.90 (m, 1H), 6.82-6.77 (m, 1H), 6.75 (s, 1H), 6.72-6.71 (m, 1H), 6.41 (dd, J = 16.9, 1.7 Hz, 1H), 5.85 (dd, J = 8.8, 4.6 Hz, 1H), 5.72 (dd, J = 10.3, 1.7 Hz, 1H), 4.15 (td, J = 7.0, 5.9, 3.1 Hz, 1H), 4.07 (q, J = 8.1 Hz, 1H), 3.85 (s, 3H), 3.16 (t, J = 5.9 Hz, 2H), 2.93 (t, J = 5.9 Hz, 2H), 2.84 (ddd, J = 10.1, 7.1, 3.2 Hz, 1H), 2.66 (s, 3H), 2.61 (s, 6H), 2.29 (dt, J = 12.5, 4.0 Hz, 1H); 572.4 [M + H]⁺ | 1.30 |
| 572 | 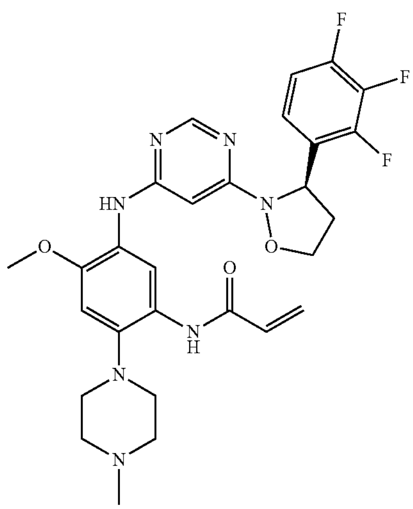 | N-(4-methoxy-2-(4-methylpiperazine-1-yl)-5-((6-((R)-3-(2,3,4-trifluorophenyl)isoxazolidine-2-yl)pyrimidine-4-yl)amino)phenyl)acrylamide | ¹H NMR (400 MHz, Chloroform-d) δ 8.75 (s, 1H), 8.42 (s, 1H), 8.29 (s, 1H), 7.71 (s, 1H), 7.33-7.27 (m, 1H), 6.96-6.90 (m, 1H), 6.82 (s, 1H), 6.66 (s, 1H), 6.37 (d, J = 16.7 Hz, 1H), 6.28 (dd, J = 16.8, 9.9 Hz, 1H), 5.84 (dd, J = 8.3, 4.5 Hz, 1H), 5.76 (dd, J = 9.8, 1.7 Hz, 1H), 4.13 (td, J = 8.0, 4.1 Hz, 1H), 4.04 (q, J = 8.1 Hz, 1H), 3.86 (s, 3H), 3.01 (q, J = 4.1 Hz, 4H), 2.84 (dq, J = 8.4, 4.2 Hz, 5H), 2.49 (s, 3H), 2.28 (dtd, J = 12.7, 8.2, 4.7 Hz, 1H); 570.4 [M + H]⁺ | 1.27 |
| 573 | 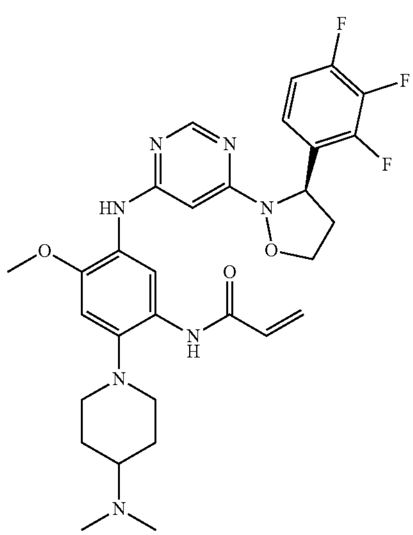 | N-(2-(4-(dimethylamino)piperidine-1-yl)-4-methoxy-5-((6-((R)-3-(2,3,4-trifluorophenyl)isoxazolidine-2-yl)pyrimidine-4-yl)amino)phenyl)acrylamide | ¹H NMR (400 MHz, Chloroform-d) δ 8.75 (s, 1H), 8.46 (s, 1H), 8.30 (d, J = 1.0 Hz, 1H), 7.50 (s, 1H), 7.33-7.28 (m, 1H), 6.93 (tdd, J = 9.2, 6.9, 2.1 Hz, 1H), 6.74 (s, 1H), 6.69 (s, 1H), 6.40-6.34 (m, 2H), 5.85 (dd, J = 8.8, 4.6 Hz, 1H), 5.75 (dd, J = 7.3, 4.2 Hz, 1H), 4.13 (td, J = 8.0, 4.2 Hz, 1H), 4.05 (q, J = 8.0 Hz, 1H), 3.85 (s, 3H), 3.12 (d, J = 11.8 Hz, 2H), 2.87-2.70 (m, 4H), 2.60 (s, 6H), 2.28 (dq, J = 8.7, 4.7, 4.0 Hz, 1H), 2.17-2.10 (m, 2H), 1.89 (qd, J = 10.8, 9.6, 5.9 Hz, 2H); 598.5 [M + H]⁺ | 1.28 |

TABLE 1-continued

| Example Compound | Structure | Name of Compound | ¹H NMR[[:]]; MS [M + H]⁺ | UPLC r.t. (min) |
|---|---|---|---|---|
| 574 | 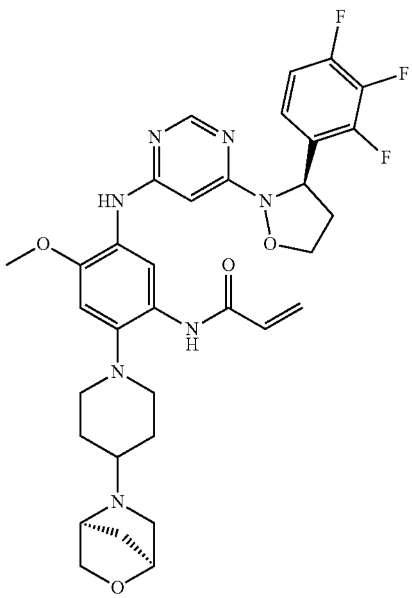 | N-(2-(4-((1S,4S)-2-oxa-5-azabicyclo[2.2.1]heptane-5-yl)piperidine-1-yl)-4-methoxy-5-((6-((R)-3-(2,3,4-trifluorophenyl)isoxazolidine-2-yl)pyrimidine-4-yl)amino)phenyl)acrylamide | ¹H NMR (400 MHz, DMSO-$d_6$) δ 10.14 (s, 1H), 9.31 (d, J = 35.5 Hz, 1H), 8.33 (s, 1H), 7.87 (d, J = 12.0 Hz, 1H), 7.37-7.20 (m, 2H), 6.94 (d, J = 10.8 Hz, 1H), 6.62 (ddd, J = 21.3, 17.0, 10.2 Hz, 1H), 6.28-6.15 (m, 2H), 5.78 (s, 1H), 5.70 (dd, J = 8.6, 5.6 Hz, 1H), 4.73-4.68 (m, 1H), 4.61 (d, J = 29.7 Hz, 1H), 4.36-4.29 (m, 1H), 4.21 (d, J = 10.3 Hz, 1H), 4.10-4.01 (m, 1H), 3.83 (d, J = 2.3 Hz, 3H), 3.70 (dd, J = 9.3, 5.0 Hz, 1H), 3.53-3.41 (m, 2H), 3.25 (d, J = 13.0 Hz, 3H), 3.19-3.10 (m, 1H), 2.90 (ddd, J = 26.1, 15.2, 7.3 Hz, 3H), 2.37-2.28 (m, 2H), 2.19 (d, J = 11.5 Hz, 1H), 2.14-2.03 (m, 3H), ; 652.3 [M + H]⁺ | 1.28 |
| 575 | 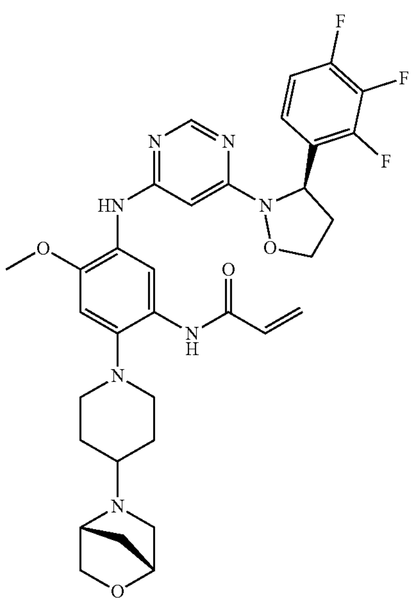 | N-(2-(4-((1R,4R)-2-oxa-5-azabicyclo[2.2.1]heptane-5-yl)piperidine-1-yl)-4-methoxy-5-((6-((R)-3-(2,3,4-trifluorophenyl)isoxazolidine-2-yl)pyrimidine-4-yl)amino)phenyl)acrylamide | ¹H NMR (400 MHz, DMSO-$d_6$) δ 9.72 (s, 1H), 9.23 (d, J = 32.9 Hz, 1H), 8.29 (s, 1H), 7.92 (d, J = 12.2 Hz, 1H), 7.29 (dt, J = 20.3, 8.0 Hz, 2H), 6.90 (d, J = 7.4 Hz, 1H), 6.58 (dt, J = 16.2, 8.1 Hz, 1H), 6.28-6.19 (m, 2H), 5.78-5.65 (m, 2H), 4.68 (d, J = 22.6 Hz, 2H), 4.58 (s, 1H), 4.01 (d, J = 7.9 Hz, 2H), 3.82 (d, J = 2.0 Hz, 3H), 3.70 (d, J = 9.6 Hz, 1H), 3.45 (d, J = 8.0 Hz, 2H), 3.37-3.13 (m, 4H), 2.94-2.68 (m, 4H), 2.31 (dt, J = 13.6, 5.6 Hz, 2H), 2.08 (d, J = 11.4 Hz, 3H), ; 652.3 [M + H]⁺ | 1.26 |

TABLE 1-continued

| Example Compound | Structure | Name of Compound | ¹H NMR[:]; MS [M + H]⁺ | UPLC r.t. (min) |
|---|---|---|---|---|
| 576 | 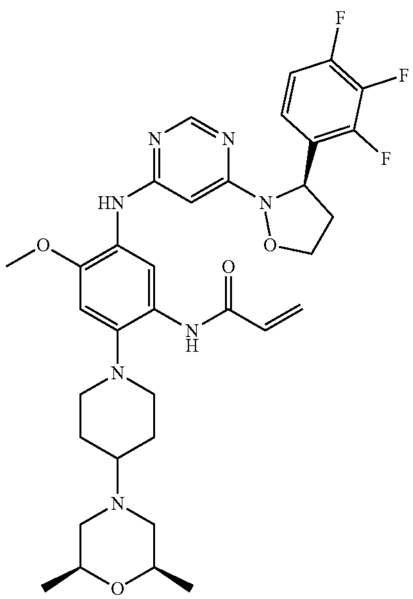 | N-(2-(4-((2S,6R)-2,6-dimethylmorpholino)piperidine-1-yl)-4-methoxy-5-((6-((R)-3-(2,3,4-trifluorophenyl)isoxazolidine-2-yl)pyrimidine-4-yl)amino)phenyl)acrylamide | ¹H NMR (400 MHz, DMSO-d₆) δ 10.16 (s, 1H), 9.23 (s, 1H), 8.33 (s, 1H), 7.89 (s, 1H), 7.32 (ddd, J = 9.4, 7.2, 1.9 Hz, 1H), 7.25 (dd, J = 11.3, 4.7 Hz, 1H), 6.94 (s, 1H), 6.70 (dd, J = 17.0, 10.2 Hz, 1H), 6.29-6.22 (m, 1H), 6.18 (s, 1H), 5.75 (d, J = 5.1 Hz, 1H), 5.72-5.68 (m, 1H), 4.33 (q, J = 3.7 Hz, 1H), 4.19-4.11 (m, 2H), 4.06 (d, J = 7.6 Hz, 2H), 3.82 (s, 3H), 3.46 (d, J = 11.7 Hz, 1H), 3.30-3.21 (m, 3H), 3.01-2.90 (m, 1H), 2.85-2.76 (m, 2H), 2.69 (d, J = 10.7 Hz, 3H), 2.33 (d, J = 7.7 Hz, 1H), 2.24 (d, J = 10.4 Hz, 2H), 2.09 (d, J = 12.6 Hz, 2H), 1.17 (d, J = 6.3 Hz, 6H), ; 668.3 [M + H]⁺ | 1.35 |
| 577 | 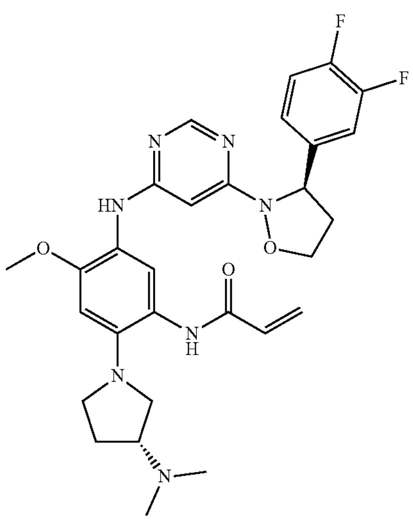 | N-(5-((6-((R)-3-(3,4-difluorophenyl)isoxazolidine-2-yl)pyrimidine-4-yl)amino)-2-((R)-3-(dimethylamino)pyrolidine-1-yl)-4-methoxyphenyl)acrylamide | ¹H NMR (400 MHz, Methanol-d₄) δ 8.04 (s, 1H), 7.86 (s, 1H), 7.25-7.17 (m, 1H), 7.12-7.08 (m, H), 6.64 (s, 1H), 6.31-6.20 (m, 2H), 5.68-5.64 (m, 1H), 5.38 (dd, J = 8.4, 4.7 Hz, 1H), 4.00 (td, J = 7.8, 4.3 Hz, 1H), 3.84-3.77 (m, 2H), 3.75 (s, 3H), 3.47 (dd, J = 10.7, 4.4 Hz, 1H), 3.34-3.23 (m, 2H), 3.23-3.16 (m, 1H), 3.01 (d, J = 2.2 Hz, 2H), 2.78 (s, 5H), 2.69-2.56 (m, 2H), 2.32 (ddd, J = 19.2, 9.4, 5.4 Hz, 1H), 2.22-2.03 (m, 2H); 566.4 [M + H]⁺ | 1.20 |

TABLE 1-continued

| Example Compound | Structure | Name of Compound | ¹H NMR[[:]]; MS [M + H]⁺ | UPLC r.t. (min) |
|---|---|---|---|---|
| 578 | 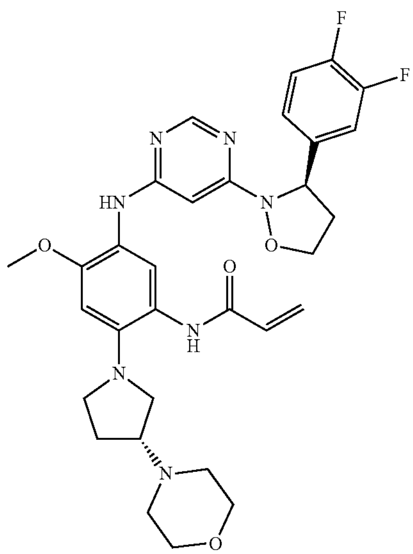 | N-(5-((6-((R)-3-(3,4-difluorophenyl)isoxazolidine-2-yl)pyrimidine-4-yl)amino)-4-methoxy-2-((R)-3-morpholinopyrrolidine-1-yl)phenyl)acrylamide | ¹H NMR (400 MHz, Methanol-d₄) δ 8.02 (s, 1H), 7.69 (s, 1H), 7.25-7.17 (m, 1H), 7.12-7.04 (m, 2H), 6.55-6.42 (m, 2H), 6.22 (td, J = 4.1, 1.8 Hz, 2H), 5.64 (dd, J = 10.3, 1.4 Hz, 1H), 5.38 (dd, J = 8.5, 4.6 Hz, 1H), 3.99 (td, J = 7.8, 4.3 Hz, 1H), 3.84-3.75 (m, 1H), 3.72 (s, 3H), 3.67 (t, J = 4.6 Hz, 4H), 3.28 (dd, J = 9.4, 6.5 Hz, 1H), 3.21-3.12 (m, 3H), 2.72-2.55 (m, 5H), 2.55 (d, J = 8.4 Hz, 9H), 2.23-2.07 (m, 2H), 1.86 (dq, J = 12.2, 8.5 Hz, 1H); 608.4 [M + H]⁺ | 1.18 |
| 579 | 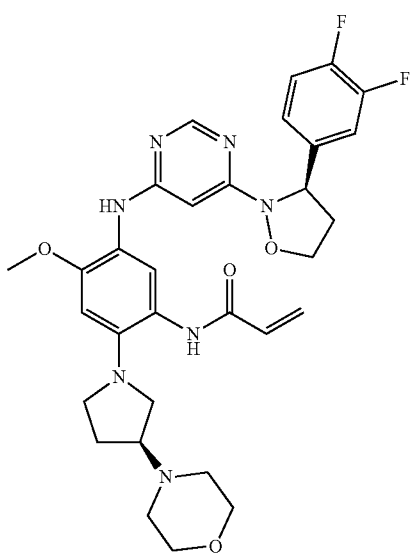 | N-(5-((6-((R)-3-(3,4-difluorophenyl)isoxazolidine-2-yl)pyrimidine-4-yl)amino)-4-methoxy-2-((S)-3-morpholinopyrrolidine-1-yl)phenyl)acrylamide | ¹H NMR (400 MHz, Methanol-d₄) δ 8.14 (s, 1H), 7.69 (s, 1H), 7.39-7.32 (m, 1H), 7.27-7.19 (m, 2H), 6.66 (s, 1H), 6.53 (dd, 17.0, 10.2 Hz, 1H), 6.40-6.30 (m, 2H), 5.79 (dd, J = 10.2, 1.5 Hz, 1H), 5.53 (dd, J = 8.5, 4.7 Hz, 1H), 4.13 (td, J = 7.9, 4.2 Hz, 1H), 3.95 (d, J = 7.9 Hz, 1H), 3.86 (s, 3H), 3.75 (t, J = 4.6 Hz, 4H), 3.39-3.24 (m, 8H), 3.01-2.91 (m, 1H), 2.84-2.73 (m, 1H), 2.68 (s, 1H), 2.66-2.49 (m, 4H), 2.38-2.27 (m, 1H), 2.27-2.18 (m, 1H), 1.91 (dq, J = 17.6, 8.8 Hz, 1H); 608.4 [M + H]⁺ | 1.17 |

| Example Compound | Structure | Name of Compound | ¹H NMR[:]; MS [M + H]⁺ | UPLC r.t. (min) |
|---|---|---|---|---|
| 580 | 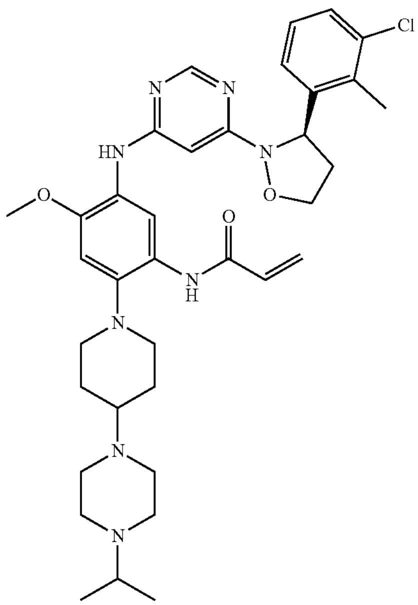 | N-(5-((6-((R)-3-(3-chloro-2-methylphenyl)isoxazolidine-2-yl)pyrimidine-4-yl)amino)-2-(4-(4-isopropylpiperazine-1-yl)piperidine-1-yl)-4-methoxyphenyl)acrylamide | ¹H NMR (400 MHz, DMSO-$d_6$) δ 8.95 (s, 1H), 8.59 (s, 1H), 8.14 (s, 1H), 7.40 (d, J = 7.7 Hz, 2H), 7.34 (d, J = 7.9 Hz, 2H), 7.20 (t, J = 7.9 Hz, 2H), 6.82 (s, 1H), 6.65 (dd, J = 16.8, 10.2 Hz, 2H), 6.34 (s, 1H), 6.20 (dd, J = 17.0, 2.0 Hz, 1H), 5.69 (dd, J = 9.2, 5.0 Hz, 2H), 4.19-4.10 (m, 2H), 3.79 (s, 3H), 3.15 (s, 4H), 3.09 (s, 3H), 3.00 (s, 2H), 2.43 (d, J = 8.1 Hz, 9H), 1.84 (d, J = 12.1 Hz, 3H), 1.68 (s, 6H), 0.96 (d, J = 6.5 Hz, 7H), ; 675.5 [M + H]⁺ | 1.25 |
| 581 | 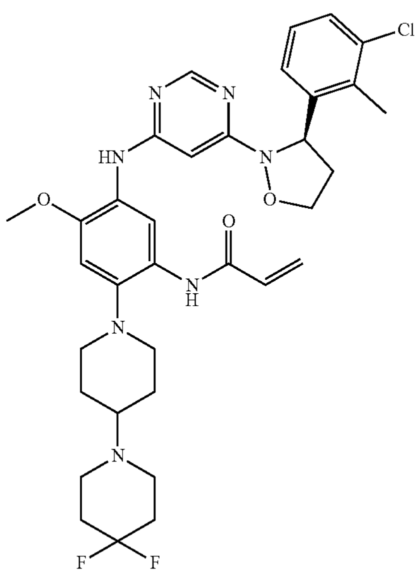 | N-(5-((6-((R)-3-(3-chloro-2-methylphenyl)isoxazolidine-2-yl)pyrimidine-4-yl)amino)-2-(4,4-difluoro-[1,4'-bipiperidine]-1'-yl)-4-methoxyphenyl)acrylamide | ¹H NMR (400 MHz, DMSO-$d_6$) δ 8.95 (s, 1H), 8.59 (s, 1H), 8.17-8.12 (m, 2H), 7.40 (dd, J = 7.8, 1.3 Hz, 1H), 7.34 (dd, J = 8.0, 1.3 Hz, 1H), 7.20 (t, J = 7.9 Hz, 1H), 6.82 (s, 1H), 6.66 (dd, J = 16.9, 10.2 Hz, 1H), 6.35 (s, 1H), 6.21 (dd, J = 17.0, 2.0 Hz, 1H), 5.75-5.67 (m, 2H), 4.15 (td, J = 7.9, 3.9 Hz, 1H), 3.79 (s, 3H), 3.32 (s, 4H), 3.06 (d, J = 11.2 Hz, 2H), 2.82 (tq, J = 8.1, 4.1 Hz, 1H), 2.66 (t, J = 5.7 Hz, 5H), 2.42 (s, 4H), 2.08 (ddt, J = 11.7, 7.8, 4.1 Hz, 1H), 2.00 (s, 1H), 1.95 (td, J = 13.2, 12.4, 6.2 Hz, 5H), 1.77 (dd, J = 14.2, 8.5 Hz, 5H), ; 668.5 [M + H]⁺ | 1.36 |

TABLE 1-continued

| Example Compound | Structure | Name of Compound | ¹H NMR[[:]]; MS [M + H]⁺ | UPLC r.t. (min) |
|---|---|---|---|---|
| 582 | 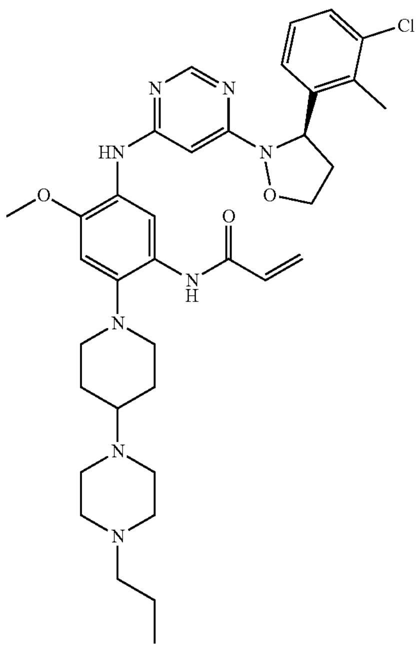 | N-(5-((6-((R)-3-(3-chloro-2-methylphenyl) isoxazolidine-2-yl)pyrimidine-4-yl)amino)-4-methoxy-2-(4-(4-propylpiperazine-1-yl)piperidine-1-yl)phenyl)acrylamide | ¹H NMR (400 MHz, DMSO-d6) δ 8.95 (s, 1H), 8.59 (s, 1H), 8.16-8.12 (m, 2H), 7.40 (dd, J = 7.8, 1.3 Hz, 1H), 7.34 (dd, J = 8.0, 1.4 Hz, 1H), 7.20 (t, J = 7.9 Hz, 1H), 6.82 (s, 1H), 6.65 (dd, J = 17.0, 10.2 Hz, 1H), 6.35 (s, 1H), 6.20 (dd, J = 16.9, 2.0 Hz, 1H), 5.74-5.66 (m, 2H), 4.14 (td, J = 7.9, 3.8 Hz, 1H), 3.79 (s, 3H), 3.04 (d, J = 10.7 Hz, 3H), 2.83 (dtd, J = 11.9, 8.0, 3.8 Hz, 2H), 2.66 (t, J = 11.6 Hz, 3H), 2.54 (s, 2H), 2.42 (s, 4H), 2.37 (d, J = 7.9 Hz, 4H), 2.24-2.17 (m, 3H), 2.13-2.01 (m, 2H), 1.84 (d, J = 13.9 Hz, 3H), 1.78 (s, 3H), 1.71 (t, J = 11.8 Hz, 3H), 1.42 (h, J = 7.3 Hz, 3H), 0.85 (t, J = 7.4 Hz, 4H), ; 675.6 [M + H]⁺ | 1.26 |
| 583 | 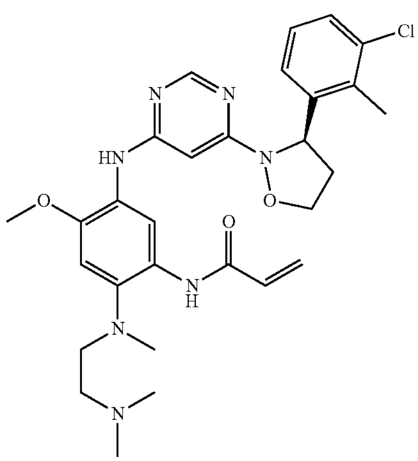 | N-(5-((6-((R)-3-(3-chloro-2-methylphenyl) isoxazolidine-2-yl)pyrimidine-4-yl)amino)-2-((2-(dimethylamino) ethyl)(methyl)amino)-4-methoxyphenyl) acrylamide | ¹H NMR (400 MHz, DMSO-d₆) δ 10.06 (s, 1H), 8.47 (s, 1H), 8.16 (d, J = 1.0 Hz, 1H), 7.40 (dd, J = 7.9, 1.3 Hz, 1H), 7.34 (dd, J = 8.0, 1.4 Hz, 1H), 7.20 (t, J = 7.9 Hz, 1H), 6.99 (s, 1H), 6.43-6.33 (m, 2H), 6.21 (dd, J = 17.0, 2.2 Hz, 1H), 5.74-5.67 (m, 2H), 4.15 (td, J = 7.9, 3.8 Hz, 1H), 3.80 (s, 3H), 2.84 (dt, J = 12.9, 4.8 Hz, 4H), 2.71 (s, 3H), 2.43 (s, 4H), 2.32 (t, J = 5.8 Hz, 2H), 2.20 (s, 7H), 2.08 (tdd, J = 11.5, 8.3, 4.1 Hz, 2H), 1.86 (s, 4H), ; 566.4 [M + H]⁺ | 1.31 |
| 584 | 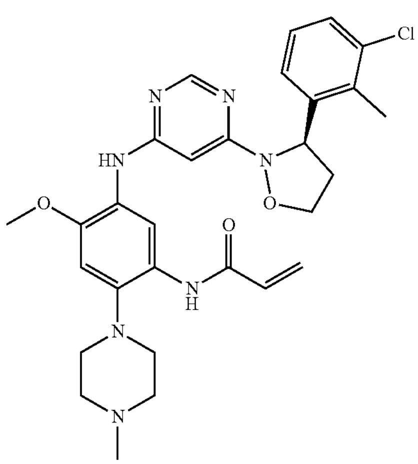 | N-(5-((6-((R)-3-(3-chloro-2-methylphenyl) isoxazolidine-2-yl)pyrimidine-4-yl)amino)-4-methoxy-2-(4-methylpiperazine-1-yl)phenyl)acrylamide | ¹H NMR (400 MHz, DMSO-d₆) δ 8.97 (s, 1H), 8.60 (s, 1H), 8.15 (d, J = 0.9 Hz, 1H), 7.40 (dd, J = 7.7, 1.3 Hz, 1H), 7.34 (dd, J = 8.0, 1.4 Hz, 1H), 7.20 (t, J = 7.9 Hz, 1H), 6.84 (s, 1H), 6.59 (dd, J = 17.0, 10.2 Hz, 1H), 6.36 (s, 1H), 6.20 (dd, J = 17.0, 2.0 Hz, 1H), 5.71 (td, J = 9.0, 8.3, 3.5 Hz, 2H), 4.15 (td, J = 7.9, 3.9 Hz, 1H), 3.81 (s, 3H), 2.90-2.76 (m, 6H), 2.42 (s, 4H), 2.25 (s, 3H), 2.14-2.00 (m, 2H), 1.82 (s, 4H), ; 564.4 [M + H]⁺ | 1.25 |

TABLE 1-continued

| Example Compound | Structure | Name of Compound | ¹H NMR[[:]]; MS [M + H]⁺ | UPLC r.t. (min) |
|---|---|---|---|---|
| 585 | 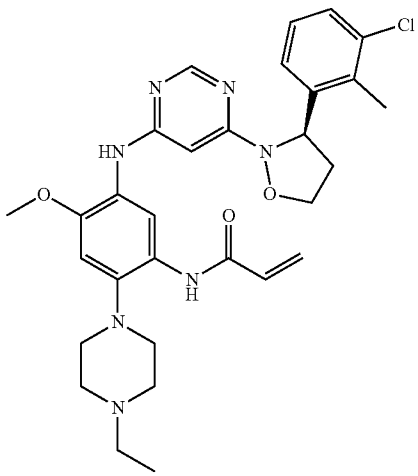 | N-(5-((6-((R)-3-(3-chloro-2-methylphenyl)isoxazolidine-2-yl)pyrimidine-4-yl)amino)-2-(4-ethylpiperazine-1-yl)-4-methoxyphenyl)acrylamide | ¹H NMR (400 MHz, DMSO-d₆) δ 8.98 (s, 1H), 8.60 (s, 1H), 8.15 (d, J = 1.0 Hz, 1H), 7.40 (dd, J = 7.8, 1.4 Hz, 1H), 7.34 (dd, J = 8.0, 1.4 Hz, 1H), 7.20 (t, J = 7.9 Hz, 1H), 6.86 (s, 1H), 6.59 (dd, J = 17.0, 10.1 Hz, 1H), 6.36 (s, 1H), 6.20 (dd, J = 17.0, 2.0 Hz, 1H), 5.71 (td, J = 8.6, 7.5, 3.4 Hz, 2H), 4.15 (td, J = 7.8, 3.8 Hz, 1H), 3.81 (s, 4H), 2.91-2.77 (m, 6H), 2.41 (d, J = 13.2 Hz, 6H), 2.07 (dtd, J = 19.3, 7.4, 6.6, 4.5 Hz, 2H), 1.87 (s, 4H), 1.03 (t, J = 7.2 Hz, 4H), ; 578.4 [M + H]⁺ | 1.26 |
| 586 | 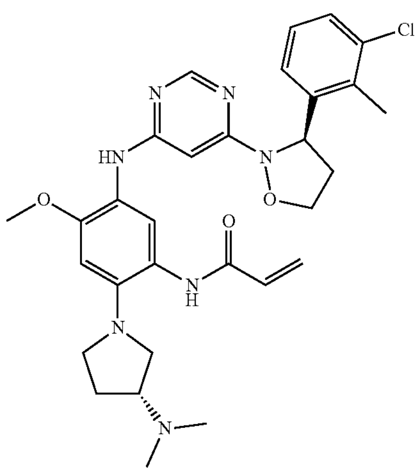 | N-(5-((6-((R)-3-(3-chloro-2-methylphenyl)isoxazolidine-2-yl)pyrimidine-4-yl)amino)-2-((R)-3-(dimethylamino)pyrrolidine-1-yl)-4-methoxyphenyl)acrylamide | ¹H NMR (400 MHz, DMSO-d₆) δ 9.37 (s, 1H), 8.46 (s, 1H), 8.11 (d, J = 0.9 Hz, 1H), 7.39 (dd, J = 7.8, 1.3 Hz, 1H), 7.34 (dd, J = 7.9, 1.3 Hz, 2H), 7.19 (t, J = 7.8 Hz, 2H), 6.53-6.41 (m, 2H), 6.18 (dd, J = 17.0, 2.1 Hz, 2H), 5.71-5.68 (m, 1H), 4.13 (td, J = 7.9, 3.8 Hz, 2H), 3.79 (s, 4H), 3.37 (td, J = 9.5, 6.4 Hz, 2H), 3.26-3.16 (m, 4H), 2.81 (dtd, J = 12.0, 8.0, 3.8 Hz, 2H), 2.42 (s, 4H), 2.16 (s, 7H), 2.07 (tdt, J = 10.8, 7.0, 3.4 Hz, 4H), 1.71 (p, J = 10.6, 10.0 Hz, 2H), ; 578.4 [M + H]⁺ | 1.22 |

TABLE 1-continued

| Example Compound | Structure | Name of Compound | ¹H NMR[[:]]; MS [M + H]⁺ | UPLC r.t. (min) |
|---|---|---|---|---|
| 587 | 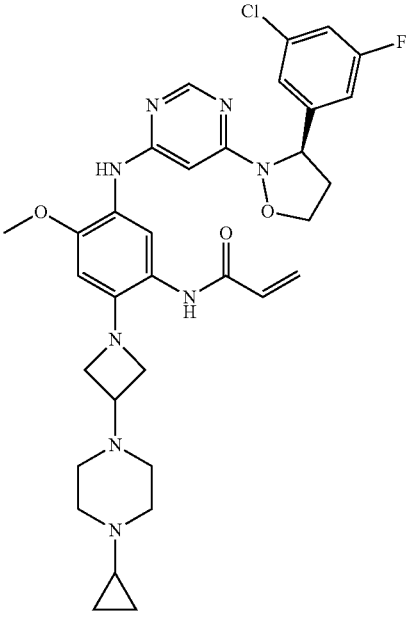 | N-(5-(((6-((R)-3-(3-chloro-5-fluorophenyl)isoxazolidine-2-yl)pyrimidine-4-yl)amino)-2-(3-(4-cyclopropylpiperazine-1-yl)azetidine-1-yl)-4-methoxyphenyl)acrylamide | ¹H NMR (400 MHz, CDCl₃) δ 8.31 (s, 1H), 8.04 (s, 1H), 7.13-7.05 (m, 2H), 7.00-6.93 (m, 1H), 6.75-6.66 (m, 1H), 6.49 (s, 1H), 6.42-6.36 (m, 1H), 6.36-6.22 (m, 2H), 5.81-5.71 (m, 1H), 5.64 (dd, J = 8.6, 4.6 Hz, 1H), 4.17-3.90 (m, 4H), 3.85 (s, 3H), 3.83-3.65 (m, 3H), 3.29-3.19 (m, 1H), 2.80-2.57 (m, 5H), 2.55-2.23 (m, 5H), 0.50-0.37 (m, 4H), ; 649.40 [M + H]⁺ | 1.24 |
| 588 | 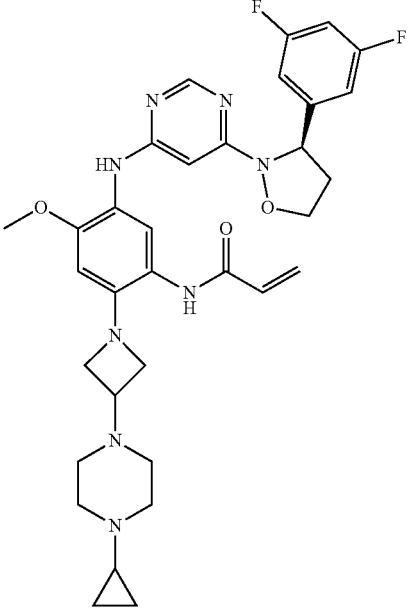 | N-(2-(3-(4-cyclopropylpiperazine-1-yl)azetidine-1-yl)-5-((6-((R)-3-(3,5-difluorophenyl)isoxazolidine-2-yl)pyrimidine-4-yl)amino)-4-methoxyphenyl)acrylamide | ¹H NMR (400 MHz, CDCl₃) δ 8.31 (s, 1H), 8.03 (s, 1H), 7.08 (s, 1H), 7.04-6.93 (m, 2H), 6.75-6.63 (m, 2H), 6.48 (s, 1H), 6.44-6.35 (m, 1H), 6.35-6.19 (m, 2H), 5.80-5.71 (m, 1H), 5.65 (dd, J = 8.6, 4.4 Hz, 1H), 4.16-3.89 (m, 4H), 3.85 (s, 3H), 3.80-3.55 (m, 3H), 3.29-3.19 (m, 1H), 2.85-2.57 (m, 5H), 2.49-2.27 (m, 5H), 0.52-0.35 (m, 4H); 633.48 [M + H]⁺ | 1.18 |

TABLE 1-continued

| Example Compound | Structure | Name of Compound | ¹H NMR[[:]]; MS [M + H]⁺ | UPLC r.t. (min) |
|---|---|---|---|---|
| 589 | 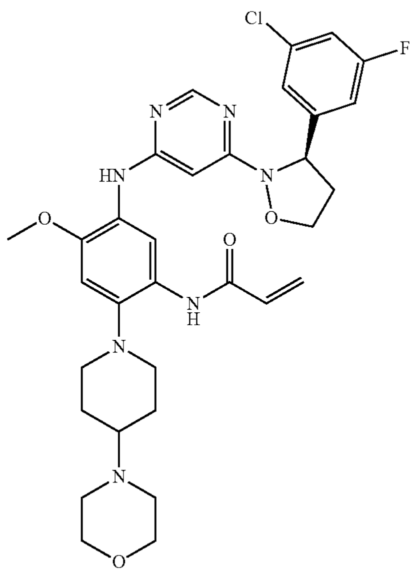 | N-(5-(((6-((R)-3-(3-chloro-5-fluorophenyl)isoxazolidine-2-yl)pyrimidine-4-yl)amino)-4-methoxy-2-(4-morpholinopiperidine-1-yl)phenyl)acrylamide | ¹H NMR (400 MHz, CDCl₃) δ 8.86 (s, 1H), 8.44 (s, 1H), 8.36 (s, 1H), 7.10 (d, J = 9.4 Hz, 1H), 7.00-6.91 (m, 2H), 6.75 (s, 1H), 6.72 (s, 1H), 6.40-6.18 (m, 2H), 5.74 (dd, J = 10.1, 1.0 Hz, 1H), 5.66 (dd, J = 8.7, 4.5 Hz, 1H), 4.16 (td, J = 8.0, 4.2 Hz, 1H), 4.06 (q, J = 8.1 Hz, 1H), 3.85 (s, 3H), 3.82-3.74 (m, 4H), 3.12-3.02 (m, J = 10.2 Hz, 2H), 2.82-2.67 (m, 3H), 2.67-2.56 (m, 4H), 2.38-2.24 (m, 2H), 2.13-2.04 (m, 2H), 1.75-1.56 (m, 2H); 638.42 [M + H]⁺ | 1.30 |
| 590 | 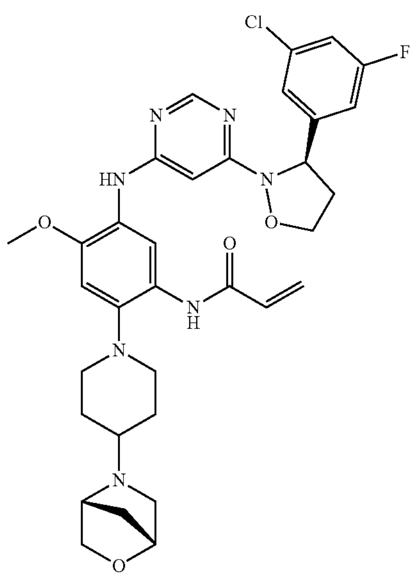 | N-(2-(4-((1R,4R)-2-oxa-5-azabicyclo[2.2.1]heptane-5-yl)piperidine-1-yl)-5-((6-((R)-3-(3-chloro-5-fluorophenyl)isoxazolidine-2-yl)pyrimidine-4-yl)amino)-4-methoxyphenyl)acrylamide | ¹H NMR (400 MHz, CDCl₃) δ 8.84 (s, 1H), 8.49 (s, 1H), 8.35 (s, 1H), 7.14-7.06 (m, 2H), 6.97 (d, J = 8.3 Hz, 1H), 6.75 (s, 1H), 6.71 (s, 1H), 6.44-6.12 (m, 3H), 5.76-5.70 (m, 1H), 5.65 (dd, J = 8.7, 4.5 Hz, 1H), 4.47 (s, 1H), 4.19-4.01 (m, 3H), 3.91-3.82 (m, 4H), 3.72-3.65 (m, 1H), 3.27-3.17 (m, 1H), 3.08-3.00 (m, 2H), 2.82-2.70 (m, 3H), 2.70-2.60 (m, 1H), 2.59-2.51 (m, 1H), 2.38-2.28 (m, 1H), 2.07-1.93 (m, 3H), 1.90-1.74 (m, 3H); 650.42 [M + H]⁺ | 1.30 |

TABLE 1-continued

| Example Compound | Structure | Name of Compound | ¹H NMR[:]; MS [M + H]⁺ | UPLC r.t. (min) |
|---|---|---|---|---|
| 591 | 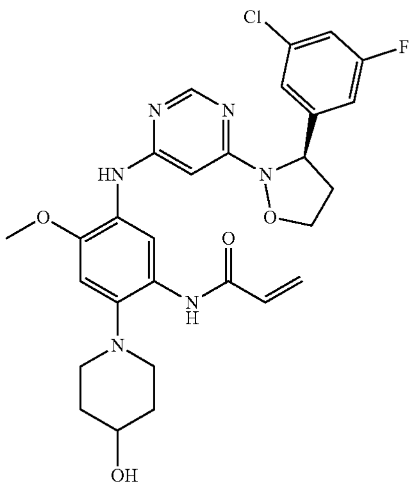 | N-(5-((6-((R)-3-(3-chloro-5-fluorophenyl)isoxazolidine-2-yl)pyrimidine-4-yl)amino)-2-(4-hydroxypiperidine-1-yl)-4-methoxyphenyl)acrylamide | ¹H NMR (400 MHz, CDCl₃) δ 8.87 (s, 1H), 8.50 (s, 1H), 8.36 (s, 1H), 7.10 (d, J = 9.4 Hz, 1H), 7.04-6.98 (m, 1H), 6.99-6.94 (m, 1H), 6.77 (s, 1H), 6.71 (s, 1H), 6.40-6.22 (m, 2H), 5.75 (dd, J = 9.9, 1.4 Hz, 1H), 5.66 (dd, J = 8.7, 4.6 Hz, 1H), 4.16 (td, J = 8.1, 4.2 Hz, 1H), 4.06 (q, J = 8.1 Hz, 1H), 3.98-3.89 (m, 1H), 3.85 (s, 3H), 3.09-3.00 (m, 2H), 2.82-2.71 (m, 3H), 2.39-2.28 (m, 1H), 2.12-2.02 (m, 2H), 1.82-1.71 (m, 2H), ; 569.32 [M + H]⁺ | 1.47 |
| 592 | 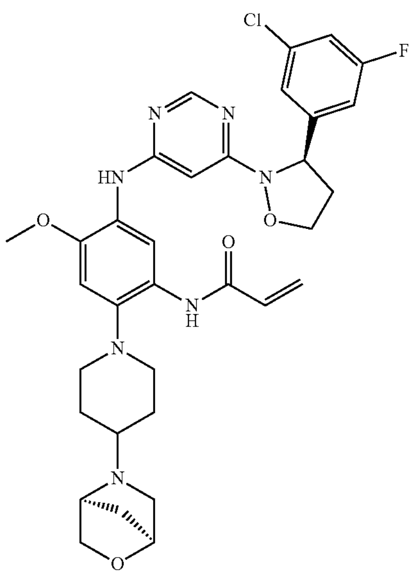 | N-(2-(4-((1S,4S)-2-oxa-5-azabicyclo[2.2.1]heptane-5-yl)piperidine-1-yl)-5-((6-((R)-3-(3-chloro-5-fluorophenyl)isoxazolidine-2-yl)pyrimidine-4-yl)amino)-4-methoxyphenyl)acrylamide | ¹H NMR (400 MHz, Chloroform-d) δ 8.87 (s, 1H), 8.48 (s, 1H), 8.36 (d, J = 1.0 Hz, 1H), 7.10 (dt, J = 9.5, 2.2 Hz, 1H), 7.00-6.92 (m, 2H), 6.76 (s, 1H), 6.72 (d, J = 1.0 Hz, 1H), 6.35 (dd, J = 17.0, 1.5 Hz, 1H), 6.23 (dd, J = 16.9, 10.1 Hz, 1H), 5.73 (dd, J = 10.0, 1.5 Hz, 1H), 5.66 (dd, J = 8.8, 4.6 Hz, 1H), 4.44 (t, J = 2.0 Hz, 1H), 4.20-4.00 (m, 3H), 3.85 (s, 3H), 3.77 (s, 1H), 3.66 (dd, J = 7.9, 1.6 Hz, 1H), 3.14 (dd, J = 9.9, 1.7 Hz, 1H), 3.07-2.99 (m, 2H), 2.84-2.71 (m, 3H), 2.63-2.54 (m, 1H), 2.51 (d, J = 9.9 Hz, 1H), 2.40-2.27 (m, 1H), 2.08-2.00 (m, 1H), 1.99-1.88 (m, 2H), 1.86-1.79 (m, 1H), 1.75-1.70 (m, 1H), 1.70-1.63 (m, 2H), ; 650.4 [M + H]⁺ | 1.26 |

TABLE 1-continued

| Example Compound | Structure | Name of Compound | ¹H NMR[:]; MS [M + H]⁺ | UPLC r.t. (min) |
|---|---|---|---|---|
| 593 | 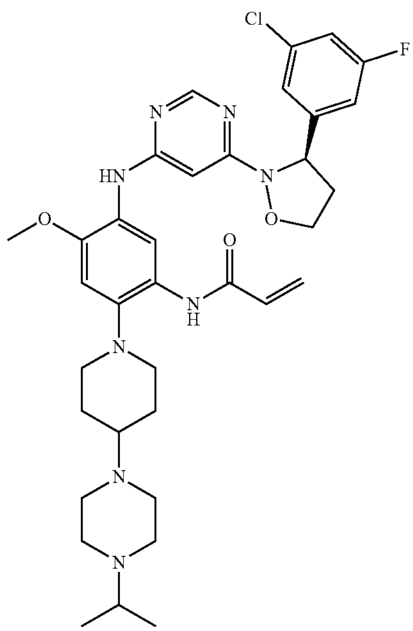 | N-(5-((6-((R)-3-(3-chloro-5-fluorophenyl)isoxazolidine-2-yl)pyrimidine-4-yl)amino)-2-(4-(4-isopropylpiperazine-1-yl)piperidine-1-yl)-4-methoxyphenyl)acrylamide | ¹H NMR (400 MHz, Chloroform-d) δ 8.86 (s, 1H), 8.46 (s, 1H), 8.36 (d, J = 1.0 Hz, 1H), 7.10 (dt, J = 9.4, 2.1 Hz, 1H), 7.00-6.88 (m, 2H), 6.78-6.69 (m, 2H), 6.35 (dd, J = 17.0, 1.5 Hz, 1H), 6.24 (dd, J = 16.9, 10.0 Hz, 1H), 5.74 (dd, J = 10.0, 1.5 Hz, 1H), 5.66 (dd, J = 8.7, 4.6 Hz, 1H), 4.20-4.11 (m, 1H), 4.11-4.00 (m, 1H), 3.84 (s, 3H), 3.09-3.02 (m, 2H), 2.82-2.55 (m, 12H), 2.37-2.27 (m, 2H), 2.14-2.06 (m, 2H), 1.74-1.70 (m, 1H), 1.69-1.60 (m, 2H), 1.08 (d, J = 6.5 Hz, 6H), ; 679.4 [M + H]⁺ | 1.23 |
| 594 | 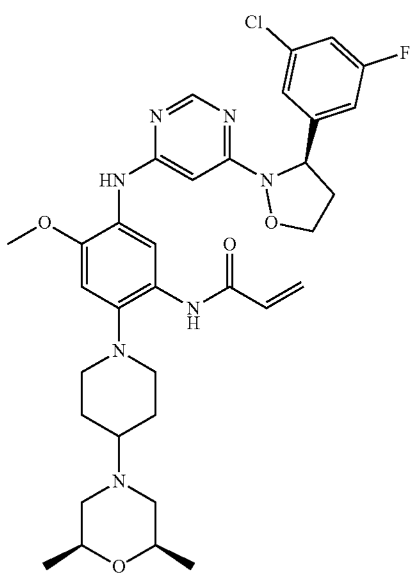 | N-(5-((6-((R)-3-(3-chloro-5-fluorophenyl)isoxazolidine-2-yl)pyrimidine-4-yl)amino)-2-(4-((2S,6R)-2,6-dimethylmorpholino)piperidine-1-yl)-4-methoxyphenyl)acrylamide | ¹H NMR (400 MHz, Chloroform-d) δ 8.86 (s, 1H), 8.43 (s, 1H), 8.36 (d, J = 1.0 Hz, 1H), 7.10 (dt, J = 9.5, 2.1 Hz, 1H), 7.00-6.93 (m, 2H), 6.73 (d, J = 14.5 Hz, 2H), 6.37 (dd, J = 16.9, 1.5 Hz, 1H), 6.25 (dd, J = 17.0, 10.0 Hz, 1H), 5.75 (dd, J = 10.0, 1.6 Hz, 1H), 5.66 (dd, J = 8.7, 4.6 Hz, 1H), 4.20-4.11 (m, 1H), 4.11-4.00 (m, 1H), 3.85 (s, 3H), 3.77-3.65 (m, 2H), 3.10-3.03 (m, 2H), 2.88 (d, J = 10.8 Hz, 2H), 2.82-2.76 (m, 1H), 2.76-2.66 (m, 2H), 2.40-2.25 (m, 2H), 2.11-2.02 (m, 2H), 1.90 (t, J = 10.6 Hz, 2H), 1.83-1.72 (m, 1H), 1.70-1.59 (m, 2H), 1.21 (d, 6H), ; 666.4 [M + H]⁺ | 1.33 |

TABLE 1-continued

| Example Compound | Structure | Name of Compound | ¹H NMR[[:]]; MS [M + H]⁺ | UPLC r.t. (min) |
|---|---|---|---|---|
| 595 | 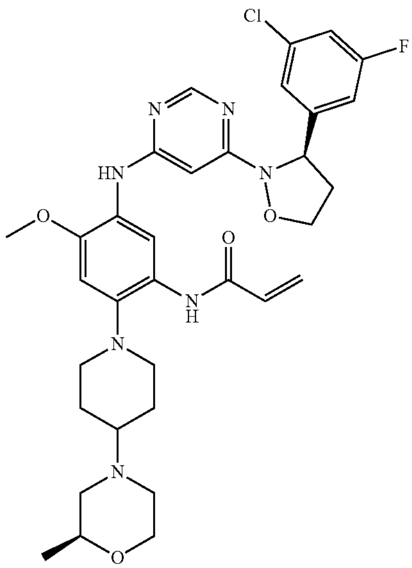 | N-(5-((6-((R)-3-(3-chloro-5-fluorophenyl)isoxazolidine-2-yl)pyrimidine-4-yl)amino)-4-methoxy-2-(4-((S)-2-methylmorpholino)piperidine-1-yl)phenyl)acrylamide | ¹H NMR (400 MHz, Chloroform-d) δ 8.86 (s, 1H), 8.44 (s, 1H), 8.36 (d, J = 1.0 Hz, 1H), 7.10 (dt, J = 9.6, 2.1 Hz, 1H), 7.01-6.88 (m, 2H), 6.77-6.68 (m, 2H), 6.37 (dd, J = 16.9, 1.5 Hz, 1H), 6.25 (dd, J = 16.9, 10.0 Hz, 1H), 5.74 (dd, J = 10.0, 1.5 Hz, 1H), 5.66 (dd, J = 8.7, 4.6 Hz, 1H), 4.20-4.11 (m, 1H), 4.11-3.99 (m, 1H), 3.97-3.88 (m, 1H), 3.85 (s, 3H), 3.76-3.69 (m, 1H), 3.69-3.61 (m, 1H), 3.07 (d, J = 11.3 Hz, 2H), 2.87 (dd, J = 22.0, 11.1 Hz, 2H), 2.82-2.67 (m, 3H), 2.38-2.26 (m, 3H), 2.11-2.04 (m, 2H), 2.02-1.92 (m, 1H), 1.72-1.65 (m, 2H), 1.65-1.62 (m, 1H), 1.19 (d, 3H), ; 652.4 [M + H]⁺ | 1.30 |
| 596 | 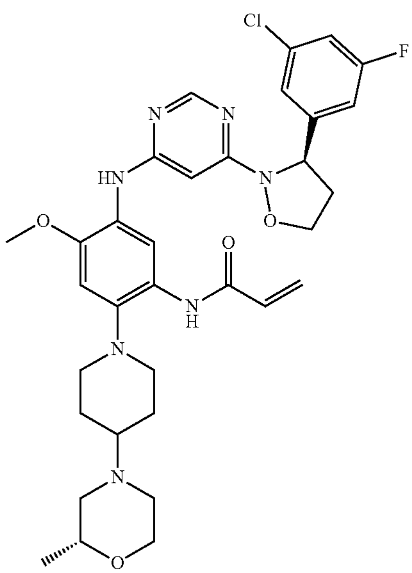 | N-(5-((6-((R)-3-(3-chloro-5-fluorophenyl)isoxazolidine-2-yl)pyrimidine-4-yl)amino)-4-methoxy-2-(4-((R)-2-methylmorpholino)piperidine-1-yl)phenyl)acrylamide | ¹H NMR (400 MHz, Chloroform-d) δ 8.86 (s, 1H), 8.44 (s, 1H), 8.36 (d, J = 1.0 Hz, 1H), 7.10 (dt, J = 9.4, 2.1 Hz, 1H), 7.01-6.93 (m, 2H), 6.73 (d, J = 14.4 Hz, 2H), 6.37 (dd, J = 17.0, 1.5 Hz, 1H), 6.25 (dd, J = 16.9, 10.1 Hz, 1H), 5.74 (dd, J = 10.0, 1.5 Hz, 1H), 5.66 (dd, J = 8.8, 4.6 Hz, 1H), 4.20-4.13 (m, 1H), 4.13-4.00 (m, 1H), 3.97-3.88 (m, 1H), 3.85 (s, 3H), 3.77-3.69 (m, 1H), 3.69-3.61 (m, 1H), 3.11-3.03 (m, 2H), 2.94-2.81 (m, 2H), 2.81-2.76 (m, 1H), 2.76-2.66 (m, 2H), 2.40-2.16 (m, 3H), 2.11-2.02 (m, 2H), 2.01-1.92 (m, 1H), 1.73-1.59 (m, 3H), 1.19 (d, 3H), ; 652.4 [M + H]⁺ | 1.28 |

TABLE 1-continued

| Example Compound | Structure | Name of Compound | ¹H NMR[:]; MS [M + H]⁺ | UPLC r.t. (min) |
|---|---|---|---|---|
| 597 | 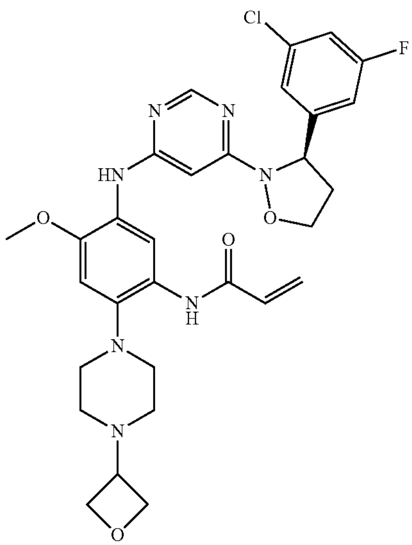 | N-(5-((6-((R)-3-(3-chloro-5-fluorophenyl)isoxazolidine-2-yl)pyrimidine-4-yl)amino)-4-methoxy-2-(4-(oxetane-3-yl)piperazine-1-yl)phenyl)acrylamide | ¹H NMR (400 MHz, Chloroform-d) δ 8.91 (s, 1H), 8.49 (s, 1H), 8.37 (d, J = 1.0 Hz, 1H), 7.10 (dt, J = 9.5, 2.0 Hz, 1H), 7.02-6.93 (m, 2H), 6.82 (s, 1H), 6.72 (s, 1H), 6.36 (dd, J = 16.9, 1.5 Hz, 1H), 6.25 (dd, J = 16.9, 10.0 Hz, 1H), 5.75 (dd, J = 10.0, 1.5 Hz, 1H), 5.66 (dd, J = 8.7, 4.6 Hz, 1H), 4.69 (dt, J = 21.2, 6.3 Hz, 4H), 4.21-4.11 (m, 1H), 4.11-4.00 (m, 1H), 3.85 (s, 3H), 3.61 (p, J = 6.4 Hz, 1H), 3.01-2.89 (m, 4H), 2.84-2.71 (m, 1H), 2.64-2.42 (m, 4H), 2.40-2.27 (m, 1H), 1.76-1.68 (m, 1H), ; 610.4 [M + H]⁺ | 1.25 |
| 598 | 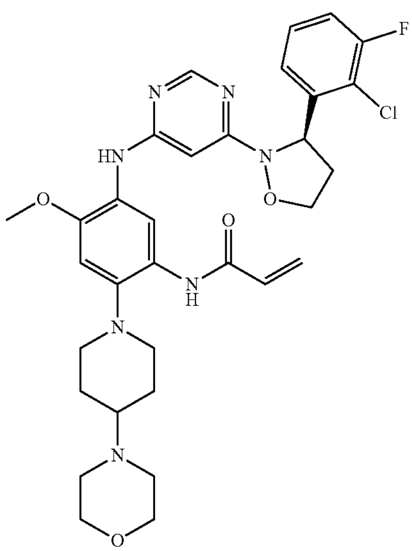 | N-(5-((6-((R)-3-(2-chloro-3-fluorophenyl)isoxazolidine-2-yl)pyrimidine-4-yl)amino)-4-methoxy-2-(4-morpholinopiperidine-1-yl)phenyl)acrylamide | ¹H NMR (400 MHz, DMSO-d₆) δ 10.04 (s, 1H), 9.06 (s, 1H), 8.98 (s, 1H), 8.21 (s, 1H), 8.11 (s, 1H), 7.37 (td, J = 7.9, 2.4 Hz, 2H), 6.86 (s, 1H), 6.61 (dd, J = 17.0, 10.2 Hz, 1H), 6.34 (s, 1H), 6.23 (dd, J = 17.0, 1.9 Hz, 1H), 5.83-5.69 (m, 2H), 4.18 (td, J = 7.8, 3.8 Hz, 1H), 4.08-4.01 (m, 2H), 3.93 (q, J = 8.0 Hz, 1H), 3.82 (s, 3H), 3.72 (t, J = 12.2 Hz, 2H), 3.49 (d, J = 12.1 Hz, 2H), 3.34 (d, J = 12.5 Hz, 1H), 3.25-3.10 (m, 4H), 2.93 (dtd, J = 12.1, 8.0, 3.9 Hz, 1H), 2.75 (t, J = 11.8 Hz, 2H), 2.13 (ddq, J = 12.9, 8.2, 4.9 Hz, 3H), 1.91 (s, 2H), ; 638.5 [M + H]⁺ | 1.25 |

TABLE 1-continued

| Example Compound | Structure | Name of Compound | ¹H NMR[:]; MS [M + H]⁺ | UPLC r.t. (min) |
|---|---|---|---|---|
| 599 | 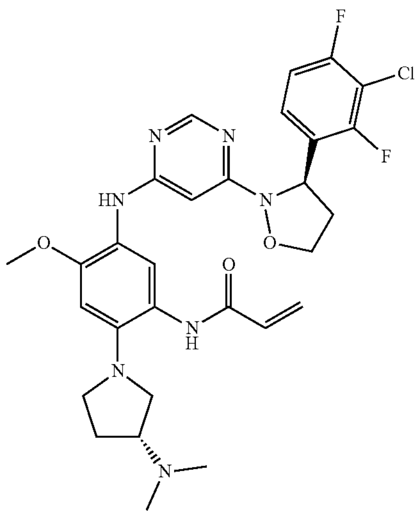 | N-(5-((6-((R)-3-(3-chloro-2,4-difluorophenyl)isoxazolidine-2-yl)pyrimidine-4-yl)amino)-2-((R)-3-(dimethylamino)pyrolidine-1-yl)-4-methoxyphenyl)acrylamide | ¹H NMR (400 MHz, DMSO-d₆) δ 9.31 (s, 1H), 8.64 (s, 1H), 8.15 (s, 1H), 7.66 (s, 1H), 7.48 (td, J = 8.5, 6.2 Hz, 1H), 7.31 (td, J = 8.8, 1.7 Hz, 1H), 6.65 (s, 1H), 6.50 (dd, 17.0, 10.2 Hz, 1H), 6.31 (s, 1H), 6.21 (dd, J = 17.0, 2.1 Hz, 1H), 5.71 (td, J = 9.5, 3.6 Hz, 2H), 4.17 (td, J = 7.9, 3.7 Hz, 1H), 3.93 (d, J = 6.5 Hz, 1H), 3.82 (s, 4H), 3.37 (s, 2H), 3.32 (d, J = 3.6 Hz, 1H), 3.20 (q, J = 10.8, 9.5 Hz, 1H), 2.83 (d, J = 5.3 Hz, 7H), 2.34 (d, J = 11.0 Hz, 1H), 2.27-2.17 (m, 1H), 2.15-2.06 (m, 1H), ; 600.4 [M + H]⁺ | 1.28 |
| 600 | 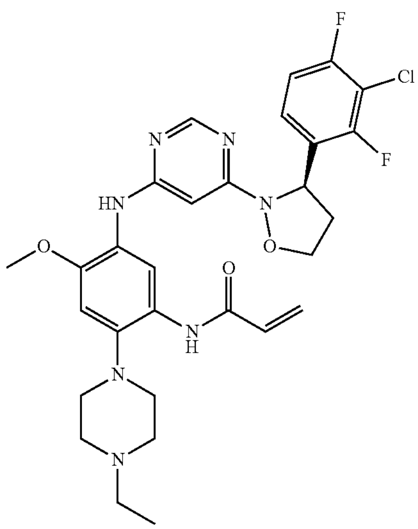 | N-(5-((6-((R)-3-(3-chloro-2,4-difluorophenyl)isoxazolidine-2-yl)pyrimidine-4-yl)amino)-2-(4-ethylpiperazine-1-yl)-4-methoxyphenyl)acrylamide | ¹H NMR (400 MHz, DMSO-d₆) δ 9.06 (s, 1H), 8.81 (s, 1H), 8.27 (s, 1H), 8.19 (s, 1H), 7.48 (td, J = 8.5, 6.2 Hz, 1H), 7.32 (td, J = 8.8, 1.7 Hz, 1H), 6.84 (s, 1H), 6.66 (dd, J = 17.0, 10.1 Hz, 1H), 6.41 (s, 1H), 6.24 (dd, J = 17.0, 2.0 Hz, 1H), 5.73 (ddd, J = 19.1, 9.4, 3.6 Hz, 2H), 4.20 (td, J = 7.8, 3.6 Hz, 1H), 3.89 (q, J = 7.8 Hz, 1H), 3.83 (s, 3H), 3.58 (d, J = 11.5 Hz, 2H), 3.31-3.18 (m, 6H), 3.04 (t, J = 12.3 Hz, 2H), 2.80 (tt, J = 8.0, 4.0 Hz, 1H), 2.28-2.16 (m, 1H), 1.28 (t, J = 7.2 Hz, 3H), ; 600.4 [M + H]⁺ | 1.31 |

TABLE 1-continued

| Example Compound | Structure | Name of Compound | ¹H NMR[[:]]; MS [M + H]⁺ | UPLC r.t. (min) |
|---|---|---|---|---|
| 601 | 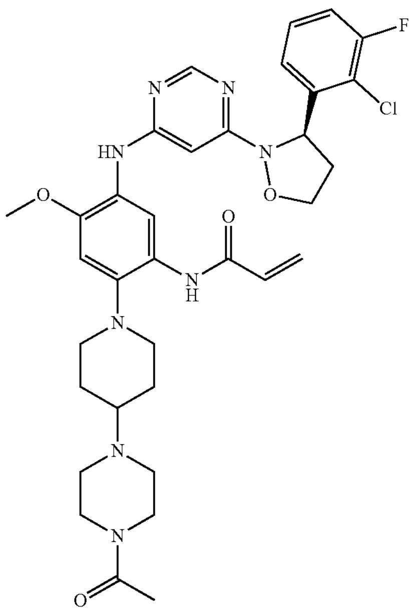 | N-(2-(4-(4-acetylpiperazine-1-yl)piperidine-1-yl)-5-((6-((R)-3-(2-chloro-3-fluorophenyl)isoxazolidine-2-yl)pyrimidine-4-yl)amino)-4-methoxyphenyl)acrylamide | ¹H NMR (400 MHz, DMSO-d$_6$) δ 9.04 (s, 1H), 8.76 (s, 1H), 8.16 (d, J = 13.4 Hz, 2H), 7.43-7.30 (m, 3H), 6.84 (s, 1H), 6.61 (dd, J = 17.3, 9.8 Hz, 1H), 6.39 (s, 1H), 6.23 (d, J = 17.0 Hz, 1H), 5.84-5.68 (m, 2H), 4.53 (d, J = 13.7 Hz, 1H), 4.20-4.12 (m, 1H), 4.06 (d, J = 13.5 Hz, 1H), 3.90 (d, J = 8.4 Hz, 1H), 3.82 (s, 3H), 3.52 (s, 2H), 3.45-3.32 (m, 2H), 3.17 (s, 3H), 3.02 (s, 1H), 2.91 (d, J = 10.7 Hz, 2H), 2.73 (d, J = 12.1 Hz, 2H), 2.08 (d, J = 7.1 Hz, 6H), 1.91 (s, 2H), ; 679.4 [M + H]⁺ | 1.23 |
| 602 | 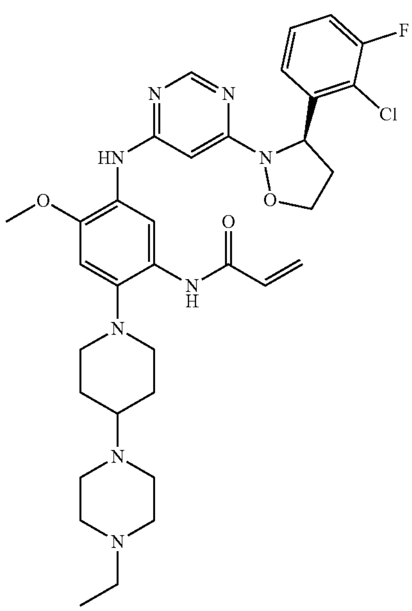 | N-(5-((6-((R)-3-(2-chloro-3-fluorophenyl)isoxazolidine-2-yl)pyrimidine-4-yl)amino)-2-(4-(4-ethylpiperazine-1-yl)piperidine-1-yl)-4-methoxyphenyl)acrylamide | ¹H NMR (400 MHz, Methanol-d$_4$) δ 8.30 (s, 1H), 8.14 (d, J = 1.0 Hz, 1H), 7.43 (d, J = 7.9 Hz, 1H), 7.30 (td, J = 8.1, 5.3 Hz, 1H), 7.15 (td, J = 8.8, 8.2, 1.5 Hz, 1H), 6.90 (s, 1H), 6.54 (dd, J = 16.9, 10.3 Hz, 1H), 6.37 (ddd, J = 25.3, 16.8, 1.7 Hz, 1H), 6.17-6.12 (m, 1H), 5.89-5.75 (m, 2H), 4.12 (td, J = 8.0, 4.1 Hz, 1H), 3.98 (q, J = 8.0 Hz, 1H), 3.86 (s, 4H), 3.72 (hept, J = 6.3 Hz, 2H), 3.22 (d, J = 7.4 Hz, 2H), 3.18-3.10 (m, 3H), 3.02-2.88 (m, 6H), 2.86-2.76 (m, 4H), 2.61-2.54 (m, 1H), 2.19 (ddd, J = 16.2, 8.1, 4.3 Hz, 1H), 2.04 (d, J = 12.3 Hz, 2H), 1.84-1.74 (m, 2H), 1.18 (tt, J = 7.4, 1.3 Hz, 1H), ; 665.5 [M + H]⁺ | 1.19 |

TABLE 1-continued

| Example Compound | Structure | Name of Compound | ¹H NMR[[:]]; MS [M + H]⁺ | UPLC r.t. (min) |
|---|---|---|---|---|
| 603 | 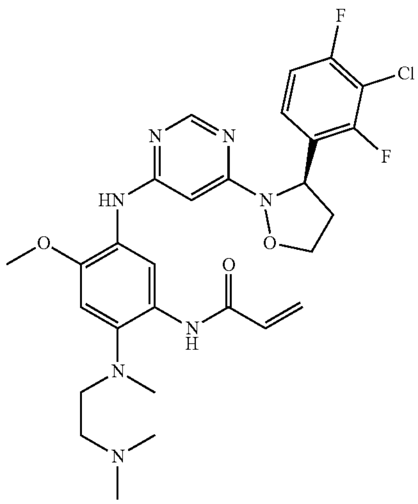 | N-(5-((6-((R)-3-(3-chloro-2,4-difluorophenyl)isoxazolidine-2-yl)pyrimidine-4-yl)amino)-2-((2-(dimethylamino)ethyl)(methyl)amino)-4-methoxyphenyl)acrylamide | ¹H NMR (400 MHz, DMSO-d$_6$) δ 9.93 (s, 1H), 8.71 (d, J = 9.5 Hz, 1H), 8.35 (s, 1H), 7.50 (td, J = 8.5, 6.2 Hz, 1H), 7.32 (td, J = 8.8, 1.7 Hz, 1H), 6.95 (s, 1H), 6.46 (d, J = 25.1 Hz, 1H), 6.23 (ddd, J = 17.1, 5.5, 2.1 Hz, 1H), 6.09 (dd, J = 17.3, 10.1 Hz, 1H), 5.77-5.65 (m, 2H), 4.19 (tt, J = 7.9, 3.9 Hz, 1H), 3.93-3.78 (m, 4H), 3.62-3.47 (m, 3H), 3.16 (d, J = 5.3 Hz, 1H), 3.06 (dd, J = 14.9, 7.5 Hz, 4H), 2.96 (s, 1H), 2.81 (dp, J = 12.6, 3.9 Hz, 1H), 2.68-2.60 (m, 3H), 2.51 (p, J = 1.9 Hz, 2H), 2.23 (ddd, J = 12.9, 8.5, 5.1 Hz, 1H), ; 588.3 [M + H]⁺ | 1.36 |
| 604 | 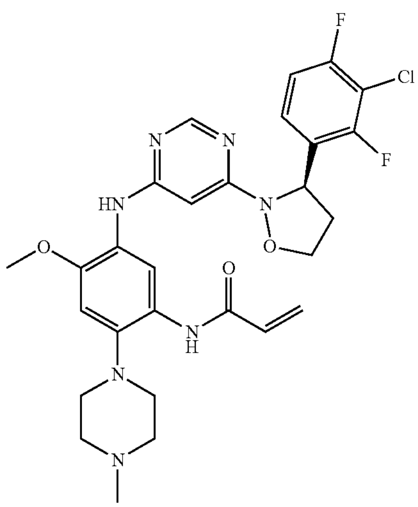 | N-(5-((6-((R)-3-(3-chloro-2,4-difluorophenyl)isoxazolidine-2-yl)pyrimidine-4-yl)amino)-4-methoxy-2-(4-methylpiperazine-1-yl)phenyl)acrylamide | ¹H NMR (400 MHz, Methanol-d$_4$) δ 8.43 (d, J = 31.7 Hz, 1H), 8.18 (dd, J = 3.3, 1.0 Hz, 1H), 7.50 (td, J = 8.6, 6.1 Hz, 1H), 7.19-6.91 (m, 2H), 6.53 (dd, J = 7.6, 1.1 Hz, 1H), 6.40-6.05 (m, 2H), 5.84-5.70 (m, 2H), 4.15 (td, J = 7.9, 4.0 Hz, 1H), 3.99 (td, J = 8.0, 2.1 Hz, 1H), 3.91 (d, J = 9.9 Hz, 3H), 3.81 (t, J = 7.6 Hz, 1H), 3.66 (t, J = 7.9 Hz, 1H), 3.34 (s, 3H), 3.17 (t, J = 4.9 Hz, 1H), 2.86 (d, J = 8.4 Hz, 2H), 2.75 (t, J = 7.6 Hz, 1H), 2.26 (ddd, J = 12.8, 8.5, 4.8 Hz, 1H), 1.38 (s, 6H), ; 586.3 [M + H]⁺ | 1.30 |

TABLE 1-continued

| Example Compound | Structure | Name of Compound | ¹H NMR[[:]]; MS [M + H]⁺ | UPLC r.t. (min) |
|---|---|---|---|---|
| 605 | 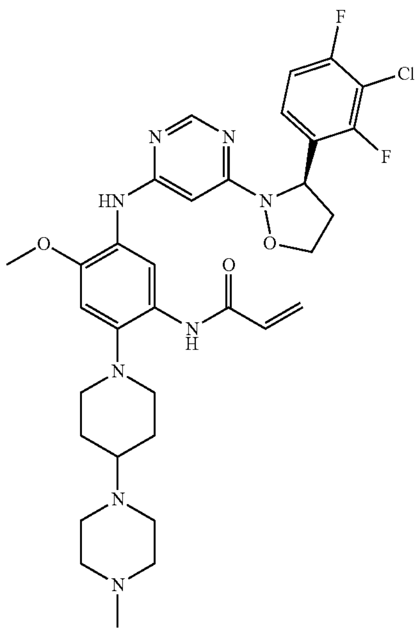 | N-(5-((6-((R)-3-(3-chloro-2,4-difluorophenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, DMSO-$d_6$) δ 8.83 (d, J = 8.4 Hz, 1H), 8.68 (d, J = 4.5 Hz, 1H), 8.59 (d, J = 8.3 Hz, 1H), 8.44 (d, J = 2.2 Hz, 1H), 8.12 (t, J = 7.7 Hz, 1H), 8.00 (dq, J = 8.1, 5.6, 3.8 Hz, 3H), 7.95-7.82 (m, 4H), 5.07 (p, J = 7.2 Hz, 1H), 3.67 (s, 4H), 3.48 (d, J = 7.3 Hz, 2H), 3.20 (s, 4H), 3.11 (dtd, J = 15.2, 8.4, 8.0, 3.7 Hz, 2H), 2.07 (dd, J = 13.4, 2.8 Hz, 1H), 2.01 (dd, J = 15.3, 3.5 Hz, 2H), 1.91 (qd, J = 13.2, 10.6, 5.1 Hz, 5H), 1.79 (td, J = 13.1, 12.7, 5.4 Hz, 2H), 1.69 (td, J = 13.6, 4.3 Hz, 2H), 1.48 (d, J = 7.0 Hz, 4H), ; 669.4 [M + H]⁺ | 1.28 |
| 606 | 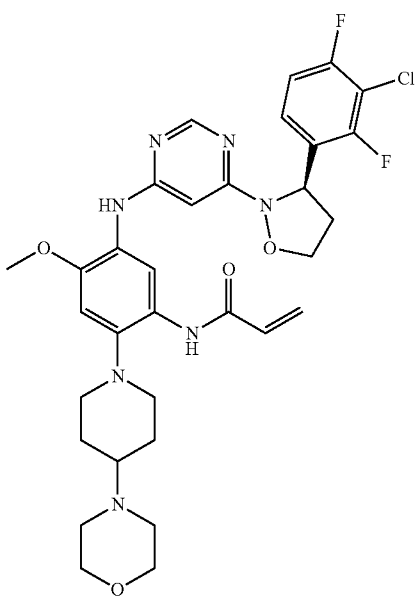 | N-(5-((6-((R)-3-(3-chloro-2,4-difluorophenyl)isoxazolidine-2-yl)pyrimidine-4-yl)amino)-4-methoxy-2-(4-morpholinopiperidine-1-yl)phenyl)acrylamide | ¹H NMR (400 MHz, DMSO-$d_6$) δ 9.04 (s, 1H), 8.21 (s, 1H), 8.11 (s, 1H), 7.47 (td, J = 8.5, 6.2 Hz, 1H), 7.32 (td, J = 8.8, 1.7 Hz, 1H), 6.85 (s, 1H), 6.62 (dd, J = 17.0, 10.2 Hz, 1H), 6.33 (s, 1H), 6.23 (dd, J = 16.9, 2.0 Hz, 1H), 5.77-5.67 (m, 2H), 4.21 (td, J = 7.9, 3.7 Hz, 1H), 3.91 (q, J = 8.2 Hz, 1H), 3.81 (s, 3H), 3.68-3.34 (m, 4H), 3.16 (d, J = 10.9 Hz, 4H), 2.85 (s, 4H), 2.74 (t, J = 11.7 Hz, 3H), 2.30-2.19 (m, 1H), 2.03 (s, 2H), 1.88 (d, J = 20.1 Hz, 2H), ; 656.4 [M + H]⁺ | 1.35 |

TABLE 1-continued

| Example Compound | Structure | Name of Compound | ¹H NMR[[:]]; MS [M + H]⁺ | UPLC r.t. (min) |
|---|---|---|---|---|
| 607 | 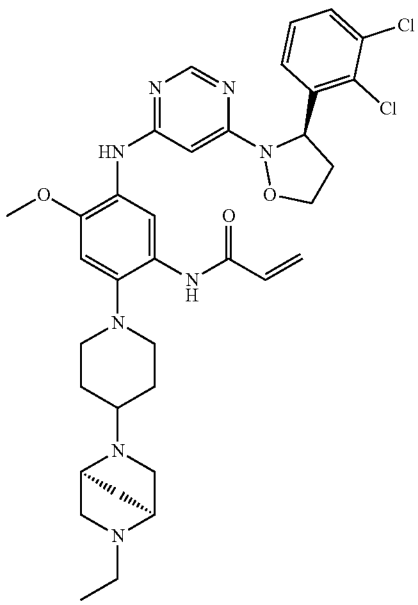 | N-(5-((6-((R)-3-(2,3-dichlorophenyl)isoxazolidine-2-yl)pyrimidine-4-yl)amino)-2-(4-((1S,4S)-5-ethyl-2,5-diazabicyclo[2.2.1]heptane-2-yl)piperidine-1-yl)-4-methoxyphenyl)acrylamide | ¹H NMR (400 MHz, Chloroform-d) δ 8.88 (s, 1H), 8.47 (s, 1H), 8.36 (d, J = 1.0 Hz, 1H), 7.60 (dd, J = 8.1, 1.6 Hz, 1H), 7.37 (dd, J = 7.9, 1.6 Hz, 1H), 7.19 (t, J = 7.9 Hz, 1H), 6.94 (s, 1H), 6.76 (d, J = 3.0 Hz, 2H), 6.40-6.32 (m, 1H), 6.25 (dd, J = 17.4, 10.5 Hz, 1H), 5.96 (dd, J = 8.9, 4.4 Hz, 1H), 5.73 (dd, J = 9.9, 1.6 Hz, 1H), 4.14-4.04 (m, 2H), 3.85 (s, 3H), 3.31 (dd, J = 10.3, 4.4 Hz, 1H), 3.22-3.15 (m, 1H), 3.01 (s, 2H), 2.94 (dq, J = 8.1, 4.0 Hz, 1H), 2.79 (d, J = 11.9 Hz, 2H), 2.50 (s, 1H), 2.28-2.16 (m, 2H), 2.05 (d, J = 9.7 Hz, 3H), 1.90 (t, J = 12.4 Hz, 2H), 1.86-1.80 (m, 1H), 1.76-1.66 (m, 2H), 1.36 (s, 2H), 1.32-1.23 (m, 4H), ; 693.4 [M + H] | 1.22 |
| 608 | 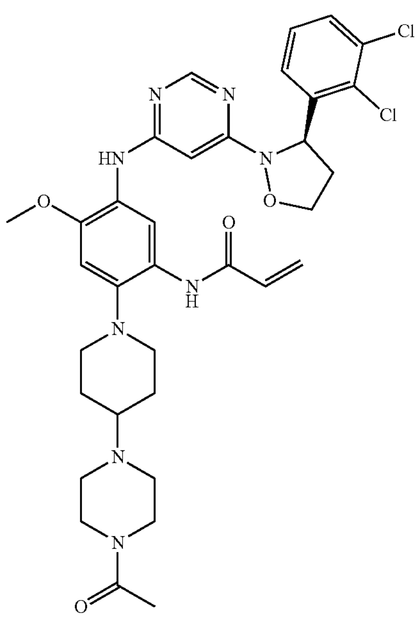 | N-(2-(4-(4-acetylpiperazine-1-yl)piperidine-1-yl)-5-((6-((R)-3-(2,3-dichlorophenyl)isoxazolidine-2-yl)pyrimidine-4-yl)amino)-4-methoxyphenyl)acrylamide | ¹H NMR (400 MHz, Chloroform-d) δ 11.33 (s, 1H), 8.85 (s, 1H), 8.42-8.22 (m, 2H), 7.62-7.54 (m, 1H), 7.37 (dd, J = 8.0, 1.6 Hz, 1H), 7.19 (t, J = 7.9 Hz, 1H), 6.74 (d, J = 3.6 Hz, 2H), 6.42-6.23 (m, 2H), 5.96 (dd, J = 8.8, 4.4 Hz, 1H), 5.76 (dd, J = 9.8, 1.7 Hz, 1H), 4.16-4.04 (m, 2H), 3.85 (s, 3H), 3.66 (td, J = 6.7, 4.0 Hz, 2H), 3.09 (qd, J = 7.5, 4.1 Hz, 4H), 2.99-2.92 (m, 1H), 2.12 (s, 3H), 1.56 (dd, J = 12.2, 7.1 Hz, 8H), 1.45 (d, J = 6.6 Hz, 4H), ; 695.4 [M + H] | 1.31 |

TABLE 1-continued

| Example Compound | Structure | Name of Compound | ¹H NMR[[:]]; MS [M + H]⁺ | UPLC r.t. (min) |
|---|---|---|---|---|
| 609 | 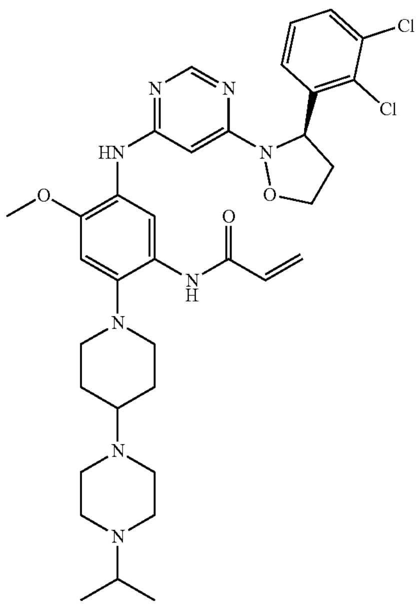 | N-(5-((6-((R)-3-(2,3-dichlorophenyl)isoxazolidine-2-yl)pyrimidine-4-yl)amino)-2-(4-(4-isopropylpiperazine-1-yl)piperidine-1-yl)-4-methoxyphenyl)acrylamide | ¹H NMR (400 MHz, Chloroform-d) δ 8.86 (s, 1H), 8.44 (s, 1H), 8.36 (d, J = 1.0 Hz, 1H), 7.60 (d, J = 7.8 Hz, 1H), 7.37 (dd, J = 8.0, 1.6 Hz, 1H), 7.19 (t, J = 7.9 Hz, 1H), 6.92 (s, 1H), 6.75 (s, 2H), 6.40-6.31 (m, 1H), 6.24 (dd, J = 17.0, 9.9 Hz, 1H), 5.96 (dd, J = 8.8, 4.4 Hz, 1H), 5.74 (dd, J = 9.9, 1.6 Hz, 1H), 4.17-4.04 (m, 2H), 3.85 (s, 3H), 3.31 (dd, J = 7.3, 5.3 Hz, 1H), 3.06 (d, J = 11.6 Hz, 2H), 2.98-2.88 (m, 2H), 2.74 (q, J = 12.5 Hz, 8H), 2.33 (s, 2H), 2.25 (s, 2H), 2.09 (d, J = 12.4 Hz, 2H), 1.84 (t, J = 6.9 Hz, 1H), 1.67 (d, J = 12.3 Hz, 6H), ; 695.5 [M + H] | 1.28 |
| 610 | 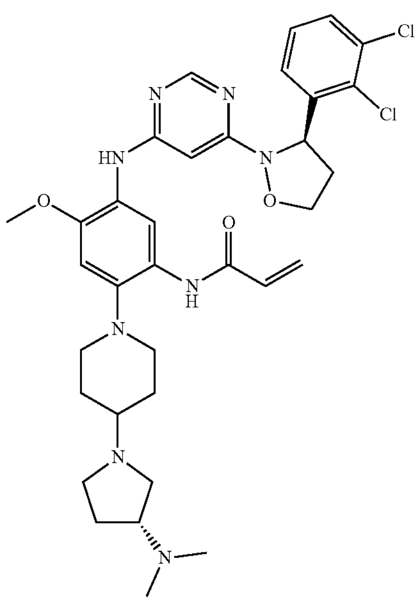 | N-(5-((6-((R)-3-(2,3-dichlorophenyl)isoxazolidine-2-yl)pyrimidine-4-yl)amino)-2-(4-((R)-3-(dimethylamino)pyrolidine-1-yl)piperidine-1-yl)-4-methoxyphenyl)acrylamide | ¹H NMR (400 MHz, Chloroform-d) δ 8.86 (s, 1H), 8.46 (s, 1H), 8.37-8.32 (m, 1H), 7.59 (t, J = 7.5 Hz, 1H), 7.37 (dd, J = 8.0, 1.6 Hz, 1H), 7.19 (td, J = 7.9, 3.3 Hz, 1H), 6.94 (s, 1H), 6.76 1.19 (s, 1H), 6.61 (d, J = 54.6 Hz, 1H), 6.43-6.17 (m, 2H), 5.96 (dt, J = 10.8, 5.3 Hz, 1H), 5.74 (dd, J = 9.9, 1.6 Hz, 1H), 4.17-4.02 (m, 2H), 3.85 (s, 3H), 3.27 (d, J = 7.4 Hz, 2H), 3.19 (q, J = 5.9 Hz, 2H), 3.04 (d, J = 11.0 Hz, 2H), 2.95 (dd, J = 8.5, 4.5 Hz, 1H), 2.79-2.70 (m, 2H), 2.62 (s, 6H), 2.37 (d, J = 8.1 Hz, 4H), 2.08 (d, J = 13.2 Hz, 2H), 1.94-1.83 (m, 2H), 1.47 (d, J = 6.5 Hz, 1H), ; 681.4 [M + H] | 1.19 |

TABLE 1-continued

| Example Compound | Structure | Name of Compound | ¹H NMR[:]; MS [M + H]⁺ | UPLC r.t. (min) |
|---|---|---|---|---|
| 611 | 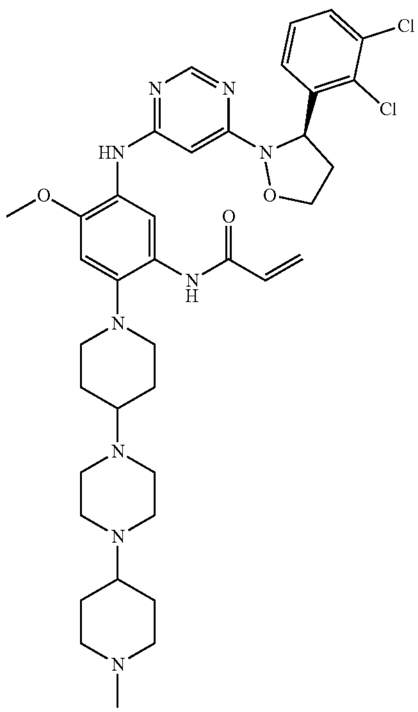 | N-(5-((6-((R)-3-(2,3-dichlorophenyl)isoxazolidine-2-yl)pyrimidine-4-yl)amino)-4-methoxy-2-(4-(4-(1-methylpiperidine-4-yl)piperazine-1-yl)piperidine-1-yl)phenyl)acrylamide | ¹H NMR (400 MHz, Chloroform-d) δ 8.86 (s, 1H), 8.34 (d, J = 8.5 Hz, 1H), 7.58 (t, J = 8.3 Hz, 1H), 7.41-7.32 (m, 1H), 7.19 (td, J = 7.9, 4.5 Hz, 1H), 6.96 (dd, J = 17.1, 11.1 Hz, 2H), 6.75 (s, 1H), 6.43-6.17 (m, 2H), 5.95 (t, J = 9.9 Hz, 1H), 5.74 (d, J = 9.4 Hz, 1H), 5.35 (s, 1H), 4.12-4.06 (m, 1H), 3.95-3.89 (m, 2H), 3.85 (d, J = 1.2 Hz, 2H), 3.39-3.32 (m, 4H), 3.30 (s, 3H), 3.21-3.16 (m, 4H), 3.05 (t, J = 12.1 Hz, 4H), 2.79 (d, J = 6.7 Hz, 2H), 2.73 (d, J = 17.7 Hz, 4H), 2.56 (s, 3H), 2.21 (d, J = 4.3 Hz, 1H), 2.09 (d, J = 12.7 Hz, 2H), 2.02 (d, J = 10.0 Hz, 2H), 1.85 (t, J = 6.2 Hz, 2H), ; 750.5 [M + H] | 1.19 |
| 612 | 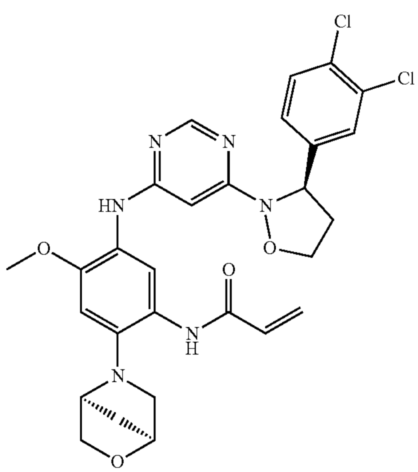 | N-(2-((1S,4S)-2-oxa-5-azabicyclo[2.2.1]heptane-5-yl)-5-((6-((R)-3-(3,4-dichlorophenyl)isoxazolidine-2-yl)pyrimidine-4-yl)amino)-4-methoxyphenyl)acrylamide | ¹H NMR (400 MHz, Chloroform-d) δ 8.68 (s, 1H), 8.35 (s, 1H), 7.96 (s, 1H), 7.58 (d, J = 2.1 Hz, 1H), 7.41 (d, J = 8.3 Hz, 1H), 7.32-7.28 (m, 1H), 6.88 (s, 1H), 6.71 (s, 1H), 6.64 (s, 1H), 6.39 (d, J = 16.9 Hz, 1H), 6.28 (dd, J = 16.8, 10.0 Hz, 1H), 5.76 (d, J = 10.0 Hz, 1H), 5.64 (dd, J = 8.7, 4.6 Hz, 1H), 4.65 (s, 1H), 4.18-4.10 (m, 1H), 4.03 (dd, J = 14.8, 7.9 Hz, 2H), 3.86 (s, 3H), 3.75 (d, J = 7.8 Hz, 1H), 3.43 (d, J = 10.2 Hz, 1H), 3.23 (d, J = 10.1 Hz, 1H), 2.81-2.70 (m, 1H), 2.61 (s, 1H), 2.37-2.27 (m, 1H), 2.08 (d, J = 10.0 Hz, 1H), 1.99 (d, J = 10.1 Hz, 1H), ; 583.2 [M + H] | 1.46 |

TABLE 1-continued

| Example Compound | Structure | Name of Compound | $^1$H NMR[:]; MS [M + H]$^+$ | UPLC r.t. (min) |
|---|---|---|---|---|
| 613 | 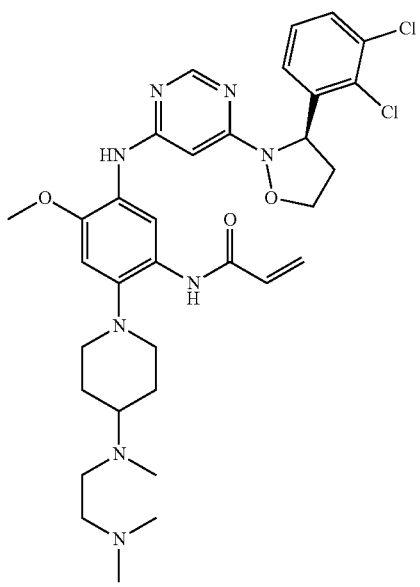 | N-(5-((6-((R)-3-(2,3-dichlorophenyl)isoxazolidine-2-yl)pyrimidine-4-yl)amino)-2-((2-(dimethylamino)ethyl)(methyl)amino)piperidine-1-yl)-4-methoxyphenyl)acrylamide | $^1$H NMR (400 MHz, Chloroform-d) δ 8.87 (s, 1H), 8.40 (s, 1H), 8.36 (d, J = 1.0 Hz, 1H), 7.60 (d, J = 7.9 Hz, 1H), 7.37 (dd, J = 8.0, 1.5 Hz, 1H), 7.19 (t, J = 7.9 Hz, 1H), 6.94 (s, 1H), 6.75 (s, 2H), 6.38-6.32 (m, 2H), 6.00-5.95 (m, 1H), 5.76 (dd, J = 8.6, 3.0 Hz, 1H), 4.17-4.04 (m, 3H), 3.85 (s, 3H), 3.12-3.04 (m, 4H), 3.00-2.92 (m, 3H), 2.72 (s, 6H), 2.43 (s, 3H), 2.27-2.17 (m, 2H), 2.04-1.97 (m, 3H), 1.83-1.77 (m, 2H), ; 669.4 [M + H]$^+$ | 1.21 |
| 614 | 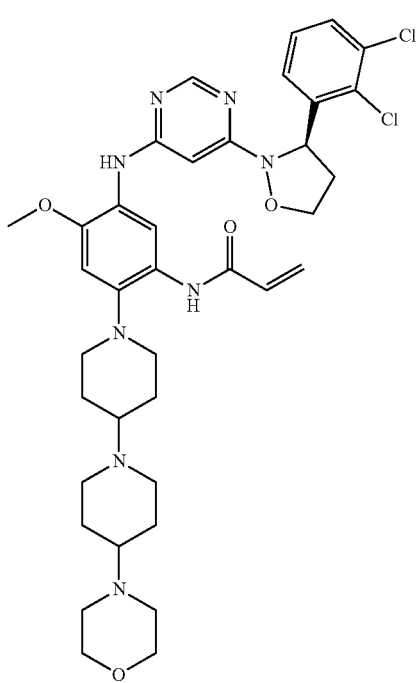 | N-(5-((6-((R)-3-(2,3-dichlorophenyl)isoxazolidine-2-yl)pyrimidine-4-yl)amino)-4-methoxy-2-(4-morpholino-[1,4'-bipiperidine]-1'-yl)phenyl)acrylamide | $^1$H NMR (400 MHz, Chloroform-d) δ 8.86 (s, 1H), 8.44 (s, 1H), 8.35 (s, 1H), 7.59 (d, J = 7.9 Hz, 1H), 7.36 (d, J = 8.0 Hz, 1H), 7.19 (t, J = 7.9 Hz, 1H), 6.95 (s, 1H), 6.75 (s, 2H), 6.40-6.31 (m, 1H), 6.25 (dd, J = 16.8, 10.0 Hz, 1H), 5.96 (dd, J = 8.7, 4.4 Hz, 1H), 5.74 (dd, J = 9.9, 1.6 Hz, 1H), 4.16-4.03 (m, 2H), 3.85 (s, 3H), 3.73 (t, J = 4.6 Hz, 4H), 3.10 (dd, J = 26.9, 11.1 Hz, 4H), 2.99-2.90 (m, 1H), 2.72 (q, J = 12.3 Hz, 2H), 2.57 (t, J = 4.7 Hz, 4H), 2.40 (s, 1H), 2.25-2.19 (m, 3H), 2.05 (d, J = 12.3 Hz, 2H), 1.88 (d, J = 12.6 Hz, 3H), 1.72-1.57 (m, 4H), ; 737.47 [M + H]$^+$ | 1.22 |

TABLE 1-continued

| Example Compound | Structure | Name of Compound | ¹H NMR[[:]]; MS [M + H]⁺ | UPLC r.t. (min) |
|---|---|---|---|---|
| 615 | 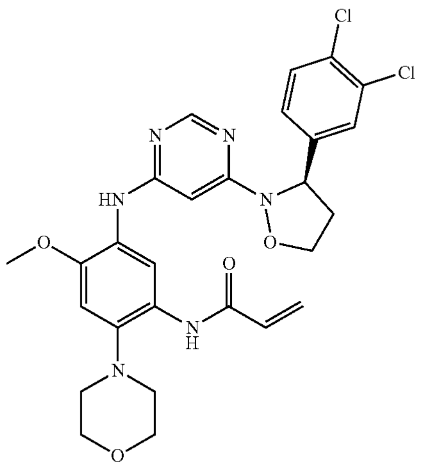 | N-(5-((6-((R)-3-(3,4-dichlorophenyl)isoxazolidine-2-yl)pyrimidine-4-yl)amino)-4-methoxy-2-morpholinophenyl)acrylamide | ¹H NMR (400 MHz, Chloroform-d) δ 8.92 (s, 1H), 8.51 (s, 1H), 8.37 (s, 1H), 7.58 (d, J = 2.1 Hz, 1H), 7.41 (d, J = 8.2 Hz, 1H), 7.30 (dd, J = 8.2, 2.1 Hz, 1H), 6.97 (s, 1H), 6.78 (s, 1H), 6.72 (s, 1H), 6.37 (d, J = 16.9 Hz, 1H), 6.27 (dd, J = 16.9, 10.0 Hz, 1H), 5.76 (d, J = 10.0 Hz, 1H), 5.65 (dd, J = 8.7, 4.6 Hz, 1H), 4.21-4.13 (m, 1H), 4.06 (q, J = 8.0 Hz, 1H), 3.91-3.87 (m, 4H), 3.87 (s, 3H), 2.94-2.84 (m, 4H), 2.82-2.72 (m, 1H), 2.38-2.28 (m, 1H), ; 571.2 [M + H]⁺ | 1.62 |
| 616 | 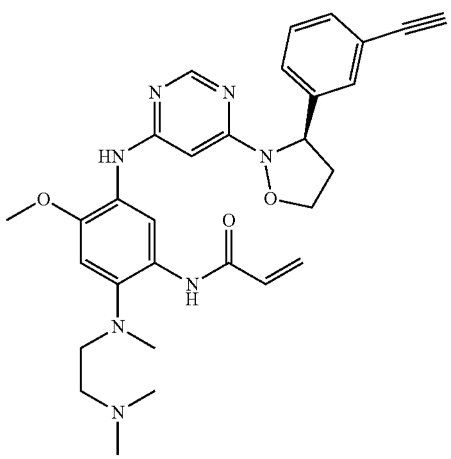 | N-(2-((2-(dimethylamino)ethyl)(methyl)amino)-5-((6-((R)-3-(3-ethynylphenyl)isoxazolidine-2-yl)pyrimidine-4-yl)amino)-4-methoxyphenyl)acrylamide | ¹H NMR (400 MHz, Chloroform-d) δ 9.59 (s, 1H), 8.89 (s, 1H), 8.32 (s, 1H), 7.60 (s, 1H), 7.46 (d, J = 7.4 Hz, 2H), 7.38 (d, J = 7.6 Hz, 1H), 7.29 (t, J = 7.8 Hz, 1H), 6.76 (s, 1H), 6.70 (s, 1H), 6.56 (dd, J = 16.9, 10.1 Hz, 1H), 6.41 (dd, J = 16.9, 1.9 Hz, 1H), 5.69 (td, J = 10.1, 3.2 Hz, 2H), 4.15 (dd, J = 8.0, 4.4 Hz, 1H), 4.09 (q, J = 8.0 Hz, 1H), 3.84 (s, 3H), 3.05 (s, 1H), 3.03 (t, J = 5.9 Hz, 2H), 2.78 (dq, J = 12.0, 3.7 Hz, 1H), 2.67 (s, 3H), 2.63 (t, J = 6.0 Hz, 2H), 2.43 (s, 6H), 2.36 (dt, J = 12.2, 4.0 Hz, 1H); 542.4 [M + H]⁺ | 1.20 |
| 617 | 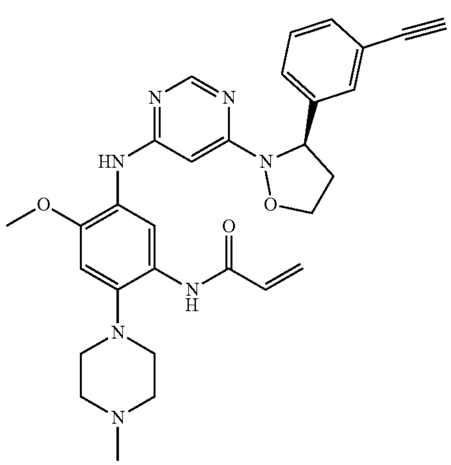 | N-(5-((6-((R)-3-(3-ethynylphenyl)isoxazolidine-2-yl)pyrimidine-4-yl)amino)-4-methoxy-2-(4-methylpiperazine-1-yl)phenyl)acrylamide | ¹H NMR (400 MHz, Chloroform-d) δ 8.87-8.66 (m, 1H), 8.48-8.37 (m, 1H), 8.35-8.26 (m, 1H), 7.59 (d, J = 1.8 Hz, 1H), 7.55 (s, 1H), 7.45 (d, J = 7.7 Hz, 1H), 7.37 (dt, J = 7.8, 1.4 Hz, 1H), 7.32-7.27 (m, 1H), 6.80 (d, J = 2.4 Hz, 1H), 6.63 (d, J = 6.7 Hz, 1H), 6.42-6.31 (m, 1H), 6.27 (dd, J = 16.9, 9.9 Hz, 1H), 5.75 (dd, J = 9.9, 1.6 Hz, 1H), 5.66 (dd, J = 8.7, 4.6 Hz, 1H), 4.14 (td, J = 8.0, 4.3 Hz, 1H), 4.04 (q, J = 8.2 Hz, 1H), 3.85 (s, 3H), 3.05 (s, 1H), 3.04-2.89 (m, 4H), 2.84 (td, J = 6.2, 2.2 Hz, 1H), 2.76 (dq, J = 7.7, 3.8, 3.3 Hz, 4H), 2.45 (d, J = 2.9 Hz, 3H), 2.35 (dtd, J = 12.5, 8.1, 4.6 Hz, 1H), ; 540.4 [M + H]⁺ | 1.13 |

TABLE 1-continued

| Example Compound | Structure | Name of Compound | ¹H NMR[[:]]; MS [M + H]⁺ | UPLC r.t. (min) |
|---|---|---|---|---|
| 618 | 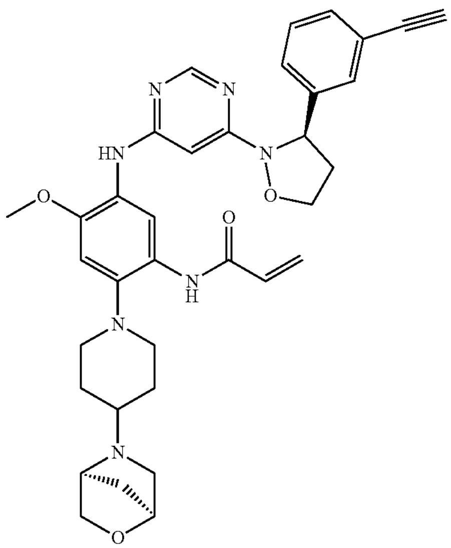 | N-(2-(4-((1S,4S)-2-oxa-5-azabicyclo[2.2.1]heptane-5-yl)piperidine-1-yl)-5-((6-((R)-3-(3-ethynylphenyl)isoxazolidine-2-yl)pyrimidine-4-yl)amino)-4-methoxyphenyl)acrylamide | ¹H NMR (400 MHz, DMSO-d₆) δ 9.98 (s, 1H), 9.24 (d, J = 30.9 Hz, 1H), 8.31 (s, 1H), 7.86 (d, J = 13.3 Hz, 1H), 7.49-7.37 (m, 4H), 6.90 (d, J = 6.6 Hz, 1H), 6.60 (dt, J = 17.7, 8.9 Hz, 1H), 6.26-6.21 (m, 1H), 6.08 (s, 1H), 5.79-5.73 (m, 1H), 5.51 (t, J = 7.3 Hz, 1H), 4.72-4.62 (m, 2H), 4.57 (s, 1H), 4.44 (d, J = 9.2 Hz, 1H), 4.31 (d, J = 4.3 Hz, 2H), 4.24 (s, 2H), 4.04 (d, J = 7.8 Hz, 1H), 3.81 (s, 3H), 3.70 (d, J = 10.1 Hz, 1H), 3.49-3.43 (m, 1H), 3.20 (d, J = 22.6 Hz, 3H), 2.93 (dd, J = 7.9, 4.1 Hz, 1H), 2.82 (s, 2H), 2.38-2.26 (m, 2H), 2.08 (d, J = 8.7 Hz, 3H), ; 622.3 [M + H]⁺ | 1.11 |
| 619 | 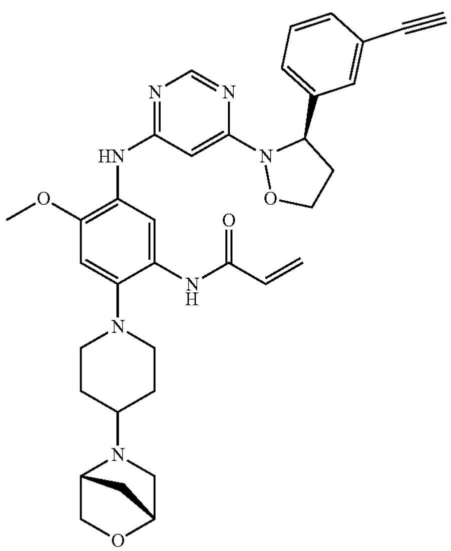 | N-(2-(4-((1R,4R)-2-oxa-5-azabicyclo[2.2.1]heptane-5-yl)piperidine-1-yl)-5-((6-((R)-3-(3-ethynylphenyl)isoxazolidine-2-yl)pyrimidine-4-yl)amino)-4-methoxyphenyl)acrylamide | ¹H NMR (400 MHz, DMSO-d₆) δ 9.88 (s, 1H), 9.23 (d, J = 30.8 Hz, 1H), 8.30 (s, 1H), 7.88 (d, J = 12.9 Hz, 1H), 7.48-7.36 (m, 4H), 6.90 (d, J = 6.7 Hz, 1H), 6.61 (td, J = 17.4, 10.2 Hz, 1H), 6.28-6.22 (m, 1H), 6.10 (s, 1H), 5.76 (t, J = 5.2 Hz, 1H), 5.55-5.46 (m, 1H), 4.73-4.62 (m, 2H), 4.57 (s, 1H), 4.30 (d, J = 4.3 Hz, 2H), 4.24 (s, 1H), 4.20 (d, J = 10.4 Hz, 1H), 4.03 (d, J = 7.8 Hz, 2H), 3.81 (d, J = 2.1 Hz, 3H), 3.70 (d, J = 9.9 Hz, 1H), 3.51-3.41 (m, 2H), 3.29-3.13 (m, 3H), 2.92 (d, J = 7.8 Hz, 1H), 2.83-2.67 (m, 2H), 2.30 (dd, J = 13.1, 5.1 Hz, 2H), 2.08 (d, J = 10.3 Hz, 2H), ; 622.3 [M + H]⁺ | 1.11 |

TABLE 1-continued

| Example Compound | Structure | Name of Compound | ¹H NMR[[:]]; MS [M + H]⁺ | UPLC r.t. (min) |
|---|---|---|---|---|
| 620 | 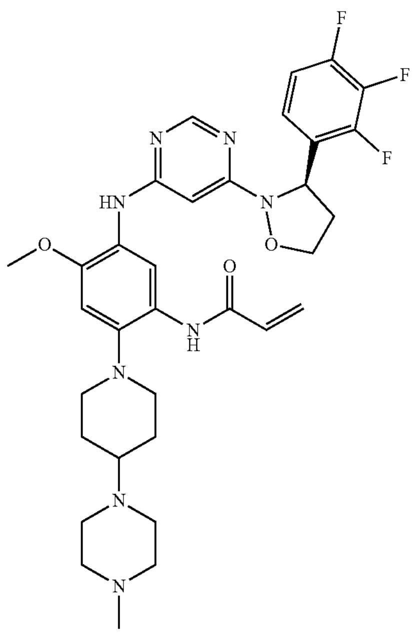 | N-(4-methoxy-2-(4-(4-methylpiperazine-1-yl)piperidine-1-yl)-5-((6-((R)-3-(2,3,4-trifluorophenyl)isoxazolidine-2-yl)pyrimidine-4-yl)amino)phenyl)acrylamide | 653.5 [M + H]⁺ | 1.18 |
| 621 | 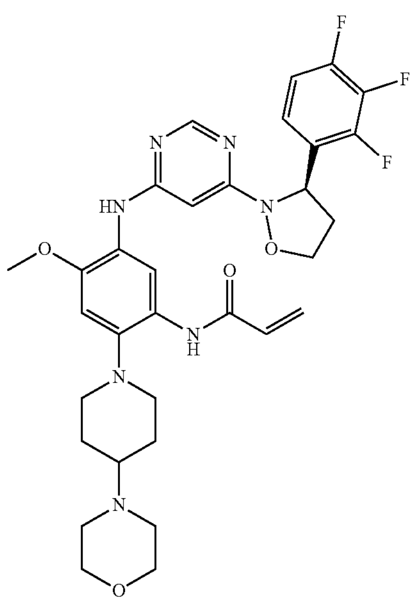 | N-(4-methoxy-2-(4-morpholinopiperidine-1-yl)-5-((6-((R)-3-(2,3,4-trifluorophenyl)isoxazolidine-2-yl)pyrimidine-4-yl)amino)phenyl)acrylamide | 640.5 [M + H]⁺ | 1.27 |

TABLE 1-continued

| Example Compound | Structure | Name of Compound | ¹H NMR[[:]]; MS [M + H]⁺ | UPLC r.t. (min) |
|---|---|---|---|---|
| 622 | 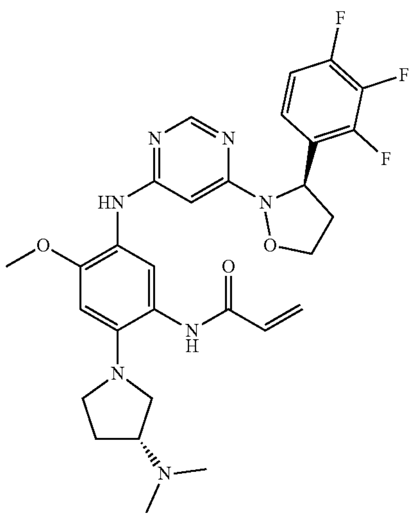 | N-(2-((R)-3-(dimethylamino)pyrolidine-1-yl)-4-methoxy-5-((6-((R)-3-(2,3,4-trifluorophenyl)isoxazolidine-2-yl)pyrimidine-4-yl)amino)phenyl)acrylamide | 584.5 [M + H]⁺ | 1.18 |
| 623 | 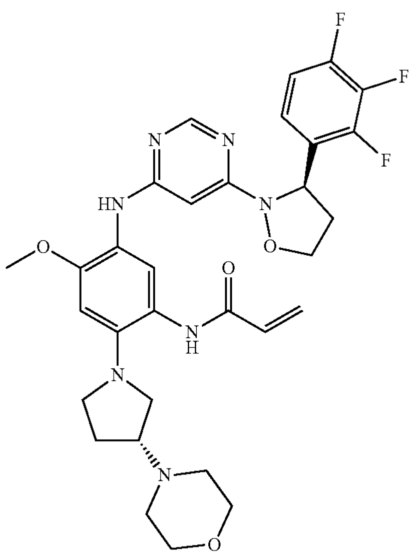 | N-(4-methoxy-2-((R)-3-morpholinopyrolidine-1-yl)-5-((6-((R)-3-(2,3,4-trifluorophenyl)isoxazolidine-2-yl)pyrimidine-4-yl)amino)phenyl)acrylamide | ¹H NMR (400 MHz, Methanol-d₄) δ 8.15 (s, 1H), 7.77 (s, 1H), 7.33 (td, J = 8.2, 2.0 Hz, 1H), 7.09 (td, J = 9.3, 1.8 Hz, 1H), 6.68 (s, 1H), 6.59 (dd, J = 17.0, 10.3 Hz, 1H), 6.41-6.32 (m, 2H), 5.81-5.72 (m, 2H), 4.15 (td, J = 7.9, 4.1 Hz, 1H), 3.98 (d, J = 8.0 Hz, 1H), 3.87 (s, 3H), 3.81 (t, J = 4.4 Hz, 4H), 3.41 (dd, J = 9.3, 6.7 Hz, 1H), 3.31 (ddd, J = 16.1, 7.6, 3.3 Hz, 5H), 2.89-2.69 (m, 5H), 2.67 (s, 8H), 2.33-2.21 (m, 2H), 2.01 (td, J = 16.9, 8.4 Hz, 1H), 1.43-1.35 (m, 4H), ; 626.4 [M + H]⁺ | 1.25 |

TABLE 1-continued

| Example Compound | Structure | Name of Compound | ¹H NMR[[:]]; MS [M + H]⁺ | UPLC r.t. (min) |
|---|---|---|---|---|
| 624 | 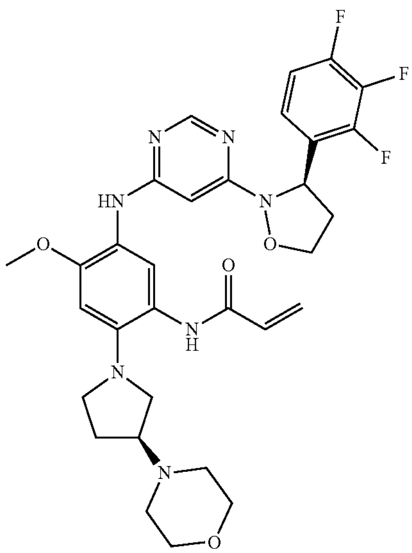 | N-(4-methoxy-2-((S)-3-morpholinopyrrolidine-1-yl)-5-((6-((R)-3-(2,3,4-trifluorophenyl)isoxazolidine-2-yl)pyrimidine-4-yl)amino)phenyl)acrylamide | 626.4 [M + H]⁺ | 1.22 |
| 625 | 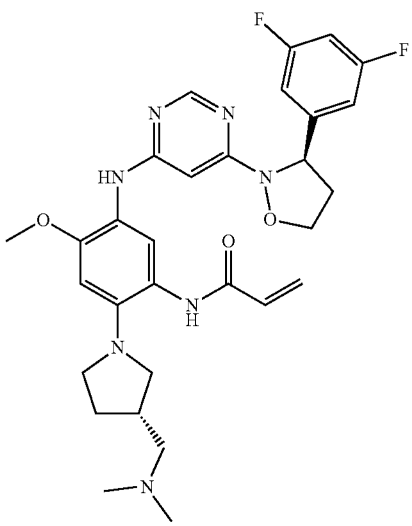 | N-(5-((6-((R)-3-(3,5-difluorophenyl)isoxazolidine-2-yl)pyrimidine-4-yl)amino)-2-((S)-3-((dimethylamino)methyl)pyrrolidine-1-yl)-4-methoxyphenyl)acrylamide | ¹H NMR (400 MHz, DMSO-d₆) δ 9.33 (s, 1H), 8.53 (s, 1H), 8.13 (d, J = 1.0 Hz, 1H), 7.37 (s, 1H), 7.13-7.09 (m, 3H), 6.53-6.43 (m, 2H), 6.20 (d, J = 2.1 Hz, 1H), 5.68 (dd, J = 10.2, 2.1 Hz, 1H), 5.55 (dd, J = 8.7, 5.0 Hz, 1H), 4.11 (td, J = 7.8, 3.8 Hz, 1H), 3.79 (s, 3H), 3.39-3.16 (m, 5H), 3.00 (dd, J = 9.3, 6.6 Hz, 1H), 2.75 (dtd, J = 12.0, 7.8, 3.8 Hz, 1H), 2.24 (dd, J = 7.7, 5.2 Hz, 2H), 2.14 (s, 7H), 2.05-1.93 (m, 1H), 1.56 (dq, 12.1, 7.8 Hz, 1H), ; 580.4 [M + H]⁺ | 1.14 |

TABLE 1-continued

| Example Compound | Structure | Name of Compound | $^1$H NMR[[:]]; MS [M + H]$^+$ | UPLC r.t. (min) |
|---|---|---|---|---|
| 626 | 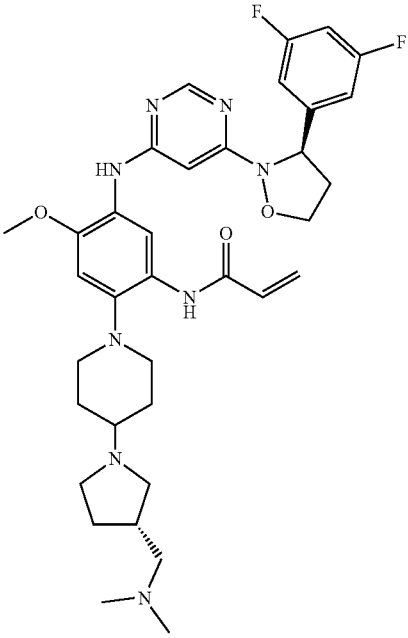 | N-(5-((6-((R)-3-(3,5-difluorophenyl)isoxazolidine-2-yl)pyrimidine-4-yl)amino)-2-(4-((S)-3-((dimethylamino)methyl)pyrrolidine-1-yl)piperidine-1-yl)-4-methoxyphenyl)acrylamide | $^1$H NMR (400 MHz, DMSO-d$_6$) δ 8.96 (s, 1H), 8.66 (s, 1H), 8.17 (s, 1H), 7.13 (td, J = 7.8, 7.2, 3.1 Hz, 4H), 6.82 (s, 1H), 6.65 (dd, J = 16.9, 10.1 Hz, 1H), 6.35 (s, 1H), 6.21 (dd, J = 16.9, 2.0 Hz, 1H), 5.72 (dd, J = 10.2, 2.0 Hz, 1H), 5.56 (dd, J = 8.7, 5.0 Hz, 1H), 4.13 (td, J = 7.9, 3.9 Hz, 1H), 3.80 (s, 3H), 3.01-2.97 (m, 2H), 2.81-2.61 (m, 5H), 2.54 (d, J = 7.3 Hz, 2H), 2.25 (ddd, J = 12.8, 8.5, 4.8 Hz, 4H), 2.11 (d, J = 7.3 Hz, 14H), 1.95-1.87 (m, 2H), 1.68 (h, J = 8.7, 7.8 Hz, 2H), 1.36 (h, J = 6.9 Hz, 1H), ; 663.5 [M + H]$^+$ | 1.05 |
| 627 | 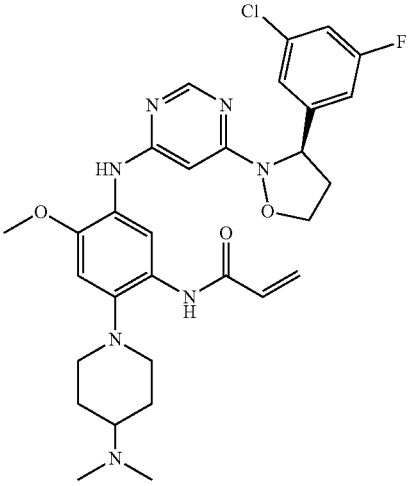 | N-(5-((6-((R)-3-(3-chloro-5-fluorophenyl)isoxazolidine-2-yl)pyrimidine-4-yl)amino)-2-(4-(dimethylamino)piperidine-1-yl)-4-methoxyphenyl)acrylamide | $^1$H NMR (400 MHz, Chloroform-d) δ 8.86 (s, 1H), 8.50 (s, 1H), 8.36 (d, J = 1.0 Hz, 1H), 7.10 (dt, J = 9.4, 2.2 Hz, 1H), 7.00-6.88 (m, 2H), 6.78-6.69 (m, 2H), 6.35 (dd, J = 17.0, 1.5 Hz, 1H), 6.25 (dd, J = 17.0, 10.0 Hz, 1H), 5.74 (dd, J = 9.9, 1.6 Hz, 1H), 5.66 (dd, J = 8.7, 4.6 Hz, 1H), 4.20-4.11 (m, 1H), 4.11-4.00 (m, 1H), 3.85 (s, 3H), 3.09-3.02 (m, 2H), 2.84-2.77 (m, 1H), 2.76-2.66 (m, 2H), 2.35 (s, 6H), 2.34-2.28 (m, 1H), 2.27-2.17 (m, 1H), 2.09-2.01 (m, 2H), 1.70-1.61 (m, 2H), 1.62-1.53 (m, 1H), ; 596.4 [M + H]$^+$ | 1.27 |

TABLE 1-continued

| Example Compound | Structure | Name of Compound | ¹H NMR[[:]]; MS [M + H]⁺ | UPLC r.t. (min) |
|---|---|---|---|---|
| 628 | 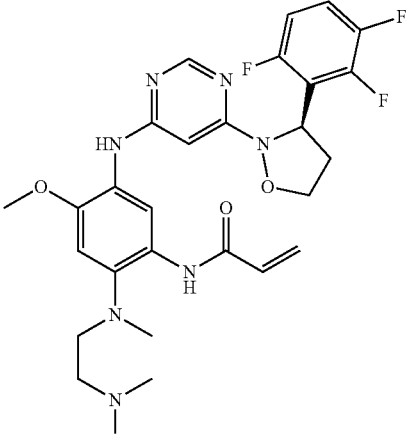 | N-(2-((2-(dimethylamino)ethyl)(methyl)amino)-4-methoxy-5-((6-((R)-3-(2,3,6-trifluorophenyl)isoxazolidine-2-yl)pyrimidine-4-yl)amino)phenyl)acrylamide | ¹H NMR (400 MHz, Chloroform-d) δ 10.09 (s, 1H), 8.94 (s, 1H), 8.37 (d, J = 1.0 Hz, 1H), 7.05 (qd, J = 9.1, 4.9 Hz, 1H), 6.88 (s, 1H), 6.86-6.80 (m, 1H), 6.79 (s, 1H), 6.68 (d, J = 1.1 Hz, 1H), 6.40 (dd, J = 17.0, 1.9 Hz, 1H), 6.27 (dd, J = 17.0, 10.0 Hz, 1H), 5.91 (dd, J = 9.1, 6.5 Hz, 1H), 5.67 (dd, J = 10.0, 1.9 Hz, 1H), 4.42-4.33 (m, 1H), 4.07-3.96 (m, 1H), 3.82 (s, 3H), 2.93-2.81 (m, 2H), 2.81-2.74 (m, 1H), 2.71 (s, 3H), 2.63-2.50 (m, 1H), 2.35-2.28 (m, 2H), 2.27 (s, 6H), ; 572.4 [M + H]⁺ | 1.19 |
| 629 | 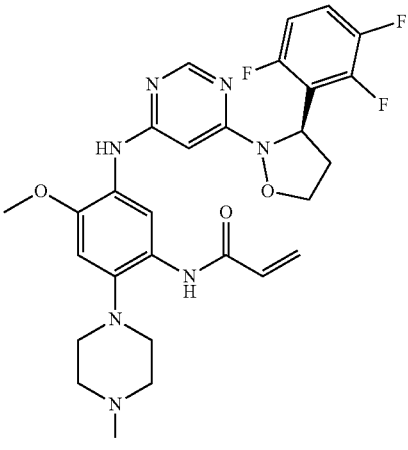 | N-(4-methoxy-2-(4-methylpiperazine-1-yl)-5-((6-((R)-3-(2,3,6-trifluorophenyl)isoxazolidine-2-yl)pyrimidine-4-yl)amino)phenyl)acrylamide | ¹H NMR (400 MHz, Chloroform-d) δ 8.88 (s, 1H), 8.52 (s, 1H), 8.37 (d, J = 1.0 Hz, 1H), 7.06 (qd, J = 9.1, 4.8 Hz, 1H), 6.88 (s, 1H), 6.87-6.79 (m, 1H), 6.78 (s, 1H), 6.64 (s, 1H), 6.37 (dd, J = 17.0, 1.6 Hz, 1H), 6.26 (dd, J = 16.9, 9.9 Hz, 1H), 5.90 (dd, J = 9.1, 6.5 Hz, 1H), 5.75 (dd, J = 9.9, 1.6 Hz, 1H), 4.41-4.32 (m, 1H), 4.04-3.94 (m, 1H), 3.82 (s, 3H), 2.97-2.85 (m, 4H), 2.80-2.72 (m, 1H), 2.71-2.47 (m, 5H), 2.39 (s, 3H), ; 570.4 [M + H]⁺ | 1.14 |
| 630 | 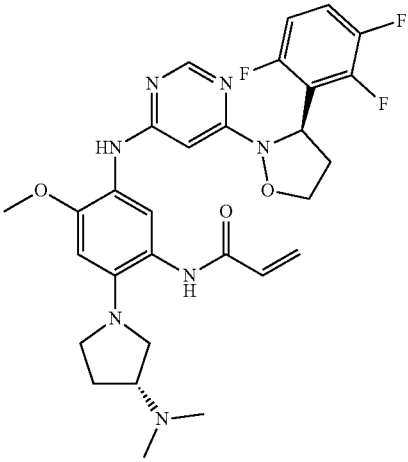 | N-(2-((R)-3-(dimethylamino)pyrolidine-1-yl)-4-methoxy-5-((6-((R)-3-(2,3,6-trifluorophenyl)isoxazolidine-2-yl)pyrimidine-4-yl)amino)phenyl)acrylamide | ¹H NMR (400 MHz, Chloroform-d) δ 8.61 (s, 1H), 8.35 (s, 1H), 8.11 (s, 1H), 7.06 (qd, J = 9.1, 4.8 Hz, 1H), 6.89-6.78 (m, 2H), 6.73 (s, 1H), 6.60 (s, 1H), 6.38 (dd, J = 16.9, 1.7 Hz, 1H), 6.28 (dd, J = 16.9, 10.0 Hz, 1H), 5.90 (dd, J = 9.0, 6.6 Hz, 1H), 5.73 (dd, J = 10.0, 1.7 Hz, 1H), 4.41-4.32 (m, 1H), 4.03-3.92 (m, 1H), 3.82 (s, 3H), 3.24-3.17 (m, 1H), 3.17-3.04 (m, 3H), 2.92-2.81 (m, 1H), 2.81-2.69 (m, 1H), 2.63-2.49 (m, 1H), 2.29 (s, 6H), 2.24-2.11 (m, 1H), 1.99-1.85 (m, 1H), ; 584.4 [M + H]⁺ | 1.11 |

TABLE 1-continued

| Example Compound | Structure | Name of Compound | ¹H NMR[[:]]; MS [M + H]⁺ | UPLC r.t. (min) |
|---|---|---|---|---|
| 631 | 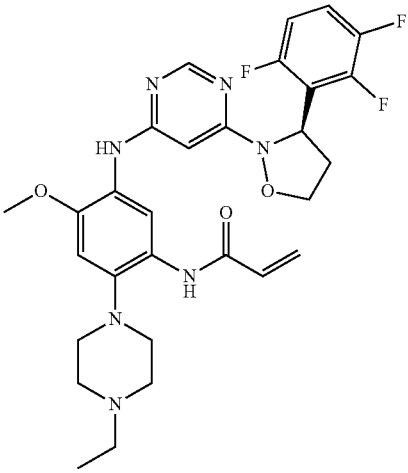 | N-(2-(4-ethylpiperazine-1-yl)-4-methoxy-5-((6-((R)-3-(2,3,6-trifluorophenyl)isoxazolidine-2-yl)pyrimidine-4-yl)amino)phenyl)acrylamide | ¹H NMR (400 MHz, Chloroform-d) δ 8.88 (s, 1H), 8.56 (s, 1H), 8.37 (d, J = 1.0 Hz, 1H), 7.06 (qd, J = 9.1, 4.8 Hz, 1H), 6.90-6.79 (m, 3H), 6.64 (s, 1H), 6.37 (dd, J = 17.0, 1.6 Hz, 1H), 6.26 (dd, J = 17.0, 9.9 Hz, 1H), 5.90 (dd, J = 9.0, 6.6 Hz, 1H), 5.75 (dd, J = 10.0, 1.6 Hz, 1H), 4.42-4.33 (m, 1H), 4.04-3.94 (m, 1H), 3.81 (s, 3H), 2.99-2.88 (m, 4H), 2.80-2.72 (m, 2H), 2.78-2.58 (m, 4H), 2.62-2.56 (m, 1H), 2.52 (q, J = 7.2 Hz, 2H), 1.16 (t, J = 7.8, 7.2 Hz, 3H), ; 584.3 [M + H]⁺ | 1.14 |
| 632 | 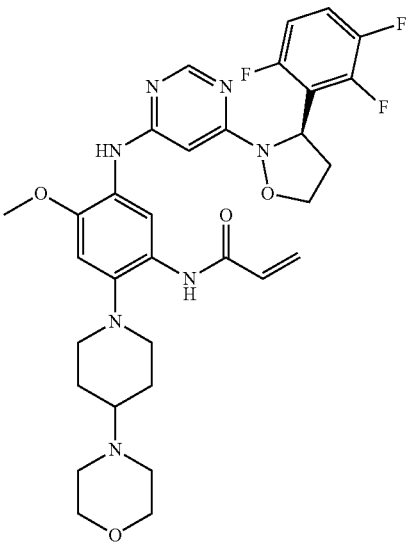 | N-(4-methoxy-2-(4-morpholinopiperidine-1-yl)-5-((6-((R)-3-(2,3,6-trifluorophenyl)isoxazolidine-2-yl)pyrimidine-4-yl)amino)phenyl)acrylamide | ¹H NMR (400 MHz, Chloroform-d) δ 8.85 (s, 1H), 8.42 (s, 1H), 8.37 (d, J = 1.0 Hz, 1H), 7.12-7.00 (m, 1H), 6.89-6.79 (m, 2H), 6.74 (s, 1H), 6.66-6.61 (m, 1H), 6.36 (dd, J = 16.9, 1.5 Hz, 1H), 6.24 (dd, J = 16.9, 10.1 Hz, 1H), 5.90 (dd, J = 9.0, 6.6 Hz, 1H), 5.74 (dd, J = 10.1, 1.5 Hz, 1H), 4.41-4.32 (m, 1H), 3.99 (q, J = 8.3 Hz, 1H), 3.83 (s, 3H), 3.78 (t, J = 4.6 Hz, 4H), 3.10-3.03 (m, 2H), 2.80-2.68 (m, 3H), 2.65-2.50 (m, 5H), 2.35-2.24 (m, 1H), 2.13-2.03 (m, 2H), 1.72-1.64 (m, 2H), ; 640.4 [M + H]⁺ | 1.15 |
| 633 | 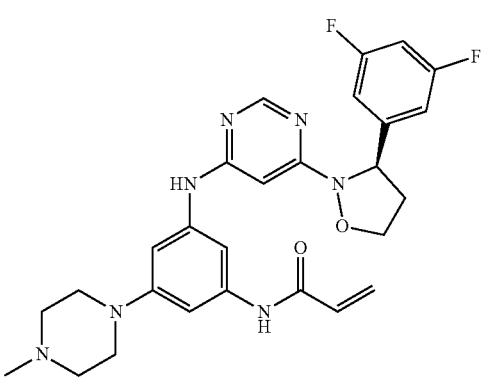 | N-(3-((6-((R)-3-(3,5-difluorophenyl)isoxazolidine-2-yl)pyrimidine-4-yl)amino)-5-(4-methylpiperazine-1-yl)phenyl)acrylamide | ¹H NMR (400 MHz, Methanol-d₄) δ 8.24 (s, 1H), 7.39 (s, 1H), 7.16 (s, 1H), 7.07 (d, J = 7.1 Hz, 2H), 6.95 (s, 1H), 6.88-6.80 (m, 1H), 6.56 (s, 1H), 6.49-6.32 (m, 2H), 5.79 (dd, J = 2.1, 9.7 Hz, 1H), 5.61-5.52 (m, 1H), 4.20-4.12 (m, 1H), 3.97 (q, J = 7.9 Hz, 1H), 3.38-3.34 (m, 4H), 2.98-2.91 (m, 4H), 2.89-2.82 (m, 1H), 2.60 (s, 3H), 2.39-2.31 (m, 1H); 522.3 [M + H]⁺ | 1.19 |

TABLE 1-continued

| Example Compound | Structure | Name of Compound | $^1$H NMR[[:]]; MS [M + H]$^+$ | UPLC r.t. (min) |
|---|---|---|---|---|
| 634 | 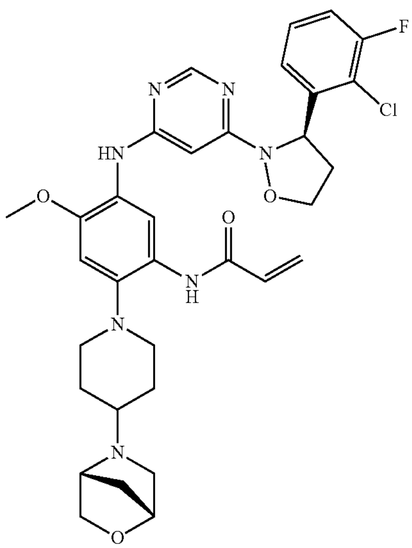 | N-(2-(4-((1R,4R)-2-oxa-5-azabicyclo[2.2.1]heptane-5-yl)piperidine-1-yl)-5-((6-((R)-3-(2-chloro-3-fluorophenyl)isoxazolidine-2-yl)pyrimidine-4-yl)amino)-4-methoxyphenyl)acrylamide | $^1$H NMR (400 MHz, DMSO-d$_6$) δ 8.98 (s, 1H), 8.65 (s, 1H), 8.15 (d, J = 6.0 Hz, 2H), 7.45-7.31 (m, 3H), 6.84 (s, 1H), 6.61 (s, 1H), 6.39 (s, 1H), 6.21 (d, J = 16.9 Hz, 1H), 5.86-5.66 (m, 2H), 4.36 (s, 1H), 4.18-4.11 (m, 1H), 3.88 (q, J = 8.0 Hz, 2H), 3.81 (s, 3H), 3.54 (s, 1H), 3.02 (s, 3H), 2.95-2.82 (m, 2H), 2.73 (t, J = 10.9 Hz, 3H), 2.10 (d, J = 8.5 Hz, 2H), 1.91 (s, 2H), 1.66 (s, 4H), ; 650.4 [M + H]$^+$ | 1.25 |
| 635 | 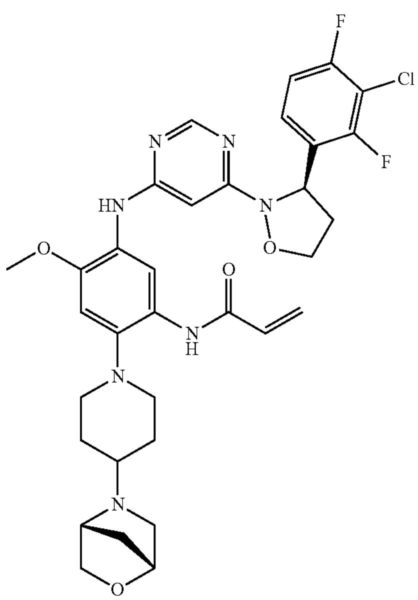 | N-(2-(4-((1R,4R)-2-oxa-5-azabicyclo[2.2.1]heptane-5-yl)piperidine-1-yl)-5-((6-((R)-3-(3-chloro-2,4-difluorophenyl)isoxazolidine-2-yl)pyrimidine-4-yl)amino)-4-methoxyphenyl)acrylamide | $^1$H NMR (400 MHz, DMSO-d$_6$) δ 8.94 (s, 1H), 8.64 (s, 1H), 8.15 (d, J = 3.7 Hz, 2H), 7.49 (td, J = 8.6, 6.2 Hz, 1H), 7.31 (td, J = 8.8, 1.7 Hz, 1H), 6.84 (s, 1H), 6.64 (dd, J = 16.9, 10.2 Hz, 1H), 6.35 (s, 1H), 6.20 (dd, J = 16.9, 2.0 Hz, 1H), 5.71 (dd, J = 9.0, 5.2 Hz, 2H), 4.33 (s, 1H), 4.17 (td, J = 7.9, 3.7 Hz, 1H), 3.87 (dd, J = 11.7, 7.8 Hz, 2H), 3.80 (s, 3H), 3.70 (s, 1H), 3.51 (d, J = 7.3 Hz, 1H), 3.03-2.92 (m, 3H), 2.79 (dt, J = 8.1, 3.9 Hz, 1H), 2.75-2.65 (m, 2H), 2.44 (d, J = 10.2 Hz, 1H), 2.34 (d, J = 9.6 Hz, 1H), 2.25-2.15 (m, 1H), 1.87 (s, 2H), 1.72-1.56 (m, 4H), ; 668.4 [M + H]$^+$ | 1.32 |

TABLE 1-continued

| Example Compound | Structure | Name of Compound | ¹H NMR[[:]]; MS [M + H]⁺ | UPLC r.t. (min) |
|---|---|---|---|---|
| 636 | 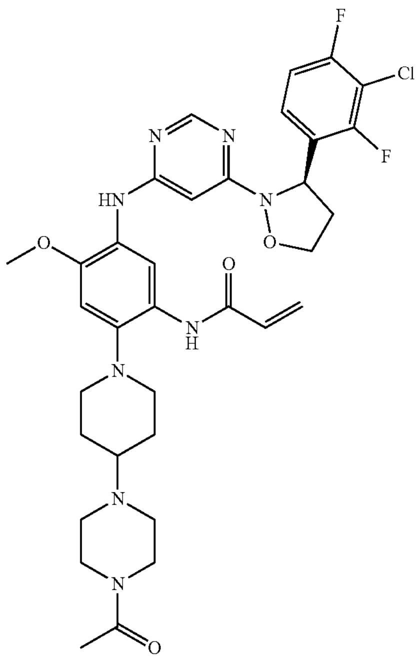 | N-(2-(4-(4-acetylpiperazine-1-yl)piperidine-1-yl)-5-((6-((R)-3-(3-chloro-2,4-difluorophenyl)isoxazolidine-2-yl)pyrimidine-4-yl)amino)-4-methoxyphenyl)acrylamide | ¹H NMR (400 MHz, Chloroform-d) δ 11.26 (s, 1H), 8.82 (s, 1H), 8.37-8.27 (m, 2H), 7.46 (td, J = 8.4, 6.0 Hz, 1H), 6.95 (td, J = 8.5, 1.8 Hz, 1H), 6.72 (s, 2H), 6.48-6.27 (m, 2H), 5.89-5.82 (m, 1H), 5.77 (dd, J = 9.3, 2.2 Hz, 1H), 4.15 (td, J = 8.0, 4.1 Hz, 1H), 4.07 (q, J = 8.1 Hz, 1H), 3.85 (s, 4H), 3.70-3.62 (m, 1H), 3.16 (d, J = 11.7 Hz, 1H), 3.08 (dd, J = 8.9, 6.5 Hz, 1H), 2.90-2.83 (m, 1H), 2.83-2.71 (m, 1H), 2.34-2.19 (m, 4H), 2.13 (s, 3H), 2.06 (d, J = 14.5 Hz, 2H), 1.58-1.52 (m, 4H), 1.45 (d, J = 6.6 Hz, 3H), ; 697.4 [M + H]⁺ | 1.31 |
| 637 | 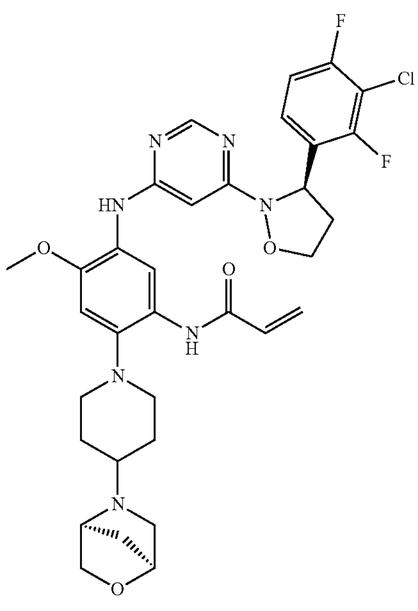 | N-(2-(4-((1S,4S)-2-oxa-5-azabicyclo[2.2.1]heptane-5-yl)piperidine-1-yl)-5-((6-((R)-3-(3-chloro-2,4-difluorophenyl)isoxazolidine-2-yl)pyrimidine-4-yl)amino)-4-methoxyphenyl)acrylamide | ¹H NMR (400 MHz, DMSO-d₆) δ 8.94 (s, 1H), 8.64 (s, 1H), 8.15 (d, J = 3.8 Hz, 2H), 7.49 (td, J = 8.5, 6.2 Hz, 1H), 7.31 (td, J = 8.8, 1.6 Hz, 1H), 6.84 (s, 1H), 6.64 (dd, J = 17.0, 10.2 Hz, 1H), 6.35 (s, 1H), 6.20 (dd, J = 17.0, 2.0 Hz, 1H), 5.71 (dd, J = 9.3, 5.4 Hz, 2H), 4.33 (s, 1H), 4.16 (dd, J = 8.0, 3.8 Hz, 1H), 3.92-3.83 (m, 2H), 3.80 (s, 3H), 3.70 (s, 1H), 3.51 (d, J = 7.3 Hz, 1H), 3.02-2.92 (m, 3H), 2.79 (dt, J = 8.1, 4.0 Hz, 1H), 2.71 (t, J = 12.1 Hz, 2H), 2.34 (d, J = 9.5 Hz, 1H), 2.26-2.16 (m, 1H), 1.85 (s, 3H), 1.74-1.56 (m, 4H), ; 668.5 [M + H]⁺ | 1.33 |

TABLE 1-continued

| Example Compound | Structure | Name of Compound | ¹H NMR[:]; MS [M + H]⁺ | UPLC r.t. (min) |
|---|---|---|---|---|
| 638 | 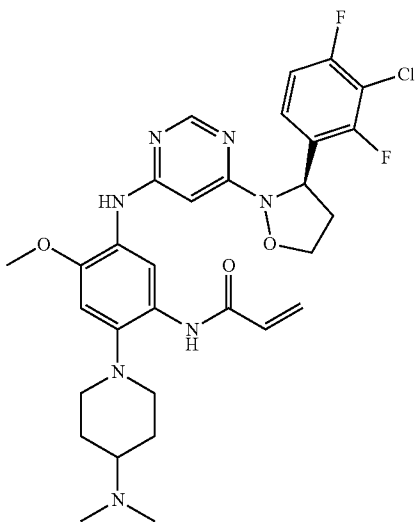 | N-(5-((6-((R)-3-(3-chloro-2,4-difluorophenyl)isoxazolidine-2-yl)pyrimidine-4-yl)amino)-2-(4-(dimethylamino)piperidine-1-yl)-4-methoxyphenyl)acrylamide | ¹H NMR (400 MHz, DMSO-d$_6$) δ 8.98 (s, 1H), 8.65 (s, 1H), 8.27-8.06 (m, 2H), 7.49 (td, J = 8.6, 6.2 Hz, 1H), 7.31 (td, J = 8.8, 1.7 Hz, 1H), 6.83 (s, 1H), 6.65 (dd, J = 17.0, 10.2 Hz, 1H), 6.38 (d, J = 12.7 Hz, 1H), 6.28-6.15 (m, 1H), 5.72 (ddd, J = 8.7, 5.8, 3.3 Hz, 2H), 4.17 (td, J = 7.9, 3.7 Hz, 1H), 3.93-3.75 (m, 4H), 3.15-3.00 (m, 3H), 2.79 (qd, J = 7.5, 3.4 Hz, 1H), 2.72-2.60 (m, 2H), 2.34-2.16 (m, 7H), 1.89-1.60 (m, 4H), ; 614.4 [M + H]⁺ | 1.31 |
| 639 | 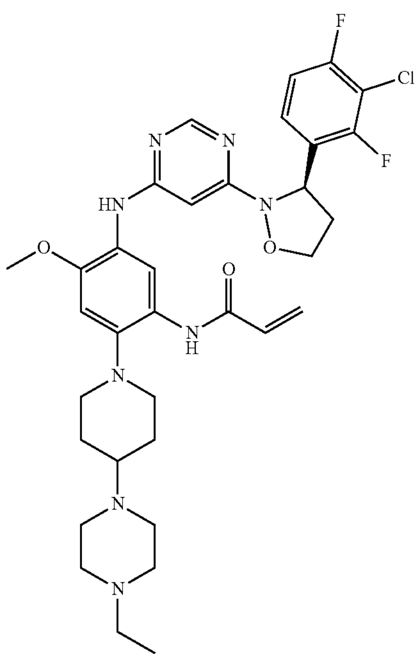 | N-(5-((6-((R)-3-(3-chloro-2,4-difluorophenyl)isoxazolidine-2-yl)pyrimidine-4-yl)amino)-2-(4-(4-ethylpiperazine-1-yl)piperidine-1-yl)-4-methoxyphenyl)acrylamide | ¹H NMR (400 MHz, DMSO-d$_6$) δ 8.98 (s, 1H), 8.66 (s, 1H), 8.16 (d, J = 6.4 Hz, 1H), 7.49 (td, J = 8.5, 6.2 Hz, 1H), 7.31 (t, J = 8.8 Hz, 1H), 6.83 (s, 1H), 6.68 (ddd, J = 19.1, 16.6, 10.2 Hz, 1H), 6.22-6.03 (m, 2H), 5.81-5.66 (m, 3H), 3.80 (s, 3H), 3.27-3.12 (m, 2H), 3.04 (d, J = 24.7 Hz, 5H), 2.62 (dd, J = 11.1, 5.5 Hz, 4H), 2.43 (dd, J = 14.5, 7.1 Hz, 3H), 1.97-1.65 (m, 6H), 1.13-1.01 (m, 6H), ; 683.4 [M + H]⁺ | 1.25 |

TABLE 1-continued

| Example Compound | Structure | Name of Compound | ¹H NMR[[:]]; MS [M + H]⁺ | UPLC r.t. (min) |
|---|---|---|---|---|
| 640 | 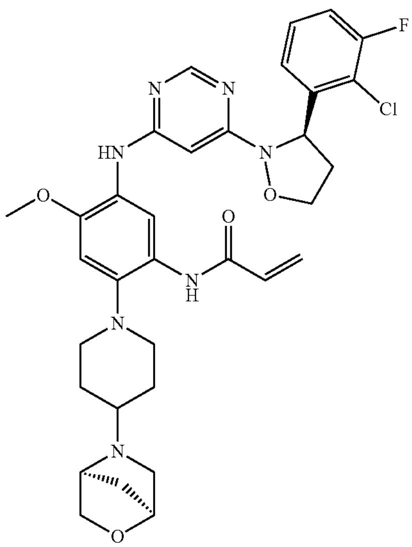 | N-(2-(4-((1S,4S)-2-oxa-5-azabicyclo[2.2.1]heptane-5-yl)piperidine-1-yl)-5-((6-((R)-3-(2-chloro-3-fluorophenyl)isoxazolidine-2-yl)pyrimidine-4-yl)amino)-4-methoxyphenyl)acrylamide | ¹H NMR (400 MHz, DMSO-d₆) δ 9.13 (s, 1H), 8.68 (s, 1H), 8.16 (s, 1H), 7.46-7.28 (m, 3H), 6.85 (s, 1H), 6.60 (t, J = 13.6 Hz, 1H), 6.42 (s, 1H), 6.24 (ddd, J = 17.0, 11.6, 1.9 Hz, 1H), 5.84-5.70 (m, 2H), 4.15 (td, J = 7.9, 3.8 Hz, 1H), 3.88 (q, J = 8.0 Hz, 1H), 3.82 (s, 3H), 3.72-3.64 (m, 2H), 3.59 (d, J = 6.6 Hz, 5H), 2.89 (dtd, J = 12.4, 8.3, 4.3 Hz, 2H), 2.73 (d, J = 12.2 Hz, 2H), 2.32-1.94 (m, 7H), 1.06 (t, J = 7.0 Hz, 2H), ; 650.4 [M + H]⁺ | 1.23 |
| 641 | 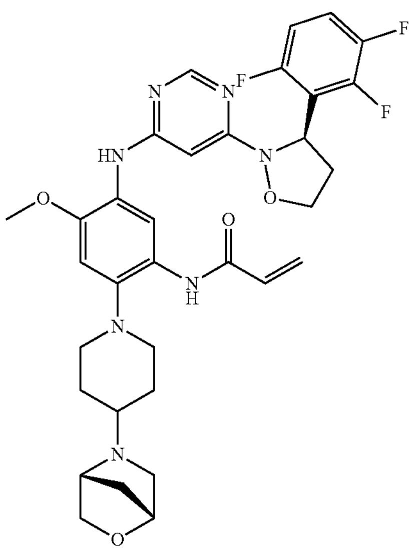 | N-(2-(4-((1R,4R)-2-oxa-5-azabicyclo[2.2.1]heptane-5-yl)piperidine-1-yl)-4-methoxy-5-((6-((R)-3-(2,3,6-trifluorophenyl)isoxazolidine-2-yl)pyrimidine-4-yl)amino)phenyl)acrylamide | ¹H NMR (400 MHz, Chloroform-d) δ 8.84 (s, 1H), 8.46 (s, 1H), 8.36 (d, J = 1.0 Hz, 1H), 7.12-6.99 (m, 1H), 6.87-6.78 (m, 2H), 6.75 (s, 1H), 6.66-6.61 (m, 1H), 6.35 (dd, J = 17.0, 1.5 Hz, 1H), 6.23 (dd, J = 16.9, 10.1 Hz, 1H), 5.90 (dd, J = 9.1, 6.5 Hz, 1H), 5.73 (dd, J = 10.1, 1.5 Hz, 1H), 4.44 (t, J = 2.0 Hz, 1H), 4.36 (td, J = 8.1, 2.5 Hz, 1H), 4.11 (dd, J = 12.7, 7.5 Hz, 1H), 4.07-3.94 (m, 1H), 3.83 (s, 3H), 3.79-3.74 (m, 1H), 3.66 (dd, J = 8.0, 1.6 Hz, 1H), 3.13 (dd, J = 10.0, 1.8 Hz, 1H), 3.06-2.98 (m, 2H), 2.83-2.69 (m, 3H), 2.63-2.51 (m, 2H), 2.51-2.46 (m, 1H), 2.04-2.00 (m, 1H), 1.99-1.86 (m, 2H), 1.86-1.79 (m, 1H), 1.72-1.59 (m, 2H), ; 652.5 [M + H]⁺ | 1.18 |

TABLE 1-continued

| Example Compound | Structure | Name of Compound | ¹H NMR[:]; MS [M + H]⁺ | UPLC r.t. (min) |
|---|---|---|---|---|
| 642 | 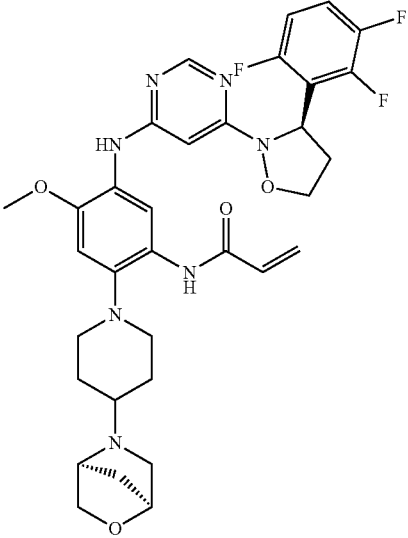 | N-(2-(4-((1S,4S)-2-oxa-5-azabicyclo[2.2.1]heptane-5-yl)piperidine-1-yl)-4-methoxy-5-((6-((R)-3-(2,3,6-trifluorophenyl)isoxazolidine-2-yl)pyrimidine-4-yl)amino)phenyl) acrylamide | ¹H NMR (400 MHz, Chloroform-d) δ 8.84 (s, 1H), 8.46 (s, 1H), 8.36 (d, J = 1.0 Hz, 1H), 7.12-6.99 (m, 1H), 6.91-6.78 (m, 2H), 6.75 (s, 1H), 6.63 (d, J = 1.0 Hz, 1H), 6.35 (dd, J = 17.0, 1.5 Hz, 1H), 6.23 (dd, J = 16.9, 10.1 Hz, 1H), 5.90 (dd, J = 9.1, 6.5 Hz, 1H), 5.72 (dd, J = 10.1, 1.5 Hz, 1H), 4.44 (t, J = 2.0 Hz, 1H), 4.36 (td, J = 8.1, 2.5 Hz, 1H), 4.10 (dd, J = 13.3, 7.5 Hz, 1H), 4.04-3.93 (m, 1H), 3.83 (s, 3H), 3.79-3.74 (m, 1H), 3.66 (dd, J = 8.0, 1.7 Hz, 1H), 3.13 (dd, J = 9.9, 1.8 Hz, 1H), 3.07-2.97 (m, 2H), 2.82-2.69 (m, 3H), 2.63-2.54 (m, 2H), 2.50 (dd, J = 9.9, 1.5 Hz, 1H), 2.08-2.00 (m, 1H), 1.98-1.89 (m, 2H), 1.84-1.80 (m, 1H), 1.72-1.60 (m, 2H), ; 652.5 [M + H]⁺ | 1.19 |
| 643 | 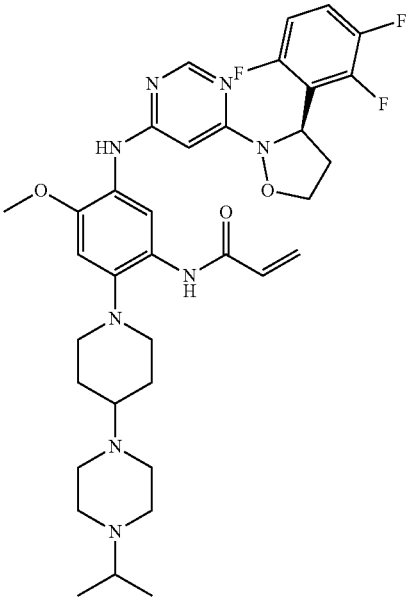 | N-(2-(4-(4-isopropylpiperazine-1-yl)piperidine-1-yl)-4-methoxy-5-((6-((R)-3-(2,3,6-trifluorophenyl)isoxazolidine-2-yl)pyrimidine-4-yl)amino)phenyl) acrylamide | ¹H NMR (400 MHz, Chloroform-d) δ 8.84 (s, 1H), 8.44 (s, 1H), 8.36 (d, J = 1.0 Hz, 1H), 7.12-6.99 (m, 1H), 6.88-6.78 (m, 2H), 6.74 (s, 1H), 6.63 (s, 1H), 6.35 (dd, J = 16.9, 1.6 Hz, 1H), 6.23 (dd, J = 16.9, 10.0 Hz, 1H), 5.90 (dd, J = 9.0, 6.5 Hz, 1H), 5.73 (dd, J = 10.0, 1.6 Hz, 1H), 4.36 (td, J = 8.1, 2.5 Hz, 1H), 3.99 (q, J = 8.3 Hz, 1H), 3.82 (s, 3H), 3.05 (d, J = 11.3 Hz, 2H), 2.82-2.49 (m, 13H), 2.37-2.25 (m, 1H), 2.07 (dd, J = 14.4, 10.7 Hz, 2H), 1.73-1.59 (m, 2H), 1.08 (d, J = 6.5 Hz, 6H), ; 681.5 [M + H]⁺ | 1.16 |

TABLE 1-continued

| Example Compound | Structure | Name of Compound | ¹H NMR[[:]]; MS [M + H]⁺ | UPLC r.t. (min) |
|---|---|---|---|---|
| 644 | 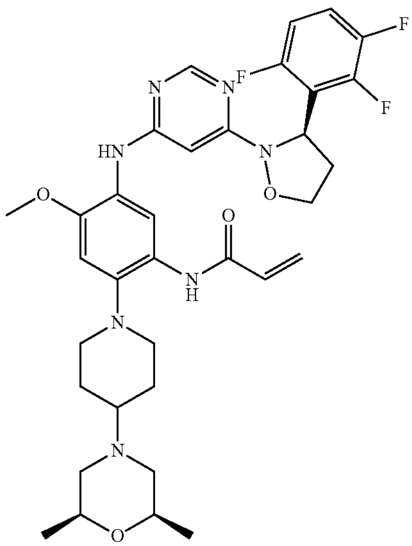 | N-(2-(4-((2S,6R)-2,6-dimethylmorpholino)piperidine-1-yl)-4-methoxy-5-((6-((R)-3-(2,3,6-trifluorophenyl)isoxazolidine-2-yl)pyrimidine-4-yl)amino)phenyl)acrylamide | ¹H NMR (400 MHz, Chloroform-d) δ 8.84 (s, 1H), 8.41 (s, 1H), 8.36 (d, J = 1.0 Hz, 1H), 7.12-6.99 (m, 1H), 6.89 (s, 1H), 6.88-6.78 (m, 1H), 6.74 (s, 1H), 6.63 (s, 1H), 6.37 (dd, J = 16.9, 1.5 Hz, 1H), 6.25 (dd, J = 16.9, 10.0 Hz, 1H), 5.90 (dd, J = 9.1, 6.6 Hz, 1H), 5.74 (dd, J = 10.0, 1.5 Hz, 1H), 4.36 (td, J = 8.1, 2.5 Hz, 1H), 3.99 (q, J = 8.5 Hz, 1H), 3.83 (s, 3H), 3.77-3.65 (m, 2H), 3.10-3.02 (m, 2H), 2.88 (d, J = 10.8 Hz, 2H), 2.82-2.64 (m, 3H), 2.63-2.49 (m, 1H), 2.35-2.23 (m, 1H), 2.10-2.02 (m, 2H), 1.90 (t, J = 10.6 Hz, 2H), 1.73-1.58 (m, 2H), 1.20 (d, J = 6.3 Hz, 6H), ; 668.5 [M + H]⁺ | 1.25 |
| 645 | 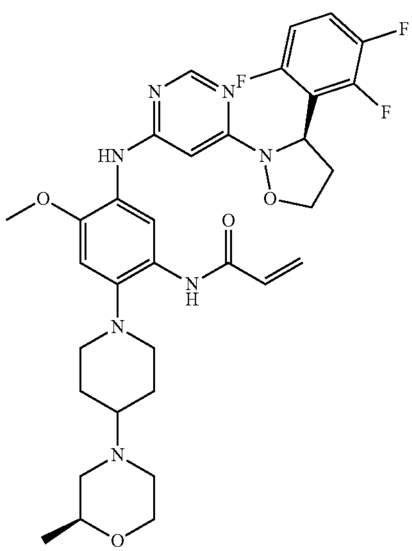 | N-(4-methoxy-2-(4-((S)-2-methylmorpholino)piperidine-1-yl)-5-((6-((R)-3-(2,3,6-trifluorophenyl)isoxazolidine-2-yl)pyrimidine-4-yl)amino)phenyl)acrylamide | ¹H NMR (400 MHz, Chloroform-d) δ 8.84 (s, 1H), 8.42 (s, 1H), 8.36 (d, J = 1.1 Hz, 1H), 7.12-6.99 (m, 1H), 6.88-6.78 (m, 2H), 6.74 (s, 1H), 6.63 (s, 1H), 6.36 (dd, J = 16.9, 1.5 Hz, 1H), 6.25 (dd, J = 16.9, 10.1 Hz, 1H), 5.90 (dd, J = 9.1, 6.6 Hz, 1H), 5.74 (dd, J = 10.1, 1.5 Hz, 1H), 4.41-4.32 (m, 1H), 4.04-3.86 (m, 2H), 3.83 (s, 3H), 3.76-3.60 (m, 2H), 3.10-3.02 (m, 2H), 2.90 (d, J = 11.3 Hz, 1H), 2.84 (d, J = 11.3 Hz, 1H), 2.81-2.66 (m, 3H), 2.63-2.50 (m, 1H), 2.35-2.23 (m, 2H), 2.11-2.02 (m, 2H), 1.97 (t, J = 10.5 Hz, 1H), 1.72-1.60 (m, 2H), 1.19 (d, J = 6.3 Hz, 3H), ; 654.5 [M + H]⁺ | 1.21 |

TABLE 1-continued

| Example Compound | Structure | Name of Compound | $^1$H NMR[[:]]; MS [M + H]$^+$ | UPLC r.t. (min) |
|---|---|---|---|---|
| 646 | 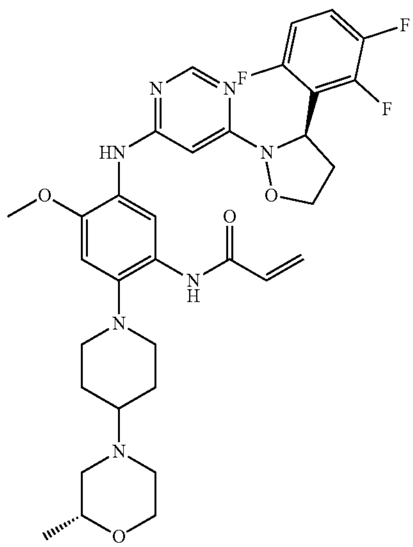 | N-(4-methoxy-2-(4-((R)-2-methylmorpholino)piperidine-1-yl)-5-((6-((R)-3-(2,3,6-trifluorophenyl)isoxazolidine-2-yl)pyrimidine-4-yl)amino)phenyl)acrylamide | $^1$H NMR (400 MHz, Chloroform-d) δ 8.84 (s, 1H), 8.42 (s, 1H), 8.36 (d, J = 1.0 Hz, 1H), 7.12-6.99 (m, 1H), 6.89 (s, 1H), 6.88-6.78 (m, 1H), 6.74 (s, 1H), 6.63 (s, 1H), 6.36 (dd, J = 16.9, 1.6 Hz, 1H), 6.25 (dd, J = 16.9, 10.0 Hz, 1H), 5.90 (dd, J = 9.1, 6.6 Hz, 1H), 5.74 (dd, J = 10.0, 1.5 Hz, 1H), 4.41-4.32 (m, 1H), 4.04-3.86 (m, 2H), 3.83 (s, 3H), 3.74-3.62 (m, 2H), 3.10-3.02 (m, 2H), 2.91 (d, 1H), 2.84 (d, J = 11.2 Hz, 1H), 2.81-2.65 (m, 3H), 2.63-2.50 (m, 1H), 2.35-2.24 (m, 2H), 2.11-2.02 (m, 2H), 1.97 (t, J = 10.5 Hz, 1H), 1.73-1.58 (m, 2H), 1.19 (d, J = 6.3 Hz, 3H), ; 654.5 [M + H]$^+$ | 1.22 |
| 647 | 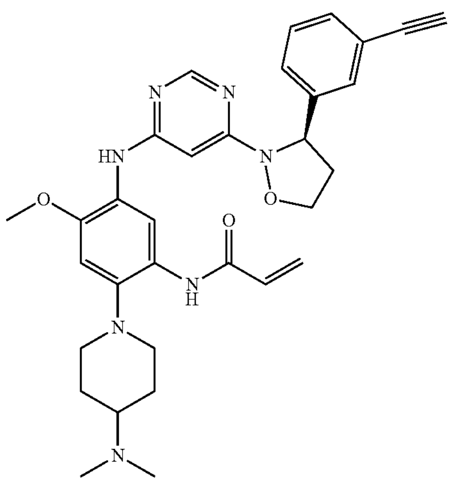 | N-(2-(4-(dimethylamino)piperidine-1-yl)-5-((6-((R)-3-(3-ethynylphenyl)isoxazolidine-2-yl)pyrimidine-4-yl)amino)-4-methoxyphenyl)acrylamide | $^1$H NMR (400 MHz, Chloroform-d) δ 8.87 (s, 1H), 8.49 (s, 1H), 8.40-8.33 (m, 1H), 7.61 (d, J = 1.8 Hz, 1H), 7.46 (dt, J = 7.6, 1.6 Hz, 1H), 7.37 (dt, J = 7.7, 1.5 Hz, 1H), 7.30 (d, J = 7.7 Hz, 1H), 6.96 (s, 1H), 6.75 (s, 1H), 6.70 (s, 1H), 6.35 (dd, J = 17.1, 1.7 Hz, 1H), 6.25 (dd, J = 17.0, 9.9 Hz, 1H), 5.73 (dd, J = 9.9, 1.7 Hz, 1H), 5.67 (dd, J = 8.7, 4.5 Hz, 1H), 4.15 (td, J = 7.9, 4.3 Hz, 1H), 4.06 (q, J = 8.0 Hz, 1H), 3.84 (s, 3H), 3.09-3.00 (m, 3H), 2.74 (tt, J = 12.3, 7.1 Hz, 4H), 2.36 (s, 6H), 2.34-2.29 (m, 1H), 2.05 (d, J = 12.8 Hz, 2H), 1.64 (td, J = 12.1, 3.7 Hz, 2H), ; 568.4 [M + H]$^+$ | 1.18 |
| 648 | 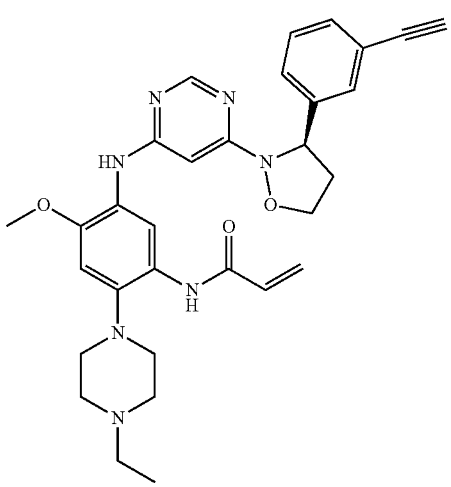 | N-(2-(4-ethylpiperazine-1-yl)-5-((6-((R)-3-(3-ethynylphenyl)isoxazolidine-2-yl)pyrimidine-4-yl)amino)-4-methoxyphenyl)acrylamide | $^1$H NMR (400 MHz, Chloroform-d) δ 8.91 (s, 1H), 8.56 (s, 1H), 8.37 (s, 1H), 7.61 (d, J = 1.8 Hz, 1H), 7.46 (dd, J = 7.8, 1.6 Hz, 1H), 7.37 (dd, J = 7.6, 1.5 Hz, 1H), 7.32-7.27 (m, 1H), 7.01 (d, J = 3.8 Hz, 1H), 6.81 (s, 1H), 6.70 (s, 1H), 6.36 (dd, J = 16.9, 1.7 Hz, 1H), 6.27 (dd, J = 17.0, 10.0 Hz, 1H), 5.74 (dd, J = 9.9, 1.7 Hz, 1H), 5.68 (dd, J = 8.7, 4.5 Hz, 1H), 4.15 (td, J = 8.0, 4.3 Hz, 1H), 4.06 (q, J = 8.0 Hz, 1H), 3.82 (s, 3H), 3.05 (s, 1H), 2.94 (t, J = 5.0 Hz, 4H), 2.79-2.73 (m, 1H), 2.74-2.54 (m, 4H), 2.52 (q, J = 7.2 Hz, 2H), 2.35 (dtd, J = 12.4, 8.1, 4.5 Hz, 1H), 1.15 (t, J = 7.2 Hz, 3H); 554.4 [M + H]$^+$ | 1.17 |

TABLE 1-continued

| Example Compound | Structure | Name of Compound | ¹H NMR[[:]]; MS [M + H]⁺ | UPLC r.t. (min) |
|---|---|---|---|---|
| 649 | 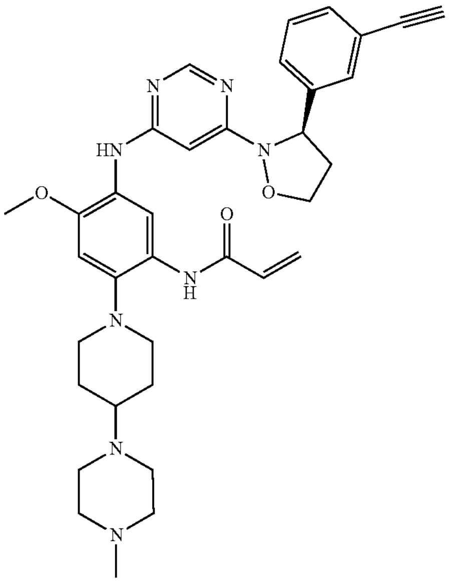 | N-(5-((6-((R)-3-(3-ethynylphenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, Chloroform-d) δ 8.87 (s, 1H), 8.46 (s, 1H), 8.36 (s, 1H), 7.61 (d, J = 1.8 Hz, 1H), 7.46 (dt, J = 7.8, 1.6 Hz, 1H), 7.37 (dt, J = 7.8, 1.5 Hz, 1H), 7.31-7.27 (m, 1H), 7.02 (s, 1H), 6.75 (s, 1H), 6.69 (s, 1H), 6.38-6.32 (m, 1H), 6.25 (dd, J = 16.9, 9.9 Hz, 1H), 5.75-5.71 (m, 1H), 5.67 (dd, J = 8.7, 4.5 Hz, 1H), 4.14 (td, J = 7.9, 4.3 Hz, 1H), 4.06 (q, J = 8.0 Hz, 1H), 3.83 (s, 3H), 3.05 (d, J = 6.6 Hz, 3H), 2.83-2.59 (m, 7H), 2.51 (s, 4H), 2.36 (d, J = 4.3 Hz, 1H), 2.32 (d, J = 2.5 Hz, 3H), 2.30 (d, J = 6.5 Hz, 1H), 2.08 (d, J = 12.2 Hz, 2H), 1.66 (tt, J = 12.1, 7.2 Hz, 2H); 623.5 [M + H]⁺ | 1.10 |
| 650 | 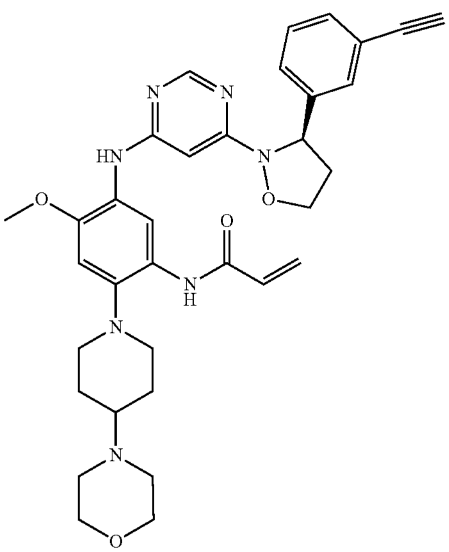 | N-(5-((6-((R)-3-(3-ethynylphenyl)isoxazolidine-2-yl)pyrimidine-4-yl)amino)-4-methoxy-2-(4-morpholinopiperidine-1-yl)phenyl)acrylamide | ¹H NMR (400 MHz, Chloroform-d) δ 8.87 (s, 1H), 8.44 (s, 1H), 8.36 (d, J = 1.0 Hz, 1H), 7.60 (d, J = 1.8 Hz, 1H), 7.46 (dt, J = 7.8, 1.7 Hz, 1H), 7.37 (dt, J = 7.7, 1.5 Hz, 1H), 7.29 (t, J = 7.7 Hz, 1H), 6.98 (s, 1H), 6.75 (s, 1H), 6.69 (s, 1H), 6.36 (dd, J = 17.0, 1.5 Hz, 1H), 6.25 (dd, J = 16.9, 10.0 Hz, 1H), 5.74 (dd, J = 10.0, 1.6 Hz, 1H), 5.67 (dd, J = 8.7, 4.5 Hz, 1H), 4.15 (td, J = 8.0, 4.3 Hz, 1H), 4.06 (q, J = 8.0 Hz, 1H), 3.84 (s, 3H), 3.77 (t, J = 4.6 Hz, 4H), 3.13-2.99 (m, 3H), 2.81-2.67 (m, 3H), 2.66-2.57 (m, 4H), 2.41-2.25 (m, 2H), 2.07 (d, J = 12.5 Hz, 2H), 1.65 (qd, J = 12.0, 3.9 Hz, 2H); 610.5 [M + H]⁺ | 1.19 |

649

650

TABLE 1-continued

| Example Compound | Structure | Name of Compound | ¹H NMR[[:]]; MS [M + H]⁺ | UPLC r.t. (min) |
|---|---|---|---|---|
| 651 | 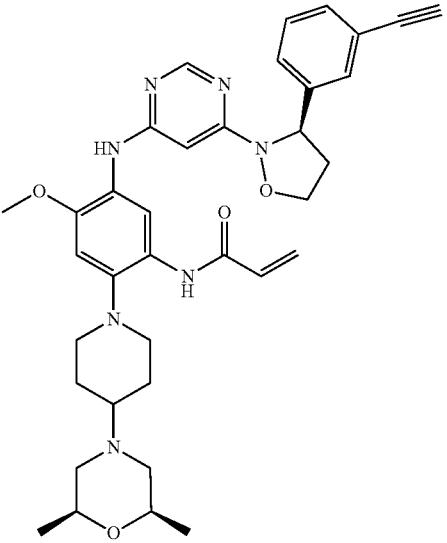 | N-(2-(4-((2S,6R)-2,6-dimethylmorpholino)piperidine-1-yl)-5-((6-((R)-3-(3-ethynylphenyl)isoxazolidine-2-yl)pyrimidine-4-yl)amino)-4-methoxyphenyl)acrylamide | ¹H NMR (400 MHz, Methanol-d₄) δ 8.18 (s, 1H), 7.94 (s, 1H), 7.46 (s, 1H), 7.39-7.36 (m, 2H), 6.94 (s, 1H), 6.60 (dd, J = 16.9, 10.2 Hz, 1H), 6.40 (dd, J = 16.9, 1.3 Hz, 1H), 5.96 (s, 1H), 5.86-5.80 (m, 1H), 5.52-5.45 (m, 1H), 4.43 (td, J = 7.6, 4.3 Hz, 1H), 4.18 (dd, J = 15.0, 8.2 Hz, 1H), 4.00 (s, 2H), 3.84 (s, 3H), 3.58 (t, J = 5.8 Hz, 3H), 3.33 (dt, J = 3.2, 1.6 Hz, 5H), 3.08-2.98 (m, 1H), 2.90-2.75 (m, 4H), 2.45 (dt, J = 13.0, 7.2 Hz, 1H), 2.29 (d, J = 11.2 Hz, 2H), 2.12-2.03 (m, 2H), 1.30 (d, J = 6.3 Hz, 6H); 638.5 [M + H]⁺ | 1.19 |
| 652 | 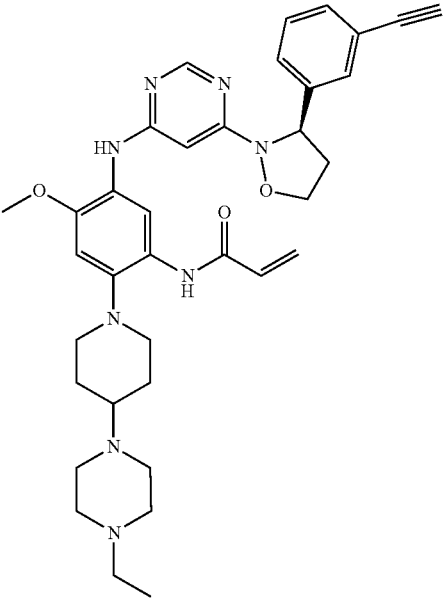 | N-(2-(4-(4-ethylpiperazine-1-yl)piperidine-1-yl)-5-((6-((R)-3-(3-ethynylphenyl)isoxazolidine-2-yl)pyrimidine-4-yl)amino)-4-methoxyphenyl)acrylamide | ¹H NMR (400 MHz, Methanol-d₄) δ 7.97 (s, 1H), 7.46 (s, 1H), 7.42-7.33 (m, 3H), 6.93 (s, 1H), 6.59 (dd, J = 16.9, 10.2 Hz, 1H), 6.39 (dd, J = 17.0, 1.1 Hz, 1H), 5.82 (d, J = 11.1 Hz, 1H), 5.50 (d, J = 4.5 Hz, 1H), 4.41 (s, 1H), 4.17 (s, 1H), 3.84 (s, 2H), 3.56 (s, 1H), 3.35-3.30 (m, 5H), 3.24 (dd, J = 14.6, 7.4 Hz, 3H), 2.87 (q, J = 11.1 Hz, 2H), 2.44 (s, 1H), 2.17 (d, J = 11.2 Hz, 2H), 2.01 (s, 2H), 1.37 (t, J = 7.2 Hz, 3H); 637.5 [M + H]⁺ | 1.11 |

TABLE 1-continued

| Example Compound | Structure | Name of Compound | ¹H NMR[[:]]; MS [M + H]⁺ | UPLC r.t. (min) |
|---|---|---|---|---|
| 653 | 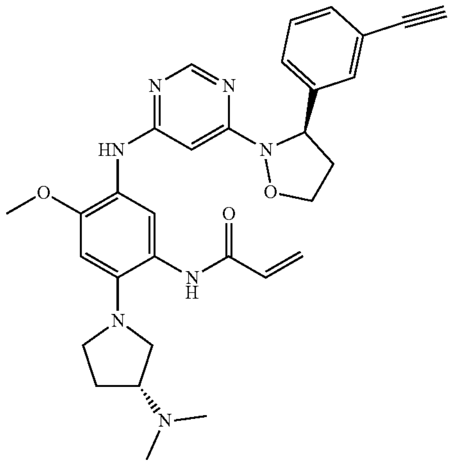 | N-(2-((R)-3-(dimethylamino)pyrolidine-1-yl)-5-((6-((R)-3-(3-ethynylphenyl)isoxazolidine-2-yl)pyrimidine-4-yl)amino)-4-methoxyphenyl)acrylamide | ¹H NMR (400 MHz, Methanol-$d_4$) δ 8.16 (s, 1H), 7.84 (s, 1H), 7.55 (s, 1H), 7.45 (d, J = 7.3 Hz, 1H), 7.37-7.33 (m, 2H), 6.75 (s, 1H), 6.55 (dd, J = 17.0, 10.2 Hz, 1H), 6.41-6.34 (m, 2H), 5.81 (dd, J = 10.2, 1.2 Hz, 1H), 5.53 (dd, J = 8.5, 4.8 Hz, 1H), 4.15 (td, J = 7.8, 4.3 Hz, 1H), 4.00-3.91 (m, 2H), 3.89 (s, 3H), 3.56-3.39 (m, 4H), 3.33 (dd, J = 3.2, 1.6 Hz, 3H), 3.23 (dd, J = 16.7, 8.0 Hz, 1H), 2.94 (s, 6H), 2.80 (tdd, J = 13.8, 9.0, 5.1 Hz, 1H), 2.47 (dtd, J = 11.6, 7.7, 3.7 Hz, 1H), 2.38-2.28 (m, 1H), 2.21 (dt, J = 14.7, 8.0 Hz, 1H); 554.4 [M + H]⁺ | 1.11 |
| 654 | 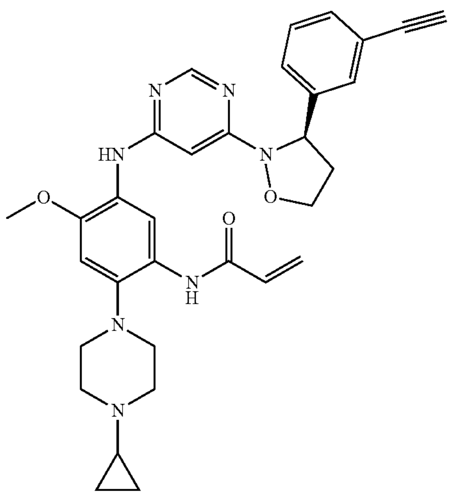 | N-(2-(4-cyclopropylpiperazine-1-yl)-5-((6-((R)-3-(3-ethynylphenyl)isoxazolidine-2-yl)pyrimidine-4-yl)amino)-4-methoxyphenyl)acrylamide | ¹H NMR (400 MHz, DMSO-$d_6$) δ 10.09 (s, 1H), 9.27 (s, 1H), 8.31 (s, 1H), 8.01 (s, 1H), 7.46 (s, 1H), 7.40 (d, J = 1.3 Hz, 3H), 6.84 (d, J = 5.9 Hz, 2H), 6.25 (dd, J = 16.9, 2.0 Hz, 1H), 6.08 (s, 1H), 5.78-5.74 (m, 1H), 5.52 (dd, J = 8.5, 5.5 Hz, 1H), 4.31 (d, J = 4.3 Hz, 1H), 4.26 (s, 1H), 4.05 (d, J = 7.8 Hz, 1H), 3.80 (s, 3H), 3.56 (t, J = 16.1 Hz, 4H), 3.25 (t, J = 7.9 Hz, 4H), 2.92 (td, J = 7.8, 4.2 Hz, 2H), 2.36-2.27 (m, 1H), 1.28-1.19 (m, 2H), 0.83 (d, J = 7.0 Hz, 2H), ; 566.3 [M + H]⁺ | 1.19 |
| 655 | 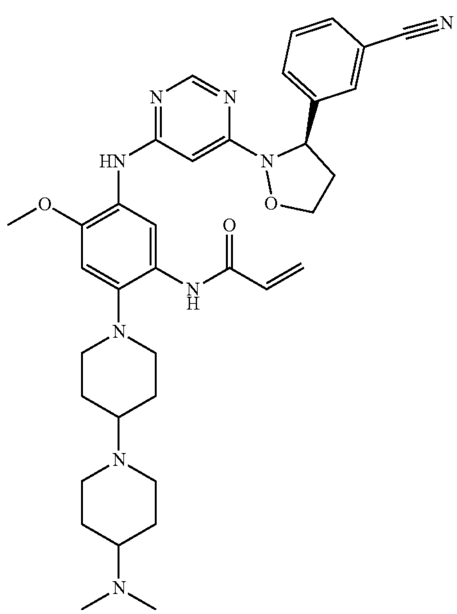 [SMILES: C=CC(=O)Nc1cc(Nc2cc(N3OCC[C@@H]3c3cccc(C#N)c3)ncn2)c(OC)cc1N1CCC(N2CCC(N(C)C)CC2)CC1] | N-(2-(4-(dimethylamino)-[1,4'-bipiperidine]-1'-yl)-5-((6-((R)-3-(3-ethynylphenyl)isoxazolidine-2-yl)pyrimidine-4-yl)amino)-4-methoxyphenyl)acrylamide | ¹H NMR (400 MHz, DMSO-$d_6$) δ 10.39 (s, 1H), 9.33 (s, 1H), 8.34 (s, 1H), 7.86 (s, 1H), 7.45 (s, 1H), 7.40 (s, 3H), 6.92 (s, 1H), 6.79 (dd, J = 16.9, 10.2 Hz, 1H), 6.26 (dd, J = 17.0, 1.9 Hz, 1H), 6.07 (s, 1H), 5.76 (dd, J = 8.7, 3.0 Hz, 1H), 5.53 (d, J = 2.9 Hz, 1H), 4.33 (d, J = 4.4 Hz, 1H), 4.25 (s, 1H), 4.08 (d, J = 7.7 Hz, 1H), 3.81 (s, 3H), 3.62 (d, J = 11.5 Hz, 2H), 3.53 (s, 1H), 3.37 (s, 1H), 3.25 (d, J = 11.1 Hz, 2H), 3.16 (d, J = 7.5 Hz, 2H), 3.00-2.93 (m, 1H), 2.85 (d, J = 11.9 Hz, 2H), 2.71 (d, J = 4.8 Hz, 6H), 2.35-2.27 (m, 5H), 2.22-2.08 (m, 4H), ; 651.4 [M + H]⁺ | 1.04 |

TABLE 1-continued

| Example Compound | Structure | Name of Compound | ¹H NMR[[:]]; MS [M + H]⁺ | UPLC r.t. (min) |
|---|---|---|---|---|
| 656 | 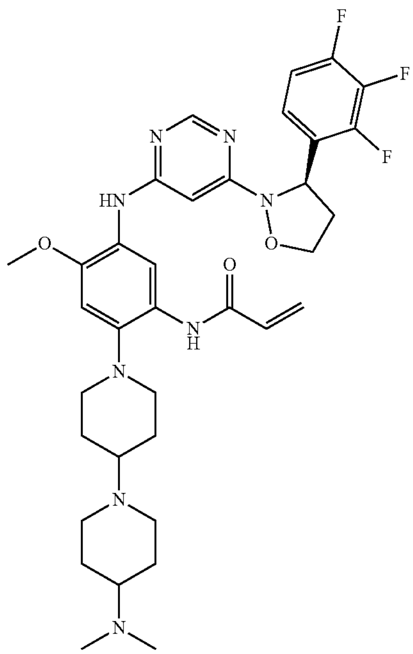 [SMILES: C=CC(=O)Nc1cc(Nc2cc(N3OCC[C@@H]3c3ccc(F)c(F)c3F)ncn2)c(OC)cc1N1CCC(N2CCC(N(C)C)CC2)CC1] | N-(2-(4-(dimethylamino)-[1,4'-bipiperidine]-1'-yl)-4-methoxy-5-((6-((R)-3-(2,3,4-trifluorophenyl)isoxazolidine-2-yl)pyrimidine-4-yl)amino)phenyl)acrylamide | ¹H NMR (400 MHz, DMSO-d₆) δ 10.22 (s, 1H), 9.27 (s, 1H), 8.34 (s, 1H), 7.89 (s, 1H), 7.32 (ddd, J = 9.6, 7.2, 1.9 Hz, 1H), 7.24 (t, J = 6.8 Hz, 1H), 6.92 (s, 1H), 6.79-6.72 (m, 1H), 6.25 (dd, J = 17.0, 1.9 Hz, 1H), 6.18 (s, 1H), 5.76 (dd, J = 10.1, 2.0 Hz, 1H), 5.70 (dd, J = 8.6, 5.6 Hz, 1H), 4.32 (dd, J = 7.7, 4.0 Hz, 1H), 4.06 (d, J = 8.0 Hz, 1H), 3.82 (s, 3H), 3.62 (d, J = 11.7 Hz, 2H), 3.51 (s, 1H), 3.36 (s, 1H), 3.24 (d, J = 11.2 Hz, 2H), 3.17-3.09 (m, 2H), 2.96 (d, J = 3.8 Hz, 1H), 2.85-2.78 (m, 2H), 2.71 (d, J = 4.8 Hz, 6H), 2.35-2.28 (m, 5H), 2.17 (s, 2H), 2.09 (d, J = 11.6 Hz, 2H), ; 681.3 [M + H]⁺ | 1.12 |
| 657 | 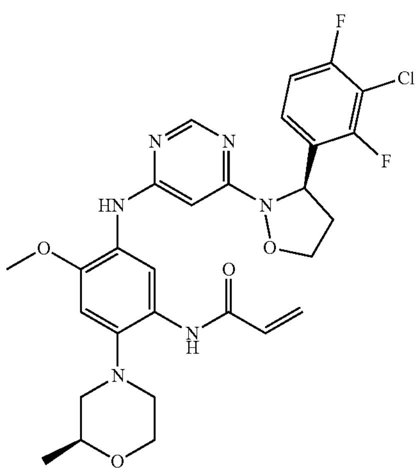 [SMILES: C=CC(=O)Nc1cc(Nc2cc(N3OCC[C@@H]3c3ccc(F)c(Cl)c3F)ncn2)c(OC)cc1N1CCO[C@@H](C)C1] | N-(5-((6-((R)-3-(3-chloro-2,4-difluorophenyl)isoxazolidine-2-yl)pyrimidine-4-yl)amino)-4-methoxy-2-((S)-2-methylmorpholino)phenyl)acrylamide | ¹H NMR (400 MHz, DMSO-d₆) δ 9.11 (s, 1H), 8.24 (d, J = 4.1 Hz, 1H), 8.05 (s, 1H), 7.45 (q, J = 7.8 Hz, 1H), 7.32 (td, J = 8.8, 1.7 Hz, 1H), 6.89 (s, 1H), 6.63 (dd, J = 16.9, 10.2 Hz, 1H), 6.29-6.17 (m, 2H), 5.71 (ddd, J = 14.9, 9.4, 3.6 Hz, 2H), 4.24 (dd, J = 7.9, 4.2 Hz, 1H), 3.96 (d, J = 8.2 Hz, 1H), 3.90-3.73 (m, 6H), 2.96-2.74 (m, 4H), 2.57-2.51 (m, 2H), 2.26 (dd, J = 12.7, 6.1 Hz, 1H), 1.11 (d, = 6.3 Hz, 3H), ; 587.3 [M + H]⁺ | 1.68 |

TABLE 1-continued

| Example Compound | Structure | Name of Compound | ¹H NMR[[:]]; MS [M + H]⁺ | UPLC r.t. (min) |
|---|---|---|---|---|
| 658 | 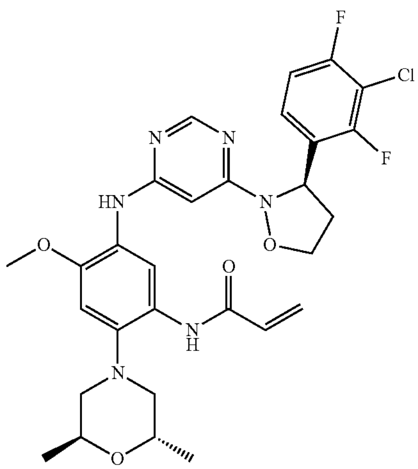 [SMILES: C=CC(=O)Nc1cc(Nc2cc(N3OCC[C@@H]3c3ccc(F)c(Cl)c3F)ncn2)c(OC)cc1N1C[C@H](C)O[C@@H](C)C1] | N-(5-((6-((R)-3-(3-chloro-2,4-difluorophenyl)isoxazolidine-2-yl)pyrimidine-4-yl)amino)-2-((2S,6S)-2,6-dimethylmorpholino)-4-methoxyphenyl)acrylamide | $^1$H NMR (400 MHz, DMSO-d$_6$) δ 9.06 (s, 1H), 8.24 (s, 1H), 7.91 (s, 1H), 7.45 (td, J = 8.5, 6.1 Hz, 1H), 7.32 (td, J = 8.8, 1.6 Hz, 1H), 6.86 (s, 1H), 6.51 (dd, J = 17.0, 10.2 Hz, 1H), 6.31-6.13 (m, 2H), 5.72 (ddd, J = 20.1, 9.4, 3.7 Hz, 2H), 4.25 (td, J = 7.8, 3.8 Hz, 1H), 4.06 (tt, J = 9.7, 4.7 Hz, 2H), 3.96 (dp, J = 8.1, 4.4, 3.9 Hz, 1H), 3.82 (s, 3H), 2.85 (dt, J = 11.5, 5.6 Hz, 4H), 2.64 (dd, J = 11.4, 5.7 Hz, 2H), 2.34-2.18 (m, 1H), 1.26 (d, J = 6.4 Hz, 6H), ; 601.4 [M + H]⁺ | 1.72 |
| 659 | 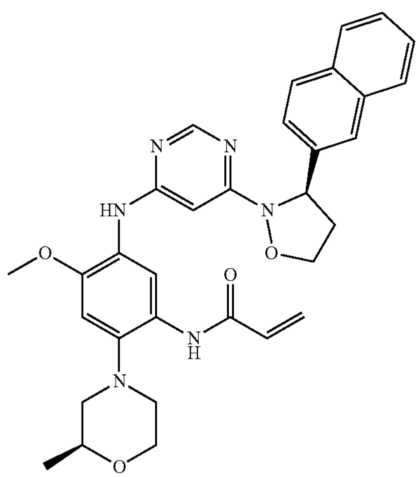 [SMILES: C=CC(=O)Nc1cc(Nc2cc(N3OCC[C@@H]3c3ccc4ccccc4c3)ncn2)c(OC)cc1N1CCO[C@@H](C)C1] | N-(4-methoxy-2-((S)-2-methylmorpholino)-5-((6-((R)-3-(naphthalene-2-yl)isoxazolidine-2-yl)pyrimidine-4-yl)amino)phenyl)acrylamide | $^1$H NMR (400 MHz, DMSO-d$_6$) δ 9.12 (s, 1H), 8.25 (d, J = 3.7 Hz, 1H), 8.02 (s, 1H), 7.97-7.85 (m, 4H), 7.52 (td, J = 6.3, 5.7, 3.4 Hz, 3H), 6.87 (s, 1H), 6.64 (dd, J = 17.0, 10.2 Hz, 1H), 6.28-6.13 (m, 2H), 5.71 (ddd, J = 27.0, 9.4, 3.7 Hz, 2H), 4.32 (td, J = 7.6, 4.0 Hz, 1H), 4.04 (d, J = 7.9 Hz, 1H), 3.85 (td, J = 8.9, 8.1, 3.2 Hz, 2H), 3.79 (s, 4H), 3.00-2.72 (m, 4H), 2.60-2.51 (m, 2H), 2.39 (dq, J = 8.6, 5.1, 3.8 Hz, 1H), 1.12 (d, J = 6.3 Hz, 3H), ; 567.4 [M + H]⁺ | 1.56 |
| 660 | 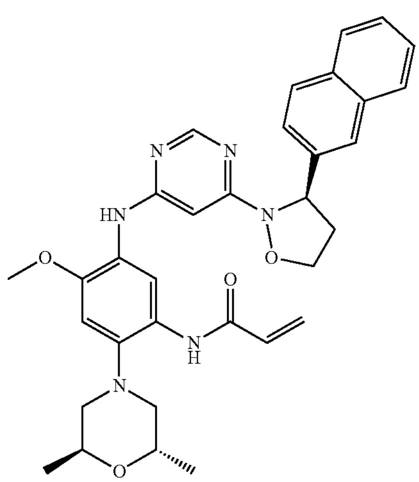 [SMILES: C=CC(=O)Nc1cc(Nc2cc(N3OCC[C@@H]3c3ccc4ccccc4c3)ncn2)c(OC)cc1N1C[C@H](C)O[C@@H](C)C1] | N-(2-((2S,6S)-2,6-dimethylmorpholino)-4-methoxy-5-((6-((R)-3-(naphthalene-2-yl)isoxazolidine-2-yl)pyrimidine-4-yl)amino)phenyl)acrylamide | $^1$H NMR (400 MHz, DMSO-d$_6$) δ 9.06 (s, 1H), 8.25 (s, 1H), 7.91 (dd, J = 15.3, 7.8 Hz, 5H), 7.52 (ddt, J = 10.7, 6.9, 3.4 Hz, 3H), 6.85 (d, J = 2.6 Hz, 1H), 6.51 (dd, J = 17.0, 10.2 Hz, 1H), 6.30-6.13 (m, 2H), 5.71 (ddd, J = 29.8, 9.4, 3.8 Hz, 2H), 4.37-4.25 (m, 1H), 4.12-3.95 (m, 4H), 3.79 (d, J = 2.8 Hz, 3H), 2.94 (d, J = 9.5 Hz, 1H), 2.84 (dd, J = 11.6, 3.1 Hz, 2H), 2.64 (dd, J = 11.4, 5.6 Hz, 2H), 2.39 (dt, J = 13.0, 3.7 Hz, 1H), 1.27 (d, J = 6.4 Hz, 6H), ; 581.5 [M + H]⁺ | 1.59 |

| Example Compound | Structure | Name of Compound | ¹H NMR[[:]]; MS [M + H]⁺ | UPLC r.t. (min) |
|---|---|---|---|---|
| 661 | 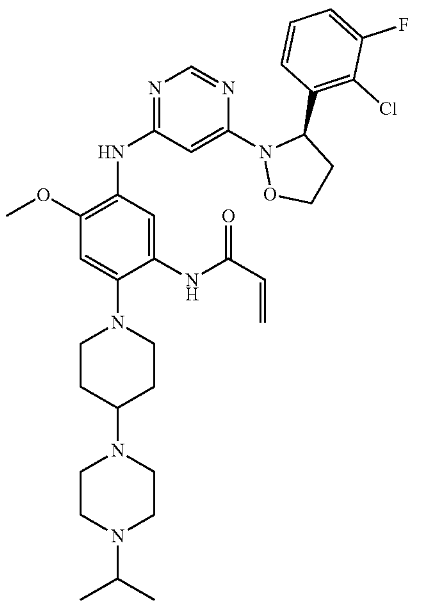 [SMILES: C=CC(=O)Nc1cc(Nc2cc(N3OCC[C@@H]3c3cccc(F)c3Cl)ncn2)c(OC)cc1N1CCC(N2CCN(C(C)C)CC2)CC1] | N-(5-((6-((R)-3-(2-chloro-3-fluorophenyl)isoxazolidine-2-yl)pyrimidine-4-yl)amino)-2-(4-(4-isopropylpiperazine-1-yl)piperidine-1-yl)-4-methoxyphenyl)acrylamide | ¹H NMR (400 MHz, Methanol-d₄) δ 8.15 (d, J = 1.1 Hz, 1H), 7.43 (d, J = 7.9 Hz, 1H), 7.30 (td, J = 8.1, 5.3 Hz, 1H), 7.20-7.10 (m, 1H), 6.84-6.70 (m, 1H), 6.54 (dd, J = 17.0, 10.3 Hz, 1H), 6.43-6.34 (m, 2H), 5.91-5.82 (m, 2H), 5.60 (ddd, J = 8.0, 5.6, 2.6 Hz, 1H), 4.12 (td, J = 8.0, 4.2 Hz, 1H), 3.85 (d, J = 12.7 Hz, 6H), 3.68 (s, 2H), 3.37 (dq, J = 6.4, 3.5 Hz, 2H), 3.17-3.11 (m, 4H), 2.99-2.93 (m, 4H), 2.57 (dt, J = 11.1, 7.3 Hz, 3H), 2.07-2.00 (m, 2H), 1.99-1.90 (m, 2H), 1.26 (d, J = 6.5 Hz, 6H), ; 679.5 [M + H]⁺ | 1.20 |
| 662 | 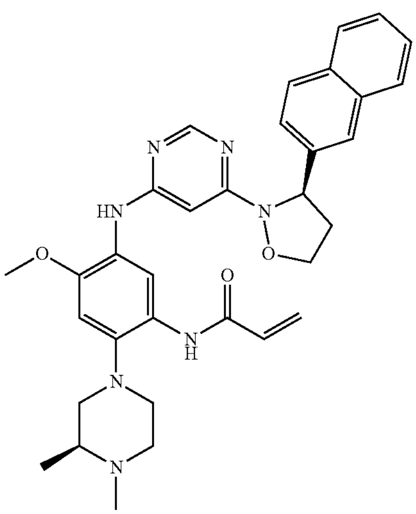 [SMILES: C=CC(=O)Nc1cc(Nc2cc(N3OCC[C@@H]3c3ccc4ccccc4c3)ncn2)c(OC)cc1N1CCN(C)[C@@H](C)C1] | N-(2-((S)-3,4-dimethylpiperazine-1-yl)-4-methoxy-5-((6-((R)-3-(naphthalene-2-yl)isoxazolidine-2-yl)pyrimidine-4-yl)amino)phenyl)acrylamide | ¹H NMR (400 MHz, DMSO-d₆) δ 9.02 (s, 1H), 8.64 (s, 1H), 8.18 (s, 1H), 7.95-7.85 (m, 4H), 7.57 (dd, J = 8.6, 1.7 Hz, 1H), 7.54-7.45 (m, 2H), 6.86 (s, 1H), 6.61 (dd, J = 17.0, 10.2 Hz, 1H), 6.43 (s, 1H), 6.23 (dd, J = 17.0, 2.0 Hz, 1H), 5.72 (ddd, J = 15.8, 9.3, 3.6 Hz, 2H), 4.20 (td, J = 7.8, 3.7 Hz, 1H), 3.86 (d, J = 24.8 Hz, 4H), 3.17 (s, 4H), 3.04 (s, 4H), 2.84 (dtd, J = 11.9, 7.9, 3.6 Hz, 2H), 2.41-2.29 (m, 1H), 1.91 (s, 2H), 1.21 (d, J = 20.2 Hz, 3H), ; 580.5 [M + H]⁺ | 1.23 |

TABLE 1-continued

| Example Compound | Structure | Name of Compound | $^1$H NMR[[:]]; MS [M + H]$^+$ | UPLC r.t. (min) |
|---|---|---|---|---|
| 663 | 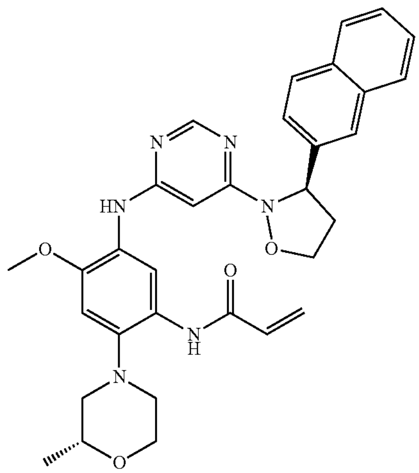 [SMILES: C=CC(=O)Nc1cc(Nc2cc(N3OCC[C@@H]3c3ccc4ccccc4c3)ncn2)c(OC)cc1N1CCO[C@H](C)C1] | N-(4-methoxy-2-((R)-2-methylmorpholino)-5-((6-((R)-3-(naphthalene-2-yl)isoxazolidine-2-yl)pyrimidine-4-yl)amino)phenyl) acrylamide | $^1$H NMR (400 MHz, DMSO-d$_6$) δ 9.07 (s, 1H), 8.61 (s, 1H), 8.19 (d, J = 11.6 Hz, 2H), 7.96-7.85 (m, 4H), 7.57 (dd, J = 8.6, 1.7 Hz, 1H), 7.49 (ddt, J = 9.6, 7.1, 3.5 Hz, 2H), 6.86 (s, 1H), 6.62 (dd, J = 17.0, 10.2 Hz, 1H), 6.41 (s, 1H), 6.21 (dd, J = 16.9, 2.0 Hz, 1H), 5.71 (td, J = 8.9, 8.1, 3.4 Hz, 2H), 4.19 (td, J = 7.9, 3.8 Hz, 1H), 3.98-3.72 (m, 7H), 2.94-2.74 (m, 4H), 2.34 (dtd, J = 12.9, 8.2, 5.0 Hz, 1H), 1.91 (s, 1H), 1.11 (d, J = 6.3 Hz, 3H), ; 567.4 [M + H]$^+$ | 1.54 |
| 664 | 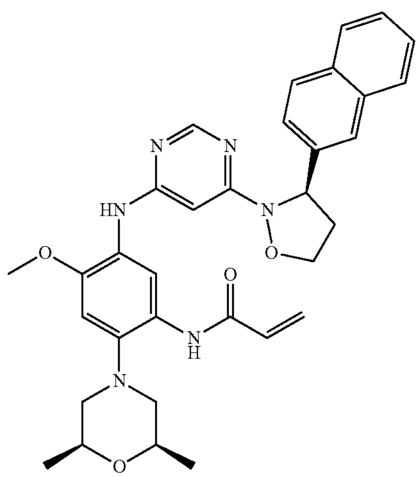 [SMILES: C=CC(=O)Nc1cc(Nc2cc(N3OCC[C@@H]3c3ccc4ccccc4c3)ncn2)c(OC)cc1N1C[C@@H](C)O[C@@H](C)C1] | N-(2-((2S,6R)-2,6-dimethylmorpholino)-4-methoxy-5-((6-((R)-3-(naphthalene-2-yl)isoxazolidine-2-yl)pyrimidine-4-yl)amino)phenyl) acrylamide | $^1$H NMR (400 MHz, DMSO-d$_6$) δ 9.06 (s, 1H), 8.61 (s, 1H), 8.27-8.10 (m, 2H), 7.97-7.85 (m, 4H), 7.57 (dd, J = 8.6, 1.7 Hz, 1H), 7.54-7.44 (m, 2H), 6.86 (s, 1H), 6.61 (dd, J = 17.0, 10.2 Hz, 1H), 6.40 (s, 1H), 6.21 (dd, J = 16.9, 2.0 Hz, 1H), 5.80-5.63 (m, 2H), 4.19 (td, = 7.8, 3.8 Hz, 1H), 3.90-3.80 (m, 5H), 2.94-2.77 (m, 3H), 2.48-2.27 (m, 3H), 1.86 (s, 1H), 1.10 (d, J = 6.2 Hz, 6H), ; 581.4 [M + H]$^+$ | 1.60 |
| 665 | 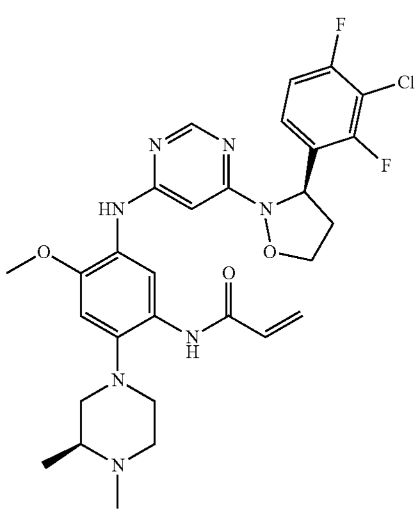 [SMILES: C=CC(=O)Nc1cc(Nc2cc(N3OCC[C@@H]3c3ccc(F)c(Cl)c3F)ncn2)c(OC)cc1N1CCN(C)[C@@H](C)C1] | N-(5-((6-((R)-3-(3-chloro-2,4-difluorophenyl)isoxazolidine-2-yl)pyrimidine-4-yl)amino)-2-((S)-3,4-dimethylpiperazine-1-yl)-4-methoxyphenyl) acrylamide | $^1$H NMR (400 MHz, DMSO-d$_6$) δ 9.05 (s, 1H), 8.82 (s, 1H), 8.27 (s, 1H), 8.19 (s, 1H), 7.48 (q, J = 7.9 Hz, 1H), 7.31 (t, J = 8.8 Hz, 1H), 6.85 (s, 1H), 6.63 (dd, J = 16.9, 10.3 Hz, 1H), 6.40 (s, 1H), 6.24 (d, J = 16.9 Hz, 1H), 5.79-5.66 (m, 2H), 4.19 (dd, J = 8.0, 3.7 Hz, 1H), 3.90 (t, J = 8.0 Hz, 1H), 3.83 (s, 3H), 3.57 (d, J = 12.0 Hz, 1H), 3.47 (s, 1H), 3.38 (q, J = 7.8, 7.3 Hz, 1H), 3.26-3.15 (m, 2H), 3.02 (t, J = 11.9 Hz, 1H), 2.90 (d, J = 4.2 Hz, 3H), 2.83 (q, J = 9.8, 9.4 Hz, 2H), 2.23 (dq, J = 13.4, 7.7 Hz, 1H), 1.32 (d, J = 6.5 Hz, 3H), ; 600.4 [M + H]$^+$ | 1.35 |

TABLE 1-continued

| Example Compound | Structure | Name of Compound | ¹H NMR[:]; MS [M + H]⁺ | UPLC r.t. (min) |
|---|---|---|---|---|
| 666 | 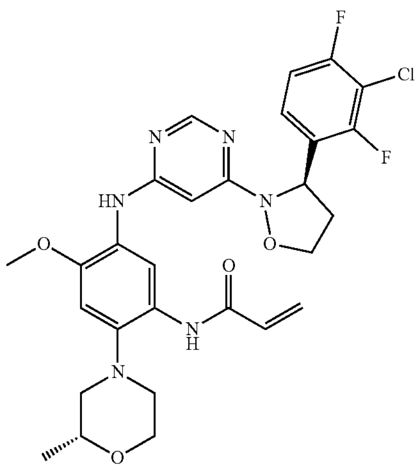 [SMILES: C=CC(=O)Nc1cc(Nc2cc(N3OCC[C@@H]3c3ccc(F)c(Cl)c3F)ncn2)c(OC)cc1N1CCO[C@H](C)C1] | N-(5-((6-((R)-3-(3-chloro-2,4-difluorophenyl)isoxazolidine-2-yl)pyrimidine-4-yl)amino)-4-methoxy-2-((R)-2-methylmorpholino)phenyl)acrylamide | ¹H NMR (400 MHz, DMSO-d₆) δ 9.07 (s, 1H), 8.80 (s, 1H), 8.17 (d, J = 14.1 Hz, 2H), 7.48 (q, J = 8.0 Hz, 1H), 7.31 (t, J = 8.8 Hz, 1H), 6.87 (s, 1H), 6.62 (dd, J = 17.1, 10.2 Hz, 1H), 6.36 (s, 1H), 6.21 (d, J = 17.3 Hz, 1H), 5.71 (t, J = 9.4 Hz, 2H), 4.19 (td, J = 8.0, 3.6 Hz, 1H), 3.92-3.75 (m, 8H), 2.92-2.76 (m, 4H), 2.27-2.16 (m, 1H), 1.11 (d, J = 6.2 Hz, 3H), ; 587.4 [M + H]⁺ | 1.70 |
| 667 | 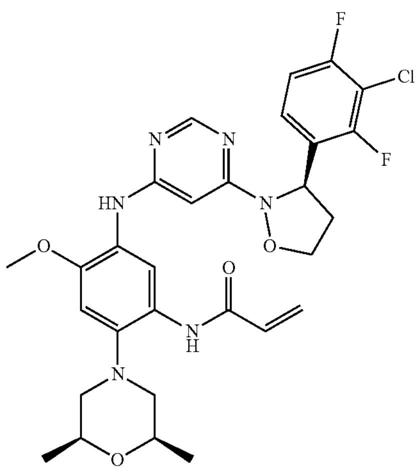 [SMILES: C=CC(=O)Nc1cc(Nc2cc(N3OCC[C@@H]3c3ccc(F)c(Cl)c3F)ncn2)c(OC)cc1N1C[C@@H](C)O[C@@H](C)C1] | N-(5-((6-((R)-3-(3-chloro-2,4-difluorophenyl)isoxazolidine-2-yl)pyrimidine-4-yl)amino)-2-((2S,6R)-2,6-dimethylmorpholino)-4-methoxyphenyl)acrylamide | ¹H NMR (400 MHz, DMSO-d₆) δ 9.05 (s, 1H), 8.66 (s, 1H), 8.18 (d, J = 7.0 Hz, 2H), 7.49 (td, J = 8.6, 6.2 Hz, 1H), 7.31 (td, J = 8.8, 1.7 Hz, 1H), 6.85 (s, 1H), 6.61 (dd, J = 17.0, 10.2 Hz, 1H), 6.38 (s, 1H), 6.20 (dd, J = 17.0, 2.0 Hz, 1H), 5.71 (dt, J = 8.4, 4.2 Hz, 2H), 4.17 (td, J = 8.0, 3.7 Hz, 1H), 3.87 (q, J = 6.8, 5.0 Hz, 3H), 3.81 (s, 3H), 2.87 (d, J = 11.2 Hz, 2H), 2.79 (qd, J = 8.2, 3.9 Hz, 1H), 2.42 (td, J = 10.7, 4.8 Hz, 2H), 2.20 (tt, J = 8.2, 4.9 Hz, 1H), 1.10 (d, J = 6.3 Hz, 6H), ; 601.4 [M + H]⁺ | 1.77 |

TABLE 1-continued

| Example Compound | Structure | Name of Compound | ¹H NMR[[:]]; MS [M + H]⁺ | UPLC r.t. (min) |
|---|---|---|---|---|
| 668 | 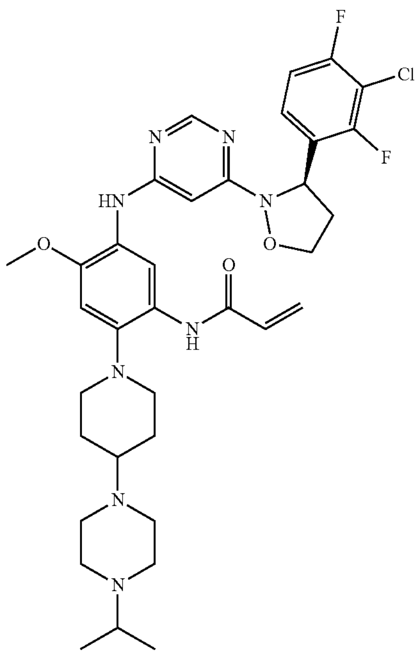 [SMILES: C=CC(=O)Nc1cc(Nc2cc(N3OCC[C@@H]3c3ccc(F)c(Cl)c3F)ncn2)c(OC)cc1N1CCC(N2CCN(C(C)C)CC2)CC1] | N-(5-((6-((R)-3-(3-chloro-2,4-difluorophenyl)isoxazolidine-2-yl)pyrimidine-4-yl)amino)-2-(4-(4-isopropylpiperazine-1-yl)piperidine-1-yl)-4-methoxyphenyl)acrylamide | ¹H NMR (400 MHz, DMSO-d₆) δ 8.98 (s, 1H), 8.66 (s, 1H), 8.16 (d, J = 3.7 Hz, 2H), 7.49 (td, J = 8.5, 6.2 Hz, 1H), 7.31 (t, J = 8.8 Hz, 1H), 6.82 (s, 1H), 6.64 (dd, J = 16.9, 10.3 Hz, 1H), 6.38 (s, 1H), 6.22 (d, J = 17.0 Hz, 1H), 5.72 (td, J = 10.6, 8.7, 6.1 Hz, 2H), 4.17 (q, J = 7.1, 6.4 Hz, 1H), 3.86 (q, J = 8.0 Hz, 2H), 3.80 (s, 3H), 3.42-3.35 (m, 2H), 3.14 (d, J = 25.2 Hz, 5H), 2.86-2.64 (m, 11H), 2.22 (dt, J = 9.3, 6.7 Hz, 2H), 1.75 (s, 5H), ; 697.5 [M + H]⁺ | 1.23 |
| 669 | 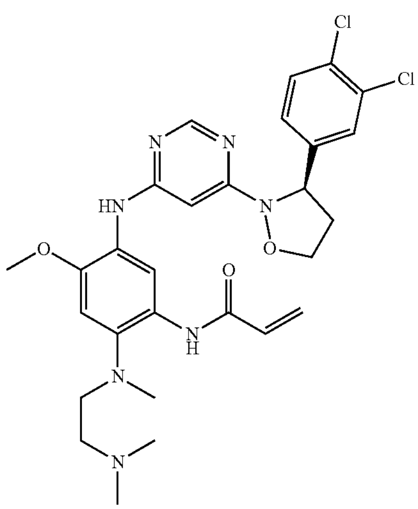 [SMILES: C=CC(=O)Nc1cc(Nc2cc(N3OCC[C@@H]3c3ccc(Cl)c(Cl)c3)ncn2)c(OC)cc1N(C)CCN(C)C] | N-(5-((6-((R)-3-(3,4-dichlorophenyl)isoxazolidine-2-yl)pyrimidine-4-yl)amino)-2-((2-(dimethylamino)ethyl)(methyl)amino)-4-methoxyphenyl)acrylamide | ¹H NMR (400 MHz, Chloroform-d) δ 12.67-12.39 (m, 1H), 9.46 (s, 1H), 8.89 (d, J = 12.7 Hz, 1H), 8.36 (d, J = 1.0 Hz, 1H), 7.59 (d, J = 2.1 Hz, 1H), 7.41 (d, J = 8.3 Hz, 1H), 7.30 (dd, J = 8.4, 2.1 Hz, 1H), 6.93 (s, 1H), 6.78 (s, 1H), 6.71 (s, 1H), 6.41 (d, J = 16.8 Hz, 1H), 5.71 (d, J = 10.2 Hz, 1H), 5.65 (dd, J = 8.6, 4.6 Hz, 1H), 4.17 (dd, J = 8.0, 4.2 Hz, 1H), 4.10 (q, J = 8.1 Hz, 1H), 3.85 (s, 3H), 3.36-3.23 (m, 2H), 3.12 (s, 2H), 2.79 (dt, J = 8.2, 3.9 Hz, 4H), 2.74 (s, 3H), 2.33 (dtd, J = 12.6, 8.2, 4.6 Hz, 4H), ; 586.3 [M + H]⁺ | 1.35 |

TABLE 1-continued

| Example Compound | Structure | Name of Compound | ¹H NMR[[:]]; MS [M + H]⁺ | UPLC r.t. (min) |
|---|---|---|---|---|
| 670 | 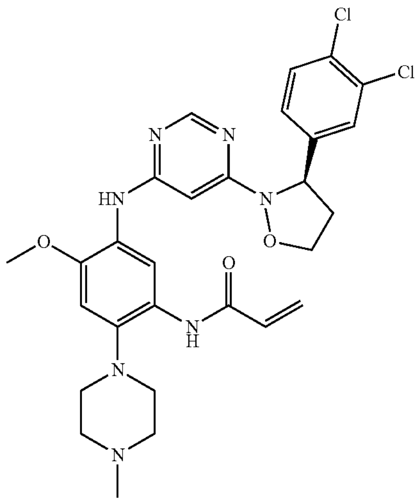 [SMILES: C=CC(=O)Nc1cc(Nc2cc(N3OCC[C@@H]3c3ccc(Cl)c(Cl)c3)ncn2)c(OC)cc1N1CCN(C)CC1] | N-(5-((6-((R)-3-(3,4-dichlorophenyl)isoxazolidine-2-yl)pyrimidine-4-yl)amino)-4-methoxy-2-(4-methylpiperazine-1-yl)phenyl)acrylamide | ¹H NMR (400 MHz, Chloroform-d) δ 8.92 (s, 1H), 8.37 (s, 1H), 8.33 (s, 1H), 7.57 (d, J = 2.1 Hz, 1H), 7.41 (d, J = 8.3 Hz, 1H), 7.30 (dd, J = 8.3, 2.1 Hz, 1H), 7.04-6.98 (m, 1H), 6.81 (s, 1H), 6.69 (s, 1H), 6.43-6.32 (m, 2H), 5.76 (dd, J = 9.6, 1.9 Hz, 1H), 5.64 (dd, J = 8.7, 4.7 Hz, 1H), 4.22-4.13 (m, 2H), 4.04 (q, J = 8.0 Hz, 2H), 3.87 (s, 3H), 3.70-3.60 (m, 4H), 3.13-3.02 (m, 5H), 2.33 (dt, J = 8.5, 4.5 Hz, 2H), ; 584.3 [M + H]⁺ | 1.31 |
| 671 | 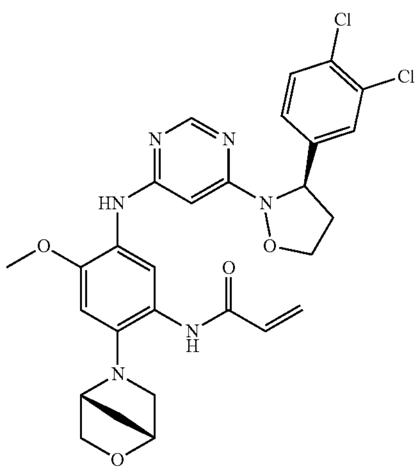 [SMILES: C=CC(=O)Nc1cc(Nc2cc(N3OCC[C@@H]3c3ccc(Cl)c(Cl)c3)ncn2)c(OC)cc1N1C[C@H]2C[C@@H]1CO2] | N-(2-((1R,4R)-2-oxa-5-azabicyclo[2.2.1]heptane-5-yl)-5-((6-((R)-3-(3,4-dichlorophenyl)isoxazolidine-2-yl)pyrimidine-4-yl)amino)-4-methoxyphenyl)acrylamide | ¹H NMR (400 MHz, Chloroform-d) δ 8.64 (s, 1H), 8.35 (s, 1H), 7.96 (s, 1H), 7.58 (d, J = 2.1 Hz, 1H), 7.41 (d, J = 8.3 Hz, 1H), 7.30 (dd, J = 8.3, 2.1 Hz, 1H), 6.89 (s, 1H), 6.71 (d, J = 13.5 Hz, 2H), 6.38 (d, J = 16.8 Hz, 1H), 6.28 (dd, J = 16.9, 9.9 Hz, 1H), 5.79-5.74 (m, 1H), 5.65 (dd, J = 8.7, 4.6 Hz, 1H), 4.67-4.62 (m, 1H), 4.21-4.13 (m, 1H), 4.08-4.02 (m, 2H), 3.88-3.85 (m, 4H), 3.75 (d, J = 7.9 Hz, 1H), 3.45 (d, J = 10.2 Hz, 1H), 3.20 (d, J = 10.1 Hz, 1H), 2.77 (ddt, J = 12.1, 8.1, 4.0 Hz, 1H), 2.33 (ddt, J = 11.8, 7.9, 4.0 Hz, 1H), 2.09 (d, J = 9.9 Hz, 1H), 2.00 (d, J = 9.9 Hz, 1H), ; 583.3 [M + H]⁺ | 1.44 |
| 672 | 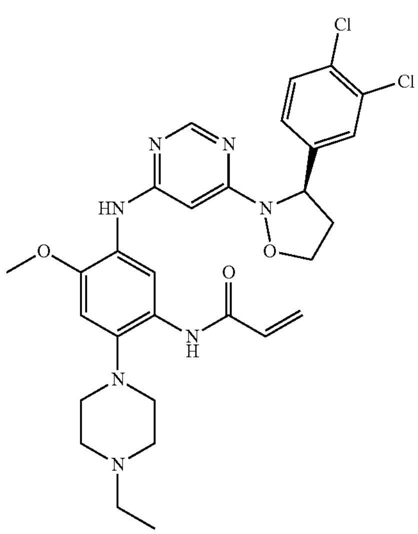 [SMILES: C=CC(=O)Nc1cc(Nc2cc(N3OCC[C@@H]3c3ccc(Cl)c(Cl)c3)ncn2)c(OC)cc1N1CCN(CC)CC1] | N-(5-((6-((R)-3-(3,4-dichlorophenyl)isoxazolidine-2-yl)pyrimidine-4-yl)amino)-2-(4-ethylpiperazine-1-yl)-4-methoxyphenyl)acrylamide | ¹H NMR (400 MHz, Chloroform-d) δ 8.92 (s, 1H), 8.45 (s, 1H), 8.37 (s, 1H), 7.58 (s, 1H), 7.41 (d, J = 8.3 Hz, 1H), 7.30 (d, J = 10.2 Hz, 1H), 6.98 (s, 1H), 6.83 (s, 1H), 6.70 (s, 1H), 6.38 (d, J = 16.5 Hz, 1H), 6.32-6.21 (m, 1H), 5.76 (d, J = 10.0 Hz, 1H), 5.68-5.61 (m, 1H), 4.20-4.13 (m, 1H), 4.09-4.01 (m, 1H), 3.85 (s, 3H), 3.70-3.62 (m, 1H), 3.37-3.29 (m, 1H), 3.14-3.03 (m, 3H), 2.85-2.67 (m, 4H), 2.42-2.25 (m, 2H), 1.54 (t, 2H), 1.45 (d, J = 6.5 Hz, 2H), ; 598.3 [M + H]⁺ | 1.32 |

TABLE 1-continued

| Example Compound | Structure | Name of Compound | ¹H NMR[[:]]; MS [M + H]⁺ | UPLC r.t. (min) |
|---|---|---|---|---|
| 673 | 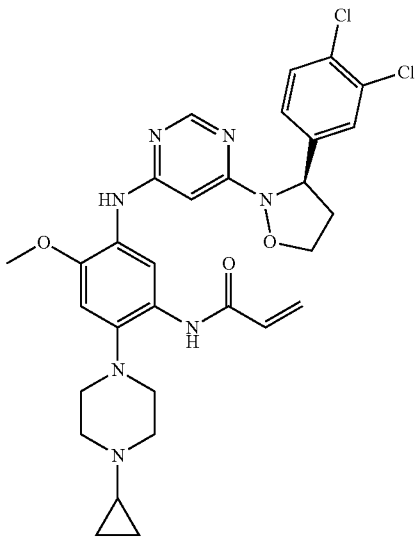 [SMILES: C=CC(=O)Nc1cc(Nc2cc(N3OCC[C@@H]3c3ccc(Cl)c(Cl)c3)ncn2)c(OC)cc1N1CCN(C2CC2)CC1] | N-(2-(4-cyclopropylpiperazine-1-yl)-5-((6-((R)-3-(3,4-dichlorophenyl)isoxazolidine-2-yl)pyrimidine-4-yl)amino)-4-methoxyphenyl)acrylamide | ¹H NMR (400 MHz, Chloroform-d) δ 8.90 (s, 1H), 8.60 (s, 1H), 8.36 (s, 1H), 7.58 (s, 1H), 7.41 (d, J = 8.3 Hz, 1H), 7.30 (d, J = 10.3 Hz, 1H), 6.92 (s, 1H), 6.79 (s, 1H), 6.72 (s, 1H), 6.40-6.33 (m, 1H), 6.32-6.24 (m, 1H), 5.76 (d, J = 9.8 Hz, 1H), 5.67-5.63 (m, 1H), 4.19-4.13 (m, 1H), 4.11-4.03 (m, 1H), 3.81 (s, 3H), 2.93-2.86 (m, 4H), 2.84-2.73 (m, 3H), 2.37-2.27 (m, 2H), 1.77-1.68 (m, 2H), 0.52 (d, J = 6.5 Hz, 2H), 0.47 (d, J = 3.3 Hz, 2H), ; 610.4 [M + H]⁺ | 1.47 |
| 674 | 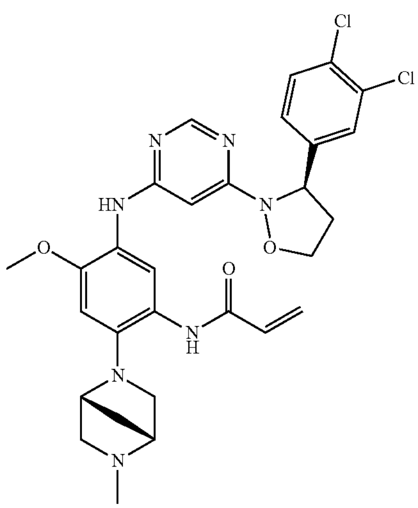 [SMILES: C=CC(=O)Nc1cc(Nc2cc(N3OCC[C@@H]3c3ccc(Cl)c(Cl)c3)ncn2)c(OC)cc1N1C[C@H]2C[C@@H]1CN2C] | N-(5-((6-((R)-3-(3,4-dichlorophenyl)isoxazolidine-2-yl)pyrimidine-4-yl)amino)-4-methoxy-2-((1R,4R)-5-methyl-2,5-diazabicyclo[2.2.1]heptane-2-yl)phenyl)acrylamide | ¹H NMR (400 MHz, Chloroform-d) δ 8.68 (s, 1H), 8.34 (s, 1H), 8.13 (s, 1H), 7.58 (s, 1H), 7.41 (d, J = 8.3 Hz, 1H), 7.30 (d, J = 8.4 Hz, 1H), 6.96 (s, 1H), 6.85 (s, 1H), 6.62 (s, 1H), 6.30 (d, J = 15.4 Hz, 1H), 6.21-6.13 (m, 1H), 5.77-5.70 (m, 1H), 5.66-5.60 (m, 1H), 4.18-4.10 (m, 2H), 4.05-3.97 (m, 2H), 3.89 (s, 3H), 3.82 (s, 2H), 3.61 (s, 2H), 3.20-3.12 (m, 1H), 2.80-2.73 (m, 1H), 2.70 (s, 3H), 2.38-2.27 (m, 1H), 2.13 (s, 1H), ; 596.3 [M + H]⁺ | 1.25 |
| 675 | 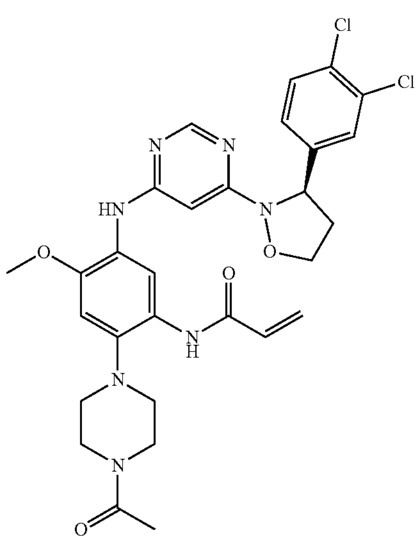 [SMILES: C=CC(=O)Nc1cc(Nc2cc(N3OCC[C@@H]3c3ccc(Cl)c(Cl)c3)ncn2)c(OC)cc1N1CCN(C(C)=O)CC1] | N-(2-(4-acetylpiperazine-1-yl)-5-((6-((R)-3-(3,4-dichlorophenyl)isoxazolidine-2-yl)pyrimidine-4-yl)amino)-4-methoxyphenyl)acrylamide | ¹H NMR (400 MHz, Chloroform-d) δ 8.94 (s, 1H), 8.44 (s, 1H), 8.38 (d, J = 1.0 Hz, 1H), 7.58 (d, J = 2.0 Hz, 1H), 7.41 (d, J = 8.3 Hz, 1H), 7.30 (dd, J = 8.4, 2.1 Hz, 1H), 6.97 (s, 1H), 6.72 (s, 2H), 6.38 (d, J = 16.9 Hz, 1H), 6.26 (dd, J = 16.9, 10.1 Hz, 1H), 5.77 (dd, J = 10.0, 1.5 Hz, 1H), 5.65 (dd, J = 8.7, 4.6 Hz, 1H), 4.17 (td, J = 8.0, 4.2 Hz, 1H), 4.06 (q, J = 8.1 Hz, 1H), 3.85 (s, 3H), 3.65 (s, 2H), 2.88 (d, J = 5.3 Hz, 4H), 2.78 (ddt, J = 12.1, 8.0, 4.0 Hz, 1H), 2.34 (ddd, J = 12.4, 8.3, 4.6 Hz, 1H), 2.17 (s, 3H), 1.25 (s, 2H), ; 612.3 [M + H] | 1.51 |

TABLE 1-continued

| Example Compound | Structure | Name of Compound | ¹H NMR[:]; MS [M + H]⁺ | UPLC r.t. (min) |
|---|---|---|---|---|
| 676 | 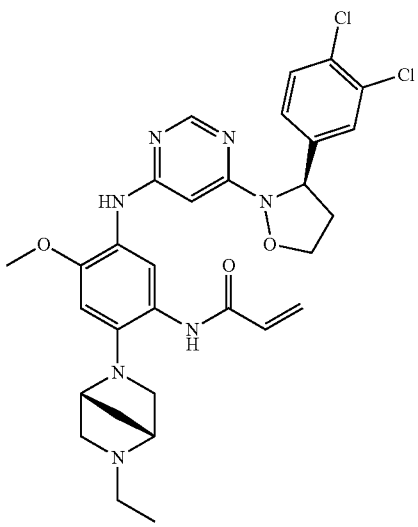 [SMILES: C=CC(=O)Nc1cc(Nc2cc(N3OCC[C@@H]3c3ccc(Cl)c(Cl)c3)ncn2)c(OC)cc1N1C[C@H]2C[C@@H]1CN2CC] | N-(5-((6-((R)-3-(3,4-dichlorophenyl)isoxazolidine-2-yl)pyrimidine-4-yl)amino)-2-((1R,4R)-5-ethyl-2,5-diazabicyclo[2.2.1]heptane-2-yl)-4-methoxyphenyl)acrylamide | ¹H NMR (400 MHz, Chloroform-d) δ 8.59 (s, 1H), 8.33 (s, 1H), 8.12 (s, 1H), 7.58 (d, J = 2.0 Hz, 1H), 7.41 (d, J = 8.3 Hz, 1H), 7.30 (dd, J = 8.3, 2.2 Hz, 1H), 6.90 (s, 1H), 6.76 (s, 1H), 6.67 (s, 1H), 6.40 (s, 1H), 6.25-6.18 (m, 1H), 5.75-5.70 (m, 1H), 5.64 (dd, J = 8.4, 5.2 Hz, 1H), 4.19-4.12 (m, 1H), 4.05 (q, J = 8.0 Hz, 1H), 3.86 (s, 3H), 3.37-3.23 (m, 2H), 3.08 (d, J = 10.1 Hz, 1H), 2.94 (s, 2H), 2.82-2.69 (m, 4H), 2.33-2.26 (m, 2H), 2.03 (s, 3H), 1.82 (dt, J = 23.4, 7.2 Hz, 1H), ; 610.3 [M + H] | 1.27 |
| 677 | 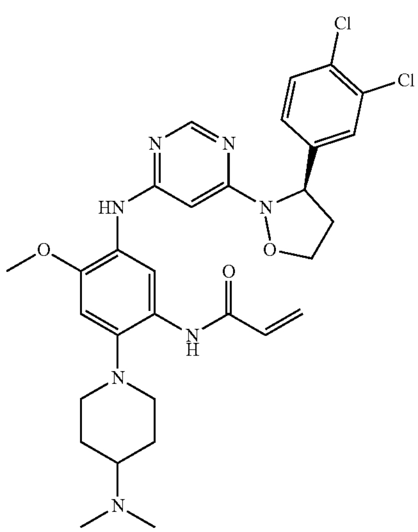 [SMILES: C=CC(=O)Nc1cc(Nc2cc(N3OCC[C@@H]3c3ccc(Cl)c(Cl)c3)ncn2)c(OC)cc1N1CCC(N(C)C)CC1] | N-(5-((6-((R)-3-(3,4-dichlorophenyl)isoxazolidine-2-yl)pyrimidine-4-yl)amino)-2-(4-(dimethylamino)piperidine-1-yl)-4-methoxyphenyl)acrylamide | ¹H NMR (400 MHz, Chloroform-d) δ 8.87 (s, 1H), 8.42 (s, 1H), 8.36 (d, J = 1.0 Hz, 1H), 7.58 (d, J = 2.1 Hz, 1H), 7.41 (d, J = 8.3 Hz, 1H), 7.30 (dd, J = 8.4, 2.1 Hz, 1H), 6.96 (s, 1H), 6.73 (d, J = 13.2 Hz, 2H), 6.41-6.33 (m, 1H), 6.28 (dd, J = 17.0, 9.7 Hz, 1H), 5.75 (dd, J = 9.8, 1.7 Hz, 1H), 5.65 (dd, J = 8.7, 4.6 Hz, 1H), 4.16 (td, J = 8.0, 4.2 Hz, 1H), 4.06 (q, J = 8.1 Hz, 1H), 3.85 (s, 3H), 3.34-3.27 (m, 1H), 3.10 (d, J = 11.7 Hz, 2H), 2.75 (q, J = 11.5 Hz, 4H), 2.51 (s, 6H), 2.37-2.30 (m, 2H), 2.14 (d, J = 12.5 Hz, 2H), ; 612.4 [M + H] | 1.32 |

TABLE 1-continued

| Example Compound | Structure | Name of Compound | ¹H NMR[[:]]; MS [M + H]⁺ | UPLC r.t. (min) |
|---|---|---|---|---|
| 678 | 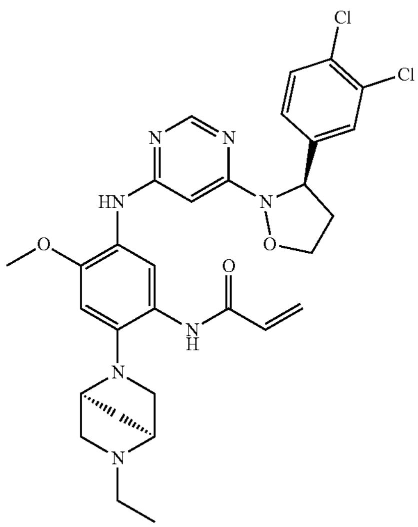 [SMILES: C=CC(=O)Nc1cc(Nc2cc(N3OCC[C@@H]3c3ccc(Cl)c(Cl)c3)ncn2)c(OC)cc1N1C[C@@H]2C[C@H]1CN2CC] | N-(5-((6-((R)-3-(3,4-dichlorophenyl)isoxazolidine-2-yl)pyrimidine-4-yl)amino)-2-((1S,4S)-5-ethyl-2,5-diazabicyclo[2.2.1]heptane-2-yl)-4-methoxyphenyl)acrylamide | ¹H NMR (400 MHz, Chloroform-d) δ 9.36 (s, 1H), 8.66 (s, 1H), 8.35 (s, 1H), 8.03 (s, 1H), 7.58 (d, J = 2.0 Hz, 1H), 7.41 (d, J = 8.3 Hz, 1H), 7.30 (dd, J = 8.2, 2.1 Hz, 1H), 6.88 (s, 1H), 6.63 (s, 1H), 6.40 (q, J = 7.6, 6.2 Hz, 2H), 5.75 (d, J = 11.3 Hz, 1H), 5.64 (dd, J = 8.7, 4.6 Hz, 1H), 4.14 (td, J = 7.9, 4.1 Hz, 1H), 4.02 (q, J = 8.0 Hz, 1H), 3.89 (s, 3H), 3.39-3.27 (m, 1H), 3.13 (d, J = 10.2 Hz, 1H), 2.76 (dtd, J = 12.2, 8.1, 4.2 Hz, 2H), 2.38-2.28 (m, 2H), 2.04 (s, 2H), 1.83 (dd, J = 18.7, 11.5 Hz, 2H), 1.48 (d, J = 24.4 Hz, 2H), 1.26 (d, J = 6.0 Hz, 3H), ; 610.3 [M + H] | 1.28 |
| 679 | 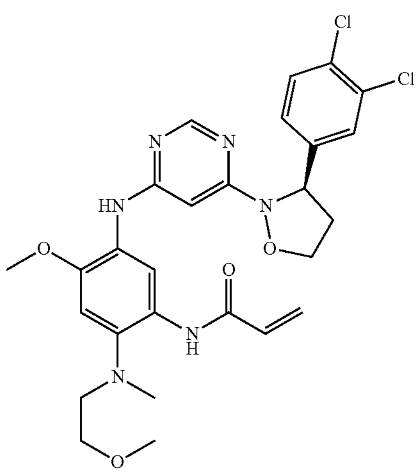 [SMILES: C=CC(=O)Nc1cc(Nc2cc(N3OCC[C@@H]3c3ccc(Cl)c(Cl)c3)ncn2)c(OC)cc1N(C)CCOC] | N-(5-((6-((R)-3-(3,4-dichlorophenyl)isoxazolidine-2-yl)pyrimidine-4-yl)amino)-4-methoxy-2-((2-methoxyethyl)(methyl)amino)phenyl)acrylamide | ¹H NMR (400 MHz, Chloroform-d) δ 9.14 (s, 1H), 8.98 (s, 1H), 8.36 (d, J = 1.1 Hz, 1H), 7.58 (d, J = 2.1 Hz, 1H), 7.40 (d, J = 8.3 Hz, 1H), 7.30 (dd, J = 8.4, 2.1 Hz, 1H), 6.92 (s, 1H), 6.81-6.71 (m, 2H), 6.40 (dd, J = 17.0, 2.0 Hz, 1H), 6.30 (dd, J = 17.0, 9.8 Hz, 1H), 5.67 (ddd, J = 18.7, 9.3, 3.3 Hz, 2H), 4.19-4.04 (m, 2H), 3.84 (s, 3H), 3.45 (d, J = 15.5 Hz, 5H), 2.97 (dt, J = 7.4, 3.2 Hz, 2H), 2.75 (s, 4H), 2.32 (dtd, J = 12.4, 8.1, 4.6 Hz, 1H), ; 573.3 [M + H] | 1.69 |
| 680 | 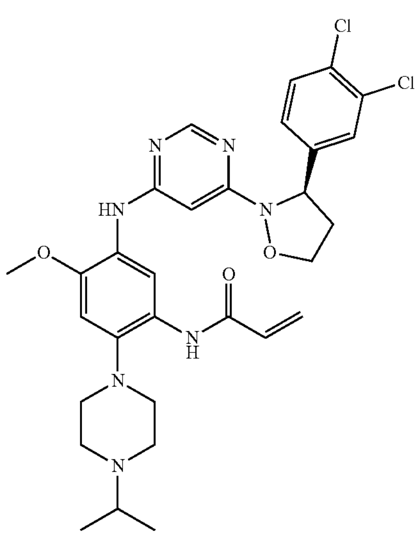 [SMILES: C=CC(=O)Nc1cc(Nc2cc(N3OCC[C@@H]3c3ccc(Cl)c(Cl)c3)ncn2)c(OC)cc1N1CCN(C(C)C)CC1] | N-(5-((6-((R)-3-(3,4-dichlorophenyl)isoxazolidine-2-yl)pyrimidine-4-yl)amino)-2-(4-isopropylpiperazine-1-yl)-4-methoxyphenyl)acrylamide | ¹H NMR (400 MHz, Chloroform-d) δ 8.92 (s, 1H), 8.55 (s, 1H), 8.37 (s, 1H), 7.58 (s, 1H), 7.41 (d, J = 8.3 Hz, 1H), 7.30 (d, J = 10.1 Hz, 1H), 6.96 (s, 1H), 6.85 (s, 1H), 6.71 (s, 1H), 6.38 (d, J = 17.1 Hz, 1H), 6.33-6.26 (m, 1H), 5.76 (d, J = 11.2 Hz, 1H), 5.69-5.62 (m, 1H), 4.19-4.11 (m, 2H), 4.10-4.01 (m, 2H), 3.84 (s, 3H), 3.72-3.61 (m, 1H), 3.37-3.27 (m, 2H), 3.12-3.05 (m, 1H), 2.96 (s, 5H), 2.82-2.73 (m, 3H), 2.62 (s, 1H), 2.38-2.28 (m, 2H), ; 612.4 [M + H]⁺ | 1.47 |

TABLE 1-continued

| Example Compound | Structure | Name of Compound | ¹H NMR[:]; MS [M + H]⁺ | UPLC r.t. (min) |
|---|---|---|---|---|
| 681 | 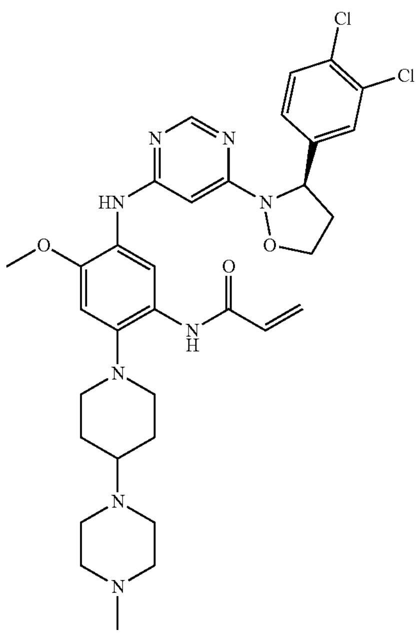 [SMILES: C=CC(=O)Nc1cc(Nc2cc(N3OCC[C@@H]3c3ccc(Cl)c(Cl)c3)ncn2)c(OC)cc1N1CCC(N2CCN(C)CC2)CC1] | N-(5-((6-((R)-3-(3,4-dichlorophenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, Chloroform-d) δ 8.86 (s, 1H), 8.45 (s, 1H), 8.36 (s, 1H), 7.58 (s, 1H), 7.40 (d, J = 8.3 Hz, 1H), 7.30 (d, J = 8.3 Hz, 1H), 6.92 (s, 1H), 6.75 (s, 1H), 6.71 (s, 1H), 6.36 (d, J = 16.9 Hz, 1H), 6.29-6.25 (m, 1H), 5.74 (d, J = 10.0 Hz, 1H), 5.67-5.62 (m, 1H), 4.18-4.12 (m, 1H), 4.10-4.03 (m, 1H), 3.84 (s, 3H), 3.40-3.27 (m, 2H), 3.22-3.15 (m, 1H), 3.11-3.02 (m, 2H), 2.80-2.65 (m, 6H), 2.59-2.49 (m, 3H), 2.38-2.29 (m, 6H), 2.08 (d, J = 14.7 Hz, 2H), ; 667.4 [M + H]⁺ | 1.25 |
| 682 | 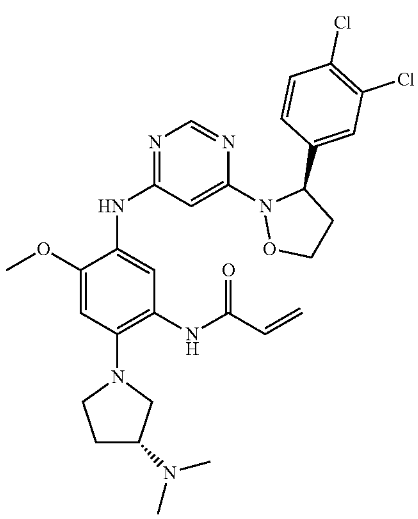 [SMILES: C=CC(=O)Nc1cc(Nc2cc(N3OCC[C@@H]3c3ccc(Cl)c(Cl)c3)ncn2)c(OC)cc1N1CC[C@@H](N(C)C)C1] | N-(5-((6-((R)-3-(3,4-dichlorophenyl)isoxazolidine-2-yl)pyrimidine-4-yl)amino)-2-((R)-3-(dimethylamino)pyrolidine-1-yl)-4-methoxyphenyl)acrylamide | ¹H NMR (400 MHz, Chloroform-d) δ 11.35 (s, 1H), 8.57 (s, 1H), 8.33 (s, 1H), 7.58 (s, 1H), 7.40 (d, J = 8.3 Hz, 1H), 7.30 (d, J = 7.5 Hz, 1H), 6.86 (s, 1H), 6.68 (d, J = 6.6 Hz, 2H), 6.40 (d, J = 16.7 Hz, 2H), 5.74 (s, 1H), 5.67-5.61 (m, 1H), 4.21-4.13 (m, 1H), 4.05 (q, J = 8.1 Hz, 1H), 3.83 (s, 3H), 3.70-3.60 (m, 1H), 3.37-3.27 (m, 1H), 3.13-2.98 (m, 3H), 2.82-2.70 (m, 2H), 2.63 (s, 6H), 2.37-2.24 (m, 2H), ; 598.4 [M + H]⁺ | 1.27 |

TABLE 1-continued

| Example Compound | Structure | Name of Compound | ¹H NMR[[:]]; MS [M + H]⁺ | UPLC r.t. (min) |
|---|---|---|---|---|
| 683 | 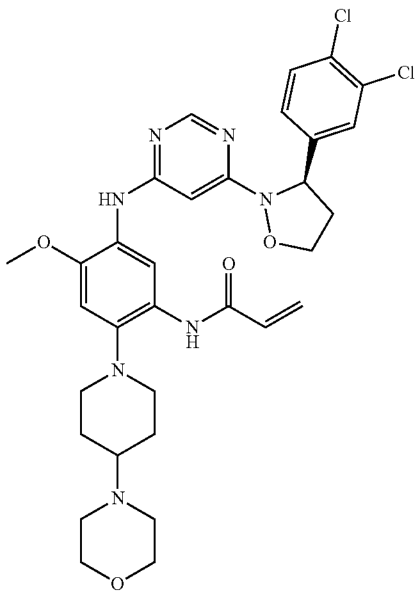 [SMILES: C=CC(=O)Nc1cc(Nc2cc(N3OCC[C@@H]3c3ccc(Cl)c(Cl)c3)ncn2)c(OC)cc1N1CCC(N2CCOCC2)CC1] | N-(5-((6-((R)-3-(3,4-dichlorophenyl)isoxazolidine-2-yl)pyrimidine-4-yl)amino)-4-methoxy-2-(4-morpholinopiperidine-1-yl)phenyl)acrylamide | ¹H NMR (400 MHz, Chloroform-d) δ 8.87 (s, 1H), 8.44 (s, 1H), 8.36 (s, 1H), 7.58 (s, 1H), 7.41 (d, J = 8.3 Hz, 1H), 7.29 (d, J = 1.7 Hz, 1H), 6.92 (s, 1H), 6.75 (s, 1H), 6.71 (s, 1H), 6.36 (d, J = 15.9 Hz, 1H), 6.29-6.20 (m, 1H), 5.74 (d, J = 10.1 Hz, 1H), 5.68-5.61 (m, 1H), 4.19-4.12 (m, 1H), 4.11-4.03 (m, 1H), 3.85 (s, 3H), 3.79-3.75 (m, 4H), 3.36-3.28 (m, 1H), 3.22-3.16 (m, 1H), 3.12-3.04 (m, 2H), 2.75 (t, J = 11.0 Hz, 3H), 2.62 (s, 4H), 2.37-2.25 (m, 3H), 2.08 (d, J = 13.9 Hz, 2H), ; 654.4 [M + H]⁺ | 1.33 |
| 684 | 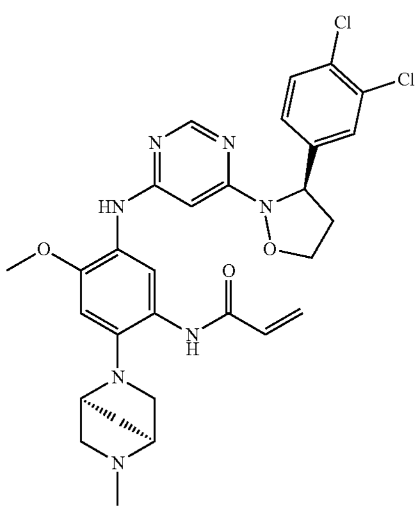 [SMILES: C=CC(=O)Nc1cc(Nc2cc(N3OCC[C@@H]3c3ccc(Cl)c(Cl)c3)ncn2)c(OC)cc1N1C[C@@H]2C[C@H]1CN2C] | N-(5-((6-((R)-3-(3,4-dichlorophenyl)isoxazolidine-2-yl)pyrimidine-4-yl)amino)-4-methoxy-2-((1S,4S)-5-methyl-2,5-diazabicyclo[2.2.1]heptane-2-yl)phenyl)acrylamide | ¹H NMR (400 MHz, Chloroform-d) δ 8.67 (s, 1H), 8.35 (s, 1H), 8.10 (s, 1H), 7.58 (d, J = 2.0 Hz, 1H), 7.41 (d, J = 8.3 Hz, 1H), 7.33-7.28 (m, 1H), 6.93 (s, 1H), 6.86 (s, 1H), 6.62 (s, 1H), 6.42 (d, J = 10.1 Hz, 2H), 5.77-5.72 (m, 1H), 5.64 (dd, J = 8.7, 4.7 Hz, 1H), 4.14 (td, J = 7.8, 4.0 Hz, 1H), 4.01 (q, J = 8.0 Hz, 1H), 3.89 (s, 3H), 3.77 (s, 1H), 3.67-3.59 (m, 1H), 3.33-3.27 (m, 1H), 3.21-3.13 (m, 2H), 3.06 (s, 1H), 2.92-2.85 (m, 1H), 2.76 (dt, J = 8.4, 4.3 Hz, 2H), 2.68 (s, 3H), 2.33 (dt, J = 12.4, 4.0 Hz, 1H); , 596.3 [M + H] | 1.26 |

TABLE 1-continued

| Example Compound | Structure | Name of Compound | ¹H NMR[[:]]; MS [M + H]⁺ | UPLC r.t. (min) |
|---|---|---|---|---|
| 685 | 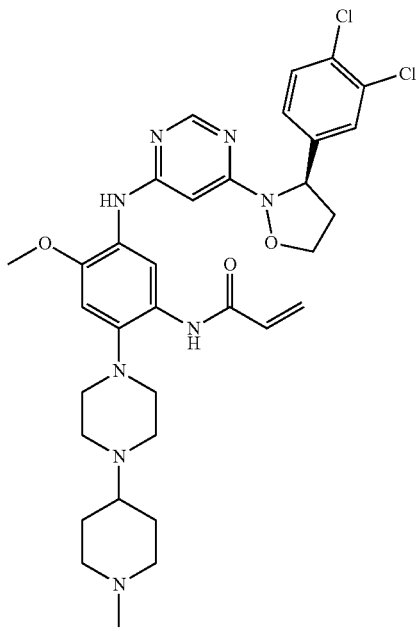 | N-(5-((6-((R)-3-(3,4-dichlorophenyl)isoxazolidine-2-yl)pyrimidine-4-yl)amino)-4-methoxy-2-(4-(1-methylpiperidine-4-yl)piperazine-1-yl)phenyl)acrylamide | ¹H NMR (400 MHz, Chloroform-d) δ 8.90 (s, 1H), 8.56 (s, 1H), 8.36 (d, J = 1.0 Hz, 1H), 7.58 (d, J = 2.1 Hz, 1H), 7.40 (d, J = 8.3 Hz, 1H), 7.30 (dd, J = 8.5, 2.1 Hz, 1H), 6.93 (s, 1H), 6.82 (s, 1H), 6.72 (s, 1H), 6.41-6.32 (m, 1H), 6.26 (dd, J = 16.9, 10.0 Hz, 1H), 5.75 (dd, J = 9.9, 1.6 Hz, 1H), 5.65 (dd, J = 8.7, 4.6 Hz, 1H), 4.15 (td, J = 8.1, 4.2 Hz, 1H), 4.06 (q, J = 8.1 Hz, 1H), 3.83 (s, 3H), 2.95-2.88 (m, 4H), 2.79-2.69 (m, 4H), 2.31 (d, J = 14.6 Hz, 4H), 1.99 (t, J = 11.7 Hz, 2H), 1.86 (d, J = 12.6 Hz, 2H), 1.66 (s, 4H), 1.25 (s, 2H), ; 667.4 [M + H] | 1.15 |
| 686 | 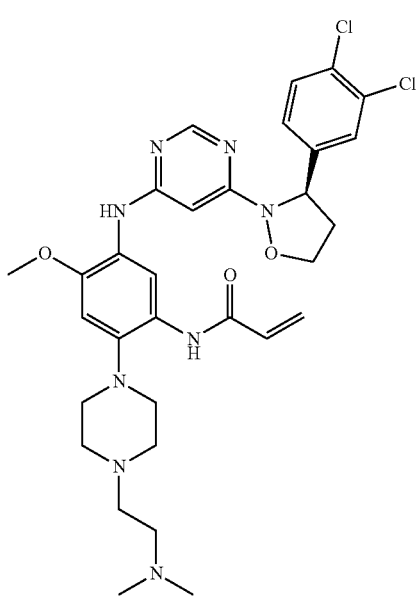 [SMILES: C=CC(=O)Nc1cc(Nc2cc(N3OCC[C@@H]3c3ccc(Cl)c(Cl)c3)ncn2)c(OC)cc1N1CCN(CCN(C)C)CC1] | N-(5-((6-((R)-3-(3,4-dichlorophenyl)isoxazolidine-2-yl)pyrimidine-4-yl)amino)-2-(4-(2-(dimethylamino)ethyl)piperazine-1-yl)-4-methoxyphenyl)acrylamide | ¹H NMR (400 MHz, Chloroform-d) δ 8.89 (s, 1H), 8.56 (s, 1H), 8.39-8.29 (m, 1H), 7.57 (d, J = 5.8 Hz, 1H), 7.45-7.37 (m, 1H), 7.30 (d, J = 7.1 Hz, 1H), 7.07-6.92 (m, 2H), 6.83-6.70 (m, 1H), 6.53 (d, J = 9.1 Hz, 1H), 6.37 (d, J = 17.0 Hz, 1H), 5.75 (d, J = 10.5 Hz, 1H), 5.64 (dd, J = 12.9, 7.8 Hz, 1H), 4.15 (s, 1H), 4.06 (d, J = 8.2 Hz, 1H), 3.84 (s, 3H), 3.43 (s, 2H), 3.33 (d, J = 6.4 Hz, 4H), 3.28 (s, 3H), 3.21 (d, J = 1.8 Hz, 2H), 2.95 (d, J = 7.0 Hz, 2H), 2.68 (s, 3H), ; 641.4 [M + H] | 1.26 |

TABLE 1-continued

| Example Compound | Structure | Name of Compound | $^1$H NMR[:]; MS [M + H]$^+$ | UPLC r.t. (min) |
|---|---|---|---|---|
| 687 | 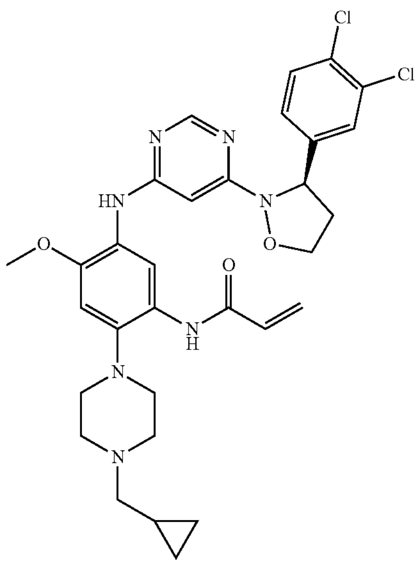 [SMILES: C=CC(=O)Nc1cc(Nc2cc(N3OCC[C@@H]3c3ccc(Cl)c(Cl)c3)ncn2)c(OC)cc1N1CCN(CC2CC2)CC1] | N-(2-(4-(cyclopropylmethyl)piperazine-1-yl)-5-((6-((R)-3-(3,4-dichlorophenyl)isoxazolidine-2-yl)pyrimidine-4-yl)amino)-4-methoxyphenyl)acrylamide | $^1$H NMR (400 MHz, Chloroform-d) δ 8.90 (s, 1H), 8.58 (s, 1H), 8.36 (d, J = 1.0 Hz, J), 7.58 (d, J = 2.1 Hz, 1H), 7.41 (d, J = 8.3 Hz, 1H), 7.30 (dd, J = 8.4, 2.1 Hz, 1H), 6.94 (s, 1H), 6.83 (s, 1H), 6.72 (s, 1H), 6.40-6.32 (m, 1H), 6.26 (dd, J = 16.9, 10.1 Hz, 1H), 5.75 (dd, J = 9.9, 1.6 Hz, 1H), 5.65 (dd, J = 8.7, 4.6 Hz, 1H), 4.16 (td, J = 8.1, 4.2 Hz, 1H), 4.06 (q, J = 8.0 Hz, 1H), 3.83 (s, 3H), 2.95 (t, J = 4.7 Hz, 4H), 2.76 (ddt, J = 12.3, 8.1, 4.2 Hz, 2H), 2.36 (d, J = 6.7 Hz, 2H), 2.30 (ddd, J = 13.7, 8.8, 5.0 Hz, 1H), 1.60 (s, 4H), 0.61-0.53 (m, 2H), 0.16 (q, J = 5.1 Hz, 2H), ; 624.4 [M + H] | 1.37 |
| 688 | 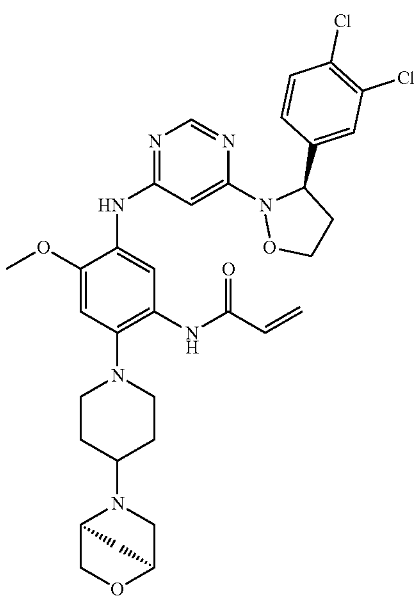 [SMILES: C=CC(=O)Nc1cc(Nc2cc(N3OCC[C@@H]3c3ccc(Cl)c(Cl)c3)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((R)-3-(3,4-dichlorophenyl)isoxazolidine-2-yl)pyrimidine-4-yl)amino)-4-methoxyphenyl)acrylamide | $^1$H NMR (400 MHz, Chloroform-d) δ 11.35 (s, 1H), 8.87 (s, 1H), 8.45 (s, 1H), 8.36 (s, 1H), 7.58 (s, 1H), 7.41 (d, J = 8.3 Hz, 1H), 7.30 (d, J = 8.4 Hz, 1H), 6.93 (s, 1H), 6.75-6.70 (m, 1H), 6.43-6.32 (m, 2H), 5.82-5.73 (m, 1H), 5.69-5.63 (m, 1H), 4.20-4.13 (m, 2H), 4.10-4.03 (m, 1H), 3.85 (s, 3H), 3.70-3.61 (m, 2H), 3.52-3.45 (m, 1H), 3.34-3.28 (m, 1H), 3.13-3.05 (m, 3H), 2.82-2.70 (m, 4H), 2.38-2.27 (m, 2H), 2.11-1.96 (m, 3H), 1.24-1.17 (m, 2H), ; 666.4 [M + H]$^+$ | 1.30 |

TABLE 1-continued

| Example Compound | Structure | Name of Compound | ¹H NMR[[:]]; MS [M + H]⁺ | UPLC r.t. (min) |
|---|---|---|---|---|
| 689 | 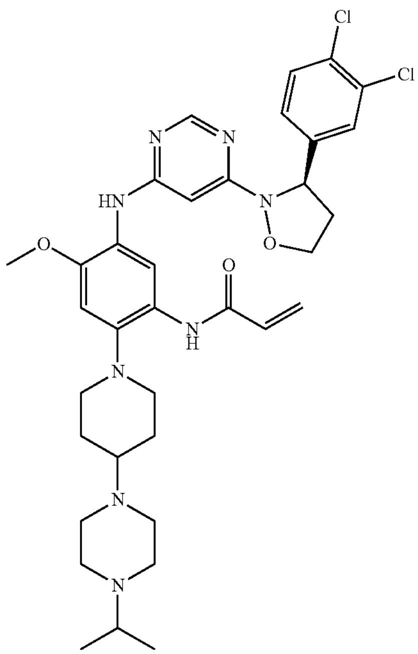 [SMILES: C=CC(=O)Nc1cc(Nc2cc(N3OCC[C@@H]3c3ccc(Cl)c(Cl)c3)ncn2)c(OC)cc1N1CCC(N2CCN(C(C)C)CC2)CC1] | N-(5-((6-((R)-3-(3,4-dichlorophenyl)isoxazolidine-2-yl)pyrimidine-4-yl)amino)-2-(4-(4-isopropylpiperazine-1-yl)piperidine-1-yl)-4-methoxyphenyl)acrylamide | ¹H NMR (400 MHz, Chloroform-d) δ 8.86 (s, 1H), 8.43 (s, 1H), 8.36 (s, 1H), 7.58 (s, 1H), 7.40 (d, J = 8.3 Hz, 1H), 7.30 (d, J = 8.5 Hz, 1H), 6.92 (s, 1H), 6.74 (s, 1H), 6.71 (s, 1H), 6.36 (d, J = 17.4 Hz, 1H), 6.28-6.24 (m, 1H), 5.74 (d, J = 11.0 Hz, 1H), 5.68-5.62 (m, 1H), 4.19-4.12 (m, 2H), 4.10-4.02 (m, 2H), 3.84 (s, 3H), 3.35-3.26 (m, 1H), 3.06 (d, J = 14.2 Hz, 3H), 2.82-2.57 (m, 9H), 2.37-2.28 (m, 2H), 2.13-2.02 (m, 3H), 1.09 (s, 6H), ; 695.5 [M + H]⁺ | 1.29 |
| 690 | 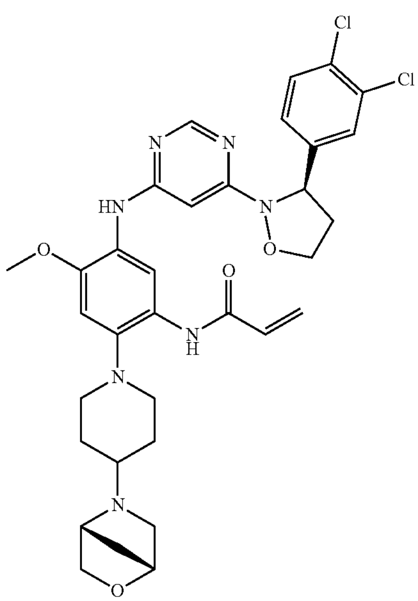 [SMILES: C=CC(=O)Nc1cc(Nc2cc(N3OCC[C@@H]3c3ccc(Cl)c(Cl)c3)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-5-((6-((R)-3-(3,4-dichlorophenyl)isoxazolidine-2-yl)pyrimidine-4-yl)amino)-4-methoxyphenyl)acrylamide | ¹H NMR (400 MHz, Chloroform-d) δ 8.86 (s, 1H), 8.44 (s, 1H), 8.36 (s, 1H), 7.58 (s, 1H), 7.41 (d, J = 8.3 Hz, 1H), 7.30 (d, J = 8.4 Hz, 1H), 6.93 (s, 1H), 6.73 (s, 2H), 6.37 (s, 2H), 5.79-5.74 (m, 1H), 5.69-5.61 (m, 1H), 4.20-4.11 (m, 2H), 4.11-4.03 (m, 2H), 3.93-3.88 (m, 1H), 3.85 (s, 3H), 3.45-3.39 (m, 1H), 3.37-3.29 (m, 1H), 3.09 (s, 2H), 2.83-2.70 (m, 4H), 2.38-2.27 (m, 2H), 2.10-1.95 (m, 3H), 1.55 (d, J = 11.7 Hz, 2H), 1.45 (d, J = 6.6 Hz, 1H), ; 666.4 [M + H]⁺ | 1.32 |

TABLE 1-continued

| Example Compound | Structure | Name of Compound | ¹H NMR[[:]]; MS [M + H]⁺ | UPLC r.t. (min) |
|---|---|---|---|---|
| 691 | 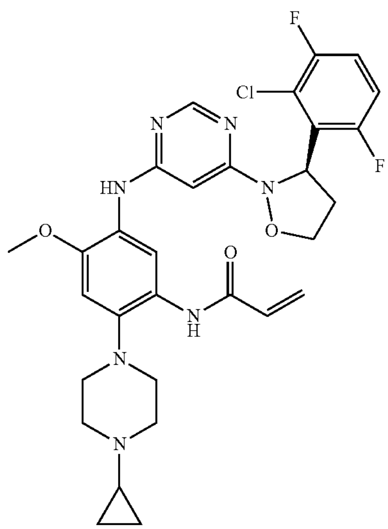 [SMILES: C=CC(=O)Nc1cc(Nc2cc(N3OCC[C@@H]3c3c(F)ccc(F)c3Cl)ncn2)c(OC)cc1N1CCN(C2CC2)CC1] | N-(5-((6-((R)-3-(2-chloro-3,6-difluorophenyl)isoxazolidine-2-yl)pyrimidine-4-yl)amino)-2-(4-cyclopropylpiperazine-1-yl)-4-methoxyphenyl)acrylamide | ¹H NMR (400 MHz, Chloroform-d) δ 8.87 (s, 1H), 8.58 (s, 1H), 8.34 (d, J = 1.0 Hz, 1H), 7.10-7.01 (m, 1H), 7.01-6.92 (m, 1H), 6.87 (s, 1H), 6.78 (s, 1H), 6.62 (s, 1H), 6.37 (dd, J = 16.9, 1.7 Hz, 1H), 6.28 (dd, J = 17.0, 9.8 Hz, 1H), 5.93 (t, J = 8.3 Hz, 1H), 5.75 (dd, J = 9.8, 1.8 Hz, 1H), 4.38 (td, J = 8.0, 1.9 Hz, 1H), 4.02-3.91 (m, 1H), 3.79 (s, 3H), 2.89-2.74 (m, 9H), 2.61-2.47 (m, 1H), 1.77-1.67 (m, 1H), 0.57-0.42 (m, 4H), ; 612.4 [M + H]⁺ | 1.18 |
| 692 | 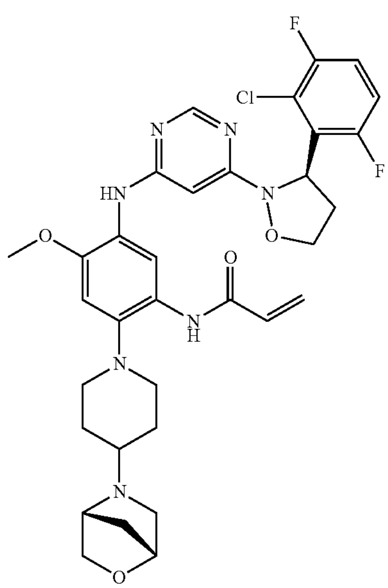 [SMILES: C=CC(=O)Nc1cc(Nc2cc(N3OCC[C@@H]3c3c(F)ccc(F)c3Cl)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-5-((6-((R)-3-(2-chloro-3,6-difluorophenyl)isoxazolidine-2-yl)pyrimidine-4-yl)amino)-4-methoxyphenyl)acrylamide | ¹H NMR (400 MHz, Chloroform-d) δ 8.83 (s, 1H), 8.46 (s, 1H), 8.33 (d, J = 1.1 Hz, 1H), 7.10-7.01 (m, 1H), 7.01-6.92 (m, 1H), 6.85 (s, 1H), 6.75 (s, 1H), 6.65-6.60 (m, 1H), 6.35 (dd, J = 17.0, 1.5 Hz, 1H), 6.23 (dd, J = 16.9, 10.1 Hz, 1H), 5.93 (t, J = 8.3 Hz, 1H), 5.72 (dd, J = 10.0, 1.5 Hz, 1H), 4.44 (t, J = 2.0 Hz, 1H), 4.37 (td, J = 8.0, 1.9 Hz, 1H), 4.09 (d, J = 7.9 Hz, 1H), 3.97 (td, J = 9.0, 8.6, 6.0 Hz, 1H), 3.83 (s, 3H), 3.77 (d, J = 2.2 Hz, 1H), 3.66 (dd, J = 8.0, 1.6 Hz, 1H), 3.14 (dd, J = 9.9, 1.8 Hz, 1H), 3.06-2.97 (m, 2H), 2.83-2.75 (m, 2H), 2.73 (dd, J = 12.0, 2.5 Hz, 1H), 2.62-2.46 (m, 3H), 2.04 (d, J = 13.0 Hz, 1H), 1.99-1.88 (m, 2H), 1.86-1.79 (m, 1H), 1.73-1.60 (m, 2H), ; 668.4 [M + H]⁺ | 1.17 |

TABLE 1-continued

| Example Compound | Structure | Name of Compound | ¹H NMR[[:]]; MS [M + H]⁺ | UPLC r.t. (min) |
|---|---|---|---|---|
| 693 | 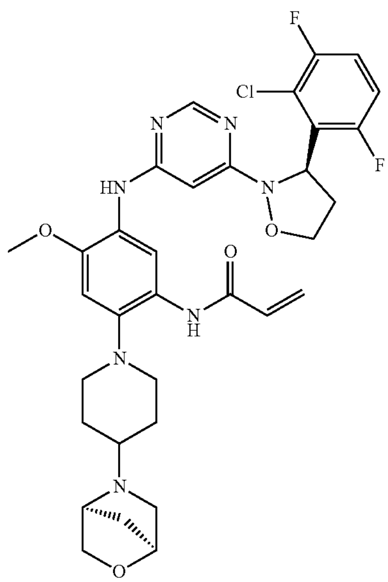 [SMILES: C=CC(=O)Nc1cc(Nc2cc(N3OCC[C@@H]3c3c(F)ccc(F)c3Cl)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((R)-3-(2-chloro-3,6-difluorophenyl)isoxazolidine-2-yl)pyrimidine-4-yl)amino)-4-methoxyphenyl)acrylamide | ¹H NMR (400 MHz, Chloroform-d) δ 8.84 (s, 1H), 8.46 (s, 1H), 8.33 (d, J = 1.0 Hz, 1H), 7.10-7.00 (m, 1H), 7.00-6.92 (m, 1H), 6.84 (s, 1H), 6.75 (s, 1H), 6.66-6.60 (m, 1H), 6.35 (dd, J = 17.0, 1.5 Hz, 1H), 6.23 (dd, J = 16.9, 10.0 Hz, 1H), 5.93 (t, J = 8.3 Hz, 1H), 5.72 (dd, J = 10.0, 1.5 Hz, 1H), 4.44 (t, J = 2.1 Hz, 1H), 4.37 (td, J = 8.0, 1.8 Hz, 1H), 4.09 (d, J = 7.9 Hz, 1H), 4.01-3.86 (m, 1H), 3.83 (s, 3H), 3.76 (s, 1H), 3.66 (dd, J = 8.0, 1.6 Hz, 1H), 3.14 (dd, J = 9.9, 1.8 Hz, 1H), 3.06-2.98 (m, 2H), 2.83-2.69 (m, 3H), 2.62-2.52 (m, 2H), 2.50 (d, J = 10.2 Hz, 1H), 2.04 (d, J = 12.9 Hz, 1H), 1.99-1.88 (m, 2H), 1.82 (d, J = 10.9 Hz, 1H), 1.72-1.60 (m, 2H), ; 668.4 [M + H]⁺ | 1.16 |
| 694 | 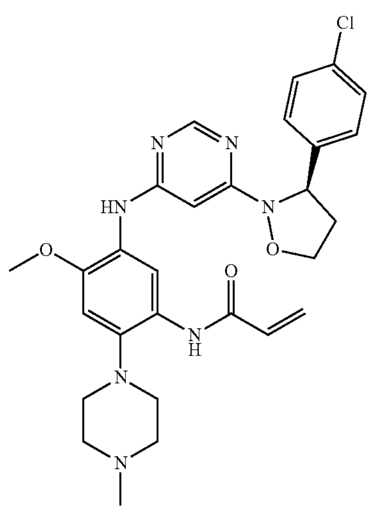 [SMILES: C=CC(=O)Nc1cc(Nc2cc(N3OCC[C@@H]3c3ccc(Cl)cc3)ncn2)c(OC)cc1N1CCN(C)CC1] | N-(5-((6-((R)-3-(4-chlorophenyl)isoxazolidine-2-yl)pyrimidine-4-yl)amino)-4-methoxy-2-(4-methylpiperazine-1-yl)phenyl)acrylamide | ¹H NMR (400 MHz, Methanol-d₄) δ 8.38 (s, 1H), 8.18 (s, 1H), 7.45-7.31 (m, 4H), 6.95 (s, 1H), 6.49-6.33 (m, 2H), 5.82 (d, J = 10.9 Hz, 1H), 5.54-5.49 (m, 1H), 4.14 (td, J = 7.7, 4.5 Hz, 1H), 4.00-3.94 (m, 1H), 3.89 (s, 3H), 3.33 (dd, J = 3.2, 1.6 Hz, 2H), 3.25-3.18 (m, 4H), 3.15 (d, J = 13.0 Hz, 5H), 2.84 (s, 1H), 2.76 (d, J = 14.0 Hz, 3H); 550.5 [M + H]⁺ | 1.41 |

TABLE 1-continued

| Example Compound | Structure | Name of Compound | ¹H NMR[[:]]; MS [M + H]⁺ | UPLC r.t. (min) |
|---|---|---|---|---|
| 695 | 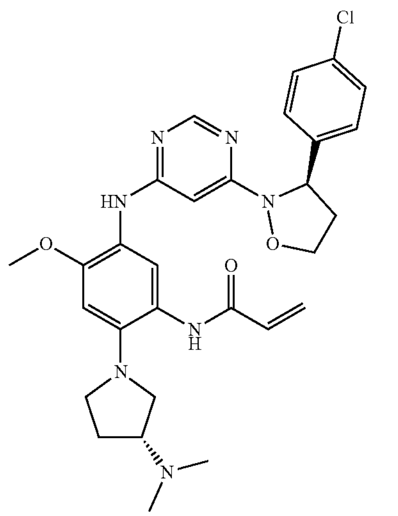 [SMILES: C=CC(=O)Nc1cc(Nc2cc(N3OCC[C@@H]3c3ccc(Cl)cc3)ncn2)c(OC)cc1N1CC[C@@H](N(C)C)C1] | N-(5-((6-((R)-3-(4-chlorophenyl)isoxazolidine-2-yl)pyrimidine-4-yl)amino)-2-((R)-3-(dimethylamino)pyrrolidine-1-yl)-4-methoxyphenyl)acrylamide | N/A; 564.5 [M + H]⁺ | 1.18 |
| 696 | 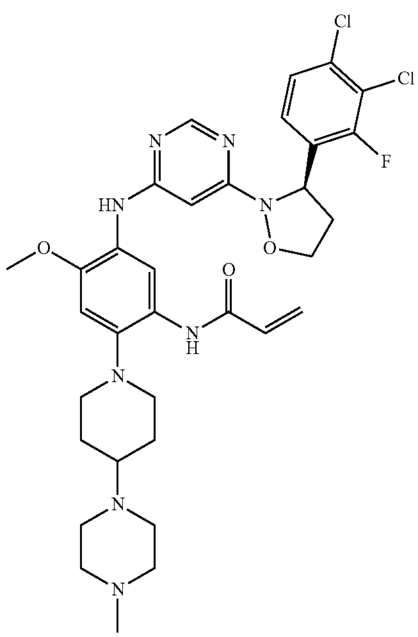 [SMILES: C=CC(=O)Nc1cc(Nc2cc(N3OCC[C@@H]3c3ccc(Cl)c(Cl)c3F)ncn2)c(OC)cc1N1CCC(N2CCN(C)CC2)CC1] | N-(5-((6-((R)-3-(3,4-dichloro-2-fluorophenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, Chloroform-d) δ 8.77 (s, 1H), 8.42 (s, 1H), 8.30 (s, 1H), 7.48 (d, J = 7.6 Hz, 1H), 7.44 (d, J = 7.9 Hz, 1H), 7.23 (dd, J = 8.5, 1.6 Hz, 1H), 6.75 (s, 1H), 6.70 (s, 1H), 6.40-6.32 (m, 1H), 6.27 (dd, J = 16.9, 9.8 Hz, 1H), 5.85 (dd, J = 9.0, 4.7 Hz, 1H), 5.75 (dd, J = 9.8, 1.7 Hz, 1H), 4.13 (dt, J = 8.1, 4.1 Hz, 1H), 4.05 (q, J = 8.0 Hz, 1H), 3.85 (s, 3H), 3.07 (d, J = 11.9 Hz, 2H), 2.83 (dd, J = 8.5, 4.5 Hz, 7H), 2.73 (q, J = 12.3 Hz, 4H), 2.55-2.48 (m, 1H), 2.45 (s, 3H), 2.29-2.24 (m, 1H), 2.08 (s, 2H), 1.71 (h, J = 7.8 Hz, 2H); 685.5 [M + H]⁺ | 1.59 |

TABLE 1-continued

| Example Compound | Structure | Name of Compound | ¹H NMR[[:]]; MS [M + H]⁺ | UPLC r.t. (min) |
|---|---|---|---|---|
| 697 | 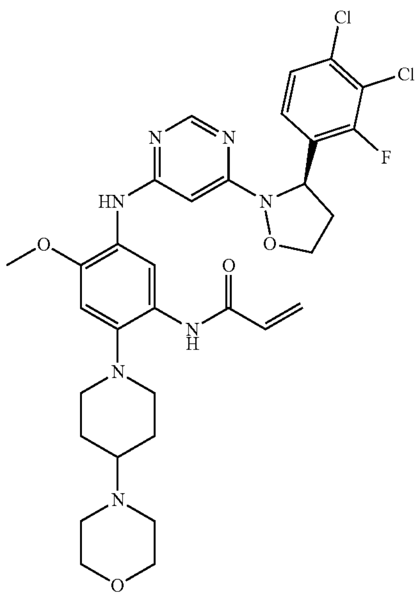 [SMILES: C=CC(=O)Nc1cc(Nc2cc(N3OCC[C@@H]3c3ccc(Cl)c(Cl)c3F)ncn2)c(OC)cc1N1CCC(N2CCOCC2)CC1] | N-(5-((6-((R)-3-(3,4-dichloro-2-fluorophenyl)isoxazolidine-2-yl)pyrimidine-4-yl)amino)-4-methoxy-2-(4-morpholinopiperidine-1-yl)phenyl)acrylamide | ¹H NMR (400 MHz, Chloroform-d) δ 8.85 (s, 1H), 8.43 (s, 1H), 8.34 (s, 1H), 7.46 (t, J = 8.0 Hz, 1H), 7.23 (d, J = 8.7 Hz, 1H), 6.75 (d, J = 4.1 Hz, 2H), 6.36 (d, J = 16.7 Hz, 1H), 6.25 (dd, J = 16.9, 10.0 Hz, 1H), 5.87 (dd, J = 9.0, 4.7 Hz, 1H), 5.74 (d, J = 9.8 Hz, 1H), 4.14-4.11 (m, 1H), 4.06 (d, J = 8.1 Hz, 1H), 3.85 (s, 3H), 3.78 (t, J = 4.6 Hz, 4H), 3.07 (d, J = 11.5 Hz, 2H), 2.85 (d, J = 9.7 Hz, 1H), 2.73 (d, J = 12.3 Hz, 2H), 2.63 (t, J = 4.5 Hz, 4H), 2.28 (d, J = 7.7 Hz, 2H), 2.08 (d, J = 10.9 Hz, 2H), 1.66 (d, J = 11.0 Hz, 2H); 672.4 [M + H]⁺ | 1.59 |
| 698 | 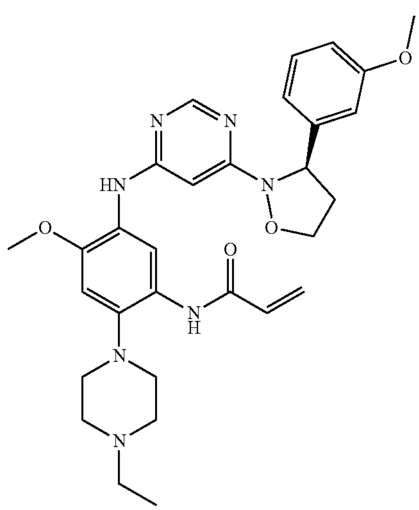 | N-(2-(4-ethylpiperazine-1-yl)-4-methoxy-5-((6-((R)-3-(3-methoxyphenyl)isoxazolidine-2-yl)pyrimidine-4-yl)amino)phenyl)acrylamide | ¹H NMR (400 MHz, Methanol-d₄) δ 8.33 (s, 1H), 8.15 (s, 1H), 7.24 (t, J = 8.1 Hz, 1H), 7.01-6.98 (m, 2H), 6.92 (s, 1H), 6.83-6.77 (m, 1H), 6.55 (dd, J = 17.0, 10.2 Hz, 1H), 6.43 (s, 1H), 6.36 (dd, J = 17.0, 1.6 Hz, 1H), 5.80 (dd, J = 10.2, 1.6 Hz, 1H), 5.49 (dd, J = 8.5, 4.7 Hz, 1H), 4.13 (td, J = 7.9, 4.4 Hz, 1H), 3.96 (q, J = 7.9 Hz, 1H), 3.88 (s, 3H), 3.78 (s, 3H), 3.10 (s, 4H), 2.93 (q, J = 7.3 Hz, 2H), 2.78 (dtd, J = 12.2, 7.9, 4.3 Hz, 1H), 2.37-2.28 (m, 1H), 1.97 (s, 4H), 1.29 (t, J = 7.3 Hz, 3H); 560.5 [M + H]⁺ | 1.03 |

TABLE 1-continued

| Example Compound | Structure | Name of Compound | ¹H NMR[:]; MS [M + H]⁺ | UPLC r.t. (min) |
|---|---|---|---|---|
| 699 | 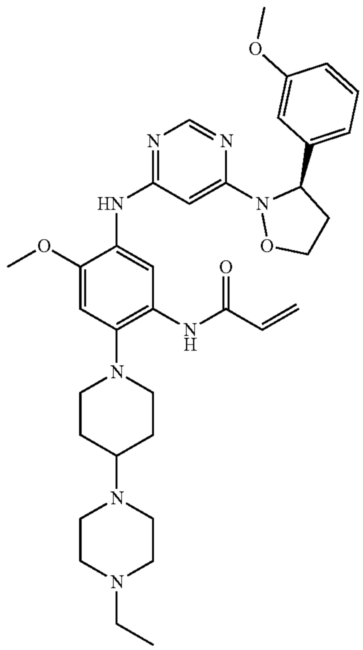 [SMILES: C=CC(=O)Nc1cc(Nc2cc(N3OCC[C@@H]3c3cccc(OC)c3)ncn2)c(OC)cc1N1CCC(N2CCN(CC)CC2)CC1] | N-(2-(4-(4-ethylpiperazine-1-yl)piperidine-1-yl)-4-methoxy-5-((6-((R)-3-(3-methoxyphenyl)isoxazolidine-2-yl)pyrimidine-4-yl)amino)phenyl)acrylamide | ¹H NMR (400 MHz, DMSO-d₆) δ 10.24 (s, 2H), 10.01 (s, 1H), 9.19 (s, 1H), 8.30 (s, 1H), 7.28 (t, J = 7.9 Hz, 1H), 6.94-6.83 (m, 4H), 6.71 (t, J = 13.8 Hz, 1H), 6.25 (dd, J = 16.9, 1.9 Hz, 1H), 6.04 (s, 1H), 5.76 (d, J = 11.3 Hz, 1H), 5.47 (s, 1H), 4.29 (d, J = 7.6 Hz, 2H), 4.04 (t, J = 7.6 Hz, 2H), 3.79 (s, 2H), 3.78-3.76 (m, 2H), 3.75 (s, 3H), 3.65 (d, J = 14.4 Hz, 2H), 3.57 (s, 3H), 3.23 (s, 1H), 3.21-3.18 (m, 2H), 2.95-2.85 (m, 1H), 2.79 (t, J = 11.5 Hz, 2H), 2.31 (dd, J = 12.8, 5.6 Hz, 1H), 2.19 (d, J = 11.1 Hz, 2H), 2.13-2.04 (m, 2H), 1.29 (dd, J = 11.1, 3.3 Hz, 5H); 643.6 [M + H]⁺ | 1.27 |
| 700 | 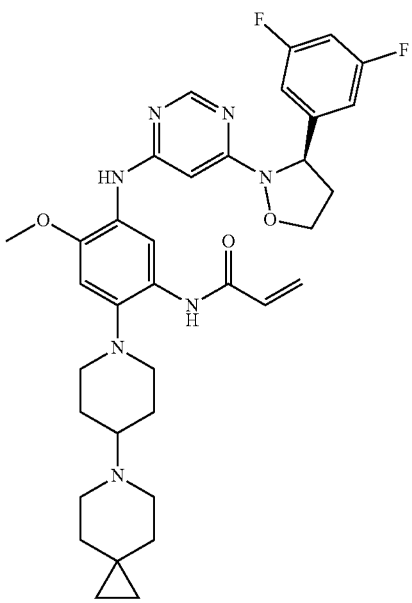 [SMILES: C=CC(=O)Nc1cc(Nc2cc(N3OCC[C@@H]3c3cc(F)cc(F)c3)ncn2)c(OC)cc1N1CCC(N2CCC3(CC2)CC3)CC1] | N-(2-(4-(6-azaspiro[2.5]octan-6-yl)piperidine-1-yl)-5-((6-((R)-3-(3,5-difluorophenyl)isoxazolidine-2-yl)pyrimidine-4-yl)amino)-4-methoxyphenyl)acrylamide | ¹H NMR (400 MHz, Methanol-d₄) δ 8.19 (s, 1H), 8.07 (s, 1H), 7.00-6.89 (m, 2H), 6.81 (s, 1H), 6.73 (tt, J = 2.5, 9.1 Hz, 1H), 6.52-6.40 (m, 1H), 6.36 (s, 1H), 6.33-6.20 (m, 1H), 5.70 (d, J = 10.3 Hz, 1H), 5.45 (dd, J = 4.8, 8.7 Hz, 1H), 4.04 (td, J = 4.2, 7.9 Hz, 1H), 3.86 (q, J = 7.9 Hz, 1H), 3.78 (s, 3H), 3.17-3.09 (m, 6H), 2.80-2.67 (m, 3H), 2.26-2.17 (m, 1H), 2.12-2.05 (m, 2H), 1.96-1.87 (m, 2H), 1.67-1.55 (m, 3H), 0.83-0.74 (m, 2H), 0.39 (s, 4H); 646.3 [M + H]⁺ | 1.59 |

TABLE 1-continued

| Example Compound | Structure | Name of Compound | ¹H NMR[[:]]; MS [M + H]⁺ | UPLC r.t. (min) |
|---|---|---|---|---|
| 701 | 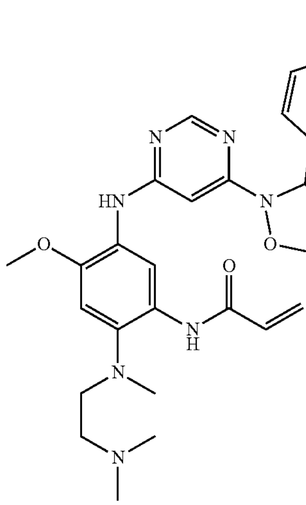 | N-(5-((6-((R)-3-(3-chloro-4-fluorophenyl)isoxazolidine-2-yl)pyrimidine-4-yl)amino)-2-((2-(dimethylamino)ethyl)(methyl)amino)-4-methoxyphenyl)acrylamide | ¹H NMR (400 MHz, MeOD) δ 8.19 (s, 1H), 7.99 (s, 1H), 7.56 (dd, J = 7.1, 2.1 Hz, 1H), 7.45-7.37 (m, 1H), 7.24 (t, J = 8.9 Hz, 1H), 6.96 (s, 1H), 6.62-6.39 (m, 3H), 5.87 (dd, J = 10.1, 1.6 Hz, 1H), 5.54 (dd, J = 8.5, 4.8 Hz, 1H), 4.18 (td, J = 7.9, 4.2 Hz, 1H), 3.98 (dd, J = 16.0, 8.0 Hz, 1H), 3.93 (s, 3H), 3.43 (t, J = 5.8 Hz, 2H), 3.19 (dd, J = 7.1, 4.2 Hz, 2H), 2.84 (dd, J = 8.1, 4.0 Hz, 1H), 2.80 (s, 6H), 2.73 (s, 3H), 2.39-2.29 (m, 1H), ; 570.5 [M + H]⁺ | 1.11 |
| 702 | 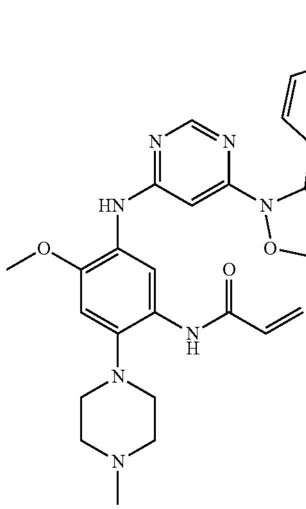 | N-(5-((6-((R)-3-(3-chloro-4-fluorophenyl)isoxazolidine-2-yl)pyrimidine-4-yl)amino)-4-methoxy-2-(4-methylpiperazine-1-yl)phenyl)acrylamide | ¹H NMR (400 MHz, MeOD) δ 8.28 (s, 1H), 8.18 (s, 1H), 7.56 (dd, J = 7.1, 2.1 Hz, 1H), 7.44-7.38 (m, 1H), 7.23 (t, J = 8.9 Hz, 1H), 6.95 (s, 1H), 6.57 (dd, J = 17.1, 10.3 Hz, 1H), 6.48-6.34 (m, 2H), 5.84 (d, J = 10.3 Hz, 1H), 5.53 (dd, J = 8.4, 4.7 Hz, 1H), 4.17 (td, J = 7.9, 4.3 Hz, 1H), 3.98 (dd, J = 16.0, 8.0 Hz, 1H), 3.90 (s, 3H), 3.10 (d, J = 15.7 Hz, 8H), 2.83 (dt, J = 16.1, 6.0 Hz, 1H), 2.72 (s, 3H), 2.35 (dt, J = 8.7, 6.4 Hz, 1H), ; 568.4 [M + H]⁺ | 1.25 |

TABLE 1-continued

| Example Compound | Structure | Name of Compound | ¹H NMR[:]; MS [M + H]⁺ | UPLC r.t. (min) |
|---|---|---|---|---|
| 703 | 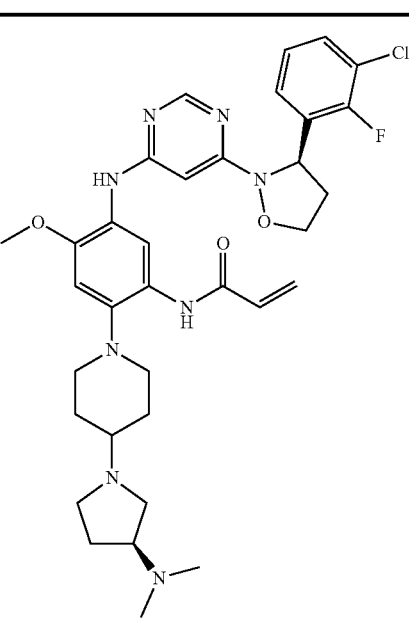 | N-(5-((6-((R)-3-(3-chloro-2-fluorophenyl)isoxazolidine-2-yl)pyrimidine-4-yl)amino)-2-(4-((S)-3-(dimethylamino)pyrolidine-1-yl)piperidine-1-yl)-4-methoxyphenyl)acrylamide | ¹H NMR (400 MHz, MeOD) δ 8.01 (d, J = 4.4 Hz, 1H), 7.71 (s, 1H), 7.34-7.17 (m, 1H), 7.13 (t, J = 7.5 Hz, 1H), 7.06-6.85 (m, 2H), 6.48 (dd, J = 16.9, 10.3 Hz, 1H), 6.26 (dd, J = 16.9, 1.6 Hz, 1H), 5.94 (s, 1H), 5.68 (dd, J = 10.2, 1.6 Hz, 1H), 5.63-5.47 (m, 1H), 4.25 (td, J = 7.7, 4.1 Hz, 1H), 4.02 (q, J = 7.9 Hz, 2H), 3.72 (d, J = 3.9 Hz, 4H), 3.64-3.37 (m, 4H), 3.36-3.23 (m, 2H), 3.17 (s, 1H), 2.82-2.61 (m, 2H), 2.29-2.15 (m, 3H), 2.09 (d, J = 14.0 Hz, 2H), 1.20 (dd, J = 6.7, 5.1 Hz, 7H), 1.11 (d, J = 2.9 Hz, 2H), ; 665.56 [M + H] | 1.38 |
| 704 | 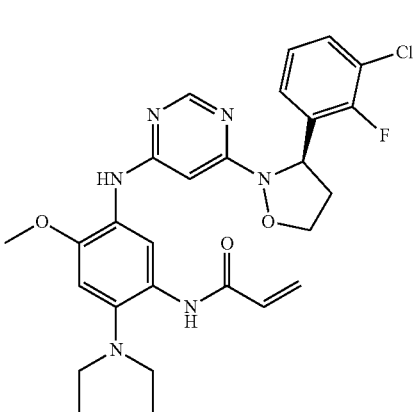 | N-(2-(4-((1S,4S)-2-oxa-5-azabicyclo[2.2.1]heptane-5-yl)piperidine-1-yl)-5-((6-((R)-3-(3-chloro-2-fluorophenyl)isoxazolidine-2-yl)pyrimidine-4-yl)amino)-4-methoxyphenyl)acrylamide | ¹H NMR (400 MHz, MeOD) δ 8.06 (s, 1H), 7.76 (s, 1H), 7.34 (t, J = 7.6 Hz, 1H), 7.21 (t, J = 7.1 Hz, 1H), 7.07 (t, J = 7.9 Hz, 1H), 6.88 (d, J = 17.8 Hz, 1H), 6.51 (d, J = 10.8 Hz, 1H), 6.30 (d, J = 17.1 Hz, 1H), 6.00 (s, 1H), 5.70 (dd, J = 26.0, 9.1 Hz, 2H), 4.66 (s, 1H), 4.58 (d, J = 14.4 Hz, 1H), 4.38-4.29 (m, 1H), 4.22 (d, J = 10.7 Hz, 1H), 4.09 (q, J = 7.9 Hz, 1H), 3.78 (t, J = 3.0 Hz, 4H), 3.54 (d, J = 11.5 Hz, 2H), 3.42-3.23 (m, 2H), 3.09-2.68 (m, 4H), 2.34 (dq, J = 13.6, 7.2 Hz, 2H), 2.23-1.81 (m, 6H), 1.19 (s, 2H), ; 650.5 [M + H] | 1.53 |

TABLE 1-continued

| Example Compound | Structure | Name of Compound | ¹H NMR[[:]]; MS [M + H]⁺ | UPLC r.t. (min) |
|---|---|---|---|---|
| 705 | 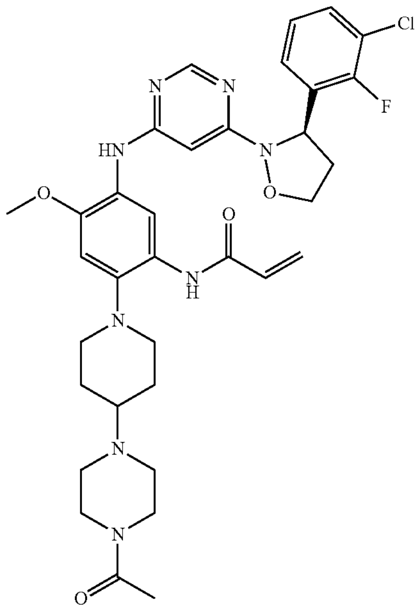 [SMILES: C=CC(=O)Nc1cc(Nc2cc(N3OCC[C@@H]3c3cccc(Cl)c3F)ncn2)c(OC)cc1N1CCC(N2CCN(C(C)=O)CC2)CC1] | N-(2-(4-(4-acetylpiperazine-1-yl)piperidine-1-yl)-5-((6-((R)-3-(3-chloro-2-fluorophenyl)isoxazolidine-2-yl)pyrimidine-4-yl)amino)-4-methoxyphenyl)acrylamide | ¹H NMR (400 MHz, MeOD) δ 8.19 (d, J = 7.2 Hz, 1H), 7.91 (d, J = 6.5 Hz, 1H), 7.50-7.42 (m, 1H), 7.33 (t, J = 7.2 Hz, 1H), 7.19 (t, J = 7.9 Hz, 1H), 7.08 (s, 1H), 6.66 (s, 1H), 6.43 (dd, J = 16.6, 7.6 Hz, 1H), 6.12 (s, 1H), 5.78 (s, 1H), 4.76 (s, 1H), 4.45 (s, 1H), 4.21 (q, J = 7.3 Hz, 2H), 3.90 (d, J = 7.1 Hz, 5H), 3.75 (s, 3H), 3.67 (s, 2H), 3.42 (s, 2H), 3.11 (s, 5H), 2.47 (dt, J = 13.0, 6.6 Hz, 1H), 2.36 (s, 3H), 2.20 (s, 2H), 2.03 (d, J = 12.5 Hz, 1H), 1.31 (s, 1H), ; 679.6 [M + H] | 1.51 |
| 706 | 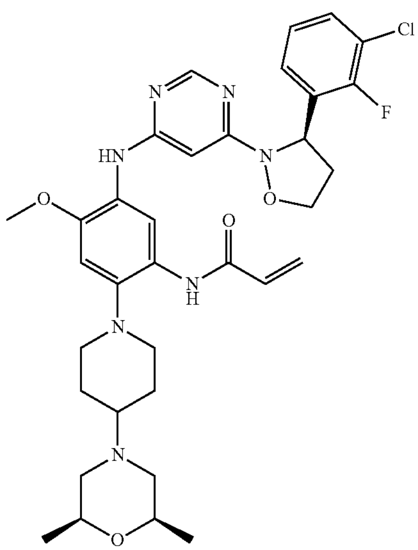 [SMILES: C=CC(=O)Nc1cc(Nc2cc(N3OCC[C@@H]3c3cccc(Cl)c3F)ncn2)c(OC)cc1N1CCC(N2C[C@@H](C)O[C@@H](C)C2)CC1] | N-(5-((6-((R)-3-(3-chloro-2-fluorophenyl)isoxazolidine-2-yl)pyrimidine-4-yl)amino)-2-(4-((2S,6R)-2,6-dimethylmorpholino)piperidine-1-yl)-4-methoxyphenyl)acrylamide | ; 666.5 [M + H]⁺ | 1.52 |

TABLE 1-continued

| Example Compound | Structure | Name of Compound | ¹H NMR[[:]]; MS [M + H]⁺ | UPLC r.t. (min) |
|---|---|---|---|---|
| 707 | 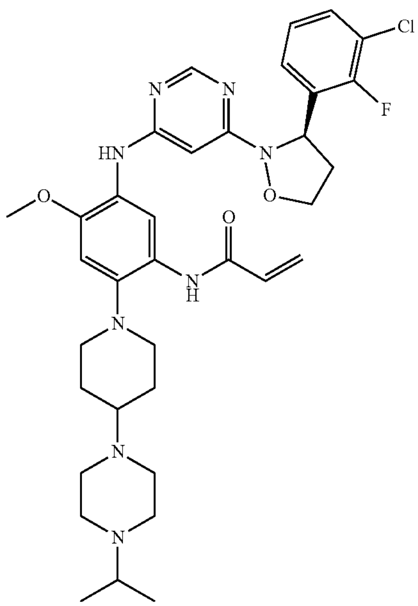 [SMILES: C=CC(=O)Nc1cc(Nc2cc(N3OCC[C@@H]3c3cccc(Cl)c3F)ncn2)c(OC)cc1N1CCC(N2CCN(C(C)C)CC2)CC1] | N-(5-((6-((R)-3-(3-chloro-2-fluorophenyl)isoxazolidine-2-yl)pyrimidine-4-yl)amino)-2-(4-(4-isopropylpiperazine-1-yl)piperidine-1-yl)-4-methoxyphenyl)acrylamide | ¹H NMR (400 MHz, DMSO-d₆) δ 9.15 (s, 1H), 8.26 (s, 1H), 8.01 (s, 1H), 7.54 (t, J = 7.6 Hz, 1H), 7.38 (t, J = 7.3 Hz, 1H), 7.24 (t, J = 7.9 Hz, 1H), 6.89 (s, 1H), 6.74-6.63 (m, 1H), 6.30-6.17 (m, 2H), 5.85-5.67 (m, 2H), 4.27 (d, J = 9.0 Hz, 1H), 4.00 (q, J = 7.7 Hz, 1H), 3.81 (s, 3H), 3.26-3.18 (m, 4H), 2.73 (d, J = 4.7 Hz, 4H), 1.34-1.30 (m, 7H), 1.30-1.22 (m, 8H), 1.09 (p, J = 7.2, 6.6 Hz, 4H), ; 679.5 [M + H]⁺ | 1.29 |
| 708 | 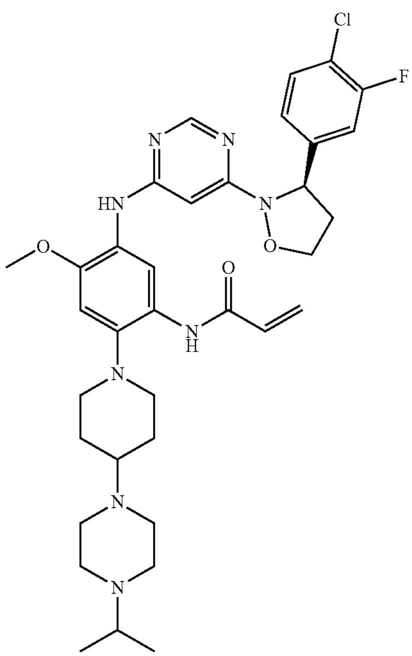 | N-(5-((6-((R)-3-(4-chloro-3-fluorophenyl)isoxazolidine-2-yl)pyrimidine-4-yl)amino)-2-(4-(4-isopropylpiperazine-1-yl)piperidine-1-yl)-4-methoxyphenyl)acrylamide | ¹H NMR (400 MHz, DMSO-d₆) δ 8.95 (s, 1H), 8.62 (s, 1H), 8.16 (d, J = 0.9 Hz, 1H), 7.56 (t, J = 8.1 Hz, 1H), 7.41 (dd, J = 10.6, 2.0 Hz, 1H), 7.29 (dd, J = 8.4, 2.0 Hz, 1H), 6.82 (s, 1H), 6.74-6.57 (m, 1H), 6.34 (s, 1H), 6.20 (dd, J = 16.9, 2.0 Hz, 1H), 5.73 (ddd, J = 10.4, 8.7, 2.2 Hz, 1H), 5.55 (dd, J = 8.7, 5.0 Hz, 1H), 4.13 (td, J = 7.9, 3.9 Hz, 1H), 3.93-3.72 (m, 4H), 3.04 (d, J = 10.8 Hz, 2H), 2.67 (dddd, J = 47.8, 24.7, 12.0, 6.5 Hz, 5H), 2.45 (s, 3H), 2.35-2.16 (m, 2H), 1.90 (m, 7H), 1.69 (q, J = 13.6 Hz, 2H), 0.97 (d, J = 6.5 Hz, 6H), ; 679.5 [M + H]⁺ | 1.23 |

TABLE 1-continued

| Example Compound | Structure | Name of Compound | $^1$H NMR[[:]]; MS [M + H]$^+$ | UPLC r.t. (min) |
|---|---|---|---|---|
| 709 | 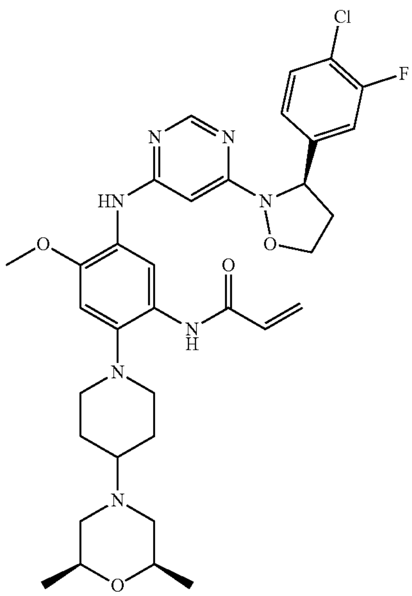 | N-(5-((6-((R)-3-(4-chloro-3-fluorophenyl)isoxazolidine-2-yl)pyrimidine-4-yl)amino)-2-(4-((2S,6R)-2,6-dimethylmorpholino)piperidine-1-yl)-4-methoxyphenyl)acrylamide | $^1$H NMR (400 MHz, Methanol-d$_4$) δ 8.20 (d, J = 9.6 Hz, 1H), 7.91 (s, 1H), 7.50 (t, J = 7.9 Hz, 1H), 7.26 (dd, J = 32.3, 9.2 Hz, 2H), 7.07 (d, J = 34.4 Hz, 1H), 6.68 (dd, J = 17.3, 10.6 Hz, 1H), 6.53-6.36 (m, 1H), 6.07 (s, 1H), 5.88 (d, J = 8.8 Hz, 1H), 5.53 (s, 1H), 4.44 (td, J = 7.7, 4.1 Hz, 1H), 4.19 (q, J = 7.7 Hz, 1H), 4.03 (s, 2H), 3.90 (d, J = 6.2 Hz, 3H), 3.61 (d, J = 12.1 Hz, 2H), 3.39 (d, J = 40.6 Hz, 4H), 3.19-2.95 (m, 3H), 2.81 (t, J = 11.5 Hz, 2H), 2.55-1.98 (m, 5H), 1.30 (d, J = 6.3 Hz, 6H), ; 666.5 [M + H]$^+$ | 1.34 |
| 710 | 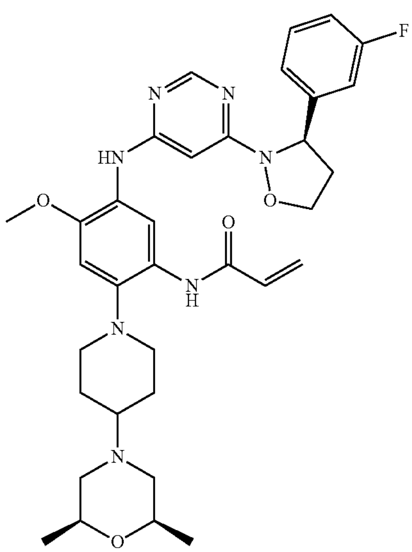 [SMILES: C=CC(=O)Nc1cc(Nc2cc(N3OCC[C@@H]3c3cccc(F)c3)ncn2)c(OC)cc1N1CCC(N2C[C@@H](C)O[C@@H](C)C2)CC1] | N-(2-(4-((2S,6R)-2,6-dimethylmorpholino)piperidine-1-yl)-5-((6-((R)-3-(3-fluorophenyl)isoxazolidine-2-yl)pyrimidine-4-yl)amino)-4-methoxyphenyl)acrylamide | $^1$H NMR (400 MHz, DMSO-d$_6$) δ 11.61 (s, 1H), 9.94 (s, 1H), 9.16 (s, 1H), 8.31 (s, 1H), 7.90 (s, 1H), 7.42 (td, J = 8.1, 6.2 Hz, 1H), 7.23-7.16 (m, 2H), 7.13 (td, J = 8.6, 8.0, 2.5 Hz, 1H), 6.91 (s, 1H), 6.68 (dd, J = 16.9, 10.2 Hz, 1H), 6.25 (dd, J = 17.0, 1.9 Hz, 1H), 6.09 (s, 1H), 5.76 (dd, J = 10.2, 1.9 Hz, 1H), 5.54 (t, J = 7.1 Hz, 1H), 4.29 (dd, J = 7.6, 4.4 Hz, 1H), 4.18-4.08 (m, 2H), 4.04 (q, J = 7.7 Hz, 1H), 3.81 (s, 3H), 3.46 (d, J = 11.8 Hz, 2H), 3.22 (q, J = 15.5 Hz, 3H), 3.00-2.86 (m, 1H), 2.72 (dq, J = 21.6, 11.3, 10.7 Hz, 4H), 2.37-2.27 (m, 1H), 2.23 (d, J = 11.5 Hz, 2H), 2.06 (d, J = 10.2 Hz, 2H), 1.17 (d, J = 6.3 Hz, 6H), ; 632.5 [M + H]$^+$ | 1.21 |

TABLE 1-continued

| Example Compound | Structure | Name of Compound | $^1$H NMR[[:]]; MS [M + H]$^+$ | UPLC r.t. (min) |
|---|---|---|---|---|
| 711 | 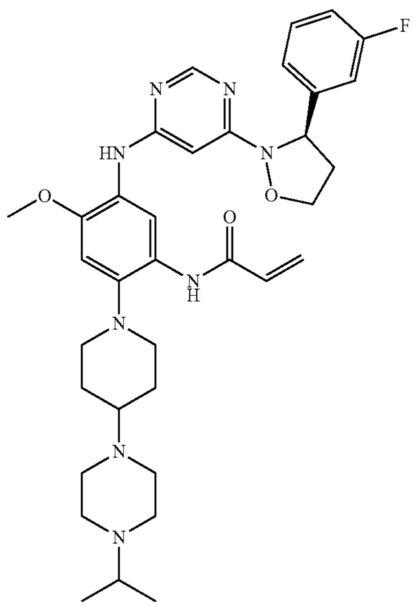 [SMILES: C=CC(=O)Nc1cc(Nc2cc(N3OCC[C@@H]3c3cccc(F)c3)ncn2)c(OC)cc1N1CCC(N2CCN(C(C)C)CC2)CC1] | N-(5-((6-((R)-3-(3-fluorophenyl)isoxazolidine-2-yl)pyrimidine-4-yl)amino)-2-(4-(4-isopropylpiperazine-1-yl)piperidine-1-yl)-4-methoxyphenyl)acrylamide | $^1$H NMR (400 MHz, DMSO-d$_6$) δ 12.22 (s, 1H), 11.88 (s, 1H), 9.69 (s, 1H), 9.15 (s, 1H), 8.28 (s, 1H), 7.98 (s, 1H), 7.42 (td, J = 8.0, 6.1 Hz, 1H), 7.28-7.16 (m, 2H), 7.12 (td, J = 8.7, 2.6 Hz, 1H), 6.89 (s, 1H), 6.69 (dd, J = 16.8, 10.3 Hz, 1H), 6.25 (dd, J = 16.8, 1.9 Hz, 1H), 6.14 (s, 1H), 5.76 (d, J = 10.3 Hz, 1H), 5.59-5.44 (m, 1H), 4.27 (s, 1H), 4.00 (s, 3H), 3.80 (s, 3H), 3.77 (s, 1H), 3.68 (s, 4H), 3.61 (d, J = 7.0 Hz, 1H), 3.46 (s, 1H), 3.21 (d, J = 11.9 Hz, 2H), 2.89 (s, 1H), 2.78 (dd, J = 19.8, 8.6 Hz, 2H), 2.31 (dd, J = 12.1, 5.0 Hz, 1H), 2.15 (s, 2H), 2.05 (s, 2H), 1.31 (d, J = 6.6 Hz, 6H), ; 645.6 [M + H]$^+$ | 1.11 |
| 712 | 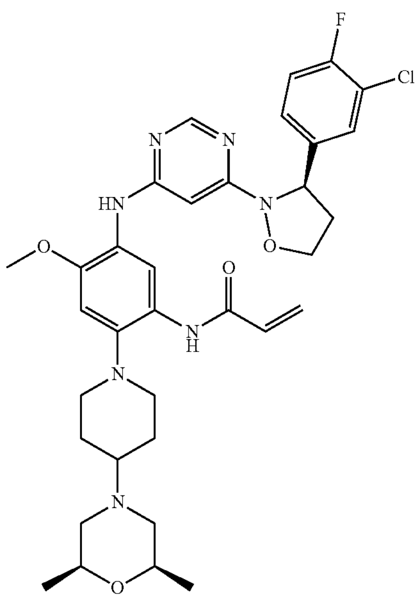 [SMILES: C=CC(=O)Nc1cc(Nc2cc(N3OCC[C@@H]3c3ccc(F)c(Cl)c3)ncn2)c(OC)cc1N1CCC(N2C[C@@H](C)O[C@@H](C)C2)CC1] | N-(5-((6-((R)-3-(3-chloro-4-fluorophenyl)isoxazolidine-2-yl)pyrimidine-4-yl)amino)-2-(4-((2S,6R)-2,6-dimethylmorpholino)piperidine-1-yl)-4-methoxyphenyl)acrylamide | $^1$H NMR (400 MHz, Methanol-d$_4$) δ 8.30 (s, 1H), 8.18 (s, 1H), 7.61-7.51 (m, 1H), 7.46-7.36 (m, 1H), 7.23 (t, J = 8.9 Hz, 1H), 6.92 (s, 1H), 6.57 (dd, J = 10.2, 17.0 Hz, 1H), 6.45 (s, 1H), 6.42-6.31 (m, 1H), 5.82 (d, J = 10.3 Hz, 1H), 5.57-5.49 (m, 1H), 4.18-4.12 (m, 1H), 3.98 (q, J = 8.0 Hz, 1H), 3.88 (s, 3H), 3.81-3.74 (m, 2H), 3.21-3.09 (m, 4H), 2.84-2.78 (m, 2H), 2.64-2.57 (m, 1H), 2.40-2.28 (m, 1H), 2.15-2.09 (m, 3H), 1.86-1.76 (m, 2H), 1.23 (s, 3H), 1.21 (s, 3H); 665.3 [M + H]$^+$ | 1.66 |

TABLE 1-continued

| Example Compound | Structure | Name of Compound | ¹H NMR[[:]]; MS [M + H]⁺ | UPLC r.t. (min) |
|---|---|---|---|---|
| 713 | 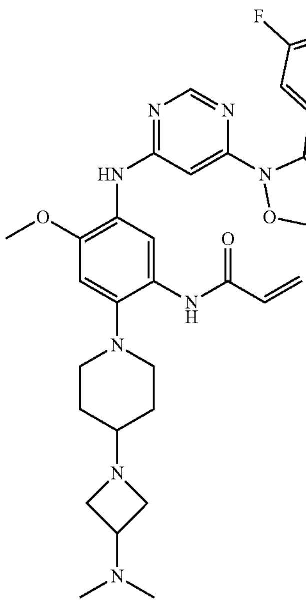 | N-(5-((6-((R)-3-(3,5-difluorophenyl)isoxazolidine-2-yl)pyrimidine-4-yl)amino)-2-(4-(3-(dimethylamino)azetidine-1-yl)piperidine-1-yl)-4-methoxyphenyl)acrylamide | ¹H NMR (400 MHz, Methanol-d₄) δ 8.29 (s, 1H), 8.17 (s, 1H), 7.11-7.04 (m, 2H), 6.92 (s, 1H), 6.88-6.80 (m, 1H), 6.61-6.43 (m, 2H), 6.41-6.29 (m, 1H), 5.84-5.75 (m, 1H), 5.60-5.51 (m, 1H), 4.18-4.12 (m, 1H), 3.88 (s, 3H), 3.26-3.16 (m, 3H), 3.16-3.03 (m, 5H), 2.88-2.73 (m, 4H), 2.37-2.29 (m, 1H), 2.25-2.19 (m, 7H), 1.63-1.50 (m, 2H); 665.3 [M + H]⁺ | 1.73 |
| 714 | 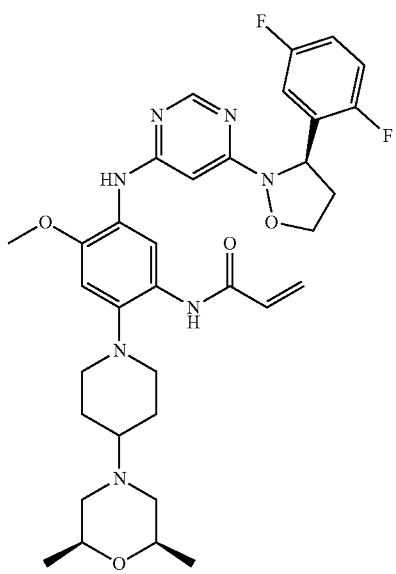 [SMILES: C=CC(=O)Nc1cc(Nc2cc(N3OCC[C@@H]3c3cc(F)ccc3F)ncn2)c(OC)cc1N1CCC(N2C[C@@H](C)O[C@@H](C)C2)CC1] | N-(5-((6-((R)-3-(2,5-difluorophenyl)isoxazolidine-2-yl)pyrimidine-4-yl)amino)-2-(4-((2S,6R)-2,6-dimethylmorpholino)piperidine-1-yl)-4-methoxyphenyl)acrylamide | ¹H NMR (400 MHz, Methanol-d₄) δ 8.30 (s, 1H), 8.18 (s, 1H), 7.28-7.21 (m, 1H), 7.20-7.11 (m, 1H), 7.09-6.99 (m, 1H), 6.92 (s, 1H), 6.62-6.48 (m, 2H), 6.42-6.32 (m, 1H), 5.86-5.72 (m, 2H), 4.18-4.11 (m, 1H), 4.03-3.94 (m, 1H), 3.89 (s, 3H), 3.80-3.72 (m, 2H), 3.21-3.14 (m, 2H), 3.10-3.05 (m, 2H), 2.87-2.77 (m, 2H), 2.59-2.51 (m, 1H), 2.35-2.20 (m, 1H), 2.12-2.06 (m, 3H), 1.85-1.72 (m, 2H), 1.22 (s, 3H), 1.20 (s, 3H); 650.3 [M + H]⁺ | 1.82 |

TABLE 1-continued

| Example Compound | Structure | Name of Compound | ¹H NMR[:]; MS [M + H]⁺ | UPLC r.t. (min) |
|---|---|---|---|---|
| 715 | 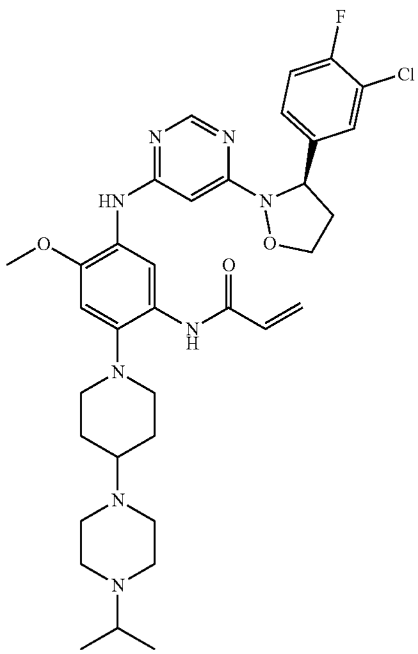 [SMILES: C=CC(=O)Nc1cc(Nc2cc(N3OCC[C@@H]3c3ccc(F)c(Cl)c3)ncn2)c(OC)cc1N1CCC(N2CCN(C(C)C)CC2)CC1] | N-(5-((6-((R)-3-(3-chloro-4-fluorophenyl)isoxazolidine-2-yl)pyrimidine-4-yl)amino)-2-(4-(4-isopropylpiperazine-1-yl)piperidine-1-yl)-4-methoxyphenyl)acrylamide | ¹H NMR (400 MHz, Methanol-d₄) δ 8.29 (s, 1H), 8.18 (s, 1H), 7.59-7.53 (m, 1H) 7.44-7.37 (m, 1H), 7.23 (t, J = 8.8 Hz, 1H), 6.92 (s, 1H), 6.62-6.50 (m, 1H), 6.45 (s, 1H), 6.42-6.30 (m, 1H), 5.86-5.76 (m, 1H), 5.56-5.49 (m, 1H), 4.18-4.13 (m, 1H), 3.98 (q, J = 8.0 Hz, 1H), 3.88 (s, 3H), 3.20-3.14 (m, 3H), 3.09-3.00 (m, 4H), 2.98-2.90 (m, 3H), 2.86-2.76 (m, 4H), 2.62-2.54 (m, 1H), 2.38-2.29 (m, 1H), 2.10-2.02 (m, 2H), 1.86-1.73 (m, 2H), 1.29 (s, 3H), 1.27 (s, 2H); 679.3 [M + H]⁺ | 1.54 |
| 716 | 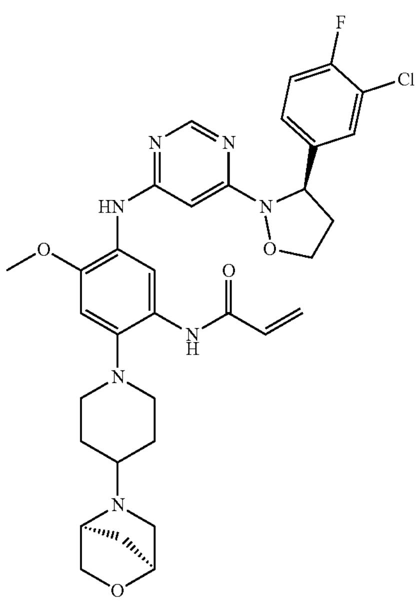 [SMILES: C=CC(=O)Nc1cc(Nc2cc(N3OCC[C@@H]3c3ccc(F)c(Cl)c3)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((R)-3-(3-chloro-4-fluorophenyl)isoxazolidine-2-yl)pyrimidine-4-yl)amino)-4-methoxyphenyl)acrylamide | ¹H NMR (400 MHz, Methanol-d₄) δ 8.29 (s, 1H), 8.18 (s, 1H), 7.59-7.50 (m, 1H), 7.49-7.35 (m, 1H), 7.23 (t, J = 8.8 Hz, 1H), 6.93 (s, 1H), 6.64-6.50 (m, 1H), 6.45 (s, 1H), 6.42-6.30 (m, 1H), 5.81 (d, J = 10.3 Hz, 1H), 5.58-5.48 (m, 1H), 4.18-4.13 (m, 3H), 3.98 (q, J = 8.0 Hz, 1H), 3.89 (s, 3H), 3.77-3.70 (m, 1H), 3.29-3.22 (m, 1H), 3.19-3.12 (m, 2H), 2.90-2.79, (m, 4H), 2.39-2.28 (m, 1H), 2.21-2.09 (m, 1H), 2.09-2.00 (m, 3H), 1.82-1.76 (m, 1H); 650.3 [M + H]⁺ | 2.27 |

TABLE 1-continued

| Example Compound | Structure | Name of Compound | ¹H NMR[[:]]; MS [M + H]⁺ | UPLC r.t. (min) |
|---|---|---|---|---|
| 717 | 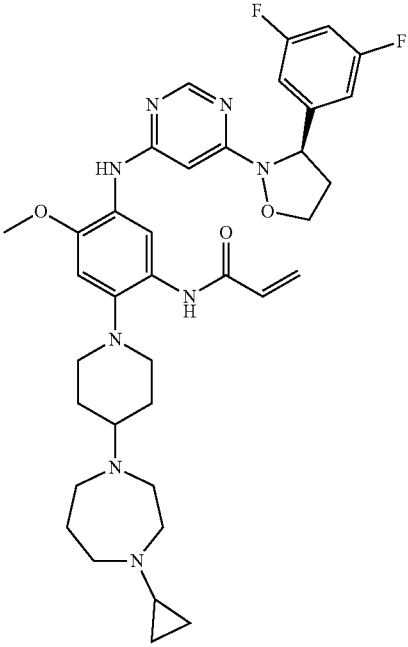 [SMILES: C=CC(=O)Nc1cc(Nc2cc(N3OCC[C@@H]3c3cc(F)cc(F)c3)ncn2)c(OC)cc1N1CCC(N2CCCN(C3CC3)CC2)CC1] | N-(2-(4-(4-cyclopropyl-1,4-diazepane-1-yl)piperidine-1-yl)-5-((6-((R)-3-(3,5-difluorophenyl)isoxazolidine-2-yl)pyrimidine-4-yl)amino)-4-methoxyphenyl)acrylamide | ¹H NMR (400 MHz, Methanol-d₄) δ 8.25 (s, 1H), 8.11 (s, 1H), 7.04-6.94 (m, 2H), 6.84 (s, 1H), 6.77 (tt, J = 2.5, 9.1 Hz, 1H), 6.51 (dd, J = 10.2, 17.0 Hz, 1H), 6.40 (s, 1H), 6.31 (d, J = 16.8 Hz, 1H), 5.75 (d, J = 10.3 Hz, 1H), 5.50 (dd, J = 4.8, 8.7 Hz, 1H), 4.09 (td, J = 4.2, 7.9 Hz, 1H), 3.93-3.85 (m, 1H), 3.82 (s, 3H), 3.21 (d, J = 5.4 Hz, 2H), 3.13 (ddq, J = 4.4, 8.7, 12.6 Hz, 4H), 3.04 (q, J = 5.1 Hz, 3H), 2.91 (t, J = 5.8 Hz, 2H), 2.76 (ddt, J = 5.1, 9.9, 14.4 Hz, 4H), 2.33-2.20 (m, 1H), 2.09-1.98 (m, 3H), 1.94 (dt, J = 5.3, 11.1 Hz, 3H), 0.51 (dd, J = 4.3, 6.4 Hz, 2H), 0.49-0.40 (m, 2H); 675.4 [M + H]⁺ | 2.07 |
| 718 | 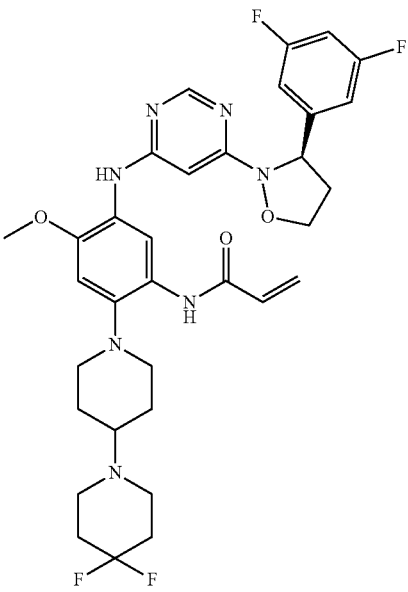 [SMILES: C=CC(=O)Nc1cc(Nc2cc(N3OCC[C@@H]3c3cc(F)cc(F)c3)ncn2)c(OC)cc1N1CCC(N2CCC(F)(F)CC2)CC1] | N-(2-(4,4-difluoro-[1,4'-bipiperidine]-1'-yl)-5-((6-((R)-3-(3,5-difluorophenyl)isoxazolidine-2-yl)pyrimidine-4-yl)amino)-4-methoxyphenyl)acrylamide | ¹H NMR (400 MHz, DMSO-d₆) δ 10.10 (s, 1H), 9.20 (s, 1H), 8.32 (s, 1H), 7.90 (s, 1H), 7.17 (tt, J = 9.2, 2.4 Hz, 1H), 7.10 (h, J = 4.7 Hz, 2H), 6.90 (s, 1H), 6.71 (dd, J = 17.0, 10.2 Hz, 1H), 6.25 (dd, J = 17.1, 1.9 Hz, 1H), 6.13 (s, 1H), 5.79-5.71 (m, 1H), 5.55 (dd, J = 8.6, 5.4 Hz, 1H), 4.04 (q, J = 7.7 Hz, 3H), 3.81 (s, 4H), 3.65 (d, J = 12.2 Hz, 3H), 3.41 (d, J = 21.8 Hz, 2H), 3.28-3.11 (m, 4H), 2.93 (tq, J = 12.0, 6.8, 5.7 Hz, 2H), 2.84-2.57 (m, 5H), 2.44-2.28 (m, 4H), 2.23 (d, J = 10.2 Hz, 2H), 2.08 (d, J = 9.8 Hz, 2H), ; 656.5 [M + H]⁺ | 1.52 |

TABLE 1-continued

| Example Compound | Structure | Name of Compound | ¹H NMR[:]; MS [M + H]⁺ | UPLC r.t. (min) |
|---|---|---|---|---|
| 719 | 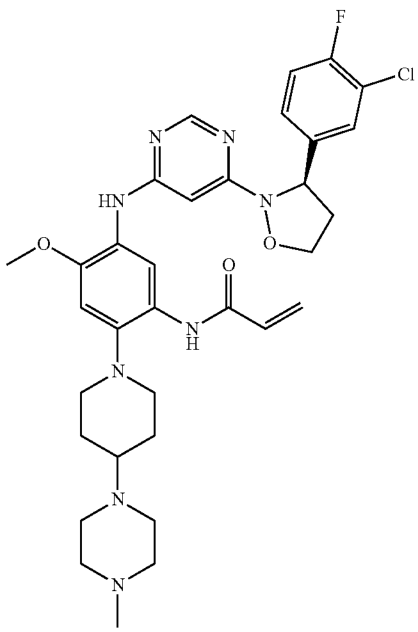 [SMILES: C=CC(=O)Nc1cc(Nc2cc(N3OCC[C@@H]3c3ccc(F)c(Cl)c3)ncn2)c(OC)cc1N1CCC(N2CCN(C)CC2)CC1] | N-(5-((6-((R)-3-(3-chloro-4-fluorophenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, Chloroform-d) δ 8.75 (s, 1H), 8.41 (s, 1H), 8.29 (d, J = 1.0 Hz, 1H), 7.50 (dd, J = 7.0, 2.2 Hz, 1H), 7.30 (ddd, J = 8.6, 4.6, 2.3 Hz, 1H), 7.09 (t, J = 8.7 Hz, 2H), 6.73 (s, 1H), 6.64 (s, 1H), 6.27 (dd, J = 16.9, 9.8 Hz, 1H), 5.74 (dd, J = 9.8, 1.8 Hz, 1H), 5.62 (dd, J = 8.7, 4.6 Hz, 1H), 5.29 (s, 1H), 4.14 (td, J = 8.0, 4.2 Hz, 1H), 3.83 (s, 4H), 3.10-3.00 (m, 3H), 2.80-2.67 (m, 5H), 2.56-2.46 (m, 2H), 2.46 (s, 3H), 2.31 (dtd, J = 12.5, 8.1, 4.6 Hz, 2H), 2.03 (s, 8H), 1.76-1.63 (m, 3H), ; 651.5 [M + H]⁺ | 1.51 |
| 720 | 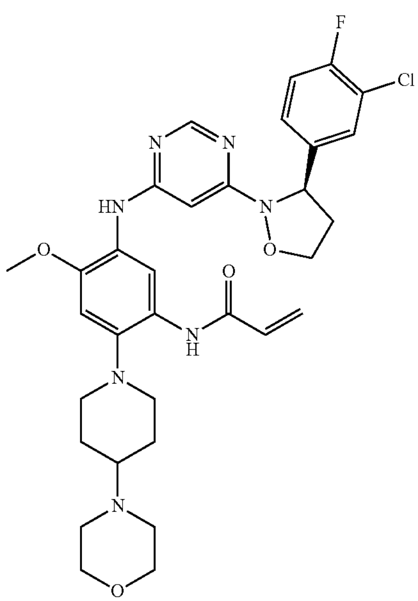 [SMILES: C=CC(=O)Nc1cc(Nc2cc(N3OCC[C@@H]3c3ccc(F)c(Cl)c3)ncn2)c(OC)cc1N1CCC(N2CCOCC2)CC1] | N-(5-((6-((R)-3-(3-chloro-4-fluorophenyl)isoxazolidine-2-yl)pyrimidine-4-yl)amino)-4-methoxy-2-(4-morpholinopiperidine-1-yl)phenyl)acrylamide | 638.5 [M + H]⁺ | 1.58 |

TABLE 1-continued

| Example Compound | Structure | Name of Compound | $^1$H NMR[[:]]; MS [M + H]$^+$ | UPLC r.t. (min) |
|---|---|---|---|---|
| 721 | 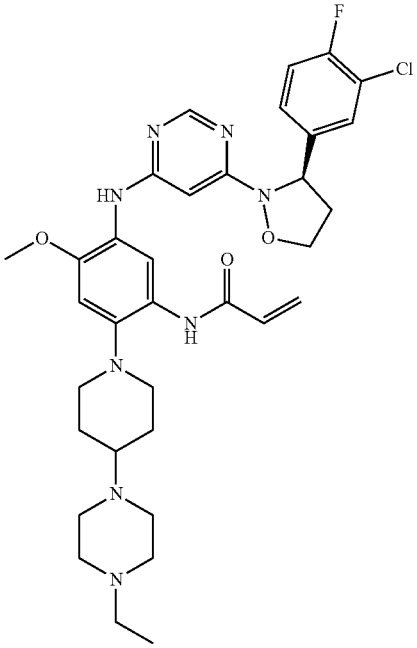 | N-(5-((6-((R)-3-(3-chloro-4-fluorophenyl)isoxazolidine-2-yl)pyrimidine-4-yl)amino)-2-(4-(4-ethylpiperazine-1-yl)piperidine-1-yl)-4-methoxyphenyl)acrylamide | $^1$H NMR (400 MHz, DMSO-d$_6$) δ 10.05 (s, 1H), 9.22 (s, 1H), 8.31 (s, 1H), 7.58 (dd, J = 7.1, 2.0 Hz, 1H), 7.46-7.36 (m, 3H), 6.89 (d, J = 12.7 Hz, 1H), 6.72 (dd, J = 16.8, 10.2 Hz, 1H), 6.25 (dd, J = 17.0, 1.9 Hz, 1H), 6.13 (s, 1H), 5.80-5.72 (m, 1H), 5.54 (dd, J = 8.5, 5.4 Hz, 1H), 4.04 (q, J = 7.7 Hz, 5H), 3.81 (s, 3H), 3.67 (s, 4H), 3.57 (d, J = 4.7 Hz, 3H), 3.46 (d, J = 9.0 Hz, 1H), 3.31-3.15 (m, 5H), 2.98-2.74 (m, 5H), 2.39-2.24 (m, 2H), 2.24-2.01 (m, 5H), 1.29 (t, J = 7.2 Hz, 4H), ; 665.6 [M + H]$^+$ | 1.52 |
| 722 | 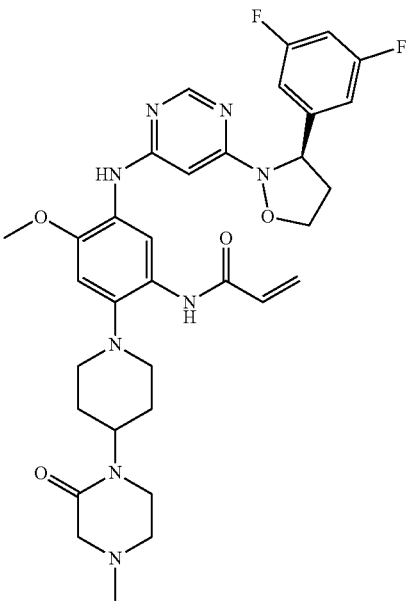 [SMILES: C=CC(=O)Nc1cc(Nc2cc(N3OCC[C@@H]3c3cc(F)cc(F)c3)ncn2)c(OC)cc1N1CCC(N2CCN(C)CC2=O)CC1] | N-(5-((6-((R)-3-(3,5-difluorophenyl)isoxazolidine-2-yl)pyrimidine-4-yl)amino)-4-methoxy-2-(4-(4-methyl-2-oxopiperazine-1-yl)piperidine-1-yl)phenyl)acrylamide | $^1$H NMR (400 MHz, DMSO-d$_6$) δ 12.15 (s, 1H), 10.15 (s, 1H), 8.34 (s, 1H), 7.97 (s, 1H), 7.16 (tt, J = 9.3, 2.4 Hz, 1H), 7.12-6.99 (m, 3H), 6.75 (dd, J = 16.9, 10.3 Hz, 1H), 6.30-6.21 (m, 1H), 5.80-5.74 (m, 1H), 5.56 (dd, J = 8.6, 5.4 Hz, 1H), 4.04 (q, J = 7.7 Hz, 1H), 3.83 (s, 4H), 3.77-3.66 (m, 2H), 3.60 (s, 1H), 3.56 (s, 2H), 3.38 (s, 2H), 3.22 (s, 3H), 3.08 (d, J = 10.2 Hz, 2H), 2.94 (ttd, J = 12.2, 7.5, 4.6 Hz, 2H), 2.81 (s, 3H), 2.37-2.08 (m, 3H), 1.65 (s, 2H), ; 649.5 [M + H]$^+$ | 1.59 |

TABLE 1-continued

| Example Compound | Structure | Name of Compound | $^1$H NMR[[:]]; MS [M + H]$^+$ | UPLC r.t. (min) |
|---|---|---|---|---|
| 723 | 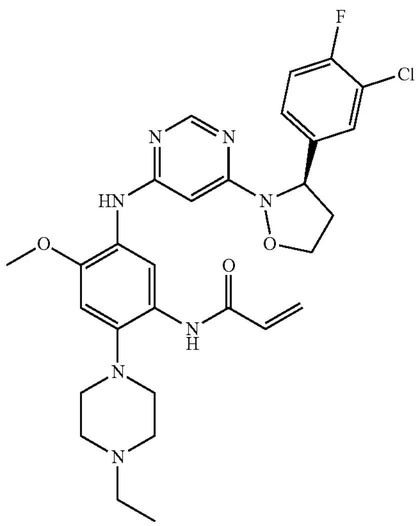 [SMILES: C=CC(=O)Nc1cc(Nc2cc(N3OCC[C@@H]3c3ccc(F)c(Cl)c3)ncn2)c(OC)cc1N1CCN(CC)CC1] | N-(5-((6-((R)-3-(3-chloro-4-fluorophenyl)isoxazolidine-2-yl)pyrimidine-4-yl)amino)-2-(4-ethylpiperazine-1-yl)-4-methoxyphenyl)acrylamide | $^1$H NMR (400 MHz, MeOD) δ 8.34 (s, 1H), 8.18 (s, 1H), 7.57 (dd, J = 7.1, 2.1 Hz, 1H), 7.44-7.37 (m, 1H), 7.23 (t, J = 8.9 Hz, 1H), 6.96 (s, 1H), 6.59-6.43 (m, 2H), 6.36 (dd, J = 17.0, 1.5 Hz, 1H), 5.81 (d, J = 10.3 Hz, 1H), 5.55 (dd, J = 8.3, 4.7 Hz, 1H), 4.16 (td, J = 7.8, 4.1 Hz, 1H), 4.03-3.93 (m, 1H), 3.90 (s, 3H), 3.00 (t, J = 4.7 Hz, 4H), 2.81 (ddd, J = 25.7, 16.6, 12.7 Hz, 5H), 2.59 (q, J = 7.2 Hz, 2H), 2.41-2.27 (m, 1H), 1.20 (t, J = 7.2 Hz, 3H), ; 582.2 [M + H]$^+$ | 1.16 |
| 724 | 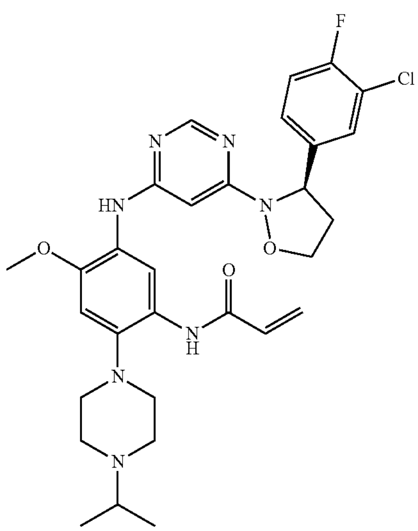 [SMILES: C=CC(=O)Nc1cc(Nc2cc(N3OCC[C@@H]3c3ccc(F)c(Cl)c3)ncn2)c(OC)cc1N1CCN(C(C)C)CC1] | N-(5-((6-((R)-3-(3-chloro-4-fluorophenyl)isoxazolidine-2-yl)pyrimidine-4-yl)amino)-2-(4-isopropylpiperazine-1-yl)-4-methoxyphenyl)acrylamide | $^1$H NMR (400 MHz, MeOD) δ 8.34 (s, 1H), 8.18 (s, 1H), 7.57 (dd, J = 7.1, 2.1 Hz, 1H), 7.44-7.37 (m, 1H), 7.23 (t, J = 8.9 Hz, 1H), 6.95 (s, 1H), 6.59-6.43 (m, 2H), 6.36 (dd, J = 17.0, 1.5 Hz, 1H), 5.81 (d, J = 10.2 Hz, 1H), 5.55 (dd, J = 8.4, 4.7 Hz, 1H), 4.16 (td, J = 7.9, 4.3 Hz, 1H), 4.01-3.94 (m, 1H), 3.89 (d, J = 5.2 Hz, 3H), 3.07-2.95 (m, 4H), 2.82 (p, J = 12.5 Hz, 6H), 2.34 (ddd, J = 15.6, 7.9, 4.1 Hz, 1H), 1.17 (t, J = 10.7 Hz, 6H), ; 596.4 [M + H]$^+$ | 1.25 |

TABLE 1-continued

| Example Compound | Structure | Name of Compound | ¹H NMR[:]; MS [M + H]⁺ | UPLC r.t. (min) |
|---|---|---|---|---|
| 725 | 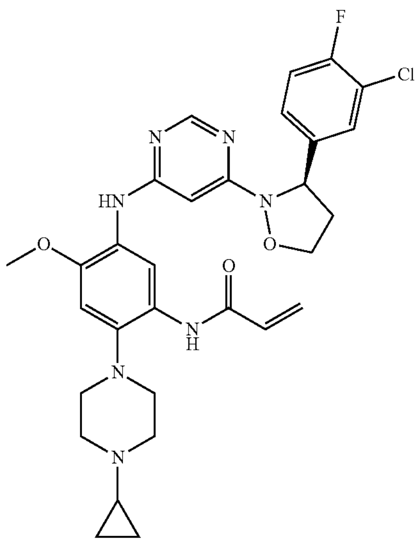 [SMILES: C=CC(=O)Nc1cc(Nc2cc(N3OCC[C@@H]3c3ccc(F)c(Cl)c3)ncn2)c(OC)cc1N1CCN(C2CC2)CC1] | N-(5-((6-((R)-3-(3-chloro-4-fluorophenyl)isoxazolidine-2-yl)pyrimidine-4-yl)amino)-2-(4-cyclopropylpiperazine-1-yl)-4-methoxyphenyl)acrylamide | ¹H NMR (400 MHz, MeOD) δ 8.34 (s, 1H), 8.18 (d, J = 0.7 Hz, 1H), 7.57 (dd, J = 7.1, 2.1 Hz, 1H), 7.45-7.38 (m, 1H), 7.23 (t, J = 8.8 Hz, 1H), 6.92 (s, 1H), 6.60-6.44 (m, 2H), 6.37 (dd, J = 17.0, 1.5 Hz, 1H), 5.82 (dd, J = 10.2, 1.3 Hz, 1H), 5.55 (dd, J = 8.5, 4.7 Hz, 1H), 4.16 (td, J = 7.9, 4.2 Hz, 1H), 3.98 (dd, J = 16.1, 8.1 Hz, 1H), 3.89 (s, 3H), 2.98-2.75 (m, 9H), 2.39-2.27 (m, 1H), 1.85-1.76 (m, 1H), 0.61-0.44 (m, 4H), ; 594.3 [M + H]⁺ | 1.30 |
| 726 | 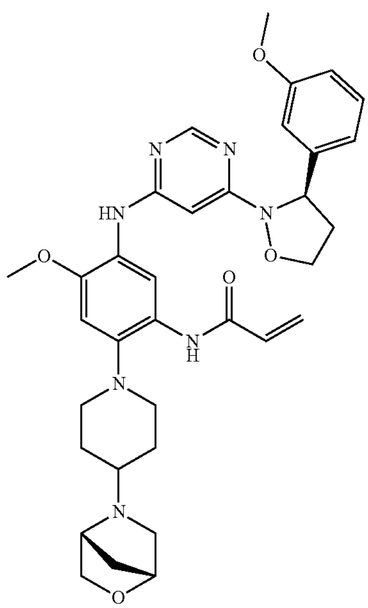 [SMILES: C=CC(=O)Nc1cc(Nc2cc(N3OCC[C@@H]3c3cccc(OC)c3)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-4-methoxy-5-((6-((R)-3-(3-methoxyphenyl)isoxazolidine-2-yl)pyrimidine-4-yl)amino)phenyl)acrylamide | ¹H NMR (400 MHz, DMSO-d₆) δ 9.75 (s, 1H), 9.20 (d, J = 29.9 Hz, 1H), 8.28 (s, 1H), 7.88 (d, J = 12.9 Hz, 1H), 7.28 (t, J = 7.9 Hz, 1H), 6.95-6.83 (m, 4H), 6.65-6.53 (m, 1H), 6.28-6.20 (m, 1H), 6.06 (s, 1H), 5.76 (d, J = 10.3 Hz, 1H), 5.51-5.42 (m, 1H), 4.71 (s, 1H), 4.62 (d, J = 27.3 Hz, 1H), 4.28 (d, J = 5.5 Hz, 1H), 4.21 (d, J = 10.2 Hz, 1H), 4.02 (s, 1H), 3.80 (s, 3H), 3.75 (s, 3H), 3.71 (d, J = 9.7 Hz, 1H), 3.47 (t, J = 9.4 Hz, 2H), 3.26-3.16 (m, 2H), 2.91-2.76 (m, 2H), 2.76-2.65 (m, 1H), 2.36-2.24 (m, 2H), 2.09 (d, J = 14.7 Hz, 4H); 628.6 [M + H]⁺ | 1.41 |

TABLE 1-continued

| Example Compound | Structure | Name of Compound | ¹H NMR[[:]]; MS [M + H]⁺ | UPLC r.t. (min) |
|---|---|---|---|---|
| 727 | 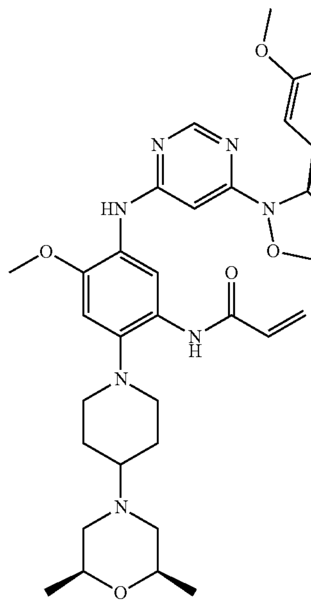 | N-(2-(4-((2S,6R)-2,6-dimethylmorpholino)piperidine-1-yl)-4-methoxy-5-((6-((R)-3-(3-methoxyphenyl)isoxazolidine-2-yl)pyrimidine-4-yl)amino)phenyl)acrylamide | ¹H NMR (400 MHz, DMSO-$d_6$) δ 9.79 (s, 1H), 9.13 (s, 1H), 8.28 (s, 1H), 7.91 (s, 1H), 7.28 (t, J = 7.9 Hz, 1H), 6.94-6.85 (m, 4H), 6.67 (dd, J = 17.0, 10.2 Hz, 1H), 6.25 (dd, J = 17.0, 1.9 Hz, 1H), 6.04 (s, 1H), 5.76 (d, J = 10.2 Hz, 1H), 5.51-5.42 (m, 1H), 4.28 (t, J = 6.1 Hz, 2H), 4.09 (s, 2H), 3.79 (s, 3H), 3.75 (s, 3H), 3.47 (d, J = 11.7 Hz, 2H), 3.27 (s, 1H), 3.21 (d, J = 12.0 Hz, 2H), 2.95-2.86 (m, 1H), 2.72 (dt, J = 30.7, 11.2 Hz, 4H), 2.35-2.27 (m, 1H), 2.22 (d, J = 11.6 Hz, 2H), 2.10-1.98 (m, 2H), 1.18 (s, 3H), 1.16 (s, 3H); 644.6 [M + H]⁺ | 1.55 |
| 728 | 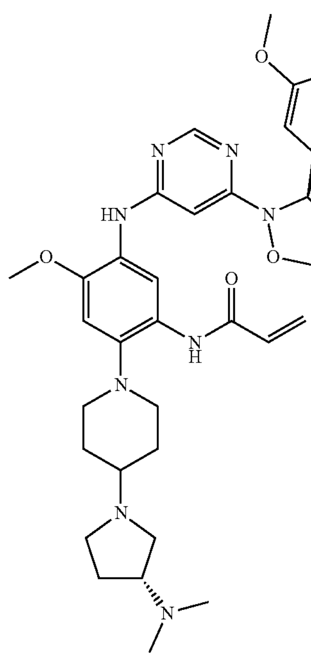 | N-(2-(4-((R)-3-(dimethylamino)pyrolidine-1-yl)piperidine-1-yl)-4-methoxy-5-((6-((R)-3-(3-methoxyphenyl)isoxazolidine-2-yl)pyrimidine-4-yl)amino)phenyl)acrylamide | ¹H NMR (400 MHz, DMSO-$d_6$) δ 9.51 (s, 1H), 9.21 (s, 1H), 8.26 (s, 1H), 7.95 (s, 1H), 7.28 (t, J = 7.9 Hz, 1H), 6.95-6.89 (m, 3H), 6.85 (dd, J = 8.3, 2.6 Hz, 1H), 6.64 (dd, J = 17.0, 10.2 Hz, 1H), 6.24 (dd, J = 17.0, 1.9 Hz, 1H), 6.13 (s, 1H), 5.75 (d, J = 10.3 Hz, 1H), 5.48 (t, J = 6.8 Hz, 1H), 4.30-4.20 (m, 1H), 3.98 (s, 1H), 3.80 (s, 3H), 3.75 (s, 3H), 3.63 (d, J = 4.1 Hz, 2H), 3.37 (s, 2H), 3.23-3.18 (m, 2H), 2.84 (s, 8H), 2.78-2.70 (m, 2H), 2.39 (dd, J = 9.7, 7.5 Hz, 1H), 2.29 (dd, J = 12.7, 5.0 Hz, 1H), 2.22-2.13 (m, 2H), 2.12-2.00 (m, 2H); 643.6 [M + H]⁺ | 1.36 |

TABLE 1-continued

| Example Compound | Structure | Name of Compound | ¹H NMR[[:]]; MS [M + H]⁺ | UPLC r.t. (min) |
|---|---|---|---|---|
| 729 | 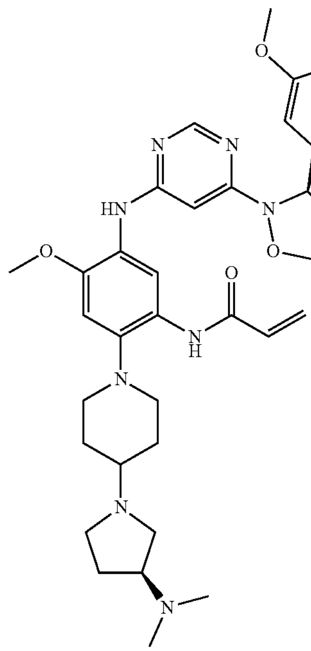 | N-(2-(4-((S)-3-(dimethylamino)pyrolidine-1-yl)piperidine-1-yl)-4-methoxy-5-((6-((R)-3-(3-methoxyphenyl)isoxazolidine-2-yl)pyrimidine-4-yl)amino)phenyl)acrylamide | ¹H NMR (400 MHz, DMSO-d₆) δ 9.69 (s, 1H), 9.22 (s, 1H), 8.27 (s, 1H), 7.91 (s, 1H), 7.28 (t, J = 7.9 Hz, 1H), 6.92 (t, J = 6.3 Hz, 3H), 6.85 (dd, J = 8.3, 2.6 Hz, 1H), 6.64 (dd, J = 17.0, 10.2 Hz, 1H), 6.24 (dd, J = 16.9, 1.9 Hz, 1H), 6.08 (s, 1H), 5.76 (d, J = 10.3 Hz, 1H), 5.52-5.42 (m, 1H), 4.30-4.24 (m, 1H), 4.01-3.99 (m, 1H), 3.80 (s, 3H), 3.75 (s, 3H), 3.57-3.48 (m, 2H), 3.44-3.28 (m, 2H), 3.25-3.19 (m, 2H), 2.84 (s, 8H), 2.80-2.69 (m, 2H), 2.45-2.36 (m, 1H), 2.34-2.27 (m, 1H), 2.16 (d, J = 19.9 Hz, 2H), 2.07 (d, J = 16.0 Hz, 2H); 643.6 [M + H]⁺ | 1.36 |
| 730 | 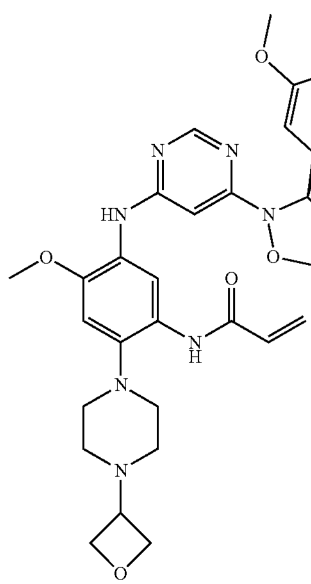 | N-(4-methoxy-5-((6-((R)-3-(3-methoxyphenyl)isoxazolidine-2-yl)pyrimidine-4-yl)amino)-2-(4-(oxetane-3-yl)piperazine-1-yl)phenyl)acrylamide | ¹H NMR (400 MHz, Methanol-d4) δ 8.29 (s, 1H), 8.14 (s, 1H), 7.24 (t, J = 8.1 Hz, 1H), 6.99 (dd, J = 5.0, 2.9 Hz, 2H), 6.92 (d, J = 8.1 Hz, 1H), 6.82-6.78 (m, 1H), 6.56-6.46 (m, 1H), 6.39 (s, 1H), 6.37-6.30 (m, 1H), 5.81-5.76 (m, 1H), 5.49-5.45 (m, 1H), 4.74 (t, J = 6.7 Hz, 2H), 4.66 (t, J = 6.2 Hz, 2H), 4.13 (td, J = 7.8, 4.4 Hz, 1H), 3.96 (q, J = 7.9 Hz, 1H), 3.90 (s, 1H), 3.86 (s, 3H), 3.78 (s, 3H), 3.69-3.61 (m, 1H), 2.99 (t, J = 4.8 Hz, 4H), 2.78 (dtd, J = 12.3, 8.0, 4.4 Hz, 1H), 2.60 (s, 3H), 2.37-2.28 (m, 1H); 588.5 [M + H]⁺ | 1.11 |

TABLE 1-continued

| Example Compound | Structure | Name of Compound | ¹H NMR[:]; MS [M + H]⁺ | UPLC r.t. (min) |
|---|---|---|---|---|
| 731 | 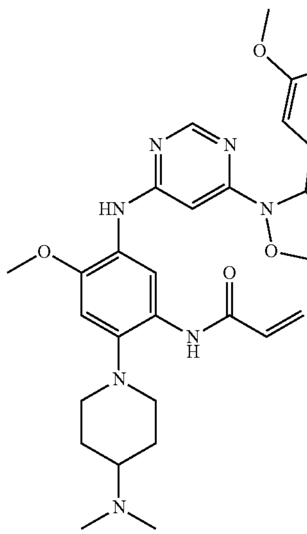 | N-(2-(4-(dimethylamino)piperidine-1-yl)-4-methoxy-5-((6-((R)-3-(3-methoxyphenyl)isoxazolidine-2-yl)pyrimidine-4-yl)amino)phenyl)acrylamide | ¹H NMR (400 MHz, Chloroform-d) δ 8.82 (s, 1H), 8.44 (s, 1H), 8.33 (s, 1H), 7.24 (d, J = 7.9 Hz, 2H), 7.06-7.01 (m, 2H), 6.79 (dd, J = 8.1, 2.5 Hz, 1H), 6.73 (s, 1H), 6.66 (s, 1H), 6.37 (d, J = 16.4 Hz, 1H), 6.30 (dd, J = 16.5, 9.8 Hz, 1H), 5.75 (dd, J = 9.5, 2.0 Hz, 1H), 5.66 (dd, J = 8.7, 4.4 Hz, 1H), 4.15 (td, J = 8.0, 4.4 Hz, 1H), 4.05 (q, J = 8.2 Hz, 1H), 3.84 (s, 3H), 3.80 (s, 3H), 3.09 (d, J = 11.4 Hz, 2H), 2.82-2.70 (m, 4H), 2.49 (s, 6H), 2.41-2.35 (m, 1H), 2.12 (s, 2H), 1.80 (dd, J = 12.0, 4.0 Hz, 2H); 574.5 [M + H]⁺ | 1.23 |
| 732 | 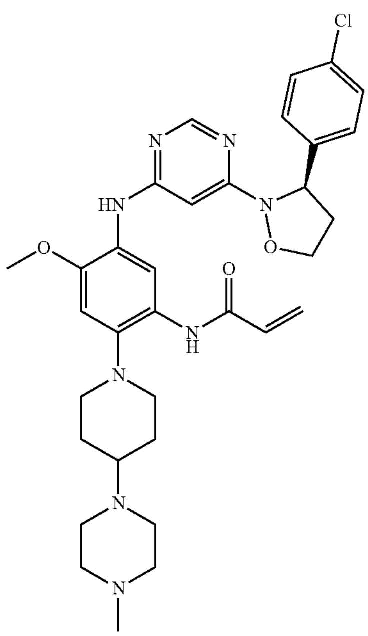 [SMILES: C=CC(=O)Nc1cc(Nc2cc(N3OCC[C@@H]3c3ccc(Cl)cc3)ncn2)c(OC)cc1N1CCC(N2CCN(C)CC2)CC1] | N-(5-((6-((R)-3-(4-chlorophenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, Methanol-d₄) δ 8.23 (s, 1H), 8.06 (s, 1H), 7.26 (dd, J = 37.4, 8.4 Hz, 4H), 6.77 (s, 1H), 6.35 (d, J = 16.7 Hz, 1H), 5.41 (dd, J = 8.4, 4.6 Hz, 1H), 4.01 (dd, J = 11.9, 7.6 Hz, 1H), 3.86 (d, J = 7.9 Hz, 1H), 3.74 (s, 3H), 3.44 (s, 1H), 3.21 (dt, J = 3.2, 1.6 Hz, 2H), 3.09-2.89 (m, 8H), 2.71-2.60 (m, 4H), 2.54 (s, 1H), 2.19 (ddd, J = 17.9, 12.7, 6.7 Hz, 1H), 1.91 (d, J = 11.7 Hz, 2H); 633.6 [M + H]⁺ | 1.20 |

TABLE 1-continued

| Example Compound | Structure | Name of Compound | ¹H NMR[[:]]; MS [M + H]⁺ | UPLC r.t. (min) |
|---|---|---|---|---|
| 733 | 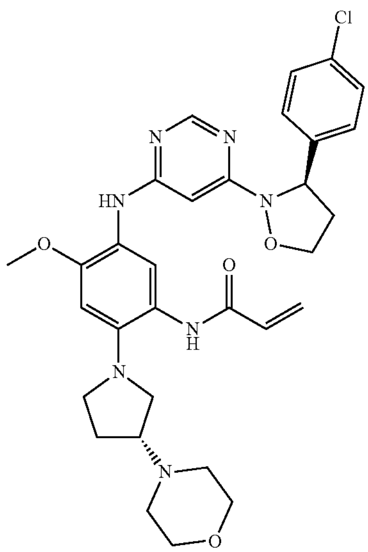 [SMILES: C=CC(=O)Nc1cc(Nc2cc(N3OCC[C@@H]3c3ccc(Cl)cc3)ncn2)c(OC)cc1N1CC[C@@H](N2CCOCC2)C1] | N-(5-((6-((R)-3-(4-chlorophenyl)isoxazolidine-2-yl)pyrimidine-4-yl)amino)-4-methoxy-2-((R)-3-morpholinopyrrolidine-1-yl)phenyl)acrylamide | ¹H NMR (400 MHz, CDCl₃) δ 8.68 (s, 1H), 8.35 (s, 1H), 8.12 (s, 1H), 7.40 (d, J = 8.4 Hz, 2H), 7.30 (d, J = 8.5 Hz, 2H), 6.90 (s, 1H), 6.75 (s, 1H), 6.67 (s, 1H), 6.31 (dt, J = 16.9, 13.3 Hz, 2H), 5.74 (d, J = 10.8 Hz, 1H), 5.66 (dd, J = 8.5, 4.5 Hz, 1H), 4.18-4.10 (m, 1H), 4.06 (dd, J = 15.7, 7.8 Hz, 1H), 3.83 (s, 3H), 3.76 (t, J = 4.5 Hz, 4H), 3.26-3.04 (m, 4H), 3.03-2.93 (m, 1H), 2.74 (ddd, J = 16.3, 7.9, 4.0 Hz, 1H), 2.63-2.43 (m, 4H), 2.38-2.28 (m, 1H), 2.18 (dd, J = 12.1, 7.5 Hz, 1H), 1.94 (dt, J = 19.8, 7.8 Hz, 1H), 1.25 (s, 1H); 606.4 [M + H] | 1.17 |
| 734 | 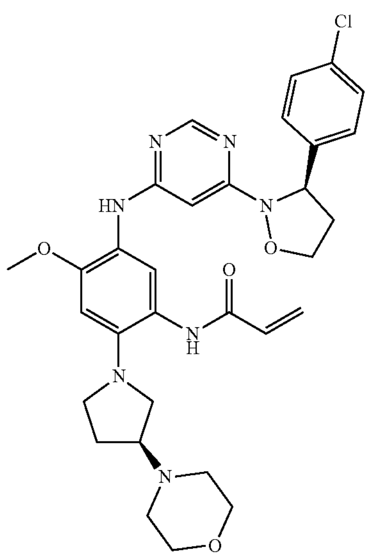 [SMILES: C=CC(=O)Nc1cc(Nc2cc(N3OCC[C@@H]3c3ccc(Cl)cc3)ncn2)c(OC)cc1N1CC[C@H](N2CCOCC2)C1] | N-(5-((6-((R)-3-(4-chlorophenyl)isoxazolidine-2-yl)pyrimidine-4-yl)amino)-4-methoxy-2-((S)-3-morpholinopyrrolidine-1-yl)phenyl)acrylamide | ¹H NMR (400 MHz, Methanol-d₄) δ 8.00 (s, 1H), 7.55 (s, 1H), 7.27 (dd, J = 36.0, 8.5 Hz, 4H), 6.54 (s, 1H), 6.41 (dd, J = 17.0, 10.2 Hz, 1H), 6.24 (dd, J = 17.0, 1.4 Hz, 1H), 6.18 (s, 1H), 5.67 (dd, J = 10.2, 1.4 Hz, 1H), 5.40 (dd, J = 8.4, 4.6 Hz, 1H), 4.00 (dt, J = 7.8, 3.9 Hz, 1H), 3.81 (q, J = 7.9 Hz, 1H), 3.74 (s, 3H), 3.63 (t, J = 4.6 Hz, 4H), 3.27-3.12 (m, 11H), 2.88-2.79 (m, 1H), 2.72-2.61 (m, 1H), 2.56-2.36 (m, 4H), 2.25-2.15 (m, 1H), 2.14-2.05 (m, 1H), 1.84-1.72 (m, 1H); 606.5 [M + H]⁺ | 1.18 |

TABLE 1-continued

| Example Compound | Structure | Name of Compound | ¹H NMR[[:]]; MS [M + H]⁺ | UPLC r.t. (min) |
|---|---|---|---|---|
| 735 | 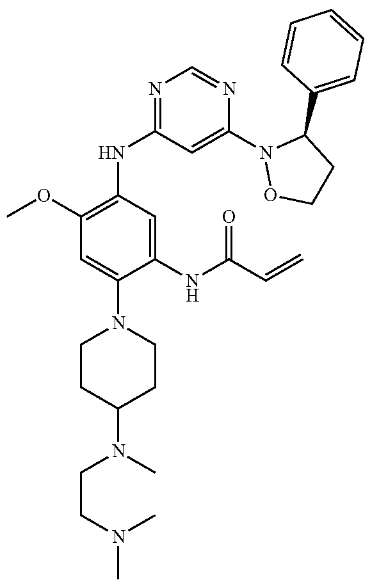 [SMILES: C=CC(=O)Nc1cc(Nc2cc(N3OCC[C@@H]3c3ccccc3)ncn2)c(OC)cc1N1CCC(N(C)CCN(C)C)CC1] | N-(2-(4-((2-(dimethylamino)ethyl)(methyl)amino)piperidine-1-yl)-4-methoxy-5-((6-((R)-3-phenylisoxazolidine-2-yl)pyrimidine-4-yl)amino)phenyl)acrylamide | ¹H NMR (400 MHz, Chloroform-d) δ 8.88 (s, 1H), 0 8.47 (s, 1H), 8.36 (s, 1H), 7.46 (d, J = 7.6 Hz, 2H), 7.33 (t, J = 7.5 Hz, 2H), 7.25 (d, J = 7.3 Hz, 1H), 6.95 (s, 1H), 6.75 (s, 1H), 6.68 (d, J = 6.9 Hz, 1H), 6.34 (d, J = 1.8 Hz, 1H), 6.29 (d, J = 9.8 Hz, 1H), 5.75 (dd, J = 9.7, 1.8 Hz, 1H), 5.70 (dd, J = 8.7, 4.5 Hz, 1H), 4.14 (dd, J = 8.0, 4.5 Hz, 1H), 4.07 (d, J = 7.9 Hz, 1H), 3.83 (s, 3H), 3.57 (s, 2H), 3.05 (d, J = 11.7 Hz, 2H), 2.78-2.65 (m, 4H), 2.51 (q, J = 8.1, 7.0 Hz, 3H), 2.35 (d, J = 14.5 Hz, 9H), 1.98 (d, J = 12.7 Hz, 2H), 1.75-1.64 (m, 2H), ; 601.6 [M + H]⁺ | 1.35 |
| 736 | 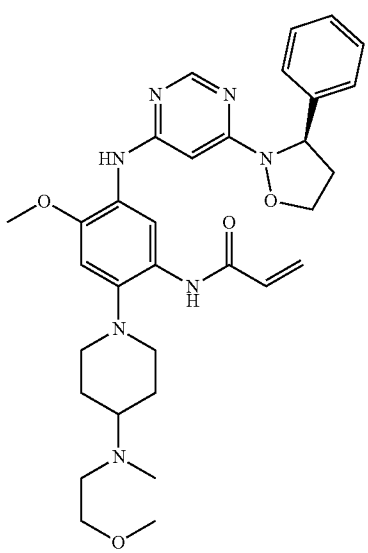 [SMILES: C=CC(=O)Nc1cc(Nc2cc(N3OCC[C@@H]3c3ccccc3)ncn2)c(OC)cc1N1CCC(N(C)CCOC)CC1] | N-(4-methoxy-2-(4-((2-methoxyethyl)(methyl)amino)piperidine-1-yl)-5-((6-((R)-3-phenylisoxazolidine-2-yl)pyrimidine-4-yl)amino)phenyl)acrylamide | ¹H NMR (400 MHz, DMSO-d₆) δ 10.01 (s, 1H), 9.17 (s, 1H), 8.30 (s, 1H), 7.93 (s, 1H), 7.37 (m, 4H), 7.30 (m, 1H), 6.87 (m, 1H), 6.76 (dd, J = 17.0, 10.2 Hz, 1H), 6.25 (dd, J = 17.0, 2.0 Hz, 1H), 6.04 (s, 1H), 5.76 (dd, J = 10.1, 2.0 Hz, 1H), 5.54-5.48 (m, 1H), 4.30 (dd, J = 7.7, 4.6 Hz, 1H), 4.06 (q, J = 7.7 Hz, 2H), 3.79 (s, 3H), 3.60 (m, 6H), 3.34 (s, 3H), 3.17 (s, 3H), 3.11 (m, 4H), 2.78 (m, 3H), 2.72 (m, 1H), ; 588.6 [M + H]⁺ | 1.87 |

TABLE 1-continued

| Example Compound | Structure | Name of Compound | ¹H NMR[[:]]; MS [M + H]⁺ | UPLC r.t. (min) |
|---|---|---|---|---|
| 737 | 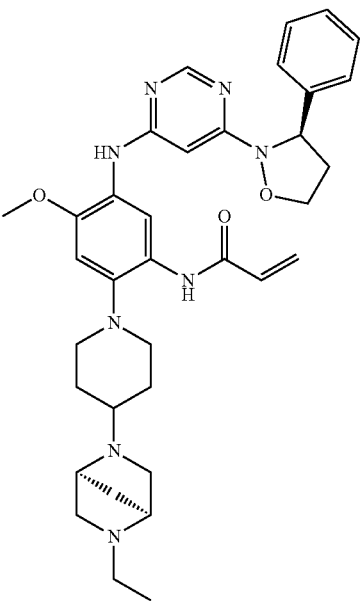 [SMILES: C=CC(=O)Nc1cc(Nc2cc(N3OCC[C@@H]3c3ccccc3)ncn2)c(OC)cc1N1CCC(N2C[C@@H]3C[C@H]2CN3CC)CC1] | N-(2-(4-((1S,4S)-5-ethyl-2,5-diazabicyclo[2.2.1]heptane-2-yl)piperidine-1-yl)-4-methoxy-5-((6-((R)-3-phenylisoxazolidine-2-yl)pyrimidine-4-yl)amino)phenyl) acrylamide | ¹H NMR (400 MHz, DMSO-d₆) δ 9.79 (s, 1H), 9.24 (s, 1H), 8.28 (s, 1H), 7.86 (s, 1H), 7.37 (m, 4H), 7.33-7.25 (m, 1H), 6.90 (d, J = 16.8 Hz, 1H), 6.66-6.51 (m, 1H), 6.24 (dd, J = 17.0, 1.8 Hz, 1H), 6.07 (m, 1H), 5.76 (d, J = 10.3 Hz, 1H), 5.51 (m, 1H), 4.56 (s, 1H), 4.29 (s, 1H), 4.04 (dd, J = 15.3, 7.5 Hz, 2H), 3.80 (s, 3H), 3.13 (m, 1H), 3.01 (m, 2H), 2.90 (m, 2H), 2.73 (m, 4H), 2.37-2.24 (m, 2H), 2.18-1.95 (m, 4H), 1.78-1.68 (m, 1H), 1.33-1.21 (m, 6H), ; 625.7 [M + H]⁺ | 1.76 |
| 738 | 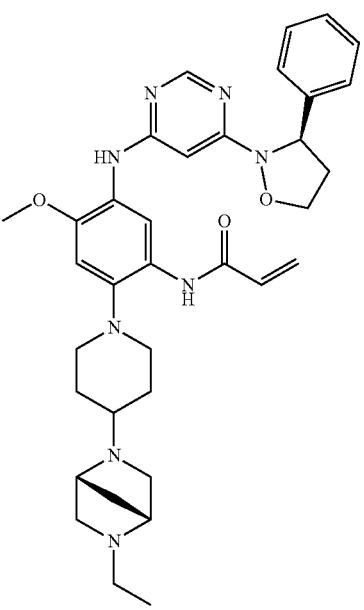 [SMILES: C=CC(=O)Nc1cc(Nc2cc(N3OCC[C@@H]3c3ccccc3)ncn2)c(OC)cc1N1CCC(N2C[C@H]3C[C@@H]2CN3CC)CC1] | N-(2-(4-((1R,4R)-5-ethyl-2,5-diazabicyclo[2.2.1]heptane-2-yl)piperidine-1-yl)-4-methoxy-5-((6-((R)-3-phenylisoxazolidine-2-yl)pyrimidine-4-yl)amino)phenyl) acrylamide | ¹H NMR (400 MHz, DMSO-d₆) δ 9.76 (s, 1H), 9.25 (s, 1H), 8.28 (s, 1H), 7.86 (s, 1H), 7.37 (m, 4H), 7.29 (m, 1H), 6.89 (d, J = 17.2 Hz, 1H), 6.57 (m, 1H), 6.24 (dd, J = 17.1, 1.8 Hz, 1H), 6.06 (m, 1H), 5.76 (d, J = 10.3 Hz, 1H), 5.50 (s, 1H), 4.61-4.51 (m, 1H), 4.34-4.25 (m, 1H), 4.04 (m, 2H), 3.80 (s, 3H), 3.17 (m, 1H), 3.02 (m, 2H), 2.91 (m, 2H), 2.74 (m, 4H), 2.34-2.29 (m, 2H), 2.06 (m, 4H), 1.73 (dt, J = 14.0, 6.5 Hz, 1H), 1.28 (m, 6H), ; 625.7 [M + H]⁺ | 1.80 |

TABLE 1-continued

| Example Compound | Structure | Name of Compound | ¹H NMR[[:]]; MS [M + H]⁺ | UPLC r.t. (min) |
|---|---|---|---|---|
| 739 | 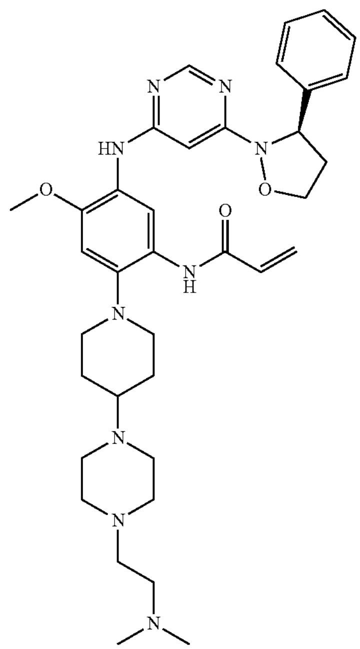 [SMILES: C=CC(=O)Nc1cc(Nc2cc(N3OCC[C@@H]3c3ccccc3)ncn2)c(OC)cc1N1CCC(N2CCN(CCN(C)C)CC2)CC1] | N-(2-(4-(4-(2-(dimethylamino)ethyl)piperazine-1-yl)piperidine-1-yl)-4-methoxy-5-((6-((R)-3-phenylisoxazolidine-2-yl)pyrimidine-4-yl)amino)phenyl)acrylamide | ¹H NMR (400 MHz, Chloroform-d) δ 8.87 (s, 1H), 8.44 (s, 1H), 8.36 (s, 1H), 7.46 (d, J = 7.5 Hz, 2H), 7.34 (t, J = 7.6 Hz, 2H), 7.24 (t, J = 7.3 Hz, 1H), 6.95 (s, 1H), 6.74 (s, 1H), 6.68 (s, 1H), 6.34 (s, 1H), 6.27 (s, 1H), 5.75 (s, 1H), 5.68 (s, 1H), 4.16 (s, 1H), 4.07 (s, 1H), 3.84 (s, 3H), 3.58 (s, 1H), 3.30 (t, J = 6.1 Hz, 1H), 3.23-3.13 (m, 1H), 3.04 (s, 2H), 2.95 (t, J = 6.9 Hz, 1H), 2.74 (m, 6H), 2.65 (m, 7H), 2.45 (s, 6H), 2.40 (s, 2H), 2.08 (d, J = 12.5 Hz, 2H), ; 656.7 [M + H]⁺ | 1.72 |
| 740 | 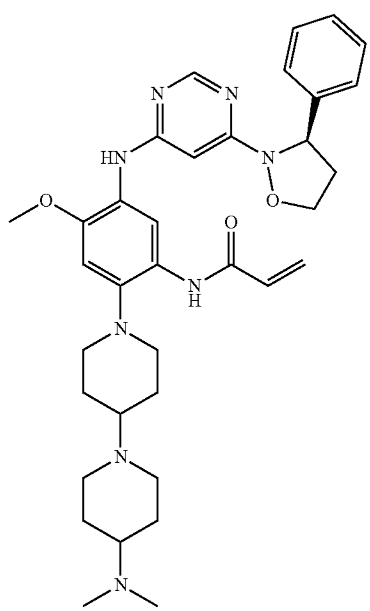 [SMILES: C=CC(=O)Nc1cc(Nc2cc(N3OCC[C@@H]3c3ccccc3)ncn2)c(OC)cc1N1CCC(N2CCC(N(C)C)CC2)CC1] | N-(2-(4-(dimethylamino)-[1,4'-bipiperidine]-1'-yl)-4-methoxy-5-((6-((R)-3-phenylisoxazolidine-2-yl)pyrimidine-4-yl)amino)phenyl)acrylamide | ¹H NMR (400 MHz, Chloroform-d) δ 8.86 (s, 1H), 8.45 (s, 1H), 8.36 (s, 1H), 7.46 (d, J = 7.4 Hz, 2H), 7.34 (t, J = 7.5 Hz, 2H), 7.24 (t, J = 7.4 Hz, 1H), 6.94 (s, 1H), 6.74 (s, 1H), 6.69 (s, 1H), 6.36 (dd, J = 17.0, 1.6 Hz, 1H), 6.25 (dd, J = 16.9, 10.0 Hz, 1H), 5.74 (dd, J = 9.9, 1.6 Hz, 1H), 5.70 (dd, J = 8.6, 4.5 Hz, 1H), 4.14 (dd, J = 7.9, 4.5 Hz, 1H), 4.07 (q, J = 8.0 Hz, 1H), 3.84 (s, 3H), 3.23 (t, J = 6.2 Hz, 2H), 2.75-2.70 (m, 2H), 2.33 (s, 6H), 2.28 (s, 3H), 2.08-2.02 (m, 2H), 1.89 (d, J = 12.4 Hz, 2H), 1.67 (t, J = 6.2 Hz, 2H), 1.58 (dd, J = 11.9, 3.5 Hz, 2H), 1.26 (s, 3H), 1.12 (t, J = 7.2 Hz, 2H), ; 627.6 [M + H] | 1.02 |

TABLE 1-continued

| Example Compound | Structure | Name of Compound | ¹H NMR[[:]]; MS [M + H]⁺ | UPLC r.t. (min) |
|---|---|---|---|---|
| 741 | 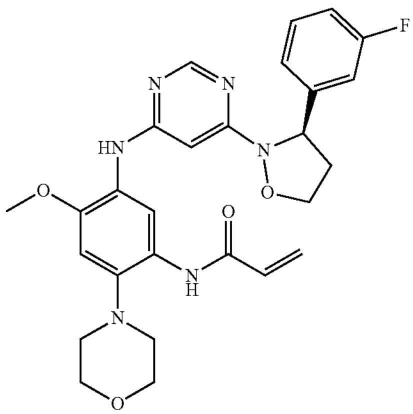 | N-(2-(4-(4-acetylpiperazine-1-yl)piperidine-1-yl)-5-((6-((R)-3-(3-fluorophenyl)isoxazolidine-2-yl)pyrimidine-4-yl)amino)-4-methoxyphenyl)acrylamide | ¹H NMR (400 MHz, DMSO-d$_6$) δ 11.60 (d, J = 51.9 Hz, 1H), 9.95 (s, 1H), 9.19 (s, 1H), 8.31 (d, J = 3.5 Hz, 1H), 7.90 (s, 1H), 7.42 (q, J = 7.3 Hz, 1H), 7.20 (t, J = 9.5 Hz, 2H), 7.13 (t, J = 8.7 Hz, 1H), 6.89 (s, 1H), 6.77-6.59 (m, 1H), 6.25 (d, J = 16.9 Hz, 1H), 6.09 (s, 1H), 5.76 (d, J = 10.2 Hz, 1H), 5.54 (t, J = 7.0 Hz, 1H), 4.50 (d, J = 13.8 Hz, 1H), 4.30 (s, 2H), 4.03 (d, J = 15.2 Hz, 3H), 3.80 (s, 3H), 3.71 (s, 1H), 3.49 (s, 2H), 3.37 (d, J = 16.8 Hz, 1H), 3.22 (d, J = 12.1 Hz, 3H), 2.97 (d, J = 28.0 Hz, 2H), 2.78 (s, 2H), 2.32 (q, J = 6.0 Hz, 1H), 2.19 (s, 2H), 2.06 (s, 3H), ; 645.6 [M + H]⁺ | 1.44 |
| 742 | 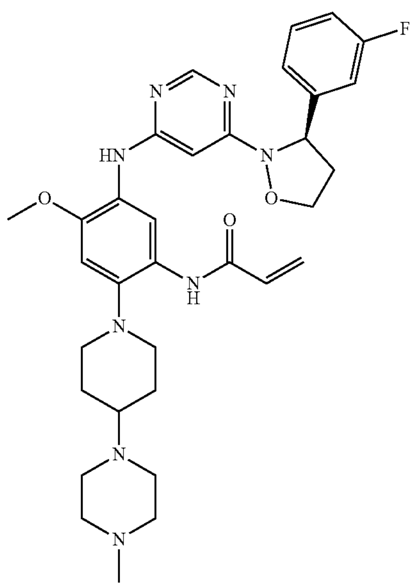 [SMILES: C=CC(=O)Nc1cc(Nc2cc(N3OCC[C@@H]3c3cccc(F)c3)ncn2)c(OC)cc1N1CCC(N2CCN(C)CC2)CC1] | N-(5-((6-((R)-3-(3-fluorophenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, DMSO-d$_6$) δ 9.88 (s, 1H), 9.18 (s, 1H), 8.30 (s, 1H), 7.92 (d, J = 15.7 Hz, 1H), 7.42 (td, J = 8.1, 6.2 Hz, 1H), 7.24-7.16 (m, 2H), 7.13 (td, J = 8.8, 2.6 Hz, 1H), 6.89 (s, 1H), 6.69 (dd, J = 16.9, 10.1 Hz, 1H), 6.25 (dd, J = 17.0, 2.0 Hz, 1H), 6.10 (s, 1H), 5.80-5.71 (m, 1H), 5.54 (dd, J = 8.5, 5.6 Hz, 1H), 4.28 (dd, J = 7.7, 4.2 Hz, 2H), 4.07-4.00 (m, 4H), 3.80 (s, 3H), 3.75 (d, J = 9.1 Hz, 2H), 3.57 (s, 2H), 3.22 (d, J = 11.9 Hz, 2H), 2.97-2.89 (m, 1H), 2.83 (d, J = 13.2 Hz, 3H), 2.80-2.70 (m, 2H), 2.32 (h, J = 7.5 Hz, 2H), 2.18 (s, 2H), 2.06 (d, J = 11.9 Hz, 2H), ; 617.6 [M + H]⁺ | 1.10 |
| 743 | 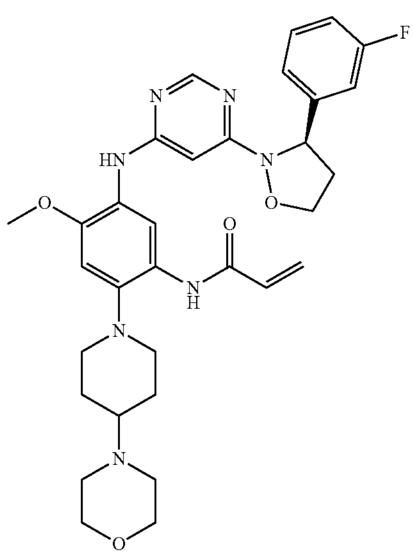 [SMILES: C=CC(=O)Nc1cc(Nc2cc(N3OCC[C@@H]3c3cccc(F)c3)ncn2)c(OC)cc1N1CCC(N2CCOCC2)CC1] | N-(5-((6-((R)-3-(3-fluorophenyl)isoxazolidine-2-yl)pyrimidine-4-yl)amino)-4-methoxy-2-(4-morpholinopiperidine-1-yl)phenyl)acrylamide | ¹H NMR (400 MHz, DMSO-d$_6$) δ 11.34 (s, 1H), 9.84 (s, 1H), 9.17 (s, 1H), 8.30 (s, 1H), 7.92 (s, 1H), 7.42 (td, J = 7.9, 6.1 Hz, 1H), 7.24-7.16 (m, 2H), 7.13 (td, J = 8.6, 2.7 Hz, 1H), 6.90 (s, 1H), 6.66 (dd, J = 17.0, 10.3 Hz, 1H), 6.25 (dd, J = 16.9, 1.9 Hz, 1H), 6.11 (s, 1H), 5.80-5.70 (m, 1H), 5.54 (t, J = 7.1 Hz, 1H), 4.31-4.26 (m, 2H), 4.03-3.94 (m, 4H), 3.81 (s, 3H), 3.45 (d, J = 12.0 Hz, 2H), 3.30 (s, 1H), 3.22 (d, J = 11.5 Hz, 2H), 3.14 (d, J = 11.6 Hz, 2H), 2.97-2.87 (m, 1H), 2.77 (t, J = 11.8 Hz, 2H), 2.32 (td, J = 13.0, 7.7 Hz, 1H), 2.20 (d, J = 11.7 Hz, 2H), 2.02 (d, J = 9.9 Hz, 2H), ; 604.6 [M + H]⁺ | 1.13 |

TABLE 1-continued

| Example Compound | Structure | Name of Compound | ¹H NMR[[:]]; MS [M + H]⁺ | UPLC r.t. (min) |
|---|---|---|---|---|
| 744 | 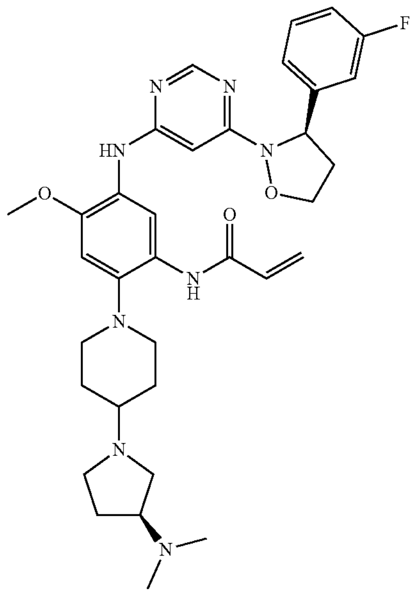 [SMILES: C=CC(=O)Nc1cc(Nc2cc(N3OCC[C@@H]3c3cccc(F)c3)ncn2)c(OC)cc1N1CCC(N2CC[C@H](N(C)C)C2)CC1] | N-(2-(4-((S)-3-(dimethylamino)pyrolidine-1-yl)piperidine-1-yl)-5-((6-((R)-3-(3-fluorophenyl)isoxazolidine-2-yl)pyrimidine-4-yl)amino)-4-methoxyphenyl)acrylamide | ¹H NMR (400 MHz, DMSO-d₆) δ 9.21 (d, J = 8.8 Hz, 1H), 8.26 (d, J = 7.9 Hz, 1H), 7.95 (s, 1H), 7.42 (q, J = 7.6 Hz, 1H), 7.26-7.15 (m, 2H), 7.12 (t, J = 8.8 Hz, 1H), 6.91 (s, 1H), 6.63 (s, 1H), 6.28-6.10 (m, 2H), 5.75 (d, J = 10.5 Hz, 1H), 5.54 (dd, J = 8.7, 5.4 Hz, 1H), 4.25 (s, 1H), 3.99 (s, 3H), 3.81 (s, 3H), 3.22 (s, 3H), 2.84 (s, 8H), 2.78-2.70 (m, 3H), 2.31 (d, J = 15.1 Hz, 3H), 2.18 (s, 3H), 2.06 (d, J = 22.5 Hz, 3H), ; 631.6 [M + H]⁺ | 1.38 |
| 745 | 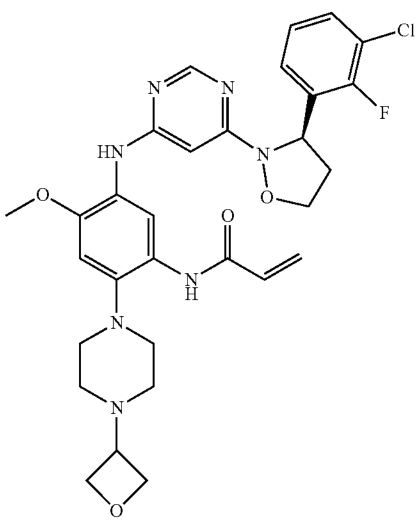 [SMILES: C=CC(=O)Nc1cc(Nc2cc(N3OCC[C@@H]3c3cccc(Cl)c3F)ncn2)c(OC)cc1N1CCN(C2COC2)CC1] | N-(5-((6-((R)-3-(3-chloro-2-fluorophenyl)isoxazolidine-2-yl)pyrimidine-4-yl)amino)-4-methoxy-2-(4-(oxetane-3-yl)piperazine-1-yl)phenyl)acrylamide | ¹H NMR (400 MHz, DMSO-d₆) δ 9.05 (s, 1H), 8.92 (s, 1H), 8.25 (d, J = 11.3 Hz, 1H), 8.20 (s, 1H), 7.57-7.47 (m, 1H), 7.43 (t, J = 7.3 Hz, 1H), 7.23 (t, J = 7.9 Hz, 1H), 6.84 (d, J = 8.6 Hz, 1H), 6.66 (dd, J = 17.1, 10.0 Hz, 1H), 6.37 (s, 1H), 6.24 (dd, J = 16.8, 2.0 Hz, 1H), 5.81-5.67 (m, 2H), 4.21 (q, J = 7.2, 6.8 Hz, 1H), 3.90 (d, J = 8.1 Hz, 2H), 3.83 (s, 3H), 3.36 (t, J = 5.6 Hz, 4H), 3.24-3.07 (m, 8H), 2.86 (t, J = 11.7 Hz, 1H), 2.28-2.17 (m, 1H), ; 610.5 [M + H]⁺ | 1.27 |
| 746 | 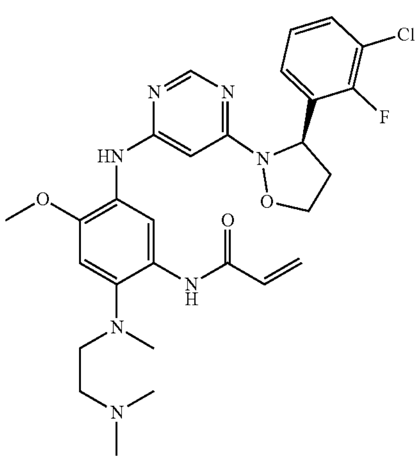 [SMILES: C=CC(=O)Nc1cc(Nc2cc(N3OCC[C@@H]3c3cccc(Cl)c3F)ncn2)c(OC)cc1N(C)CCN(C)C] | N-(5-((6-((R)-3-(3-chloro-2-fluorophenyl)isoxazolidine-2-yl)pyrimidine-4-yl)amino)-2-((2-(dimethylamino)ethyl)(methyl)amino)-4-methoxyphenyl)acrylamide | ¹H NMR (400 MHz, DMSO-d₆) δ 9.89 (s, 1H), 8.29 (s, 1H), 8.07 (s, 1H), 7.54 (td, J = 7.6, 1.7 Hz, 1H), 7.37 (t, J = 7.3 Hz, 1H), 7.24 (t, J = 7.9 Hz, 2H), 6.96 (s, 1H), 6.27-6.18 (m, 2H), 5.75-5.67 (m, 2H), 4.31 (s, 2H), 4.05 (d, J = 8.2 Hz, 2H), 3.82 (s, 4H), 2.97 (d, J = 19.4 Hz, 1H), 2.72 (d, J = 4.8 Hz, 7H), 2.61 (s, 4H), 2.30 (tt, J = 13.1, 6.1 Hz, 1H), ; 570.5 [M + H]⁺ | 1.34 |

TABLE 1-continued

| Example Compound | Structure | Name of Compound | ¹H NMR[[:]]; MS [M + H]⁺ | UPLC r.t. (min) |
|---|---|---|---|---|
| 747 | 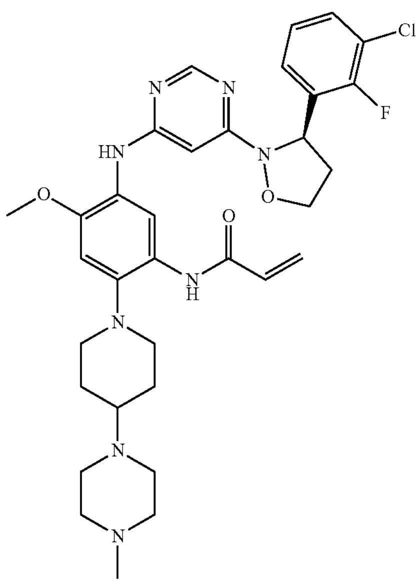 [SMILES: C=CC(=O)Nc1cc(Nc2cc(N3OCC[C@@H]3c3cccc(Cl)c3F)ncn2)c(OC)cc1N1CCC(N2CCN(C)CC2)CC1] | N-(5-((6-((R)-3-(3-chloro-2-fluorophenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, DMSO-d₆) δ 9.15 (s, 1H), 8.26 (d, J = 4.1 Hz, 1H), 7.99 (s, 1H), 7.54 (t, J = 7.6 Hz, 1H), 7.44-7.34 (m, 1H), 7.24 (t, J = 7.9 Hz, 1H), 6.89 (s, 1H), 6.67 (dd, J = 17.4, 9.9 Hz, 1H), 6.28-6.18 (m, 2H), 5.79-5.67 (m, 2H), 4.33-4.22 (m, 1H), 4.01 (d, J = 9.9 Hz, 2H), 3.83-3.78 (m, 3H), 3.78-3.70 (m, 4H), 3.21 (d, J = 12.0 Hz, 3H), 2.93 (d, J = 8.0 Hz, 2H), 2.86 (s, 3H), 2.83-2.71 (m, 4H), 2.28 (d, J = 12.7 Hz, 2H), 2.17 (s, 2H), 2.03 (s, 2H), ; 651.6 [M + H]⁺ | 1.24 |
| 748 | 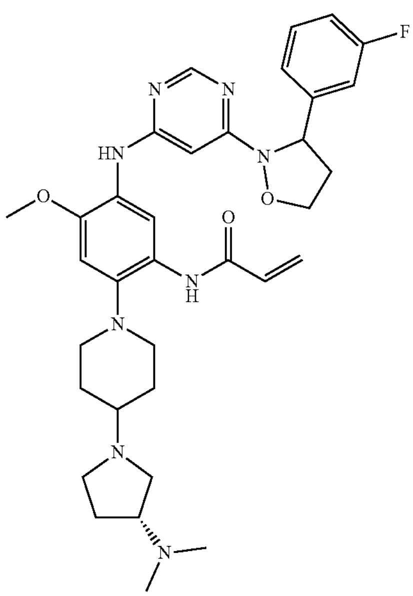 [SMILES: C=CC(=O)Nc1cc(Nc2cc(N3OCCC3c3cccc(F)c3)ncn2)c(OC)cc1N1CCC(N2CC[C@@H](N(C)C)C2)CC1] | N-(2-(4-((R)-3-(dimethylamino)pyrolidine-1-yl)piperidine-1-yl)-5-((6-(3-(3-fluorophenyl)isoxazolidine-2-yl)pyrimidine-4-yl)amino)-4-methoxyphenyl)acrylamide | ¹H NMR (400 MHz, MeOD) δ 8.21 (s, 1H), 7.92 (s, 1H), 7.41 (td, J = 7.9, 5.7 Hz, 1H), 7.21 (d, J = 7.7 Hz, 1H), 7.17-6.97 (m, 3H), 6.68 (dd, J = 16.9, 10.1 Hz, 1H), 6.46 (d, J = 16.8 Hz, 1H), 6.02 (s, 1H), 5.88 (d, J = 10.3 Hz, 1H), 5.52 (s, 1H), 4.51-4.39 (m, 1H), 4.21 (q, J = 7.7 Hz, 3H), 3.90 (s, 6H), 3.70-3.50 (m, 2H), 3.43 (s, 2H), 3.05 (s, 9H), 2.62-2.11 (m, 6H), 1.31 (s, 1H), ; 632.5 [M + H]⁺ | 1.07 |

| Example Compound | Structure | Name of Compound | ¹H NMR[:]; MS [M + H]⁺ | UPLC r.t. (min) |
|---|---|---|---|---|
| 749 | 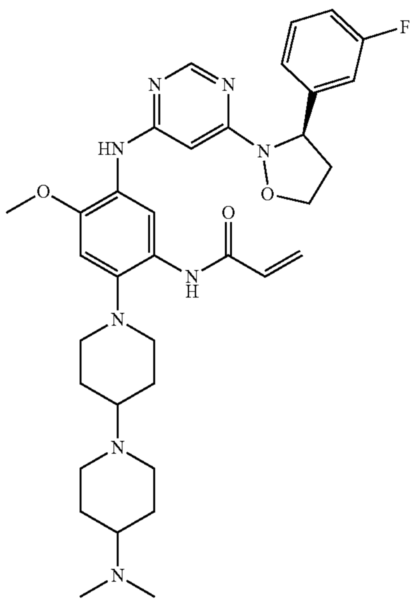 [SMILES: C=CC(=O)Nc1cc(Nc2cc(N3OCC[C@@H]3c3cccc(F)c3)ncn2)c(OC)cc1N1CCC(N2CCC(N(C)C)CC2)CC1] | N-(2-(4-(dimethylamino)-[1,4'-bipiperidine]-1'-yl)-5-((6-((R)-3-(3-fluorophenyl)isoxazolidine-2-yl)pyrimidine-4-yl)amino)-4-methoxyphenyl)acrylamide | ¹H NMR (400 MHz, MeOD) δ 8.13 (s, 1H), 7.80 (s, 1H), 7.40-7.19 (m, 1H), 7.19-6.84 (m, 4H), 6.68-6.47 (m, 1H), 6.37 (d, J = 16.5 Hz, 1H), 6.10-5.83 (m, 1H), 5.83-5.70 (m, 1H), 5.41 (s, 1H), 4.34 (d, J = 5.3 Hz, 1H), 4.11 (t, J = 7.6 Hz, 1H), 3.81 (s, 6H), 3.56-3.23 (m, 6H), 3.06-2.89 (m, 2H), 2.85 (s, 6H), 237 (d, J = 14.1 Hz, 4H), 2.20 (s, 4H), 1.33-1.13 (m, 2H), ; 646.5 [M + H]⁺ | 1.06 |
| 750 | 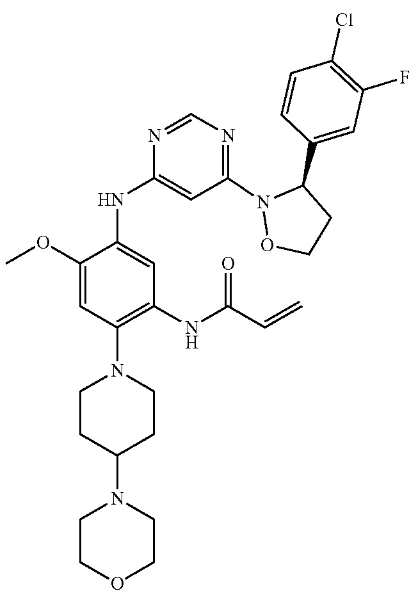 [SMILES: C=CC(=O)Nc1cc(Nc2cc(N3OCC[C@@H]3c3ccc(Cl)c(F)c3)ncn2)c(OC)cc1N1CCC(N2CCOCC2)CC1] | N-(5-((6-((R)-3-(4-chloro-3-fluorophenyl)isoxazolidine-2-yl)pyrimidine-4-yl)amino)-4-methoxy-2-(4-morpholinopiperidine-1-yl)phenyl)acrylamide | ¹H NMR (400 MHz, MeOD) δ 8.11 (s, 1H), 7.79 (s, 1H), 7.39 (t, J = 7.9 Hz, 1H), 7.26-6.94 (m, 3H), 6.56 (dd, J = 16.9, 10.2 Hz, 1H), 6.35 (dd, J = 16.9, 1.6 Hz, 1H), 5.97 (s, 1H), 5.78 (dd, J = 10.1, 1.6 Hz, 1H), 5.41 (t, J = 7.2 Hz, 1H), 4.33 (td, J = 7.6, 4.1 Hz, 1H), 4.05 (ddd, J = 30.5, 10.7, 4.9 Hz, 3H), 3.81 (d, J = 6.0 Hz, 5H), 3.60-3.49 (m, 2H), 3.47-3.27 (m, 3H), 3.23 (d, J = 12.2 Hz, 2H), 3.15 (dd, J = 13.9, 5.1 Hz, 3H), 3.00-2.85 (m, 1H), 2.45-2.21 (m, 3H), 2.18-1.99 (m, 2H), ; 639.4 [M + H]⁺ | 1.28 |

TABLE 1-continued

| Example Compound | Structure | Name of Compound | ¹H NMR[:]; MS [M + H]⁺ | UPLC r.t. (min) |
|---|---|---|---|---|
| 751 | 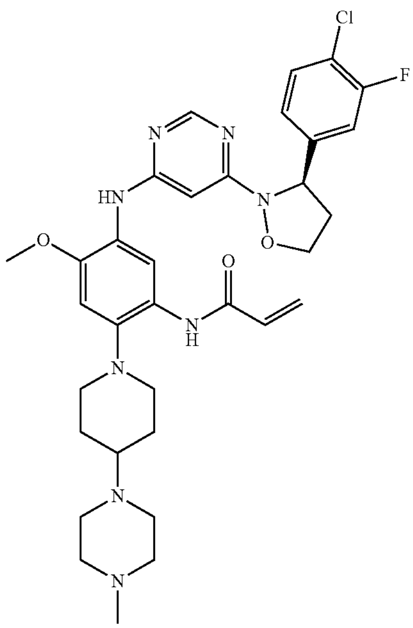 [SMILES: C=CC(=O)Nc1cc(Nc2cc(N3OCC[C@@H]3c3ccc(Cl)c(F)c3)ncn2)c(OC)cc1N1CCC(N2CCN(C)CC2)CC1] | N-(5-((6-((R)-3-(4-chloro-3-fluorophenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, MeOD) δ 8.22 (s, 1H), 7.93 (s, 1H), 7.50 (t, J = 7.9 Hz, 1H), 7.31 (dd, J = 10.0, 2.0 Hz, 1H), 7.23 (dd, J = 8.3, 2.0 Hz, 1H), 7.13 (s, 1H), 6.69 (dd, J = 16.9, 10.2 Hz, 1H), 6.46 (dd, J = 16.9, 1.6 Hz, 1H), 6.08 (s, 1H), 5.88 (dd, J = 10.2, 1.6 Hz, 1H), 5.54 (t, J = 7.3 Hz, 1H), 4.44 (td, J = 7.6, 4.1 Hz, 1H), 4.20 (td, J = 8.3, 6.5 Hz, 1H), 4.16-3.55 (m, 12H), 3.54-3.39 (m, 2H), 3.32-3.11 (m, 3H), 3.08 (s, 4H), 2.56-2.37 (m, 3H), 2.35-2.20 (m, 2H), ; 652.4 [M + H]⁺ | 1.23 |
| 752 | 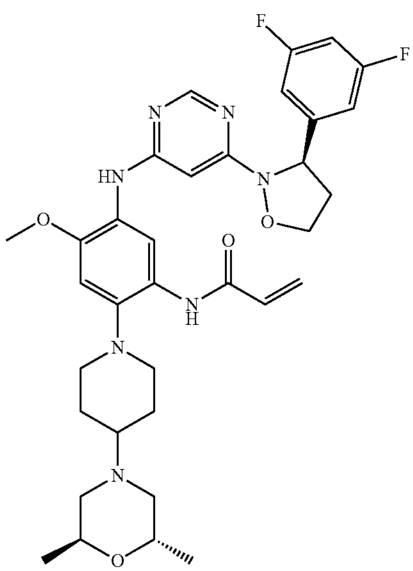 [SMILES: C=CC(=O)Nc1cc(Nc2cc(N3OCC[C@@H]3c3cc(F)cc(F)c3)ncn2)c(OC)cc1N1CCC(N2C[C@H](C)O[C@@H](C)C2)CC1] | N-(5-((6-((R)-3-(3,5-difluorophenyl)isoxazolidine-2-yl)pyrimidine-4-yl)amino)-2-(4-((2S,6S)-2,6-dimethylmorpholino)piperidine-1-yl)-4-methoxyphenyl)acrylamide | ¹H NMR (400 MHz, Methanol-d₄) δ 8.30 (s, 1H), 8.18 (s, 1H), 7.11-7.04 (m, 2H), 6.92 (s, 1H), 6.89-6.79 (m, 1H), 6.59-6.50 (m, 1H), 6.45 (s, 1H), 6.41-6.30 (m, 1H), 5.82 (d, J = 10.3 Hz, 1H), 5.61-5.51 (m, 1H), 4.19-4.04 (m, 4H), 3.98 (q, J = 7.9 Hz, 1H), 3.88 (s, 3H), 3.20-3.10 (m, 3H), 2.84-2.72 (m, 5H), 2.50-2.43 (m, 3H), 2.38-2.28 (m, 1H), 1.84-1.73 (m, 2H), 1.29 (s, 3H), 1.28 (s, H); 650.3 [M + H]⁺ | 1.28 |

TABLE 1-continued

| Example Compound | Structure | Name of Compound | ¹H NMR[[:]]; MS [M + H]⁺ | UPLC r.t. (min) |
|---|---|---|---|---|
| 753 | 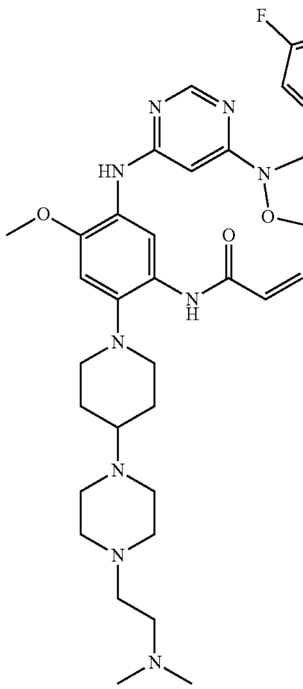 | N-(5-((6-((R)-3-(3,5-difluorophenyl)isoxazolidine-2-yl)pyrimidine-4-yl)amino)-2-(4-(4-(2-(dimethylamino)ethyl)piperazine-1-yl)piperidine-1-yl)-4-methoxyphenyl)acrylamide | ¹H NMR (400 MHz, Methanol-d₄) δ 8.17 (s, 1H), 8.09-8.03 (m, 1H), 6.98-6.91 (m, 2H), 6.82-6.77 (m, 1H), 6.75-6.68 (m, 1H), 6.50-6.37 (m, 1H), 6.34 (s, 1H), 6.30-6.20 (m, 1H), 5.69 (d, J = 10.3 Hz, 1H), 5.50-5.41 (m, 1H), 4.06-4.01 (m, 1H), 3.90-3.81 (m, 2H), 3.77 (s, 3H), 3.15-3.09 (m, 3H), 3.09-3.00 (m, 6H), 2.99-2.93 (m, 2H), 2.73-2.70 (m, 8H), 2.68-2.53 (m, 9H), 2.25-2.20 (m, 1H), 2.03-1.95 (m, 2H); 692.4 [M + H]⁺ | 1.13 |
| 754 | 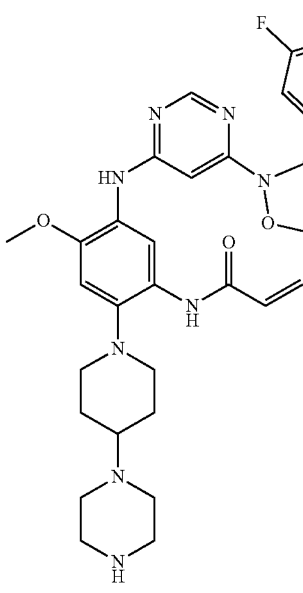 | N-(5-((6-((R)-3-(3,5-difluorophenyl)isoxazolidine-2-yl)pyrimidine-4-yl)amino)-4-methoxy-2-(4-(piperazine-1-yl)piperidine-1-yl)phenyl)acrylamide | ¹H NMR (400 MHz, Methanol-d₄) δ 8.17 (s, 0H), 8.08-8.04 (m, 1H), 6.98-6.90 (m, 2H), 6.81-6.68 (m, 2H), 6.47-6.37 (m, 1H), 6.37-6.30 (m, 1H), 6.28-6.19 (m, 1H), 5.74-5.61 (m, 1H), 5.48-5.43 (m, 1H), 4.05-4.00 (m, 1H), 3.88-3.81 (m, 1H), 3.76 (s, 3H), 3.18-2.96 (m, 5H), 2.81-2.56 (m, 10H), 2.50-2.39 (m, 1H), 2.29-2.16 (m, 1H), 1.73-1.62 (m, 2H); 621.3 [M + H]⁺ | 1.09 |

TABLE 1-continued

| Example Compound | Structure | Name of Compound | ¹H NMR[:]; MS [M + H]⁺ | UPLC r.t. (min) |
|---|---|---|---|---|
| 755 | 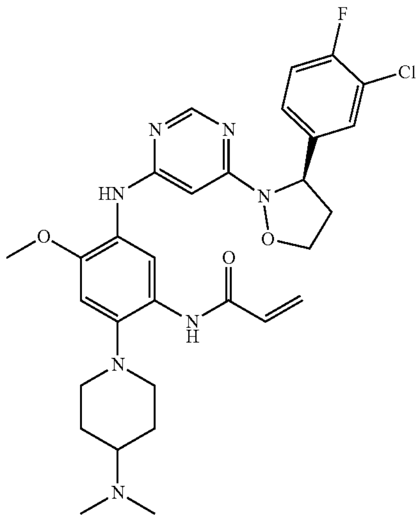 [SMILES: C=CC(=O)Nc1cc(Nc2cc(N3OCC[C@@H]3c3ccc(F)c(Cl)c3)ncn2)c(OC)cc1N1CCC(N(C)C)CC1] | N-(5-((6-((R)-3-(3-chloro-4-fluorophenyl)isoxazolidine-2-yl)pyrimidine-4-yl)amino)-2-(4-(dimethylamino)piperidine-1-yl)-4-methoxyphenyl)acrylamide | ¹H NMR (400 MHz, MeOD) δ 8.32 (s, 1H), 8.18 (d, J = 0.8 Hz, 1H), 7.57 (dd, J = 7.1, 2.1 Hz, 1H), 7.41 (ddd, J = 8.4, 4.5, 2.2 Hz, 1H), 7.23 (t, J = 8.9 Hz, 1H), 6.92 (s, 1H), 6.58 (dd, J = 16.9, 10.3 Hz, 1H), 6.46 (d, J = 0.8 Hz, 1H), 6.37 (dd, J = 17.0, 1.5 Hz, 1H), 5.81 (dd, J = 10.3, 1.3 Hz, 1H), 5.55 (dd, J = 8.5, 4.7 Hz, 1H), 4.16 (td, J = 7.8, 4.2 Hz, 1H), 3.98 (q, J = 8.0 Hz, 1H), 3.88 (s, 3H), 3.19-3.09 (m, 2H), 2.88-2.73 (m, 3H), 2.43-2.27 (m, 8H), 2.05 (d, J = 10.7 Hz, 2H), 1.75 (dt, J = 11.8, 8.3 Hz, 2H), ; 596.4 [M + H]⁺ | 1.27 |
| 756 | 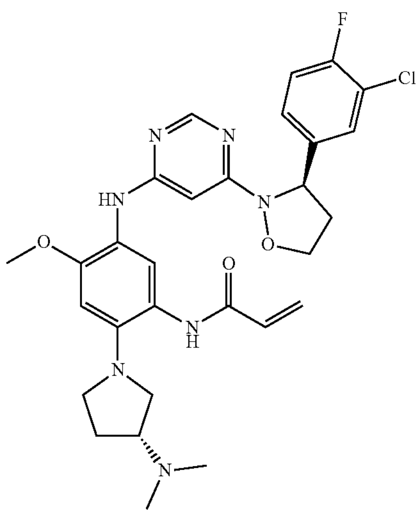 [SMILES: C=CC(=O)Nc1cc(Nc2cc(N3OCC[C@@H]3c3ccc(F)c(Cl)c3)ncn2)c(OC)cc1N1CC[C@@H](N(C)C)C1] | N-(5-((6-((R)-3-(3-chloro-4-fluorophenyl)isoxazolidine-2-yl)pyrimidine-4-yl)amino)-2-((R)-3-(dimethylamino)pyrolidine-1-yl)-4-methoxyphenyl)acrylamide | ¹H NMR (400 MHz, MeOD) δ 8.14 (s, 1H), 7.68 (s, 1H), 7.56 (dd, J = 7.2, 2.1 Hz, 1H), 7.44-7.37 (m, 1H), 7.22 (t, J = 8.9 Hz, 1H), 6.67 (s, 1H), 6.54 (dd, J = 17.0, 10.2 Hz, 1H), 6.42-6.30 (m, 2H), 5.79 (dd, J = 10.2, 1.6 Hz, 1H), 5.53 (dd, J = 8.5, 4.5 Hz, 1H), 4.14 (td, J = 7.8, 4.2 Hz, 1H), 3.95 (q, J = 7.9 Hz, 1H), 3.88 (s, 3H), 3.26 (m, J = 9.3 Hz, 3H), 2.95-2.86 (m, 1H), 2.86-2.75 (m, 1H), 2.39-2.16 (m, 9H), 1.97-1.84 (m, 1H), ; 582.4 [M + H]⁺ | 1.25 |

TABLE 1-continued

| Example Compound | Structure | Name of Compound | ¹H NMR[[:]]; MS [M + H]⁺ | UPLC r.t. (min) |
|---|---|---|---|---|
| 757 | 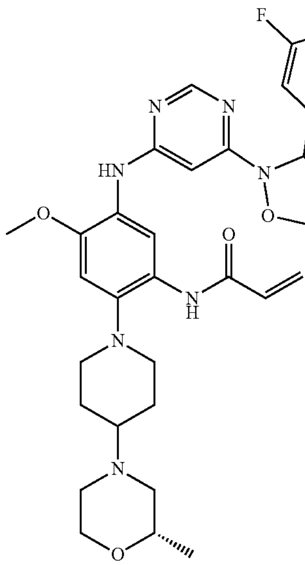 | N-(5-(((6-((R)-3-(3,5-difluorophenyl)isoxazolidine-2-yl)pyrimidine-4-yl)amino)-4-methoxy-2-(4-((S)-2-methylmorpholino)piperidine-1-yl)phenyl)acrylamide | ¹H NMR (400 MHz, Chloroform-d) δ 8.85 (s, 1H), 8.44 (s, 1H), 8.37 (d, J = 1.0 Hz, 1H), 7.07-6.89 (m, 3H), 6.75 (s, 1H), 6.73-6.63 (m, 2H), 6.37 (dd, J = 17.0, 1.5 Hz, 1H), 6.25 (dd, J = 16.9, 10.0 Hz, 1H), 5.75 (dd, J = 10.0, 1.5 Hz, 1H), 5.66 (dd, J = 8.8, 4.6 Hz, 1H), 4.15 (td, J = 8.1, 4.2 Hz, 1H), 4.06 (q, J = 8.1 Hz, 1H), 3.97-3.88 (m, 1H), 3.85 (s, 3H), 3.77-3.63 (m, 2H), 3.07 (d, J = 11.4 Hz, 2H), 2.91 (d, J = 11.1 Hz, 1H), 2.85 (d, J = 11.2 Hz, 1H), 2.82-2.73 (m, 2H), 2.73-2.67 (m, 1H) 2.40-2.25 (m, 3H), 2.12-2.02 (m, 2H), 1.97 (t, J = 10.5 Hz, 1H), 1.70-1.65 (m, 2H), 1.19 (d, J = 6.3 Hz, 3H), ; 636.5 [M + H]⁺ | 1.23 |
| 758 | 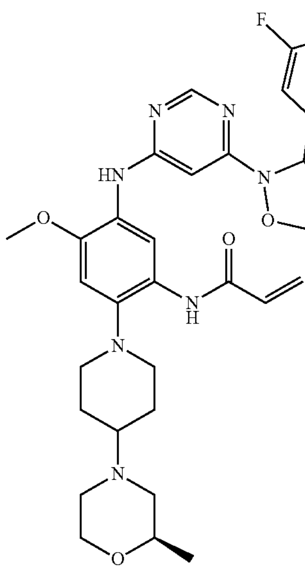 | N-(5-(((6-((R)-3-(3,5-difluorophenyl)isoxazolidine-2-yl)pyrimidine-4-yl)amino)-4-methoxy-2-(4-((R)-2-methylmorpholino)piperidine-1-yl)phenyl)acrylamide | ¹H NMR (400 MHz, Chloroform-d) δ 8.86 (s, 1H) 8.44 (s, 1H), 8.36 (d, J = 1.0 Hz, 1H), 7.06-6.98 (m, 2H), 6.96 (s, 1H), 6.75 (s, 1H), 6.73-6.63 (m, 2H), 6.37 (dd, J = 17.0, 1.5 Hz, 1H), 6.25 (dd, J = 16.9, 10.0 Hz, 1H), 5.74 (dd, J = 10.0, 1.6 Hz, 1H), 5.67 (dd, J = 8.7, 4.5 Hz, 1H), 4.15 (td, J = 8.1, 4.2 Hz, 1H), 4.06 (q, J = 8.1 Hz, 1H), 3.93 (dd, J = 11.4, 3.4, 1.5 Hz, 1H), 3.85 (s, 3H), 3.76-3.60 (m, 2H), 3.11-3.02 (m, 2H), 2.94-2.66 (m, 5H), 2.40-2.24 (m, 3H), 2.08 (d, J = 12.3 Hz, 2H), 1.97 (t, J = 10.5 Hz, 1H), 1.68-1.63 (m, 2H), 1.19 (d, J = 6.2 Hz, 3H), ; 636.5 [M + H]⁺ | 1.20 |

TABLE 1-continued

| Example Compound | Structure | Name of Compound | ¹H NMR[[:]]; MS [M + H]⁺ | UPLC r.t. (min) |
|---|---|---|---|---|
| 759 | 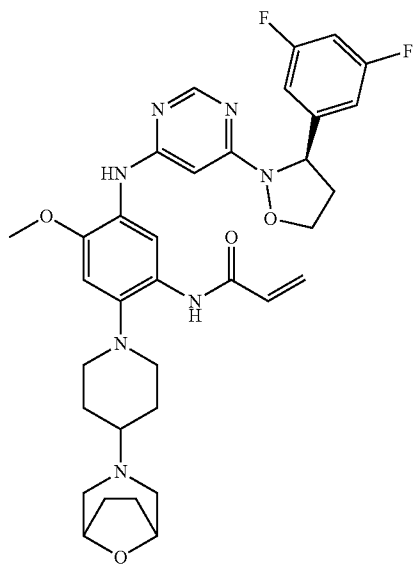 [SMILES: C=CC(=O)Nc1cc(Nc2cc(N3OCC[C@@H]3c3cc(F)cc(F)c3)ncn2)c(OC)cc1N1CCC(N2CC3CCC(C2)O3)CC1] | N-(2-(4-((1R,5S)-8-oxa-3-azabicyclo[3.2.1]octan-3-yl)piperidine-1-yl)-5-((6-((R)-3-(3,5-difluorophenyl)isoxazolidine-2-yl)pyrimidine-4-yl)amino)-4-methoxyphenyl)acrylamide | ¹H NMR (400 MHz, Chloroform-d) δ 8.86 (s, 1H), 8.45 (s, 1H), 8.36 (d, J = 1.0 Hz, 1H), 7.06-6.97 (m, 2H), 6.96 (s, 1H), 6.75 (s, 1H), 6.72-6.63 (m, 2H), 6.38 (dd, J = 16.9, 1.7 Hz, 1H), 6.28 (dd, J = 16.9, 9.9 Hz, 1H), 5.75 (dd, J = 9.8, 1.7 Hz, 1H), 5.67 (dd, J = , 8.7, 4.5 Hz, 1H), 4.33 (dt, J = 4.5, 2.3 Hz, 2H), 4.20-4.10 (m, 1H), 4.06 (q, J = 8.1 Hz, 1H), 3.84 (s, 3H), 3.09-2.98 (m, 2H), 2.82-2.65 (m, 5H), 2.48 (dd, J = 10.9, 2.2 Hz, 2H), 2.40-2.21 (m, 2H), 1.96-1.93 (m, 2H), 1.91-1.84 (m, 2H), 1.77-1.68 (m, 1H), 1.67-1.55 (m, 3H), 1.55-1.47 (m, 1H), ; 648.5 [M + H]⁺ | 1.15 |
| 760 | 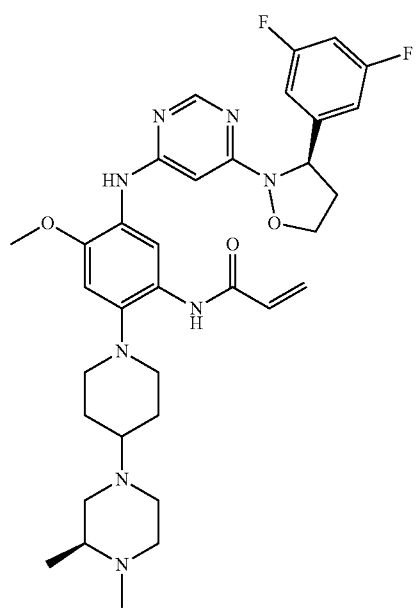 [SMILES: C=CC(=O)Nc1cc(Nc2cc(N3OCC[C@@H]3c3cc(F)cc(F)c3)ncn2)c(OC)cc1N1CCC(N2CCN(C)[C@@H](C)C2)CC1] | N-(5-((6-((R)-3-(3,5-difluorophenyl)isoxazolidine-2-yl)pyrimidine-4-yl)amino)-2-(4-((S)-3,4-dimethylpiperazine-1-yl)piperidine-1-yl)-4-methoxyphenyl)acrylamide | ¹H NMR (400 MHz, Chloroform-d) δ 8.86 (s, 1H), 8.45 (s, 1H), 8.36 (d, J = 1.0 Hz, 1H), 7.06-6.98 (m, 2H), 6.96 (s, 1H), 6.75 (s, 1H), 6.73-6.61 (m, 2H), 6.36 (dd, J = 17.0, 1.6 Hz, 1H), 6.25 (dd, J = 16.9, 10.0 Hz, 1H), 5.74 (dd, J = 10.0, 1.6 Hz, 1H), 5.66 (dd, J = 8.7, 4.6 Hz, 1H), 4.15 (td, J = 8.0, 4.2 Hz, 1H), 4.06 (q, J = 8.0 Hz, 1H), 3.84 (s, 3H), 3.06 (d, J = 10.4 Hz, 2H), 3.01-2.96 (m, 1H), 2.94-2.84 (m, 2H), 2.82-2.68 (m, 3H), 2.44-2.34 (m, 3H), 2.32 (s, 3H), 2.31-2.27 (m, 1H), 2.13-2.00 (m, 4H), 1.74-1.59 (m, 2H), 1.11 (d, J = 6.2 Hz, 3H), ; 649.5 [M + H]⁺ | 1.15 |

TABLE 1-continued

| Example Compound | Structure | Name of Compound | $^1$H NMR[:]; MS [M + H]$^+$ | UPLC r.t. (min) |
|---|---|---|---|---|
| 761 | 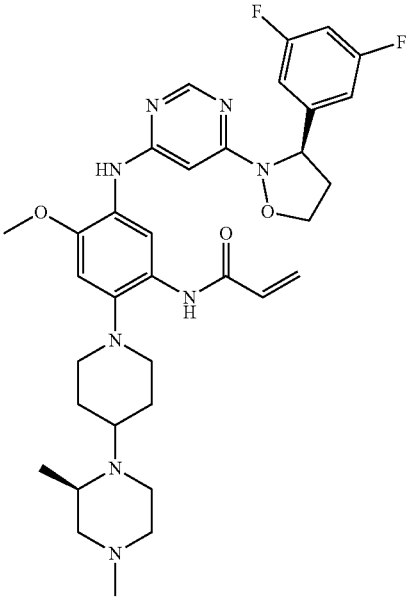 [SMILES: C=CC(=O)Nc1cc(Nc2cc(N3OCC[C@@H]3c3cc(F)cc(F)c3)ncn2)c(OC)cc1N1CCC(N2CCN(C)C[C@H]2C)CC1] | N-(5-((6-((R)-3-(3,5-difluorophenyl)isoxazolidine-2-yl)pyrimidine-4-yl)amino)-2-(4-((R)-2,4-dimethylpiperazine-1-yl)piperidine-1-yl)-4-methoxyphenyl)acrylamide | $^1$H NMR (400 MHz, Chloroform-d) δ 8.87 (s, 1H), 8.45 (s, 1H), 8.36 (d, J = 1.0 Hz, 1H), 7.04-6.98 (m, 2H), 6.96 (s, 1H), 6.76 (s, 1H), 6.74-6.63 (m, 2H), 6.37 (dd, J = 16.9, 1.7 Hz, 1H), 6.27 (dd, J = 16.9, 9.9 Hz, 1H), 5.75 (dd, J = 9.9, 1.7 Hz, 1H), 5.67 (dd, J = 8.8, 4.6 Hz, 1H), 4.15 (td, J = 8.1, 4.2 Hz, 1H), 4.06 (q, J = 8.0 Hz, 1H), 3.85 (s, 3H), 3.07 (dt, J = 11.3, 5.1 Hz, 2H), 2.99-2.84 (m, 3H), 2.83-2.59 (m, 6H), 2.40-2.30 (m, 2H), 2.30 (s, 3H), 2.09-2.03 (m, 1H), 1.95-1.80 (m, 3H), 1.63 (qd, J = 12.0, 3.9 Hz, 1H), 1.11 (d, J = 6.3 Hz, 3H), ; 649.5 [M + H]$^+$ | 1.15 |
| 762 | 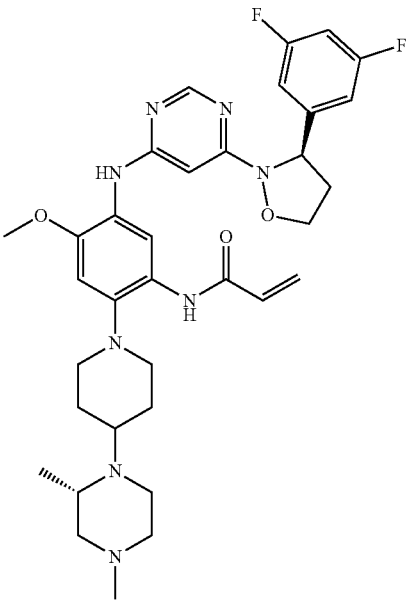 [SMILES: C=CC(=O)Nc1cc(Nc2cc(N3OCC[C@@H]3c3cc(F)cc(F)c3)ncn2)c(OC)cc1N1CCC(N2CCN(C)C[C@@H]2C)CC1] | N-(5-((6-((R)-3-(3,5-difluorophenyl)isoxazolidine-2-yl)pyrimidine-4-yl)amino)-2-(4-((S)-2,4-dimethylpiperazine-1-yl)piperidine-1-yl)-4-methoxyphenyl)acrylamide | $^1$H NMR (400 MHz, Chloroform-d) δ 8.87 (s, 1H), 8.44 (s, 1H), 8.37 (d, J = 1.0 Hz, 1H), 7.06-6.96 (m, 2H), 6.94 (s, 1H), 6.76 (s, 1H), 6.76-6.63 (m, 2H), 6.37 (dd, J = 16.9, 1.6 Hz, 1H), 6.27 (dd, J = 16.9, 9.9 Hz, 1H), 5.75 (dd, J = 9.9, 1.6 Hz, 1H), 5.67 (dd, J = 8.8, 4.5 Hz, 1H), 4.15 (td, J = 8.1, 4.2 Hz, 1H), 4.06 (q, J = 8.1 Hz, 1H), 3.85 (s, 3H), 3.07 (d, J = 11.5 Hz, 2H), 2.99-2.84 (m, 3H), 2.84-2.73 (m, 3H), 2.73-2.60 (m, 3H), 2.40-2.31 (m, 2H), 2.30 (s, 3H), 2.10-2.06 (m, 1H), 1.89 (dd, J = 22.0, 9.7 Hz, 3H), 1.63 (q, J = 12.2, 11.7 Hz, 1H), 1.12 (d, J = 6.3 Hz, 3H), ; 649.5 [M + H]$^+$ | 1.16 |

TABLE 1-continued

| Example Compound | Structure | Name of Compound | $^1$H NMR[:]; MS [M + H]$^+$ | UPLC r.t. (min) |
|---|---|---|---|---|
| 763 | 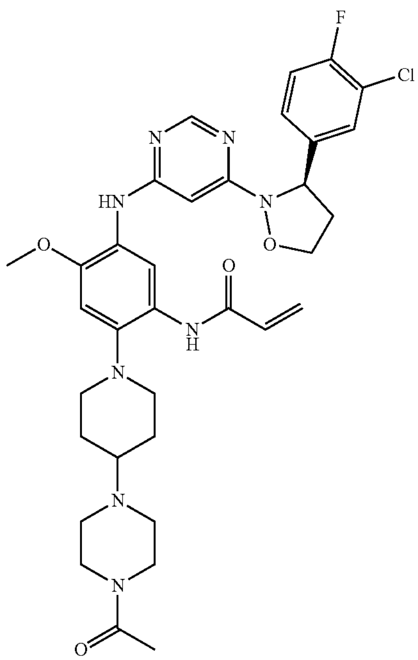 [SMILES: C=CC(=O)Nc1cc(Nc2cc(N3OCC[C@@H]3c3ccc(F)c(Cl)c3)ncn2)c(OC)cc1N1CCC(N2CCN(C(C)=O)CC2)CC1] | N-(2-(4-(4-acetylpiperazine-1-yl)piperidine-1-yl)-5-((6-((R)-3-(3-chloro-4-fluorophenyl)isoxazolidine-2-yl)pyrimidine-4-yl)amino)-4-methoxyphenyl)acrylamide | $^1$H NMR (400 MHz, DMSO-d$_6$) δ 10.26 (s, 1H), 9.27 (s, 1H), 8.33 (s, 1H), 7.86 (s, 1H), 7.58 (dd, J = 7.1, 2.1 Hz, 1H), 7.42 (t, J = 8.8 Hz, 1H), 7.40-7.35 (m, 1H), 6.90 (d, J = 11.0 Hz, 1H), 6.72 (dd, J = 17.0, 10.2 Hz, 1H), 6.24 (dd, J = 17.0, 1.9 Hz, 1H), 6.11 (s, 1H), 5.79-5.71 (m, 1H), 5.54 (dd, J = 8.5, 5.5 Hz, 2H), 3.89 (t, J = 6.1 Hz, 1H), 3.80 (d, J = 2.6 Hz, 4H), 3.56 (s, 6H), 3.48 (s, 3H), 3.36 (dd, J = 16.4, 10.4 Hz, 2H), 3.20 (d, J = 28.8 Hz, 5H), 3.04-2.87 (m, 4H), 2.81 (s, 3H), 2.39-2.27 (m, 2H), 2.06 (s, 4H), ; 679.5 [M + H]$^+$ | 1.25 |
| 764 | 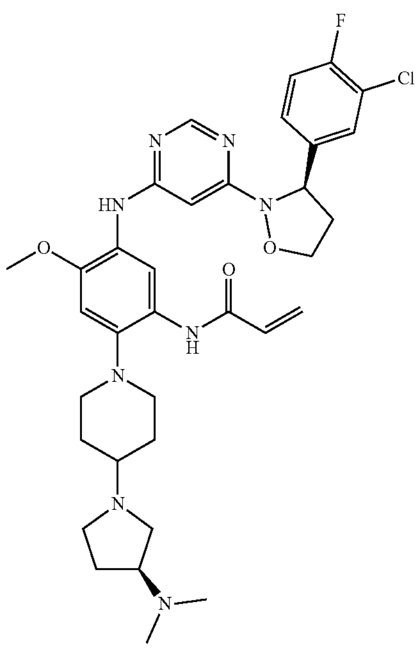 [SMILES: C=CC(=O)Nc1cc(Nc2cc(N3OCC[C@@H]3c3ccc(F)c(Cl)c3)ncn2)c(OC)cc1N1CCC(N2CC[C@H](N(C)C)C2)CC1] | N-(5-((6-((R)-3-(3-chloro-4-fluorophenyl)isoxazolidine-2-yl)pyrimidine-4-yl)amino)-2-(4-((S)-3-(dimethylamino)pyrolidine-1-yl)piperidine-1-yl)-4-methoxyphenyl)acrylamide | $^1$H NMR (400 MHz, DMSO-d$_6$) δ 10.12 (s, 1H), 9.31 (s, 1H), 8.32 (s, 1H), 7.86 (s, 1H), 7.58 (dd, J = 7.1, 2.2 HZ, 1H), 7.47-7.34 (m, 3H), 6.96 (s, 1H), 6.67 (dd, J = 16.7, 10.6 Hz, 1H), 6.24 (dd, J = 17.1, 1.9 Hz, 1H), 6.10 (d, J = 9.8 Hz, 1H), 5.75 (dd, J = 7.7, 3.8 Hz, 1H), 5.53 (dd, J = 8.5, 5.5 Hz, 2H), 4.02 (dq, J = 18.8, 10.0, 8.8 Hz, 6H), 3.81 (s, 5H), 3.56 (s, 5H), 3.25 (s, 6H), 3.17-3.06 (m, 2H), 2.92 (t J = 6.4 Hz, 2H), 2.89-2.69 (m, 9H), 2.47-2.26 (m, 3H), 2.27-2.02 (m, 5H), ; 665.6 [M + H]$^+$ | 1.13 |

TABLE 1-continued

| Example Compound | Structure | Name of Compound | ¹H NMR[[:]]; MS [M + H]⁺ | UPLC r.t. (min) |
|---|---|---|---|---|
| 765 | 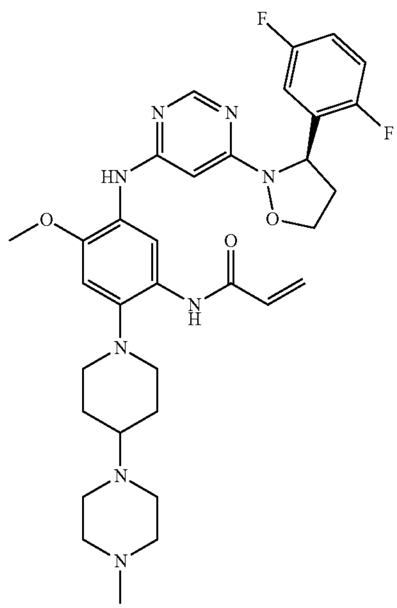 [SMILES: C=CC(=O)Nc1cc(Nc2cc(N3OCC[C@@H]3c3cc(F)ccc3F)ncn2)c(OC)cc1N1CCC(N2CCN(C)CC2)CC1] | N-(5-((6-((R)-3-(2,5-difluorophenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, DMSO-d$_6$) δ 10.38 (s, 1H), 9.29 (s, 1H), 8.34 (s, 1H), 7.32 (td, J = 9.3, 4.5 Hz, 1H), 7.26-7.10 (m, 3H), 6.93 (s, 1H), 6.74 (dd, J = 17.0, 10.2 Hz, 1H), 6.25 (dd, J = 17.0, 1.9 Hz, 1H), 6.16 (s, 1H), 5.79-5.71 (m, 1H), 5.66 (dd, J = 8.7, 5.6 Hz, 2H), 4.07 (q, J = 7.8 Hz, 2H), 3.81 (d, J = 2.5 Hz, 5H), 3.45 (s, 2H), 3.35-3.14 (m, 4H), 2.95 (dq, J = 12.0, 6.0 Hz, 3H), 2.84 (s, 6H), 2.71 (d, J = 4.9 Hz, 1H), 2.36-2.09 (m, 6H), 1.35-1.24 (m, 3H), ; 635.5 [M + H]⁺ | 1.33 |
| 766 | 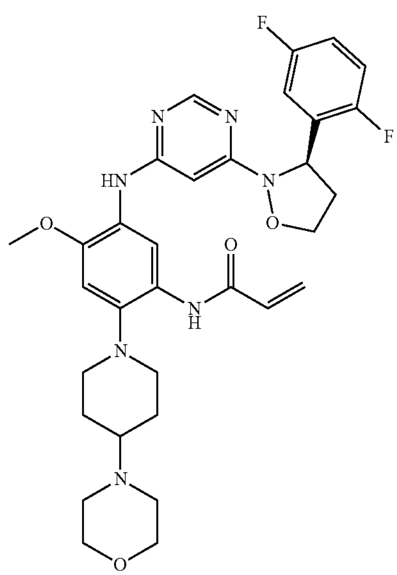 [SMILES: C=CC(=O)Nc1cc(Nc2cc(N3OCC[C@@H]3c3cc(F)ccc3F)ncn2)c(OC)cc1N1CCC(N2CCOCC2)CC1] | N-(5-((6-((R)-3-(2,5-difluorophenyl)isoxazolidine-2-yl)pyrimidine-4-yl)amino)-4-methoxy-2-(4-morpholinopiperidine-1-yl)phenyl)acrylamide | 622.5 [M + H]⁺ | 1.36 |

TABLE 1-continued

| Example Compound | Structure | Name of Compound | $^1$H NMR[:]; MS [M + H]$^+$ | UPLC r.t. (min) |
|---|---|---|---|---|
| 767 | 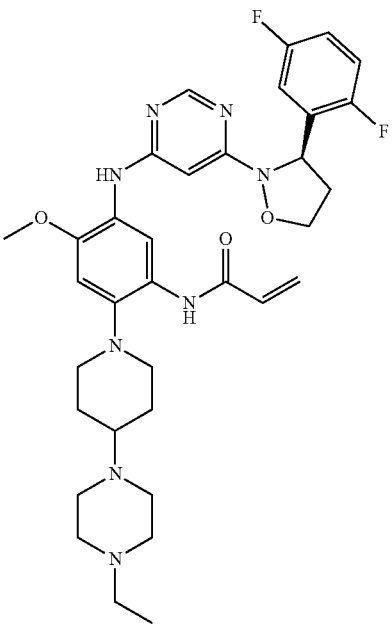 [SMILES: C=CC(=O)Nc1cc(Nc2cc(N3OCC[C@@H]3c3cc(F)ccc3F)ncn2)c(OC)cc1N1CCC(N2CCN(CC)CC2)CC1] | N-(5-((6-((R)-3-(2,5-difluorophenyl)isoxazolidine-2-yl)pyrimidine-4-yl)amino)-2-(4-(4-ethylpiperazine-1-yl)piperidine-1-yl)-4-methoxyphenyl)acrylamide | $^1$H NMR (400 MHz, Chloroform-d) δ 8.79 (s, 1H), 8.41 (d, J = 9.9 Hz, 2H), 8.32 (d, J = 1.2 Hz, 2H), 7.40 (s, 2H), 7.30 (ddd, J = 9.3, 5.8, 3.3 Hz, 2H), 6.99 (td, J = 9.2, 4.3 Hz, 2H), 6.89 (ddd, J = 8.7, 6.3, 3.6 Hz, 2H), 6.26 (dd, J = 16.9, 9.8 Hz, 1H), 5.74 (dt, J = 9.9, 1.9 Hz, 1H), 4.07-3.99 (m, 2H), 3.84 (d, J = 1.5 Hz, 5H), 3.42 (s, 3H), 3.08 (dd, J = 15.5, 10.3 Hz, 5H), 2.80-2.62 (m, 10H), 2.55 (d, J = 3.3 Hz, 3H), 2.44 (s, 2H), 2.29 (ddd, J = 12.3, 9.8, 3.9 Hz, 2H), 2.03 (s, 12H), 1.70 (q, J = 10.8, 10.3 Hz, 3H), ; 649.5 [M + H]$^+$ | 1.36 |
| 768 | 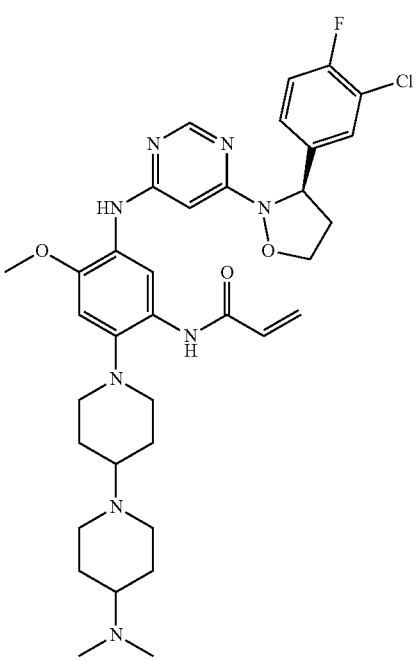 [SMILES: C=CC(=O)Nc1cc(Nc2cc(N3OCC[C@@H]3c3ccc(F)c(Cl)c3)ncn2)c(OC)cc1N1CCC(N2CCC(N(C)C)CC2)CC1] | N-(5-((6-((R)-3-(3-chloro-4-fluorophenyl)isoxazolidine-2-yl)pyrimidine-4-yl)amino)-2-(4-(dimethylamino)-[1,4'-bipiperidine]-1'-yl)-4-methoxyphenyl)acrylamide | $^1$H NMR (400 MHz, Methanol-d$_4$) δ 8.16 (s, 1H), 8.05 (s, 1H), 7.47-7.41 (m, 1H), 7.33-7.25 (m, 1H), 7.16-7.05 (m, 1H), 6.80 (s, 1H), 6.50-6.37 (m, 1H), 6.36-6.30 (m, 1H), 6.30-6.19 (m, 1H), 5.73-5.64 (m, 1H), 5.47-5.39 (m, 1H), 4.06-4.00 (m, 1H), 3.89-3.82 (m, 1H), 3.76 (s, 3H), 3.13-3.08 (m, 3H), 3.08-2.99 (m, 6H), 2.95-2.88 (m, 2H), 2.75-2.64 (m, 8H), 2.43-2.37 (m, 1H), 2.26-2.18 (m, 1H), 1.98-1.91 (m, 2H), 1.80-1.70 (m, 3H); 679.3 [M + H]$^+$ | 1.33 |

TABLE 1-continued

| Example Compound | Structure | Name of Compound | ¹H NMR[[:]]; MS [M + H]⁺ | UPLC r.t. (min) |
|---|---|---|---|---|
| 769 | 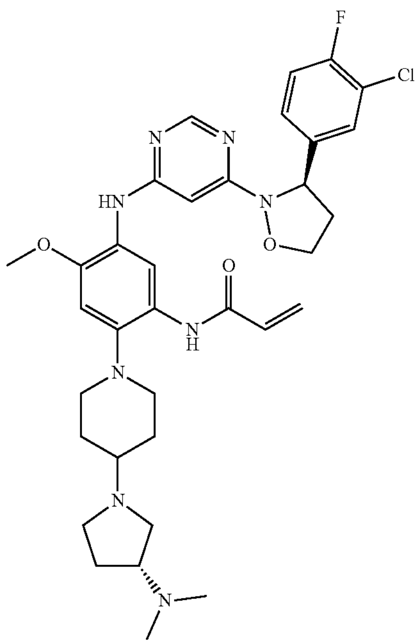 [SMILES: C=CC(=O)Nc1cc(Nc2cc(N3OCC[C@@H]3c3ccc(F)c(Cl)c3)ncn2)c(OC)cc1N1CCC(N2CC[C@@H](N(C)C)C2)CC1] | N-(5-((6-((R)-3-(3-chloro-4-fluorophenyl)isoxazolidine-2-yl)pyrimidine-4-yl)amino)-2-((R)-3-(dimethylamino)pyrolidine-1-yl)piperidine-1-yl)-4-methoxyphenyl)acrylamide | ¹H NMR (400 MHz, Methanol-$d_4$) δ 8.16 (s, 1H), 8.06 (s, 1H), 7.48-7.40 (m, 1H), 7.31-7.25 (m, 1H), 7.14-7.04 (m, 1H), 6.80 (s, 1H), 6.51-6.38 (m, 1H), 6.33 (s, 1H), 6.31-6.18 (m, 1H), 5.74-5.63 (m, 1H), 5.48-5.36 (m, 1H), 4.07-4.01 (m, 1H), 3.89-3.81 (m, 1H), 3.77 (s, 3H), 3.11 (s, 1H), 3.05-3.00 (m, 3H), 2.93-2.85 (m, 2H), 2.77-2.64 (m, 5H), 2.45 (s, 6H), 2.27-2.10 (m, 3H), 2.05-1.98 (m, 2H), 1.73-1.64 (m, 2H); 665.3 [M + H]⁺ | 1.33 |
| 770 | 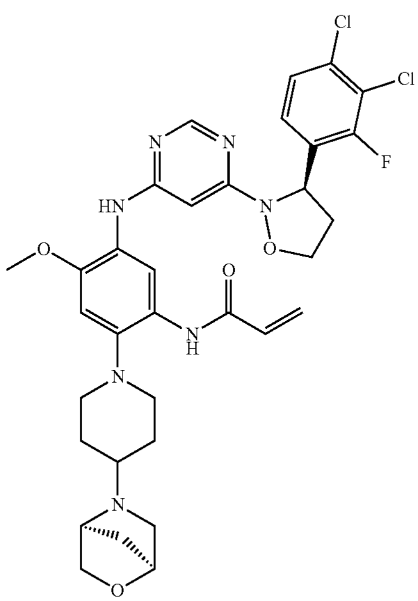 [SMILES: C=CC(=O)Nc1cc(Nc2cc(N3OCC[C@@H]3c3ccc(Cl)c(Cl)c3F)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((R)-3-(3,4-dichloro-2-fluorophenyl)isoxazolidine-2-yl)pyrimidine-4-yl)amino)-4-methoxyphenyl)acrylamide | ¹H NMR (400 MHz, DMSO-$d_6$) δ 9.73 (s, 1H), 9.24 (d, J = 31.7 Hz, 1H), 8.28 (s, 1H), 7.93 (d, J = 12.1 Hz, 1H), 7.53 (dd, J = 8.7, 1.5 Hz, 1H), 7.41 (t, J = 8.1 Hz, 1H), 6.90 (d, J = 7.6 Hz, 1H), 6.58 (dd, J = 17.4, 10.3 Hz, 1H), 6.27-6.19 (m, 2H), 5.79-5.65 (m, 2H), 4.74-4.53 (m, 3H), 4.29 (d, J = 4.6 Hz, 1H), 4.20 (d, J = 10.3 Hz, 1H), 4.01 (d, J = 7.9 Hz, 1H), 3.82 (d, J = 1.7 Hz, 3H), 3.69 (s, 2H), 3.47 (d, J = 8.6 Hz, 2H), 3.38 (d, J = 6.0 Hz, 1H), 3.22 (d, J = 10.8 Hz, 2H), 2.92-2.72 (m, 3H), 2.31 (d, J = 11.5 Hz, 2H), 2.08 (d, J = 10.5 Hz, 3H), ; 684.2 [M + H]⁺ | 1.54 |

TABLE 1-continued

| Example Compound | Structure | Name of Compound | $^1$H NMR[[:]]; MS [M + H]$^+$ | UPLC r.t. (min) |
|---|---|---|---|---|
| 771 | 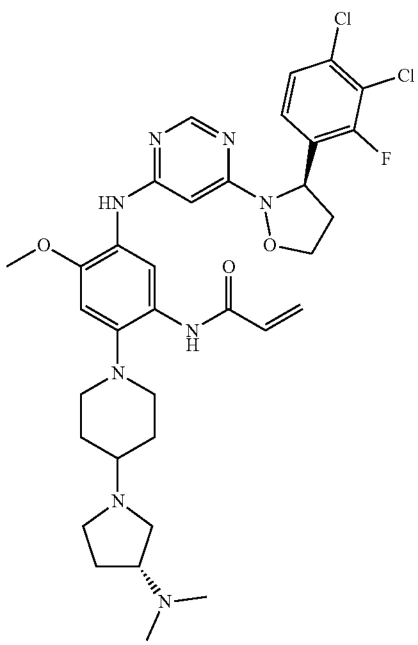 [SMILES: C=CC(=O)Nc1cc(Nc2cc(N3OCC[C@@H]3c3ccc(Cl)c(Cl)c3F)ncn2)c(OC)cc1N1CCC(N2CC[C@@H](N(C)C)C2)CC1] | N-(5-((6-((R)-3-(3,4-dichloro-2-fluorophenyl)isoxazolidine-2-yl)pyrimidine-4-yl)amino)-2-(4-((R)-3-(dimethylamino)pyrolidine-1-yl)piperidine-1-yl)-4-methoxyphenyl)acrylamide | 699.5 [M + H]$^+$ | 1.47 |
| 772 | 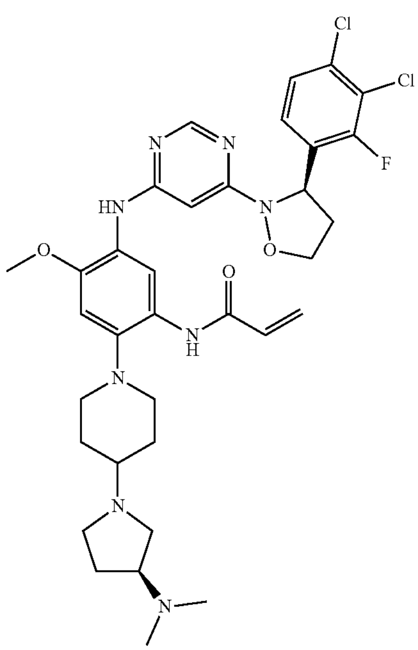 | N-(5-((6-((R)-3-(3,4-dichloro-2-fluorophenyl)isoxazolidine-2-yl)pyrimidine-4-yl)amino)-2-(4-((S)-3-(dimethylamino)pyrolidine-1-yl)piperidine-1-yl)-4-methoxyphenyl)acrylamide | 669.3 [M + H]$^+$ | 1.49 |

TABLE 1-continued

| Example Compound | Structure | Name of Compound | ¹H NMR[[:]]; MS [M + H]⁺ | UPLC r.t. (min) |
|---|---|---|---|---|
| 773 | 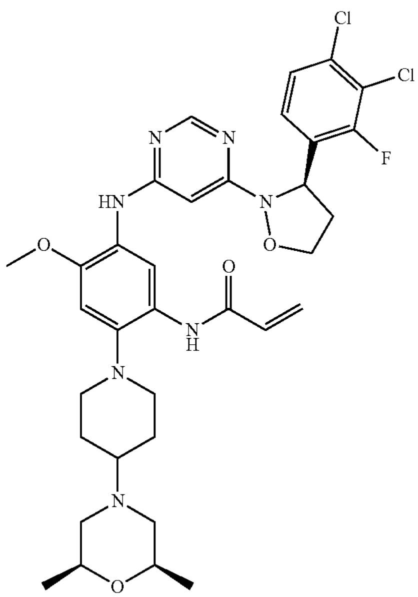 [SMILES: C=CC(=O)Nc1cc(Nc2cc(N3OCC[C@@H]3c3ccc(Cl)c(Cl)c3F)ncn2)c(OC)cc1N1CCC(N2C[C@@H](C)O[C@@H](C)C2)CC1] | N-(5-((6-((R)-3-(3,4-dichloro-2-fluorophenyl)isoxazolidine-2-yl)pyrimidine-4-yl)amino)-2-(4-((2S,6R)-2,6-dimethylmorpholino)piperidine-1-yl)-4-methoxyphenyl)acrylamide | ¹H NMR (400 MHz, DMSO-$d_6$) δ 9.61 (s, 1H), 9.13 (s, 1H), 8.27 (s, 1H), 7.97 (s, 1H), 7.53 (dd, J = 8.6, 1.5 Hz, 1H), 7.41 (t, J = 8.1 Hz, 1H), 6.90 (s, 1H), 6.66 (dd, J = 17.0, 10.3 Hz, 1H), 6.29-6.17 (m, 2H), 5.78-5.64 (m, 2H), 4.28 (d, J = 4.3 Hz, 1H), 4.11 (s, 2H), 4.00 (d, J = 8.0 Hz, 1H), 3.82 (s, 3H), 3.48 (s, 2H), 3.21 (d, J = 11.6 Hz, 3H), 2.95-2.88 (m, 1H), 2.72 (dd, J = 22.5, 11.6 Hz, 4H), 2.33-2.27 (m, 1H), 2.22 (d, J = 11.7 Hz, 2H), 2.03 (d, J = 11.5 Hz, 2H), 1.17 (d, J = 6.2 Hz, 6H), ; 700.5 [M + H]⁺ | 1.62 |
| 774 | 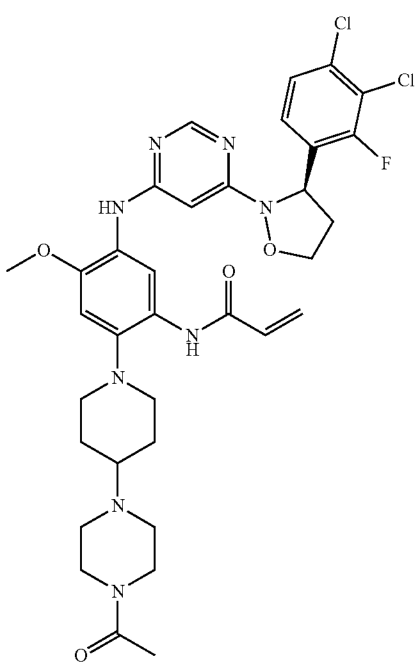 [SMILES: C=CC(=O)Nc1cc(Nc2cc(N3OCC[C@@H]3c3ccc(Cl)c(Cl)c3F)ncn2)c(OC)cc1N1CCC(N2CCN(C(C)=O)CC2)CC1] | N-(2-(4-(4-acetylpiperazine-1-yl)piperidine-1-yl)-5-((6-((R)-3-(3,4-dichloro-2-fluorophenyl)isoxazolidine-2-yl)pyrimidine-4-yl)amino)-4-methoxyphenyl)acrylamide | 713.3 [M + H]⁺ | 1.54 |

TABLE 1-continued

| Example Compound | Structure | Name of Compound | ¹H NMR[:]; MS [M + H]⁺ | UPLC r.t. (min) |
|---|---|---|---|---|
| 775 | 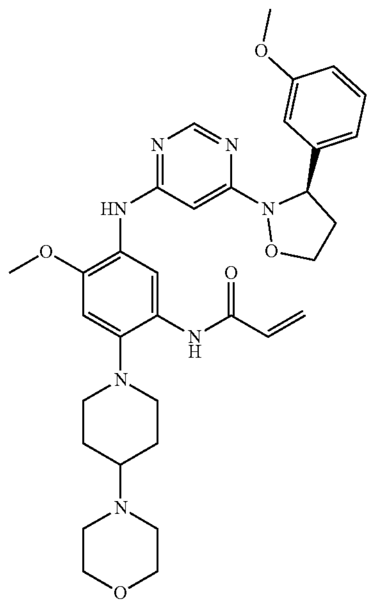 [SMILES: C=CC(=O)Nc1cc(Nc2cc(N3OCC[C@@H]3c3cccc(OC)c3)ncn2)c(OC)cc1N1CCC(N2CCOCC2)CC1] | N-(4-methoxy-5-((6-((R)-3-(3-methoxyphenyl)isoxazolidine-2-yl)pyrimidine-4-yl)amino)-2-(4-morpholinopiperidine-1-yl)phenyl)acrylamide | ¹H NMR (400 MHz, Methanol-d4) δ 8.28 (s, 1H), 8.14 (s, 1H), 7.24 (t, J = 8.0 Hz, 1H), 6.99 (dd, J = 5.0, 3.0 Hz, 2H), 6.89 (s, 1H), 6.82-6.78 (m, 1H), 6.55 (dd, J = 17.0, 10.3 Hz, 1H), 6.40-6.32 (m, 2H), 5.79 (dd, J = 10.3, 1.5 Hz, 1H), 5.48 (dd, J = 8.5, 4.7 Hz, 1H), 4.13 (td, J = 7.8, 4.4 Hz, 1H), 3.96 (q, J = 7.9 Hz, 1H), 3.85 (s, 3H), 3.79 (d, J = 4.7 Hz, 7H), 3.17-3.11 (m, 2H), 2.82-2.74 (m, 7H), 2.56 (tt, J = 11.6, 4.0 Hz, 1H), 2.37-2.28 (m, 1H), 2.12-2.06 (m, 2H), 1.80-1.74 (m, 2H); 616.5 [M + H]⁺ | 1.03 |
| 776 | 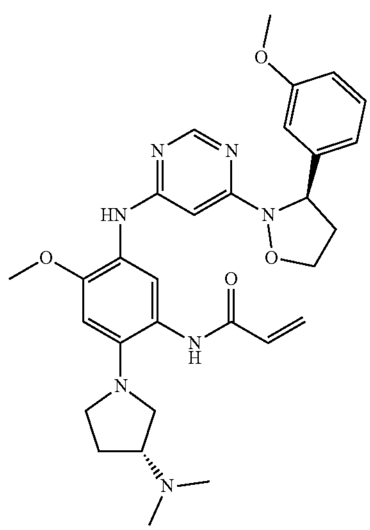 [SMILES: C=CC(=O)Nc1cc(Nc2cc(N3OCC[C@@H]3c3cccc(OC)c3)ncn2)c(OC)cc1N1CC[C@@H](N(C)C)C1] | N-(2-((R)-3-(dimethylamino)pyrolidine-1-yl)-4-methoxy-5-((6-((R)-3-(3-methoxyphenyl)isoxazolidine-2-yl)pyrimidine-4-yl)amino)phenyl)acrylamide | ¹H NMR (400 MHz, Methanol-d4) δ 8.11 (s, 1H), 7.70 (s, 1H), 7.24 (t, J = 8.0 Hz, 1H), 6.99 (dd, J = 5.0, 3.0 Hz, 2H), 6.83-6.78 (m, 1H), 6.68 (s, 1H), 6.52 (dd, J = 17.0, 10.2 Hz, 1H), 6.36 (dd, J = 17.1, 1.7 Hz, 1H), 6.30 (s, 1H), 5.79 (dd, J = 10.1, 1.7 Hz, 1H), 5.50-5.46 (m, 1H), 4.12 (td, J = 7.8, 4.4 Hz, 1H), 3.93 (q, J = 7.9 Hz, 1H), 3.86 (s, 3H), 3.78 (s, 3H), 3.42-3.32 (m, 5H), 2.81-2.73 (m, 1H), 2.59 (s, 6H), 2.37-2.28 (m, 2H), 2.07-2.01 (m, 1H), ; 560.5 [M + H]⁺ | 1.00 |

TABLE 1-continued

| Example Compound | Structure | Name of Compound | ¹H NMR[[:]]; MS [M + H]⁺ | UPLC r.t. (min) |
|---|---|---|---|---|
| 777 | 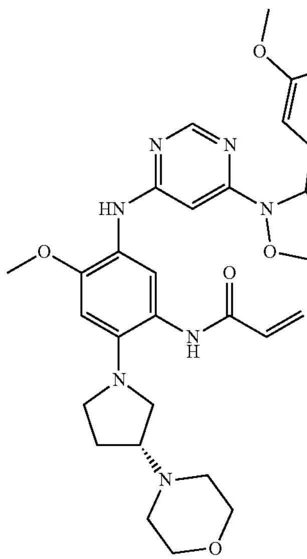 | N-(4-methoxy-5-((6-((R)-3-(3-methoxyphenyl)isoxazolidine-2-yl)pyrimidine-4-yl)amino)-2-((R)-3-morpholinopyrolidine-1-yl)phenyl)acrylamide | ¹H NMR (400 MHz, Methanol-d4) δ 8.10 (s, 1H), 7.64 (s, 1H), 7.24 (t, J = 8.0 Hz, 1H), 6.99 (dd, J = 5.1, 3.1 Hz, 2H), 6.82-6.78 (m, 1H), 6.64 (s, 1H), 6.52 (dd, J = 17.0, 10.2 Hz, 1H), 6.34 (dd, J = 17.0, 1.7 Hz, 1H), 6.27 (s, 1H), 5.77 (dd, J = 10.3, 1.7 Hz, 1H), 5.49-5.45 (m, 1H), 4.11 (td, J = 7.8, 4.4 Hz, 1H), 3.93 (q, J = 7.9 Hz, 1H), 3.84 (s, 3H), 3.78 (s, 3H), 3.74 (t, J = 4.8 Hz, 4H), 3.39-3.32 (m, 2H), 3.30-3.26 (m, 2H), 2.98 (p, J = 7.3 Hz, 1H), 2.76 (tq, J = 8.0, 4.5, 4.0 Hz, 1H), 2.64 (dt, J = 10.2, 4.8 Hz, 2H), 2.55 (dt, J = 11.8, 5.1 Hz, 2H), 2.32 (ddt, J = 11.6, 7.7, 3.9 Hz, 1H), 2.23 (dtd, J = 13.8, 6.7, 2.7 Hz, 1H), 1.94-1.86 (m, 1H); 602.5 [M + H]⁺ | 1.06 |
| 778 | 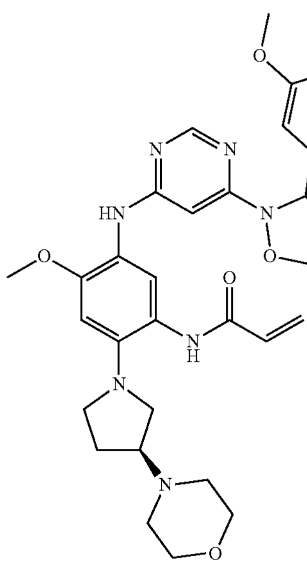 | N-(4-methoxy-5-((6-((R)-3-(3-methoxyphenyl)isoxazolidine-2-yl)pyrimidine-4-yl)amino)-2-((S)-3-morpholinopyrolidine-1-yl)phenyl)acrylamide | ¹H NMR (400 MHz, Methanol-d4) δ 8.10 (s, 1H), 7.63 (s, 1H), 7.24 (t, J = 8.1 Hz, 1H), 7.02-6.95 (m, 2H), 6.82-6.78 (m, 1H), 6.64 (s, 1H), 6.52 (dd, J = 17.0, 10.2 Hz, 1H), 6.39-6.21 (m, 2H), 5.78 (dd, J = 10.2, 1.7 Hz, 1H), 5.46 (dd, J = 8.5, 4.7 Hz, 1H), 4.11 (td, J = 7.8, 4.4 Hz, 1H), 3.92 (q, J = 7.8 Hz, 1H), 3.84 (s, 3H), 3.78 (s, 3H), 3.74 (t, J = 4.8 Hz, 4H), 3.36-3.32 (m, 2H), 3.27 (dt, J = 9.3, 4.4 Hz, 2H), 3.00 (p, J = 7.2 Hz, 1H), 2.76 (ddt, J = 12.3, 8.0, 3.9 Hz, 1H), 2.66 (dt, J = 9.7, 4.6 Hz, 2H), 2.56 (dt, J = 11.3, 4.8 Hz, 2H), 2.32 (ddt, J = 11.7, 7.8, 3.9 Hz, 1H), 2.23 (dtd, J = 13.7, 6.8, 2.9 Hz, 1H), 1.94-1.87 (m, 1H); 602.5 [M + H]⁺ | 1.02 |

| Example Compound | Structure | Name of Compound | ¹H NMR[[:]]; MS [M + H]⁺ | UPLC r.t. (min) |
|---|---|---|---|---|
| 779 | 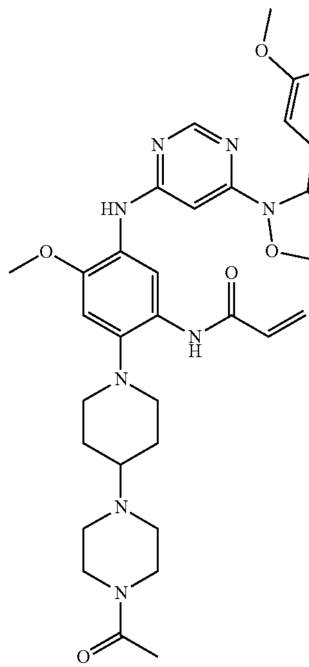 | N-(2-(4-(4-acetylpiperazine-1-yl)piperidine-1-yl)-4-methoxy-5-((6-((R)-3-(3-methoxyphenyl)isoxazolidine-2-yl)pyrimidine-4-yl)amino)phenyl)acrylamide | ¹H NMR (400 MHz, Methanol-d4) δ 8.27 (s, 1H), 8.14 (s, 1H), 7.24 (t, J = 8.1 Hz, 1H), 6.99 (dd, J = 5.0, 2.9 Hz, 2H), 6.89 (s, 1H), 6.83-6.78 (m, 1H), 6.54 (dd, J = 17.0, 10.3 Hz, 1H), 6.41-6.30 (m, 2H), 5.79 (d, J = 10.3 Hz, 1H), 5.51-5.45 (m, 1H), 4.13 (td, J = 7.8, 4.3 Hz, 1H), 3.96 (q, J = 7.9 Hz, 1H), 3.85 (s, 3H), 3.78 (s, 3H), 3.63 (dt, J = 15.5, 5.3 Hz, 4H), 3.13 (d, J = 11.3 Hz, 2H), 2.83-2.72 (m, 5H), 2.69 (t, J = 5.2 Hz, 2H), 2.53 (tt, J = 11.5, 3.9 Hz, 1H), 2.38-2.28 (m, 1H), 2.11 (s, 3H), 2.06-2.00 (m, 2H), 1.83-1.73 (m, 2H); 657.6 [M + H]⁺ | 1.12 |
| 780 | 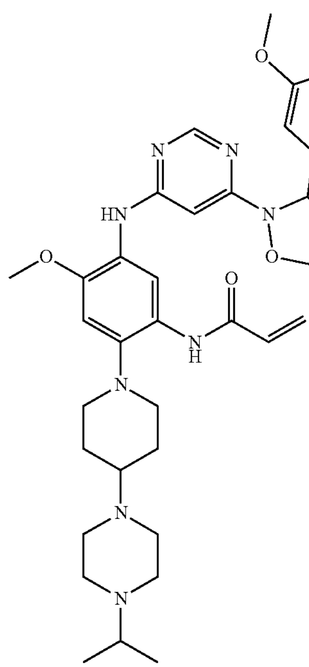 | N-(2-(4-(4-isopropylpiperazine-1-yl)piperidine-1-yl)-4-methoxy-5-((6-((R)-3-(3-methoxyphenyl)isoxazolidine-2-yl)pyrimidine-4-yl)amino)phenyl)acrylamide | 657.6 [M + H]⁺ | 1.12 |

TABLE 1-continued

| Example Compound | Structure | Name of Compound | ¹H NMR[:]; MS [M + H]⁺ | UPLC r.t. (min) |
|---|---|---|---|---|
| 781 | 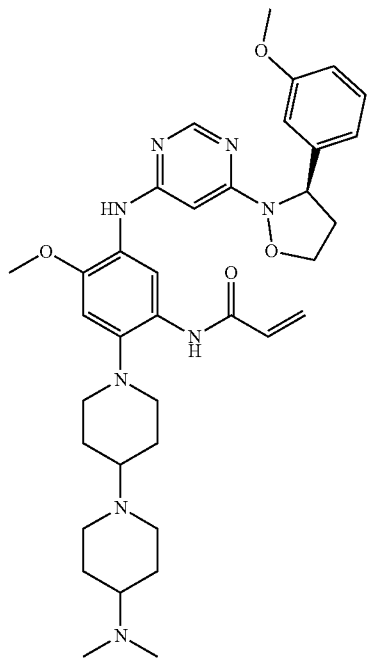 [SMILES: C=CC(=O)Nc1cc(Nc2cc(N3OCC[C@@H]3c3cccc(OC)c3)ncn2)c(OC)cc1N1CCC(N2CCC(N(C)C)CC2)CC1] | N-(2-(4-(dimethylamino)-[1,4'-bipiperidine]-1'-yl)-4-methoxy-5-((6-((R)-3-(3-methoxyphenyl)isoxazolidine-2-yl)pyrimidine-4-yl)amino)phenyl)acrylamide | 657.7 [M + H]⁺ | 1.04 |
| 782 | 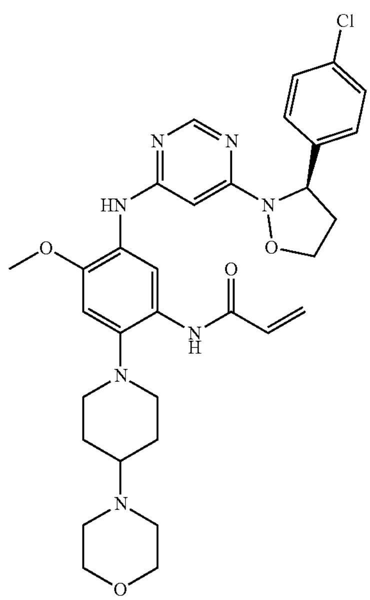 [SMILES: C=CC(=O)Nc1cc(Nc2cc(N3OCC[C@@H]3c3ccc(Cl)cc3)ncn2)c(OC)cc1N1CCC(N2CCOCC2)CC1] | N-(5-((6-((R)-3-(4-chlorophenyl)isoxazolidine-2-yl)pyrimidine-4-yl)amino)-4-methoxy-2-(4-morpholinopiperidine-1-yl)phenyl)acrylamide | 620.5 [M + H]⁺ | 1.38 |

TABLE 1-continued

| Example Compound | Structure | Name of Compound | ¹H NMR[[:]]; MS [M + H]⁺ | UPLC r.t. (min) |
|---|---|---|---|---|
| 783 | 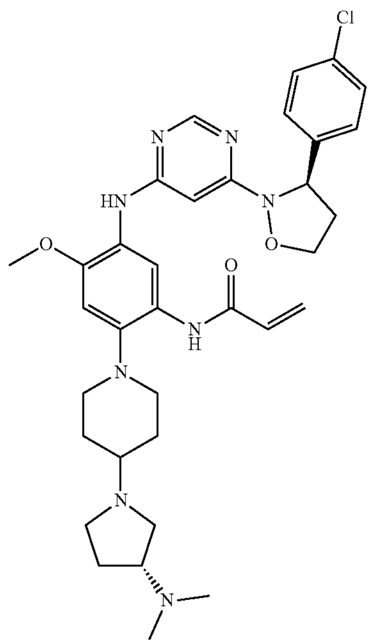 [SMILES: C=CC(=O)Nc1cc(Nc2cc(N3OCC[C@@H]3c3ccc(Cl)cc3)ncn2)c(OC)cc1N1CCC(N2CC[C@@H](N(C)C)C2)CC1] | N-(5-((6-((R)-3-(4-chlorophenyl) isoxazolidine-2-yl)pyrimidine-4-yl)amino)-2-(4-((R)-3-(dimethylamino) pyrolidine-1-yl)piperidine-1-yl)-4-methoxyphenyl) acrylamide | 647.6 [M + H]⁺ | 1.12 |
| 784 | 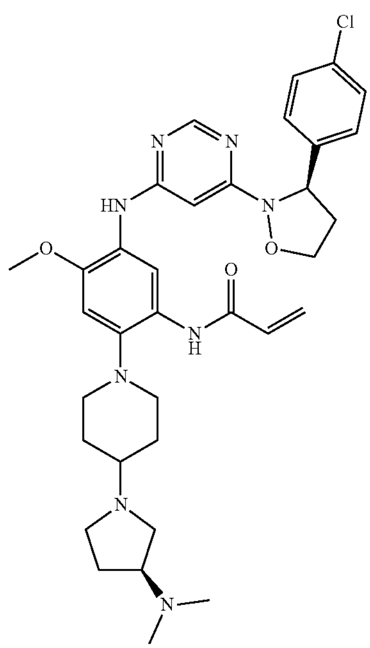 [SMILES: C=CC(=O)Nc1cc(Nc2cc(N3OCC[C@@H]3c3ccc(Cl)cc3)ncn2)c(OC)cc1N1CCC(N2CC[C@H](N(C)C)C2)CC1] | N-(5-((6-((R)-3-(4-chlorophenyl) isoxazolidine-2-yl)pyrimidine-4-yl)amino)-2-(4-((S)-3-(dimethylamino) pyrolidine-1-yl) piperidine-1-yl)-4-methoxyphenyl) acrylamide | 647.6 [M + H]⁺ | 1.13 |

TABLE 1-continued

| Example Compound | Structure | Name of Compound | ¹H NMR[[:]]; MS [M + H]⁺ | UPLC r.t. (min) |
|---|---|---|---|---|
| 785 | 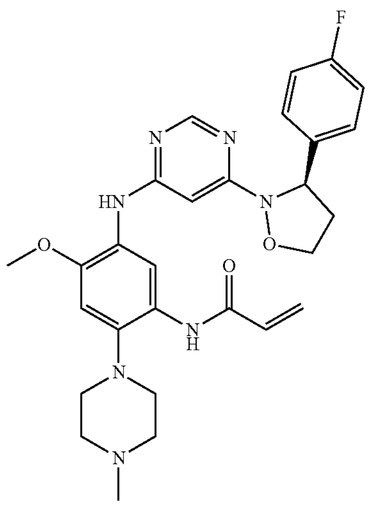 [SMILES: C=CC(=O)Nc1cc(Nc2cc(N3OCC[C@@H]3c3ccc(F)cc3)ncn2)c(OC)cc1N1CCN(C)CC1] | N-(5-((6-((R)-3-(4-fluorophenyl)isoxazolidine-2-yl)pyrimidine-4-yl)amino)-4-methoxy-2-(4-methylpiperazine-1-yl)phenyl)acrylamide | $^1$H NMR (400 MHz, DMSO-$d_6$) δ 9.41 (s, 1H), 9.11 (s, 1H), 8.25 (s, 1H), 8.13 (s, 1H), 7.42 (dd, J = 8.6, 5.6 Hz, 2H), 7.19 (t, J = 8.8 Hz, 2H), 6.87 (s, 1H), 6.74 (dd, J = 17.0, 10.3 Hz, 1H), 6.28-6.15 (m, 2H), 5.76 (dd, J = 10.3, 2.0 Hz, 1H), 5.52 (dd, J = 8.6, 5.2 Hz, 1H), 4.25-4.21 (m, 1H), 3.97 (d, J = 7.8 Hz, 1H), 3.82 (s, 3H), 3.33 (d, J = 10.5 Hz, 3H), 3.18 (d, J = 5.9 Hz, 4H), 2.87 (d, J = 14.9 Hz, 1H), 2.83 (d, J = 4.7 Hz, 3H), 2.34-2.24 (m, 2H), ; 534.4 [M + H]⁺ | 1.28 |
| 786 | 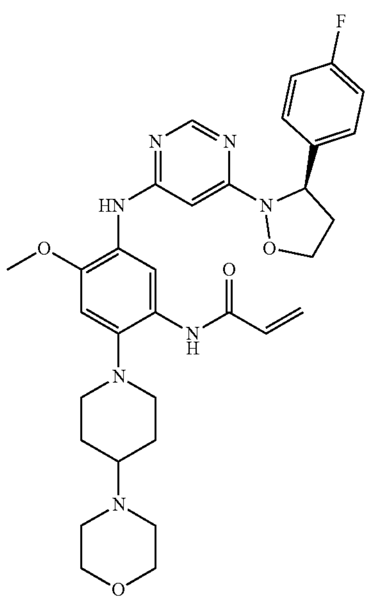 [SMILES: C=CC(=O)Nc1cc(Nc2cc(N3OCC[C@@H]3c3ccc(F)cc3)ncn2)c(OC)cc1N1CCC(N2CCOCC2)CC1] | N-(5-((6-((R)-3-(4-fluorophenyl)isoxazolidine-2-yl)pyrimidine-4-yl)amino)-4-methoxy-2-(4-morpholinopiperidine-1-yl)phenyl)acrylamide | 604.5 [M + H]⁺ | 1.3 |

TABLE 1-continued

| Example Compound | Structure | Name of Compound | ¹H NMR[:]; MS [M + H]⁺ | UPLC r.t. (min) |
|---|---|---|---|---|
| 787 | 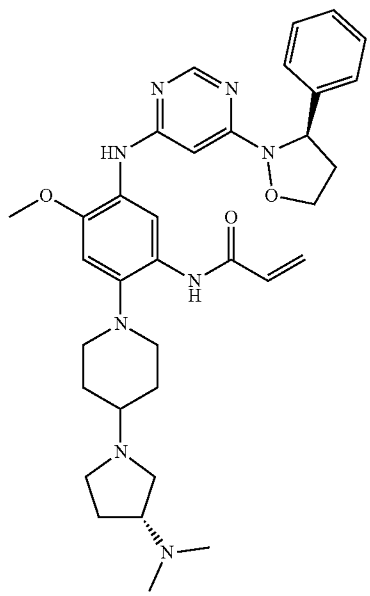 [SMILES: C=CC(=O)Nc1cc(Nc2cc(N3OCC[C@@H]3c3ccccc3)ncn2)c(OC)cc1N1CCC(N2CC[C@@H](N(C)C)C2)CC1] | N-(2-(4-((R)-3-(dimethylamino)pyrolidine-1-yl)piperidine-1-yl)-4-methoxy-5-((6-((R)-3-phenylisoxazolidine-2-yl)pyrimidine-4-yl)amino)phenyl)acrylamide | ¹H NMR (400 MHz, DMSO-$d_6$) δ 9.71 (s, 1H), 9.23 (s, 1H), 8.27 (s, 1H), 7.90 (s, 1H), 7.37 (m, 4H), 7.29 (td, J = 5.3, 3.0 Hz, 1H), 6.91 (m, 1H), 6.64 (dd, J = 17.0, 10.2 Hz, 1H), 6.24 (dd, J = 17.1, 1.9 Hz, 1H), 6.07 (s, 1H), 5.82-5.70 (m, 1H), 5.51 (d, J = 9.1 Hz, 1H), 4.29 (m, 2H), 4.03 (m, 4H), 3.80 (s, 3H), 3.23 (m, 3H), 2.95-2.69 (m, 12H), 2.36-2.26 (m, 1H), 2.18 (m, 2H), 2.06 (m, 2H), ; 613.6 [M + H]⁺ | 1.00 |
| 788 | 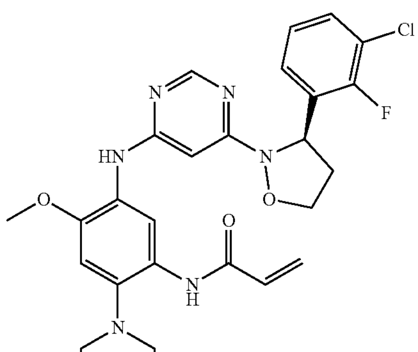 | N-(5-((6-((R)-3-(3-chloro-2-fluorophenyl)isoxazolidine-2-yl)pyrimidine-4-yl)amino)-4-methoxy-2-(4-morpholinopiperidine-1-yl)phenyl)acrylamide | ¹H NMR (400 MHz, DMSO-$d_6$) δ 9.20 (s, 1H), 8.29 (d, J = 4.6 Hz, 1H), 7.92 (s, 1H), 7.55 (t, J = 7.5 Hz, 1H), 7.36 (t, J = 7.3 Hz, 1H), 7.24 (t, J = 7.9 Hz, 1H), 6.91 (s, 1H), 6.67 (dd, J = 17.3, 10.5 Hz, 1H), 6.25 (d, J = 16.6 Hz, 1H), 6.17 (s, 1H), 5.81-5.66 (m, 2H), 4.31 (t, J = 6.0 Hz, 1H), 4.04 (dt, J = 10.7, 5.9 Hz, 1H), 4.01-3.90 (m, 4H), 3.81 (s, 3H), 3.22 (d, J = 11.4 Hz, 3H), 3.18-3.10 (m, 3H), 3.01-2.90 (m, 2H), 2.78 (t, J = 12.0 Hz, 2H), 2.30 (dt, J = 12.9, 6.5 Hz, 1H), 2.21 (d, J = 11.7 Hz, 3H), 2.05 (t, J = 12.4 Hz, 2H), ; 638.5 [M + H]⁺ | 1.28 |

TABLE 1-continued

| Example Compound | Structure | Name of Compound | ¹H NMR[[:]]; MS [M + H]⁺ | UPLC r.t. (min) |
|---|---|---|---|---|
| 789 | 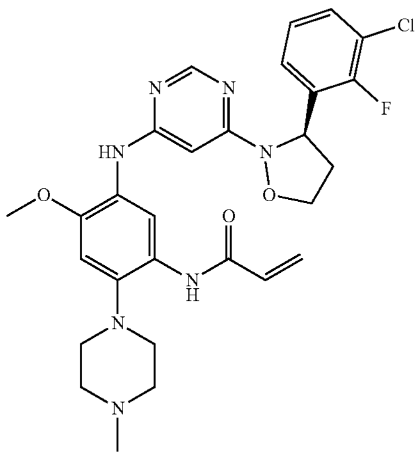 [SMILES: C=CC(=O)Nc1cc(Nc2cc(N3OCC[C@@H]3c3cccc(Cl)c3F)ncn2)c(OC)cc1N1CCN(C)CC1] | N-(5-((6-((R)-3-(3-chloro-2-fluorophenyl)isoxazolidine-2-yl)pyrimidine-4-yl)amino)-4-methoxy-2-(4-methylpiperazine-1-yl)phenyl)acrylamide | ¹H NMR (400 MHz, DMSO-d₆) δ 9.15 (d, J = 11.3 Hz, 1H), 8.26 (q, J = 5.7 Hz, 1H), 7.58-7.50 (m, 1H), 7.42-7.34 (m, 1H), 7.24 (t, J = 7.9 Hz, 1H), 6.86 (d, J = 15.2 Hz, 1H), 6.29-6.18 (m, 2H), 5.74 (dt, J = 13.0, 5.2 Hz, 2H), 4.32-4.23 (m, 1H), 4.00 (d, J = 7.6 Hz, 2H), 3.83 (d, J = 2.7 Hz, 3H), 3.80-3.71 (m, 4H), 3.31 (d, J = 12.4 Hz, 1H), 3.19 (dd, J = 10.3, 6.1 Hz, 4H), 3.16-3.07 (m, 3H), 2.82 (d, J = 4.6 Hz, 2H), 2.27 (s, 1H), ; 568.5 [M + H]⁺ | 1.41 |
| 790 | 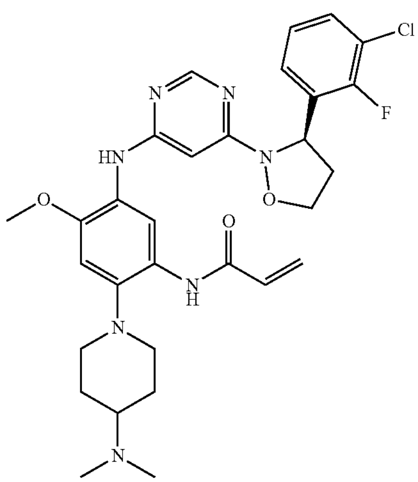 [SMILES: C=CC(=O)Nc1cc(Nc2cc(N3OCC[C@@H]3c3cccc(Cl)c3F)ncn2)c(OC)cc1N1CCC(N(C)C)CC1] | N-(5-((6-((R)-3-(3-chloro-2-fluorophenyl)isoxazolidine-2-yl)pyrimidine-4-yl)amino)-2-(4-(dimethylamino)piperidine-1-yl)-4-methoxyphenyl)acrylamide | ; 596.5 [M + H]⁺ | 1.41 |
| 791 | 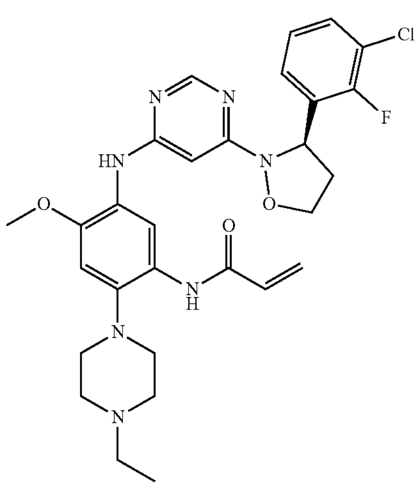 | N-(5-((6-((R)-3-(3-chloro-2-fluorophenyl)isoxazolidine-2-yl)pyrimidine-4-yl)amino)-2-(4-ethylpiperazine-1-yl)-4-methoxyphenyl)acrylamide | ¹H NMR (400 MHz, DMSO-d₆) δ 9.57 (d, J = 11.0 Hz, 1H), 8.25 (d, J = 5.0 Hz, 1H), 7.54 (t, J = 7.9 Hz, 1H), 7.38 (d, J = 8.0 Hz, 1H), 7.24 (t, J = 7.9 Hz, 1H), 6.82 (t, J = 8.8 Hz, 1H), 6.66 (d, J = 20.8 Hz, 1H), 6.23 (ddd, J = 16.5, 14.4, 2.0 Hz, 1H), 6.08 (dd, J = 17.3, 10.2 Hz, 1H), 5.78-5.67 (m, 2H), 4.34-4.22 (m, 1H), 4.06-3.93 (m, 1H), 3.81 (d, J = 3.4 Hz, 3H), 3.75 (q, J = 6.1 Hz, 1H), 3.61 (td, J = 6.6, 3.9 Hz, 3H), 3.16-3.10 (m, 4H), 2.80 (dd, J = 8.1, 4.6 Hz, 6H), 2.73 (dd, J = 6.0, 3.8 Hz, 1H), 2.34-2.23 (m, 2H), ; 596.5 [M + H]⁺ | 1.39 |

TABLE 1-continued

| Example Compound | Structure | Name of Compound | $^1$H NMR[[:]]; MS [M + H]$^+$ | UPLC r.t. (min) |
|---|---|---|---|---|
| 792 | 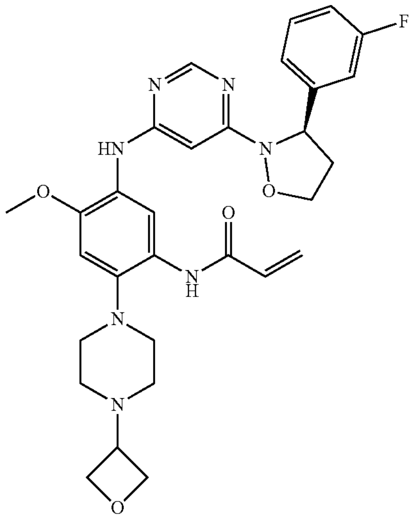 [SMILES: C=CC(=O)Nc1cc(Nc2cc(N3OCC[C@@H]3c3cccc(F)c3)ncn2)c(OC)cc1N1CCN(C2COC2)CC1] | N-(5-((6-((R)-3-(3-fluorophenyl)isoxazolidine-2-yl)pyrimidine-4-yl)amino)-4-methoxy-2-(4-(oxetane-3-yl)piperazine-1-yl)phenyl)acrylamide | $^1$H NMR (400 MHz, DMSO-d$_6$) δ 10.64 (s, 1H), 9.68 (s, 1H), 9.16 (d, J = 19.0 Hz, 1H), 8.29 (s, 1H), 8.06 (s, 1H), 7.42 (td, J = 7.9, 6.1 Hz, 1H), 7.20 (t, J = 10.1 Hz, 2H), 7.17-7.08 (m, 1H), 6.88 (s, 1H), 6.67 (dd, J 16.9, 10.0 Hz, 1H), 6.25 (dd, J = 17.0, 2.3 Hz, 1H), 5.81-5.69 (m, 1H), 5.53 (t, J = 7.0 Hz, 1H), 4.81 (d, J = 6.5 Hz, 3H), 4.66 (t, J = 5.3 Hz, 2H), 4.52 (s, 1H), 4.28 (s, 1H), 4.02 (s, 1H), 3.82 (d, J = 2.3 Hz, 3H), 3.57 (d, J = 24.1 Hz, 3H), 3.36 (s, 1H), 3.24 (s, 3H), 3.12 (d, J = 11.4 Hz, 1H), 2.91 (s, 1H), ; 576.5 [M + H]$^+$ | 1.29 |
| 793 | 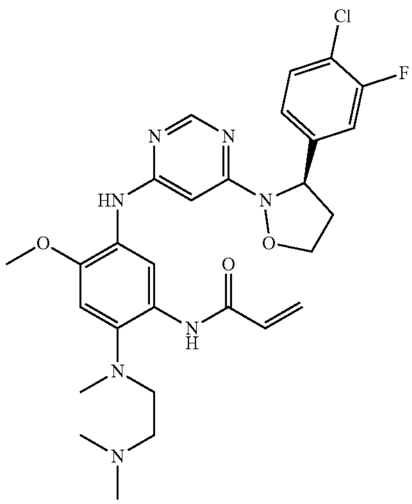 [SMILES: C=CC(=O)Nc1cc(Nc2cc(N3OCC[C@@H]3c3ccc(Cl)c(F)c3)ncn2)c(OC)cc1N(C)CCN(C)C] | N-(5-((6-((R)-3-(4-chloro-3-fluorophenyl)isoxazolidine-2-yl)pyrimidine-4-yl)amino)-2-((2-(dimethylamino)ethyl)(methyl)amino)-4-methoxyphenyl)acrylamide | $^1$H NMR (400 MHz, MeOD) δ 8.09 (s, 1H), 7.57 (s, 1H), 7.38 (t, J = 7.9 Hz, 1H), 7.18 (dd, J = 10.1, 2.0 Hz, 1H), 7.10 (dd, J = 8.3, 2.0 Hz, 1H), 6.92 (s, 1H), 6.71 (dd, J = 16.9, 10.2 Hz, 1H), 6.32 (dd, J = 16.9, 1.6 Hz, 1H), 5.97 (s, 1H), 5.73 (dd, J = 10.3, 1.6 Hz, 1H), 5.44 (t, J = 7.1 Hz, 1H), 4.32 (td, J = 7.5, 3.9 Hz, 1H), 4.07 (q, J = 7.7 Hz, 1H), 3.80 (s, 3H), 3.44 (t, J = 5.7 Hz, 2H), 3.27 (t, J = 5.6 Hz, 2H), 3.20 (s, 1H), 2.94 (q, J = 8.9, 7.3 Hz, 1H), 2.85-2.73 (m, 6H), 2.67 (s, 3H), 2.41-2.28 (m, 1H), ; 571.3 [M + H]$^+$ | 1.31 |
| 794 | 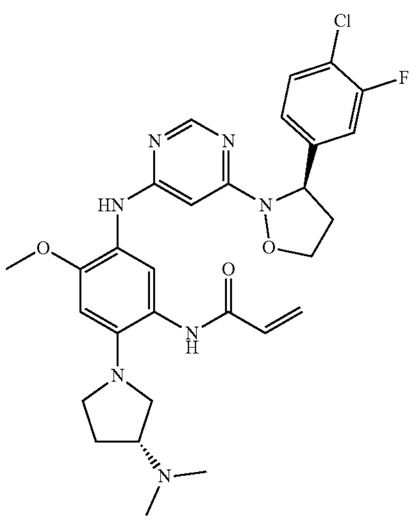 [SMILES: C=CC(=O)Nc1cc(Nc2cc(N3OCC[C@@H]3c3ccc(Cl)c(F)c3)ncn2)c(OC)cc1N1CC[C@@H](N(C)C)C1] | N-(5-((6-((R)-3-(4-chloro-3-fluorophenyl)isoxazolidine-2-yl)pyrimidine-4-yl)amino)-2-((R)-3-(dimethylamino)pyrolidine-1-yl)-4-methoxyphenyl)acrylamide | $^1$H NMR (400 MHz, MeOD) δ 8.04 (s, 1H), 7.45-7.27 (m, 2H), 7.17 (dd, J = 10.1, 2.1 Hz, 1H), 7.09 (dd, J = 8.3, 2.0 Hz, 1H), 6.65 (s, 1H), 6.60 (dd, J = 17.0, 10.3 Hz, 1H), 6.28 (dd, J = 17.0, 1.7 Hz, 1H), 5.95 (s, 1H), 5.72 (dd, J = 10.3, 1.7 Hz, 1H), 5.43 (d, J = 7.3 Hz, 1H), 4.30 (td, J = 7.6, 4.2 Hz, 1H), 4.06 (td, J = 8.2, 6.6 Hz, 1H), 3.91 (q, J = 6.5 Hz, 1H), 3.77 (s, 3H), 3.59 (dd, J = 10.9, 4.8 Hz, 1H), 3.54-3.43 (m, 2H), 3.20 (s, 1H), 3.19-3.13 (m, 1H), 2.97-2.90 (m, 1H), 2.86 (d, J = 10.8 Hz, 6H), 2.47-2.30 (m, 2H), 2.22 (dd, J = 13.9, 6.7 Hz, 1H), ; 583.4 [M + H]$^+$ | 1.24 |

TABLE 1-continued

| Example Compound | Structure | Name of Compound | ¹H NMR[[:]]; MS [M + H]⁺ | UPLC r.t. (min) |
|---|---|---|---|---|
| 795 | 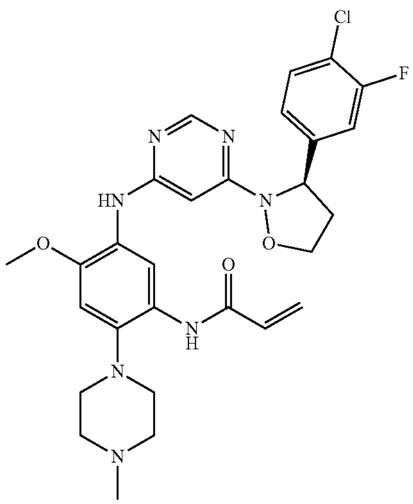 [SMILES: C=CC(=O)Nc1cc(Nc2cc(N3OCC[C@@H]3c3ccc(Cl)c(F)c3)ncn2)c(OC)cc1N1CCN(C)CC1] | N-(5-((6-((R)-3-(4-chloro-3-fluorophenyl)isoxazolidine-2-yl)pyrimidine-4-yl)amino)-4-methoxy-2-(4-methylpiperazine-1-yl)phenyl)acrylamide | ¹H NMR (400 MHz, MeOD) δ 8.08 (s, 1H), 7.87 (s, 1H), 7.38 (t, J = 7.9 Hz, 1H), 7.18 (dd, J = 10.1, 2.0 Hz, 1H), 7.10 (dd, J = 8.3, 2.0 Hz, 1H), 6.91 (s, 1H), 6.59 (dd, J = 16.9, 10.2 Hz, 1H), 6.30 (dd, J = 17.0, 1.6 Hz, 1H), 5.95 (s, 1H), 5.73 (dd, J = 10.2, 1.6 Hz, 1H), 5.42 (d, J = 7.7 Hz, 1H), 4.31 (td, J = 7.6, 4.1 Hz, 1H), 4.07 (q, J = 7.9 Hz, 1H), 3.78 (s, 3H), 3.53 (d, J = 11.9 Hz, 2H), 3.42-3.31 (m, 2H), 3.22-3.17 (m, 6H), 2.90 (s, 3H), 2.41-2.29 (m, 1H), ; 568.3 [M + H]⁺ | 1.27 |
| 796 | 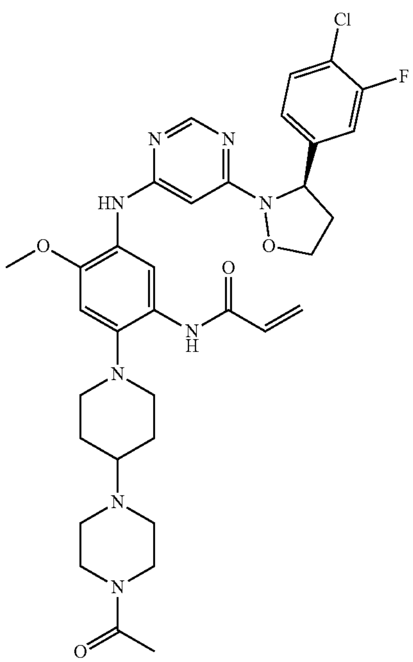 [SMILES: C=CC(=O)Nc1cc(Nc2cc(N3OCC[C@@H]3c3ccc(Cl)c(F)c3)ncn2)c(OC)cc1N1CCC(N2CCN(C(C)=O)CC2)CC1] | N-(2-(4-(4-acetylpiperazine-1-yl)piperidine-1-yl)-5-((6-((R)-3-(4-chloro-3-fluorophenyl)isoxazolidine-2-yl)pyrimidine-4-yl)amino)-4-methoxyphenyl)acrylamide | ¹H NMR (400 MHz, MeOD) δ 8.20 (s, 1H), 8.06 (s, 1H), 7.33 (t, J = 8.0 Hz, 1H), 7.22 (dd, J = 10.5, 2.0 Hz, 1H), 7.15 (dd, J = 8.5, 2.0 Hz, 1H), 6.80 (s, 1H), 6.44 (dd, J = 17.0, 10.3 Hz, 1H), 6.34 (s, 1H), 6.24 (dd, J = 17.0, 1.6 Hz, 1H), 5.69 (dd, J = 10.2, 1.6 Hz, 1H), 5.44 (dd, J = 8.7, 4.7 Hz, 1H), 4.10-3.98 (m, 1H), 3.86 (d, J = 8.0 Hz, 1H), 3.76 (s, 3H), 3.50 (dt, J = 16.1, 5.4 Hz, 4H), 3.03 (d, J = 11.4 Hz, 2H), 2.76-2.61 (m, 3H), 2.60-2.45 (m, 4H), 2.35 (s, 1H), 2.28-2.13 (m, 1H), 2.01 (s, 3H), 1.91 (d, J = 11.7 Hz, 2H), 1.74-1.60 (m, 2H), ; 679.4 [M + H]⁺ | 1.28 |

TABLE 1-continued

| Example Compound | Structure | Name of Compound | $^1$H NMR[:]; MS [M + H]$^+$ | UPLC r.t. (min) |
|---|---|---|---|---|
| 797 | 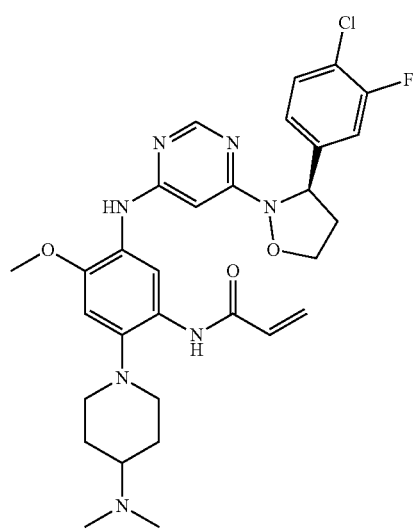 [SMILES: C=CC(=O)Nc1cc(Nc2cc(N3OCC[C@@H]3c3ccc(Cl)c(F)c3)ncn2)c(OC)cc1N1CCC(N(C)C)CC1] | N-(5-((6-((R)-3-(4-chloro-3-fluorophenyl)isoxazolidine-2-yl)pyrimidine-4-yl)amino)-2-(4-(dimethylamino)piperidine-1-yl)-4-methoxyphenyl)acrylamide | $^1$H NMR (400 MHz, MeOD) δ 8.24 (s, 1H), 7.92 (s, 1H), 7.51 (t, J = 7.9 Hz, 1H), 7.31 (dd, J = 10.0, 2.0 Hz, 1H), 7.26-7.05 (m, 2H), 6.70 (dd, J = 17.0, 10.2 Hz, 1H), 6.47 (dd, J = 16.8, 1.5 Hz, 1H), 6.10 (s, 1H), 5.99-5.80 (m, 1H), 5.54 (t, J = 7.1 Hz, 1H), 4.45 (td, J = 7.5, 3.9 Hz, 1H), 4.20 (q, J = 7.7 Hz, 1H), 3.93 (s, 3H), 3.75 (p, J = 6.6 Hz, 1H), 3.65-3.34 (m, 4H), 3.13-3.05 (m, 1H), 2.98 (s, 6H), 2.91 (d, J = 3.1 Hz, 1H), 2.48 (dd, J = 13.0, 6.6 Hz, 1H), 2.35 (d, J = 12.3 Hz, 2H), 2.27-2.12 (m, 2H), ; 597.4 [M + H]$^+$ | 1.28 |
| 798 | 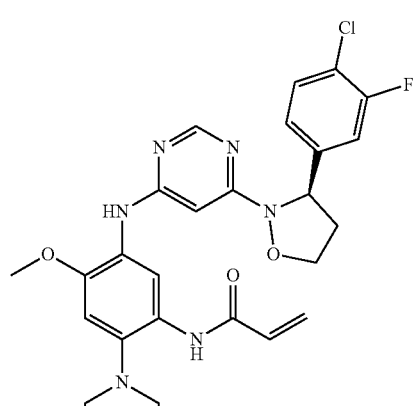 | N-(5-((6-((R)-3-(4-chloro-3-fluorophenyl)isoxazolidine-2-yl)pyrimidine-4-yl)amino)-2-(4-ethylpiperazine-1-yl)-4-methoxyphenyl)acrylamide | $^1$H NMR (400 MHz, MeOD) δ 8.08 (s, 1H), 7.88 (s, 1H), 7.38 (t, J = 7.9 Hz, 1H), 7.18 (dd, J = 10.1, 2.0 Hz, 1H), 7.10 (dd, J = 8.3, 2.0 Hz, 1H), 6.92 (s, 1H), 6.60 (dd, J = 16.9, 10.3 Hz, 1H), 6.29 (dd, J = 16.9, 1.6 Hz, 1H), 5.96 (s, 1H), 5.73 (dd, J = 10.2, 1.6 Hz, 1H), 5.42 (d, J = 7.4 Hz, 1H), 4.31 (td, J = 7.6, 4.2 Hz, 1H), 4.07 (q, J = 7.9 Hz, 1H), 3.78 (s, 3H), 3.58 (d, J = 11.9 Hz, 2H), 3.41-3.27 (m, 2H), 3.21 (tt, J = 4.4, 2.1 Hz, 7H), 3.00-2.84 (m, 1H), 2.42-2.23 (m, 1H), 1.34 (t, J = 7.3 Hz, 3H), ; 582.3 [M + H]$^+$ | 1.28 |

TABLE 1-continued

| Example Compound | Structure | Name of Compound | ¹H NMR[[:]]; MS [M + H]⁺ | UPLC r.t. (min) |
|---|---|---|---|---|
| 799 | 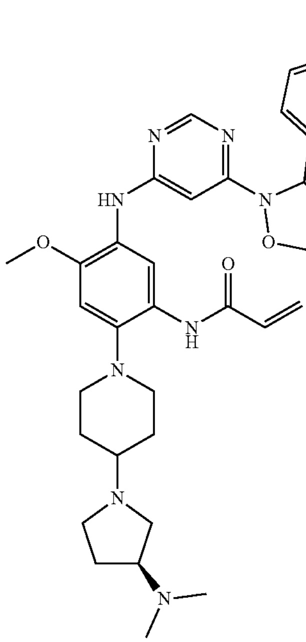 | N-(5-((6-((R)-3-(4-chloro-3-fluorophenyl)isoxazolidine-2-yl)pyrimidine-4-yl)amino)-2-(4-((S)-3-(dimethylamino)pyrolidine-1-yl)piperidine-1-yl)-4-methoxyphenyl)acrylamide | ¹H NMR (400 MHz, MeOD) δ 8.09 (s, 1H), 7.80 (s, 1H), 7.38 (t, 7.9 Hz, 1H), 7.14 (ddd, J = 31.8, 9.2, 2.0 Hz, 2H), 6.98 (s, 1H), 6.56 (dd, J = 16.9, 10.2 Hz, 1H), 6.33 (dd, J = 17.0, 1.6 Hz, 1H), 5.95 (s, 1H), 5.75 (dd, J = 10.2, 1.6 Hz, 1H), 5.41 (s, 1H), 4.32 (td, J = 7.5, 4.1 Hz, 1H), 4.08 (td, J = 8.3, 6.6 Hz, 2H), 3.79 (s, 5H), 3.66-3.40 (m, 3H), 3.38-3.24 (m, 3H), 3.06-2.77 (m, 9H), 2.60 (s, 1H), 2.33 (ddd, J = 37.1, 18.9, 9.9 Hz, 4H), 2.13 (s, 2H), ; 666.5 [M + H]⁺ | 1.17 |
| 800 | 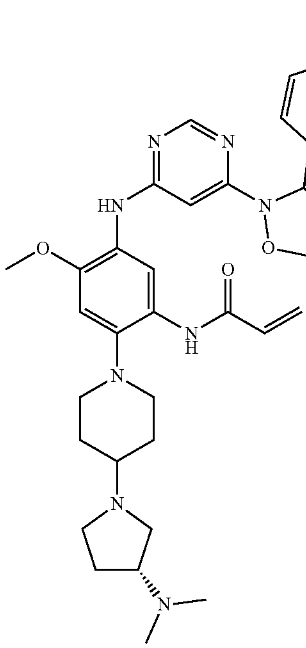 | N-(5-((6-((R)-3-(4-chloro-3-fluorophenyl)isoxazolidine-2-yl)pyrimidine-4-yl)amino)-2-(4-((R)-3-(dimethylamino)pyrolidine-1-yl)piperidine-1-yl)-4-methoxyphenyl)acrylamide | ¹H NMR (400 MHz, DMSO-d₆) δ 10.36 (s, 1H), 9.39 (s, 1H), 8.35 (s, 1H), 7.85 (s, 1H), 7.60 (t, J = 8.1 Hz, 1H), 7.42 (dd, J = 10.4, 2.0 Hz, 1H), 7.25 (dd, J = 8.4, 2.0 Hz, 1H), 6.98 (d, J = 7.0 Hz, 1H), 6.72 (dt, J = 17.1, 8.4 Hz, 1H), 6.25 (dd, J = 17.0, 1.9 Hz, 1H), 6.13 (s, 1H), 5.81-5.73 (m, 1H), 5.56 (dd, J = 8.5, 5.4 Hz, 1H), 4.32 (td, J = 7.6, 4.4 Hz, 2H), 4.21 (s, 1H), 4.05 (dq, J = 26.8, 9.7, 8.7 Hz, 3H), 3.70-3.50 (m, 2H), 3.40 (s, 1H), 3.28 (d, J = 12.1 Hz, 2H), 2.95 (tq, J = 12.2, 7.3, 5.9 Hz, 1H), 2.88-2.75 (m, 8H), 2.48-2.40 (m, 1H), 2.33 (dtd, J = 12.7, 7.5, 5.2 Hz, 1H), 2.15 (dd, J = 30.8, 18.7 Hz, 4H), ; 665.5 [M + H]⁺ | 1.37 |

TABLE 1-continued

| Example Compound | Structure | Name of Compound | $^1$H NMR[[:]]; MS [M + H]$^+$ | UPLC r.t. (min) |
|---|---|---|---|---|
| 801 | 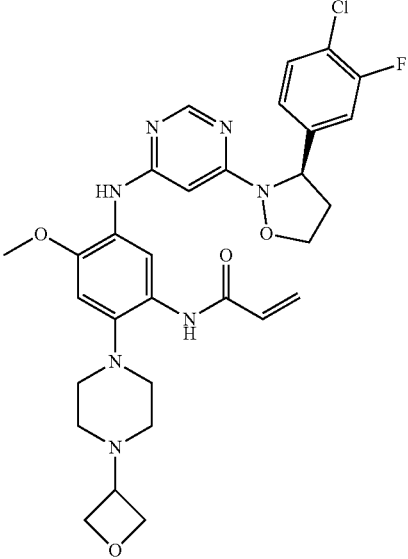 [SMILES: C=CC(=O)Nc1cc(Nc2cc(N3OCC[C@@H]3c3ccc(Cl)c(F)c3)ncn2)c(OC)cc1N1CCN(C2COC2)CC1] | N-(5-((6-((R)-3-(4-chloro-3-fluorophenyl)isoxazolidine-2-yl)pyrimidine-4-yl)amino)-4-methoxy-2-(4-(oxetane-3-yl)piperazine-1-yl)phenyl)acrylamide | $^1$H NMR (400 MHz, DMSO-d$_6$) δ 9.22 (dd, J = 15.0, 7.8 Hz, 1H), 8.32 (d, J = 4.0 Hz, 1H), 8.01 (d, J = 7.9 Hz, 1H), 7.60 (t, J = 8.0 Hz, 1H), 7.42 (dd, J = 10.4, 2.0 Hz, 1H), 7.25 (d, J = 8.4 Hz, 1H), 6.93 (d, J = 3.9 Hz, 1H), 6.73 (dt, J = 17.2, 8.5 Hz, 1H), 6.25 (dt, J = 17.1, 2.5 Hz, 1H), 6.08 (d, J = 8.3 Hz, 1H), 5.83-5.71 (m, 1H), 5.54 (dd, J = 8.5, 5.5 Hz, 1H), 4.81 (q, J = 7.8 Hz, 2H), 4.69 (h, J = 7.8, 6.3 Hz, 1H), 4.56 (s, 1H), 4.31 (tt, J = 7.5, 3.8 Hz, 1H), 4.08 (q, J = 7.2 Hz, 1H), 3.83 (s, 3H), 3.63 (s, 1H), 3.56-3.47 (m, 1H), 2.98-2.87 (m, 1H), 2.40 (d, J = 7.2 Hz, 7H), ; 610.4 [M + H]$^+$ | 1.46 |
| 802 | 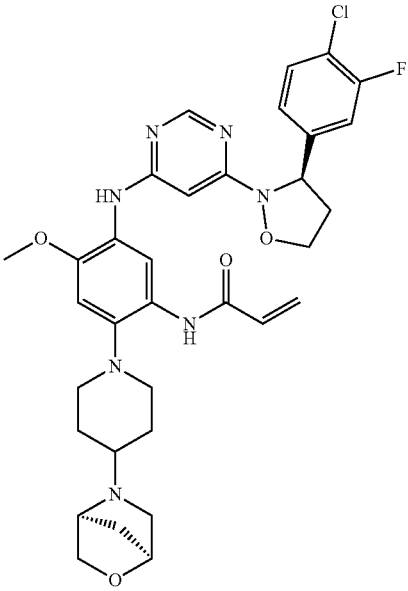 [SMILES: C=CC(=O)Nc1cc(Nc2cc(N3OCC[C@@H]3c3ccc(Cl)c(F)c3)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((R)-3-(4-chloro-3-fluorophenyl)isoxazolidine-2-yl)pyrimidine-4-yl)amino)-4-methoxyphenyl)acrylamide | $^1$H NMR (400 MHz, DMSO-d$_6$) δ 10.17 (s, 1H), 9.30 (d, J = 32.5 Hz, 1H), 8.33 (t, J = 2.9 Hz, 1H), 7.85 (d, J = 12.8 Hz, 1H), 7.60 (t, J = 8.0 Hz, 1H), 7.42 (dd J = 10.4, 2.0 Hz, 1H), 7.30-7.16 (m, 1H), 6.92 (d, J = 7.2 Hz, 1H), 6.61 (dt, J = 17.7, 10.2 Hz, 1H), 6.25 (dt, J = 17.1, 2.2 Hz, 1H), 6.13 (s, 1H), 5.76 (dd, J = 10.1, 1.8 Hz, 2H), 5.55 (dd, J = 8.6, 5.5 Hz, 1H), 4.80-4.40 (m, 3H), 4.30 (q, J = 6.9 Hz, 1H), 4.21 (d, J = 10.3 Hz, 1H), 4.06 (q, J = 5.4, 3.2 Hz, 2H), 3.82 (d, J = 2.2 Hz, 3H), 3.70 (dd, J = 9.6, 5.2 Hz, 1H), 3.57-3.08 (m, 5H), 3.02-2.63 (m, 3H), 2.32 (dtd, J = 12.8, 7.5, 5.0 Hz, 2H), 2.20-1.91 (m, 5H), ; 650.4 [M + H]$^+$ | 1.46 |

TABLE 1-continued

| Example Compound | Structure | Name of Compound | ¹H NMR[[:]]; MS [M + H]⁺ | UPLC r.t. (min) |
|---|---|---|---|---|
| 803 | 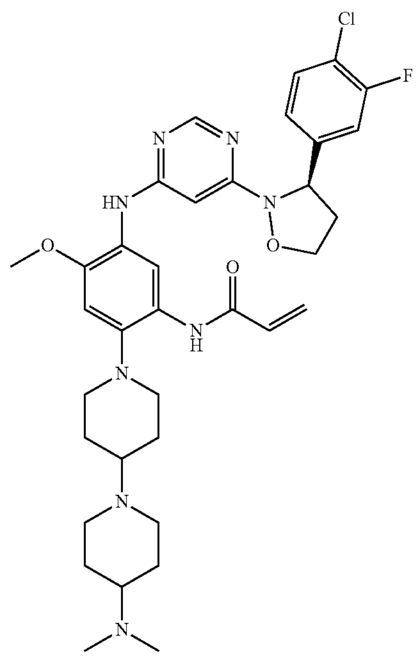 | N-(5-((6-((R)-3-(4-chloro-3-fluorophenyl)isoxazolidine-2-yl)pyrimidine-4-yl)amino)-2-(4-(dimethylamino)-[1,4'-bipiperidine]-1'-yl)-4-methoxyphenyl)acrylamide | ¹H NMR (400 MHz, DMSO-d₆) δ 9.37-9.18 (m, 1H), 8.34 (s, 1H), 7.87 (s, 1H), 7.60 (t, J = 8.0 Hz, 1H), 7.42 (dd, J = 10.4, 2.0 Hz, 1H), 7.24 (dd, J = 8.4, 2.0 Hz, 1H), 6.92 (s, 1H), 6.78 (dd, = 16.9, 10.2 Hz, 1H), 6.25 (dd, J = 16.9, 2.0 Hz, 1H), 6.18-6.03 (m, 1H), 5.76 (dd, J = 10.1, 2.1 Hz, 1H), 5.55 (dd, J = 8.5, 5.4 Hz, 1H), 4.31 (td, J = 7.6, 4.4 Hz, 1H), 4.07 (q, J = 7.7 Hz, 1H), 3.81 (s, 3H), 3.62 (d, J = 11.6 Hz, 2H), 3.52 (s, 1H), 3.38 (d, J = 12.2 Hz, 1H), 3.24 (d, J = 11.3 Hz, 2H), 3.20-3.08 (m, 2H), 3.07-2.90 (m, 2H), 2.81 (d, J = 13.2 Hz, 2H), 2.71 (d, J = 4.8 Hz, 6H), 2.33 (dd, J = 12.2, 5.7 Hz, 5H), 2.22-2.03 (m, 4H), ; 679.6 [M + H]⁺ | 1.34 |
| 804 | 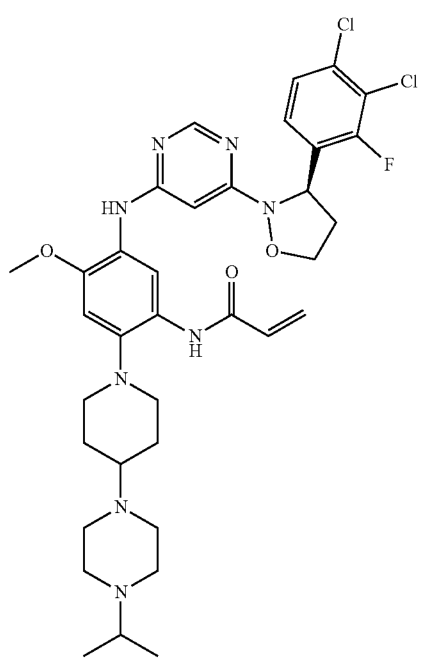 [SMILES: C=CC(=O)Nc1cc(Nc2cc(N3OCC[C@@H]3c3ccc(Cl)c(Cl)c3F)ncn2)c(OC)cc1N1CCC(N2CCN(C(C)C)CC2)CC1] | N-(5-((6-((R)-3-(3,4-dichloro-2-fluorophenyl)isoxazolidine-2-yl)pyrimidine-4-yl)amino)-2-(4-(4-isopropylpiperazine-1-yl)piperidine-1-yl)-4-methoxyphenyl)acrylamide | ¹H NMR (400 MHz, DMSO-d₆) δ 9.87 (s, 1H), 9.19 (s, 1H), 8.29 (s, 1H), 7.98 (s, 1H), 7.53 (dd, J = 8.6, 1.5 Hz, 1H), 7.41 (d, J = 8.0 Hz, 1H), 6.90 (s, 1H), 6.71 (dd, = 16.9, 10.2 Hz, 1H), 6.25 (dd, J = 17.0, 2.0 Hz, 2H), 5.73 (ddd, J = 25.8, 9.3, 3.8 Hz, 2H), 4.30 (d, J = 4.1 Hz, 1H), 4.03 (d, J = 7.9 Hz, 3H), 3.82 (s, 3H), 3.60 (t, J = 6.4 Hz, 2H), 3.48 (d, J = 7.0 Hz, 2H), 3.22 (d, J = 11.3 Hz, 3H), 3.00-2.88 (m, 2H), 2.85-2.76 (m, 2H), 2.31 (dd, J = 13.2, 6.0 Hz, 2H), 2.21-2.02 (m, 5H), 1.32 (d, J = 6.6 Hz, 6H), ; 713.6 [M + H]⁺ | 1.53 |

TABLE 1-continued

| Example Compound | Structure | Name of Compound | $^1$H NMR[[:]]; MS [M + H]$^+$ | UPLC r.t. (min) |
|---|---|---|---|---|
| 805 | 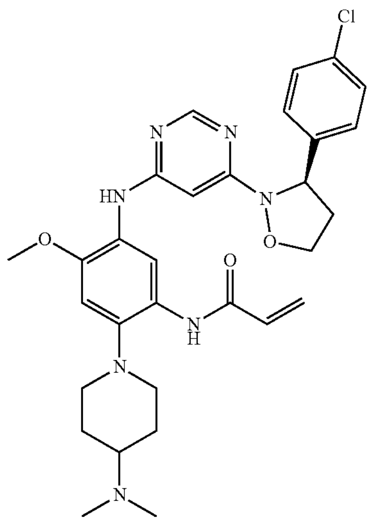 [SMILES: C=CC(=O)Nc1cc(Nc2cc(N3OCC[C@@H]3c3ccc(Cl)cc3)ncn2)c(OC)cc1N1CCC(N(C)C)CC1] | N-(5-((6-((R)-3-(4-chlorophenyl)isoxazolidine-2-yl)pyrimidine-4-yl)amino)-2-(4-(dimethylamino)piperidine-1-yl)-4-methoxyphenyl)acrylamide | $^1$H NMR (400 MHz, Chloroform-d) δ 8.78 (s, 1H), 8.43 (s, 1H), 8.31 (d, J = 1.0 Hz, 1H), 7.47 (s, 1H), 7.39 (d, J = 8.5 Hz, 2H), 7.30 (d, J = 8.5 Hz, 2H), 6.73 (s, 1H), 6.64 (s, 1H), 6.43-6.28 (m, 2H), 5.75 (dd, J = 8.9, 2.7 Hz, 1H), 5.65 (dd, J = 8.6, 4.5 Hz, 1H), 4.14 (td, J = 8.0, 4.4 Hz, 1H), 4.05 (q, J = 8.0 Hz, 1H), 3.84 (s, 3H), 3.11 (d, J = 11.4 Hz, 2H), 2.82-2.71 (m, 4H), 2.57 (s, 6H), 2.33 (dp, J = 12.4, 4.4, 3.9 Hz, 1H), 2.12 (d, J = 12.4 Hz, 2H), 1.86 (tt, J = 13.0, 7.6 Hz, 2H); 578.5 [M + H]$^+$ | 1.21 |
| 806 | 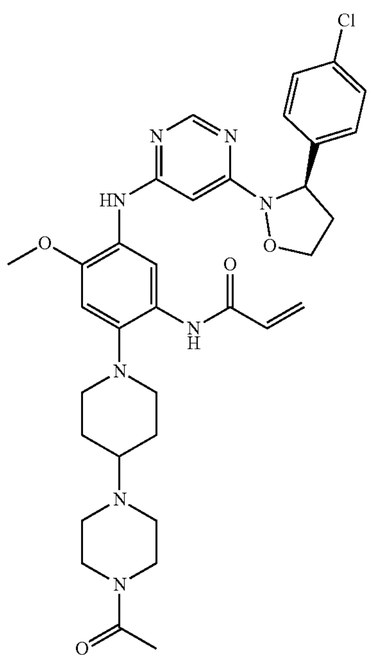 [SMILES: C=CC(=O)Nc1cc(Nc2cc(N3OCC[C@@H]3c3ccc(Cl)cc3)ncn2)c(OC)cc1N1CCC(N2CCN(C(C)=O)CC2)CC1] | N-(2-(4-(4-acetylpiperazine-1-yl)piperidine-1-yl)-5-((6-((R)-3-(4-chlorophenyl)isoxazolidine-2-yl)pyrimidine-4-yl)amino)-4-methoxyphenyl)acrylamide | $^1$H NMR (400 MHz, Methanol-d$_4$) δ 8.26 (d, J = 3.5 Hz, 1H), 8.14 (s, 1H), 7.42 (d, J = 8.4 Hz, 2H), 7.33 (d, J = 8.5 Hz, 2H), 6.90 (s, 1H), 6.54 (dd, J = 17.0, 10.2 Hz, 1H), 6.41-6.31 (m, 2H), 5.79 (d, J = 10.3 Hz, 1H), 5.52 (dd, J = 8.6, 4.7 Hz, 1H), 4.13 (td, J = 7.9, 4.3 Hz, 1H), 3.96 (q, J = 7.9 Hz, 1H), 3.85 (s, 3H), 3.62 (dt, J = 14.9, 5.0 Hz, 4H), 3.17-3.10 (m, 2H), 2.78 (ddd, J = 11.9, 7.8, 4.2 Hz, 3H), 2.70 (dt, J = 21.8, 5.2 Hz, 4H), 2.50 (tt, J = 11.4, 3.8 Hz, 1H), 2.35-2.28 (m, 1H), 2.11 (s, 3H), 2.06-2.00 (m, 2H), 1.78 (dd, J = 12.4, 4.0 Hz, 2H); 661.5 [M + H]$^+$ | 1.22 |

TABLE 1-continued

| Example Compound | Structure | Name of Compound | $^1$H NMR[:]; MS [M + H]$^+$ | UPLC r.t. (min) |
|---|---|---|---|---|
| 807 | 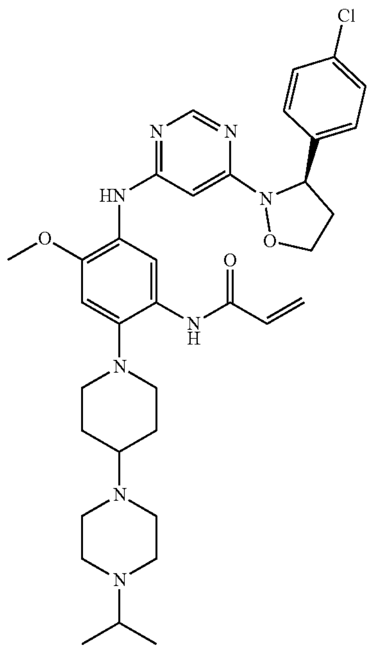 [SMILES: C=CC(=O)Nc1cc(Nc2cc(N3OCC[C@@H]3c3ccc(Cl)cc3)ncn2)c(OC)cc1N1CCC(N2CCN(C(C)C)CC2)CC1] | N-(5-((6-((R)-3-(4-chlorophenyl)isoxazolidine-2-yl)pyrimidine-4-yl)amino)-2-(4-(4-isopropylpiperazine-1-yl)piperidine-1-yl)-4-methoxyphenyl)acrylamide | 661.6 [M + H]$^+$ | 1.18 |
| 808 | 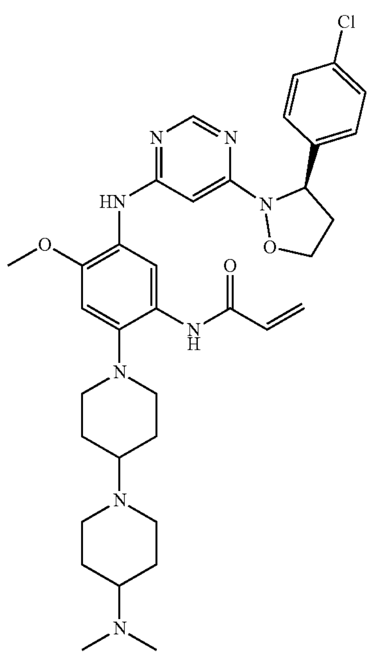 [SMILES: C=CC(=O)Nc1cc(Nc2cc(N3OCC[C@@H]3c3ccc(Cl)cc3)ncn2)c(OC)cc1N1CCC(N2CCC(N(C)C)CC2)CC1] | N-(5-((6-((R)-3-(4-chlorophenyl)isoxazolidine-2-yl)pyrimidine-4-yl)amino)-2-(4-(dimethylamino)-[1,4'-bipiperidine]-1'-yl)-4-methoxyphenyl)acrylamide | 661.6 [M + H]$^+$ | 1.13 |

TABLE 1-continued

| Example Compound | Structure | Name of Compound | ¹H NMR[[:]]; MS [M + H]⁺ | UPLC r.t. (min) |
|---|---|---|---|---|
| 809 | 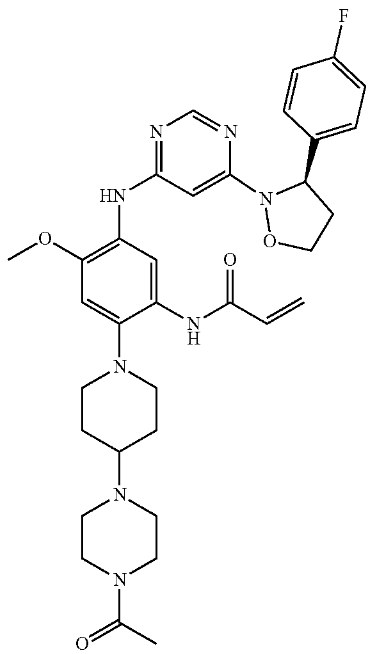 [SMILES: C=CC(=O)Nc1cc(Nc2cc(N3OCC[C@@H]3c3ccc(F)cc3)ncn2)c(OC)cc1N1CCC(N2CCN(C(C)=O)CC2)CC1] | N-(2-(4-(4-acetylpiperazine-1-yl)piperidine-1-yl)-5-((6-((R)-3-(4-fluorophenyl)isoxazolidine-2-yl)pyrimidine-4-yl)amino)-4-methoxyphenyl)acrylamide | ¹H NMR (400 MHz, DMSO-d$_6$) δ 10.00 (s, 1H), 9.21 (s, 1H), 8.30 (s, 1H), 7.89 (s, 1H), 7.41 (dt, J = 6.5, 2.7 Hz, 2H), 7.18 (d, J = 8.8 Hz, 2H), 6.90 (s, 1H), 6.70 (dd, J = 17.0, 10.1 Hz, 1H), 6.25 (dd, J = 17.0, 1.9 Hz, 1H), 6.08 (s, 1H), 5.75 (dd, J = 10.0, 2.0 Hz, 1H), 5.53 (dd, 8.5, 5.2 Hz, 1H), 4.49 (d, J = 13.6 Hz, 1H), 4.33-4.28 (m, 1H), 4.04 (s, 1H), 3.80 (s, 3H), 3.48 (d, J = 5.1 Hz, 2H), 3.19 (d, J = 17.9 Hz, 6H), 3.04-2.88 (m, 4H), 2.78 (s, 2H), 2.30 (d, J = 7.6 Hz, 2H), 2.20 (d, J = 11.7 Hz, 2H), 2.06 (s, 3H), ; 645.6 [M + H]⁺ | 1.12 |
| 810 | 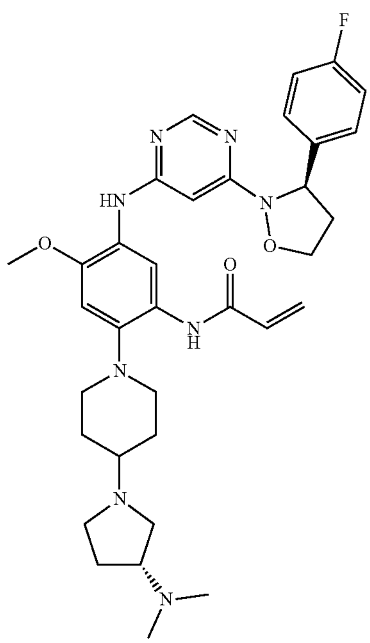 [SMILES: C=CC(=O)Nc1cc(Nc2cc(N3OCC[C@@H]3c3ccc(F)cc3)ncn2)c(OC)cc1N1CCC(N2CC[C@@H](N(C)C)C2)CC1] | N-(2-(4-((R)-3-(dimethylamino)pyrolidine-1-yl)piperidine-1-yl)-5-((6-((R)-3-(4-fluorophenyl)isoxazolidine-2-yl)pyrimidine-4-yl)amino)-4-methoxyphenyl)acrylamide | ¹H NMR (400 MHz, DMSO-d$_6$) δ 10.25 (s, 1H), 9.34 (s, 1H), 8.33 (s, 1H), 7.83 (s, 1H), 7.40 (dd, J = 8.6, 5.5 Hz, 2H), 7.20 (t, J = 8.8 Hz, 2H), 6.96 (d, J = 7.6 Hz, 1H), 6.69 (dd, J = 17.0, 10.0 Hz, 1H), 6.29-6.23 (m, 1H), 6.06 (s, 1H), 5.79-5.72 (m, 1H), 5.53 (dd, J = 8.4, 5.4 Hz, 1H), 4.33 (s, 1H), 4.08 (d, J = 7.6 Hz, 2H), 4.00 (d, J = 3.7 Hz, 2H), 3.89 (d, J = 5.9 Hz, 1H), 3.75 (s, 1H), 3.64 (d, J = 8.8 Hz, 1H), 3.59-3.51 (m, 1H), 3.39 (s, 1H), 3.28-3.21 (m, 2H), 2.95 (td, J = 7.5, 4.1 Hz, 1H), 2.85-2.75 (m, 8H), 2.46-2.38 (m, 1H), 2.31 (d, J = 7.6 Hz, 1H), 2.23-2.08 (m, 4H), 1.65-1.56 (m, 1H), 1.47-1.37 (m, 1H), ; 631.3 [M + H]⁺ | 1.04 |

TABLE 1-continued

| Example Compound | Structure | Name of Compound | ¹H NMR[[:]]; MS [M + H]⁺ | UPLC r.t. (min) |
|---|---|---|---|---|
| 811 | 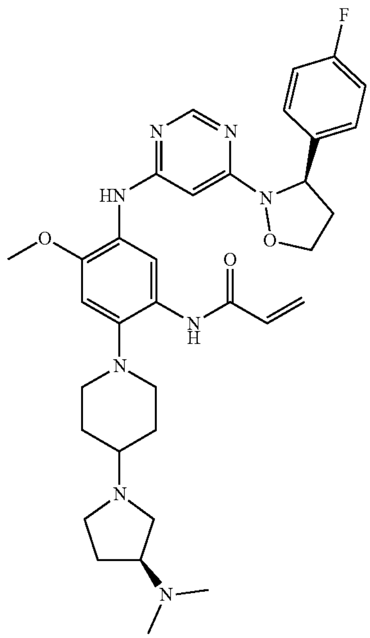 [SMILES: C=CC(=O)Nc1cc(Nc2cc(N3OCC[C@@H]3c3ccc(F)cc3)ncn2)c(OC)cc1N1CCC(N2CC[C@H](N(C)C)C2)CC1] | N-(2-(4-((S)-3-(dimethylamino)pyrolidine-1-yl)piperidine-1-yl)-5-((6-((R)-3-(4-fluorophenyl)isoxazolidine-2-yl)pyrimidine-4-yl)amino)-4-methoxyphenyl)acrylamide | $^1$H NMR (400 MHz, DMSO-$d_6$) δ 9.87 (s, 1H), 9.26 (s, 1H), 8.29 (s, 1H), 7.89 (s, 1H), 7.46-7.37 (m, 2H), 7.20 (t, J = 8.8 Hz, 2H), 6.93 (d, J = 7.6 Hz, 1H), 6.66 (dd, J = 17.0, 10.2 Hz, 1H), 6.24 (dd, J = 16.9, 1.9 Hz, 1H), 6.11-5.97 (m, 1H), 5.76 (d, J = 10.7 Hz, 1H), 5.52 (t, J = 7.0 Hz, 1H), 4.29 (d, J = 4.8 Hz, 1H), 4.06-3.96 (m, 3H), 3.93 (s, 2H), 3.81 (s, 3H), 3.39 (s, 1H), 3.20 (d, J = 25.1 Hz, 4H), 3.07-2.99 (m, 1H), 2.87-2.81 (m, 6H), 2.72 (d, J = 4.9 Hz, 2H), 2.33-2.26 (m, 2H), 2.20-2.01 (m, 4H); 631.3 [M + H]⁺ | 1.03 |
| 812 | 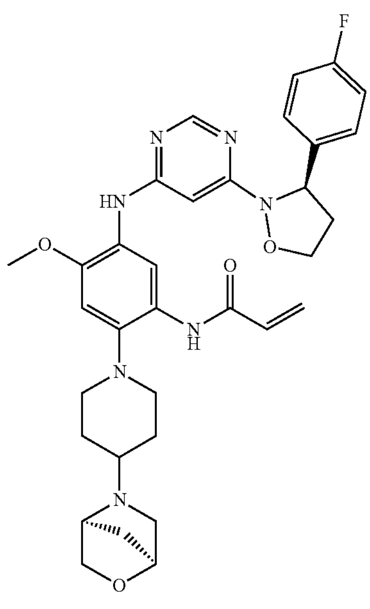 [SMILES: C=CC(=O)Nc1cc(Nc2cc(N3OCC[C@@H]3c3ccc(F)cc3)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((R)-3-(4-fluorophenyl)isoxazolidine-2-yl)pyrimidine-4-yl)amino)-4-methoxyphenyl)acrylamide | 616.3 [M + H]⁺ | 1.11 |

TABLE 1-continued

| Example Compound | Structure | Name of Compound | ¹H NMR[[:]]; MS [M + H]⁺ | UPLC r.t. (min) |
|---|---|---|---|---|
| 813 | 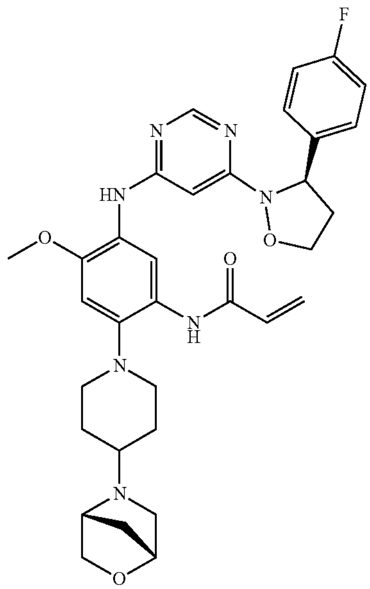 [SMILES: C=CC(=O)Nc1cc(Nc2cc(N3OCC[C@@H]3c3ccc(F)cc3)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-5-((6-((R)-3-(4-fluorophenyl)isoxazolidine-2-yl)pyrimidine-4-yl)amino)-4-methoxyphenyl)acrylamide | ¹H NMR (400 MHz, DMSO-d₆) δ 10.08 (s, 1H), 9.28 (d, J = 30.5 Hz, 1H), 8.32 (s, 1H), 7.85 (d, J = 13.4 Hz, 1H), 7.44-7.36 (m, 2H), 7.20 (t, J = 8.8 Hz, 2H), 6.91 (d, J = 7.5 Hz, 1H), 6.69-6.54 (m, 1H), 6.24 (dd, J = 17.0, 2.1 Hz, 1H), 6.07 (s, 1H), 5.79-5.71 (m, 1H), 5.53 (dd, J = 8.5, 5.3 Hz, 1H), 4.73-4.53 (m, 3H), 4.31 (d, J = 4.5 Hz, 1H), 4.19 (s, 1H), 4.05 (s, 1H), 3.81 (s, 3H), 3.73-3.67 (m, 2H), 3.52-3.42 (m, 2H), 3.23 (d, J = 10.8 Hz, 2H), 2.95-2.71 (m, 4H), 2.32 (t, J = 3.9 Hz, 2H), 2.11-2.01 (m, 3H), ; 616.3 [M + H]⁺ | 1.13 |
| 814 | 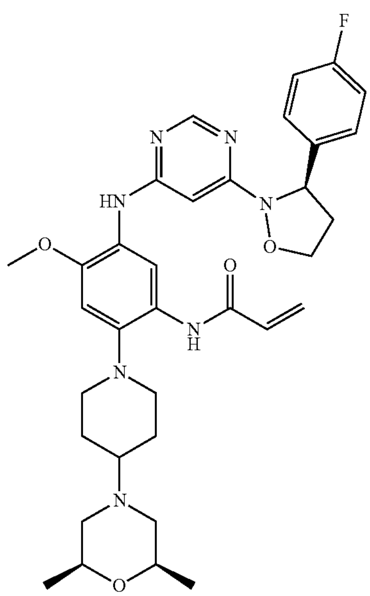 [SMILES: C=CC(=O)Nc1cc(Nc2cc(N3OCC[C@@H]3c3ccc(F)cc3)ncn2)c(OC)cc1N1CCC(N2C[C@@H](C)O[C@@H](C)C2)CC1] | N-(2-(4-((2S,6R)-2,6-dimethylmorpholino)piperidine-1-yl)-5-((6-((R)-3-(4-fluorophenyl)isoxazolidine-2-yl)pyrimidine-4-yl)amino)-4-methoxyphenyl)acrylamide | 632.3 [M + H]⁺ | 1.18 |

TABLE 1-continued

| Example Compound | Structure | Name of Compound | $^1$H NMR[[:]]; MS [M + H]$^+$ | UPLC r.t. (min) |
|---|---|---|---|---|
| 815 | 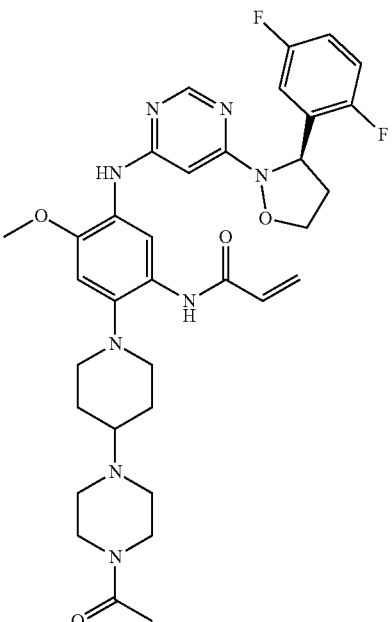 | N-(2-(4-(4-acetylpiperazine-1-yl)piperidine-1-yl)-5-((6-((R)-3-(2,5-difluorophenyl)isoxazolidine-2-yl)pyrimidine-4-yl)amino)-4-methoxyphenyl)acrylamide | $^1$H NMR (400 MHz, DMSO-d$_6$) δ 11.75 (s, 1H), 10.12 (s, 1H), 9.24 (s, 1H), 8.32 (s, 1H), 7.89 (s, 1H), 7.32 (td, J = 9.4, 4.4 Hz, 1H), 7.24-7.19 (m, 1H), 7.16 (ddt, J = 9.1, 5.9, 2.7 Hz, 1H), 6.91 (s, 1H), 6.70 (dd, J = 17.0, 10.1 Hz, 1H), 6.24 (dd, J = 17.0, 1.9 Hz, 1H), 5.75 (dd, J = 10.2, 1.9 Hz, 1H), 5.66 (dd, J = 8.7, 5.6 Hz, 1H), 4.53-4.46 (m, 2H), 4.32 (td, J = 7.6, 4.0 Hz, 3H), 4.09-3.96 (m, 4H), 3.81 (s, 4H), 3.73 (t, J = 13.0 Hz, 2H), 3.35 (t, J = 13.1 Hz, 2H), 3.29-3.17 (m, 4H), 2.96 (dtd, J = 19.3, 11.7, 9.7, 4.7 Hz, 3H), 2.80 (s, 2H), 2.06 (s, 4H), ; 663.6 [M + H]$^+$ | 1.18 |
| 816 | 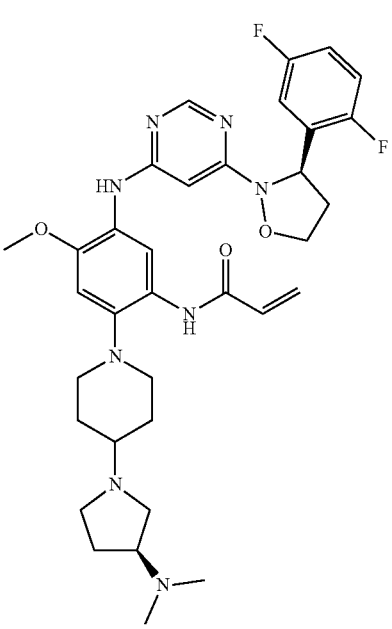 [SMILES: C=CC(=O)Nc1cc(Nc2cc(N3OCC[C@@H]3c3cc(F)ccc3F)ncn2)c(OC)cc1N1CCC(N2CC[C@H](N(C)C)C2)CC1] | N-(5-((6-((R)-3-(2,5-difluorophenyl)isoxazolidine-2-yl)pyrimidine-4-yl)amino)-2-(4-((S)-3-(dimethylamino)pyrolidine-1-yl)piperidine-1-yl)-4-methoxyphenyl)acrylamide | $^1$H NMR (400 MHz, DMSO-d$_6$) δ 9.77 (s, 1H), 9.14 (s, 1H), 8.29 (s, 1H), 7.96 (s, 1H), 7.32 (td, J = 9.3, 4.4 Hz, 1H), 7.26-7.13 (m, 2H), 6.88 (d, J = 13.3 Hz, 1H), 6.68 (dd, J = 16.9, 10.2 Hz, 1H), 6.26 (d, J = 1.9 Hz, 1H), 5.78-5.72 (m, 1H), 5.67 (dd, J = 8.7, 5.5 Hz, 1H), 4.01 (q, J = 7.8 Hz, 6H), 3.81 (s, 5H), 3.71-3.60 (m, 3H), 3.43 (s, 2H), 3.20 (t, J = 12.0 Hz, 5H), 2.91 (dt, J = 11.8, 4.7 Hz, 2H), 2.83-2.55 (m, 5H), 2.44-2.16 (m, 6H), 2.05 (d, J = 11.9 Hz, 2H), ; 649.5 [M + H]$^+$ | 1.10 |

TABLE 1-continued

| Example Compound | Structure | Name of Compound | ¹H NMR[[:]]; MS [M + H]⁺ | UPLC r.t. (min) |
|---|---|---|---|---|
| 817 | 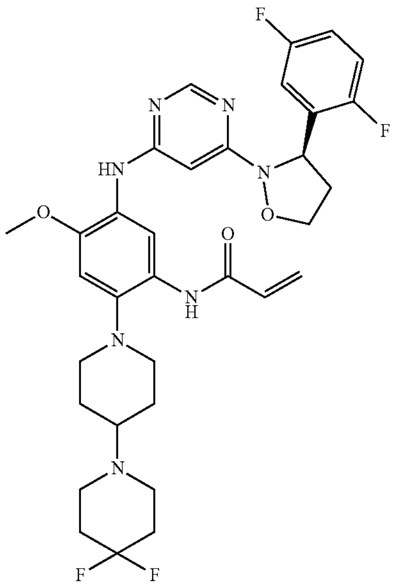 [SMILES: C=CC(=O)Nc1cc(Nc2cc(N3OCC[C@@H]3c3cc(F)ccc3F)ncn2)c(OC)cc1N1CCC(N2CCC(F)(F)CC2)CC1] | N-(2-(4,4-difluoro-[1,4'-bipiperidine]-1'-yl)-5-((6-((R)-3-(2,5-difluorophenyl)isoxazolidine-2-yl)pyrimidine-4-yl)amino)-4-methoxyphenyl)acrylamide | 656.5 [M + H]⁺ | 1.27 |
| 818 | 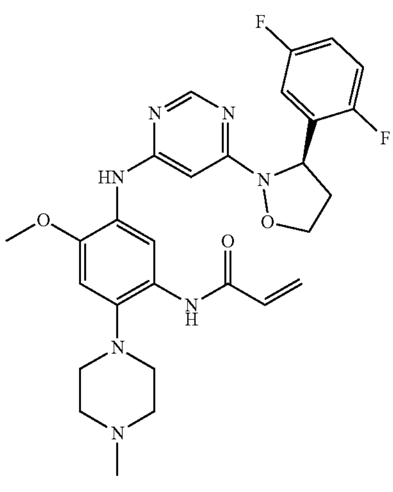 [SMILES: C=CC(=O)Nc1cc(Nc2cc(N3OCC[C@@H]3c3cc(F)ccc3F)ncn2)c(OC)cc1N1CCN(C)CC1] | N-(5-((6-((R)-3-(2,5-difluorophenyl)isoxazolidine-2-yl)pyrimidine-4-yl)amino)-4-methoxy-2-(4-methylpiperazine-1-yl)phenyl)acrylamide | ¹H NMR (400 MHz, Chloroform-d) δ 8.91 (s, 1H), 8.53 (s, 1H), 8.38 (d, J = 1.0 Hz, 1H), 7.37-7.28 (m, 1H), 7.03-6.94 (m, 2H), 6.93-6.86 (m, 1H), 6.78 (d, J = 16.4 Hz, 2H), 6.37 (dd, J = 17.0, 1.6 Hz, 1H), 6.27 (dd, J = 16.9, 10.0 Hz, 1H), 5.90 (dd, J = 8.8, 4.4 Hz, 1H), 5.75 (dd, J = 10.0, 1.6 Hz, 1H), 4.16-4.02 (m, 2H), 3.85 (s, 3H), 2.95-2.89 (m, 4H), 2.87-2.79 (m, 1H), 2.40 (s, 3H), 2.34-2.25 (m, 1H), 1.66-1.62 (m, 4H), ; 552.4 [M + H]⁺ | 1.18 |
| 819 | 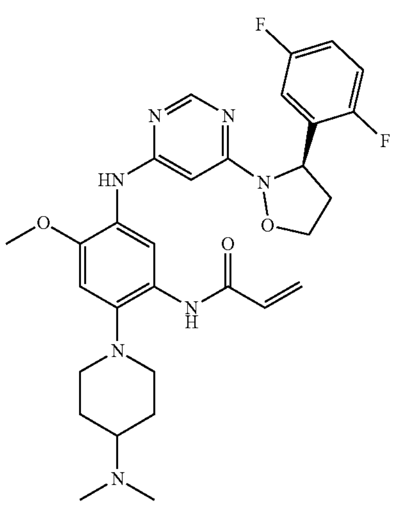 [SMILES: C=CC(=O)Nc1cc(Nc2cc(N3OCC[C@@H]3c3cc(F)ccc3F)ncn2)c(OC)cc1N1CCC(N(C)C)CC1] | N-(5-((6-((R)-3-(2,5-difluorophenyl)isoxazolidine-2-yl)pyrimidine-4-yl)amino)-2-(4-(dimethylamino)piperidine-1-yl)-4-methoxyphenyl)acrylamide | ¹H NMR (400 MHz, Chloroform-d) δ 8.88 (s, 1H), 8.46 (s, 1H), 8.37 (d, J = 1.0 Hz, 1H), 7.37-7.28 (m, 1H), 7.03-6.97 (m, 1H), 6.95 (s, 1H), 6.93-6.87 (m, 1H), 6.76 (d, J = 2.4 Hz, 2H), 6.41-6.32 (m, 1H), 6.26 (dd, J = 16.9, 9.9 Hz, 1H), 5.90 (dd, J = 8.8, 4.4 Hz, 1H), 5.74 (dd, J = 9.9, 1.6 Hz, 1H), 4.16-4.05 (m, 2H), 3.85 (s, 3H), 3.08 (d, J = 11.5 Hz, 2H), 2.88-2.80 (m, 1H), 2.79-2.70 (m, 2H), 2.43 (s, 6H), 2.32-2.25 (m, 2H), 2.09 (d, J = 12.6 Hz, 2H), 1.74-1.70 (m, 2H), ; 580.4 [M + H]⁺ | 1.19 |

TABLE 1-continued

| Example Compound | Structure | Name of Compound | ¹H NMR[[:]]; MS [M + H]⁺ | UPLC r.t. (min) |
|---|---|---|---|---|
| 820 | 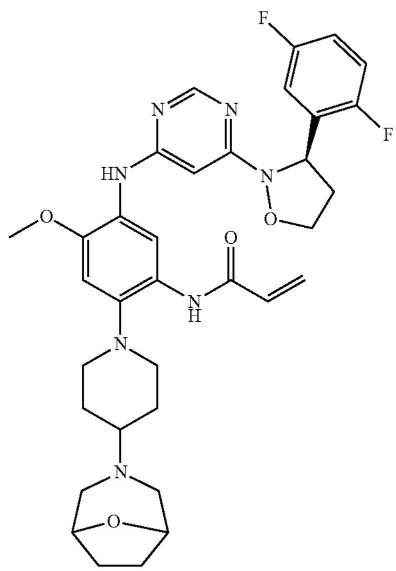 [SMILES: C=CC(=O)Nc1cc(Nc2cc(N3OCC[C@@H]3c3cc(F)ccc3F)ncn2)c(OC)cc1N1CCC(N2CC3CCC(C2)O3)CC1] | N-(2-(4-(8-oxa-3-azabicyclo[3.2.1]octan-3-yl)piperidine-1-yl)-5-((6-((R)-3-(2,5-difluorophenyl)isoxazolidine-2-yl)pyrimidine-4-yl)amino)-4-methoxyphenyl)acrylamide | ; 648.5 [M + H]⁺ | 1.25 |
| 821 | 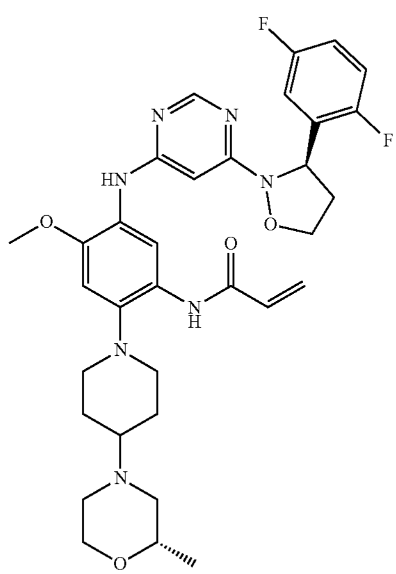 [SMILES: C=CC(=O)Nc1cc(Nc2cc(N3OCC[C@@H]3c3cc(F)ccc3F)ncn2)c(OC)cc1N1CCC(N2CCO[C@@H](C)C2)CC1] | N-(5-((6-((R)-3-(2,5-difluorophenyl)isoxazolidine-2-yl)pyrimidine-4-yl)amino)-4-methoxy-2-(4-((S)-2-methylmorpholino)piperidine-1-yl)phenyl)acrylamide | 636.5 [M + H]⁺ | 1.23 |

TABLE 1-continued

| Example Compound | Structure | Name of Compound | ¹H NMR[[:]]; MS [M + H]⁺ | UPLC r.t. (min) |
|---|---|---|---|---|
| 822 | 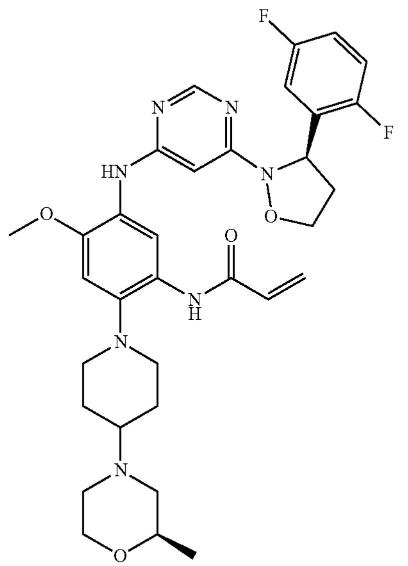 [SMILES: C=CC(=O)Nc1cc(Nc2cc(N3OCC[C@@H]3c3cc(F)ccc3F)ncn2)c(OC)cc1N1CCC(N2CCO[C@H](C)C2)CC1] | N-(5-((6-((R)-3-(2,5-difluorophenyl)isoxazolidine-2-yl)pyrimidine-4-yl)amino)-4-methoxy-2-(4-((R)-2-methylmorpholino)piperidine-1-yl)phenyl)acrylamide | 636.5 [M + H]⁺ | 1.22 |
| 823 | 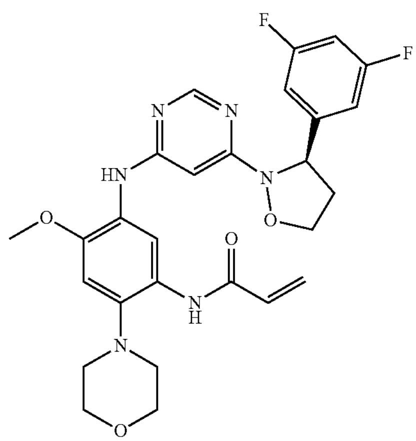 [SMILES: C=CC(=O)Nc1cc(Nc2cc(N3OCC[C@@H]3c3cc(F)cc(F)c3)ncn2)c(OC)cc1N1CCOCC1] | N-(5-((6-((R)-3-(3,5-difluorophenyl)isoxazolidine-2-yl)pyrimidine-4-yl)amino)-4-methoxy-2-morpholinophenyl)acrylamide | ¹H NMR (400 MHz, MeOD) δ 8.34 (s, 1H), 8.19 (s, 1H), 7.07 (d, J = 6.7 Hz, 2H), 6.95 (s, 1H), 6.87-6.80 (m, 1H), 6.56 (dd, J = 16.9, 10.2 Hz, 1H), 6.48 (s, 1H), 6.36 (dd, J = 17.0, 1.5 Hz, 1H), 5.81 (d, J = 11.5 Hz, 1H), 5.59-5.54 (m, 1H), 4.15 (td, J = 7.9, 4.3 Hz, 1H), 3.98 (dd, J = 16.0, 8.0 Hz, 1H), 3.90 (d, J = 5.9 Hz, 7H), 2.98-2.91 (m, 4H), 2.88-2.79 (m, 1H), 2.41-2.29 (m, 1H), ; 539.4 [M + H]⁺ | 1.46 |
| 824 | 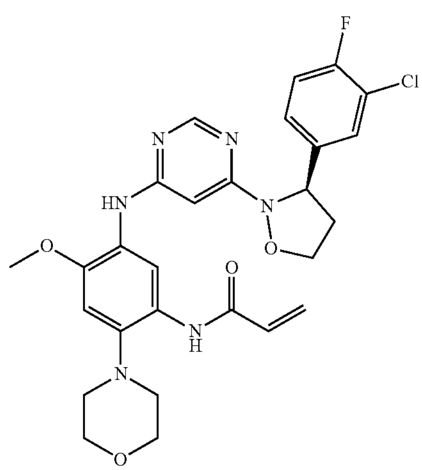 [SMILES: C=CC(=O)Nc1cc(Nc2cc(N3OCC[C@@H]3c3ccc(F)c(Cl)c3)ncn2)c(OC)cc1N1CCOCC1] | N-(5-((6-((R)-3-(3-chloro-4-fluorophenyl)isoxazolidine-2-yl)pyrimidine-4-yl)amino)-4-methoxy-2-morpholinophenyl)acrylamide | ¹H NMR (400 MHz, MeOD) δ 8.34 (s, 1H), 8.18 (s, 1H), 7.58-7.54 (m, 1H), 7.45-7.37 (m, 1H), 7.22 (d, J = 8.8 Hz, 1H), 6.95 (s, 1H), 6.60-6.53 (m, 1H), 6.48 (s, 1H), 6.36 (dd, J = 17.0, 1.5 Hz, 1H), 5.81 (d, J = 10.3 Hz, 1H), 5.55 (dd, J = 8.4, 4.9 Hz, 1H), 4.16 (td, J = 7.8, 4.1 Hz, 1H), 3.98 (q, J = 8.0 Hz, 1H), 3.90 (d, J = 5.5 Hz, 7H), 2.98-2.91 (m, 4H), 2.82 (dtd, J = 12.2, 8.0, 4.2 Hz, 1H), 2.34 (ddd, J = 16.4, 10.4, 6.5 Hz, 1H), ; 555.4 [M + H]⁺ | 1.50 |

TABLE 1-continued

| Example Compound | Structure | Name of Compound | ¹H NMR[[:]]; MS [M + H]⁺ | UPLC r.t. (min) |
|---|---|---|---|---|
| 825 | 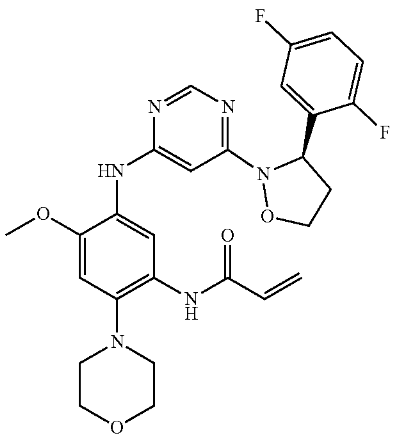 [SMILES: C=CC(=O)Nc1cc(Nc2cc(N3OCC[C@@H]3c3cc(F)ccc3F)ncn2)c(OC)cc1N1CCOCC1] | N-(5-((6-((R)-3-(2,5-difluorophenyl)isoxazolidine-2-yl)pyrimidine-4-yl)amino)-4-methoxy-2-morpholinophenyl)acrylamide | ¹H NMR (400 MHz, MeOD) δ 8.35 (s, 1H), 8.19 (s, 1H), 7.26 (ddd, J = 9.1, 5.8, 3.2 Hz, 1H), 7.15 (td, J = 9.3, 4.3 Hz, 1H), 7.07-7.00 (m, 1H), 6.95 (s, 1H), 6.61-6.49 (m, 2H), 6.36 (dd, J = 17.0, 1.5 Hz, 1H), 5.84-5.73 (m, 2H), 4.15 (td, J = 7.9, 4.2 Hz, 1H), 4.00 (q, J = 8.0 Hz, 1H), 3.92-3.86 (m, 7H), 2.98-2.93 (m, 4H), 2.86 (ddd, J = 16.7, 8.2, 4.2 Hz, 1H), 2.34-2.22 (m, 1H), ; 539.4 [M + H]⁺ | 1.46 |
| 826 | 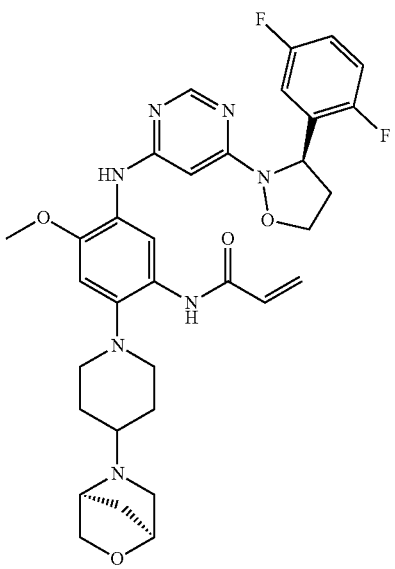 [SMILES: C=CC(=O)Nc1cc(Nc2cc(N3OCC[C@@H]3c3cc(F)ccc3F)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((R)-3-(2,5-difluorophenyl)isoxazolidine-2-yl)pyrimidine-4-yl)amino)-4-methoxyphenyl)acrylamide | ¹H NMR (400 MHz, Methanol-d₄) δ 8.30 (s, 1H), 8.18 (s, 1H), 7.29-7.21 (m, 1H), 7.20-7.10 (m, 1H), 7.08-7.00 (m, 1H), 6.94 (s, 1H), 6.62-6.46 (m, 2H), 6.41-6.31 (m, 1H), 5.87-5.70 (m, 2H), 4.21-4.13 (m, 3H), 4.02-3.96 (m, 1H), 3.90 (s, 3H), 3.80-3.72 (m, 1H), 3.19-3.13 (m, 2H), 3.02-2.91 (m, 2H), 2.90-2.80 (m, 3H), 2.32-2.23 (m, 1H), 2.20-2.13 (m, 1H), 2.13-2.07 (m, 1H), 2.07-2.02 (m, 2H), 1.86-1.76 (m, 2H); 634.3 [M + H]⁺ | 1.22 |

TABLE 1-continued

| Example Compound | Structure | Name of Compound | ¹H NMR[[:]]; MS [M + H]⁺ | UPLC r.t. (min) |
|---|---|---|---|---|
| 827 | 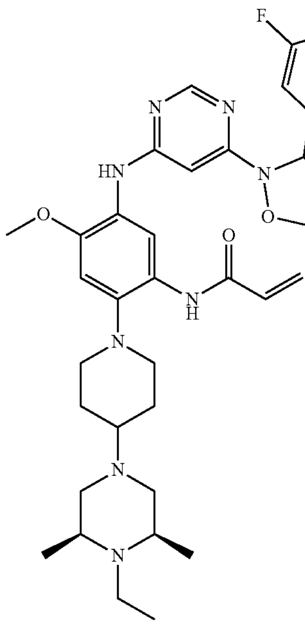 | N-(5-((6-((R)-3-(3,5-difluorophenyl)isoxazolidine-2-yl)pyrimidine-4-yl)amino)-2-(4-((3S,5R)-4-ethyl-3,5-dimethylpiperazine-1-yl)piperidine-1-yl)-4-methoxyphenyl)acrylamide | ¹H NMR (400 MHz, Methanol-$d_4$) δ 8.29 (s, 1H), 8.18 (s, 1H), 7.11-7.01 (m, 2H), 6.92 (s, 1H), 6.90-6.78 (m, 1H), 6.64-6.50 (m, 1H), 6.46 (s, 1H), 6.41-6.31 (m, 1H), 5.86-5.78 (m, 1H), 5.61-5.51 (m, 1H), 4.18-4.13 (m, 1H), 4.00-3.94 (m, 1H), 3.88 (s, 3H), 3.30-3.27 (m, 3H), 3.24-3.13 (m, 6H), 2.86-2.76 (m, 4H), 2.60-2.52 (m, 1H), 2.43-2.32 (m, 3H), 1.84-1.76 (m, 2H), 1.35-1.33 (m, 6H), 1.25-1.21 (m, 3H); 677.4 [M + H]⁺ | 1.23 |
| 828 | 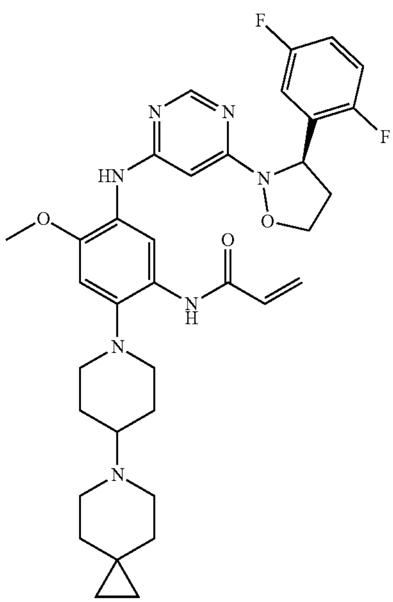 [SMILES: C=CC(=O)Nc1cc(Nc2cc(N3OCC[C@@H]3c3cc(F)ccc3F)ncn2)c(OC)cc1N1CCC(N2CCC3(CC2)CC3)CC1] | N-(2-(4-(6-azaspiro[2.5]octan-6-yl)piperidine-1-yl)-5-((6-((R)-3-(2,5-difluorophenyl)isoxazolidine-2-yl)pyrimidine-4-yl)amino)-4-methoxyphenyl)acrylamide | ¹H NMR (400 MHz, Methanol-$d_4$) δ 8.31 (s, 1H), 8.19 (s, 1H), 7.31-7.21 (m, 1H), 7.21-7.10 (m, 1H), 7.08-7.00 (m, 1H), 6.93 (s, 1H), 6.65-6.48 (m, 2H), 6.41-6.33 (m, 1H), 5.86-5.72 (m, 2H), 4.19-4.12 (m, 1H), 4.01-3.96 (m, 1H), 3.90 (s, 3H), 3.31-3.21 (m, 5H), 2.96-2.79 (m, 4H), 2.36-2.15 (m, 4H), 2.12-1.99 (m, 3H), 1.82-1.68 (m, 3H), 0.53 (s, 4H); 646.3 [M + H]⁺ | 1.33 |

TABLE 1-continued

| Example Compound | Structure | Name of Compound | ¹H NMR[[:]]; MS [M + H]⁺ | UPLC r.t. (min) |
|---|---|---|---|---|
| 829 | 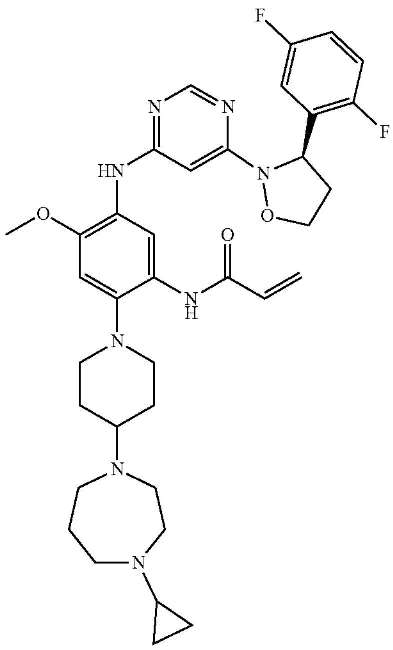 [SMILES: C=CC(=O)Nc1cc(Nc2cc(N3OCC[C@@H]3c3cc(F)ccc3F)ncn2)c(OC)cc1N1CCC(N2CCCN(C3CC3)CC2)CC1] | N-(2-(4-(4-cyclopropyl-1,4-diazepane-1-yl)piperidine-1-yl)-5-((6-((R)-3-(2,5-difluorophenyl)isoxazolidine-2-yl)pyrimidine-4-yl)amino)-4-methoxyphenyl)acrylamide | ¹H NMR (400 MHz, Methanol-d₄) δ 8.25 (d, J = 3.8 Hz, 1H), 8.11 (s, 1H), 7.18 (ddd, J = 3.2, 5.8, 9.2 Hz, 1H), 7.08 (td, J = 4.3, 9.3 Hz, 1H), 6.97 (dt, J = 4.2, 8.7 Hz, 1H), 6.85 (s, 1H), 6.57-6.41 (m, 2H), 6.31 (d, J = 16.9 Hz, 1H), 5.80-5.64 (m, 2H), 4.07 (dd, J = 4.2, 8.0 Hz, 1H), 3.92 (q, J = 8.0 Hz, 1H), 3.82 (s, 3H), 3.34-3.27 (m, 3H), 3.15 (d, J = 12.1 Hz, 3H), 3.08-3.04 (m, 2H), 2.93 (q, J = 5.8, 6.2 Hz, 3H), 2.79 (ddd, J = 6.2, 9.9, 15.1 Hz, 3H), 2.21 (dtd, J = 4.5, 8.0, 12.6 Hz, 1H), 2.11-1.92 (m, 7H), 0.52 (dd, J = 4.3, 6.4 Hz, 2H), 0.49-0.42 (m, 2H); 675.4 [M + H]⁺ | 1.14 |
| 830 | 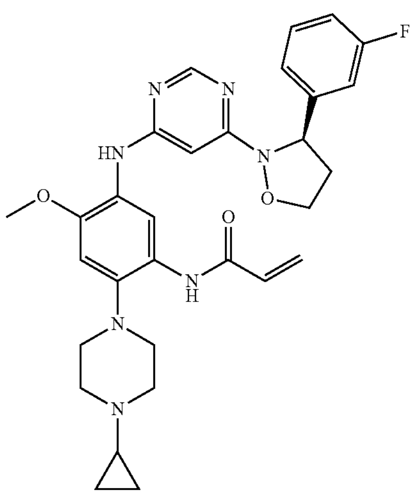 [SMILES: C=CC(=O)Nc1cc(Nc2cc(N3OCC[C@@H]3c3cccc(F)c3)ncn2)c(OC)cc1N1CCN(C2CC2)CC1] | N-(2-(4-cyclopropylpiperazine-1-yl)-5-((6-((R)-3-(3-fluorophenyl)isoxazolidine-2-yl)pyrimidine-4-yl)amino)-4-methoxyphenyl)acrylamide | ¹H NMR (400 MHz, DMSO-d₆) δ 10.84 (s, 1H), 9.45 (s, 1H), 9.13 (s, 1H), 8.26 (s, 1H), 8.13 (s, 1H), 7.42 (td, J = 7.9, 6.0 Hz, 1H), 7.31-7.17 (m, 2H), 7.11 (td, J = 8.5, 2.7 Hz, 1H), 6.84 (s, 1H), 6.74 (dd, J = 17.0, 10.2 Hz, 1H), 6.33-6.12 (m, 2H), 5.77 (dd, J = 10.1, 2.0 Hz, 1H), 5.54 (dd, J = 8.5, 5.3 Hz, 1H), 4.25 (q, J = 7.2, 6.7 Hz, 1H), 3.97 (q, J = 7.8 Hz, 1H), 3.82 (s, 3H), 3.55 (s, 3H), 3.21 (d, J = 4.7 Hz, 4H), 2.96-2.81 (m, 2H), 2.36-2.22 (m, 2H), 1.22-1.11 (m, 2H), 0.85 (d, J = 7.1 Hz, 2H), ; 560.4 [M + H]⁺ | 1.14 |

TABLE 1-continued

| Example Compound | Structure | Name of Compound | ¹H NMR[[:]]; MS [M + H]⁺ | UPLC r.t. (min) |
|---|---|---|---|---|
| 831 | 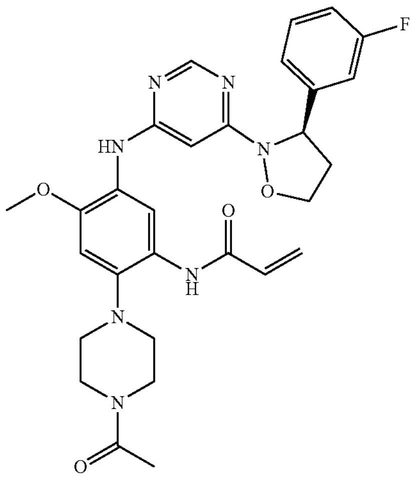 [SMILES: C=CC(=O)Nc1cc(Nc2cc(N3OCC[C@@H]3c3cccc(F)c3)ncn2)c(OC)cc1N1CCN(C(C)=O)CC1] | N-(2-(4-acetylpiperazine-1-yl)-5-((6-((R)-3-(3-fluorophenyl)isoxazolidine-2-yl)pyrimidine-4-yl)amino-4-methoxyphenyl)acrylamide | $^1$H NMR (400 MHz, DMSO-$d_6$) δ 9.80 (s, 1H), 9.18 (s, 1H), 8.29 (s, 1H), 8.00 (s, 1H), 7.42 (td, J = 8.0, 6.1 Hz, 1H), 7.20 (dd, J = 14.6, 5.3 Hz, 2H), 7.12 (td, J = 8.6, 2.6 Hz, 1H), 6.92 (s, 1H), 6.69 (dd, J = 17.0, 10.1 Hz, 1H), 6.24 (dd, J = 17.0, 2.0 Hz, 1H), 6.12 (s, 1H), 5.75 (dd, J = 10.2, 2.0 Hz, 1H), 5.59-5.47 (m, 1H), 4.29 (dt, J = 7.9, 3.9 Hz, 1H), 4.03 (d, J = 7.7 Hz, 1H), 3.79 (s, 3H), 3.66 (d, J = 4.8 Hz, 4H), 2.87 (dt, J = 16.2, 4.9 Hz, 5H), 2.32 (h, J = 7.4 Hz, 1H), 2.05 (s, 3H), ; 562.4 [M + H]⁺ | 1.30 |
| 832 | 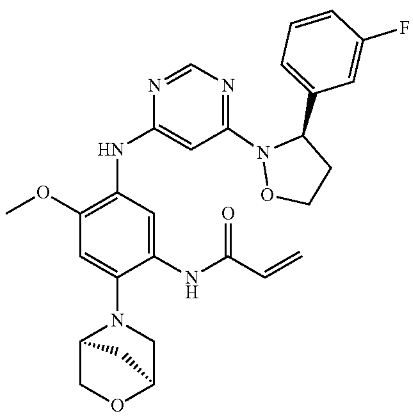 [SMILES: C=CC(=O)Nc1cc(Nc2cc(N3OCC[C@@H]3c3cccc(F)c3)ncn2)c(OC)cc1N1C[C@@H]2C[C@H]1CO2] | N-(2-((1S,4S)-2-oxa-5-azabicyclo[2.2.1]heptane-5-yl)-5-((6-((R)-3-(3-fluorophenyl)isoxazolidine-2-yl)pyrimidine-4-yl)amino)-4-methoxyphenyl)acrylamide | $^1$H NMR (400 MHz, DMSO-$d_6$) δ 9.77 (s, 1H), 9.37 (s, 1H), 8.27 (s, 1H), 7.42 (td, J = 8.0, 6.2 Hz, 1H), 7.24-7.08 (m, 4H), 6.52-6.39 (m, 2H), 6.19 (dd, J = 17.1, 2.1 Hz, 1H), 6.01 (s, 1H), 5.70 (dd, J = 10.2, 2.1 Hz, 1H), 5.54 (t, J = 7.0 Hz, 1H), 4.53 (d, J = 21.0 Hz, 2H), 4.29 (t, J = 6.2 Hz, 1H), 4.05-4.01 (m, 1H), 3.95 (d, J = 7.7 Hz, 1H), 3.79 (s, 4H), 3.56 (d, J = 9.3 Hz, 1H), 2.93 (d, J = 9.9 Hz, 2H), 2.32 (q, J = 5.4 Hz, 1H), 1.85 (q, J = 9.8 Hz, 2H), ; 533.4 [M + H]⁺ | 1.29 |
| 833 | 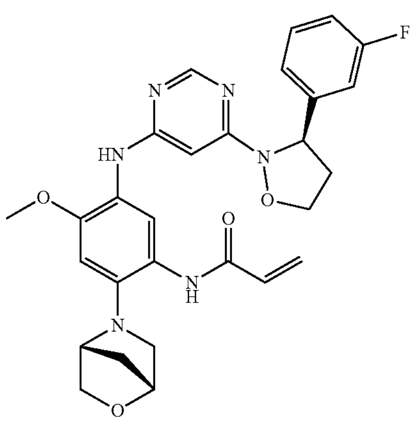 [SMILES: C=CC(=O)Nc1cc(Nc2cc(N3OCC[C@@H]3c3cccc(F)c3)ncn2)c(OC)cc1N1C[C@H]2C[C@@H]1CO2] | N-(2-((1R,4R)-2-oxa-5-azabicyclo[2.2.1]heptane-5-yl)-5-((6-((R)-3-(3-fluorophenyl)isoxazolidine-2-yl)pyrimidine-4-yl)amino)-4-methoxyphenyl)acrylamide | $^1$H NMR (400 MHz, DMSO-$d_6$) δ 9.92 (s, 1H), 9.40 (s, 1H), 8.29 (s, 1H), 7.42 (td, J = 8.1, 6.2 Hz, 1H), 7.28-7.04 (m, 4H), 6.54-6.41 (m, 2H), 6.19 (dd, J = 17.1, 2.1 Hz, 1H), 5.99 (s, 1H), 5.70 (dd, J = 10.1, 2.1 Hz, 1H), 5.54 (dd, J = 8.5, 5.4 Hz, 1H), 4.53 (d, J = 18.2 Hz, 2H), 4.31 (q, J = 3.2 Hz, 1H), 4.05 (q, J = 7.7 Hz, 1H), 3.95 (d, J = 7.6 Hz, 1H), 3.77 (d, J = 9.2 Hz, 4H), 3.56 (d, J = 9.4 Hz, 1H), 2.92 (t, J = 10.6 Hz, 2H), 2.32 (dq, J = 12.8, 7.3, 6.5 Hz, 1H), 1.88 (dd, J = 17.8, 8.3 Hz, 2H); 533.5 [M + H]⁺ | 1.29 |

TABLE 1-continued

| Example Compound | Structure | Name of Compound | $^1$H NMR[[:]]; MS [M + H]$^+$ | UPLC r.t. (min) |
|---|---|---|---|---|
| 834 | 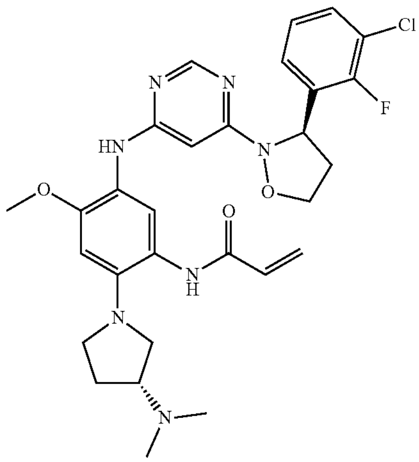 [SMILES: C=CC(=O)Nc1cc(Nc2cc(N3OCC[C@@H]3c3cccc(Cl)c3F)ncn2)c(OC)cc1N1CC[C@@H](N(C)C)C1] | N-(5-((6-((R)-3-(3-chloro-2-fluorophenyl)isoxazolidine-2-yl)pyrimidine-4-yl)amino)-2-((R)-3-(dimethylamino)pyrolidine-1-yl)-4-methoxyphenyl)acrylamide | $^1$H NMR (400 MHz, DMSO-d$_6$) δ 9.57 (d, J = 9.7 Hz, 1H), 8.24 (d, J = 4.4 Hz, 1H), 7.63 (s, 1H), 7.59-7.50 (m, 1H), 7.37 (t, J = 7.1 Hz, 1H), 7.23 (t, J = 7.9 Hz, 1H), 6.89-6.76 (m, 1H), 6.71 (d, J = 21.2 Hz, 1H), 6.26-6.10 (m, 2H), 5.71 (td, J = 6.0, 2.6 Hz, 2H), 4.32-4.21 (m, 1H), 3.98 (d, J = 7.5 Hz, 1H), 3.92-3.86 (m, 1H), 3.83 (d, J = 7.8 Hz, 3H), 3.13 (dt, J = 11.7, 4.1 Hz, 2H), 3.07 (t, J = 7.8 Hz, 2H), 2.91 (t, J = 8.1 Hz, 2H), 2.80 (dd, J = 8.0, 4.7 Hz, 6H), 2.38-2.20 (m, 3H), ; 582.4 [M + H]$^+$ | 1.21 |
| 835 | 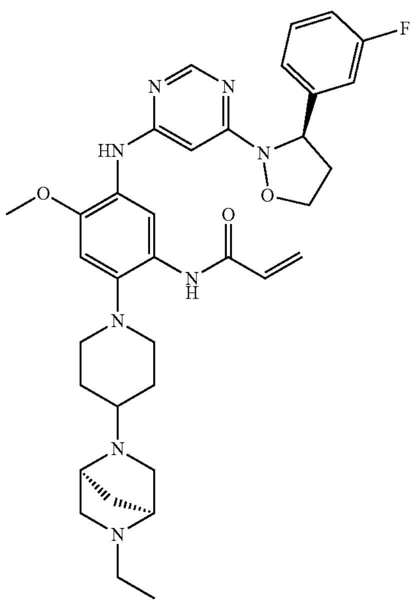 [SMILES: C=CC(=O)Nc1cc(Nc2cc(N3OCC[C@@H]3c3cccc(F)c3)ncn2)c(OC)cc1N1CCC(N2C[C@@H]3C[C@H]2CN3CC)CC1] | N-(2-(4-((1S,4S)-5-ethyl-2,5-diazabicyclo[2.2.1]heptane-2-yl)piperidine-1-yl)-5-((6-((R)-3-(3-fluorophenyl)isoxazolidine-2-yl)pyrimidine-4-yl)amino)-4-methoxyphenyl)acrylamide | $^1$H NMR (400 MHz, DMSO-d$_6$) δ 9.24 (d, J = 12.7 Hz, 1H), 8.28 (s, 1H), 7.90 (s, 1H), 7.42 (td, J = 8.0, 6.1 Hz, 1H), 7.26-7.17 (m, 2H), 7.12 (td, J = 8.7, 2.7 Hz, 1H), 6.90 (d, J = 17.0 Hz, 1H), 6.58 (t, J = 13.9 Hz, 1H), 6.25 (ddd, J = 17.1, 4.8, 1.9 Hz, 1H), 6.19-6.01 (m, 1H), 5.76 (d, J = 10.5 Hz, 1H), 5.54 (dd, J = 8.5, 5.3 Hz, 1H), 4.56 (s, 1H), 4.27 (td, J = 7.9, 7.4, 4.7 Hz, 1H), 4.01 (q, J = 7.8 Hz, 2H), 3.82 (s, 3H), 3.76 (t, J = 6.3 Hz, 1H), 3.61 (dqd, J = 13.2, 6.6, 3.7 Hz, 8H), 3.12 (qd, J = 7.4, 4.2 Hz, 7H), 2.90 (d, J = 7.7 Hz, 1H), 2.77-2.67 (m, 2H), 2.31 (tdd, J = 12.7, 8.8, 5.3 Hz, 2H), 2.19-1.95 (m, 2H), ; 643.6 [M + H]$^+$ | 1.05 |

TABLE 1-continued

| Example Compound | Structure | Name of Compound | ¹H NMR[[:]]; MS [M + H]⁺ | UPLC r.t. (min) |
|---|---|---|---|---|
| 836 | 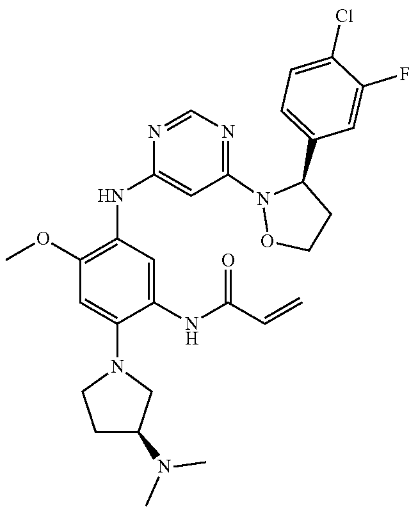 | N-(5-((6-((R)-3-(4-chloro-3-fluorophenyl)isoxazolidine-2-yl)pyrimidine-4-yl)amino)-2-((S)-3-(dimethylamino)pyrolidine-1-yl)-4-methoxyphenyl)acrylamide | ¹H NMR (400 MHz, DMSO-d₆) δ 9.54 (s, 1H), 8.24 (d, J = 4.6 Hz, 1H), 7.68-7.55 (m, 2H), 7.41 (dd, J = 10.5, 2.0 Hz, 1H), 7.26 (d, J = 8.5 Hz, 1H), 6.81 (s, 1H), 6.68 (s, 1H), 6.30-6.04 (m, 2H), 5.79-5.67 (m, 1H), 5.54 (dd, J = 8.8, 5.4 Hz, 1H), 3.82 (d, J = 7.8 Hz, 3H), 3.39 (t, J = 6.9 Hz, 2H), 3.19-3.13 (m, 4H), 3.08 (s, 4H), 2.80 (dd, J = 8.1, 4.7 Hz, 6H), 2.39-2.22 (m, 2H), ; 585.2 [M + H]⁺ | 1.23 |
| 837 | 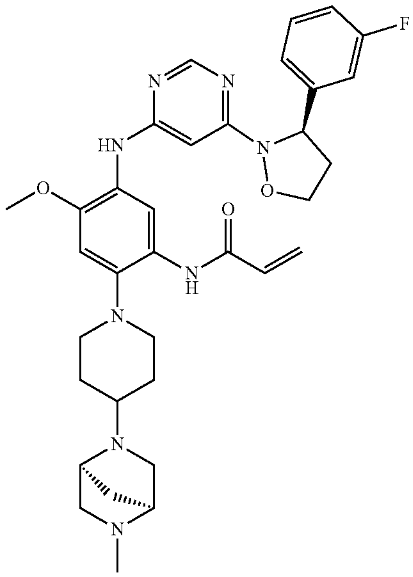 [SMILES: C=CC(=O)Nc1cc(Nc2cc(N3OCC[C@@H]3c3cccc(F)c3)ncn2)c(OC)cc1N1CCC(N2C[C@@H]3C[C@H]2CN3C)CC1] | N-(5-((6-((R)-3-(3-fluorophenyl)isoxazolidine-2-yl)pyrimidine-4-yl)amino)-4-methoxy-2-(4-((1S,4S)-5-methyl-2,5-diazabicyclo[2.2.1]heptane-2-yl)piperidine-1-yl)phenyl)acrylamide | ¹H NMR (400 MHz, DMSO-d₆) δ 9.26 (s, 1H), 8.30 (s, 1H), 7.87 (s, 1H), 7.42 (td, J = 8.0, 6.0 Hz, 1H), 7.25-7.16 (m, 2H), 7.12 (td, J = 8.6, 2.7 Hz, 1H), 6.91 (d, J = 23.6 Hz, 1H), 6.67-6.50 (m, 1H), 6.24 (dd, J = 17.3, 1.7 Hz, 1H), 6.12 (s, 1H), 5.81-5.71 (m, 1H), 5.59-5.49 (m, 1H), 4.47 (s, 1H), 4.28 (s, 2H), 3.66 (d, J = 4.3 Hz, 3H), 3.55-3.47 (m, 1H), 3.38 (q, J = 7.1 Hz, 2H), 3.27 (t, J = 8.4 Hz, 4H), 3.05-2.98 (m, 5H), 2.88 (t, J = 3.9 Hz, 2H), 2.72 (d, J = 5.0 Hz, 2H), 2.33 (dq, J = 13.3, 5.9 Hz, 2H), 2.19-2.00 (m, 2H), 1.77 (ddd, J = 22.2, 15.4, 8.2 Hz, 2H), ; 629.6 [M + H]⁺ | 1.04 |
| 838 | 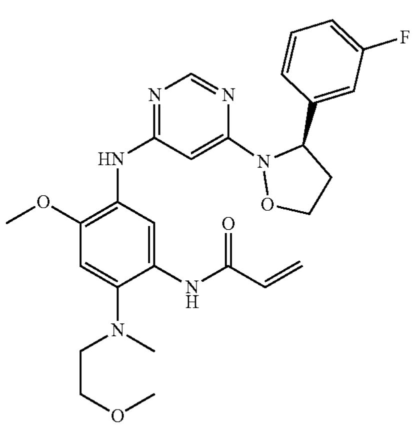 [SMILES: C=CC(=O)Nc1cc(Nc2cc(N3OCC[C@@H]3c3cccc(F)c3)ncn2)c(OC)cc1N(C)CCOC] | N-(5-((6-((R)-3-(3-fluorophenyl)isoxazolidine-2-yl)pyrimidine-4-yl)amino)-4-methoxy-2-((2-methoxyethyl)(methyl)amino)phenyl)acrylamide | ¹H NMR (400 MHz, DMSO-d₆) δ 10.38 (s, 1H), 8.37 (s, 1H), 8.08 (d, J = 8.3 Hz, 1H), 7.43 (td, J = 8.0, 5.9 Hz, 1H), 7.32 (s, 1H), 7.25-7.17 (m, 2H), 7.13 (td, J = 8.7, 2.6 Hz, 1H), 6.58 (dd, J = 17.1, 10.1 Hz, 1H), 6.33-6.15 (m, 2H), 5.81 (dd, J = 10.1, 1.9 Hz, 1H), 5.57 (dd, J = 8.5, 5.4 Hz, 1H), 4.32 (td, J = 7.6, 4.3 Hz, 1H), 4.07 (q, J = 7.7 Hz, 1H), 3.86 (s, 3H), 3.49 (t, J = 5.0 Hz, 2H), 3.05 (s, 2H), 2.94 (ddd, J = 12.3, 8.0, 4.6 Hz, 1H), 2.33 (dtd, J = 12.8, 7.7, 5.3 Hz, 1H), 1.26 (dd, J = 10.5, 4.3 Hz, 2H), 0.85 (q, J = 5.2, 4.0 Hz, 2H), ; 523.4 [M + H]⁺ | 1.49 |

TABLE 1-continued

| Example Compound | Structure | Name of Compound | ¹H NMR[[:]]; MS [M + H]⁺ | UPLC r.t. (min) |
|---|---|---|---|---|
| 839 | 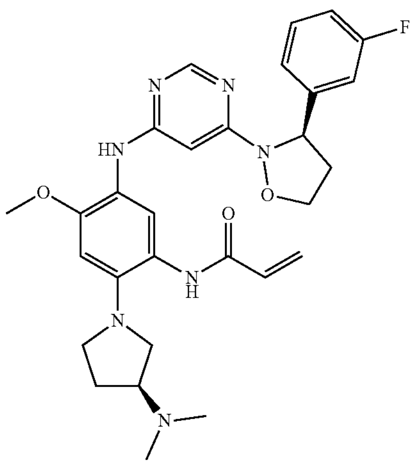 [SMILES: C=CC(=O)Nc1cc(Nc2cc(N3OCC[C@@H]3c3cccc(F)c3)ncn2)c(OC)cc1N1CC[C@H](N(C)C)C1] | N-(2-((S)-3-(dimethylamino)pyrolidine-1-yl)-5-((6-((R)-3-(3-fluorophenyl)isoxazolidine-2-yl)pyrimidine-4-yl)amino)-4-methoxyphenyl)acrylamide | ¹H NMR (400 MHz, DMSO-d₆) δ 11.33 (s, 1H), 9.99 (s, 1H), 9.66 (d, J = 6.9 Hz, 1H), 8.30 (d, J = 2.4 Hz, 1H), 7.58 (d, J = 2.7 Hz, 1H), 7.42 (td, J = 8.2, 6.3 Hz, 1H), 7.24-7.09 (m, 3H), 6.90 (ddd, J = 17.1, 10.2, 3.1 Hz, 1H), 6.69 (s, 1H), 6.22 (dd, J = 17.0, 2.1 Hz, 1H), 6.13-5.97 (m, 1H), 5.71 (dd, J = 10.1, 2.1 Hz, 1H), 5.55 (dd, J = 8.5, 5.3 Hz, 1H), 4.29 (td, J = 7.6, 4.4 Hz, 2H), 4.04 (q, J = 7.7 Hz, 1H), 3.89 (q, J = 6.1 Hz, 1H), 3.63 (dd, J = 11.1, 4.2 Hz, 1H), 3.52 (q, J = 7.6, 7.0 Hz, 1H), 3.41 (dd, J = 11.2, 6.4 Hz, 1H), 3.04 (q, J = 8.2 Hz, 1H), 2.92 (dtd, J = 12.6, 7.7, 4.6 Hz, 1H), 2.80 (dd, J = 7.4, 4.8 Hz, 6H), 2.38-2.24 (m, 3H), ; 548.5 [M + H]⁺ | 1.07 |
| 840 | 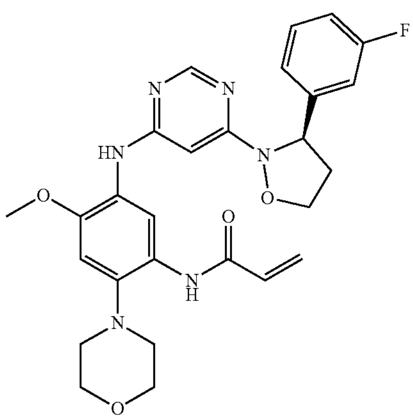 [SMILES: C=CC(=O)Nc1cc(Nc2cc(N3OCC[C@@H]3c3cccc(F)c3)ncn2)c(OC)cc1N1CCOCC1] | N-(5-((6-((R)-3-(3-fluorophenyl)isoxazolidine-2-yl)pyrimidine-4-yl)amino)-4-methoxy-2-morpholinophenyl)acrylamide | ¹H NMR (400 MHz, DMSO-d₆) δ 10.39 (s, 1H), 9.36-9.24 (m, 1H), 8.35 (s, 1H), 7.86 (s, 1H), 7.43 (td, J = 8.0, 5.9 Hz, 1H), 7.24-7.09 (m, 3H), 6.94 (s, 1H), 6.69 (dd, J = 17.0, 10.2 Hz, 1H), 6.24 (dd, J = 16.9, 2.0 Hz, 1H), 6.08 (s, 1H), 5.75 (dd, J = 10.1, 2.0 Hz, 1H), 5.55 (dd, J = 8.5, 5.4 Hz, 1H), 4.33 (td, J = 7.5, 4.3 Hz, 1H), 4.09 (q, J = 7.7 Hz, 1H), 3.82 (d, J = 5.1 Hz, 7H), 3.00-2.88 (m, 5H), 2.33 (dtd, J = 12.7, 7.6, 5.3 Hz, 1H), ; 521.4 [M + H]⁺ | 1.41 |
| 841 | 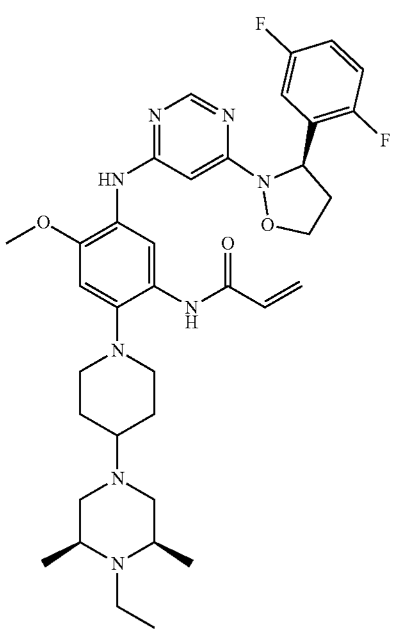 [SMILES: C=CC(=O)Nc1cc(Nc2cc(N3OCC[C@@H]3c3cc(F)ccc3F)ncn2)c(OC)cc1N1CCC(N2C[C@@H](C)N(CC)[C@@H](C)C2)CC1] | N-(5-((6-((R)-3-(2,5-difluorophenyl)isoxazolidine-2-yl)pyrimidine-4-yl)amino)-2-(4-((3S,5R)-4-ethyl-3,5-dimethylpiperazine-1-yl)piperidine-1-yl)-4-methoxyphenyl)acrylamide | ¹H NMR (400 MHz, Methanol-d₄) δ 8.30 (s, 1H), 8.18 (s, 1H), 7.29-7.21 (m, 1H), 7.21-7.10 (m, 1H), 7.10-6.99 (m, 1H), 6.92 (s, 1H), 6.61-6.46 (m, 2H), 6.41-6.31 (m, 1H), 5.89-5.72 (m, 2H), 4.17-4.12 (m, 1H), 4.03-3.96 (m, 1H), 3.89 (s, 3H), 3.30-3.26 (m, 3H), 3.26-3.11 (m, 5H), 2.89-2.76 (m, 3H), 2.60-2.51 (m, 1H), 2.43-2.35 (m, 2H), 2.32-2.23 (m, 1H), 2.07-2.00 (m, 2H), 1.87-1.73 (m, 2H), 1.34 (s, 3H), 1.33 (s, 3H), 1.22 (t, J = 7.3 Hz, 3H); 677.4 [M + H]⁺ | 1.36 |

TABLE 1-continued

| Example Compound | Structure | Name of Compound | ¹H NMR[[:]]; MS [M + H]⁺ | UPLC r.t. (min) |
|---|---|---|---|---|
| 842 | 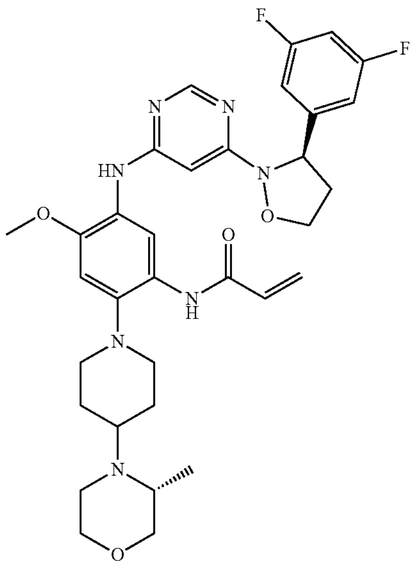 [SMILES: C=CC(=O)Nc1cc(Nc2cc(N3OCC[C@@H]3c3cc(F)cc(F)c3)ncn2)c(OC)cc1N1CCC(N2CCOC[C@H]2C)CC1] | N-(5-((6-((R)-3-(3,5-difluorophenyl)isoxazolidine-2-yl)pyrimidine-4-yl)amino)-4-methoxy-2-(4-((R)-3-methylmorpholino)piperidine-1-yl)phenyl)acrylamide | ¹H NMR (400 MHz, Methanol-d₄) δ 8.30 (s, 1H), 8.18 (s, 1H), 7.12-7.02 (m, 2H), 6.94 (s, 1H), 6.87-6.78 (m, 1H), 6.57 (dd, J = 10.2, 17.0 Hz, 1H), 6.46 (s, 1H), 6.42-6.31 (m, 1H), 5.82 (d, J = 10.2 Hz, 1H), 5.60-5.51 (m, 1H), 4.19-4.13 (m, 1H), 3.98 (q, J = 8.0 Hz, 1H), 3.89 (s, 4H), 3.83-3.71 (m, 2H), 3.51-3.41 (m, 1H), 3.23-3.04 (m, 5H), 3.03-2.92 (m, 1H), 2.92-2.75 (m, 5H), 2.38-2.29 (m, 1H), 1.93-1.84 (m, 1H), 1.84-1.75 (m, 1H), 1.16 (d, J = 6.4 Hz, 3H); 636.3 [M + H]⁺ | 1.24 |
| 843 | 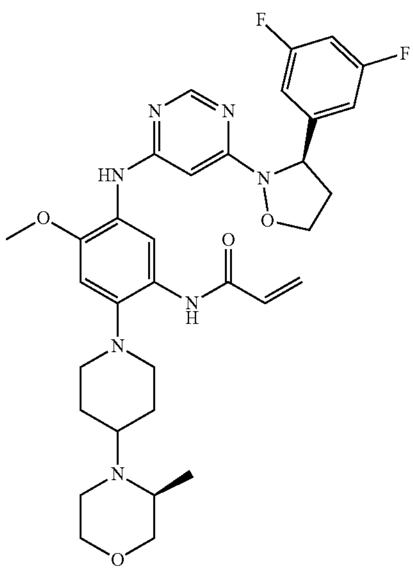 [SMILES: C=CC(=O)Nc1cc(Nc2cc(N3OCC[C@@H]3c3cc(F)cc(F)c3)ncn2)c(OC)cc1N1CCC(N2CCOC[C@@H]2C)CC1] | N-(5-((6-((R)-3-(3,5-difluorophenyl)isoxazolidine-2-yl)pyrimidine-4-yl)amino)-4-methoxy-2-(4-((S)-3-methylmorpholino)piperidine-1-yl)phenyl)acrylamide | ¹H NMR (400 MHz, Methanol-d₄) δ 8.30 (s, 1H), 8.18 (s, 1H), 7.12-7.02 (m, 2H), 6.94 (s, 1H), 6.89-6.78 (m, 1H), 6.63-6.50 (m, 1H), 6.46 (s, 1H), 6.42-6.31 (m, 1H), 5.82 (d, J = 10.2 Hz, 1H), 5.62-5.50 (m, 1H), 4.18-4.12 (m, 1H), 3.98 (q, J = 8.0 Hz, 1H), 3.89 (s, 4H), 3.82-3.71 (m, 2H), 3.48-3.40 (m, 1H), 3.22-3.05 (m, 5H), 2.98-2.91 (m, 1H), 2.92-2.73 (m, 5H), 2.38-2.30 (m, 1H), 1.93-1.86 (m, 1H), 1.84-1.76 (m, 1H), 1.15 (d, J = 6.4 Hz, 3H); 636.3 [M + H]⁺ | 1.24 |
| 844 | 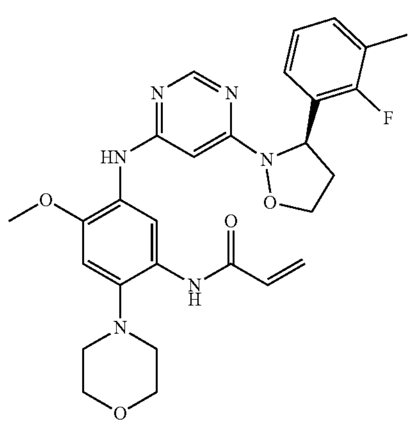 | N-(5-((6-((R)-3-(2-fluoro-3-methylphenyl)isoxazolidine-2-yl)pyrimidine-4-yl)amino)-4-methoxy-2-morpholinophenyl)acrylamide | ¹H NMR (400 MHz, MeOD) δ 8.34 (s, 1H), 8.16 (s, 1H), 7.35 (t, J = 7.3 Hz, 1H), 7.15 (t, J = 7.3 Hz, 1H), 7.03 (t, J = 7.6 Hz, 1H), 6.95 (s, 1H), 6.56 (dd, J = 17.0, 10.3 Hz, 1H), 6.49 (s, 1H), 6.36 (d, J = 17.0 Hz, 1H), 5.79 (dd, J = 15.2, 7.2 Hz, 2H), 4.13 (td, J = 7.7, 4.3 Hz, 1H), 3.99 (q, J = 7.9 Hz, 1H), 3.93-3.79 (m, 7H), 2.99-2.90 (m, 4H), 2.88-2.80 (m, 1H), 2.32-2.22 (m, 4H), ; 535.5 [M + H]⁺ | 1.64 |

TABLE 1-continued

| Example Compound | Structure | Name of Compound | ¹H NMR[[:]]; MS [M + H]⁺ | UPLC r.t. (min) |
|---|---|---|---|---|
| 845 | 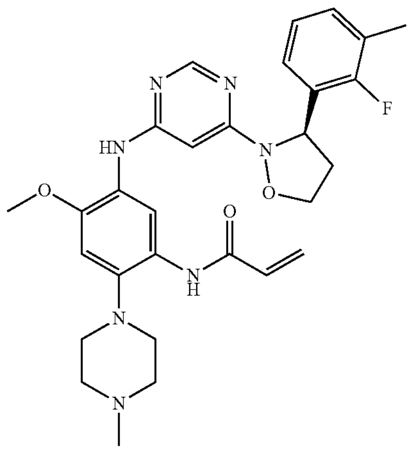 | N-(5-((6-((R)-3-(2-fluoro-3-methylphenyl)isoxazolidine-2-yl)pyrimidine-4-yl)amino)-4-methoxy-2-(4-methylpiperazine-1-yl)phenyl)acrylamide | ¹H NMR (400 MHz, MeOD) δ 8.34 (s, 1H), 8.16 (s, 1H), 7.35 (t, J = 7.0 Hz, 1H), 7.15 (t, J = 7.4 Hz, 1H), 7.03 (t, J = 7.6 Hz, 1H), 6.95 (s, 1H), 6.58-6.47 (m, 2H), 6.36 (d, J = 17.0 Hz, 1H), 5.84-5.74 (m, 2H), 4.13 (td, J = 7.8, 4.5 Hz, 1H), 3.99 (dd, J = 16.4, 8.5 Hz, 1H), 3.90 (s, 3H), 2.99 (t, J = 4.5 Hz, 4H), 2.84 (dt, J = 16.4, 6.3 Hz, 1H), 2.70 (s, 4H), 2.41 (s, 3H), 2.31-2.22 (m, 4H), ; 548.5 [M + H]⁺ | 1.37 |
| 846 | 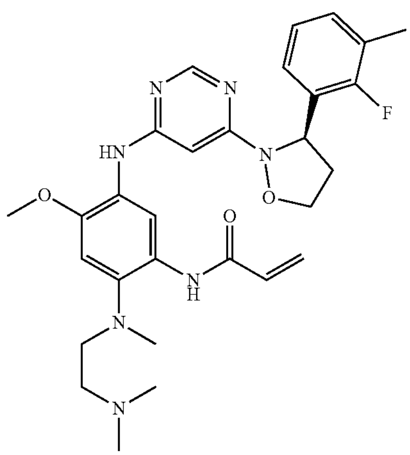 | N-(2-((2-(dimethylamino)ethyl)(methyl)amino)-5-((6-((R)-3-(2-fluoro-3-methylphenyl)isoxazolidine-2-yl)pyrimidine-4-yl)amino)-4-methoxyphenyl)acrylamide | ¹H NMR (400 MHz, MeOD) δ 8.34 (s, 1H), 8.16 (s, 1H), 7.35 (t, J = 7.0 Hz, 1H), 7.15 (t, J = 7.4 Hz, 1H), 7.03 (t, J = 7.6 Hz, 1H), 6.95 (s, 1H), 6.58-6.47 (m, 2H), 6.36 (d, J = 17.0 Hz, 1H), 5.84-5.74 (m, 2H), 4.13 (td, J = 7.8, 4.5 Hz, 1H), 3.99 (dd, J = 16.4, 8.5 Hz, 1H), 3.90 (s, 3H), 2.99 (t, J = 4.5 Hz, 4H), 2.84 (dt, J = 16.4, 6.3 Hz, 1H), 2.70 (s, 4H), 2.41 (s, 3H), 2.31-2.22 (m, 4H), ; 550.5 [M + H]⁺ | 1.38 |
| 847 | 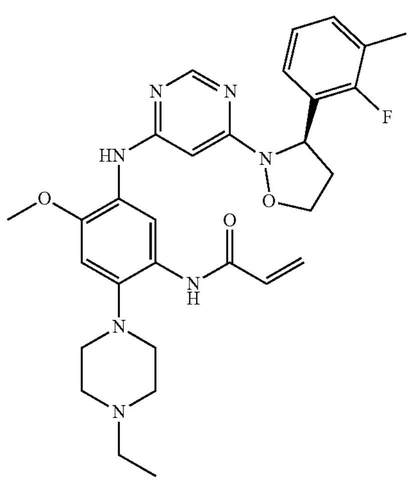 | N-(2-(4-ethylpiperazine-1-yl)-5-((6-((R)-3-(2-fluoro-3-methylphenyl)isoxazolidine-2-yl)pyrimidine-4-yl)amino)-4-methoxyphenyl)acrylamide | ¹H NMR (400 MHz, MeOD) δ 8.34 (s, 1H), 8.16 (s, 1H), 7.35 (t, J = 7.1 Hz, 1H), 7.15 (t, J = 7.4 Hz, 1H), 7.03 (t, J = 7.6 Hz, 1H), 6.96 (s, 1H), 6.58-6.46 (m, 2H), 6.36 (d, J = 15.7 Hz, 1H), 5.85-5.74 (m, 2H), 4.13 (td, J = 7.9, 4.6 Hz, 1H), 3.99 (dd, J = 16.0, 8.1 Hz, 1H), 3.90 (s, 3H), 3.00 (t, J = 4.7 Hz, 4H), 2.90-2.81 (m, 1H), 2.74 (s, 4H), 2.58 (q, J = 7.3 Hz, 2H), 2.33-2.20 (m, 4H), 1.19 (t, J = 7.2 Hz, 3H), ; 562.5 [M + H]⁺ | 1.23 |

TABLE 1-continued

| Example Compound | Structure | Name of Compound | ¹H NMR[[:]]; MS [M + H]⁺ | UPLC r.t. (min) |
|---|---|---|---|---|
| 848 | 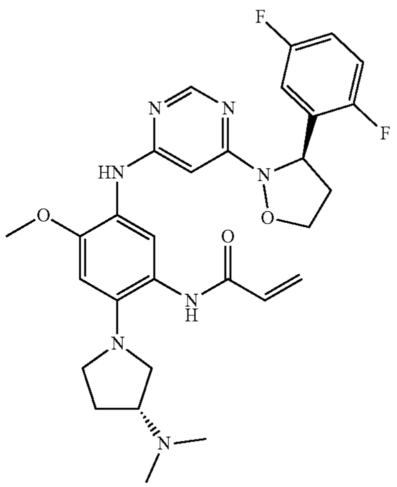 [SMILES: C=CC(=O)Nc1cc(Nc2cc(N3OCC[C@@H]3c3cc(F)ccc3F)ncn2)c(OC)cc1N1CC[C@@H](N(C)C)C1] | N-(5-((6-((R)-3-(2,5-difluorophenyl)isoxazolidine-2-yl)pyrimidine-4-yl)amino)-2-((R)-3-(dimethylamino)pyrolidine-1-yl)-4-methoxyphenyl)acrylamide | ¹H NMR (400 MHz, DMSO-d$_6$) δ 11.06 (s, 1H), 9.74 (s, 1H), 9.58 (s, 1H), 8.27 (s, 1H), 7.59 (s, 1H), 7.37-7.27 (m, 1H), 7.26-7.12 (m, 2H), 6.83 (dd, J = 17.0, 10.2 Hz, 1H), 6.69 (s, 1H), 6.22 (dd, J = 17.0, 2.1 Hz, 1H), 6.12 (s, 1H), 5.78-5.62 (m, 2H), 4.33-4.26 (m, 1H), 4.06-3.98 (m, 1H), 3.82 (s, 3H), 3.60 (s, 6H), 3.39-3.37 (m, 1H), 3.10-3.04 (m, 1H), 2.95-2.88 (m, 1H), 2.82-2.78 (m, 4H), 2.30-2.27 (m, 1H), ; 566.5 [M + H]⁺ | 1.16 |
| 849 | 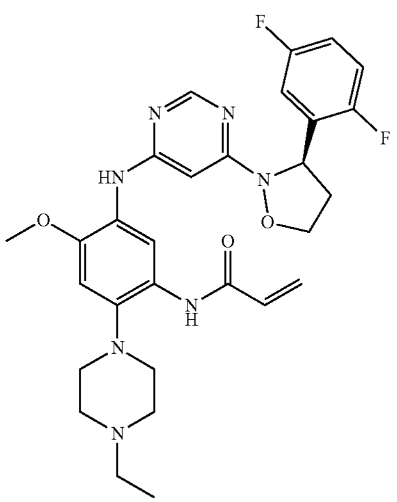 [SMILES: C=CC(=O)Nc1cc(Nc2cc(N3OCC[C@@H]3c3cc(F)ccc3F)ncn2)c(OC)cc1N1CCN(CC)CC1] | N-(5-((6-((R)-3-(2,5-difluorophenyl)isoxazolidine-2-yl)pyrimidine-4-yl)amino)-2-(4-ethylpiperazine-1-yl)-4-methoxyphenyl)acrylamide | ¹H NMR (400 MHz, DMSO-d$_6$) δ 10.72 (s, 1H), 9.57 (s, 1H), 9.15 (d, J = 5.6 Hz, 1H), 8.27 (d, J = 3.0 Hz, 1H), 8.11 (s, 1H), 7.37-7.27 (m, 1H), 7.26-7.13 (m, 2H), 6.85 (d, J = 13.3 Hz, 1H), 6.74 (dd, J = 17.0, 10.2 Hz, 1H), 6.29-6.18 (m, 2H), 5.80-5.72 (m, 1H), 5.67 (dd, J = 8.7, 5.4 Hz, 1H), 4.33-4.23 (m, 1H), 4.04-3.95 (m, 1H), 3.83 (s, 3H), 3.40-3.37 (m, 2H), 3.30-3.25 (m, 2H), 3.21-3.16 (m, 4H), 2.99-2.82 (m, 2H), 2.31-2.21 (m, 1H), 1.31 (t, J = 7.3 Hz, 3H), ; 566.5 [M + H]⁺ | 1.22 |

TABLE 1-continued

| Example Compound | Structure | Name of Compound | $^1$H NMR[[:]]; MS [M + H]$^+$ | UPLC r.t. (min) |
|---|---|---|---|---|
| 850 | 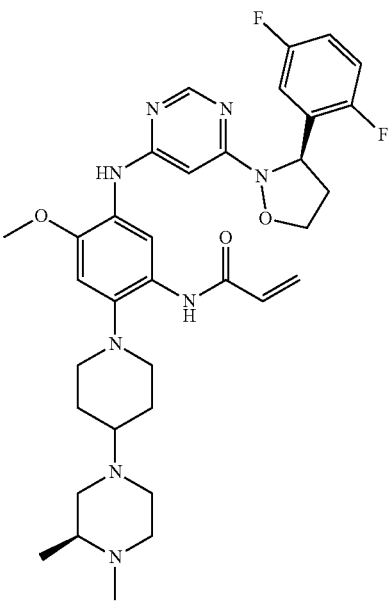 [SMILES: C=CC(=O)Nc1cc(Nc2cc(N3OCC[C@@H]3c3cc(F)ccc3F)ncn2)c(OC)cc1N1CCC(N2CCN(C)[C@@H](C)C2)CC1] | N-(5-((6-((R)-3-(2,5-difluorophenyl)isoxazolidine-2-yl)pyrimidine-4-yl)amino)-2-(4-((S)-3,4-dimethylpiperazine-1-yl)piperidine-1-yl)-4-methoxyphenyl)acrylamide | $^1$H NMR (400 MHz, Chloroform-d) δ 8.87 (s, 1H), 8.44 (s, 1H), 8.37 (d, J = 1.0 Hz, 1H), 7.36-7.27 (m, 1H), 7.00 (td, J = 9.2, 4.4 Hz, 1H), 6.94 (s, 1H), 6.93-6.84 (m, 1H), 6.76 (d, J = 1.4 Hz, 2H), 6.36 (d, J = 17.0, 1.6 Hz, 1H), 6.25 (dd, J = 16.9, 9.9 Hz, 1H), 5.90 (dd, J = 8.9, 4.3 Hz, 1H), 5.74 (dd, J = 10.0, 1.6 Hz, 1H), 4.17-4.02 (m, 2H), 3.85 (s, 3H), 3.06 (d, J = 11.4 Hz, 2H), 3.02-2.95 (m, 1H), 2.93-2.78 (m, 3H), 2.78-2.66 (m, 2H), 2.44-2.34 (m, 2H), 2.32 (s, 3H), 2.31-2.26 (m, 2H), 2.17 (s, 1H), 2.13-2.04 (m, 2H), 2.03-1.96 (m, 1H), 1.69-1.63 (m, 2H), 1.10 (d, J = 6.1 Hz, 3H), ; 649.5 [M + H]$^+$ | 1.17 |
| 851 | 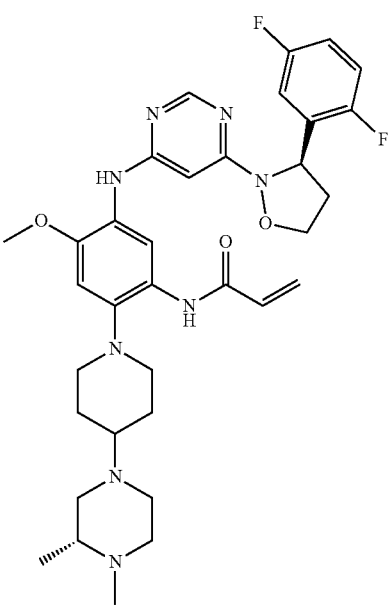 [SMILES: C=CC(=O)Nc1cc(Nc2cc(N3OCC[C@@H]3c3cc(F)ccc3F)ncn2)c(OC)cc1N1CCC(N2CCN(C)[C@H](C)C2)CC1] | N-(5-((6-((R)-3-(2,5-difluorophenyl)isoxazolidine-2-yl)pyrimidine-4-yl)amino)-2-(4-((R)-3,4-dimethylpiperazine-1-yl)piperidine-1-yl)-4-methoxyphenyl)acrylamide | $^1$H NMR (400 MHz, Chloroform-d) δ 8.87 (s, 1H), 8.44 (s, 1H), 8.37 (d, J = 1.0 Hz, 1H), 7.36-7.27 (m, 1H), 7.00 (td, J = 9.2, 4.4 Hz, 1H), 6.95 (s, 1H), 6.94-6.84 (m, 1H), 6.79-6.72 (m, 2H), 6.41-6.32 (m, 1H), 6.25 (dd, J = 16.9, 10.0 Hz, 1H), 5.90 (dd, J = 8.8, 4.3 Hz, 1H), 5.74 (dd, J = 10.0, 1.6 Hz, 1H), 4.17-4.02 (m, 2H), 3.85 (s, 3H), 3.06 (d, J = 11.6 Hz, 2H), 3.02-2.96 (m, 1H), 2.95-2.87 (m, 2H), 2.87-2.79 (m, 1H), 2.73 (q, J = 12.1 Hz, 2H), 2.41 (s, 2H), 2.34 (s, 3H), 2.32-2.25 (m, 2H), 2.21 (d, J = 23.1 Hz, 1H), 2.12-2.02 (m, 3H), 1.69-1.64 (m, 2H), 1.12 (d, J = 6.2 Hz, 3H), ; 649.5 [M + H]$^+$ | 1.18 |

| Example Compound | Structure | Name of Compound | ¹H NMR[[:]]; MS [M + H]⁺ | UPLC r.t. (min) |
|---|---|---|---|---|
| 852 | 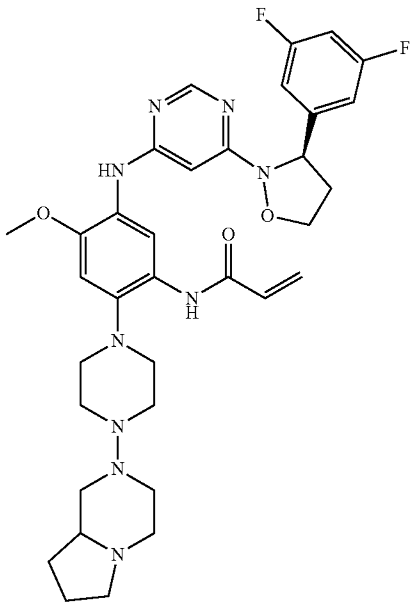 [SMILES: C=CC(=O)Nc1cc(Nc2cc(N3OCC[C@@H]3c3cc(F)cc(F)c3)ncn2)c(OC)cc1N1CCN(N2CCN3CCCC3C2)CC1] | N-(5-((6-((R)-3-(3,5-difluorophenyl)isoxazolidine-2-yl)pyrimidine-4-yl)amino)-2-(4-(hexahydropyrrolo[1,2-a]pyrazine-2(1H)-yl)piperidine-1-yl)-4-methoxyphenyl)acrylamide | ¹H NMR (400 MHz, Chloroform-d) δ 8.86 (s, 1H), 8.45 (s, 1H), 8.36 (d, J = 1.0 Hz, 1H), 7.06-6.96 (m, 2H), 6.94 (s, 1H), 6.75 (s, 1H), 6.74-6.63 (m, 2H), 6.36 (dd, J = 16.9, 1.5 Hz, 1H), 6.25 (dd, J = 16.9, 10.0 Hz, 1H), 5.74 (dd, J = 10.0, 1.6 Hz, 1H), 5.67 (dd, J = 8.8, 4.6 Hz, 1H), 4.15 (td, J = 8.1, 4.2 Hz, 1H), 4.06 (q, J = 8.0 Hz, 1H), 3.84 (s, 3H), 3.19-3.13 (m, 1H), 3.13-3.03 (m, 4H), 3.03-2.96 (m, 1H), 2.84-2.68 (m, 3H), 2.52-2.39 (m, 2H), 2.39-2.27 (m, 2H), 2.20-2.14 (m, 1H), 2.10-2.06 (m, 2H), 1.88-1.66 (m, 8H), ; 661.6 [M + H]⁺ | 1.18 |
| 853 | 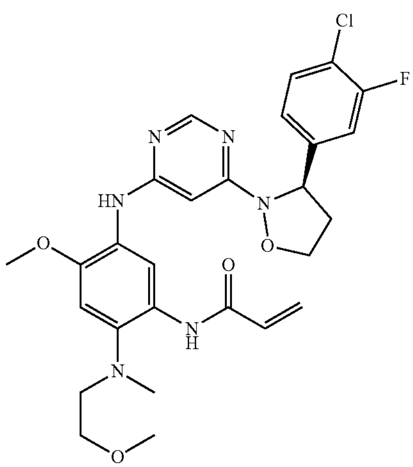 [SMILES: C=CC(=O)Nc1cc(Nc2cc(N3OCC[C@@H]3c3ccc(Cl)c(F)c3)ncn2)c(OC)cc1N(C)CCOC] | N-(5-((6-((R)-3-(4-chloro-3-fluorophenyl)isoxazolidine-2-yl)pyrimidine-4-yl)amino)-4-methoxy-2-((2-methoxyethyl)(methyl)amino)phenyl)acrylamide | ¹H NMR (400 MHz, DMSO-d₆) δ 9.34 (s, 1H), 8.37-8.20 (m, 1H), 7.58 (t, J = 8.1 Hz, 1H), 7.42 (dd, J = 10.5, 2.0 Hz, 1H), 7.27 (d, J = 8.3 Hz, 1H), 7.03 (s, 1H), 6.44 (dd, J = 16.9, 10.1 Hz, 1H), 6.23 (d, J = 17.2 Hz, 2H), 5.77 (d, J = 10.2 Hz, 1H), 5.54 (dd, J = 8.6, 5.2 Hz, 1H), 4.22 (td, J = 8.0, 4.1 Hz, 1H), 3.95 (q, J = 7.8 Hz, 1H), 3.81 (s, 3H), 3.49 (t, J = 5.2 Hz, 2H), 3.32 (s, 2H), 3.04 (s, 1H), 2.82 (s, 2H), 2.50 (p, J = 1.9 Hz, 6H), 2.35-2.21 (m, 1H), ; 557.4 [M + H]⁺ | 1.63 |
| 854 | 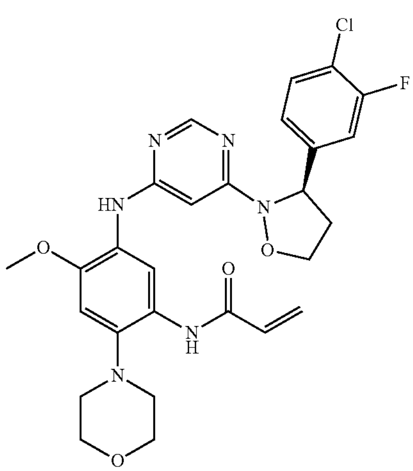 [SMILES: C=CC(=O)Nc1cc(Nc2cc(N3OCC[C@@H]3c3ccc(Cl)c(F)c3)ncn2)c(OC)cc1N1CCOCC1] | N-(5-((6-((R)-3-(4-chloro-3-fluorophenyl)isoxazolidine-2-yl)pyrimidine-4-yl)amino)-4-methoxy-2-morpholinophenyl)acrylamide | ¹H NMR (400 MHz, DMSO-d₆) δ 9.11 (s, 1H), 8.22 (s, 1H), 8.06 (s, 1H), 7.58 (t, J = 8.0 Hz, 1H), 7.41 (dd, J = 10.5, 2.0 Hz, 1H), 7.27 (dd, J = 8.4, 2.0 Hz, 1H), 6.89 (s, 1H), 6.64 (dd, J = 16.9, 10.2 Hz, 1H), 6.24 (d, J = 2.0 Hz, 1H), 6.19 (d, J = 2.0 Hz, 1H), 5.73 (dd, J = 10.2, 2.0 Hz, 1H), 5.54 (dd, J = 8.6, 5.2 Hz, 1H), 4.21 (td, J = 7.7, 4.1 Hz, 2H), 3.93 (q, J = 7.9 Hz, 1H), 3.81 (d, J = 6.5 Hz, 7H), 2.87 (t, J = 4.6 Hz, 4H), 2.82 (td, J = 7.7, 3.9 Hz, 1H), 2.29 (ddd, J = 12.6, 8.4, 5.1 Hz, 1H), ; 555.4 [M + H]⁺ | 1.55 |

TABLE 1-continued

| Example Compound | Structure | Name of Compound | $^1$H NMR[[:]]; MS [M + H]$^+$ | UPLC r.t. (min) |
|---|---|---|---|---|
| 855 | 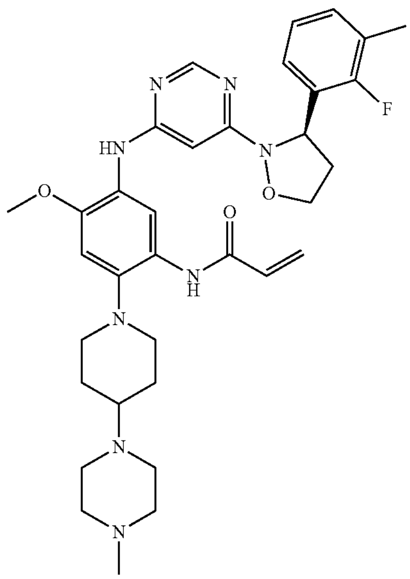 | N-(5-((6-((R)-3-(2-fluoro-3-methylphenyl)isoxazolidine-2-yl)pyrimidine-4-yl)amino)-4-methoxy-2-(4-(4-methylpiperazine-1-yl)piperidine-1-yl)phenyl)acrylamide | $^1$H NMR (400 MHz, DMSO-d$_6$) δ 9.07 (s, 1H), 8.81 (s, 1H), 8.13 (d, J = 31.2 Hz, 1H), 7.26 (t, J = 7.4 Hz, 1H), 7.23-7.15 (m, 1H), 7.07 (t, J = 7.5 Hz, 1H), 6.90 (d, J = 38.3 Hz, 1H), 6.72-6.59 (m, 1H), 6.40-6.17 (m, 2H), 5.80-5.64 (m, 2H), 4.21-4.12 (m, 1H), 3.85-3.79 (m, 3H), 3.59 (dh, J = 9.7, 3.2 Hz, 3H), 3.13 (dh, J = 11.0, 3.6 Hz, 4H), 3.03 (d, J = 12.9 Hz, 1H), 2.91 (s, 1H), 2.87-2.76 (m, 3H), 2.26 (d, J = 2.2 Hz, 3H), 2.21-2.10 (m, 2H), 1.28 (ddd, J = 8.4, 6.4, 3.0 Hz, 8H), 1.18-1.03 (m, 2H), ; 555.4 [M + H]$^+$ | 1.17 |
| 856 | 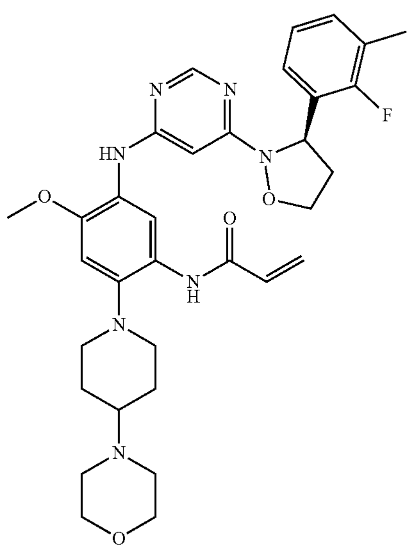 | N-(5-((6-((R)-3-(2-fluoro-3-methylphenyl)isoxazolidine-2-yl)pyrimidine-4-yl)amino)-4-methoxy-2-(4-morpholinopiperidine-1-yl)phenyl)acrylamide | $^1$H NMR (400 MHz, DMSO-d$_6$) δ 9.49 (s, 1H), 9.14 (s, 1H), 8.23 (s, 1H), 8.03 (s, 1H), 7.27-7.16 (m, 2H), 7.07 (t, J = 7.6 Hz, 1H), 6.89 (s, 1H), 6.66 (dd, J = 16.9, 10.2 Hz, 1H), 6.31-6.18 (m, 2H), 5.72 (ddd, J = 17.5, 9.4, 3.6 Hz, 2H), 4.23 (td, J = 7.7, 4.0 Hz, 1H), 4.06-3.92 (m, 7H), 3.81 (s, 3H), 3.59 (pd, J = 6.6, 3.9 Hz, 4H), 3.44 (d, J = 12.1 Hz, 3H), 3.11 (dq, J = 7.4, 3.2 Hz, 5H), 2.26 (d, J = 2.0 Hz, 4H), ; 618.5 [M + H]$^+$ | 1.27 |

TABLE 1-continued

| Example Compound | Structure | Name of Compound | $^1$H NMR[[:]]; MS [M + H]$^+$ | UPLC r.t. (min) |
|---|---|---|---|---|
| 857 | 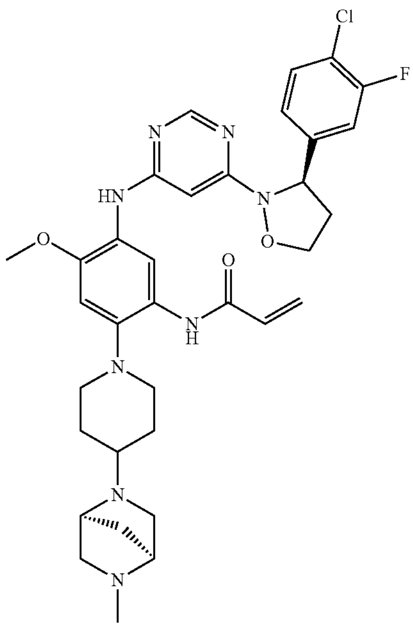 [SMILES: C=CC(=O)Nc1cc(Nc2cc(N3OCC[C@@H]3c3ccc(Cl)c(F)c3)ncn2)c(OC)cc1N1CCC(N2C[C@@H]3C[C@H]2CN3C)CC1] | N-(5-((6-((R)-3-(4-chloro-3-fluorophenyl)isoxazolidine-2-yl)pyrimidine-4-yl)amino)-4-methoxy-2-(4-((1S,4S)-5-methyl-2,5-diazabicyclo[2.2.1]heptane-2-yl)piperidine-1-yl)phenyl)acrylamide | $^1$H NMR (400 MHz, DMSO-d$_6$) δ 10.41 (s, 1H), 9.37 (s, 1H), 8.35 (s, 1H), 7.81 (s, 1H), 7.60 (t, J = 8.0 Hz, 1H), 7.42 (dd, J = 10.3, 2.0 Hz, 1H), 7.24 (dd, J = 8.4, 2.0 Hz, 1H), 6.96 (d, J = 20.1 Hz, 1H), 6.75-6.52 (m, 1H), 6.25 (dd, J = 17.0, 1.8 Hz, 1H), 6.12 (s, 1H), 5.82-5.70 (m, 1H), 5.56 (dd, J = 8.5, 5.4 Hz, 1H), 4.82 (s, 1H), 4.71 (s, 1H), 4.49 (s, 2H), 4.32 (td, J = 7.5, 4.3 Hz, 1H), 4.08 (q, J = 7.6 Hz, 2H), 3.83 (s, 3H), 3.79-3.61 (m, 2H), 3.36-3.16 (m, 3H), 3.01-2.63 (m, 7H), 2.42-1.98 (m, 6H), ; 663.5 [M + H]$^+$ | 1.17 |
| 858 | 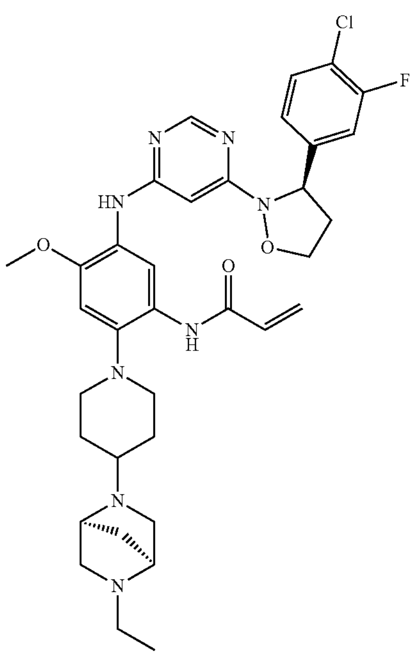 [SMILES: C=CC(=O)Nc1cc(Nc2cc(N3OCC[C@@H]3c3ccc(Cl)c(F)c3)ncn2)c(OC)cc1N1CCC(N2C[C@@H]3C[C@H]2CN3CC)CC1] | N-(5-((6-((R)-3-(4-chloro-3-fluorophenyl)isoxazolidine-2-yl)pyrimidine-4-yl)amino)-2-(4-((1S,4S)-5-ethyl-2,5-diazabicyclo[2.2.1]heptane-2-yl)piperidine-1-yl)-4-methoxyphenyl)acrylamide | $^1$H NMR (400 MHz, DMSO-d$_6$) δ 10.37 (s, 1H), 9.36 (s, 1H), 8.35 (s, 1H), 7.81 (s, 1H), 7.60 (t, J = 8.1 Hz, 1H), 7.42 (dd, J = 10.4, 2.0 Hz, 1H), 7.25 (dd, J = 8.4, 2.0 Hz, 1H), 6.95 (d, J = 15.4 Hz, 1H), 6.64 (ddd, J = 27.1, 16.8, 10.5 Hz, 1H), 6.25 (dd, J = 16.9, 1.8 Hz, 1H), 6.12 (s, 1H), 5.83-5.69 (m, 1H), 5.56 (dd, J = 8.5, 5.4 Hz, 1H), 4.84 (s, 1H), 4.71 (s, 1H), 4.58 (d, J = 8.9 Hz, 2H), 4.32 (td, J = 7.6, 4.4 Hz, 2H), 4.08 (q, J = 7.5 Hz, 2H), 3.38 (s, 3H), 3.72-3.55 (m, 2H), 3.46-3.14 (m, 5H), 2.95 (ddp, J = 12.2, 7.3, 4.4 Hz, 1H), 2.77 (p, J = 13.6, 12.9 Hz, 2H), 2.58 (d, J = 12.5 Hz, 1H), 2.33 (dtd, J = 12.7, 7.5, 5.1 Hz, 1H), 2.09 (d, J = 38.9 Hz, 3H), 1.30 (dd, J = 8.7, 5.0 Hz, 3H), ; 677.5 [M + H]$^+$ | 1.15 |

TABLE 1-continued

| Example Compound | Structure | Name of Compound | ¹H NMR[[:]]; MS [M + H]⁺ | UPLC r.t. (min) |
|---|---|---|---|---|
| 859 | 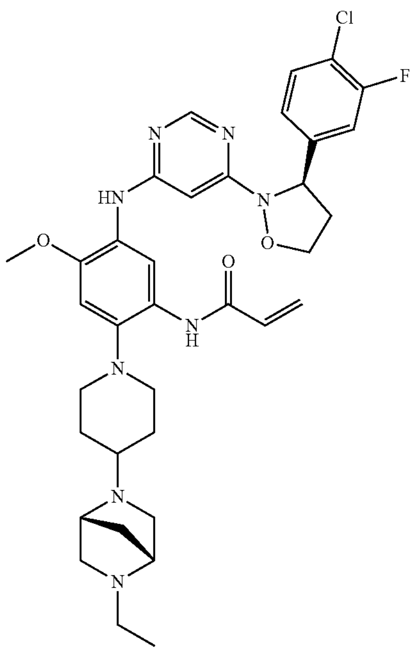 [SMILES: C=CC(=O)Nc1cc(Nc2cc(N3OCC[C@@H]3c3ccc(Cl)c(F)c3)ncn2)c(OC)cc1N1CCC(N2C[C@H]3C[C@@H]2CN3CC)CC1] | N-(5-((6-((R)-3-(4-chloro-3-fluorophenyl)isoxazolidine-2-yl)pyrimidine-4-yl)amino)-2-(4-((1R,4R)-5-ethyl-2,5-diazabicyclo[2.2.1]heptane-2-yl)piperidine-1-yl)-4-methoxyphenyl)acrylamide | ¹H NMR (400 MHz, DMSO-d₆) δ 10.41 (s, 1H), 9.38 (s, 1H), 8.35 (s, 1H), 7.81 (s, 1H), 7.60 (t, J = 8.0 Hz, 1H), 7.42 (dd, J = 10.4, 2.0 Hz, 1H), 7.25 (dd, J = 8.3, 2.0 Hz, 1H), 6.96 (d, J = 14.3 Hz, 1H), 6.63 (td, J = 16.3, 8.2 Hz, 1H), 6.25 (dd, J = 17.1, 1.8 Hz, 1H), 6.12 (d, J = 9.8 Hz, 1H), 5.77 (d, J = 10.5 Hz, 1H), 5.56 (dd, J = 8.5, 5.4 Hz, 1H), 4.84 (s, 1H), 4.71 (s, 1H), 4.58 (d, J = 9.9 Hz, 2H), 4.32 (td, J = 7.6, 4.4 Hz, 1H), 4.08 (q, J = 7.5 Hz, 2H), 3.83 (s, 3H), 3.71-3.58 (m, 1H), 3.45-3.12 (m, 5H), 2.96 (ddp, J = 12.3, 7.4, 4.6 Hz, 1H), 2.77 (ddd, J = 23.2, 16.4, 8.4 Hz, 2H), 2.40-2.26 (m, 2H), 2.21-2.02 (m, 3H), 1.36-1.22 (m, 4H), ; 677.5 [M + H]⁺ | 1.17 |
| 860 | 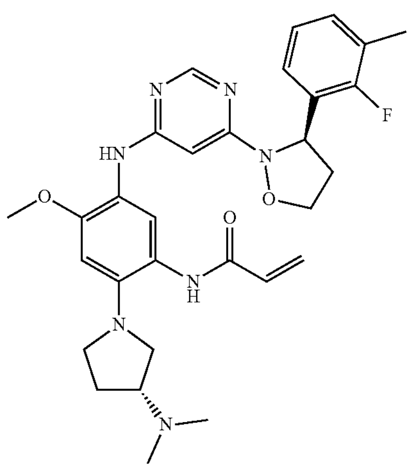 | N-(2-((R)-3-(dimethylamino)pyrolidine-1-yl)-5-((6-((R)-3-(2-fluoro-3-methylphenyl)isoxazolidine-2-yl)pyrimidine-4-yl)amino)-4-methoxyphenyl)acrylamide | ¹H NMR (400 MHz, MeOD) δ 8.06-7.93 (m, 1H), 7.56 (s, 1H), 7.27-7.15 (m, 1H), 7.08-6.96 (m, 1H), 6.90 (t, J = 7.6 Hz, 1H), 6.54 (s, 1H), 6.42 (dd, J = 17.0, 10.2 Hz, 1H), 6.29-6.17 (m, 2H), 5.72-5.57 (m, 2H), 3.98 (td, J = 7.9, 4.4 Hz, 1H), 3.83 (q, J = 7.9 Hz, 1H), 3.75 (s, 3H), 3.20-3.08 (m, 4H), 2.83-2.61 (m, 2H), 2.55 (s, 1H), 2.19 (d, J = 13.3 Hz, 9H), 2.10 (ddd, J = 12.3, 7.9, 4.4 Hz, 2H), 1.84-1.72 (m, 1H), ; 562.4 [M + H]⁺ | 1.19 |
| 861 | 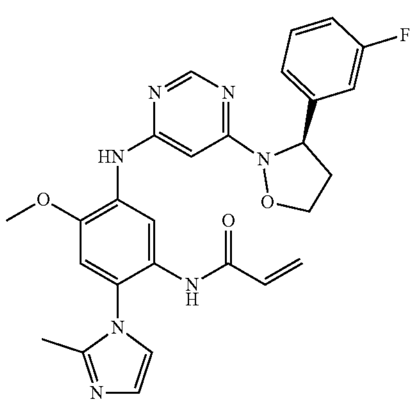 [SMILES: C=CC(=O)Nc1cc(Nc2cc(N3OCC[C@@H]3c3cccc(F)c3)ncn2)c(OC)cc1-n1ccnc1C] | N-(5-((6-((R)-3-(3-fluorophenyl)isoxazolidine-2-yl)pyrimidine-4-yl)amino)-4-methoxy-2-(2-methyl-1H-imidazole-1-yl)phenyl)acrylamide | ¹H NMR (400 MHz, DMSO-d₆) δ 14.80 (s, 1H), 10.08 (s, 1H), 9.23 (s, 1H), 8.36 (d, J = 8.6 Hz, 2H), 7.60 (dd, J = 46.0, 2.1 Hz, 2H), 7.47-7.34 (m, 2H), 7.30-7.20 (m, 2H), 7.11 (td, J = 8.7, 2.8 Hz, 1H), 6.78 (s, 1H), 6.31 (dd, J = 17.1, 10.2 Hz, 1H), 6.09 (dd, J = 17.1, 1.9 Hz, 1H), 5.68 (dd, J = 10.2, 2.0 Hz, 1H), 5.56 (dd, J = 8.7, 5.2 Hz, 1H), 4.24 (td, J = 7.8, 3.7 Hz, 1H), 3.89 (s, 4H), 2.83 (tq, J = 8.3, 4.3 Hz, 1H), 2.54 (s, 3H), 2.30 (dtd, J = 11.8, 7.8, 3.7 Hz, 1H), ; 516.4 [M + H]⁺ | 1.31 |

TABLE 1-continued

| Example Compound | Structure | Name of Compound | ¹H NMR[[:]]; MS [M + H]⁺ | UPLC r.t. (min) |
|---|---|---|---|---|
| 862 | 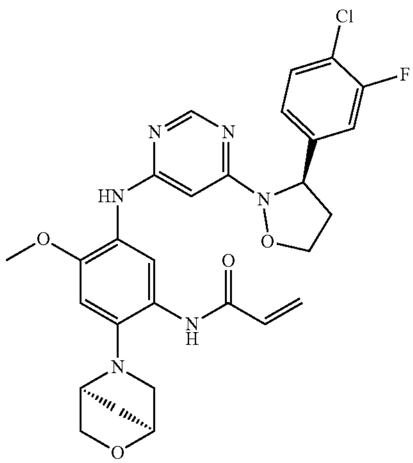 [SMILES: C=CC(=O)Nc1cc(Nc2cc(N3OCC[C@@H]3c3ccc(Cl)c(F)c3)ncn2)c(OC)cc1N1C[C@@H]2C[C@H]1CO2] | N-(2-((1S,4S)-2-oxa-5-azabicyclo[2.2.1]heptane-5-yl)-5-((6-((R)-3-(4-chloro-3-fluorophenyl)isoxazolidine-2-yl)pyrimidine-4-yl)amino)-4-methoxyphenyl)acrylamide | ¹H NMR (400 MHz, DMSO-d₆) δ 9.93 (s, 1H), 9.40 (s, 1H), 8.28 (s, 1H), 7.59 (t, J = 8.0 Hz, 1H), 7.41 (dd, J = 10.4, 2.0 Hz, 1H), 7.24 (dd, J = 8.5, 2.0 Hz, 1H), 7.15 (s, 1H), 6.54-6.40 (m, 2H), 6.19 (dd, J = 17.1, 2.1 Hz, 1H), 6.12-5.94 (m, 1H), 5.70 (dd, J = 10.2, 2.1 Hz, 1H), 5.54 (dd, J = 8.5, 5.4 Hz, 1H), 4.51 (s, 2H), 4.32-4.29 (m, 1H), 4.05 (q, J = 7.7 Hz, 1H), 3.95 (d, J = 7.7 Hz, 1H), 3.78 (d, J = 7.3 Hz, 4H), 3.57 (d, J = 9.3 Hz, 1H), 2.93 (dd, J = 11.3, 5.7 Hz, 2H), 2.37-2.26 (m, 1H), 1.87 (p, J = 10.2, 9.5 Hz, 2H), ; 567.4 [M + H]⁺ | 1.44 |
| 863 | 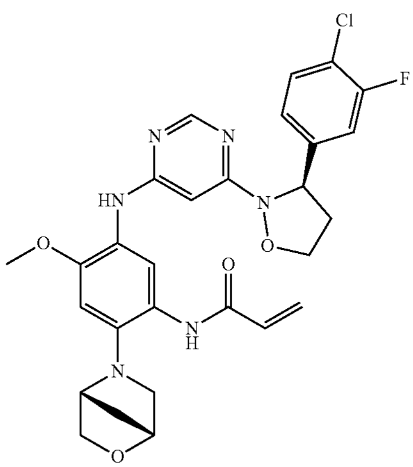 [SMILES: C=CC(=O)Nc1cc(Nc2cc(N3OCC[C@@H]3c3ccc(Cl)c(F)c3)ncn2)c(OC)cc1N1C[C@H]2C[C@@H]1CO2] | N-(2-((1R,4R)-2-oxa-5-azabicyclo[2.2.1]heptane-5-yl)-5-((6-((R)-3-(4-chloro-3-fluorophenyl)isoxazolidine-2-yl)pyrimidine-4-yl)amino)-4-methoxyphenyl)acrylamide | ¹H NMR (400 MHz, DMSO-d₆) δ 9.88 (s, 1H), 9.39 (s, 1H), 8.28 (s, 1H), 7.59 (t, J = 8.0 Hz, 1H), 7.41 (dd, J = 10.4, 2.1 Hz, 1H), 7.24 (dd, J = 8.3, 2.0 Hz, 1H), 7.16 (s, 1H), 6.52-6.42 (m, 2H), 6.19 (dd, J = 17.1, 2.1 Hz, 1H), 6.02 (s, 1H), 5.70 (dd, J = 10.1, 2.1 Hz, 1H), 5.53 (dd, J = 8.6, 5.4 Hz, 1H), 4.51 (s, 2H), 4.32-4.28 (m, 1H), 4.04 (q, J = 7.6 Hz, 1H), 3.95 (d, J = 7.7 Hz, 1H), 3.78 (d, J = 5.1 Hz, 4H), 3.60-3.51 (m, 1H), 2.93 (t, J = 8.2 Hz, 2H), 2.32 (td, J = 12.9, 7.5 Hz, 1H), 1.85 (q, J = 9.4 Hz, 2H), ; 567.4 [M + H]⁺ | 1.45 |
| 864 | 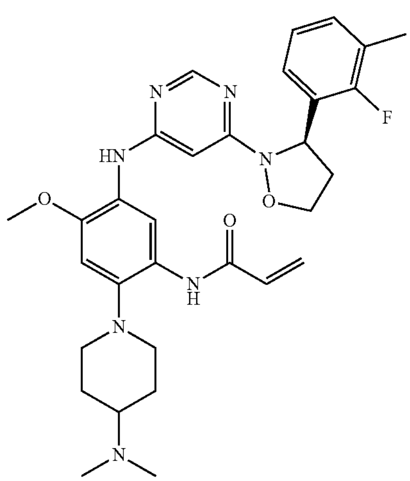 | N-(2-(4-(dimethylamino)piperidine-1-yl)-5-((6-((R)-3-(2-fluoro-3-methylphenyl)isoxazolidine-2-yl)pyrimidine-4-yl)amino)-4-methoxyphenyl)acrylamide | ¹H NMR (400 MHz, DMSO-d₆) δ 10.96 (s, 1H), 9.92 (s, 1H), 9.17 (s, 1H), 8.29 (s, 1H), 7.94 (s, 1H), 7.20 (dt, J = 22.2, 7.1 Hz, 2H), 7.08 (t, J = 7.6 Hz, 1H), 6.90 (s, 1H), 6.72 (dd, J = 17.0, 10.2 Hz, 1H), 6.25 (dd, J = 16.9, 2.0 Hz, 1H), 6.13 (s, 1H), 5.76 (dd, J = 10.1, 2.0 Hz, 1H), 5.68 (t, J = 7.2 Hz, 1H), 4.30 (td, J = 7.7, 4.2 Hz, 2H), 4.05 (d, J = 7.8 Hz, 2H), 3.81 (s, 3H), 3.28 (d, J = 3.8 Hz, 1H), 3.20 (d, J = 11.4 Hz, 2H), 2.92 (dd, J = 8.4, 4.3 Hz, 1H), 2.75 (d, J = 4.9 Hz, 6H), 2.26 (d, J = 1.9 Hz, 4H), 2.11 (d, J = 9.6 Hz, 2H), 2.01 (t, J = 12.0 Hz, 2H), ; 576.5 [M + H]⁺ | 1.27 |

TABLE 1-continued

| Example Compound | Structure | Name of Compound | ¹H NMR[[:]]; MS [M + H]⁺ | UPLC r.t. (min) |
|---|---|---|---|---|
| 865 | 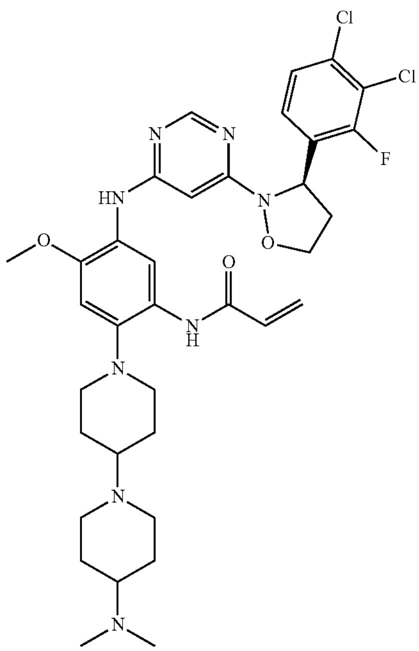 [SMILES: C=CC(=O)Nc1cc(Nc2cc(N3OCC[C@@H]3c3ccc(Cl)c(Cl)c3F)ncn2)c(OC)cc1N1CCC(N2CCC(N(C)C)CC2)CC1] | N-(5-((6-((R)-3-(3,4-dichloro-2-fluorophenyl)isoxazolidine-2-yl)pyrimidine-4-yl)amino)-2-(4-(dimethylamino)-[1,4'-bipiperidine]-1'-yl)-4-methoxyphenyl)acrylamide | ¹H NMR (400 MHz, DMSO-d₆) δ 10.04 (s, 1H), 9.23 (s, 1H), 8.31 (s, 1H), 7.92 (s, 1H), 7.53 (dd, J = 8.6, 1.5 Hz, 1H), 7.39 (t, J = 8.1 Hz, 1H), 6.90 (s, 1H), 6.74 (dd, J = 17.0, 10.3 Hz, 1H), 6.31-6.12 (m, 2H), 5.77-5.60 (m, 2H), 4.32 (d, J = 4.0 Hz, 1H), 4.05 (d, J = 7.9 Hz, 1H), 3.82 (s, 3H), 3.61 (s, 1H), 3.50 (s, 1H), 3.35 (d, J = 3.4 Hz, 1H), 3.23 (d, J = 11.1 Hz, 2H), 3.13 (s, 1H), 3.00-2.89 (m, 1H), 2.86-2.76 (m, 2H), 2.72 (d, J = 4.8 Hz, 6H), 2.35-2.26 (m, 5H), 2.17 (d, J = 9.4 Hz, 2H), 2.12-2.02 (m, 2H), 1.62 (d, J = 2.7 Hz, 1H), 1.49-1.36 (m, 1H), ; 613.3 [M + H]⁺ | 1.27 |
| 866 | 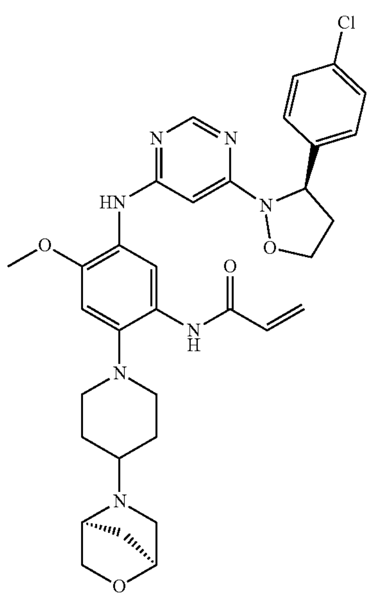 [SMILES: C=CC(=O)Nc1cc(Nc2cc(N3OCC[C@@H]3c3ccc(Cl)cc3)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((R)-3-(4-chlorophenyl)isoxazolidine-2-yl)pyrimidine-4-yl)amino)-4-methoxyphenyl)acrylamide | ¹H NMR (400 MHz, CDCl₃) δ 8.86 (s, 1H), 8.48 (s, 1H), 8.36 (s, 1H), 7.40 (d, J = 8.4 Hz, 2H), 7.30 (d, J = 8.4 Hz, 2H), 6.96 (s, 1H), 6.75 (s, 1H), 6.69 (s, 1H), 6.29 (dt, J = 17.0, 13.1 Hz, 2H), 5.74 (d, J = 11.0 Hz, 1H), 5.66 (d, J = 8.5, 4.5 Hz, 1H), 4.47 (s, 1H), 4.18-4.01 (m, 3H), 3.85 (s, 3H), 3.69 (d, J = 7.9 Hz, 1H), 3.21 (d, J = 10.2 Hz, 1H), 3.04 (dd, J = 10.6, 5.0 Hz, 2H), 2.81-2.71 (m, 4H), 2.67 (d, J = 10.6 Hz, 1H), 2.57 (d, J = 10.0 Hz, 1H), 2.38-2.27 (m, 1H), 2.09-1.90 (m, 4H), 1.83 (dd, J = 33.8, 9.8 Hz, 3H), 1.26 (s, 1H); 632.5 [M + H]⁺ | 1.23 |

TABLE 1-continued

| Example Compound | Structure | Name of Compound | ¹H NMR[[:]]; MS [M + H]⁺ | UPLC r.t. (min) |
|---|---|---|---|---|
| 867 | 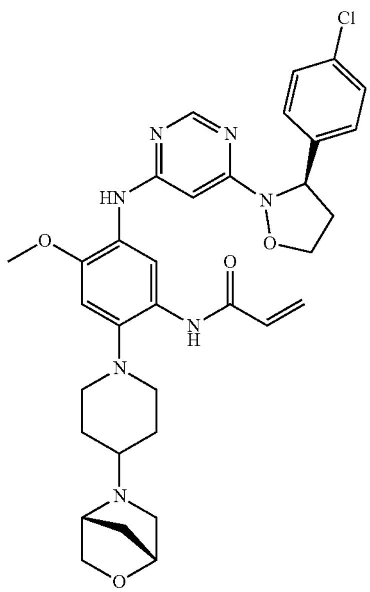 | N-(2-(4-((1R,4R)-2-oxa-5-azabicyclo[2.2.1]heptane-5-yl)piperidine-1-yl)-5-((6-((R)-3-(4-chlorophenyl)isoxazolidine-2-yl)pyrimidine-4-yl)amino)-4-methoxyphenyl)acrylamide | ¹H NMR (400 MHz, CDCl₃) δ 8.86 (s, 1H), 8.48 (s, 1H), 8.35 (s, 1H), 7.40 (d, J = 8.4 Hz, 2H), 7.30 (d, J = 8.5 Hz, 2H), 6.97 (s, 1H), 6.76 (s, 1H), 6.70 (s, 1H), 6.35 (d, J = 16.3 Hz, 1H), 6.24 (dd, J = 16.9, 10.0 Hz, 1H), 5.73 (d, J = 11.1 Hz, 1H), 5.66 (dd, J = 8.6, 4.5 Hz, 1H), 4.44 (s, 1H), 4.18-4.03 (m, 3H), 3.85 (s, 3H), 3.77 (s, 1H), 3.66 (d, J = 7.4 Hz, 1H), 3.14 (d, J = 9.0 Hz, 1H), 3.02 (d, J = 11.7 Hz, 2H), 2.76 (ddd, J = 12.1, 9.6, 3.3 Hz, 3H), 2.63-2.54 (m, 1H), 2.51 (d, J = 9.9 Hz, 1H), 2.38-2.26 (m, 1H), 2.04 (d, J = 12.4 Hz, 1H), 1.92 (d, J = 10.0 Hz, 2H), 1.83 (d, J = 9.8 Hz, 1H), 1.74-1.60 (m, 2H), 1.25 (s, 1H); 632.4 [M + H]⁺ | 1.38 |
| 868 | 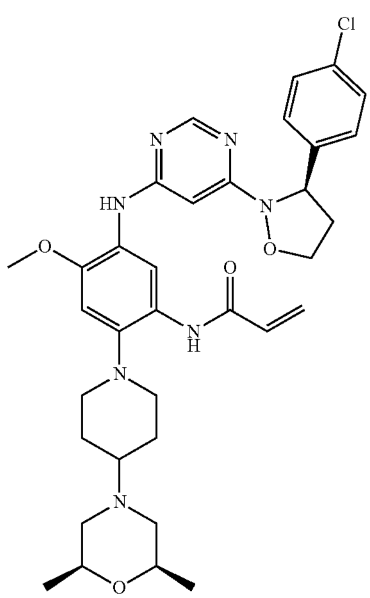 | N-(5-((6-((R)-3-(4-chlorophenyl)isoxazolidine-2-yl)pyrimidine-4-yl)amino)-2-(4-((2S,6R)-2,6-dimethylmorpholino)piperidine-1-yl)-4-methoxyphenyl)acrylamide | ¹H NMR (400 MHz, CDCl₃) δ 8.87 (s, 1H), 8.43 (s, 1H), 8.36 (s, 1H), 7.40 (d, J = 8.5 Hz, 2H), 7.30 (d, J = 8.4 Hz, 1H), 6.94 (s, 1H), 6.72 (d, J = 19.8 Hz, 2H), 6.29 (dt, J = 16.9, 13.2 Hz, 2H), 5.74 (d, J = 11.0 Hz, 1H), 5.66 (dd, J = 8.6, 4.5 Hz, 1H), 4.18-4.02 (m, 2H), 3.84 (s, 3H), 3.77-3.65 (m, 2H), 3.06 (d, J = 11.0 Hz, 2H), 2.88 (d, J = 10.8 Hz, 2H), 2.80-2.66 (m, 3H), 2.39-2.24 (m, 2H), 2.07 (d, J = 12.5 Hz, 2H), 1.90 (t, J = 10.6 Hz, 2H), 1.66 (dd, J = 21.1, 11.0 Hz, 2H), 1.26 (s, 1H), 1.20 (d, J = 6.3 Hz, 6H); 648.4 [M + H]⁺ | 1.21 |

TABLE 1-continued

| Example Compound | Structure | Name of Compound | ¹H NMR[[:]]; MS [M + H]⁺ | UPLC r.t. (min) |
|---|---|---|---|---|
| 869 | 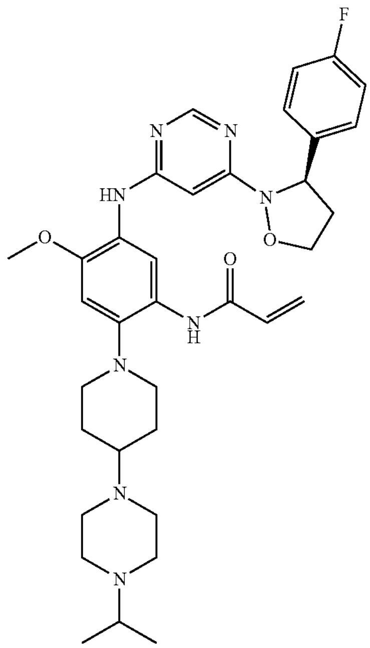 [SMILES: C=CC(=O)Nc1cc(Nc2cc(N3OCC[C@@H]3c3ccc(F)cc3)ncn2)c(OC)cc1N1CCC(N2CCN(C(C)C)CC2)CC1] | N-(5-((6-((R)-3-(4-fluorophenyl)isoxazolidine-2-yl)pyrimidine-4-yl)amino)-2-(4-(dimethylamino)-[1,4'-bipiperidine]-1'-yl)-4-methoxyphenyl)acrylamide | ¹H NMR (400 MHz, DMSO-d₆) δ 9.97 (s, 1H), 9.19 (s, 1H), 8.30 (s, 1H), 7.93 (s, 1H), 7.43-7.37 (m, 2H), 7.20 (t, J = 8.8 Hz, 2H), 6.90 (s, 1H), 6.72 (dd, J = 17.0, 10.2 Hz, 1H), 6.25 (dd, J = 17.0, 2.0 Hz, 1H), 6.07 (s, 1H), 5.76 (dd, J = 10.1, 2.0 Hz, 1H), 5.52 (t, J = 6.9 Hz, 1H), 4.31 (d, J = 4.5 Hz, 1H), 4.05 (d, J = 7.7 Hz, 2H), 3.80 (s, 3H), 3.77 (s, 2H), 3.69 (s, 4H), 3.62-3.58 (m, 1H), 3.47 (d, J = 5.4 Hz, 2H), 3.22 (d, J = 11.5 Hz, 2H), 2.91 (d, J = 7.6 Hz, 1H), 2.80 (t, J = 11.5 Hz, 2H), 2.35-2.28 (m, 1H), 2.21-2.04 (m, 4H), 1.32 (d, J = 6.5 Hz, 6H), ; 645.4 [M + H]⁺ | 1.08 |
| 870 | 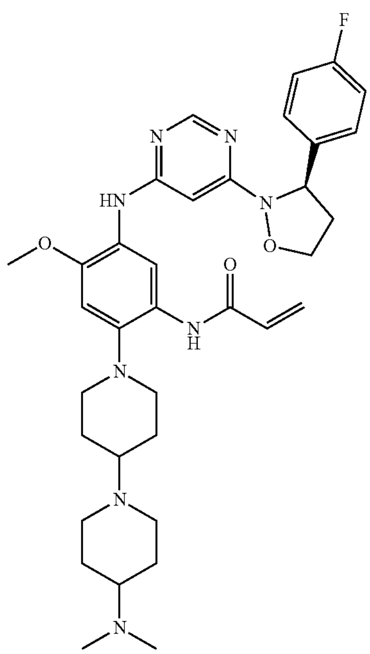 [SMILES: C=CC(=O)Nc1cc(Nc2cc(N3OCC[C@@H]3c3ccc(F)cc3)ncn2)c(OC)cc1N1CCC(N2CCC(N(C)C)CC2)CC1] | N-(2-(4-(dimethylamino)-[1,4'-bipiperidine]-1'-yl)-5-((6-((R)-3-(4-fluorophenyl)isoxazolidine-2-yl)pyrimidine-4-yl)amino)-4-methoxyphenyl)acrylamide | ¹H NMR (400 MHz, DMSO-d₆) δ 10.34 (s, 1H), 9.31 (s, 1H), 8.34 (s, 1H), 7.85 (s, 1H), 7.40 (dd, J = 8.5, 5.4 Hz, 2H), 7.20 (t, J = 8.8 Hz, 2H), 6.91 (s, 1H), 6.79 (dd, J = 17.0, 10.2 Hz, 1H), 6.25 (dd, J = 16.9, 1.9 Hz, 1H), 6.06 (s, 1H), 5.76 (dd, J = 9.4, 2.5 Hz, 1H), 5.54 (dd, J = 8.4, 5.3 Hz, 1H), 4.35-4.30 (m, 1H), 4.08 (d, J = 7.7 Hz, 1H), 3.81 (s, 3H), 3.62 (d, J = 11.6 Hz, 2H), 3.53 (s, 1H), 3.37 (t, J = 3.5 Hz, 1H), 3.24 (d, J = 11.1 Hz, 2H), 3.18-3.08 (m, 2H), 2.98-2.89 (m, 1H), 2.86-2.77 (m, 2H), 2.71 (d, J = 4.8 Hz, 6H), 2.37-2.24 (m, 5H), 2.15 (d, J = 17.8 Hz, 4H), ; 645.4 [M + H]⁺ | 1.01 |

TABLE 1-continued

| Example Compound | Structure | Name of Compound | ¹H NMR[[:]]; MS [M + H]⁺ | UPLC r.t. (min) |
|---|---|---|---|---|
| 871 | 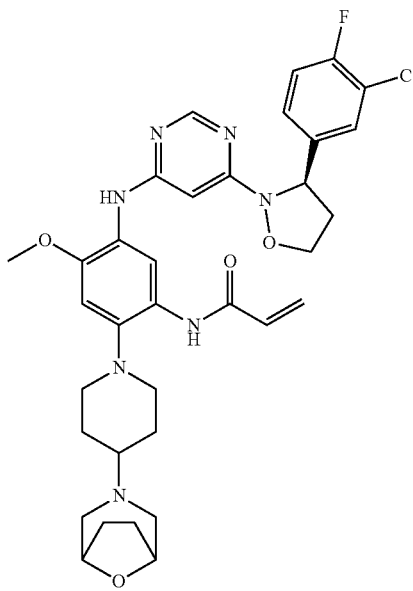 | N-(2-(4-((1R,5S)-8-oxa-3-azabicyclo[3.2.1]octan-3-yl)piperidine-1-yl)-5-((6-((R)-3-(3-chloro-4-fluorophenyl)isoxazolidine-2-yl)pyrimidine-4-yl)amino)-4-methoxyphenyl)acrylamide | ¹H NMR (400 MHz, Methanol-d₄) δ 8.23 (s, 1H), 7.89 (s, 1H), 7.52 (dd, J = 6.9, 1.8 Hz, 1H), 7.39-7.32 (m, 1H), 7.26 (t, J = 8.8 Hz, 1H), 7.19 (s, 1H), 6.68 (dd, J = 16.9, 10.2 Hz, 1H), 6.48 (d, J = 16.7 Hz, 1H), 6.09 (s, 1H), 5.89 (d, J = 10.7 Hz, 1H), 5.50 (t, J = 6.9 Hz, 1H), 4.57 (s, 2H), 4.44 (td, J = 7.6, 4.1 Hz, 1H), 4.18 (dd, J = 15.1, 8.2 Hz, 1H), 3.92 (s, 3H), 3.54 (d, J = 12.3 Hz, 4H), 3.31 (s, 5H), 3.05 (q, J = 12.1 Hz, 1H), 2.49-2.23 (m, 7H), 2.17-2.11 (m, 2H), ; 664.5 [M + H]⁺ | 1.27 |
| 872 | 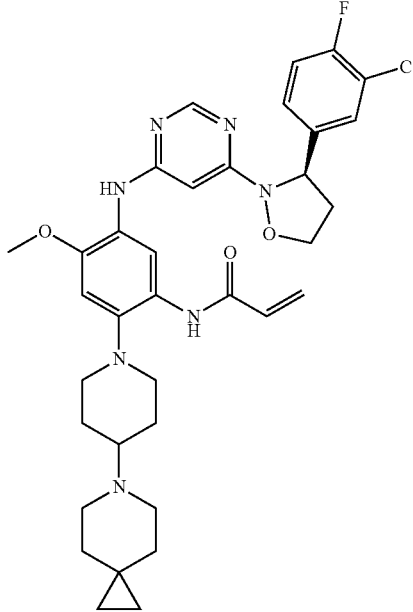 | N-(2-(4-(6-azaspiro[2.5]octan-6-yl)piperidine-1-yl)-5-((6-((R)-3-(3-chloro-4-fluorophenyl)isoxazolidine-2-yl)pyrimidine-4-yl)amino)-4-methoxyphenyl)acrylamide | 662.6 [M + H]⁺ | 1.37 |

TABLE 1-continued

| Example Compound | Structure | Name of Compound | ¹H NMR[[:]]; MS [M + H]⁺ | UPLC r.t. (min) |
|---|---|---|---|---|
| 873 | 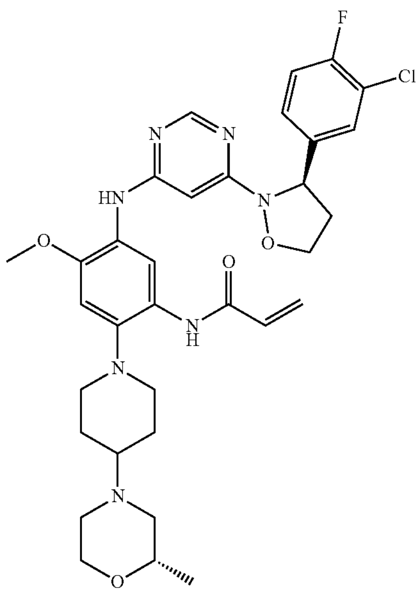 [SMILES: C=CC(=O)Nc1cc(Nc2cc(N3OCC[C@@H]3c3ccc(F)c(Cl)c3)ncn2)c(OC)cc1N1CCC(N2CCO[C@@H](C)C2)CC1] | N-(5-((6-((R)-3-(3-chloro-4-fluorophenyl)isoxazolidine-2-yl)pyrimidine-4-yl)amino)-4-methoxy-2-(4-((S)-2-methylmorpholino)piperidine-1-yl)phenyl)acrylamide | ¹H NMR (400 MHz, Chloroform-d) δ 9.88 (s, 1H), 8.20 (s, 1H), 7.85 (s, 1H), 7.34 (d, J = 6.7 Hz, 1H), 7.14 (d, J = 11.8 Hz, 2H), 6.62 (s, 1H), 6.38 (d, J = 15.6 Hz, 1H), 6.03 (s, 1H), 5.76 (d, J = 8.5 Hz, 1H), 5.57 (s, 1H), 4.36 (s, 4H), 4.00 (d, J = 48.1 Hz, 1H), 3.54 - 3.32 (m, 3H), 2.91 (d, J = 20.6 Hz, 4H), 2.72 (s, 2H), 2.43 (s, 2H), 1.77 (s, 2H), 1.57 (s, 1H), 1.27 (s, 3H), 1.21 (t, J = 7.0 Hz, 1H), ; 652.3 [M + H]⁺ | 1.26 |
| 874 | 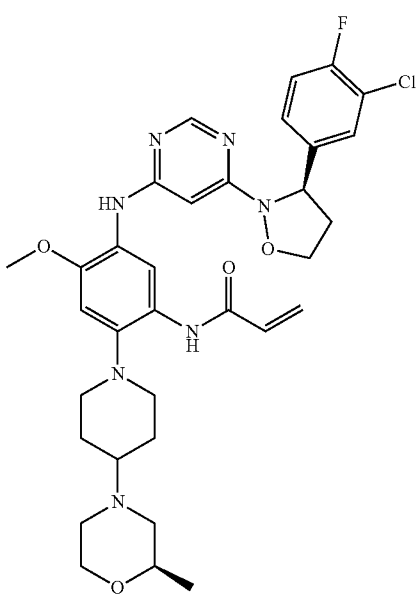 [SMILES: C=CC(=O)Nc1cc(Nc2cc(N3OCC[C@@H]3c3ccc(F)c(Cl)c3)ncn2)c(OC)cc1N1CCC(N2CCO[C@H](C)C2)CC1] | N-(5-((6-((R)-3-(3-chloro-4-fluorophenyl)isoxazolidine-2-yl)pyrimidine-4-yl)amino)-4-methoxy-2-(4-((R)-2-methylmorpholino)piperidine-1-yl)phenyl)acrylamide | 652.3 [M + H]⁺ | 1.3 |

| Example Compound | Structure | Name of Compound | ¹H NMR[[:]]; MS [M + H]⁺ | UPLC r.t. (min) |
|---|---|---|---|---|
| 875 | 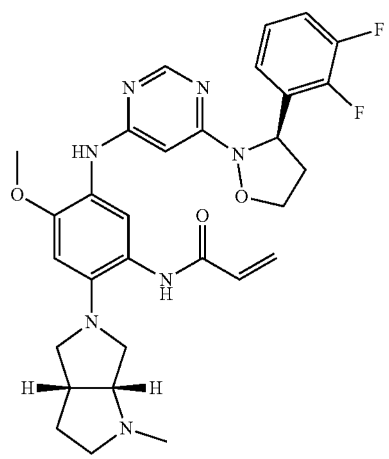 [SMILES: C=CC(=O)Nc1cc(Nc2cc(N3OCC[C@@H]3c3cccc(F)c3F)ncn2)c(OC)cc1N1C[C@H]2CCN(C)[C@H]2C1] | N-(5-((6-((R)-3-(2,3-difluorophenyl)isoxazolidine-2-yl)pyrimidine-4-yl)amino)-4-methoxy-2-((3aR,6aR)-1-methylhexahydropyrrolo[3,4-b]pyrrole-5(1H)-yl)phenyl)acrylamide | ¹H NMR (400 MHz, CDCl₃) δ 8.82 (s, 1H), 8.72 (s, 1H), 8.35 (s, 1H), 7.36 (t, J = 6.6 Hz, 1H), 7.09-6.99 (m, 2H), 6.86 (s, 1H), 6.73 (s, 1H), 6.68 (s, 1H), 6.42 (d, J = 16.9 Hz, 1H), 6.34-6.23 (m, 1H), 5.93 (dd, J = 8.6, 4.4 Hz, 1H), 5.74-5.67 (m, 1H), 4.17-4.03 (m, 2H), 3.83 (s, 3H), 3.24-3.14 (m, 1H), 3.11-2.99 (m, 2H), 2.94-2.80 (m, 4H), 2.61-2.50 (m, 1H), 2.43 (s, 3H), 2.35-2.25 (m, 2H), 2.21-2.13 (m, 1H), 1.65-1.53 (m, 1H); 578.46 [M + H]⁺ | 1.22 |
| 876 | 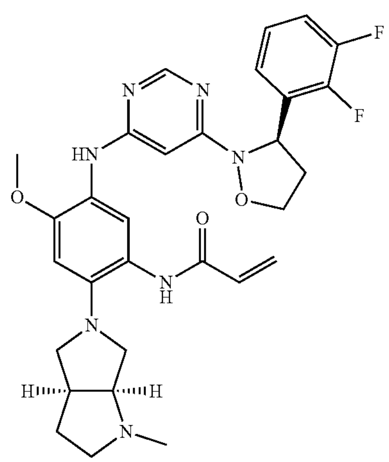 [SMILES: C=CC(=O)Nc1cc(Nc2cc(N3OCC[C@@H]3c3cccc(F)c3F)ncn2)c(OC)cc1N1C[C@@H]2CCN(C)[C@@H]2C1] | N-(5-((6-((R)-3-(2,3-difluorophenyl)isoxazolidine-2-yl)pyrimidine-4-yl)amino)-4-methoxy-2-((3aS,6aS)-1-methylhexahydropyrrolo[3,4-b]pyrrole-5(1H)-yl)phenyl)acrylamide | ¹H NMR (400 MHz, CDCl₃) δ 8.83 (s, 1H), 8.72 (s, 1H), 8.35 (s, 1H), 7.36 (t, J = 6.9 Hz, 1H), 7.10-6.98 (m, 2H), 6.88 (s, 1H), 6.71 (s, 1H), 6.69 (s, 1H), 6.42 (d, J = 16.0 Hz, 1H), 6.35-6.24 (m, 1H), 5.93 (dd, J = 8.6, 4.5 Hz, 1H), 5.74-5.67 (m, 1H), 4.13 (td, J = 8.0, 4.3 Hz, 1H), 4.05 (q, J = 8.1 Hz, 1H), 3.83 (s, 3H), 3.22-3.05 (m, 2H), 2.98-2.80 (m, 5H), 2.68-2.58 (m, 1H), 2.45 (s, 3H), 2.36-2.27 (m, 2H), 2.24-2.14 (m, 1H), 1.76-1.66 (m, 1H); 578.46 [M + H]⁺ | 1.22 |
| 877 | 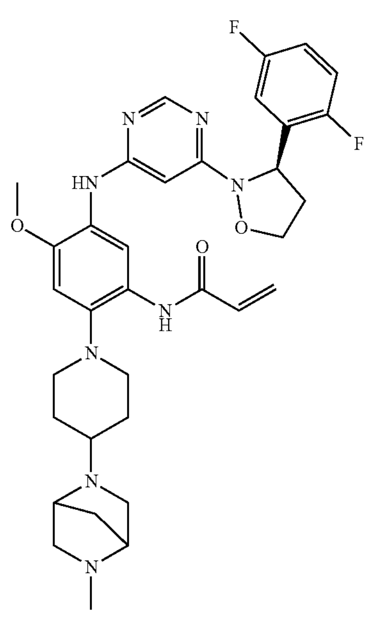 [SMILES: C=CC(=O)Nc1cc(Nc2cc(N3OCC[C@@H]3c3cc(F)ccc3F)ncn2)c(OC)cc1N1CCC(N2CC3CC2CN3C)CC1] | N-(5-((6-((R)-3-(2,5-difluorophenyl)isoxazolidine-2-yl)pyrimidine-4-yl)amino)-4-methoxy-2-(4-(5-methyl-2,5-diazabicyclo[2.2.1]heptane-2-yl)piperidine-1-yl)phenyl)acrylamide | ¹H NMR (400 MHz, CDCl₃) δ 8.87 (s, 1H), 8.47 (s, 1H), 8.37 (s, 1H), 7.35-7.29 (m, 1H), 7.03-6.86 (m, 3H), 6.76 (s, 2H), 6.35 (d, J = 16.3 Hz, 1H), 6.24 (dd, J = 16.9, 10.0 Hz, 1H), 5.90 (dd, J = 8.6, 4.2 Hz, 1H), 5.75-5.69 (m, 1H), 4.16-4.03 (m, 2H), 3.86 (s, 3H), 3.08-2.99 (m, 3H), 2.87-2.71 (m, 4H), 2.64-2.56 (m, 2H), 2.49 (s, 3H), 2.34-2.24 (m, 2H), 2.07-2.02 (m, 1H), 1.94-1.83 (m, 3H), 1.72-1.63 (m, 2H); 647.56 [M + H]⁺ | 1.14 |

| Example Compound | Structure | Name of Compound | $^1$H NMR[[:]]; MS [M + H]$^+$ | UPLC r.t. (min) |
|---|---|---|---|---|
| 878 | 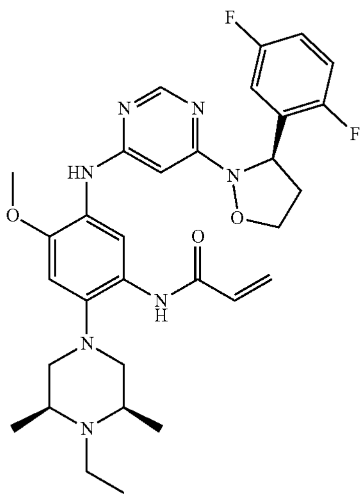 [SMILES: C=CC(=O)Nc1cc(Nc2cc(N3OCC[C@@H]3c3cc(F)ccc3F)ncn2)c(OC)cc1N1C[C@@H](C)N(CC)[C@@H](C)C1] | N-(5-((6-((R)-3-(2,5-difluorophenyl)isoxazolidine-2-yl)pyrimidine-4-yl)amino)-2-((3S,5R)-4-ethyl-3,5-dimethylpiperazine-1-yl)-4-methoxyphenyl)acrylamide | $^1$H NMR (400 MHz, CDCl$_3$) δ 8.90 (s, 1H), 8.57 (s, 1H), 8.37 (s, 1H), 7.35-7.29 (m, 1H), 7.03-6.95 (m, 2H), 6.93-6.86 (m, 1H), 6.79 (s, 1H), 6.77 (s, 1H), 6.37 (d, J = 16.2 Hz, 1H), 6.27 (dd, J = 16.9, 10.0 Hz, 1H), 5.90 (dd, J = 8.7, 4.2 Hz, 1H), 5.75 (dd, J = 10.0, 1.2 Hz, 1H), 4.16-4.04 (m, 2H), 3.84 (s, 3H), 3.06-2.96 (m, 2H), 2.88-2.78 (m, 5H), 2.70-2.59 (m, 1H), 2.34-2.23 (m, 1H), 1.18-1.10 (m, 7H), 1.00 (t, J = 6.9 Hz, 3H); 594.52 [M + H]$^+$ | 1.26 |
| 879 | 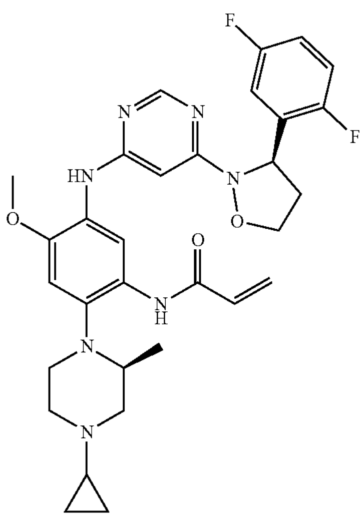 [SMILES: C=CC(=O)Nc1cc(Nc2cc(N3OCC[C@@H]3c3cc(F)ccc3F)ncn2)c(OC)cc1N1CCN(C2CC2)C[C@@H]1C] | N-(2-((S)-4-cyclopropyl-2-methylpiperazine-1-yl)-5-((6-((R)-3-(2,5-difluorophenyl)isoxazolidine-2-yl)pyrimidine-4-yl)amino)-4-methoxyphenyl)acrylamide | $^1$H NMR (400 MHz, CDCl$_3$) δ 9.02 (s, 1H), 8.97 (s, 1H), 8.39 (s, 1H), 7.36-7.28 (m, 1H), 7.06 (s, 1H), 7.04-6.96 (m, 1H), 6.94-6.85 (m, 1H), 6.82 (s, 1H), 6.80 (s, 1H), 6.38-6.24 (m, 2H), 5.90 (dd, J = 8.6, 4.2 Hz, 1H), 5.74 (dd, J = 9.6, 1.8 Hz, 1H), 4.17-4.07 (m, 2H), 3.80 (s, 3H), 3.14-3.00 (m, 3H), 2.90-2.78 (m, 3H), 2.52-2.44 (m, 1H), 2.34-2.25 (m, 1H), 2.23-2.16 (m, 1H), 1.72-1.66 (m, 1H), 0.82 (d, J = 6.2 Hz, 3H), 0.56-0.44 (m, 4H); 592.45 [M + H]$^+$ | 1.30 |
| 880 | 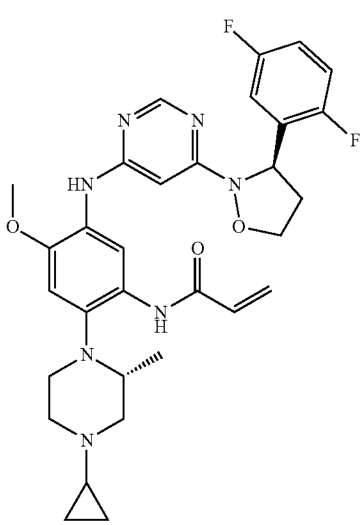 [SMILES: C=CC(=O)Nc1cc(Nc2cc(N3OCC[C@@H]3c3cc(F)ccc3F)ncn2)c(OC)cc1N1CCN(C2CC2)C[C@H]1C] | N-(2-((R)-4-cyclopropyl-2-methylpiperazine-1-yl)-5-((6-((R)-3-(2,5-difluorophenyl)isoxazolidine-2-yl)pyrimidine-4-yl)amino)-4-methoxyphenyl)acrylamide | $^1$H NMR (400 MHz, CDCl$_3$) δ 9.05 (s, 1H), 8.98 (s, 1H), 8.39 (s, 1H), 7.36-7.28 (m, 1H), 7.06 (s, 1H), 7.03-6.97 (m, 1H), 6.93-6.87 (m, 1H), 6.82 (s, 2H), 6.38-6.24 (m, 2H), 5.91 (dd, J = 8.7, 4.2 Hz, 1H), 5.74 (dd, J = 9.7, 1.8 Hz, 1H), 4.18-4.06 (m, 2H), 3.81 (s, 3H), 3.15-2.99 (m, 3H), 2.91-2.77 (m, 3H), 2.52-2.45 (m, 1H), 2.35-2.25 (m, 1H), 2.23-2.16 (m, 1H), 1.73-1.66 (m, 1H), 0.83 (d, J = 6.2 Hz, 3H), 0.57-0.44 (m, 4H); 592.45 [M + H]$^+$ | 1.31 |

TABLE 1-continued

| Example Compound | Structure | Name of Compound | ¹H NMR[[:]]; MS [M + H]⁺ | UPLC r.t. (min) |
|---|---|---|---|---|
| 881 | 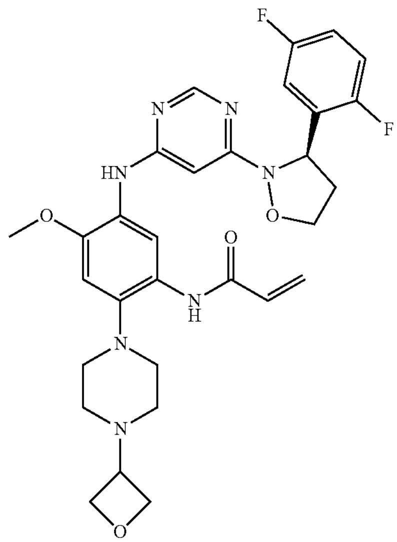 [SMILES: C=CC(=O)Nc1cc(Nc2cc(N3OCC[C@@H]3c3cc(F)ccc3F)ncn2)c(OC)cc1N1CCN(C2COC2)CC1] | N-(5-((6-((R)-3-(2,5-difluorophenyl)isoxazolidine-2-yl)pyrimidine-4-yl)amino)-4-methoxy-2-(4-(oxetane-3-yl)piperazine-1-yl)phenyl)acrylamide | ¹H NMR (400 MHz, Chloroform-d) δ 8.92 (s, 1H), 8.49 (s, 1H), 8.38 (d, J = 0.9 Hz, 1H), 7.32 (ddd, J = 9.1, 5.9, 3.2 Hz, 1H), 7.05-6.95 (m, 2H), 6.90 (ddd, J = 8.8, 7.3, 3.6 Hz, 1H), 6.82 (s, 1H), 6.77 (s, 1H), 6.36 (dd, J = 17.0, 1.6 Hz, 1H), 6.25 (dd, J = 17.0, 10.0 Hz, 1H), 5.90 (dd, J = 8.7, 4.4 Hz, 1H), 5.74 (dd, J = 9.9, 1.5 Hz, 1H), 4.72 (t, J = 6.5 Hz, 2H), 4.67 (t, J = 6.2 Hz, 2H), 4.18-4.02 (m, 2H), 3.85 (s, 3H), 3.66-3.55 (m, 1H), 3.03-2.90 (m, 4H), 2.89-2.76 (m, 1H), 2.64-2.43 (m, 4H), 2.36-2.23 (m, 1H), ; 594.4 [M + H]⁺ | 1.24 |
| 882 | 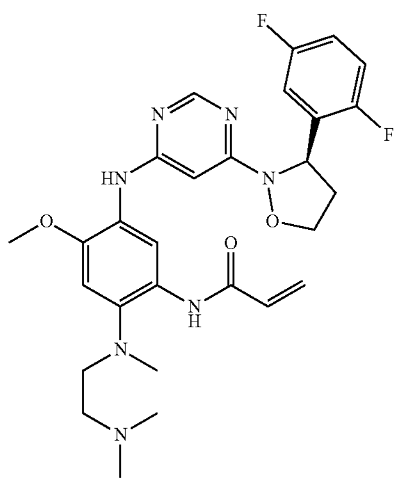 [SMILES: C=CC(=O)Nc1cc(Nc2cc(N3OCC[C@@H]3c3cc(F)ccc3F)ncn2)c(OC)cc1N(C)CCN(C)C] | N-(5-((6-((R)-3-(2,5-difluorophenyl)isoxazolidine-2-yl)pyrimidine-4-yl)amino)-2-((2-(dimethylamino)ethyl)(methyl)amino)-4-methoxyphenyl)acrylamide | ¹H NMR (400 MHz, Chloroform-d) δ 10.09 (s, 1H), 8.96 (s, 1H), 8.37 (d, J = 1.0 Hz, 1H), 7.33 (ddd, J = 9.1, 5.9, 3.2 Hz, 1H), 7.05-6.95 (m, 2H), 6.95-6.84 (m, 1H), 6.83-6.78 (m, 2H), 6.40 (dd, J = 16.9, 2.1 Hz, 1H), 6.34 (d, J = 9.6 Hz, 1H), 5.90 (dd, J = 8.9, 4.3 Hz, 1H), 5.71-5.64 (m, 1H), 4.19-4.07 (m, 2H), 3.85 (s, 3H), 2.93-2.85 (m, 2H), 2.85-2.77 (m, 1H), 2.72 (s, 3H), 2.41-2.33 (m, 2H), 2.30 (s, 6H), 2.28-2.24 (m, 1H), ; 554.4 [M + H]⁺ | 1.25 |
| 883 | 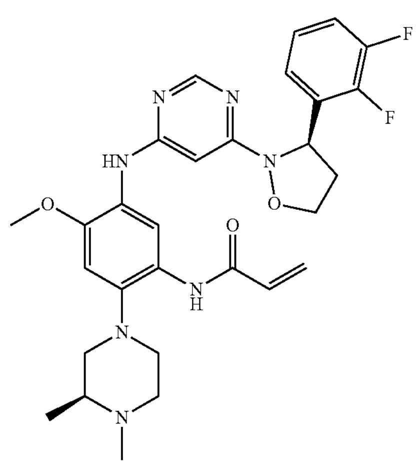 [SMILES: C=CC(=O)Nc1cc(Nc2cc(N3OCC[C@@H]3c3cccc(F)c3F)ncn2)c(OC)cc1N1CCN(C)[C@@H](C)C1] | N-(5-((6-((R)-3-(2,3-difluorophenyl)isoxazolidine-2-yl)pyrimidine-4-yl)amino)-2-((S)-3,4-dimethylpiperazine-1-yl)-4-methoxyphenyl)acrylamide | ¹H NMR (400 MHz, Chloroform-d) δ 8.90 (s, 1H), 8.54 (s, 1H), 8.37 (d, J = 1.0 Hz, 1H), 7.40-7.32 (m, 1H), 7.12-6.99 (m, 2H), 6.97 (s, 1H), 6.77 (d, J = 16.1 Hz, 2H), 6.37 (dd, J = 17.0, 1.6 Hz, 1H), 6.26 (dd, J = 16.9, 10.0 Hz, 1H), 5.93 (dd, J = 8.9, 4.5 Hz, 1H), 5.75 (dd, J = 10.0, 1.5 Hz, 1H), 4.19-4.11 (m, 1H), 4.07 (q, J = 8.1 Hz, 1H), 3.85 (s, 3H), 3.03-2.78 (m, 5H), 2.64 (dd, J = 11.4, 9.5 Hz, 1H), 2.52-2.42 (m, 1H), 2.39 (s, 3H), 2.38-2.25 (m, 2H), 1.14 (d, J = 6.3 Hz, 3H), ; 566.4 [M + H]⁺ | 1.22 |

TABLE 1-continued

| Example Compound | Structure | Name of Compound | ¹H NMR[:]; MS [M + H]⁺ | UPLC r.t. (min) |
|---|---|---|---|---|
| 884 | 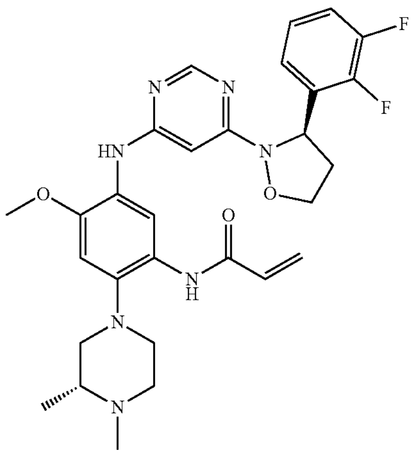 [SMILES: C=CC(=O)Nc1cc(Nc2cc(N3OCC[C@@H]3c3cccc(F)c3F)ncn2)c(OC)cc1N1CCN(C)[C@H](C)C1] | N-(5-((6-((R)-3-(2,3-difluorophenyl)isoxazolidine-2-yl)pyrimidine-4-yl)amino)-2-((R)-3,4-dimethylpiperazine-1-yl)-4-methoxyphenyl)acrylamide | ¹H NMR (400 MHz, Chloroform-d) δ 8.90 (s, 1H), 8.54 (s, 1H), 8.37 (d, J = 1.0 Hz, 1H), 7.40-7.31 (m, 1H), 7.12-6.99 (m, 2H), 6.97 (s, 1H), 6.77 (d, J = 14.8 Hz, 2H), 6.37 (dd, J = 17.0, 1.5 Hz, 1H), 6.26 (dd, J = 16.9, 10.0 Hz, 1H), 5.93 (dd, J = 8.9, 4.6 Hz, 1H), 5.75 (dd, J = 10.0, 1.5 Hz, 1H), 4.19-4.02 (m, 2H), 3.84 (s, 3H), 3.06-2.93 (m, 2H), 2.93-2.79 (m, 3H), 2.61 (dd, J = 11.5, 9.5 Hz, 1H), 2.47 (td, J = 11.5, 11.0, 3.0 Hz, 1H), 2.40 (s, 3H), 2.38-2.25 (m, 2H), 1.14 (d, J = 6.3 Hz, 3H), ; 566.4 [M + H]⁺ | 1.23 |
| 885 | 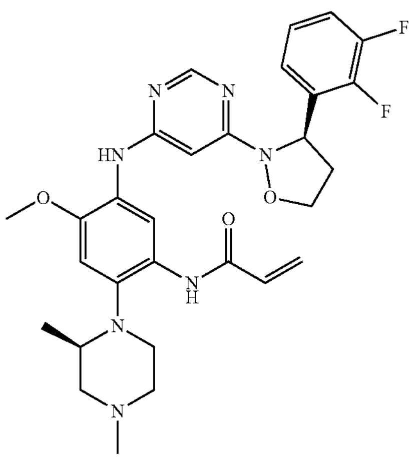 [SMILES: C=CC(=O)Nc1cc(Nc2cc(N3OCC[C@@H]3c3cccc(F)c3F)ncn2)c(OC)cc1N1CCN(C)C[C@H]1C] | N-(5-((6-((R)-3-(2,3-difluorophenyl)isoxazolidine-2-yl)pyrimidine-4-yl)amino)-2-((R)-2,4-dimethylpiperazine-1-yl)-4-methoxyphenyl)acrylamide | ¹H NMR (400 MHz, Chloroform-d) δ 9.05 (s, 1H), 8.92 (s, 1H), 8.39 (d, J = 1.0 Hz, 1H), 7.40-7.32 (m, 1H), 7.12-6.99 (m, 3H), 6.85-6.77 (m, 2H), 6.35 (dd, J = 16.9, 1.7 Hz, 1H), 6.26 (dd, J = 17.0, 9.8 Hz, 1H), 5.94 (dd, J = 8.8, 4.5 Hz, 1H), 5.74 (dd, J = 9.8, 1.7 Hz, 1H), 4.16 (td, J = 8.1, 4.3 Hz, 1H), 4.09 (q, J = 8.0 Hz, 1H), 3.83 (s, 3H), 3.19-3.06 (m, 1H), 3.02-2.92 (m, 2H), 2.91-2.77 (m, 3H), 2.39 (s, 3H), 2.37-2.21 (m, 2H), 1.98 (t, J = 10.4 Hz, 1H), 0.83 (d, J = 6.2 Hz, 3H), ; 566.4 [M + H]⁺ | 1.27 |
| 886 | 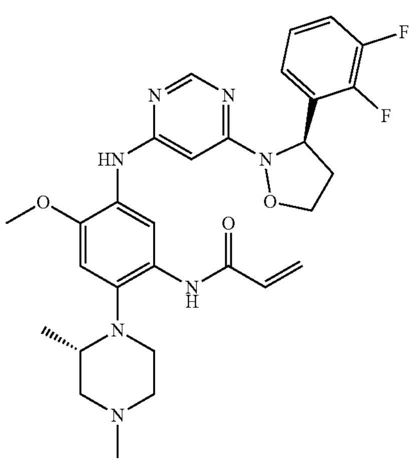 [SMILES: C=CC(=O)Nc1cc(Nc2cc(N3OCC[C@@H]3c3cccc(F)c3F)ncn2)c(OC)cc1N1CCN(C)C[C@@H]1C] | N-(5-((6-((R)-3-(2,3-difluorophenyl)isoxazolidine-2-yl)pyrimidine-4-yl)amino)-2-((S)-2,4-dimethylpiperazine-1-yl)-4-methoxyphenyl)acrylamide | ¹H NMR (400 MHz, Chloroform-d) δ 9.03 (s, 1H), 8.91 (s, 1H), 8.39 (d, J = 1.0 Hz, 1H), 7.40-7.32 (m, 1H), 7.12-6.99 (m, 3H), 6.85-6.77 (m, 2H), 6.35 (dd, J = 16.9, 1.7 Hz, 1H), 6.26 (dd, J = 16.9, 9.8 Hz, 1H), 5.94 (dd, J = 8.8, 4.5 Hz, 1H), 5.74 (dd, J = 9.8, 1.8 Hz, 1H), 4.21-4.04 (m, 2H), 3.83 (s, 3H), 3.19-3.07 (m, 1H), 3.01-2.78 (m, 5H), 2.38 (s, 3H), 2.37-2.21 (m, 2H), 1.98 (t, J = 10.4 Hz, 1H), 0.82 (d, J = 6.2 Hz, 3H), ; 566.4 [M + H]⁺ | 1.24 |

TABLE 1-continued

| Example Compound | Structure | Name of Compound | ¹H NMR[[:]]; MS [M + H]⁺ | UPLC r.t. (min) |
|---|---|---|---|---|
| 887 | 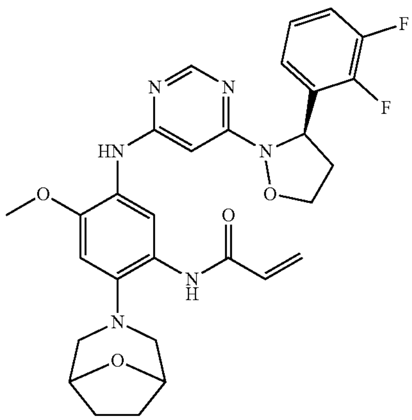 [SMILES: C=CC(=O)Nc1cc(Nc2cc(N3OCC[C@@H]3c3cccc(F)c3F)ncn2)c(OC)cc1N1CC2CCC(C1)O2] | N-(2-(8-oxa-3-azabicyclo[3.2.1]oct-3-yl)-5-((6-((R)-3-(2,3-difluorophenyl)isoxazolidine-2-yl)pyrimidine-4-yl)amino)-4-methoxyphenyl)acrylamide | ¹H NMR (400 MHz, Chloroform-d) δ 8.92 (s, 1H), 8.60 (s, 1H), 8.38 (d, J = 1.0 Hz, 1H), 7.39-7.31 (m, 1H), 7.12-6.99 (m, 2H), 6.98 (s, 1H), 6.82 (s, 1H), 6.76 (s, 1H), 6.41 (dd, J = 16.9, 1.4 Hz, 1H), 6.26 (dd, J = 16.9, 10.2 Hz, 1H), 5.93 (dd, J = 8.7, 4.6 Hz, 1H), 5.77 (dd, J = 10.1, 1.4 Hz, 1H), 4.49-4.44 (m, 2H), 4.15 (td, J = 8.0, 4.2 Hz, 1H), 4.07 (q, J = 8.0 Hz, 1H), 3.85 (s, 3H), 3.12 (td, J = 11.2, 2.1 Hz, 2H), 2.86 (dtd, J = 12.5, 8.1, 4.1 Hz, 1H), 2.65 (d, J = 11.2 Hz, 2H), 2.32 (dtd, J = 12.7, 8.4, 5.3 Hz, 1H), 2.17-2.10 (m, 2H), 2.10-2.02 (m, 2H), ; 565.4 [M + H]⁺ | 1.55 |
| 888 | 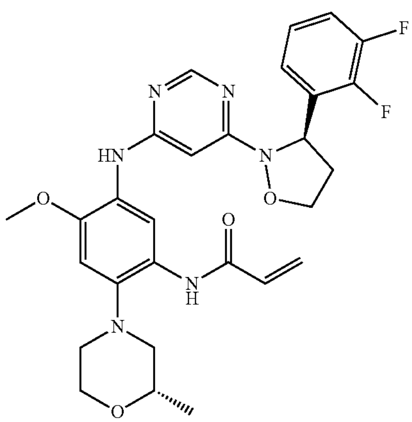 [SMILES: C=CC(=O)Nc1cc(Nc2cc(N3OCC[C@@H]3c3cccc(F)c3F)ncn2)c(OC)cc1N1CCO[C@@H](C)C1] | N-(5-((6-((R)-3-(2,3-difluorophenyl)isoxazolidine-2-yl)pyrimidine-4-yl)amino)-4-methoxy-2-((S)-2-methylmorpholino)phenyl)acrylamide | ¹H NMR (400 MHz, Chloroform-d) δ 8.92 (s, 1H), 8.51 (s, 1H), 8.38 (d, J = 1.0 Hz, 1H), 7.40-7.31 (m, 1H), 7.12-7.00 (m, 2H), 6.98 (s, 1H), 6.76 (d, J = 1.6 Hz, 2H), 6.37 (dd, J = 17.0, 1.5 Hz, 1H), 6.26 (dd, J = 16.9, 10.0 Hz, 1H), 5.93 (dd, J = 8.7, 4.6 Hz, 1H), 5.76 (dd, J = 10.0, 1.5 Hz, 1H), 4.20-4.12 (m, 1H), 4.12-4.00 (m, 2H), 3.87 (s, 3H), 3.83-3.72 (m, 2H), 2.94-2.75 (m, 4H), 2.60 (dd, J = 11.4, 9.7 Hz, 1H), 2.38-2.25 (m, 1H), 1.24 (d, J = 6.3 Hz, 3H), ; 553.4 [M + H]⁺ | 1.58 |
| 889 | 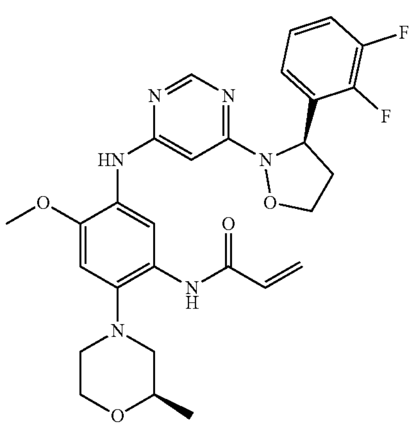 [SMILES: C=CC(=O)Nc1cc(Nc2cc(N3OCC[C@@H]3c3cccc(F)c3F)ncn2)c(OC)cc1N1CCO[C@H](C)C1] | N-(5-((6-((R)-3-(2,3-difluorophenyl)isoxazolidine-2-yl)pyrimidine-4-yl)amino)-4-methoxy-2-((R)-2-methylmorpholino)phenyl)acrylamide | ¹H NMR (400 MHz, Chloroform-d) δ 8.92 (s, 1H), 8.51 (s, 1H), 8.38 (d, J = 1.0 Hz, 1H), 7.40-7.31 (m, 1H), 7.12-7.01 (m, 2H), 6.99 (s, 1H), 6.76 (d, J = 2.5 Hz, 2H), 6.37 (dd, J = 16.9, 1.5 Hz, 1H), 6.26 (dd, J = 16.9, 10.0 Hz, 1H), 5.93 (dd, J = 8.8, 4.6 Hz, 1H), 5.76 (dd, J = 10.0, 1.5 Hz, 1H), 4.20-4.11 (m, 1H), 4.11-4.00 (m, 2H), 3.87 (s, 3H), 3.85-3.74 (m, 2H), 2.97-2.74 (m, 4H), 2.57 (dd, J = 11.6, 9.8 Hz, 1H), 2.38-2.25 (m, 1H), 1.24 (d, J = 6.3 Hz, 3H), ; 553.4 [M + H]⁺ | 1.58 |

TABLE 1-continued

| Example Compound | Structure | Name of Compound | ¹H NMR[[:]]; MS [M + H]⁺ | UPLC r.t. (min) |
|---|---|---|---|---|
| 890 | 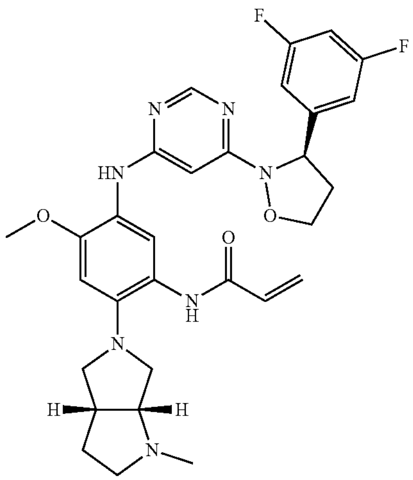 [SMILES: C=CC(=O)Nc1cc(Nc2cc(N3OCC[C@@H]3c3cc(F)cc(F)c3)ncn2)c(OC)cc1N1C[C@H]2CCN(C)[C@H]2C1] | N-(5-((6-((R)-3-(3,5-difluorophenyl)isoxazolidine-2-yl)pyrimidine-4-yl)amino)-4-methoxy-2-((3aR,6aR)-1-methylhexahydro-pyrrolo[3,4-b]pyrrole-5(1H)-yl)phenyl)acrylamide | ¹H NMR (400 MHz, DMSO-d₆) δ 9.18 (s, 1H), 8.58 (s, 1H), 8.15 (s, 1H), 7.80 (s, 1H), 7.15-7.07 (m, 3H), 6.67 (s, 1H), 6.43 (dd, J = 17.1, 10.2 Hz, 1H), 6.21 (dd, J = 17.0, 2.0 Hz, 1H), 5.72 (dd, J= 10.1, 2.0 Hz, 1H), 5.55 (dd, J = 8.7, 5.0 Hz, 1H), 4.12 (td, J = 7.9, 3.9 Hz, 1H), 3.79 (s, 4H), 2.99-2.82 (m, 4H), 2.76 (ddp, J = 11.9, 7.7, 3.7 Hz, 3H), 2.36-2.17 (m, 6H), 2.06-1.95 (m, 1H), 1.84 (s, 1H), 1.63 (tt, J = 12.3, 6.9 Hz, 2H), 1.23 (s, 1H), ; 578.4 [M + H]⁺ | 1.24 |
| 891 | 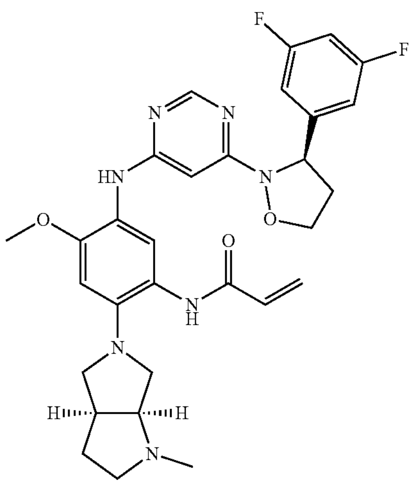 [SMILES: C=CC(=O)Nc1cc(Nc2cc(N3OCC[C@@H]3c3cc(F)cc(F)c3)ncn2)c(OC)cc1N1C[C@@H]2CCN(C)[C@@H]2C1] | N-(5-((6-((R)-3-(3,5-difluorophenyl)isoxazolidine-2-yl)pyrimidine-4-yl)amino)-4-methoxy-2-((3aS,6aS)-1-methylhexahydro-pyrrolo[3,4-b]pyrrole-5(1H)-yl)phenyl)acrylamide | ¹H NMR (400 MHz, DMSO-d₆) δ 9.19 (s, 1H), 8.58 (s, 1H), 8.15 (d, J = 0.9 Hz, 1H), 7.80 (s, 1H), 7.15-7.06 (m, 5H), 6.67 (s, 1H), 6.44 (dd, J = 17.1, 10.2 Hz, 1H), 6.21 (dd, J = 17.1, 1.9 Hz, 2H), 5.72 (dd, J = 10.2, 2.0 Hz, 1H), 5.55 (dd, J = 8.7, 5.0 Hz, 2H), 4.12 (td, J = 7.9, 3.9 Hz, 2H), 3.79 (s, 4H), 3.00-2.88 (m, 4H), 2.76 (dp, J = 8.4, 4.2 Hz, 4H), 2.31-2.21 (m, 8H), 2.00 (q, J = 9.5, 6.8 Hz, 2H), 1.87 (s, 5H), 1.63 (tt, J = 12.4, 6.9 Hz, 2H), 1.23 (s, 2H), ; 578.5 [M + H]⁺ | 1.25 |
| 892 | 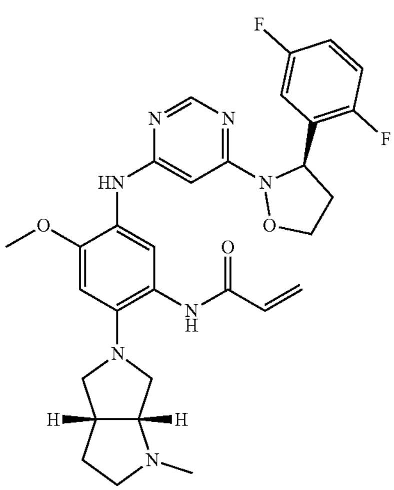 [SMILES: C=CC(=O)Nc1cc(Nc2cc(N3OCC[C@@H]3c3cc(F)ccc3F)ncn2)c(OC)cc1N1C[C@H]2CCN(C)[C@H]2C1] | N-(5-((6-((R)-3-(2,5-difluorophenyl)isoxazolidine-2-yl)pyrimidine-4-yl)amino)-4-methoxy-2-((3aR,6aR)-1-methylhexahydro-pyrrolo[3,4-b]pyrrole-5(1H)-yl)phenyl)acrylamide | ¹H NMR (400 MHz, DMSO-d₆) δ 9.19 (s, 1H), 8.60 (s, 1H), 8.14 (s, 1H), 7.79 (s, 1H), 7.29 (td, J = 9.3, 4.5 Hz, 2H), 7.18 (tdt, J = 11.9, 7.4, 3.3 Hz, 3H), 6.67 (s, 1H), 6.44 (dd, J = 17.1, 10.2 Hz, 1H), 6.21 (dd, J = 17.1, 1.9 Hz, 1H), 5.71 (td, J = 9.6, 9.1, 3.5 Hz, 2H), 4.16 (td, J = 7.9, 3.8 Hz, 1H), 3.79 (s, 3H), 3.00-2.82 (m, 5H), 2.77 (tt, J = 8.4, 4.2 Hz, 3H), 2.37-2.20 (m, 6H), 2.00 (q, J = 9.4, 7.2 Hz, 2H), 1.78 (s, 3H), 1.63 (tt, J = 11.4, 6.9 Hz, 2H), 1.23 (s, 3H), ; 578.4 [M + H]⁺ | 1.24 |

TABLE 1-continued

| Example Compound | Structure | Name of Compound | ¹H NMR[[:]]; MS [M + H]⁺ | UPLC r.t. (min) |
|---|---|---|---|---|
| 893 | 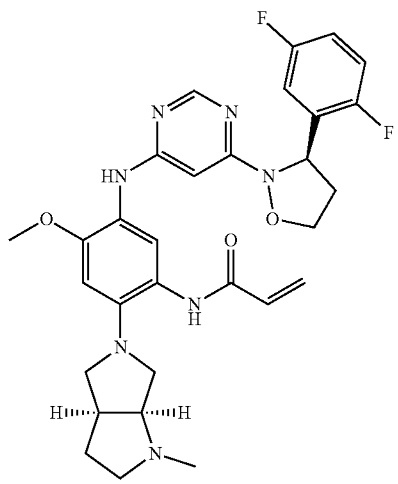 [SMILES: C=CC(=O)Nc1cc(Nc2cc(N3OCC[C@@H]3c3cc(F)ccc3F)ncn2)c(OC)cc1N1C[C@@H]2CCN(C)[C@@H]2C1] | N-(5-((6-((R)-3-(2,5-difluorophenyl)isoxazolidine-2-yl)pyrimidine-4-yl)amino)-4-methoxy-2-((3aS,6aS)-1-methylhexahydro-pyrrolo[3,4-b]pyrrole-5(1H)-yl)phenyl)acrylamide | ¹H NMR (400 MHz, DMSO-d₆) δ 9.20 (s, 1H), 8.60 (s, 1H), 8.14 (d, J = 0.9 Hz, 1H), 7.80 (s, 1H), 7.29 (td, J = 9.2, 4.4 Hz, 1H), 7.24-7.13 (m, 3H), 6.67 (s, 1H), 6.44 (dd, J = 17.1, 10.2 Hz, 1H), 6.21 (dd, J = 17.1, 1.9 Hz, 1H), 5.71 (td, J = 9.7, 3.5 Hz, 2H), 4.16 (td, J = 7.9, 3.9 Hz, 2H), 3.79 (s, 3H), 3.01-2.83 (m, 5H), 2.78 (qd, J = 8.2, 4.0 Hz, 3H), 2.35-2.11 (m, 7H), 2.00 (q, J = 9.6, 6.8 Hz, 1H), 1.89 (s, 4H), 1.63 (tt, J = 11.9, 6.9 Hz, 1H), 1.23 (s, 1H), ; 578.4 [M + H]⁺ | 1.23 |
| 894 | 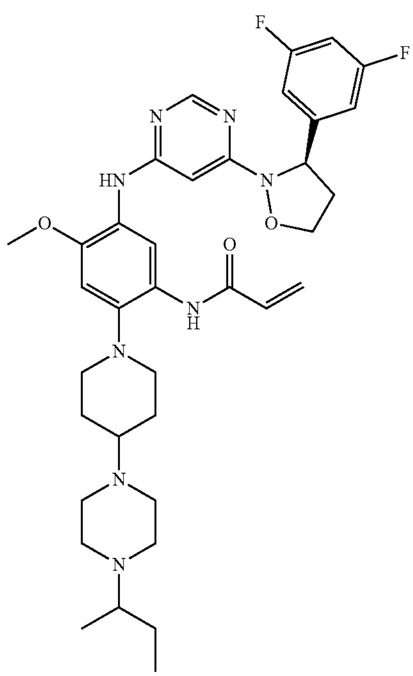 [SMILES: C=CC(=O)Nc1cc(Nc2cc(N3OCC[C@@H]3c3cc(F)cc(F)c3)ncn2)c(OC)cc1N1CCC(N2CCN(C(C)CC)CC2)CC1] | N-(2-(4-(4-(sec-butyl)piperazine-1-yl)piperidine-1-yl)-5-((6-((R)-3-(3,5-difluorophenyl)isoxazolidine-2-yl)pyrimidine-4-yl)amino)-4-methoxyphenyl)acrylamide | ¹H NMR (400 MHz, Chloroform-d) δ 8.81 (s, 1H), 8.43 (s, 1H), 8.33 (d, J = 1.0 Hz, 1H), 7.17 (s, 1H), 6.99 (h, J = 4.4 Hz, 2H), 6.74 (s, 1H), 6.68 (s, 1H), 6.33 (d, J = 1.7 Hz, 1H), 6.25 (dd, J = 16.9, 9.9 Hz, 2H), 5.73 (dd, J = 9.8, 1.7 Hz, 1H), 5.65 (dd, J = 8.7, 4.5 Hz, 1H), 4.07-4.00 (m, 1H), 3.83 (s, 3H), 3.05 (d, J = 11.2 Hz, 2H), 2.77 (d, J = 3.0 Hz, 8H), 2.67-2.58 (m, 1H), 2.42 (td, J = 11.9, 11.4, 6.2 Hz, 1H), 2.33 (q, J = 4.2 Hz, 2H), 2.11-2.05 (m, 2H), 1.72-1.64 (m, 3H), 1.28 (d, J = 6.7 Hz, 5H), 1.07 (d, J = 6.5 Hz, 3H), 0.92 (t, J = 7.4 Hz, 3H), ; 677.6 [M + H]⁺ | 1.23 |

TABLE 1-continued

| Example Compound | Structure | Name of Compound | ¹H NMR[:]; MS [M + H]⁺ | UPLC r.t. (min) |
|---|---|---|---|---|
| 895 | 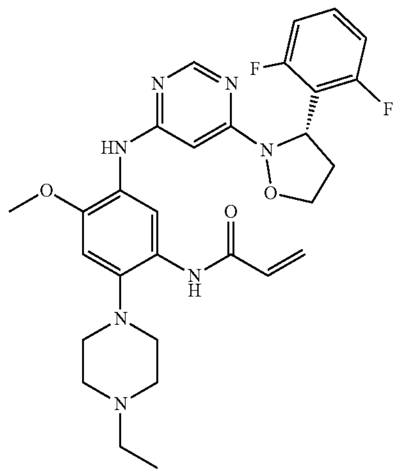 [SMILES: C=CC(=O)Nc1cc(Nc2cc(N3OCC[C@H]3c3c(F)cccc3F)ncn2)c(OC)cc1N1CCN(CC)CC1] | N-(5-((6-((S)-3-(2,6-difluorophenyl)isoxazolidine-2-yl)pyrimidine-4-yl)amino)-2-(4-ethylpiperazine-1-yl)-4-methoxyphenyl)acrylamide | ¹H NMR (400 MHz, Methanol-d₄) δ 8.31 (s, 1H), 8.16 (s, 1H), 7.34 (tt, J = 8.5, 6.2 Hz, 1H), 6.96 (dd, J = 15.5, 7.2 Hz, 3H), 6.56 (dd, J = 17.0, 10.3 Hz, 1H), 6.42-6.31 (m, 2H), 5.81 (dd, J = 10.2, 1.6 Hz, 1H), 5.76 (dd, J = 8.9, 7.0 Hz, 1H), 4.34 (td, J = 7.9, 2.5 Hz, 1H), 3.97-3.90 (m, 1H), 3.89 (s, 3H), 3.11 (s, 4H), 2.93 (q, J = 7.3 Hz, 2H), 2.80 (dddd, J = 11.9, 9.1, 6.5, 2.5 Hz, 1H), 2.59-2.48 (m, 1H), 1.98 (s, 4H), 1.30 (t, J = 7.3 Hz, 3H); 566.4 [M + H]⁺ | 1.12 |
| 896 | 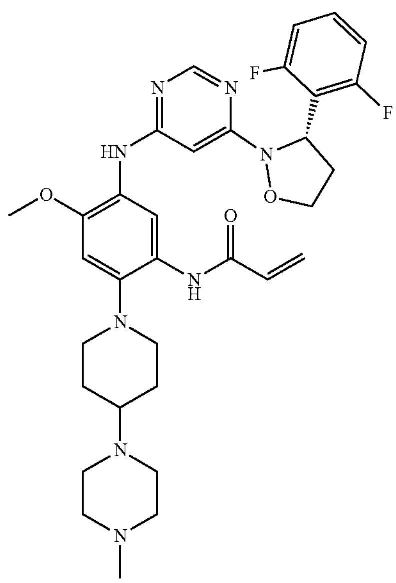 [SMILES: C=CC(=O)Nc1cc(Nc2cc(N3OCC[C@H]3c3c(F)cccc3F)ncn2)c(OC)cc1N1CCC(N2CCN(C)CC2)CC1] | N-(5-((6-((S)-3-(2,6-difluorophenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, Methanol-d₄) δ 8.28 (s, 1H), 8.16 (s, 1H), 7.34 (tt, J = 8.5, 6.2 Hz, 1H), 6.97 (t, J = 8.4 Hz, 2H), 6.92 (s, 1H), 6.53 (dd, J = 17.0, 10.2 Hz, 1H), 6.41-6.31 (m, 2H), 5.81 (d, J = 10.3 Hz, 1H), 5.76 (dd, J = 8.9, 7.0 Hz, 1H), 4.34 (td, J = 7.9, 2.4 Hz, 1H), 3.95-3.89 (m, 1H), 3.88 (s, 3H), 3.49-3.36 (m, 2H), 3.00 (t, J = 4.8 Hz, 4H), 2.85 (qq, J = 6.1, 2.9 Hz, 6H), 2.78 (dt, J = 9.9, 3.0 Hz, 2H), 2.74 (s, 3H), 2.63 (tq, J = 11.7, 4.2 Hz, 1H), 2.57-2.48 (m, 1H), 2.15 (dd, J = 12.8, 3.1 Hz, 2H), 1.84 (td, J = 13.8, 13.2, 6.9 Hz, 2H); 635.5 [M + H]⁺ | 1.00 |

TABLE 1-continued

| Example Compound | Structure | Name of Compound | ¹H NMR[[:]]; MS [M + H]⁺ | UPLC r.t. (min) |
|---|---|---|---|---|
| 897 | 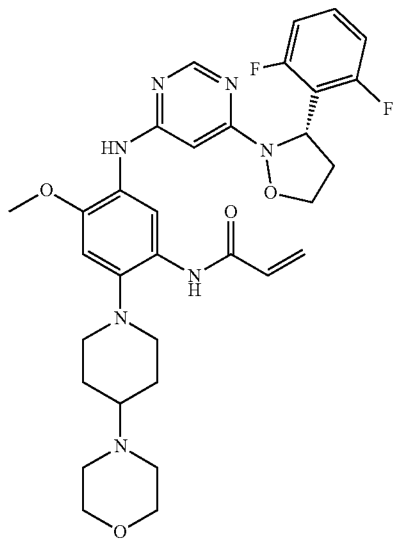 [SMILES: C=CC(=O)Nc1cc(Nc2cc(N3OCC[C@H]3c3c(F)cccc3F)ncn2)c(OC)cc1N1CCC(N2CCOCC2)CC1] | N-(5-((6-((S)-3-(2,6-difluorophenyl)isoxazolidine-2-yl)pyrimidine-4-yl)amino)-4-methoxy-2-(4-morpholinopiperidine-1-yl)phenyl)acrylamide | ¹H NMR (400 MHz, Methanol-d₄) δ 8.15 (s, 1H), 8.03 (s, 1H), 7.22 (tt, J = 8.4, 6.2 Hz, 1H), 6.85 (t, J = 8.4 Hz, 2H), 6.78 (s, 1H), 6.44 (dd, J = 17.0, 10.3 Hz, 1H), 6.31-6.17 (m, 2H), 5.72-5.66 (m, 1H), 5.63 (dd, J = 8.9, 7.0 Hz, 1H), 4.22 (td, J = 7.9, 2.4 Hz, 1H), 3.79 (td, J = 9.0, 8.3, 6.6 Hz, 1H), 3.74 (s, 3H), 3.70 (t, J = 4.7 Hz, 4H), 3.04 (d, J = 11.7 Hz, 2H), 2.83-2.60 (m, 7H), 2.44 (ttd, J = 16.8, 11.3, 9.5, 5.7 Hz, 2H), 1.99 (dd, J = 12.6, 3.5 Hz, 2H), 1.72-1.62 (m, 2H); 622.4 [M + H]⁺ | 1.14 |
| 898 | 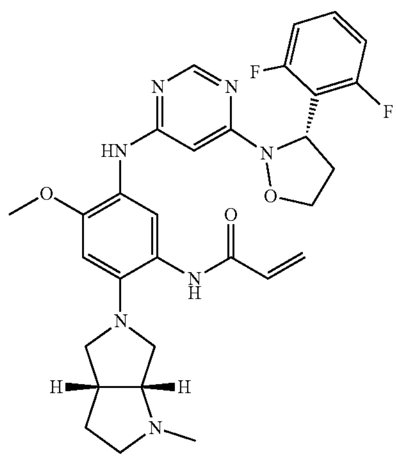 [SMILES: C=CC(=O)Nc1cc(Nc2cc(N3OCC[C@H]3c3c(F)cccc3F)ncn2)c(OC)cc1N1C[C@H]2CCN(C)[C@H]2C1] | N-(5-((6-((S)-3-(2,6-difluorophenyl)isoxazolidine-2-yl)pyrimidine-4-yl)amino)-4-methoxy-2-((3aR,6aR)-1-methylhexahydropyrrolo[3,4-b]pyrrole-5(1H)-yl)phenyl)acrylamide | ¹H NMR (400 MHz, DMSO-d₆) δ 10.04 (s, 1H), 9.94 (s, 1H), 8.25 (s, 1H), 7.71 (s, 1H), 7.46-7.36 (m, 1H), 7.17-7.03 (m, 3H), 6.86 (s, 1H), 6.27-6.21 (m, 1H), 5.98 (s, 1H), 5.74-5.64 (m, 2H), 4.47 (d, J = 2.2 Hz, 1H), 4.06-3.99 (m, 2H), 3.78 (s, 3H), 3.69 (d, J = 11.7 Hz, 1H), 3.53 (d, J = 6.7 Hz, 1H), 3.15-3.01 (m, 4H), 2.86 (d, J = 5.0 Hz, 5H), 2.44 (dd, J = 12.1, 7.8 Hz, 2H), 1.83 (dd, J = 13.5, 6.5 Hz, 1H), ; 578.5 [M + H]⁺ | 1.14 |
| 899 | 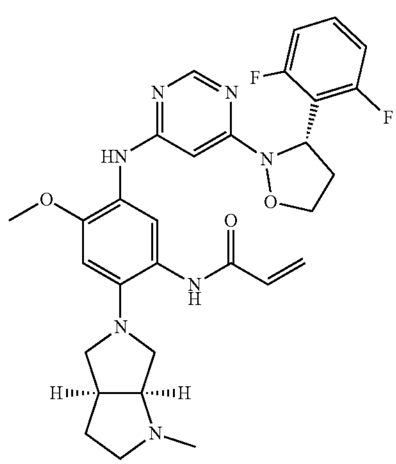 [SMILES: C=CC(=O)Nc1cc(Nc2cc(N3OCC[C@H]3c3c(F)cccc3F)ncn2)c(OC)cc1N1C[C@@H]2CCN(C)[C@@H]2C1] | N-(5-((6-((S)-3-(2,6-difluorophenyl)isoxazolidine-2-yl)pyrimidine-4-yl)amino)-4-methoxy-2-((3aS,6aS)-1-methylhexahydropyrrolo[3,4-b]pyrrole-5(1H)-yl)phenyl)acrylamide | 1H NMR (400 MHz, DMSO-d₆) δ 10.04 (s, 1H), 9.97 (s, 1H), 8.26 (s, 1H), 7.71 (s, 1H), 7.42 (tt, J = 8.3, 6.3 Hz, 1H), 7.17-7.09 (m, 2H), 7.08-7.01 (m, 1H), 6.86 (s, 1H), 6.25 (dd, J = 17.0, 2.1 Hz, 1H), 5.96 (s, 1H), 5.72 (dt, J = 11.8, 8.7 Hz, 2H), 4.47 (d, J = 2.3 Hz, 1H), 4.04-3.99 (m, 2H), 3.78 (s, 3H), 3.69 (d, J = 11.7 Hz, 1H), 3.55-3.49 (m, 1H), 3.39 (s, 1H), 3.16-2.98 (m, 5H), 2.95-2.89 (m, 1H), 2.86 (d, J = 4.9 Hz, 2H), 2.47-2.35 (m, 2H), 1.88-1.77 (m, 1H), ; 578.5 [M + H]⁺ | 1.13 |

TABLE 1-continued

| Example Compound | Structure | Name of Compound | ¹H NMR[[:]]; MS [M + H]⁺ | UPLC r.t. (min) |
|---|---|---|---|---|
| 900 | 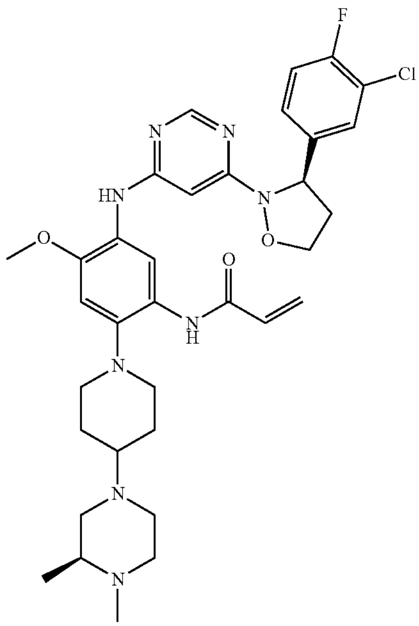 [SMILES: C=CC(=O)Nc1cc(Nc2cc(N3OCC[C@@H]3c3ccc(F)c(Cl)c3)ncn2)c(OC)cc1N1CCC(N2CCN(C)[C@@H](C)C2)CC1] | N-(5-((6-((R)-3-(3-chloro-4-fluorophenyl)isoxazolidine-2-yl)pyrimidine-4-yl)amino)-2-(4-((S)-3,4-dimethylpiperazine-1-yl)piperidine-1-yl)-4-methoxyphenyl)acrylamide | ¹H NMR (400 MHz, Chloroform-d) δ 8.32 (s, 1H), 8.02 (s, 1H), 7.35 (d, J = 6.8 Hz, 1H), 7.19-7.10 (m, 2H), 6.80 (s, 2H), 6.40 (d, J = 16.1 Hz, 1H), 6.24 (s, 1H), 5.81 (d, J = 9.1 Hz, 1H), 5.56 (s, 1H), 4.24 (d, J = 62.7 Hz, 6H), 3.75 (s, 4H), 3.48 (d, J = 7.3 Hz, 3H), 2.92 (s, 4H), 2.68 (s, 3H), 2.41 (s, 3H), 1.31-1.13 (m, 6H), ; 665.6 [M + H]⁺ | 1.23 |
| 901 | 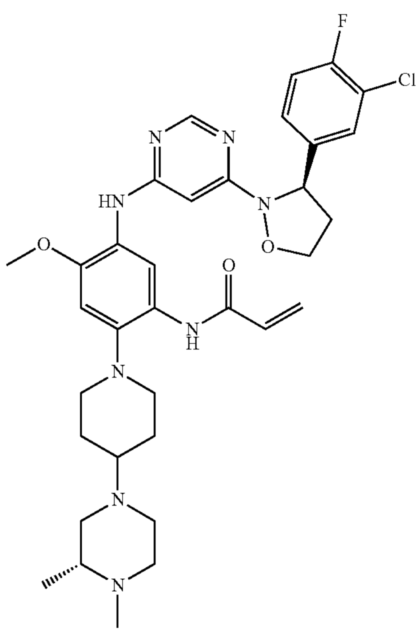 [SMILES: C=CC(=O)Nc1cc(Nc2cc(N3OCC[C@@H]3c3ccc(F)c(Cl)c3)ncn2)c(OC)cc1N1CCC(N2CCN(C)[C@H](C)C2)CC1] | N-(5-((6-((R)-3-(3-chloro-4-fluorophenyl)isoxazolidine-2-yl)pyrimidine-4-yl)amino)-2-(4-((R)-3,4-dimethylpiperazine-1-yl)piperidine-1-yl)-4-methoxyphenyl)acrylamide | ¹H NMR (400 MHz, Chloroform-d) δ 8.18 (s, 1H), 7.96 (s, 1H), 7.35 (d, J = 6.8 Hz, 1H), 7.21-7.10 (m, 3H), 6.69 (dd, J = 16.9, 10.2 Hz, 1H), 6.42 (d, J = 17.0 Hz, 1H), 6.14 (s, 1H), 5.81 (d, J = 10.2 Hz, 1H), 5.55 (d, J = 7.7 Hz, 1H), 4.36 (s, 1H), 4.29 (s, 2H), 4.19 (d, J = 7.6 Hz, 2H), 3.98 (s, 1H), 3.86 (s, 3H), 3.65 (s, 4H), 3.49 (s, 2H), 2.92 (s, 3H), 2.60 (s, 3H), 2.46-2.40 (m, 1H), 1.77 (s, 1H), 1.62 (d, J = 6.3 Hz, 3H), 1.27-1.18 (m, 3H), ; 665.6 [M + H]⁺ | 1.24 |

TABLE 1-continued

| Example Compound | Structure | Name of Compound | ¹H NMR[[:]]; MS [M + H]⁺ | UPLC r.t. (min) |
|---|---|---|---|---|
| 902 | 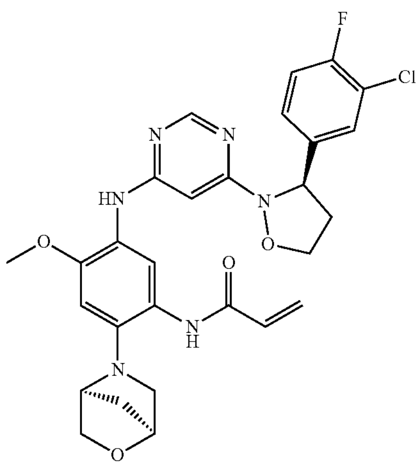 [SMILES: C=CC(=O)Nc1cc(Nc2cc(N3OCC[C@@H]3c3ccc(F)c(Cl)c3)ncn2)c(OC)cc1N1C[C@@H]2C[C@H]1CO2] | N-(2-((1S,4S)-2-oxa-5-azabicyclo[2.2.1]heptane-5-yl)-5-((6-((R)-3-(3-chloro-4-fluorophenyl)isoxazolidine-2-yl)pyrimidine-4-yl)amino)-4-methoxyphenyl)acrylamide | ¹H NMR (400 MHz, Methanol-d₄) δ 8.11 (s, 1H), 7.54 (dd, J = 7.1, 2.2 Hz, 1H), 7.47 (s, 1H), 7.38 (ddd, J = 7.3, 4.5, 2.2 Hz, 1H), 7.20 (t, J = 8.8 Hz, 1H), 6.54 (s, 1H), 6.46 (dd, J = 17.0, 10.1 Hz, 1H), 6.34 (dd, J = 17.1, 1.8 Hz, 1H), 6.29 (s, 1H), 5.77 (dd, J = 10.1, 1.8 Hz, 1H), 5.53-5.48 (m, 1H), 4.58 (s, 1H), 4.36 (s, 1H), 4.14 (dd, J = 8.0, 4.3 Hz, 1H), 4.10 (d, J = 7.6 Hz, 1H), 3.93 (q, J = 8.0 Hz, 1H), 3.85 (s, 4H), 3.51 (d, J = 9.6 Hz, 1H), 3.10 (d, J = 9.6 Hz, 1H), 2.78 (dtd, J = 12.3, 8.0, 4.2 Hz, 1H), 2.31 (ddt, J = 11.8, 7.8, 4.1 Hz, 1H), 2.04 (dd, J = 9.9, 2.2 Hz, 1H), 1.92 (dd, J = 9.8, 2.5 Hz, 1H); 567.3 [M + H]⁺ | 1.41 |
| 903 | 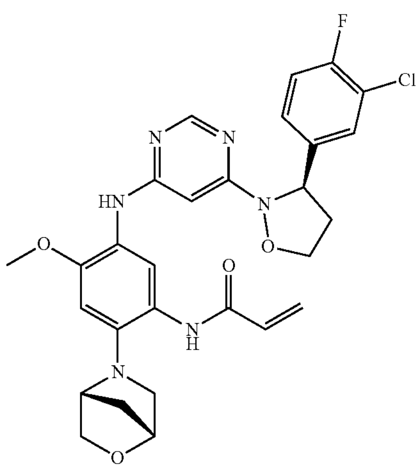 [SMILES: C=CC(=O)Nc1cc(Nc2cc(N3OCC[C@@H]3c3ccc(F)c(Cl)c3)ncn2)c(OC)cc1N1C[C@H]2C[C@@H]1CO2] | N-(2-((1R,4R)-2-oxa-5-azabicyclo[2.2.1]heptane-5-yl)-5-((6-((R)-3-(3-chloro-4-fluorophenyl)isoxazolidine-2-yl)pyrimidine-4-yl)amino)-4-methoxyphenyl)acrylamide | ¹H NMR (400 MHz, Methanol-d₄) δ 8.11 (s, 1H), 7.53 (dd, J = 7.1, 2.2 Hz, 1H), 7.47 (s, 1H), 7.38 (ddd, J = 8.6, 4.6, 2.3 Hz, 1H), 7.20 (t, J = 8.8 Hz, 1H), 6.54 (s, 1H), 6.46 (dd, J = 17.0, 10.1 Hz, 1H), 6.34 (dd, J = 17.1, 1.8 Hz, 1H), 6.29 (s, 1H), 5.77 (dd, J = 10.1, 1.8 Hz, 1H), 5.51-5.47 (m, 1H), 4.58 (t, J = 1.9 Hz, 1H), 4.35 (s, 1H), 4.13 (dt, J = 7.9, 3.9 Hz, 1H), 4.09 (d, J = 7.5 Hz, 1H), 3.91 (q, J = 7.9 Hz, 1H), 3.84 (s, 4H), 3.49 (dd, J = 9.7, 1.7 Hz, 1H), 3.12 (d, J = 9.7 Hz, 1H), 2.78 (dtd, J = 12.3, 8.0, 4.2 Hz, 1H), 2.35-2.25 (m, 1H), 2.03 (dd, J = 9.9, 2.3 Hz, 1H), 1.91 (dd, J = 9.4, 2.6 Hz, 1H); 567.3 [M + H]⁺ | 1.40 |
| 904 | 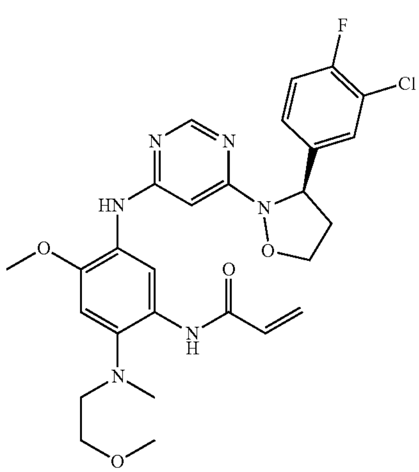 [SMILES: C=CC(=O)Nc1cc(Nc2cc(N3OCC[C@@H]3c3ccc(F)c(Cl)c3)ncn2)c(OC)cc1N(C)CCOC] | N-(5-((6-((R)-3-(3-chloro-4-fluorophenyl)isoxazolidine-2-yl)pyrimidine-4-yl)amino)-4-methoxy-2-((2-methoxyethyl)(methyl)amino)phenyl)acrylamide | ¹H NMR (400 MHz, Methanol-d₄) δ 8.50 (s, 1H), 8.06 (s, 1H), 7.44 (dd, J = 7.1, 2.2 Hz, 1H), 7.28 (ddd, J = 8.7, 4.6, 2.3 Hz, 1H), 7.10 (t, J = 8.8 Hz, 1H), 6.87 (s, 1H), 6.41-6.29 (m, 2H), 6.23 (dd, J = 17.0, 1.8 Hz, 1H), 5.68 (dd, J = 10.0, 1.8 Hz, 1H), 5.41 (dd, J = 8.6, 4.8 Hz, 1H), 4.04 (td, J = 7.9, 4.2 Hz, 1H), 3.87 (q, J = 7.9 Hz, 1H), 3.75 (s, 3H), 3.43 (t, J = 4.9 Hz, 2H), 3.32 (s, 3H), 2.93 (t, J = 4.9 Hz, 2H), 2.72 (td, J = 8.0, 4.0 Hz, 1H), 2.67 (s, 3H), 2.26-2.16 (m, 1H); 557.4 [M + H]⁺ | 1.65 |

TABLE 1-continued

| Example Compound | Structure | Name of Compound | ¹H NMR[[:]]; MS [M + H]⁺ | UPLC r.t. (min) |
|---|---|---|---|---|
| 905 | 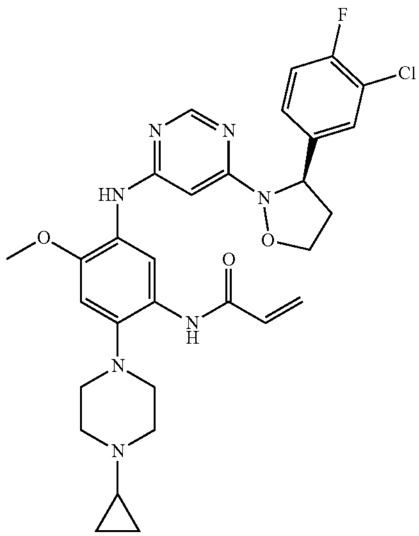 [SMILES: C=CC(=O)Nc1cc(Nc2cc(N3OCC[C@@H]3c3ccc(F)c(Cl)c3)ncn2)c(OC)cc1N1CCN(C2CC2)CC1] | N-(5-((6-((R)-3-(3-chloro-4-fluorophenyl)isoxazolidine-2-yl)pyrimidine-4-yl)amino)-2-(4-cyclopropylpiperazine-1-yl)-4-methoxyphenyl)acrylamide | 594.4 [M + H]⁺ | 1.28 |
| 906 | 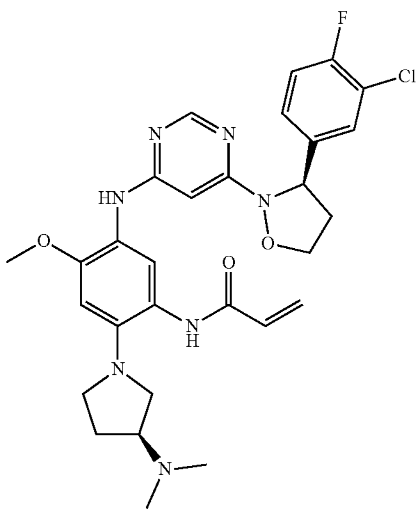 [SMILES: C=CC(=O)Nc1cc(Nc2cc(N3OCC[C@@H]3c3ccc(F)c(Cl)c3)ncn2)c(OC)cc1N1CC[C@H](N(C)C)C1] | N-(5-((6-((R)-3-(3-chloro-4-fluorophenyl)isoxazolidine-2-yl)pyrimidine-4-yl)amino)-2-((S)-3-(dimethylamino)pyrolidine-1-yl)-4-methoxyphenyl)acrylamide | ¹H NMR (400 MHz, Chloroform-d) δ 8.69 (s, 1H), 8.35 (s, 1H), 8.22 (s, 1H), 7.53 (dd, J = 7.0, 2.3 Hz, 1H), 7.32 (ddd, J = 8.6, 4.6, 2.3 Hz, 1H), 7.10 (t, J = 8.7 Hz, 1H), 6.92 (s, 1H), 6.75 (s, 1H), 6.67 (s, 1H), 6.43-6.35 (m, 1H), 6.30 (dd, J = 16.9, 9.7 Hz, 1H), 5.73 (dd, J = 9.7, 2.0 Hz, 1H), 5.64 (dd, J = 8.7, 4.5 Hz, 1H), 4.15 (td, J = 8.0, 4.2 Hz, 1H), 4.04 (q, J = 8.0 Hz, 1H), 3.84 (s, 3H), 3.13 (q, J = 8.4, 7.8 Hz, 4H), 2.91 (t, J = 7.2 Hz, 1H), 2.79-2.71 (m, 1H), 2.31 (s, 7H), 2.22-2.14 (m, 1H), 2.02-1.94 (m, 1H); 582.4 [M + H]⁺ | 1.23 |
| 907 | 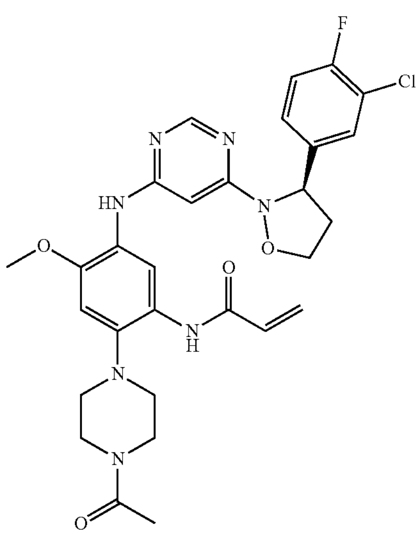 [SMILES: C=CC(=O)Nc1cc(Nc2cc(N3OCC[C@@H]3c3ccc(F)c(Cl)c3)ncn2)c(OC)cc1N1CCN(C(C)=O)CC1] | N-(2-(4-acetylpiperazine-1-yl)-5-((6-((R)-3-(3-chloro-4-fluorophenyl)isoxazolidine-2-yl)pyrimidine-4-yl)amino)-4-methoxyphenyl)acrylamide | ¹H NMR (400 MHz, Methanol-d₄) δ 8.33 (s, 1H), 8.17 (s, 1H), 7.54 (dd, J = 7.1, 2.2 Hz, 1H), 7.39 (ddd, J = 7.3, 4.6, 2.2 Hz, 1H), 7.20 (t, J = 8.8 Hz, 1H), 6.90 (s, 1H), 6.57 (dd, J = 17.0, 10.3 Hz, 1H), 6.45 (s, 1H), 6.36 (dd, J = 17.0, 1.5 Hz, 1H), 5.80 (d, J = 10.4 Hz, 1H), 5.52 (dd, J = 8.6, 4.7 Hz, 1H), 4.14 (td, J = 7.9, 4.2 Hz, 1H), 3.96 (q, J = 8.0 Hz, 1H), 3.86 (s, 3H), 3.78 (t, J = 5.1 Hz, 2H), 3.73 (t, J = 5.0 Hz, 2H), 2.95 (t, J = 5.0 Hz, 2H), 2.90 (t, J = 5.1 Hz, 2H), 2.80 (dtd, J = 12.3, 8.0, 4.2 Hz, 1H), 2.36-2.26 (m, 1H), 2.16 (s, 3H); 596.3 [M + H]⁺ | 1.41 |

TABLE 1-continued

| Example Compound | Structure | Name of Compound | ¹H NMR[:]; MS [M + H]⁺ | UPLC r.t. (min) |
|---|---|---|---|---|
| 908 | 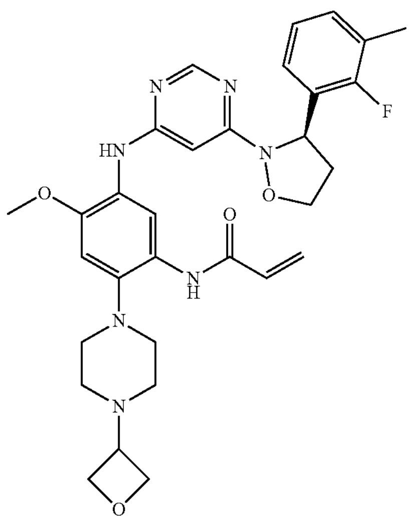 | N-(5-((6-((R)-3-(2-fluoro-3-methylphenyl)isoxazolidine-2-yl)pyrimidine-4-yl)amino)-4-methoxy-2-(4-(oxetane-3-yl)piperazine-1-yl)phenyl)acrylamide | ¹H NMR (400 MHz, DMSO-d₆) δ 9.10 (s, 1H), 9.05 (s, 1H), 8.21 (s, 1H), 7.23 (dt, J = 15.8, 7.3 Hz, 2H), 7.07 (t, J = 7.6 Hz, 1H), 6.86 (s, 1H), 6.65 (dd, J = 17.0, 10.1 Hz, 1H), 6.32 (s, 1H), 6.24 (dd, J = 17.0, 2.0 Hz, 1H), 5.78-5.73 (m, 1H), 5.71 (dd, J = 8.7, 5.2 Hz, 1H), 4.80 (d, J = 6.4 Hz, 4H), 4.47 (t, J = 6.6 Hz, 1H), 4.20 (td, J = 7.8, 3.9 Hz, 2H), 3.84 (s, 7H), 3.17 (s, 5H), 2.83 (dq, J = 8.1, 4.2 Hz, 1H), 2.26 (d, J = 1.9 Hz, 3H), 2.19 (ddt, J = 11.6, 7.7, 3.9 Hz, 1H), ; 590.4 [M + H]⁺ | 1.25 |
| 909 | 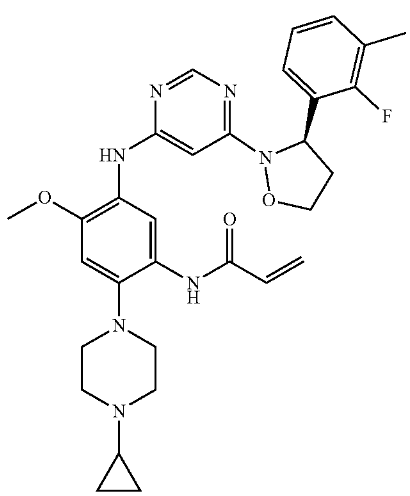 | N-(2-(4-cyclopropylpiperazine-1-yl)-5-((6-((R)-3-(2-fluoro-3-methylphenyl)isoxazolidine-2-yl)pyrimidine-4-yl)amino)-4-methoxyphenyl)acrylamide | ¹H NMR (400 MHz, DMSO-d₆) δ 8.99 (s, 1H), 8.60 (s, 1H), 8.15 (d, J = 2.9 Hz, 2H), 7.28 (t, J = 7.4 Hz, 1H), 7.19 (t, J = 7.3 Hz, 1H), 7.06 (t, J = 7.6 Hz, 1H), 6.85 (s, 1H), 6.61 (dd, J = 17.0, 10.2 Hz, 1H), 6.37 (s, 1H), 6.27-6.16 (m, 2H), 6.13-5.81 (m, 1H), 5.72 (dd, J = 9.2, 4.4 Hz, 2H), 4.14 (td, J = 7.9, 3.8 Hz, 1H), 3.85 (q, J = 7.9 Hz, 1H), 3.79 (s, 3H), 2.88-2.69 (m, 10H), 2.54 (s, 1H), 2.26 (d, J = 2.0 Hz, 3H), 2.13 (ddt, J = 12.8, 8.2, 4.1 Hz, 1H), 1.71 (dq, J = 6.8, 3.4 Hz, 1H), ; 574.5 [M + H]⁺ | 1.29 |

TABLE 1-continued

| Example Compound | Structure | Name of Compound | ¹H NMR[:]; MS [M + H]⁺ | UPLC r.t. (min) |
|---|---|---|---|---|
| 910 | 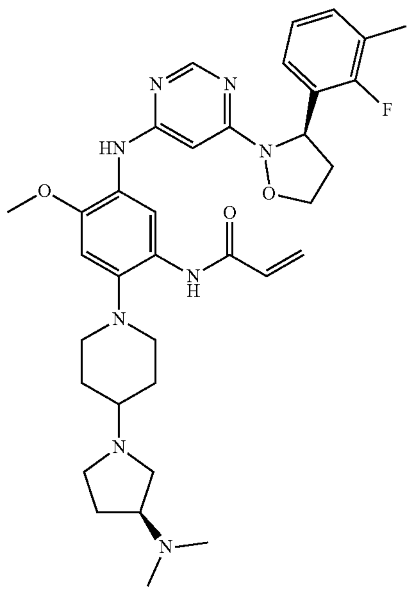 | N-(2-(4-((S)-3-(dimethylamino)pyrolidine-1-yl)piperidine-1-yl)-5-((6-((R)-3-(2-fluoro-3-methylphenyl)isoxazolidine-2-yl)pyrimidine-4-yl)amino)-4-methoxyphenyl)acrylamide | ¹H NMR (400 MHz, DMSO-d₆) δ 8.95 (s, 1H), 8.60 (s, 1H), 8.14 (s, 1H), 7.28 (t, J = 7.1 Hz, 1H), 7.19 (t, J = 7.0 Hz, 1H), 7.06 (t, J = 7.6 Hz, 1H), 6.82 (s, 1H), 6.69-6.59 (m, 1H), 6.35 (s, 1H), 6.20 (dt, J = 17.3, 2.4 Hz, 2H), 5.72 (dd, J = 9.1, 4.9 Hz, 2H), 4.14 (td, J = 7.9, 3.9 Hz, 1H), 3.85 (t, J = 8.0 Hz, 2H), 3.80 (d, J = 2.1 Hz, 3H), 3.46 (q, J = 8.9, 8.0 Hz, 2H), 3.06-2.93 (m, 8H), 2.78 (dt, J = 9.8, 6.0 Hz, 2H), 2.71-2.62 (m, 4H), 2.36-2.30 (m, 1H), 2.26 (d, J = 2.0 Hz, 3H), 2.12 (d, J = 4.0 Hz, 6H), ; 645.6 [M + H]⁺ | 1.12 |
| 911 | 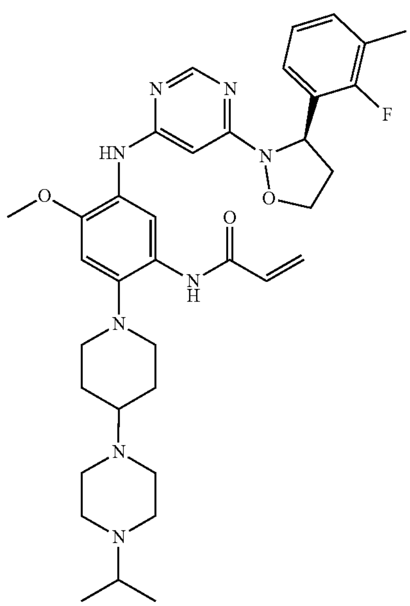 | N-(5-((6-((R)-3-(2-fluoro-3-methylphenyl)isoxazolidine-2-yl)pyrimidine-4-yl)amino)-2-(4-(4-isopropylpiperazine-1-yl)piperidine-1-yl)-4-methoxyphenyl)acrylamide | ¹H NMR (400 MHz, DMSO-d₆) δ 8.95 (s, 1H), 8.60 (s, 1H), 8.14 (s, 1H), 7.28 (t, J = 7.3 Hz, 1H), 7.19 (t, J = 7.2 Hz, 1H), 7.06 (t, J = 7.6 Hz, 1H), 6.82 (s, 1H), 6.69 (ddt, J = 21.3, 16.9, 6.5 Hz, 1H), 6.35 (s, 1H), 6.27-6.00 (m, 1H), 5.73 (ddd, J = 9.7, 6.9, 3.3 Hz, 2H), 4.14 (td, J = 7.9, 3.9 Hz, 1H), 3.85 (t, J = 8.0 Hz, 1H), 3.80 (s, 3H), 3.65 (t, J = 7.0 Hz, 2H), 3.45 (t, J = 7.8 Hz, 2H), 3.23 (t, J = 6.3 Hz, 3H), 3.17 (ddt, J = 12.6, 10.3, 6.4 Hz, 4H), 3.05 (d, J = 10.4 Hz, 3H), 2.98 (dd, J = 11.5, 3.6 Hz, 4H), 2.78 (dd, J = 8.1, 4.2 Hz, 2H), 2.71-2.61 (m, 2H), 2.26 (d, J = 2.0 Hz, 2H), 2.12 (s, 6H), ; 659.6 [M + H]⁺ | 1.23 |

TABLE 1-continued

| Example Compound | Structure | Name of Compound | ¹H NMR[[:]]; MS [M + H]⁺ | UPLC r.t. (min) |
|---|---|---|---|---|
| 912 | 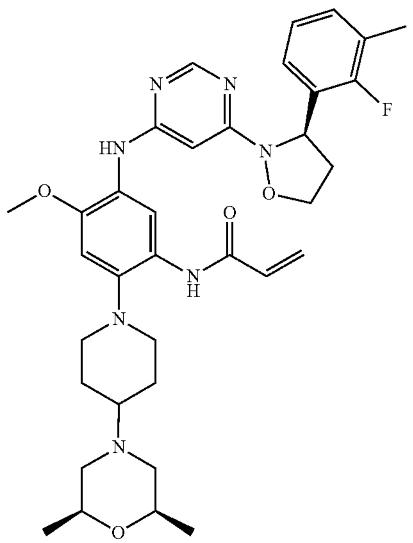 | N-(2-(4-((2S,6R)-2,6-dimethylmorpholino)piperidine-1-yl)-5-((6-((R)-3-(2-fluoro-3-methylphenyl)isoxazolidine-2-yl)pyrimidine-4-yl)amino)-4-methoxyphenyl)acrylamide | ¹H NMR (400 MHz, DMSO-d₆) δ 8.91 (s, 1H), 8.62 (s, 1H), 8.15 (s, 1H), 7.31-7.25 (m, 1H), 7.19 (t, J = 7.4 Hz, 1H), 7.06 (t, J = 7.6 Hz, 1H), 6.83 (s, 1H), 6.63 (d, J = 11.6 Hz, 1H), 6.37 (s, 1H), 6.28-6.19 (m, 1H), 5.72 (dd, J = 9.1, 5.4 Hz, 2H), 4.14 (td, J = 7.9, 3.8 Hz, 1H), 3.86 (t, J = 8.0 Hz, 1H), 3.81 (s, 3H), 3.60 (ddt, J = 13.0, 9.8, 4.8 Hz, 4H), 3.13 (qd, J = 7.1, 3.4 Hz, 4H), 2.77 (dq, J = 8.2, 4.1 Hz, 2H), 2.74-2.63 (m, 4H), 2.26 (d, J = 2.0 Hz, 3H), 2.20-2.08 (m, 2H), 1.83 (s, 2H) 1.13 (s, 6H), ; 630.4 [M + H]⁺ | 1.32 |
| 913 | 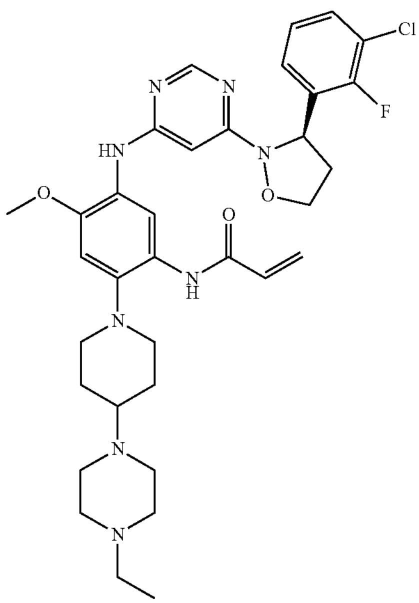 [SMILES: C=CC(=O)Nc1cc(Nc2cc(N3OCC[C@@H]3c3cccc(Cl)c3F)ncn2)c(OC)cc1N1CCC(N2CCN(CC)CC2)CC1] | N-(5-((6-((R)-3-(3-chloro-2-fluorophenyl)isoxazolidine-2-yl)pyrimidine-4-yl)amino)-2-(4-(4-ethylpiperazine-1-yl)piperidine-methoxyphenyl)acrylamide | ¹H NMR (400 MHz, DMSO-d₆) δ 8.95 (s, 1H), 8.63 (s, 1H), 8.14 (d, J = 6.5 Hz, 2H), 7.55-7.48 (m, 1H), 7.48-7.40 (m, 1H), 7.22 (t, J = 7.9 Hz, 1H), 6.82 (s, 1H), 6.76-6.58 (m, 1H), 6.36 (s, 1H), 6.22 (td, J = 16.7, 16.1, 2.0 Hz, 2H), 5.87 (dt, J = 10.3, 1.5 Hz, 1H), 4.16 (dt, J = 8.1, 4.0 Hz, 1H), 3.85 (q, J = 8.0 Hz, 1H), 3.80 (s, 3H), 3.67 (q, J = 7.9, 7.3 Hz, 1H), 3.22 (dd, J = 12.7, 6.3 Hz, 3H), 3.19-3.12 (m, 2H), 3.05 (d, J = 10.7 Hz, 3H), 3.00 (s, 1H), 2.81 (dq, J = 8.3, 4.2 Hz, 1H), 2.67 (t, J = 11.9 Hz, 4H) 2.37-2.29 (m, 2H), 2.20 (dq, J = 12.9, 4.9, 4.4 Hz, 3H), 1.85 (d, J = 12.1 Hz, 2H), 1.71 (d, J = 11.6 Hz, 2H), ; 665.5 [M + H]⁺ | 1.25 |

TABLE 1-continued

| Example Compound | Structure | Name of Compound | ¹H NMR[:]; MS [M + H]⁺ | UPLC r.t. (min) |
|---|---|---|---|---|
| 914 | 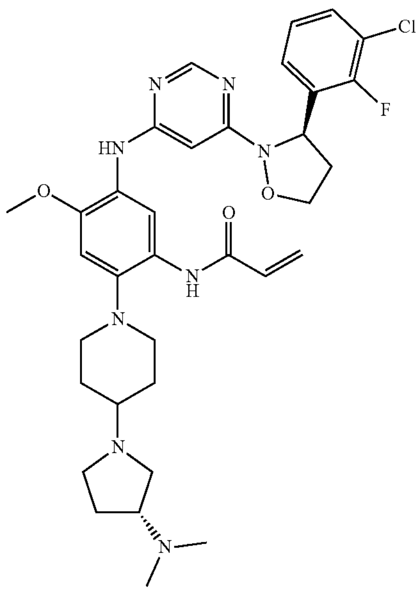 [SMILES: C=CC(=O)Nc1cc(Nc2cc(N3OCC[C@@H]3c3cccc(Cl)c3F)ncn2)c(OC)cc1N1CCC(N2CC[C@@H](N(C)C)C2)CC1] | N-(5-((6-((R)-3-(3-chloro-2-fluorophenyl)isoxazolidine-2-yl)pyrimidine-4-yl)amino)-2-(4-((R)-3-(dimethylamino)pyrolidine-1-yl)piperidine-1-yl)-4-methoxyphenyl)acrylamide | ¹H NMR (400 MHz, DMSO-d₆) δ 8.95 (s, 1H), 8.63 (s, 1H), 8.15 (s, 1H), 7.55-7.48 (m, 1H), 7.48-7.40 (m, 1H), 7.22 (t, J = 7.9 Hz, 1H), 6.82 (s, 1H), 6.64 (dd, J = 16.8, 10.1 Hz, 1H), 6.35 (s, 1H), 6.24-6.17 (m, 1H), 5.72 (dt, J = 9.3, 5.0 Hz, 2H), 4.17 (td, J = 7.9, 3.7 Hz, 1H), 3.85 (q, J = 8.1 Hz, 1H), 3.80 (s, 3H), 3.20-3.13 (m, 1H), 3.01 (td, J = 15.7, 14.1, 6.8 Hz, 4H), 2.82 (dq, J = 8.3, 4.8 Hz, 2H), 2.73-2.62 (m, 4H), 2.37 (t, J = 7.6 Hz, 1H), 2.14 (s, 7H), 1.87 (d, J = 28.6 Hz, 3H), 1.73-1.57 (m, 3H), ; 665.5 [M + H]⁺ | 1.19 |
| 915 | 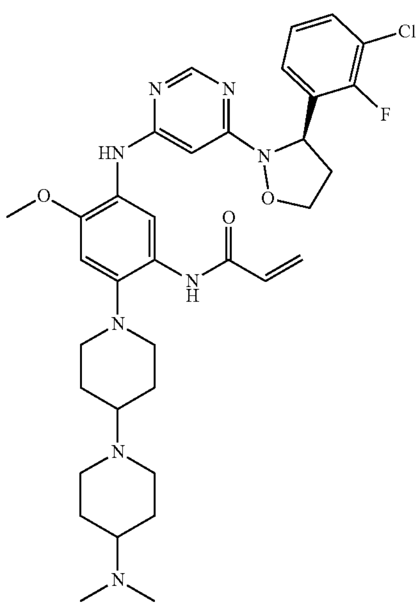 [SMILES: C=CC(=O)Nc1cc(Nc2cc(N3OCC[C@@H]3c3cccc(Cl)c3F)ncn2)c(OC)cc1N1CCC(N2CCC(N(C)C)CC2)CC1] | N-(5-((6-((R)-3-(3-chloro-2-fluorophenyl)isoxazolidine-2-yl)pyrimidine-4-yl)amino)-2-(4-(dimethylamino)-[1,4'-bipiperidine]-1'-yl)-4-methoxyphenyl)acrylamide | ¹H NMR (400 MHz, DMSO-d₆) δ 9.08 (d, J = 11.8 Hz, 1H), 8.65 (s, 1H), 8.15 (d, J = 5.0 Hz, 1H), 8.05 (d, J = 3.7 Hz, 1H), 7.55-7.48 (m, 1H), 7.44 (t, J = 7.2 Hz, 1H), 7.23 (t, J = 7.9 Hz, 1H), 6.82 (s, 1H), 6.38 (s, 1H), 6.30-6.16 (m, 1H), 6.04 (dq, J = 30.3, 6.5 Hz, 1H), 5.72 (dd, J = 8.8, 5.1 Hz, 1H), 4.18 (td, J = 8.0, 3.6 Hz, 1H), 3.85 (q, J = 7.9 Hz, 1H), 3.80 (s, 3H), 3.62 (t, J = 7.6 Hz, 1H), 3.07 (d, J = 2.9 Hz, 4H), 3.01 (dt, J = 13.1, 6.2 Hz, 5H), 2.91 (t, J = 7.7 Hz, 4H), 2.66 (s, 6H), 2.25-2.14 (m, 1H), 1.75-1.66 (m, 6H), ; 679.5 [M + H]⁺ | 1.20 |

TABLE 1-continued

| Example Compound | Structure | Name of Compound | ¹H NMR[[:]]; MS [M + H]⁺ | UPLC r.t. (min) |
|---|---|---|---|---|
| 916 | 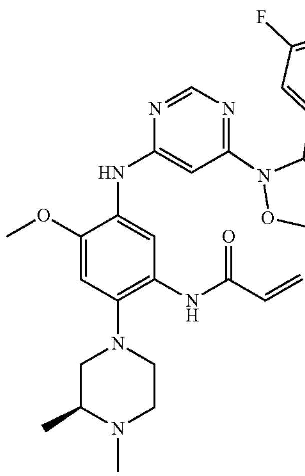 | N-(5-((6-((R)-3-(3,5-difluorophenyl)isoxazolidine-2-yl)pyrimidine-4-yl)amino)-2-((S)-3,4-dimethylpiperazine-1-yl)-4-methoxyphenyl)acrylamide | ¹H NMR (400 MHz, DMSO-d₆) δ 9.01 (s, 1H), 8.66 (s, 1H), 8.17 (d, J = 4.8 Hz, 2H), 7.12 (dp, J = 7.7, 2.5, 2.1 Hz, 3H), 6.83 (s, 1H), 6.61 (dd, J = 17.0, 10.2 Hz, 1H), 6.38 (s, 1H), 6.21 (dd, J = 17.0, 2.0 Hz, 1H), 5.77-5.68 (m, 1H), 5.56 (dd, J = 8.7, 5.0 Hz, 1H), 4.13 (td, J = 7.9, 3.9 Hz, 1H), 3.82 (s, 3H), 3.34 (s, 3H), 2.95 (d, J = 13.0 Hz, 4H), 2.76 (dtd, J = 12.1, 7.9, 3.8 Hz, 2H), 2.40 (s, 2H), 2.30-2.18 (m, 1H), 1.32-1.21 (m, 2H), 1.11 (d, J = 7.4 Hz, 3H), ; 566.4 [M + H]⁺ | 1.21 |
| 917 | 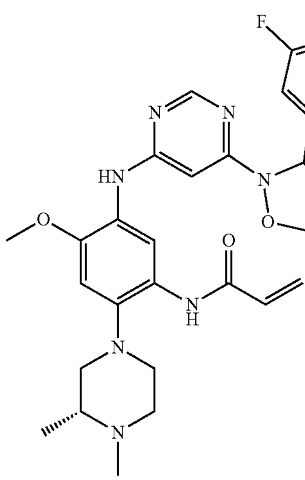 | N-(5-((6-((R)-3-(3,5-difluorophenyl)isoxazolidine-2-yl)pyrimidine-4-yl)amino)-2-((R)-3,4-dimethylpiperazine-1-yl)-4-methoxyphenyl)acrylamide | ¹H NMR (400 MHz, DMSO-d₆) δ 8.99 (s, 1H), 8.64 (s, 1H), 8.17 (s, 1H), 8.13 (s, 1H), 7.12 (dq, J = 9.4, 3.2 Hz, 3H), 6.83 (s, 1H), 6.58 (dd, J = 17.0, 10.2 Hz, 1H), 6.36 (s, 1H), 6.20 (dd, J = 17.0, 2.0 Hz, 1H), 5.72 (dd, J = 10.2, 2.0 Hz, 1H), 5.56 (dd, J = 8.7, 5.0 Hz, 1H), 4.13 (td, J = 7.9, 3.9 Hz, 1H), 3.81 (s, 4H), 3.32 (s, 10H), 2.98-2.71 (m, 5H), 2.24 (ddd, J = 20.7, 10.1, 6.2 Hz, 4H), 1.32-1.19 (m, 3H), 1.09-0.97 (m, 3H), ; 566.4 [M + H]⁺ | 1.23 |
| 918 | 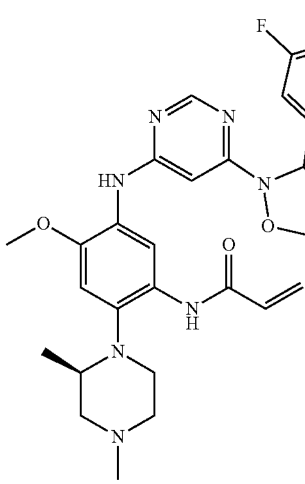 | N-(5-((6-((R)-3-(3,5-difluorophenyl)isoxazolidine-2-yl)pyrimidine-4-yl)amino)-2-((R)-2,4-dimethylpiperazine-1-yl)-4-methoxyphenyl)acrylamide | 566.5 [M + H]⁺ | 1.27 |

TABLE 1-continued

| Example Compound | Structure | Name of Compound | ¹H NMR[[:]]; MS [M + H]⁺ | UPLC r.t. (min) |
|---|---|---|---|---|
| 919 | 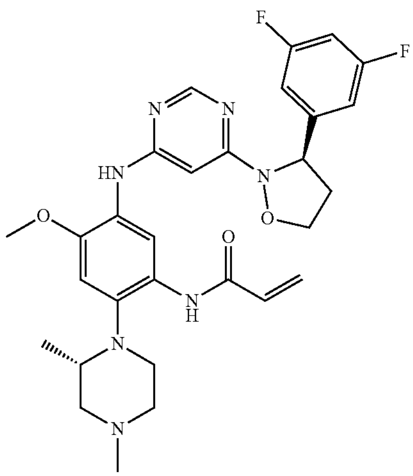 [SMILES: C=CC(=O)Nc1cc(Nc2cc(N3OCC[C@@H]3c3cc(F)cc(F)c3)ncn2)c(OC)cc1N1CCN(C)C[C@@H]1C] | N-(5-((6-((R)-3-(3,5-difluorophenyl)isoxazolidine-2-yl)pyrimidine-4-yl)amino)-2-((S)-2,4-dimethylpiperazine-1-yl)-4-methoxyphenyl)acrylamide | 566.5 [M + H]⁺ | 1.27 |
| 920 | 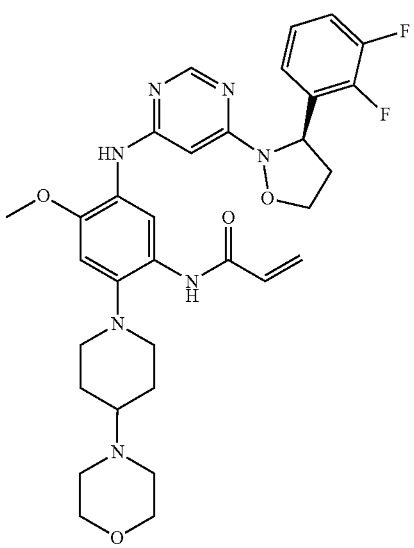 [SMILES: C=CC(=O)Nc1cc(Nc2cc(N3OCC[C@@H]3c3cccc(F)c3F)ncn2)c(OC)cc1N1CCC(N2CCOCC2)CC1] | N-(5-((6-((R)-3-(2,3-difluorophenyl)isoxazolidine-2-yl)pyrimidine-4-yl)amino)-4-methoxy-2-(4-morpholinopiperidine-1-yl)phenyl)acrylamide | ¹H NMR (400 MHz, DMSO-d₆) δ 8.95 (s, 1H), 8.63 (s, 1H), 8.16 (s, 1H), 7.35 (ddd, J = 10.4, 6.3, 1.9 Hz, 1H), 7.32-7.26 (m, 1H), 7.23-7.15 (m, 1H), 6.83 (s, 1H), 6.65 (dd, J = 16.9, 10.2 Hz, 1H), 6.36 (s, 1H), 6.21 (dd, J = 17.0, 2.0 Hz, 1H), 5.79-5.68 (m, 2H), 3.86 (d, J = 8.2 Hz, 1H), 3.80 (s, 3H), 3.59 (t, J = 4.5 Hz, 4H), 3.33 (s, 4H), 3.05 (d, J = 11.1 Hz, 2H), 2.81 (dtd, J = 12.0, 7.9, 3.7 Hz, 1H), 2.66 (tt, J = 11.7, 2.5 Hz, 2H), 2.22 (dddq, J = 16.8, 12.9, 8.2, 5.0, 4.3 Hz, 2H), 1.91-1.81 (m, 2H), 1.69 (tdd, J = 15.1, 9.1, 3.4 Hz, 2H), 1.30-1.20 (m, 2H), 0.85 (td, J = 7.9, 7.3, 3.1 Hz, 1H), ; 622.4 [M + H]⁺ | 1.21 |

TABLE 1-continued

| Example Compound | Structure | Name of Compound | ¹H NMR[[:]]; MS [M + H]⁺ | UPLC r.t. (min) |
|---|---|---|---|---|
| 921 | 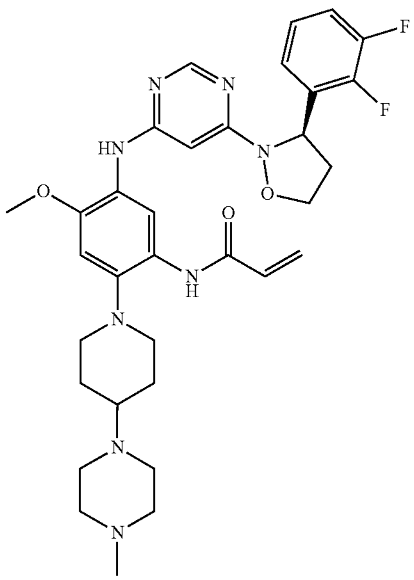 [SMILES: C=CC(=O)Nc1cc(Nc2cc(N3OCC[C@@H]3c3cccc(F)c3F)ncn2)c(OC)cc1N1CCC(N2CCN(C)CC2)CC1] | N-(5-((6-((R)-3-(2,3-difluorophenyl)isoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, DMSO-d₆) δ 8.97 (s, 1H), 8.64 (s, 1H), 8.16 (s, 1H), 7.40-7.25 (m, 2H), 7.26-7.15 (m, 1H), 6.82 (s, 1H), 6.68 (ddd, J = 19.3, 17.0, 10.3 Hz, 1H), 6.36 (s, 1H), 6.29-6.16 (m, 2H), 5.78-5.68 (m, 3H), 4.17 (td, J = 8.0, 3.8 Hz, 1H), 3.80 (s, 3H), 3.07 (d, J = 11.0 Hz, 3H), 2.87-2.61 (m, 11H), 2.56 (s, 1H), 1.92-1.66 (m, 5H), 1.31-1.20 (m, 5H), ; 635.5 [M + H]⁺ | 1.16 |
| 922 | 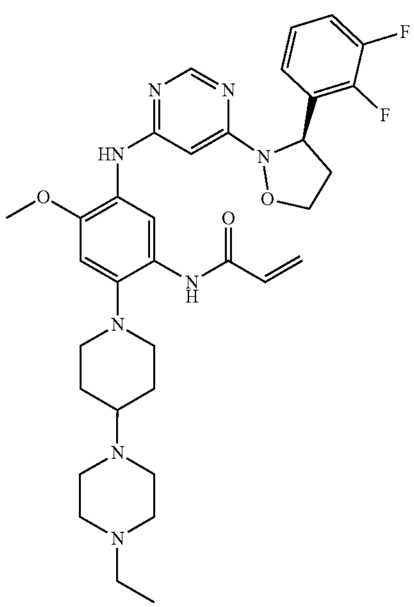 [SMILES: C=CC(=O)Nc1cc(Nc2cc(N3OCC[C@@H]3c3cccc(F)c3F)ncn2)c(OC)cc1N1CCC(N2CCN(CC)CC2)CC1] | N-(5-((6-((R)-3-(2,3-difluorophenyl)isoxazolidine-2-yl)pyrimidine-4-yl)amino)-2-(4-(4-ethylpiperazine-1-yl)piperidine-1-yl)-4-methoxyphenyl)acrylamide | 649.5 [M + H]⁺ | 1.17 |

TABLE 1-continued

| Example Compound | Structure | Name of Compound | ¹H NMR[[:]]; MS [M + H]⁺ | UPLC r.t. (min) |
|---|---|---|---|---|
| 923 | 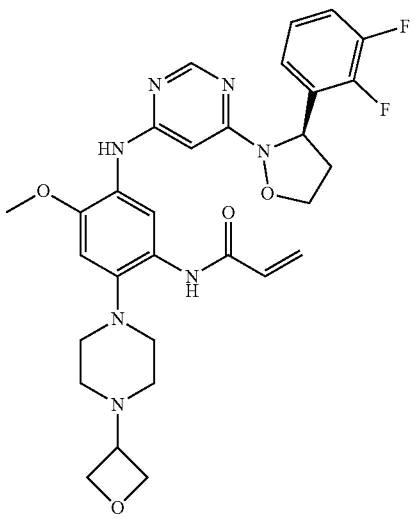 [SMILES: C=CC(=O)Nc1cc(Nc2cc(N3OCC[C@@H]3c3cccc(F)c3F)ncn2)c(OC)cc1N1CCN(C2COC2)CC1] | N-(5-((6-((R)-3-(2,3-difluorophenyl)isoxazolidine-2-yl)pyrimidine-4-yl)amino)-4-methoxy-2-(4-(oxetane-3-yl)piperazine-1-yl)phenyl)acrylamide | ¹H NMR (400 MHz, Chloroform-d) δ 8.91 (s, 1H), 8.49 (s, 1H), 8.37 (d, J = 1.0 Hz, 1H), 7.39-7.31 (m, 1H), 7.12-7.00 (m, 2H), 7.00 (s, 1H), 6.82 (s, 1H), 6.75 (s, 1H), 6.36 (dd, J = 17.0, 1.6 Hz, 1H), 6.25 (dd, J = 16.9, 10.0 Hz, 1H), 5.93 (dd, J = 8.8, 4.6 Hz, 1H), 5.74 (dd, J = 10.0, 1.5 Hz, 1H), 4.72 (t, J = 6.5 Hz, 2H), 4.67 (t, J = 6.2 Hz, 2H), 4.14 (td, J = 8.1, 4.2 Hz, 1H), 4.06 (q, J = 8.1 Hz, 1H), 3.85 (s, 3H), 3.61 (p, J = 6.4 Hz, 1H), 3.03-2.91 (m, 4H), 2.91-2.79 (m, 1H), 2.63-2.41 (m, 4H), 2.38-2.25 (m, 1H), ; 594.5 [M + H]⁺ | 1.26 |
| 924 | 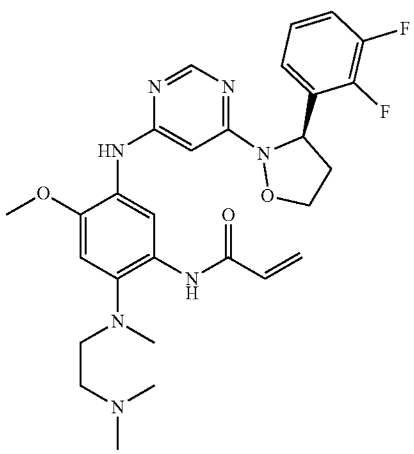 [SMILES: C=CC(=O)Nc1cc(Nc2cc(N3OCC[C@@H]3c3cccc(F)c3F)ncn2)c(OC)cc1N(C)CCN(C)C] | N-(5-((6-((R)-3-(2,3-difluorophenyl)isoxazolidine-2-yl)pyrimidine-4-yl)amino)-2-(2-(dimethylamino)ethyl)(methyl)amino)-4-methoxyphenyl)acrylamide | ¹H NMR (400 MHz, Chloroform-d) δ 10.10 (s, 1H), 8.95 (s, 1H), 8.37 (d, J = 1.0 Hz, 1H), 7.41-7.32 (m, 1H), 7.12-6.99 (m, 2H), 6.98 (s, 1H), 6.80 (d, J = 1.3 Hz, 2H), 6.40 (dd, J = 17.0, 2.0 Hz, 1H), 6.29 (dd, J = 17.0, 9.8 Hz, 1H), 5.94 (dd, J = 8.8, 4.5 Hz, 1H), 5.68 (dd, J = 9.8, 2.0 Hz, 1H), 4.20-4.05 (m, 2H), 3.85 (s, 3H), 2.94-2.80 (m, 3H), 2.72 (s, 3H), 2.37-2.31 (m, 3H), 2.28 (s, 6H), ; 554.4 [M + H]⁺ | 1.21 |
| 925 | 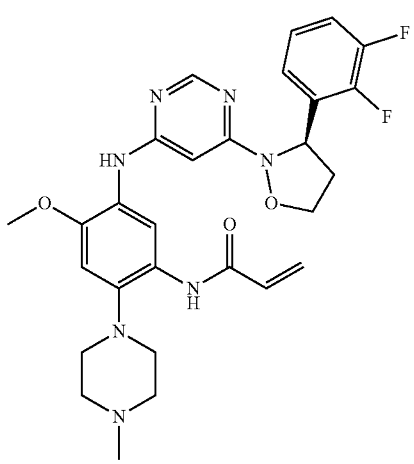 [SMILES: C=CC(=O)Nc1cc(Nc2cc(N3OCC[C@@H]3c3cccc(F)c3F)ncn2)c(OC)cc1N1CCN(C)CC1] | N-(5-((6-((R)-3-(2,3-difluorophenyl)isoxazolidine-2-yl)pyrimidine-4-yl)amino)-4-methoxy-2-(4-methylpiperazine-1-yl)phenyl)acrylamide | ¹H NMR (400 MHz, Chloroform-d) δ 8.90 (s, 1H), 8.53 (s, 1H), 8.37 (d, J = 1.0 Hz, 1H), 7.40-7.31 (m, 1H), 7.12-7.00 (m, 2H), 6.98 (s, 1H), 6.80 (s, 1H), 6.75 (s, 1H), 6.37 (dd, J = 16.9, 1.6 Hz, 1H), 6.27 (dd, J = 16.9, 9.9 Hz, 1H), 5.93 (dd, J = 8.9, 4.5 Hz, 1H), 5.75 (dd, J = 9.9, 1.6 Hz 1H), 4.14 (td, J = 8.1, 4.2 Hz, 1H), 4.07 (q, J = 8.1 Hz, 1H), 3.84 (s, 3H), 2.99-2.88 (m, 4H), 2.88-2.79 (m, 1H), 2.73-2.49 (m, 4H), 2.40 (s, 3H), 2.34-2.25 (m, 1H), ; 552.4 [M + H]⁺ | 1.17 |

TABLE 1-continued

| Example Compound | Structure | Name of Compound | ¹H NMR[[:]]; MS [M + H]⁺ | UPLC r.t. (min) |
|---|---|---|---|---|
| 926 | 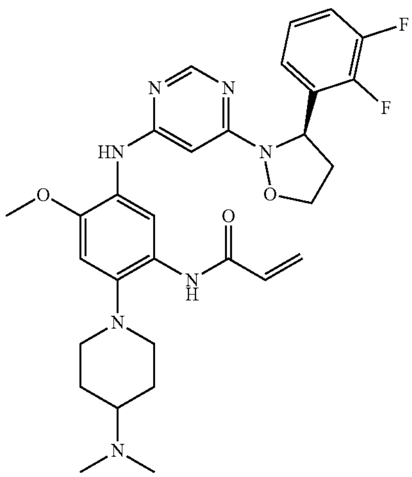 [SMILES: C=CC(=O)Nc1cc(Nc2cc(N3OCC[C@@H]3c3cccc(F)c3F)ncn2)c(OC)cc1N1CCC(N(C)C)CC1] | N-(5-((6-((R)-3-(2,3-difluorophenyl)isoxazolidine-2-yl)pyrimidine-4-yl)amino)-2-(4-(dimethylamino)piperidine-1-yl)-4-methoxyphenyl)acrylamide | ¹H NMR (400 MHz, Chloroform-d) δ 8.87 (s, 1H), 8.46 (s, 1H), 8.36 (d, J = 1.0 Hz, 1H), 7.36 (dt, J = 9.7, 3.5 Hz, 1H), 7.12-6.99 (m, 2H), 6.96 (s, 1H), 6.75 (d, J = 3.5 Hz, 2H), 6.36 (dd, J = 16.9, 1.6 Hz, 1H), 6.26 (dd, J = 16.9, 9.9 Hz, 1H), 5.93 (dd, J = 8.9, 4.6 Hz, 1H), 5.74 (dd, J = 9.9, 1.6 Hz, 1H), 4.14 (td, J = 8.1, 4.3 Hz, 1H), 4.07 (q, J = 8.0 Hz, 1H), 3.85 (s, 3H), 3.11-3.04 (m, 2H), 2.86 (dtd, J = 12.4, 8.1, 4.2 Hz, 1H), 2.77 (dd, J = 12.3, 2.3 Hz, 1H), 2.71 (dd, J = 12.1, 2.3 Hz, 1H), 2.42 (s, 6H), 2.36-2.26 (m, 2H), 2.09 (d, J = 12.6 Hz, 2H), 1.71 (dtd, J = 14.7, 12.0, 4.0 Hz, 2H), ; 580.5 [M + H]⁺ | 1.20 |
| 927 | 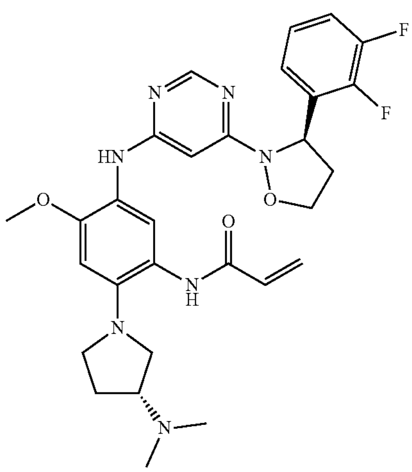 [SMILES: C=CC(=O)Nc1cc(Nc2cc(N3OCC[C@@H]3c3cccc(F)c3F)ncn2)c(OC)cc1N1CC[C@@H](N(C)C)C1] | N-(5-((6-((R)-3-(2,3-difluorophenyl)isoxazolidine-2-yl)pyrimidine-4-yl)amino)-2-((R)-3-(dimethylamino)pyrrolidine-1-yl)-4-methoxyphenyl)acrylamide | ¹H NMR (400 MHz, Chloroform-d) δ 8.65 (s, 1H), 8.35 (s, 1H), 8.17 (s, 1H), 7.40-7.31 (m, 1H), 7.12-6.98 (m, 2H), 6.91 (s, 1H), 6.73 (d, J = 11.0 Hz, 2H), 6.38 (dd, J = 17.0, 1.9 Hz, 1H), 6.30 (dd, J = 16.9, 9.7 Hz, 1H), 5.93 (dd, J = 8.8, 4.5 Hz, 1H), 5.73 (dd, J = 9.7, 1.9 Hz, 1H), 4.14 (td, J = 8.0, 4.2 Hz, 1H), 4.06 (q, J = 8.1 Hz, 1H), 3.84 (s, 3H), 3.23-3.14 (m, 1H), 3.14-3.06 (m, 3H), 2.94-2.78 (m, 2H), 2.37-2.31 (m, 1H), 2.30 (s, 6H), 2.24-2.12 (m, 1H), 2.00-1.92 (m, 1H), ; 566.4 [M + H]⁺ | 1.13 |
| 928 | 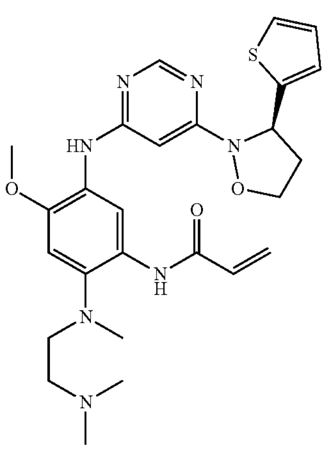 [SMILES: C=CC(=O)Nc1cc(Nc2cc(N3OCC[C@@H]3c3cccs3)ncn2)c(OC)cc1N(C)CCN(C)C] | N-(2-((2-(dimethylamino)ethyl)(methyl)amino)-4-methoxy-5-((6-((R)-3-(thiophene-2-yl)isoxazolidine-2-yl)pyrimidine-4-yl)amino)phenyl)acrylamide | ¹H NMR (400 MHz, CDCl₃) δ 10.06 (s, 1H), 8.96 (s, 1H), 8.41 (s, 1H), 7.20 (dd, J = 5.1, 1.1 Hz, 1H), 7.07 (d, J = 3.5 Hz, 1H), 6.98-6.91 (m, 2H), 6.79 (s, 1H), 6.71 (s, 1H), 6.43-6.24 (m, 2H), 6.01 (dd, J = 8.2, 3.3 Hz, 1H), 5.68 (dd, J = 9.8, 2.0 Hz, 1H), 4.26-4.12 (m, 2H), 3.84 (s, 3H), 2.92-2.83 (m, 2H), 2.75-2.62 (m, 4H), 2.55-2.45 (m, 1H), 2.38-2.31 (m, 2H), 2.29 (s, 6H); 524.36 [M + H]⁺ | 1.16 |

TABLE 1-continued

| Example Compound | Structure | Name of Compound | ¹H NMR[[:]]; MS [M + H]⁺ | UPLC r.t. (min) |
|---|---|---|---|---|
| 929 | 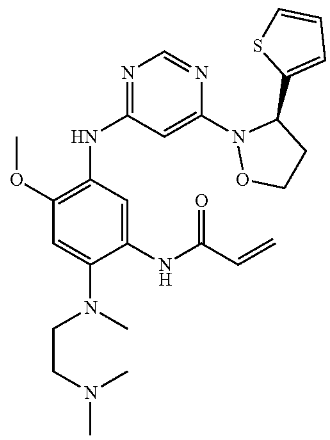 [SMILES: C=CC(=O)Nc1cc(Nc2cc(N3OCC[C@@H]3c3cccs3)ncn2)c(OC)cc1N(C)CCN(C)C] | N-(4-methoxy-2-(4-methylpiperazine-1-yl)-5-((6-((R)-3-(thiophene-2-yl)isoxazolidine-2-yl)pyrimidine-4-yl)amino)phenyl) acrylamide | ¹H NMR (400 MHz, CDCl₃) δ 8.91 (s, 1H), 8.52 (s, 1H), 8.41 (s, 1H), 7.20 (dd, J = 5.1, 1.0 Hz, 1H), 7.07 (d, J = 3.5 Hz, 1H), 6.98-6.91 (m, 2H), 6.79 (s, 1H), 6.67 (s, 1H), 6.40-6.22 (m, 2H), 6.00 (dd, J = 8.2, 3.3 Hz, 1H), 5.75 (dd, J = 10.0, 1.3 Hz, 1H), 4.21 (td, J = 8.0, 5.5 Hz, 1H), 4.13 (q, J = 7.9 Hz, 1H), 3.83 (s, 3H), 2.97-2.87 (m, 4H), 2.73-2.63 (m, 1H), 2.57-2.46 (m, 1H), 2.39 (s, 3H); 522.33 [M + H]⁺ | 1.13 |
| 930 | 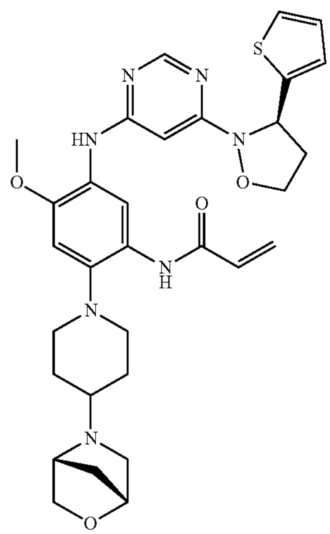 [SMILES: C=CC(=O)Nc1cc(Nc2cc(N3OCC[C@@H]3c3cccs3)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-4-methoxy-5-((6-((R)-3-(thiophene-2-yl)isoxazolidine-2-yl)pyrimidine-4-yl)amino)phenyl) acrylamide | ¹H NMR (400 MHz, CDCl₃) δ 8.86 (s, 1H), 8.48 (s, 1H), 8.40 (s, 1H), 7.20 (dd, J = 5.1, 1.0 Hz, 1H), 7.07 (d, J = 3.5 Hz, 1H), 6.98-6.93 (m, 2H), 6.75 (s, 1H), 6.67 (s, 1H), 6.38-6.20 (m, 2H), 6.00 (dd, J = 8.3, 3.3 Hz, 1H), 5.73 (dd, J = 10.0, 1.3 Hz, 1H), 4.45 (s, 1H), 4.24-4.07 (m, 3H), 3.84 (s, 3H), 3.80 (s, 1H), 3.69-3.63 (m, 1H), 3.19-3.14 (m, 1H), 3.06-2.99 (m, 2H), 2.81-2.65 (m, 3H), 2.64-2.56 (m, 1H), 2.56-2.46 (m, 2H), 2.08-1.65 (m, 6H); 604.45 [M + H]⁺ | 1.16 |

TABLE 1-continued

| Example Compound | Structure | Name of Compound | ¹H NMR[[:]]; MS [M + H]⁺ | UPLC r.t. (min) |
|---|---|---|---|---|
| 931 | 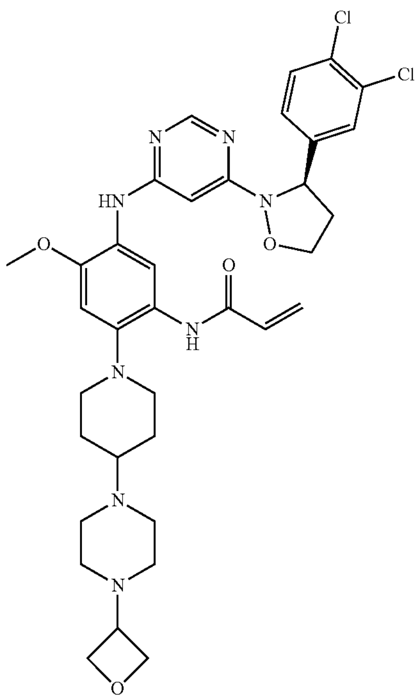 [SMILES: C=CC(=O)Nc1cc(Nc2cc(N3OCC[C@@H]3c3ccc(Cl)c(Cl)c3)ncn2)c(OC)cc1N1CCC(N2CCN(C3COC3)CC2)CC1] | N-(5-((6-((R)-3-(3,4-dichlorophenyl)isoxazolidine-2-yl)pyrimidine-4-yl)amino)-4-methoxy-2-(4-(4-(oxetane-3-yl)piperazine-1-yl)piperidine-1-yl)phenyl)acrylamide | ¹H NMR (400 MHz, Chloroform-d) δ 8.87 (s, 1H), 8.36 (s, 1H), 7.58 (s, 1H), 7.41 (d, J = 8.3 Hz, 1H), 7.30 (d, J = 8.6 Hz, 1H), 6.93 (s, 1H), 6.71 (s, 2H), 6.38 (d, J = 16.1 Hz, 3H), 5.76 (d, J = 11.1 Hz, 1H), 5.65 (s, 1H), 4.70 (t, J = 6.6 Hz, 2H), 4.66-4.56 (m, 2H), 4.16 (d, J = 4.3 Hz, 1H), 4.06 (d, J = 8.2 Hz, 1H), 3.92 (s, 1H), 3.85 (s, 3H), 3.61 (d, J = 33.0 Hz, 2H), 3.45-3.29 (m, 4H), 3.26-3.06 (m, 4H), 2.86 (s, 1H), 2.78 (d, J = 18.0 Hz, 5H), 2.39-2.26 (m, 3H), ; 709.4 [M + H]⁺ | 1.31 |
| 932 | 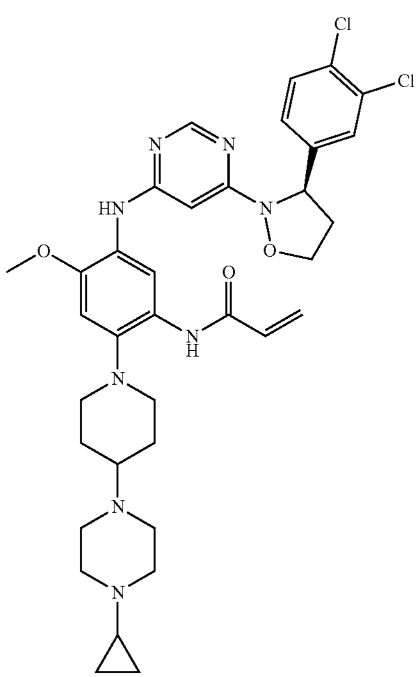 [SMILES: C=CC(=O)Nc1cc(Nc2cc(N3OCC[C@@H]3c3ccc(Cl)c(Cl)c3)ncn2)c(OC)cc1N1CCC(N2CCN(C3CC3)CC2)CC1] | N-(2-(4-(4-cyclopropylpiperazine-1-yl)piperidine-1-yl)-5-((6-((R)-3-(3,4-dichlorophenyl)isoxazolidine-2-yl)pyrimidine-4-yl)amino)-4-methoxyphenyl)acrylamide | ¹H NMR (400 MHz, Chloroform-d) δ 9.13 (s, 1H), 8.84 (s, 1H), 8.35 (s, 1H), 8.31 (s, 1H), 7.57 (s, 1H), 7.41 (d, J = 8.3 Hz, 1H), 7.29 (dd, J = 8.8, 2.2 Hz, 1H), 6.70 (m, 2H), 6.38 (s, 2H), 5.80-5.73 (m, 1H), 5.64 (dd, J = 8.8, 4.6 Hz, 1H), 4.17 (td, J = 7.9, 4.2 Hz, 1H), 4.06 (q, J = 8.2 Hz, 1H), 3.95-3.90 (m, 2H), 3.84 (s, 3H), 3.66 (d, J = 17.4 Hz, 4H), 3.33 (t, J = 6.3 Hz, 4H), 3.13-3.04 (m, 6H), 2.33 (dd, J = 12.3, 4.3 Hz, 2H), 2.29-2.22 (m, 2H), 0.55 (s, 2H), 0.39 (s, 2H), ; 693.5 [M + H]⁺ | 1.38 |

TABLE 1-continued

| Example Compound | Structure | Name of Compound | ¹H NMR[[:]]; MS [M + H]⁺ | UPLC r.t. (min) |
|---|---|---|---|---|
| 933 | 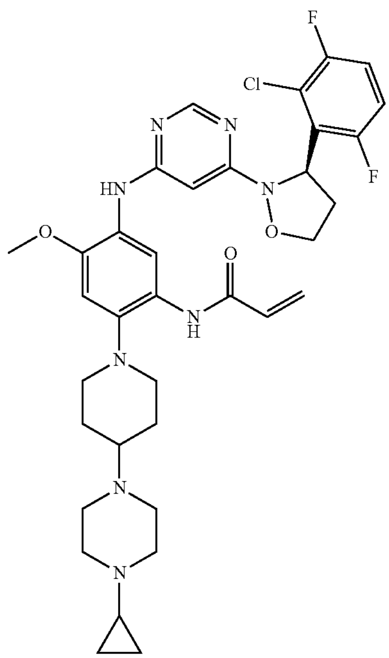 [SMILES: C=CC(=O)Nc1cc(Nc2cc(N3OCC[C@@H]3c3c(F)ccc(F)c3Cl)ncn2)c(OC)cc1N1CCC(N2CCN(C3CC3)CC2)CC1] | N-(5-((6-((R)-3-(2-chloro-3,6-difluorophenyl)isoxazolidine-2-yl)pyrimidine-4-yl)amino)-2-(4-(4-cyclopropylpiperazine-1-yl)piperidine-1-yl)-4-methoxyphenyl)acrylamide | ¹H NMR (400 MHz, Chloroform-d) δ 8.82 (s, 1H), 8.43 (s, 1H), 8.33 (d, J = 1.0 Hz, 1H), 7.08-7.01 (m, 1H), 7.00-6.93 (m, 1H), 6.84 (s, 1H), 6.73 (s, 1H), 6.62 (s, 1H), 6.37-6.20 (m, 2H), 5.94 (d, J = 8.3 Hz, 1H), 5.75-5.71 (m, 1H), 4.39-4.35 (m, 1H), 3.99-3.93 (m, 1H), 3.82 (s, 3H), 3.05 (d, J = 11.4 Hz, 2H), 2.78-2.59 (m, 11H), 2.56-2.49 (m, 1H), 2.32 (td, J = 7.5, 3.8 Hz, 1H), 2.07 (d, J = 12.6 Hz, 2H), 1.72-1.65 (m, 2H), 1.64-1.60 (m, 1H), 0.48-0.41 (m, 4H), ; 695.5 [M + H]⁺ | 1.20 |
| 934 | 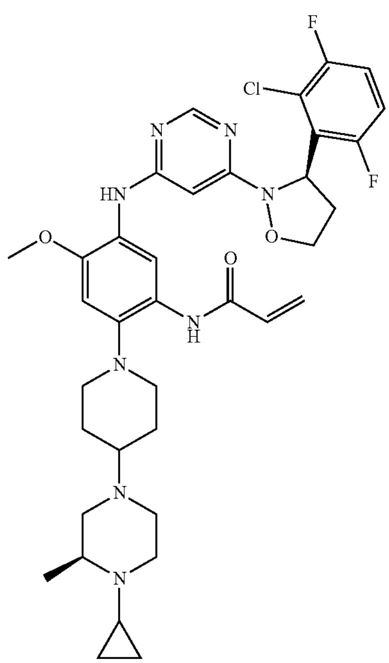 [SMILES: C=CC(=O)Nc1cc(Nc2cc(N3OCC[C@@H]3c3c(F)ccc(F)c3Cl)ncn2)c(OC)cc1N1CCC(N2CCN(C3CC3)[C@@H](C)C2)CC1] | N-(5-((6-((R)-3-(2-chloro-3,6-difluorophenyl)isoxazolidine-2-yl)pyrimidine-4-yl)amino)-2-(4-((S)-4-cyclopropyl-3-methylpiperazine-1-yl)piperidine-1-yl)-4-methoxyphenyl)acrylamide | ¹H NMR (400 MHz, Chloroform-d) δ 8.83 (s, 1H), 8.42 (s, 1H), 8.33 (d, J = 1.1 Hz, 1H), 7.05 (ddd, J = 9.0, 7.9, 4.5 Hz, 1H), 6.97 (td, J = 9.5, 4.3 Hz, 1H), 6.83 (s, 1H), 6.73 (s, 1H), 6.62 (s, 1H), 6.35 (dd, J = 17.0, 1.5 Hz, 1H), 6.24 (dd, J = 17.0, 10.1 Hz, 1H), 5.93 (t, J = 8.3 Hz, 1H), 5.79-5.70 (m, 1H), 4.42-4.33 (m, 1H), 3.96 (td, J = 8.9, 6.0 Hz, 1H), 3.82 (s, 3H), 3.08-2.99 (m, 3H), 2.96 (d, J = 10.7 Hz, 1H), 2.87 (d, J = 10.8 Hz, 1H), 2.83-2.65 (m, 3H), 2.60-2.42 (m, 3H), 2.36-2.24 (m, 2H), 2.07 (d, J = 12.1 Hz, 2H), 2.00 (t, J = 10.4 Hz, 1H), 1.72-1.62 (m, 2H), 1.58-1.48 (m, 1H), 1.21 (d, 3H), 0.70-0.55 (m, 2H), 0.49-0.38 (m, 1H), 0.37-0.26 (m, 1H), ; 709.5 [M + H]⁺ | 1.22 |

TABLE 1-continued

| Example Compound | Structure | Name of Compound | ¹H NMR[[:]]; MS [M + H]⁺ | UPLC r.t. (min) |
|---|---|---|---|---|
| 935 | 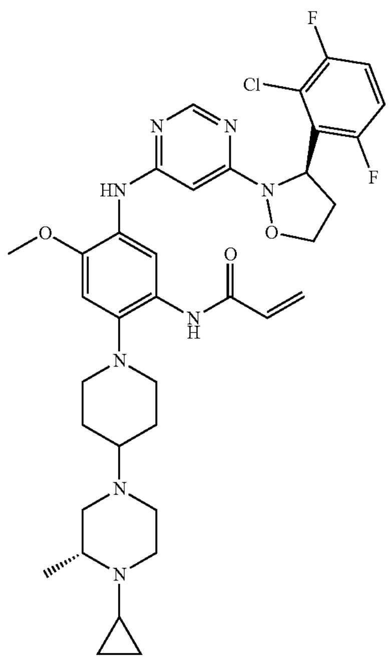 [SMILES: C=CC(=O)Nc1cc(Nc2cc(N3OCC[C@@H]3c3c(F)ccc(F)c3Cl)ncn2)c(OC)cc1N1CCC(N2CCN(C3CC3)[C@H](C)C2)CC1] | N-(5-((6-((R)-3-(2-chloro-3,6-difluorophenyl)isoxazolidine-2-yl)pyrimidine-4-yl)amino)-2-(4-((R)-4-cyclopropyl-3-methylpiperazine-1-yl)piperidine-1-yl)-4-methoxyphenyl)acrylamide | ¹H NMR (400 MHz, Chloroform-d) δ 8.80 (s, 1H), 8.43 (s, 1H), 8.32 (d, J = 1.0 Hz, 1H), 7.05 (ddd, J = 9.1, 7.9, 4.5 Hz, 1H), 6.97 (td, J = 9.5, 4.4 Hz, 1H), 6.87 (s, 1H), 6.73 (s, 1H), 6.62 (s, 1H), 6.36 (dd, J = 16.9, 1.5 Hz, 1H), 6.25 (dd, J = 16.9, 10.0 Hz, 1H), 5.93 (t, J = 8.3 Hz, 1H), 5.74 (dd, J = 9.9, 1.5 Hz, 1H), 4.37 (td, J = 8.0, 1.9 Hz, 1H), 4.01-3.90 (m, 1H), 3.82 (s, 3H), 3.03 (td, J = 11.3, 10.8, 5.1 Hz, 3H), 2.96 (d, J = 10.8 Hz, 1H), 2.92-2.84 (m, 1H), 2.84-2.64 (m, 3H), 2.60-2.42 (m, 3H), 2.36-2.23 (m, 2H), 2.11-1.95 (m, 3H), 1.73-1.58 (m, 2H), 1.58-1.49 (m, 1H), 1.21 (d, 3H), 0.71-0.55 (m, 2H), 0.49-0.38 (m, 1H), 0.37-0.26 (m, 1H), ; 709.5 [M + H]⁺ | 1.22 |
| 936 | 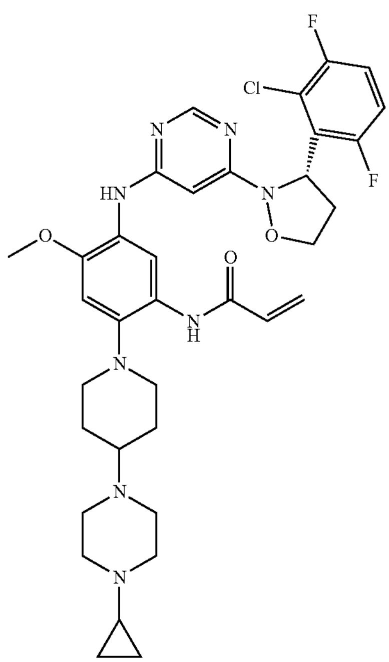 [SMILES: C=CC(=O)Nc1cc(Nc2cc(N3OCC[C@H]3c3c(F)ccc(F)c3Cl)ncn2)c(OC)cc1N1CCC(N2CCN(C3CC3)CC2)CC1] | N-(5-((6-((S)-3-(2-chloro-3,6-difluorophenyl)isoxazolidine-2-yl)pyrimidine-4-yl)amino)-2-(4-(4-cyclopropylpiperazine-1-yl)piperidine-1-yl)-4-methoxyphenyl)acrylamide | ¹H NMR (400 MHz, DMSO-d₆) δ 9.04 (s, 2H), 8.16 (s, 1H), 8.04 (s, 1H), 7.44 (td, J = 8.9, 4.4 Hz, 1H), 7.30 (td, J = 9.7, 4.4 Hz, 1H), 6.84 (s, 1H), 6.62 (dd, J = 16.9, 10.2 Hz, 1H), 6.28-6.06 (m, 3H), 5.78-5.68 (m, 3H), 4.39 (t, J = 7.6 Hz, 1H), 3.79 (s, 3H), 3.46 (s, 2H), 3.27 (s, 2H), 3.15 (d, J = 11.5 Hz, 4H), 3.02 (d, J = 24.8 Hz, 3H), 2.89-2.66 (m, 6H), 2.41 (ddd, J = 19.2, 11.3, 7.8 Hz, 2H), 2.08 (d, J = 3.5 Hz, 3H), 1.91 (s, 3H), 0.55 (d, J = 6.9 Hz, 2H), 0.48 (s, 2H), ; 695.5 [M + H]⁺ | 1.15 |

TABLE 1-continued

| Example Compound | Structure | Name of Compound | ¹H NMR[:]; MS [M + H]⁺ | UPLC r.t. (min) |
|---|---|---|---|---|
| 937 | 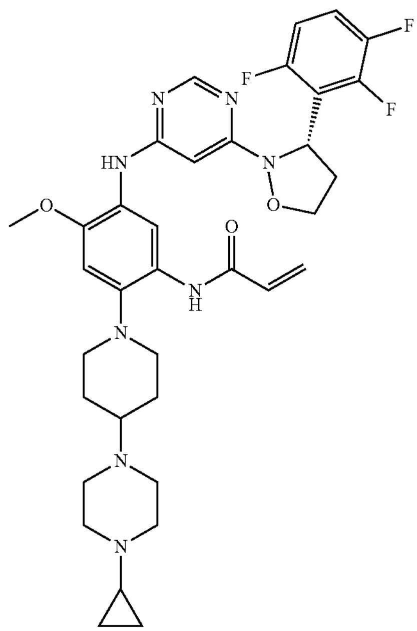 [SMILES: C=CC(=O)Nc1cc(Nc2cc(N3OCC[C@H]3c3c(F)ccc(F)c3F)ncn2)c(OC)cc1N1CCC(N2CCN(C3CC3)CC2)CC1] | N-(2-(4-(4-cyclopropylpiperazine-1-yl)piperidine-1-yl)-4-methoxy-5-((6-((S)-3-(2,3,6-trifluorophenyl)isoxazolidine-2-yl)pyrimidine-4-yl)amino)phenyl)acrylamide | ¹H NMR (400 MHz, DMSO-d$_6$) δ 8.97 (s, 1H), 8.58 (s, 1H), 8.14 (s, 1H), 7.45 (qd, J = 9.4, 4.8 Hz, 1H), 7.13 (tdd, J = 9.5, 3.9, 2.0 Hz, 1H), 6.81 (s, 1H), 6.65 (dd, J = 17.0, 10.2 Hz, 1H), 6.27 (d, J = 5.4 Hz, 1H), 6.22 (t, J = 1.7 Hz, 1H), 5.74-5.64 (m, 2H), 4.32 (td, J = 8.1, 2.2 Hz, 1H), 3.78 (s, 3H), 3.56 (p, J = 6.6 Hz, 2H), 3.07 (q, J = 7.5 Hz, 4H), 2.79 (ddt, J = 13.9, 10.4, 5.6 Hz, 2H), 2.65 (d, J = 9.6 Hz, 10H), 2.41 (ddd, J = 18.7, 11.0, 7.8 Hz, 2H), 1.95-1.85 (m, 2H), 1.76 (q, J = 12.5, 11.3 Hz, 2H), 0.41 (dt, J = 6.2, 3.0 Hz, 2H), 0.31 (p, J = 3.9 Hz, 2H), ; 679.5 [M + H]⁺ | 1.18 |
| 938 | 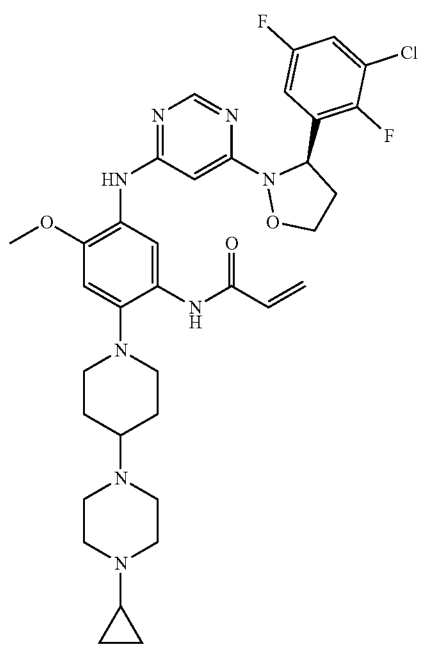 [SMILES: C=CC(=O)Nc1cc(Nc2cc(N3OCC[C@@H]3c3cc(F)cc(Cl)c3F)ncn2)c(OC)cc1N1CCC(N2CCN(C3CC3)CC2)CC1] | N-(5-((6-((R)-3-(3-chloro-2,5-difluorophenyl)isoxazolidine-2-yl)pyrimidine-4-yl)amino)-2-(4-(4-cyclopropylpiperazine-1-yl)piperidine-1-yl)-4-methoxyphenyl)acrylamide | ¹H NMR (400 MHz, DMSO-d$_6$) δ 8.95 (s, 1H), 8.66 (s, 1H), 8.16 (s, 1H), 7.57 (ddd, J = 8.4, 5.5, 3.2 Hz, 1H), 7.22 (ddd, J = 8.7, 5.3, 3.2 Hz, 1H), 6.82 (s, 1H), 6.65 (dd, J = 16.9, 10.2 Hz, 1H), 6.36 (s, 1H), 6.20 (dd, J = 17.0, 2.0 Hz, 1H), 5.71 (dd, J = 9.2, 3.8 Hz, 2H), 4.18 (td, J = 7.9, 3.7 Hz, 1H), 3.79 (s, 3H), 3.04 (d, J = 11.2 Hz, 2H), 2.81 (dtd, J = 12.1, 8.0, 3.6 Hz, 1H), 2.66 (t, J = 11.7 Hz, 2H), 2.54 (s, 2H), 2.32-2.14 (m, 3H), 2.09 (s, 2H), 1.86 (s, 8H), 1.76-1.62 (m, 3H), 1.58 (tt, J = 6.7, 3.6 Hz, 2H), 0.39 (dt, J = 6.2, 3.0 Hz, 2H), 0.27 (p, J = 3.9 Hz, 2H), ; 695.5 [M + H]⁺ | 1.37 |

TABLE 1-continued

| Example Compound | Structure | Name of Compound | ¹H NMR[[:]]; MS [M + H]⁺ | UPLC r.t. (min) |
|---|---|---|---|---|
| 939 | 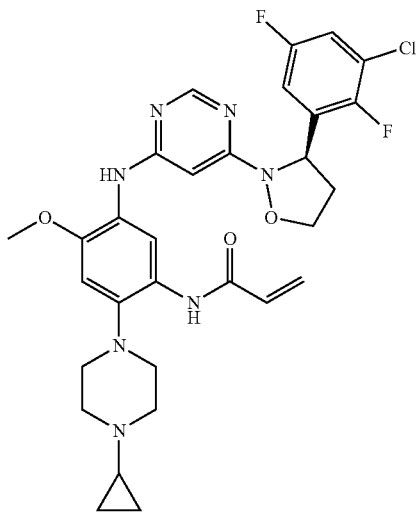 [SMILES: C=CC(=O)Nc1cc(Nc2cc(N3OCC[C@@H]3c3cc(F)cc(Cl)c3F)ncn2)c(OC)cc1N1CCN(C2CC2)CC1] | N-(5-((6-((R)-3-(3-chloro-2,5-difluorophenyl)isoxazolidine-2-yl)pyrimidine-4-yl)amino)-2-(4-cyclopropylpiperazine-1-yl)-4-methoxyphenyl)acrylamide | ¹H NMR (400 MHz, DMSO-d₆) δ 8.99 (s, 1H), 8.67 (s, 1H), 8.17 (s, 1H), 7.57 (ddd, J = 8.4, 5.6, 3.2 Hz, 1H), 7.22 (ddd, J = 8.7, 5.2, 3.2 Hz, 1H), 6.85 (s, 1H), 6.61 (dd, J = 17.0, 10.2 Hz, 1H), 6.38 (s, 1H), 6.20 (dd, J = 17.0, 1.9 Hz, 1H), 5.76-5.67 (m, 2H), 4.18 (td, J = 7.9, 3.7 Hz, 1H), 3.79 (s, 3H), 2.78 (dt, J = 34.1, 4.9 Hz, 10H), 2.21 (dtd, J = 13.0, 8.2, 4.9 Hz, 1H), 1.76 (s, 1H), 1.70 (dq, J = 6.9, 3.7, 3.3 Hz, 1H), 0.44 (dt, J = 6.3, 3.0 Hz, 2H), 0.32 (p, J = 4.0 Hz, 2H), ; 612.3 [M + H]⁺ | 1.35 |
| 940 | 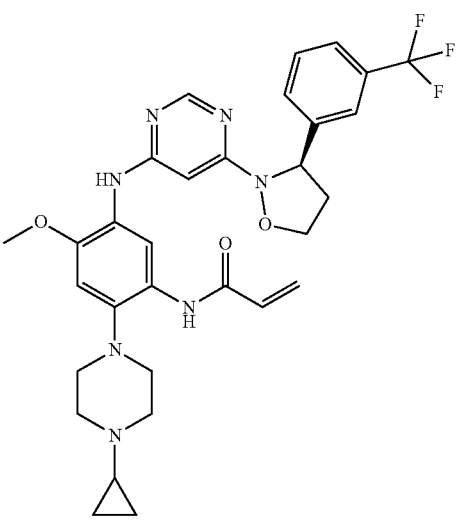 [SMILES: C=CC(=O)Nc1cc(Nc2cc(N3OCC[C@@H]3c3cccc(C(F)(F)F)c3)ncn2)c(OC)cc1N1CCN(C2CC2)CC1] | N-(2-(4-cyclopropylpiperazine-1-yl)-4-methoxy-5-((6-((R)-3-(3-(trifluoromethyl)phenyl)isoxazolidine-2-yl)pyrimidine-4-yl)amino)phenyl)acrylamide | ¹H NMR (400 MHz, Chloroform-d) δ 8.90 (s, 1H), 8.60 (s, 1H), 8.37 (s, 1H), 7.73 (s, 1H), 7.66 (d, J = 7.6 Hz, 1H), 7.52-7.43 (m, 2H), 7.03 (s, 1H), 6.79 (s, 1H), 6.74 (s, 1H), 6.37 (dd, J = 16.9, 1.7 Hz, 1H), 6.29 (dd, J = 16.9, 9.9 Hz, 1H), 5.80-5.73 (m, 2H), 4.23-4.14 (m, 1H), 4.14-4.02 (m, 1H), 3.81 (s, 3H), 2.92-2.75 (m, 9H), 2.43-2.30 (m, 1H), 1.77-1.68 (m, 1H), 0.57-0.42 (m, 4H), ; 610.4 [M + H]⁺ | 1.31 |

TABLE 1-continued

| Example Compound | Structure | Name of Compound | ¹H NMR[[:]]; MS [M + H]⁺ | UPLC r.t. (min) |
|---|---|---|---|---|
| 941 | 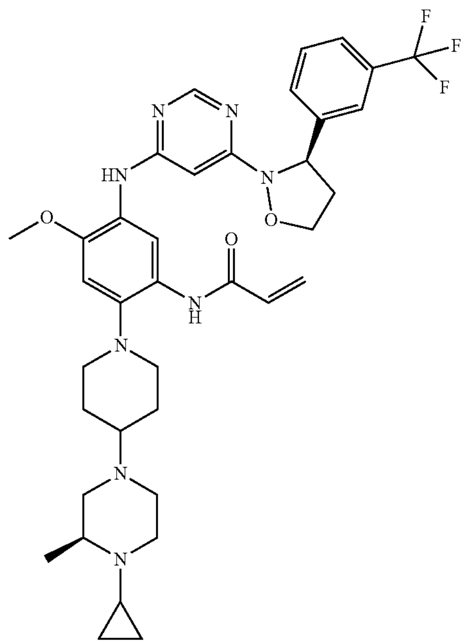 [SMILES: C=CC(=O)Nc1cc(Nc2cc(N3OCC[C@@H]3c3cccc(C(F)(F)F)c3)ncn2)c(OC)cc1N1CCC(N2CCN(C3CC3)[C@@H](C)C2)CC1] | N-(2-(4-((S)-4-cyclopropyl-3-methylpiperazine-1-yl)piperidine-1-yl)-4-methoxy-5-((6-((R)-3-(3-(trifluoromethyl)phenyl)isoxazolidine-2-yl)pyrimidine-4-yl)amino)phenyl)acrylamide | ¹H NMR (400 MHz, Chloroform-d) δ 8.86 (s, 1H), 8.45 (s, 1H) 8.39-8.29 (m, 1H), 7.73 (s, 1H), 7.66 (d, J = 7.6 Hz, 1H), 7.54-7.47 (m, 1H), 7.47-7.41 (m, 1H), 6.96 (s, 1H), 6.74 (d, J = 6.4 Hz, 2H), 6.36 (dd, J = 16.9, 1.6 Hz, 1H), 6.25 (dd, J = 17.0, 10.0 Hz, 1H), 5.80-5.69 (m, 2H), 4.16 (td, J = 8.0, 4.2 Hz, 1H), 4.09 (q, J = 8.0 Hz, 1H), 3.84 (s, 3H), 3.09-3.00 (m, 3H), 2.97 (d, J = 10.8 Hz, 1H), 2.92-2.66 (m, 4H), 2.58-2.43 (m, 2H), 2.42-2.24 (m, 3H), 2.12-1.96 (m, 3H), 1.74-1.59 (m, 2H), 1.59-1.49 (m, 1H), 1.21 (d, 3H), 0.71-0.55 (m, 2H), 0.49-0.38 (m, 1H), 0.37-0.27 (m, 1H), ; 707.5 [M + H]⁺ | 1.34 |
| 942 | 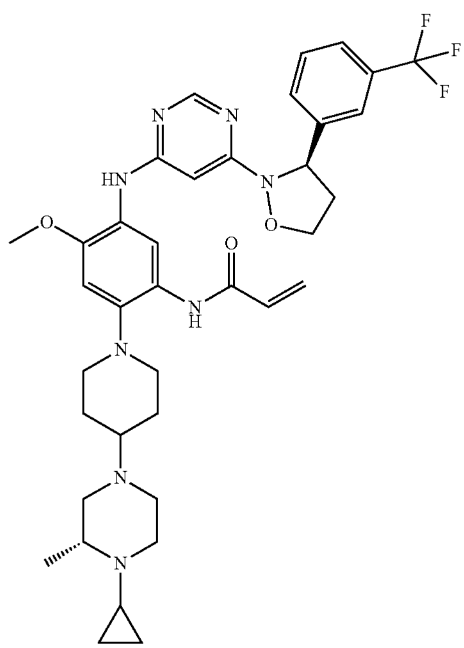 [SMILES: C=CC(=O)Nc1cc(Nc2cc(N3OCC[C@@H]3c3cccc(C(F)(F)F)c3)ncn2)c(OC)cc1N1CCC(N2CCN(C3CC3)[C@H](C)C2)CC1] | N-(2-(4-((R)-4-cyclopropyl-3-methylpiperazine-1-yl)piperidine-1-yl)-4-methoxy-5-((6-((R)-3-(3-(trifluoromethyl)phenyl)isoxazolidine-2-yl)pyrimidine-4-yl)amino)phenyl)acrylamide | ¹H NMR (400 MHz, Chloroform-d) δ 8.86 (s, 1H), 8.45 (s, 1H), 8.36 (s, 1H), 7.73 (s, 1H), 7.66 (d, J = 7.5 Hz, 1H), 7.54-7.48 (m, 1H), 7.48-7.41 (m, 1H), 6.98 (s, 1H), 6.74 (d, J = 6.4 Hz, 2H), 6.36 (dd, J = 17.1, 1.6 Hz, 1H), 6.25 (dd, J = 16.9, 10.0 Hz, 1H), 5.81-5.70 (m, 2H), 4.21-4.12 (m, 1H), 4.12-4.03 (m, 1H), 3.84 (s, 3H), 3.09-2.99 (m, 3H), 2.96 (d, J = 10.8 Hz, 1H), 2.88 (dd, J = 10.8, 2.7 Hz, 1H), 2.84-2.65 (m, 3H), 2.59-2.42 (m, 2H), 2.42-2.23 (m, 3H), 2.10-1.96 (m, 3H), 1.66 (qt, J = 12.1, 3.3 Hz, 2H), 1.58-1.48 (m, 1H), 1.21 (d, 3H), 0.70-0.55 (m, 2H), 0.49-0.38 (m, 1H), 0.37-0.26 (m, 1H), ; 707.5 [M + H]⁺ | 1.33 |

TABLE 1-continued

| Example Compound | Structure | Name of Compound | ¹H NMR[[:]]; MS [M + H]⁺ | UPLC r.t. (min) |
|---|---|---|---|---|
| 943 | 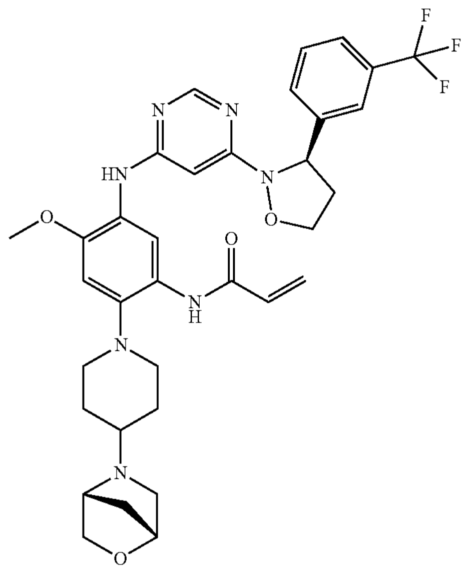 [SMILES: C=CC(=O)Nc1cc(Nc2cc(N3OCC[C@@H]3c3cccc(C(F)(F)F)c3)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-4-methoxy-5-((6-((R)-3-(3-(trifluoromethyl)phenyl)isoxazolidine-2-yl)pyrimidine-4-yl)amino)phenyl)acrylamide | ¹H NMR (400 MHz, Chloroform-d) δ 8.87 (s, 1H), 8.48 (s, 1H), 8.39-8.34 (m, 1H), 7.73 (s, 1H), 7.66 (d, J = 7.5 Hz, 1H), 7.54-7.43 (m, 2H), 6.98 (s, 1H), 6.75 (d, J = 9.5 Hz, 2H), 6.35 (dd, J = 16.9, 1.5 Hz, 1H), 6.24 (dd, J = 16.9, 10.0 Hz, 1H), 5.80-5.69 (m, 2H), 4.44 (t, J = 2.0 Hz, 1H), 4.21-4.12 (m, 1H), 4.12-4.04 (m, 2H), 3.85 (s, 3H), 3.77 (s, 1H), 3.66 (dd, J = 8.0, 1.6 Hz, 1H), 3.14 (dd, J = 9.9, 1.8 Hz, 1H), 3.07-2.98 (m, 2H), 2.87-2.77 (m, 2H), 2.77-2.69 (m, 1H), 2.64-2.54 (m, 1H), 2.51 (d, J = 9.9 Hz, 1H), 2.43-2.30 (m, 1H), 2.04 (d, J = 12.7 Hz, 1H), 1.99-1.88 (m, 2H), 1.83 (d, J = 9.9 Hz, 1H), 1.75-1.62 (m, 2H), ; 666.5 [M + H]⁺ | 1.28 |
| 944 | 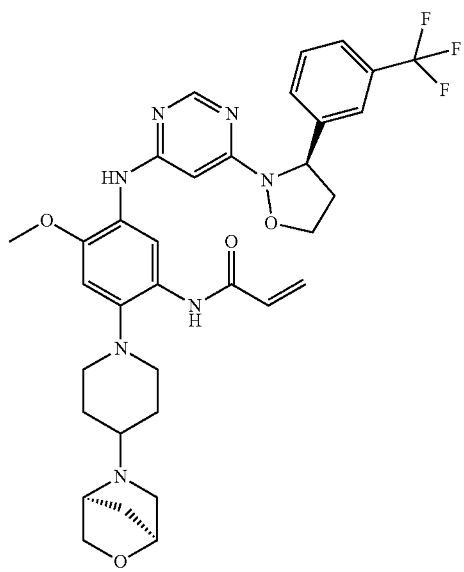 [SMILES: C=CC(=O)Nc1cc(Nc2cc(N3OCC[C@@H]3c3cccc(C(F)(F)F)c3)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-4-methoxy-5-((6-((R)-3-(3-(trifluoromethyl)phenyl)isoxazolidine-2-yl)pyrimidine-4-yl)amino)phenyl)acrylamide | ¹H NMR (400 MHz, Chloroform-d) δ 8.87 (s, 1H), 8.49 (s, 1H), 8.36 (d, J = 1.0 Hz, 1H), 7.73 (s, 1H), 7.66 (d, J = 7.6 Hz, 1H), 7.54-7.43 (m, 2H), 7.00 (s, 1H), 6.75 (d, J = 11.5 Hz, 2H), 6.35 (dd, J = 17.0, 1.5 Hz, 1H), 6.24 (dd, J = 16.9, 10.0 Hz, 1H), 5.80-5.69 (m, 2H), 4.44 (t, J = 2.0 Hz, 1H), 4.21-4.13 (m, 1H), 4.13-4.03 (m, 2H), 3.85 (s, 3H), 3.77 (s, 1H), 3.66 (dd, J = 7.9, 1.7 Hz, 1H), 3.14 (dd, J = 9.9, 1.7 Hz, 1H), 3.08-2.97 (m, 2H), 2.87-2.70 (m, 3H), 2.64-2.56 (m, 1H), 2.56-2.47 (m, 1H), 2.42-2.30 (m, 1H), 2.04 (d, J = 12.8 Hz, 1H), 1.99-1.88 (m, 2H), 1.86-1.79 (m, 1H), 1.75-1.62 (m, 2H), ; 666.5 [M + H]⁺ | 1.28 |
| 945 | 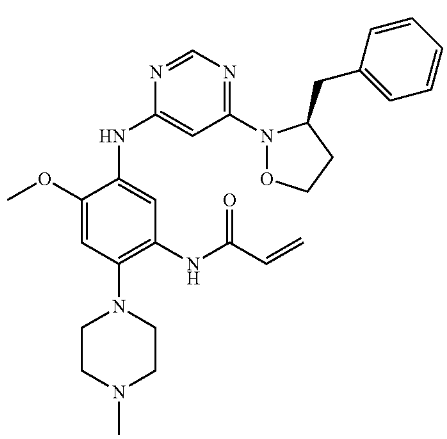 [SMILES: C=CC(=O)Nc1cc(Nc2cc(N3OCC[C@@H]3Cc3ccccc3)ncn2)c(OC)cc1N1CCN(C)CC1] | N-(5-((6-((S)-3-benzylisoxazolidine-2-yl)pyrimidine-4-yl)amino)-4-methoxy-2-(4-methylpiperazine-1-yl)phenyl)acrylamide | ¹H NMR (400 MHz, Chloroform-d) δ 8.88 (s, 1H), 8.42 (s, 1H), 8.38 (s, 1H), 7.34-7.28 (m, 4H), 7.24-7.20 (m, 1H), 7.01 (m, 1H), 6.79 (s, 1H), 6.57 (s, 1H), 6.47-6.23 (m, 2H), 5.75 (dd, J = 9.8, 1.7 Hz, 1H), 4.92-4.84 (m, 1H), 4.06 (td, J = 8.1, 4.7 Hz, 1H), 3.95 (q, J = 8.1 Hz, 1H), 3.84 (s, 3H), 3.66 (p, J = 6.7 Hz, 1H), 3.26 (dd, J = 13.7, 5.8 Hz, 1H), 3.07 (dd, J = 16.9, 9.4 Hz, 4H), 2.80 (d, J = 4.8 Hz, 2H), 2.53 (s, 3H), 2.21-2.14 (m, 4H), ; 530.5 [M + H]⁺ | 1.11 |

TABLE 1-continued

| Example Compound | Structure | Name of Compound | ¹H NMR[[:]]; MS [M + H]⁺ | UPLC r.t. (min) |
|---|---|---|---|---|
| 946 | 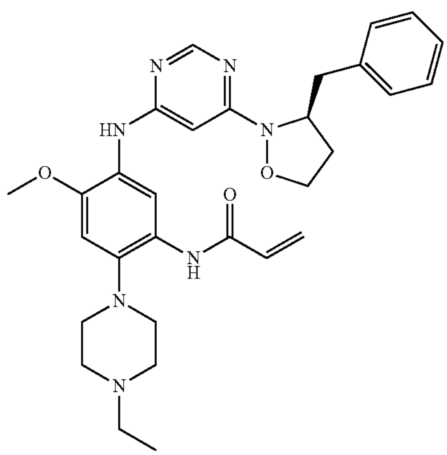 [SMILES: C=CC(=O)Nc1cc(Nc2cc(N3OCC[C@@H]3Cc3ccccc3)ncn2)c(OC)cc1N1CCN(CC)CC1] | N-(5-((6-((S)-3-benzylisoxazolidine-2-yl)pyrimidine-4-yl)amino)-2-(4-ethylpiperazine-1-yl)-4-methoxyphenyl)acrylamide | ¹H NMR (400 MHz, Chloroform-d) δ 8.87 (s, 1H), 8.50 (s, 1H), 8.37 (s, 1H), 7.36-7.29 (m, 4H), 7.23 (dd, J = 5.9, 2.7 Hz, 1H), 7.03 (s, 1H), 6.81 (s, 1H), 6.57 (s, 1H), 6.40-6.11 (m, 2H), 5.76 (m, 1H), 4.88 (m, 1H), 4.06 (td, J = 8.0, 4.6 Hz, 1H), 3.96 (q, J = 8.1 Hz, 1H), 3.83 (s, 3H), 3.65 (m, 2H), 3.26 (m, 1H), 3.08 (t, J = 7.4 Hz, 2H), 3.04-2.96 (m, 4H), 2.80 (m, 3H), 2.18 (dtd, J = 12.6, 8.1, 4.7 Hz, 1H), 2.06 (dtd, J = 11.9, 7.9, 3.9 Hz, 1H), 1.54 (d, J = 7.4 Hz, 3H), ; 544.5 [M + H]⁺ | 1.07 |
| 947 | 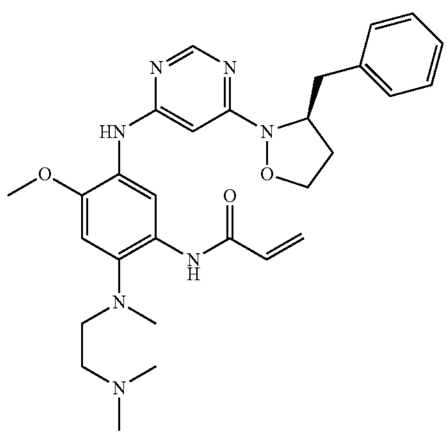 [SMILES: C=CC(=O)Nc1cc(Nc2cc(N3OCC[C@@H]3Cc3ccccc3)ncn2)c(OC)cc1N(C)CCN(C)C] | N-(5-((6-((S)-3-benzylisoxazolidine-2-yl)pyrimidine-4-yl)amino)-2-((2-(dimethylamino)ethyl)(methyl)amino)-4-methoxyphenyl)acrylamide | ¹H NMR (400 MHz, DMSO-d₆) δ 9.85 (s, 1H), 8.55 (s, 1H), 8.30 (s, 1H), 8.19 (s, 1H), 7.30 (d, J = 4.4 Hz, 4H), 7.24-7.17 (m, 1H), 6.93 (s, 1H), 6.32 (s, 1H), 6.27-6.15 (m, 2H), 5.71 (dd, J = 10.1, 2.2 Hz, 1H), 4.75 (td, J = 7.4, 3.7 Hz, 1H), 4.05 (m, 1H), 3.86-3.72 (m, 4H), 3.62-3.53 (m, 1H), 3.16-3.01 (m, 4H), 2.75 (dd, J = 13.7, 7.9 Hz, 1H), 2.62 (s, 3H), 2.52-2.49 (m, 6H), 2.19-2.08 (m, 1H), 2.05-1.94 (m, 1H), ; 532.5 [M + H]⁺ | 1.15 |
| 948 | 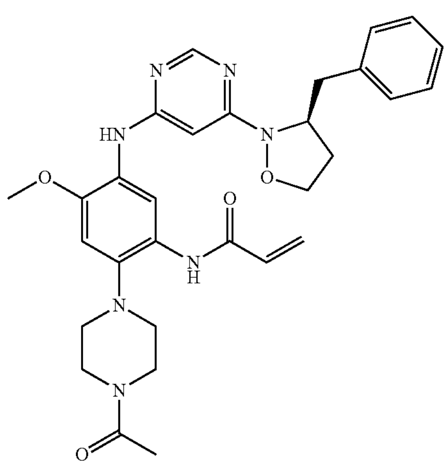 [SMILES: C=CC(=O)Nc1cc(Nc2cc(N3OCC[C@@H]3Cc3ccccc3)ncn2)c(OC)cc1N1CCN(C(C)=O)CC1] | N-(2-(4-acetylpiperazine-1-yl)-5-((6-((S)-3-benzylisoxazolidine-2-yl)pyrimidine-4-yl)amino)-4-methoxyphenyl)acrylamide | ¹H NMR (400 MHz, Chloroform-d) δ 8.93 (s, 1H), 8.43 (s, 1H), 8.40 (s, 1H), 7.35-7.28 (m, 4H), 7.24-7.19 (m, 1H), 6.90 (s, 1H), 6.71 (s, 1H), 6.60 (s, 1H), 6.41-6.20 (m, 2H), 5.76 (dd, J = 10.1, 1.5 Hz, 1H), 4.93-4.84 (m, 1H), 4.07 (m, 1H), 3.96 (q, J = 8.0 Hz, 1H), 3.84-3.80 (m, 4H), 3.64 (m, 2H), 3.26 (dd, J = 13.7, 5.8 Hz, 1H), 3.08 (d, J = 6.6 Hz, 1H), 2.91-2.85 (m, 4H), 2.80 (dd, J = 13.7, 8.9 Hz, 1H), 2.17 (m, 4H), 2.12-2.02 (m, 1H), ; 558.5 [M + H]⁺ | 1.28 |

TABLE 1-continued

| Example Compound | Structure | Name of Compound | ¹H NMR[:]; MS [M + H]⁺ | UPLC r.t. (min) |
|---|---|---|---|---|
| 949 | 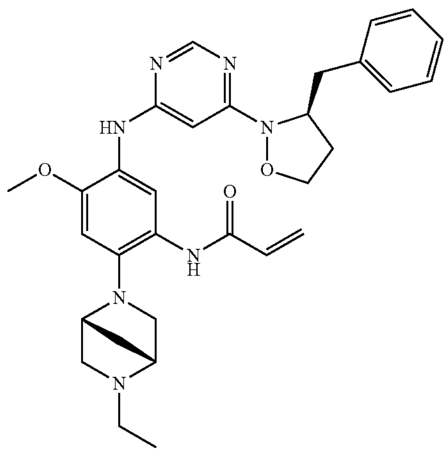 [SMILES: C=CC(=O)Nc1cc(Nc2cc(N3OCC[C@@H]3Cc3ccccc3)ncn2)c(OC)cc1N1C[C@H]2C[C@@H]1CN2CC] | N-(5-((6-((S)-3-benzylisoxazolidine-2-yl)pyrimidine-4-yl)amino)-2-((1R,4R)-5-ethyl-2,5-diazabicyclo[2.2.1]heptane-2-yl)-4-methoxyphenyl) acrylamide | ¹H NMR (400 MHz, Chloroform-d) δ 8.58 (s, 1H), 8.35 (s, 1H), 8.13 (s, 1H), 7.37-7.28 (m, 4H), 7.24-7.18 (m, 1H), 6.89 (s, 1H), 6.79 (s, 1H), 6.54 (s, 1H), 6.32-6.11 (m, 2H), 5.72 (dd, J = 9.7, 1.9 Hz, 1H), 4.88 (m, 1H), 4.07 (m, 1H), 3.99-3.89 (m, 4H), 3.86 (s, 3H), 3.26 (dd, J = 13.7, 5.7 Hz, 1H), 3.14-2.98 (m, 3H), 2.81 (m, 2H), 2.22-2.13 (m, 1H), 2.07 (m, 4H), 1.31 (t, J = 7.3 Hz, 3H), ; 556.5 [M + H]⁺ | 0.96 |
| 950 | 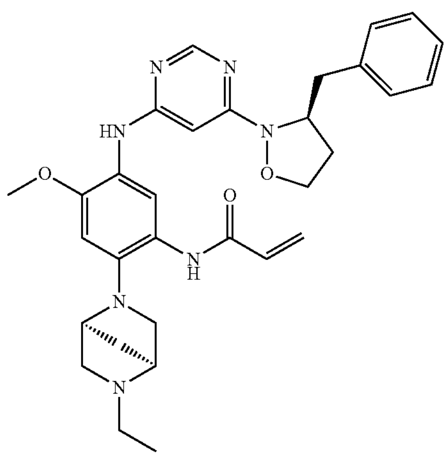 [SMILES: C=CC(=O)Nc1cc(Nc2cc(N3OCC[C@@H]3Cc3ccccc3)ncn2)c(OC)cc1N1C[C@@H]2C[C@H]1CN2CC] | N-(5-((6-((S)-3-benzylisoxazolidine-2-yl)pyrimidine-4-yl)amino)-2-((1S,4S)-5-ethyl-2,5-diazabicyclo[2.2.1]heptane-2-yl)-4-methoxyphenyl) acrylamide | ¹H NMR (400 MHz, Chloroform-d) δ 8.61 (s, 1H), 8.36 (s, 1H) 8.10 (s, 1H), 7.31 (m, 4H), 7.23 (m, 1H), 6.86 (s, 1H), 6.74 (s, 1H), 6.50 (s, 1H), 6.30-6.13 (m, 2H), 5.75-5.70 (m, 1H), 4.88 (m, 1H), 4.03 (m, 1H), 3.95-2.85 (s, 7H), 3.26 (dd, J = 13.7, 5.7 Hz, 1H), 2.97 (m, 3H), 2.84-2.77 (m, 2H), 2.15 (m, 1H), 2.05 (m, 4H), 1.26 (t, J = 7.5 Hz, 3H), ; 556.5 [M + H]⁺ | 1.10 |
| 951 | 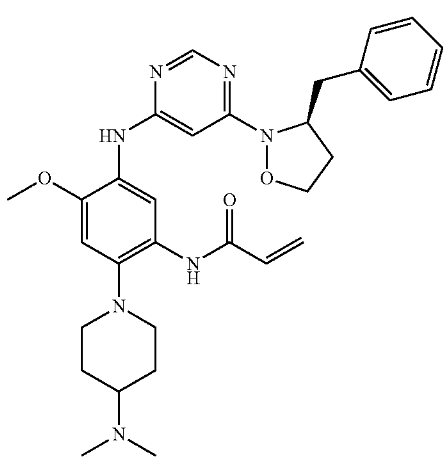 [SMILES: C=CC(=O)Nc1cc(Nc2cc(N3OCC[C@@H]3Cc3ccccc3)ncn2)c(OC)cc1N1CCC(N(C)C)CC1] | N-(5-((6-((S)-3-benzylisoxazolidine-2-yl)pyrimidine-4-yl)amino)-2-(4-(dimethylamino)piperidine-1-yl)-4-methoxyphenyl) acrylamide | ¹H NMR (400 MHz, Chloroform-d) δ 8.86 (s, 1H), 8.45 (s, 1H), 8.38 (s, 1H), 7.35-7.29 (m, 4H), 7.21 (d, J = 6.8 Hz, 1H), 6.88 (s, 1H), 6.74 (s, 1H), 6.59 (s, 1H), 6.33-6.13 (m, 2H), 5.73 (dd, J = 9.8, 1.7 Hz, 1H), 4.93-4.84 (m, 1H), 4.06 (td, J = 8.1, 4.8 Hz, 1H), 3.96 (q, J = 8.0 Hz, 1H), 3.83 (s, 3H), 3.26 (dd, J = 13.7, 5.8 Hz, 1H), 3.07 (m, 2H), 2.84-2.68 (m, 4H), 2.43 (s, 6H), 2.23-2.13 (m, 2H), 2.13-2.02 (m, 4H), ; 558.5 [M + H]⁺ | 1.11 |

TABLE 1-continued

| Example Compound | Structure | Name of Compound | ¹H NMR[[:]]; MS [M + H]⁺ | UPLC r.t. (min) |
|---|---|---|---|---|
| 952 | 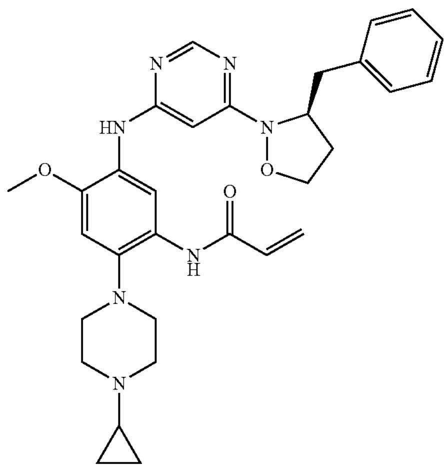 [SMILES: C=CC(=O)Nc1cc(Nc2cc(N3OCC[C@@H]3Cc3ccccc3)ncn2)c(OC)cc1N1CCN(C2CC2)CC1] | N-(5-((6-((S)-3-benzylisoxazolidine-2-yl)pyrimidine-4-yl)amino)-2-(4-cyclopropylpiperazine-1-yl)-4-methoxyphenyl) acrylamide | ¹H NMR (400 MHz, Chloroform-d) δ 8.89 (s, 1H), 8.59 (s, 1H), 8.38 (s, 1H), 7.36-7.27 (m, 4H), 7.24-7.18 (m, 1H), 6.86 (s, 1H), 6.78 (s, 1H), 6.59 (s, 1H), 6.40-6.23 (m, 2H), 5.75 (dd, J = 9.8, 1.7 Hz, 1H), 4.93-4.85 (m, 1H), 4.06 (td, J = 8.1, 4.7 Hz, 1H), 3.97 (q, J = 8.0 Hz, 1H), 3.80 (s, 3H), 3.26 (dd, J = 13.7, 5.7 Hz, 1H), 2.90-2.75 (m, 9H), 2.23-2.13 (m, 1H), 2.07 (m, 1H), 1.72 (mz, 1H), 0.52 (m, 2H), 0.47 (m, 2H), ; 556.5 [M + H]⁺ | 1.15 |
| 953 | 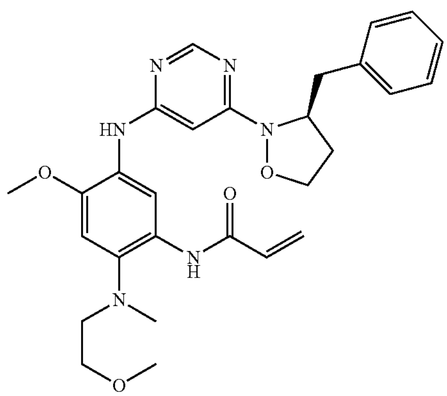 [SMILES: C=CC(=O)Nc1cc(Nc2cc(N3OCC[C@@H]3Cc3ccccc3)ncn2)c(OC)cc1N(C)CCOC] | N-(5-((6-((S)-3-benzylisoxazolidine-2-yl)pyrimidine-4-yl)amino)-4-methoxy-2-((2-methoxyethyl)(methyl)amino)phenyl) acrylamide | ¹H NMR (400 MHz, Chloroform-d) δ 9.12 (s, 1H), 8.97 (s, 1H), 8.38 (s, 1H), 7.35-7.27 (m, 4H), 7.23-7.17 (m, 1H), 6.86 (s, 1H), 6.76 (s, 1H), 6.61 (s, 1H), 6.45-6.24 (m, 2H), 5.68 (dd, J = 9.8, 2.0 Hz, 1H), 4.89 (m, 1H), 4.10-3.94 (m, 2H), 3.83 (s, 3H), 3.45 (t, J = 4.9 Hz, 2H), 3.42 (s, 3H), 3.26 (dd, J = 13.6, 5.7 Hz, 1H), 2.96 (m, 2H), 2.80 (dd, J = 13.7, 8.9 Hz, 1H), 2.75 (s, 3H), 2.23-2.13 (m, 1H), 2.06 (m, 1H), ; 519.47 [M + H]⁺ | 1.51 |
| 954 | 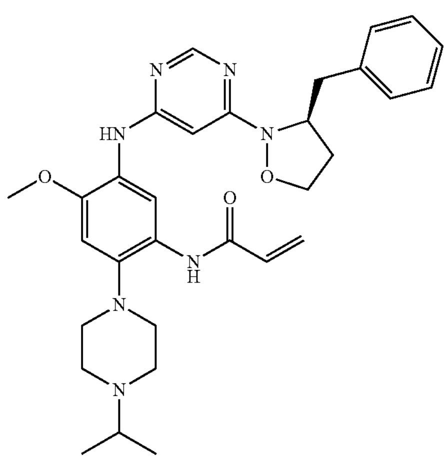 [SMILES: C=CC(=O)Nc1cc(Nc2cc(N3OCC[C@@H]3Cc3ccccc3)ncn2)c(OC)cc1N1CCN(C(C)C)CC1] | N-(5-((6-((S)-3-benzylisoxazolidine-2-yl)pyrimidine-4-yl)amino)-2-(4-isopropylpiperazine-1-yl)-4-methoxyphenyl) acrylamide | ¹H NMR (400 MHz, Chloroform-d) δ 8.89 (s, 1H), 8.57 (s, 1H), 8.38 (d, J = 1.0 Hz, 1H), 7.36-7.27 (m, 4H), 7.25-7.19 (m, 1H), 6.86 (s, 1H), 6.82 (s, 1H), 6.59 (s, 1H), 6.39-6.22 (m, 2H) 5.74 (dd, J = 9.9, 1.7 Hz, 1H), 4.88 (m, 1H), 4.06 (td, J = 8.1, 4.7 Hz, 1H), 3.97 (q, J = 8.0 Hz, 1H), 3.81 (s, 3H), 3.26 (dd, J = 13.7, 5.8 Hz, 1H), 2.92 (m, 4H), 2.84-2.75 (m, 2H), 2.72 (m, 4H), 2.17 (m, 1H), 2.07 (m, 1H), 1.12 (d, J = 6.5 Hz, 6H), ; 558.5 [M + H]⁺ | 1.15 |

TABLE 1-continued

| Example Compound | Structure | Name of Compound | ¹H NMR[[:]]; MS [M + H]⁺ | UPLC r.t. (min) |
|---|---|---|---|---|
| 955 | 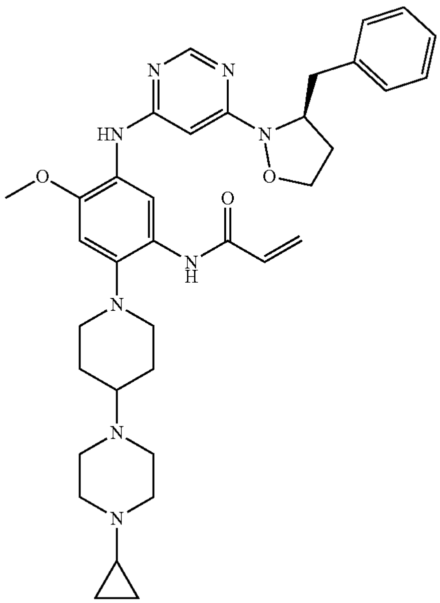 [SMILES: C=CC(=O)Nc1cc(Nc2cc(N3OCC[C@@H]3Cc3ccccc3)ncn2)c(OC)cc1N1CCC(N2CCN(C3CC3)CC2)CC1] | N-(5-((6-((S)-3-benzylisoxazolidine-2-yl)pyrimidine-4-yl)amino)-2-(4-(4-cyclopropylpiperazine-1-yl)piperidine-1-yl)-4-methoxyphenyl) acrylamide | ¹H NMR (400 MHz, Chloroform-d) δ 8.85 (s, 1H), 8.44 (s, 1H), 8.38 (s, 1H), 7.33-7.29 (m, 4H), 7.24-7.21 (m, 1H), 6.84 (s, 1H), 6.73 (s, 1H), 6.59 (s, 1H), 6.37-6.31 (m, 1H), 6.23 (dd, J = 16.9, 10.0 Hz, 1H), 5.73 (dd, J = 9.9, 1.6 Hz, 1H), 4.91-4.85 (m, 1H), 4.04 (dd, J = 8.1, 4.7 Hz, 1H), 3.96 (q, J = 8.0 Hz, 1H), 3.83 (s, 3H), 3.26 (dd, J = 13.7, 5.8 Hz, 1H), 3.05 (d, J = 11.5 Hz, 2H), 2.83-2.75 (m, 2H), 2.63 (s, 4H), 2.32 (s, 1H), 2.16 (dt, J = 7.8, 3.8 Hz, 1H), 2.10-2.05 (m, 3H), 1.64 (s, 4H), 1.26 (d, J = 4.3 Hz, 3H), 0.89-0.85 (m, 1H), 0.48-0.41 (m, 4H); 639.6 [M + H]⁺ | 1.18 |
| 956 | 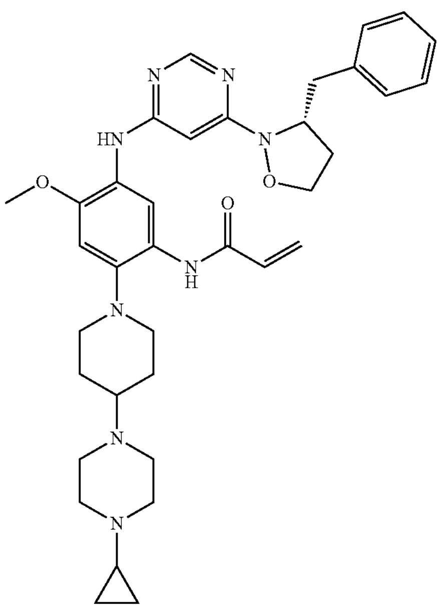 | N-(5-((6-((R)-3-benzylisoxazolidine-2-yl)pyrimidine-4-yl)amino)-2-(4-(4-cyclopropylpiperazine-1-yl)piperidine-1-yl)-4-methoxyphenyl) acrylamide | ¹H NMR (400 MHz, Chloroform-d) δ 8.85 (s, 1H), 8.43 (s, 1H), 8.38 (s, 1H), 7.33-7.28 (m, 4H), 7.24-7.19 (m, 1H), 6.84 (s, 1H), 6.73 (s, 1H), 6.58 (s, 1H), 6.38-6.31 (m, 1H), 6.24 (dd, J = 16.9, 10.0 Hz, 1H), 5.73 (dd, J = 9.9, 1.6 Hz, 1H), 4.95-4.79 (m, 1H), 4.05 (td, J = 8.1, 4.7 Hz, 1H), 3.96 (q, J = 8.0 Hz, 1H), 3.83 (s, 3H), 3.26 (dd, J = 13.7, 5.7 Hz, 1H), 3.05 (d, J = 11.5 Hz, 2H), 2.85-2.76 (m, 2H), 2.64 (s, 4H), 2.33 (s, 1H), 2.17 (tq, J = 8.2, 4.8, 4.0 Hz, 1H), 2.07 (tt, J = 8.0, 3.9 Hz, 3H), 1.63 (s, 4H), 1.26 (s, 3H), 0.88-0.85 (m, 1H), 0.49-0.41 (m, 4H); 639.6 [M + H]⁺ | 1.18 |

TABLE 1-continued

| Example Compound | Structure | Name of Compound | ¹H NMR[[:]]; MS [M + H]⁺ | UPLC r.t. (min) |
|---|---|---|---|---|
| 957 | 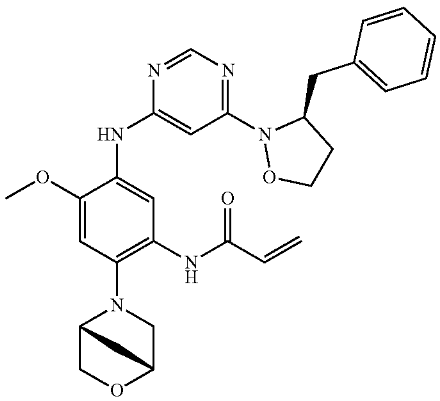 [SMILES: C=CC(=O)Nc1cc(Nc2cc(N3OCC[C@@H]3Cc3ccccc3)ncn2)c(OC)cc1N1C[C@H]2C[C@@H]1CO2] | N-(5-((6-((S)-3-benzylisoxazolidine-2-yl)pyrimidine-4-yl)amino)-2-((1R,4R)-2-oxa-5-azabicyclo[2.2.1]heptane-5-yl)-4-methoxyphenyl)acrylamide | ¹H NMR (400 MHz, Chloroform-d) δ 8.63 (s, 1H), 8.37 (s, 1H), 7.95 (s, 1H), 7.35-7.31 (m, 4H), 7.24-7.18 (m, 1H), 6.81 (s, 1H), 6.71 (s, 1H), 6.56 (s, 1H), 6.38 (d, J = 17.0 Hz, 1H), 6.27 (dd, J = 16.8, 10.0 Hz, 1H), 5.75 (d, J = 9.8 Hz, 1H), 4.93-4.83 (m, 1H), 4.65 (s, 1H), 4.09-4.02 (m, 2H), 4.00-3.92 (m, 1H), 3.89-3.86 (m, 1H), 3.85 (s, 3H), 3.74 (d, J = 8.0 Hz, 1H), 3.44 (d, J = 10.2 Hz, 1H), 3.29-3.18 (m, 2H), 2.80 (dd, J = 13.7, 9.0 Hz, 1H), 2.12-1.96 (m, 4H), ; 529.4 [M + H]⁺ | 1.28 |
| 958 | 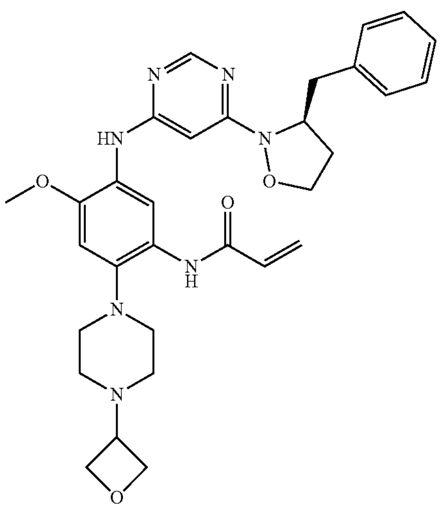 [SMILES: C=CC(=O)Nc1cc(Nc2cc(N3OCC[C@@H]3Cc3ccccc3)ncn2)c(OC)cc1N1CCN(C2COC2)CC1] | N-(5-((6-((S)-3-benzylisoxazolidine-2-yl)pyrimidine-4-yl)amino)-4-methoxy-2-(4-(oxetane-3-yl)piperazine-1-yl)phenyl)acrylamide | ¹H NMR (400 MHz, Chloroform-d) δ 8.90 (s, 1H), 8.48 (s, 1H), 8.39 (d, J = 0.9 Hz, 1H), 7.34-7.27 (m, 4H), 7.22 (t, J = 6.6 Hz, 1H), 6.88 (s, 1H), 6.80 (s, 1H), 6.60 (s, 1H), 6.35 (dd, J = 16.9, 1.5 Hz, 1H), 6.24 (dd, J = 16.9, 9.9 Hz, 1H), 5.74 (dd, J = 10.0, 1.5 Hz, 1H), 4.89 (tt, J = 9.1, 4.4 Hz, 1H), 4.72 (t, J = 6.5 Hz, 2H), 4.66 (t, J = 6.2 Hz, 2H), 4.06 (td, J = 8.1, 4.7 Hz, 1H), 3.96 (q, J = 8.0 Hz, 1H), 3.83 (s, 3H), 3.60 (p, J = 6.4 Hz, 1H), 3.26 (dd, J = 13.7, 5.8 Hz, 1H), 2.95 (t, J = 4.8 Hz, 4H), 2.80 (dd, J = 13.7, 8.9 Hz, 1H), 2.53 (s, 3H), 2.18 (dtd, J = 12.6, 8.2, 4.8 Hz, 1H), 2.06 (dtd, J = 12.3, 8.1, 4.1 Hz, 1H), 1.25 (s, 1H), ; 572.4 [M + H]⁺ | 1.15 |
| 959 | 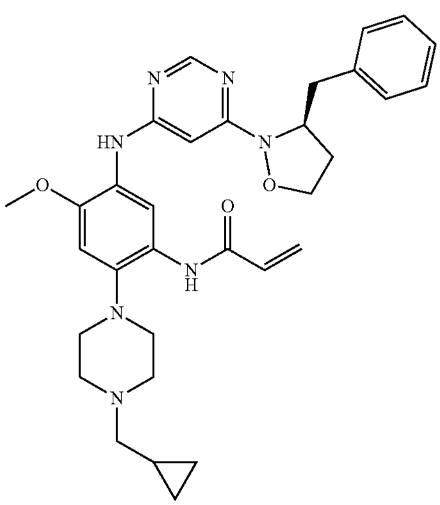 [SMILES: C=CC(=O)Nc1cc(Nc2cc(N3OCC[C@@H]3Cc3ccccc3)ncn2)c(OC)cc1N1CCN(CC2CC2)CC1] | N-(5-((6-((S)-3-benzylisoxazolidine-2-yl)pyrimidine-4-yl)amino)-2-(4-(cyclopropylmethyl)piperazine-1-yl)-4-methoxyphenyl)acrylamide | ¹H NMR (400 MHz, Chloroform-d) δ 8.90 (s, 1H), 8.57 (s, 1H), 8.38 (s, 1H), 7.34-7.29 (m, 4H), 7.22 (t, J = 6.6 Hz, 1H), 6.86 (s, 1H), 6.82 (s, 1H), 6.60 (s, 1H), 6.36 (d, J = 16.4 Hz, 1H), 6.25 (dd, J = 17.0, 9.9 Hz, 1H), 5.73 (dd, J = 9.9, 1.6 Hz, 1H), 4.93-4.85 (m, 1H), 4.06 (td, J = 8.1, 4.7 Hz, 1H), 3.97 (q, J = 8.1 Hz, 1H), 3.82 (s, 3H), 3.26 (dd, J = 13.7, 5.7 Hz, 1H), 2.93 (d, J = 5.6 Hz, 4H), 2.80 (dd, J = 13.7, 8.9 Hz, 2H), 2.72 (s, 3H), 2.35 (d, J = 6.6 Hz, 2H), 2.17 (ddt, J = 12.5, 8.0, 3.9 Hz, 1H), 2.07 (tt, J = 8.0, 4.0 Hz, 1H), 0.98-0.81 (m, 1H), 0.60-0.53 (m, 2H), 0.16 (q, J = 4.9 Hz, 2H), ; 570.5 [M + H]⁺ | 1.18 |

TABLE 1-continued

| Example Compound | Structure | Name of Compound | $^1$H NMR[[:]]; MS [M + H]$^+$ | UPLC r.t. (min) |
|---|---|---|---|---|
| 960 | 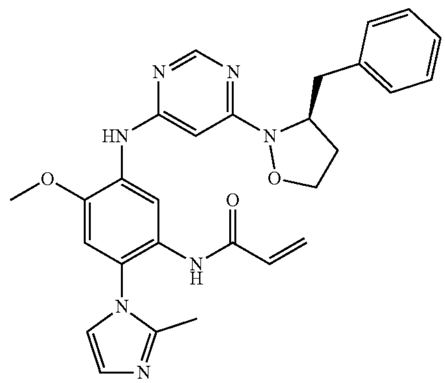 [SMILES: C=CC(=O)Nc1cc(Nc2cc(N3OCC[C@@H]3Cc3ccccc3)ncn2)c(OC)cc1-n1ccnc1C] | N-(5-((6-((S)-3-benzylisoxazolidine-2-yl)pyrimidine-4-yl)amino)-4-methoxy-2-(2-methyl-1H-imidazole-1-yl)phenyl)acrylamide | $^1$H NMR (400 MHz, Chloroform-d) δ 9.10 (s, 1H), 8.46 (s, 1H), 7.32 (d, J = 6.3 Hz, 4H), 7.23 (s, 1H), 7.14 (d, J = 5.9 Hz, 2H), 6.94 (s, 1H), 6.73 (s, 1H), 6.70 (s, 1H), 6.65 (s, 1H), 6.27 (d, J = 16.9 Hz, 1H), 6.04 (dd, J = 16.7, 10.2 Hz, 1H), 5.70 (d, J = 10.4 Hz, 1H), 4.89 (s, 1H), 4.11 (d, J = 8.1 Hz, 1H), 3.94 (d, J = 8.0 Hz, 1H), 3.88 (s, 3H), 3.29 (dd, J = 13.6, 5.7 Hz, 1H), 2.82 (dd, J = 13.6, 8.9 Hz, 1H), 2.24 (s, 3H), 2.20 (s, 1H), 2.12 (s, 1H); 512.5 [M + H]$^+$ | 1.38 |
| 961 | 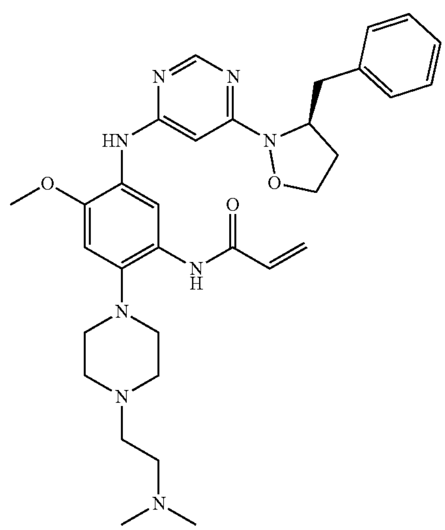 [SMILES: C=CC(=O)Nc1cc(Nc2cc(N3OCC[C@@H]3Cc3ccccc3)ncn2)c(OC)cc1N1CCN(CCN(C)C)CC1] | N-(5-((6-((S)-3-benzylisoxazolidine-2-yl)pyrimidine-4-yl)amino)-2-(4-(2-(dimethylamino)ethyl)piperazine-1-yl)-4-methoxyphenyl)acrylamide | $^1$H NMR (400 MHz, Chloroform-d) δ 8.88 (s, 1H), 8.49 (s, 1H), 8.38 (s, 1H), 7.32 (m, 4H), 7.22 (s, 1H), 6.90 (s, 1H), 6.79 (s, 1H), 6.59 (s, 1H), 6.35 (d, J = 17.2 Hz, 1H), 6.26 (s, 1H), 5.74 (d, J = 11.2 Hz, 1H), 4.88 (d, J = 13.0 Hz, 1H), 4.05 (d, J = 3.2 Hz, 1H), 3.96 (d, J = 8.0 Hz, 1H), 3.83 (s, 3H), 3.36 (d, J = 15.0 Hz, 2H), 3.26 (dd, J = 13.6, 5.7 Hz, 2H), 2.93 (s, 4H), 2.83-2.76 (m, 4H), 2.72 (s, 3H), 2.57 (s, 3H), 2.16 (d, J = 4.5 Hz, 2H), 2.06 (d, J = 8.1 Hz, 2H), ; 587.5 [M + H]$^+$ | 1.07 |
| 962 | 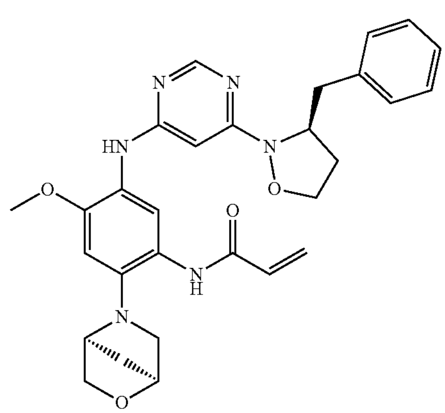 [SMILES: C=CC(=O)Nc1cc(Nc2cc(N3OCC[C@@H]3Cc3ccccc3)ncn2)c(OC)cc1N1C[C@@H]2C[C@H]1CO2] | N-(5-((6-((S)-3-benzylisoxazolidine-2-yl)pyrimidine-4-yl)amino)-2-((1S,4S)-2-oxa-5-azabicyclo[2.2.1]heptane-5-yl)-4-methoxyphenyl)acrylamide | $^1$H NMR (400 MHz, Chloroform-d) δ 8.66 (s, 1H), 8.37 (s, 1H), 7.95 (s, 1H), 7.32-7.29 (m, 4H), 7.23 (dd, J = 6.0, 2.7 Hz, 1H), 6.81 (s, 1H), 6.70 (s, 1H), 6.52 (s, 1H), 6.38 (d, J = 16.8 Hz, 1H), 6.27 (dd, J = 16.9, 10.0 Hz, 1H), 5.75 (d, J = 10.0 Hz, 1H), 4.87 (dd, J = 11.4, 6.2 Hz, 1H), 4.65 (s, 1H), 4.05 (d, J = 7.8 Hz, 2H), 3.94-3.88 (m, 1H), 3.85 (s, 3H), 3.75 (d, J = 7.8 Hz, 1H), 3.42 (d, J = 10.2 Hz, 1H), 3.29-3.21 (m, 2H), 2.79 (dd, J = 13.7, 8.9 Hz, 1H), 2.61 (s, 1H), 2.18-2.13 (m, 1H), 2.07 (ddd, J = 11.9, 7.8, 3.7 Hz, 2H), 1.99 (d, J = 9.9 Hz, 1H), ; 529.4 [M + H] | 1.29 |

TABLE 1-continued

| Example Compound | Structure | Name of Compound | ¹H NMR[[:]]; MS [M + H]⁺ | UPLC r.t. (min) |
|---|---|---|---|---|
| 963 | 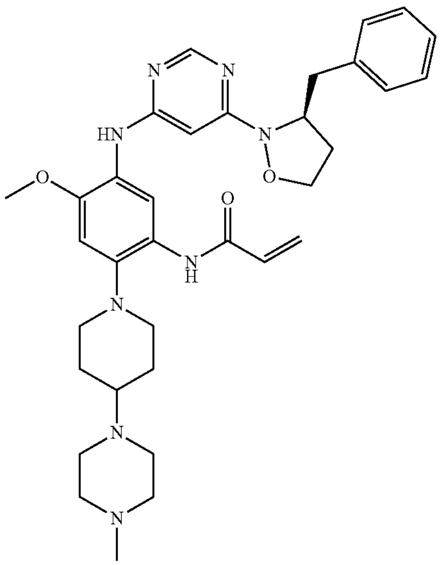 | N-(5-((6-((S)-3-benzylisoxazolidine-2-yl)pyrimidine-4-yl)amino)-4-methoxy-2-(4-(4-methylpiperazine-1-yl)piperidine-1-yl)phenyl)acrylamide | ¹H NMR (400 MHz, Chloroform-d) δ 8.84 (s, 1H), 8.39 (d, J = 10.9 Hz, 2H), 7.31 (d, J = 6.7 Hz, 4H), 7.24-7.21 (m, 1H), 6.93 (s, 1H), 6.73 (s, 1H), 6.58 (s, 1H), 6.39-6.33 (m, 1H), 6.25 (dd, J = 16.9, 9.9 Hz, 1H), 5.76-5.71 (m, 1H), 4.87 (dd, J = 11.2, 6.2 Hz, 1H), 4.05 (dd, J = 8.1, 4.7 Hz, 1H), 3.96 (d, J = 8.0 Hz, 1H), 3.83 (s, 3H), 3.65 (p, J = 6.7 Hz, 2H), 3.24 (d, J = 5.7 Hz, 1H), 3.08 (d, J = 7.4 Hz, 2H), 2.83-2.71 (m, 6H), 2.48 (s, 3H), 2.16 (tt, J = 8.1, 4.5 Hz, 3H), 2.07 (dt, J = 7.8, 4.2 Hz, 3H), 1.71 (d, J = 12.6 Hz, 2H), 1.55 (t, J = 7.4 Hz, 2H), ; 613.6 [M + H] | 1.09 |
| 964 | 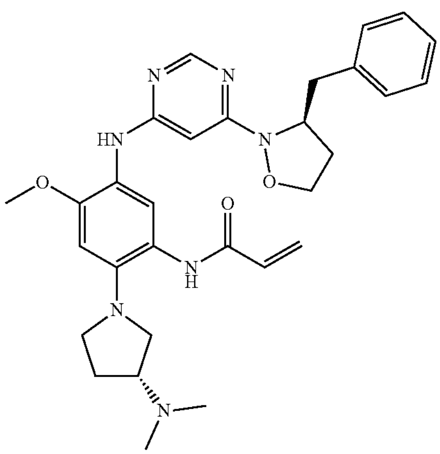 [SMILES: C=CC(=O)Nc1cc(Nc2cc(N3OCC[C@@H]3Cc3ccccc3)ncn2)c(OC)cc1N1CC[C@@H](N(C)C)C1] | N-(5-((6-((S)-3-benzylisoxazolidine-2-yl)pyrimidine-4-yl)amino)-2-((R)-3-(dimethylamino)pyrolidine-1-yl)-4-methoxyphenyl)acrylamide | ¹H NMR (400 MHz, Chloroform-d) δ 8.68 (s, 1H), 8.53 (s, 1H), 8.35 (d, J = 0.9 Hz, 1H), 7.34-7.27 (m, 4H), 7.24-7.20 (m, 1H), 6.92 (s, 1H), 6.65 (s, 1H), 6.54 (s, 1H), 6.43-6.28 (m, 2H), 5.71 (dd, J = 10.2, 1.8 Hz, 1H), 4.91-4.82 (m, 1H), 4.05 (dd, J = 8.1, 4.8 Hz, 1H), 3.95 (q, J = 8.0 Hz, 1H), 3.82 (s, 3H), 3.65 (p, J = 6.7 Hz, 2H), 3.28-3.23 (m, 1H), 3.09 (q, J = 7.5 Hz, 2H), 2.79 (dd, J = 13.7, 8.9 Hz, 1H), 2.62 (s, 3H), 2.30 (s, 2H), 2.16 (ddt, J = 12.6, 8.1, 4.5 Hz, 2H), 2.06 (dq, J = 8.0, 4.0 Hz, 2H), 1.55 (t, J = 7.4 Hz, 2H), 544.5 [M + H] | 1.13 |
| 965 | 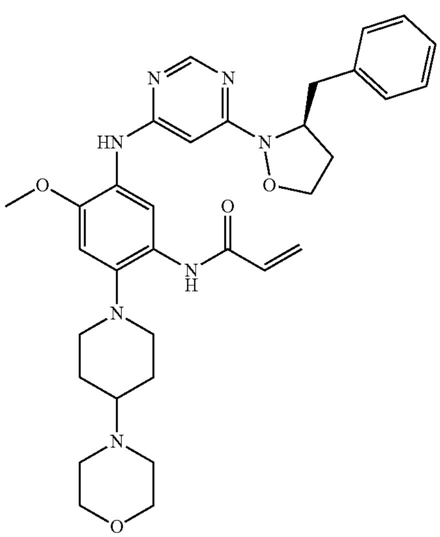 | N-(5-((6-((S)-3-benzylisoxazolidine-2-yl)pyrimidine-4-yl)amino)-4-methoxy-2-(4-morpholinopiperidine-1-yl)phenyl)acrylamide | ¹H NMR (400 MHz, Chloroform-d) δ 8.86 (s, 1H), 8.43 (s, 1H), 8.38 (d, J = 1.0 Hz, 1H), 7.34-7.27 (m, 4H), 7.24-7.20 (m, 1H), 6.85 (s, 1H), 6.74 (s, 1H), 6.59 (s, 1H), 6.39-6.32 (m, 1H), 6.24 (dd, J = 16.9, 10.0 Hz, 1H), 5.73 (dd, J = 10.0, 1.6 Hz, 1H), 4.92-4.85 (m, 1H), 4.06 (td, J = 8.0, 4.7 Hz, 1H), 3.96 (q, J = 8.0 Hz, 1H), 3.83 (s, 3H), 3.78 (s, 3H), 3.29-3.24 (m, 1H), 3.07 (d, J = 11.5 Hz, 2H), 2.80 (dd, J = 13.7, 8.9 Hz, 1H), 2.72 (dd, J = 12.0, 9.5 Hz, 2H), 2.63 (s, 3H), 2.21-2.14 (m, 1H), 2.07 (tt, J = 8.0, 3.8 Hz, 3H), 1.57-1.53 (m, 3H), 1.45 (d, J = 6.7 Hz, 2H), ; 600.5 [M + H] | 1.15 |

TABLE 1-continued

| Example Compound | Structure | Name of Compound | ¹H NMR[[:]]; MS [M + H]⁺ | UPLC r.t. (min) |
|---|---|---|---|---|
| 966 | 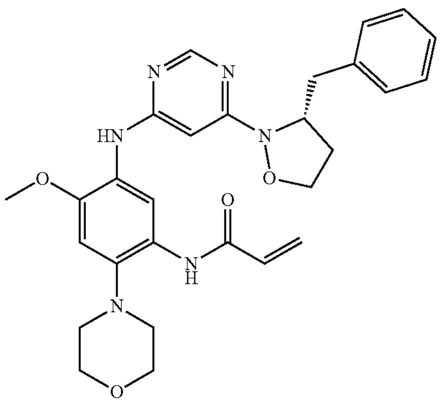 [SMILES: C=CC(=O)Nc1cc(Nc2cc(N3OCC[C@H]3Cc3ccccc3)ncn2)c(OC)cc1N1CCOCC1] | N-(5-((6-((R)-3-benzylisoxazolidine-2-yl)pyrimidine-4-yl)amino)-4-methoxy-2-morpholinophenyl)acrylamide | ¹H NMR (400 MHz, Chloroform-d) δ 8.92 (s, 1H), 8.50 (s, 1H), 8.39 (d, J = 0.9 Hz, 1H), 7.34-7.28 (m, 4H), 7.24-7.20 (m, 1H), 6.89 (s, 1H), 6.76 (s, 1H), 6.60 (s, 1H), 6.40-6.31 (m, 1H), 6.26 (dd, J = 17.0, 9.9 Hz, 1H), 5.75 (dd, J = 9.9, 1.5 Hz, 1H), 4.89 (tq, J = 8.9, 4.1 Hz, 1H), 4.06 (td, J = 8.1, 4.7 Hz, 1H), 3.97 (t, J = 8.0 Hz, 1H), 3.88 (t, J = 4.6 Hz, 3H), 3.85 (s, 2H), 3.26 (dd, J = 13.7, 5.8 Hz, 1H), 2.88 (dd, J = 6.0, 3.5 Hz, 3H), 2.80 (dd, J = 13.7, 8.9 Hz, 1H), 2.23-2.13 (m, 1H), 2.07 (dtd, J = 12.0, 7.9, 3.9 Hz, 1H), 1.59 (s, 3H), ; 517.4 [M + H] | 1.53 |
| 967 | 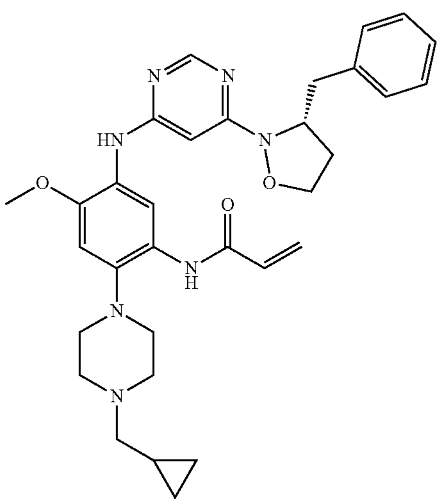 [SMILES: C=CC(=O)Nc1cc(Nc2cc(N3OCC[C@H]3Cc3ccccc3)ncn2)c(OC)cc1N1CCN(CC2CC2)CC1] | N-(5-((6-((R)-3-benzylisoxazolidine-2-yl)pyrimidine-4-yl)amino)-2-(4-(cyclopropylmethyl)piperazine-1-yl)-4-methoxyphenyl)acrylamide | ¹H NMR (400 MHz, Chloroform-d) δ 8.89 (s, 1H), 8.52 (s, 1H), 8.38 (d, J = 1.0 Hz, 1H), 7.34-7.27 (m, 4H), 7.24-7.20 (m, 1H), 6.89 (s, 1H), 6.79 (s, 1H), 6.59 (s, 1H), 6.36 (dd, J = 17.0, 1.6 Hz, 1H), 6.26 (dd, J = 17.2, 9.6 Hz, 1H), 5.74 (dd, J = 9.9, 1.6 Hz, 1H), 4.88 (tt, J = 8.9, 4.9 Hz, 1H), 4.06 (td, J = 8.0, 4.7 Hz, 1H), 3.96 (q, J = 8.1 Hz, 1H), 3.83 (s, 3H), 3.62-3.57 (m, 1H), 3.26 (dd, J = 13.7, 5.9 Hz, 1H), 3.03 (d, J = 7.7 Hz, 1H), 2.92 (t, J = 4.9 Hz, 4H), 2.80 (dd, J = 13.7, 8.9 Hz, 1H), 2.62 (s, 3H), 2.40 (s, 3H), 2.27 (s, 1H), 2.19-2.12 (m, 1H), 2.10-2.01 (m, 2H), 1.85 (p, J = 6.9 Hz, 1H), ; 570.5 [M + H] | 1.30 |
| 968 | 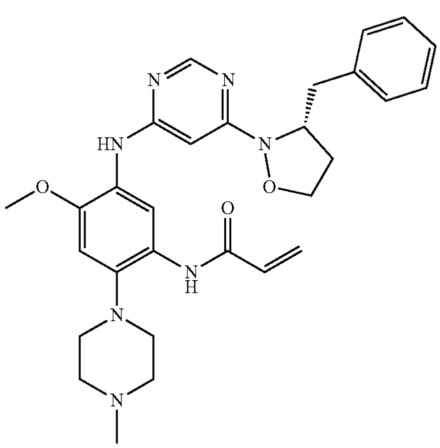 [SMILES: C=CC(=O)Nc1cc(Nc2cc(N3OCC[C@H]3Cc3ccccc3)ncn2)c(OC)cc1N1CCN(C)CC1] | N-(5-((6-((R)-3-benzylisoxazolidine-2-yl)pyrimidine-4-yl)amino)-4-methoxy-2-(4-methylpiperazine-1-yl)phenyl)acrylamide | ¹H NMR (400 MHz, Chloroform-d) δ 8.90 (s, 1H), 8.56 (s, 1H), 8.39 (d, J = 0.9 Hz, 1H), 7.34-7.28 (m, 4H), 7.24-7.19 (m, 1H), 6.87 (s, 1H), 6.82 (s, 1H), 6.59 (s, 1H), 6.39-6.32 (m, 1H), 6.25 (dd, J = 16.9, 10.0 Hz, 1H), 5.74 (dd, J = 9.9, 1.6 Hz, 1H), 4.88 (dp, J = 9.0, 4.4 Hz, 1H), 4.06 (td, J = 8.1, 4.7 Hz, 1H), 3.96 (q, J = 8.1 Hz, 1H), 3.82 (s, 3H), 3.26 (dd, J = 13.7, 5.8 Hz, 1H), 2.95 (s, 3H), 2.80 (dd, J = 13.6, 8.9 Hz, 2H), 2.37 (d, J = 6.5 Hz, 2H), 2.17 (h, J = 3.9, 3.4 Hz, 1H), 2.09-2.03 (m, 1H), 1.63 (s, 3H), 1.54 (d, J = 7.6 Hz, 2H), ; 530.5 [M + H] | 1.26 |

TABLE 1-continued

| Example Compound | Structure | Name of Compound | ¹H NMR[[:]]; MS [M + H]⁺ | UPLC r.t. (min) |
|---|---|---|---|---|
| 969 | 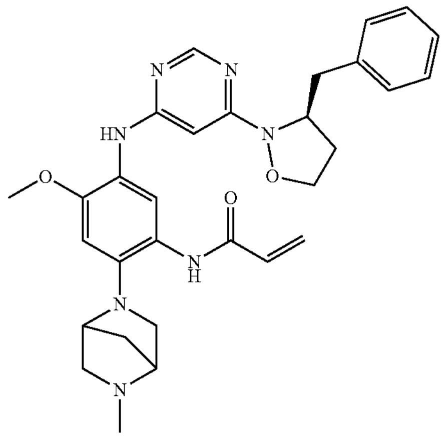 [SMILES: C=CC(=O)Nc1cc(Nc2cc(N3OCC[C@@H]3Cc3ccccc3)ncn2)c(OC)cc1N1CC2CC1CN2C] | N-(5-((6-((S)-3-benzylisoxazolidine-2-yl)pyrimidine-4-yl)amino)-4-methoxy-2-(5-methyl-2,5-diazabicyclo[2.2.1]heptane-2-yl)phenyl)acrylamide | ¹H NMR (400 MHz, DMSO-d6) δ 9.24 (s, 1H), 8.37 (s, 1H), 8.13 (s, 1H), 7.30 (d, J = 4.4 Hz, 5H), 7.21 (h, J = 4.2 Hz, 1H), 6.44 (dd, J = 17.1, 10.2 Hz, 1H), 6.37 (s, 1H), 6.23-6.07 (m, 2H), 5.67 (dd, J = 10.2, 2.1 Hz, 1H), 4.74 (qd, J = 7.6, 3.6 Hz, 1H), 4.16 (s, 1H), 4.04 (td, J = 8.0, 4.7 Hz, 1H), 3.76 (s, 4H), 3.11-2.98 (m, 2H), 2.80-2.69 (m, 3H), 2.10 (dq, J = 7.8, 3.9, 3.5 Hz, 1H), 1.98 (ddd, J = 11.8, 7.8, 3.7 Hz, 1H), 1.80 (d, J = 9.3 Hz, 1H), 1.68 (d, J = 9.2 Hz, 1H), 1.24 (s, 3H), 0.92-0.76 (m, 2H), ; 542.5 [M + H]⁺ | 1.12 |
| 970 | 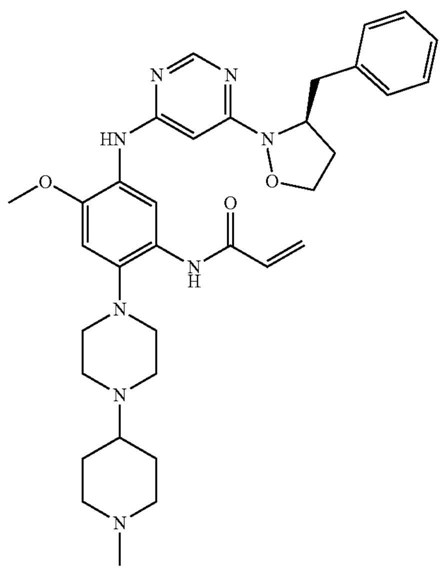 [SMILES: C=CC(=O)Nc1cc(Nc2cc(N3OCC[C@@H]3Cc3ccccc3)ncn2)c(OC)cc1N1CCN(C2CCN(C)CC2)CC1] | N-(5-((6-((S)-3-benzylisoxazolidine-2-yl)pyrimidine-4-yl)amino)-4-methoxy-2-(4-(1-methylpiperidine-4-yl)piperazine-1-yl)phenyl)acrylamide | ¹H NMR (400 MHz, Chloroform-d) δ 8.89 (s, 1H), 8.54 (s, 1H), 8.38 (s, 1H), 7.34-7.27 (m, 4H), 7.22 (t, J = 6.6 Hz, 1H), 6.86 (s, 1H), 6.80 (s, 1H), 6.59 (s, 1H), 6.39-6.32 (m, 1H), 6.25 (dd, J = 17.0, 9.9 Hz, 1H), 5.74 (dd, J = 9.9, 1.7 Hz, 1H), 4.92-4.83 (m, 1H), 4.06 (td, J = 8.0, 4.7 Hz, 1H), 3.96 (q, J = 7.9 Hz, 1H), 3.81 (s, 3H), 3.26 (dd, J = 13.6, 5.8 Hz, 2H), 3.00 (d, J = 11.6 Hz, 2H), 2.93-2.89 (m, 4H), 2.83-2.77 (m, 2H), 2.75 (s, 2H), 2.34 (s, 3H), 2.17 (s, 2H), 2.06 (d, J = 8.1 Hz, 3H), 1.88 (d, J = 13.7 Hz, 2H), 1.46 (s, 2H), ; 613.6 [M + H]⁺ | 1.03 |
| 971 | 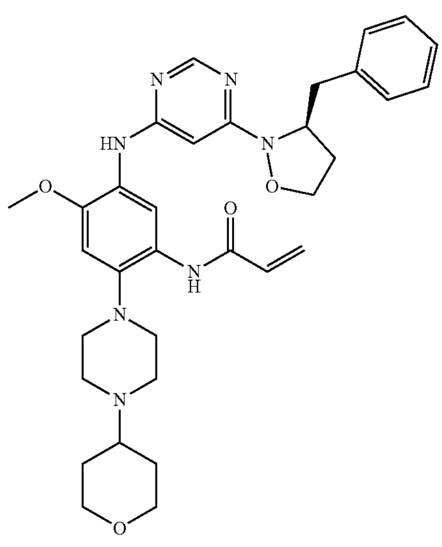 [SMILES: C=CC(=O)Nc1cc(Nc2cc(N3OCC[C@@H]3Cc3ccccc3)ncn2)c(OC)cc1N1CCN(C2CCOCC2)CC1] | N-(5-((6-((S)-3-benzylisoxazolidine-2-yl)pyrimidine-4-yl)amino)-4-methoxy-2-(4-(tetrahydro-2H-pyran-4-yl)piperazine-1-yl)phenyl)acrylamide | ¹H NMR (400 MHz, Chloroform-d) δ 8.89 (s, 1H), 8.54 (s, 1H), 8.39 (s, 1H), 7.32 (s, 4H), 7.23 (d, J = 6.7 Hz, 1H), 6.87 (s, 1H), 6.80 (s, 1H), 6.59 (s, 1H), 6.36 (d, J = 16.1 Hz, 1H), 6.30-6.20 (m, 1H), 5.74 (d, J = 11.4 Hz, 1H), 4.90 (s, 1H), 4.06 (d, J = 4.4 Hz, 3H), 3.96 (d, J = 8.1 Hz, 1H), 3.82 (s, 3H), 3.42 (t, J = 11.1 Hz, 2H), 3.26 (dd, J = 13.7, 5.8 Hz, 1H), 2.93 (s, 4H), 2.84-2.69 (m, 5H), 2.52 (s, 1H), 2.17 (s, 2H), 2.06 (s, 2H), 1.83 (d, J = 10.8 Hz, 2H), ; 600.5 [M + H]⁺ | 1.16 |

TABLE 1-continued

| Example Compound | Structure | Name of Compound | ¹H NMR[[:]]; MS [M + H]⁺ | UPLC r.t. (min) |
|---|---|---|---|---|
| 972 | 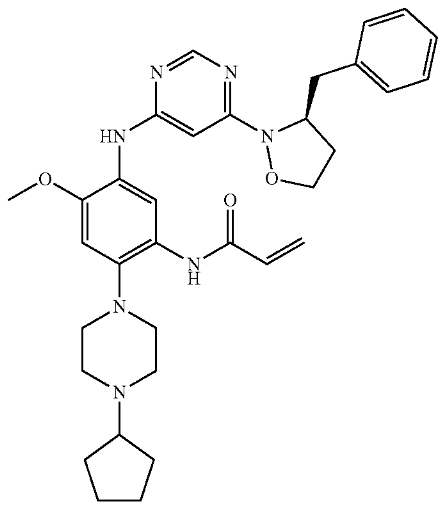 [SMILES: C=CC(=O)Nc1cc(Nc2cc(N3OCC[C@@H]3Cc3ccccc3)ncn2)c(OC)cc1N1CCN(C2CCCC2)CC1] | N-(5-((6-((S)-3-benzylisoxazolidine-2-yl)pyrimidine-4-yl)amino)-2-(4-cyclopentylpiperazine-1-yl)-4-methoxyphenyl)acrylamide | ¹H NMR (400 MHz, Chloroform-d) δ 8.89 (s, 1H), 8.58 (s, 1H), 8.38 (s, 1H), 7.31 (s, 4H), 7.22 (s, 1H), 6.87 (s, 1H), 6.81 (s, 1H), 6.59 (s, 1H), 6.35 (d, J = 16.0 Hz, 1H), 6.26 (dd, J = 16.9, 9.8 Hz, 1H), 5.74 (d, J = 9.9 Hz, 1H), 4.87 (s, 1H), 4.03 (s, 1H), 3.95 (s, 1H), 3.81 (s, 3H), 3.26 (dd, J = 13.7, 5.8 Hz, 1H), 2.93 (s, 4H), 2.80 (dd, J = 13.7, 8.9 Hz, 2H), 2.70 (s, 2H), 2.62-2.55 (m, 2H), 2.17 (s, 3H), 2.10-2.03 (m, 1H), 1.92 (s, 2H), 1.74 (s, 2H), 1.52-1.40 (m, 2H), ; 584.5 [M + H]⁺ | 1.22 |
| 973 | 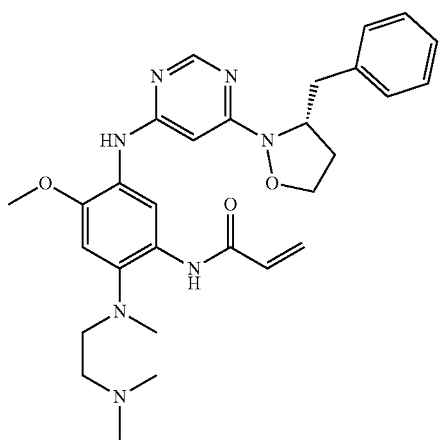 [SMILES: C=CC(=O)Nc1cc(Nc2cc(N3OCC[C@H]3Cc3ccccc3)ncn2)c(OC)cc1N(C)CCN(C)C] | N-(5-((6-((R)-3-benzylisoxazolidine-2-yl)pyrimidine-4-yl)amino)-2-((2-(dimethylamino)ethyl)(methyl)amino)-4-methoxyphenyl)acrylamide | ¹H NMR (400 MHz, Chloroform-d) δ 10.08 (s, 1H), 8.94 (s, 1H), 8.38 (s, 1H), 7.36-7.27 (m, 4H), 7.24-7.19 (m, 1H), 6.87 (s, 1H), 6.78 (s, 1H), 6.63 (s, 1H), 6.39 (dd, J = 16.9, 1.9 Hz, 1H), 6.29 (d, J = 11.0 Hz, 1H), 5.67 (dd, J = 9.8, 2.0 Hz, 1H), 4.93-4.85 (m, 1H), 4.10-3.96 (m, 2H), 3.83 (s, 3H), 3.26 (dd, J = 13.7, 5.8 Hz, 1H), 2.87 (s, 2H), 2.83 (s, 1H), 2.71 (s, 3H), 2.27 (s, 8H), 2.20-2.14 (m, 1H), 2.06 (dtd, J = 11.6, 7.8, 3.6 Hz, 1H), ; 532.5 [M + H] | 1.17 |
| 974 | 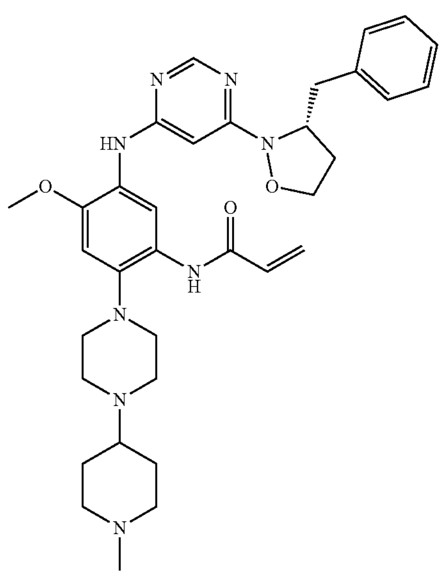 [SMILES: C=CC(=O)Nc1cc(Nc2cc(N3OCC[C@H]3Cc3ccccc3)ncn2)c(OC)cc1N1CCN(C2CCN(C)CC2)CC1] | N-(5-((6-((R)-3-benzylisoxazolidine-2-yl)pyrimidine-4-yl)amino)-4-methoxy-2-(4-(1-methylpiperidine-4-yl)piperazine-1-yl)phenyl)acrylamide | ¹H NMR (400 MHz, Chloroform-d) δ 8.88 (s, 1H), 8.47 (s, 1H), 8.38 (s, 1H), 7.31 (d, J = 6.9 Hz, 4H), 7.22 (t, J = 6.6 Hz, 1H), 6.88 (s, 1H), 6.78 (s, 1H), 6.59 (s, 1H), 6.36 (d, J = 17.1 Hz, 1H), 6.25 (dd, J = 17.0, 9.9 Hz, 1H), 5.77-5.72 (m, 1H), 4.91-4.85 (m, 1H), 4.05 (dd, J = 8.0, 4.8 Hz, 1H), 3.96 (q, J = 8.1 Hz, 1H), 3.83 (s, 3H), 3.37-3.33 (m, 1H), 3.28 (d, J = 5.8 Hz, 1H), 3.24 (d, J = 5.7 Hz, 1H), 3.22-3.18 (m, 2H), 3.17 (s, 1H), 3.00 (t, J = 6.4 Hz, 1H), 2.92 (s, 3H), 2.72 (s, 2H), 2.56 (s, 2H), 2.17 (s, 2H), 1.26 (s, 3H), 1.12 (t, J = 7.2 Hz, 1H), 1.07 (t, J = 7.2 Hz, 1H), 0.97 (d, J = 6.6 Hz, 1H), 0.90-0.86 (m, 2H), ; 613.6 [M + H] | 1.04 |

TABLE 1-continued

| Example Compound | Structure | Name of Compound | ¹H NMR[[:]]; MS [M + H]⁺ | UPLC r.t. (min) |
|---|---|---|---|---|
| 975 | 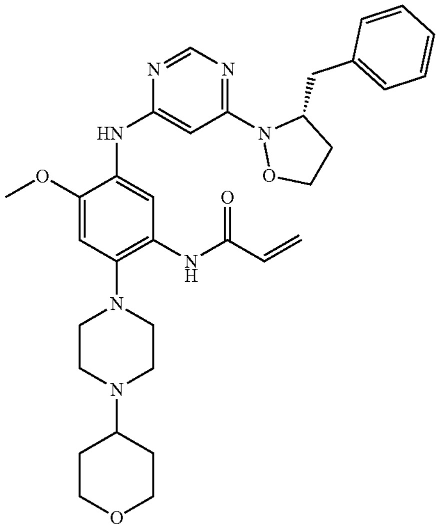 [SMILES: C=CC(=O)Nc1cc(Nc2cc(N3OCC[C@H]3Cc3ccccc3)ncn2)c(OC)cc1N1CCN(C2CCOCC2)CC1] | N-(5-((6-((R)-3-benzylisoxazolidine-2-yl)pyrimidine-4-yl)amino)-4-methoxy-2-(4-(tetrahydro-2H-pyran-4-yl)piperazine-1-yl)phenyl)acrylamide | ¹H NMR (400 MHz, Chloroform-d) δ 8.89 (s, 1H), 8.53 (s, 1H), 8.38 (s, 1H), 7.31 (d, J = 6.8 Hz, 4H), 7.24-7.20 (m, 1H), 6.88 (s, 1H), 6.80 (s, 1H), 6.59 (s, 1H), 6.36 (d, J = 16.8 Hz, 1H), 6.25 (dd, J = 16.9, 10.0 Hz, 1H), 5.77-5.71 (m, 1H), 4.93-4.85 (m, 1H), 4.09-4.04 (m, 2H), 3.96 (q, J = 8.1 Hz, 1H), 3.82 (s, 2H), 3.42 (t, J = 11.6 Hz, 2H), 3.26 (dd, J = 13.7, 5.7 Hz, 1H), 2.92 (d, J = 4.8 Hz, 3H), 2.76 (d, J = 5.9 Hz, 2H), 2.50 (d, J = 11.7 Hz, 1H), 2.17 (td, J = 8.6, 7.7, 3.8 Hz, 1H), 2.09-2.03 (m, 1H), 1.84 (d, J = 12.4 Hz, 2H), 1.69-1.63 (m, 2H), 1.26 (s, 4H), 0.90-0.83 (m, 2H), ; 600.5 [M + H] | 1.18 |
| 976 | 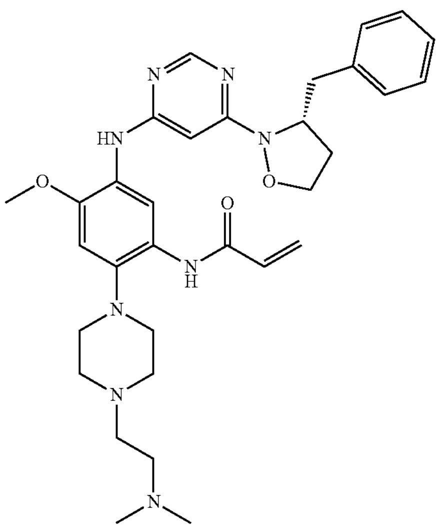 [SMILES: C=CC(=O)Nc1cc(Nc2cc(N3OCC[C@H]3Cc3ccccc3)ncn2)c(OC)cc1N1CCN(CCN(C)C)CC1] | N-(5-((6-((R)-3-benzylisoxazolidine-2-yl)pyrimidine-4-yl)amino)-2-(4-(2-(dimethylamino)ethyl)piperazine-1-yl)-4-methoxyphenyl)acrylamide | ¹H NMR (400 MHz, Chloroform-d) δ 8.88 (s, 1H), 8.50 (s, 1H), 8.38 (s, 1H), 7.31 (d, J = 6.8 Hz, 4H), 7.23 (d, J = 6.5 Hz, 1H), 6.89 (s, 1H), 6.79 (s, 1H), 6.59 (s, 1H), 6.33 (s, 1H), 6.27 (d, J = 10.1 Hz, 1H), 5.74 (d, J = 10.0 Hz, 1H), 4.88 (s, 1H), 4.05 (dd, J = 8.1, 4.7 Hz, 2H), 3.96 (d, J = 8.0 Hz, 1H), 3.83 (s, 3H), 3.37-3.32 (m, 3H), 3.28 (d, J = 5.8 Hz, 1H), 3.24 (d, J = 5.7 Hz, 1H), 2.93 (d, J = 4.9 Hz, 3H), 2.71 (s, 3H), 2.54 (s, 4H), 2.17 (s, 3H), 1.25 (s, 3H), ; 587.5 [M + H] | 1.08 |
| 977 | 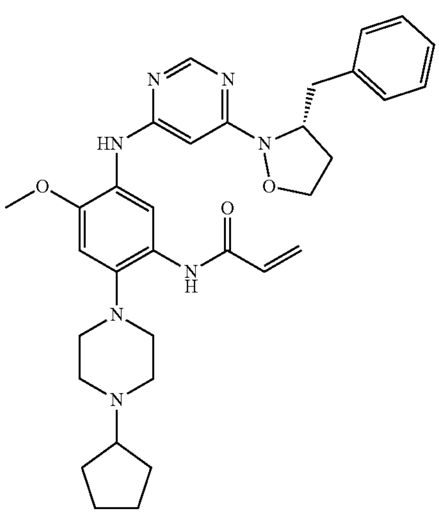 [SMILES: C=CC(=O)Nc1cc(Nc2cc(N3OCC[C@H]3Cc3ccccc3)ncn2)c(OC)cc1N1CCN(C2CCCC2)CC1] | N-(5-((6-((R)-3-benzylisoxazolidine-2-yl)pyrimidine-4-yl)amino)-2-(4-cyclopentylpiperazine-1-yl)-4-methoxyphenyl)acrylamide | ¹H NMR (400 MHz, Chloroform-d) δ 8.89 (s, 1H), 8.58 (s, 1H), 8.38 (d, J = 1.0 Hz, 1H), 7.35-7.27 (m, 4H), 7.24-7.19 (m, 1H), 6.86 (s, 1H), 6.81 (s, 1H), 6.59 (s, 1H), 6.39-6.32 (m, 1H), 6.26 (dd, J = 17.0, 9.9 Hz, 1H), 5.74 (dd, J = 9.8, 1.7 Hz, 1H), 4.87 (dd, J = 11.4, 6.2 Hz, 1H), 4.06 (td, J = 8.1, 4.6 Hz, 1H), 3.97 (q, J = 6.7, 5.5 Hz, 1H), 3.81 (s, 3H), 3.26 (dd, J = 13.7, 5.8 Hz, 1H), 2.92 (d, J = 5.1 Hz, 3H), 2.80 (dd, J = 13.7, 8.9 Hz, 1H), 2.62 (s, 1H), 2.17 (s, 2H), 2.02 (s, 1H), 1.92 (s, 2H), 1.74 (s, 2H), 1.58 (s, 8H), ; 584.5 [M + H] | 1.23 |

TABLE 1-continued

| Example Compound | Structure | Name of Compound | ¹H NMR[[:]]; MS [M + H]⁺ | UPLC r.t. (min) |
|---|---|---|---|---|
| 978 | 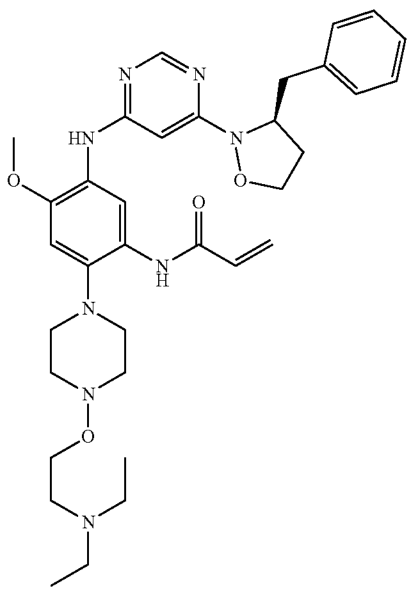 [SMILES: C=CC(=O)Nc1cc(Nc2cc(N3OCC[C@@H]3Cc3ccccc3)ncn2)c(OC)cc1N1CCN(OCCN(CC)CC)CC1] | N-(5-((6-((S)-3-benzylisoxazolidine-2-yl)pyrimidine-4-yl)amino)-2-(4-(2-(diethylamino)ethoxy)piperidine-1-yl)-4-methoxyphenyl)acrylamide | 630.57 [M + H]⁺ | 1.23 |
| 979 | 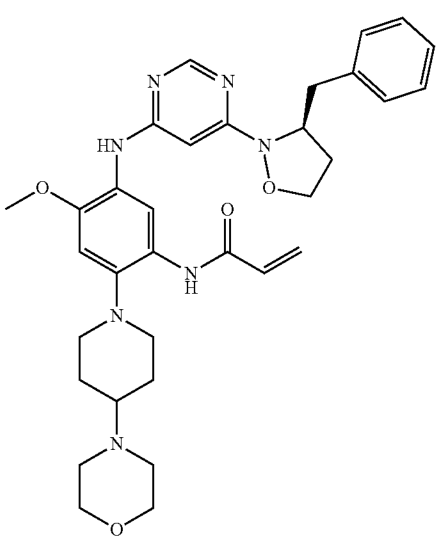 | N-(5-((6-((S)-3-(2,3-dichlorobenzyl)isoxazolidine-2-yl)pyrimidine-4-yl)amino)-4-methoxy-2-(4-morpholinopiperidine-1-yl)phenyl)acrylamide | 668.4 [M + H]⁺ | 1.25 |

TABLE 1-continued

| Example Compound | Structure | Name of Compound | ¹H NMR[[:]]; MS [M + H]⁺ | UPLC r.t. (min) |
|---|---|---|---|---|
| 980 | 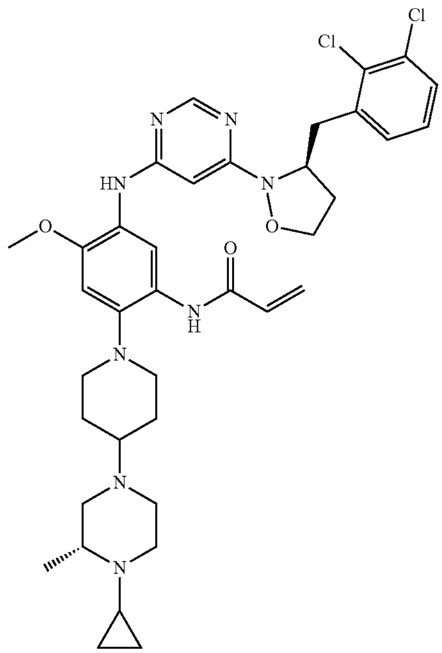 [SMILES: C=CC(=O)Nc1cc(Nc2cc(N3OCC[C@@H]3Cc3cccc(Cl)c3Cl)ncn2)c(OC)cc1N1CCC(N2CCN(C3CC3)[C@H](C)C2)CC1] | N-(2-(4-((R)-4-cyclopropyl-3-methylpiperazine-1-yl)piperidine-1-yl)-5-((6-((S)-3-(2,3-dichlorobenzyl)isoxazolidine-2-yl)pyrimidine-4-yl)amino)-4-methoxyphenyl) acrylamide | ¹H NMR (400 MHz, DMSO-$d_6$) δ 8.94 (s, 1H), 8.56 (s, 1H), 8.12 (s, 1H), 7.48 (ddd, J = 21.1, 7.9, 1.6 Hz, 2H), 7.29 (t, J = 7.8 Hz, 1H), 6.79 (s, 1H), 6.66 (dd, J = 16.9, 10.2 Hz, 1H), 6.30-6.14 (m, 2H), 5.71 (dd, J = 10.2, 2.0 Hz, 1H), 4.92 (qd, J = 8.0, 3.1 Hz, 1H), 3.77 (s, 3H), 3.35 (s, 1H), 3.13-2.91 (m, 5H), 2.84 (dt, J = 10.8, 2.8 Hz, 1H), 2.73 (t, J = 11.5 Hz, 2H), 2.63 (qd, J = 9.8, 9.4, 5.2 Hz, 2H), 2.45-2.35 (m, 1H), 2.35-2.13 (m, 5H), 2.02 (dtd, J = 11.6, 8.0, 3.0 Hz, 1H), 1.96-1.86 (m, 1H), 1.86-1.77 (m, 2H), 1.69 (tq, J = 11.9, 8.3, 6.1 Hz, 3H), 1.49 (dh, J = 7.6, 3.6 Hz, 2H), 1.09 (d, J = 6.3 Hz, 3H), 0.57 (dtd, J = 10.1, 6.6, 4.1 Hz, 1H), 0.44-0.30 (m, 2H), 0.17 (dq, J = 9.2, 3.9 Hz, 1H), ; 721.5 [M + H]⁺ | 1.29 |
| 981 | 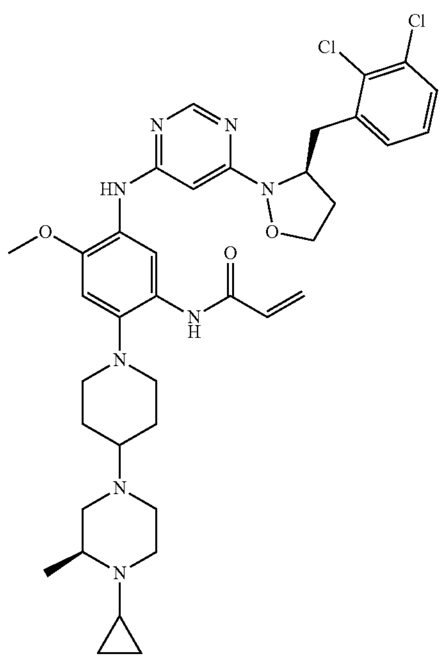 | N-(2-(4-((S)-4-cyclopropyl-3-methylpiperazine-1-yl)piperidine-1-yl)-5-((6-((S)-3-(2,3-dichlorobenzyl)isoxazolidine-2-yl)pyrimidine-4-yl)amino)-4-methoxyphenyl) acrylamide | ¹H NMR (400 MHz, DMSO-$d_6$) δ 9.01 (s, 1H), 8.59 (s, 1H), 8.13 (s, 2H), 7.48 (ddd, J = 21.8, 7.9, 1.6 Hz, 2H), 7.29 (t, J = 7.8 Hz, 1H), 6.81 (s, 1H), 6.62 (dd, J = 17.0, 10.2 Hz, 1H), 6.29 (s, 1H), 6.21 (dd, J = 16.9, 1.9 Hz, 1H), 5.74-5.69 (m, 1H), 4.92 (qd, J = 8.0, 3.1 Hz, 1H), 3.79 (s, 4H), 3.37 (s, 2H), 3.09 (dt, J = 18.5, 9.2 Hz, 5H), 2.96 (dd, J = 14.1, 6.4 Hz, 2H), 2.70 (t, J = 11.6 Hz, 4H), 2.59 (s, 2H), 2.25-1.96 (m, 5H), 1.91 (s, 5H), 1.74-1.41 (m, 2H), 1.19 (s, 3H), 0.65 (s, 1H), 0.45 (s, 2H), 0.25 (s, 1H), ; 721.4 [M + H]⁺ | 1.45 |

TABLE 1-continued

| Example Compound | Structure | Name of Compound | ¹H NMR[[:]]; MS [M + H]⁺ | UPLC r.t. (min) |
|---|---|---|---|---|
| 982 | 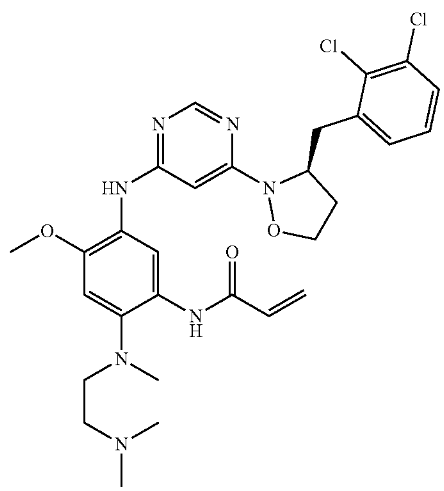 [SMILES: C=CC(=O)Nc1cc(Nc2cc(N3OCC[C@@H]3Cc3cccc(Cl)c3Cl)ncn2)c(OC)cc1N(C)CCN(C)C] | N-(5-((6-((S)-3-(2,3-dichlorobenzyl)isoxazolidine-2-yl)pyrimidine-4-yl)amino)-2-((2-(dimethylamino)ethyl)(methyl)amino)-4-methoxyphenyl)acrylamide | ¹H NMR (400 MHz, DMSO-d₆) δ 10.04 (s, 1H), 8.42 (s, 1H), 8.13 (d, J = 1.0 Hz, 1H), 7.51 (dd, J = 8.0, 1.6 Hz, 1H), 7.45 (dd, J = 7.8, 1.6 Hz, 1H), 7.29 (t, J = 7.8 Hz, 1H), 6.97 (s, 1H), 6.39 (dd, J = 16.9, 10.1 Hz, 1H), 6.30 (s, 1H), 6.21 (dd, J = 16.9, 2.1 Hz, 1H), 5.78-5.71 (m, 1H), 4.93 (dq, J = 11.9, 5.1, 4.0 Hz, 1H), 3.78 (s, 3H), 2.96 (dd, J = 14.1, 6.5 Hz, 2H), 2.88 (t, J = 5.8 Hz, 3H), 2.69 (s, 4H), 2.38 (t, J = 5.8 Hz, 2H), 2.18 (dt, J = 8.2, 4.4 Hz, 1H), 2.02 (dtd, J = 11.6, 8.0, 3.0 Hz, 2H), 1.90 (s, 6H), 1.00-0.91 (m, 1H), 0.85 (td, J = 8.0, 7.3, 3.1 Hz, 1H), ; 600.3 [M + H]⁺ | 1.31 |
| 983 | 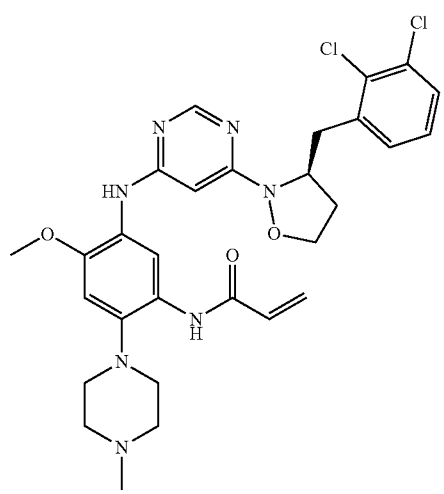 [SMILES: C=CC(=O)Nc1cc(Nc2cc(N3OCC[C@@H]3Cc3cccc(Cl)c3Cl)ncn2)c(OC)cc1N1CCN(C)CC1] | N-(5-((6-((S)-3-(2,3-dichlorobenzyl)isoxazolidine-2-yl)pyrimidine-4-yl)amino)-4-methoxy-2-(4-methylpiperazine-1-yl)phenyl)acrylamide | ¹H NMR (400 MHz, DMSO-d₆) δ 8.98 (s, 1H), 8.58 (s, 1H), 8.12 (s, 1H), 7.51 (dd, J = 8.0, 1.6 Hz, 2H), 7.45 (dd, J = 7.8, 1.6 Hz, 2H), 7.29 (t, J = 7.8 Hz, 2H), 6.82 (s, 1H), 6.59 (dd, J = 17.0, 10.2 Hz, 1H), 6.28 (s, 1H), 6.19 (dd, J = 16.9, 1.9 Hz, 1H), 5.71 (dd, J = 10.2, 1.9 Hz, 1H), 4.92 (qd, J = 8.0, 3.0 Hz, 2H), 3.79 (s, 3H), 3.16-2.90 (m, 6H), 2.85 (t, J = 4.8 Hz, 4H), 2.24 (s, 4H), 2.10 (ddtd, J = 60.6, 11.6, 7.9, 3.3 Hz, 5H), ; 598.3 [M + H]⁺ | 1.25 |
| 984 | 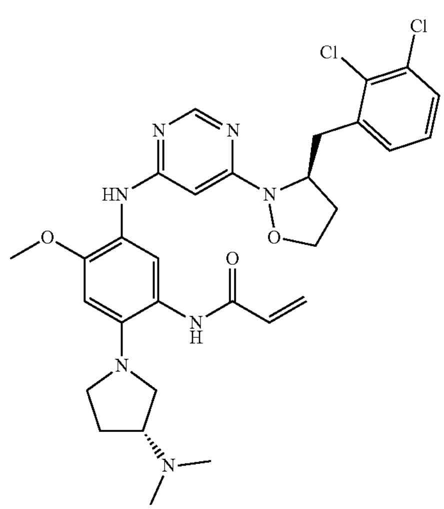 [SMILES: C=CC(=O)Nc1cc(Nc2cc(N3OCC[C@@H]3Cc3cccc(Cl)c3Cl)ncn2)c(OC)cc1N1CC[C@@H](N(C)C)C1] | N-(5-((6-((S)-3-(2,3-dichlorobenzyl)isoxazolidine-2-yl)pyrimidine-4-yl)amino)-2-((R)-3-(dimethylamino)pyrolidine-1-yl)-4-methoxyphenyl)acrylamide | ¹H NMR (400 MHz, DMSO-d₆) δ 11.26 (s, 1H), 9.58 (s, 1H), 8.57 (s, 1H), 8.12 (s, 1H), 7.81 (s, 1H), 7.51 (dd, J = 8.0, 1.5 Hz, 1H), 7.47-7.43 (m, 1H), 7.30 (t, J = 7.8 Hz, 1H), 6.90 (dd, J = 17.0, 10.2 Hz, 1H), 6.68 (s, 1H), 6.24-6.14 (m, 2H), 5.68 (dd, J = 10.2, 2.1 Hz, 1H), 4.92 (qd, J = 7.9, 3.0 Hz, 1H), 3.80 (s, 3H), 3.60 (dt, J = 9.4, 2.7 Hz, 2H), 3.48-3.39 (m, 1H), 3.37 (s, 2H), 3.32 (dd, J = 11.0, 6.4 Hz, 1H), 3.11 (dd, J = 7.5, 4.4 Hz, 3H), 2.96 (dd, J = 14.2, 6.7 Hz, 2H), 2.78 (d, J = 4.7 Hz, 6H), 2.29 (dq, J = 12.7, 7.3, 5.6 Hz, 2H), 2.19 (dtd, J = 12.9, 8.3, 5.0 Hz, 1H), 2.02 (dtd, J = 11.6, 7.9, 3.0 Hz, 1H), ; 612.3 [M + H]⁺ | 1.24 |

TABLE 1-continued

| Example Compound | Structure | Name of Compound | ¹H NMR[[:]]; MS [M + H]⁺ | UPLC r.t. (min) |
|---|---|---|---|---|
| 985 | 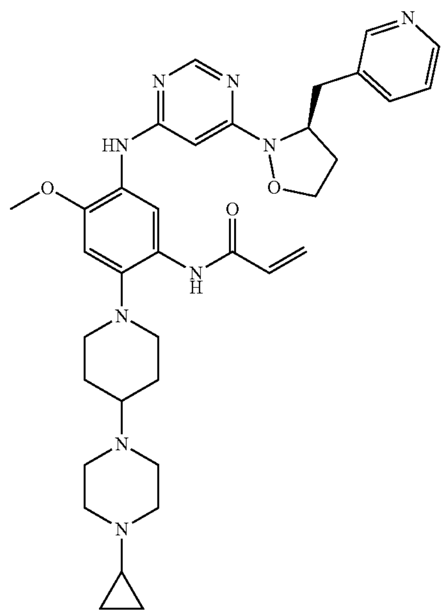 [SMILES: C=CC(=O)Nc1cc(Nc2cc(N3OCC[C@@H]3Cc3cccnc3)ncn2)c(OC)cc1N1CCC(N2CCN(C3CC3)CC2)CC1] | N-(2-(4-(4-cyclopropylpiperazine-1-yl)piperidine-1-yl)-4-methoxy-5-((6-((S)-3-(pyridine-3-ylmethyl)isoxazolidine-2-yl)pyrimidine-4-yl)amino)phenyl)acrylamide | ¹H NMR (400 MHz, Chloroform-d) δ 8.79 (s, 1H), 8.52 (d, J = 2.3 Hz, 1H), 8.45 (dd, J = 4.9, 1.6 Hz, 1H), 8.31 (s, 1H), 7.70 (dt, J = 7.9, 2.1 Hz, 1H), 7.22 (dd, J = 7.8, 4.8 Hz, 1H), 7.01 (s, 1H), 6.69 (s, 1H), 6.57 (s, 1H), 6.39-6.30 (m, 2H), 5.74 (td, J = 9.6, 9.2, 2.1 Hz, 2H), 4.88 (qd, J = 7.3, 3.8 Hz, 1H), 3.81 (s, 3H), 3.17-3.02 (m, 5H), 2.72 (q, J = 11.6 Hz, 4H), 2.62 (s, 1H), 2.26 (dtd, J = 12.2, 8.1, 4.2 Hz, 2H), 2.17 (d, J = 12.0 Hz, 2H), 2.12-1.99 (m, 2H), 1.98-1.85 (m, 3H), 1.79 (t, J = 5.1 Hz, 1H), 1.47 (d, J = 6.7 Hz, 3H), 1.24 (s, 4H), 0.51 (t, J = 7.0 Hz, 5H), ; 640.5 [M + H]⁺ | 1.09 |
| 986 | 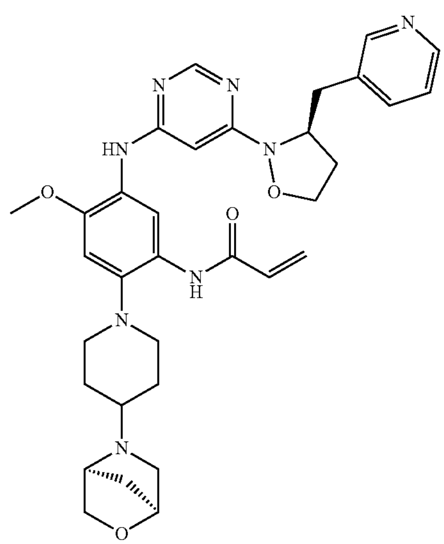 [SMILES: C=CC(=O)Nc1cc(Nc2cc(N3OCC[C@@H]3Cc3cccnc3)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-4-methoxy-5-((6-((S)-3-(pyridine-3-ylmethyl)isoxazolidine-2-yl)pyrimidine-4-yl)amino)phenyl)acrylamide | ¹H NMR (400 MHz, Chloroform-d) δ 8.81 (s, 1H), 8.53 (d, J = 2.2 Hz, 1H), 8.46 (q, J = 1.8 Hz, 2H), 8.32 (s, 1H), 7.70 (dt, J = 7.9, 2.0 Hz, 1H), 7.22 (dd, J = 7.8, 4.8 Hz, 1H), 6.94 (s, 1H), 6.73 (s, 1H), 6.59 (s, 1H), 6.35-6.25 (m, 2H), 5.72 (dd, J = 9.7, 1.9 Hz, 1H), 4.89 (qd, J = 7.2, 3.8 Hz, 1H), 3.83 (s, 3H), 3.73-3.66 (m, 2H), 3.39 (q, J = 6.5 Hz, 1H), 3.30 (td, J = 7.3, 5.2 Hz, 1H), 3.23 (d, J = 10.1 Hz, 2H), 3.14 (dd, J = 14.0, 6.7 Hz, 2H), 2.81-2.59 (m, 6H), 2.45 (s, 1H), 2.27 (dtd, J = 12.3, 8.2, 4.3 Hz, 2H), 2.09-1.99 (m, 4H), 1.99-1.91 (m, 2H), 1.88 (d, J = 9.9 Hz, 2H), 1.25 (s, 2H), ; 613.3 [M + H]⁺ | 1.03 |

TABLE 1-continued

| Example Compound | Structure | Name of Compound | ¹H NMR[[:]]; MS [M + H]⁺ | UPLC r.t. (min) |
|---|---|---|---|---|
| 987 | 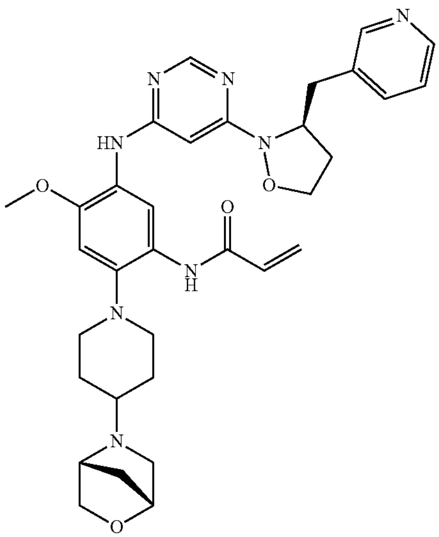 [SMILES: C=CC(=O)Nc1cc(Nc2cc(N3OCC[C@@H]3Cc3cccnc3)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-4-methoxy-5-((6-((S)-3-(pyridine-3-ylmethyl)isoxazolidine-2-yl)pyrimidine-4-yl)amino)phenyl)acrylamide | ¹H NMR (400 MHz, Chloroform-d) δ 8.81 (s, 1H), 8.50-8.42 (m, 2H), 8.32 (s, 1H), 7.69 (d, J = 7.9 Hz, 1H), 7.21 (dd, J = 7.8, 4.8 Hz, 1H), 6.92 (s, 1H), 6.72 (s, 1H), 6.58 (s, 1H), 6.34-6.23 (m, 2H), 5.72 (dd, J = 9.6, 1.9 Hz, 1H), 4.88 (qd, J = 7.3, 3.8 Hz, 1H), 3.99-3.88 (m, 2H), 3.82 (s, 3H), 3.69 (d, J = 8.4 Hz, 1H), 3.13 (dd, J = 14.0, 6.8 Hz, 1H), 3.09-2.97 (m, 3H), 2.74 (tdd, J = 12.1, 6.9, 3.3 Hz, 4H), 2.61 (d, J = 10.3 Hz, 2H), 2.49 (s, 1H), 2.26 (dtd, J = 12.5, 8.2, 4.3 Hz, 2H), 2.03 (dq, J = 11.6, 3.8 Hz, 4H), 1.89 (d, J = 10.3 Hz, 2H), 1.34-1.21 (m, 4H), ; 613.5 [M + H]⁺ | 1.05 |
| 988 | 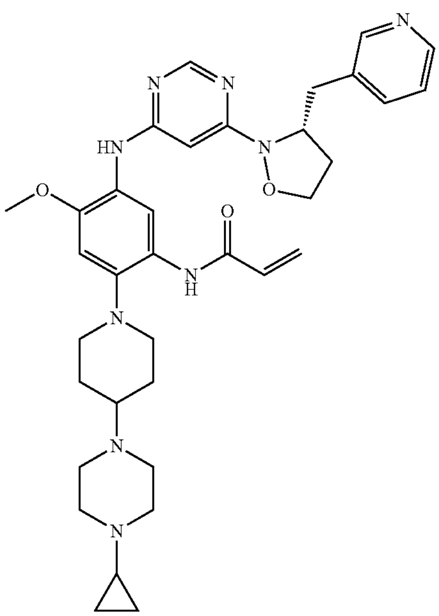 [SMILES: C=CC(=O)Nc1cc(Nc2cc(N3OCC[C@H]3Cc3cccnc3)ncn2)c(OC)cc1N1CCC(N2CCN(C3CC3)CC2)CC1] | N-(2-(4-(4-cyclopropylpiperazine-1-yl)piperidine-1-yl)-4-methoxy-5-((6-((R)-3-(pyridine-3-ylmethyl)isoxazolidine-2-yl)pyrimidine-4-yl)amino)phenyl)acrylamide | ¹H NMR (400 MHz, Chloroform-d) δ 8.77 (s, 1H), 8.33 (s, 1H), 8.30 (s, 1H), 7.70 (d, J = 7.7 Hz, 1H), 7.09 (s, 1H), 6.67 (s, 1H), 6.55 (s, 1H), 6.36 (d, J = 5.7 Hz, 2H), 5.74 (t, J = 5.8 Hz, 1H), 5.29 (s, 1H), 4.88 (dq, J = 7.5, 3.5 Hz, 1H), 4.52 (t, J = 16.1 Hz, 1H), 3.81 (s, 4H), 3.64 (h, J = 6.7 Hz, 2H), 3.32-3.27 (m, 1H), 3.10-3.03 (m, 3H), 2.90-2.66 (m, 8H), 2.27 (dhept, J = 11.9, 3.9 Hz, 5H), 2.04 (dtt, J = 14.7, 10.5, 5.1 Hz, 2H), 1.92 (s, 2H), 0.86-0.80 (m, 5H), 0.57 (d, J = 6.4 Hz, 4H), ; 640.5 [M + H]⁺ | 1.09 |

TABLE 1-continued

| Example Compound | Structure | Name of Compound | ¹H NMR[[:]]; MS [M + H]⁺ | UPLC r.t. (min) |
|---|---|---|---|---|
| 989 | 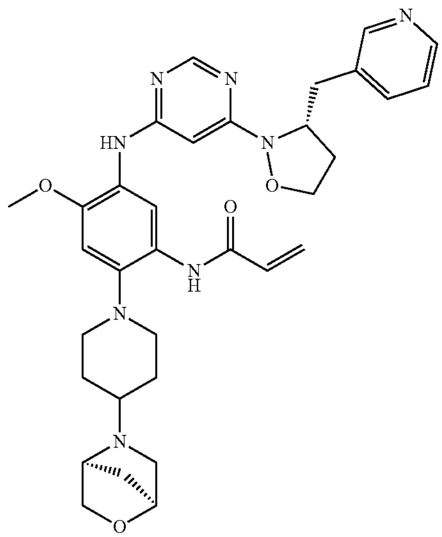 [SMILES: C=CC(=O)Nc1cc(Nc2cc(N3OCC[C@H]3Cc3cccnc3)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-4-methoxy-5-((6-((R)-3-(pyridine-3-ylmethyl)isoxazolidine-2-yl)pyrimidine-4-yl)amino)phenyl)acrylamide | ¹H NMR (400 MHz, Chloroform-d) δ 8.80 (s, 1H), 8.43 (s, 1H), 8.32 (s, 1H), 7.70 (d, J = 7.8 Hz, 1H), 6.99 (s, 1H), 6.71 (d, J = 4.0 Hz, 1H), 6.59 (s, 1H), 6.39-6.32 (m, 2H), 5.77-5.72 (m, 1H), 5.29 (s, 1H), 4.89 (tt, J = 11.1, 5.5 Hz, 1H), 4.57 (s, 1H), 3.99-3.86 (m, 3H), 3.82 (s, 3H), 3.65 (p, J = 6.7 Hz, 2H), 3.31 (td, J = 7.3, 5.3 Hz, 2H), 3.11 (ddd, J = 25.4, 14.4, 7.1 Hz, 5H), 2.99 (dt, J = 15.0, 7.8 Hz, 2H), 2.27 (dtd, J = 12.4, 8.1, 4.2 Hz, 3H), 2.17 (dt, J = 14.9, 7.4 Hz, 2H), 1.55 (t, J = 7.4 Hz, 2H), 1.50-1.46 (m, 5H), 0.90 0.78 (m, 2H), ; 613.4 [M + H]⁺ | 1.02 |
| 990 | 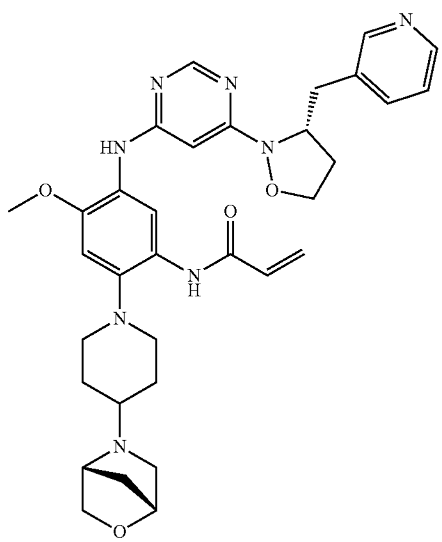 [SMILES: C=CC(=O)Nc1cc(Nc2cc(N3OCC[C@H]3Cc3cccnc3)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-4-methoxy-5-((6-((R)-3-(pyridine-3-ylmethyl)isoxazolidine-2-yl)pyrimidine-4-yl)amino)phenyl)acrylamide | ¹H NMR (400 MHz, Chloroform-d) δ 8.81 (s, 1H), 8.43 (s, 1H), 8.32 (s, 1H), 7.70 (d, J = 7.8 Hz, 1H), 7.23 (s, 1H), 6.92 (s, 1H), 6.70 (s, 1H), 6.60 (s, 1H), 6.37-6.32 (m, 2H), 5.74 (dd, J = 7.2, 4.3 Hz, 1H), 4.89 (qd, J = 7.3, 3.8 Hz, 1H), 4.56 (s, 1H), 3.95 (q, J = 8.1 Hz, 1H), 3.87 (dt, J = 13.9, 7.1 Hz, 2H), 3.82 (s, 3H), 3.77 (d, J = 9.2 Hz, 1H), 3.43 (p, J = 7.4, 6.4 Hz, 2H), 3.37-3.25 (m, 2H), 3.11 (ddd, J = 25.4, 14.5, 7.2 Hz, 4H), 2.96 (dt, J = 22.6, 7.8 Hz, 2H), 2.86 (dd, J = 14.1, 7.3 Hz, 2H), 2.26 (ddd, J = 12.9, 8.5, 4.5 Hz, 2H), 2.15 (td, J = 15.7, 14.2, 6.7 Hz, 2H), 1.48 (s, 3H), 1.29-1.22 (m, 4H), 1.19 (t, J = 7.3 Hz, 2H), ; 613.5 [M + H]⁺ | 1.03 |
| 991 | 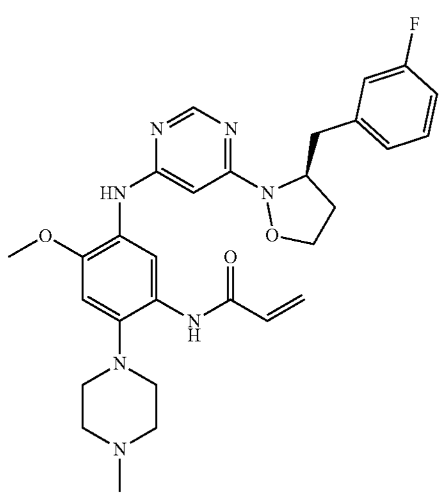 [SMILES: C=CC(=O)Nc1cc(Nc2cc(N3OCC[C@@H]3Cc3cccc(F)c3)ncn2)c(OC)cc1N1CCN(C)CC1] | N-(5-((6-((S)-3-(3-fluorobenzyl)isoxazolidine-2-yl)pyrimidine-4-yl)amino)-4-methoxy-2-(4-methylpiperazine-1-yl)phenyl)acrylamide | ¹H NMR (400 MHz, CDCl₃) δ 8.88 (s, 1H), 8.51 (s, 1H), 8.37 (s, 1H), 7.29-7.22 (m, 1H), 7.10 (d, J = 7.6 Hz, 1H), 7.04 (d, J = 9.9 Hz, 1H), 6.94-6.87 (m, 2H), 6.79 (s, 1H), 6.59 (s, 1H), 6.39-6.21 (m, 2H), 5.74 (dd, J = 9.9, 1.4 Hz, 1H), 4.92-4.83 (m, 1H), 4.07 (td, J = 8.1, 4.6 Hz, 1H), 3.96 (q, J = 8.1 Hz, 1H), 3.83 (s, 3H), 3.23 (dd, J = 13.8, 6.2 Hz, 1H), 2.97-2.88 (m, 4H), 2.80 (dd, J = 13.8, 8.3 Hz, 1H), 2.70-2.56 (m, 3H), 2.41 (s, 3H), 2.27-2.17 (m, 1H), 2.09-1.99 (m, 1H), 1.77-1.62 (m, 2H); 548.32 [M + H]⁺ | 1.14 |

TABLE 1-continued

| Example Compound | Structure | Name of Compound | ¹H NMR[[:]]; MS [M + H]⁺ | UPLC r.t. (min) |
|---|---|---|---|---|
| 992 | 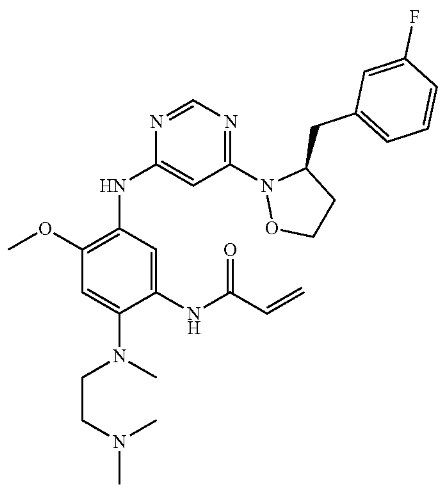 [SMILES: C=CC(=O)Nc1cc(Nc2cc(N3OCC[C@@H]3Cc3cccc(F)c3)ncn2)c(OC)cc1N(C)CCN(C)C] | N-(2-((2-(dimethylamino)ethyl)(methyl)amino)-5-((6-((S)-3-(3-fluorobenzyl)isoxazolidine-2-yl)pyrimidine-4-yl)amino)-4-methoxyphenyl)acrylamide | ¹H NMR (400 MHz, CDCl₃) δ 9.47 (s, 1H), 8.81 (s, 1H), 8.36 (s, 1H), 7.29-7.21 (m, 1H), 7.10 (d, J = 7.7 Hz, 1H), 7.04 (d, J = 9.9 Hz, 1H), 7.00-6.87 (m, 2H), 6.68 (s, 1H), 6.63 (s, 1H), 6.40 (dd, J = 16.8, 1.9 Hz, 1H), 5.70 (dd, J = 10.2, 1.9 Hz, 1H), 4.94-4.80 (m, 1H), 4.09 (td, J = 8.1, 4.6 Hz, 1H), 3.99 (q, J = 8.1 Hz, 1H), 3.84 (s, 3H), 3.49 (s, 3H), 3.33-3.25 (m, 2H), 3.22 (dd, J = 13.8, 6.3 Hz, 1H), 2.85-2.77 (m, 6H), 2.74 (s, 3H), 2.31-2.17 (m, 1H), 2.10-2.01 (m, 1H); 550.39 [M + H]⁺ | 1.18 |
| 993 | 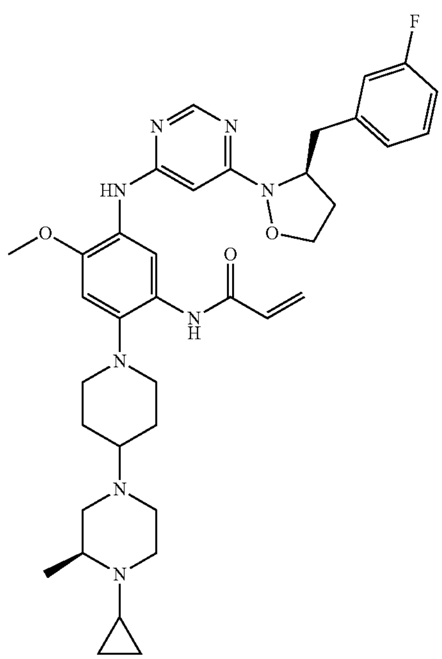 [SMILES: C=CC(=O)Nc1cc(Nc2cc(N3OCC[C@@H]3Cc3cccc(F)c3)ncn2)c(OC)cc1N1CCC(N2CCN(C3CC3)[C@@H](C)C2)CC1] | N-(2-(4-((S)-4-cyclopropyl-3-methylpiperazine-1-yl)piperidine-1-yl)-5-((6-((S)-3-(3-fluorobenzyl)isoxazolidine-2-yl)pyrimidine-4-yl)amino)-4-methoxyphenyl)acrylamide | ¹H NMR (400 MHz, CDCl₃) δ 8.84 (s, 1H), 8.42 (s, 1H), 8.37 (s, 1H), 7.29-7.21 (m, 5H), 7.10 (d, J = 7.7 Hz, 1H), 7.04 (d, J = 9.8 Hz, 1H), 6.90 (td, J = 8.5, 2.2 Hz, 1H), 6.86 (s, 1H), 6.73 (s, 1H), 6.59 (s, 1H), 6.38-6.20 (m, 2H), 5.76-5.71 (m, 1H), 4.92-4.83 (m, 1H), 4.06 (td, J = 8.1, 4.5 Hz, 1H), 3.96 (q, J = 8.1 Hz, 1H), 3.83 (s, 3H), 3.22 (dd, J = 13.8, 6.2 Hz, 1H), 3.10-2.86 (m, 5H), 2.83-2.49 (m, 5H), 2.43-2.16 (m, 3H), 2.14-1.99 (m, 4H), 1.77-1.52 (m, 3H), 1.22 (d, J = 5.9 Hz, 3H), 0.71-0.55 (m, 2H), 0.50-0.28 (m, 2H); 671.61 [M + H]⁺ | 1.19 |

TABLE 1-continued

| Example Compound | Structure | Name of Compound | ¹H NMR[[:]]; MS [M + H]⁺ | UPLC r.t. (min) |
|---|---|---|---|---|
| 994 | 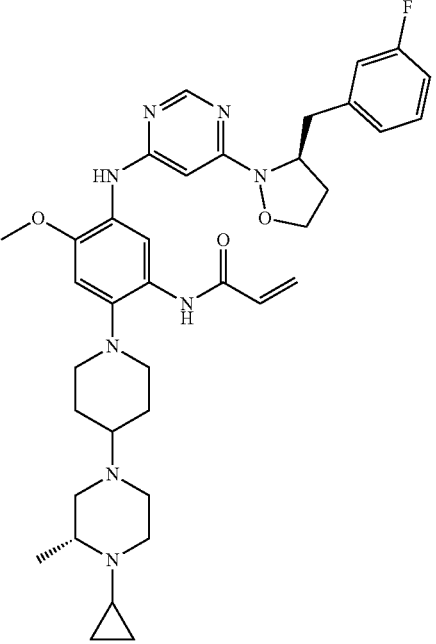 [SMILES: C=CC(=O)Nc1cc(Nc2cc(N3OCC[C@@H]3Cc3cccc(F)c3)ncn2)c(OC)cc1N1CCC(N2CCN(C3CC3)[C@H](C)C2)CC1] | N-(2-(4-((R)-4-cyclopropyl-3-methylpiperazine-1-yl)piperidine-1-yl)-5-((6-((S)-3-(3-fluorobenzyl)isoxazolidine-2-yl)pyrimidine-4-yl)amino)-4-methoxyphenyl)acrylamide | ¹H NMR (400 MHz, CDCl₃) δ 8.84 (s, 1H), 8.42 (s, 1H), 8.37 (s, 1H), 7.28-7.22 (m, 1H), 7.10 (d, J = 7.7 Hz, 1H), 7.04 (d, J = 9.9 Hz, 1H), 6.91 (td, J = 8.5, 2.1 Hz, 1H), 6.85 (s, 1H), 6.73 (s, 1H), 6.59 (s, 1H), 6.38-6.19 (m, 2H), 5.77-5.70 (m, 1H), 4.92-4.83 (m, 1H), 4.06 (td, J = 8.1, 4.6 Hz, 1H), 3.96 (q, J = 8.1 Hz, 1H), 3.83 (s, 3H), 3.22 (dd, J = 13.8, 6.2 Hz, 1H), 3.09-2.85 (m, 5H), 2.83-2.67 (m, 3H), 2.64-2.42 (m, 2H), 2.41-2.17 (m, 3H), 2.13-1.97 (m, 4H), 1.73-1.50 (m, 3H), 1.22 (d, J = 6.1 Hz, 3H), 0.71-0.54 (m, 2H), 0.49-0.29 (m, 2H); 671.51 [M + H]⁺ | 1.19 |
| 995 | 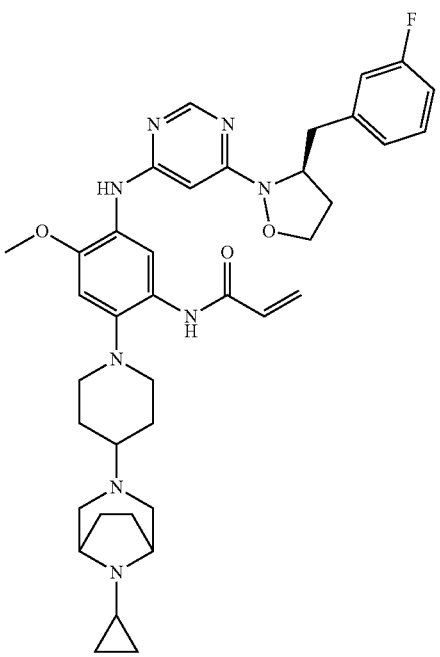 [SMILES: C=CC(=O)Nc1cc(Nc2cc(N3OCC[C@@H]3Cc3cccc(F)c3)ncn2)c(OC)cc1N1CCC(N2CC3CCC(C2)N3C2CC2)CC1] | N-(2-(4-((1R,5S)-8-cyclopropyl-3,8-diazabicyclo[3.2.1]octan-3-yl)piperidine-1-yl)-5-((6-((S)-3-(3-fluorobenzyl)isoxazolidine-2-yl)pyrimidine-4-yl)amino)-4-methoxyphenyl)acrylamide | ¹H NMR (400 MHz, CDCl₃) δ 8.83 (s, 1H), 8.45 (s, 1H), 8.36 (s, 1H), 7.28-7.21 (m, 1H), 7.10 (d, J = 7.6 Hz, 1H), 7.04 (d, J = 9.8 Hz, 1H), 6.90 (td, J = 8.4, 2.1 Hz, 1H), 6.85 (s, 1H), 6.73 (s, 1H), 6.59 (s, 1H), 6.39-6.21 (m, 2H), 5.74 (dd, J = 9.8, 1.6 Hz, 1H), 4.93-4.83 (m, 1H), 4.06 (td, J = 8.1, 4.6 Hz, 1H), 3.96 (q, J = 8.1 Hz, 1H), 3.83 (s, 3H), 3.35-3.17 (m, 3H), 3.06-2.96 (m, 2H), 2.80 (dd, J = 13.8, 8.3 Hz, 1H), 2.73-2.63 (m, 4H), 2.47-2.17 (m, 4H), 2.09-1.80 (m, 8H), 1.73-1.54 (m, 2H), 0.59-0.27 (m, 4H); 683.47 [M + H]⁺ | 1.22 |

TABLE 1-continued

| Example Compound | Structure | Name of Compound | ¹H NMR[:]; MS [M + H]⁺ | UPLC r.t. (min) |
|---|---|---|---|---|
| 996 | 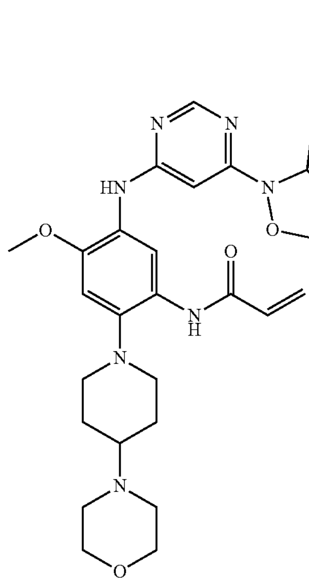 | N-(5-((6-((S)-3-(3-fluorobenzyl)isoxazolidine-2-yl)pyrimidine-4-yl)amino)-4-methoxy-2-(4-morpholinopiperidine-1-yl)phenyl)acrylamide | ¹H NMR (400 MHz, CDCl₃) δ 8.85 (s, 1H), 8.42 (s, 1H), 8.37 (s, 1H), 7.29-7.20 (m, 1H), 7.10 (d, J = 7.6 Hz, 1H), 7.04 (d, J = 9.9 Hz, 1H), 6.94-6.85 (m, 2H), 6.74 (s, 1H), 6.59 (s, 1H), 6.39-6.20 (m, 2H), 5.73 (dd, J = 10.0, 1.3 Hz, 1H), 4.92-4.83 (m, 1H), 4.06 (td, J = 8.1, 4.6 Hz, 1H), 3.96 (q, J = 8.1 Hz, 1H), 3.83 (s, 3H), 3.83-3.73 (m, 4H), 3.22 (dd, J = 13.8, 6.2 Hz, 1H), 3.12-3.02 (m, 2H), 2.84-2.60 (m, 7H), 2.41-2.28 (m, 1H), 2.26-2.17 (m, 1H), 2.13-2.00 (m, 3H), 1.73-1.57 (m, 2H); 618.48 [M + H]⁺ | 1.14 |
| 997 | 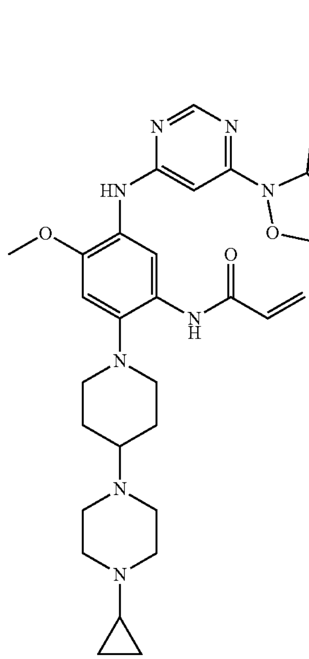 | N-(2-(4-(4-cyclopropylpiperazine-1-yl)piperidine-1-yl)-5-((6-((S)-3-(3-fluorobenzyl)isoxazolidine-2-yl)pyrimidine-4-yl)amino)-4-methoxyphenyl)acrylamide | ; 657.44 [M + H]⁺ | 1.21 |

TABLE 1-continued

| Example Compound | Structure | Name of Compound | ¹H NMR[[:]]; MS [M + H]⁺ | UPLC r.t. (min) |
|---|---|---|---|---|
| 998 | 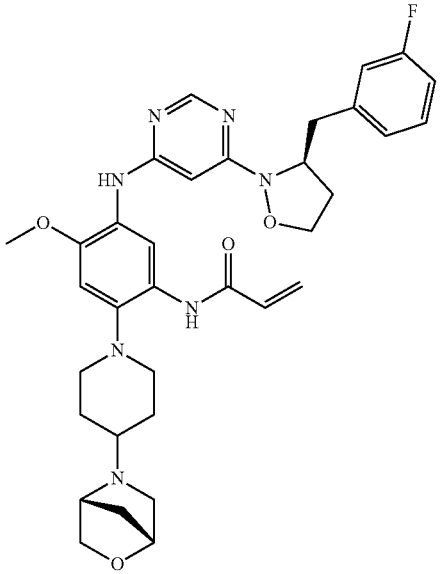 [SMILES: C=CC(=O)Nc1cc(Nc2cc(N3OCC[C@@H]3Cc3cccc(F)c3)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-5-((6-((S)-3-(3-fluorobenzyl)isoxazolidine-2-yl)pyrimidine-4-yl)amino)-4-methoxyphenyl)acrylamide | ; 630.53 [M + H]⁺ | 1.17 |
| 999 | 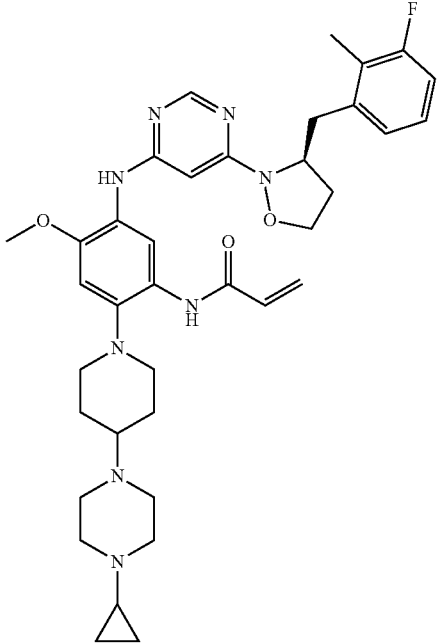 [SMILES: C=CC(=O)Nc1cc(Nc2cc(N3OCC[C@@H]3Cc3cccc(F)c3C)ncn2)c(OC)cc1N1CCC(N2CCN(C3CC3)CC2)CC1] | N-(2-(4-(4-cyclopropylpiperazine-1-yl)piperidine-1-yl)-5-((6-((S)-3-(3-fluoro-2-methylbenzyl)isoxazolidine-2-yl)pyrimidine-4-yl)amino)-4-methoxyphenyl)acrylamide | ¹H NMR (400 MHz, Methanol-d₄) δ 8.25 (s, 1H), 8.16 (s, 1H), 7.13-7.08 (m, 2H), 6.95-6.87 (m, 2H), 6.61-6.48 (m, 1H), 6.40-6.32 (m, 1H), 6.29 (s, 1H), 5.81 (d, J = 10.2 Hz, 1H), 4.14-4.09 (m, 1H), 3.93-3.86 (m, 5H), 3.22-3.17 (m, 3H), 3.04-2.97 (m, 3H), 2.91-2.80 (m, 8H), 2.33 (d, 3H), 2.27-2.21 (m, 1H), 2.17-2.11 (m, 3H), 1.90-1.78 (m, 4H), 0.60-0.53 (m, 2H), 0.53-0.43 (m, 2H); 671.4 [M + H]⁺ | 1.22 |

TABLE 1-continued

| Example Compound | Structure | Name of Compound | ¹H NMR[:]; MS [M + H]⁺ | UPLC r.t. (min) |
|---|---|---|---|---|
| 1000 | 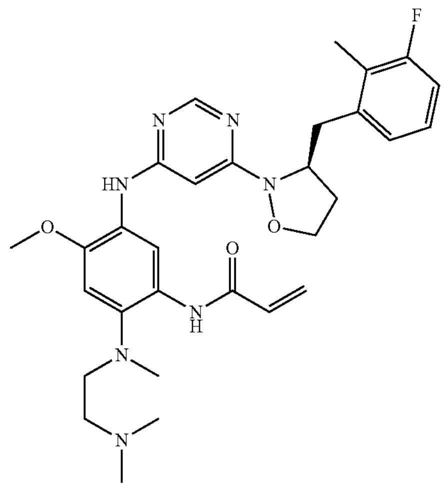 [SMILES: C=CC(=O)Nc1cc(Nc2cc(N3OCC[C@@H]3Cc3cccc(F)c3C)ncn2)c(OC)cc1N(C)CCN(C)C] | N-(2-((2-(dimethylamino)ethyl)(methyl)amino)-5-((6-((S)-3-(3-fluoro-2-methylbenzyl)isoxazolidine-2-yl)pyrimidine-4-yl)amino)-4-methoxyphenyl)acrylamide | ¹H NMR (400 MHz, Methanol-d₄) δ 8.18 (s, 1H), 7.98 (s, 1H), 7.14-7.09 (m, 2H), 6.97-6.86 (m, 2H), 6.60-6.49 (m, 1H), 6.47-6.36 (m, 2H), 5.91-5.81 (m, 1H), 4.17-4.11 (m, 1H), 3.95-3.84 (m, 5H), 3.45-3.38 (m, 2H), 3.25-3.19 (m, 1H), 3.16-3.12 (m, 2H), 2.90-2.82 (m, 1H), 2.77 (s, 6H), 2.73 (s, 3H), 2.34 (d, J = 2.2 Hz, 3H), 2.29-2.20 (m, 1H), 2.20-2.09 (m, 1H); 564.3 [M + H]⁺ | 1.23 |
| 1001 | 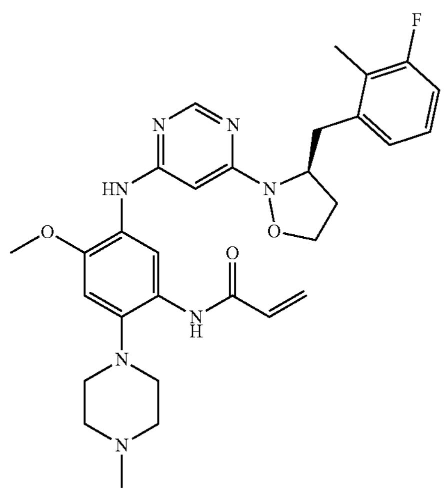 | N-(5-((6-((S)-3-(3-fluoro-2-methylbenzyl)isoxazolidine-2-yl)pyrimidine-4-yl)amino)-4-methoxy-2-(4-methylpiperazine-1-yl)phenyl)acrylamide | ¹H NMR (400 MHz, Methanol-d₄) δ 8.30 (s, 1H), 8.17 (s, 1H), 7.15-7.05 (m, 2H), 6.97-6.84 (m, 2H), 6.63-6.44 (m, 1H), 6.40-6.29 (m, 2H), 5.82 (d, J = 10.3 Hz, 1H), 4.16-4.09 (m, 1H), 3.95-3.83 (m, 5H), 3.24-3.17 (m, 1H), 3.10-3.04 (m, 4H), 3.04-2.93 (m, 4H), 2.89-2.81 (m, 1H), 2.62 (s, 3H), 2.33 (s, 3H), 2.30-2.19 (m, 1H), 2.19-2.09 (m, 1H); 645.3 [M + H]⁺ | 1.16 |
| 1002 | 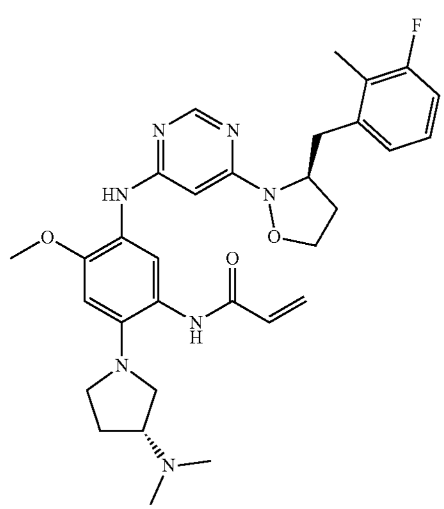 [SMILES: C=CC(=O)Nc1cc(Nc2cc(N3OCC[C@@H]3Cc3cccc(F)c3C)ncn2)c(OC)cc1N1CC[C@@H](N(C)C)C1] | N-(2-((R)-3-(dimethylamino)pyrolidine-1-yl)-5-((6-((S)-3-(3-fluoro-2-methylbenzyl)isoxazolidine-2-yl)pyrimidine-4-yl)amino)-4-methoxyphenyl)acrylamide | ¹H NMR (400 MHz, Methanol-d₄) δ 8.14 (s, 1H), 7.70 (s, 1H), 7.15-7.06 (m, 2H), 6.95-6.86 (m, 1H), 6.71 (s, 1H), 6.62-6.48 (m, 1H), 6.42-6.30 (m, 1H), 6.20 (s, 1H), 5.81 (dd, J = 1.7, 10.2 Hz, 1H), 4.14-4.06 (m, 1H), 3.94-3.81 (m, 4H), 3.78-3.70 (m, 1H), 3.47-3.34 (m, 4H), 3.32-3.16 (m, 3H), 2.89-2.80 (m, 1H), 2.32 (d, J = 2.2 Hz, 3H), 2.27-2.18 (m, 1H), 2.18-2.04 (m, 2H), 1.43-1.35 (m, 6H); 576.3 [M + H]⁺ | 1.15 |

TABLE 1-continued

| Example Compound | Structure | Name of Compound | ¹H NMR[[:]]; MS [M + H]⁺ | UPLC r.t. (min) |
|---|---|---|---|---|
| 1003 | 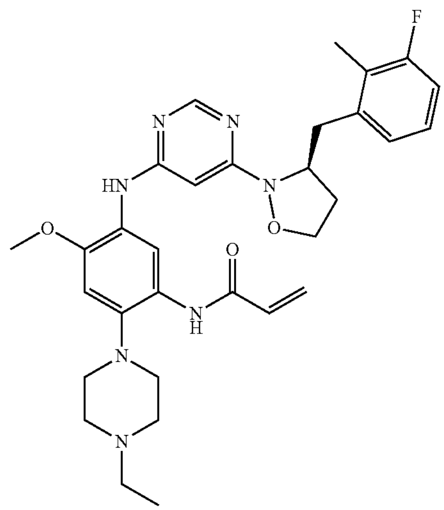 [SMILES: C=CC(=O)Nc1cc(Nc2cc(N3OCC[C@@H]3Cc3cccc(F)c3C)ncn2)c(OC)cc1N1CCN(CC)CC1] | N-(2-(4-ethylpiperazine-1-yl)-5-((6-(S)-(3-(3-fluoro-2-methylbenzyl)isoxazolidine-2-yl)pyrimidine-4-yl)amino)-4-methoxyphenyl)acrylamide | ¹H NMR (400 MHz, Methanol-d₄) δ 8.31 (s, 1H), 8.17 (s, 1H), 7.17-7.05 (m, 2H), 6.98-6.83 (m, 2H), 6.64-6.49 (m, 1H), 6.42-6.28 (m, 2H), 5.82 (d, J = 10.4 Hz, 1H), 4.13 (td, J = 4.5, 7.9 Hz, 1H), 4.00-3.79 (m, 5H), 3.23-3.17 (m, 1H), 3.17-3.06 (m, 8H), 2.99-2.93 (m, 2H), 2.89-2.80 (m, 1H), 2.33 (d, J = 2.8 Hz, 3H), 2.26-2.20 (m, 1H), 2.17-2.09 (m, 1H), 1.33-1.30 (m, 3H); 576.3 [M + H]⁺ | 1.19 |
| 1004 | 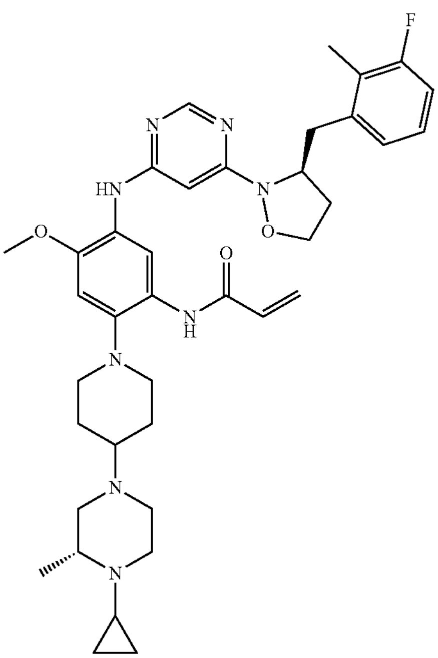 [SMILES: C=CC(=O)Nc1cc(Nc2cc(N3OCC[C@@H]3Cc3cccc(F)c3C)ncn2)c(OC)cc1N1CCC(N2CCN(C3CC3)[C@H](C)C2)CC1] | N-(2-(4-((R)-4-cyclopropyl-3-methylpiperazine-1-yl)piperidine-1-yl)-5-((6-((S)-3-(3-fluoro-2-methylbenzyl)isoxazolidine-2-yl)pyrimidine-4-yl)amino)-4-methoxyphenyl)acrylamide | ¹H NMR (400 MHz, Methanol-d₄) δ 8.26 (s, 1H), 8.16 (s, 1H), 7.17-7.04 (m, 2H), 6.96-6.84 (m, 2H), 6.56 (dd, J = 10.2, 17.0 Hz, 1H), 6.40-6.26 (m, 2H), 5.81 (d, J = 10.3 Hz, 1H), 4.15-4.09 (m, 1H), 3.96-3.79 (m, 5H), 3.23-3.17 (m, 4H), 2.88-2.70 (m, 6H), 2.69-2.59 (m, 2H), 2.46-2.37 (m, 1H), 2.33 (d, J = 2.2 Hz, 3H), 2.30-2.18 (m, 1H), 2.18-2.09 (m, 3H), 1.92-1.82 (m, 2H), 1.77-1.71 (m, 1H), 1.30 (d, J = 6.2 Hz, 3H), 0.81-0.72 (m, 1H), 0.72-0.62 (m, 1H), 0.62-0.52 (m, 1H), 0.45-0.32 (m, 1H); 685.4 [M + H]⁺ | 1.23 |

TABLE 1-continued

| Example Compound | Structure | Name of Compound | ¹H NMR[:]; MS [M + H]⁺ | UPLC r.t. (min) |
|---|---|---|---|---|
| 1005 | 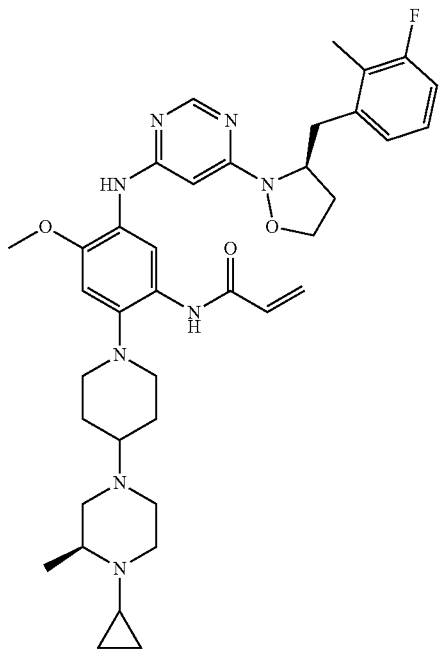 [SMILES: C=CC(=O)Nc1cc(Nc2cc(N3OCC[C@@H]3Cc3cccc(F)c3C)ncn2)c(OC)cc1N1CCC(N2CCN(C3CC3)[C@@H](C)C2)CC1] | N-(2-(4-((S)-4-cyclopropyl-3-methylpiperazine-1-yl)piperidine-1-yl)-5-((6-((S)-3-(3-fluoro-2-methylbenzyl)isoxazolidine-2-yl)pyrimidine-4-yl)amino)-4-methoxyphenyl)acrylamide | ¹H NMR (400 MHz, Methanol-$d_4$) δ 8.27 (s, 1H), 8.16 (s, 1H), 7.16-7.03 (m, 2H), 6.95-6.84 (m, 2H), 6.64-6.47 (m, 1H), 6.41-6.23 (m, 2H), 5.87-5.74 (m, 1H), 4.15-4.08 (m, 1H), 3.93-3.84 (m, 4H), 3.30-3.23 (m, 1H), 3.22-3.12 (m, 5H), 2.88-2.61 (m, 7H), 2.47-2.37 (m, 1H), 2.32 (d, J = 2.2 Hz, 3H), 2.30-2.19 (m, 1H), 2.19-2.10 (m, 3H), 1.93-1.81 (m, 2H), 1.76-1.72 (m, 1H), 1.30 (d, J = 6.3 Hz, 3H), 0.80-0.70 (m, 1H), 0.70-0.62 (m, 1H), 0.62-0.51 (m, 1H), 0.44-0.36 (m, 1H); 685.4 [M + H]⁺ | 1.23 |
| 1006 | 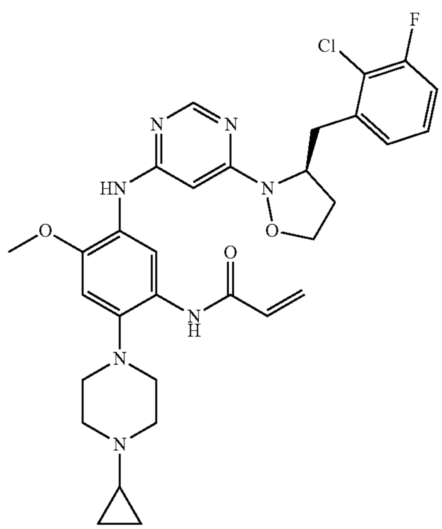 [SMILES: C=CC(=O)Nc1cc(Nc2cc(N3OCC[C@@H]3Cc3cccc(F)c3Cl)ncn2)c(OC)cc1N1CCN(C2CC2)CC1] | N-(5-((6-((S)-3-(2-chloro-3-fluorobenzyl)isoxazolidine-2-yl)pyrimidine-4-yl)amino)-2-(4-cyclopropylpiperazine-1-yl)-4-methoxyphenyl)acrylamide | ¹H NMR (400 MHz, Methanol-$d_4$) δ 8.28 (s, 1H), 8.14 (s, 1H), 7.32-7.20 (m, 2H), 7.17-7.04 (m, 1H), 6.92 (s, 1H), 6.54 (dd, J = 10.2, 17.0 Hz, 1H), 6.39-6.25 (m, 2H), 5.82 (d, J = 10.2 Hz, 1H), 4.14 (td, J = 4.7, 8.0 Hz, 1H), 3.96-3.83 (m, 4H), 3.39-3.34 (m, 1H), 3.23-3.16 (m, 1H), 3.11-3.04 (m, 1H), 3.01-2.87 (m, 8H), 2.33-2.23 (m, 1H), 2.18-2.07 (m, 1H), 1.92-1.85 (m, 1H), 0.63-0.56 (m, 2H), 0.56-0.49 (m, 2H); 608.3 [M + H]⁺ | 1.21 |

TABLE 1-continued

| Example Compound | Structure | Name of Compound | ¹H NMR[[:]]; MS [M + H]⁺ | UPLC r.t. (min) |
|---|---|---|---|---|
| 1007 | 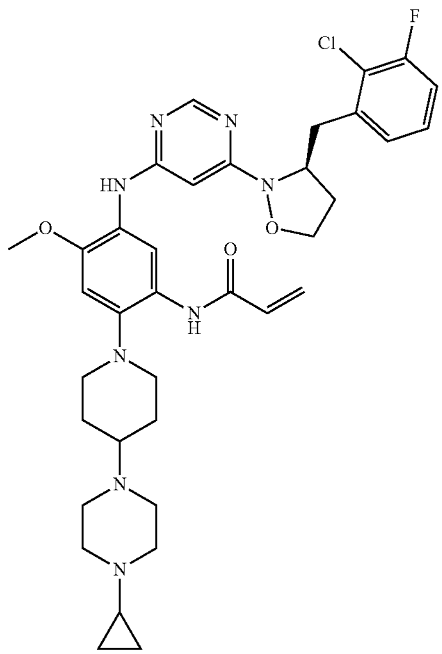 [SMILES: C=CC(=O)Nc1cc(Nc2cc(N3OCC[C@@H]3Cc3cccc(F)c3Cl)ncn2)c(OC)cc1N1CCC(N2CCN(C3CC3)CC2)CC1] | N-(5-((6-((S)-3-(2-chloro-3-fluorobenzyl)isoxazolidine-2-yl)pyrimidine-4-yl)amino)-2-(4-(4-cyclopropylpiperazine-1-yl)piperidine-1-yl)-4-methoxyphenyl)acrylamide | ¹H NMR (400 MHz, Methanol-d₄) δ 8.26 (s, 1H), 8.14 (s, 1H), 7.33-7.20 (m, 2H), 7.17-7.04 (m, 1H), 6.91 (s, 1H), 6.56 (dd, J = 10.2, 17.0 Hz, 1H), 6.44-6.23 (m, 2H), 5.81 (d, J = 10.2 Hz, 1H), 4.17-4.10 (m, 1H), 3.97-3.80 (m, 5H), 3.24-3.14 (m, 3H), 3.14-3.03 (m, 2H), 3.03-2.92 (m, 3H), 2.92-2.76 (m, 7H), 2.33-2.22 (m, 1H), 2.18-2.07 (m, 3H), 1.90-1.78 (m, 3H), 0.60-0.50 (m, 2H), 0.50-0.43 (m, 2H); 691.3 [M + H]⁺ | 1.19 |
| 1008 | 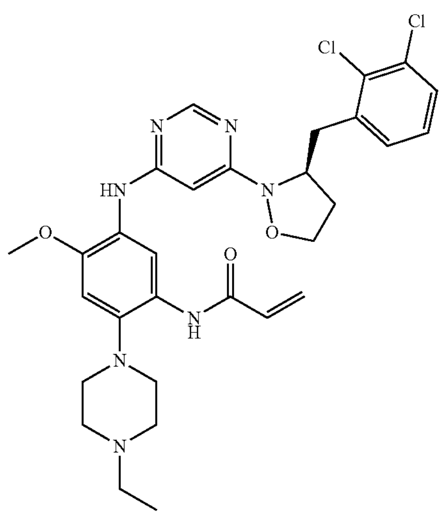 [SMILES: C=CC(=O)Nc1cc(Nc2cc(N3OCC[C@@H]3Cc3cccc(Cl)c3Cl)ncn2)c(OC)cc1N1CCN(CC)CC1] | N-(5-((6-((S)-3-(2,3-dichlorobenzyl)isoxazolidine-2-yl)pyrimidine-4-yl)amino)-2-(4-ethylpiperazine-1-yl)-4-methoxyphenyl)acrylamide | ¹H NMR (400 MHz, Chloroform-d) δ 8.85 (s, 1H), 8.55 (s, 1H), 8.32 (s, 1H), 7.34 (ddd, J = 13.6, 7.8, 1.6 Hz, 2H), 7.12 (t, J = 7.8 Hz, 1H), 6.92 (s, 1H), 6.80 (s, 1H), 6.59 (s, 1H), 6.25 (dd, J = 16.9, 9.9 Hz, 1H), 5.73 (dd, J = 9.8, 1.7 Hz, 1H), 5.00 (qd, J = 7.4, 3.3 Hz, 1H), 3.80 (s, 3H), 3.24 (dd, J = 14.2, 7.4 Hz, 1H), 3.07 (dd, J = 14.2, 7.1 Hz, 1H), 2.92 (t, J = 4.9 Hz, 5H), 2.76-2.56 (m, 4H), 2.51 (q, J = 7.2 Hz, 3H), 2.25 (dtd, J = 12.9, 8.3, 4.9 Hz, 2H), 2.07 (dtd, J = 11.8, 7.8, 3.4 Hz, 1H), 1.25 (d, J = 2.9 Hz, 2H), 1.14 (t, J = 7.2 Hz, 4H), ; 612.3 [M + H]⁺ | 1.41 |

TABLE 1-continued

| Example Compound | Structure | Name of Compound | ¹H NMR[[:]]; MS [M + H]⁺ | UPLC r.t. (min) |
|---|---|---|---|---|
| 1009 | 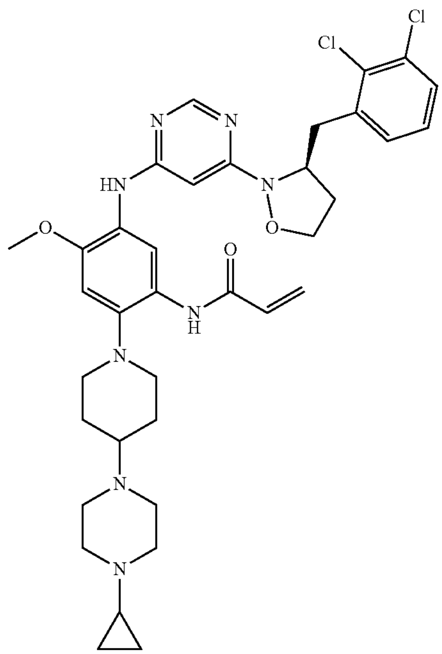 [SMILES: C=CC(=O)Nc1cc(Nc2cc(N3OCC[C@@H]3Cc3cccc(Cl)c3Cl)ncn2)c(OC)cc1N1CCC(N2CCN(C3CC3)CC2)CC1] | N-(2-(4-(4-cyclopropylpiperazine-1-yl)piperidine-1-yl)-5-((6-((S)-3-(2,3-dichlorobenzyl)isoxazolidine-2-yl)pyrimidine-4-yl)amino)-4-methoxyphenyl)acrylamide | ¹H NMR (400 MHz, Chloroform-d) δ 8.81 (s, 1H), 8.42 (s, 1H), 8.32 (s, 1H), 7.34 (ddd, J = 12.7, 7.8, 1.6 Hz, 2H), 7.12 (t, J = 7.8 Hz, 1H), 6.89 (s, 1H), 6.72 (s, 1H), 6.58 (s, 1H), 6.24 (dd, J = 16.9, 9.9 Hz, 1H), 5.72 (dd, J = 9.9, 1.7 Hz, 1H), 5.00 (qd, J = 3.24 (dd, J = 14.2, 7.4 Hz, 1H), 7.5, 3.4 Hz, 1H), 3.81 (s, 3H), 3.06 (dt, J = 13.6, 5.4 Hz, 4H), 2.78-2.62 (m, 10H), 2.38 (s, 1H), 2.25 (dtd, J = 12.8, 8.3, 4.8 Hz, 2H), 2.07 (tt, J = 11.8, 3.4 Hz, 3H), 1.77-1.64 (m, 4H), 1.31-1.21 (m, 4H), 0.86 (dtd, J = 12.7, 6.5, 1.9 Hz, 3H), 0.51-0.40 (m, 4H), ; 707.4 [M + H]⁺ | 1.31 |
| 1010 | 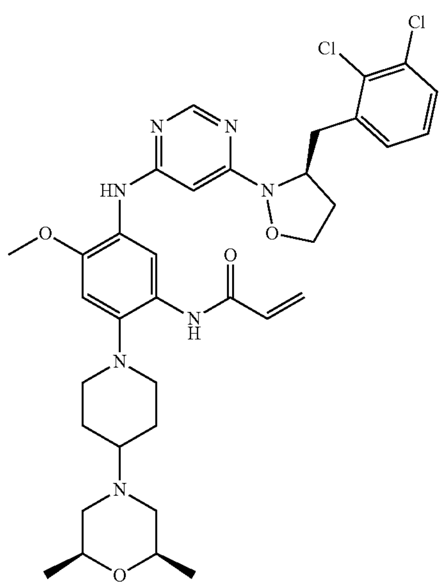 [SMILES: C=CC(=O)Nc1cc(Nc2cc(N3OCC[C@@H]3Cc3cccc(Cl)c3Cl)ncn2)c(OC)cc1N1CCC(N2C[C@@H](C)O[C@@H](C)C2)CC1] | N-(5-((6-((S)-3-(2,3-dichlorobenzyl)isoxazolidine-2-yl)pyrimidine-4-yl)amino)-2-(4-((2S,6R)-2,6-dimethylmorpholino)piperidine-1-yl)-4-methoxyphenyl)acrylamide | ¹H NMR (400 MHz, Chloroform-d) δ 8.82 (s, 1H), 8.41 (s, 1H), 8.32 (d, J = 1.0 Hz, 1H), 7.34 (ddd, J = 12.9, 7.9, 1.6 Hz, 2H), 7.12 (t, J = 7.8 Hz, 1H), 6.88 (s, 1H), 6.73 (s, 1H), 6.58 (s, 1H), 6.24 (dd, J = 16.9, 10.0 Hz, 1H), 5.73 (dd, J = 10.0, 1.6 Hz, 1H), 5.00 (qd, J = 7.4, 3.4 Hz, 1H), 3.82 (s, 3H), 3.70 (dqd, J = 12.4, 6.2, 1.9 Hz, 2H), 3.24 (dd, J = 14.2, 7.4 Hz, 1H), 3.11-3.02 (m, 3H), 2.87 (d, J = 10.8 Hz, 2H), 2.76-2.65 (m, 2H), 2.32-2.19 (m, 2H), 2.07 (dtd, J = 12.0, 7.4, 7.0, 3.1 Hz, 4H), 1.89 (t, J = 10.6 Hz, 3H), 1.65 (qd, J = 12.1, 3.9 Hz, 2H), 1.20 (d, J = 6.3 Hz, 6H), ; 696.4 [M + H]⁺ | 1.27 |

TABLE 1-continued

| Example Compound | Structure | Name of Compound | ¹H NMR[:]; MS [M + H]⁺ | UPLC r.t. (min) |
|---|---|---|---|---|
| 1011 | 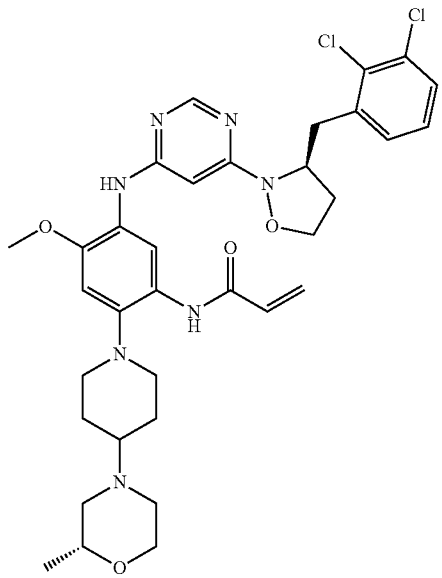 [SMILES: C=CC(=O)Nc1cc(Nc2cc(N3OCC[C@@H]3Cc3cccc(Cl)c3Cl)ncn2)c(OC)cc1N1CCC(N2CCO[C@H](C)C2)CC1] | N-(5-((6-((S)-3-(2,3-dichlorobenzyl)isoxazolidine-2-yl)pyrimidine-4-yl)amino)-4-methoxy-2-(4-((R)-2-methylmorpholino)piperidine-1-yl)phenyl)acrylamide | ¹H NMR (400 MHz, Chloroform-d) δ 8.82 (s, 1H), 8.42 (s, 1H), 8.32 (d, J = 1.0 Hz, 1H), 7.34 (ddd, J = 12.9, 7.9, 1.6 Hz, 2H), 7.12 (t, J = 7.8 Hz, 1H), 6.88 (s, 1H), 6.73 (s, 1H), 6.58 (s, 1H), 6.23 (dd, J = 16.9, 10.0 Hz, 1H), 5.72 (dd, J = 9.9, 1.6 Hz, 1H), 5.00 (qd, J = 7.4, 3.3 Hz, 1H), 4.11 (td, J = 8.1, 4.8 Hz, 1H), 4.00 (q, J = 8.1 Hz, 1H), 3.92 (ddd, J = 11.3, 3.4, 1.5 Hz, 1H), 3.82 (s, 3H), 3.75-3.60 (m, 2H), 3.24 (dd, J = 14.2, 7.4 Hz, 1H), 3.06 (dt, J = 15.4, 6.0 Hz, 3H), 2.92-2.79 (m, 2H), 2.76-2.66 (m, 2H), 2.27 (ddt, J = 25.5, 12.9, 4.5 Hz, 4H), 2.17-2.01 (m, 4H), 1.96 (t, J = 10.5 Hz, 2H), 1.64 (qt, J = 12.1, 3.6 Hz, 2H), 1.18 (d, J = 6.3 Hz, 4H), ; 682.4 [M + H]⁺ | 1.26 |
| 1012 | 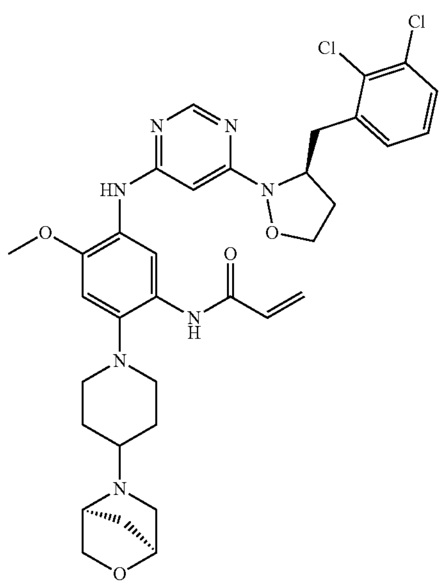 [SMILES: C=CC(=O)Nc1cc(Nc2cc(N3OCC[C@@H]3Cc3cccc(Cl)c3Cl)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((S)-3-(2,3-dichlorobenzyl)isoxazolidine-2-yl)pyrimidine-4-yl)amino)-4-methoxyphenyl)acrylamide | 680.4 [M + H]⁺ | 1.24 |

TABLE 1-continued

| Example Compound | Structure | Name of Compound | $^1$H NMR[:]; MS [M + H]$^+$ | UPLC r.t. (min) |
|---|---|---|---|---|
| 1013 | 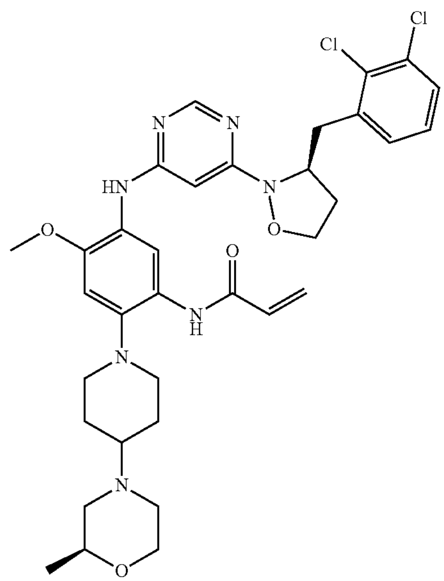 [SMILES: C=CC(=O)Nc1cc(Nc2cc(N3OCC[C@@H]3Cc3cccc(Cl)c3Cl)ncn2)c(OC)cc1N1CCC(N2CCO[C@@H](C)C2)CC1] | N-(5-((6-((S)-3-(2,3-dichlorobenzyl)isoxazolidine-2-yl)pyrimidine-4-yl)amino)-4-methoxy-2-(4-((S)-2-methylmorpholino)piperidine-1-yl)phenyl)acrylamide | $^1$H NMR (400 MHz, Chloroform-d) δ 8.83 (s, 1H), 8.43 (s, 1H), 8.33 (d, J = 1.0 Hz, 1H), 7.35 (ddd, J = 12.6, 7.8, 1.5 Hz, 2H), 7.13 (t, J = 7.8 Hz, 1H), 6.85 (s, 1H), 6.74 (d, J = 4.6 Hz, 1H), 6.59 (s, 1H), 6.24 (dd, J = 16.9, 10.0 Hz, 1H), 5.73 (dd, J = 10.0, 1.5 Hz, 1H), 5.01 (qd, J = 7.4, 3.4 Hz, 1H), 3.83 (s, 4H), 3.74-3.61 (m, 3H), 3.25 (dd, J = 14.2, 7.4 Hz, 1H), 3.08 (dd, J = 15.0, 8.5 Hz, 4H), 2.87 (dd, J = 22.8, 11.2 Hz, 2H), 2.72 (q, J = 11.3 Hz, 3H), 2.29 (ddt, J = 13.8, 8.6, 3.8 Hz, 4H), 2.08-2.04 (m, 2H), 1.96 (t, J = 10.5 Hz, 1H), 1.25 (s, 3H), 1.21-1.15 (m, 4H), ; 684.2 [M + H]$^+$ | 1.31 |
| 1014 | 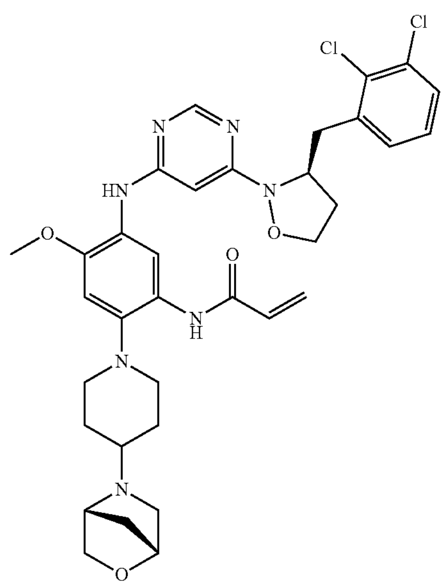 | N-(2-(4-((1R,4R)-2-oxa-5-azabicyclo[2.2.1]heptane-5-yl)piperidine-1-yl)-5-((6-((S)-3-(2,3-dichlorobenzyl)isoxazolidine-2-yl)pyrimidine-4-yl)amino)-4-methoxyphenyl)acrylamide | $^1$H NMR (400 MHz, Chloroform-d) δ 8.82 (s, 1H), 8.46 (s, 1H), 8.32 (d, J = 1.0 Hz, 1H), 7.34 (ddd, J = 13.4, 7.8, 1.6 Hz, 2H), 7.12 (t, J = 7.8 Hz, 1H), 6.89 (s, 1H), 6.74 (s, 1H), 6.58 (d, J = 1.1 Hz, 1H), 6.21 (dd, J = 17.0, 10.0 Hz, 1H), 5.71 (dd, J = 10.0, 1.5 Hz, 1H), 5.00 (qd, J = 7.4, 3.4 Hz, 1H), 4.09 (td, J = 8.1, 3.3 Hz, 2H), 3.82 (s, 3H), 3.77-3.73 (m, 1H), 3.65 (dd, J = 7.9, 1.6 Hz, 1H), 3.27-2.97 (m, 1H), 2.75 (qd, J = 11.4, 2.5 Hz, 2H), 2.56 (tt, J = 10.1, 3.9 Hz, 1H), 2.49 (dd, J = 10.0, 1.4 Hz, 1H), 2.24-2.19 (m, 2H), 2.07 (ddd, J = 16.4, 8.1, 3.8 Hz, 2H), 2.02-1.94 (m, 1H), 1.94-1.87 (m, 2H), 1.84-1.77 (m, 1H), 1.72-1.58 (m, 3H), ; 680.4 [M + H]$^+$ | 1.25 |

TABLE 1-continued

| Example Compound | Structure | Name of Compound | ¹H NMR[[:]]; MS [M + H]⁺ | UPLC r.t. (min) |
|---|---|---|---|---|
| 1015 | 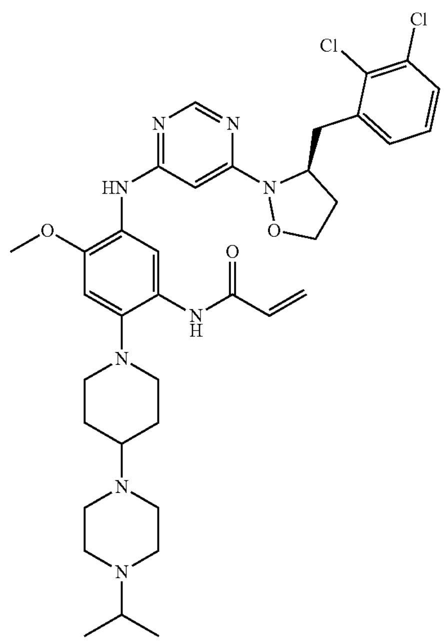 [SMILES: C=CC(=O)Nc1cc(Nc2cc(N3OCC[C@@H]3Cc3cccc(Cl)c3Cl)ncn2)c(OC)cc1N1CCC(N2CCN(C(C)C)CC2)CC1] | N-(5-((6-((S)-3-(2,3-dichlorobenzyl)isoxazolidine-2-yl)pyrimidine-4-yl)amino)-2-(4-(4-isopropylpiperazine-1-yl)piperidine-1-yl)-4-methoxyphenyl)acrylamide | ¹H NMR (400 MHz, Chloroform-d) δ 8.80 (s, 1H), 8.37 (s, 1H), 8.31 (s, 1H), 7.39-7.31 (m, 2H), 7.14 (d, J = 7.9 Hz, 1H), 6.72 (s, 1H), 6.57 (s, 1H), 6.36 (ddd, J = 17.0, 6.6, 1.8 Hz, 2H), 6.26 (dd, J = 16.9, 9.8 Hz, 1H), 5.74 (dd, J = 9.8, 1.7 Hz, 1H), 5.00 (qd, J = 7.4, 3.4 Hz, 1H), 3.83 (s, 3H), 3.65 (h, J = 6.7 Hz, 3H), 3.33 (qd, J = 7.2, 5.1 Hz, 2H), 3.23 (d, J = 7.4 Hz, 1H), 3.16 (s, 4H), 3.09 (qd, J = 7.1, 5.2 Hz, 8H), 2.72 (s, 2H), 2.26 (qd, J = 8.0, 4.1 Hz, 1H), 2.09 (ddt, J = 12.2, 8.2, 4.0 Hz, 4H), 1.76-1.67 (m, 3H), 1.56 (t, J = 7.5 Hz, 5H), 1.41 (d, J = 6.6 Hz, 6H), ; 709.5 [M + H]⁺ | 1.23 |
| 1016 | 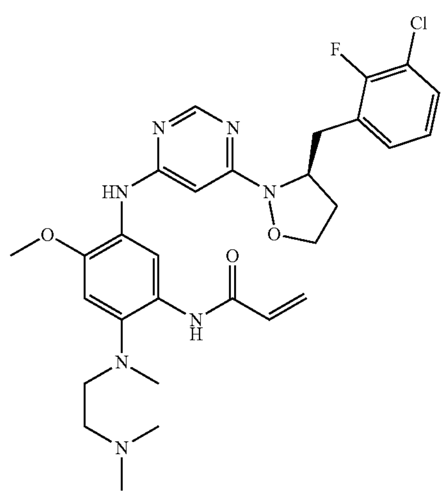 [SMILES: C=CC(=O)Nc1cc(Nc2cc(N3OCC[C@@H]3Cc3cccc(Cl)c3F)ncn2)c(OC)cc1N(C)CCN(C)C] | N-(5-((6-((S)-3-(3-chloro-2-fluorobenzyl)isoxazolidine-2-yl)pyrimidine-4-yl)amino)-2-((2-(dimethylamino)ethyl)(methyl)amino)-4-methoxyphenyl)acrylamide | ; 584.41 [M + H]⁺ | 1.32 |

TABLE 1-continued

| Example Compound | Structure | Name of Compound | ¹H NMR[[:]]; MS [M + H]⁺ | UPLC r.t. (min) |
|---|---|---|---|---|
| 1017 | 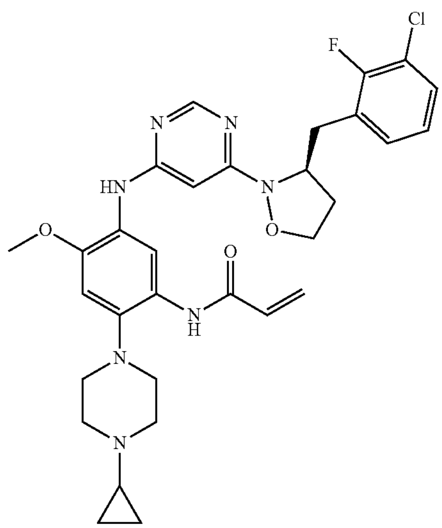 [SMILES: C=CC(=O)Nc1cc(Nc2cc(N3OCC[C@@H]3Cc3cccc(Cl)c3F)ncn2)c(OC)cc1N1CCN(C2CC2)CC1] | N-(5-((6-((S)-3-(3-chloro-2-fluorobenzyl)isoxazolidine-2-yl)pyrimidine-4-yl)amino)-2-(4-cyclopropylpiperazine-1-yl)-4-methoxyphenyl)acrylamide | ¹H NMR (400 MHz, CDCl₃) δ 8.87 (s, 1H), 8.58 (s, 1H), 8.34 (s, 1H), 7.30 (t, J = 7.1 Hz, 1H), 7.28-7.23 (m, 1H), 7.01 (t, J = 7.8 Hz, 1H), 6.91 (s, 1H), 6.78 (s, 1H), 6.60 (s, 1H), 6.39-6.22 (m, 2H), 5.74 (dd, J = 9.8, 1.5 Hz, 1H), 4.96-4.88 (m, 1H), 4.09 (td, J = 8.1, 4.7 Hz, 1H), 3.98 (q, J = 8.1 Hz, 1H), 3.80 (s, 3H), 3.15 (dd, J = 14.0, 6.6 Hz, 1H), 2.98 (dd, J = 13.9, 7.6 Hz, 1H), 2.89-2.84 (m, 4H), 2.31-2.20 (m, 1H), 2.10-2.00 (m, 1H), 1.75-1.69 (m, 1H), 0.56-0.50 (m, 2H), 0.50-0.44 (m, 2H), ; 608.42 [M + H]⁺ | 1.31 |
| 1018 | 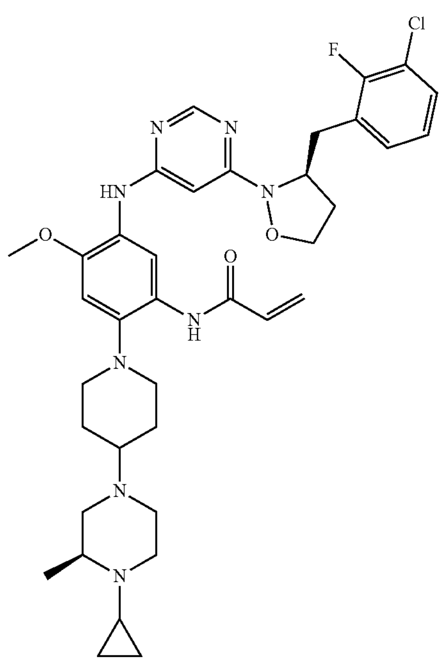 [SMILES: C=CC(=O)Nc1cc(Nc2cc(N3OCC[C@@H]3Cc3cccc(Cl)c3F)ncn2)c(OC)cc1N1CCC(N2CCN(C3CC3)[C@@H](C)C2)CC1] | N-(5-((6-((S)-3-(3-chloro-2-fluorobenzyl)isoxazolidine-2-yl)pyrimidine-4-yl)amino)-2-(4-((S)-4-cyclopropyl-3-methylpiperazine-1-yl)piperidine-1-yl)-4-methoxyphenyl)acrylamide | ¹H NMR (400 MHz, CDCl₃) δ 8.83 (s, 1H), 8.43 (s, 1H), 8.34 (s, 1H), 7.30 (t, J = 7.1 Hz, 1H), 7.28-7.23 (m, 1H), 7.01 (t, J = 7.8 Hz, 1H), 6.85 (d, J = 4.6 Hz, 1H), 6.73 (s, 1H), 6.59 (s, 1H), 6.38-6.19 (m, 2H), 5.73 (dd, J = 10.0, 1.2 Hz, 1H), 4.96-4.88 (m, 1H), 4.08 (td, J = 8.1, 4.7 H, 1H), 3.97 (q, J = 8.0 Hz, 1H), 3.82 (s, 3H), 3.15 (dd, J = 14.0, 7.0 Hz, 1H), 3.08-2.93 (m, 5H), 2.91-2.84 (m, 1H), 2.77-2.66 (m, 2H), 2.58-2.43 (m, 2H), 2.34-2.21 (m, 3H), 2.10-1.97 (m, 4H), 1.71-1.50 (m, 3H), 1.21 (d, J = 6.3 Hz, 3H), 0.69-0.56 (m, 2H), 0.48-0.40 (m, 1H), 0.36-0.28 (m, 1H); 705.53 [M + H]⁺ | 1.33 |

TABLE 1-continued

| Example Compound | Structure | Name of Compound | ¹H NMR[[:]]; MS [M + H]⁺ | UPLC r.t. (min) |
|---|---|---|---|---|
| 1019 | 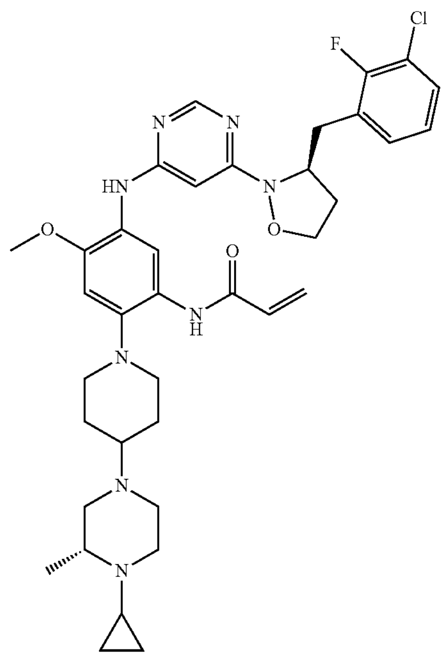 [SMILES: C=CC(=O)Nc1cc(Nc2cc(N3OCC[C@@H]3Cc3cccc(Cl)c3F)ncn2)c(OC)cc1N1CCC(N2CCN(C3CC3)[C@H](C)C2)CC1] | N-(5-((6-((S)-3-(3-chloro-2-fluorobenzyl)isoxazolidine-2-yl)pyrimidine-4-yl)amino)-2-(4-((R)-4-cyclopropyl-3-methylpiperazine-1-yl)piperidine-1-yl)-4-methoxyphenyl)acrylamide | ¹H NMR (400 MHz, CDCl$_3$) δ 8.83 (s, 1H), 8.43 (s, 1H), 8.34 (s, 1H), 7.30 (t, J = 7.1 Hz, 1H), 7.28-7.23 (m, 1H), 7.01 (t, J = 7.8 Hz, 1H), 6.85 (s, 1H), 6.73 (s, 1H), 6.59 (s, 1H), 6.37-6.18 (m, 2H), 5.73 (dd, J = 10.1, 1.1 Hz, 1H), 4.96-4.87 (m, 1H), 4.08 (td, J = 8.1, 4.7 Hz, 1H), 3.97 (q, J = 7.9 Hz, 1H), 3.82 (s, 3H), 3.15 (dd, J = 14.0, 6.7 Hz, 1H), 3.08-2.93 (m, 5H), 2.91-2.84 (m, 1H), 2.76-2.65 (m, 2H), 2.57-2.43 (m, 2H), 2.35-2.20 (m, 3H), 2.10-1.96 (m, 4H), 1.76-1.50 (m, 3H), 1.21 (d, J = 6.3 Hz, 3H), 0.69-0.56 (m, 2H), 0.47-0.39 (m, 1H), 0.36-0.28 (m, 1H); 705.53 [M + H]⁺ | 1.34 |
| 1020 | 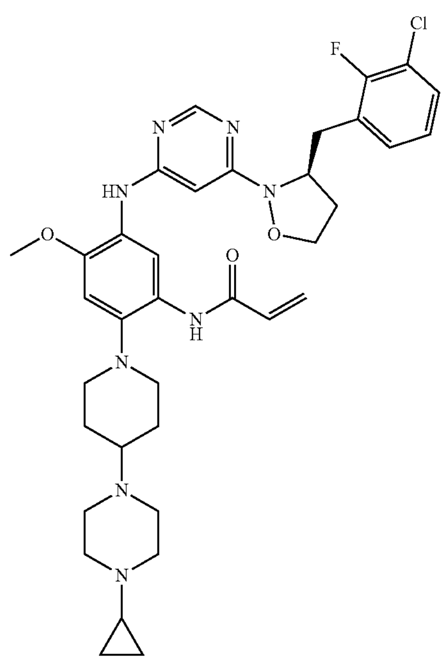 [SMILES: C=CC(=O)Nc1cc(Nc2cc(N3OCC[C@@H]3Cc3cccc(Cl)c3F)ncn2)c(OC)cc1N1CCC(N2CCN(C3CC3)CC2)CC1] | N-(5-((6-((S)-3-(3-chloro-2-fluorobenzyl)isoxazolidine-2-yl)pyrimidine-4-yl)amino)-2-(4-cyclopropylpiperazine-1-yl)piperidine-1-methoxyphenyl)acrylamide | ¹H NMR (400 MHz, CDCl$_3$) δ 8.83 (s, 1H), 8.43 (s, 1H), 8.34 (s, 1H), 7.30 (t, J = 7.1 Hz, 1H), 7.28-7.23 (m, 1H), 7.01 (t, J = 7.8 Hz, 1H), 6.85 (s, 1H), 6.73 (s, 1H), 6.59 (s, 1H), 6.37-6.19 (m, 2H), 5.73 (dd, J = 10.0, 1.3 Hz, 1H), 4.96-4.87 (m, 1H), 4.08 (td, J = 8.1, 4.7 Hz, 1H), 3.97 (q, J = 8.0 Hz, 1H), 3.82 (s, 3H), 3.15 (dd, J = 14.2, 6.5 Hz, 1H), 3.08-3.01 (m, 2H), 2.98 (dd, J = 14.0, 7.6 Hz, 1H), 2.78-2.58 (m, 9H), 2.37-2.20 (m, 2H), 2.11-2.01 (m, 3H), 1.73-1.54 (m, 4H), 0.50-0.39 (m, 4H); 691.50 [M + H]⁺ | 1.31 |

TABLE 1-continued

| Example Compound | Structure | Name of Compound | ¹H NMR[[:]]; MS [M + H]⁺ | UPLC r.t. (min) |
|---|---|---|---|---|
| 1021 | 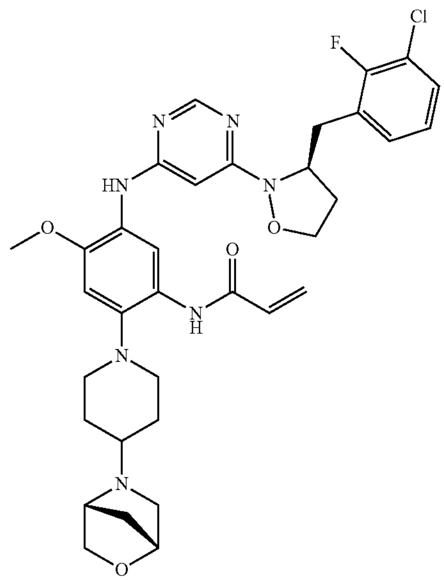 [SMILES: C=CC(=O)Nc1cc(Nc2cc(N3OCC[C@@H]3Cc3cccc(Cl)c3F)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-5-((6-((S)-3-(3-chloro-2-fluorobenzyl)isoxazolidine-2-yl)pyrimidine-4-yl)amino)-4-methoxyphenyl)acrylamide | ¹H NMR (400 MHz, CDCl₃) δ 8.83 (s, 1H), 8.47 (s, 1H), 8.34 (s, 1H), 7.30 (t, J = 7.1 Hz, 1H), 7.28-7.23 (m, 1H), 7.01 (t, J = 7.8 Hz, 1H), 6.93 (s, 1H), 6.74 (s, 1H), 6.59 (s, 1H), 6.36-6.19 (m, 2H), 5.75-5.69 (m, 1H), 4.97-4.87 (m, 1H), 4.45 (s, 1H), 4.12-4.04 (m, 2H), 3.98 (q, J = 8.0 Hz, 1H), 3.85-3.78 (m, 4H), 3.71-3.64 (m, 1H), 3.21-3.10 (m, 2H), 3.06-2.94 (m, 3H), 2.81-2.69 (m, 2H), 2.66-2.57 (m, 1H), 2.57-2.49 (m, 1H), 2.31-2.20 (m, 1H), 2.09-1.82 (m, 5H), 1.78-1.66 (m, 2H); 664.45 [M + H]⁺ | 1.24 |
| 1022 | 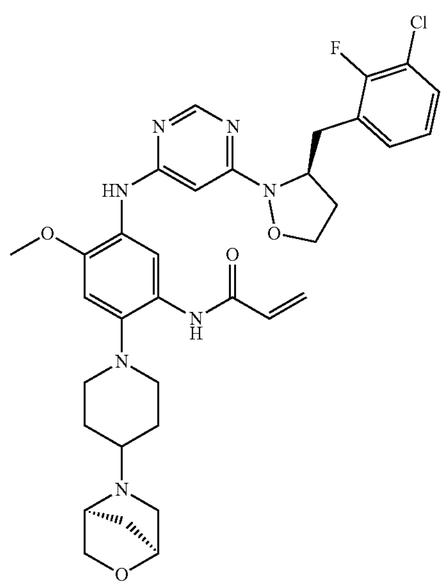 [SMILES: C=CC(=O)Nc1cc(Nc2cc(N3OCC[C@@H]3Cc3cccc(Cl)c3F)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((S)-3-(3-chloro-2-fluorobenzyl)isoxazolidine-2-yl)pyrimidine-4-yl)amino)-4-methoxyphenyl)acrylamide | ¹H NMR (400 MHz, CDCl₃) δ 8.84 (s, 1H), 8.47 (s, 1H), 8.34 (s, 1H), 7.30 (t, J = 7.1 Hz, 1H), 7.28-7.23 (m, 1H), 7.01 (t, J = 7.8 Hz, 1H), 6.86 (s, 1H), 6.75 (s, 1H), 6.60 (s, 1H), 6.37-6.18 (m, 2H), 5.72 (dd, J = 10.1, 1.3 1H), 4.96-4.88 (m, 1H), 4.44 (s, 1H), 4.12-4.05 (m, 2H), 3.98 (q, J = 8.1 Hz, 1H), 3.84 (s, 3H), 3.77 (s, 1H), 3.66 (d, J = 7.5 Hz, 1H), 3.20-3.11 (m, 2H), 3.06-2.94 (m, 3H), 2.81-2.70 (m, 2H), 2.63-2.54 (m, 1H), 2.53 2.47 (m, 1H), 2.31-2.21 (m, 1H), 2.10-2.01 (m, 2H), 1.98-1.89 (m, 2H), 1.86-1.80 (m, 1H), 1.73-1.66 (m, 2H); 664.45 [M + H]⁺ | 1.23 |

TABLE 1-continued

| Example Compound | Structure | Name of Compound | $^1$H NMR[:]; MS [M + H]$^+$ | UPLC r.t. (min) |
|---|---|---|---|---|
| 1023 | 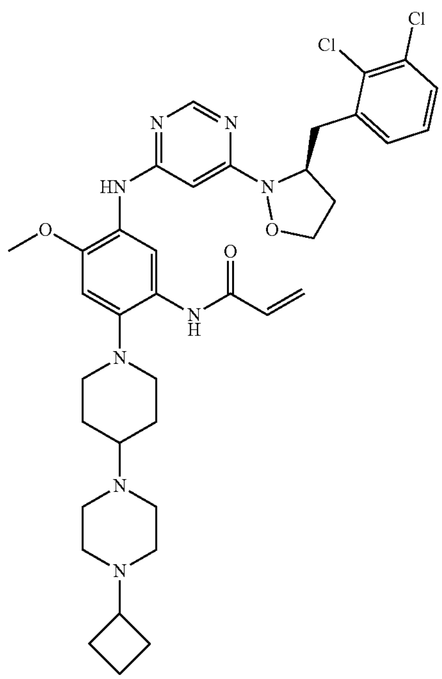 [SMILES: C=CC(=O)Nc1cc(Nc2cc(N3OCC[C@@H]3Cc3cccc(Cl)c3Cl)ncn2)c(OC)cc1N1CCC(N2CCN(C3CCC3)CC2)CC1] | N-(2-(4-(4-cyclobutylpiperazine-1-yl)piperidine-1-yl)-5-((6-((S)-3-(2,3-dichlorobenzyl)isoxazolidine-2-yl)pyrimidine-4-yl)amino)-4-methoxyphenyl)acrylamide | $^1$H NMR (400 MHz, Chloroform-d) δ 8.82 (s, 1H), 8.43 (s, 1H), 8.32 (d, J = 1.0 Hz, 1H), 7.34 (ddd, J = 12.8, 7.9, 1.6 Hz, 2H), 7.12 (t, J = 7.8 Hz, 1H), 6.86 (s, 1H), 6.73 (s, 1H), 6.58 (s, 1H), 6.23 (dd, J = 16.9, 10.0 Hz, 1H), 5.72 (dd, J = 10.0, 1.6 Hz, 1H), 5.00 (qd, J = 7.4, 3.4 Hz, 1H), 4.00 (q, J = 8.1 Hz, 1H), 3.82 (s, 3H), 3.24 (dd, J = 14.2, 7.4 Hz, 1H), 3.11-3.00 (m, 3H), 2.83-2.54 (m, 8H), 2.44 (s, 2H), 2.38-2.29 (m, 2H), 2.25 (dt, J = 12.0, 3.9 Hz, 2H), 2.05 (ddt, J = 15.8, 9.5, 3.2 Hz, 7H), 1.91 (t, J = 9.8 Hz, 3H), 1.68 (dtd, J = 27.2, 12.0, 11.0, 5.5 Hz, 5H), ; 721.5 [M + H]$^+$ | 1.27 |
| 1024 | 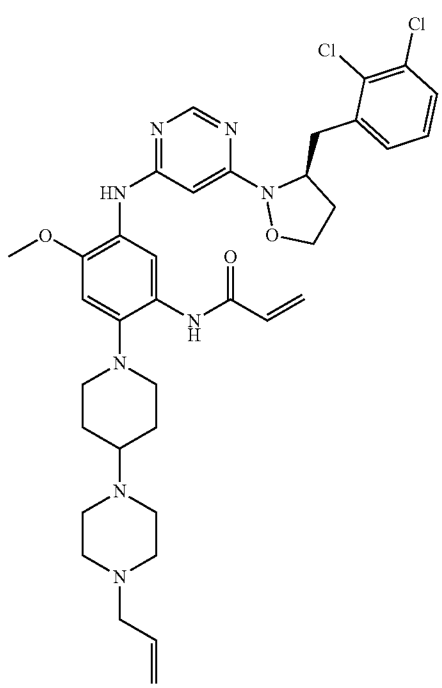 [SMILES: C=CCN1CCN(C2CCN(c3cc(OC)c(Nc4cc(N5OCC[C@@H]5Cc5cccc(Cl)c5Cl)ncn4)cc3NC(=O)C=C)CC2)CC1] | N-(2-(4-(4-allylpiperazine-1-yl)piperidine-1-yl)-5-((6-((S)-3-(2,3-dichlorobenzyl)isoxazolidine-2-yl)pyrimidine-4-yl)amino)-4-methoxyphenyl)acrylamide | 707.3 [M + H]$^+$ | 1.40 |

TABLE 1-continued

| Example Compound | Structure | Name of Compound | ¹H NMR[[:]]; MS [M + H]⁺ | UPLC r.t. (min) |
|---|---|---|---|---|
| 1025 | 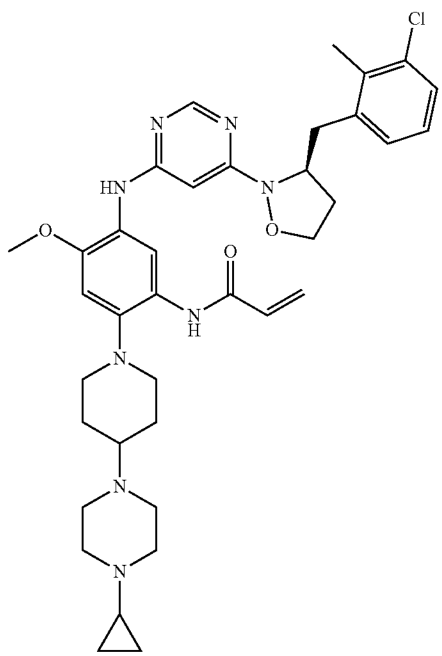 [SMILES: C=CC(=O)Nc1cc(Nc2cc(N3OCC[C@@H]3Cc3cccc(Cl)c3C)ncn2)c(OC)cc1N1CCC(N2CCN(C3CC3)CC2)CC1] | N-(5-((6-((S)-3-(3-chloro-2-methylbenzyl)isoxazolidine-2-yl)pyrimidine-4-yl)amino)-2-(4-(4-cyclopropylpiperazine-1-yl)piperidine-1-yl)-4-methoxyphenyl)acrylamide | ¹H NMR (400 MHz, Chloroform-d) δ 10.67 (s, 1H), 8.27 (d, J = 6.4 Hz, 2H), 8.13 (s, 1H), 7.10-7.00 (m, 2H), 6.67 (s, 1H), 6.48-6.30 (m, 2H), 5.98 (s, 1H), 5.77 (dd, J = 9.7, 1.8 Hz, 1H), 4.74 (tt, J = 9.2, 5.0 Hz, 1H), 4.00 (q, J = 7.6 Hz, 1H), 3.77 (s, 4H), 3.72 (s, 8H), 3.37 (dd, J = 13.8, 5.5 Hz, 1H), 3.24 (d, J = 11.9 Hz, 1H), 3.16 (d, J = 11.6 Hz, 2H) 2.76 (dt, J = 11.1, 8.5 Hz, 3H), 2.53 (td, J = 7.1, 3.5 Hz, 1H), 2.45 (s, 3H), 2.34 (dtd, J = 13.4, 7.9, 5.6 Hz, 1H), 2.20 (dt, J = 11.7, 6.2 Hz, 3H), 2.16-2.01 (m, 3H), 1.17 (d, J = 4.0 Hz, 2H), 0.98-0.78 (m, 4H), ; 687.5 | 1.34 |
| 1026 | 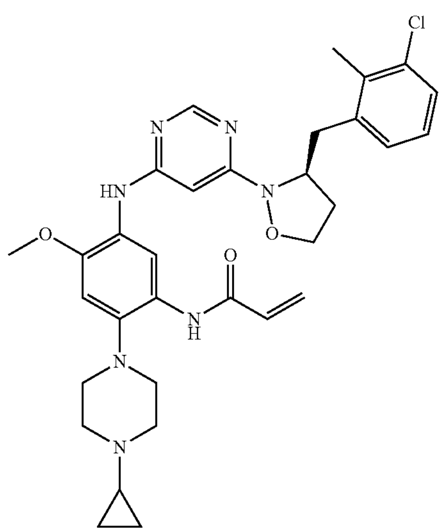 [SMILES: C=CC(=O)Nc1cc(Nc2cc(N3OCC[C@@H]3Cc3cccc(Cl)c3C)ncn2)c(OC)cc1N1CCN(C2CC2)CC1] | N-(5-((6-((S)-3-(3-chloro-2-methylbenzyl)isoxazolidine-2-yl)pyrimidine-4-yl)amino)-2-(4-cyclopropylpiperazine-1-yl)-4-methoxyphenyl)acrylamide | ¹H NMR (400 MHz, Chloroform-d) δ 8.65 (s, 1H), 8.46 (s, 1H), 8.24-8.22 (m, 1H), 7.23 (d, J = 1.4 Hz, 1H), 7.13 (dd, J = 7.8, 1.4, 1H), 7.05 (t, J = 7.8, 1H), 6.77 (s, 1H), 6.40-6.23 (m, 3H), 5.75 (dd, J = 9.6, 2.0 Hz, 1H), 4.84-4.74 (m, 1H) 3.80 (s, 3H), 2.96 (s, 6H), 2.80 (dd, J = 14.0, 8.7 Hz, 2H), 2.47 (s, 3H), 2.22 (dtd, J = 12.4, 7.9, 4.6 Hz, 1H), 2.14-2.07 (m, 1H), 2.06 (s, 4H), 1.91 (d, J = 10.0 Hz, 1H), 1.26 (d, J = 2.6 Hz, 1H), 0.91-0.80 (m, 1H), 0.71 (s, 2H), 0.61 (d, J = 6.6 Hz, 2H), ; 604.4 [M + H]⁺ | 1.33 |

TABLE 1-continued

| Example Compound | Structure | Name of Compound | ¹H NMR[[:]]; MS [M + H]⁺ | UPLC r.t. (min) |
|---|---|---|---|---|
| 1027 | 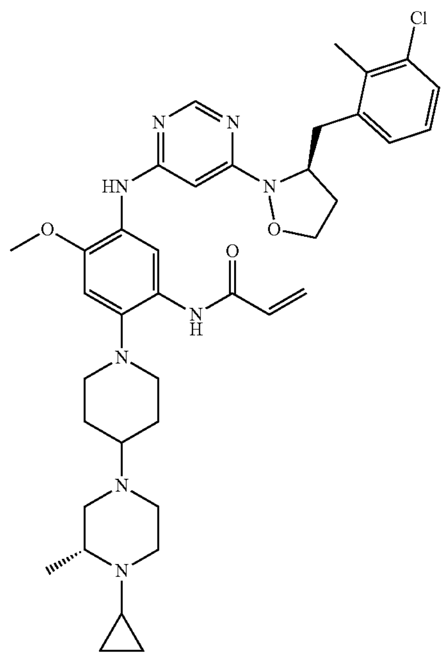 | N-(5-((6-((S)-3-(3-chloro-2-methylbenzyl)isoxazolidine-2-yl)pyrimidine-4-yl)amino)-2-(4-((R)-4-cyclopropyl-3-methylpiperazine-1-yl)piperidine-1-yl)-4-methoxyphenyl)acrylamide | 701.6 [M + H]⁺ | 1.32 |
| 1028 | 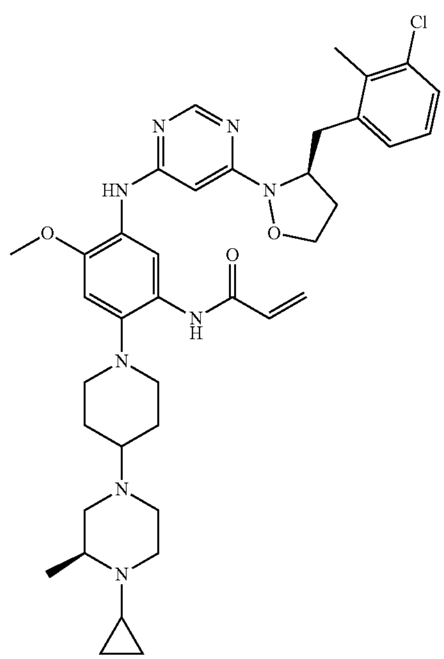 | N-(5-((6-((S)-3-(3-chloro-2-methylbenzyl)isoxazolidine-2-yl)pyrimidine-4-yl)amino)-2-(4-((S)-4-cyclopropyl-3-methylpiperazine-1-yl)piperidine-1-yl)-4-methoxyphenyl)acrylamide | ¹H NMR (400 MHz, Chloroform-d) δ 8.72 (s, 1H), 8.45 (s, 1H), 8.28 (d, J = 1.0 Hz, 1H), 7.22 (d, J = 1.3, Hz, 1H), 7.15 (dd, J = 7.7, 1.4 Hz, 1H), 7.04 (t, J = 7.7 Hz, 1H), 6.67 (s, 1H), 6.52-6.47 (m, 1H), 6.42-6.26 (m, 2H), 5.73 (dd, J = 9.3, 2.2 Hz, 1H), 4.81 (tdd, J = 8.3, 6.1, 4.1 Hz, 1H), 4.09 (td, J = 8.0, 4.5 Hz, 1H), 3.96 (q, J = 8.1 Hz, 1H), 3.80 (s, 3H), 3.57 (d, J = 10.6 Hz, 1H), 3.29 (dd, J = 14.0, 6.1 Hz, 1H), 3.12-3.02 (m, 3H), 2.97 (s, 1H), 2.88 (d, J = 10.2 Hz, 1H), 2.84-2.62 (m, 4H), 2.47 (s, 3H), 2.30-2.11 (m, 4H), 2.11-2.06 (m, 2H), 1.33-1.22 (m, 2H), 0.92-0.77 (m, 2H), ; 701.6 [M + H]⁺ | 1.36 |

TABLE 1-continued

| Example Compound | Structure | Name of Compound | ¹H NMR[:]; MS [M + H]⁺ | UPLC r.t. (min) |
|---|---|---|---|---|
| 1029 | 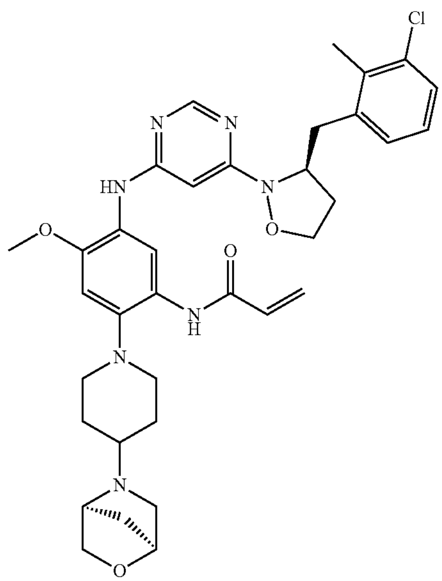 [SMILES: C=CC(=O)Nc1cc(Nc2cc(N3OCC[C@@H]3Cc3cccc(Cl)c3C)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((S)-3-(3-chloro-2-methylbenzyl)isoxazolidine-2-yl)pyrimidine-4-yl)amino)-4-methoxyphenyl)acrylamide | ¹H NMR (400 MHz, Chloroform-d) δ 8.72 (s, 1H), 8.45 (s, 1H), 8.28 (d, J = 1.0 Hz, 1H), 7.22 (d, J = 1.3, 1H), 7.15 (dd, J = 7.7, 1.4 Hz, 1H), 7.04 (t, J = 7.7 Hz, 1H), 6.67 (s, 1H), 6.52-6.47 (m, 1H), 6.42-6.26 (m, 2H), 5.73 (dd, J = 9.3, 2.2 Hz, 1H), 4.81 (tdd, J = 8.3, 6.1, 4.1 Hz, 1H), 4.09 (td, J = 8.0, 4.5 Hz, 1H), 3.96 (q, J = 8.1 Hz, 1H), 3.80 (s, 3H), 3.57 (d, J = 10.6 Hz, 1H), 3.29 (dd, J = 14.0, 6.1 Hz, 1H), 3.12-3.02 (m, 3H), 2.97 (s, 1H), 2.88 (d, J = 10.2 Hz, 1H), 2.84-2.62 (m, 4H), 2.47 (s, 3H), 2.30-2.11 (m, 4H), 2.11-2.06 (m, 2H), 1.33-1.22 (m, 2H), 0.92-0.77 (m, 2H), ; 660.4 [M + H]⁺ | 1.23 |
| 1030 | 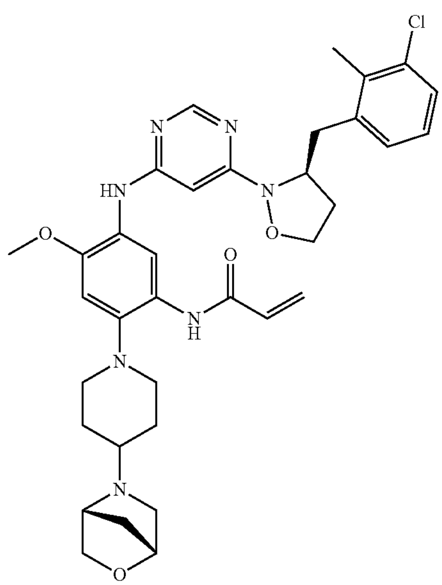 | N-(2-(4-((1R,4R)-2-oxa-5-azabicyclo[2.2.1]heptane-5-yl)piperidine-1-yl)-5-((6-((S)-3-(3-chloro-2-methylbenzyl)isoxazolidine-2-yl)pyrimidine-4-yl)amino)-4-methoxyphenyl)acrylamide | ¹H NMR (400 MHz, Chloroform-d) δ 8.74 (s, 1H), 8.48 (d, J = 1.0 Hz, 1H), 7.24 (dd, J = 7.9, 1.3 Hz, 1H), 7.16 (dd, J = 7.7, 1.4 Hz, 1H), 7.05 (t, J = 7.8 Hz, 1H), 6.72 (s, 1H), 6.53 (s, 1H), 6.34 (s, 1H), 6.32 (d, J = 2.1 Hz, 1H), 5.73 (dd, J = 6.9, 4.7 Hz, 1H), 4.87-4.77 (m, 1H), 4.11-4.04 (m, 2H), 3.83 (s, 3H), 3.75-3.71 (m, 1H), 3.39 (d, J = 10.4 Hz, 1H), 3.30 (dd, J = 14.0, 6.1 Hz, 1H), 3.06 (d, J = 11.8 Hz, 2H), 2.85-2.62 (m, 6H), 2.48 (s, 3H), 2.20 (dtd, J = 12.4, 8.1, 4.6 Hz, 2H), 2.06 (s, 5H), 1.94 (d, J = 11.2 Hz, 5H), 1.34-1.22 (m, 2H), ; 660.4 [M + H]⁺ | 1.25 |

TABLE 1-continued

| Example Compound | Structure | Name of Compound | ¹H NMR[:]; MS [M + H]⁺ | UPLC r.t. (min) |
|---|---|---|---|---|
| 1031 | 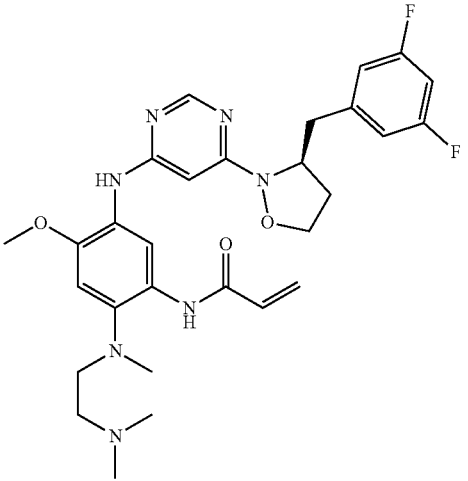 [SMILES: C=CC(=O)Nc1cc(Nc2cc(N3OCC[C@@H]3Cc3cc(F)cc(F)c3)ncn2)c(OC)cc1N(C)CCN(C)C] | N-(5-((6-((S)-3-(3,5-difluorobenzyl)isoxazolidine-2-yl)pyrimidine-4-yl)amino)-2-((2-(dimethylamino)ethyl)(methyl)amino)-4-methoxyphenyl)acrylamide | ; 568.40 [M + H]+ | 1.24 |
| 1032 | 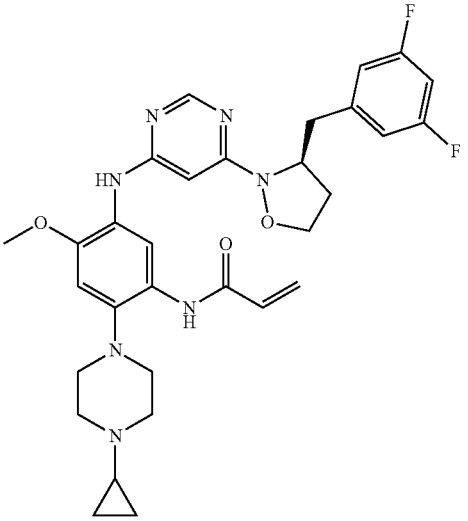 [SMILES: C=CC(=O)Nc1cc(Nc2cc(N3OCC[C@@H]3Cc3cc(F)cc(F)c3)ncn2)c(OC)cc1N1CCN(C2CC2)CC1] | N-(2-(4-cyclopropylpiperazine-1-yl)-5-((6-(S)-3-(3,5-difluorobenzyl)isoxazolidine-2-yl)pyrimidine-4-yl)amino)-4-methoxyphenyl)acrylamide | ¹H NMR (400 MHz, CDCl₃) δ 8.87 (s, 1H), 8.59 (s, 1H), 8.36 (s, 1H), 6.91-6.83 (m, 3H), 6.78 (s, 1H), 6.70-6.62 (m, 1H), 6.61 (s, 1H), 6.39-6.23 (m, 2H), 5.75 (dd, J = 9.8, 1.6 Hz, 1H), 4.88 (qd, J = 7.5, 3.9 Hz, 1H), 4.08 (td, J = 8.2, 4.4 Hz, 1H), 3.97 (q, J = 8.2 Hz, 1H), 3.80 (s, 3H), 3.18 (dd, J = 13.9, 6.7 Hz, 1H), 2.94-2.72 (m, 9H), 2.32-2.20 (m, 1H), 2.08-1.98 (m, 1H), 1.75-1.68 (m, 1H), 0.56-0.49 (m, 2H), 0.49-0.43 (m, 2H); 592.45 [M + H]⁺ | 1.22 |

TABLE 1-continued

| Example Compound | Structure | Name of Compound | ¹H NMR[[:]]; MS [M + H]⁺ | UPLC r.t. (min) |
|---|---|---|---|---|
| 1033 | 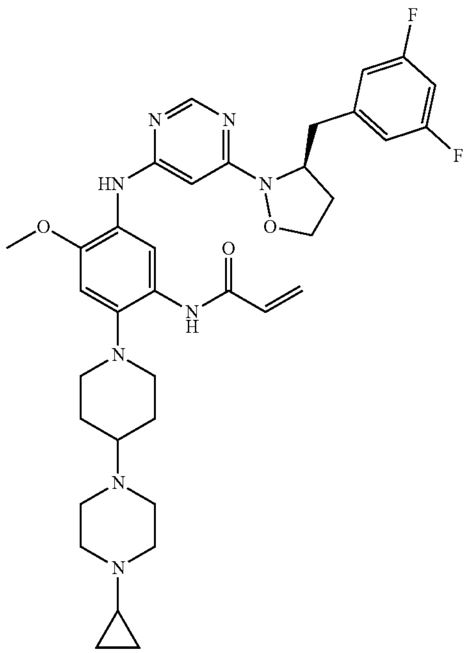 [SMILES: C=CC(=O)Nc1cc(Nc2cc(N3OCC[C@@H]3Cc3cc(F)cc(F)c3)ncn2)c(OC)cc1N1CCC(N2CCN(C3CC3)CC2)CC1] | N-(2-(4-(4-cyclopropyl piperazine-1-yl)piperidine-1-yl)-5-((6-((S)-3-(3,5-difluorobenzyl) isoxazolidine-2-yl)pyrimidine-4-yl)amino)-4-methoxyphenyl) acrylamide | ¹H NMR (400 MHz, CDCl₃) δ 8.83 (s, 1H), 8.44 (s, 1H), 8.36 (s, 1H), 6.90-6.82 (m, 3H), 6.73 (s, 1H), 6.69-6.62 (m, 1H), 6.60 (s, 1H), 6.38-6.19 (m, 2H), 5.73 (dd, J = 10.0, 1.3 Hz, 1H), 4.92-4.83 (m, 1H), 4.07 (td, J = 8.2, 4.5 Hz, 1H), 3.97 (q, J = 8.1 Hz, 1H), 3.83 (s, 3H), 3.17 (dd, J = 14.0, 6.7 Hz, 1H), 3.10-3.00 (m, 2H), 2.83-2.58 (m, 10H), 2.38-2.21 (m, 2H), 2.11-1.97 (m, 3H), 1.72-1.62 (m, 4H), 0.51-0.38 (m, 4H); 675.53 [M + H]⁺ | 1.23 |
| 1034 | 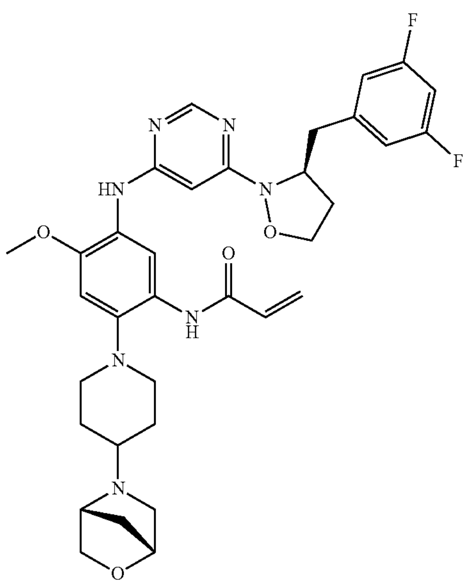 [SMILES: C=CC(=O)Nc1cc(Nc2cc(N3OCC[C@@H]3Cc3cc(F)cc(F)c3)ncn2)c(OC)cc1N1CCC(N2C[C@H]3C[C@@H]2CO3)CC1] | N-(2-(4-((1R,4R)-2-oxa-5-azabicyclo[2.2.1] heptane-5-yl)piperidine-1-yl)-5-((6-((S)-3-(3,5-difluorobenzyl) isoxazolidine-2-yl)pyrimidine-4-yl)amino)-4-methoxyphenyl) acrylamide | ¹H NMR (400 MHz, CDCl₃) δ 8.84 (s, 1H), 8.47 (s, 1H), 8.36 (s, 1H), 6.91-6.83 (m, 3H), 6.75 (s, 1H), 6.70-6.62 (m, 1H), 6.61 (s, 1H), 6.38-6.18 (m, 2H), 5.72 (dd, J = 10.0, 1.3 Hz, 1H), 4.88 (qd, J = 7.6, 3.9 Hz, 1H), 4.44 (s, 1H), 4.12-4.03 (m, 2H), 3.97 (q, J = 8.1 Hz, 1H), 3.84 (s, 3H), 3.81-3.74 (m, 1H), 3.70-3.63 (m, 1H), 3.21-3.11 (m, 2H), 3.07-2.97 (m, 2H), 2.83-2.70 (m, 3H), 2.63-2.54 (m, 1H), 2.54-2.47 (m, 1H), 2.31-2.19 (m, H), 2.07-1.99 (m, 2H), 1.98-1.89 (m, 2H), 1.87-1.79 (m, 1H), 1.75-1.67 (m, 2H); 648.44 [M + H]⁺ | 1.20 |

TABLE 1-continued

| Example Compound | Structure | Name of Compound | ¹H NMR[[:]]; MS [M + H]⁺ | UPLC r.t. (min) |
|---|---|---|---|---|
| 1035 | 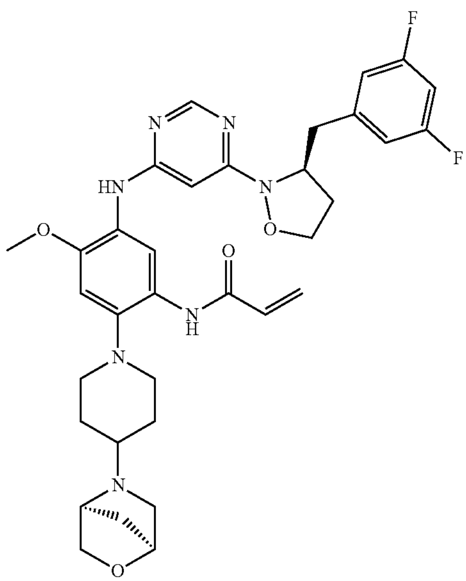 [SMILES: C=CC(=O)Nc1cc(Nc2cc(N3OCC[C@@H]3Cc3cc(F)cc(F)c3)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((S)-3-(3,5-difluorobenzyl)isoxazolidine-2-yl)pyrimidine-4-yl)amino)-4-methoxyphenyl)acrylamide | ¹H NMR (400 MHz, CDCl₃) δ 8.84 (s, 1H), 8.47 (s, 1H), 8.36 (s, 1H), 6.91-6.84 (m, 3H), 6.75 (s, 1H), 6.69-6.62 (m, 1H), 6.60 (s, 1H), 6.37-6.19 (m, 2H), 5.72 (dd, J = 10.0, 1.2 Hz, 1H), 4.88 (qd, J = 7.6, 3.9 Hz, 1H), 4.45 (s, 1H), 4.13-4.04 (m, 2H), 3.97 (q, J = 8.1 Hz, 1H), 3.84 (s, 3H), 3.82-3.74 (m, 1H), 3.71-3.63 (m, 1H), 3.22-3.12 (m, 2H), 3.07-2.98 (m, 2H), 2.83-2.70 (m, 3H), 2.64-2.55 (m, 1H), 2.55-2.48 (m, 1H), 2.30-2.20 (m, 1H), 2.09-1.99 (m, 2H), 1.99-1.89 (m, 2H), 1.88-1.80 (m, 1H), 1.77-1.68 (m, 2H); 648.44 [M + H]⁺ | 1.19 |
| 1036 | 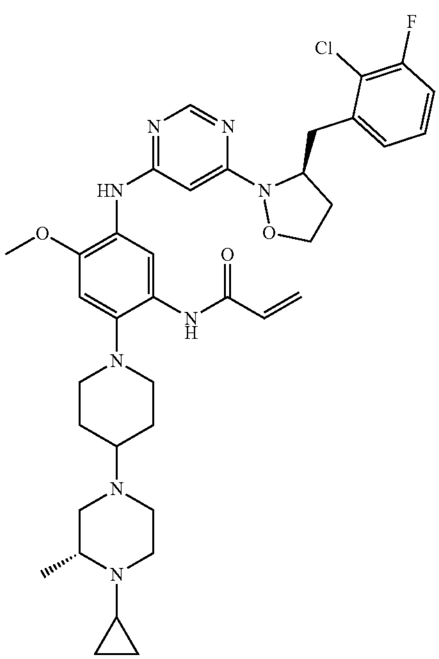 [SMILES: C=CC(=O)Nc1cc(Nc2cc(N3OCC[C@@H]3Cc3cccc(F)c3Cl)ncn2)c(OC)cc1N1CCC(N2CCN(C3CC3)[C@H](C)C2)CC1] | N-(5-((6-((S)-3-(2-chloro-3-fluorobenzyl)isoxazolidine-2-yl)pyrimidine-4-yl)amino)-2-(4-((R)-4-cyclopropyl-3-methylpiperazine-1-yl)piperidine-1-yl)-4-methoxyphenyl)acrylamide | ¹H NMR (400 MHz, Methanol-d₄) δ 8.27 (s, 1H), 8.14 (s, 1H), 7.32-7.19 (m, 2H), 7.15-7.07 (m, 1H), 6.91 (s, 1H), 6.63-6.49 (m, 1H), 6.39-6.27 (m, 2H), 5.81 (dd, J = 1.5, 10.2 Hz, 1H), 6.39-6.27 (m, 2H), 5.81 ( dd, J = 1.5, 10.2 Hz, 1H), 4.17-4.11 (m, 1H), 3.97-3.82 (m, 4H), 3.30-3.25 (m, 1H), 3.24-3.13 (m, 5H), 3.11-3.02 (m, 1H), 2.86-2.60 (m, 6H), 2.44-2.37 (m, 1H), 2.33-2.23 (m, 1H), 2.17-2.10 (m, 3H), 1.94-1.79 (m, 2H), 1.79-1.67 (m, 1H), 1.30 (d, J = 6.3 Hz, 3H), 0.81-0.70 (m, 1H), 0.70-0.62 (m, 1H), 0.62-0.51 (m, 1H), 0.45-0.35 (m, 1H); 705.3 [M + H]⁺ | 1.23 |

TABLE 1-continued

| Example Compound | Structure | Name of Compound | ¹H NMR[[:]]; MS [M + H]⁺ | UPLC r.t. (min) |
|---|---|---|---|---|
| 1037 | 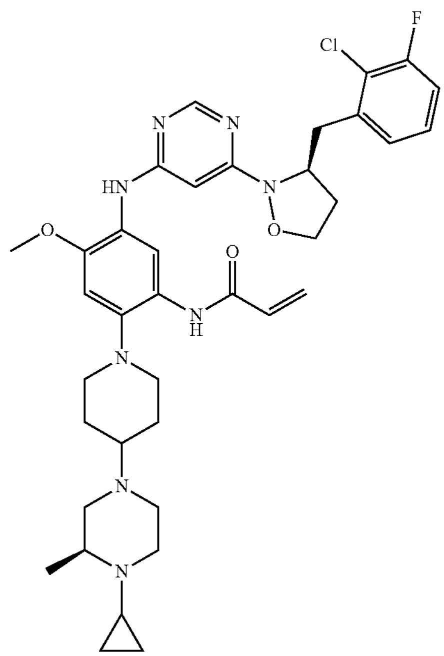 [SMILES: C=CC(=O)Nc1cc(Nc2cc(N3OCC[C@@H]3Cc3cccc(F)c3Cl)ncn2)c(OC)cc1N1CCC(N2CCN(C3CC3)[C@@H](C)C2)CC1] | N-(5-((6-((S)-3-(2-chloro-3-fluorobenzyl)isoxazolidine-2-yl)pyrimidine-4-yl)amino)-2-(4-((S)-4-cyclopropyl-3-methylpiperazine-1-yl)piperidine-1-yl)-4-methoxyphenyl)acrylamide | ¹H NMR (400 MHz, Methanol-$d_4$) δ 8.27 (s, 1H), 8.15 (s, 1H), 7.33-7.20 (m, 2H), 7.18-7.06 (m, 1H), 6.91 (s, 1H), 6.63-6.48 (m, 1H), 6.41-6.25 (m, 2H), 5.84-5.76 (m, 1H), 4.17-4.10 (m, 1H), 3.94-3.84 (m, 4H), 3.30-3.25 (m, 1H), 3.25-3.15 (m, 5H), 3.10-3.03 (m, 1H), 2.85-2.64 (m, 6H), 2.47-2.38 (m, 1H), 2.33-2.24 (m, 1H), 2.17-2.08 (m, 3H), 1.93-1.81 (m, 2H), 1.77-1.69 (m, 1H), 1.30 (d, J = 6.2 Hz, 3H), 0.80-0.71 (m, 1H), 0.70-0.62 (m, 1H), 0.60-0.52 (m, 1H), 0.43-0.35 (m, 1H), ; 705.3 [M + H]⁺ | 1.24 |
| 1038 | 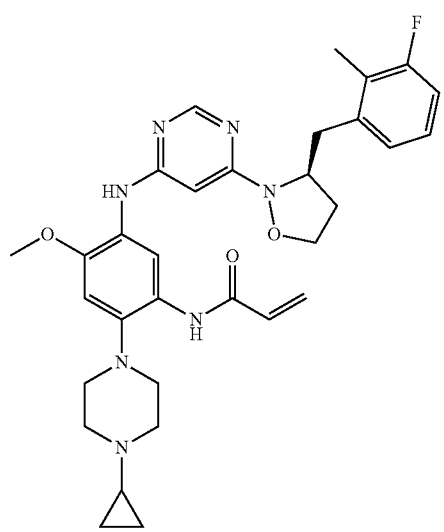 | N-(2-(4-cyclopropylpiperazine-1-yl)-5-((6-((S)-3-(3-fluoro-2-methylbenzyl)isoxazolidine-2-yl)pyrimidine-4-yl)amino)-4-methoxyphenyl)acrylamide | ¹H NMR (400 MHz, Methanol-$d_4$) δ 8.29 (s, 1H), 8.16 (s, 1H), 7.15-7.02 (m, 2H), 6.96-6.81 (m, 2H), 6.60-6.49 (m, 1H), 6.40-6.25 (m, 2H), 5.82 (dd, J = 1.5, 10.2 Hz, 1H), 4.15-4.07 (m, 1H), 3.93-3.85 (m, 4H), 3.24-3.16 (m, 1H), 3.01-2.90 (m, 8H), 2.88-2.81 (m, 1H), 2.32 (d, J = 2.2 Hz, 3H), 2.27-2.20 (m, 1H), 2.17-2.09 (m, 1H), 1.94-1.88 (m, 1H), 0.64-0.57 (m, 2H), 0.57-0.50 (m, 2H); 588.3 [M + H]⁺ | 1.19 |

TABLE 1-continued

| Example Compound | Structure | Name of Compound | ¹H NMR[[:]]; MS [M + H]⁺ | UPLC r.t. (min) |
|---|---|---|---|---|
| 1039 | 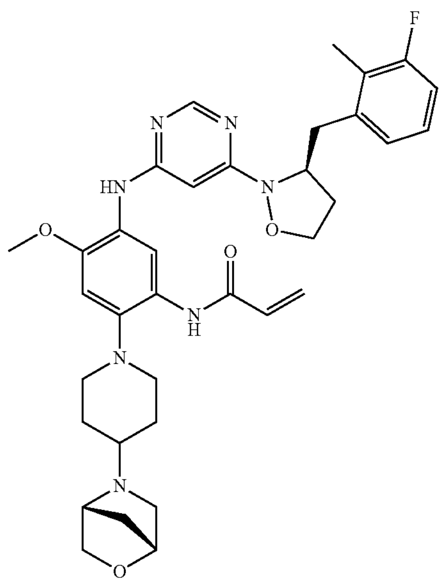 [SMILES: C=CC(=O)Nc1cc(Nc2cc(N3OCC[C@@H]3Cc3cccc(F)c3C)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-5-((6-((S)-3-(3-fluoro-2-methylbenzyl)isoxazolidine-2-yl)pyrimidine-4-yl)amino)-4-methoxyphenyl)acrylamide | ¹H NMR (400 MHz, Methanol-d₄) δ 8.26 (s, 1H), 8.17 (s, 1H), 7.17-7.04 (m, 2H), 6.97-6.83 (m, 2H), 6.63-6.49 (m, 1H), 6.41-6.25 (m, 2H), 5.81 (d, J = 10.2 Hz, 1H), 4.61-4.58 (m, 1H), 4.29-4.24 (m, 1H), 4.20-4.09 (m, 2H), 3.95-3.84 (m, 4H), 3.81-3.75 (m, 1H), 3.32-3.28 (m, 1H), 3.24-3.12 (m, 3H), 3.07-2.95 (m, 2H), 2.90-2.78 (m, 3H), 2.32 (d, J = 2.2 Hz, 3H), 2.29-2.02 (m, 7H), 1.89-1.77 (m, 2H); 644.3 [M + H]⁺ | 1.18 |
| 1040 | 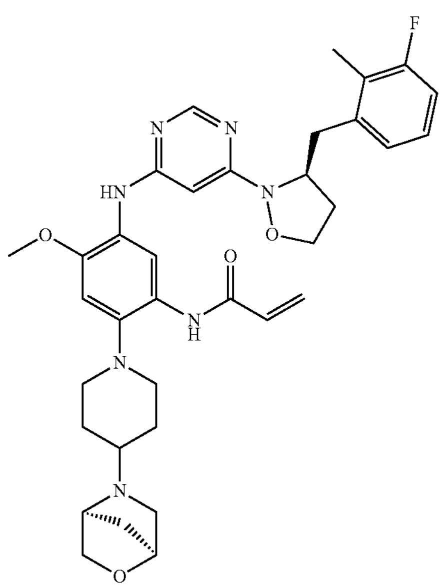 [SMILES: C=CC(=O)Nc1cc(Nc2cc(N3OCC[C@@H]3Cc3cccc(F)c3C)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((S)-3-(3-fluoro-2-methylbenzyl)isoxazolidine-2-yl)pyrimidine-4-yl)amino)-4-methoxyphenyl)acrylamide | ¹H NMR (400 MHz, Methanol-d₄) δ 8.26 (s, 1H), 8.17 (s, 1H), 7.16-7.04 (m, 2H), 6.97-6.84 (m, 2H), 6.63-6.47 (m, 1H), 6.42-6.26 (m, 2H), 5.86-5.75 (m, 1H), 4.59 (s, 1H), 4.27 (s, 1H), 4.20-4.08 (m, 2H), 3.95-3.84 (m, 4H), 3.82-3.74 (m, 1H), 3.32 (d, J = 3.0 Hz, 1H), 3.24-3.11 (m, 3H), 3.08-2.96 (m, 2H), 2.89-2.78 (m, 3H), 2.32 (d, J = 2.2 Hz, 3H), 2.30-2.01 (m, 7H), 1.90-1.76 (m, 2H); 644.3 [M + H]⁺ | 1.18 |

TABLE 1-continued

| Example Compound | Structure | Name of Compound | ¹H NMR[[:]]; MS [M + H]⁺ | UPLC r.t. (min) |
|---|---|---|---|---|
| 1041 | 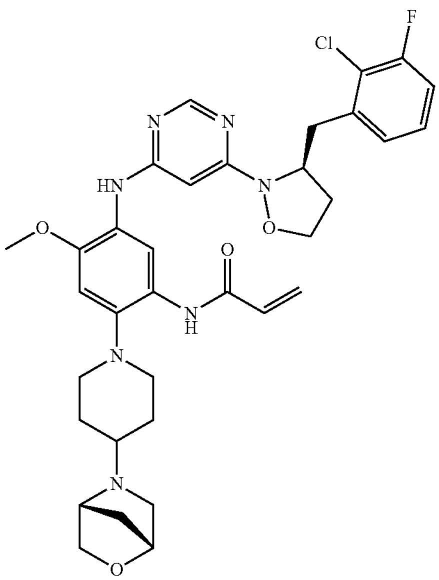 [SMILES: C=CC(=O)Nc1cc(Nc2cc(N3OCC[C@@H]3Cc3cccc(F)c3Cl)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-5-((6-((S)-3-(2-chloro-3-fluorobenzyl)isoxazolidine-2-yl)pyrimidine-4-yl)amino)-4-methoxyphenyl)acrylamide | ¹H NMR (400 MHz, Methanol-d₄) δ 8.26 (s, 1H), 8.15 (s, 1H), 7.29-7.22 (m, 2H), 7.14-7.08 (m, 1H), 6.92 (s, 1H), 6.55 (dd, J = 10.3, 17.0 Hz, 1H), 6.38-6.30 (m, 2H), 5.81 (d, J = 10.4 Hz, 1H), 4.60-4.58 (m, 1H), 4.28-4.24 (m, H1), 4.19-4.11 (m, 2H), 3.95-3.89 (m, 1H), 3.87 (s, 3H), 3.80-3.75 (m, 1H), 3.31-3.30 (m, 1H), 3.22-3.14 (m, 3H), 3.10-2.97 (m, 3H), 2.89-2.80 (m, 2H), 2.32-2.24 (m, 1H), 2.21-2.04 (m, 6H), 1.87-1.79 (m, 2H), ; 663.3 [M + H]⁺ | 1.18 |
| 1042 | 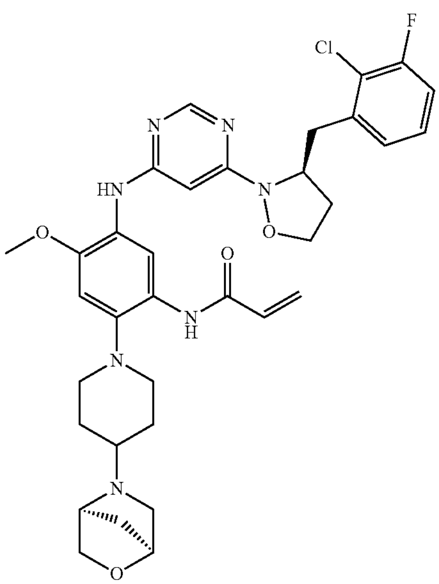 [SMILES: C=CC(=O)Nc1cc(Nc2cc(N3OCC[C@@H]3Cc3cccc(F)c3Cl)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-5-((6-((S)-3-(2-chloro-3-fluorobenzyl)isoxazolidine-2-yl)pyrimidine-4-yl)amino)-4-methoxyphenyl)acrylamide | ¹H NMR (400 MHz, Methanol-d₄) δ 8.26 (s, 1H), 8.15 (s, 1H), 7.31-7.21 (m, 2H), 7.14-7.07 (m, 1H), 6.92 (s, 1H), 6.55 (dd, J = 10.2, 17.0 Hz, 1H), 6.40-6.28 (m, 2H), 5.81 (d, J = 10.2 Hz, 1H), 4.60-4.58 (m, 1H), 4.27-4.25 (m, 1H), 4.19-4.11 (m, 2H), 3.96-3.89 (m, 1H), 3.87 (s, 3H), 3.80-3.75 (m, 1H), 3.31-3.29 (m, 1H), 3.22-3.14 (m, 3H), 3.10-2.97 (m, 3H), 2.89-2.81 (m, 2H), 2.33-2.24 (m, 1H), 2.23-2.01 (m, 6H), 1.88-1.76 (m, 2H); 663.3 [M + H]⁺ | 1.18 |

TABLE 1-continued

| Example Compound | Structure | Name of Compound | ¹H NMR[[:]]; MS [M + H]⁺ | UPLC r.t. (min) |
|---|---|---|---|---|
| 1043 | 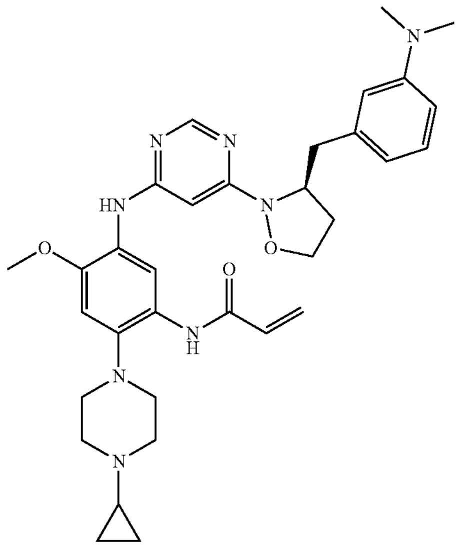 | N-(2-(4-cyclopropylpiperazine-1-yl)-5-((6-((S)-3-(3-(dimethylamino)benzyl)isoxazolidine-2-yl)pyrimidine-4-yl)amino)-4-methoxyphenyl)acrylamide | ¹H NMR (400 MHz, Chloroform-d) δ 8.91 (s, 1H), 8.59 (s, 1H), 8.40 (d, J = 1.0 Hz, 1H), 7.17 (t, J = 7.8 Hz, 1H), 6.88 (s, 1H), 6.78 (s, 1H), 6.75-6.65 (m, 2H), 6.65-6.57 (m, 2H), 6.36 (dd, J = 17.0, 1.7 Hz, 1H), 6.27 (dd, J = 17.0, 9.8 Hz, 1H), 5.74 (dd, J = 9.8, 1.7 Hz, 1H), 4.96-4.85 (m, 1H), 4.07 (td, J = 8.0, 5.0 Hz, 1H), 3.98 (q, J = 8.0 Hz, 1H), 3.80 (s, 3H), 3.27 (dd, J = 13.7, 5.6 Hz, 1H), 2.95 (s, 6H), 2.89-2.85 (m, 4H), 2.85-2.75 (m, 4H), 2.75-2.67 (m, 1H), 2.22-2.03 (m, 2H), 1.77-1.67 (m, 1H), 0.57-0.42 (m, 4H), ; 599.5 [M + H]⁺ | 1.12 |
| 1044 | 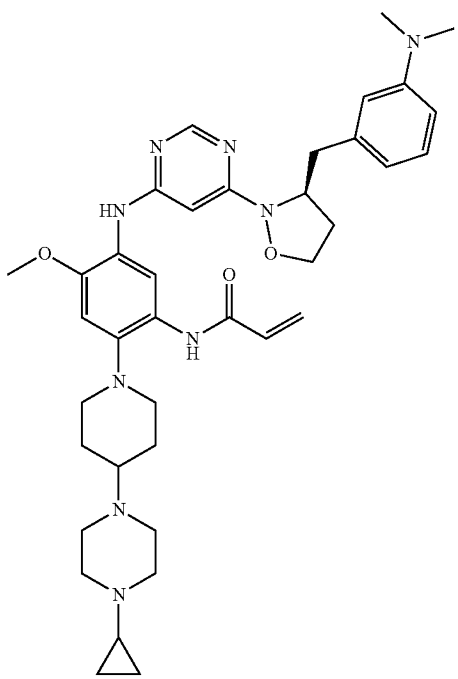 | N-(2-(4-(4-cyclopropylpiperazine-1-yl)piperidine-1-yl)-5-((6-((S)-3-(3-(dimethylamino)benzyl)isoxazolidine-2-yl)pyrimidine-4-yl)amino)-4-methoxyphenyl)acrylamide | ¹H NMR (400 MHz, Chloroform-d) δ 8.86 (s, 1H), 8.46-8.37 (m, 2H), 7.17 (t, J = 7.8 Hz, 1H), 6.85 (s, 1H), 6.76-6.57 (m, 5H), 6.34 (dd, J = 17.0, 1.6 Hz, 1H), 6.23 (dd, J = 16.9, 10.0 Hz, 1H), 5.72 (dd, J = 10.0, 1.6 Hz, 1H), 4.91 (ddt, J = 13.4, 9.6, 5.2 Hz, 1H), 4.07 (td, J = 8.0, 5.0 Hz, 1H), 3.98 (q, J = 7.9 Hz, 1H), 3.83 (s, 3H), 3.26 (dd, J = 13.7, 5.6 Hz, 1H), 3.05 (d, J = 11.6 Hz, 2H), 2.95 (s, 6H), 2.78-2.68 (m, 6H), 2.68-2.53 (m, 4H), 2.37-2.27 (m, 1H), 2.22-2.03 (m, 4H), 1.71-1.61 (m, 3H), 0.51-0.38 (m, 4H), ; 682.5 [M + H]⁺ | 1.14 |

TABLE 1-continued

| Example Compound | Structure | Name of Compound | ¹H NMR[[:]]; MS [M + H]⁺ | UPLC r.t. (min) |
|---|---|---|---|---|
| 1045 | 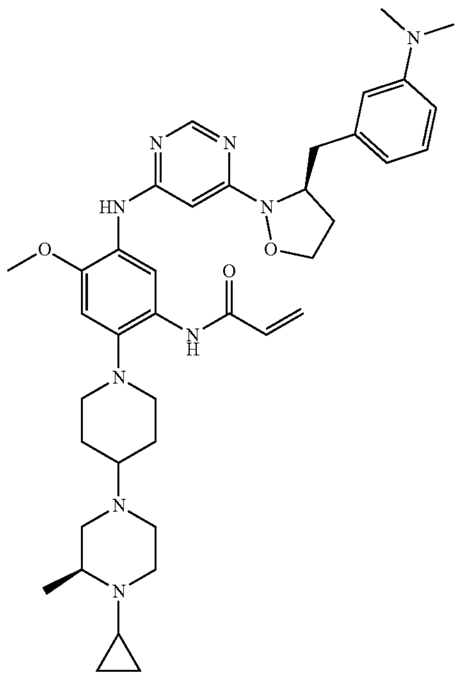 | N-(2-(4-((S)-4-cyclopropyl-3-methylpiperazine-1-yl)piperidine-1-yl)-5-((6-((S)-3-(3-(dimethylamino)benzyl)isoxazolidine-2-yl)pyrimidine-4-yl)amino)-4-methoxyphenyl)acrylamide | ¹H NMR (400 MHz, Chloroform-d) δ 8.86 (s, 1H), 8.43 (s, 1H), 8.39 (d, J = 1.0 Hz, 1H), 7.17 (t, J = 7.8 Hz, 1H), 6.87 (s, 1H), 6.75-6.71 (m, 2H), 6.68 (d, J = 7.4 Hz, 1H), 6.65-6.57 (m, 2H), 6.35 (dd, J = 17.0, 1.6 Hz, 1H), 6.24 (dd, J = 16.9, 10.0 Hz, 1H), 5.73 (dd, J = 10.0, 1.6 Hz, 1H), 4.96-4.85 (m, 1H), 4.07 (td, J = 8.0, 5.0 Hz, 1H), 3.98 (q, J = 7.9 Hz, 1H), 3.83 (s, 3H), 3.26 (dd, J = 13.6, 5.6 Hz, 1H), 3.08-2.95 (m, 4H), 2.94 (s, 6H), 2.87 (d, J = 10.8 Hz, 1H), 2.77-2.65 (m, 3H), 2.59-2.42 (m, 2H), 2.30 (tt, J = 11.5, 4.7 Hz, 2H), 2.22-2.03 (m, 4H), 2.00 (t, J = 10.3 Hz, 1H), 1.66 (qd, J = 11.8, 5.9 Hz, 2H), 1.58-1.48 (m, 1H), 1.21 (d, J = 6.4 Hz, 3H), 0.70-0.55 (m, 2H), 0.49-0.38 (m, 1H), 0.37-0.26 (m, 1H), ; 696.5 [M + H]⁺ | 1.17 |
| 1046 | 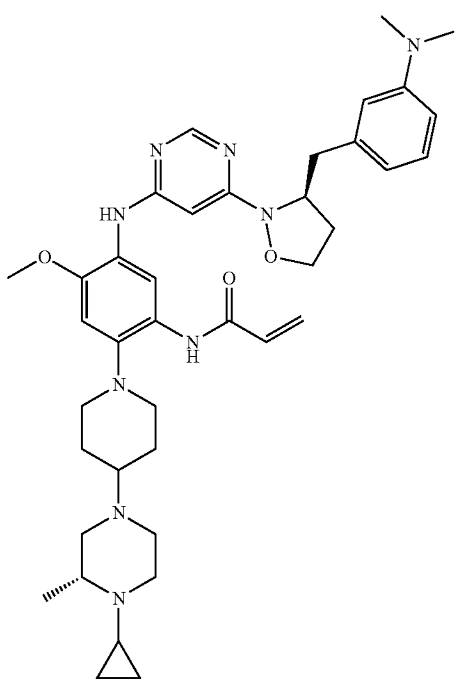 | N-(2-(4-((R)-4-cyclopropyl-3-methylpiperazine-1-yl)piperidine-(dimethylamino)benzyl)isoxazolidine-2-yl)pyrimidine-4-yl)amino)-4-methoxyphenyl)acrylamide | ¹H NMR (400 MHz, Chloroform-d) δ 8.86 (s, 1H), 8.44 (s, 1H), 8.40-8.37 (m, 1H), 7.16 (t, J = 7.8 Hz, 1H), 6.90 (s, 1H), 6.75-6.71 (m, 2H), 6.68 (d, J = 7.4 Hz, 1H), 6.62 (d, J = 2.6 Hz, 1H), 6.59 (d, J = 2.6 Hz, 1H), 6.35 (dd, J = 16.9, 1.6 Hz, 1H), 6.24 (dd, J = 16.9, 10.0 Hz, 1H), 5.72 (dd, J = 9.9, 1.6 Hz, 1H), 4.90 (tt, J = 9.1, 5.0 Hz, 1H), 4.07 (td, J = 8.0, 5.0 Hz, 1H), 3.98 (q, J = 7.9 Hz, 1H), 3.82 (s, 3H), 3.26 (dd, J = 13.7, 5.6 Hz, 1H), 3.08-2.96 (m, 4H), 2.94 (s, 6H), 2.87 (d, J = 10.9 Hz, 1H), 2.78-2.65 (m, 3H), 2.57-2.42 (m, 2H), 2.35-2.23 (m, 2H), 2.21-2.03 (m, 4H), 2.00 (t, J = 10.4 Hz, 1H), 1.73-1.58 (m, 2H), 1.57-1.48 (m, 1H), 1.22-1.19 (m, 3H), 0.70-0.54 (m, 2H), 0.49-0.38 (m, 1H), 0.37-0.26 (m, 1H), ; 696.5 [M + H]⁺ | 1.17 |

TABLE 1-continued

| Example Compound | Structure | Name of Compound | ¹H NMR[[:]]; MS [M + H]⁺ | UPLC r.t. (min) |
|---|---|---|---|---|
| 1047 | 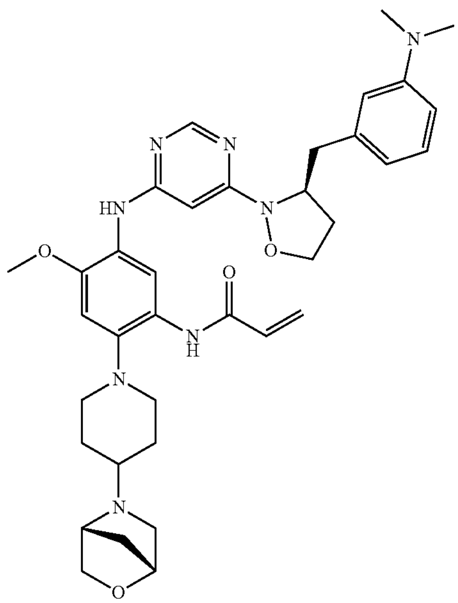 | N-(2-(4-((1R,4R)-2-oxa-5-azabicyclo[2.2.1]heptane-5-yl)piperidine-1-yl)-5-((6-((S)-3-(3-(dimethylamino)benzyl)isoxazolidine-2-yl)pyrimidine-4-yl)amino)-4-methoxyphenyl)acrylamide | ¹H NMR (400 MHz, Chloroform-d) δ 8.87 (s, 1H), 8.47 (s, 1H), 8.40 (d, J = 1.0 Hz, 1H), 7.17 (t, J = 7.8 Hz, 1H), 6.88 (s, 1H), 6.77-6.65 (m, 3H), 6.65-6.57 (m, 2H), 6.34 (dd, J = 16.9, 1.5 Hz, 1H), 6.22 (dd, J = 16.9, 10.0 Hz, 1H), 5.72 (dd, J = 10.0, 1.5 Hz, 1H), 4.96-4.85 (m, 1H), 4.46-4.41 (m, 1H), 4.07 (td, J = 7.9, 5.0 Hz, 2H), 3.98 (q, J = 8.0 Hz, 1H), 3.84 (s, 3H), 3.79-3.73 (m, 1H), 3.66 (dd, J = 7.9, 1.6 Hz, 1H), 3.26 (dd, J = 13.6, 5.6 Hz, 1H), 3.13 (dd, J = 10.0, 1.8 Hz, 1H), 3.10-2.97 (m, 2H), 2.95 (s, 6H), 2.82-2.73 (m, 2H), 2.72-2.66 (m, 1H), 2.63-2.46 (m, 2H), 2.22-2.00 (m, 3H), 1.99-1.89 (m, 2H), 1.84-1.80 (m, 1H), 1.74-1.59 (m, 2H), ; 655.5 [M + H]⁺ | 1.13 |
| 1048 | 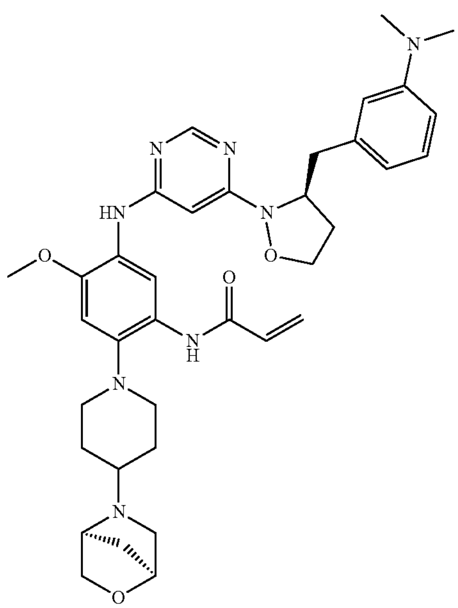 | N-(2-(4-((1S,4S)-2-oxa-5-azabicyclo[2.2.1]heptane-5-yl)piperidine-1-yl)-5-((6-((S)-3-(3-(dimethylamino)benzyl)isoxazolidine-2-yl)pyrimidine-4-yl)amino)-4-methoxyphenyl)acrylamide | ¹H NMR (400 MHz, Chloroform-d) δ 8.87 (s, 1H), 8.47 (s, 1H), 8.40 (d, J = 1.0 Hz, 1H), 7.17 (t, J = 7.8 Hz, 1H), 6.89 (s, 1H), 6.77-6.70 (m, 2H), 6.68 (d, J = 7.4 Hz, 1H), 6.65-6.57 (m, 2H), 6.34 (dd, J = 16.9, 1.6 Hz, 1H), 6.22 (dd, J = 17.0, 10.0 Hz, 1H), 5.72 (dd, J = 10.0, 1.5 Hz, 1H), 4.96-4.85 (m, 1H), 4.44 (t, J = 2.0 Hz, 1H), 4.12-4.04 (m, 2H), 3.98 (q, J = 8.0 Hz, 1H), 3.84 (s, 3H), 3.76 (s, 1H), 3.66 (dd, J = 7.9, 1.6 Hz, 1H), 3.26 (dd, J = 13.7, 5.6 Hz, 1H), 3.13 (dd, J = 9.9, 1.8 Hz, 1H), 3.02 (dd, J = 12.0, 4.5 Hz, 2H), 2.94 (s, 6H), 2.82-2.66 (m, 3H), 2.62-2.54 (m, 1H), 2.50 (d, J = 9.9 Hz, 1H), 2.22-2.00 (m, 3H), 1.97-1.87 (m, 2H), 1.86-1.78 (m, 1H), 1.72-1.60 (m, 2H), ; 655.5 [M + H]⁺ | 1.11 |

TABLE 1-continued

| Example Compound | Structure | Name of Compound | ¹H NMR[:]; MS [M + H]⁺ | UPLC r.t. (min) |
|---|---|---|---|---|
| 1049 | 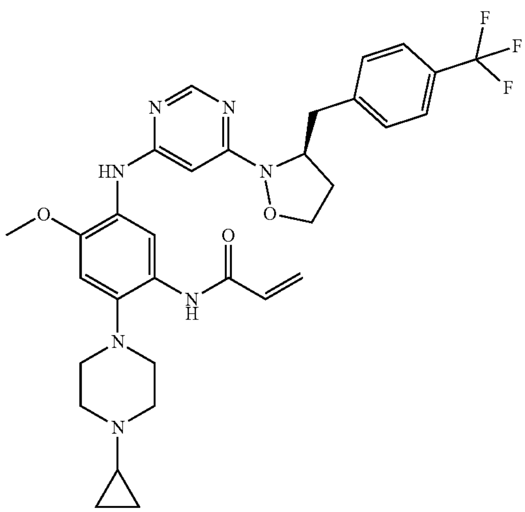 [SMILES: C=CC(=O)Nc1cc(Nc2cc(N3OCC[C@@H]3Cc3ccc(C(F)(F)F)cc3)ncn2)c(OC)cc1N1CCN(C2CC2)CC1] | N-(2-(4-cyclopropylpiperazine-1-yl)-4-methoxy-5-((6-((S)-3-(4-(trifluoromethyl)benzyl)isoxazolidine-2-yl)pyrimidine-4-yl)amino)phenyl)acrylamide | ¹H NMR (400 MHz, CDCl₃) δ 8.87 (s, 1H), 8.59 (s, 1H), 8.37 (d, J = 5.7 Hz, 1H), 7.54 (d, J = 8.1 Hz, 2H), 7.44 (d, J = 8.0 Hz, 2H), 6.88 (s, 1H), 6.78 (s, 1H), 6.59 (s, 1H), 6.39-6.23 (m, 2H), 5.75 (dd, J = 9.8, 1.6 Hz, 1H), 4.92 (qd, J = 7.5, 3.9 Hz, 1H), 4.06 (td, J = 8.1, 4.5 Hz, 1H), 3.97 (q, J = 8.2 Hz, 1H), 3.80 (s, 3H), 3.25 (dd, J = 13.8, 6.6 Hz, 1H), 2.93-2.71 (m, 9H), 2.29-2.19 (m, 1H), 2.09-1.99 (m, 1H), 1.75-1.69 (m, 1H), 0.55-0.42 (m, 4H); 624.48 [M + H]⁺ | 1.29 |
| 1050 | 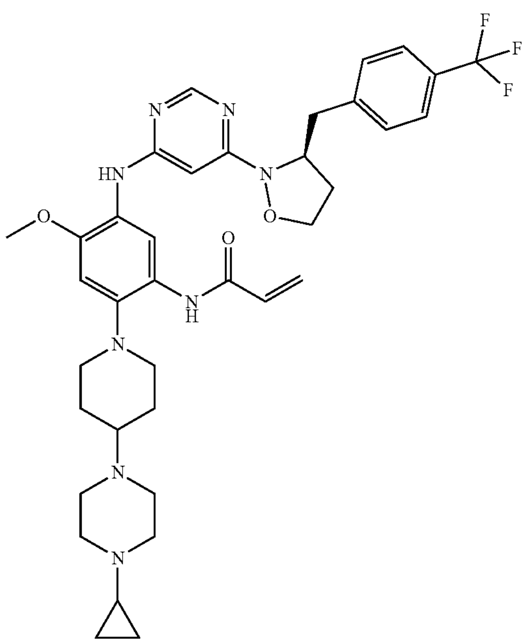 [SMILES: C=CC(=O)Nc1cc(Nc2cc(N3OCC[C@@H]3Cc3ccc(C(F)(F)F)cc3)ncn2)c(OC)cc1N1CCC(N2CCN(C3CC3)CC2)CC1] | N-(2-(4-(4-cyclopropylpiperazine-1-yl)piperidine-1-yl)-4-methoxy-5-((6-((S)-3-(4-(trifluoromethyl)benzyl)isoxazolidine-2-yl)pyrimidine-4-yl)amino)phenyl)acrylamide | ¹H NMR (400 MHz, CDCl₃) δ 8.82 (s, 1H), 8.44 (s, 1H), 8.35 (s, 1H), 7.54 (d, J = 8.1 Hz, 2H), 7.44 (d, J = 8.0 Hz, 2H), 6.86 (s, 1H), 6.73 (s, 1H), 6.59 (s, 1H), 6.38-6.19 (m, 2H), 5.73 (dd, J = 10.0, 1.3 Hz, 1H), 4.95-4.86 (m, 1H), 4.06 (td, J = 8.1, 4.5 Hz, 1H), 3.96 (q, J = 8.1 Hz, 1H), 3.83 (s, 3H), 3.24 (dd, J = 13.8, 6.6 Hz, 1H), 3.08-3.01 (m, 2H), 2.89 (dd, J = 13.8, 7.7 Hz, 1H), 2.79-2.58 (m, 9H), 2.37-2.29 (m, 1H), 2.27-2.21 (m, 1H), 2.11-1.99 (m, 3H), 1.72-1.64 (m, 4H), 0.51-0.39 (m, 4H); 707.52 [M + H]⁺ | 1.30 |

TABLE 1-continued

| Example Compound | Structure | Name of Compound | ¹H NMR[:]; MS [M + H]⁺ | UPLC r.t. (min) |
|---|---|---|---|---|
| 1051 | 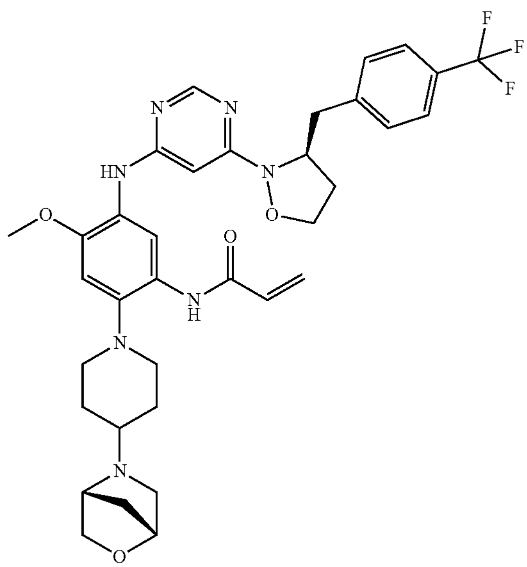 [SMILES: C=CC(=O)Nc1cc(Nc2cc(N3OCC[C@@H]3Cc3ccc(C(F)(F)F)cc3)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-4-methoxy-5-((6-((S)-3-(4-(trifluoromethyl)benzyl)isoxazolidine-2-yl)pyrimidine-4-yl)amino)phenyl)acrylamide | ¹H NMR (400 MHz, CDCl$_3$) δ 8.83 (s, 1H), 8.47 (s, 1H), 8.35 (s, 1H), 7.54 (d, J = 7.9 Hz, 2H), 7.44 (d, J = 7.9 Hz, 2H), 6.89 (d, J = 9.4 Hz, 1H), 6.75 (s, 1H), 6.59 (s, 1H), 6.38-6.19 (m, 2H), 5.76-5.70 (m, 1H), 4.96-4.85 (m, 1H), 4.45 (s, 1H), 4.12-4.02 (m, 2H), 3.97 (q, J = 8.0 Hz, 1H), 3.86-3.76 (m, 4H), 3.70-3.64 (m, 1H), 3.24 (dd, J = 13.8, 6.6 Hz, 1H), 3.20-3.12 (m, 1H), 3.07-2.99 (m, 2H), 2.89 (dd, J = 13.8, 7.7 Hz, 1H), 2.80-2.69 (m, 2H), 2.65-2.49 (m, 2H), 2.30-2.19 (m, 1H), 2.08-2.00 (m, 2H), 2.00-1.90 (m, 2H), 1.88-1.81 (m, 1H), 1.76-1.66 (m, 2H); 680.47 [M + H]⁺ | 1.25 |
| 1052 | 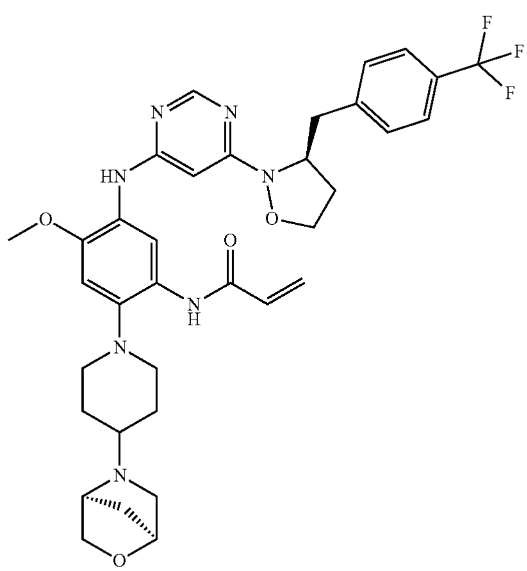 [SMILES: C=CC(=O)Nc1cc(Nc2cc(N3OCC[C@@H]3Cc3ccc(C(F)(F)F)cc3)ncn2)c(OC)cc1N1CCC(N2C[C@@H]3C[C@H]2CO3)CC1] | N-(2-(4-((1S,4S)-2-oxa-5-azabicyclo[2.2.1]heptane-5-yl)piperidine-1-yl)-4-methoxy-5-((6-((S)-3-(4-(trifluoromethyl)benzyl)isoxazolidine-2-yl)pyrimidine-4-yl)amino)phenyl)acrylamide | ¹H NMR (400 MHz, CDCl$_3$) δ 8.83 (s, 1H), 8.47 (s, 1H), 8.35 (s, 1H), 7.54 (d, J = 8.0 Hz, 2H), 7.44 (d, J = 8.0 Hz, 2H), 6.88 (s, 1H), 6.75 (s, 1H), 6.59 (s, 1H), 6.37-6.19 (m, 2H), 5.75-5.69 (m, 1H), 4.96-4.86 (m, 1H), 4.45 (s, 1H), 4.12-4.03 (m, 2H), 3.97 (q, J = 8.1 Hz, 1H), 3.84 (s, 3H), 3.78 (s, 1H), 3.70-3.63 (m, 1H), 3.24 (dd, J = 13.8, 6.6 Hz, 1H), 3.19-3.11 (m, 1H), 3.06-2.98 (m, 2H), 2.89 (dd, J = 13.8, 7.7 Hz, 1H), 2.81-2.70 (m, 2H), 2.63-2.49 (m, 2H), 2.29-2.20 (m, 1H), 2.08-1.99 (m, 2H), 1.99-1.90 (m, 2H), 1.85-1.80 (m, 1H), 1.73-1.66 (m, 2H); 680.47 [M + H]⁺ | 1.25 |

TABLE 1-continued

| Example Compound | Structure | Name of Compound | $^1$H NMR[:]; MS [M + H]$^+$ | UPLC r.t. (min) |
|---|---|---|---|---|
| 1053 | 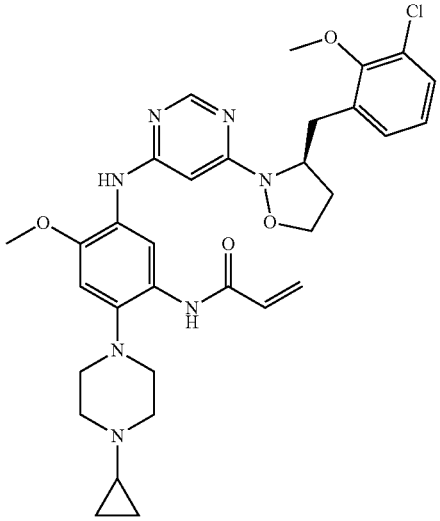 [SMILES: C=CC(=O)Nc1cc(Nc2cc(N3OCC[C@@H]3Cc3cccc(Cl)c3OC)ncn2)c(OC)cc1N1CCN(C2CC2)CC1] | N-(5-((6-((S)-3-(3-chloro-2-methoxybenzyl)isoxazolidine-2-yl)pyrimidine-4-yl)amino)-2-(4-cyclopropylpiperazine-1-yl)-4-methoxyphenyl)acrylamide | $^1$H NMR (400 MHz, Methanol-d$_4$) δ 8.18 (s, 1H), 8.05 (s, 1H), 7.19 (dd, J = 7.7, 20.0 Hz, 2H), 6.93 (t, J = 7.8 Hz, 1H), 6.81 (s, 1H), 6.42 (dd, J = 10.2, 17.0 Hz, 1H), 6.24 (d, J = 15.2 Hz, 2H), 5.70 (d, J = 10.3 Hz, 1H), 4.02-3.96 (m, 1H), 3.83-3.73 (m, 7H), 3.07-2.98 (m, 1H), 2.87-2.76 (m, 9H), 2.15-2.06 (m, 1H), 2.06-1.97 (m, 1H), 1.80-1.74 (m, 1H), 0.82-0.77 (m, 1H), 0.51-0.45 (m, 2H), 0.45-0.39 (m, 2H); 620.3 [M + H]$^+$ | 1.2 |
| 1054 | 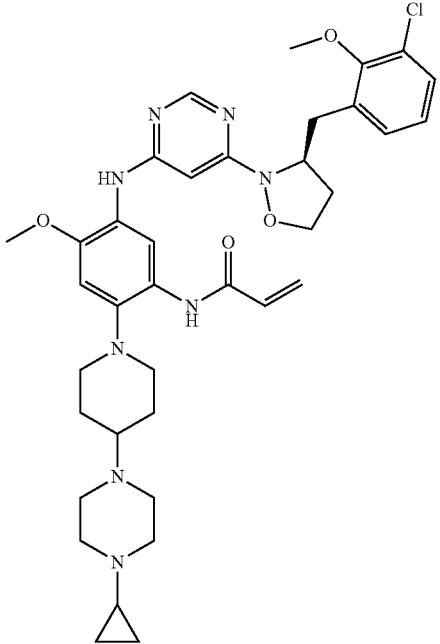 [SMILES: C=CC(=O)Nc1cc(Nc2cc(N3OCC[C@@H]3Cc3cccc(Cl)c3OC)ncn2)c(OC)cc1N1CCC(N2CCN(C3CC3)CC2)CC1] | N-(5-((6-((S)-3-(3-chloro-2-methoxybenzyl)isoxazolidine-2-yl)pyrimidine-4-yl)amino)-2-(4-(4-cyclopropylpiperazine-1-yl)piperidine-1-yl)-4-methoxyphenyl)acrylamide | $^1$H NMR (400 MHz, Methanol-d$_4$) δ 8.15 (s, 1H), 8.05 (s, 1H), 7.25-7.14 (m, 2H), 6.93 (t, J = 7.8 Hz, 1H), 6.80 (s, 1H), 6.43 (dd, J = 10.2, 16.9 Hz, 1H), 6.30-6.18 (m, 2H), 5.69 (d, J = 9.9 Hz, 1H), 4.01-3.96 (m, 1H), 3.81-3.75 (m, 7H), 3.09-3.01 (m, 3H), 2.93-2.85 (m, 3H), 2.82-2.62 (m, 8H), 2.13-2.07 (m, 1H), 2.06-1.96 (m, 3H), 1.95-1.92 (m, 1H), 1.79-1.67 (m, 3H), 1.54-1.47 (m, 1H), 0.49-0.40 (m, 2H), 0.40-0.31 (m, 2H); 703.3 [M + H]$^+$ | 1.21 |

TABLE 1-continued

| Example Compound | Structure | Name of Compound | ¹H NMR[[:]]; MS [M + H]⁺ | UPLC r.t. (min) |
|---|---|---|---|---|
| 1055 | 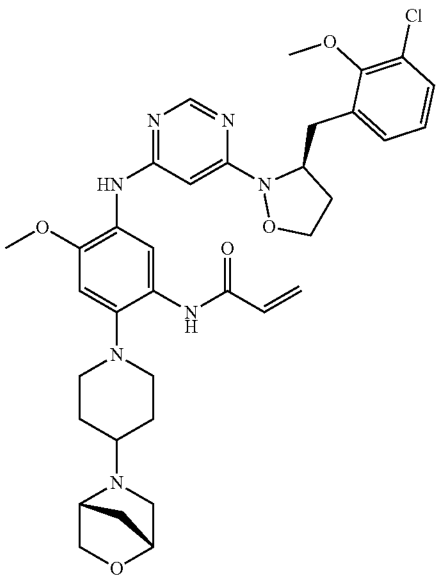 [SMILES: C=CC(=O)Nc1cc(Nc2cc(N3OCC[C@@H]3Cc3cccc(Cl)c3OC)ncn2)c(OC)cc1N1CCC(N2C[C@H]3C[C@@H]2CO3)CC1] | N-(2-(4-((1R,4R)-2-oxa-5-azabicyclo[2.2.1]heptane-5-yl)piperidine-1-yl)-5-((6-((S)-3-(3-chloro-2-methoxybenzyl)isoxazolidine-2-yl)pyrimidine-4-yl)amino)-4-methoxyphenyl)acrylamide | ¹H NMR (400 MHz, Methanol-$d_4$) δ 8.14 (s, 1H), 8.05 (s, 1H), 7.25-7.19 (m, 1H), 7.19-7.14 (m, 1H), 6.93 (t, J = 7.8 Hz, 1H), 6.81 (s, 1H), 6.42 (dd, J = 10.3, 17.0 Hz, 1H), 6.28-6.20 (m, 2H), 5.69 (d, J = 10.2 Hz, 1H), 4.18-4.13 (m, 1H), 4.07-4.03 (m, 1H), 4.02-3.96 (m, 1H), 3.81-3.74 (m, 7H), 3.68-3.65 (m, 1H), 3.08-3.01 (m, 3H), 2.96-2.86 (m, 2H), 2.83-2.71 (m, 3H), 2.13-2.06 (m, 2H), 2.01-1.94 (m, 4H), 1.73-1.67 (m, 2H), 0.82-0.74 (m, 3H), ; 676.3 [M + H]⁺ | 1.18 |
| 1056 | 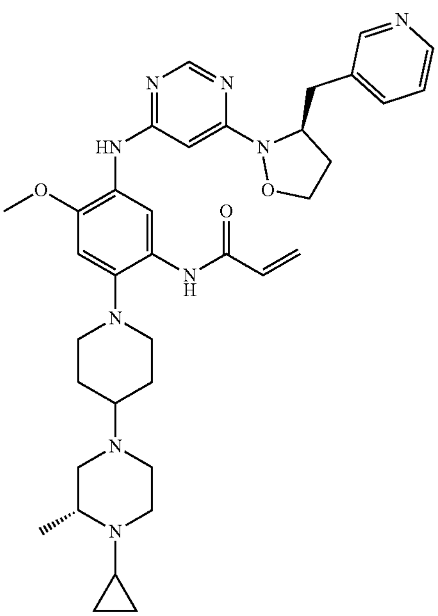 [SMILES: C=CC(=O)Nc1cc(Nc2cc(N3OCC[C@@H]3Cc3cccnc3)ncn2)c(OC)cc1N1CCC(N2CCN(C3CC3)[C@H](C)C2)CC1] | N-(2-(4-((R)-4-cyclopropyl-3-methylpiperazine-1-yl)piperidine-1-yl)-4-methoxy-5-((6-((S)-3-(pyridine-3-ylmethyl)isoxazolidine-2-yl)pyrimidine-4-yl)amino)phenyl)acrylamide | ¹H NMR (400 MHz, Chloroform-d) δ 8.72 (s, 1H), 8.52 (d, J = 2.3 Hz, 2H), 8.46 (dd, J = 4.9, 1.6 Hz, 2H), 8.40 (s, 2H), 8.27 (s, 1H), 7.73 (dt, J = 7.8, 2.0 Hz, 2H), 7.25-7.22 (m, 1H), 6.72 (s, 2H), 6.53 (s, 1H), 6.33-6.25 (m, 3H), 5.73 (dd, J = 9.5, 2.1 Hz, 2H), 4.87 (qd, J = 7.2, 3.8 Hz, 2H), 3.81 (s, 4H), 3.43 (s, 1H), 3.17-3.10 (m, 4H), 3.10-2.99 (m, 7H), 2.86 (dd, J = 14.1, 7.1 Hz, 2H), 2.72 (q, J = 11.0, 10.5 Hz, 6H), 2.27 (dtd, J = 12.4, 8.2, 4.3 Hz, 2H), 2.09 (d, J = 12.6 Hz, 4H), 1.77 (qd, J = 12.2, 3.9 Hz, 4H), 1.60 (tt, J = 6.8, 3.9 Hz, 2H), 0.65 (dp, J = 15.3, 5.5, 4.8 Hz, 4H), 0.45 (td, J = 10.6, 9.0, 5.9 Hz, 2H), 0.37 (p, J = 4.8 Hz, 2H), ; 654.6 [M + H]⁺ | 0.87 |

TABLE 1-continued

| Example Compound | Structure | Name of Compound | ¹H NMR[[:]]; MS [M + H]⁺ | UPLC r.t. (min) |
|---|---|---|---|---|
| 1057 | 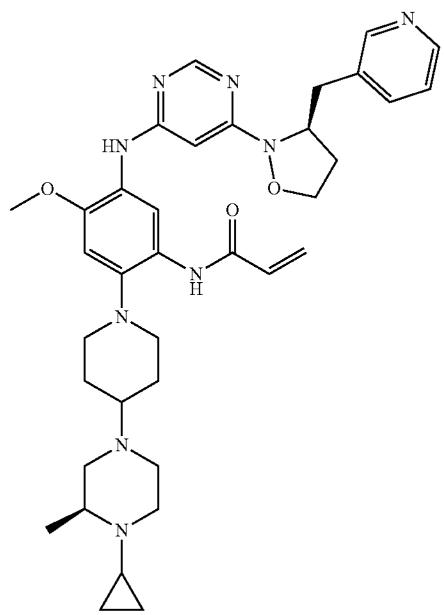 [SMILES: C=CC(=O)Nc1cc(Nc2cc(N3OCC[C@@H]3Cc3cccnc3)ncn2)c(OC)cc1N1CCC(N2CCN(C3CC3)[C@@H](C)C2)CC1] | N-(2-(4-((S)-4-cyclopropyl-3-methylpiperazine-1-yl)piperidine-1-yl)-4-methoxy-5-((6-((S)-3-(pyridine-3-ylmethyl)isoxazolidine-2-yl)pyrimidine-4-yl)amino)phenyl)acrylamide | ¹H NMR (400 MHz, Chloroform-d) δ 8.75 (s, 1H), 8.53 (d, J = 2.2 Hz, 1H), 8.46 (dd, J = 4.9, 1.6 Hz, 2H), 8.41 (s, 1H), 8.28 (d, J = 0.9 Hz, 1H), 7.72 (dt, J = 7.9, 1.9 Hz, 1H), 7.25-7.21 (m, 1H), 6.72 (s, 1H), 6.55 (s, 1H), 6.37-6.20 (m, 3H), 5.73 (dd, J = 9.7, 1.9 Hz, 1H), 4.87 (dt, J = 11.2, 5.5 Hz, 2H), 3.82 (s, 4H), 3.14 (dd, J = 14.1, 6.7 Hz, 3H), 3.10-3.02 (m, 5H), 2.86 (dd, J = 14.0, 7.3 Hz, 2H), 2.78-2.63 (m, 5H), 2.63-2.50 (m, 3H), 2.45 (dd, J = 12.5, 9.6 Hz, 2H), 2.27 (dtd, J = 12.4, 8.3, 4.4 Hz, 2H), 2.19-2.06 (m, 5H), 1.75 (q, J = 11.9 Hz, 3H), 1.60 (dd, J = 6.9, 3.4 Hz, 2H), 1.23 (d, J = 6.3 Hz, 4H), 0.71-0.59 (m, 3H), 0.46 (p, J = 6.1 Hz, 1H), 0.36 (d, J = 8.2 Hz, 1H), ; 654.6 [M + H]⁺ | 0.92 |
| 1058 | 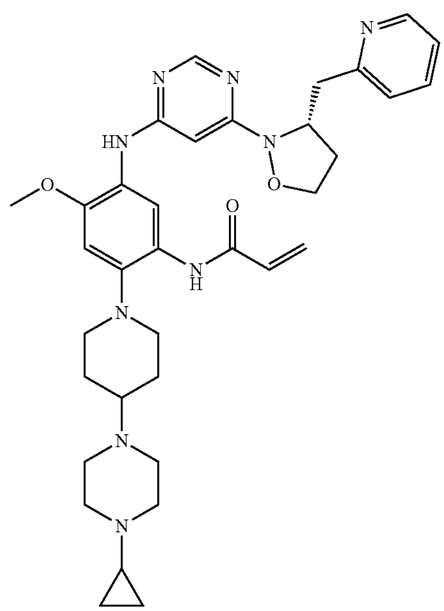 [SMILES: C=CC(=O)Nc1cc(Nc2cc(N3OCC[C@H]3Cc3ccccn3)ncn2)c(OC)cc1N1CCC(N2CCN(C3CC3)CC2)CC1] | N-(2-(4-(4-cyclopropylpiperazine-1-yl)piperidine-1-yl)-4-methoxy-5-((6-((R)-3-(pyridine-2-ylmethyl)isoxazolidine-2-yl)pyrimidine-4-yl)amino)phenyl)acrylamide | ¹H NMR (400 MHz, Methanol-d₄) δ 8.51-8.42 (m, 1H), 8.26 (s, 1H), 8.14 (s, 1H), 7.83-7.71 (m, 1H), 7.49 (d, J = 7.9 Hz, 1H), 7.29 (dd, J = 5.1, 7.5 Hz, 1H), 6.91 (s, 1H), 6.56 (dd, J = 10.2, 17.0 Hz, 1H), 6.36 (d, J = 18.2 Hz, 2H), 5.81 (d, J = 10.2 Hz, 1H), 4.09 (dd, J = 4.7, 8.2 Hz, 1H), 3.94-3.84 (m, 4H), 3.32-3.30 (m, 1H), 3.29-3.23 (m, 1H), 3.23-3.14 (m, 2H), 3.06-2.96 (m, 4H), 2.92-2.76 (m, 7H), 2.32-2.26 (m, 1H), 2.21-2.11 (m, 3H), 1.92-1.77 (m, 3H), 0.94-0.88 (m, 1H), 0.60-0.53 (m, 2H), 0.52-0.45 (m, 2H); 640.4 [M + H]⁺ | 0.85 |

TABLE 1-continued

| Example Compound | Structure | Name of Compound | $^1$H NMR[[:]]; MS [M + H]$^+$ | UPLC r.t. (min) |
|---|---|---|---|---|
| 1059 | 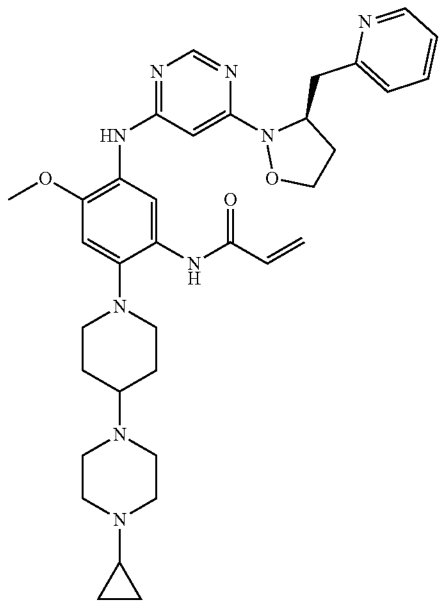 [SMILES: C=CC(=O)Nc1cc(Nc2cc(N3OCC[C@@H]3Cc3ccccn3)ncn2)c(OC)cc1N1CCC(N2CCN(C3CC3)CC2)CC1] | N-(2-(4-(4-cyclopropylpiperazine-1-yl)piperidine-1-yl)-4-methoxy-5-((6-((S)-3-(pyridine-2-ylmethyl) isoxazolidine-2-yl)pyrimidine-4-yl)amino)phenyl) acrylamide | $^1$H NMR (400 MHz, Methanol-d$_4$) δ 8.49-8.42 (m, 1H), 8.26 (s, 1H), 8.14 (s, 1H), 7.79-7.74 (m, 1H), 7.49 (d, J = 7.9 Hz, 1H), 7.31-7.27 (m, 1H), 6.91 (s, 1H), 6.55 (dd, J = 10.2, 17.0 Hz, 1H), 6.40-6.30 (m, 2H), 5.81 (d, J = 10.3 Hz, 1H), 4.12-4.07 (m, 1H), 3.92-3.85 (m, 4H), 3.28-3.24 (m, 1H), 3.22-3.17 (m, 2H), 3.06-2.98 (m, 4H), 2.93-2.75 (m, 8H), 2.33-2.25 (m, 1H), 2.21-2.12 (m, 3H), 1.91-1.80 (m, 3H), 0.93-0.89 (m, 1H), 0.61-0.55 (m, 2H), 0.53-0.45 (m, 2H); 640.4 [M + H]$^+$ | 0.86 |

<Experimental Example 1> Evaluation of Ba/F3 and Lung Cancer Cell Proliferation Suppression Activity The following experiment was carried out to evaluate the suppression activity of the compounds according to the present invention against proliferation of Ba/F3 and lung cancer cells which express EGFR mutations.

Of the cancer cell lines expressing the EGFR gene, A549 was cultured after adding 10% FBS (HyClone) to DMEM (Invitrogen), and RPMI-1640 (Invitrogen) with 10% FBS was used for the other cancer cells. For the Ba/F3 cells, RPMI-1640 with 10% FBS and 5 ng/ml IL-3 (R&D Systems) was used. The transduced Ba/F3 cells were cultured by adding 1 ug/ml puromycin (Invitrogen) to the same medium.

24 hours before treatment with the compounds, 3000 to 5000 cells were distributed into each well of a white clear bottom 96 well plate (Corning). The compounds were diluted in dimethylsulfoxide (dilution ratio 3:1; 12 concentrations total) and injected 0.5 ul each for a final concentration of 0.3 nM to 50 um. As for measurement of live cells, 72 hours after treatment with the compounds, a CellTiter-Glo luminescent cell-viability reagent (Promega) was used to store the cells at room temperature for 10 minutes, followed by measurement of luminescence using a reader (SynergyNeo, Biotek). Each test was repeated three times.

The result was calculated as a cell growth ratio (%) compared to a control. The program GraphPad Prism version 5.0 was used to draw the graphs and calculate the GI$_{50}$ values.

Table 2 below shows the results of proliferation suppression for Ba/F3 cells which express EGFR (HER2) mutations.

TABLE 2

| | Ba/F3 cell (GI$_{50}$ (μM)) | | | | | | | | | |
|---|---|---|---|---|---|---|---|---|---|---|
| Example Compound | EGFR L858R/ T790M/ | EGFR Del19/ T790M | EGFR L858R | EGFR Exon20 ins NPH | EGFR Exon20 ins SVD | EGFR Exon20 ins FQEA | EGFR Exon20 ins H | EGFR Exon20 ins ASV | HER2 Exon20 ins YVMA | naive |
| 1 | B | B | A | — | — | — | — | — | — | D |
| 2 | C | C | B | — | — | — | — | — | — | D |
| 3 | C | B | — | B | B | A | C | B | B | D |
| 4 | A | A | A | A | A | A | A | A | A | D |
| 5 | B | B | A | — | — | — | — | — | — | D |
| 6 | A | A | A | A | A | A | A | A | A | D |
| 7 | B | A | — | — | — | — | — | — | — | D |
| 8 | B | B | — | — | — | — | — | — | — | C |
| 9 | A | A | A | A | A | A | A | A | A | D |
| 10 | A | A | A | A | A | A | A | A | A | D |
| 12 | A | A | A | A | A | A | A | A | A | D |
| 13 | A | A | A | A | A | A | A | A | A | D |
| 15 | A | A | A | A | A | A | A | A | A | D |

TABLE 2-continued

| Example Compound | EGFR L858R/ T790M/ | EGFR Del19/ T790M | EGFR L858R | EGFR Exon20 ins NPH | EGFR Exon20 ins SVD | EGFR Exon20 ins FQEA | EGFR Exon20 ins H | EGFR Exon20 ins ASV | HER2 Exon20 ins YVMA | naive |
|---|---|---|---|---|---|---|---|---|---|---|
| 26 | A | — | — | A | A | — | — | — | A | D |
| 28 | A | A | A | A | A | A | A | A | A | C |
| 29 | A | A | A | A | A | A | A | A | A | D |
| 30 | A | A | A | A | A | A | — | A | A | D |
| 57 | A | A | A | A | A | A | — | A | A | D |
| 236 | A | A | A | A | A | A | — | A | A | C |
| 237 | A | — | — | A | — | — | — | A | — | D |
| 238 | A | A | A | A | A | A | — | A | A | C |
| 239 | A | A | A | A | A | A | — | A | A | D |
| 240 | A | — | — | A | — | — | — | A | — | D |
| 241 | A | A | A | A | A | A | — | A | A | C |
| 242 | A | B | A | A | A | A | — | A | A | C |
| 249 | A | — | — | A | — | — | — | — | — | D |
| 250 | A | — | — | A | — | — | — | — | — | D |
| 251 | A | — | — | A | — | — | — | — | — | D |
| 252 | A | — | — | A | — | — | — | — | — | C |
| 253 | A | — | — | A | — | — | — | — | — | C |

A: $GI_{50} < 50$ nM,
B: $50$ nM $\leq GI_{50} < 500$ nM,
C: $500$ nM $\leq GI_{50} < 5000$ nM,
D: $5000$ nM $\leq GI_{50}$ Additionally, Table 3 below shows the activity of the respective example compounds against the Ba/F3 cell line wherein NPH has been inserted (ins) at Exon20 of EGFR.

TABLE 3

| Example Compound | Ba/F3 (NPH) Activity |
|---|---|
| 1 |  |
| 2 |  |
| 3 | B |
| 4 | A |
| 5 |  |
| 6 | A |
| 7 |  |
| 8 |  |
| 9 | A |
| 10 | A |
| 11 | A |
| 12 | A |
| 13 | A |
| 14 |  |
| 15 | A |
| 16 |  |
| 17 |  |
| 18 | A |
| 19 |  |
| 20 |  |
| 21 |  |
| 22 |  |
| 23 |  |
| 24 | A |
| 25 | B |
| 26 | A |
| 27 | A |
| 28 | A |
| 29 | A |
| 30 | A |
| 31 | A |
| 32 |  |
| 33 | A |
| 34 |  |
| 35 | B |
| 36 | A |
| 37 |  |
| 38 | A |
| 39 | A |
| 40 | B |
| 41 | B |
| 42 | B |
| 43 | B |
| 44 | B |
| 45 | B |
| 46 | C |
| 47 | B |
| 48 | B |
| 49 | C |
| 50 | B |
| 51 | C |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | B |
| 68 | A |
| 69 |  |
| 70 |  |
| 71 | A |
| 72 |  |
| 73 | A |
| 74 | B |
| 75 | A |
| 76 | A |
| 77 | A |
| 78 | A |
| 79 | A |
| 80 | A |
| 81 | B |
| 82 | A |
| 83 | A |
| 84 | B |

TABLE 3-continued

| Example Compound | Ba/F3 (NPH) Activity |
|---|---|
| 85 | A |
| 86 | A |
| 87 | A |
| 88 | A |
| 89 | A |
| 90 | A |
| 91 | A |
| 92 | A |
| 93 | A |
| 94 | A |
| 95 | C |
| 96 | A |
| 97 | A |
| 98 | A |
| 99 | A |
| 100 | A |
| 101 | A |
| 102 | A |
| 103 | A |
| 104 | |
| 105 | A |
| 106 | A |
| 107 | A |
| 108 | A |
| 109 | A |
| 110 | A |
| 111 | A |
| 112 | A |
| 113 | A |
| 114 | A |
| 115 | A |
| 116 | C |
| 117 | A |
| 118 | C |
| 119 | A |
| 120 | C |
| 121 | A |
| 122 | A |
| 123 | A |
| 124 | A |
| 125 | A |
| 126 | A |
| 127 | A |
| 128 | A |
| 129 | C |
| 130 | A |
| 131 | A |
| 132 | B |
| 133 | B |
| 134 | A |
| 135 | A |
| 136 | B |
| 137 | B |
| 138 | A |
| 139 | A |
| 140 | A |
| 141 | A |
| 142 | A |
| 143 | A |
| 144 | A |
| 145 | A |
| 146 | B |
| 147 | A |
| 148 | A |
| 149 | A |
| 150 | A |
| 151 | B |
| 152 | A |
| 153 | A |
| 154 | A |
| 155 | A |
| 156 | A |
| 157 | A |
| 158 | A |
| 159 | A |
| 160 | A |
| 161 | A |
| 162 | A |
| 163 | A |
| 164 | A |
| 165 | A |
| 166 | A |
| 167 | A |
| 168 | A |
| 169 | A |
| 170 | A |
| 171 | A |
| 172 | A |
| 173 | A |
| 174 | A |
| 175 | A |
| 176 | A |
| 177 | A |
| 178 | A |
| 179 | A |
| 180 | A |
| 181 | A |
| 182 | A |
| 183 | A |
| 184 | B |
| 185 | A |
| 186 | A |
| 187 | A |
| 188 | A |
| 189 | A |
| 190 | B |
| 191 | A |
| 192 | A |
| 193 | A |
| 194 | A |
| 195 | A |
| 196 | A |
| 197 | A |
| 198 | A |
| 199 | A |
| 200 | B |
| 201 | A |
| 202 | A |
| 203 | A |
| 204 | A |
| 205 | A |
| 206 | B |
| 207 | A |
| 208 | A |
| 209 | A |
| 210 | A |
| 211 | A |
| 212 | A |
| 213 | A |
| 214 | A |
| 215 | C |
| 216 | A |
| 217 | |
| 218 | B |
| 219 | B |
| 220 | B |
| 221 | B |
| 222 | B |
| 223 | B |
| 224 | C |
| 225 | B |
| 226 | C |
| 227 | B |
| 228 | A |
| 229 | B |
| 230 | B |
| 231 | B |
| 232 | B |
| 233 | C |
| 234 | C |
| 235 | B |
| 236 | A |
| 237 | A |
| 238 | A |

TABLE 3-continued

| Example Compound | Ba/F3 (NPH) Activity |
|---|---|
| 239 | A |
| 240 | A |
| 241 | A |
| 242 | A |
| 243 | A |
| 244 | A |
| 245 | A |
| 246 | A |
| 247 | A |
| 248 | A |
| 249 | A |
| 250 | A |
| 251 | A |
| 252 | A |
| 253 | A |
| 254 | A |
| 255 | A |
| 256 | A |
| 257 | A |
| 258 | A |
| 259 | A |
| 260 | A |
| 261 | C |
| 262 | A |
| 263 | A |
| 264 | A |
| 265 | A |
| 266 | A |
| 267 | A |
| 268 | A |
| 269 | C |
| 270 | B |
| 271 | B |
| 272 | B |
| 273 | B |
| 274 | |
| 275 | |
| 276 | |
| 277 | A |
| 278 | A |
| 279 | A |
| 280 | |
| 281 | |
| 282 | |
| 283 | A |
| 284 | A |
| 285 | A |
| 286 | A |
| 287 | |
| 288 | |
| 289 | |
| 290 | |
| 291 | B |
| 292 | |
| 293 | |
| 294 | B |
| 295 | C |
| 296 | |
| 297 | A |
| 298 | A |
| 299 | A |
| 300 | A |
| 301 | A |
| 302 | B |
| 303 | A |
| 304 | A |
| 305 | A |
| 306 | B |
| 307 | C |
| 308 | C |
| 309 | C |
| 310 | C |
| 311 | C |
| 312 | C |
| 313 | C |
| 314 | C |
| 315 | C |

TABLE 3-continued

| Example Compound | Ba/F3 (NPH) Activity |
|---|---|
| 316 | A |
| 317 | A |
| 318 | A |
| 319 | B |
| 320 | A |
| 321 | B |
| 322 | A |
| 323 | A |
| 324 | A |
| 325 | A |
| 326 | A |
| 327 | B |
| 328 | A |
| 329 | A |
| 330 | A |
| 331 | A |
| 332 | A |
| 333 | A |
| 334 | A |
| 335 | A |
| 336 | A |
| 337 | B |
| 338 | B |
| 339 | A |
| 340 | A |
| 341 | A |
| 342 | A |
| 343 | A |
| 344 | A |
| 345 | A |
| 346 | A |
| 347 | A |
| 348 | A |
| 349 | A |
| 350 | A |
| 351 | A |
| 352 | A |
| 353 | A |
| 354 | A |
| 355 | A |
| 356 | A |
| 357 | A |
| 358 | A |
| 359 | A |
| 360 | A |
| 361 | A |
| 362 | A |
| 363 | A |
| 364 | A |
| 365 | B |
| 366 | |
| 367 | |
| 368 | |
| 369 | C |
| 370 | A |
| 371 | A |
| 372 | A |
| 373 | A |
| 374 | A |
| 375 | A |
| 376 | A |
| 377 | B |
| 378 | A |
| 379 | A |
| 380 | A |
| 381 | A |
| 382 | A |
| 383 | A |
| 384 | A |
| 385 | A |
| 386 | B |
| 387 | A |
| 388 | A |
| 389 | A |
| 390 | B |
| 391 | B |
| 392 | A |

TABLE 3-continued

| Example Compound | Ba/F3 (NPH) Activity |
|---|---|
| 393 | B |
| 394 | A |
| 395 | B |
| 396 | B |
| 397 | A |
| 398 | A |
| 399 | B |
| 400 | A |
| 401 | A |
| 402 | A |
| 403 | A |
| 404 | B |
| 405 | B |
| 406 | A |
| 407 | B |
| 408 | A |
| 409 | A |
| 410 | B |
| 411 | A |
| 412 | A |
| 413 | A |
| 414 | A |
| 415 | A |
| 416 | A |
| 417 | A |
| 418 | A |
| 419 | A |
| 420 | A |
| 421 | A |
| 422 | A |
| 423 | A |
| 424 | A |
| 425 | A |
| 426 | A |
| 427 | A |
| 428 | A |
| 429 | A |
| 430 | A |
| 431 | A |
| 432 | A |
| 433 | A |
| 434 | A |
| 435 | B |
| 436 | B |
| 437 | B |
| 438 | A |
| 439 | A |
| 440 | A |
| 441 | B |
| 442 | A |
| 443 | A |
| 444 | B |
| 445 | A |
| 446 | A |
| 447 | A |
| 448 | A |
| 449 | A |
| 450 | A |
| 451 | A |
| 452 | A |
| 453 | A |
| 454 | A |
| 455 | A |
| 456 | A |
| 457 | A |
| 458 | A |
| 459 | A |
| 460 | A |
| 461 | A |
| 462 | A |
| 463 | B |
| 464 | A |
| 465 | A |
| 466 | B |
| 467 | A |
| 468 | A |
| 469 | A |
| 470 | A |
| 471 | A |
| 472 | A |
| 473 | A |
| 474 | A |
| 475 | A |
| 476 | A |
| 477 | A |
| 478 | A |
| 479 | A |
| 480 | A |
| 481 | A |
| 482 | A |
| 483 | A |
| 484 | B |
| 485 | A |
| 486 | A |
| 487 | A |
| 488 | A |
| 489 | A |
| 490 | B |
| 491 | B |
| 492 | B |
| 493 | A |
| 494 | A |
| 495 | C |
| 496 | B |
| 497 | A |
| 498 | A |
| 499 | A |
| 500 | A |
| 501 | A |
| 502 | A |
| 503 | A |
| 504 | A |
| 505 | A |
| 506 | A |
| 507 | B |
| 508 | A |
| 509 | B |
| 510 | B |
| 511 | A |
| 512 | A |
| 513 | B |
| 514 | B |
| 515 | B |
| 516 | A |
| 517 | A |
| 518 | A |
| 519 | A |
| 520 | A |
| 521 | A |
| 522 | B |
| 523 | A |
| 524 | A |
| 525 | A |
| 526 | A |
| 527 | A |
| 528 | A |
| 529 | A |
| 530 | A |
| 531 | A |
| 532 | A |
| 533 | A |
| 534 | A |
| 535 | A |
| 536 | A |
| 537 | A |
| 538 | A |
| 539 | A |
| 540 | A |
| 541 | A |
| 542 | B |
| 543 | A |
| 544 | A |
| 545 | A |
| 546 | A |

TABLE 3-continued

| Example Compound | Ba/F3 (NPH) Activity |
|---|---|
| 547 | A |
| 548 | A |
| 549 | A |
| 550 | B |
| 551 | A |
| 552 | A |
| 553 | A |
| 554 | B |
| 555 | B |
| 556 | B |
| 557 | B |
| 558 | A |
| 559 | A |
| 560 | A |
| 561 | A |
| 562 | B |
| 563 | A |
| 564 | A |
| 565 | A |
| 566 | B |
| 567 | A |
| 568 | A |
| 569 | A |
| 570 | A |
| 571 | A |
| 572 | A |
| 573 | A |
| 574 | A |
| 575 | A |
| 576 | A |
| 577 | A |
| 578 | B |
| 579 | C |
| 580 | A |
| 581 | A |
| 582 | A |
| 583 | A |
| 584 | A |
| 585 | A |
| 586 | A |
| 587 | B |
| 588 | B |
| 589 | A |
| 590 | A |
| 591 | A |
| 592 | A |
| 593 | A |
| 594 | A |
| 595 | A |
| 596 | A |
| 597 | A |
| 598 | A |
| 599 | A |
| 600 | A |
| 601 | A |
| 602 | A |
| 603 | A |
| 604 | A |
| 605 | A |
| 606 | A |
| 607 | A |
| 608 | A |
| 609 | A |
| 610 | B |
| 611 | B |
| 612 | A |
| 613 | B |
| 614 | B |
| 615 | A |
| 616 | A |
| 617 | A |
| 618 | A |
| 619 | A |
| 620 | A |
| 621 | A |
| 622 | C |
| 623 | C |
| 624 | C |
| 625 | A |
| 626 | A |
| 627 | A |
| 628 | A |
| 629 | B |
| 630 | B |
| 631 | B |
| 632 | A |
| 633 | B |
| 634 | A |
| 635 | A |
| 636 | A |
| 637 | A |
| 638 | A |
| 639 | A |
| 640 | A |
| 641 | A |
| 642 | A |
| 643 | A |
| 644 | A |
| 645 | A |
| 646 | A |
| 647 | A |
| 648 | A |
| 649 | A |
| 650 | A |
| 651 | A |
| 652 | B |
| 653 | A |
| 654 | B |
| 655 | B |
| 656 | B |
| 657 | A |
| 658 | B |
| 659 | B |
| 660 | C |
| 661 | A |
| 662 | B |
| 663 | B |
| 664 | C |
| 665 | B |
| 666 | B |
| 667 | B |
| 668 | B |
| 669 | A |
| 670 | A |
| 671 | A |
| 672 | A |
| 673 | A |
| 674 | A |
| 675 | A |
| 676 | A |
| 677 | A |
| 678 | A |
| 679 | B |
| 680 | A |
| 681 | A |
| 682 | A |
| 683 | A |
| 684 | A |
| 685 | A |
| 686 | B |
| 687 | A |
| 688 | A |
| 689 | B |
| 690 | A |
| 691 | B |
| 692 | A |
| 693 | A |
| 694 | |
| 695 | B |
| 696 | |
| 697 | |
| 698 | |
| 699 | |
| 700 | A |

TABLE 3-continued

| Example Compound | Ba/F3 (NPH) Activity |
|---|---|
| 701 | A |
| 702 | A |
| 703 | |
| 704 | |
| 705 | |
| 706 | A |
| 707 | A |
| 708 | A |
| 709 | A |
| 710 | |
| 711 | |
| 712 | A |
| 713 | A |
| 714 | A |
| 715 | A |
| 716 | A |
| 717 | A |
| 718 | A |
| 719 | A |
| 720 | A |
| 721 | A |
| 722 | B |
| 723 | A |
| 724 | A |
| 725 | A |
| 726 | A |
| 727 | A |
| 728 | A |
| 729 | A |
| 730 | B |
| 731 | B |
| 732 | A |
| 733 | A |
| 734 | B |
| 735 | A |
| 736 | A |
| 737 | A |
| 738 | A |
| 739 | A |
| 740 | B |
| 741 | A |
| 742 | A |
| 743 | A |
| 744 | A |
| 745 | A |
| 746 | A |
| 747 | A |
| 748 | A |
| 749 | A |
| 750 | A |
| 751 | A |
| 752 | A |
| 753 | A |
| 754 | A |
| 755 | A |
| 756 | A |
| 757 | A |
| 758 | B |
| 759 | B |
| 760 | A |
| 761 | A |
| 762 | A |
| 763 | A |
| 764 | A |
| 765 | A |
| 766 | A |
| 767 | A |
| 768 | A |
| 769 | A |
| 770 | A |
| 771 | B |
| 772 | B |
| 773 | B |
| 774 | B |
| 775 | A |
| 776 | A |
| 777 | B |
| 778 | B |
| 779 | A |
| 780 | B |
| 781 | B |
| 782 | A |
| 783 | A |
| 784 | A |
| 785 | A |
| 786 | A |
| 787 | A |
| 788 | A |
| 789 | A |
| 790 | A |
| 791 | B |
| 792 | A |
| 793 | A |
| 794 | B |
| 795 | B |
| 796 | A |
| 797 | A |
| 798 | A |
| 799 | A |
| 800 | A |
| 801 | A |
| 802 | A |
| 803 | A |
| 804 | A |
| 805 | A |
| 806 | A |
| 807 | A |
| 808 | B |
| 809 | A |
| 810 | A |
| 811 | A |
| 812 | A |
| 813 | A |
| 814 | A |
| 815 | A |
| 816 | A |
| 817 | A |
| 818 | A |
| 819 | A |
| 820 | A |
| 821 | A |
| 822 | A |
| 823 | A |
| 824 | A |
| 825 | A |
| 826 | A |
| 827 | A |
| 828 | A |
| 829 | A |
| 830 | A |
| 831 | A |
| 832 | A |
| 833 | A |
| 834 | A |
| 835 | A |
| 836 | A |
| 837 | A |
| 838 | A |
| 839 | A |
| 840 | A |
| 841 | A |
| 842 | A |
| 843 | A |
| 844 | A |
| 845 | A |
| 846 | A |
| 847 | A |
| 848 | A |
| 849 | A |
| 850 | A |
| 851 | A |
| 852 | A |
| 853 | B |
| 854 | A |

TABLE 3-continued

| Example Compound | Ba/F3 (NPH) Activity |
|---|---|
| 855 | A |
| 856 | A |
| 857 | A |
| 858 | A |
| 859 | A |
| 860 | A |
| 861 | B |
| 862 | A |
| 863 | A |
| 864 | A |
| 865 | B |
| 866 | A |
| 867 | A |
| 868 | A |
| 869 | A |
| 870 | A |
| 871 | A |
| 872 | A |
| 873 | A |
| 874 | A |
| 875 | A |
| 876 | A |
| 877 | A |
| 878 | A |
| 879 | A |
| 880 | A |
| 881 | A |
| 882 | A |
| 883 | A |
| 884 | A |
| 885 | A |
| 886 | A |
| 887 | A |
| 888 | A |
| 889 | A |
| 890 | A |
| 891 | A |
| 892 | A |
| 893 | A |
| 894 | A |
| 895 | C |
| 896 | C |
| 897 | C |
| 898 | C |
| 899 | C |
| 900 | A |
| 901 | A |
| 902 | A |
| 903 | A |
| 904 | A |
| 905 | A |
| 906 | A |
| 907 | A |
| 908 | A |
| 909 | A |
| 910 | A |
| 911 | A |
| 912 | A |
| 913 | A |
| 914 | A |
| 915 | B |
| 916 | A |
| 917 | A |
| 918 | A |
| 919 | A |
| 920 | A |
| 921 | A |
| 922 | A |
| 923 | A |
| 924 | A |
| 925 | A |
| 926 | A |
| 927 | A |
| 928 | A |
| 929 | A |
| 930 | A |
| 931 | A |
| 932 | B |
| 933 | A |
| 934 | A |
| 935 | A |
| 936 | B |
| 937 | B |
| 938 | A |
| 939 | B |
| 940 | B |
| 941 | A |
| 942 | A |
| 943 | A |
| 944 | A |
| 945 | A |
| 946 | A |
| 947 | A |
| 948 | A |
| 949 | A |
| 950 | A |
| 951 | A |
| 952 | A |
| 953 | B |
| 954 | A |
| 955 | A |
| 956 | C |
| 957 | A |
| 958 | A |
| 959 | A |
| 960 | B |
| 961 | A |
| 962 | A |
| 963 | A |
| 964 | A |
| 965 | A |
| 966 | C |
| 967 | C |
| 968 | C |
| 969 | A |
| 970 | A |
| 971 | A |
| 972 | A |
| 973 | B |
| 974 | C |
| 975 | C |
| 976 | C |
| 977 | C |
| 978 | C |
| 979 | A |
| 980 | A |
| 981 | A |
| 982 | A |
| 983 | A |
| 984 | A |
| 985 | C |
| 986 | |
| 987 | C |
| 988 | B |
| 989 | B |
| 990 | B |
| 991 | A |
| 992 | A |
| 993 | A |
| 994 | A |
| 995 | A |
| 996 | A |
| 997 | A |
| 998 | A |
| 999 | A |
| 1000 | A |
| 1001 | A |
| 1002 | A |
| 1003 | A |
| 1004 | A |
| 1005 | A |
| 1006 | A |
| 1007 | A |
| 1008 | A |

TABLE 3-continued

| Example Compound | Ba/F3 (NPH) Activity |
|---|---|
| 1009 | A |
| 1010 | A |
| 1011 | A |
| 1012 | A |
| 1013 | A |
| 1014 | A |
| 1015 | A |
| 1016 | A |
| 1017 | A |
| 1018 | A |
| 1019 | A |
| 1020 | A |
| 1021 | A |
| 1022 | A |
| 1023 | |
| 1024 | A |
| 1025 | A |
| 1026 | B |
| 1027 | A |
| 1028 | A |
| 1029 | A |
| 1030 | A |
| 1031 | A |
| 1032 | B |
| 1033 | A |
| 1034 | A |
| 1035 | A |
| 1036 | A |
| 1037 | A |
| 1038 | A |
| 1039 | A |
| 1040 | A |
| 1041 | A |
| 1042 | A |
| 1043 | C |
| 1044 | B |
| 1045 | B |
| 1046 | B |
| 1047 | B |
| 1048 | B |
| 1049 | C |
| 1050 | B |
| 1051 | A |
| 1052 | A |
| 1053 | A |
| 1054 | A |
| 1055 | A |
| 1056 | B |
| 1057 | B |
| 1058 | C |
| 1059 | A |

A: $GI_{50} < 50$ nM,
B: $50$ nM $\leq GI_{50} < 500$ nM,
C: $500$ nM $\leq GI_{50} < 5000$ nM,
D: $5000$ nM $\leq GI_{50}$ As shown in Table 2 and Table 3 above, the example compounds of the present invention exhibit high suppression activity against EGFR single or double mutations or ERBB2 mutations in the Ba/F3 cell line.

Table 4 below shows the results of evaluating proliferation suppression activity ($GI_{50}$) against the EGFR mutant lung cancer cell lines PC9, PC9GR and H1975.

TABLE 4

| Example Compound | cancer cell ($GI_{50}$(nM)) | | | |
|---|---|---|---|---|
| | PC9GR | H1975 | PC9 | A519 |
| 4 | 20 | 28 | 1 | >15000 |
| 6 | 32 | 60 | 1 | >15000 |
| 9 | 4 | 6 | 1 | >15000 |
| 10 | 10 | 13 | 14 | >15000 |
| 11 | 7 | 9 | 2 | >15000 |
| 12 | 5 | 8 | 12 | >15000 |
| 13 | 64 | 63 | 12 | >15000 |
| 15 | 6 | 13 | 7 | >15000 |
| 30 | 6 | 1 | 1 | — |
| 57 | 4 | 1 | 1 | — |
| 236 | 7 | 1 | 1 | — |
| 238 | 4 | 1 | 1 | — |
| 239 | 5 | 1 | 1 | — |
| 241 | 12 | 1 | 1 | — |
| 242 | 23 | 4 | 1 | — |
| Poziotinib | 20 | 34 | 1 | >15000 |
| Osimertinib | 16 | 36 | 7 | 2414 |
| Lazertinib | 14 | 24 | 5 | 4819 |

In Table 4, it can be seen that the example compounds of the present invention exhibit good proliferation suppression activity against the EGFR mutant lung cancer cell lines PC9, PC9GR and H1975.

FIG. 1 shows experimental data results examining whether or not cancer was suppressed when the example compounds were orally administered to a PDX (Exon20ins V769_D770ins ASV) cell line xenograft in vivo model for 28 days, then observed for 21 days without administration. (Testing consigned to Champions Oncology, Inc.)

Referring to FIG. 1, it can be seen that the example compounds of the present invention reduce tumor size in an animal model, thereby exhibiting effective suppression of cancer.

TABLE 5

| | % inhibition of scanMAX Kinase profiling | | | | | | | | | |
|---|---|---|---|---|---|---|---|---|---|---|
| | Example Compound | | | | | | | | | |
| Protein | 4 | 6 | 9 | 30 | 57 | 236 | 238 | 239 | 241 | 242 |
| EGFR(E746-A750del) | 100 | 100 | 100 | 95 | 98 | 89 | 100 | 96 | 100 | 50 |
| EGFR(G719C) | 100 | 100 | 100 | 100 | 100 | 100 | 100 | 100 | 100 | 100 |
| EGFR(G719S) | 100 | 100 | 100 | 100 | 100 | 100 | 100 | 99 | 99 | 100 |
| EGFR(L747-E749del, A750P) | 97 | 100 | 100 | 100 | 98 | 98 | 91 | 95 | 98 | 99 |
| EGFR(L747-T751ldel, Sins) | 100 | 100 | 100 | 96 | 100 | 100 | 92 | 93 | 96 | 100 |
| EGFR(L858R) | 100 | 100 | 100 | 100 | 100 | 100 | 99 | 100 | 100 | 100 |
| EGFR(L858R, T790M) | 96 | 85 | 96 | 97 | 96 | 98 | 98 | 98 | 98 | 96 |
| EGFR(L861Q) | 100 | 100 | 100 | 100 | 100 | 98 | 98 | 97 | 98 | 100 |
| EGFR(S752-1759del) | 100 | 96 | 100 | 99 | 98 | 89 | 91 | 82 | 95 | 100 |
| EGFR(T790M) | 99 | 100 | 99 | 100 | 100 | 100 | 100 | 100 | 100 | 100 |

TABLE 5-continued

| % inhibition of scanMAX Kinase profiling | | | | | | | | | | |
|---|---|---|---|---|---|---|---|---|---|---|
| | Example Compound | | | | | | | | | |
| Protein | 4 | 6 | 9 | 30 | 57 | 236 | 238 | 239 | 241 | 242 |
| ERBB2 | 100 | 100 | 100 | 100 | 100 | 100 | 100 | 100 | 100 | 100 |
| ERBB4 | 100 | 100 | 100 | 100 | 100i | 100 | 100 | 100 | 94 | 100 |

Table 5 above shows the results of DiscoverX (eurofin) KINOMEscan (scanMAX platform) kinase profiling testing on compounds 4, 6, 9, 30, 57, 236, 238, 239, 241 and 242. As can be seen in Table 5, high suppression activity was exhibited against the EGFR mutant and ERBB2 and ERBB4. It was confirmed that the above example compounds had high selectivity against EGFR series genes. Accordingly, these can be useful in the treating of cancers wherein this kinase is expressed. In particular, as they have substantially outstanding lung cancer cell line proliferation suppression, they can be useful in the treatment of lung cancer, breast cancer, and brain cancer.

Whereas the present invention has been explained in detail in the above through preferred preparation examples, example compounds and experimental examples, the scope of the present invention is not limited to these specific example compounds and shall be defined by the appended claims. Further, it shall be understood that a person having ordinary skill in the art may make various modifications and changes without departing from the scope of the present invention.

What is claimed is:

1. A compound of Formula 8,

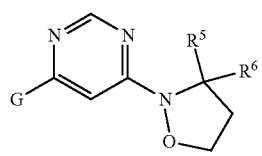

Formula 8 wherein:
$R^5$ is $C_1$-8 alkyl, aryl of 3 to 12 atoms, heteroaryl of 3 to 12 atoms, or heterocycloalkyl of 3 to 12 atoms, wherein the $C_{1-8}$ alkyl, aryl, heteroaryl, and heterocycloalkyl are independently unsubstituted or substituted by at least one substituent J;
J is selected from the group consisting of halogen, cyano, $C_{1-8}$ alkyl substituted or unsubstituted by halogen, aryl of 3 to 12 atoms, heteroaryl of 3 to 12 atoms, heterocycloalkyl of 3 to 12 atoms, $C_{2-8}$ alkenyl, $C_{1-8}$ alkoxy, $C_{2-8}$ alkynyl and $C_{1-8}$ alkylamino, wherein each of the substituents J are independently unsubstituted or substituted with one or more substituents selected from the group consisting of halogen, $C_{1-8}$ alkyl substituted or unsubstituted by halogen, $C_{1-8}$ alkoxy, and $C_{1-8}$ alkylamino;
$R^6$ is hydrogen or $C_{1-8}$ alkyl; and
G is halogen, a sulfonic acid, an ester, or an alkoxy.

2. The compound according to claim 1, wherein $R^5$ is $C_{1-8}$ alkyl unsubstituted or substituted by at least one substituent J.

3. The compound according to claim 1, wherein $R^5$ is aryl of 3 to 12 atoms unsubstituted or substituted by at least one substituent J.

4. The compound according to claim 3, wherein $R^5$ is phenyl unsubstituted or substituted by at least one substituent J.

5. The compound according to claim 4, wherein J is selected from the group consisting of halogen, cyano, $C_{1-8}$ alkyl substituted and unsubstituted by halogen, $C_{2-8}$ alkenyl, and $C_{1-8}$ alkoxy.

6. The compound according to claim 5, wherein J is halogen.

7. The compound according to claim 6, wherein the halogen is selected from the group consisting of fluoro and chloro.

8. The compound according to claim 7, wherein the halogen is fluoro.

9. The compound according to claim 7, wherein the halogen is chloro.

10. The compound according to claim 5, wherein J is cyano.

11. The compound according to claim 5, wherein J is $C_{1-8}$ alkyl substituted or unsubstituted by halogen.

12. The compound according to claim 11, wherein J is —$CF_3$.

13. The compound according to claim 5, wherein J is $C_{2-8}$ alkenyl.

14. The compound according to claim 5, wherein J is $C_{1-8}$ alkoxy.

15. The compound according to claim 14, wherein $C_{1-8}$ alkoxy is —$OCH_3$.

16. The compound according to claim 1, wherein the compound is

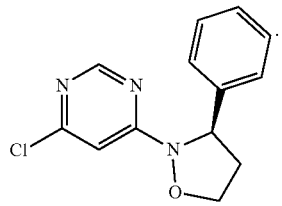 [SMILES: Clc1cc(N2OCC[C@@H]2c2ccccc2)ncn1]

17. The compound according to claim 1, wherein $R^5$ is heteroaryl of 3 to 12 atoms unsubstituted or substituted by at least one substituent J.

18. The compound according to claim 17, wherein J is selected from the group consisting of halogen, cyano, $C_{1-8}$ alkyl substituted and unsubstituted by halogen, $C_{2-8}$ alkenyl, and $C_{1-8}$ alkoxy.

19. The compound according to claim 18, wherein J is halogen.

20. The compound according to claim 19, wherein the halogen is selected from the group consisting of fluoro and chloro.

21. The compound according to claim 20, wherein the halogen is fluoro.

22. The compound according to claim 20, wherein the halogen is chloro.

23. The compound according to claim 18, wherein J is cyano.

24. The compound according to claim 18, wherein J is $C_{1-8}$ alkyl substituted or unsubstituted by halogen.

25. The compound according to claim 24, wherein J is —$CF_3$.

26. The compound according to claim 18, wherein J is $C_{2-8}$ alkenyl.

27. The compound according to claim 18, wherein J is $C_{1-8}$ alkoxy.

28. The compound according to claim 27, wherein $C_{1-8}$ alkoxy is —$OCH_3$.

29. The compound according to claim 1, wherein $R^5$ is heterocycloalkyl of 3 to 12 atoms unsubstituted or substituted by at least one substituent J.

\* \* \* \* \*